(12) United States Patent
Vogelstein et al.

(10) Patent No.: US 12,195,803 B2
(45) Date of Patent: Jan. 14, 2025

(54) METHODS AND MATERIALS FOR ASSESSING AND TREATING CANCER

(71) Applicants: The Johns Hopkins University, Baltimore, MD (US); BOARD OF REGENTS, THE UNIVERSITY OF TEXAS SYSTEM, Austin, TX (US); THE RESEARCH FOUNDATION FOR THE STATE UNIVERSITY OF NEW YORK, Albany, NY (US)

(72) Inventors: Bert Vogelstein, Baltimore, MD (US); Kenneth W. Kinzler, Baltimore, MD (US); Joshua Cohen, Baltimore, MD (US); Nickolas Papadopoulos, Towson, MD (US); Anne Marie Lennon, Baltimore, MD (US); Cristian Tomasetti, Baltimore, MD (US); Yuxuan Wang, Baltimore, MD (US); Georges Jabboure Netto, Baltimore, MD (US); Rachel Karchin, Baltimore, MD (US); Christopher Douville, Baltimore, MD (US); Samir Hanash, Houston, TX (US); Simeon Springer, Baltimore, MD (US); Arthur P. Grollman, Albany, NY (US); Kathleen Dickman, Albany, NY (US)

(73) Assignees: The Johns Hopkins University, Baltimore, MD (US); Board of Regents, The University of Texas System, Austin, TX (US); The Research Foundation for The State University of New York, Albany, NY (US)

( * ) Notice: Subject to any disclaimer, the term of this patent is extended or adjusted under 35 U.S.C. 154(b) by 307 days.

(21) Appl. No.: 16/637,372

(22) PCT Filed: Aug. 7, 2018

(86) PCT No.: PCT/US2018/045669
§ 371 (c)(1),
(2) Date: Feb. 7, 2020

(87) PCT Pub. No.: WO2019/067092
PCT Pub. Date: Apr. 4, 2019

(65) Prior Publication Data
US 2020/0377956 A1    Dec. 3, 2020

Related U.S. Application Data

(60) Provisional application No. 62/629,870, filed on Feb. 13, 2018, provisional application No. 62/628,759, filed on Feb. 9, 2018, provisional application No. 62/618,232, filed on Jan. 17, 2018, provisional application No. 62/594,245, filed on Dec. 4, 2017, provisional application No. 62/542,167, filed on Aug.
(Continued)

(51) Int. Cl.
| | |
|---|---|
| C12Q 1/6886 | (2018.01) |
| C12Q 1/6827 | (2018.01) |
| C12Q 1/6858 | (2018.01) |
| C12Q 1/686 | (2018.01) |
| C12Q 1/6869 | (2018.01) |

(52) U.S. Cl.
CPC ......... *C12Q 1/6886* (2013.01); *C12Q 1/6827* (2013.01); *C12Q 1/6858* (2013.01); *C12Q 1/686* (2013.01); *C12Q 1/6869* (2013.01); *C12Q 2531/113* (2013.01); *C12Q 2565/30* (2013.01); *C12Q 2565/514* (2013.01); *C12Q 2565/625* (2013.01); *C12Q 2600/112* (2013.01); *C12Q 2600/156* (2013.01); *C12Q 2600/158* (2013.01); *C12Q 2600/16* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,750,341 A | 5/1998 | Macevicz |
| 6,090,935 A | 7/2000 | Breivik et al. |

(Continued)

FOREIGN PATENT DOCUMENTS

| | | |
|---|---|---|
| CN | 1360059 | 7/2002 |
| CN | 102241772 | 11/2011 |

(Continued)

OTHER PUBLICATIONS

US 9,115,403 B2, 08/2015, Vogelstein et al. (withdrawn)
(Continued)

*Primary Examiner* — Katherine D Salmon
(74) *Attorney, Agent, or Firm* — Fish & Richardson P.C.

(57) ABSTRACT

Provided herein are methods and materials for detecting and/or treating subject (e.g. a human) having cancer. In some embodiments, methods and materials for identifying a subject as having cancer (e.g., a localized cancer) are provided in which the presence of member(s) of two or more classes of biomarkers are detected. In some embodiments, methods and materials for identifying a subject as having cancer (e.g. a localized cancer) are provided in which the presence of member(s) of at least one class of biomarkers and the presence of aneuploidy are detected. In some embodiments, methods described herein provide increased sensitivity and/or specificity in the detection of cancer in a subject (e.g. a human).

15 Claims, 88 Drawing Sheets
Specification includes a Sequence Listing.

Related U.S. Application Data 7, 2017, provisional application No. 62/542,164, filed on Aug. 7, 2017, provisional application No. 62/542,144, filed on Aug. 7, 2017.

(56) References Cited

U.S. PATENT DOCUMENTS

| | | | |
|---|---|---|---|
| 6,156,504 A | 12/2000 | Gocke et al. |
| 6,190,857 B1 | 2/2001 | Ralph et al. |
| 6,248,521 B1 | 6/2001 | Van Ness et al. |
| 6,306,597 B1 | 10/2001 | Macevicz |
| 6,361,940 B1 | 3/2002 | Van Ness et al. |
| 6,514,736 B1 | 2/2003 | Erlich et al. |
| 6,576,420 B1 | 6/2003 | Carson et al. |
| 6,686,157 B2 | 2/2004 | Ward et al. |
| 6,746,845 B2 | 6/2004 | Kinzler et al. |
| 6,815,212 B2 | 11/2004 | Ness et al. |
| 6,890,764 B2 | 5/2005 | Chee et al. |
| 6,942,968 B1 | 9/2005 | Dickinson et al. |
| 6,977,153 B2 | 12/2005 | Kumar et al. |
| 7,056,660 B1 | 6/2006 | Diehl et al. |
| 7,060,431 B2 | 6/2006 | Chee et al. |
| 7,115,400 B1 | 10/2006 | Adessi et al. |
| 7,211,390 B2 | 5/2007 | Rothberg et al. |
| 7,232,656 B2 | 6/2007 | Balsubramanian et al. |
| 7,264,929 B2 | 9/2007 | Rothberg et al. |
| 7,323,305 B2 | 1/2008 | Leamon et al. |
| 7,323,310 B2 | 1/2008 | Peters et al. |
| 7,332,270 B1 | 2/2008 | Ralph et al. |
| 7,499,806 B2 | 3/2009 | Kermani et al. |
| 7,682,790 B2 | 3/2010 | Hollander et al. |
| 7,683,035 B1 | 3/2010 | Erbacher et al. |
| 7,700,286 B2 | 4/2010 | Stroun et al. |
| 7,702,468 B2 | 4/2010 | Chinitz et al. |
| 7,704,687 B2 | 4/2010 | Wang et al. |
| 7,745,125 B2 | 6/2010 | Gelfand et al. |
| 7,754,429 B2 | 7/2010 | Rigatti et al. |
| 7,776,531 B1 | 8/2010 | Black et al. |
| 7,811,759 B2 | 10/2010 | Han |
| 7,899,626 B2 | 3/2011 | Kruglyak et al. |
| 7,901,897 B2 | 3/2011 | Stuelpnagel et al. |
| 7,948,015 B2 | 5/2011 | Rothberg et al. |
| 7,957,913 B2 | 6/2011 | Chinitz et al. |
| 7,977,108 B2 | 7/2011 | Newhouse et al. |
| 8,021,888 B2 | 9/2011 | Mohammed et al. |
| 8,026,053 B2 | 9/2011 | Samuels et al. |
| 8,043,834 B2 | 10/2011 | Abarzua et al. |
| 8,076,074 B2 | 12/2011 | Mohammed |
| 8,093,063 B2 | 1/2012 | Albitar |
| 8,150,626 B2 | 4/2012 | Fan et al. |
| 8,168,602 B2 | 5/2012 | DePinho et al. |
| 8,190,373 B2 | 5/2012 | Huang et al. |
| 8,288,103 B2 | 10/2012 | Oliphant et al. |
| 8,323,896 B2 | 12/2012 | Tanabe et al. |
| 8,343,718 B2 | 1/2013 | Van Der Werf et al. |
| 8,372,637 B2 | 2/2013 | Hollander |
| 8,481,292 B2 | 7/2013 | Casbon et al. |
| 8,492,089 B2 | 7/2013 | Owen et al. |
| 8,658,572 B2 | 2/2014 | Albert et al. |
| 8,697,350 B2 | 4/2014 | Ruegg et al. |
| 8,715,926 B2 | 5/2014 | Duerksen-Hughes et al. |
| 8,728,732 B2 | 5/2014 | Preston et al. |
| 8,741,630 B2 | 6/2014 | Dickinson et al. |
| 8,765,419 B2 | 7/2014 | Hirschbein et al. |
| 8,822,158 B2 | 9/2014 | Froehlich et al. |
| 8,865,410 B2 | 10/2014 | Shendure et al. |
| 8,871,687 B2 | 10/2014 | Strom |
| 8,877,436 B2 | 11/2014 | Eder et al. |
| 8,911,942 B2 | 12/2014 | Mohammed et al. |
| 8,962,250 B2 | 2/2015 | Stanley |
| 9,012,149 B2 | 4/2015 | Kim et al. |
| 9,029,103 B2 | 5/2015 | Rigatti et al. |
| 9,045,796 B2 | 6/2015 | Gunderson et al. |
| 9,051,606 B2 | 6/2015 | Liu et al. |
| 9,074,206 B2 | 7/2015 | Wu et al. |
| 9,085,798 B2 | 7/2015 | Chee et al. |
| 9,109,256 B2 | 8/2015 | Shuber |
| 9,115,410 B2 | 8/2015 | Nazarenko et al. |
| 9,133,524 B2 | 9/2015 | You et al. |
| 9,140,687 B2 | 9/2015 | Blonder et al. |
| 9,163,283 B2 | 10/2015 | Chee et al. |
| 9,222,134 B2 | 12/2015 | Mann |
| 9,228,234 B2 | 1/2016 | Rabinowitz et al. |
| 9,233,125 B2 | 1/2016 | Davila et al. |
| 9,238,832 B2 | 1/2016 | Will et al. |
| 9,279,146 B2 | 3/2016 | Gupta et al. |
| 9,315,868 B2 | 4/2016 | Vogelstein et al. |
| 9,340,830 B2 | 5/2016 | Lipson et al. |
| 9,382,581 B2 | 7/2016 | Froehner et al. |
| 9,389,234 B2 | 7/2016 | Von Hoff et al. |
| 9,399,794 B2 | 7/2016 | Liu |
| 9,404,156 B2 | 8/2016 | Hicks et al. |
| 9,410,206 B2 | 8/2016 | Hoon et al. |
| 9,410,956 B1 | 8/2016 | Cheng |
| 9,422,593 B2 | 8/2016 | Rothmann et al. |
| 9,424,392 B2 | 8/2016 | Rabinowitz et al. |
| 9,441,267 B2 | 9/2016 | Gunderson et al. |
| 9,453,258 B2 | 9/2016 | Kain et al. |
| 9,476,095 B2 | 10/2016 | Vogelstein et al. |
| 9,476,098 B2 | 10/2016 | Mann et al. |
| 9,487,823 B2 | 11/2016 | Lasken et al. |
| 9,546,399 B2 | 1/2017 | Amorese et al. |
| 9,546,404 B2 | 1/2017 | Sanders et al. |
| 9,556,491 B2 | 1/2017 | Hoon |
| 9,567,640 B2 | 2/2017 | Hoon |
| 9,574,234 B2 | 2/2017 | Straus et al. |
| 9,587,273 B2 | 3/2017 | Stuelpnagel et al. |
| 9,593,366 B2 | 3/2017 | Nazarenko et al. |
| 9,598,731 B2 | 3/2017 | Talasaz |
| 9,670,530 B2 | 6/2017 | Kostem et al. |
| 9,689,047 B2 | 6/2017 | O'Neil et al. |
| 9,701,741 B2 | 7/2017 | Eberhard et al. |
| 9,702,004 B2 | 7/2017 | Van Eijk et al. |
| 9,708,655 B2 | 7/2017 | Mandell et al. |
| 9,745,632 B2 | 8/2017 | Parr et al. |
| 9,760,530 B2 | 9/2017 | Harsha et al. |
| 9,783,847 B2 | 10/2017 | Chee |
| 9,783,854 B2 | 10/2017 | Sanders et al. |
| 9,792,403 B2 | 10/2017 | Sun et al. |
| 9,797,000 B2 | 10/2017 | Lowe et al. |
| 9,797,016 B2 | 10/2017 | Lind et al. |
| 9,816,139 B2 | 11/2017 | Breen |
| 9,822,417 B2 | 11/2017 | Lothe et al. |
| 9,828,672 B2 | 11/2017 | Varadarajan et al. |
| 9,834,822 B2 | 12/2017 | Talasaz et al. |
| 9,846,159 B2 | 12/2017 | Shaw et al. |
| 9,873,908 B2 | 1/2018 | Gupta et al. |
| 9,879,312 B2 | 1/2018 | Steemers et al. |
| 9,902,992 B2 | 2/2018 | Talasaz et al. |
| 9,914,973 B2 | 3/2018 | Cheng |
| 9,920,366 B2 | 3/2018 | Eltoukhy et al. |
| 9,944,924 B2 | 4/2018 | Rigatti et al. |
| 9,957,570 B2 | 5/2018 | Mori et al. |
| 9,992,598 B2 | 6/2018 | Reiche |
| 10,011,826 B2 | 7/2018 | Hollander et al. |
| 10,011,870 B2 | 7/2018 | Zimmermann et al. |
| 10,017,759 B2 | 7/2018 | Kaper et al. |
| 10,023,904 B2 | 7/2018 | Villahermosa Jaen et al. |
| 10,023,917 B2 | 7/2018 | Buettner et al. |
| 9,965,585 B2 | 8/2018 | Lo et al. |
| 10,041,127 B2 | 8/2018 | Talasaz |
| 10,047,356 B2 | 8/2018 | Altschuler et al. |
| 10,100,366 B2 | 10/2018 | Davare |
| 10,102,337 B2 | 10/2018 | Scolnick et al. |
| 10,113,199 B2 | 10/2018 | Morin et al. |
| 10,131,957 B2 | 11/2018 | Akbari |
| 10,227,652 B2 | 3/2019 | Rabinowitz et al. |
| 10,240,202 B2 | 3/2019 | Rabinowitz et al. |
| 10,260,103 B2 | 4/2019 | Gonzalez Diaz et al. |
| 10,266,893 B2 | 4/2019 | Rabinowitz et al. |
| 10,388,403 B2 | 8/2019 | Rava et al. |
| 10,407,737 B2 | 9/2019 | Cohen et al. |
| 10,422,006 B2 | 9/2019 | Samuels et al. |
| 10,457,995 B2 | 10/2019 | Talasaz |
| 10,494,678 B2 | 12/2019 | Talasaz |

(56) References Cited

U.S. PATENT DOCUMENTS

| | | | |
|---|---|---|---|
| 10,501,793 B2 | 12/2019 | Chee et al. |
| 10,501,810 B2 | 12/2019 | Talasaz |
| 10,522,242 B2 | 12/2019 | Rabinowitz et al. |
| 10,526,658 B2 | 1/2020 | Babiarz et al. |
| 10,538,759 B2 | 1/2020 | Stuelpnagel et al. |
| 10,538,814 B2 | 1/2020 | Babiarz et al. |
| 10,539,566 B2 | 1/2020 | Narain et al. |
| 10,557,172 B2 | 2/2020 | Babiarz et al. |
| 10,577,601 B2 | 3/2020 | Shendure et al. |
| 10,590,482 B2 | 3/2020 | Ryan et al. |
| 10,597,653 B2 | 3/2020 | Sabot et al. |
| 10,619,214 B2 | 4/2020 | Lo et al. |
| 10,689,709 B2 | 6/2020 | Song et al. |
| 10,704,085 B2 | 7/2020 | Talasaz et al. |
| 10,704,086 B2 | 7/2020 | Talasaz et al. |
| 10,704,105 B2 | 7/2020 | Samuels et al. |
| 10,704,108 B2 | 7/2020 | Vogelstein et al. |
| 10,731,220 B2 | 8/2020 | Babiarz et al. |
| 10,732,220 B2 | 8/2020 | Tamura et al. |
| 10,783,364 B2 | 9/2020 | Gao |
| 10,787,713 B2 | 9/2020 | Samuels et al. |
| 10,801,063 B2 | 10/2020 | Eltoukhy et al. |
| 10,822,663 B2 | 11/2020 | Talasaz |
| 10,894,987 B2 | 1/2021 | Vogelstein et al. |
| 10,941,450 B2 | 3/2021 | Hayashi et al. |
| 10,947,597 B2 | 3/2021 | Panka |
| 11,001,898 B2 | 5/2021 | Bitene et al. |
| 11,060,152 B2 | 7/2021 | Roperch |
| 11,098,372 B2 | 8/2021 | Stern et al. |
| 11,118,234 B2 | 9/2021 | Quinn et al. |
| 11,142,797 B2 | 10/2021 | Moynahan et al. |
| 11,193,175 B2 | 12/2021 | Chudova |
| 11,211,144 B2 | 12/2021 | Zhu et al. |
| 11,339,447 B2 | 5/2022 | Mao et al. |
| 11,345,968 B2 | 5/2022 | Mortimer et al. |
| 11,384,382 B2 | 7/2022 | Kennedy et al. |
| 2002/0160404 A1 | 10/2002 | Dietmaier et al. |
| 2003/0148335 A1 | 8/2003 | Shen et al. |
| 2005/0136405 A1 | 6/2005 | Linder et al. |
| 2005/0153313 A1 | 7/2005 | Endege et al. |
| 2005/0244847 A1 | 11/2005 | Domanico et al. |
| 2006/0127918 A1 | 6/2006 | Mohammed et al. |
| 2006/0263789 A1 | 11/2006 | Kincaid |
| 2006/0292576 A1 | 12/2006 | Albitar et al. |
| 2007/0020640 A1 | 1/2007 | McCloskey |
| 2007/0269805 A1 | 11/2007 | Hogers |
| 2008/0160580 A1 | 7/2008 | Adessi et al. |
| 2008/0286795 A1 | 11/2008 | Kawashima et al. |
| 2009/0088328 A1 | 4/2009 | Mohammed et al. |
| 2009/0105081 A1 | 4/2009 | Rodesch et al. |
| 2009/0215062 A1 | 8/2009 | Lee |
| 2009/0233802 A1 | 9/2009 | Bignell |
| 2009/0298187 A1 | 12/2009 | Nazarenko et al. |
| 2010/0041048 A1 | 2/2010 | Diehl et al. |
| 2010/0113758 A1 | 5/2010 | Wilmer et al. |
| 2010/0127186 A1 | 5/2010 | Bykanov et al. |
| 2010/0129874 A1 | 5/2010 | Mitra et al. |
| 2010/0248991 A1 | 9/2010 | Roesler et al. |
| 2010/0273219 A1 | 10/2010 | May et al. |
| 2011/0152111 A1 | 6/2011 | Fan et al. |
| 2011/0217309 A1 | 9/2011 | Buck et al. |
| 2011/0319415 A1 | 12/2011 | Thomas et al. |
| 2012/0010091 A1 | 1/2012 | Linnarson |
| 2012/0156753 A1 | 6/2012 | Jendrisak et al. |
| 2012/0225428 A1 | 9/2012 | Beck et al. |
| 2013/0059741 A1 | 3/2013 | Weiner |
| 2013/0266938 A1 | 10/2013 | Will |
| 2014/0011199 A1 | 1/2014 | Speiser et al. |
| 2014/0038837 A1 | 2/2014 | Fung et al. |
| 2014/0050788 A1 | 2/2014 | Daniel et al. |
| 2014/0066317 A1 | 3/2014 | Talasaz |
| 2014/0128270 A1 | 5/2014 | Nakao |
| 2014/0271635 A1 | 9/2014 | Brogdon et al. |
| 2014/0336996 A1 | 11/2014 | Sun et al. |
| 2014/0364323 A1 | 12/2014 | Fan et al. |
| 2015/0011416 A1 | 1/2015 | Lei et al. |
| 2015/0024948 A1 | 1/2015 | Dugas et al. |
| 2015/0051085 A1 | 2/2015 | Vogelstein et al. |
| 2015/0087535 A1 | 3/2015 | Patel |
| 2015/0093756 A1 | 4/2015 | Wolff et al. |
| 2015/0176071 A1 | 6/2015 | Fisher et al. |
| 2015/0197787 A1 | 7/2015 | Welder et al. |
| 2015/0225775 A1 | 8/2015 | Satya |
| 2015/0252415 A1 | 9/2015 | Vogelstein et al. |
| 2015/0275267 A1 | 10/2015 | O'Neil et al. |
| 2015/0307947 A1 | 10/2015 | Basu et al. |
| 2015/0324519 A1 | 11/2015 | Liu |
| 2015/0360193 A1 | 12/2015 | Fan et al. |
| 2016/0017320 A1 | 1/2016 | Wang et al. |
| 2016/0026758 A1 | 1/2016 | Jabara et al. |
| 2016/0048564 A1 | 2/2016 | Bassett, Jr. et al. |
| 2016/0092630 A1 | 3/2016 | Chen et al. |
| 2016/0122831 A1* | 5/2016 | West .............. G16B 45/00 514/49 |
| 2016/0194404 A1 | 7/2016 | June et al. |
| 2016/0201131 A1* | 7/2016 | Wang ............ C12Q 1/6809 506/2 |
| 2016/0251704 A1 | 9/2016 | Talasaz et al. |
| 2016/0273049 A1 | 9/2016 | Velculescu et al. |
| 2016/0281154 A1 | 9/2016 | So et al. |
| 2016/0304954 A1* | 10/2016 | Lin .............. C12Q 1/6874 |
| 2016/0319345 A1 | 11/2016 | Gnerre et al. |
| 2016/0374330 A1 | 12/2016 | Grolz |
| 2017/0009287 A1 | 1/2017 | Brastaad et al. |
| 2017/0039328 A1 | 2/2017 | Kathleen et al. |
| 2017/0058332 A1 | 3/2017 | Kermani et al. |
| 2017/0061072 A1 | 3/2017 | Kermani et al. |
| 2017/0101676 A1 | 4/2017 | Teng et al. |
| 2017/0137876 A1 | 5/2017 | Rigatti et al. |
| 2017/0141793 A1 | 5/2017 | Straus et al. |
| 2017/0165289 A1 | 6/2017 | Minomi et al. |
| 2017/0175197 A1 | 6/2017 | Gatalica et al. |
| 2017/0183742 A1 | 6/2017 | Thierry et al. |
| 2017/0240972 A1 | 8/2017 | Mokhtari et al. |
| 2017/0240974 A1 | 8/2017 | Eltoukhy et al. |
| 2017/0260590 A1 | 9/2017 | Eltoukhy et al. |
| 2017/0314081 A1 | 11/2017 | Gutin et al. |
| 2017/0316149 A1 | 11/2017 | Maston |
| 2017/0356030 A1 | 12/2017 | Boyanov et al. |
| 2017/0356053 A1 | 12/2017 | Otto et al. |
| 2018/0002738 A1 | 1/2018 | Wang et al. |
| 2018/0002749 A1 | 1/2018 | Larson et al. |
| 2018/0016640 A1 | 1/2018 | Xu et al. |
| 2018/0023119 A1 | 1/2018 | Adey et al. |
| 2018/0037950 A1 | 2/2018 | Gunderson et al. |
| 2018/0051329 A1 | 2/2018 | Elzinga |
| 2018/0087105 A1 | 3/2018 | Larson et al. |
| 2018/0095969 A1 | 4/2018 | Jung et al. |
| 2018/0100859 A1 | 4/2018 | Cardone et al. |
| 2018/0119216 A1 | 5/2018 | Jamshidi et al. |
| 2018/0120291 A1 | 5/2018 | Eltoukhy et al. |
| 2018/0135044 A1 | 5/2018 | Sausen et al. |
| 2018/0135103 A1 | 5/2018 | Furlan et al. |
| 2018/0141020 A1 | 5/2018 | Gunderson et al. |
| 2018/0142304 A1 | 5/2018 | Sanders et al. |
| 2018/0148716 A1 | 5/2018 | Heitz et al. |
| 2018/0155705 A1 | 6/2018 | Wolf et al. |
| 2018/0155774 A1 | 6/2018 | Gunderson et al. |
| 2018/0163201 A1 | 6/2018 | Larson |
| 2018/0171337 A1 | 6/2018 | O'Neil et al. |
| 2018/0195131 A1 | 7/2018 | Mortimer |
| 2018/0201974 A1 | 7/2018 | Fraser |
| 2018/0201992 A1 | 7/2018 | Wu et al. |
| 2018/0203974 A1 | 7/2018 | Venn |
| 2018/0208999 A1 | 7/2018 | Lo et al. |
| 2018/0258490 A1 | 9/2018 | Wang |
| 2019/0206510 A1 | 7/2019 | Jiang et al. |
| 2019/0256924 A1 | 8/2019 | Vogelstein et al. |
| 2019/0287654 A1 | 9/2019 | Curtis et al. |
| 2019/0355438 A1 | 11/2019 | Venn et al. |
| 2019/0376137 A1 | 12/2019 | Vogelstein et al. |
| 2020/0013482 A1 | 1/2020 | Sikora |
| 2020/0131568 A1 | 4/2020 | Talasz et al. |
| 2020/0157636 A1 | 5/2020 | Velculescu et al. |

(56) References Cited

U.S. PATENT DOCUMENTS

| | | |
|---|---|---|
| 2021/0254153 A1 | 8/2021 | Vogelstein et al. |
| 2021/0277467 A1 | 9/2021 | Vogelstein et al. |
| 2021/0277468 A1 | 9/2021 | Vogelstein et al. |

FOREIGN PATENT DOCUMENTS

| | | |
|---|---|---|
| EP | 1910560 | 12/2010 |
| EP | 3443119 | 2/2019 |
| EP | 3177740 | 1/2021 |
| WO | WO 2001023618 | 4/2001 |
| WO | WO 2002012897 | 2/2002 |
| WO | WO 2002016649 | 2/2002 |
| WO | WO 2002059355 | 8/2002 |
| WO | WO 2002099982 | 12/2002 |
| WO | WO 2008030186 | 3/2008 |
| WO | WO 2008118877 | 10/2008 |
| WO | WO 2009092068 | 7/2009 |
| WO | WO 2009152928 | 12/2009 |
| WO | WO 2010028098 | 3/2010 |
| WO | WO 2010126614 | 11/2010 |
| WO | WO 2010127186 | 11/2010 |
| WO | WO 2010141955 | 12/2010 |
| WO | WO 2012038839 | 3/2012 |
| WO | WO 2012092336 | 7/2012 |
| WO | WO 2012142213 | 10/2012 |
| WO | WO 2013113816 | 8/2013 |
| WO | WO 2013148496 | 10/2013 |
| WO | WO 2014183078 | 11/2014 |
| WO | WO 2015198074 | 12/2015 |
| WO | WO 2016130704 | 8/2016 |
| WO | WO 2016135300 | 9/2016 |
| WO | WO 2016140974 | 9/2016 |
| WO | WO 2016141169 | 9/2016 |
| WO | WO 2016141324 | 9/2016 |
| WO | WO 2016170147 | 10/2016 |
| WO | WO 2016/134136 | 11/2016 |
| WO | WO 2016193490 | 12/2016 |
| WO | WO 2017019456 | 2/2017 |
| WO | WO 2017032808 | 3/2017 |
| WO | WO 2017053915 | 3/2017 |
| WO | WO 2017085321 | 5/2017 |
| WO | WO 2017123316 | 7/2017 |
| WO | WO 2017127741 | 7/2017 |
| WO | WO 2017132276 | 8/2017 |
| WO | WO 2017132438 | 8/2017 |
| WO | WO 2017136603 | 8/2017 |
| WO | WO 2017151524 | 9/2017 |
| WO | WO 2017181134 | 10/2017 |
| WO | WO 2017181146 | 10/2017 |
| WO | WO 2017197027 | 11/2017 |
| WO | WO 2017201315 | 11/2017 |
| WO | WO 2017205686 | 11/2017 |
| WO | WO 2017218512 | 12/2017 |
| WO | WO 2018009723 | 1/2018 |
| WO | WO 2018013598 | 1/2018 |
| WO | WO 2018057770 | 3/2018 |
| WO | WO 2018064229 | 4/2018 |
| WO | WO 2018064629 | 4/2018 |
| WO | WO 2018068014 | 4/2018 |
| WO | WO 2018077847 | 5/2018 |
| WO | WO 2018081130 | 5/2018 |
| WO | WO 2018085862 | 5/2018 |
| WO | WO 2018093780 | 5/2018 |
| WO | WO 2018111872 | 6/2018 |
| WO | WO 2018119399 | 6/2018 |
| WO | WO 2018119438 | 6/2018 |
| WO | WO 2018119452 | 6/2018 |
| WO | WO 2018125892 | 7/2018 |
| WO | WO 2018136416 | 7/2018 |
| WO | WO 2018/093744 | 8/2018 |
| WO | WO 2018137826 | 8/2018 |
| WO | WO 2018177847 | 10/2018 |
| WO | WO 2018/204657 | 11/2018 |
| WO | WO 2018218113 | 11/2018 |
| WO | WO 2020021119 | 1/2020 |

OTHER PUBLICATIONS

Yamao et al. (Jpn J Clin Oncol 1999 vol. 29 p. 550) (Year: 1999).*
Porika et al. (Asian Pacific J Cancer Prev 2010 vol. 11 p. 157) (Year: 2010).*
Cohen et al (Science Feb. 2018 vol. 23 p. 926) (Year: 2018).*
Gaspari et al. "Fetal ovarian cysts: an early manifestation of McCune-Albright syndrome?, "Prenatal Diagnosis, 2012, 32:859-863.
Khalid et al., "Pancreatic cyst fluid DNA analysis in evaluating pancreatic cysts: a report of the PANDA study," Gastrointestinal Endoscopy, 2009, 69(6):1095-1102.
Troiano et al., "Sonographically guided therapeutic aspiration of benign-appearing ovarian cysts and endometriomas," AJR, 1998, 171:1601-1605.
Urick et al., "PIK3R1 (p85α) Is Somatically Mutated at High Frequency in Primary Endometrial Cancer," Cancer Research, 2011, 71(12):4061.
Bettegowda et al. "Detection of circulating tumor DNA in early- and late-stage human malignancies," Sci Transl Med, 2014, 6(224):1-25.
Color Hereditary Cancer Test, "A pathogenic mutation was identified in the BRCA1 gene," tm Clinical Grade testing (www.color.com), 2015, 1-12.
Gardner et al., "Evaluation of a 27-gene inherited cancer panel across 630 consecutive patients referred for testing in a clinical diagnostic laboratory," Hereditary Cancer in Clinical Practice, 2018, 16(1):1-10.
Gudmundsson et al. "Genome-Wide Association and Replication Studies Identify Four Variants Associated with Prostate Cancer Susceptibility," Nat. Genet. 2009 41:1122-6.
Haber et al. "Blood-based analyses of cancer: circulating tumor cells and circulating tumor DNA," Cancer Discov, 2014, 4(6):650-661.
Heitzer et al., "Current and future perspectives of liquid bipsies in genomics-driven oncology", Nature Reviews Genetics, 2018, 20(2):71-88.
Huber et al., "High-Resolution Liquid Chromatography of DNA Fragments on Non-Porous Poly(Styrene-Divinylbenzene) Particles," Nucleic Acids Res., 1993, 21:1061-6.
International Search Report and Written Opinion in International Application No. PCT/US2019/017973, dated May 17, 2019, 7 pages.
International Search Report and Written Opinion in International Application No. PCT/US2018/030905, dated Oct. 2, 2018, 23 pages.
International Search Report and Written Opinion in International Application No. PCT/US2017/061447, Feb. 19, 2018, 10 pages.
International Search Report and Written Opinion in International Application No. PCT/US2020/014172, dated Apr. 30, 2020, 18 pages.
Jain et al., "Personalized Therapy of Cancer," Textbook of Personalized Medicine, 2015, Chapter 10, pp. 199-381.
Kato et al., "A new Packing for Separation of DNA Restriction Fragments by High Performance Liquid Chromatography," J. Biochem, 1984, 95:83-86.
Kinde et al., 'Detection and quantification of rare mutations with massively parallel sequencing', PNAS, 2011, 108(23):9530-9535.
Leary et al. "Detection of chromosomal alterations in the circulation of cancer patients with whole-genome sequencing," Sci Transl Med, 2012, 4(162):1-21.
Martinez et al., "Computational optimisation of targeted DNA sequencing for cancer detection," Sci. Rep., 2013, 3(3309):sertp03309 1-8.
Newman et al., 'Integrated digital error suppression for improved detection of circulating tumor DNA', Nature Biotechnology, 2016, 34(5):547-555.
"Nextera XT DNA Sample Preparation Guide," Illumina, Oct. 1, 2012 (Oct. 1, 2012), Part# 15031942, Rev. C, pp. 1-48. Retrieved from the Internet:<http://cmore.soest.hawaii.edu/summercourse/2015/documents/Metagenomics_06-22/nextera_xt_sample_preparation_guide_15031942_c.pdf> on Sep. 19, 2010 (Sep. 19, 2010).

(56) References Cited

OTHER PUBLICATIONS

Out et al., "Deep Sequencing to Reveal New Variants in Pooled DNA Samples," Hum. Mutat. 2009, 30:1703-1712.
Peng et al., Reducing amplification artifacts in high multiplex amplicon sequencing by using molecular barcodes, BMC Genomics, 2015, 16(589):1-12.
Turner et al., "Massively parallel exon capture and library-free resequencing across 16 genomes," Nat. Methods, 2009, 6:315-316.
Peng et al., "Targeted Single Primer Enrichment Sequencing with Single End Duplex-UMI," Scientific Reports, 2019, 9:4810, 10 pages.
Abbosh et al., "Phylogenetic ctDNA analysis depicts early-stage lung cancer evolution", Nature 545: 446-451, 2017.
Abdel-Rahman, "Denosumab versus zoledronic acid to prevent aromatase inhibitors-associated fractures in postmenopausal early breast cancer; a mixed treatment meta-analysis.", Expert Rev Anticancer Ther 16(8): 885-91, 2016.
ACOG Practice Bulletin. Clinical Management Guidelines for Obstetrician-Gynecologists. No. 60, Mar. 2005. "Pregestational diabetes mellitus.", Obstet Gynecol 1 05, 675-685, 2005.
Affymetrix Human Genome U133 Plus 2.0 Array, Public on Nov. 7, 2003, Gene Expression Omnibus URL: https://www.ncbi.nlm.nih.gov/geo/query/acc.cgi?acc=GPL570> [Retrieved from the internet Jun. 7, 2018].
Agus et al., "Targeting ligand-activated ErbB2 signaling inhibits breast and prostate tumor growth", Cancer Cell 2: 127-137, 2002.
Albert et al., "Direct selection of human genomic loci by microarray hybridization", Nat. Methods 4: 903-905, 2007.
Albertini et al., "In vivo somatic mutations in humans: measurement and analysis.", Annu Rev Genet 24: 305-326, 1990.
Alhilli et al., "Incidence and factors associated with synchronous ovarian and endometrial cancer: a population-based case-control study.", Gynecologic oncology 125: 109-113, 2012.
Alizadeh et al., "The Lymphochip: A Specialized cDNA Microarray for the Genomic-scale Analysis of Gene Expression in Normal and Malignant Lymphocytes," Cold Spring Harbor Symposia on Quantitative Biology, 1999, vol. LXIV:71-78.
Allegra et al., "American Society of Clinical Oncology provisional clinical opinion: testing for KRAS gene mutations in patients with metastatic colorectal carcinoma to predict response to anti-epidermal growth factor receptor monoclonal antibody therapy.", J. Clin. Oncol. 27: 2091-2096, 2009.
Allen et al., "Multi-institutional Validation Study of the American Joint Commission on Cancer (8th Edition) Changes for T and N Staging in Patients With Pancreatic Adenocarcinoma.", Ann Surg 265(1): 185-191, 2017.
Allory et al., "Telomerase Reverse Transcriptase Promoter Mutations in Bladder Cancer: High Frequency Across Stages, Detection in Urine, and Lack of Association with Outcome", Eur Urol 65: 360-366, 2014.
Alvarez et al., "Widespread Hypomethylation Occurs Early and Synergizes with Gene Amplification duting Esophageal Carcinogenesis", PLOS Genetics, vol. 7, issue 3, e1001356, 1-14 pages, 2011.
Alvarez-Chaver et al., "Proteornics for discovery of candidate colorectal cancer biornarkers", World J. Gastroenterol. 20(14): 3804-3824, 2014.
American Cancer Society, "Can ovarian cancer be found early?", (Available at http://www.cancer.org/Cancer/OvarianCancer/DetailedGuide/ovariancancer-detection), 4 pages, 2017.
American College of Obstetricians and Gynecologists, ACOG Committee Opinion: No. 280, Dec. 2002. "The role of the generalist obstetrician-gynecologist in the early detection of ovarian cancer.", Obstet Gynecol., 2002, 100(6):1413-1416.
Andre et al., "Improved overall survival with oxaliplatirl, fluorouracil, and leucovorin as adjuvan treatment in stage II or III colon cancer in the MOSAIC trial.", J Clin Oncol 27(19): 3109-3116, 2009.
Anglesio et al., "Cancer-Associated Mutations in Endometriosis without Cancer", N Engl J Med 376: 1835-1848, 2017.

Ansari et al.,"Relationship between tumour size and outcome in pancreatic ductal adenocarcinoma", Br J Surg 104(5): 600-607, 2017.
Antoni et al., "Bladder Cancer Incidence and Mortality: A Global Overview and Recent Trends.", Eur Urol, 71(1), 96-108, 2017.
Araten et al., A quantitative measurement of the human somatic mutation rate., Cancer Res 65: 8111-8117, 2005.
Arbyn et al., "European Guidelines for Quality Assurance in Cervical Cancer Screening. Second edition—summary document.", Ann Oncol 21, 448-458 2010.
Arnold et al., "Global burden of cancer attributable to high body-mass index in 2012: a population-based study.", The Lancet. Oncology 16, 36-46, 2015.
Audeh et al., "Oral poly(ADP-ribose) polymerase inhibitor olaparib in patients with BRCA1 or BRCA2 mutations and recurrent ovarian cancer: a proof-of-concept trial.", Lancet 376: 245-251, 2010.
Australian Office Action in Australian Application No. 2017203206, dated Jan. 23, 2018.
Awada et al., "An open-label, dose-escalation study to evaluate the safety and pharmacokinetics of CEP-9722 (a PARP-1 and PARP-2 inhibitor) in combination with gemcitabine and cisplatin in patients with advanced solid tumors", Anticancer Drugs 27(4): 342-8, 2016.
Baard et al., Diagnostic dilemmas in patients with upper tract urothelial carcinoma., Nat Rev Urol, 14(3), 181-191, 2017.
Baehner, "The analytical validation of the Oncotype DX Recurrence Score assay", Ecancermedicalscience 10: 675, 2016.
Bahuva et al., "Morphologic abnormalities are poorly predictive of Visceral pain in chronic pancreatitis.", Pancreas 42(1): 6-10, 2013
Bainbridge et al., "Whole exome capture in solution with 3 Gbp of data" Genome Biology, 11(6): R62, 2010.
Bandiera et al., "Cancer antigen 125, human epididymis 4, kal-likrein 6, osteopontin and soluble mesothelin-related peptide immunocomplexed with immunoglobulin Min epithelial ovarian cancer diagnosis.", Clinical chemistry and laboratory medicine: CCLM I FESCC 51, 1815-1824, 2013.
Bang et al., "Trastuzumab in combination with chemotherapy versus chemotherapy alone for treatment of HER2-positive advanced gastric or gastro-oesophageal junction cancer (ToGA): a phase 3, open-label, randomised controlled trial", Lancet 376: 687-697, 2010.
Bansal et al., "Low- and high-grade bladder cancer appraisal via serum-based proteomics approach.", Clin Chim Acta 436: 97-103, 2014.
Bardelli et al., "Liquid Biopsies, What We Do Not Know (Yet)", Cell Press, 31, 172-179, 2017.
Baretton et al., "Inerphase Cytogenetic Analysis of Prostatic Carcinomas by Use of Nonisotopic in Situ Hybridization", Cancer Research 54, 4472-4480, 1994.
Barkan et al., "The Paris System for Reporting Urinary Cytology: The Quest to Develop a Standardized Terminology.", Adv AnatPathol 23:193-201, 2016.
Barnes, "The fidelity of Taq polymerase catalyzing PCR is improved by an N-terminal deletion", Gene 112:29-35, 1992.
Barollo et al., "Prevalence, tumorigenic role, and biochemical implications of rare BRAF alterations", Thyroid: offical journal of the american thyroid association 24, 809-819, 2014.
Barroso-Sousa et al., "Clinical Development of the CDK4/6 Inhibitors Ribociclib and Abemaciclib in Breast Cancer", Breast Care 11(3): 167-173, 2016.
Barrow et al., "Cumulative lifetime incidence of extracolonic cancers in Lynch syndrome: a report of 121 families with proven mutations.", Clin. Genet. 75, 141-149, 2009.
Baselga et al., "Pertuzumab plus Trastuzumab plus Docetaxel for Metastatic Breast Cancer", N Engl J Med 366: 109-119, 2012.
Bashashati et al., "Distinct evolutionary trajectories of primary high-grade serous ovarian cancers revealed through spatial mutational profiling.", The Journal of pathology, 231: 21-34, 2013.
Bast et al., "A radioimmunoassay using a monoclonal antibody to monitor the course of epithelial ovarian cancer", The New England journal of medicine 309, 883-887, 1983.
Beddowes et al., "Predicting treatment resistance and relapse through circulating DNA.", Breast 34(Suppl 1): S31-S35, 2017.

(56) References Cited

OTHER PUBLICATIONS

Beers et al., "Array-CGH and breast cancer," Breast Cancer Res., 2006, 8(3):210, 10 pages.
Bell et al., "A simple way to treat PCR products prior to sequencing using ExoSAP-IT" Bio Techniques, 2008.
Bell et al., "Integrated genomic analyses of ovarian carcinoma.", Nature 474, 609-615, 2011.
Benson et al., "Colon Cancer, Version 1.2017", NCCN, vol. 15, No. 3, 370-398, 2017.
Beroukhim et al., "Assessing the significance of chromosomal aberrations in cancer: Methodology and application to glioma", Proceedings of the National Academy of Sciences, 104: 20007-20012, 2007.
Bertone et al., "Design optimization methods for genomic DNA tiling arrays", Genome Res 16(2): 271-281, 2006.
Bertotti et al., "The genomic landscape of response to EGFR blockade in colorectal cancer.", Nature, 526: 263-7, 2015.
Bettegowda et al., "Detection of Circulating Tumor DNA in Early- and Late-Stage Human Malignancies", Science translational medicine 6(224): 224ra224, 2014.
Biankin et al., "Pancreatic cancer genomes reveal aberrations in axon guidance pathway genes.", Nature 491(7424): 399-405, 2012.
Bielas et al., "Quantification of random genomic mutations.", Nat. Methods, 2: 285-290, 2005.
Binladen et al., "The Use of Coded PCR Primers Enables High-Throughput Sequencing of Multiple Homolog Amplification Products by 454 Parallel Sequencing" PLoS One, 9 pages, Feb. 14, 2007.
Bowtell et al., "Rethinking ovarian cancer II: reducing mortality from high-grade serous ovarian cancer.", Nature reviews Cancer, 15: 668-79, 2015.
Boyd et al., "Measurement and clinical monitoring of human lymphocyte clonality by massively parallel VDJ pyrosequencing.", Science Translat. Med., vol. 1, 12ra23, Supplementary material, pp. 1-30, 2009.
Bozic et al., "Evolutionary dynamics of cancer in response to targeted combination therapy", Elife 2: e00747, 2013.
Brahmer et al., "Safety and activity of anti-PD-L1 antibody in patients with advanced cancer.", N Engl J Med, 366(26): 2455-65, 2012.
Bray et al., "Global estimates of cancer prevalence for 27 sites in the adult population in 2008.", Int. J. Cancer, 2012.
Bristow et al., "Survival effect of maximal cytoreductive surgery for advanced ovarian carcinoma during the platinum era: a meta-analysis." J. Clin. Oncol. 20, 1248-1259, 2002.
Burris et al., "Phase I trial of novel kinesin spindle protein (KSP) inhibitor SB-715992 IV days 1, 8, 15 q 28 days", J. Clin. Oncol. 22: 128, 2004.
Buys et al., "Ovarian cancer screening in the Prostate, Lung, Colorectal and Ovarian (PLCO) cancer screening trial: findings from the initial screen of a randomized trial", American journal of obstetrics and gynecology 193, 1630-1639, 2005.
Buys et al., Effect of screening on ovarian cancer mortality: the Prostate, Lung, Colorectal and Ovarian (PLCO) Cancer Screening Randomized Controlled Trial. JAMA 305, 2295-2303, 2011.
Byron et al., "FGFR2 mutations are rare across histologic subtypes of ovarian cancer," Gynecologic Oncology 117, 125-129, 2010.
Calvez-Kelm et al., "KRAS mutations in blood circulating cell-free DNA: a pancreatic cancer case-control", Oncotarget, vol. 7, No. 48, 2016.
Camidge et al., "A phase I safety, tolerability, and pharmacokinetic study of enzastaurin combined with capecitabine in patients with advanced solid tumors", Anticancer Drugs 19: 77-84, 2008.
Campbell et al., "No difference in stem cell somatic mutation between the background mucosa of right- and left-sided sporadic colorectal carcinomas.", J Pathol 186: 31-35, 1998.
Cancer Genome Atlas Research Network, "Comprehensive molecular characterization of urothelial bladder carcinoma.", Nature 507: 315-322, 2014.
Cancer Genome Atlas Research, "Integrated genomic analyses of ovarian carcinoma.", Nature 474: 609-615, 2011.

Cancer Genome Atlas Research, "Integrated genomic characterization of endometrial carcinoma.", Nature 497: 67-73, 2013.
Cancer.gov [online], "NCI Dictionary of Cancer Terms, Definition of Biomarker," available on or before Apr. 5, 2018, [retrieved on Feb. 26, 2020], retrieved from: URL<https://www.cancer.gov/publications/dictionaries/cancer-terms/def/biomarker>, 1 page.
Capello et al., "Sequential Validation of Blood-Based Protein Biomarker Candidates for Early-Stage Pancreatic Cancer.", J Natl Cancer Inst 109(4), 2017.
Carlson et al., "Screening for ovarian cancer.", Ann. Intern. Afrd. 121, 124-132, 1994.
Casbon et al., "A method for counting PCR template molecules with application to next-generation sequencing," Nucleic Acids Research, 1-8, 2011.
Cass et al., BRCA-mutation-associated fallopian tube carcinoma: a distinct clinical phenotype? Obstetrics and Gynecology 106: 1327-34, 2005.
Castelo-Branco et al., "Methylation of the TERT promoter and risk stratification of childhood brain tumours: an integrative genomic and molecular study," Lancet Oncol., 2013, 14(6):534-542.
Chai et al., Field effect in cancer-an update. Ann Clin Lab Sci 39: 331-337, 2009.
Chan et al., "Size Distributions of Maternal and Fetal DNA in Maternal Plasma", Clinical chemistry 50: 88-92, 2004.
Chan, "Consolidated guidelines on the use of antiretroviral drugs for treating and preventing HIV infection Recommendations for a public health approach", Second Edition, Book, 2016.
Chang et al., "CARs: Synthetic Immunoreceptors for Cancer Therapy and Beyond", Trends Mol Med 23(5): 430-450, 2017.
Chang et al., "The clinical utility of endoscopic ultrasound-guided fine-needle aspiration in the diagnosis and staging of pancreatic carcinoma.", Gastrointestinal endoscopy 45, 387-393, 1997.
Chari et al., "Probability of pancreatic cancer following diabetes: a population based study". Gastroenterology 129(2): 504-511, 2005.
Chen et al., "Aristolochic acid-associated urothelial cancer in Taiwan", Proc Natl Acad Sci US A, 109(21): 8241-8246, 2012.
Chen et al., "CAR T-cell intrinsic PD-1 checkpoint blockade: A two-in-one approach for solid tumor immunotherapy", Oncoimmunology 6(2): el273302, 2016.
Chen, "Immune checkpoint inhibitors for nonsmall cell lung cancer treatment", J. Chin Med Assoc 80(1): 7-14, 2017.
Cheng et al., "Molecular genetic analysis of ovarian serous cystadenomas", Laboratory investigation; a journal of technical methods and pathology 84, 778-784, 2004.
Cheng et al., "TERT Promoter Mutations Occur Frequently in Urothelial Papilloma and Papillary Urothelial Neoplasm of Low Malignant Potential.", Eur Urol 71 :497-498, 2017.
Chetverina et al., "Molecular colony diagnostics: detection and quantitation of viral nucleic acids by in-gel PCR.", Biotechniques 33: 150-152, 154, 156, 2002.
Cheung et al., "High frequency of PIK3R1 and PIK3R2 mutations in endometrial cancer elucidates a novel mechanism for regulation of PTEN protein stability.", Cancer Discov 1, 170-185, 2011.
Chinese Office Action issued Mar. 3, 2017 in related Chinese Application No. 201380068411.8.
Chiu et al., "Noninvasive prenatal diagnosis of fetal chromosomal aneuploidy by massively parallel genomic sequencing of DNA in maternal plasma", Proc Natl Acad Sci US A 105: 20458-20463, 2008.
Christensen et al., "Functional ovarian cysts in premenopausal and gynecologically healthy women", Contraception 66, 153-157, 2002.
Chu et al., J. Clin. Oncol. 22:14S, abstr 2078, 2004.
Chung et al., "A whole-genome mouse BAC microarray with 1-Mb resolution for analysis of DNA copy number changes by array comparative genomic hybridization.", Genome Res. 14(1): 188-196, 2004.
Clarke-Pearson, "Clinical Practice, Screening for ovarian cancer.", N Engl J Med., 361(2): 170-177, 2009.
Cobb et al., "Adenocarcinoma of Mullerian origin: review of pathogenesis, molecular biology, and emerging treatment paradigms" Gynecologic Oncology Research and Practice, May 12, 2015 (online), vol. 5, pp. 1-16.

(56) References Cited

OTHER PUBLICATIONS

Cohen et al., "Combined circulating tumor DNA and protein biomarker-based liquid biopsy for the earlier detection of pancreatic cancers", PNAS, vol. 114, No. 38, 10202-10207, 2017.
Cohen et al., "Detection and localization of surgically resectable cancers with a multi-analyte blood test", Science, 359(6378): 926-930, 2018.
Cole et al., "Working paper No. 3 Somatic mutant frequency, mutation rates and mutational spectra in the human population in vivo", Mutat Res 304: 33-105, 1994.
Conner et al., "Outcome of unexpected adnexal neoplasia discovered during risk reduction salpingo-oophorectomy in women with germ-line BRCA1 or BRCA2 mutations.", Gynecol Oncol 132: 280-6, 2014.
Coombs et al., "Therapy-Related Clonal Hematopoiesis in Patients with Non-hematologic Cancers Is Common and Associated with Adverse Clinical Outcomes", Cell Stem Cell 21(3): 374-382, 2017.
"Consensus sequence" (online) Oct. 4, 2011 <https://en.wikipedia.org/w/index.php?title=Consensus_sequence&oldid=423354064>.
Cooper et al., "Endometrial sampling techniques in the diagnosis of abnormal uterine bleeding.", Obstet Gynecol Clin North Am 27, 235-244, 2000.
Corona et al., "CDK4/6 inhibitors in HER2-positive breast cancer", Cri Rev Oncol Hematol 112: 208-214, 2017.
Cortes et al., "Support-Vector Networks", Machine learning 20: 273-297, 1995.
Costello et al., "Discovery and characterization of artifactual mutations in deep coverage targeted capture sequencing data due to oxidative DNA damage during sample preparation.", Nucleic acids research 41: e67, 2013.
Cowan et al., "Detection of TERT promoter mutations in primary adenocarcinoma of the urinary bladder.", Hum Pathol., 53: 8-13, 2016.
Craig et al., "Identification of genetic variants using bar-coded multiplexed sequencing.", Nat Methods 5: 887-893, 2008.
Cree et al., "The evidence base for circulating tumour DNA blood-based biomarkers for the early detection of cancer: a systematic mapping review", BMC Cancer, 17: 697, 1-17, 2017.
Cruz et al., "Absence of BRAF and NRAS mutations in uveal melanoma", Cancer research 63, 5761-5766, 2003.
Cunningham et al., Cetuximab Monotherapy and Cetuximab plus Irinotecan in Irinotecan-Refractory Metastatic Colorectal Cancer, N. Engl. J. Med., 2004, 351(4):337-345.
D'Souza et al., "Tumor characterization by ultrasound-release of multiple protein and microRNA biomarkers, preclinical and clinical evidence", PLOS One, 1-17 pp. 2018.
Dalma-Weiszhausz et al., "The affymetrix GeneChip platform: an overview.", Methods Enzymol. 410: 3-28, 2006.
Darragh et al., "Tumor Detection by Imaging Proteolytic Activity", Cancer Res 70: 1505-12, 2010.
Davies et al., "Mutations of the BRAF gene in human cancer", Nature 417, 949-954, 2002.
Davis et al., "Diagnosis, evaluation and follow-up of asymptomatic microhematuria (AMH) in adults: AUA guideline.", J Urol 188: 2473-2481, 2012.
Dawson et al., "Analysis of Circulating Tumor DNA to Monitor Metastatic Breast Cancer", N Engl J Med 368(13): 1199-1209, 2013.
De Boer et al., "An in vitro assay for frameshift mutations: hotspots for deletions of 1 bp by Klenow-fragment polymerase share a consensus DNA sequence.", Genetics 118: 181-191, 1988.
De Vos et al., "Novel PMS2 Pseudogenes Can Conceal Recessive Mutations Causing a Distinctive Childhood Cancer Syndrome", American journal of human genetic, 74: 954-964, 2004.
Demeure et al., "Whole-genome Sequencing of an Aggressive BRAF Wild-type Papillary Thyroid Cancer Identified EML4-ALK Translocation as a Therapeutic Target", World J Surg., 38: 1296-305, 2014.
Demirol et al., "Effect of endometrioma cystectomy on IVF outcome: a prospective randomized study", Reproductive biomedicine online 12, 639-643, 2006.
DeRisi et al., "Use of a cDNA microarray to analyse gene expression patterns in human cancer.", Nat. Genet., 14: 457-460, 1996.
DeSimone et al., "Rate of pathology from atypical glandular cell Pap tests classified by the Bethesda 2001 nomenclature.", Obstet Gynecol 107, 1285-1291, 2006.
Di Renzo et al., "Expression of the MetfHepatocyte Growth Factor Receptor in Human Pancreatic Cancer", Cancer Res 55(5): 1129-1138, 1995.
Di Renzo et al., "Overexpression and amplification of the met/HGF receptor gene during the progression of colorectal cancer.", Clin Cancer Res 1(2): 147-154, 1995.
Diehl et al., "Analysis of mutations in DNA isolated from plasma and stool of colorectal cancer patients." Gastroenterology 135: 489-498, 2008.
Diehl et al., "Detection and quantification of mutations in the plasma of patients with colorectal tumors", Proceedings of the National Academy of Sciences of the United States of America, 102: 16368-16373, 2005.
Dimashkieh et al., "Evaluation of Uro Vysion and Cytology for Bladder Cancer Detection", Cancer Cytopathol 121: 591-597, 2013.
Dinkelspiel et al., "Long-term mortality among women with epithelial ovarian cancer.", Gynecologic oncology 138: 421-8, 2015.
Dizon et al., "A Phase II Evaluation of Belinostat and Carboplatin in the Treatment of Recurrent or Persistent Platinum-Resistant Ovarian, Fallopian Tube, or Primary Peritoneal Carcinoma: A Gynecologic Oncology Group Study", Gynecol. Oncol. 125(2): 367-371, 2012.
Dizon et al., "Phase II Activity of Belinostat (PXD-101), Carboplatin, and Paclitaxel in Women With Previously Treated Ovarian Cancer", Int J. Gynecol. Cancer 23(3): 533-539, 2012.
Dohm et al., "Substantial biases in ultrashort read data sets from high-throughput DNA sequencing.", Nucleic Acids Res 36:e105, 2008.
Dokianakis et al., "Ras gene activation in malignant cells of human ovarian carcinoma peritoneal fluids," Clin & Exp. Metastasis, 1999, 17(4):293-297.
Dong et al., "Combining markers with and without the limit of detection.", Stat Med 33(8): 1307-1320, 2014.
Douville et al., "Detection of aneuploidy in patients with cancer through amplification of long interspersed nucleotide elements (LINEs)", PNAS, vol. 115, No. 8, 1871-1876, 2018.
Dressman et al., Transforming single DNA molecules into fluorescent magnetic particles for detection and enumeration of genetic variations. Proc Natl Acad Sci US A 100(15): 8817-8822, 2003.
Drevis et al., "Phase I Clinical Study of AZD2171, an Oral Vascular Endothelial Growth Factor Signaling Inhibitor, in Patients With Advanced Solid Tumors", 25: 3045-2054, 2007.
Druley et al., "Quantification of rare allelic variants from pooled genomic DNA.", Nat Methods 6: 263-265, 2009.
Duke et al., "Transvaginal aspiration of ovarian cysts: long-term follow-up", Cardiovascular and interventional radiology 29, 401-405, 2006.
Durbin et al., "A map of human genome variation from population-scale sequencing.", Nature 467:1061-1073, 2010.
Dy et al., "Long-Term Survivors of Metastatic Colorectal Cancer Treated with Systemic Chemotherapy Alone: A North Central Cancer Treatment Group Review of 3811 Patients, N0144", Clin Colorectal Cancer 8(2): 88-93, 2009.
Eastman et al., "Maternal viral genotypic zidovudine resistance and infrequent failure of zidovudine therapy to prevent perinatal transmission of human immunodeficiency virus type 1 in pediatric AIDS Clinical Trials Group Protocol 076.", J Infect Dis 177:557-564, 1998.
Easton et al., "Breast and Ovarian Cancer Incidence in BRCA I-Mutation Carriers", Am. J. Hum. Genet. 56: 265-271, 1995.
Eberle et al., "Immunoguided laser assisted microdissection techniques for DNA methylation analysis of archival tissue specimens.", The Journal of molecular diagnostics: JMD 12: 394-401, 2010.

(56) References Cited

OTHER PUBLICATIONS

Eckert et al., "Genomics of Ovarian Cancer Progression Reveals Diverse Metastatic Trajectories Including Intraepithelial Metastasis to the Fallopian Tube," Cancer Discov., 2016, 6(12):1342-1351.
Eckert et al., "High fidelity DNA synthesis by the Thermus aquaticus DNA polymerase.", Nucleic Acids Res 18: 3739-3744, 1990.
Egawa et al., "Clinicopathological aspects of small pancreatic cancer. Pancreas", 28(3): 235-240, 2004.
Ehab et al., "Profile of palbociclib in the treatment of metastatic breast cancer", Breast Cancer 8: 83-91, 2016.
Eid et al., "Real-time DNA sequencing from single polymerase molecules", Science 323: 133-138, 2009.
Eliassen et al., "Urinary Estrogens and Estrogen Metabolites and Subsequent Risk of Breast Cancer among Premenopausal Women", Cancer Research, vol. 72, issue 3, 696-706, 2012.
Ellinger et al., "Epigenetic biomarkers in the blood of patients with urological malignancies", Expert Rev Mal Diagn 15: 505-516, 2015.
Ellis et al., "Immune Checkpoint Inhibitors for Patients With Advanced NoneSmall-Cell Lung Cancer: A Systematic Review", Clin Lung Cancer pii: S1525-7304(17)30043-8, 2017.
Elmasry et al., "Genetic mutations in gynaecological cancers," Reviews in Gynaecological and Preinatal Practice, vol. 6, No. 3-4, pp. 115-125, 2006.
Eloubeidi et al., "Endoscopic ultrasound-guided fine needle aspiration biopsy of patients with suspected pancreatic cancer: diagnostic accuracy and acute and 30-day complications.", The American journal of gastroenterology 98, 2663-2668, 2003.
El-Tanani et al., "The regulation and role of osteopontin in malignant transformation and cancer.", Cytokine Growth Factor Rev 17(6): 463-474, 2006.
Elzek et al., "Proteomics of ovarian cancer: functional insights and clinical applications", Cancer Metastasis Rev., 34(1): 83-96, 2015.
Erickson et al., "Detection of somatic TP53 mutations in tampons of patients with highgrade serous ovarian cancer.", Obstetrics and gynecology 124, 881-885, 2014.
Erlich et al., "Alta-Cyclic: a self-optimizing base caller for next-generation sequencing.", Nat Methods 5: 679-682, 2008.
Ernani et al., "Agilent's SureSelect Target Enrichment System: Brining Cost and Process Efficiency to Next-Generation Sequencing," Agilent Technologies—Product Notes, pp. 1-8, 2009.
Ethier et al., "Bone Modifier Use as Adjuvant Therapy for Early Breast Cancer", Curr Oncol Rep 19(3): 15, 2017.
European Office Action issued in related European Application No. 13851273.6, dated Apr. 19, 2017.
Extended European Search Report in Application No. 18193794.7, dated Dec. 19, 2018.
Extended European Search Report issued in related European Application No. 12772013.4, dated Sep. 17, 2014.
Extended European Search Report issued in related European Application No. 13851273.6, dated Jun. 1, 2016.
Extended European Search Report issued in related European Application No. 17154750.8, dated Aug. 17, 2017.
Faias et al., "Clinical Impact of KRAS and GNAS Analysis Added to CEA and Cytology in Pancreatic Cystic Fluid Obtained by EUS-FNA", Digestive Diseases and Sciences, vol. 63, No. 9, pp. 2351-2361, 2018.
Falchook et al., "Methylation and histone deacetylase inhibition in combination with platinum treatment in patients with advanced malignancies", Investig. New Drugs 31(5): 1192-1200, 2013.
Falconer et al., "Ovarian cancer risk after salpingectomy: a nationwide population-based study.", J. Natl. Cancer Inst., 107,vol. 2, 2015.
Falzoi et al., "Multiplex genotyping of CYP3A4, CYP3A5, CYP2C9 and CYP2C19 SNPs using MALDI-TOF mass spectrometry", Pharmacogenomics 11: 559-571, 2010.
Fan et al., "Noninvasive diagnosis of fetal aneuploidy by shotgun sequencing DNA from maternal blood.", Proc Natl Acad Sci US A 105: 16266-16271, 2008.

Ferlay et al., "Cancer incidence and mortality patterns in Europe: estimates for 40 countries in 2012.", European Journal of cancer 49: 1374-403, 2013.
Finn et al., "Palbociclib and Letrozole in Advanced Breast Cancer", N Eng J Med 375: 1925-1936, 2016.
Fishman et al., "The role of ultrasound evaluation in the detection of early-stage epithelial ovarian cancer.", Am J Obstet Gynecol 192, 1214-1221; discussion 1221-1212, 2005.
Fong et al., "Inhibition of poly(ADP-ribose) polymerase in tumors from BRCA mutation carriers.", N Engl J Med 361: 123-134, 2009.
Forbes et al., "COSMIC: mining complete cancer genomes in the Catalogue of Somatic Mutations in Cancer.", Nucleic Acids Res 39, D945-950, 2011.
Forbes et al., "COSMIC: somatic cancer genetics at high-resolution", Nucleic Acids Res 45: D777-D783, 2017.
Forshew et al., "Noninvasive identification and monitoring of cancer mutations by targeted deep sequencing of plasma DNA", Sci Transl Med; 4: 136ra68, 2012.
Fradet et al., "Performance characteristics of a new monoclonal antibody test for bladder cancer: ImmunoCyt trade mark.", Can J Urol 4: 400-405, 1997 Abstract.
Friedman et al., "Regularization Paths for Generalized Linear Models via Coordinate Descent", Journal of Statistical Software 33 :74862, 22 pages, 2010.
Frokjaer et al., "Fibrosis, atrophy, and ductal pathology in chronic pancreatitis are associated with pancreatic function but independent of symptoms.", Pancreas 42(7): 1182-1187, 2013.
Frossard et al., "Performance of endosonography-guided fine needle aspiration and biopsy in the diagnosis of pancreatic cystic lesions", The american journal of gastroenterology 98, 1516-1524, 2003.
Fu et al., "Phase 1b-2a study to reverse platinum resistance through use of a hypomethylating agent, azacitidine, in patients with platinum-resistant or platinum-refractory epithelial ovarian cancer.", Cancer 117(8): 1661-1669, 2011.
Fujiwara et al., "Evaluation of Matrix Metalloproteinase-2 (MMP-2) Activity with Film in situ Zymography for Improved Cytological Diagnosis of Breast Tumors", Breast cancer 13: 272-8, 2006.
Fukagawa et al., "MicroRNA-135a-3p as a promising biomarker and nucleic acid therapeutic agent for ovarian cancer", Cancer Science, 108, 886-896, 2017.
Fullwood et al., "Next-generation DNA sequencing of paired-end tags (PET) for transcriptome and genome analyses" Genome Research, 19: 521-532, 2009.
Gam et al., "Breast cancer and protein biomarkers", World J. Exp. Med. 2(5): 86-91, 2012.
Gangi et al., "Metabolomic profile in pancreatic cancer patients: a consensusbased approach to identify highly discriminating metabolites", Oncotarget, 7(5):5815-5829, 2016.
Gasi et al., "Overexpression of Full-Length ETV1 Transcripts in Clinical Prostate Cancer Due to Gene Translocation", PLOS One, vol. 6, issue 1, e16332, 7 pages, 2011.
Geier et al., "Clinical evaluation of atypical glandular cells of undetermined significance.", Am. J. Obstet. Gynecol. 184, 64-69, 2001.
Geldenhuys et al., "Sensitivity and specificity of the Pap smear for glandular lesions of the cervix and endometrium.", Acta cytologica 51, 47-50, 2007.
Gelmon et al., "Olaparib in patients with recurrent high-grade serous or poorly differentiated ovarian carcinoma or triple-negative breast cancer: a phase 2, multicentre, open-label, non-randomised study", Lancet Oncol. 12: 852-61, 2011.
GenBank Accession No. NM_ 006218, "phosphatidylinositol-4,5-bisphosphate 3-kinase catalytic subunit alpha (PIK3CA), mRNA," Feb. 16, 2020, 7 pages.
GenBank Accession No. NM_ 058197, "*Homo sapiens* cyclin dependent kinase inhibitor 2A (CDKN2A), transcript variant 3, mRNA," Dec. 29, 2019, 5 pages.
GenBank Accession No. NM_000546, "*Homo sapiens* tumor protein p53 (TP53), transcript variant 1, mRNA," Feb. 13, 2020, 11 pages.
GenBank Accession No. NM_001126112, "*Homo sapiens* tumor protein p53 (TP53), transcript variant 2, mRNA," Dec. 28, 2019, 11 pages.

(56) References Cited

OTHER PUBLICATIONS

GenBank Accession No. NM_001126113, "*Homo sapiens* tumor protein p53 (TP53), transcript variant 4, mRNA," Dec. 8, 2019, 6 pages.
GenBank Accession No. NM_001126114, "*Homo sapiens* tumor protein p53 (TP53), transcript variant 3, mRNA," Dec. 29, 2019, 9 pages.
GenBank Accession No. NM_001276761, "*Homo sapiens* tumor protein p53 (TP53), transcript variant 2, mRNA," Dec. 23, 2019, 5 pages.
GenBank Accession No. NM000077, "*Homo sapiens* cyclin dependent kinase inhibitor 2A (CDKN2A), transcript variant 1, mRNA", dated Oct. 21, 2018, 7 pages.
GenBank Accession No. NM000142, "*Homo sapiens* fibroblast growth factor receptor 3 (FGFR3), transcript variant 1, mRNA", dated Dec. 23, 2018, 8 pages.
GenBank Accession No. NM000245, "*Homo sapiens* MET proto-oncogene, receptor tyrosine kinase (MET), transcript variant 2, mRNA", dated Jan. 13, 2019, 7 pages.
GenBank Accession No. NM000551, "*Homo sapiens* von Hippel-Lindau tumor suppressor (VHL), transcript variant 1, mRNA", dated Dec. 23, 2018, 7 pages.
GenBank Accession No. NM001005862, "*Homo sapiens* erb-b2 receptor tyrosine kinase 2 (ERBB2), transcript variant 2, mRNA", dated Jan. 13, 2019, 8 pages.
GenBank Accession No. NM001127500, "*Homo sapiens* MET proto-oncogene, receptor tyrosine kinase (MET), transcript variant 1, mRNA", dated Jan. 13, 2019, 7 pages.
GenBank Accession No. NM001130442, "*Homo sapiens* HRas proto-oncogene, GTPase (HRAS), transcript variant 3, mRNA", dated Dec. 23, 2018, 5 pages.
GenBank Accession No. NM001163213, "*Homo sapiens* fibroblast growth factor receptor 3 (FGFR3), transcript variant 3, mRNA", dated Dec. 23, 2018, 7 pages.
GenBank Accession No. NM001195132, "*Homo sapiens* cyclin dependent kinase inhibitor 2A (CDKN2A), transcript variant 5, mRNA", dated Oct. 21, 2018, 7 pages.
GenBank Accession No. NM001289936, "*Homo sapiens* erb-b2 receptor tyrosine kinase 2 (ERBB2), transcript variant 3, mRNA", dated Jan. 13, 2019, 8 pages.
GenBank Accession No. NM001289937, "*Homo sapiens* erb-b2 receptor tyrosine kinase 2 (ERBB2), transcript variant 4, mRNA", dated Jan. 13, 2019, 8 pages.
GenBank Accession No. NM001289938, "*Homo sapiens* erb-b2 receptor tyrosine kinase 2 (ERBB2), transcript variant 5, mRNA", dated Jan. 13, 2019, 6 pages.
GenBank Accession No. NM001318054, "*Homo sapiens* HRas proto-oncogene, GTPase (HRAS), transcript variant 4, mRNA", dated Dec. 23, 2018, 5 pages.
GenBank Accession No. NM001324401, "*Homo sapiens* MET proto-oncogene, receptor tyrosine kinase (MET), transcript variant 3, mRNA", dated Jan. 13, 2019, 5 pages.
GenBank Accession No. NM001324402, "*Homo sapiens* MET proto-oncogene, receptor tyrosine kinase (MET), transcript variant 4, mRNA", dated Jan. 13, 2019, 6 pages.
GenBank Accession No. NM001354723, "*Homo sapiens* von Hippel-Lindau tumor suppressor (VHL), transcript variant 3, mRNA", dated Dec. 23, 2018, 4 pages.
GenBank Accession No. NM001354809, "*Homo sapiens* fibroblast growth factor receptor 3 (FGFR3), transcript variant 4, mRNA", dated Dec. 23, 2018, 6 pages.
GenBank Accession No. NM001354810, "*Homo sapiens* fibroblast growth factor receptor 3 (FGFR3), transcript variant 5, mRNA", dated Dec. 23, 2018, 6 pages.
GenBank Accession No. NM003482, "*Homo sapiens* lysine methyltransferase 2D (KMT2D), mRNA", dated Jan. 13, 2019, 21 pages.
GenBank Accession No. NM004448, "*Homo sapiens* erb-b2 receptor tyrosine kinase 2 (ERBB2), transcript variant 1, mRNA", dated Jan. 13, 2019, 10 pages.
GenBank Accession No. NM004985, "*Homo sapiens* KRAS proto-oncogene, GTPase (KRAS), transcript variant b, mRNA", dated Jan. 13, 2019, 7 pages.
GenBank Accession No. NM005343, "*Homo sapiens* HRas proto-oncogene, GTPase (HRAS), transcript variant 1, mRNA", dated Dec. 29, 2018, 5 pages.
GenBank Accession No. NM022965, "*Homo sapiens* fibroblast growth factor receptor 3 (FGFR3), transcript variant 2, mRNA", dated Dec. 23, 2018, 6 pages.
GenBank Accession No. NM033360, "*Homo sapiens* KRAS proto-oncogene, GTPase (KRAS), transcript variant a, mRNA", dated Jan. 13, 2019, 8 pages.
GenBank Accession No. NM058195, "*Homo sapiens* cyclin dependent kinase inhibitor 2A (CDKN2A), transcript variant 4, mRNA", dated Aug. 4, 2018, 6 pages.
GenBank Accession No. NM058196, "*Homo sapiens* cyclin-dependent kinase inhibitor 2A (melanoma, p16, inhibits CDK4) (CDKN2A), transcript variant 2, mRNA", dated Dec. 21, 2003, 19 pages.
GenBank Accession No. NM176795, "*Homo sapiens* HRas proto-oncogene, GTPase (HRAS), transcript variant 2, mRNA", dated Dec. 23, 2018, 5 pages.
GenBank Accession No. NM198156, "*Homo sapiens* von Hippel-Lindau tumor suppressor (VHL), transcript variant 2, mRNA", dated Dec. 23, 2018, 7 pages.
GenBank Release Note v. 220, p. 1 (Jun. 2017).
Geng et al., "Function and clinical significance of circRNAs in solid tumors", Journal of Hematology and Oncology, 11; 98, 20 pages, 2018.
Genovese et al., "Clonal hematopoiesis and blood-cancer risk inferred from blood DNA sequence.", N Engl J Med 371(26): 2477-2487, 2014.
Gerlinger et al., "Intratumor heterogeneity and branched evolution revealed by multiregion sequencing.", N Engl J Med 366, 883-892, 2012.
Ghosh et al., "Quantifying the sensitivities of EGF receptor (EGFR) tyrosine kinase inhibitors in drug resistant non-small cell lung cancer (NSCLC) cells using hydrogel-based peptide array.", Biosensors & Bioelectronics 26: 424-31, 2010.
Giacona et al., "Cell-free DNA in human blood plasma: length measurements in patients with pancreatic cancer and healthy controls.", Pancreas 17: 89-97, 1998.
Gilbert et al., "Assessment of symptomatic women for early diagnosis of ovarian cancer: results from the prospective DOvE pilot project.", The Lancet. Oncology 13, 285-291, 2012.
Giligan et al., "American Society of Clinical Oncology Clinical Practice Guideline on uses of serum tumor markers in adult males with germ cell tumors.", J. Clin. Oncol. 28: 3388-3404, 2010.
Giraldez et al., "Droplet Digital PCR for Absolute Quantification of Extracellular MicroRNAs in Plasma and Serum: Quantification of the Cancer Biomarker hsa-miR-141.", Methods Mol. Biol., 1768: 459-74, 2018.
Gomez et al., "Efficacy and safety of lapatinib as first-line therapy for ErbB2-amplified locally advanced or metastatic breast cancer.", J Clin Oncol 26: 2999-3005, 2008.
Gong et al., "Efficacy and safety of everolimus in Chinese metastatic HR positive, HER2 negative breast cancer patients: a real-world retrospective study", Oncotarget, 8(35): 59810-59822, 2017.
Gonzalez-Pons "Colorectal Cancer Biomarkers: Where Are We Now?", Biomed. Res. Int. 2015: 149014, 2015.
Goodison et al., "A multi-analyte assay for the non-invasive detection of bladder cancer.", PLoS One, 7: e47469, 2012.
Gopalakrishna et al., "Anticipatory Positive Urine Tests for Bladder Cancer.", Ann Surg Oncol., 24: 1747-1753, 2017.
Gore et al., "Somatic coding mutations in human induced pluripotent stem cells.", Nature 471: 63-67, 2011.
Grisham et al., "BRAF mutation is associated with early stage disease and improved outcome in patients with low-grade serous ovarian cancer", Cancer 119, 548-554, 2013.
Grist et al., "In vivo human somatic mutation: frequency and spectrum with age.", Mutat Res 266: 189-196, 1992.
Grollman et al., "Aristolochic acid nephropathy: Harbinger of a global iatrogenic disease.", Environ Mal Mutagen, 54(1): 1-7, 2013.

(56) References Cited

OTHER PUBLICATIONS

Gruenberger et al., "Bevacizumab, Capecitabine, and Oxaliplatin as Neoadjuvant Therapy for Patients With Potentially Curable Metastatic Colorectal Cancer", J. Clin. Oncol. 26: 1830-1835, 2008.
Guetschow et al., "Detection of prolactin inducible protein mRNA, a biomarker for breast cancer metastasis, using a molecular beacon-based assay.", Anal. Bioanaly. Chem., 404: 399-406, 2012.
Gunderson et al., "Oncologic and reproductive outcomes with progestin therapy in women with endometrial hyperplasia and grade 1 adenocarcinoma: a systematic review," Gynecol Oncol 125, 477-482, 2012.
Haber et al., "Blood-based analyses of cancer: circulating tumor cells and circulating tumor DNA", Cancer Discov 4(6): 650-661, 2014.
Hajdinjak, "Uro Vysion FISH test for detecting urothelial cancers: meta-analysis of diagnostic accuracy and comparison with urinary cytology testing.", Urol Oncol 26: 646-651, 2008.
Halama et al., "Nesting of colon and ovarian cancer cells in the endothelial niche is associated with alterations in glycan and lipid metabolism", Scientific Reports, 7:39999, 10 pages, 2017.
Hall et al., "Linkage of Early-Onset Familial Breast Cancer to Chromosome 17q21", Science 250: 1684-1689, 1990.
Hamanishi et al., "Safety and Antitumor Activity of Anti-PD-1 Antibody, Nivolumab, in Patients With Platinum-Resistant Ovarian Cancer.", J. Clin. Oncol. 33(34): 4015-4022, 2015.
Hamilton et al., "The Molecular Basis of Turcot's Syndrome", The New England Journal of Medicine 332: 839-847, 1995.
Hamilton et al., "Uterine papillary serous and clear cell carcinomas predict for poorer survival compared to grade 3 endometrioid corpus cancers", British journal of cancer 94: 642-646, 2006.
Hare et al., "mTOR function and therapeutic targeting in breast cancer", Am J Cancer Res 7(3): 383-404, 2017.
Harris et al., "American Society of Clinical Oncology 2007 Update of Recommendations for the Use of Tumor Markers in Breast Cancer", J. Clin. Oncol. 25: 5287-5312, 2007.
Havrilesky et al., "Predictors of clinical outcomes in the laparoscopic management of adnexal masses.", Obstetrics and gynecology 102, 243-251, 2003.
He et al., "Heteroplasmic mitochondrial DNA mutations in normal and tumour cells.", Nature 464: 610-614, 2010.
He et al., "IgH gene rearrangements as plasma biomarkers in Non-Hodgkin's lymphoma patients.", Oncotarget 2, 178-185, 2011.
Hecht et al., "A randomized, double-blind, placebo-controlled, phase III study in patients (Pts) with metastatic adenocarcinoma of the colon or rectum receiving fifirst-line chemotherapy with oxaliplatin/5-flfluorouracil/leucovorin and PTK787/ZK 222584 or placebo (CONFIRM-1)", ASCO Annual Meeting Proceedings J. Clin. Oncol. 23: 16S, abstr. LBA3, 2005.
Hellmann et al., "Nivolumab plus ipilimumab as first-line treatment for advanced non-small-cell lung cancer (CheckMate 012): results of an open-label, phase 1, multicohort study", Lancet Oncol. 18(1): 31-41, 2017.
Hellstrom et al., "The HE4 (WFDC2) protein is a biomarker for ovarian carcinoma", Cancer research 63, 3695-3700, 2003.
Hennessy et al., "Ovarian cancer," Lancet, vol. 374, Oct. 17, 2009.
Henrique et al., "DNA hypomethylation in plasma as a cancer biomarker: when less is more?", Expert Rev. Mol. Diagn., 14: 419-22, 2014.
Henry et al., "Cancer biomarkers", Mol. Oncol. 6: 140-146, 2012.
Herbst et al., "Lung cancer.", N Engl J Med, 359(13): 1367-1380, 2008.
Herman et al., "Filter-based hybridization capture of subgenomes enables resequencing and copy-number detection.", Nat Methods 6: 507-510, 2009.
Hiatt et al., "Parallel, tag-directed assembly of locallt dreived short sequence reads.", Nat Methods, (7) 119-122, 2010.
Hiatt et al., "Single molecule molecular inversion probes for targeted, high-accuracy detection of low-frequency variation.", Genome research 23, 843-854, 2013.
Hilger et al., "Laparoscopic management of the adnexal mass.", Clinical obstetrics and gynecology 49, 535-548, 2006.
Hoang et al., "Mutational Signature of Aristolochic Acid Exposure as Revealed by Whole-Exome Sequencing", 2013 Science translational medicine 5: 197ra102, 2013.
Hodges et al., "High definition profiling of mammalian DNA methylation by array capture and single molecule bisulfite sequencing," Genome Research, 19: 1593-1605, 2009.
Hogenbirk et al., "Defining chromosomal translocation risks in cancer", PNAS, E3649-E3656, 2016.
Hoque et al., "High-throughput molecular analysis of urine sediment for the detection of bladder cancer by high-density single-nucleotide polymorphism array.", Cancer Res 63: 5723-5726, 2003.
Horn et al., "TERT promoter mutations in familial and sporadic melanoma." Science 339: 959-961, 2013.
Hosein et al., "Evaluating the repair of DNA derived from formalin-fixed paraffin-embedded tissues prior to genomic profiling by SNP-CGH analysis", Lab. Invest., 93, 701-710, 2013.
Hosgood et al., "Mitochondrial DNA copy number and lung cancer risk in a prospective cohort study", Carcinogen., 31: 847-9, 2010.
Howlader et al., SEER Cancer Statistics Review, 1975-2009, National Cancer Institute Bethesda, MD, 2012.
Hsieh et al., "Prescription profile of potentially aristolochic acid containing Chinese herbal products: an analysis of National Health Insurance data in Taiwan between 1997 and 2003", Chin Med, 3: 13, 6 pages, 2008.
Huang et al., "Comparison of Central HER2 Testing With Quantitative Total HER2 Expression and HER2 Homodimer Measurements Using a Novel Proximity-Based Assay", Am. J. Clin. Pathol. 134: 303-11, 2010.
Huang et al., "Highly recurrent TERT promoter mutations in human melanoma.", Science 339: 957-959, 2013.
Huang et al., "T-cell invigoration to tumour burden ratio associated with antiPD-1 response.", Nature 545(7652): 60-65, 2017.
Hughes et al., "Expression profiling using microarrays fabricated by an ink-jet oligonucleotide synthesizer.", Nat. Biotechnol. 19(4): 342-347, 2001.
Hui et al., "Pembrolizumab as first-line therapy for patients with PD-L1-positive advanced non-small cell lung cancer: a phase 1 trial", Ann Oncol 28(4): 874-881, 2017.
Hun et al., "Systems approach to characterize the metabolism of liver cancer stem cells expressing CD133", Sci. Rep. 7: 45557, 2017.
Huntsman et al. "MLL2, the second human homolog of the *Drosophila trithorax* gene, maps to 19q13.1 and is amplified in solid tumor cell lines," Oncogene, 18, 7975-7984, 1999.
Hurst et al., "Comprehensive mutation analysis of the TERT promoter in bladder cancer and detection of mutations in voided urine.", Eur Urol 65: 367-369, 2014.
Hurwitz et al., "Bevacizumab plus Irinotecan, Fluorouracil, and Leucovorin for Metastatic Colorectal Cancer", N. Engl. J. Med. 350: 2335-2342, 2004.
Ikediobi et al., "Mutation analysis of 24 known cancer genes in the NCI-60 cell line set,", Molecular Cancer Therapeutics, 5(11), 2006.
Ikematsu et al., "Serum midkine levels are increased in patients with various types of carcinomas", Br J Cancer 83(6): 701-706, 2000.
Ingvarsson et al., "Detection of pancreatic cancer using antibody microarray-based serum protein profiling.", Proteomics 8: 2211-9, 2008.
Innis et al., "Protocols for functional genomics" PCR application, (1999).
Insinga et al., "Diagnoses and outcomes in cervical cancer screening: a population-based study.", Am. J. Obstet. Gynecol. 191, 105-113, 2004.
International Preliminary Report on Patentability in PCT Appln. No. PCT/US2018/045669, dated Feb. 11, 2020, 7 pages.
International Preliminary Report on Patentability issued in PCT/US2013/065342, issued May 5, 2015, 7 pages.
International Search Report and Written Opinion for PCT/US2013/065342, mailed Apr. 1, 2014.
International Search Report and Written Opinion in International Application No. PCT/US2012/033207, dated Nov. 28, 2012.

(56) References Cited

OTHER PUBLICATIONS

International Search Report and Written Opinion in International Application No. PCT/US2016/046453, dated Nov. 1, 2016, 11 pages.
International Search Report and Written Opinion in PCT Appln. No. PCT/US2018/045669, dated Nov. 26, 2018, 15 pages.
Irizarry et al., "Summaries of Affymetrix GeneChip probe level data", Nucleic Acids Res 31, 4 :e15, 2003.
Isakoff et al., "P3-16-05: A Phase II Trial Expansion Cohort of the PARP Inhibitor Veliparib (ABT888) and Temozolomide in BRCA1/2 Associated Metastatic Breast Cancer.", Cancer Res 71: P3-16-05, 2011.
Ishikawa et al., "Minute carcinoma of the pancreas measuring 1 cm or less in diameter—collective review of Japanese case reports.", Hepatogastroenterology 46(25): 8-15, 1999.
Jabara et al., "Accurate sampling and deep sequencing of the HIV-1 protease gene using a Primer ID.", Proceedings of the National Academy of Sciences of the United States of America 108, 20166-20171, 2011.
Jacobs et al., "Ovarian cancer screening and mortality in the UK Collaborative Trial of Ovarian Cancer Screening UKCTOCS): a randomised controlled trial.", Lancet 387: 945-956, 2016.
Jacobs et al., Sensitivity of transvaginal ultrasound screening for endometrial cancer in postmenopausal women: a case-control study within the UKCTOCS cohort. The Lancet. Oncology 12, 38-48, 2011.
Jahr et al., "DNA Fragments in the Blood Plasma of Cancer Patients: Quantitations and Evidence for Their Origin from Apoptotic and Necrotic Cells", Cancer Research 61: 1659-1665, 2001.
Jaiswal et al., "Age-related clonal hematopoiesis associated with adverse outcomes.", N Engl J Med 371(26): 2488-2498, 2014.
Jasmine et al., "A Genome-Wide Study of Cytogenetic Changes in Colorectal Cancer Using SNP Microarrays: Opportunities for Future Personalized Treatment", PLoS One 7(2): e31968, 18 pages, 2012.
Jelakovic et al., "Aristolactam-DNA adducts are a biomarker of environmental exposure to aristolochic acid", Kidney Int. 81(6): 559-67, 2012.
Jiao et al., "DAXX/ATRX, MEN1, and mTOR Pathway Genes Are Frequently Altered in Pancreatic Neuroendocrine Tumors", Science 331: 1199-1203, 2011.
Jones et al., "Comparative lesion sequencing provides insights into tumor evolution.", Proceedings of the National Academy of Sciences of the United States of America 105: 4283-4288, 2008.
Jones et al., "Core signaling pathways in human pancreatic cancers revealed by global genomic analyses.", Science 321(5897): 1801-1806, 2008.
Jones et al., "Frequent mutations of chromatin remodeling gene ARIDIA in ovarian clear cell carcinoma.", Science 330, 228-231, 2010.
Jones et al., "Low-grade serous carcinomas of the ovary contain very few point mutations", The Journal of pathology 226, 413-420, 2012.
Jones et al., "Personalized genomic analyses for cancer mutation discovery and interpretation.", Science translational medicine, 7: 283ra53, 2015.
Jones et al., "The epigenomics of cancer.", Cell 128: 683-692, 2007.
Ju et al., "Origins and functional consequences of somatic mitochondrial DNA mutations in human cancer", eLife 3, 28 pages, 2014.
Jung et al., "Intron retention is a widespread mechanism of tumor-suppressor inactivation.", Nat Genet 47, 1242-1248, 2015.
Jung et al.,. (2007) Clinicopathological aspects of 542 cases of pancreatic cancer: a special emphasis on small pancreatic cancer. J Korean Med Sci 22 Suppl:S79-85.
Kalinich et al., "An RNA-based signature enables high specificity detection of circulating tumor cells in hepatocellular carcinoma.", Proc Natl Acad Sci USA, 114(5): 1123-1128, 2017.
Kandoth et al., "Integrated genomic characterization of endometrial carcinoma.", Nature 497, 67-73, 2013.
Kandoth et al., "Mutational landscape and significance across 12 major cancer types", Nature 502: 333-339, 2013.
Kang et al., "Inverse correlation between RASSF1A hypermethylation, KRAS and BRAF mutations in cervical adenocarcinoma," Gynecology Oncology, 105, 662-666, 2007.
Karow, "Hopkins Team Develops method to Improve Rare Mutation Detection for Early Cancer Dx," Genomeweb, 3 pages, Jun. 1, 2011.
Karst et al., "Modeling high-grade serous ovarian carcinogenesis from the fallopian tube", Proc. Natl Acad Sci USA 108, 7547-7552, 2011.
Karst et al., "Ovarian cancer pathogenesis: a model in evolution.", Journal of oncology 932371, 13 pages, 2010.
Kaufamn et al., "Olaparib monotherapy in patients with advanced cancer and a germline BRCA1/2 mutation.", J Clin. Oncol. 33: 244-250, 2015.
Kauff et al., "Risk-reducing salpingooophorectomy in women with a BRCA1 or BRCA2 mutation.", The New England journal of medicine, 346: 1609-15, 2002.
Kawauchi et al., "9p21 index as estimated by dual-color fluorescence in situ hybridization is useful to predict urothelial carcinoma recurrence in bladder washing cytology.", Hum Pathol 40: 1783-1789, 2009.
Kennedy et al., "Detecting ultralow-frequency mutations by Duplex Sequencing.", Nature protocols 9, 2586-2606, 2014.
Kennedy et al., "Somatic mutations in aging, cancer and neurodegeneration", MechAgeing Dev 133: 118-126, 2012.
Keohavong et al., "Fidelity of DNA polymerases in DNA amplification.", Proc Natl Acad Sci US A 86: 9253-9257, 1989.
Kesmodel et al., "Gastrointestinal Cancers Symposium: Multidisciplinary Approaches to the Prevention, Diagnosis, and Therapy of GI Cancers", 2007, abstr 234, 4 pages.
Keys et al., "Primer ID Informs Next-Generation Sequencing Platforms and Reveals Preexisting Drug Resistance Mutations in the HIV-1 Reverse Transcriptase Coding Domain.", AIDS Res Hum Retroviruses 31, 658-668, 2015.
Khadra et al., "A prospective analysis of 1,930 patients with hematuria to evaluate current diagnostic practice.", J Urol 163: 524-527, 2000.
Kidd et al., "Developing a SNP panel for forensic identification of individuals", Forensic science international 164: 20-32, 2006.
Killela et al., "TERT promoter mutations occur frequently in gliomas and a subset of tumors derived from cells with low rates of self-renewal.", Proc Natl Acad Sci USA 110:6021-6026, 2013.
Kim et al., "Clinical usefulness of carbohydrate antigen 19-9 as a screening test for pancreatic cancer in an asymptomatic population.", J Gastroenterol Hepatol 19(2): 182-186, 2004.
Kim et al., "Impact of intraoperative rupture of the ovarian capsule on prognosis in patients with early-stage epithelial ovarian cancer: a meta-analysis.", European journal of surgical oncology : the journal of the European Society of Surgical Oncology and the British Association of Surgical Oncology 39, 279-289, 2013.
Kim et al., "Oligonucleotide microarray analysis of distinct gene expression patterns in colorectal cancer tissues harboring BRAF and K-ras mutations.", Carcinogenesis 27(3): 392-404, 2006.
Kinde et al., "Detection and quantification of rare mutations with massively parallel sequencing", Proceedings of the National Academy of Sciences of the United States of America 108, 9530-9535, 2011.
Kinde et al., "FAST-SeqS: a simple and efficient method for the detection of aneuploidy by massively parallel sequencing.", PloS One 7:e41162, 2012.
Kinde et al., "TERT promoter mutations occur early in urothelial neoplasia and are biomarkers of early disease and disease recurrence in urine.", Cancer Res 73 :7162-7167, 2013.
Kinde et al., 'Evaluation of DNA from the Papanicolaou test to detect ovarian and endometrial cancers' Science Translational Medicine. vol. 5, Issue 167, Article No. 164ra164, pp. 1-10, 2013.
Kindelberger et al., "Intraepithelial carcinoma of the fimbria and pelvic serous carcinoma: Evidence for a causal relationship.", The American journal of surgical pathology 31: 161-9, 2007.
Kivioja et al., "Counting absolute numbers of molecules using unique molecular identifiers," Nature Methods, vol. 9, No. 1, pp. 72-74, 2011 (there are two Kivioja references—2011 and 2012).

(56) References Cited

OTHER PUBLICATIONS

Kobayashi et al., "A randomized study of screening for ovarian cancer: a multi center study in Japan.", Int J Gynecol Cancer 18, 414-420, 2008.
Konecny et al., "Activity of the Dual Kinase Inhibitor Lapatinib (GW572016) against HER-2-Overexpressing and Trastuzumab-Treated Breast Cancer Cells", Cancer Res 66: 1630-1639, 2006.
Koopmann et al., "Evaluation of Osteopontin as Biomarker for Pancreatic Adenocarcinoma", Cancer Epidemiol Biomarkers Prev 13(3): 487-491, 2004.
Korpanty et al., "Biomarkers that currently affect clinical practice in lung cancer: EGFR, ALK, MET, ROS-1, and KRAS", Front Oncol. 4: 204, 2014.
Kosuri et al., "Scalable gene synthesis by selective amplification of DNA pools from high-fidelity microchips.", Nat Biotechnol 28: 1295-1299, 2010.
Kou et al., "Benefits and Challenges with Applying Unique Molecular Identifiers in Next Generation Sequencing to Detect Low Frequency Mutations", PLoS One., vol. 11, No. 1, p. e0146638, 2016.
Kozarewa et al., "Amplification-free Illumina sequencing-library preparation facilitates improved mapping and assembly of (G+C)-biased genomes", Nature Methods, vol. 6, No. 4, pp. 291-295, 2009.
Kozarewa et al., "Amplification-free library preparation for paired-end illumina sequencing", chapter 18, pp. 257-266, 2011.
Kraystberg et al., "Single-molecuke PCR: an artifact-free PCR approach for the analysis of somatic mutations" Expert Rev. Mol. Diagn. 5(5), 809-815, 2005.
Kraystberg et al., "Single molecule PCR in mtDNA mutational analysis: genuine mutations vs. damage bypass-derived arttifacts" NIH Public Access Methods, 46(4): 269-273, 2008.
Krimmel et al., "Ultra-deep sequencing detects ovarian cancer cells in peritoneal fluid and reveals somatic TP53 mutations in noncancerous tissues.", Proc Natl Acad Sci USA 113, 6005-6010, 2016.
Kristjansdottir et al., "Ovarian cyst fluid is a rich proteome resource for detection of new tumor biomarkers", Clinical Proteomics, vol. 9, internal pp. 1-9, 2012.
Kristjansdottir et al., "Potential tumor biomarkers identified in ovarian cyst fluid by quantitative proteomic analysis, iTRAQ.", Clinical proteomics 10, 4, 2013.
Kruger et al., "Numerical aberrations of chromosome 17 and the 9p2 1 locus are independent predictors of tumor recurrence in noninvasive transitional cell carcinoma of the urinary bladder.", Int J Oncol 23 :41-48, 2003.
Kuhn et al., "Identification of Molecular Pathway Aberrations in Uterine Serous Carcinoma by Genome-wide Analyses," Journal of the National Cancer Institute, 104(19):1503-1513, 2012.
Kuhn et al., "TP53 mutations in serous tubal intraepithelial carcinoma and concurrent pelvic high-grade serous carcinoma-evidence supporting the clonal relationship of the two lesions.", The Journal of pathology, 226: 421-6, 2012.
Kumar et al., "Application of microarray in breast cancer: An overview", J. Pharm. Bioallied Sci. 4(1):21-26, 2012.
Kumar et al., "Association of mitochondrial copy number variation and T16189C polymorphism with colorectal cancer in North Indian population.", Tumour Biol, 39: 1010428317740296, 2017.
Kumar et al., "Cell-free mitochondrial DNA copy number variation in head and neck squamous cell carcinoma: A study of non-invasive biomarker from Northeast India.", Tumor Biol., 39: 1010428317736643, 2017.
Kumar et al., "Deep sequencing of multiple regions of glial tumors reveals spatial heterogeneity for mutations in clinically relevant genes.", Genome biology 15, 530, 2014.
Kumar et al., "Serum and Plasma Metabolomic Biomarkers for Lung Cancer", Bioinformation, 13(6); 202-208, 2017.
Kunkel, "The mutational specificity of DNA polymerase-beta during in vitro DNA synthesis.", J Biol Chem 260: 5787-5796, 1985.
Kuppusamy et al., "Proteins are potent biomarkers to detect colon cancer progression", Saudi Journal of Biological Sciences, 24, 1212-1221, 2017.
Kurman et al., "Molecular pathogenesis and extraovarian origin of epithelial ovarian cancer—Shilling the paradigm," Human Pathology, 42, 918-931, 2011.
Kurman et al., "The Dualistic Model of Ovarian Carcinogenesis: Revisited, Revised, and Expanded.", Am J Pathol 186, 733-747, 2016.
Kurman et al., "The origin and pathogenesis of epithelial ovarian cancer: a proposed unifying theory", The American journal of surgical pathology 34, 433-443, 2010.
Kwon et al., "Prophylactic salpingectomy and delayed pophorectomy as an alternative for BRCA mutation carriers.", Obstetrics and gynecology, 121:14-24, 2013.
Laddha et al., "Mutational Landscape of the Essential Autophagy Gene BECN1 in Human Cancers", Molecular cancer research 12: 485-490, 2014.
Laere et al., "cDNA Microarray Analysis of Inflammatory Breast Cancer Signatures", Methods Mol. Biol. 512: 71-98, 2009.
Lai et al., "Population-Based Case-Control Study of Chinese Herbal Products Containing Aristolochic Acid and Urinary Tract Cancer Risk", J Natl Cancer Inst, 102(3): 179-186, 2010.
Lalkhen et al., "Clinical tests: sensitivity and specificity", Continuing Education in Anaesthesia, Critical Care & Pain, vol. 8, No. 6, 221-223, 2008.
Langmead et al., "Fast gapped-read alignment with Bowtie 2", Nature Methods 9: 357-359, 2012.
Lee et al., "A candidate precursor to serous carcinoma that originates in the distal fallopian tube", The journal of pathology 211, 26-35, 2007.
Lee et al., "Quantification of kinase activity in cell lysates via photopatterned macroporous poly(ethylene glycol) hydrogel arrays in microfluidic channels", Biomed. Microdevices 14: 247-57, 2012.
Lennon et al., "Diagnostic and Therapeutic Response Markers.", Pancreatic Cancer, (Springer New York, New York, NY), pp. 675-701, 2010.
Lennon et al., "The Early Detection of Pancreatic Cancer: What Will It Take to Diagnose and Treat Curable Pancreatic Neoplasia?", Cancer Res 74(13): 3381-3389, 2014.
Levanon et al., "New insights into the pathogenesis of serous ovarian cancer and its clinical impact.", Journal of clinical oncology : official journal of the American Society of Clinical Oncology, 26: 5284-93, 2008.
Levey et al., "Definition and classification of chronic kidney disease: a position statement from Kidney Disease: Improving Global Outcomes (KDIGO).", Kidney Int. 67(6): 2089-100, 2005.
Levey et al., "Using Standardized Serum Creatinine Values in the Modification of Diet in Renal Disease Study Equation for Estimating Glomerular Filtration Rate", Ann Intern Med. 145(4): 247-54, 2006.
Levina et al., "Biological significance of prolactin in gynecologic cancers.", Cancer Res 69(12): 5226-5233, 2009.
Levine et al., "Management of asymptomatic pvarian and other adnexal cysts imaged at US: Society of Radiologists in Ultrasound Consensus Conference Statement", Radiology 256, 943-954, 2010.
Li et al., "DNA Methylation in Peripheral Blood: A Potential Biomarker for Cancer Molecular Epidemiology", J. Epidemoil, 22(5): 384-394, 2012.
Li et al., "Replacing PCR with COLD-PCR enriches variant DNA sequences and redefines the sensitivity of genetic testing", Nat Med 14: 579-584, 2008.
Li et al., "Significant Predictive Factors for Prognosis of Primary Upper Urinary Tract Cancer after Radical Nephroureterectomy in Taiwanese Patients", Eur Ural. 54(5): 1127-1134, 2008.
Li et al., "Toward better understanding of artifacts in variant calling from high-coverage samples.", Bioinformatics 30: 2843-2851, 2014.
Liaw et al., "Classification and Regression by random Forest", R news 2: 18-22, 2001.
Lin et al., "A molecular inversion probe assay for detecting alternative splicing", BMC Genomics 11: 712, 2010.
Lin et al., "Benefits and harms of prostate-specific antigen screening for prostate cancer: an evidence update for the U.S. Preventive Services Task Force.", Ann. Intern. Med. 149: 192-199, 2008.

(56) References Cited

OTHER PUBLICATIONS

Lin et al., "Increase sensitivity in detecting superficial, low grade bladder cancer by combination analysis of hypermethylation of E-cadherin, p16, p14, RASSFIA genes in urine.", Ural Oncol 28: 597-602, 2010.

Lin et al., "Thyroid cancer in the thyroid nodules evaluated by ultrasonography and fine-needle aspiration cytology", Thyroid: official journal of the american thyroid association 15, 708-717, 2005.

Lindor et al., Press, "Recommendations for the care of individuals with an inherited predisposition to Lynch syndrome: a systematic review.", JA,HA 296, 1507-1517, 2006.

Linnarsson et al., "Recent advances in DNA sequencing methods—general principles of sample preparation", Experimental cell research., 316, 1339-1343, 2010.

Liotta et al., "The promise of proteomics.", Clin Adv Hematol Oncol 1(8): 460-462, 2003.

Liscia et al., "Prognostic significance of loss of heterozygosity at loci on chromosome 17p13.3-ter in sporadic breast cancer is evidence for a putative tumour suppressor gene", British Journal of Cancer, 80 (5/6) 821-826, 1999.

Liu et al., "Comparison of Next-Generation Sequencing Systems," Journal of Biomedicine and Biotechnology, 2012, 2012(251364) 11 pages.

Liu et al., "Detection of extremely rare alleles by bidirectional pyrophosphorolysis-activated polymerization allele-specific amplification (Bi-PAP-A): measurement of mutation load in mammalian tissues.", Biotechniques 36: 156-166, 2004.

Liu et al., "Digital quantification of gene methylation in stool DNA by emulsion-PCR coupled with hydrogel immobilized bead-array.", Biosens Bioelectron 92: 596-601, 2017.

Livrahi et al., "PARP inhibitors in the management of breast cancer: current data and future prospects.", BMC Medicine 13: 188, 2015.

Locker et al., "ASCO 2006 Update of Recommendations for the Use of Tumor Markers in Gastrointestinal Cancer ", J. Clin. Oncol. 24: 5313-5327, 2006.

Lodato et al., "Somatic mutation in single human neurons tracks developmental and transcriptional history.", Science 350, 94-98, 2015.

Lodes et al., "Detection of Cancer with Serum miRNAs on an Oligonucleotide Microarray", PLoS One 4(7): e6229, 2009.

Loh et al., "Ovarian response after laparoscopic ovarian cystectomy for endometriotic cysts in 132 monitored cycles", Fertility and sterility 72, 316-321, 1999.

Longacre et al., "Recommendations for the reporting of fallopian tube neoplasms.", Hum Pathol., 38: 1160-3, 2007.

Lotan et al., "Sensitivity and Specificity of Commonly Available Bladder Tumor Markers Versus Cytology: Results of a Comprehensive Literature Review and Meta-Analyses", Urology 61: 109-18, 2003.

Lou et al., "Biomarkers for Hepatocellular Carcinoma", Biomark Cancer, 9: 1-9, 2017.

Louseberg et al., "Safety, Efficacy, and Patient Acceptability of Everolimus in the Treatment of Breast Cancer.", Breast Cancer 10: 239-252, 2017.

Lowe et al., "Multiplex Sensing of Protease and Kinase Enzyme Activity via Orthogonal Coupling of Quantum Dot-Peptide Conjugates", ACS nano. 6: 851-7, 2012.

Luria et al., "Mutations of Bacteria from Virus Sensitivity to Virus Resistance.", Genetics 28: 491-511, 1943.

Mackay et al., "cDNA microarray analysis of genes associated with ERBB2 (HER2/neu) overexpression in human mammary luminal epithelial cells", Oncogene 22: 2680-2688, 2003.

Mackay et al., "Phase II trial of the histone deacetylase inhibitor belinostat in women with platinum resistant epithelial ovarian cancer and micropapillary (LMP) ovarian tumours.", Eur. J. Cancer 46(9): 1573-1579, 2010.

Madabhushi et al., "DNA damage and its links to neurodegeneration.", Neuron 83, 266-282, 2014.

Makohon-Moore et al., "Limited heterogeneity of known driver gene mutations among the metastases of individual patients with pancreatic cancer", Nat Genet., 49(3): 358-366, 2017.

Malpica et al., "Grading ovarian serous carcinoma using a two-tier system," Am. J. Surg. Pathol. 28, 496-504, 2004.

Mao et al., "The Application of Single Nucleotide Polymorphism Microarrays in Cancer Research", Curr. Genomics 8(4): 219-228, 2007.

Mao, "Recent advances in the molecular diagnosis of lung cancer.", Oncogene 21: 45, 6960-6969, 2002.

Maragh et al., "Evaluation of two mitochondrial DNA biomarkers for prostate cancer detection.", Cancer Biomark., 15: 763-73, 2015.

Marques et al., "A"typical glandular cells and cervical cancer: systematic review.", Rev Assoc Af ed Bras 57, 234-238, 2011.

Martinez-Onsurbe et al., "Aspiration cytology of 147 adnexal cysts with histologic correlation", Acta. Cytologica 45, 941-947, 2001.

Matei et al., "Epigenetic Resensitization to Platinum in Ovarian Cancer", Cancer Res. 72(9): 2197-2205, 2012.

Matzas et al., "High-fidelity gene synthesis by retrieval of sequence-verified DNA identified using high-throughput pyrosequencing.", Nat Biotechnol 28: 1291-1294, 2010.

Mayr et al., "KRAS and BRAF mutations in ovarian tumors: a comprehensive study of invasive carcinomas, borderline tumors and extraovarian implants", Gyencologic oncology 103, 883-887, 2006.

Mayrand et al., "Human papillomavirus DNA versus Papanicolaou screening tests for cervical cancer.", N. Engl. J. Med. 357, 1579-1588, 2007.

McAlpine et al., "Opportunistic salpingectomy: uptake, risks, and complications of a regional initiative for ovarian cancer prevention.", American journal of obstetrics and gynecology 210: 471 e1-11, 2014.

McCloskey et al., "Encoding PCR products with batch-stamps and barcodes", Biochem Genet 45: 761-767, 2007.

McConechy et al., "Use of mutation profiles to refine the classification of endometrial carcinomas," J. Path, 2012, 228:20-30 and supplementary table, pp. 1-11.

McDaniel et al., "Next-Generation Sequencing of Tubal Intraepithelial Carcinomas." JAMA oncology 1: 1128-32, 2015.

McMahon et al., "The HBV drug entecavir—effects on HIV-1 replication and resistance.", N Engl J Med 356: 2614-2621, 2007.

Medeiros et al., "The tubal fimbria is a preferred site for early adenocarcinoma in women with familial ovarian cancer syndrome.", The American journal, vol. 30, issue 2, pp. 230-236, 2006.

Meden et al., "CA 125 in benign gynecological conditions.", Int J Biol Alarkers 13, 231-237, 1998.

Meldrum et al., "Next-Generation Sequencing for Cancer Diagnostics: a Practical Perspective", Clin. Biochem. Rev. 32(4): 177-195, 2011.

Mendivil et al., "Increased incidence of severe gastrointestinal events with first-line paclitaxel, carboplatin, and vorinostat chemotherapy for advanced-stage epithelial ovarian, primary peritoneal, and fallopian tube cancer.", Int. J. Gynecol. Cancer 23(3): 533-539, 2013.

Menon et al., "Ovarian cancer screening-current status, future directions.", Gynecologic oncology 132: 490-5, 2014.

Menon et al., "Risk Algorithm Using Serial Biomarker Measurements Doubles the Number of Screen-Detected Cancers Compared With a Single-Threshold Rule in the United Kingdom Collaborative Trial of Ovarian Cancer Screening.", J Clin Oncol 33, 2062-2071, 2015.

Mermel et al., "GISTIC2.0 facilitates sensitive and confident localization of the targets of focal somatic copy-number alteration in human cancers", Genome biology 12: R41, 2011.

Metzker et al., "Sequencing technologies—the next generation" Nature reviews, 2010.

Michels et al., "Detection of DNA copy number alterations in cancer by array comparative genomic hybridization.", Genet. Med. 9: 574-584, 2007.

Miller et al., "Phase I trial of alvespimycin (KOS-1022; 17-DMAG) and trastuzumab (T)", J. Clin. Oncol. 25: s1115, 2007.

Miner et al., "Molecular barcodes detect redundancy and contamination in hairpin-bisulfite PCR.", Nucleic Acids Res 32:e135, 2004.

(56) References Cited

OTHER PUBLICATIONS

Mirus et al., "Cross-Species Antibody Microarray Interrogation Identifies a 3-Protein Panel of Plasma Biomarkers for Early Diagnosis of Pancreas Cancer", Clin. Cancer Res. 21(7): 1764-1771, 2015.
Misek et al., "Protein Biomarkers for the Early Detection of Breast Cancer", International Journal of Proteomics, vol. 2011, article ID 343582, 9 pages, 2011.
Mishriki et al., "Diagnosis of urologic malignancies in patients with asymptomatic dipstick hematuria: prospective study with 13 years' follow-up.", Urology 71: 13-16, 2008.
Mitchell et al., "Accuracy and survival benefit of cytological prediction of endometrial carcinoma on routine cervical smears.", Int J Gynecol Pathol 12, 34-40, 1993.
Mitra et al., "Digital genotyping and haplotyping with polymerase colonies.", Proc Natl Acad Sci USA 100: 5926-5931, 2008.
Mizutani et al., "A Novel FRET-Based Biosensor for the Measurement of BCR-ABL Activity and Its Response to Drugs in Living Cells", Clin. Cancer Res. 16: 3964-75, 2010.
Mo et al., "Hyperactivation of Haras oncogene, but not Ink4a/Arf deficiency, triggers bladder tumorigenesis.", J Clin Invest 117: 314-325, 2007.
Moch et al., "The 2016 WHO Classification of Tumours of the Urinary System and Male Genital Organs—Part A: Renal, Penile, and Testicular Tumours", EAU, 70, 93-105, 2016.
Mockler et al., "Applications of DNA tiling arrays for whole-genome analysis", Genomics, 85(1): 1-15, 2005.
Modesitt et al., "A phase II study of vorinostat in the treatment of persistent or recurrent epithelial ovarian or primary peritoneal carcinoma: a Gynecologic Oncology Group study.", 109(2): 182-186, 2008.
Modi et al., "Phase II trial of the Hsp90 inhibitor tanespimycin (Tan) + trastuzumab (T) in patients (pts) with HER2-positive metastatic breast cancer (MBC)", J. Clin Oncol. 26: s1027, 2008.
Moertel et al., "Fluorouracil plus levamisole as effective adjuvant therapy after resection of stage III colon carcinoma: a final report.", Ann Intern Med 122(5): 321-326, 1995.
Monnat et al., "Nucleotide sequence preservation of human mitochondrial DNA", Proc Natl Acad Sci USA 82: 2895-2899, 1985.
Moonen et al., "Uro Vysion compared with cytology and quantitative cytology in the surveillance of non-muscle-invasive bladder cancer.", Eur Urol 51: 1275-80, 2007.
Moore et al., "The use of multiple novel tumor biomarkers for the detection of ovarian carcinoma in patients with a pelvic mass.", Gynecologic oncology 108, 402-408, 2008.
Moore et al., "Uterine Papillary Serous Carcinoma", Clin Obstet Gynecol 54: 278-291, 2011.
Moran et al., "Cytologic examination of ovarian cyst fluid for the distinction between benign and malignant tumors", Obstetrics and gynecology 82, 444-446, 1993.
Moyer et al., "Screening for ovarian cancer: U.S. Preventive Services Task Force reaffirmation recommendation statement", Annals of internal medicine 157: 900-904, 2012.
Murtaza et al., "Non-invasive analysis of acuired resistance to cancer therapy by sequencing of plasma DNA", Nature 497, 108-112, 2013.
Nair et al., "Genomic Analysis of Uterine Lavage Fluid Detects Early Endometrial Cancers and Reveals a Prevalent Landscape of Driver Mutations in Women without Histopathologic Evidence of Cancer: A Prospective Cross-Sectional Study", PLoS Med 13: e1002206, 2016.
National Toxicology Program. Aristolochic acids. Rep Carcinog, 12, 45-49, 2011.
Naucler et al., "Human papillomavirus and Papanicolaou tests to screen for cervical cancer.", N Engl J l\fed 357, 1589-1597, 2007.
Nazarian et al., "Melanomas acquire resistance to B-RAF(V600E) inhibition by RTK or N-RAS upregulation.", Nature 468: 973-977, 2010.
Nazli et al., "The diagnostic importance of CEA and CA 19-9 for the early diagnosis of pancreatic carcinoma.", Hepatogastroenterology 47(36): 1750-1752, 2000.
Netto et al., "Emerging Bladder Cancer Biomarkers and Targets of Therapy.", Urol Clin North Am 43: 63-76, 2016.
Netto et al., "Theranostic and prognostic biomarkers: genomic applications in urological malignancies", Pathology 42: 384-394, 2010.
Netto, "Clinical applications ofrecent molecular advances in urologic malignancies: no longer chasing a "mirage"?.", Adv Anat Pathol 20: 175-203, 2013.
Netto, "Molecular biomarkers in urothelial carcinoma of the bladder: are we there yet?.", Nat Rev Urol 9: 41-51, 2011.
Newman et al., "An ultrasensitive method for quantitating circulating tumor DNA with board patient coverage", Nature medicine 20, 548-554, 2014.
Ng et al., "Significance of endometrial cells in the detection of endometrial carcinoma and its precursors.", Acta cytologica 18, 356-361, 1974.
Ngamruengphong et al., "Preoperative endoscopic ultrasound-guided fine needle aspiration does not impair survival of patients with resected pancreatic cancer.", Gut, 64: 1105-1110, 2015.
Ngan et al., "Abnormal expression and mutation of p53 in cervical cancer—a study at protein, RNA and DNA levels", Denitourin Med, 73: 54-58, 1997.
Nguyen et al., "High prevalence of TERT promoter mutations in micropapillary urothelial carcinoma.", Virchows Arch 469: 427-434, 2016.
Nik et al., "Origin and pathogenesis of pelvic (ovarian, tubal, and primary peritoneal) serous carcinoma.", Annual review of pathology 9: 27-45, 2014.
Niknafs et al., SubClonal Hierarchy Inference from Somatic Mutations: Automatic Reconstruction of Cancer Evolutionary Trees from Multi-region Next Generation Sequencing. PLoS computational biology, 11: e1004416, pp. 1-26, 2015.
Nolen et al., "Protein biomarkers of ovarian cancer: the forest and the trees", Future Oncol., 8(1): 55-71, 2012.
O'Brien et al., "Serum CA19-9 is significantly upregulated up to 2 years before diagnosis with pancreatic cancer: implications for early disease detection.", Clin Cancer Res 21(3): 622-631, 2015.
Oda et al., "High Frequency of Coexistent Mutations of PIK3CA and PTEN Genes in Endometrial Carcinoma," Cancer Research, vol. 65, No. 23, pp. 10669-10673, 2005.
Odunsi et al., "Epigenetic potentiation of NY-ESO-1 vaccine therapy in human ovarian cancer", Cancer Immunol. Res. 2(1): 37-49, 2014.
Ogiwara et al., "Unbalanced translocation, a major chromosome alteration causing loss of heterozygosity in human lung cancer.", Oncogene, 27: 4788-97, 2008.
Ottesen et al., "Microfluidic digital PCR enables multigene analysis of individual environmental bacteria.", Science 314: 1464-1467, 2006.
Paik et al., "A Multigene Assay to Predict Recurrence of Tamoxifen-Treated, Node-Negative Breast Cancer", N. Engl. J. Med. 351: 2817-2826, 2004.
Parameswaran et al., "A pyrosequencing-tailored nucleotide barcode design unveils opportunities for large-scale sample multiplexing.", Nucleic Acids Res 35: e130, 2007.
Pardall, "The blockade of immune checkpoints in cancer immunotherapy", Nat. Rev Cancer 12: 252-264, 2012.
Park et al., "Large-scale clinical validation of biomarkers for pancreatic cancer using a mass spectrometry-based proteomics approach", Oncotarget., 8(26): 42761-42771, 2017.
Parker et al., "Ovarian conservation at the time of hysterectomy and long-term health outcomes in the nurses' health study.", Obstetrics and gynecology, 113: 1027-37, 2009.
Parsons et al., "Mismatch repair deficiency in phenotypically normal human cells", Science 268: 738-740, 1995.
Partridge et al., "Results from four rounds of ovarian cancer screening in a randomized trial.", Obstet Gynecol 113, 775-782, 2009.
Patch et al., "Whole-genome characterization of chemoresistant ovarian cancer.", Nature, 521: 489-94, 2015.

(56) References Cited

OTHER PUBLICATIONS

Patel et al., "Endometrial carcinoma detected with SurePath liquid-based cervical cytology: comparison with conventional cytology", Cytopathology, vol. 20, No. 6, pp. 380-387, 2009.

Patz et al., "Panel of serum biomarkers for the diagnosis of lung cancer.", J Clin Oneal 25: 5578-5583, 2007.

Pavlik et al., "Frequency and diposition of ovarian abnormalities followed with serial transvaginal ultrasonography", Obstetrics and gynecology 122, 210-217, 2013.

Pecorelli, "Revised FIGO staging for carcinoma of the vulva, cervix, and endometrium.", Int J Gynaecol Obstet 105, 103-104, 2009.

Pengelly et al., "A SNP profiling panel for sample tracking in whole-exome sequencing studies", Genome medicine 5: 89, 2013.

Perets et al., "It's Totally Tubular . . . Riding The New Wave of Ovarian Cancer Research.", Cancer research, 76: 10-7, 2016.

Perets et al., "Transformation of the fallopian tube secretory epithelium leads to high-grade serous ovarian cancer in Brca;Tp53;Pten models.", Cancer cell, 24: 751-65, 2013.

Phallen et al., "Direct detection of early-stage cancers using circulating tumor DNA.", Science translational medicine 9, 2017.

Philips et al., "Targeting HER2-positive breast cancer with trastuzumab-DM1, an antibody-cytotoxic drug conjugate.", Cancer Res 68: 9280-9290, 2008.

Piccart-Gebhart et al., "Trastuzumab after adjuvant chemotherapy in HER2-positive breast cancer.", N. Engl. J. Med. 353: 1659-1672, 2005.

Piek et al., "BRCA1/2-related ovarian cancers are of tubal origin: a hypothesis.", Gynecologic oncology, 90: 491, 2003.

Piek et al., "Dysplastic changes in prophylactically removed Fallopian tubes of women predisposed to developing ovarian cancer.", The Journal of pathology, 195: 451-6, 2001.

Pinkel et al., "Array comparative genomic hybridization and its applications in cancer", Nature Genetics, vol. 37, S11-S17, 2005.

Pinsky et al., "Prostate Cancer Screening—A Perspective on the Current State of the Evidence", The New England Journal of Medicine, 376; 13, 1285-1289, 2017.

"Polymerase chain reaction" (online) 2011, <https://web.archive.org/web/20110203140027/https:en.wikipedia.org/wiki/Polymerase>.

Powers et al., "Protein analytical assays for diagnosing, monitoring, and choosing treatment for cancer patients.", J. Heathc Eng. 3(4): 503-534, 2015.

Proctor et al., "The promise of telomere length, telomerase activity and its regulation in the translocation-dependent cancer ESFT; clinical challenges and utility", Biochimica et Biophysica Acta, 260-274, 2009.

Qiu et al., "No evidence of clonal somatic genetic alterations in cancer-associated fibroblasts from human breast and ovarian carcinomas.", Nature Genetics, vol. 40, pp. 650-655, 2008.

Quail et al., "A large genome center's improvements to the Illumina sequencing system.", Nat Methods 5:1005-1010, 2008.

Quail et al., "Improved Protocols for the Illumina Genome Analyzer Sequencing System," Current Protocols in Humar Genetics, Supplement 62, pp. 18.2.1-18.2.27, 2009.

Rago et al., "Serial assessment of human tumor burdens in mice by the analysis of circulating DNA.", Cancer Res 67, 9364-9370, 2007.

Rahib et al., "Projecting Cancer Incidence and Deaths to 2030: The Unexpected Burden of Thyroid, Liver, and Pancreas Cancers in the United States", Cancer research 74, 2913-2921, 2014.

Ralla et al., "Nucleic acid-based biomarkers in body fluids of patients with urologic malignancies", Crit Rev Clin Lab Sci 51: 200-231, 2014.

Randerath et al., "Covalent DNA Damage in Tissues of Cigarette Smokers as Determined by 32P-Postlabeling Assay", Journal of the National Cancer Institute 81: 341-347, 1989.

Rebbeck et al., "Prophylactic oophorectomy in Carriers of BRCA 1 or BRCA2 mutations.", The New England journal of medicine, 346: 1616-22, 2002.

Resta et al., "Phase I study of enzastaurin (ENZ) and bevacizumab (BV) in patients with advanced cancer", J. Clin. Oncol. 26 (May 20 suppl), abstr 3529, 2008.

Ricciuti et al., "Long-Lasting Response to Nivolumab and Immune-Related Adverse Events in a Nonsquamous Metastatic Non-Small Cell Lung Cancer Patient.", J. Thorne Oncol. 12(5): e51-e55, 2017.

Ries et al., SEER Survival Afonograph: Cancer Survival Among Adults: US Seer Program, 1988-2001, Patient and Tumor Characteristics (NIH Pub. No. 07-6215. National Cancer Institute, Bethesda, MD, 2007).

Roach et al., "Analysis of Genetic Inheritance in a Family Quartet by Whole Genome Sequencing", Science 328: 636-639, 2010.

Rodriguez et al., Spectrum of genetic mutations in de novo PUNLMP of the urinary bladder. Virchows Arch, vol. 471, issue 6, pp. 761-767, 2017.

Roh et al., "High-grade fimbrial—Ovarian carcinomas are unified by altered p53, PTEN and PAX2 expression.", Modem pathology, 23: 1316-24, 2010.

Romond et al., "Trastuzumab plus Adjuvant Chemotherapy for Operable HER2-Positive Breast Cancer", N. Engl. J. Med. 353: 1673-1684, 2005.

Rosen et al., "Safety, pharmacokinetics, and efficacy of AMG 706, an oral multikinase inhibitor, in patients with advanced solid tumors.", J. Clin. Oncol. 25: 2369-76, 2007.

Rosenberg et al., "Adoptive cell transfer as personalized immunotherapy for human cancer", Science 348(6230): 62-68, 2015.

Rougemont et al., "Probabilistic base calling of Solexa sequencing data.", BMC Bioinformatics 9:431, 2008.

Roupret et al., "European Association of Urology Guidelines on Upper Urinary Tract Urothelial Cell Carcinoma: 2015 Update", Eur Ural. 68(5): 868-79, 2015.

Rozen et al., "Primer3 on the WWW for general users and for biologist programmers.", Methods Afol Biol 132, 365-386, 2000.

Ryan et al., "Pancreatic adenocarcinoma.", N Engl J Med 371(22): 2140-2141, 2014.

Saltz et al., "Phase II Trial of Sunitinib in Patients With Metastatic Colorectal Cancer After Failure of Standard Therapy", J. Clin. Oncol. 25: 4793-4799, 2007.

Sams et al.., "Liquid-based Papanicolaou tests in endometrial carcinoma diagnosis. Performance, error root cause analysis, and quality improvement.", Am J Clin Pathol 137, 248-254, 2012.

Sandhu et al., "The poly(ADP-ribose) polymerase inhibitor niraparib (MK4827) in BRCA mutation carriers and patients with sporadic cancer: a phase 1 dose-escalation trial.", Lancet Oncol 14: 882-92, 2013.

Saraswat et al., "Comparative proteomic profiling of the serum differentiates pancreatic cancer from chronic pancreatitis", Cancer Med., vol. 6, issue 7, 1738-1751, 2017.

Sarkis et al., "Association of P53 nuclear overexpression and tumor progression in carcinoma in situ of the bladder.", J Urol 152: 388-392, 1994.

Sarkis et al., "Nuclear overexpression ofp53 protein in transitional cell bladder carcinoma: a marker for disease progression.", J Natl Cancer Inst 85:53-59, 1993.

Sarkis et al., "Prognostic value of p53 nuclear overexpression in patients with invasive bladder cancer treated with neoadjuvant MVAC.", J Clin Oncol 13: 1384-1390, 1995.

Sarojini et al., "Early Detection Biomarkers for Ovarian Cancer", J. Oncol. 2012: 709049, 2012.

Sarosdy et al., "Use of a multitarget fluorescence in situ hybridization assay to diagnose bladder cancer in patients with hematuria.", J Urol 176: 44-47, 2006.

Schmeler et al., "Neoadjuvant chemotherapy for low-grade serous carcinoma of the ovary or peritoneum", Gynecologic oncology 108, 510-514, 2008.

Schmidt et al., "Pre-diagnostic metabolite concentrations and prostate cancer risk in 1077 cases and 1077 matched controls in the European Prospective Investigation into Cancer and Nutrition", BMC Med, 15: 122, 14 pages, 2012.

Schmitt et al., "Detection of ultra-rare mutations by next-generation sequencing", PNAS USA 109:14508-14513, 2012.

Schnatz et al., "Clinical significance of atypical glandular cells on cervical cytology.", Obstetrics and gynecology 107, 701-708, 2006.

(56) References Cited

OTHER PUBLICATIONS

Schorge et al., "ThinPrep detection of cervical and endometrial adenocarcinoma: a retrospective cohort study.", Cancer 96: 338-43, 2002.
Schroder et al., "Dual-color Proteomic Profiling of Complex Samples with a Microarray of 810 Cancer-related Antibodies",Mol. Cell. Proteomics 9: 1271-80, 2010.
Schulz et al., "Inhibiting the HSP90 chaperone destabilizes macrophage migration inhibitory factor and thereby inhibits breast tumor progression.", J Exp Med 209(2): 275-89, 2012.
Schwienbacher et al., "Abnormal RNA expression of 11p15 imprinted genes and kidney developmental genes in Wilms' tumor.", Cancer Res., 60: 1521-5, 2000.
Scott et al., "Mutations of the TERT promoter are common in basal cell carcinoma and squamous cell carcinoma.", Mod Pathol 27: 516-523, 2014.
Scott, "Niraparib: First Global Approval", Drugs, 77: 1029-1034, 2017.
Screening for ovarian cancer: recommendation statement. U.S. Preventive Services Task Force. Am Fam Physician 71, 759-762, 2005.
Semrad et al., "Integrating Chemotherapy into the Management of Oligometastatic Colorectal Cancer: Evidence-Based Approach Using Clinical Trial Findings.", Ann Surg Oncol 22(Suppl 3): S855-862, 2015.
Serizawa et al., "Integrated genetic and epigenetic analysis of bladder cancer reveals an additive diagnostic value of FGFR3 mutations and hypermethylation events.", Int J Cancer 129(1):78-87, 2010.
Sethi et al., "Evolving Concept of Cancer Stem Cells: Role of Micro-RNAs and their Implications in Tumor Aggressiveness", J. Carcinog. Mutag. S 1-005, 2011.
Shariat et al., "Gender differences in radical nephroureterectomy for upper tract urothelial carcinoma", World J Ural. 29(4): 481-486, 2011.
Sharma et al., "Risk of epithelial ovarian cancer in asymptomatic women with ultrasound-detected ovarian masses: a prospective cohort study within the UK collaborative trial of ovarian cancer screening (UKCTOCS)", Ultrasound Obstet Gynecol 40: 338-344, 2012.
Sharma et al., "Screening for gynaecological cancers," EJSO, 2006, 32(8):818-824.
Sharpless et al., "Dysplasia associated with atypical glandular cells on cervical cytology.", Obstet Gynecol 105, 494-500, 2005.
Shen et al., "BMN 673, a novel and highly potent PARP1/2 inhibitor for the treatment of human cancers with DNA repair deficiency.", Clin. Cancer Res. 19(18): 5003-5015, 2013.
Shen et al., "Mitochondrial copy number and risk of breast cancer: A pilot study", Mitochondrion, 10: 62-68, 2010.
Shendure et al., "Next-generation DNA sequencing," nature biotechnology, 2008, 26(10):1135-1145.
Sherman et al., "Survival amound women with borderline ovarian tumors and ovarian carcinoma: a population-based analysis", Cancer 100, 1045-1052, 2004.
Shi et al., "A Novel Proximity Assay for the Detection of Proteins and Protein Complexes: Quantitation of HER1 and HER2 Total Protein Expression and Homodimerization in Formalin-fixed, Paraffin-Embedded Cell Lines and Breast Cancer Tissue", Diagnostic molecular pathology: the American journal of surgical pathology, part B: 18: 11-21, 2009.
Shi et al., "LigAmp for sensitive detection of single-nucleotide differences.", Nat Methods 1: 141-147, 2004.
Shibata, "Mutation and epigenetic molecular clocks in cancer.", Carcinogenesis 32: 123-128, 2011.
Shih et al., "Risk factors for recurrence of ovarian boderline tumors", Gynecologic oncology 120, 480-484, 2011.
Shlien et al., "Combined hereditary and somatic mutations of replication error repair genes result in rapid onset of ultra-hypermutated cancers.", Nature genetics 47: 257-262, 2015.
Sidranksy, "Nucleic acid-based methods for the detection of cancer.", Science 278(5340): 1054-9, 1997.
Sidransky et al., Identification of p53 gene mutations in bladder cancers and urine samples. Science 252: 706-709, 1991.
Siegel et al., "Cancer Statistics, 2017.", CA Cancer J Clin 67: 7-30, 2017.
Siegel et al., Cancer statistics, 2015. CA: a cancer journal for clinicians, 65:5-29, 2015.
Singer et al., "Mutations in BRAF and KRAS characterize the development of low-grade ovarian serous carcinoma", Journal of National Cancer Institute, vol. 95, No. 6, pp. 484-486, 2003.
Siravegna et al., "Integrating liquid biopsies into the management of cancer.", Nat Rev Clin Oncol 14, 531-548, 2017.
Skacel et al., "Multitarget Fluorescence In Situ Hybridization Assay Detects Transitional Cell Carcinoma in the Majority of Patients with Bladder Cancer and Atypical or Negative Urine Cytology", J Urol 169: 2101-2105, 2003.
Smith et al., "Epigenetic therapy for the treatment of epithelial ovarian cancer: A clinical review", Gynecol. Oncol. Rep. 20: 81-86, 2017.
Smith et al., "Transvaginal ultrasound for identifying endometrial abnormality.", Acta Obstet Gynecol Scand 70, 591-594, 1991.
Somlo et al., "Efficacy of the combination of ABT-888 (veliparib) and carboplatin in patients with BRCA-associated breast cancer.", J. Clin. Oncol. 31: 1024, 2013.
Song et al., "Prognostic factors in women with synchronous endometrial and ovarian cancers.", Int J Gynecol Cancer 24: 520-527, 2014.
Soria et al., "Epidemiology, diagnosis, preoperative evaluation and prognostic assessment of upper-tract urothelial carcinoma (UTUC)", World J Urol, 35(3), 379-387, 2017.
Sorscher, "Pembrolizumab in Non-Small-Cell Lung Cancer.", N Engl J Med 376, 10: 996-7, 2017.
Soung et al., "Exosomes in Cancer Diagnostics", Cancers 9(1):pii:E8, 2017.
Spalding et al., "Retrospective birth dating of cells in humans.", Cell 122, 133-143, 2005.
Springer et al., "A Combination of Molecular Markers and Clinical Features Improve the Classification of Pancreatic Cysts", Gastroenterology 149(6): 1501-1510, 2015.
Springer et al., "Non-invasive detection of urothelial cancer through the analysis of driver gene mutations and aneuploidy", eLIFE, 7: e32143, 27 pages, 2018.
Steensma et al., "Clonal hematopoiesis of indeterminate potential and its distinction from myelodysplastic syndromes.", Blood 126, 9-16, 2015.
Stem et al., "Mutation of the TERT promoter, switch to active chromatin, and monoallelic TERT expression in multiple cancers.", Genes Dev 29: 2219-2224, 2015.
Stratagene Catalog, p. 39, 1988.
Stratton et al., "The cancer genome.", Nature 458: 719-724, 2009.
Stromberg et al., "A high-throughput strategy for protein profiling in cell microarrays using automated image analysis.", Proteomics 7: 2142-50, 2007.
Suh et al., Major clinical research advances in gynecologic cancer in 2011, Journal of Gynecologic Oncology, vol. 23, No. 1, pp. 53-64, 2012.
Sun et al., "Elevated expression of the centromere protein-A(CENP-A)-encoding gene as a prognostic and predictive biomarker in human cancers", Int. J. Cancer, 139, 899-907, 2016.
Sun et al., "Nivolumab effectively inhibit platinum-resistant ovarian cancer cells via induction of cell apoptosis and inhibition of ADAM17 expression", Eur Rev Med Pharmacol Sci 21(6): 1198-1205, 2017.
Sundfeldt et al., "Specific mutant tumor DNA can be detected in ovarian cystic fluid of an unknown ovarian tumor cyst", In: The American Association for Cancer Research, abstract #2839, 2015.
Tabernero et al., "Dose- and Schedule-Dependent Inhibition of the Mammalian Target of Rapamycin Pathway With Everolimus: A Phase I Tumor Pharmacodynamic Study in Patients With Advanced Solid Tumors," J. Clin. Oncol., 2008, 26: 1603-1610.

(56) References Cited

OTHER PUBLICATIONS

Tabernero et al., "Phase I study of AZD0530, an oral potent inhibitor of Src kinase: First demonstration of inhibition of Src activity in human cancers", J. Clin. Oncol. 25: 18S, abstr 3520, 2007.

Takahashi et al., "Clonal and chronological genetic analysis of multifocal cancers of the bladder and upper urinary tract.", Cancer Res 58: 5835-5841, 1998.

Tanase et al., "Prostate cancer proteomics: Current trends and future perspectives for biomarker discovery", Oncotarget., Mar. 14; 8(11): 18497-18512, 2017.

Tang et al., "A phase I study of vorinostat (VOR) in combination with capecitabine (CAP) in patients (pts) with advanced solid tumors", J. Clin. Oncol 26, May 20 suppl; abstr 4027, 2018.

Tao, "Direct intrauterine sampling: the IUMC Endometrial Sampler.", Diagnostic cytopathology 17, 153-159, 1997.

The 1000 Genomes Project Consortium, "An integrated map of genetic variation from 1,092 human genomes.", Nature 491: 56-65, 2012.

Thomas et al., "Construction of a 2-Mb resolution BAC microarray for CGH analysis of canine tumors", Genome Res. 15(12): 1831-1837, 2005.

Thomas et al., "Evaluation of serum CEA, CYFRA21-1 and CA125 for the early detection of colorectal cancer using longitudinal preclinical samples.", Br J Cancer 113(2): 268-274, 2015.

Thompson et al., "Winnowing DNA for Rare Sequences: Highly Specific Sequence and Methylation Based Enrichment", PLoS One, 7:e31597, 2012.

Thorpe et al., "Effects of blood collection conditions on ovarian cancer serum markers.", PLoS One 2(12): e1281, 2007.

Thunnissen, "Sputum examination for early detection of lung cancer.", J Clin Pathol 56: 805-810, 2003.

Thyagarajan et al., "Mitochondrial Copy Number is Associated With Colorectal Cancer Risk", Cancer Epidemiol Biomarkers Prev, 21(9): 1574-1581, 2012.

Tindall et al., "Fidelity of DNA synthesis by the Thermus aquaticus DNA polymerase.", Biochemistry 27: 6008-6013, 1988.

Tomasetti et al., "Cancer etiology. Variation in cancer risk among tissues can be explained by the number of stem cell divisions.", Science 347, 78-81, 2015.

Tomasetti et al., "Half or more of the somatic mutations in cancers of self-renewing tissues originate prior to tumor initiation.", Proceedings of the National Academy of Sciences of the United States of America 110, 1999-2004, 2013.

Tran et al., "Tract embolization with gelatin sponge slurry for prevention of pneumothorax after percutaneous computed tomography-guided lung biopsy.", Cardiovascular and interventional radiology 37, 1546-1553, 2014.

Traut et al., "Cancer of the Uterus: The Vaginal Smear in Its Diagnosis.", Cali. West. Med. 59, 121-122, 1943.

Tsang et al., "KRAS (but not BRAF) mutations in ovarian serous borderline tumour are assocaited with recurrent low-grade serous carcinoma", The Journal of pathology 231, 449-456, 2013.

Tsang et al., "Ultrasound-guided plugged percutaneous biopsy of solid organs in patients with bleeding tendencies.", Hong Kong Medical Journal, 20, 107-112, 2014.

Tsuchiya et al., "Biomarkers for the early diagnosis of hepatocellular carcinoma", World J Gastroenterol., 21(37): 10573-10583, 2015.

Tsuchiya et al., "Collective review of small carcinomas of the pancreas.", Ann Surg 203(1): 77-81, 1986.

Turner et al., "Palbociclib in Hormone-Receptor-Positive Advanced Breast Cancer", N Engl J Med 373: 209-219, 2015.

Tutt et al., "Oral poly(ADP-ribose) polymerase inhibitor olaparib in patients with BRCA1 or BRCA2 mutations and advanced breast cancer: a proof-of-concept trial", Lancet 376: 235-44, 2010.

Ueland et al., "Effectiveness of a multivariate index assay in the preoperative assessment of ovarian tumors.", Obstetrics and gynecology 117, 1289-1297, 2011.

Uhlen et al., "Tissue-based map of the human proteome.", Science 347(6220): 1260419, 2015.

Vallania et al., High-throughput discovery of rare insertions and deletions in large cohorts. Genome Res 20: 1711-1718, 2010.

Van Beers et al., "Array-CGH and breast cancer", Breast Cancer Res. 8(3): 210, 10 pages, 2006.

Van Dijk et al., "Ten years of next-generation sequencing technology," Trends in Genetics, 2014, 30(9):418-426.

Van Dongen et al., "Analysis of immunoglobulin and T cell receptor genes. Part II: Possibilities and limitations in the diagnosis and management of lymphoproliferative diseases and related disorders.", Clin Chim Acta 198: 93-174, 1991.

Van Nagell et al., "Ovarian cancer screening with annual transvaginal sonography: findings of 25,000 women screened.", Cancer 109, 1887-1896, 2007.

Vansteenkiste et al., "Prospects and progress of atezolizumab in non-small cell lung cancer", Expert Opin Biol Ther 17(6): 781-789, 2017.

Vijg et al., "Somatic mutations, genome mosaicism, cancer and aging", Current opinion in genetics & development 26: 141-149, 2014.

Vogelstein et al., "Cancer genes and the pathways they control.", Nat. Med. 10, 789-799, 2004.

Vogelstein et al., "Cancer genome landscapes", Science 339, 1546-1558, 2013.

Vogelstein et al., "Digital PCR.", Proc NatlAcad Sci US A 96: 9236-9241, 1999.

Vogelstein et al., "The Path to Cancer—Three Strikes and You're Out", N Engl J Med 3 73: 1895-1898, 2015.

Volpe et al., "Techniques, safety and accuracy of sampling of renal tumors by fine needle aspiration and core biopsy", The journal of urology 178, 379-386, 2007.

Waddell et al., "Whole genomes redefine the mutational landscape of pancreatic cancer", Nature 518(7540):495-501, 2015.

Walsh et al., Coexisting ovarian malignancy in young women with endometrial cancer. Obstetrics and gynecology 106, 693-699, 2005.

Wang et al., "Detection of somatic mutations and HPV in the saliva and plasma of patients with head and neck squamous cell carcinomas.", Science translational medicine 7(293): 293ra104, 2015.

Wang et al., "Detection of tumor-derived DNA in cerebrospinal fluid of patients with primary tumors of the brain and spinal cord.", Proc Natl Acad Sci USA 1 12(31): 9704-9709, 2015.

Wang et al., "Diagnostic potential of tumor DNA from ovarian cyst fluid.", Elife 5, 18 pages, 2016.

Wang et al., "Diagnostic significance of urinary long non-coding PCA3 RNA in prostate cancer", Oncotarget, vol. 8, No. 35, 58577-58586, 2017.

Wang et al., "Evaluation of liquid from the Papanicolaou test andother liquid biopsies for the detection of endometrial and ovarian cancers", Sci. Transl. Med., 10, eaap8796, 9 pages, 2018.

Wang et al., "Extracellular interactions and ligand degradation shape the nodal morphogen gradient", Elife 5: 10.7554/eLife. 15 175, 19 pages, 2016.

Wang et al., "Molecular inversion probes: a novel microarray technology and its application in cancer research.", Cancer Genet 205(7-8): 341-55, 2012.

Wang et al., "Molecular mechanisms and clinical applications of miR-22 in regulating malignant progression in human cancer (Review)", International Journal of Oncology, 50: 345-355, 2017.

Wang et al., "PD-L1 and intratumoral immune response in breast cancer", Oncotarget, vol. 8, (No. 31), pp. 51641-51651, 2017.

Wang et al., "TERT promoter mutations are associated with distant metastases in upper tract urothelial carcinomas and serve as urinary biomarkers detected by a sensitive castPCR.", Oncotarget, 5: 12428-12439, 2014.

Wang et al., "The clinical impact of recent advances in LC-MS for cancer biomarker discovery and verification", Expert Rev Proteomics 13: 99-114, 2016.

Wang et al., "The long non-coding RNA CYTOR drives colorectal cancer progression by interacting with NCL and Sam68", Molecular Cancer, 17: 110, 16 pages, 2018.

Wei et al., "A study of the relationships between oligonucleotide properties and hybridization signal intensities from NimbleGen microarray datasets", Nucleic Acids Res 36(9): 2926-2938, 2008.

(56) References Cited

OTHER PUBLICATIONS

Wilcox et al., "Chronic pancreatitis pain pattern and severity are independent of abdominal imaging findings.", Clin Gastroenterol Hepatol 13(3):552-560; quiz e528-559, 2015.
Wong et al., "Chronic Pancreatitis Pain Pattern and Severity are Independent of Abdominal Imaging Findings", Clin. Cancer Res. 15: 2552-2558, 2009.
Woodbury et al., "Elevated HGF Levels in Sera from Breast Cancer Patients Detected Using a Protein Microarray ELISA", J. Proteome Res. 1: 233-237, 2002.
Wu et al., "Endometrial brush biopsy (Tao brush). Histologic diagnosis of 200 cases with complementary cytology: an accurate sampling technique for the detection of endometrial abnormalities.", American journal of clinical pathology 114, 412-418, 2000.
Wu et al., "Recurrent GNAS mutations define an unexpected pathway for pancreatic cyst development.", Sci Transl Afed 3, 92ra66, 2011.
Wu et al., "Whole-exome sequencing of neoplastic cysts of the pancreas reveals recurrent mutations in components of ubiquitin-dependent pathways", PNAS 108, 21188-21193, 2011.
Wu, "Urothelial tumorigenesis: a tale of divergent pathways.", Nat Rev Cancer 5: 713-725, 2005.
Xia et al., "Lapatinib Antitumor Activity Is Not Dependent upon Phosphatase and Tensin Homologue Deleted on Chromosome 10 in ErbB2-Overexpressing Breast Cancers", Cancer Res. 67: 1170-1175, 2007.
Xie et al., "Age-related mutations associated with clonal hematopoietic expansion and malignancies.", Nat Med 20(12): 1472-1478, 2014.
Xie et al., "Lnc-PCDH9-13:1 Is a Hypersensitive and Specific Biomarker for Early Hepatocellular Carcinoma", EBioMedicine, 33, 57-67, 2018.
Xu et al., "Recent advances of highly selective CDK4/6 inhibitors in breast cancer", J Hematol. Oncol. 10(1): 97, 2017.
Yachida et al., "Clinical significance of the genetic landscape of pancreatic cancer and implications for identification of potential long-term survivors.", Clin Cancer Res 18: 6339-6347, 2012.
Yachida et al., "Distant metastasis occurs late during the Jenetic evolution of pancreatic cancer.", Nature, 467: 1114-7, 2010.
Yafi et al., "Prospective analysis of sensitivity and specificity of urinary cytology and other urinary biomarkers for bladder cancer.", Urol Oncol 33 :66.e25-66.e3 1, 2015.
Yamada et al., "It is possible to diagnose malignancy from fluid in cystic ovarian tumors?", European journal of obstetrics, gynecology, and reproductive biology 171, 96-100, 2013.
Yang et al., "Unusually high incidence of upper urinary tract urothelial carcinoma in Taiwan.", Urology, 59( 5), 681-687, 2002.
Yee et al., "Personalized Therapy Tumor Antigen Discovery for Adoptive Cellular Therapy", Cancer J. 23(2): 144-148, 2016.
Young et al., "Clonal haematopoiesis harbouring AML-associated mutations is ubiquitous in healthy adults.", Nat Commun 7, 12484, 2016.
Yousem et al., "Pulmonary Langerhans Cell Histiocytosis. Profiling of Multifocal Tumors Using Next-Generation Sequencing Identifies Concordant Occurrence of Braf V600E Mutations", Chest 143: 1679-1684, 2013.
Yu et al., "LncRNA HCP5 promotes the development of cervical cancer by regulating MACCI via suppression of microRNA-15a.", Eur. Rev. Med. Pharmacol. Sci., 22: 4812-4819, 2018.
Yu et al., "Long non-coding RNA CACNA1G-AS1 promotes cell migration, invasion and epithelial-mesenchymal transition by HNRNPA2B1 in non-small cell lung cancer", Eur. Rev. Med. Pharmacol. Sci., 22: 993-1002, 2018.
Yun et al., "Biomonitoring of aristolactam-DNA adducts in human tissues using ultra-performance liquid chromatography/ion-trap mass spectrometry.", Chem ResToxicol. 2012 25(5): 1119-31, 2012.
Zack et al., "Pan-cancer patterns of somatic copy number alteration.", Nature genetics 45: 1134-1140, 2013.
Zaino et al., "Simultaneously Detected Endometrial and Ovarian Carcinomas—A Prospective Clinicopathologic Study of 74 Cases: A Gynecologic Oncology Group Study", Gynecologic oncology 83: 355-362, 2001.
Zamay et al., "Current and Prospective Protein Biomarkers of Lung Cancer", Cancers (Basel), 9(11): 155, 2017.
Zhai et al.,"High-grade serous carcinomas arise in the mouse oviduct via defects linked to the human disease.", The Journal of pathology 243, 16-25, 2017.
Zhang "Study of Use of Liquid-based Cytologic Test in Cervical Cancer and Endometrial Carcinoma Screening," China Master Dissertations Full-text Database, No. 8, pp. 4-28, 2005.
Zhang et al., "Analysis of the complex interaction of CDR1as-miRNA-protein and detection of its novel role in melanoma", Oncology Letters, 16: 1219-1225, 2018.
Zhang et al., "LncRNA DQ786243 expression as a biomarker for assessing prognosis in patients with gastric cancer.", Eur. Rev. Med. Pharmacol. Sci., 22: 2304-2309, 2018.
Zhang et al., "LncRNA H19 regulates the expression of its target gene HOXA10 in endometrial carcinoma through competing with miR-612.", Eur. Rev. Med. Pharmacol. Sci., 22: 4820-4827, 2018.
Zhang et al., "The cytomorphological features of low-grade urothelial neoplasms vary by specimen type.", Cancer Cytopathol 124: 552-564, 2016.
Zhao et al., "Histologic follow-up results in 662 patients with Pap test findings of atypical glandular cells: results from a large academic womens hospital laboratory employing sensitive screening methods.", Gynecologic oncology 114, 383-389, 2009.
Zhou et al., "Identifying markers for pancreatic cancer by gene expression analysis.", Cancer Epidemiol Biomarkers Prev 7(2): 109-112, 1998.
Zilbermann et al., "Genome-wide analysis of Dna methylation patterns" Development 134, 2007.
Zimmermann et al., "Digital PCR: a powerful new tool for noninvasive prenatal diagnosis?", Prenat Diagn 28: 1087-1093, 2008.
Zou et al., "More valuable than platinum: first-line pembrolizumab in advanced stage non-small-cell lung cancer.", Ann Oncol 28(4): 685-687, 2017.
Hannady, M. et al., Error-correcting barcoded primers for pyrosequencing hundreds of samples in multiplex, Nature Meth., 2007, 5:235-237.
Hannady, M. et al., Error-correcting barcoded primers for pyrosequencing hundreds of samples in multiplex, Nature Meth., 2007, vol. 5:1-36.
Resaei-Matehkolaei et al., Use of Single-enzyme PCR-restriction Digestion Bardode Targeting the Internal Transcribed Spacers (ITS rDNA) to identify Dermatophyte Species, Iranian J. Publ. Health, 2012, 41(3):82-94.
Al-Shannsi et al., "Molecular spectrum of KRAS, NRAS, BRAF, PIK3CA, TP53, and APC somatic gene mutations in Arab patients with colorectal cancer: determination of frequency and distribution pattern," Journal of Gastrointestinal Oncology, 2016, 7(6):882-902.
Balmain et al., "A model for RAS mutation patterns in cancers: finding the sweet spot.," Nature Reviews, 2018, 18:767-777.
Boland et al., "Clinical next generation sequencing to identify actionable aberrations in a phase I program," Oncotarget, 2015, 6(24):20099-20110.
Ellenson and Wu, "Focus on endometrial and cervical cancer," Cancer Cell; 2004, 5:533-538.
European Search Report issued in European Application No. 21173115.3, dated Oct. 12, 2021, 9 pages.
Fujii et al., Genomic landscape of upper urinary tract urothelial carcinoma, Eur. Urol., 2017, 16:3:e900.
Giam et al., "Aneuploidy and chromosomal instability in cancer: a jackpot to chaos," Cell Division, May 2015, 10: 3.
International Preliminary Report on Patentability in International Appln. No. PCT/US2020/014172, dated Jun. 16, 2021, 9 pages.
Izquierdo et al., "Molecular characterization of upper urinary tract tumors," BJUI, Oct. 2009, 106:868-872.
Kodaz et al., Frequency of RAS Mutations (KRAS, NRAS, HRAS) in Human Solid Cancer, EJMO, 2017, 1(1):1-7.
Marengo et al., "Biomarkers for pancreatic cancer: Recent achievements in proteomics and genomics through classical and multivari-

(56) References Cited

OTHER PUBLICATIONS ate statistical methods," World J. Gastroenterol, 20(37):13325-13342, Oct. 7, 2014) (Year: 2014).

McConechy et al., "Use of mutation profiles to refine the classification of endometrial carcinomas," J. Path, 2012; 228: 20-30.

Moreno-Bueno et al., "Abnormalities of the APC/b-catenin pathway in endometrial cancer," Oncogene; 2002; 21:7981-7990.

Wang et al., "TERT promoter mutations are associated with distant metastases in upper tract urothelial carcinomas and serve as urinary biomarkers detected by a sensitive castPCR," Oncotarget, 2014, 5:23: 12428-12439.

Wang et al., "TERT promoter mutations in renal cell carcinomas and upper tract urothelial carcinomas," 2014, 5:7:1829-1836.

Young et al., Validation of Biomarkers for Early Detection of Pancreatic Cancer: Summary of the Alliance of Pancreatic Cancer Consortia for Biomarkers for Early Detection Workshop., Pancreas, 2018, 47(2): 135-141.

Yuan et al., "The genetic difference between Western and Chinese urothelial cell carcinomas: infrequent FGFR3 mutation in Han Chinese patients," Oncotarget, 2016, 7:18:25826-25835.

[No Author Listed], "Grail announces data from prototype blood tests for early cancer detection," Grail Press Release, Apr. 17, 2018, 4 pages.

Futakawan et., "Significance of K-ras mutation and CEA level in pancreatic juice in the diagnosis of pancreatic cancer," J Hepatobiliary Pancreat Surg., Mar. 1, 2000, vol. 7, No. 1, pp. 63-71.

Ghosh et al., "Diagnostic Role of Tumour Markers CEA, CA15-3, CA19-9 and CA125 in Lung Cancer," Ind J. Clin Biochem, Jan. 2013, 28(1):24-29.

Hu et al., "False-Positive Plasma Genotyping Due to Clonal Hematopoiesis," AACR Journals, Mar. 22, 2018, 4437-4443.

Kadayifci et al., "Value of adding GNAS testing to pancreatic cyst fluid KRAS and carcinoembryonic antigen analysis for the diagnosis of intraductal papillary mucinous neoplasms," Dig. Endosc. Jan. 2017, 29:111-117.

Macconaill et al., "Prospective enterprise-level molecular genotyping of a cohort of cancer patients," Journal of Molecular Diagnostics, Nov. 2014, 16(6):660-672.

Office Action in Eurasian Application No. 202090439, dated May 13, 2022, 14 pages (with English translation).

Parkinson et al., "Exploratory Analysis of TP53 Mutations in Circulating Tumour DNA as Biomarkers of Treatment Response for Patients with Relapsed High-Grade Serous Ovarian Carcinoma: A Retrospective Study," PLoS Med. Dec. 2016, 13:12:e1002198.

Wong et al., "A Phase I Study with Neratinib (HKI-272), an Irreversible Pan ErbB Receptor Tyrosine Kinase Inhibitor, in Patients with Solid Tumors," Clin. Cancer Res., Apr. 2009, 2552-2558.

Wu et al., "Evaluation of the diagnostic value of serum tumor markers, and fecal k-ras and p53 gene mutations for pancreatic cancer," Chin J. Dig Dis., 2006, 7:3:170-4.

Bettegowda et al., "Detection of circulating tumor DNA in early- and late-stage human malignancies," Sci Transl Med, Feb. 2014, 6(224):224ra24.

Chen et al., "Analysis of Cancer Mutation Signature in Blood by a Novel Ultra- sensitive assay: monitoring of therapy or recurrence in non-metastatic breast cancer," PLOS One, Sep. 2009, 4(9):e7220.

Liao et al., "Noninvasive detection of tumor-associated mutations from circulating cell-free DNA in hepatocellular carcinoma patients by targeted deep sequencing," Oncotarget, Jun. 2016, 7(26):40481-40490.

Ono et al., "Circulating Tumor DNA Analysis for Liver Cancers and Its Usefulness as a Liquid Biopsy," Cellular and Molecular Gastroenterology and Hepatology, Sep. 2015, 1(5):516-534.

Page et al., "Next Generation Sequencing of Circulating Cell-Free DNA for Evaluating Mutations and Gene Amplification in Metastatic Breast Cancer," Clinical Chemistry, Feb. 2017, 63(2):532-541.

Razavi et al., "Cell-free DNA (cfDNA) mutations from clonal hematopoiesis: Implications for interpretation of liquid biopsy tests," 2017 ASCO Annual Meeting I, Jun. 20, 2017, Meeting Abstract, 2 pages.

USPTO Patent Trial and Appeal Board, "Decision on Appeal," Appeal No. 2018-006665, U.S. Appl. No. 14/212,469, dated Mar. 19, 2019, 7 pages.

\* cited by examiner

A

| Tumor Type | SEER Incidence | Total # | # ctDNA Positive | # Protein Positive | # ctDNA + Protein Positive | % ctDNA Positive | % Protein Positive | % ctDNA + Protein Positive |
|---|---|---|---|---|---|---|---|---|
| Breast | 43.8 | 150 | 24 | 30 | 47 | 16% | 20% | 31% |
| CRC | 1.0 | 322 | 130 | 168 | 231 | 40% | 52% | 72% |
| Esophagus | 0.63 | 43 | 21 | 28 | 34 | 49% | 65% | 79% |
| Gastric | 1.34 | 65 | 20 | 38 | 39 | 31% | 58% | 60% |
| Liver | 1.5 | 53 | 39 | 43 | 50 | 74% | 81% | 94% |
| Lung | 3.31 | 109 | 43 | 30 | 61 | 39% | 28% | 56% |
| Ovarian | 3.83 | 86 | 43 | 45 | 59 | 50% | 52% | 69% |
| Pancreas | 3.8 | 412 | 91 | 248 | 271 | 22% | 60% | 66% |
| All Cancers | 68.21 | 1240 | 411 | 630 | 792 | 33% | 51% | 64% |
| All Cancers (Incidence Weighted) | 68.21 | 12239 | 3102.55 | 4341.11 | 5974.96 | 25% | 35% | 49% |

| Early Detection Cohort | | | | Surveillance Cohort | | | |
|---|---|---|---|---|---|---|---|
| Urine collected at patient presentation (n=570) | | | | Urine collected following surgery (n=322) | | | |
| Developed Bladder Cancer 31% | | Did Not Develop Bladder Cancer 69% | | Developed Bladder Cancer 58% | | Did not Develop Bladder Cancer 42% | |
| UroSEEK positive 83% | Cytology positive 43% | UroSEEK positive 7% | Cytology positive 0% | UroSEEK positive 68% | Cytology positive 25% | UroSEEK positive 20% | Cytology positive 0% |
| Sensitivity (UroSEEK/Cytology Combined) 95% | | Specificity (UroSEEK/Cytology Combined) 93% | | Sensitivity (UroSEEK/Cytology Combined) 71% | | Specificity (UroSEEK/Cytology Combined) 82% | |

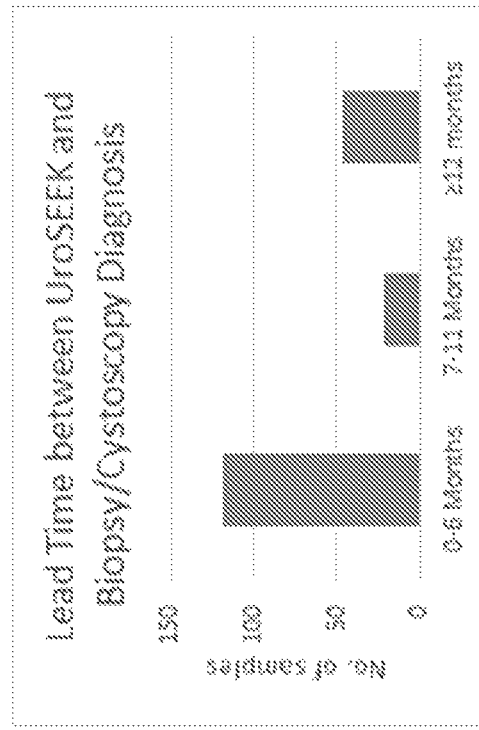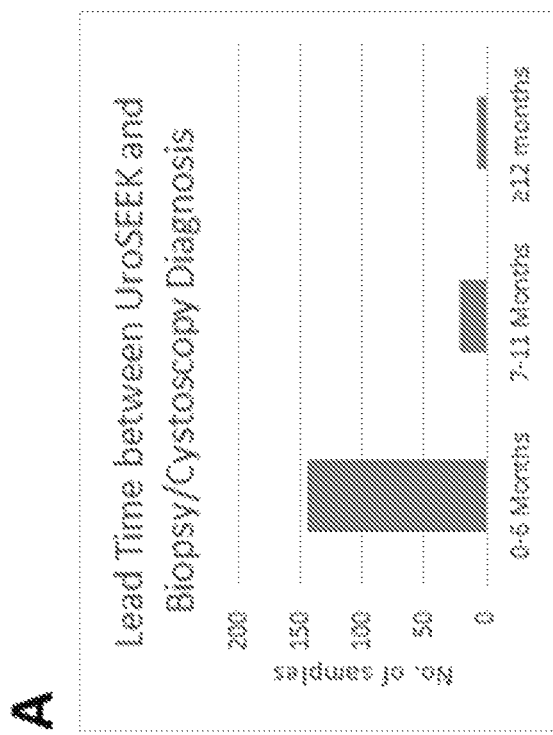
FIG. 29

A 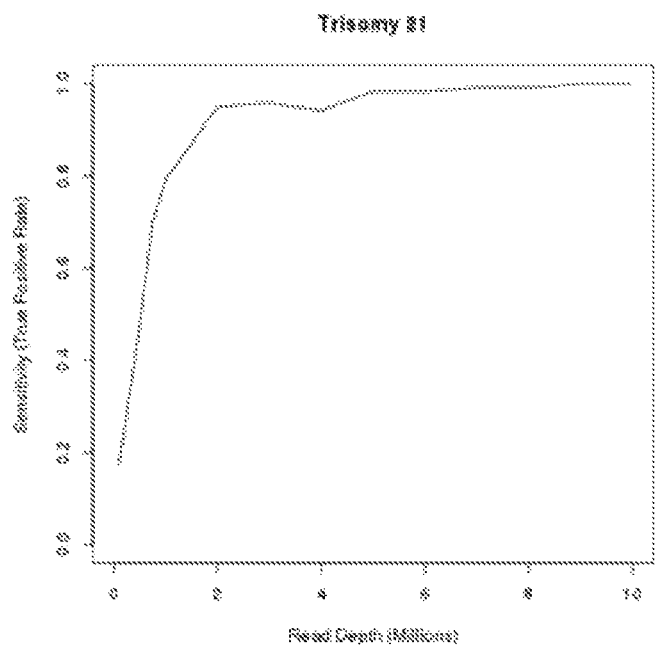
B 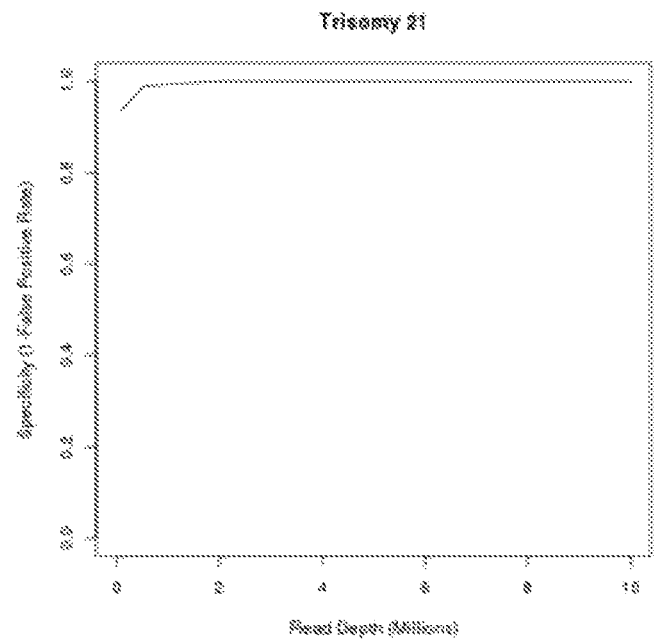
FIG. 41

Synthetics with one arm alterations

N <- number of normal WBC samples used
f <- desired neoplastic cell fraction
r <- chromosome arm (1p..22q)
r_type <- alteration type (gain or loss)
p(r) <- probability of arm gain (0.5 default)
rho <- desired unique read depth of synthetic sample (9M default)
j <- desired number of repeats

```
For j=1:5
    For i=1:N
        s <- sample[i]
        U <- get UIDs from s
        For f in 1:F
            For r in 1p:22q   #select alteration types and spike-in to t
                For r_type in gain loss
                    h <- new synthetic sample
                    t <- copy of s
                    u_ref <- get all reference allele UIDs that that map
                             to chr arm r
                    if r_type== gain
                        t <- add duplicate u_ref reads
                    else (r_type == loss)
                        t <- subtract u_ref reads
                    Endif
                    h_normal<-random select (1-f)*rho UIDs from s
                    h_aneuploid<-random select f*rho UIDs from t
                    h<-h_normal+h_aneuploid
                End
            End
        End
```

FIG. 49

```
N <- number of normal WBC samples used
d <- desired degree of aneuploidy (number arms altered)
f <- desired neoplastic cell fraction
r <- chromosome arm (1p..22q)
r_type<-arm alteration type (gain or loss)
p(r) <- probability of arm gain (0.5 default)
rho <- desired unique read depth of synthetic sample (9M default)
j<- desired number of repeats For j=1:5
    For i=1:N
        s <- sample[i]
        U <-  get UIDs from s
        For f in 1:F
            h <- new synthetic sample
            For d in (5,10,15,20,25) #desired numbers of altered arms
                t <- copy of s
                For a in 1:d   #select alteration types and spike-in to t
                    r <- random select arm
                    r_type <- alteration type with p(r)
                    u_ref <- get all reference allele UIDs that that map
                            to chr arm r
                    if r_type== gain
                        t <- add  duplicate u_ref reads
                    else (r_type == loss)
                        t <- subtract u_ref reads
                    Endif
                    h_normal<-random select (1-f)*rho UIDs from s
                    h_aneuploid<-random select f*rho UIDs from t
                    h<-h_normal+h_aneuploid
                End
            End
        End
    End
End
```

FIG. 50

A
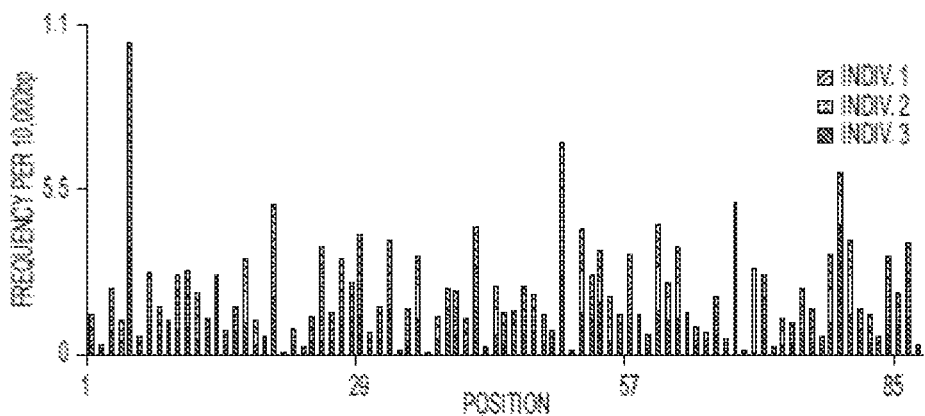
B
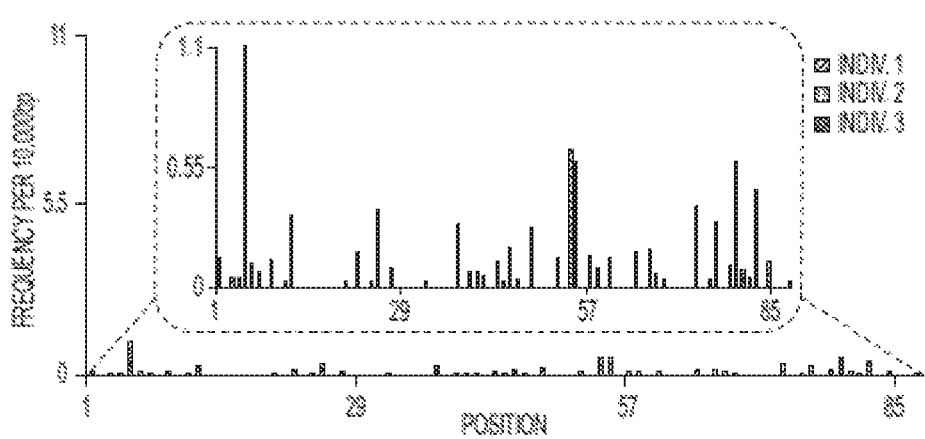
FIG. 64

```
SEQUENCE LISTING

<160> NUMBER OF SEQ ID NOS: 892

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggtctctca tggcactgta ct                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atggtgaaac ctgtttgttg g                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgctggtgt gaaatgactg a                                               21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gattgtcagt gcgcttttcc                                                 20

<210> SEQ ID NO 5
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
actggcagca acagtcttac ct                                              22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actcagagaa ggagctgtgg tagt                                            24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctggactctg gaatccattc tg                                              22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcctcagga ttgcctttac c                                               21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgaaaaagc cgaaggtcac                                                 20

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtaagtgtta ctcaagaagc agaaagg                                         27

<210> SEQ ID NO 11
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 11
cagaataaaa attctttgtg caacc                                             25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgactttacc ttatcaatgt ctcgaa                                            26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttttagcact tacctgtgac tcca                                              24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caatttctac acgagatcct ctctc                                             25

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccaatccatt tttgttgtcc a                                                 21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgagcaagag gctttggagt                                                   20

<210> SEQ ID NO 17
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 17
accctcctgc catcatattg                                              20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggccagtgtt tacatgtttt ga                                           22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtctcaata tcccaaaccc taa                                          23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20 ttgttttttct gtttctccct ctg                                         23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccatgacaag attttcccctt acc                                         23

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caccttatat gggcatactt ccact                                        25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic

```
      primer

<400> SEQUENCE: 23
tgcagagttc agttacctta ggaga                                        25

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcatacatc agacagcaca ga                                           22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatcttcagc tgacctagtt ccaa                                         24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagattctgc taataccctg caa                                          23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtccactctc tctcttttca gca                                          23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctcaaacag ctcaaaccaa g                                            21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 29
gcagcatgtc aagatcacag at                                            22

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgcctccttc tgcatggtat                                               20

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgggacccac tccatcg                                                  17

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atatttcttc atgaagacct cacagtaa                                      28

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caactgcgcc gacccc                                                   16

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cagcgtgtcc aggaagcc                                                 18

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 35
accctggctc tgaccattc                                                19

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagcagctcc gccactc                                                  17

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
accacagttg cacaatatcc ttt                                           23

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcttcacaaa agggtttgat aagttc                                        26

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgttgcag caattcactg t                                             21

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgatgtaat aaatatgcac atatcattac                                    30

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```

-continued ggaaagggac gaactggtg                                                19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tagggcctct tgtgccttta                                               20

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctctggtcct tacttcccca tag                                           23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
catatttatt acatcggggc aaa                                           23

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agtccggctt ggaggatg                                                 18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tccccactcc tcctttcttc                                               20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
gcgatgacgg aatataagct g                                              21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctggatcagc tggatggtca                                                20

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caagaagtta tggaattcct tttattga                                       28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tttatttcag tgttacttac ctgtcttg                                       28

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gagaaacctg tctcttggat attctc                                         26

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgtactggtc cctcattgca c                                              21

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgtcaaggca ctcttgcc                                                  18
```

```
<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgctgaaaat gactgaatat aaacttgt                                             28

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gccgccaggt cttgatgt                                                        18

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gggtctgacg ggtagagtgt g                                                    21

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgagtcaggc ccttctgtct                                                      20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gccacctgaa gtccaaaaag                                                      20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 tttttatggcg ggaggtagac t                                                   21
```

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcatctctcc tccctgcttc t                                           21

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccctggctcc ttcccag                                                17

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cttcgagatg ttccgagagc                                             20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tcctctgttg ctgcagatcc                                             20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgagttccaa ggcctcattc                                             20

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cacttgataa gaggtcccaa gactta                                      26

```
<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cccagccaaa gaagaaacca                                                   20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tcttctttgg ctggggaga                                                    19

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttttatcacc tttccttgcc tct                                               23

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 aaagggagc ctcaccac                                                      18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
accgcttctt gtcctgctt                                                    19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtgaggctcc cctttcttg                                                    19

<210> SEQ ID NO 72
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cgtgtttgtg cctgtcctg                                                    19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gggacggaac agctttgag                                                    19

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcggagattc tcttcctctg t                                                 21

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aacacgcacc tcaaagctg                                                    19

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgcctcttgc ttctcttttc ct                                                22

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtggcaagtg gctcctga                                                     18

<210> SEQ ID NO 78
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
catgggcggc atgaac                                                      16

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tggctctgac tgtaccacca                                                  20

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atgggcctcc ggttcat                                                     17

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cccatgcagg aactgttaca c                                                21

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggcctgtgtt atctcctagg ttg                                              23

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
taacccctcc tcccagagac                                                  20

<210> SEQ ID NO 84
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 84
ttttcgacat agtgtggtgg tg                                                    22

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttgcgtgtgg agtatttgga                                                       20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agacctcagg cggctcatag                                                       20

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgaaaagtgt ttctgtcatc ca                                                    22

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gcccctcctc agcatcttat                                                       20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgcaaatttc cttccactcg                                                       20

<210> SEQ ID NO 90
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 90
ctgattcctc actgattgct ctt                                              23

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agccccagct gctcacc                                                     17

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
acatgacgga ggttgtgagg                                                  20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggccatcta caagcagtca                                                  20

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gagcagcgct catggtg                                                     17

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgtcatgtgc tgtgactgct t                                                21

<210> SEQ ID NO 96
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 96
cagctgtggg ttgattcca                                                  19

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gaatcaaccc acagctgcac                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agtactcccc tgccctcaac                                                 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ggccagttgg caaaacatct                                                 20

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gccctgactt tcaactctgt ct                                              22

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
atacggccag gcattgaagt                                                 20

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 102
gggacagcca agtctgtga                                              19

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cccctcaggg caactgac                                               18

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
agctacggtt tccgtctgg                                              19

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggcccctgtc atcttctgt                                              19

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cagaatgcaa gaagcccaga                                             20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ttctgggaag ggacagaaga                                             20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 108
tgcaccagca gctcctacac                    20

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagcagcctc tggcattct                     19

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gtccccggac gatattgaac                    20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cctgggtctt cagtgaacca                    20

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cttgccgtcc caagcaat                      18

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggggacagca tcaaatcatc                    20

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 114
tgactgctct tttcacccat c                                              21

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
agcccaaccc ttgtccttac                                                20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccatgggact gactttctgc                                                20

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tggatccact cacagtttcc a                                              21

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gccgcagtca gatcctagc                                                 19

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tacttccgga acctgtgctc                                                20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
```
ggcaaactcc cccagctt                                                        18

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tgtttcagga cctgcttcg                                                       19

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tccacctgga acttggtctc                                                      20

<210> SEQ ID NO 123
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gagaaacctg tctcttggat attctc                                               26

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tgtactggtc cctcattgca c                                                    21

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cgtcaaggca ctcttgcc                                                        18

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tgctgaaaat gactgaatat aaacttgt                                          28

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tcctctgttg ctgcagatcc                                                   20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgagttccaa ggcctcattc                                                   20

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129 aaagggagc ctcaccac                                                      18

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
accgcttctt gtcctgctt                                                    19

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gtgaggctcc cctttcttg                                                    19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cgtgtttgtg cctgtcctg                                                    19

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gggacggaac agctttgag                                                  19

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcggagattc tcttcctctg t                                               21

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
aacacgcacc tcaaagctg                                                  19

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgcctcttgc ttctcttttc ct                                              22

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtggcaagtg gctcctga                                                   18

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
catgggcggc atgaac                                                     16

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggctctgac tgtaccacca                                                    20

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
atgggcctcc ggttcat                                                       17

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cccatgcagg aactgttaca c                                                  21

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggcctgtgtt atctcctagg ttg                                                23

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
taacccctcc tcccagagac                                                    20

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ttttcgacat agtgtggtgg tg                                                 22

```
<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ttgcgtgtgg agtatttgga                                                   20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
agacctcagg cggctcatag                                                   20

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cgaaaagtgt ttctgtcatc ca                                                22

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcccctcctc agcatcttat                                                   20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgcaaatttc cttccactcg                                                   20

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ctgattcctc actgattgct ctt                                               23

<210> SEQ ID NO 151
```

<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
agccccagct gctcacc                                                      17

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
acatgacgga ggttgtgagg                                                   20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
tggccatcta caagcagtca                                                   20

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
gagcagcgct catggtg                                                      17

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
cgtcatgtgc tgtgactgct t                                                 21

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
cagctgtggg ttgattcca                                                    19

<210> SEQ ID NO 157
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ggccagttgg caaaacatct                                              20

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gccctgactt tcaactctgt ct                                           22

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cacacaggaa acagctatga ccatgacacc cccaggattc ttacag                 46

<210> SEQ ID NO 160
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 160
cgacgtaaaa cgacggccag tnnnnnnnnn nnnnncgcct gtcctcatgt attgg       55

<210> SEQ ID NO 161
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cacacaggaa acagctatga ccatggatgt ggctcgccaa ttaac                  45

<210> SEQ ID NO 162
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g
```

<400> SEQUENCE: 162
cgacgtaaaa cgacggccag tnnnnnnnnn nnnnngattg tcagtgcgct tttcc    55

<210> SEQ ID NO 163
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cacacaggaa acagctatga ccatgagcca caggctccca gac    43

<210> SEQ ID NO 164
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 164
cgacgtaaaa cgacggccag tnnnnnnnnn nnnnntgaca gaaaggtaaa gaggagca    58

<210> SEQ ID NO 165
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cacacaggaa acagctatga ccatggctgc atatttcaga tatttctttc c    51

<210> SEQ ID NO 166
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 166
cgacgtaaaa cgacggccag tnnnnnnnnn nnnnncatca tcaatattgt tcctgtatac    60
gc    62

<210> SEQ ID NO 167
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cacacaggaa acagctatga ccatgggatt tcctgcagaa agacttg    47

<210> SEQ ID NO 168
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 168
cgacgtaaaa cgacggccag tnnnnnnnnn nnnnntcttt tctaaatgaa aacacaacat      60
ga                                                                   62

<210> SEQ ID NO 169
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cacacaggaa acagctatga ccatgaaatag ttgttttaga agatatttgc aagc           54

<210> SEQ ID NO 170
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 170
cgacgtaaaa cgacggccag tnnnnnnnnn nnnnnttaat ggtggctttt tgtttgtt       58

<210> SEQ ID NO 171
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cacacaggaa acagctatga ccatgaagat tcaggcaatg tttgttagta tt             52

<210> SEQ ID NO 172
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 172
cgacgtaaaa cgacggccag tnnnnnnnnn nnnnngcaat taaatttggc ggtgt          55

-continued

<210> SEQ ID NO 173
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cacacaggaa acagctatga ccatgcagta agatacagtc tatcgggttt aagt         54

<210> SEQ ID NO 174
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 174
cgacgtaaaa cgacggccag tnnnnnnnnn nnnnntttta aactttctct ttagttgtgc   60
tga                                                                 63

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
cacacaggaa acagctatga ccatgtttct tattctgagg ttatcttttt acca         54

<210> SEQ ID NO 176
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 176
cgacgtaaaa cgacggccag tnnnnnnnnn nnnnncatga ttgtcatctt cacttagcc    59

<210> SEQ ID NO 177
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cacacaggaa acagctatga ccatgccata acccaccaca gctaga                  46

<210> SEQ ID NO 178
<211> LENGTH: 60
<212> TYPE: DNA

<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 178
cgacgtaaaa cgacggccag tnnnnnnnnn nnnnngcaca tatcattaca ccagttcgtc     60

<210> SEQ ID NO 179
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cacacaggaa acagctatga ccatggcaat tcactgtaaa gctggaaa                   48

<210> SEQ ID NO 180
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 180
cgacgtaaaa cgacggccag tnnnnnnnnn nnnntggtc cttacttccc catagaa         57

<210> SEQ ID NO 181
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cacacaggaa acagctatga ccatgaaacc caaaatctgt tttccaa                    47

<210> SEQ ID NO 182
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 182
cgacgtaaaa cgacggccag tnnnnnnnnn nnnnaggca caagaggccc tagat           55

<210> SEQ ID NO 183
<211> LENGTH: 49
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 183
cacacaggaa acagctatga ccatgtcaat ttggcttctc ttttttttc                    49

<210> SEQ ID NO 184
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 184
cgacgtaaaa cgacggccag tnnnnnnnnn nnnnncactg gtctataatc cagatgattc        60
tt                                                                       62

<210> SEQ ID NO 185
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cacacaggaa acagctatga ccatggcgct atgtgtatta ttatagctac ctg               53

<210> SEQ ID NO 186
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 186
cgacgtaaaa cgacggccag tnnnnnnnnn nnnnncgcca ctgaacattg gaatag            56

<210> SEQ ID NO 187
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cacacaggaa acagctatga ccatggctac ctgttaaaga atcatctgga                   50

<210> SEQ ID NO 188
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
<222> LOCATION: (22)..(35)
<223> OTHER INFORMATION: a, c, t, or g

<400> SEQUENCE: 188
cgacgtaaaa cgacggccag tnnnnnnnnn nnnnnggaag gatgagaatt tcaagcac      58

<210> SEQ ID NO 189
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cacacaggaa acagctatga ccatgaggca tttcctgtga aataatactg               50

<210> SEQ ID NO 190
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 190
cgacgtaaaa cgacggccag tnnnnnnnnn nnnnntgaac ttgtcttccc gtcgt         55

<210> SEQ ID NO 191
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cacacaggaa acagctatga ccatgtgtgg tctgccagct aaagg                    45

<210> SEQ ID NO 192
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 192
cgacgtaaaa cgacggccag tnnnnnnnnn nnnnngttct gtttgtggaa gaactctact    60
tt                                                                   62

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
```

```
cacacaggaa acagctatga ccatgttgag ttccctcagc cgtta              45
```

<210> SEQ ID NO 194
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 194

```
cgacgtaaaa cgacggccag tnnnnnnnnn nnnnntttgg atatttctcc caatgaaag   59
```

<210> SEQ ID NO 195
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195

```
cacacaggaa acagctatga ccatgttttt tttttaggac aaaatgtttc ac          52
```

<210> SEQ ID NO 196
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 196

```
cgacgtaaaa cgacggccag tnnnnnnnnn nnnnntgcac gctctatact gcaaatg    57
```

<210> SEQ ID NO 197
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197

```
cacacaggaa acagctatga ccatgtctat gtgatcaaga aatcgatagc a           51
```

<210> SEQ ID NO 198
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 198

```
cgacgtaaaa cgacggccag tnnnnnnnnn nnnnnaagta tcggttggct ttgtctttt   58
```

<210> SEQ ID NO 199
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cacacaggaa acagctatga ccatgtttaa caaaaaatga tcttgacaaa gc            52

<210> SEQ ID NO 200
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 200
cgacgtaaaa cgacggccag tnnnnnnnnn nnnnnacaag tcaacaaccc ccaca          55

<210> SEQ ID NO 201
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
cacacaggaa acagctatga ccatgtgggt tttcatttta aattttcttt c              51

<210> SEQ ID NO 202
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 202
cgacgtaaaa cgacggccag tnnnnnnnnn nnnnnaggtt cattgtcact aacatctggt     60

<210> SEQ ID NO 203
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
cacacaggaa acagctatga ccatgtagag gagccgtcaa atcca                     45

<210> SEQ ID NO 204
<211> LENGTH: 60
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 204
cgacgtaaaa cgacggccag tnnnnnnnnn nnnnnctgat cttcatcaaa aggttcattc    60

<210> SEQ ID NO 205
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
cacacaggaa acagctatga ccatgggtcc attttcagtt tattcaagtt ta            52

<210> SEQ ID NO 206
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 206
cgacgtaaaa cgacggccag tnnnnnnnnn nnnnnctgac accactgact ctgatcc       57

<210> SEQ ID NO 207
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cacacaggaa acagctatga ccatggcagc cagaaatgtt ttggta                   46

<210> SEQ ID NO 208
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 208
cgacgtaaaa cgacggccag tnnnnnnnnn nnnnnactgc catcgactta cattgg        56

<210> SEQ ID NO 209
<211> LENGTH: 45
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 209
cacacaggaa acagctatga ccatggcaga gtatttgggc gaatg        45

<210> SEQ ID NO 210
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 210
cgacgtaaaa cgacggccag tnnnnnnnnn nnnnntctgg tgtcagagat ggagatg    57

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
cacacaggaa acagctatga ccatggctgg gcatcactgt aaacc        45

<210> SEQ ID NO 212
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 212
cgacgtaaaa cgacggccag tnnnnnnnnn nnnnntcttc cctctctcca ccaga    55

<210> SEQ ID NO 213
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cacacaggaa acagctatga ccatgggaaa taaatgtgat ttgccttct    49

<210> SEQ ID NO 214
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

```
<400> SEQUENCE: 214
cgacgtaaaa cgacggccag tnnnnnnnnn nnnnntttca gtgttactta cctgtcttgt    60
ctt                                                                   63

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cacacaggaa acagctatga ccatgttctc ccttctcagg attcctac                 48

<210> SEQ ID NO 216
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 216
cgacgtaaaa cgacggccag tnnnnnnnnn nnnnntgtac tggtccctca ttgcac        56

<210> SEQ ID NO 217
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cacacaggaa acagctatga ccatgtttac ctctattgtt ggatcatatt cg            52

<210> SEQ ID NO 218
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 218
cgacgtaaaa cgacggccag tnnnnnnnnn nnnnntgact gaatataaac ttgtggtagt    60
tgg                                                                   63

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
```
cacacaggaa acagctatga ccatggtctg tgtggtgccc agttt    45

<210> SEQ ID NO 220
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 220
cgacgtaaaa cgacggccag tnnnnnnnnn nnnnngactg cccacaggaa ggtaa    55

<210> SEQ ID NO 221
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
cacacaggaa acagctatga ccatgcccat cccaggagct tactt    45

<210> SEQ ID NO 222
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 222
cgacgtaaaa cgacggccag tnnnnnnnnn nnnntggca tttgacattg agacg    55

<210> SEQ ID NO 223
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cacacaggaa acagctatga ccatgtcctt gtagccaatg aaggtg    46

<210> SEQ ID NO 224
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 224
cgacgtaaaa cgacggccag tnnnnnnnnn nnnnnagggt ctgacgggta gagtgt    56

```
<210> SEQ ID NO 225
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
cacacaggaa acagctatga ccatggccac ctgaagtcca aaaag            45

<210> SEQ ID NO 226
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 226
cgacgtaaaa cgacggccag tnnnnnnnnn nnnnngaggc tgtcagtggg gaac      54

<210> SEQ ID NO 227
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cacacaggaa acagctatga ccatgatgtc atctctcctc cctgct            46

<210> SEQ ID NO 228
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 228
cgacgtaaaa cgacggccag tnnnnnnnnn nnnnnagtct gagtcaggcc cttctg     56

<210> SEQ ID NO 229
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
cacacaggaa acagctatga ccatggttcc gagagctgaa tgagg            45

<210> SEQ ID NO 230
<211> LENGTH: 55
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 230
cgacgtaaaa cgacggccag tnnnnnnnnn nnnnntagga aggcagggga gtagg         55

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cacacaggaa acagctatga ccatgccctg gctccttccc ag                       42

<210> SEQ ID NO 232
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 232
cgacgtaaaa cgacggccag tnnnnnnnnn nnnnncttct cccctcctc tgttg          55

<210> SEQ ID NO 233
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cacacaggaa acagctatga ccatgaagaa gaaaacggca ttttgag                  47

<210> SEQ ID NO 234
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 234
cgacgtaaaa cgacggccag tnnnnnnnnn nnnnnccagc caaagaagaa accac         55

<210> SEQ ID NO 235
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 235
cacacaggaa acagctatga ccatgtttta tcacctttcc ttgcctct    48

<210> SEQ ID NO 236
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 236
cgacgtaaaa cgacggccag tnnnnnnnnn nnnnncaaga cttagtacct gaagggtgaa    60

<210> SEQ ID NO 237
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cacacaggaa acagctatga ccatgcgtgt ttgtgcctgt cctg    44

<210> SEQ ID NO 238
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 238
cgacgtaaaa cgacggccag tnnnnnnnnn nnnnngcttc ttgtcctgct tgctt    55

<210> SEQ ID NO 239
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cacacaggaa acagctatga ccatgtgcct cttgcttctc ttttcc    46

<210> SEQ ID NO 240
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 240

```
cgacgtaaaa cgacggccag tnnnnnnnnn nnnnngcgga gattctcttc ctctgt        56
```

<210> SEQ ID NO 241
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241

```
cacacaggaa acagctatga ccatgtggct ctgactgtac caccatc        47
```

<210> SEQ ID NO 242
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 242

```
cgacgtaaaa cgacggccag tnnnnnnnnn nnnnngtggc aagtggctcc tga        53
```

<210> SEQ ID NO 243
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243

```
cacacaggaa acagctatga ccatgtgtga tgatggtgag gatgg        45
```

<210> SEQ ID NO 244
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 244

```
cgacgtaaaa cgacggccag tnnnnnnnnn nnnnntcatc ttgggcctgt gttatc        56
```

<210> SEQ ID NO 245
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245

```
cacacaggaa acagctatga ccatggtgga aggaaatttg cgtgt        45
```

<210> SEQ ID NO 246
<211> LENGTH: 55

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 246
cgacgtaaaa cgacggccag tnnnnnnnnn nnnnncttaa cccctcctcc cagag        55

<210> SEQ ID NO 247
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cacacaggaa acagctatga ccatggtccc caggcctctg att                     43

<210> SEQ ID NO 248
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 248
cgacgtaaaa cgacggccag tnnnnnnnnn nnnnncgaaa agtgtttctg tcatcca      57

<210> SEQ ID NO 249
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
cacacaggaa acagctatga ccatggccat ggccatctac aagc                    44

<210> SEQ ID NO 250
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 250
cgacgtaaaa cgacggccag tnnnnnnnnn nnnnnaccag ccctgtcgtc tctc         54

<210> SEQ ID NO 251
<211> LENGTH: 45
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 251
cacacaggaa acagctatga ccatgctccg tcatgtgctg tgact        45

<210> SEQ ID NO 252
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 252
cgacgtaaaa cgacggccag tnnnnnnnnn nnnnncaaca agatgttttg ccaactg        57

<210> SEQ ID NO 253
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cacacaggaa acagctatga ccatggccct gactttcaac tctgtct        47

<210> SEQ ID NO 254
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 254
cgacgtaaaa cgacggccag tnnnnnnnnn nnnnnggggg tgtggaatca acc        53

<210> SEQ ID NO 255
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
cacacaggaa acagctatga ccatggcatt gaagtctcat ggaagc        46

<210> SEQ ID NO 256
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)

<223> OTHER INFORMATION: a, c, t, or g

<400> SEQUENCE: 256
cgacgtaaaa cgacggccag tnnnnnnnnn nnnnncccctt cccagaaaac ctacc    55

<210> SEQ ID NO 257
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
cacacaggaa acagctatga ccatgctgca ccagcagctc ctac                  44

<210> SEQ ID NO 258
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 258
cgacgtaaaa cgacggccag tnnnnnnnnn nnnnncagaa tgcaagaagc ccaga      55

<210> SEQ ID NO 259
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cacacaggaa acagctatga ccatgagctc ccagaatgcc agag                  44

<210> SEQ ID NO 260
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 260
cgacgtaaaa cgacggccag tnnnnnnnnn nnnntggga agggacagaa gatga       55

<210> SEQ ID NO 261
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
cacacaggaa acagctatga ccatggcaat ggatgatttg atgctg                46

<210> SEQ ID NO 262
<211> LENGTH: 53
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(35)
<223> OTHER INFORMATION: a, c, t, or g

<400> SEQUENCE: 262
cgacgtaaaa cgacggccag tnnnnnnnnn nnnnncggtg taggagctgc tgg    53

<210> SEQ ID NO 263
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
cacacaggaa acagctatga ccatgtgact gctcttttca cccatc    46

<210> SEQ ID NO 264
<211> LENGTH: 55
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(35)
<223> OTHER INFORMATION: a, c, t, or g

<400> SEQUENCE: 264
cgacgtaaaa cgacggccag tnnnnnnnnn nnnnntcatc tggacctggg tcttc    55

<210> SEQ ID NO 265
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
cacacaggaa acagctatga ccatgagccc cctagcagag acct    44

<210> SEQ ID NO 266
<211> LENGTH: 54
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(35)
<223> OTHER INFORMATION: a, c, t, or g

<400> SEQUENCE: 266
cgacgtaaaa cgacggccag tnnnnnnnnn nnnnncagcc caaccttgt cctt    54

<210> SEQ ID NO 267

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cacacaggaa acagctatga ccatgccttc caatggatcc actcac                  46

<210> SEQ ID NO 268
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 268
cgacgtaaaa cgacggccag tnnnnnnnnn nnnnnactgc cttccgggtc act          53

<210> SEQ ID NO 269
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
cacacaggaa acagctatga ccatgcgaca cccacagagg aaaag                   45

<210> SEQ ID NO 270
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 270
cgacgtaaaa cgacggccag tnnnnnnnnn nnnnnggacc aaggatatgc cacac        55

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cacacaggaa acagctatga ccatgaatgc cagtgatgac gacaa                   45

<210> SEQ ID NO 272
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (22)..(35)
<223> OTHER INFORMATION: a, c, t, or g

<400> SEQUENCE: 272
cgacgtaaaa cgacggccag tnnnnnnnnn nnnnntgtgt agggcgaagt gtgag              55

<210> SEQ ID NO 273
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
cacacaggaa acagctatga ccatgacatg gggatgatct cactctt                      47

<210> SEQ ID NO 274
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 274
cgacgtaaaa cgacggccag tnnnnnnnnn nnnnntactt ccggaacctg tgctc              55

<210> SEQ ID NO 275
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cacacaggaa acagctatga ccatgttccc ttctgagagt gtcagtgt                     48

<210> SEQ ID NO 276
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 276
cgacgtaaaa cgacggccag tnnnnnnnnn nnnnntggtg atgcccactc tgc                53

<210> SEQ ID NO 277
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
```

```
cacacaggaa acagctatga ccatgacatt caacccacac aagagg          46
```

<210> SEQ ID NO 278
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 278

```
cgacgtaaaa cgacggccag tnnnnnnnnn nnnnnatcta tgtccctgaa gcagca    56
```

<210> SEQ ID NO 279
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279

```
cacacaggaa acagctatga ccatggccat ggaaccagac agaaa          45
```

<210> SEQ ID NO 280
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 280

```
cgacgtaaaa cgacggccag tnnnnnnnnn nnnnncctca ggattgcctt tacca     55
```

<210> SEQ ID NO 281
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281

```
cacacaggaa acagctatga ccatgccccc tccatcaact tcttc          45
```

<210> SEQ ID NO 282
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 282

```
cgacgtaaaa cgacggccag tnnnnnnnnn nnnnngaaaa agccgaaggt cacaa     55
```

<210> SEQ ID NO 283
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
cacacaggaa acagctatga ccatgttatt ccagacgcat ttccac                    46

<210> SEQ ID NO 284
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 284
cgacgtaaaa cgacggccag tnnnnnnnnn nnnnnacatt cacgtaggtt gcacaaa        57

<210> SEQ ID NO 285
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
cacacaggaa acagctatga ccatgcaatg aattaaggga aaatgacaaa                50

<210> SEQ ID NO 286
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 286
cgacgtaaaa cgacggccag tnnnnnnnnn nnnnnctcca ttttagcact tacctgtgac     60

<210> SEQ ID NO 287
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
cacacaggaa acagctatga ccatggcatg ccaatctctt cataaatc                  48

<210> SEQ ID NO 288
<211> LENGTH: 55
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 288
cgacgtaaaa cgacggccag tnnnnnnnnn nnnnntccaa agcctcttgc tcagt            55

<210> SEQ ID NO 289
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cacacaggaa acagctatga ccatgtttga tgacattgca tacattcg                    48

<210> SEQ ID NO 290
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 290
cgacgtaaaa cgacggccag tnnnnnnnnn nnnnngatcc aatccatttt tgttgtccag       60

<210> SEQ ID NO 291
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cacacaggaa acagctatga ccatgttgag acaggccagt gtttacat                    48

<210> SEQ ID NO 292
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 292
cgacgtaaaa cgacggccag tnnnnnnnnn nnnnncagtc tctggatccc acacc            55

<210> SEQ ID NO 293
<211> LENGTH: 48
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 293
cacacaggaa acagctatga ccatgttgtt tttctgtttc tccctctg        48

<210> SEQ ID NO 294
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 294
cgacgtaaaa cgacggccag tnnnnnnnnn nnnnnctgca acatgaccca tcaaa    55

<210> SEQ ID NO 295
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
cacacaggaa acagctatga ccatggaagt cccaaccatg acaaga    46

<210> SEQ ID NO 296
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 296
cgacgtaaaa cgacggccag tnnnnnnnnn nnnnncggac actcaaagtg tggaa    55

<210> SEQ ID NO 297
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
cacacaggaa acagctatga ccatgaaacc ttaagatgag cattgttttg    50

<210> SEQ ID NO 298
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

```
<400> SEQUENCE: 298
cgacgtaaaa cgacggccag tnnnnnnnnn nnnnncattt tagtagacgc atctcgtacc    60

<210> SEQ ID NO 299
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
cacacaggaa acagctatga ccatgtcagg gaagaagtga atgaaaaa                 48

<210> SEQ ID NO 300
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 300
cgacgtaaaa cgacggccag tnnnnnnnnn nnnnncagct atattccctg gcttacct      58

<210> SEQ ID NO 301
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cacacaggaa acagctatga ccatgggggtt ttgggctgat attaaaac                48

<210> SEQ ID NO 302
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 302
cgacgtaaaa cgacggccag tnnnnnnnnn nnnnnccata tttcccatct cgatgaa       57

<210> SEQ ID NO 303
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
cacacaggaa acagctatga ccatgtgttt ccatgtcagc tattttgtt                49

<210> SEQ ID NO 304
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 304
cgacgtaaaa cgacggccag tnnnnnnnnn nnnnntgtaa ttttttccct acagcttcaa      60

<210> SEQ ID NO 305
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
cacacaggaa acagctatga ccatgtctag gatcaagttg tcaaagaaga                 50

<210> SEQ ID NO 306
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 306
cgacgtaaaa cgacggccag tnnnnnnnnn nnnnctggg atgtgcgggt atatt            55

<210> SEQ ID NO 307
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
cacacaggaa acagctatga ccatgagata atattgaagc tgtagggaaa aaa             53

<210> SEQ ID NO 308
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 308
cgacgtaaaa cgacggccag tnnnnnnnnn nnnnnaaaac tcacctggga tgtgc           55

<210> SEQ ID NO 309
<211> LENGTH: 52
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 309
cacacaggaa acagctatga ccatgtgcag taagagattg ttctatgaaa gg        52

<210> SEQ ID NO 310
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 310
cgacgtaaaa cgacggccag tnnnnnnnnn nnnnngggtc tggcactgtt cttca        55

<210> SEQ ID NO 311
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cacacaggaa acagctatga ccatgccaaa tgaaaggac agctattg        48

<210> SEQ ID NO 312
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 312
cgacgtaaaa cgacggccag tnnnnnnnnn nnnnnttctt tctcattgcc ttcacg        56

<210> SEQ ID NO 313
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cacacaggaa acagctatga ccatgtttga agaacagtgc cagacc        46

<210> SEQ ID NO 314
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (22)..(35)
<223> OTHER INFORMATION: a, c, t, or g

<400> SEQUENCE: 314
cgacgtaaaa cgacggccag tnnnnnnnnn nnnnnagcac aagaacaagg gaaaca        56

<210> SEQ ID NO 315
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
cacacaggaa acagctatga ccatgtttct tttgcctgca ggatt                    45

<210> SEQ ID NO 316
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 316
cgacgtaaaa cgacggccag tnnnnnnnnn nnnntactc agctgcctgc ttcttc         56

<210> SEQ ID NO 317
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cacacaggaa acagctatga ccatgttgac agtagaagaa gattggaaga a             51

<210> SEQ ID NO 318
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 318
cgacgtaaaa cgacggccag tnnnnnnnnn nnnntggtc tctcgtcttt ctcagc         56

<210> SEQ ID NO 319
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
cacacaggaa acagctatga ccatgcctga attgtagcaa tcaccaa                  47
```

```
<210> SEQ ID NO 320
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 320
cgacgtaaaa cgacggccag tnnnnnnnnn nnnnnacgta tgaacagcat taaaccaga      59

<210> SEQ ID NO 321
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cacacaggaa acagctatga ccatggatga agatttgccc catca                    45

<210> SEQ ID NO 322
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 322
cgacgtaaaa cgacggccag tnnnnnnnnn nnnnntctcc cggacaagaa aagtg          55

<210> SEQ ID NO 323
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
cacacaggaa acagctatga ccatgcccaa ggcatctcat cgtag                    45

<210> SEQ ID NO 324
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 324
cgacgtaaaa cgacggccag tnnnnnnnnn nnnnnaggac agtcatgttg ccagtatt       58
```

```
<210> SEQ ID NO 325
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
cacacaggaa acagctatga ccatgtgatt atgtttttga caccaatcg              49

<210> SEQ ID NO 326
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 326
cgacgtaaaa cgacggccag tnnnnnnnnn nnnnngaaga ggagctgggt aacactg     57

<210> SEQ ID NO 327
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
cacacaggaa acagctatga ccatgcaaca tgactgtcct ttcacca               47

<210> SEQ ID NO 328
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 328
cgacgtaaaa cgacggccag tnnnnnnnnn nnnntagac caattccgcg ttctc       55

<210> SEQ ID NO 329
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
cacacaggaa acagctatga ccatgtgtta cccagctcct cttcatc               47

<210> SEQ ID NO 330
<211> LENGTH: 58
<212> TYPE: DNA
<213> ORGANISM: Artificial Sequence
<220> FEATURE:
<223> OTHER INFORMATION: Description of Artificial Sequence: Synthetic
``` primer
<220> FEATURE:
<221> NAME/KEY: modified_base
<222> LOCATION: (22)..(35)
<223> OTHER INFORMATION: a, c, t, or g

<400> SEQUENCE: 330
cgacgtaaaa cgacggccag tnnnnnnnnn nnnnnaagtt cctggatttt ctgttgct        58

<210> SEQ ID NO 331
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
cacacaggaa acagctatga ccatggagaa cgcggaattg gtcta                      45

<210> SEQ ID NO 332
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 332
cgacgtaaaa cgacggccag tnnnnnnnnn nnnnnccatg actttggcaa tctgg           55

<210> SEQ ID NO 333
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
cacacaggaa acagctatga ccatgggcaa ctaccatcca gcaac                      45

<210> SEQ ID NO 334
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 334
cgacgtaaaa cgacggccag tnnnnnnnnn nnnnncttct gtcttcctga gaggtatgaa      60

<210> SEQ ID NO 335
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
cacacaggaa acagctatga ccatggccaa agtcatggaa gaagtg    46

<210> SEQ ID NO 336
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 336
cgacgtaaaa cgacggccag tnnnnnnnnn nnnnngtgta tgggcagcag agctt    55

<210> SEQ ID NO 337
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
cacacaggaa acagctatga ccatggtatt ctaatttggc ataaggcata ga    52

<210> SEQ ID NO 338
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 338
cgacgtaaaa cgacggccag tnnnnnnnnn nnnnntgtgt gacagatgag agaaatgc    58

<210> SEQ ID NO 339
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
cacacaggaa acagctatga ccatgaagtc ggaaaattca aataggaca    49

<210> SEQ ID NO 340
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 340

```
cgacgtaaaa cgacggccag tnnnnnnnnn nnnnntgacc tcttttacca taaccatca      59
```

<210> SEQ ID NO 341
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341

```
cacacaggaa acagctatga ccatggttct atgccttatg ccaaattaga               50
```

<210> SEQ ID NO 342
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 342

```
cgacgtaaaa cgacggccag tnnnnnnnnn nnnnnggatt caatcgaggg tttca         55
```

<210> SEQ ID NO 343
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343

```
cacacaggaa acagctatga ccatgtgatg gttatggtaa aagaggtca                49
```

<210> SEQ ID NO 344
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 344

```
cgacgtaaaa cgacggccag tnnnnnnnnn nnnnntgcac tatgtatttt atgggctagg    60
t                                                                    61
```

<210> SEQ ID NO 345
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345

```
cacacaggaa acagctatga ccatgaagat gatgaaagta agttttgcag tt            52
```

<210> SEQ ID NO 346

```
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 346
cgacgtaaaa cgacggccag tnnnnnnnnn nnnnntggtg tatctagttc tccatcatta    60
tca                                                                 63

<210> SEQ ID NO 347
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
cacacaggaa acagctatga ccatgagccg acctagccca taaaa                   45

<210> SEQ ID NO 348
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 348
cgacgtaaaa cgacggccag tnnnnnnnnn nnnnntgaag gactttgcct tccag        55

<210> SEQ ID NO 349
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
cacacaggaa acagctatga ccatgggatg ataatgatgg agaactagat aca          53

<210> SEQ ID NO 350
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 350
cgacgtaaaa cgacggccag tnnnnnnnnn nnnnngtttg ggtcttgccc atct         54

<210> SEQ ID NO 351
```

```
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
cacacaggaa acagctatga ccatgagatg agcagttgaa ctctggaa                  48

<210> SEQ ID NO 352
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 352
cgacgtaaaa cgacggccag tnnnnnnnnn nnnnnccttg attgtctttg ctcactttt      58

<210> SEQ ID NO 353
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
cacacaggaa acagctatga ccatgatgtg gttggaactt gaggtg                    46

<210> SEQ ID NO 354
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 354
cgacgtaaaa cgacggccag tnnnnnnnnn nnnnngaccc aaacacataa tagaagatga     60
a                                                                     61

<210> SEQ ID NO 355
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
cacacaggaa acagctatga ccatgtcgat ttgtttctga accattg                   47

<210> SEQ ID NO 356
<211> LENGTH: 61
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 356
cgacgtaaaa cgacggccag tnnnnnnnnn nnnnncctgt ttatactgag agcactgatg    60
a                                                                   61

<210> SEQ ID NO 357
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
cacacaggaa acagctatga ccatgatttt ggacagcagg aatgtg                   46

<210> SEQ ID NO 358
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 358
cgacgtaaaa cgacggccag tnnnnnnnnn nnnnttctt gacacaaaga ctggcttac     59

<210> SEQ ID NO 359
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
cacacaggaa acagctatga ccatgccaat ggttcagaaa caaatcg                  47

<210> SEQ ID NO 360
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 360
cgacgtaaaa cgacggccag tnnnnnnnnn nnnntcttc agagtaacgt tcactataat    60
tgg                                                                 63

<210> SEQ ID NO 361
<211> LENGTH: 50
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 361
cacacaggaa acagctatga ccatgtttgt tggtctctct tcttcttcat            50

<210> SEQ ID NO 362
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 362
cgacgtaaaa cgacggccag tnnnnnnnnn nnnnntcaaa atgtaagcca gtctttgtg   59

<210> SEQ ID NO 363
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
cacacaggaa acagctatga ccatgtcaat aggctgatcc acatgac              47

<210> SEQ ID NO 364
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 364
cgacgtaaaa cgacggccag tnnnnnnnnn nnnnntgata agcctaccaa ttatagtgaa  60
cg                                                                62

<210> SEQ ID NO 365
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
cacacaggaa acagctatga ccatgaagaa gagagaccaa caaattatag ca          52

<210> SEQ ID NO 366
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (22)..(35)
<223> OTHER INFORMATION: a, c, t, or g

<400> SEQUENCE: 366
cgacgtaaaa cgacggccag tnnnnnnnnn nnnnnaaaat gactgtttct gtgatgaagg    60

<210> SEQ ID NO 367
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
cacacaggaa acagctatga ccatgcggtt ttactgcttt gtccag    46

<210> SEQ ID NO 368
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 368
cgacgtaaaa cgacggccag tnnnnnnnnn nnnnncgtca tgtggatcag cctatt    56

<210> SEQ ID NO 369
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
cacacaggaa acagctatga ccatgttcct tcatcacaga aacagtca    48

<210> SEQ ID NO 370
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 370
cgacgtaaaa cgacggccag tnnnnnnnnn nnnnntgatt ctgcctcttg gcatta    56

<210> SEQ ID NO 371
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
```
cacacaggaa acagctatga ccatgccgaa catatgtctt caagcag    47

<210> SEQ ID NO 372
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 372
cgacgtaaaa cgacggccag tnnnnnnnnn nnnnnagcct tttgaggctg accac    55

<210> SEQ ID NO 373
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
cacacaggaa acagctatga ccatggaaaa acatattgga gtatcttcta caca    54

<210> SEQ ID NO 374
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 374
cgacgtaaaa cgacggccag tnnnnnnnnn nnnnnccatc caagttctgc acagagt    57

<210> SEQ ID NO 375
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
cacacaggaa acagctatga ccatgcttgc aaagtttctt ctattaacca ag    52

<210> SEQ ID NO 376
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 376
cgacgtaaaa cgacggccag tnnnnnnnnn nnnnntgatt acatcctatt tcatcttcag    60

```
<210> SEQ ID NO 377
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
cacacaggaa acagctatga ccatggatgt agttcattat catctttgtc atca         54

<210> SEQ ID NO 378
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 378
cgacgtaaaa cgacggccag tnnnnnnnnn nnnnngctga cctagttcca atcttttctt   60

<210> SEQ ID NO 379
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
cacacaggaa acagctatga ccatggtgct gtgacactgc tggaa                    45

<210> SEQ ID NO 380
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 380
cgacgtaaaa cgacggccag tnnnnnnnnn nnnnncagac gacacaggaa gcaga          55

<210> SEQ ID NO 381
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
cacacaggaa acagctatga ccatgggtca gctgaagatc ctgtga                   46

<210> SEQ ID NO 382
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 382
cgacgtaaaa cgacggccag tnnnnnnnnn nnnnntcgct cctgaagaaa attcaa          56

<210> SEQ ID NO 383
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
cacacaggaa acagctatga ccatgagaat cagccaggca caaag                     45

<210> SEQ ID NO 384
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 384
cgacgtaaaa cgacggccag tnnnnnnnnn nnnnnaacat gagtggggtc tcctg          55

<210> SEQ ID NO 385
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
cacacaggaa acagctatga ccatgggtgc tcagacaccc aaaag                     45

<210> SEQ ID NO 386
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 386
cgacgtaaaa cgacggccag tnnnnnnnnn nnnnnctggc aatcgaacga ctctc          55

<210> SEQ ID NO 387
<211> LENGTH: 45
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 387
cacacaggaa acagctatga ccatgcagga gacccactc atgtt                45

<210> SEQ ID NO 388
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 388
cgacgtaaaa cgacggccag tnnnnnnnnn nnnnnatgcc acttaccatt ccactg        56

<210> SEQ ID NO 389
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
cacacaggaa acagctatga ccatggctcc gttcagagtg aaccat           46

<210> SEQ ID NO 390
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 390
cgacgtaaaa cgacggccag tnnnnnnnnn nnnnnaggag gtggtggagg tgttt         55

<210> SEQ ID NO 391
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
cacacaggaa acagctatga ccatgcatgc caccaagcag aagta             45

<210> SEQ ID NO 392
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)

<223> OTHER INFORMATION: a, c, t, or g

<400> SEQUENCE: 392
cgacgtaaaa cgacggccag tnnnnnnnnn nnnnngcagc ttgcttaggt ccactc    56

<210> SEQ ID NO 393
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
cacacaggaa acagctatga ccatgctcaa acagctcaaa ccaagc    46

<210> SEQ ID NO 394
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 394
cgacgtaaaa cgacggccag tnnnnnnnnn nnnnnagcat ctggaagaac ctgga    55

<210> SEQ ID NO 395
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
cacacaggaa acagctatga ccatgagcac tcaggctgga tgaac    45

<210> SEQ ID NO 396
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 396
cgacgtaaaa cgacggccag tnnnnnnnnn nnnnnggacc taagcaagct gcagtaa    57

<210> SEQ ID NO 397
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
cacacaggaa acagctatga ccatgtttgc cacggaaagt actcc    45

<210> SEQ ID NO 398
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 398
cgacgtaaaa cgacggccag tnnnnnnnnn nnnnncccat tgtcattttc ctgaactg    58

<210> SEQ ID NO 399
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
cacacaggaa acagctatga ccatggagcc tcgatgagcc attt                  44

<210> SEQ ID NO 400
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 400
cgacgtaaaa cgacggccag tnnnnnnnnn nnnnntggtt ttcatttgat tctttaggc   59

<210> SEQ ID NO 401
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
cacacaggaa acagctatga ccatggggaa tgaaacagaa tcagagc               47

<210> SEQ ID NO 402
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 402
cgacgtaaaa cgacggccag tnnnnnnnnn nnnnntcaat atcatcatca tctgaatcat   60
cta                                                                63

<210> SEQ ID NO 403
<211> LENGTH: 48
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 403
cacacaggaa acagctatga ccatgaaaac caagagaaag aggcagaa            48

<210> SEQ ID NO 404
<211> LENGTH: 57
<212> TYPE: DNA
<213> ORGANISM: Artificial Sequence
<220> FEATURE:
<223> OTHER INFORMATION: Description of Artificial Sequence: Synthetic
    primer
<220> FEATURE:
<221> NAME/KEY: modified_base
<222> LOCATION: (22)..(35)
<223> OTHER INFORMATION: a, c, t, or g

<400> SEQUENCE: 404
cgacgtaaaa cgacggccag tnnnnnnnnn nnnnnttggc atggcagaaa taataca    57

<210> SEQ ID NO 405
<211> LENGTH: 52
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 405
cacacaggaa acagctatga ccatgaggac ctattagatg attcagatga tg        52

<210> SEQ ID NO 406
<211> LENGTH: 57
<212> TYPE: DNA
<213> ORGANISM: Artificial Sequence
<220> FEATURE:
<223> OTHER INFORMATION: Description of Artificial Sequence: Synthetic
    primer
<220> FEATURE:
<221> NAME/KEY: modified_base
<222> LOCATION: (22)..(35)
<223> OTHER INFORMATION: a, c, t, or g

<400> SEQUENCE: 406
cgacgtaaaa cgacggccag tnnnnnnnnn nnnnnggtgg aggtaatttt gaagcag    57

<210> SEQ ID NO 407
<211> LENGTH: 49
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 407
cacacaggaa acagctatga ccatgcaacc tgttttgtga tggtagaag             49

<210> SEQ ID NO 408
<211> LENGTH: 55
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 408
cgacgtaaaa cgacggccag tnnnnnnnnn nnnnnccatg ccaacaaagt catca           55

<210> SEQ ID NO 409
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
cacacaggaa acagctatga ccatgtgtgc cagggacctt acct                      44

<210> SEQ ID NO 410
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 410
cgacgtaaaa cgacggccag tnnnnnnnnn nnnnggaga agctcccaac caag             54

<210> SEQ ID NO 411
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
cacacaggaa acagctatga ccatgctgga tcccagaagg tgaga                     45

<210> SEQ ID NO 412
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 412
cgacgtaaaa cgacggccag tnnnnnnnnn nnnncccac acagcaaagc agaa             54

<210> SEQ ID NO 413
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 413
cacacaggaa acagctatga ccatgcgatc tgcacacacc agttg   45

<210> SEQ ID NO 414
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE
<221> NAME/KEY: modified_base
<222> LOCATION: (22)..(35)
<223> OTHER INFORMATION: a, c, t, or g

<400> SEQUENCE: 414
cgacgtaaaa cgacggccag tnnnnnnnnn nnnnngcatc tgcctcacct ccac   54

<210> SEQ ID NO 415
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
cacacaggaa acagctatga ccatgtccct ggtgtcagga aaatg   45

<210> SEQ ID NO 416
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 416
cgacgtaaaa cgacggccag tnnnnnnnnn nnnnngcagc atgtcaagat cacagat   57

<210> SEQ ID NO 417
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
cacacaggaa acagctatga ccatgtgttt tcctttactt actacacctc aga   53

<210> SEQ ID NO 418
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 418
cgacgtaaaa cgacggccag tnnnnnnnnn nnnnnaactg ttcaaactga tgggacc      57

<210> SEQ ID NO 419
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
cacacaggaa acagctatga ccatgtgtgc cacacatctt tgacc      45

<210> SEQ ID NO 420
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 420
cgacgtaaaa cgacggccag tnnnnnnnnn nnnnnctgta ggaccttcgg tgactg      56

<210> SEQ ID NO 421
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
cacacaggaa acagctatga ccatgaggag ctgggccatc g      41

<210> SEQ ID NO 422
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 422
cgacgtaaaa cgacggccag tnnnnnnnnn nnnnnacaaa ttctcagatc atcagtcctc      60

<210> SEQ ID NO 423
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
cacacaggaa acagctatga ccatgcttcc tggacacgct ggt      43

<210> SEQ ID NO 424
<211> LENGTH: 53

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 424
cgacgtaaaa cgacggccag tnnnnnnnnn nnnnngcagg taccgtgcga cat          53

<210> SEQ ID NO 425
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
cacacaggaa acagctatga ccatggaccc cgccactctc ac                      42

<210> SEQ ID NO 426
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 426
cgacgtaaaa cgacggccag tnnnnnnnnn nnnnngctcc tcagccaggt cca          53

<210> SEQ ID NO 427
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
cacacaggaa acagctatga ccatgccgag tggcggagct g                       41

<210> SEQ ID NO 428
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 428
cgacgtaaaa cgacggccag tnnnnnnnnn nnnnncacca gcgtgtccag gaag         54

<210> SEQ ID NO 429
<211> LENGTH: 46
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 429
cacacaggaa acagctatga ccatgtggct ctgaccattc tgttct            46

<210> SEQ ID NO 430
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 430
cgacgtaaaa cgacggccag tnnnnnnnnn nnnnngggtc gggtgagagt gg      52

<210> SEQ ID NO 431
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
cacacaggaa acagctatga ccatggggtc gggtagagga ggtg              44

<210> SEQ ID NO 432
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 432
cgacgtaaaa cgacggccag tnnnnnnnnn nnnnnctccc gctgcagacc ct      52

<210> SEQ ID NO 433
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
cacacaggaa acagctatga ccatgagcct tcggctgact gg                42

<210> SEQ ID NO 434
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)

<223> OTHER INFORMATION: a, c, t, or g

<400> SEQUENCE: 434
cgacgtaaaa cgacggccag tnnnnnnnnn nnnnnggcct ccgaccgtaa ctatt    55

<210> SEQ ID NO 435
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
cacacaggaa acagctatga ccatggggga gagcaggcag c                   41

<210> SEQ ID NO 436
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, or g

<400> SEQUENCE: 436
cgacgtaaaa cgacggccag tnnnnnnnnn nnnnncacct cctctacccg accc    54

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
ctgtaggacc ttcggtgact g                                          21

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
tgtgccacac atctttgacc                                            20

<210> SEQ ID NO 439
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
acaaattctc agatcatcag tcctc                                      25

<210> SEQ ID NO 440
<211> LENGTH: 16
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 440
aggagctggg ccatcg                                                    16

<210> SEQ ID NO 441
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gcaggtaccg tgcgacat                                                  18

<210> SEQ ID NO 442
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
cttcctggac acgctggt                                                  18

<210> SEQ ID NO 443
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
gctcctcagc caggtcca                                                  18

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
gaccccgcca ctctcacccg                                                20

<210> SEQ ID NO 445
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
caccagcgtg tccaggaag                                                 19

<210> SEQ ID NO 446
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 446
ccgagtggcg gagctg                                                    16

<210> SEQ ID NO 447
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
gggtcgggtg agagtgg                                                   17

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
tggctctgac cattctgttc t                                              21

<210> SEQ ID NO 449
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
ctcccgctgc agaccct                                                   17

<210> SEQ ID NO 450
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
gggtcgggta gaggaggtg                                                 19

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
ggcctccgac cgtaactatt                                                20

<210> SEQ ID NO 452
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 452
agccttcggc tgactgg                                                    17

<210> SEQ ID NO 453
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
cacctcctct acccgaccc                                                  19

<210> SEQ ID NO 454
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
ggggagagca ggcagc                                                     16

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
tgttccatcc tctgctgtca                                                 20

<210> SEQ ID NO 456
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
gggtatgtgg ctacatgttc ct                                              22

<210> SEQ ID NO 457
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
gtcatctgcc cccacaga                                                   18

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 458
tgcgtcactg tacaccttgc                                              20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
accaccagga tgaacaggaa                                              20

<210> SEQ ID NO 460
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
cctcaacgcc catgtctttt                                              19

<210> SEQ ID NO 461
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
aggcgtccta ctggcatga                                               19

<210> SEQ ID NO 462
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
accgaggaca acgtgatga                                               19

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
gtggtcattg atggggagac                                              20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 464
gatggcaaac acacacagga                                              20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
gttctggatc agctggatgg                                              20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
ggcaggagac cctgtaggag                                              20

<210> SEQ ID NO 467
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
tttcagtgtt acttacctgt cttgtctt                                     28

<210> SEQ ID NO 468
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
ggaaataaat gtgatttgcc ttct                                         24

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
tgtactggtc cctcattgca c                                            21

<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 470
ttctcccttc tcaggattcc tac                                              23

<210> SEQ ID NO 471
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
tgactgaata taaacttgtg gtagttgg                                         28

<210> SEQ ID NO 472
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
tttacctcta ttgttggatc atattcg                                          27

<210> SEQ ID NO 473
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
ttttgagttt gcagactttc ca                                               22

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
tcaaggttgc tgattttggt c                                                21

<210> SEQ ID NO 475
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
gttgccttcc acaaacgtg                                                   19

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
```

```
caagtctgtt gtgagccctt c                                      21
```

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477

```
gaaaaagccg aaggtcacaa                                        20
```

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478

```
ccccctccat caacttcttc                                        20
```

<210> SEQ ID NO 479
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479

```
acattcacgt aggttgcaca aa                                     22
```

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480

```
ttattccaga cgcatttcca c                                      21
```

<210> SEQ ID NO 481
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481

```
ctccatttta gcacttacct gtgac                                  25
```

<210> SEQ ID NO 482
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
caatgaatta agggaaaatg acaaa                                          25

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
tccaaagcct cttgctcagt                                                20

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
gcatgccaat ctcttcataa atc                                            23

<210> SEQ ID NO 485
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
gatccaatcc atttttgttg tccag                                          25

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
tttgatgaca ttgcatacat tcg                                            23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
atgaagaaag tgcccataac aga                                            23

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
cttccaaggc tgggatgat                                                 19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
gaggctgtca gtggggaac                                                    19

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
gccacctgaa gtccaaaaag                                                   20

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
agtctgagtc aggcccttct g                                                 21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
atgtcatctc tcctccctgc t                                                 21

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
taggaaggca ggggagtagg                                                   20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
gttccgagag ctgaatgagg                                                   20

```
<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
cttctccccc tcctctgttg                                              20

<210> SEQ ID NO 496
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
ccctggctcc ttcccag                                                 17

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
ccagccaaag aagaaaccac                                              20

<210> SEQ ID NO 498
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
aagaagaaaa cggcattttg ag                                           22

<210> SEQ ID NO 499
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
caagacttag tacctgaagg gtgaa                                        25

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
ttttatcacc tttccttgcc tct                                          23
```

```
<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
gcttcttgtc ctgcttgctt                                               20

<210> SEQ ID NO 502
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
cgtgtttgtg cctgtcctg                                                19

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
gcggagattc tcttcctctg t                                             21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
tgcctcttgc ttctctttc c                                              21

<210> SEQ ID NO 505
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
gtggcaagtg gctcctga                                                 18

<210> SEQ ID NO 506
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
tggctctgac tgtaccacca tc                                            22

<210> SEQ ID NO 507
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
tcatcttggg cctgtgttat c                                                  21

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
tgtgatgatg gtgaggatgg                                                    20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
cttaacccct cctcccagag                                                    20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 510
gtggaaggaa atttgcgtgt                                                    20

<210> SEQ ID NO 511
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
cgaaaagtgt ttctgtcatc ca                                                 22

<210> SEQ ID NO 512
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
gtccccaggc ctctgatt                                                      18

<210> SEQ ID NO 513
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
accagccctg tcgtctctc                                                   19

<210> SEQ ID NO 514
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
gccatggcca tctacaagc                                                   19

<210> SEQ ID NO 515
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
caacaagatg ttttgccaac tg                                               22

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 516
ctccgtcatg tgctgtgact                                                  20

<210> SEQ ID NO 517
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
gggggtgtgg aatcaacc                                                    18

<210> SEQ ID NO 518
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
gccctgactt tcaactctgt ct                                               22

<210> SEQ ID NO 519
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 519
cccttcccag aaaacctacc                                               20

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 520
gcattgaagt ctcatggaag c                                             21

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 521
cagaatgcaa gaagcccaga                                               20

<210> SEQ ID NO 522
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 522
ctgcaccagc agctcctac                                                19

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
tgggaaggga cagaagatga                                               20

<210> SEQ ID NO 524
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
agctcccaga atgccagag                                                19

<210> SEQ ID NO 525
<211> LENGTH: 18
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 525
cggtgtagga gctgctgg                                                    18

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526
gcaatggatg atttgatgct g                                                21

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 527
tcatctggac ctgggtcttc                                                  20

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 528
tgactgctct tttcacccat c                                                21

<210> SEQ ID NO 529
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
cagcccaacc cttgtcctt                                                   19

<210> SEQ ID NO 530
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530 agcccctag cagagacct                                                    19

<210> SEQ ID NO 531
<211> LENGTH: 18
<212> TYPE: DNA
<213> ORGANISM: Artificial Sequence
<220> FEATURE:

<223> OTHER INFORMATION: Description of Artificial Sequence: Synthetic
       primer

<400> SEQUENCE: 531
actgccttcc gggtcact                                                  18

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 532
ccttccaatg gatccactca c                                              21

<210> SEQ ID NO 533
<211> LENGTH: 17
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 533
ccgccgtctt cttcagg                                                   17

<210> SEQ ID NO 534
<211> LENGTH: 16
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 534
cccgggtggt ctggat                                                    16

<210> SEQ ID NO 535
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 535
cggcctccat ctcctcct                                                  18

<210> SEQ ID NO 536
<211> LENGTH: 19
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 536
aggcaggcgt cgaagagta                                                 19

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic

```
                                  primer

<400> SEQUENCE: 537
ggactgcgat tgcagaagat                                            20

<210> SEQ ID NO 538
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
cggcccggaa gagtcc                                                16

<210> SEQ ID NO 539
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 539
cggcagcgtt gggtag                                                16

<210> SEQ ID NO 540
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540
gctgcgctcg gtgaact                                               17

<210> SEQ ID NO 541
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
cgtgctatcg tccctgct                                              18

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
ccgtatggct caacttcgac                                            20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 543
gctgtccgtc aacattgaga                                      20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
ccggtgtggc tctttaacaa                                      20

<210> SEQ ID NO 545
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
ccaaactgaa ttatttgtgc catc                                 24

<210> SEQ ID NO 546
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
tctatcctgt acttaccaca acaacc                               26

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
ggtggtcttc cagatcttcg t                                    21

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
gatttggttt ttgcccttcc                                      20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 549
tcaatctccc atccgttgat                                        20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
caggagactg gacatcgtca                                        20

<210> SEQ ID NO 551
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 551
tcatcagtac catcaaaagc tga                                    23

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
cccaaatgtg cagaaagacc                                        20

<210> SEQ ID NO 553
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
ggccgcggaa aggaag                                            16

<210> SEQ ID NO 554
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
cgtcctgccc cttcacc                                           17

<210> SEQ ID NO 555
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
```

```
ccgtccatac tctttcattt gc                                              22

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
agggagaact aaaggggaac c                                               21

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
gcgactgaaa gtagaagtct gtcc                                            24

<210> SEQ ID NO 558
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
gtgcttctgg gtcctggtt                                                  19

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
agcggctatc tccagagcag                                                 20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
ggattttcag ggctccgagt                                                 20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
```
agagagagcc acggtgacag                                               20

<210> SEQ ID NO 562
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
ctgcctcgtg aggttcaga                                                19

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
tgccaagtcc atagtcagtc c                                             21

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 564
tatgtcattc tgcccccaag                                               20

<210> SEQ ID NO 565
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 565
tatggaagca tggcccttt                                                19

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 566
gtgtttgttc tggcccactc                                               20

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 567
gggatgctcc cactctaaga a                                             21

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 568
cagaagggcc gtttacactc                                              20

<210> SEQ ID NO 569
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
ttgtcaaagt gccttcactg ac                                           22

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
cagggagctg ttttcaggtg                                              20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
ttggaagcag cagacatcac                                              20

<210> SEQ ID NO 572
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 572
agcatttctg gcctcctgt                                               19

<210> SEQ ID NO 573
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 573
aactaagtcc ttatctgtgg tggtg                                        25

<210> SEQ ID NO 574
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 574
gtgggagaaa gtcagtttga ataaa                                            25

<210> SEQ ID NO 575
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 575
ttttgatttt gcattgtttt gc                                               22

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 576
tttcaccctc acctccgtta                                                  20

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 577
cctcagaatg ggtcagagtc a                                                21

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
gccctagtac cctgccatct                                                  20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
actacttgct gtgcccacct                                                  20

```
<210> SEQ ID NO 580
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
aaacccaagt cacatcattg aac                                           23

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
aggtgaggtc aggtcccttt                                               20

<210> SEQ ID NO 582
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
ctgccagcca tgctcaag                                                 18

<210> SEQ ID NO 583
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 583
cactttctca gggggtgct                                                19

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
tgatggcttc catctccact                                               20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
accccaaagt tccaggagag                                               20

<210> SEQ ID NO 586
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
cactgaagtg ccccttcttc                                               20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
gatccgtctg tgttggcttc                                               20

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 588
gattggttgt agcaggctga a                                             21

<210> SEQ ID NO 589
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 589
aggtacgcta gtgataggag ttgg                                          24

<210> SEQ ID NO 590
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590
ccctaatttt tcatactaaa ggagca                                        26

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
cgctgagaaa gggagatgac                                               20

<210> SEQ ID NO 592
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
ccagatgagg gaccactaac a                                              21

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
gcccaatcct agcagaatga                                                20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 594
gaatgctctg cactctgcac                                                20

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 595
tcacctctgt tatggggctc t                                              21

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
ctgatgcaca gggacagaaa                                                20

<210> SEQ ID NO 597
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
ttttctggaa tccaacctct gt                                             22

<210> SEQ ID NO 598
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 598
tttccaaacc ggattctgtc                                              20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 599
ccacatttca gagcccagag                                              20

<210> SEQ ID NO 600
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 600
gccaaggcta cacatggttt                                              20

<210> SEQ ID NO 601
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 601
ttttaactac tcatacatcc ccatgtc                                      27

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
ccctcttcca tcccgtattt                                              20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
gtccaagaac aggccagatg                                              20

<210> SEQ ID NO 604
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 604
ggagaaaagc caagtcagca                                                    20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
tctgggaagc aagtgtgatg                                                    20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
aacccatggc cctacttgag                                                    20

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 607
ctgtaggacc ttcggtgact g                                                  21

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
tgtgccacac atctttgacc                                                    20

<210> SEQ ID NO 609
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609
acaaattctc agatcatcag tcctc                                              25

<210> SEQ ID NO 610
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 610
aggagctggg ccatcg                                                         16

<210> SEQ ID NO 611
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611
gcaggtaccg tgcgacat                                                       18

<210> SEQ ID NO 612
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612
cttcctggac acgctggt                                                       18

<210> SEQ ID NO 613
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 613
gctcctcagc caggtcca                                                       18

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 614
gaccccgcca ctctcacccg                                                     20

<210> SEQ ID NO 615
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 615
caccagcgtg tccaggaag                                                      19

<210> SEQ ID NO 616
<211> LENGTH: 16
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 616
ccgagtggcg gagctg                                                    16

<210> SEQ ID NO 617
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 617
gggtcgggtg agagtgg                                                   17

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 618
tggctctgac cattctgttc t                                              21

<210> SEQ ID NO 619
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
ctcccgctgc agaccct                                                   17

<210> SEQ ID NO 620
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
gggtcgggta gaggaggtg                                                 19

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
ggcctccgac cgtaactatt                                                20

<210> SEQ ID NO 622
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 622
agccttcggc tgactgg                                                    17

<210> SEQ ID NO 623
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
cacctcctct acccgaccc                                                  19

<210> SEQ ID NO 624
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 624
ggggagagca ggcagc                                                     16

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
tgttccatcc tctgctgtca                                                 20

<210> SEQ ID NO 626
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 626
gggtatgtgg ctacatgttc ct                                              22

<210> SEQ ID NO 627
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 627
gtcatctgcc cccacaga                                                   18

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 628
tgcgtcactg tacaccttgc                                               20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 629
accaccagga tgaacaggaa                                               20

<210> SEQ ID NO 630
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 630
cctcaacgcc catgtcttt                                                19

<210> SEQ ID NO 631
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 631
aggcgtccta ctggcatga                                                19

<210> SEQ ID NO 632
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 632
accgaggaca acgtgatga                                                19

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 633
gtggtcattg atggggagac                                               20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 634
```
gatggcaaac acacacagga                                           20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 635
gttctggatc agctggatgg                                           20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 636
ggcaggagac cctgtaggag                                           20

<210> SEQ ID NO 637
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 637
tttcagtgtt acttacctgt cttgtctt                                  28

<210> SEQ ID NO 638
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 638
ggaaataaat gtgatttgcc ttct                                      24

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 639
tgtactggtc cctcattgca c                                         21

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 640
ttctcccttc tcaggattcc tac                                        23

<210> SEQ ID NO 641
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 641
tgactgaata taaacttgtg gtagttgg                                   28

<210> SEQ ID NO 642
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 642
tttacctcta ttgttggatc atattcg                                    27

<210> SEQ ID NO 643
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 643
ttttgagttt gcagactttc ca                                         22

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 644
tcaaggttgc tgattttggt c                                          21

<210> SEQ ID NO 645
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 645
gttgccttcc acaaacgtg                                             19

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 646
caagtctgtt gtgagccctt c                                          21

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 647
gaaaaagccg aaggtcacaa                                              20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 648
ccccctccat caacttcttc                                              20

<210> SEQ ID NO 649
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 649
acattcacgt aggttgcaca aa                                           22

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 650
ttattccaga cgcatttcca c                                            21

<210> SEQ ID NO 651
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 651
ctccatttta gcacttacct gtgac                                        25

<210> SEQ ID NO 652
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 652
caatgaatta agggaaaatg acaaa                                        25

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 653
tccaaagcct cttgctcagt                                               20

<210> SEQ ID NO 654
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 654
gcatgccaat ctcttcataa atc                                           23

<210> SEQ ID NO 655
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 655
gatccaatcc attttgttg tccag                                          25

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 656
tttgatgaca ttgcatacat tcg                                           23

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 657
atgaagaaag tgcccataac aga                                           23

<210> SEQ ID NO 658
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 658
cttccaaggc tgggatgat                                                19

```
<210> SEQ ID NO 659
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 659
gaggctgtca gtggggaac                                              19

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 660
gccacctgaa gtccaaaaag                                             20

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 661
agtctgagtc aggcccttct g                                           21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 662
atgtcatctc tcctccctgc t                                           21

<210> SEQ ID NO 663
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 663
taggaaggca ggggagtagg                                             20

<210> SEQ ID NO 664
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 664
gttccgagag ctgaatgagg                                             20

<210> SEQ ID NO 665
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 665
cttctccccc tcctctgttg                                              20

<210> SEQ ID NO 666
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 666
ccctggctcc ttcccag                                                 17

<210> SEQ ID NO 667
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 667
ccagccaaag aagaaaccac                                              20

<210> SEQ ID NO 668
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 668
aagaagaaaa cggcattttg ag                                           22

<210> SEQ ID NO 669
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 669
caagacttag tacctgaagg gtgaa                                        25

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 670
ttttatcacc tttccttgcc tct                                          23

<210> SEQ ID NO 671
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 671
gcttcttgtc ctgcttgctt                                               20

<210> SEQ ID NO 672
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 672
cgtgtttgtg cctgtcctg                                                19

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 673
gcggagattc tcttcctctg t                                             21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 674
tgcctcttgc ttctcttttc c                                             21

<210> SEQ ID NO 675
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 675
gtggcaagtg gctcctga                                                 18

<210> SEQ ID NO 676
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 676
tggctctgac tgtaccacca tc                                            22

<210> SEQ ID NO 677
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 677
tcatcttggg cctgtgttat c                                           21

<210> SEQ ID NO 678
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 678
tgtgatgatg gtgaggatgg                                             20

<210> SEQ ID NO 679
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 679
cttaacccct cctcccagag                                             20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 680
gtggaaggaa atttgcgtgt                                             20

<210> SEQ ID NO 681
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 681
cgaaaagtgt ttctgtcatc ca                                          22

<210> SEQ ID NO 682
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 682
gtccccaggc ctctgatt                                               18

<210> SEQ ID NO 683
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 683
accagccctg tcgtctctc                                                    19

<210> SEQ ID NO 684
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 684
gccatggcca tctacaagc                                                    19

<210> SEQ ID NO 685
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 685
caacaagatg ttttgccaac tg                                                22

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 686
ctccgtcatg tgctgtgact                                                   20

<210> SEQ ID NO 687
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 687
gggggtgtgg aatcaacc                                                     18

<210> SEQ ID NO 688
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 688
gccctgactt tcaactctgt ct                                                22

<210> SEQ ID NO 689
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 689
cccttcccag aaaacctacc                                              20

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 690
gcattgaagt ctcatggaag c                                            21

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 691
cagaatgcaa gaagcccaga                                              20

<210> SEQ ID NO 692
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 692
ctgcaccagc agctcctac                                               19

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 693
tgggaaggga cagaagatga                                              20

<210> SEQ ID NO 694
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 694
agctcccaga atgccagag                                               19

<210> SEQ ID NO 695
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 695
cggtgtagga gctgctgg                                                 18

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 696
gcaatggatg atttgatgct g                                             21

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 697
tcatctggac ctgggtcttc                                               20

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 698
tgactgctct tttcacccat c                                             21

<210> SEQ ID NO 699
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 699
cagcccaacc cttgtccttt                                               19

<210> SEQ ID NO 700
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 700 agcccccctag cagagacct                                               19

<210> SEQ ID NO 701
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 701
actgccttcc gggtcact                                                 18

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 702
ccttccaatg gatccactca c                                             21

<210> SEQ ID NO 703
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 703
ccgccgtctt cttcagg                                                  17

<210> SEQ ID NO 704
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 704
cccgggtggt ctggat                                                   16

<210> SEQ ID NO 705
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 705
cggcctccat ctcctcct                                                 18

<210> SEQ ID NO 706
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 706
aggcaggcgt cgaagagta                                                19

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 707
ggactgcgat tgcagaagat                                              20

<210> SEQ ID NO 708
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 708
cggcccggaa gagtcc                                                  16

<210> SEQ ID NO 709
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 709
cggcagcgtt gggtag                                                  16

<210> SEQ ID NO 710
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 710
gctgcgctcg gtgaact                                                 17

<210> SEQ ID NO 711
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 711
cgtgctatcg tccctgct                                                18

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 712
ccgtatggct caacttcgac                                              20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 713
```
gctgtccgtc aacattgaga                                          20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 714
ccggtgtggc tctttaacaa                                          20

<210> SEQ ID NO 715
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 715
ccaaactgaa ttatttgtgc catc                                     24

<210> SEQ ID NO 716
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 716
tctatcctgt acttaccaca acaacc                                   26

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 717
ggtggtcttc cagatcttcg t                                        21

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 718
gatttggttt ttgcccttcc                                          20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 719
tcaatctccc atccgttgat                                              20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 720
caggagactg gacatcgtca                                              20

<210> SEQ ID NO 721
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 721
tcatcagtac catcaaaagc tga                                          23

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 722
cccaaatgtg cagaaagacc                                              20

<210> SEQ ID NO 723
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 723
ggccgcggaa aggaag                                                  16

<210> SEQ ID NO 724
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 724
cgtcctgccc cttcacc                                                 17

<210> SEQ ID NO 725
<211> LENGTH: 14
<212> TYPE: DNA
<213> ORGANISM: Homo sapiens

<400> SEQUENCE: 725
atgtagttgt agtg                                                    14

<210> SEQ ID NO 726

-continued

<210> SEQ ID NO 726
<211> LENGTH: 20
<212> TYPE: DNA
<213> ORGANISM: Homo sapiens

<400> SEQUENCE: 726
atcaaatcat ccattgcttg                                               20

<210> SEQ ID NO 727
<211> LENGTH: 25
<212> TYPE: DNA
<213> ORGANISM: Homo sapiens

<400> SEQUENCE: 727
tgcccatcat catgacctgc cagag                                         25

<210> SEQ ID NO 728
<211> LENGTH: 14
<212> TYPE: DNA
<213> ORGANISM: Homo sapiens

<400> SEQUENCE: 728
atgtagttgt agtg                                                     14

<210> SEQ ID NO 729
<211> LENGTH: 18
<212> TYPE: DNA
<213> ORGANISM: Homo sapiens

<400> SEQUENCE: 729
tcatggtggg ggcagcgc                                                 18

<210> SEQ ID NO 730
<211> LENGTH: 15
<212> TYPE: DNA
<213> ORGANISM: Homo sapiens

<400> SEQUENCE: 730
ttttcaggaa gtctg                                                    15

<210> SEQ ID NO 731
<211> LENGTH: 21
<212> TYPE: DNA
<213> ORGANISM: Homo sapiens

<400> SEQUENCE: 731
ccaggacagg cacaaacacg c                                             21

<210> SEQ ID NO 732
<211> LENGTH: 23
<212> TYPE: DNA
<213> ORGANISM: Homo sapiens

<400> SEQUENCE: 732
ggcccctgca ccagcccct cct                                            23

<210> SEQ ID NO 733
<211> LENGTH: 18
<212> TYPE: DNA
<213> ORGANISM: Homo sapiens

<400> SEQUENCE: 733
cgctgccccc accatgag                                                 18

```
<210> SEQ ID NO 734
<211> LENGTH: 29
<212> TYPE: DNA
<213> ORGANISM: Homo sapiens

<400> SEQUENCE: 734
ccaccatgag cgctgctcag atagcgatg                                          29

<210> SEQ ID NO 735
<211> LENGTH: 16
<212> TYPE: DNA
<213> ORGANISM: Homo sapiens

<400> SEQUENCE: 735
ttctgggaca gccaag                                                        16

<210> SEQ ID NO 736
<211> LENGTH: 13
<212> TYPE: DNA
<213> ORGANISM: Homo sapiens

<400> SEQUENCE: 736
cccctgcacc agc                                                           13

<210> SEQ ID NO 737
<211> LENGTH: 16
<212> TYPE: DNA
<213> ORGANISM: Homo sapiens

<400> SEQUENCE: 737
ctgcccccag ggagca                                                        16

<210> SEQ ID NO 738
<211> LENGTH: 10
<212> TYPE: DNA
<213> ORGANISM: Homo sapiens

<400> SEQUENCE: 738
ccgcccggca                                                               10

<210> SEQ ID NO 739
<211> LENGTH: 11
<212> TYPE: DNA
<213> ORGANISM: Homo sapiens

<400> SEQUENCE: 739
atttgcgtgt g                                                             11

<210> SEQ ID NO 740
<211> LENGTH: 16
<212> TYPE: DNA
<213> ORGANISM: Homo sapiens

<400> SEQUENCE: 740
gtctgtgact tgcacg                                                        16

<210> SEQ ID NO 741
<211> LENGTH: 18
<212> TYPE: DNA
<213> ORGANISM: Homo sapiens

<400> SEQUENCE: 741
cgctgccccc accatgag                                                      18
```

```
<210> SEQ ID NO 742
<211> LENGTH: 18
<212> TYPE: DNA
<213> ORGANISM: Homo sapiens

<400> SEQUENCE: 742
cgctgccccc accatgag                                                 18

<210> SEQ ID NO 743
<211> LENGTH: 28
<212> TYPE: DNA
<213> ORGANISM: Homo sapiens

<400> SEQUENCE: 743
atgttttgcc aactggccaa gacctgcc                                      28

<210> SEQ ID NO 744
<211> LENGTH: 14
<212> TYPE: DNA
<213> ORGANISM: Homo sapiens

<400> SEQUENCE: 744
ccgagtggaa ggat                                                     14

<210> SEQ ID NO 745
<211> LENGTH: 14
<212> TYPE: DNA
<213> ORGANISM: Homo sapiens

<400> SEQUENCE: 745
atccgagtgg aagg                                                     14

<210> SEQ ID NO 746
<211> LENGTH: 21
<212> TYPE: DNA
<213> ORGANISM: Homo sapiens

<400> SEQUENCE: 746
ccatcatcac actggaagac t                                             21

<210> SEQ ID NO 747
<211> LENGTH: 14
<212> TYPE: DNA
<213> ORGANISM: Homo sapiens

<400> SEQUENCE: 747
ccgagtggaa ggaa                                                     14

<210> SEQ ID NO 748
<211> LENGTH: 25
<212> TYPE: DNA
<213> ORGANISM: Homo sapiens

<400> SEQUENCE: 748
gtgggcgtga gcgcttcgag atgtt                                         25

<210> SEQ ID NO 749
<211> LENGTH: 20
<212> TYPE: DNA
<213> ORGANISM: Homo sapiens

<400> SEQUENCE: 749
ggtgcgttgg gcagcgcccc                                               20
```

<210> SEQ ID NO 750
<211> LENGTH: 20
<212> TYPE: DNA
<213> ORGANISM: Homo sapiens

<400> SEQUENCE: 750
gtcgggtgag agtggcgggg                                                   20

<210> SEQ ID NO 751
<211> LENGTH: 14
<212> TYPE: DNA
<213> ORGANISM: Homo sapiens

<400> SEQUENCE: 751
ataccctgca aata                                                         14

<210> SEQ ID NO 752
<211> LENGTH: 12
<212> TYPE: DNA
<213> ORGANISM: Homo sapiens

<400> SEQUENCE: 752
tagattatat ga                                                           12

<210> SEQ ID NO 753
<211> LENGTH: 12
<212> TYPE: DNA
<213> ORGANISM: Homo sapiens

<400> SEQUENCE: 753
tagattatat ga                                                           12

<210> SEQ ID NO 754
<211> LENGTH: 18
<212> TYPE: DNA
<213> ORGANISM: Homo sapiens

<400> SEQUENCE: 754
gtatgaacag cattaaac                                                     18

<210> SEQ ID NO 755
<211> LENGTH: 18
<212> TYPE: DNA
<213> ORGANISM: Homo sapiens

<400> SEQUENCE: 755
gtatgaacag cattaaac                                                     18

<210> SEQ ID NO 756
<211> LENGTH: 21
<212> TYPE: DNA
<213> ORGANISM: Homo sapiens

<400> SEQUENCE: 756
gctgagtatc gagaaattga c                                                 21

<210> SEQ ID NO 757
<211> LENGTH: 21
<212> TYPE: DNA
<213> ORGANISM: Homo sapiens

<400> SEQUENCE: 757
gctgagtatc gagaaattga c    21

<210> SEQ ID NO 758
<211> LENGTH: 16
<212> TYPE: DNA
<213> ORGANISM: Homo sapiens

<400> SEQUENCE: 758
ttaaagaatc atctgg    16

<210> SEQ ID NO 759
<211> LENGTH: 10
<212> TYPE: DNA
<213> ORGANISM: Homo sapiens

<400> SEQUENCE: 759
tgggggcagc    10

<210> SEQ ID NO 760
<211> LENGTH: 24
<212> TYPE: DNA
<213> ORGANISM: Homo sapiens

<400> SEQUENCE: 760
ggctccatgc tgctccccgc cgcc    24

<210> SEQ ID NO 761
<211> LENGTH: 18
<212> TYPE: DNA
<213> ORGANISM: Homo sapiens

<400> SEQUENCE: 761
agcagcgctc atggtggg    18

<210> SEQ ID NO 762
<211> LENGTH: 11
<212> TYPE: DNA
<213> ORGANISM: Homo sapiens

<400> SEQUENCE: 762
ttggaagaag a    11

<210> SEQ ID NO 763
<211> LENGTH: 24
<212> TYPE: DNA
<213> ORGANISM: Homo sapiens

<400> SEQUENCE: 763
ctgtagggaa aaaattacat gaat    24

<210> SEQ ID NO 764
<211> LENGTH: 12
<212> TYPE: DNA
<213> ORGANISM: Homo sapiens

<400> SEQUENCE: 764
gatgtaagta tt    12

<210> SEQ ID NO 765
<211> LENGTH: 14
<212> TYPE: DNA
<213> ORGANISM: Homo sapiens

<400> SEQUENCE: 765

```
gtgttgttgg gcag                                                         14

<210> SEQ ID NO 766
<211> LENGTH: 10
<212> TYPE: DNA
<213> ORGANISM: Homo sapiens

<400> SEQUENCE: 766
atgatgaaag                                                              10

<210> SEQ ID NO 767
<211> LENGTH: 21
<212> TYPE: DNA
<213> ORGANISM: Homo sapiens

<400> SEQUENCE: 767
cactcagttt caagaaaaaa g                                                 21

<210> SEQ ID NO 768
<211> LENGTH: 14
<212> TYPE: DNA
<213> ORGANISM: Homo sapiens

<400> SEQUENCE: 768
gggcgctgcc catc                                                         14

<210> SEQ ID NO 769
<211> LENGTH: 10
<212> TYPE: DNA
<213> ORGANISM: Homo sapiens

<400> SEQUENCE: 769
tatcaagagg                                                              10

<210> SEQ ID NO 770
<211> LENGTH: 11
<212> TYPE: DNA
<213> ORGANISM: Homo sapiens

<400> SEQUENCE: 770
ggcaatgaga a                                                            11

<210> SEQ ID NO 771
<211> LENGTH: 11
<212> TYPE: DNA
<213> ORGANISM: Homo sapiens

<400> SEQUENCE: 771
ccaatacttg a                                                            11

<210> SEQ ID NO 772
<211> LENGTH: 12
<212> TYPE: DNA
<213> ORGANISM: Homo sapiens

<400> SEQUENCE: 772
tatatgaaga at                                                           12

<210> SEQ ID NO 773
<211> LENGTH: 16
<212> TYPE: DNA
<213> ORGANISM: Homo sapiens
```

```
<400> SEQUENCE: 773
aagtgaagat gacaat                                              16

<210> SEQ ID NO 774
<211> LENGTH: 16
<212> TYPE: DNA
<213> ORGANISM: Homo sapiens

<400> SEQUENCE: 774
cgtgcaagtc acagac                                              16

<210> SEQ ID NO 775
<211> LENGTH: 21
<212> TYPE: DNA
<213> ORGANISM: Homo sapiens

<400> SEQUENCE: 775
gaactggtgt aatgatatgt g                                        21

<210> SEQ ID NO 776
<211> LENGTH: 14
<212> TYPE: DNA
<213> ORGANISM: Homo sapiens

<400> SEQUENCE: 776
gggcgctgcc catc                                                14

<210> SEQ ID NO 777
<211> LENGTH: 13
<212> TYPE: DNA
<213> ORGANISM: Homo sapiens

<400> SEQUENCE: 777
accagacctt atc                                                 13

<210> SEQ ID NO 778
<211> LENGTH: 15
<212> TYPE: DNA
<213> ORGANISM: Homo sapiens

<400> SEQUENCE: 778
gcacatccca ggccc                                               15

<210> SEQ ID NO 779
<211> LENGTH: 15
<212> TYPE: DNA
<213> ORGANISM: Homo sapiens

<400> SEQUENCE: 779
aacgtatgaa cagca                                               15

<210> SEQ ID NO 780
<211> LENGTH: 15
<212> TYPE: DNA
<213> ORGANISM: Homo sapiens

<400> SEQUENCE: 780
aacgtatgaa cagca                                               15

<210> SEQ ID NO 781
<211> LENGTH: 24
<212> TYPE: DNA
<213> ORGANISM: Homo sapiens
```

-continued

```
<400> SEQUENCE: 781
ctgtagggaa aaaattacat gaat                                          24

<210> SEQ ID NO 782
<211> LENGTH: 14
<212> TYPE: DNA
<213> ORGANISM: Homo sapiens

<400> SEQUENCE: 782
gtgttgttgg gcag                                                     14

<210> SEQ ID NO 783
<211> LENGTH: 14
<212> TYPE: DNA
<213> ORGANISM: Homo sapiens

<400> SEQUENCE: 783
ataccctgca aata                                                     14

<210> SEQ ID NO 784
<211> LENGTH: 15
<212> TYPE: DNA
<213> ORGANISM: Homo sapiens

<400> SEQUENCE: 784
tgtgatgatg gtgag                                                    15

<210> SEQ ID NO 785
<211> LENGTH: 30
<212> TYPE: DNA
<213> ORGANISM: Homo sapiens

<400> SEQUENCE: 785
taagatgctg aggaggggcc agacctaaga                                    30

<210> SEQ ID NO 786
<211> LENGTH: 24
<212> TYPE: DNA
<213> ORGANISM: Homo sapiens

<400> SEQUENCE: 786
ggctccatgc tgctccccgc cgcc                                          24

<210> SEQ ID NO 787
<211> LENGTH: 12
<212> TYPE: DNA
<213> ORGANISM: Homo sapiens

<400> SEQUENCE: 787
tagattatat ga                                                       12

<210> SEQ ID NO 788
<211> LENGTH: 21
<212> TYPE: DNA
<213> ORGANISM: Homo sapiens

<400> SEQUENCE: 788
ctcacaacct ccgtcatgtg c                                             21

<210> SEQ ID NO 789
<211> LENGTH: 23
<212> TYPE: DNA
```

```
<213> ORGANISM: Homo sapiens

<400> SEQUENCE: 789
ctatctgagc agcgctcatg gtg                                       23

<210> SEQ ID NO 790
<211> LENGTH: 18
<212> TYPE: DNA
<213> ORGANISM: Homo sapiens

<400> SEQUENCE: 790
agcagcgctc atggtggg                                             18

<210> SEQ ID NO 791
<211> LENGTH: 10
<212> TYPE: DNA
<213> ORGANISM: Homo sapiens

<400> SEQUENCE: 791
atgatgaaag                                                      10

<210> SEQ ID NO 792
<211> LENGTH: 12
<212> TYPE: DNA
<213> ORGANISM: Homo sapiens

<400> SEQUENCE: 792
tagattatat ga                                                   12

<210> SEQ ID NO 793
<211> LENGTH: 10
<212> TYPE: DNA
<213> ORGANISM: Homo sapiens

<400> SEQUENCE: 793
tatcaagagg                                                      10

<210> SEQ ID NO 794
<211> LENGTH: 14
<212> TYPE: DNA
<213> ORGANISM: Homo sapiens

<400> SEQUENCE: 794
gggcgctgcc catc                                                 14

<210> SEQ ID NO 795
<211> LENGTH: 11
<212> TYPE: DNA
<213> ORGANISM: Homo sapiens

<400> SEQUENCE: 795
ggcaatgaga a                                                    11

<210> SEQ ID NO 796
<211> LENGTH: 11
<212> TYPE: DNA
<213> ORGANISM: Homo sapiens

<400> SEQUENCE: 796
ccaatacttg a                                                    11

<210> SEQ ID NO 797
<211> LENGTH: 18
```

```
<212> TYPE: DNA
<213> ORGANISM: Homo sapiens

<400> SEQUENCE: 797
gtatgaacag cattaaac                                                 18

<210> SEQ ID NO 798
<211> LENGTH: 21
<212> TYPE: DNA
<213> ORGANISM: Homo sapiens

<400> SEQUENCE: 798
gctgagtatc gagaaattga c                                             21

<210> SEQ ID NO 799
<211> LENGTH: 16
<212> TYPE: DNA
<213> ORGANISM: Homo sapiens

<400> SEQUENCE: 799
aagtgaagat gacaat                                                   16

<210> SEQ ID NO 800
<211> LENGTH: 13
<212> TYPE: DNA
<213> ORGANISM: Homo sapiens

<400> SEQUENCE: 800
atcaaagaga tcg                                                      13

<210> SEQ ID NO 801
<211> LENGTH: 16
<212> TYPE: DNA
<213> ORGANISM: Homo sapiens

<400> SEQUENCE: 801
cgtgcaagtc acagac                                                   16

<210> SEQ ID NO 802
<211> LENGTH: 12
<212> TYPE: DNA
<213> ORGANISM: Homo sapiens

<400> SEQUENCE: 802
tatatgaaga at                                                       12

<210> SEQ ID NO 803
<211> LENGTH: 21
<212> TYPE: DNA
<213> ORGANISM: Homo sapiens

<400> SEQUENCE: 803
gaactggtgt aatgatatgt g                                             21

<210> SEQ ID NO 804
<211> LENGTH: 11
<212> TYPE: DNA
<213> ORGANISM: Homo sapiens

<400> SEQUENCE: 804
ggtcagttaa a                                                        11

<210> SEQ ID NO 805
```

```
<211> LENGTH: 13
<212> TYPE: DNA
<213> ORGANISM: Homo sapiens

<400> SEQUENCE: 805
accagacctt atc                                                          13

<210> SEQ ID NO 806
<211> LENGTH: 9
<212> TYPE: DNA
<213> ORGANISM: Homo sapiens

<400> SEQUENCE: 806 acgtatgaa                                                                9

<210> SEQ ID NO 807
<211> LENGTH: 15
<212> TYPE: DNA
<213> ORGANISM: Homo sapiens

<400> SEQUENCE: 807
aacgtatgaa cagca                                                        15

<210> SEQ ID NO 808
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 808
aatgatacgg cgaccaccga ga                                                22

<210> SEQ ID NO 809
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 809
caagcagaag acggcatacg ag                                                22

<210> SEQ ID NO 810
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 810
gatcggaaga gcggttcagc aggaatgccg ag                                     32

<210> SEQ ID NO 811
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 811
acactctttc cctacacgac gctcttccga tct                                    33
```

<210> SEQ ID NO 812
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 812
aatgatacgg cgaccaccga gatctacaca cactctttcc ctacacgacg ctcttccgat    60
ct                                                                   62

<210> SEQ ID NO 813
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 813
caagcagaag acggcatacg agatctcggc attcctgctg aaccgctctt ccgatct       57

<210> SEQ ID NO 814
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
aatgatacgg cgaccaccga gatctacaca cactctttcc ctacacgacg ctcttccgat    60
ct                                                                   62

<210> SEQ ID NO 815
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 815
caagcagaag acggcatacg agatctcggc attcctgctg aaccgctctt ccgatct       57

<210> SEQ ID NO 816
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 816
acactctttc cctacacgac gctcttccga tct                                 33

<210> SEQ ID NO 817
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 817
ctcggcattc ctgctgaacc gctcttccga tct                                33

<210> SEQ ID NO 818
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 818
gatcggaaga gcggttcagc aggaatgccg ag                                 32

<210> SEQ ID NO 819
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 819
acactctttc cctacacgac gctcttccga tct                                33

<210> SEQ ID NO 820
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 820
cgtgatacac tctttcccta cacgacgctc ttccgatct                          39

<210> SEQ ID NO 821
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 821
acatcgacac tctttcccta cacgacgctc ttccgatct                          39

<210> SEQ ID NO 822
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 822
gcctaaacac tctttcccta cacgacgctc ttccgatct                          39

<210> SEQ ID NO 823
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 823
```
tggtcaacac tctttcccta cacgacgctc ttccgatct                    39

<210> SEQ ID NO 824
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 824
cactgtacac tctttcccta cacgacgctc ttccgatct                    39

<210> SEQ ID NO 825
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 825
attggcacac tctttcccta cacgacgctc ttccgatct                    39

<210> SEQ ID NO 826
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 826
gatctgacac tctttcccta cacgacgctc ttccgatct                    39

<210> SEQ ID NO 827
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 827
tcaagtacac tctttcccta cacgacgctc ttccgatct                    39

<210> SEQ ID NO 828
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 828
ctgatcacac tctttcccta cacgacgctc ttccgatct                    39

<210> SEQ ID NO 829
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 829
aagctaacac tctttcccta cacgacgctc ttccgatct         39

<210> SEQ ID NO 830
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 830
gtagccacac tctttcccta cacgacgctc ttccgatct         39

<210> SEQ ID NO 831
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 831
tacaagacac tctttcccta cacgacgctc ttccgatct         39

<210> SEQ ID NO 832
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 832
ctcggcattc ctgctgaacc gctcttccga tct         33

<210> SEQ ID NO 833
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 833
aatgatacgg cgaccaccga gatctacacc agcaggcctt ataataaaaa taatga         56

<210> SEQ ID NO 834
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 834
caagcagaag acggcatacg agattgactg aatataaact tgtggtagtt g         51

<210> SEQ ID NO 835
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 835
acactctttc cctacacgac gctcttccga tct         33

<210> SEQ ID NO 836
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 836
ctcggcattc ctgctgaacc gctcttccga tct                                33

<210> SEQ ID NO 837
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 837
cggaagagcg tcgtgtaggg aaagagtgt                                     29

<210> SEQ ID NO 838
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 838
cggaagagcg gttcagcagg aatgccgag                                     29

<210> SEQ ID NO 839
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 839
ggttacaggc tcatgatgta acc                                           23

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 840
gataccagct tggtaatggc a                                             21

<210> SEQ ID NO 841
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(33)
<223> OTHER INFORMATION: a, c, t, g, unknown or other

```
<400> SEQUENCE: 841
cgacgtaaaa cgacggccag tnnnnnnnnn nnnggttaca ggctcatgat gtaacc        56

<210> SEQ ID NO 842
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 842
cacacaggaa acagctatga ccatggatac cagcttggta atggca                  46

<210> SEQ ID NO 843
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 843
aatgatacgg cgaccaccga gatctacacc gtgatcgacg taaaacgacg gccagt        56

<210> SEQ ID NO 844
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 844
aatgatacgg cgaccaccga gatctacaca catcgcgacg taaaacgacg gccagt        56

<210> SEQ ID NO 845
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 845
aatgatacgg cgaccaccga gatctacacg cctaacgacg taaaacgacg gccagt        56

<210> SEQ ID NO 846
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 846
aatgatacgg cgaccaccga gatctacact ggtcacgacg taaaacgacg gccagt        56

<210> SEQ ID NO 847
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 847
```
aatgatacgg cgaccaccga gatctacacc actgtcgacg taaaacgacg gccagt        56

<210> SEQ ID NO 848
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 848
aatgatacgg cgaccaccga gatctacaca ttggccgacg taaaacgacg gccagt        56

<210> SEQ ID NO 849
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 849
aatgatacgg cgaccaccga gatctacacg atctgcgacg taaaacgacg gccagt        56

<210> SEQ ID NO 850
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 850
aatgatacgg cgaccaccga gatctacact caagtcgacg taaaacgacg gccagt        56

<210> SEQ ID NO 851
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 851
aatgatacgg cgaccaccga gatctacacc tgatccgacg taaaacgacg gccagt        56

<210> SEQ ID NO 852
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 852
aatgatacgg cgaccaccga gatctacaca agctacgacg taaaacgacg gccagt        56

<210> SEQ ID NO 853
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 853
caagcagaag acggcatacg agatcacaca ggaaacagct atgaccatg        49

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 854
cgacgtaaaa cgacggccag t                                     21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 855
actggccgtc gttttacgtc g                                     21

<210> SEQ ID NO 856
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(35)
<223> OTHER INFORMATION: a, c, t, g, unknown or other

<400> SEQUENCE: 856
cgacgtaaaa cgacggccag tnnnnnnnnn nnnnngcagc aacagtctta cctggact    58

<210> SEQ ID NO 857
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 857
cacacaggaa acagctatga ccatgtccac atcctcttcc tcaggatt        48

<210> SEQ ID NO 858
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 858
aatgatacgg cgaccaccga gatctacacc gacgtaaaac gacggccagt       50

<210> SEQ ID NO 859
<211> LENGTH: 55
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 859
caagcagaag acggcatacg agatatcacg cacacaggaa acagctatga ccatg    55

<210> SEQ ID NO 860
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 860
caagcagaag acggcatacg agatcgatgt cacacaggaa acagctatga ccatg    55

<210> SEQ ID NO 861
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 861
caagcagaag acggcatacg agattgacca cacacaggaa acagctatga ccatg    55

<210> SEQ ID NO 862
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 862
caagcagaag acggcatacg agatgccaat cacacaggaa acagctatga ccatg    55

<210> SEQ ID NO 863
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 863
caagcagaag acggcatacg agatcagatc cacacaggaa acagctatga ccatg    55

<210> SEQ ID NO 864
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 864
caagcagaag acggcatacg agatacttga cacacaggaa acagctatga ccatg    55

<210> SEQ ID NO 865
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 865
caagcagaag acggcatacg agatgatcag cacacaggaa acagctatga ccatg      55

<210> SEQ ID NO 866
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 866
caagcagaag acggcatacg agattagctt cacacaggaa acagctatga ccatg      55

<210> SEQ ID NO 867
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 867
caagcagaag acggcatacg agatggctac cacacaggaa acagctatga ccatg      55

<210> SEQ ID NO 868
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 868
caagcagaag acggcatacg agatcttgta cacacaggaa acagctatga ccatg      55

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 869
cgacgtaaaa cgacggccag t                                           21

<210> SEQ ID NO 870
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 870
catggtcata gctgtttcct gtgtg                                       25

<210> SEQ ID NO 871
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
<222> LOCATION: (22)..(35)
<223> OTHER INFORMATION: a, c, t, g, unknown or other

<400> SEQUENCE: 871
cgacgtaaaa cgacggccag tnnnnnnnnn nnnnnttacc gagaaagctc acaagaa      57

<210> SEQ ID NO 872
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 872
cacacaggaa acagctatga ccatgatgct aaggcgagga tgaaa                   45

<210> SEQ ID NO 873
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 873
aatgatacgg cgaccaccga gatctacaca catcgcgacg taaaacgacg gccagt       56

<210> SEQ ID NO 874
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 874
aatgatacgg cgaccaccga gatctacacg cctaacgacg taaaacgacg gccagt       56

<210> SEQ ID NO 875
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 875
aatgatacgg cgaccaccga gatctacact ggtcacgacg taaaacgacg gccagt       56

<210> SEQ ID NO 876
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 876
aatgatacgg cgaccaccga gatctacaca ttggccgacg taaaacgacg gccagt       56

<210> SEQ ID NO 877
<211> LENGTH: 56
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 877
aatgatacgg cgaccaccga gatctacacg atctgcgacg taaaacgacg gccagt         56

<210> SEQ ID NO 878
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 878
aatgatacgg cgaccaccga gatctacact caagtcgacg taaaacgacg gccagt         56

<210> SEQ ID NO 879
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 879
aatgatacgg cgaccaccga gatctacacc tgatccgacg taaaacgacg gccagt         56

<210> SEQ ID NO 880
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 880
caagcagaag acggcatacg agatcacaca ggaaacagct atgaccatg                 49

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 881
cgacgtaaaa cgacggccag t                                               21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 882
cctaattccc cccatcctta c                                               21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 883
actggccgtc gttttacgtc g				21

<210> SEQ ID NO 884
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 884
ggttacaggc tcatgatgta acctctgtgt cttggtgtaa ctttaaaaca tattttgcc		60 attaccaagc tggtatc				77

<210> SEQ ID NO 885
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 885
ggttacaggc tcatgatgta acctctgtgt cttggtgsaa ctttaaaaca tattttgcc		60 attaccaagc tggtatc				77

<210> SEQ ID NO 886
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(36)
<223> OTHER INFORMATION: a, c, t, g, unknown or other

<400> SEQUENCE: 886
acactctttc cctacacgac gctcnnnnnn nnnnnnggtg agtctgtgca ggcat		55

<210> SEQ ID NO 887
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 887
ctcgagcact gtcctgactg agacgatacc agcttggtaa tggca		45

<210> SEQ ID NO 888
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 888
aatgatacgg cgaccaccga gatctacacc gtgatacact ctttccctac acgacgctc		59

```
<210> SEQ ID NO 889
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 889
caagcagaag acggcatacg agatctcgag cactgtcctg actgagac              48

<210> SEQ ID NO 890
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 890
acactctttc cctacacgac gctc                                        24

<210> SEQ ID NO 891
<211> LENGTH: 22
<212> TYPE: DNA
<213> ORGANISM: Homo sapiens

<400> SEQUENCE: 891
gaagaccata acccaccaca gc                                          22

<210> SEQ ID NO 892
<211> LENGTH: 10
<212> TYPE: DNA
<213> ORGANISM: Homo sapiens

<400> SEQUENCE: 892
cccaagtgac                                                        10
```

METHODS AND MATERIALS FOR ASSESSING AND TREATING CANCER

This application is a National Stage application under 35 U.S.C. § 371 of International Application No. PCT/US2018/045669 having an International Filing Date of Aug. 7, 2018, which claims the benefit of U.S. Patent Application Ser. Nos. 62/542,167, filed Aug. 7, 2017, 62/542,144, filed Aug. 7, 2017, 62/542,164 filed Aug. 7, 2017, 62/594,245, filed Dec. 4, 2017, 62/618,232, filed Jan. 17, 2018, 62/628,759, filed Feb. 9, 2018 and 62/629,870, filed Feb. 13, 2018. The disclosures of the prior applications are considered part of (and are incorporated by reference in) the disclosure of this application.

STATEMENT REGARDING FEDERAL FUNDING

This invention was made with U.S. government support under Grant Nos. CA062924 and HG007804 from the National Institutes of Health. The U.S. government has certain rights in the invention.

SEQUENCE LISTING

The instant application includes a Sequence Listing in electronic format submitted to the United States Patent and Trademark Office via the electronic filing system, and is hereby incorporated by reference in its entirety. Said sequence listing, created on Aug. 6, 2018, is named 448070306WO1SL.txt and is 208,305 bytes in size.

ELECTRONICALLY-FILED TABLES

The instant application includes tables in electronic format submitted to the United States Patent and Trademark Office via the electronic filing system. The ASCII text files, each of which is incorporated herein by reference in its entirety, include a text file named Table1.txt, created on Aug. 7, 2018, having a size of 152,000 bytes; a text file named Table2.txt, created on Aug. 7, 2018, having a size of 351,000 bytes; a text file named Table3.txt, created on Aug. 7, 2018, having a size of 438,000 bytes; a text file named Table4.txt, created on Aug. 7, 2018, having a size of 1,081,000 bytes; a text file named Table5.txt, created on Aug. 7, 2018, having a size of 31,000 bytes; a text file named Table6.txt, created on Aug. 7, 2018, having a size of 103,000 bytes; a text file named Table7.txt, created on Aug. 7, 2018, having a size of 25,000 bytes; a text file named Table8.txt, created on Aug. 7, 2018, having a size of 59,000 bytes; a text file named Table9.txt, created on Aug. 7, 2018, having a size of 38,000 bytes; a text file named Table10.txt, created on Aug. 7, 2018, having a size of 22,000 bytes; a text file named Table11.txt, created on Aug. 7, 2018, having a size of 17,000 bytes; a text file named Table12.txt, created on Aug. 7, 2018, having a size of 14,000 bytes; a text file named Table13.txt, created on Aug. 7, 2018, having a size of 104,000 bytes; a text file named Table14.txt, created on Aug. 7, 2018, having a size of 106,000 bytes; a text file named Table15.txt, created on Aug. 7, 2018, having a size of 370,000 bytes; a text file named Table16.txt, created on Aug. 7, 2018, having a size of 262,000 bytes; a text file named Table17.txt, created on Aug. 7, 2018, having a size of 8,000 bytes; a text file named Table18.txt, created on Aug. 7, 2018, having a size of 52,000 bytes; a text file named Table19.txt, created on Aug. 7, 2018, having a size of 41,000 bytes; a text file named Table20.txt, created on Aug. 7, 2018, having a size of 14,000 bytes; a text file named Table21.txt, created on Aug. 7, 2018, having a size of 6,000 bytes; a text file named Table22.txt, created on Aug. 7, 2018, having a size of 19,000 bytes; a text file named Table23.txt, created on Aug. 7, 2018, having a size of 6,000 bytes; a text file named Table24.txt, created on Aug. 7, 2018, having a size of 42,000 bytes; a text file named Table25.txt, created on Aug. 7, 2018, having a size of 25,000 bytes; a text file named Table26.txt, created on Aug. 7, 2018, having a size of 14,000 bytes; a text file named Table27.txt, created on Aug. 7, 2018, having a size of 5,000 bytes; a text file named Table28.txt, created on Aug. 7, 2018, having a size of 10,000 bytes; a text file named Table29.txt, created on Aug. 7, 2018, having a size of 9,000 bytes; a text file named Table30.txt, created on Aug. 7, 2018, having a size of 3,000 bytes; a text file named Table31.txt, created on Aug. 7, 2018, having a size of 2,000 bytes; a text file named Table32.txt, created on Aug. 7, 2018, having a size of 9,000 bytes; a text file named Table33.txt, created on Aug. 7, 2018, having a size of 3,000 bytes; a text file named Table34.txt, created on Aug. 7, 2018, having a size of 22,000 bytes; a text file named Table35.txt, created on Aug. 7, 2018, having a size of 1,536,000 bytes; a text file named Table36.txt, created on Aug. 7, 2018, having a size of 1,591,000 bytes; a text file named Table37.txt, created on Aug. 7, 2018, having a size of 13,000 bytes; a text file named Table38.txt, created on Aug. 7, 2018, having a size of 5,000 bytes; a text file named Table39.txt, created on Aug. 7, 2018, having a size of 30,000 bytes; a text file named Table40.txt, created on Aug. 7, 2018, having a size of 9,000 bytes; a text file named Table41.txt, created on Aug. 7, 2018, having a size of 4,000 bytes; a text file named Table42.txt, created on Aug. 7, 2018, having a size of 8,000 bytes; a text file named Table43.txt, created on Aug. 7, 2018, having a size of 25,000 bytes; a text file named Table44.txt, created on Aug. 7, 2018, having a size of 11,000 bytes; a text file named Table45.txt, created on Aug. 7, 2018, having a size of 11,000 bytes; a text file named Table46.txt, created on Aug. 7, 2018, having a size of 18,000 bytes; a text file named Table47.txt, created on Aug. 7, 2018, having a size of 18,000 bytes; a text file named Table48.txt, created on Aug. 7, 2018, having a size of 8,000 bytes; a text file named Table49.txt, created on Aug. 7, 2018, having a size of 167,000 bytes; a text file named Table50.txt, created on Aug. 7, 2018, having a size of 312,000 bytes; a text file named Table51.txt, created on Aug. 7, 2018, having a size of 20,000 bytes; a text file named Table52.txt, created on Aug. 7, 2018, having a size of 1,000 bytes; a text file named Table53.txt, created on Aug. 7, 2018, having a size of 3,000 bytes; a text file named Table54.txt, created on Aug. 7, 2018, having a size of 3,000 bytes; a text file named Table55.txt, created on Aug. 7, 2018, having a size of 8,000 bytes; a text file named Table56.txt, created on Aug. 7, 2018, having a size of 1,000 bytes; a text file named Table57.txt, created on Aug. 7, 2018, having a size of 14,000 bytes; a text file named Table58.txt, created on Aug. 7, 2018, having a size of 3,000 bytes; and a text file named Table59.txt, created on Aug. 7, 2018, having a size of 309,000 bytes.

LENGTHY TABLES

The patent contains a lengthy table section. A copy of the table is available in electronic form from the USPTO web site (https://seqdata.uspto.gov/?pageRequest=docDetail&DocID=US12195803B2). An electronic copy of the table will also be available from the USPTO upon request and payment of the fee set forth in 37 CFR 1.19(b)(3).

BACKGROUND

1. Technical Field

Provided herein are methods and materials for detecting and/or treating subject (e.g., humans) having cancer. In some embodiments, methods and materials for identifying a subject as having cancer (e.g., a localized cancer) are provided in which the presence of two or more members of two or more classes of biomarkers are detected. In some embodiments, methods and materials for identifying a subject as having cancer (e.g., a localized cancer) are provided in which the presence of two or more members of at least one class of biomarkers and the presence of aneuploidy are detected. In some embodiments, methods described herein provide increased sensitivity and/or specificity of detecting cancer in a subject (e.g. a human).

2. Background Information

Cancers will kill 592,000 Americans this year and according to the Center for Disease Control, cancers will soon be the leading cause of death in this country. How can this dire situation be averted? The vast majority of translational cancer research today is focused on prolonging survival in patients with advanced disease. Our research perspective is different: in the long term, prevention is always better than cure. Examples of the value of this perspective are abundant, ranging from infectious to cardiovascular diseases. Cardiovascular diseases are particularly relevant because the combination of primary and secondary prevention measures for this disease have reduced deaths by 75% in the last 60 years. In contrast, overall cancer deaths have barely changed over the same time period.

Earlier detection through the application of blood tests for cancer can be viewed as a form of secondary prevention. The last three letters of the word "earlier" are particularly important. For all cancers that have been studied, the probability for cure is much higher with early, localized disease than for advanced disease. The earlier the stage, the more likely the tumor can be cured by surgery alone. Moreover, cancers do not have to be detected when they are at their initial stages to be cured. Theoretically, the responses to therapy are dictated by the total number of cancer cells prior to therapy and the rates of mutation in human cells. The more cancer cells, the more likely that at least one of them will contain or develop a mutation(s) that confers resistance to any form of therapy, be it conventional chemotherapy, radiotherapy, targeted therapy, or immunotherapy. Clinically, a large number of studies have shown that drugs can be curative in the adjuvant setting but not in patients with advanced disease. For example, nearly half of the patients with Stage III colorectal cancer who would die from their disease can be cured by adjuvant therapy, but virtually no patients with Stage IV colorectal cancers can be cured with the same regimens.

There is a strong correlation between tumor stage and prognosis in many cancers (Ansari D, et al. (2017) Relationship between tumour size and outcome in pancreatic ductal adenocarcinoma. Br J Surg 104(5):600-607). Very few patients with cancers of the lung, colon, esophagus, or stomach who have distant metastasis at the time of diagnosis survive for more than five years (Howlader N, et al. (2016) SEER Cancer Statistics Review, 1975-2013, National Cancer Institute. Bethesda, MD, http://seer.cancer.gov/csr/1975_2013/, based on November 2015 SEER data submission, posted to the SEER web site, April 2016). The size of cancers is also important in a general sense, in that smaller tumors have less often metastasized than larger tumors at the time of diagnosis, and are therefore are more likely to be curable by surgery alone. Even when cancers have metastasized to distant sites, a smaller burden of disease is much more easily managed than bulky lesions (Bozic I, et al. (2013) Evolutionary dynamics of cancer in response to targeted combination therapy. Elife 2:e00747). Thus, adjuvant chemotherapeutic agents administered to patients with micro-metastases stemming from a colorectal cancer can be curative in nearly 50% of cases (Semrad T J, Fahrni A R, Gong I Y, & Khatri V P (2015) Integrating Chemotherapy into the Management of Oligometastatic Colorectal Cancer: Evidence-Based Approach Using Clinical Trial Findings. Ann Surg Oncol 22 Suppl 3:S855-862; Moertel C G, et al. (1995) Fluorouracil plus levamisole as effective adjuvant therapy after resection of stage III colon carcinoma: a final report. Ann Intern Med 122(5):321-326; Andre T, et al. (2009) Improved overall survival with oxaliplatin, fluorouracil, and leucovorin as adjuvant treatment in stage II or III colon cancer in the MOSAIC trial. J Clin Oncol 27(19): 3109-3116). The same chemotherapeutic agents delivered to patients with metastatic lesions that are radiologically visible produce virtually no cures (Dy G K, et al. (2009) Long-term survivors of metastatic colorectal cancer treated with systemic chemotherapy alone: a North Central Cancer Treatment Group review of 3811 patients, N0144. Clin Colorectal Cancer 8(2):88-93).

It is therefore evident that the earlier detection of cancers is one key to reducing deaths from these diseases, including pancreatic cancer. In addition to offering the possibility of surgical resection, newly developed adjuvant chemotherapeutic and emerging immunotherapy regimens will undoubtedly prove more efficacious in patients with minimal disease beyond that which is curable surgically (Huang A C, et al. (2017) T-cell invigoration to tumour burden ratio associated with anti-PD-1 response. Nature 545(7652):60-65). Biomarkers in the circulation provide one of the best ways, in principle, to detect cancers at an earlier stage. Historically, the type of biomarkers used to monitor cancers were proteins (Liotta L A & Petricoin E F, 3rd (2003) The promise of proteomics. Clin Adv Hematol Oncol 1(8):460-462), and included carcinoembryonic antigen (CEA), carbohydrate antigen 19-9 (CA19-9), and cancer antigen 125 (CA125). These biomarkers have proven useful for following patients with known disease but none have been approved for screening purposes, in part because of their low sensitivity or specificity (Lennon A M & Goggins M (2010) Diagnostic and Therapeutic Response Markers. Pancreatic Cancer, (Springer New York, New York, NY), pp 675-701; Clarke-Pearson D L (2009) Clinical practice. Screening for ovarian cancer. N Engl J Med 361(2):170-177; Locker G Y, et al. (2006) ASCO 2006 update of recommendations for the use of tumor markers in gastrointestinal cancer. J Clin Oncol 24(33):5313-5327). More recently, mutant DNA has been explored as a biomarker. The concept underlying this approach, often called "liquid biopsies" is that cancer cells, like normal self-renewing cells, turn over frequently. DNA released from the dying cells can escape into bodily fluids such as urine, stool, and plasma (Haber D A & Velculescu V E (2014) Blood-based analyses of cancer: circulating tumor cells and circulating tumor DNA. Cancer Discov 4(6):650-661; Dawson S J, et al. (2013) Analysis of circulating tumor DNA to monitor metastatic breast cancer. N Engl J Med 368(13):1199-1209; Bettegowda C, et al. (2014) Detection of circulating tumor DNA in early- and late-stage human malignancies. Science translational medicine 6(224):224ra224; Kinde I, et al. (2013) Evaluation of DNA from the Papanicolaou test to detect ovarian and endometrial cancers. Science translational medicine 5(167):167ra164; Wang Y, et al. (2015) Detection of somatic mutations and HPV in the saliva and plasma of patients with head and neck squamous cell carcinomas. Science translational medicine 7(293):293ra104; Wang Y, et al. (2015) Detection of tumor-derived DNA in cerebrospinal fluid of patients with primary tumors of the brain and spinal cord. Proc Natl Acad Sci USA 112(31):9704-9709; Wang Y, et al. (2016) Diagnostic potential of tumor DNA from ovarian cyst fluid. Elife 5; Springer S, et al. (2015) A Combination of Molecular Markers and Clinical Features Improve the Classification of Pancreatic Cysts. Gastroenterology 149(6):1501-1510; Forshew T, et al. (2012) Noninvasive identification and monitoring of cancer mutations by targeted deep sequencing of plasma DNA. Science translational medicine 4(136):136ra168; Vogelstein B & Kinzler K W (1999) Digital PCR. Proc Natl Acad Sci USA 96(16):9236-9241; Dressman D, Yan H, Traverso G, Kinzler K W, & Vogelstein B (2003) Transforming single DNA molecules into fluorescent magnetic particles for detection and enumeration of genetic variations. Proc Natl Acad Sci USA 100(15):8817-8822). An advantage of using mutant DNA in the circulation as a biomarker is its exquisite specificity. Every cell within a cancer has a core set of somatic mutations in driver genes that are responsible for their clonal growth (Vogelstein B, et al. (2013) Cancer genome landscapes. Science 339(6127):1546-1558). In contrast, normal cells do not clonally expand during adulthood and the fraction of normal cells that have any specific somatic mutation is extremely low.

Most studies of circulating tumor DNA (ctDNA) have focused on following patients with cancer rather than on evaluating their use in screening settings. Available data indicate that ctDNA is elevated in >85% of patients with advanced forms of many cancer types (Bettegowda C, et al. (2014) Detection of circulating tumor DNA in early- and late-stage human malignancies. Science translational medicine 6(224):224ra224; Wang Y, et al. (2015) Detection of somatic mutations and HPV in the saliva and plasma of patients with head and neck squamous cell carcinomas. Science translational medicine 7(293):293ra104). However, a considerably smaller fraction of patients with earlier stages of cancer have detectable levels of ctDNA in their plasma (Bettegowda C, et al. (2014) Detection of circulating tumor DNA in early- and late-stage human malignancies. Science translational medicine 6(224):224ra224; Wang Y, et al. (2015) Detection of somatic mutations and HPV in the saliva and plasma of patients with head and neck squamous cell carcinomas. Science translational medicine 7(293): 293ra104).

The majority of localized cancers can be cured by surgery alone, without any systemic therapy (Siegel et al., 2017 *CA Cancer J Clin* 67:7-30). Once distant metastasis has occurred, however, surgical excision is rarely curative. One major goal in cancer research is therefore the detection of cancers before they metastasize to distant sites. Depending on the cancer type, 20 to 30 years appear to be required for typical cancers in adults to progress from incipient neoplastic lesions to late stage cancers (Vogelstein et al., 2013 *Science* 339:1546-1558; Jones et al., 2008 *Proc Natl Acad Sci USA* 105:4283-4288; and Yachida et al., 2012 *Clin Cancer Res* 18:6339-6347). Only in the last few years of this long process do neoplastic cells appear to successfully seed and give rise to metastatic lesions (Vogelstein et al., 2013 *Science* 339:1546-1558; Jones et al., 2008 *Proc Natl Acad Sci USA* 105:4283-4288; Yachida et al., 2012 *Clin Cancer Res* 18:6339-6347; and Vogelstein et al., 2015 *N Engl J Med* 373:1895-1898). Thus, there is a wide window of opportunity to detect cancers prior to the onset of metastasis. Once large, metastatic tumors are formed however, current therapies are not effective (Bozic et al., 2013 *Elife* 2:e00747; Semrad et al., 2015 *Ann Surg Oncol* 22 (Suppl 3):S855-862; Moertel et al., 1995 *Ann Intern Med* 122:321-326; Huang et al., 2017 *Nature* 545:60-65).

Pancreatic ductal adenocarcinoma (hereinafter "pancreatic cancer") is the third leading cause of cancer death and is predicted to become the second most common cause in the United States by 2030 (Rahib L, et al. (2014) Projecting cancer incidence and deaths to 2030: the unexpected burden of thyroid, liver, and pancreas cancers in the United States. Cancer Res 74(11):2913-2921). Pancreatic cancer is notoriously lethal, with fewer than 9% of patients surviving five years after diagnosis (Siegel R L, Miller K D, & Jemal A (2016) Cancer statistics, 2016. CA Cancer J Clin 66(1):7-30). The poor prognosis of patients with pancreatic cancer is in part due to the fact that 80% to 85% of patients are diagnosed at advanced stages, when either tumor invasion into the surrounding major vessels or distant metastases are evident upon radiologic studies (Ryan D P, Hong T S, & Bardeesy N (2014) Pancreatic adenocarcinoma. N Engl J Med 371(22):2140-2141). At this late point in the disease, pancreatic cancer is not amenable to surgical resection, and the 3-year survival rate is <5%. In contrast, a five-year survival of almost 60% is reported for very small, localized tumors; among resectable cancers, the smaller the tumor, the better the prognosis (Ansari D, et al. (2017) Relationship between tumour size and outcome in pancreatic ductal adenocarcinoma. Br J Surg 104(5):600-607; Jung K W, et al. (2007) Clinicopathological aspects of 542 cases of pancreatic cancer: a special emphasis on small pancreatic cancer. J Korean Med Sci 22 Suppl:S79-85; Egawa S, et al. (2004) Clinicopathological aspects of small pancreatic cancer. Pancreas 28(3):235-240; Ishikawa O, et al. (1999) Minute carcinoma of the pancreas measuring 1 cm or less in diameter—collective review of Japanese case reports. Hepatogastroenterology 46(25):8-15; Tsuchiya R, et al. (1986) Collective review of small carcinomas of the pancreas. Ann Surg 203(1):77-81).

Pancreatic cancer is not different from other cancers with respect to its strong correlation between tumor stage and prognosis (Ansari D, et al. (2017) Relationship between tumour size and outcome in pancreatic ductal adenocarcinoma. Br J Surg 104(5):600-607). Very few patients with cancers of the lung, colon, esophagus, or stomach who have distant metastasis at the time of diagnosis survive for more than five years (Howlader N, et al. (2016) SEER Cancer Statistics Review, 1975-2013, National Cancer Institute. Bethesda, MD, http://scer.cancer.gov/csr/1975_2013/, based on November 2015 SEER data submission, posted to the SEER web site, April 2016). The size of cancers is also important in a general sense, in that smaller tumors have less often metastasized than larger tumors at the time of diagnosis, and are therefore are more likely to be curable by surgery alone. Even when cancers have metastasized to distant sites, a smaller burden of disease is much more easily managed than bulky lesions (Bozic I, et al. (2013) Evolutionary dynamics of cancer in response to targeted combination therapy. Elife 2:e00747). Thus, adjuvant chemotherapeutic agents administered to patients with micro-metastases stemming from a colorectal cancer can be curative in nearly 50% of cases (Semrad T J, Fahrni A R, Gong I Y, & Khatri V P (2015) Integrating Chemotherapy into the Management of Oligometastatic Colorectal Cancer: Evidence-Based Approach Using Clinical Trial Findings. Ann Surg Oncol 22 Suppl 3:S855-862; Moertel C G, et al. (1995) Fluorouracil plus levamisole as effective adjuvant therapy after resection of stage III colon carcinoma: a final report. Ann Intern Med 122(5):321-326; Andre T, et al. (2009) Improved overall survival with oxaliplatin, fluorouracil, and leucovorin as adjuvant treatment in stage II or III colon cancer in the MOSAIC trial. J Clin Oncol 27(19):3109-3116). The same chemotherapeutic agents delivered to patients with metastatic lesions that are radiologically visible produce virtually no cures (Dy G K, et al. (2009) Long-term survivors of metastatic colorectal cancer treated with systemic chemotherapy alone: a North Central Cancer Treatment Group review of 3811 patients, N0144. Clin Colorectal Cancer 8(2):88-93).

It is therefore evident that the earlier detection of cancers is one key to reducing deaths from these diseases, including pancreatic cancer. In addition to offering the possibility of surgical resection, newly developed adjuvant chemotherapeutic and emerging immunotherapy regimens will undoubtedly prove more efficacious in patients with minimal disease beyond that which is curable surgically (Huang A C, et al. (2017) T-cell invigoration to tumour burden ratio associated with anti-PD-1 response. Nature 545(7652):60-65). Biomarkers in the circulation provide one of the best ways, in principle, to detect cancers at an earlier stage. Historically, the type of biomarkers used to monitor cancers were proteins (Liotta L A & Petricoin E F, 3rd (2003) The promise of proteomics. Clin Adv Hematol Oncol 1(8):460-462), and included carcinoembryonic antigen (CEA), carbohydrate antigen 19-9 (CA19-9), and cancer antigen 125 (CA125). These biomarkers have proven useful for following patients with known disease but none have been approved for screening purposes, in part because of their low sensitivity or specificity (Lennon A M & Goggins M (2010) Diagnostic and Therapeutic Response Markers. Pancreatic Cancer, (Springer New York, New York, NY), pp 675-701; Clarke-Pearson D L (2009) Clinical practice. Screening for ovarian cancer. N Engl J Med 361(2):170-177; Locker G Y, et al. (2006) ASCO 2006 update of recommendations for the use of tumor markers in gastrointestinal cancer. J Clin Oncol 24(33):5313-5327). More recently, mutant DNA has been explored as a biomarker. The concept underlying this approach, often called "liquid biopsies" is that cancer cells, like normal self-renewing cells, turn over frequently. DNA released from the dying cells can escape into bodily fluids such as urine, stool, and plasma (Haber D A & Velculescu V E (2014) Blood-based analyses of cancer: circulating tumor cells and circulating tumor DNA. Cancer Discov 4(6):650-661; Dawson S J, et al. (2013) Analysis of circulating tumor DNA to monitor metastatic breast cancer. N Engl J Med 368(13):1199-1209; Bettegowda C, et al. (2014) Detection of circulating tumor DNA in early- and late-stage human malignancies. Science translational medicine 6(224): 224ra224; Kinde I, et al. (2013) Evaluation of DNA from the Papanicolaou test to detect ovarian and endometrial cancers. Science translational medicine 5(167):167ra164; Wang Y, et al. (2015) Detection of somatic mutations and HPV in the saliva and plasma of patients with head and neck squamous cell carcinomas. Science translational medicine 7(293): 293ra104; Wang Y, et al. (2015) Detection of tumor-derived DNA in cerebrospinal fluid of patients with primary tumors of the brain and spinal cord. Proc Natl Acad Sci USA 112(31): 9704-9709; Wang Y, et al. (2016) Diagnostic potential of tumor DNA from ovarian cyst fluid. Elife 5; Springer S, et al. (2015) A Combination of Molecular Markers and Clinical Features Improve the Classification of Pancreatic Cysts. Gastroenterology 149(6):1501-1510; Forshew T, et al. (2012) Noninvasive identification and monitoring of cancer mutations by targeted deep sequencing of plasma DNA. Science translational medicine 4(136):136ra168; Vogelstein B & Kinzler K W (1999) Digital PCR. Proc Natl Acad Sci USA 96(16):9236-9241; Dressman D, Yan H, Traverso G, Kinzler K W, & Vogelstein B (2003) Transforming single DNA molecules into fluorescent magnetic particles for detection and enumeration of genetic variations. Proc Natl Acad Sci USA 100(15):8817-882). An advantage of using mutant DNA in the circulation as a biomarker is its exquisite specificity. Every cell within a cancer has a core set of somatic mutations in driver genes that are responsible for their clonal growth (Vogelstein B, et al. (2013) Cancer genome landscapes. Science 339(6127):1546-1558). In contrast, normal cells do not clonally expand during adulthood and the fraction of normal cells that have any specific somatic mutation is extremely low.

Most studies of circulating tumor DNA (ctDNA) have focused on following patients with cancer rather than on evaluating their use in screening settings. Available data indicate that ctDNA is elevated in >85% of patients with advanced forms of many cancer types (Bettegowda C, et al. (2014) Detection of circulating tumor DNA in early- and late-stage human malignancies. Science translational medicine 6(224):224ra224; Wang Y, et al. (2015) Detection of somatic mutations and HPV in the saliva and plasma of patients with head and neck squamous cell carcinomas. Science translational medicine 7(293):293ra104). However, a considerably smaller fraction of patients with earlier stages of cancer have detectable levels of ctDNA in their plasma (Bettegowda C, et al. (2014) Detection of circulating tumor DNA in early- and late-stage human malignancies. Science translational medicine 6(224):224ra224; Wang Y, et al. (2015) Detection of somatic mutations and HPV in the saliva and plasma of patients with head and neck squamous cell carcinomas. Science translational medicine 7(293): 293ra104).

There is a continuing need in the art to increase the sensitivity of detection of resectable or otherwise treatable cancers under conditions that preserve high specificity.

The Papanicolaou (Pap) test has dramatically decreased the incidence and mortality of cervical cancer in the screened population. Unfortunately, the Pap test is generally unable to detect endometrial or ovarian cancers ((L. Geldenhuys, M. L. Murray, Sensitivity and specificity of the Pap smear for glandular lesions of the cervix and endometrium. Acta cytologica 51, 47-50 (2007); A. B. Ng, J. W. Reagan, S. Hawliczek, B. W. Wentz, Significance of endometrial cells in the detection of endometrial carcinoma and its precursors. Acta cytologica 18, 356-361 (1974); P. F. Schnatz, M. Guile, D. M. O'Sullivan, J. I. Sorosky, Clinical significance of atypical glandular cells on cervical cytology. Obstetrics and gynecology 107, 701-708 (2006); C. Zhao, A. Florea, A. Onisko, R. M. Austin, Histologic follow-up results in 662 patients with Pap test findings of atypical glandular cells: results from a large academic womens hospital laboratory employing sensitive screening methods. Gynecologic oncology 114, 383-389 (2009)). In light of the success of the Pap test in detecting early-stage, curable cervical cancers, ovarian and endometrial cancers are currently the most lethal and most common gynecologic malignancies, respectively, in countries where Pap tests are routinely performed (N. Howlader et al., SEER Cancer Statistics Review, 1975-2014, National Cancer Institute. (2017)). Together, endometrial and ovarian cancers account for approximately 25,000 deaths each year and are the third leading cause of cancer-related mortality in women in the United States (N. Howlader et al., SEER Cancer Statistics Review, 1975-2014, National Cancer Institute. (2017)). Most of these deaths are caused by high-grade tumor subtypes, which tend to metastasize prior to the onset of symptoms (R. J. Kurman, M. Shih Ie, The origin and pathogenesis of epithelial ovarian cancer: a proposed unifying theory. The American journal of surgical pathology 34, 433-443 (2010); K. N. Moore, A. N. Fader, Uterine papillary serous carcinoma. Clin Obstet Gynecol 54, 278-291 (2011)).

Endometrial cancer is the most common gynecologic malignancy, with 61,380 estimated new cases in 2017 in the United States (N. Howlader et al., SEER Cancer Statistics Review, 1975-2014, National Cancer Institute. (2017)). The incidence of endometrial cancer has been rising with increased obesity and increased life expectancy (M. Arnold et al., Global burden of cancer attributable to high body-mass index in 2012: a population-based study. The Lancet. Oncology 16, 36-46 (2015)). At the same time, relative survival has not improved over the past decades (N. Howlader et al., SEER Cancer Statistics Review, 1975-2014, National Cancer Institute. (2017); L. Rahib et al., Projecting cancer incidence and deaths to 2030: the unexpected burden of thyroid, liver, and pancreas cancers in the United States. Cancer research 74, 2913-2921 (2014)). Much effort has been directed towards developing a screening test for this cancer type. The most common diagnostic test is transvaginal ultrasound (TVUS), which measures the thickness of the endometrium. The potential of TVUS as a screening test is undermined by its inability to reliably distinguish between benign and malignant lesions, subjecting women without cancer to unnecessary invasive procedures and their associated complications. Its high false positive rate is demonstrated by the fact that as few as one in 50 women who tested positive by TVUS was proven to have endometrial cancer after undergoing additional diagnostic procedures (Jacobs et al., Sensitivity of transvaginal ultrasound screening for endometrial cancer in postmenopausal women: a case-control study within the UKCTOCS cohort. The Lancet. Oncology 12, 38-48 (2011)).

Ovarian cancer is the second most common gynecologic malignancy in the U.S. and Europe. It is often diagnosed at a late stage, when the 5-year survival is less than 30% (N. Howlader et al., SEER Cancer Statistics Review, 1975-2014, National Cancer Institute. (2017)). The high mortality has made the development of an effective screening test a high priority. Large randomized trials have assessed the use of CA-125 and TVUS as potential screening tests for ovarian cancer (Buys et al., Effect of screening on ovarian cancer mortality: the Prostate, Lung, Colorectal and Ovarian (PLCO) Cancer Screening Randomized Controlled Trial. JAMA 305, 2295-2303 (2011); Kobayashi et al., A randomized study of screening for ovarian cancer: a multicenter study in Japan. Int J Gynecol Cancer 18, 414-420 (2008); Jacobs et al., Ovarian cancer screening and mortality in the UK Collaborative Trial of Ovarian Cancer Screening (UKCTOCS): a randomised controlled trial. Lancet 387, 945-956 (2016); Menon et al., Risk Algorithm Using Serial Biomarker Measurements Doubles the Number of Screen-Detected Cancers Compared With a Single-Threshold Rule in the United Kingdom Collaborative Trial of Ovarian Cancer Screening. J Clin Oncol 33, 2062-2071 (2015)). However, screening with current diagnostic approaches is not recommended for the general population, as it leads to "important harms, including major surgical interventions in women who do not have cancer" (V. A. Moyer, U. S. P. S. T. Force, Screening for ovarian cancer: U.S. Preventive Services Task Force reaffirmation recommendation statement. Annals of internal medicine 157, 900-904 (2012)). Thus, new diagnostic approaches are urgently needed.

Among ovarian cancers, high-grade serous carcinomas (HGSC) account for 90% of all ovarian cancer deaths. Increasing evidence suggests that most HGSC arise in the fallopian tube and subsequently implant on the ovarian surface (16-21 R. J. Kurman, M. Shih Ie, Molecular pathogenesis and extraovarian origin of epithelial ovarian cancer—shifting the paradigm. Human pathology 42, 918-931 (2011); Lee et al., A candidate precursor to serous carcinoma that originates in the distal fallopian tube. The Journal of pathology 211, 26-35 (2007) A candidate precursor to serous carcinoma that originates in the distal fallopian tube. The Journal of pathology 211, 26-35 (2007); Eckert et al., Genomics of Ovarian Cancer Progression Reveals Diverse Metastatic Trajectories Including Intraepithelial Metastasis to the Fallopian Tube. Cancer Discov 6, 1342-1351 (2016); A. M. Karst, K. Levanon, R. Drapkin, Modeling high-grade serous ovarian carcinogenesis from the fallopian tube. Proc Natl Acad Sci USA 108, 7547-7552 (2011); Zhai et al., High-grade serous carcinomas arise in the mouse oviduct via defects linked to the human disease. The Journal of pathology 243, 16-25 (2017); R. J. Kurman, M. Shih Ie, The Dualistic Model of Ovarian Carcinogenesis: Revisited, Revised, and Expanded. Am J Pathol 186, 733-747(2016)). A recent prospective study of symptomatic women reported that most early diagnosed HGSCs have extra-ovarian origins (Gilbert et al. Assessment of symptomatic women for early diagnosis of ovarian cancer: results from the prospective DOVE pilot project. The Lancet. Oncology 13, 285-291 (2012)). This might explain the low sensitivity of TVUS for early disease, when no ovarian abnormalities are detectable. Multimodal screening with serum CA-125 levels improves sensitivity, however CA-125 lacks specificity and is elevated in a variety of common benign conditions (H. Meden, A. Fattahi-Meibodi, CA 125 in benign gynecological conditions. Int J Biol Markers 13, 231-237 (1998)).

Unlike markers associated with neoplasia, cancer driver gene mutations are causative agents of neoplasia and absent in non-neoplastic conditions. It has been shown that tumor DNA could be detected in the vaginal tract of women with ovarian cancer (Erickson et al., Detection of somatic TP53 mutations in tampons of patients with high-grade serous ovarian cancer. Obstetrics and gynecology 124, 881-885

(2014)). Furthermore, a recent proof-of-principle study showed that endometrial and ovarian cancers shed cells that collect at the cervix, allowing detectable levels of tumor DNA to be found in the fluids obtained during routine Pap tests (Kinde et al., Evaluation of DNA from the Papanicolaou test to detect ovarian and endometrial cancers. Sci Transl Med 5, 167ra164 (2013)). These cells are sampled with a brush (a "Pap brush") that is inserted into the endocervical canal. The brush is then dipped into preservative fluid. For the detection of cervical cancers, cells from the fluid are applied to a slide for cytologic examination (the classic Pap smear). Additionally, DNA is often purified from the fluid to search for HPV sequences.

Bladder cancer (BC) is the most common malignancy of the urinary tract. According to the American Cancer Society, 79,030 new cases of bladder cancer and 18,540 deaths are estimated to occur in the United States alone in 2017 [Siegel R L, Miller K D, Jemal A (2017) Cancer Statistics, 2017. CA Cancer J Clin 67:7-30]. Predominantly of urothelial histology, invasive BC arises from non-invasive papillary or flat precursors. Many BC patients suffer with multiple relapses prior to progression, providing ample lead-time for early detection and treatment prior to metastasis [Netto G J (2013) Clinical applications of recent molecular advances in urologic malignancies: no longer chasing a "mirage"?. Adv Anat Pathol 20:175-203]. Urine cytology and cystoscopy with transurethral biopsy (TURB) are currently the gold standard for diagnosis and follow-up in bladder cancer. While urine cytology has value for the detection of high-grade neoplasms, it is unable to detect the vast majority of low-grade tumors [Netto G J, Tafe L J (2016) Emerging Bladder Cancer Biomarkers and Targets of Therapy. Urol Clin North Am 43:63-76; Lotan Y, Roehrborn C G (2003) Sensitivity and specificity of commonly available bladder tumor markers versus cytology: results of a comprehensive literature review and meta-analyses. Urology 61:109-18; discussion 118; Zhang M L, Rosenthal D L, VandenBussche C J (2016) The cytomorphological features of low-grade urothelial neoplasms vary by specimen type. Cancer Cytopathol 124:552-564]. This fact, together with the high cost and invasive nature of repeated cystoscopy and TURB procedures, have led to many attempts to develop novel noninvasive strategies. These include urine or serum based genetic and protein assays for screening and surveillance [Kawauchi et al., (2009) 9p21 Index as Estimated by Dual-Color Fluorescence in Situ Hybridization is Useful to Predict Urothelial Carcinoma Recurrence in Bladder Washing Cytology. Hum Pathol 40:1783-1789; Kruger S, Mess F, Bohle A, Feller A C (2003) Numerical aberrations of chromosome 17 and the 9p21 locus are independent predictors of tumor recurrence in non-invasive transitional cell carcinoma of the urinary bladder. Int J Oncol 23:41-48; Skacel et al., (2003) Multitarget fluorescence in situ hybridization assay detects transitional cell carcinoma in the majority of patients with bladder cancer and atypical or negative urine cytology. J Urol 169:2101-2105; Sarosdy et al., (2006) Use of a multitarget fluorescence in situ hybridization assay to diagnose bladder cancer in patients with hematuria. J Urol 176:44-47; Moonen et al., (2007) UroVysion compared with cytology and quantitative cytology in the surveillance of non-muscle-invasive bladder cancer. Eur Urol 51:1275-80; discussion 1280; Fradet Y, Lockhard C (1997) Performance characteristics of a new monoclonal antibody test for bladder cancer: ImmunoCyt trade mark. Can J Urol 4:400-405; Yafi et al., (2015) Prospective analysis of sensitivity and specificity of urinary cytology and other urinary biomarkers for bladder cancer. Urol Oncol 33:66.e25-66.e31; Serizawa et al., (2010) Integrated genetic and epigenetic analysis of bladder cancer reveals an additive diagnostic value of FGFR3 mutations and hypermethylation events. Int J Cancer; Kinde et al., (2013) TERT promoter mutations occur early in urothelial neoplasia and are biomarkers of early disease and disease recurrence in urine. Cancer Res 73:7162-7167; Hurst C D, Platt F M, Knowles M A (2014) Comprehensive mutation analysis of the TERT promoter in bladder cancer and detection of mutations in voided urine. Eur Urol 65:367-369; Wang et al., (2014) TERT promoter mutations are associated with distant metastases in upper tract urothelial carcinomas and serve as urinary biomarkers detected by a sensitive castPCR. Oncotarget 5:12428-12439; Ralla et al., (2014) Nucleic acid-based biomarkers in body fluids of patients with urologic malignancies. Crit Rev Clin Lab Sci 51:200-231; Ellinger J, Muller S C, Dietrich D (2015) Epigenetic biomarkers in the blood of patients with urological malignancies. Expert Rev Mol Diagn 15:505-516; Bansal N, Gupta A, Sankhwar S N, Mahdi A A (2014) Low- and high-grade bladder cancer appraisal via serum-based proteomics approach. Clin Chim Acta 436:97-103; Goodison S, Chang M, Dai Y, Urquidi V, Rosser C J (2012) A multi-analyte assay for the non-invasive detection of bladder cancer. PLoS One 7:e47469; Allory et al., (2014) Telomerase reverse transcriptase promoter mutations in bladder cancer: high frequency across stages, detection in urine, and lack of association with outcome. Eur Urol 65:360-366]. Currently available U.S. Food and Drug Administration (FDA) approved assays include ImmunoCyt test (Scimedx Corp), nuclear matrix protein 22 (NMP22) immunoassay test (Matritech), and multitarget FISH (UroVysion) [Kawauchi et al., (2009) 9p21 Index as Estimated by Dual-Color Fluorescence in Situ Hybridization is Useful to Predict Urothelial Carcinoma Recurrence in Bladder Washing Cytology. Hum Pathol 40:1783-1789; Kruger S, Mess F, Bohle A, Feller A C (2003) Numerical aberrations of chromosome 17 and the 9p21 locus are independent predictors of tumor recurrence in non-invasive transitional cell carcinoma of the urinary bladder. Int J Oncol 23:41-48; Skacel et al., (2003) Multitarget fluorescence in situ hybridization assay detects transitional cell carcinoma in the majority of patients with bladder cancer and atypical or negative urine cytology. J Urol 169:2101-2105; Sarosdy et al., (2006) Use of a multitarget fluorescence in situ hybridization assay to diagnose bladder cancer in patients with hematuria. J Urol 176:44-47; Moonen et al., (2007) UroVysion compared with cytology and quantitative cytology in the surveillance of non-muscle-invasive bladder cancer. Eur Urol 51:1275-80; discussion 1280; Fradet Y, Lockhard C (1997) Performance characteristics of a new monoclonal antibody test for bladder cancer: ImmunoCyt trade mark. Can J Urol 4:400-405; Yafi et al., (2015) Prospective analysis of sensitivity and specificity of urinary cytology and other urinary biomarkers for bladder cancer. Urol Oncol 33:66.e25-66.e31]. Sensitivities between 62% and 69% and specificities between 79% and 89% have been reported for some of these tests. However, due to assay performance inconsistencies, cost or required technical expertise, integration of such assays into routine clinical practice has not yet occurred.

Bladder cancer typically falls into three types that begin in cells in the lining of the bladder. In some embodiments, bladder cancers are named for the type of cells that become malignant (cancerous) including transitional cell carcinoma, squamous cell carcinoma, and adenocarcinoma. Transitional cell carcinomas begin in cells in the innermost tissue layer of the bladder. Transitional cell carcinomas can be low-grade or high-grade. Low-grade transitional cell carcinomas can recur after treatment, but rarely spread into the muscle layer of the bladder or to other parts of the body. High-grade transitional cell carcinomas can recur after treatment and often spreads into the muscle layer of the bladder, to other parts of the body, and to lymph nodes. Almost all deaths from bladder cancer are due to high-grade disease. Squamous cell carcinomas begin in squamous cells, which are thin, flat cells that may form in the bladder after long-term infection or irritation. Adenocarcinomas begin in glandular (secretory) cells that are found in the lining of the bladder, and are a very rare type of bladder cancer.

High rates of activating mutations in the upstream promoter of the TERT gene are found in the majority of BC as well as in other cancer types [Huang F W, Hodis E, Xu M J, Kryukov G V, Chin L, Garraway L A (2013) Highly recurrent TERT promoter mutations in human melanoma. Science 339:957-959; Killela et al., (2013) TERT promoter mutations occur frequently in gliomas and a subset of tumors derived from cells with low rates of self-renewal. Proc Natl Acad Sci USA 110:6021-6026; Scott G A, Laughlin T S, Rothberg P G (2014) Mutations of the TERT promoter are common in basal cell carcinoma and squamous cell carcinoma. Mod Pathol 27:516-523]. TERT promoter mutations predominantly affect two hot spots, g.1295228 C>T and g.1295250 C>T. They lead to the generation of CCGGAA/T or GGAA/T motifs altering binding site for ETS transcription factors and subsequently increased TERT promoter activity [Huang F W, Hodis E, Xu M J, Kryukov G V, Chin L, Garraway L A (2013) Highly recurrent TERT promoter mutations in human melanoma. Science 339:957-959; Horn et al., (2013) TERT promoter mutations in familial and sporadic melanoma. Science 339:959-961]. TERT promoter mutations occur in up to 80% of invasive urothelial carcinomas of the bladder and upper urinary tract as well as in several of its histologic variants [Kinde et al., (2013) TERT promoter mutations occur early in urothelial neoplasia and are biomarkers of early disease and disease recurrence in urine. Cancer Res 73:7162-7167; Killela et al., (2013) TERT promoter mutations occur frequently in gliomas and a subset of tumors derived from cells with low rates of self-renewal. Proc Natl Acad Sci USA 110:6021-6026; Allory et al., (2014) Telomerase reverse transcriptase promoter mutations in bladder cancer: high frequency across stages, detection in urine, and lack of association with outcome. Eur Urol 65:360-366; Cowan et al., (2016) Detection of TERT promoter mutations in primary adenocarcinoma of the urinary bladder. Hum Pathol 53:8-13; Nguyen et al., (2016) High prevalence of TERT promoter mutations in micropapillary urothelial carcinoma. Virchows Arch 469: 427-434]. Moreover, TERT promoter mutations occur in 60-80% of BC precursors, including Papillary Urothelial Neoplasms of Low Malignant Potential [Rodriguez et al., (2017) Spectrum of genetic mutations in de novo PUNLMP of the urinary bladder. Virchows Arch], non-invasive Low Grade Papillary Urothelial Carcinoma, non-invasive High Grade Papillary Urothelial Carcinoma and "flat" Carcinoma in Situ (CIS), as well as in urinary cells from a subset of these patients [Kinde et al., (2013) TERT promoter mutations occur early in urothelial neoplasia and are biomarkers of early disease and disease recurrence in urine. Cancer Res 73:7162-7167]. TERT promoter mutations have thus been established as the most common genetic alteration in BC [Kinde et al., (2013) TERT promoter mutations occur early in urothelial neoplasia and are biomarkers of early disease and disease recurrence in urine. Cancer Res 73:7162-7167; Cheng L, Montironi R, Lopez-Beltran A (2017) TERT Promoter Mutations Occur Frequently in Urothelial Papilloma and Papillary Urothelial Neoplasm of Low Malignant Potential. Eur Urol 71:497-498]. Other oncogene-activating mutations include those in FGFR3, RAS and PIK3CA, which have been shown to occur in a high fraction of non-muscle invasive bladder cancers [International Agency for Research on Cancer. (2016) WHO Classification of Tumours of the Urinary System and Male Genital Organs. World Health Organization; 4 edition; Netto G J (2011) Molecular biomarkers in urothelial carcinoma of the bladder: are we there yet?. Nat Rev Urol 9:41-51]. In muscle-invasive bladder cancers, mutations in TP53, CDKN2A, MLL and ERBB2 are also frequently found [Netto G J (2011) Molecular biomarkers in urothelial carcinoma of the bladder: are we there yet?. Nat Rev Urol 9:41-51; Mo et al., (2007) Hyperactivation of Ha-ras oncogene, but not Ink4a/Arf deficiency, triggers bladder tumorigenesis. J Clin Invest 117:314-325; Sarkis et al., (1993) Nuclear overexpression of p53 protein in transitional cell bladder carcinoma: a marker for disease progression. J Natl Cancer Inst 85:53-59; Lin et al., (2010) Increase sensitivity in detecting superficial, low grade bladder cancer by combination analysis of hypermethylation of E-cadherin, p16, p14, RASSF1A genes in urine. Urol Oncol 28:597-602; Sarkis et al., (1994) Association of P53 nuclear overexpression and tumor progression in carcinoma in situ of the bladder. J Urol 152:388-392; Wu X R (2005) Urothelial tumorigenesis: a tale of divergent pathways. Nat Rev Cancer 5:713-725; Cancer Genome Atlas Research Network (2014) Comprehensive molecular characterization of urothelial bladder carcinoma. Nature 507: 315-322].

Because urine cytology is relatively insensitive for the detection of recurrence, cystoscopies are performed as often as every three months in such patients in the U.S. In fact, the cost of managing these patients is in aggregate higher than the cost of managing any other type of cancer, and amounts to 3 billion dollars annually [Netto G J, Epstein J I (2010) Theranostic and prognostic biomarkers: genomic applications in urological malignancies. Pathology 42:384-394]. A non-invasive test that could predict which of these patients were most likely to develop recurrent BC could thereby be both medically and economically important.

More than 400,000 new cases of urologic transitional cell carcinoma are diagnosed worldwide each year (Antoni, S., Ferlay, J., Soerjomataram, I., Znaor, A., Jemal, A., & Bray, F. (2017). Bladder Cancer Incidence and Mortality: A Global Overview and Recent Trends. Eur Urol, 71 (1), 96-108. doi: 10.1016/j.eururo.2016.06.010). Although most of these urothelial carcinomas arise in the bladder in the lower urinary tract, 5-10% originate in the upper urinary tract in the renal pelvis and/or ureter (Roupret, M., Babjuk, M., Comperat, E., Zigeuner, R., Sylvester, R. J., Burger, M., Cowan, N. C., Bohle, A., Van Rhijn, B. W., Kaasinen, E., Palou, J., & Shariat, S. F. (2015). European Association of Urology Guidelines on Upper Urinary Tract Urothelial Cell Carcinoma: 2015 Update. Eur Urol, 68 (5), 868-879. doi: 10.1016/j.eururo.2015.06.044; Soria, F., Shariat, S. F., Lerner, S. P., Fritsche, H. M., Rink, M., Kassouf, W., Spiess, P. E., Lotan, Y., Ye, D., Fernandez, M. I., Kikuchi, E., Chade, D. C., Babjuk, M., Grollman, A. P., & Thalmann, G. N. (2017). Epidemiology, diagnosis, preoperative evaluation and prognostic assessment of upper-tract urothelial carcinoma (UTUC). World J Urol, 35 (3), 379-387. doi: 10.1007/s00345-016-1928-x). The annual incidence of these upper tract urothelial carcinomas (UTUCs) in Western countries is 1-2 cases per 100,000, but occurs at a much higher rate in populations exposed to aristolochic acid (AA) (Chen, C. H., Dickman, K. G., Moriya, M., Zavadil, J., Sidorenko, V. S., Edwards, K. L., Gnatenko, D. V., Wu, L., Turesky, R. J., Wu, X. R., Pu, Y. S., & Grollman, A. P. (2012). Aristolochic acid-associated urothelial cancer in Taiwan. Proc Natl Acad Sci USA, 109(21), 8241-8246. doi: 10.1073/pnas. 1119920109; Grollman, A. P. (2013). Aristolochic acid nephropathy: Harbinger of a global iatrogenic disease. Environ Mol Mutagen, 54(1), 1-7. doi: 10.1002/em.21756; Lai, M. N., Wang, S. M., Chen, P. C., Chen, Y. Y., & Wang, J. D. (2010). Population-based case-control study of Chinese herbal products containing aristolochic acid and urinary tract cancer risk. J Natl Cancer Inst, 102 (3), 179-186. doi: 10.1093/jnci/djp467; Taiwan Cancer Registry. (2017). Bureau of Health Promotion, Dept. of Health, Taiwan. The incidence of renal pelvic and ureteral tumor in Taiwan. Taiwan cancer registry. Retrieved Aug. 14, 2017, from URL cris.bhp.doh.gov.tw/pagepub/Home.aspx?itemNo-cr.q.10).

AA is a carcinogenic and nephrotoxic nitrophenanthrene carboxylic acid produced by Aristolochia plants (Hsieh, S. C., Lin, I. H., Tseng, W. L., Lee, C. H., & Wang, J. D. (2008). Prescription profile of potentially aristolochic acid containing Chinese herbal products: an analysis of National Health Insurance data in Taiwan between 1997 and 2003, Chin Med, 3, 13. doi: 10.1186/1749-8546-3-13; National Toxicology Program. (2011). Aristolochic acids. Rep Carcinog, 12, 45-49). An etiological link between AA exposure and UTUC has been established in two distinct populations. The first resides in Balkan countries where Aristolochia plants grow naturally in wheat fields (Jelakovic, B., Karanovic, S., Vukovic-Lela, I., Miller, F., Edwards, K. L., Nikolic, J., Tomic, K., Slade, N., Brdar, B., Turesky, R. J., Stipancic, Z., Dittrich, D., Grollman, A. P., & Dickman, K. G. (2012). Aristolactam-DNA adducts are a biomarker of environmental exposure to aristolochic acid. Kidney Int, 81 (6), 559-567. doi: 10.1038/ki.2011.371). The second population is in Asia, where Aristolochia herbs are widely used in the practice of Traditional Chinese Medicine (Grollman, 2013; National Toxicology Program, 2011). The public health threat posed by the medicinal use of Aristolochia herbs is exemplified by Taiwan, which has the highest incidence of UTUC in the world (Chen, C. H., Dickman, K. G., Moriya, M., Zavadil, J., Sidorenko, V. S., Edwards, K. L., Gnatenko, D. V., Wu, L., Turesky, R. J., Wu, X. R., Pu, Y. S., & Grollman, A. P. (2012). Aristolochic acid-associated urothelial cancer in Taiwan. Proc Natl Acad Sci USA, 109(21), 8241-8246. doi: 10.1073/pnas. 1119920109; Yang, M. H., Chen, K. K., Yen, C. C., Wang, W. S., Chang, Y. H., Huang, W. J., Fan, F. S., Chiou, T. J., Liu, J. H., & Chen, P. M. (2002). Unusually high incidence of upper urinary tract urothelial carcinoma in Taiwan. Urology, 59 (5), 681-687). More than one-third of the adult population in Taiwan has been prescribed herbal remedies containing AA (Hsieh, S. C., Lin, I. H., Tseng, W. L., Lee, C. H., & Wang, J. D. (2008). Prescription profile of potentially aristolochic acid containing Chinese herbal products: an analysis of National Health Insurance data in Taiwan between 1997 and 2003. Chin Med, 3, 13. doi: 10.1186/1749-8546-3-13), resulting in an unusually high (37%) proportion of UTUC cases relative to all urothelial cancers (Taiwan Cancer Registry. (2017). Bureau of Health Promotion, Dept. of Health, Taiwan. The incidence of renal pelvic and ureteral tumor in Taiwan. Taiwan cancer registry. Retrieved Aug. 14, 2017, from URL cris.bhp.doh.gov.tw/pagepub/Home.aspx?itemNo=cr.q.10).

Nephroureterectomy can be curative for patients with UTUC when it is detected at an early stage (Li, C. C., Chang, T. H., Wu, W. J., Ke, H. L., Huang, S. P., Tsai, P. C., Chang, S. J., Shen, J. T., Chou, Y. H., & Huang, C. H. (2008). Significant predictive factors for prognosis of primary upper urinary tract cancer after radical nephroureterectomy in Taiwanese patients. Eur Urol, 54 (5), 1127-1134. doi: 10.1016/j.eururo.2008.01.054). However, these cancers are largely silent until the onset of overt clinical symptoms, typically hematuria, and as a result, most patients are diagnosed only at an advanced stage (Roupret, M., Babjuk, M., Comperat, E., Zigeuner, R., Sylvester, R. J., Burger, M., Cowan, N. C., Bohle, A., Van Rhijn, B. W., Kaasinen, E., Palou, J., & Shariat, S. F. (2015). European Association of Urology Guidelines on Upper Urinary Tract Urothelial Cell Carcinoma: 2015 Update. Eur Urol, 68 (5), 868-879. doi: 10.1016/j.eururo.2015.06.044). Diagnostic tests for the detection of early-stage UTUC are not currently available. There is thus a need for clinical tools that can be used to identify early UTUCs in populations at risk for developing this type of malignancy. Relapse following surgery is also a concern, as UTUC can recur in the contralateral upper urinary tract and/or in the bladder (Roupret, M., Babjuk, M., Comperat, E., Zigeuner, R., Sylvester, R. J., Burger, M., Cowan, N. C., Bohle, A., Van Rhijn, B. W., Kaasinen, E., Palou, J., & Shariat, S. F. (2015). European Association of Urology Guidelines on Upper Urinary Tract Urothelial Cell Carcinoma: 2015 Update. Eur Urol, 68 (5), 868-879. doi: 10.1016/j.eururo.2015.06.044; Soria, F., Shariat, S. F., Lerner, S. P., Fritsche, H. M., Rink, M., Kassouf, W., Spiess, P. E., Lotan, Y., Ye, D., Fernandez, M. I., Kikuchi, E., Chade, D. C., Babjuk, M., Grollman, A. P., & Thalmann, G. N. (2017). Epidemiology, diagnosis, preoperative evaluation and prognostic assessment of upper-tract urothelial carcinoma (UTUC). World J Urol, 35 (3), 379-387. doi: 10.1007/s00345-016-1928-x). Vigilant surveillance for signs of malignancy is therefore an essential part of follow-up care in UTUC patients, and non-invasive tests for recurrent disease could substantially improve post-surgical management, particularly as urine cytology cannot detect the majority of UTUCs (Baard, J., de Bruin, D. M., Zondervan, P. J., Kamphuis, G., de la Rosette, J., & Laguna, M. P. (2017). Diagnostic dilemmas in patients with upper tract urothelial carcinoma. Nat Rev Urol, 14 (3), 181-191. doi: 10.1038/nrurol.2016.252).

SUMMARY

In general, methods and materials for identifying the presence of cancer in a subject with increased sensitivity and specificity as compared to conventional methods of identifying the presence of cancer in a subject are provided herein. In some embodiments, methods provided herein for identifying the presence of cancer in a subject with increased sensitivity and specificity are performed on a liquid sample obtained from the subject (e.g., blood, plasma, or serum), whereas conventional methods of identifying the presence of cancer in a subject do not achieve the level of sensitivity, the level of specificity, or both when performed on a liquid sample obtained from the subject. In some embodiments, methods provided herein for identifying the presence of cancer in a subject with increased sensitivity and specificity are performed prior to having determined that the subject already suffers from cancer, prior to having determined that the subject harbors a cancer cell, and/or prior to the subject exhibiting symptoms associated with cancer. In some embodiments, methods provided herein for identifying the presence of cancer in a subject with increased sensitivity and specificity are used as a first line detection method, and not simply as a confirmation (e.g., an "overcall") of another detection method that the subject has cancer.

In some embodiments, provided herein are methods for identifying the presence of pancreatic cancer in a subject that include: detecting in a first biological sample obtained from the subject the presence of one or more genetic biomarkers in one or more of the following genes: KRAS, TP53, CDKN2A, or SMAD4; detecting a level of one or more of the following protein biomarkers in a second biological sample obtained from the subject: carbohydrate antigen 19-9 (CA19-9), carcinoembryonic antigen (CEA), hepatocyte growth factor (HGF), or osteopontin (OPN); comparing the detected levels of the one or more protein biomarker to one or more reference levels of the protein biomarkers; and identifying the presence of pancreatic cancer in the subject when the presence of one or more genetic biomarkers is detected, the detected levels of the one or more protein biomarkers are higher than the reference levels of the one or more protein biomarkers, or both. In some of methods for identifying the presence of pancreatic cancer in a subject, the first biological sample, the second biological sample, or both includes plasma. In some of methods for identifying the presence of pancreatic cancer in a subject, the first and second biological samples are the same. In some of methods for identifying the presence of pancreatic cancer in a subject, the presence of one or more genetic biomarkers in each of: KRAS, TP53, CDKN2A, and SMAD4 is detected. In some of methods for identifying the presence of pancreatic cancer in a subject, the level of each of carbohydrate antigen 19-9 (CA19-9), carcinoembryonic antigen (CEA), hepatocyte growth factor (HGF), and osteopontin (OPN) is detected. In some of methods for identifying the presence of pancreatic cancer in a subject, the presence of one or more genetic biomarkers in one or more of KRAS, TP53, CDKN2A, or SMAD4 is detected using a multiplex PCR-based sequencing assay that includes a. assigning a unique identifier (UID) to each of a plurality of template molecules present in the sample; b. amplifying each uniquely tagged template molecule to create UID-families; and c. redundantly sequencing the amplification products. In some of methods for identifying the presence of pancreatic cancer in a subject, detecting the presence of one or more genetic biomarkers, detecting the level of one or more protein biomarkers, or both is performed when the subject is not known to harbor a cancer cell. In some of methods for identifying the presence of pancreatic cancer in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

In some embodiments, provided herein are methods for identifying the presence of cancer in a subject that include: detecting in a first biological sample obtained from the subject the presence of one or more genetic biomarkers in one or more of the following genes: NRAS, CTNNB1, PIK3CA, FBXW7, APC, EGFR, BRAF, CDKN2A, PTEN, FGFR2, HRAS, KRAS, AKT1, TP53, PPP2R1A, or GNAS; detecting a level of one or more of the following protein biomarkers in a second biological sample obtained from the subject: CA19-9, CEA, HGF, OPN, CA125, prolactin, TIMP-1, or MPO; comparing the detected levels of the one or more protein biomarker to one or more reference levels of the protein biomarkers; and identifying the presence of cancer in the subject when the presence of one or more genetic biomarkers is detected, the detected levels of the one or more protein biomarkers are higher than the reference levels of the one or more protein biomarkers, or both. In some embodiments of methods for identifying the presence of cancer in a subject, the first biological sample, the second biological sample, or both includes plasma. In some embodiments of methods for identifying the presence of cancer in a subject, the first and second biological samples are the same. In some embodiments of methods for identifying the presence of cancer in a subject, the presence of one or more genetic biomarkers in each of: NRAS, CTNNB1, PIK3CA, FBXW7, APC, EGFR, BRAF, CDKN2A, PTEN, FGFR2, HRAS, KRAS, AKT1, TP53, PPP2R1A, and GNAS is detected. In some embodiments of methods for identifying the presence of cancer in a subject, the level of each of CA19-9, CEA, HGF, OPN, CA125, prolactin, TIMP-1, and MPO is detected. In some embodiments of methods for identifying the presence of cancer in a subject, the presence of one or more genetic biomarkers in one or more of NRAS, CTNNB1, PIK3CA, FBXW7, APC, EGFR, BRAF, CDKN2A, PTEN, FGFR2, HRAS, KRAS, AKT1, TP53, PPP2R1A, or GNAS is detected using a multiplex PCR-based sequencing assay that includes: a. assigning a unique identifier (UID) to each of a plurality of template molecules present in the sample; b. amplifying each uniquely tagged template molecule to create UID-families; and c. redundantly sequencing the amplification products. In some embodiments of methods for identifying the presence of cancer in a subject, the cancer is liver cancer, ovary cancer, esophageal cancer, stomach cancer, pancreatic cancer, colorectal cancer, lung cancer, breast cancer, or prostate cancer. In some embodiments of methods for identifying the presence of cancer in a subject, the presence of one or more genetic biomarkers, detecting the level of one or more protein biomarkers, or both is performed when the subject is not known to harbor a cancer cell. In some embodiments of methods for identifying the presence of cancer in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

In some embodiments, provided herein are methods for identifying the presence of cancer in a subject that include: detecting in a first biological sample obtained from the subject the presence of one or more genetic biomarkers in one or more of the following genes: NRAS, CTNNB1, PIK3CA, FBXW7, APC, EGFR, BRAF, CDKN2A, PTEN, FGFR2, HRAS, KRAS, AKT1, TP53, PPP2R1A, or GNAS; detecting a level of one or more of the following protein biomarkers in a second biological sample obtained from the subject: CA19-9, CEA, HGF, OPN, CA125, AFP, prolactin, TIMP-1, follistatin, G-CSF, or CA15-3; comparing the detected levels of the one or more protein biomarker to one or more reference levels of the protein biomarkers; and identifying the presence of cancer in the subject when the presence of one or more genetic biomarkers is detected, the detected levels of the one or more protein biomarkers are higher than the reference levels of the one or more protein biomarkers, or both. In some embodiments of methods for identifying the presence of cancer in a subject, the first biological sample, the second biological sample, or both includes plasma. In some embodiments of methods for identifying the presence of cancer in a subject, the first and second biological samples are the same. In some embodiments of methods for identifying the presence of cancer in a subject, the presence of one or more genetic biomarkers in each of: NRAS, CTNNB1, PIK3CA, FBXW7, APC, EGFR, BRAF, CDKN2A, PTEN, FGFR2, HRAS, KRAS, AKT1, TP53, PPP2R1A, and GNAS is detected. In some embodiments of methods for identifying the presence of cancer in a subject, the level of each of CA19-9, CEA, HGF, OPN, CA125, AFP, prolactin, TIMP-1, follistatin, G-CSF, and CA15-3 is detected. In some embodiments of methods for identifying the presence of cancer in a subject, the presence of one or more genetic biomarkers in one or more of NRAS, CTNNB1, PIK3CA, FBXW7, APC, EGFR, BRAF, CDKN2A, PTEN, FGFR2, HRAS, KRAS, AKT1, TP53, PPP2R1A, or GNAS is detected using a multiplex PCR-based sequencing assay that includes: a. assigning a unique identifier (UID) to each of a plurality of template molecules present in the sample; b. amplifying each uniquely tagged template molecule to create UID-families; and c. redundantly sequencing the amplification products. In some embodiments of methods for identifying the presence of cancer in a subject, the cancer is liver cancer, ovary cancer, esophageal cancer, stomach cancer, pancreatic cancer, colorectal cancer, lung cancer, breast cancer, or prostate cancer. In some embodiments of methods for identifying the presence of cancer in a subject, the presence of one or more genetic biomarkers, detecting the level of one or more protein biomarkers, or both is performed when the subject is not known to harbor a cancer cell. In some embodiments of methods for identifying the presence of cancer in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

In some embodiments, provided herein are methods for identifying the presence of cancer in a subject that include: detecting in a first biological sample obtained from the subject the presence of one or more genetic biomarkers in one or more of the following genes: NRAS, CTNNB1, PIK3CA, FBXW7, APC, EGFR, BRAF, CDKN2A, PTEN, FGFR2, HRAS, KRAS, AKT1, TP53, PPP2R1A, or GNAS; detecting a level of one or more of the following protein biomarkers in a second biological sample obtained from the subject: CA19-9, CEA, HGF, OPN, CA125, AFP, prolactin, TIMP-1, or CA15-3; comparing the detected levels of the one or more protein biomarker to one or more reference levels of the protein biomarkers; and identifying the presence of cancer in the subject when the presence of one or more genetic biomarkers is detected, the detected levels of the one or more protein biomarkers are higher than the reference levels of the one or more protein biomarkers, or both. In some embodiments of methods for identifying the presence of cancer in a subject, the first biological sample, the second biological sample, or both includes plasma. In some embodiments of methods for identifying the presence of cancer in a subject, the first and second biological samples are the same. In some embodiments of methods for identifying the presence of cancer in a subject, the presence of one or more genetic biomarkers in each of: NRAS, CTNNB1, PIK3CA, FBXW7, APC, EGFR, BRAF, CDKN2A, PTEN, FGFR2, HRAS, KRAS, AKT1, TP53, PPP2R1A, and GNAS is detected. In some embodiments of methods for identifying the presence of cancer in a subject, the level of each of CA19-9, CEA, HGF, OPN, CA125, AFP, prolactin, TIMP-1, and CA15-3 is detected. In some embodiments of methods for identifying the presence of cancer in a subject, the presence of one or more genetic biomarkers in one or more of NRAS, CTNNB1, PIK3CA, FBXW7, APC, EGFR, BRAF, CDKN2A, PTEN, FGFR2, HRAS, KRAS, AKT1, TP53, PPP2R1A, or GNAS is detected using a multiplex PCR-based sequencing assay that includes: a. assigning a unique identifier (UID) to each of a plurality of template molecules present in the sample; b. amplifying each uniquely tagged template molecule to create UID-families; and c. redundantly sequencing the amplification products. In some embodiments of methods for identifying the presence of cancer in a subject, the cancer is liver cancer, ovary cancer, esophageal cancer, stomach cancer, pancreatic cancer, colorectal cancer, lung cancer, breast cancer, or prostate cancer. In some embodiments of methods for identifying the presence of cancer in a subject, the presence of one or more genetic biomarkers, detecting the level of one or more protein biomarkers, or both is performed when the subject is not known to harbor a cancer cell. In some embodiments of methods for identifying the presence of cancer in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

In some embodiments, provided herein are methods for identifying the presence of bladder cancer or an upper tract urothelial carcinoma in a subject that include: detecting in a first biological sample obtained from the subject the presence of one or more genetic biomarkers in one or more of the following genes: TP53, PIK3CA, FGFR3, KRAS, ERBB2, CDKN2A, MLL, HRAS, MET, or VHL; detecting the presence of at least one mutation in a TERT promoter in a second biological sample obtained from the subject; and detecting the presence of aneuploidy in a third biological sample obtained from the subject; and identifying the presence of bladder cancer or an upper tract urothelial carcinoma in the subject when the presence of one or more genetic biomarkers is detected, the presence of the at least one mutation in the TERT promoter, the presence of aneuploidy is detected, or combinations thereof. In some embodiments of methods for identifying the presence of bladder cancer or an upper tract urothelial carcinoma in a subject, the first biological sample and the second biological sample are the same; the first biological sample and the third biological sample are the same; the second biological sample and the third biological sample are the same; or the first biological sample, the second biological sample, and the third biological sample are the same. In some embodiments of methods for identifying the presence of bladder cancer or an upper tract urothelial carcinoma in a subject, the first biological sample, the second biological sample, or the third biological sample is a urine sample. In some embodiments of methods for identifying the presence of bladder cancer or an upper tract urothelial carcinoma in a subject, the presence of aneuploidy is detected on one or more of chromosome arms 5q, 8q, or 9p. In some embodiments of methods for identifying the presence of bladder cancer or an upper tract urothelial carcinoma in a subject, the presence of one or more genetic biomarkers in each of: TP53, PIK3CA, FGFR3, KRAS, ERBB2, CDKN2A, MLL, HRAS, MET, and VHL is detected. In some embodiments of methods for identifying the presence of bladder cancer or an upper tract urothelial carcinoma in a subject, the presence of one or more genetic biomarkers in one or more of TP53, PIK3CA, FGFR3, KRAS, ERBB2, CDKN2A, MLL, HRAS, MET, or VHL is detected using a multiplex PCR-based sequencing assay that comprises: a. assigning a unique identifier (UID) to each of a plurality of template molecules present in the sample; b. amplifying each uniquely tagged template molecule to create UID-families; and c. redundantly sequencing the amplification products. In some embodiments of methods for identifying the presence of bladder cancer or an upper tract urothelial carcinoma in a subject, detecting the presence of one or more genetic biomarkers, detecting the presence of the at least one mutation in the TERT promoter, or detecting the presence of aneuploidy is performed when the subject is not known to harbor a cancer cell. In some embodiments of methods for identifying the presence of bladder cancer or an upper tract urothelial carcinoma in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

In some embodiments, provided herein are methods for identifying the presence of ovarian or endometrial cancer in a subject that include: detecting in a first biological sample obtained from the subject the presence of one or more genetic biomarkers in one or more of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A; detecting the presence of aneuploidy in a second biological sample obtained from the subject; and identifying the presence of ovarian or endometrial cancer in the subject when the presence of one or more genetic biomarkers is detected, the presence of aneuploidy is detected, or both. In some embodiments of methods for identifying the presence of ovarian or endometrial cancer in a subject, the first biological sample and the second biological sample are the same. In some embodiments of methods for identifying the presence of ovarian or endometrial cancer in a subject, the first biological sample or the second biological sample is a cervical sample or an endometrial sample. In some embodiments of methods for identifying the presence of ovarian or endometrial cancer in a subject, the presence of aneuploidy is detected on one or more of chromosome arms 4p, 7q, 8q, or 9q. In some embodiments of methods for identifying the presence of ovarian or endometrial cancer in a subject, the presence of one or more genetic biomarkers in each of: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A is detected. In some embodiments of methods for identifying the presence of ovarian or endometrial cancer in a subject, the presence of one or more genetic biomarkers in one or more of: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A is detected using a multiplex PCR-based sequencing assay that comprises: a. assigning a unique identifier (UID) to each of a plurality of template molecules present in the sample; b. amplifying each uniquely tagged template molecule to create UID-families; and c. redundantly sequencing the amplification products. In some embodiments of methods for identifying the presence of ovarian or endometrial cancer in a subject, the methods further include detecting in a circulating tumor DNA (ctDNA) sample obtained from the subject the presence of at least one genetic biomarker in one or more of the following genes: AKT1, APC, BRAF, CDKN2A, CTNNB1, EGFR, FBXW7, FGFR2, GNAS, HRAS, KRAS, NRAS, PIK3CA, PPP2R1A, PTEN, or TP53. In some embodiments of methods for identifying the presence of ovarian or endometrial cancer in a subject, the presence of one or more genetic biomarkers or detecting the presence of aneuploidy is performed when the subject is not known to harbor a cancer cell. In some embodiments of methods for identifying the presence of ovarian or endometrial cancer in a subject, the subject is administered one or more therapeutic interventions (e.g., surgery, adjuvant chemotherapy, neoadjuvant chemotherapy, radiation therapy, immunotherapy, targeted therapy, and/or an immune checkpoint inhibitor).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Headers used in various sections herein are not to be construed as limiting the disclosure of that section to the topic of the header, nor as limiting the disclosure of other sections to topics other than that of the header. Such headers are exemplary, and are simply included for ease of reading. Such headers are further not intended to restrict the applicability or generality of that section to other parts of this disclosure.

Other features and advantages of the invention will be apparent from the following detailed description and figures, and from the claims.

DESCRIPTION OF THE DRAWINGS

FIG. 26 contains a flow diagram indicating the number of patients in the Early Detection Cohort and the Surveillance Cohort with summaries of the data. Cytology was performed on a subset of the patients.

FIG. 29 contains bar graphs of the lead time between a positive UroSEEK test and the detection of disease at the clinical level in the Early Detection Cohort (A) and the Surveillance Cohort (B).

FIG. 41 contains graphs showing Trisomy 21 performance as a function of read depth. DNA samples from individuals with trisomies were physically mixed at a ratio of 2 ng of normal DNA and ~0.2 ng of Trisomy 21 DNA and normal peripheral white blood cell (WBC) samples. The mixtures were created to replicate typical fetal fractions in noninvasive prenatal testing (approximately 10%). Using polymorphisms in the LINE-amplicons, the trisomy admixture of the samples was estimated to range from 7.7% to 10.4%). Using a z threshold of 2.5, sensitivities (A) and specificities (B) were calculated for a range of read depths.

FIG. 49 shows an exemplary pseudocode to generate synthetics with one arm alteration.

FIG. 50 shows an exemplary pseudocode to generate synthetics with multiple arm alterations.

Figure 61:
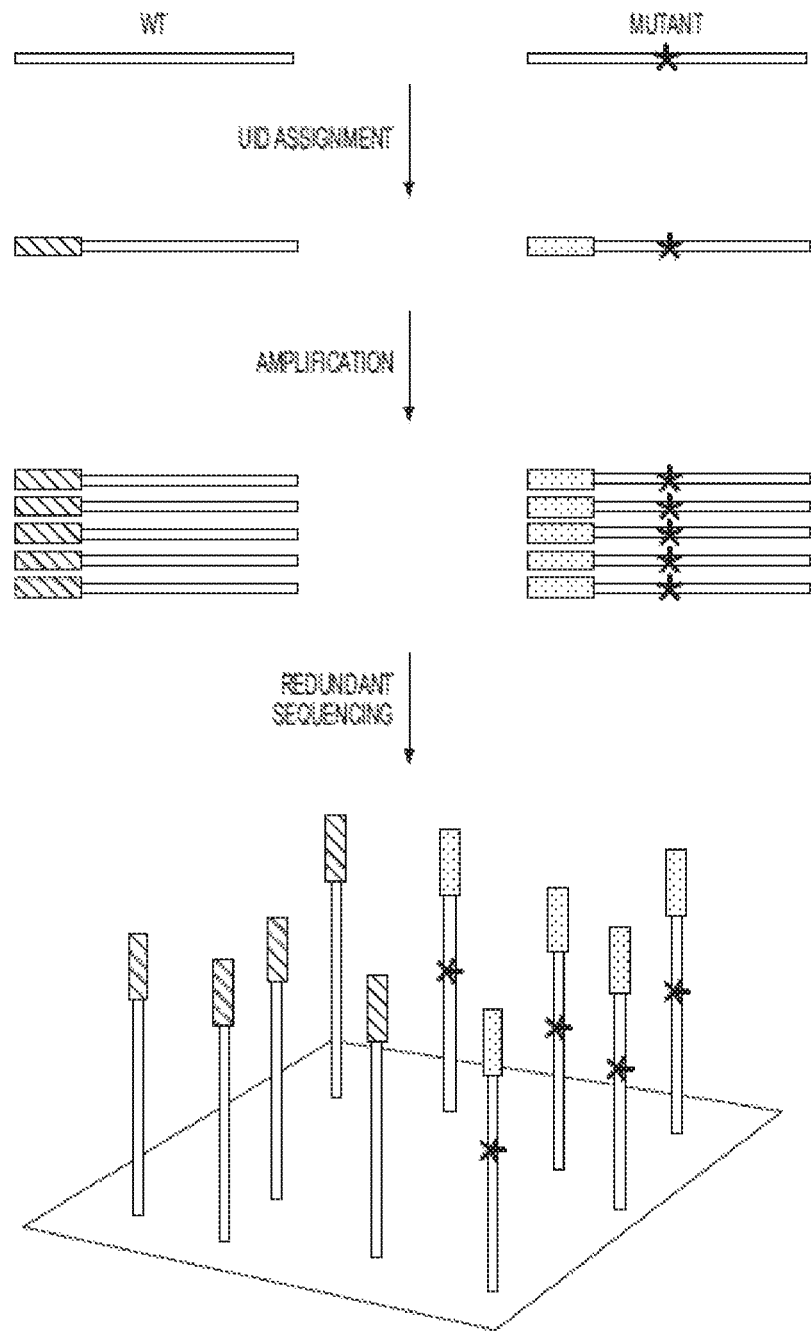
FIG. 61 contains a schematic showing elements of Safe-SeqS. In the first step, each fragment to be analyzed is assigned a unique identification (UID) sequence (metal hatch or stippled bars). In the second step, the uniquely tagged fragments are amplified, producing UID-families, each member of which has the same UID. A super-mutant is defined as a UID-family in which ≥95% of family members have the same mutation.

sequences (adhesive filled and light stippled bars), sequencing is performed and super-mutants are defined as in FIG. 61.

Figure 63:
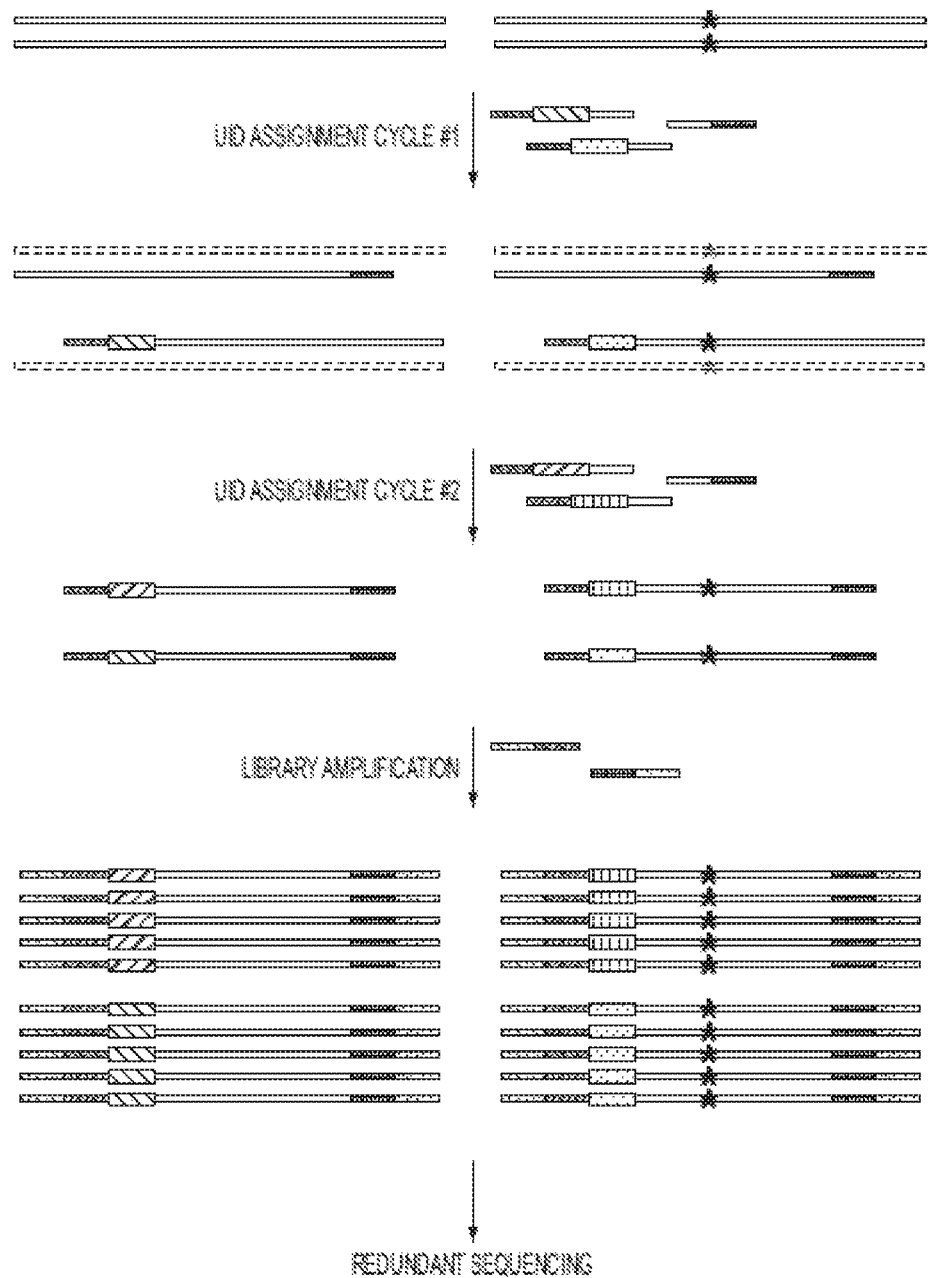

FIG. 63 contains a schematic showing an exemplary Safe-SeqS with exogenous UIDs. DNA (sheared or unsheared) is amplified with a set of gene-specific primers. One of the primers has a random DNA sequence (e.g., a set of 14 N's) that forms the unique identifier (UID; variously shaded bars), located 5' to its gene-specific sequence, and both have sequences that permit universal amplification in the next step (earth hatched and cross hatched bars). Two UID assignment cycles produce two fragments—each with a different UID—from each double-stranded template molecule, as shown. Subsequent PCR with universal primers, which also contain "grafting" sequences (adhesive filled and light stippled bars), produces UID-families which are directly sequenced. Super-mutants are defined as in the legend to FIG. 61.

FIG. 64 contains graphs showing single base substitutions identified by conventional and Safe-SeqS analysis. The exogenous UID strategy depicted in FIG. 63 was used to produce PCR fragments from the CTNNB1 gene of three normal, unrelated individuals. Each position represents one of 87 possible single base substitutions (3 possible substitutions/base×29 bases analyzed). These fragments were sequenced on an Illumina GA IIx instrument and analyzed in the conventional manner (A) or with Safe-SeqS (B). Safe-SeqS results are displayed on the same scale as conventional analysis for direct comparison; the inset is a magnified view. Note that most of the variants identified by conventional analysis are likely to represent sequencing errors, as indicated by their high frequency relative to Safe-SeqS and their consistency among unrelated samples.

Figure 65:
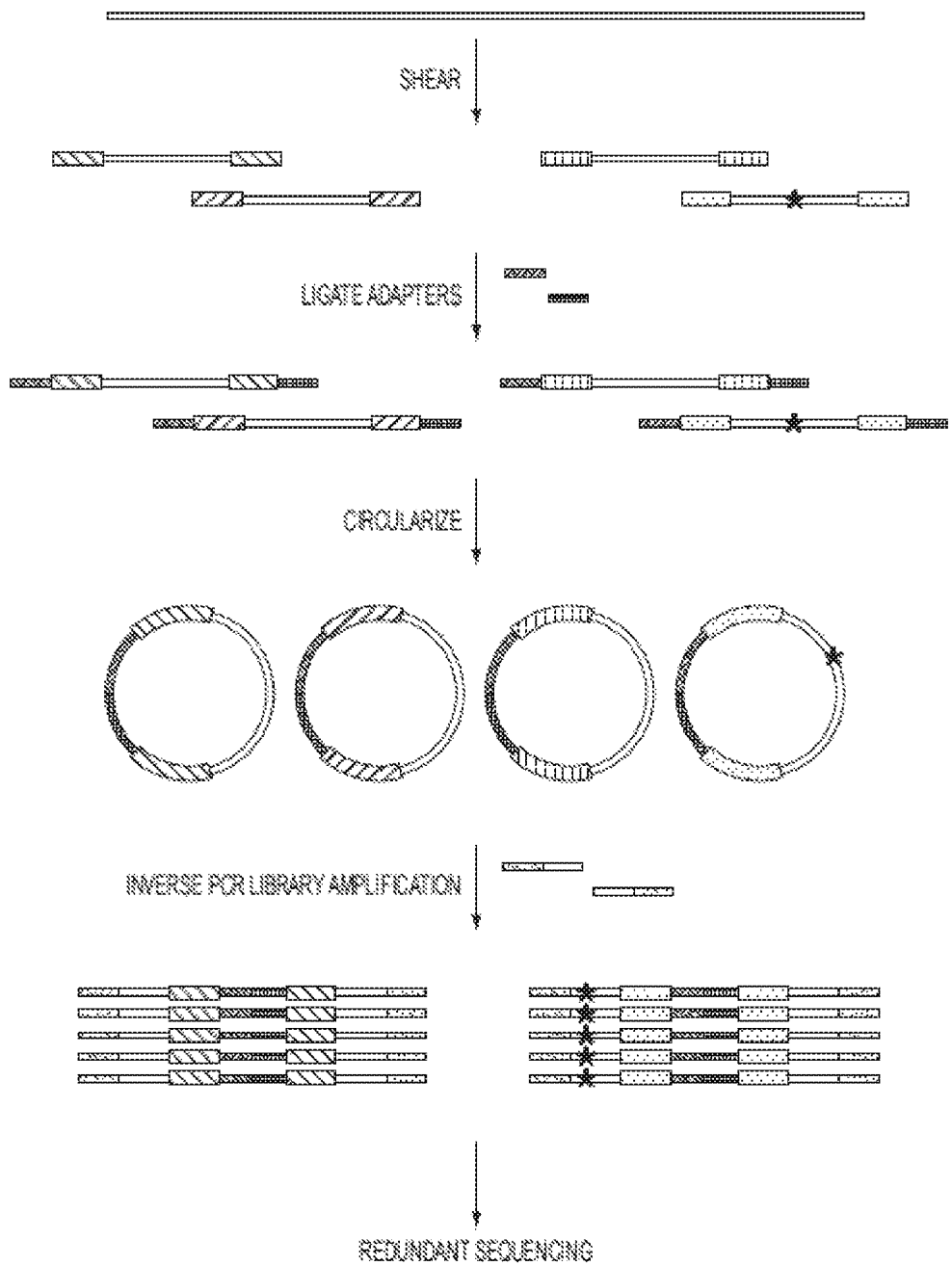

FIG. 65 contains a schematic showing an exemplary Safe-SeqS with endogenous UIDs plus inverse PCR. The sequence of the ends of each fragment produced by random shearing serve as unique identifiers (UIDs; variously shaded bars). These fragments are ligated to adapters (earth hatched and cross hatched bars) as in a standard Illumina library preparation. One uniquely tagged fragment is produced from each strand of the double-stranded template; only one strand is shown. Following circularization with a ligase, inverse PCR is performed with gene-specific primers that also contain 5' "grafting" sequences (adhesive filled and lightly stippled bars). This PCR produces UID-families which are directly sequenced. Super-mutants are defined as in FIG. 61.

Figure 66:
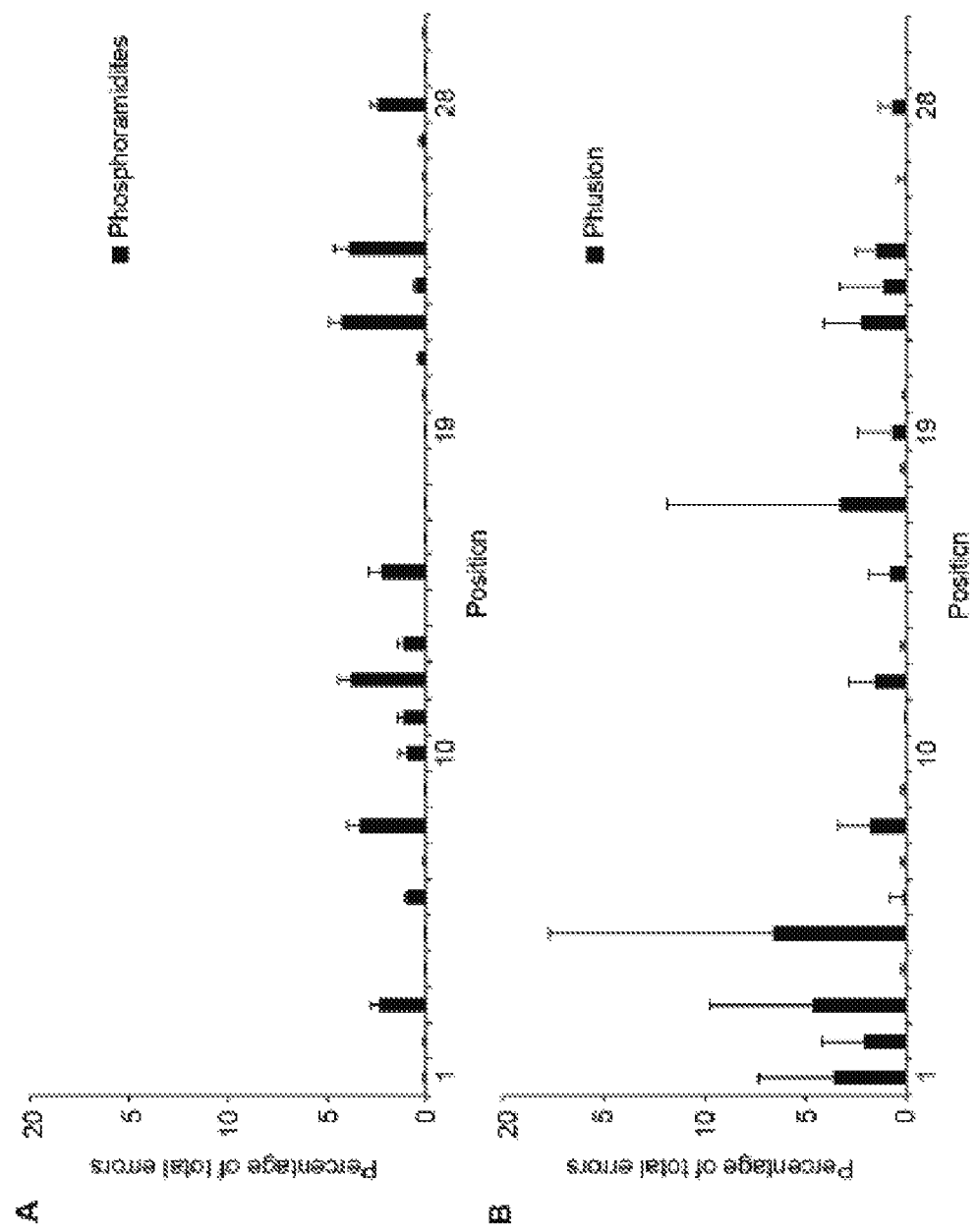

FIG. 66 contains graphs showing single base substitutions position vs. error frequency in oligonucleotides synthesized with phosphoramidites and Phusion. A representative portion of the same 31-base DNA fragment synthesized with phosphoramidites (A) or Phusion polymerase (B) was analyzed by Safe-SeqS. The means and standard deviations for seven independent experiments of each type are plotted. There was an average of 1,721±383 and 196±143 SBS super-mutants identified in the phosphoramidite-synthesized and Phusion-generated fragments, respectively. The y-axis indicates the fraction of the total errors at the indicated position. Note that the errors in the phosphoramidite-synthesized DNA fragment were consistent among the seven replicates, as would be expected if the errors were systematically introduced during the synthesis itself. In contrast, the errors in the Phusion-generated fragments appeared to be heterogeneous among samples, as expected from a stochastic process (Luria and Delbruck, 1943 *Genetics* 28:491-511).

Figure 67:
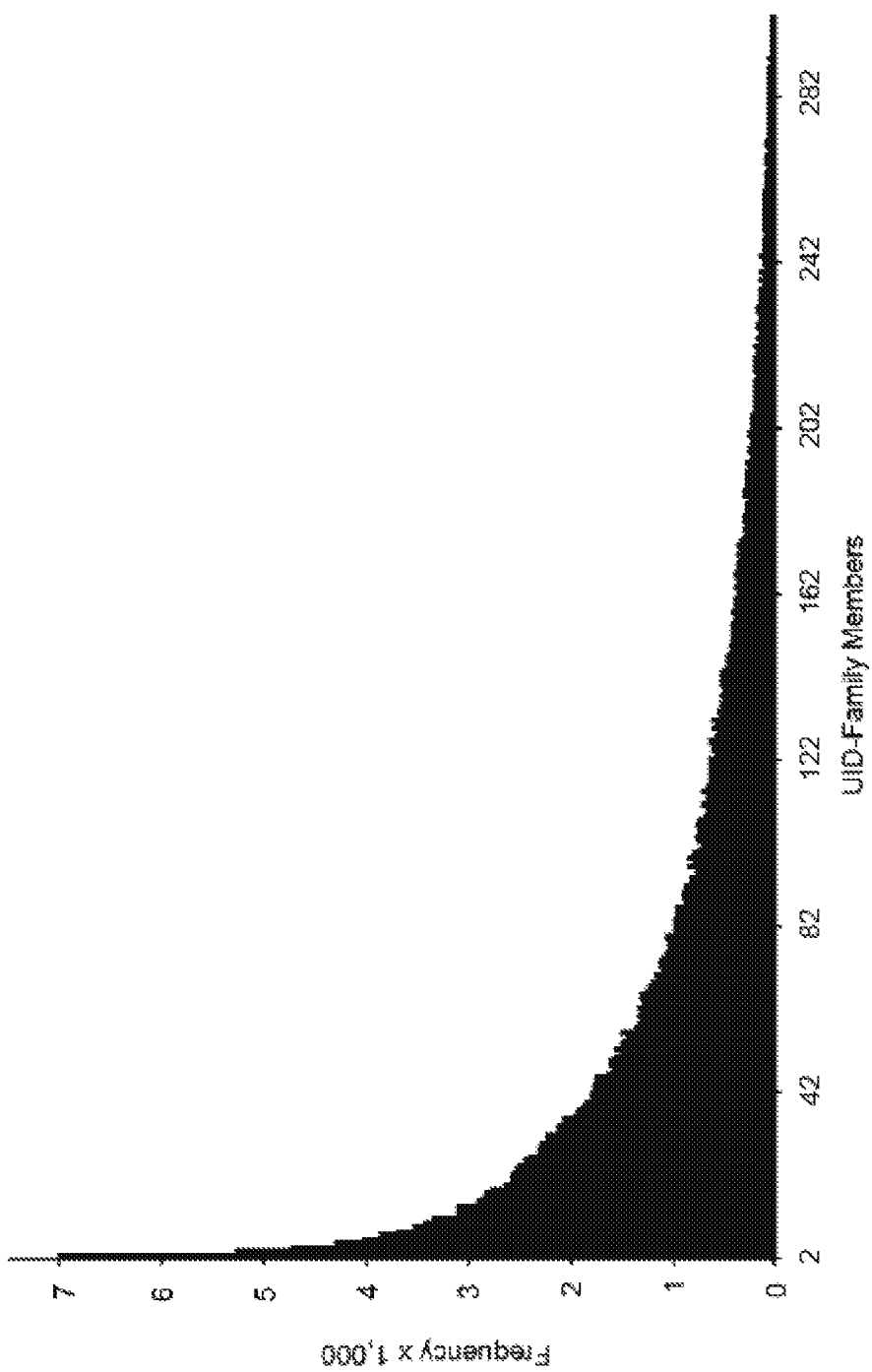
Figure 68A:
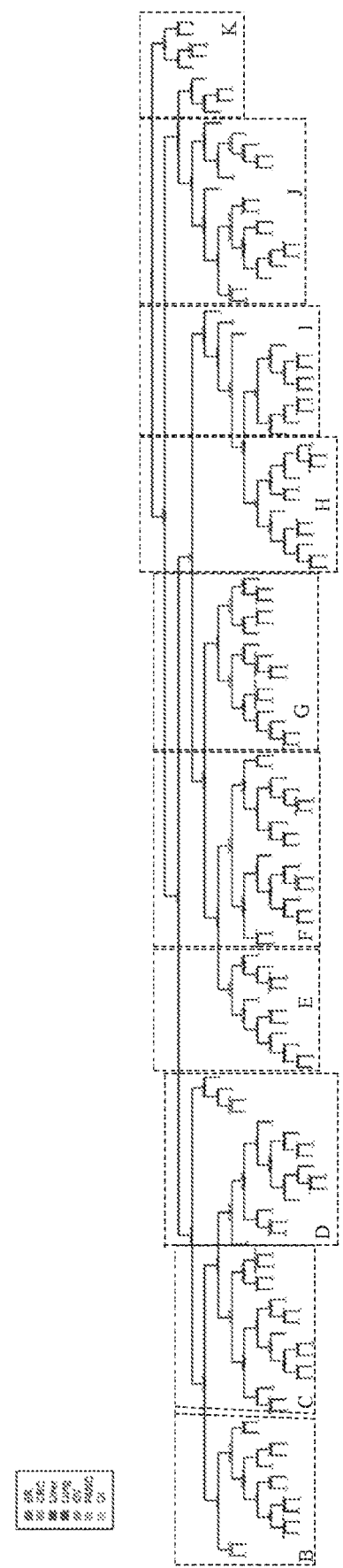
Figure 68B:
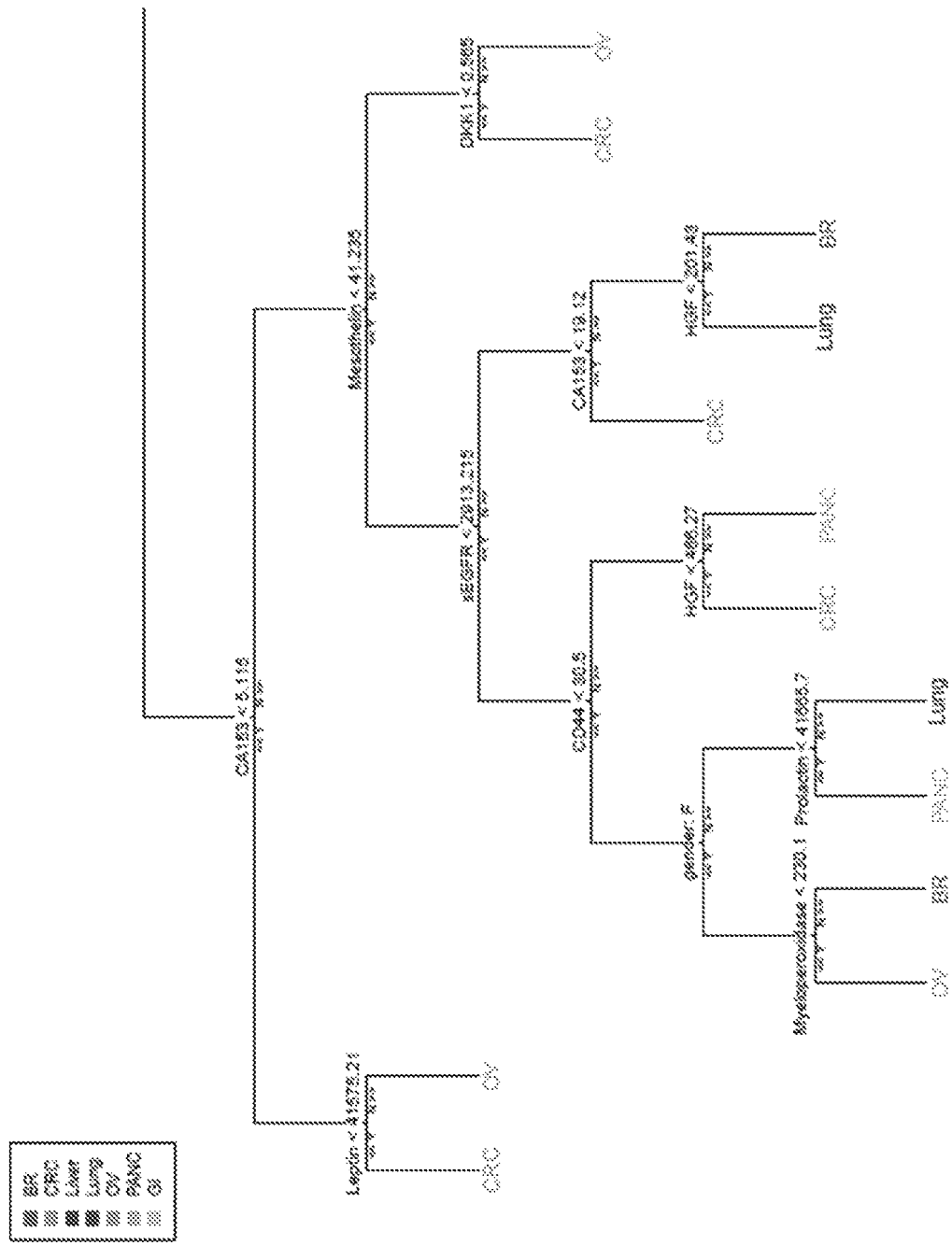
Figure 68C:
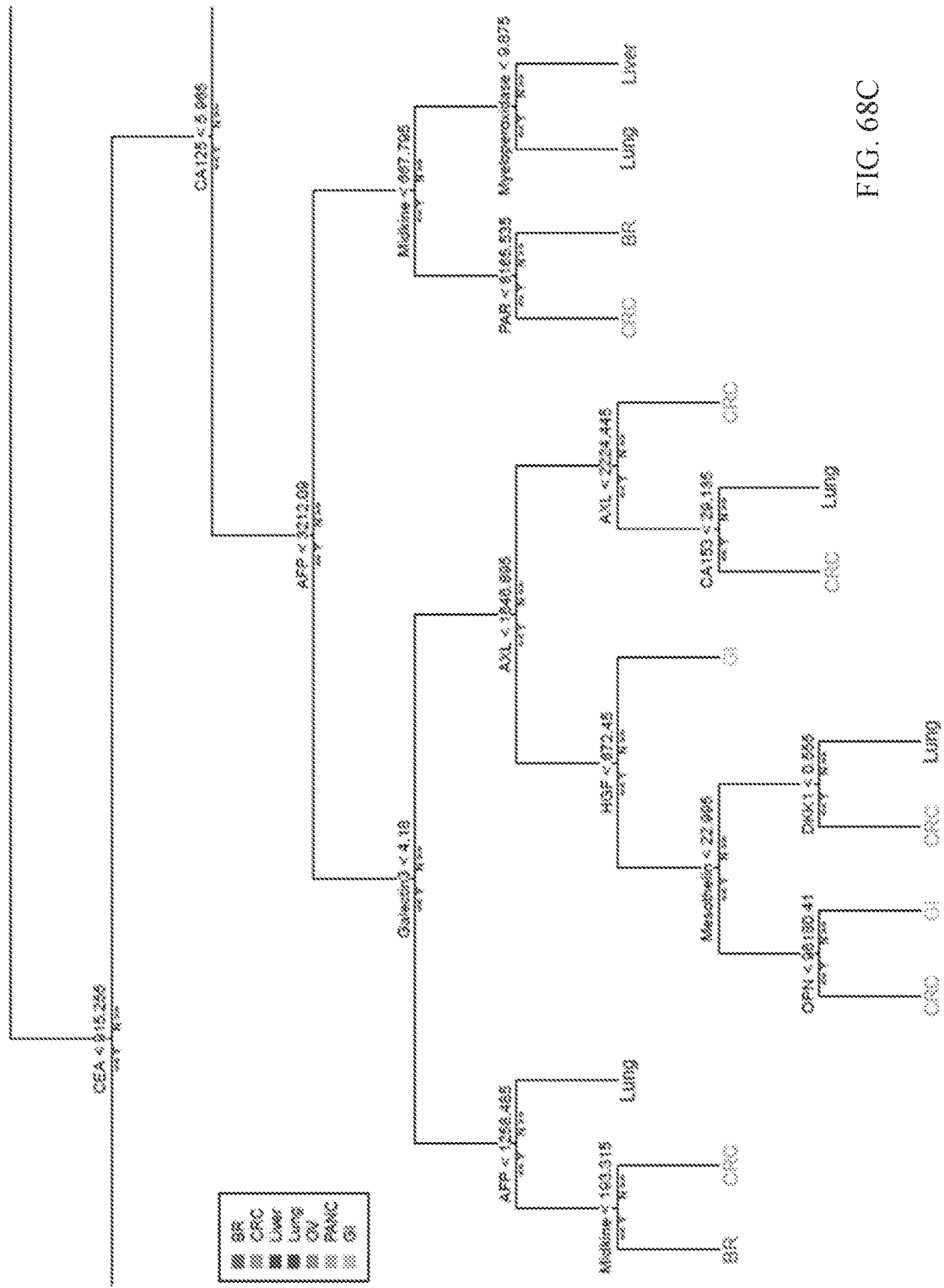
Figure 68D:
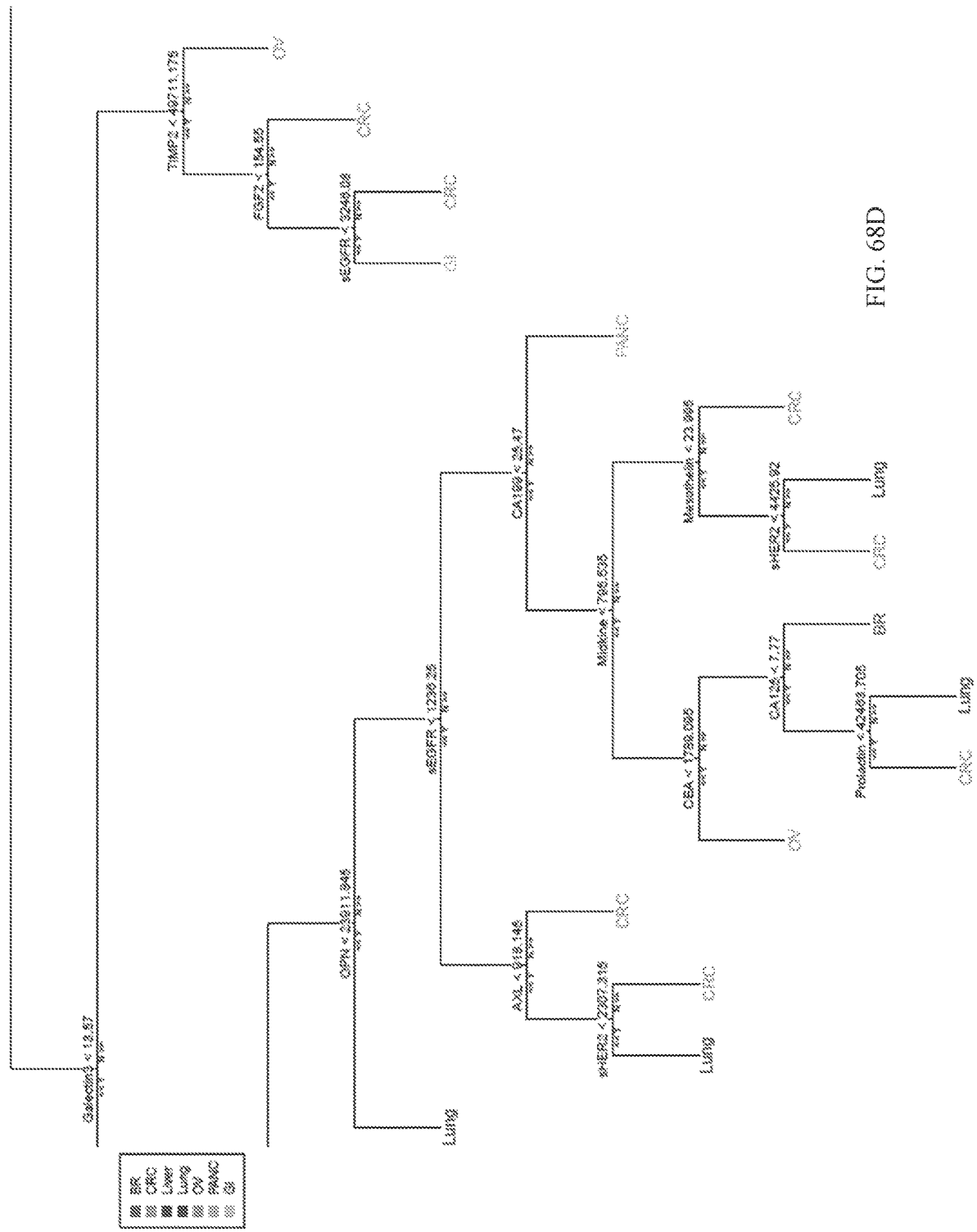
Figure 68E:
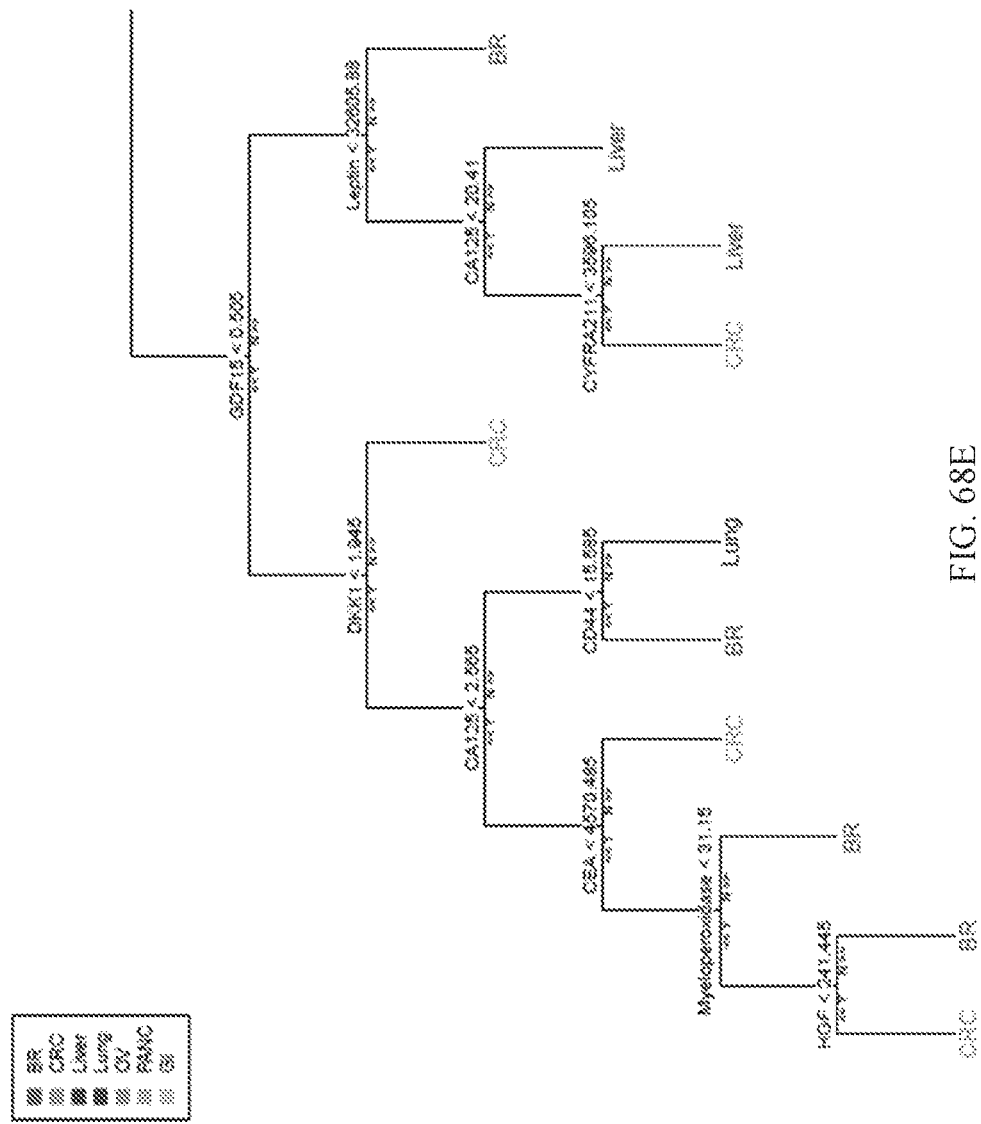
Figure 68F:
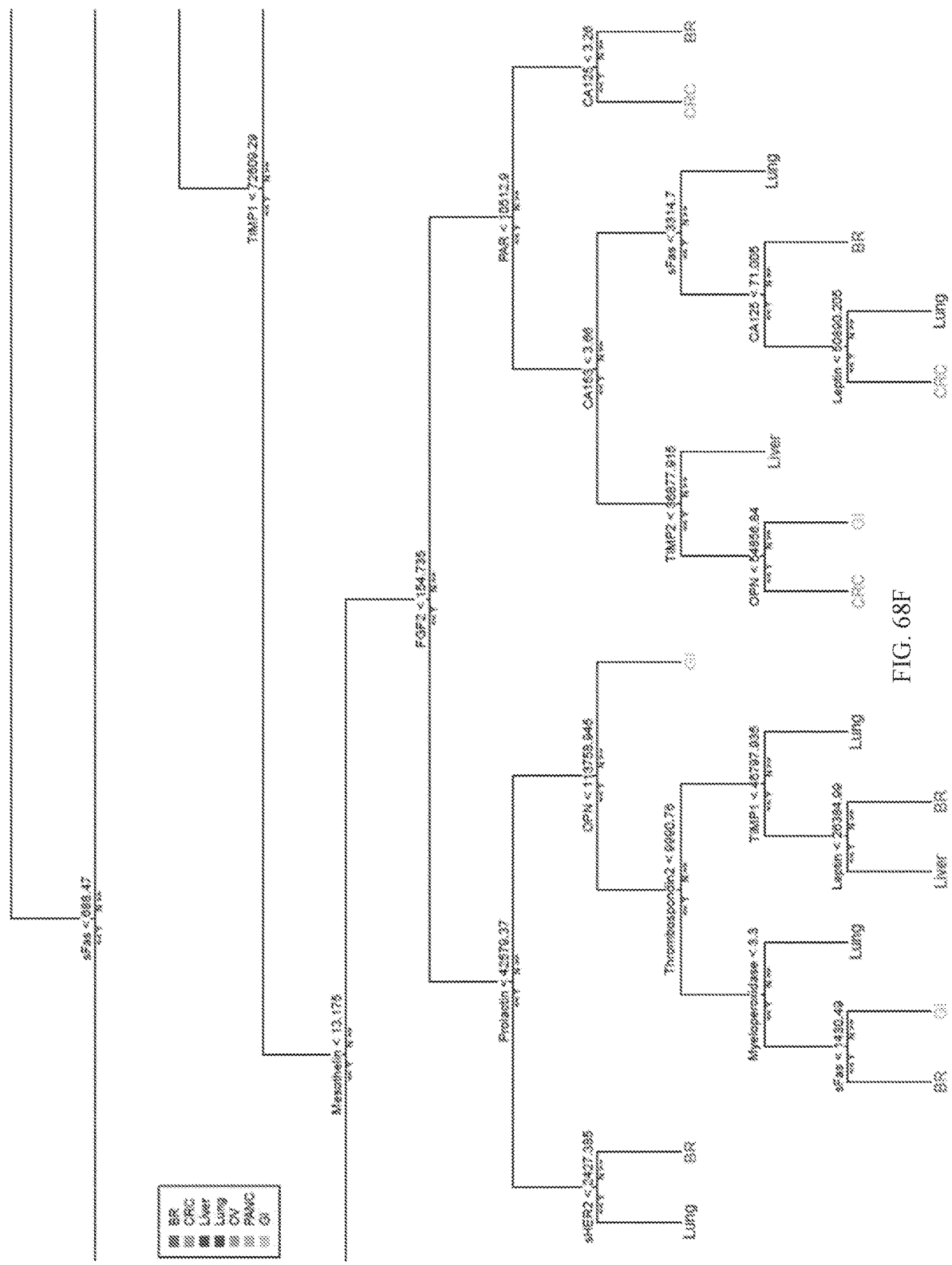
Figure 68G:
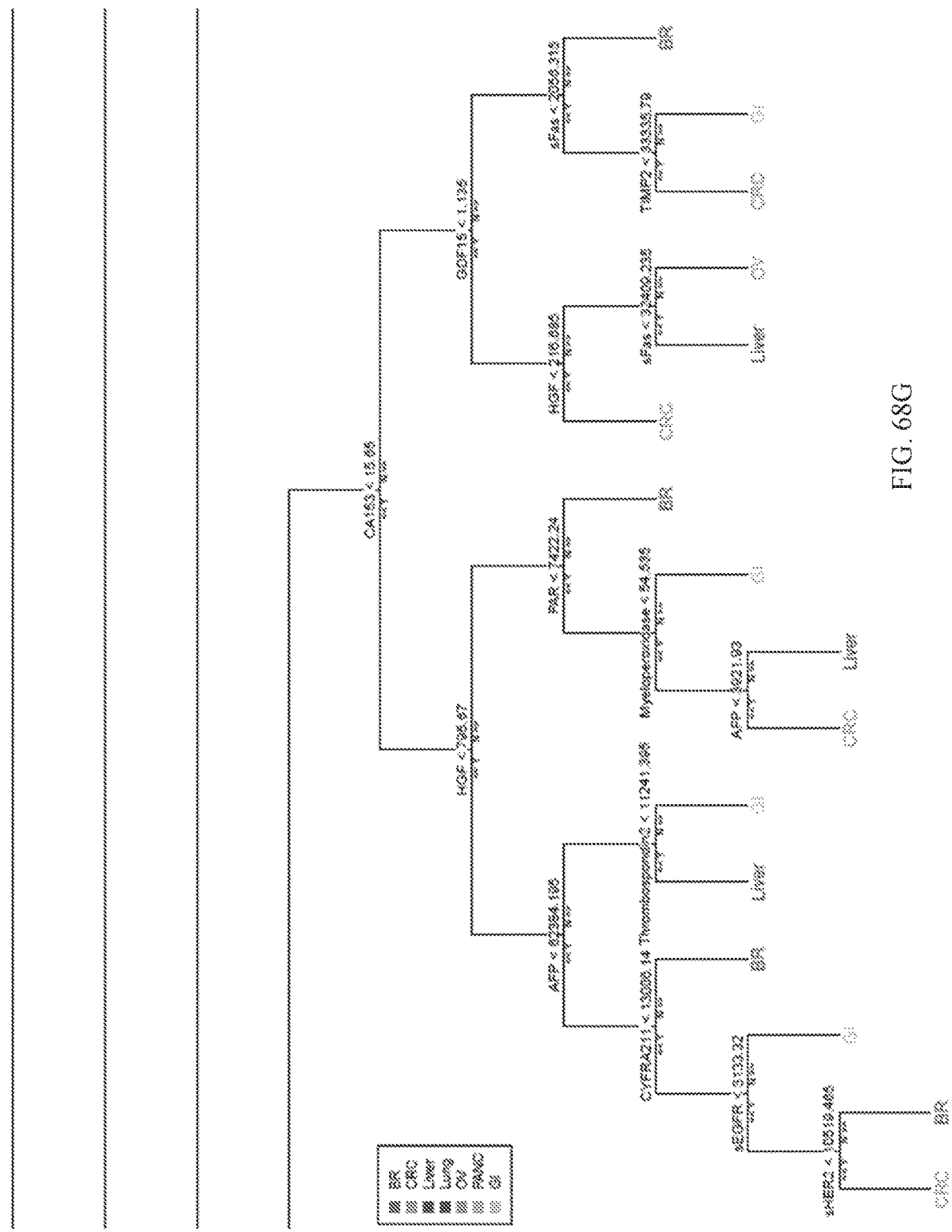
Figure 68H:
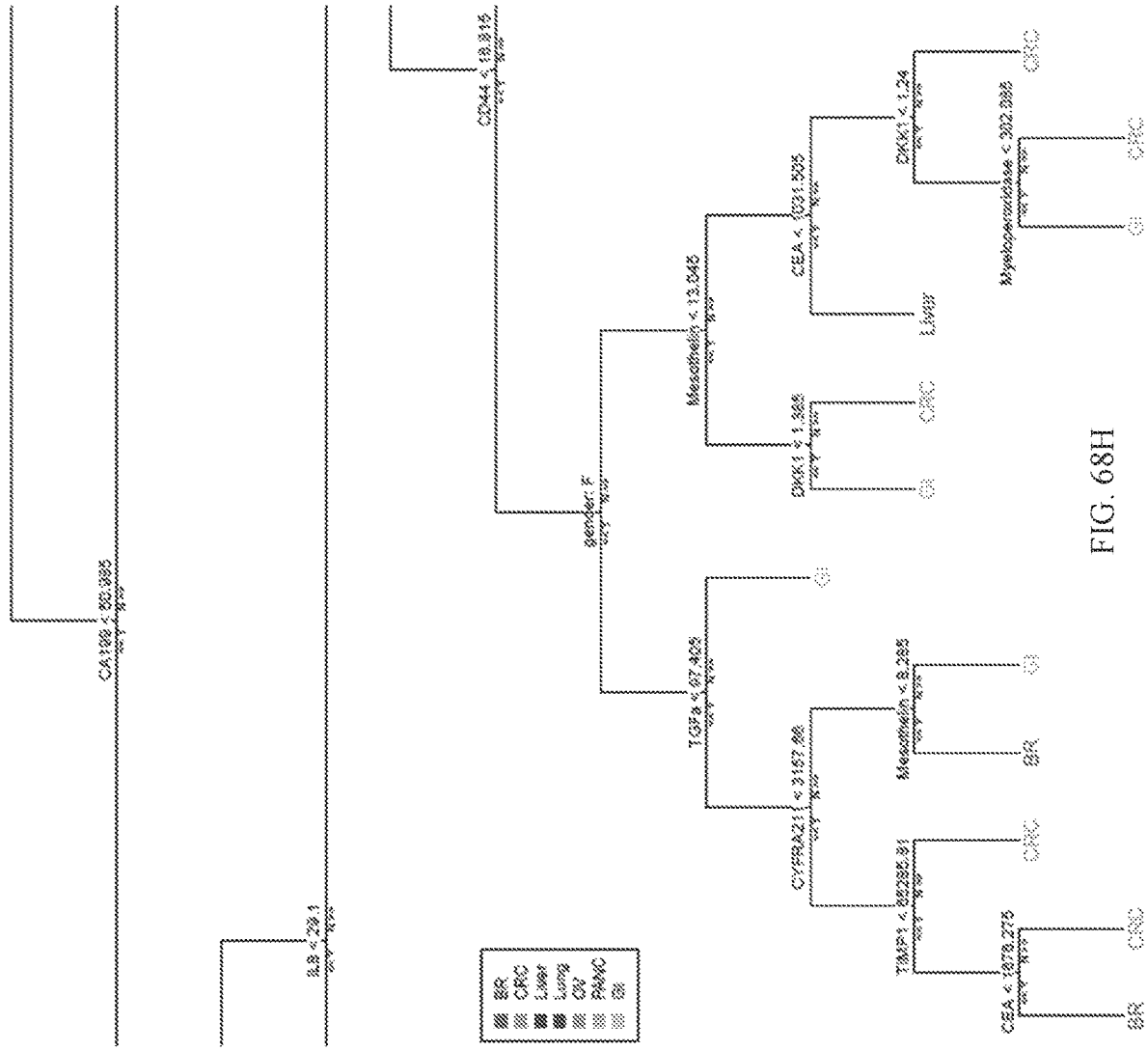
Figure 68I:
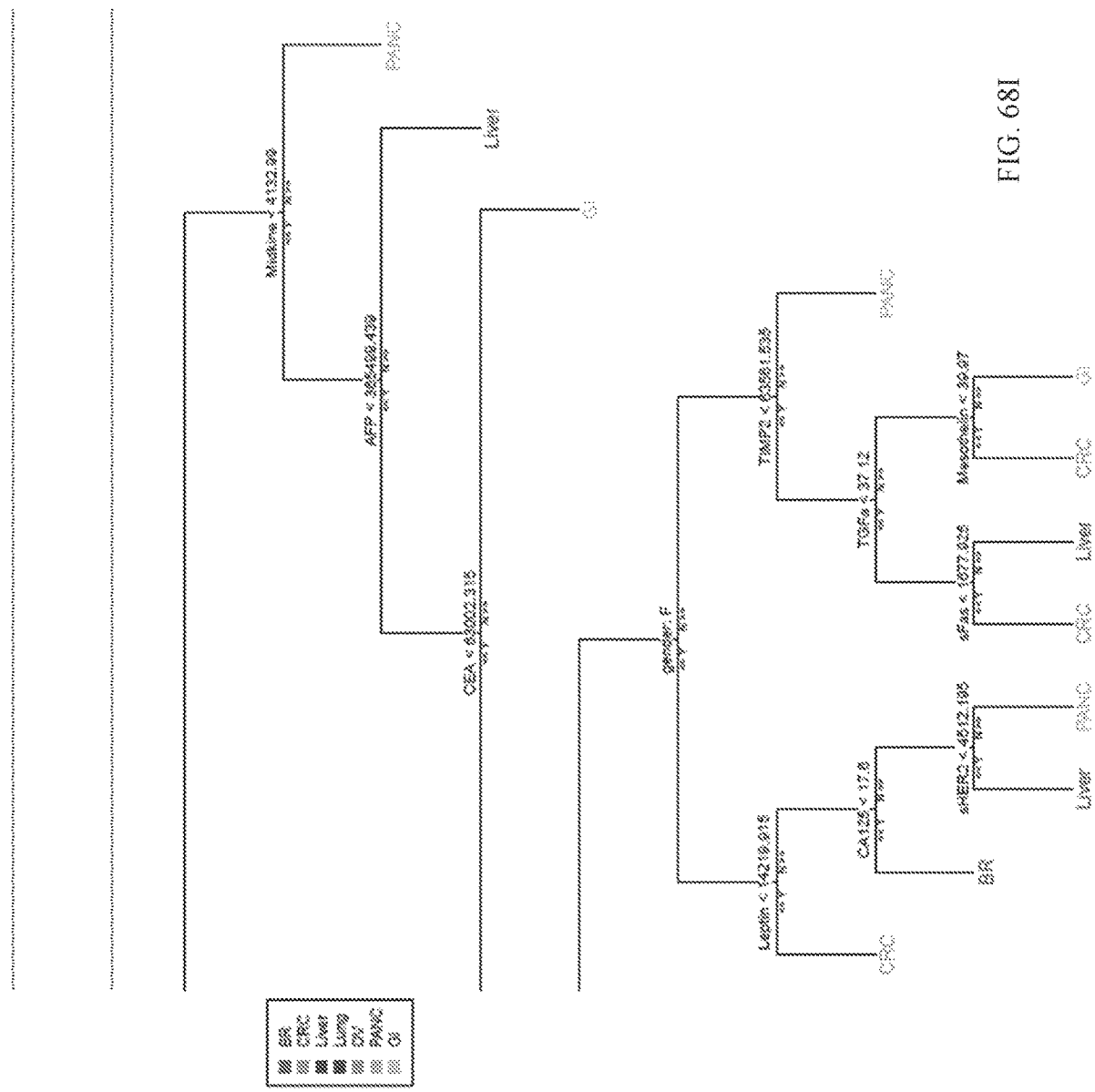
Figure 68J:
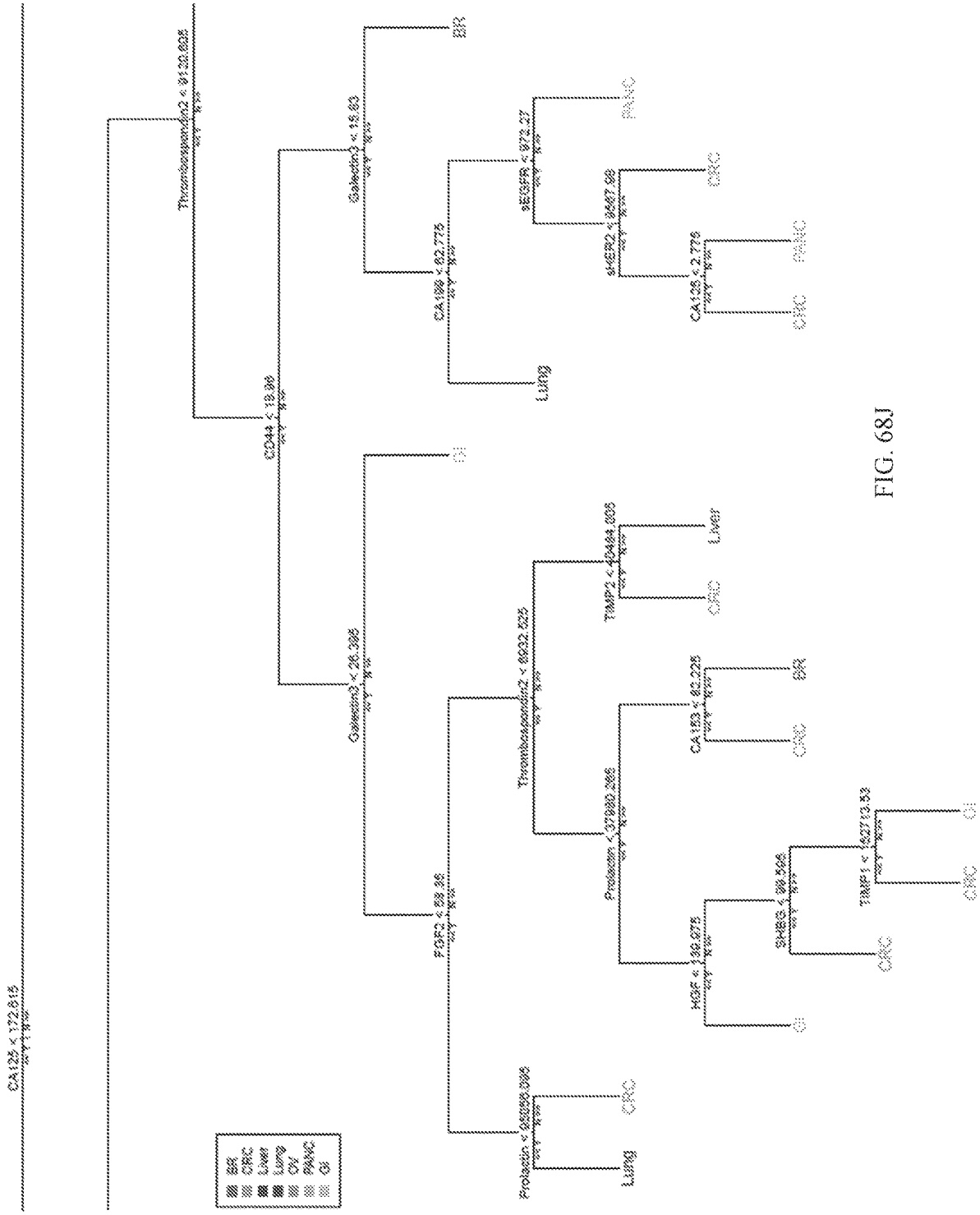
Figure 68K:
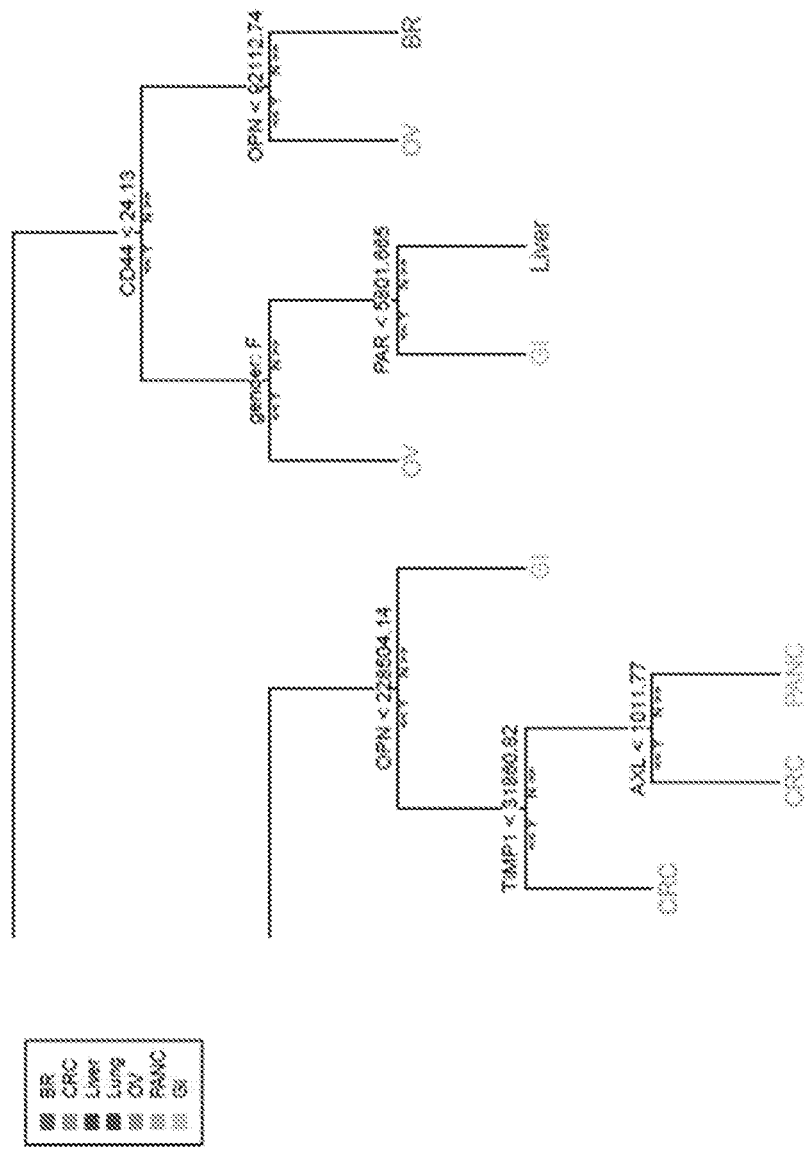

FIG. 67 contains a graph showing UID-family member distribution. The exogenous UID strategy depicted in FIG. 63 was used to produce PCR fragments from a region of CTNNB1 from three normal, unrelated individuals (Table 53); a representative example of the UID-families with ≤300 members (99% of total UID-families) generated from one individual is shown. The y-axis indicates the number of different UID-families that contained the number of family members shown on the x-axis.

FIG. 68 contains an exemplary Random Forest model tree for classification of tumor location. (A) shows the complete tree, and (B)—(K) contain magnified images of sections of the complete tree as indicated in (A).

Figure 69:
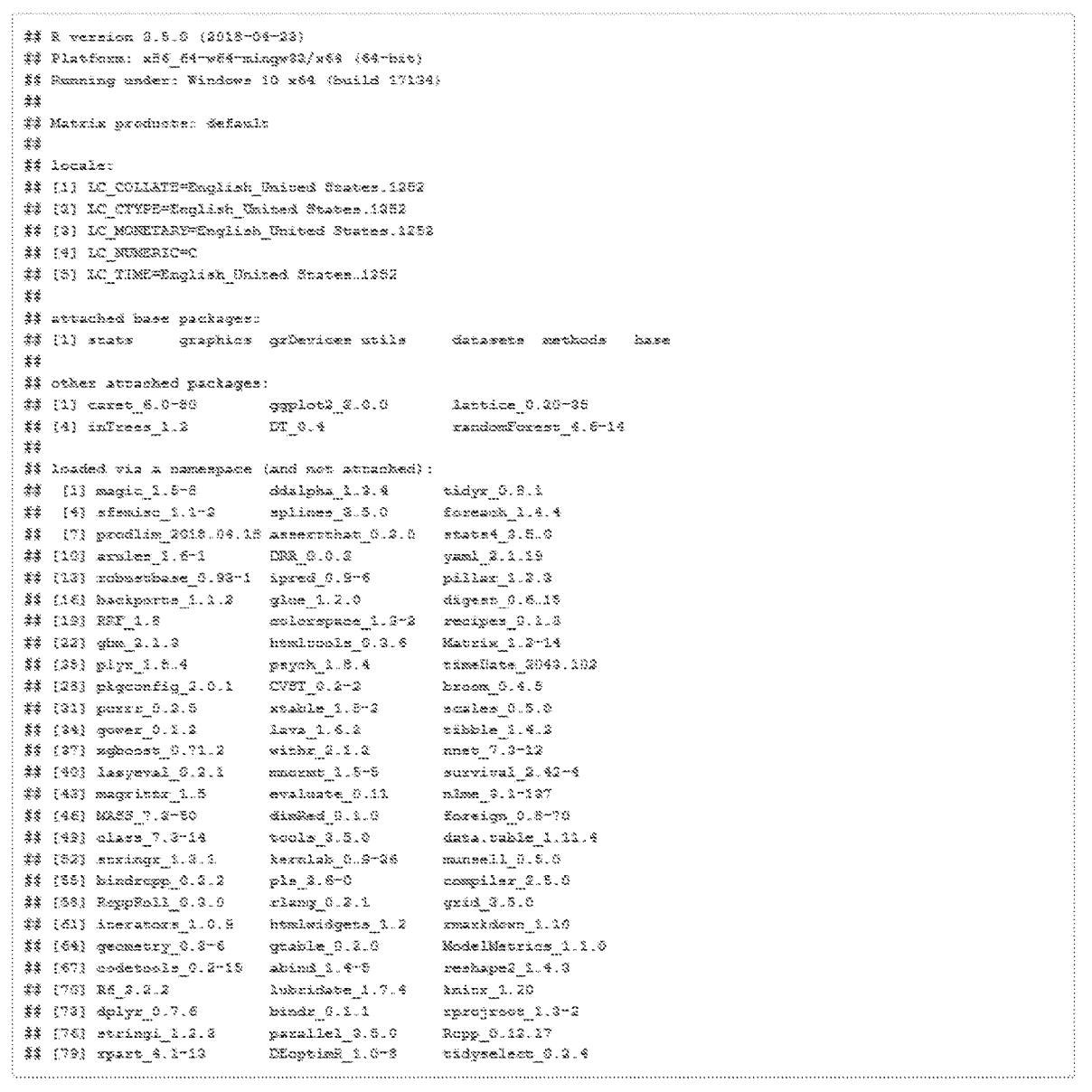
Figure 69:
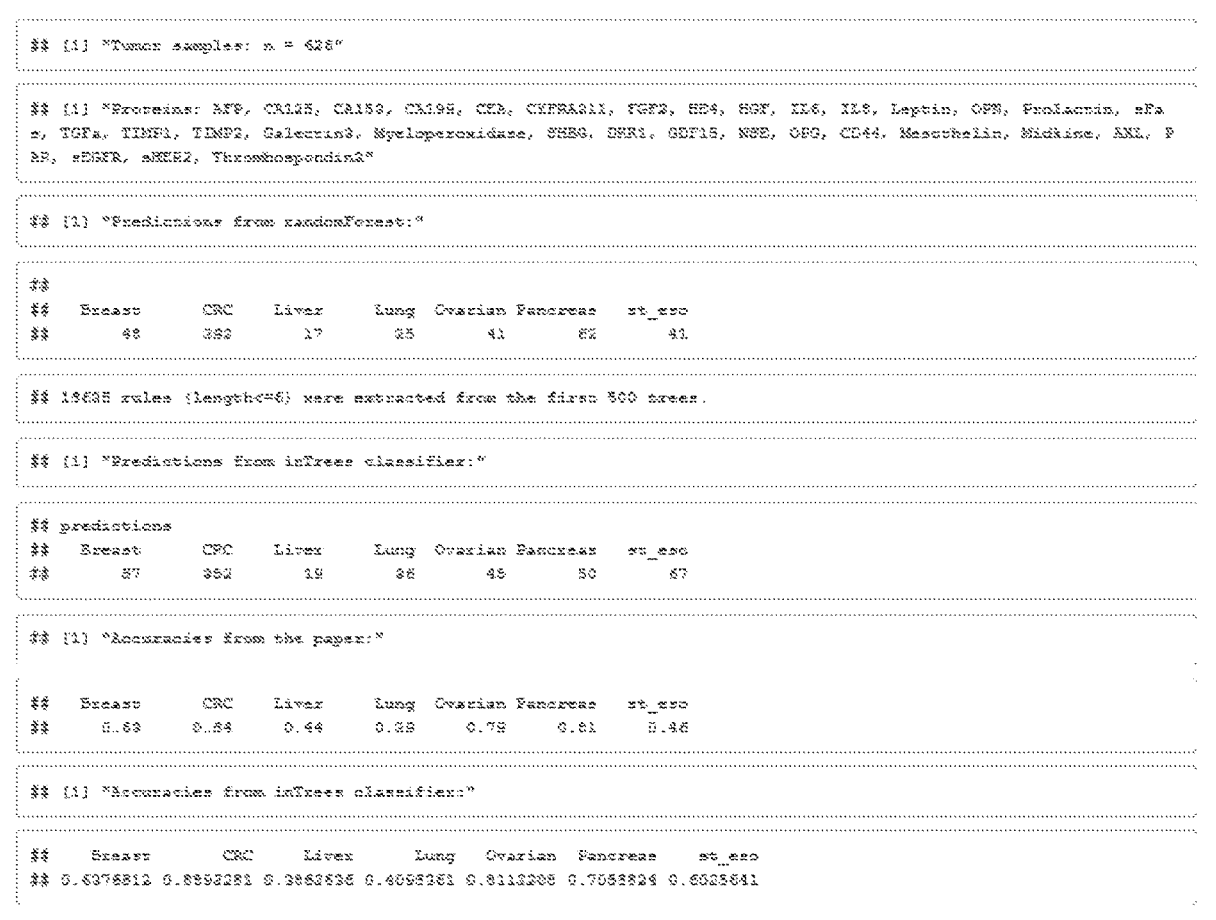

FIG. 69 contains exemplary rules for tissue recognition extracted from the random forest model. The randomForest function from the randomForest package (v4.6-14) was applied to protein data from the CancerSEEK project. The protein data have 33 proteins and the 626 tumor samples that were predicted correctly as cancer by CancerSEEK. The values of each protein were set to zero if they were less than the 25th quantile of values in the normal samples. To get the specific decision rules (Table 58), the inTrees package (v1.2) was applied to extract all rules of length less than or equal to 6 from all 500 trees created by randomForest. From this set of rules, using the functions (selectRuleRRF, buildLearner, applyLearner) from the inTrees package, relevant and non-redundant rules were selected, a classifier was created and applied to the data, and the final list of rules was extracted. This final list of rules performs similarly to the full random forest and it represents a good approximation of the full forest.

DETAILED DESCRIPTION

Definitions

As used herein, the word "a" before a noun represents one or more of the particular noun. For example, the phrase "a genetic alteration" encompasses "one or more genetic alterations."

As used herein, the term "about" means approximately, in the region of, roughly, or around. When used in conjunction with a numerical range, the term "about" modifies that range by extending the boundaries above and below the numerical values set forth. In general, the term "about" is used herein to modify a numerical value above and below the stated value by a variance of 10%.

As used herein, the term "aneuploidy" refers to the condition of having less than or more than the natural diploid number of chromosomes, or any deviation from euploidy.

As used herein in the context of circulating tumor DNA or cell-free DNA, the phrase "derived from a gene" means that the circulating tumor DNA is shed from tumor cells (e.g., tumor cells that have lysed or otherwise died). For example, circulating tumor DNA "derived from a KRAS gene" means that the circulating tumor DNA was originally present in a tumor cell. When detecting a mutation that is present in circulating tumor DNA derived from a gene, it is not necessary to have first identified the mutation in the tumor cell itself.

As used herein, the phrases "genetic biomarker" and "genetic marker" refer to a nucleic acid that is characteristic, alone in combination with other genetic or other biomarkers, of cancer in a subject. A genetic biomarker can include a modification (e.g., a mutation) in a gene. Examples of modifications include, without limitation, single base substitutions, insertions, deletions, indels, translocations, and copy number variations. In some embodiments, a genetic biomarker includes a modification (e.g., an inactivating modification) in a tumor suppressor gene. In some embodiments, a genetic biomarker includes a modification (e.g., an activating modification) in an oncogene. Various genetic biomarkers and genetic biomarker panels are described in more detail herein.

As used herein, the terms "mutation", "genetic modification", and "genetic alteration" are used interchangeably to indicate a change in a wild type nucleic acid sequence. For example, in some embodiments, methods of detecting a mutation in cell-free DNA (e.g., ctDNA) are described herein. It is to be understood that such methods can be interchangeably described as detecting mutations, genetic modifications, or genetic alterations.

As used herein, the phrases "protein biomarker", "protein marker", "peptide biomarker", and "peptide marker" refer to a protein that is characteristic, alone in combination with other protein or other biomarkers, of cancer in a subject. In some embodiments, a protein biomarker includes an elevated level of the protein in a subject (e.g., a subject having cancer regardless of whether the subject is known to have cancer) as compared to a reference subject that does not have cancer. In some embodiments, a protein biomarker includes a decreased level of the protein in a subject (e.g., a subject having cancer regardless of whether the subject is known to have cancer) as compared to a reference subject that does not have cancer. As used herein, the phrase "detecting a protein biomarker" can refer to detecting a level (e.g., an increased level or a decreased level) of the protein biomarker. Various protein biomarkers and protein biomarker panels are described in more detail herein. In some embodiments, peptides that are distinct from a protein biomarker are used in methods provided herein.

As used herein with reference to protein biomarkers, the phrase "elevated level" refers to a level of the protein biomarker that is greater than a reference level of the protein biomarker typically observed in a sample (e.g., a reference sample) from a healthy subject (e.g., a subject that does not exhibit a particular disease or condition). In some embodiments, a reference sample can be a sample obtained from a subject (e.g., a different or reference subject) that does not have a cancer. For example, for a protein biomarker associated with colorectal cancer, a reference sample can be a sample obtained from a different or reference subject that does not have colorectal cancer. In some embodiments, a reference sample can be a sample obtained from the same subject in which the elevated level of a protein biomarker is observed, where the reference sample was obtained prior to onset of the cancer. In some embodiments, such a reference sample obtained from the same subject is frozen or otherwise preserved for future use as a reference sample. In some embodiments, when reference samples have undetectable levels of a protein biomarker, an elevated level can be any detectable level of the protein biomarker. It will be appreciated that levels from comparable samples can be used when determining whether or not a particular level is an elevated level.

As used herein with reference to protein biomarkers, the phrase "reference level" refers to the level of the protein biomarker that is typically present in a healthy subject (e.g., a subject that does not exhibit a particular disease or condition). A reference level of a protein biomarker can be a level that is present in a reference subject that does not exhibit a disease or condition (e.g., cancer). For example, for a protein biomarker associated with colorectal cancer, a reference sample can be a sample obtained from a subject that does not have colorectal cancer. As another example, a reference level of a protein biomarker can be a level that is present in a subject prior to the onset of the disease or condition (e.g., cancer) in that subject. In some embodiments, a disease or condition can be identified in a subject when the measured or detected level of one or more protein biomarkers is higher than reference level(s) of the one or more protein biomarkers.

As used herein, the term "sensitivity" refers to the ability of a method to correctly identify or diagnose the presence of a disease in a subject (e.g., the sensitivity of a method can be described as the ability of the method to identify the true positive rate or probability of detecting a condition in a subject). For example, when used in reference to any of the variety of methods described herein that can detect the presence of cancer in a subject, a high sensitivity means that the method correctly identifies the presence of cancer in the subject a large percentage of the time. For example, a method described herein that correctly detects the presence of cancer in a subject 95% of the time the method is performed is said to have a sensitivity of 95%. In some embodiments, a method described herein that can detect the presence of cancer in a subject provides a sensitivity of at least 80% (e.g., at least 80%, 85%, 90%, 91%, 92%, 93%, 94%, 95%, 96%, 97%, 98%, 99%, 99.5%, or higher). In some embodiments, methods provided herein that include detecting the presence of one or more members of two or more classes of biomarkers (e.g., genetic biomarkers and/or protein biomarkers) provide a higher sensitivity than methods that include detecting the presence of one or more members of only one class of biomarkers.

As used herein, the term "specificity" refers to the ability of a method to correctly reject the presence of a disease in a subject (e.g., the specificity of a method can be described as the ability of the method to identify the true negative rate or probability of correctly determining that a condition does not exist in a subject. For example, when used in reference to any of the variety of methods described herein that can detect the presence of cancer in a subject, a high specificity means that the method correctly identifies the absence of cancer in the subject a large percentage of the time (e.g., the method does not incorrectly identify the presence of cancer in the subject a large percentage of the time). For example, a method described herein that correctly detects the absence of cancer in a subject 95% of the time the method is performed is said to have a specificity of 95%. In some embodiments, a method described herein that can detect the absence of cancer in a subject provides a specificity of at least 80% (e.g., at least 80%, 85%, 90%, 91%, 92%, 93%, 94%, 95%, 96%, 97%, 98%, 99%, 99.5%, or higher). In some embodiments, methods provided herein that include detecting the presence of one or more members of two or more classes of biomarkers (e.g., genetic biomarkers and/or protein biomarkers) provide a higher specificity than methods that include detecting the presence of one or more members of only one class of biomarkers.

As used herein, the term "subject" is used interchangeably with the term "patient" and means a vertebrate, including any member of the class mammalia, including humans, domestic and farm animals, and zoo, sports or pet animals, such as mouse, rabbit, pig, sheep, goat, cattle, horse (e.g., race horse), and higher primates. In some embodiments, the subject is a human. In some embodiments, the subject has a disease. In some embodiments, the subject has cancer. In some embodiments, the subject is a human harboring a cancer cell. In some embodiments, the subject is a human harboring a cancer cell, but is not known to harbor the cancer cell. In some embodiments, the subject has a viral disease. In some embodiments, the subject has a bacterial disease. In some embodiments, the subject has a fungal disease. In some embodiments, the subject has a parasitic disease. In some embodiments, the subject has asthma. In some embodiments, the subject has an autoimmune disease. In some embodiments, the subject has graft vs. host disease.

As used herein, the term "treatment" is used interchangeably with the phrase "therapeutic intervention."

Methods of testing DNA isolated or obtained from white blood cells (e.g., white blood cell clones arising during age-associated clonal hematopoiesis (e.g., clonal hematopoietic expansion, also known as clonal hematopoiesis of indeterminate potential or CHIP) or myelodysplasia) for the presence or absence of a genetic mutation that is associated with cancer in order to determine whether that genetic alteration originates from a cancer cell in the subject are generically described herein as "verifying a genetic alteration against white blood cells", "verifying a genetic alteration against DNA from white blood cells", "white blood cell verification", and similar phrases.

Overview

In general, methods and materials for detecting or identifying the presence of cancer in a subject with high sensitivity and specificity as compared to conventional methods of identifying the presence of cancer in a subject are provided herein. In some embodiments, methods provided herein for identifying the presence of cancer in a subject with high sensitivity and specificity are performed on a liquid sample(s) obtained from the subject (e.g., blood, plasma, or serum), whereas conventional methods of identifying the presence of cancer in a subject do not achieve the level of sensitivity, the level of specificity, or both when performed on a liquid sample obtained from the subject. In some embodiments, methods provided herein for identifying the presence of cancer in a subject with high sensitivity and specificity are performed prior to having determined that the subject already suffers from cancer, prior to having determined that the subject harbors a cancer cell, and/or prior to the subject exhibiting symptoms associated with cancer. Thus, in some embodiments, methods provided herein for identifying the presence of cancer in a subject with high sensitivity and specificity are used as a first-line detection method, and not simply as a confirmation (e.g., an "overcall") of another detection method that the subject has cancer.

In some embodiments, methods and materials provided herein provide high sensitivity in the detection or diagnosis of cancer (e.g., a high frequency or incidence of correctly identifying a subject as having cancer). In some embodiments, methods and materials provided herein provide a sensitivity of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. In some embodiments, methods and materials provided herein provide high sensitivity in detecting a single type of cancer. In some embodiments, methods and materials provided herein provide high sensitivity in detecting two or more types of cancers. Any of a variety of cancer types can be detected using methods and materials provided herein (see, e.g., the section entitled "Cancers"). In some embodiments, cancers that can be detected using methods and materials provided herein include pancreatic cancer. In some embodiments, cancers that can be detected using methods and materials provided herein include liver cancer, ovarian cancer, esophageal cancer, stomach cancer, pancreatic cancer, colorectal cancer, lung cancer, or breast cancer. In some embodiments, cancers that can be detected using methods and materials provided herein include cancers of the female reproductive tract (e.g., cervical cancer, endometrial cancer, ovarian cancer, or fallopian tubal cancer). In some embodiments, cancers that can be detected using methods and materials provided herein include bladder cancer or upper-tract urothelial carcinomas.

In some embodiments, methods and materials provided herein provide high specificity in the detection or diagnosis of cancer (e.g., a low frequency or incidence of incorrectly identifying a subject as having cancer when that subject does not have cancer). In some embodiments, methods and materials provided herein provide a specificity of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. As will be understood by those of ordinary skill in the art, a specificity of 99% means that only 1% of subjects that do not have cancer are incorrectly identified as having cancer. In some embodiments, methods and materials provided herein provide high specificity in detecting a single cancer (e.g., there is a low probability of incorrectly identifying that subject as having that single cancer type). In some embodiments, methods and materials provided herein provide high specificity in detecting two or more cancers (e.g., there is a low probability of incorrectly identifying that subject as having those two or more cancer types).

As will be appreciated by those of ordinary skill in the art, an appropriate sensitivity or specificity in the detection or diagnosis of cancer can be chosen based on a variety of factor. As one non-limiting example, a method designed to provide a lower specificity in the detection or diagnosis of cancer can be designed to have an increased sensitivity. As another non-limiting example, a method designed to provide an increased specificity in the detection or diagnosis of cancer can be designed to have a lower sensitivity. In some embodiments, even a low sensitivity can be advantageous (e.g., in screening a population that is not normally screened). In some embodiments, in populations where cancer (e.g., a particular type of cancer) is prevalent, a method to detect or diagnose the presence of cancer can be designed to have a relatively high sensitivity, even at the cost of decreased specificity. In some embodiments, the sensitivity and specificity of various detection methods provided herein is determined based on the prevalence of the disease in a specific patient population. In example, screening tests for a general patient population not known to have cancer can be chosen to have high specificity (so as to eliminate false positive diagnoses and unnecessary further diagnostic testing and/or monitoring). As another example, screening tests for high risk populations (e.g., populations in which the risk of having or developing cancer is higher than the general population overall, e.g., due to the population engaging or having engaged in in risky behaviors, having risky family histories, experiencing or having experienced risky environments, and the like) cancer can be chosen to have high sensitivity (in order to increase the provide greater certainty of detecting a cancer that is present, even at the expense of additional further diagnostic testing and/or monitoring that may not be appropriate for the general population). As one non-limiting example, a test with 90% sensitivity and 95% specificity will have positive predictive value (PPV) of 15% and a negative predictive value (NPV) of >99% in a population with prevalence of 0.01%, while both predictive values can be greater than 99% if the prevalence was 40% (high risk population). PPV can be calculated as follows: #true positives (TP)/(#true positives+#false positives). PPV can also be calculated as follows: (sensitivity×prevalence)/(sensitivity×prevalence)+((1−specificity)×(1−prevalnce)). NPV can be calculated as follows: #true negatives/# of negative calls. PPV can also be calculated as follows: specificity×(1−prevalence)/((1−sensitivity)×prevalence)+ (specificity×(1−prevalence). See, e.g., Lalkhen and Mccluskey, Clinical tests: sensitivity and specificity, Continuing Education in Anaesthesia, Critical Care & Pain, Volume 8, 2008, incorporated herein by reference in its entirety.

Methods of Detecting

Provided herein are methods and materials for detecting the presence of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from a subject. In some embodiments, the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments, the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of both simultaneous and sequential testing for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include detecting the presence of one or more members of one or more classes of biomarkers in a sample obtained from the subject further include detecting the presence of aneuploidy in a sample obtained from the subject. For example, methods that include detecting the presence of one or more members of a class of genetic biomarkers in a sample obtained from a subject can further include detecting the presence of aneuploidy in a sample obtained from the subject (e.g., the same sample or two different samples from the subject). As another example, methods that include detecting the presence of one or more members of a class of protein biomarkers in a sample obtained from a subject can further include detecting the presence of aneuploidy in a sample obtained from the subject (e.g., the same sample or two different samples from the subject). In some embodiments, methods that include detecting both the presence of one or more members of a class of genetic biomarkers and detecting the presence of one or more members of a class of protein biomarkers in a sample obtained from a subject can further include detecting the presence of aneuploidy in a sample obtained from the subject (e.g., the same sample or two or more different samples from the subject).

In some embodiments, methods provided herein include detecting the presence of one or more members of a single class of biomarkers in one or more samples obtained from a subject (e.g., genetic biomarkers or protein biomarkers). In some embodiments, methods provided herein include detecting the presence of aneuploidy in one or more samples obtained from a subject (e.g., genetic biomarkers or protein biomarkers). In some embodiments, methods provided herein include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein include detecting the presence of one or more members of two or more classes of biomarkers in one or more samples obtained from a subject (e.g., genetic biomarkers and protein biomarkers). In some embodiments, methods provided herein include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy. Alternatively, two or more samples can be obtained from a subject, and each of the two or more samples can be individually tested to detect the presence of one or more members of one or more classes of biomarkers and/or for the presence of aneuploidy. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy. As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy. As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample).

In some embodiments, the presence of one or more members of one or more classes of biomarkers and/or the presence of aneuploidy (e.g., detected by any of the variety of methods disclosed herein) in a sample obtained from a subject is associated with a disease and indicates the subject suffers from that disease. In some embodiments, a subject is diagnosed with a disease when the presence of one or more members of one or more classes of biomarkers and/or the presence of aneuploidy (which biomarkers and/or aneuploidy are associated with a disease) in a sample obtained from a subject is detected. In some embodiments, the disease is cancer (e.g., any of the variety of cancers described herein). In some embodiments, a subject is not known to have a disease (e.g., cancer) prior to detecting the presence of one or more members of one or more classes of biomarkers and/or the presence of aneuploidy. In some embodiments, a subject is not known to harbor a cancer cell prior to detecting the presence of one or more members of one or more classes of biomarkers and/or the presence of aneuploidy. In some embodiments, a subject does not exhibit symptoms associated with cancer prior to detecting the presence of one or more members of one or more classes of biomarkers and/or the presence of aneuploidy.

Methods of Diagnosis

Also provided herein are methods and materials for diagnosing or identifying the presence of a disease in a subject (e.g., identifying the subject as having cancer) by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of diagnosing or identifying the presence of a disease in a subject (e.g., identifying the subject as having cancer), the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of diagnosing or identifying the presence of a disease in a subject (e.g., identifying the subject as having cancer), the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of diagnosing or identifying the presence of a disease in a subject (e.g., identifying the subject as having cancer) that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include diagnosing the presence cancer in a subject (e.g., identifying the subject as having cancer) by detecting the presence of one or more members of one or more classes of biomarkers in a sample obtained from the subject further include detecting the presence of aneuploidy in a sample obtained from the subject. For example, methods that include diagnosing the presence cancer in a subject (e.g., identifying the subject as having cancer) by detecting the presence of one or more members of a class of genetic biomarkers in a sample obtained from the subject can further include detecting the presence of aneuploidy in a sample obtained from the subject (e.g., the same sample or two different samples from the subject). As another example, methods that include diagnosing the presence cancer in a subject (e.g., identifying the subject as having cancer) by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include diagnosing the presence cancer in a subject (e.g., identifying the subject as having cancer) by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein include diagnosing the presence cancer in a subject (e.g., identifying the subject as having cancer) by detecting the presence of one or more members of a single class of biomarkers in one or more samples obtained from the subject (e.g., genetic biomarkers or protein biomarkers). In some embodiments, methods provided herein include diagnosing the presence cancer in a subject (e.g., identifying the subject as having cancer) by detecting the presence of aneuploidy in one or more samples obtained from the subject (e.g., genetic biomarkers or protein biomarkers). In some embodiments, methods provided herein include diagnosing the presence cancer in a subject (e.g., identifying the subject as having cancer) by detecting the presence of one or more members of a single class of biomarkers in one or more samples obtained from the subject (e.g., genetic biomarkers or protein biomarkers) and detecting the presence of aneuploidy in one or more samples obtained from the subject. In some embodiments, methods provided herein include diagnosing the presence cancer in a subject (e.g., identifying the subject as having cancer) by detecting the presence of one or more members of two or more classes of biomarkers in one or more samples obtained from the subject (e.g., genetic biomarkers and protein biomarkers). In some embodiments, methods provided herein include diagnosing the presence cancer in a subject (e.g., identifying the subject as having cancer) by detecting the presence of one or more members of two or more classes of biomarkers in one or more samples obtained from the subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed as having cancer (e.g., is identified as having cancer) when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed as having cancer (e.g., is identified as having cancer) when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed as having cancer (e.g., is identified as having cancer) when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed as having cancer (e.g., is identified as having cancer) when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed as having cancer (e.g., is identified as having cancer) when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed as having cancer (e.g., is identified as having cancer) when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of diagnosing or identifying the presence of a disease (e.g., cancer) in a subject (e.g., using any of the variety of methods described herein), the subject is also identified as a candidate for further diagnostic testing. In some embodiments of diagnosing or identifying the presence of a disease (e.g., cancer) in a subject (e.g., using any of the variety of methods described herein), the subject is also identified as a candidate for increased monitoring. In some embodiments of diagnosing or identifying the presence of a disease (e.g., cancer) in a subject (e.g., using any of the variety of methods described herein), the subject is also identified as a candidate that will or is likely to respond to a treatment (e.g., any of the variety of therapeutic interventions described herein). In some embodiments of diagnosing or identifying the presence of a disease (e.g., cancer) in a subject (e.g., using any of the variety of methods described herein), the subject is also administered a treatment (e.g., any of the variety of therapeutic interventions described herein).

Methods of Identifying a Subject as being at Risk of Having or Developing a Disease Provided herein are methods and materials for identifying a subject as being at risk (e.g., increased risk) of having or developing a disease (e.g., cancer) by detecting the presence of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of identifying a subject as being at risk (e.g., increased risk) of having or developing a disease (e.g., cancer), the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of identifying a subject as being at risk (e.g., increased risk) of having or developing a disease (e.g., cancer), the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of identifying a subject as being at risk (e.g., increased risk) of having or developing a disease (e.g., cancer) that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include identifying a subject as being at risk (e.g., increased risk) of having or developing a disease (e.g., cancer) by detecting the presence of one or more members of one or more classes of biomarkers in a sample obtained from the subject further include detecting the presence of aneuploidy in a sample obtained from the subject. For example, methods that include identifying a subject as being at risk (e.g., increased risk) of having or developing a disease (e.g., cancer) by detecting the presence of one or more members of a class of genetic biomarkers in a sample obtained from the subject can further include detecting the presence of aneuploidy in a sample obtained from the subject (e.g., the same sample or two different samples from the subject). As another example, methods that include identifying a subject as being at risk (e.g., increased risk) of having or developing a disease (e.g., cancer) by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include identifying a subject as being at risk (e.g., increased risk) of having or developing a disease (e.g., cancer) by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for identifying a subject as being at risk (e.g., increased risk) of having or developing a disease (e.g., cancer) include detecting the presence of one or more members of a single class of biomarkers in one or more samples obtained from the subject (e.g., genetic biomarkers or protein biomarkers). In some embodiments, methods provided herein for identifying a subject as being at risk (e.g., increased risk) of having or developing a disease (e.g., cancer) include detecting the presence of aneuploidy in one or more samples obtained from the subject (e.g., genetic biomarkers or protein biomarkers). In some embodiments, methods provided herein for identifying a subject as being at risk (e.g., increased risk) of having or developing a disease (e.g., cancer) include detecting the presence of one or more members of a single class of biomarkers in one or more samples obtained from the subject (e.g., genetic biomarkers or protein biomarkers) and detecting the presence of aneuploidy in one or more samples obtained from the subject. In some embodiments, methods provided herein for identifying a subject as being at risk (e.g., increased risk) of having or developing a disease (e.g., cancer) include detecting the presence of one or more members of two or more classes of biomarkers in one or more samples obtained from the subject (e.g., genetic biomarkers and protein biomarkers). In some embodiments, methods provided herein for identifying a subject as being at risk (e.g., increased risk) of having or developing a disease (e.g., cancer) include detecting the presence of one or more members of two or more classes of biomarkers in one or more samples obtained from the subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be identified as being at risk (e.g., increased risk) of having or developing a disease (e.g., cancer) when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be identified as being at risk (e.g., increased risk) of having or developing a disease (e.g., cancer) when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is identified as being at risk (e.g., increased risk) of having or developing a disease (e.g., cancer) when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is identified as being at risk (e.g., increased risk) of having or developing a disease (e.g., cancer) when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is identified as being at risk (e.g., increased risk) of having or developing a disease (e.g., cancer) when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is identified as being at risk (e.g., increased risk) of having or developing a disease (e.g., cancer) when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of identifying a subject as being at risk (e.g., increased risk) of having or developing a disease (e.g., using any of the variety of methods described herein), the subject is also identified as a candidate for further diagnostic testing. In some embodiments of identifying a subject as being at risk (e.g., increased risk) of having or developing a disease (e.g., using any of the variety of methods described herein), the subject is also identified as a candidate for increased monitoring. In some embodiments of identifying a subject as being at risk (e.g., increased risk) of having or developing a disease (e.g., using any of the variety of methods described herein), the subject is also identified as a candidate that will or is likely to respond to a treatment (e.g., any of the variety of therapeutic interventions described herein including, without limitation, a chemopreventive). In some embodiments of identifying a subject as being at risk (e.g., increased risk) of having or developing a disease (e.g., using any of the variety of methods described herein), the subject is also administered a treatment (e.g., any of the variety of therapeutic interventions described herein including, without limitation, a chemopreventive).

Methods of Treatment

Also provided herein are methods and materials for treating a subject who has been diagnosed or identified as having a disease (e.g., cancer) or who has been identified as being at risk (e.g., increased risk) of having or developing a disease (e.g., cancer) by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of treating a subject who has been diagnosed or identified as having a disease (e.g., cancer) or who has been identified as being at risk (e.g., increased risk) of having or developing a disease (e.g., cancer), the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of treating a subject who has been diagnosed or identified as having a disease (e.g., cancer) or who has been identified as being at risk (e.g., increased risk) of having or developing a disease (e.g., cancer), the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of treating a subject who has been diagnosed or identified as having a disease (e.g., cancer) or who has been identified as being at risk (e.g., increased risk) of having or developing a disease (e.g., cancer) that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include treating a subject who has been diagnosed or identified as having a disease (e.g., cancer) or who has been identified as being at risk (e.g., increased risk) of having or developing a disease (e.g., cancer) by detecting the presence of one or more members of one or more classes of biomarkers in a sample obtained from the subject further include detecting the presence of aneuploidy in a sample obtained from the subject. For example, methods that include treating a subject who has been diagnosed or identified as having a disease (e.g., cancer) or who has been identified as being at risk (e.g., increased risk) of having or developing a disease (e.g., cancer) by detecting the presence of one or more members of a class of genetic biomarkers in a sample obtained from the subject can further include detecting the presence of aneuploidy in a sample obtained from the subject (e.g., the same sample or two different samples from the subject). As another example, methods that include treating a subject who has been diagnosed or identified as having a disease (e.g., cancer) or who has been identified as being at risk (e.g., increased risk) of having or developing a disease (e.g., cancer) by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include treating a subject who has been diagnosed or identified as having a disease (e.g., cancer) or who has been identified as being at risk (e.g., increased risk) of having or developing a disease (e.g., cancer) by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for treating a subject who has been diagnosed or identified as having a disease (e.g., cancer) or who has been identified as being at risk (e.g., increased risk) of having or developing a disease (e.g., cancer) include detecting the presence of one or more members of a single class of biomarkers in one or more samples obtained from a subject (e.g., genetic biomarkers or protein biomarkers). In some embodiments, methods provided herein for treating a subject who has been diagnosed or identified as having a disease (e.g., cancer) or who has been identified as being at risk (e.g., increased risk) of having or developing a disease (e.g., cancer) include detecting the presence of aneuploidy in one or more samples obtained from a subject (e.g., genetic biomarkers or protein biomarkers). In some embodiments, methods provided herein for treating a subject who has been diagnosed or identified as having a disease (e.g., cancer) or who has been identified as being at risk (e.g., increased risk) of having or developing a disease (e.g., cancer) include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein for treating a subject who has been diagnosed or identified as having a disease (e.g., cancer) or who has been identified as being at risk (e.g., increased risk) of having or developing a disease (e.g., cancer) include detecting the presence of one or more members of two or more classes of biomarkers in one or more samples obtained from a subject (e.g., genetic biomarkers and protein biomarkers). In some embodiments, methods provided herein for treating a subject who has been diagnosed or identified as having a disease (e.g., cancer) or who has been identified as being at risk (e.g., increased risk) of having or developing a disease (e.g., cancer) include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed or identified as having a disease (e.g., cancer) or as being at risk (e.g., increased risk) of having or developing a disease (e.g., cancer) and/or the subject can be treated when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed or identified as being at risk (e.g., increased risk) of having or developing a disease (e.g., cancer) and/or the subject can be treated when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed or identified as having a disease (e.g., cancer) or as being at risk (e.g., increased risk) of having or developing a disease (e.g., cancer) and/or the subject can be treated when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is treated when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is treated when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed or identified as having a disease (e.g., cancer) or as being at risk (e.g., increased risk) of having or developing a disease (e.g., cancer) and/or the subject is treated when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of treating a subject who has been diagnosed or identified as having a disease or who has been identified as being at risk (e.g., increased risk) of having or developing a disease by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject, the treatment is any of the variety of therapeutic interventions disclosed herein including without limitation, chemotherapy, neoadjuvant chemotherapy, radiation therapy, hormone therapy, cytotoxic therapy, immunotherapy, adoptive T cell therapy (e.g., chimeric antigen receptors and/or T cells having wild-type or modified T cell receptors), targeted therapy such as administration of kinase inhibitors (e.g., kinase inhibitors that target a particular genetic lesion, such as a translocation or mutation), (e.g. a kinase inhibitor, an antibody, a bispecific antibody), signal transduction inhibitors, bispecific antibodies or antibody fragments (e.g., BiTEs), monoclonal antibodies, immune checkpoint inhibitors, surgery (e.g., surgical resection), or any combination of the above. In some embodiments in which the disease is cancer, a therapeutic intervention reduces the severity of the cancer, reduces a symptom of the cancer, and/or reduces the number of cancer cells present within the subject.

In some embodiments of treating a subject who has been diagnosed or identified as having a disease or who has been identified as being at risk (e.g., increased risk) of having or developing a disease (e.g., by any of the variety of methods described herein), the subject is also identified as a subject who will or is likely to respond to that treatment. In some embodiments of treating a subject who has been diagnosed or identified as having a disease or who has been identified as being at risk (e.g., increased risk) of having or developing a disease (e.g., by any of the variety of methods described herein), the subject is also identified as a candidate for further diagnostic testing (e.g., prior to administration of the treatment and/or after administration of the treatment to determine the effect of that treatment and/or whether the subject is a candidate for additional administrations of the same or a different treatment). In some embodiments of treating a subject who has been diagnosed or identified as having a disease or who has been identified as being at risk (e.g., increased risk) of having or developing a disease (e.g., by any of the variety of methods described herein), the subject is also identified as a candidate for increased monitoring (e.g., prior to administration of the treatment and/or after administration of the treatment to determine the effect of that treatment and/or whether the subject is a candidate for additional administrations of the same or a different treatment).

Method of Identifying a Treatment

Also provided herein are methods and materials for identifying a treatment for a subject who has been diagnosed or identified as having a disease (e.g., cancer) or who has been identified as being at risk (e.g., increased risk) of having or developing a disease (e.g., cancer) by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of identifying a treatment for a subject who has been diagnosed or identified as having a disease (e.g., cancer) or who has been identified as being at risk (e.g., increased risk) of having or developing a disease (e.g., cancer), the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of identifying a treatment for a subject who has been diagnosed or identified as having a disease (e.g., cancer) or who has been identified as being at risk (e.g., increased risk) of having or developing a disease (e.g., cancer), the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of identifying a treatment for a subject who has been diagnosed or identified as having a disease (e.g., cancer) or who has been identified as being at risk (e.g., increased risk) of having or developing a disease (e.g., cancer) that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include identifying a treatment for a subject who has been diagnosed or identified as having a disease (e.g., cancer) or who has been identified as being at risk (e.g., increased risk) of having or developing a disease (e.g., cancer) by detecting the presence of one or more members of one or more classes of biomarkers in a sample obtained from the subject further include detecting the presence of aneuploidy in a sample obtained from the subject. For example, methods that include identifying a treatment for a subject who has been diagnosed or identified as having a disease (e.g., cancer) or who has been identified as being at risk (e.g., increased risk) of having or developing a disease (e.g., cancer) by detecting the presence of one or more members of a class of genetic biomarkers in a sample obtained from the subject can further include detecting the presence of aneuploidy in a sample obtained from the subject (e.g., the same sample or two different samples from the subject). As another example, methods that include identifying a treatment for a subject who has been diagnosed or identified as having a disease (e.g., cancer) or who has been identified as being at risk (e.g., increased risk) of having or developing a disease (e.g., cancer) by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include identifying a treatment for a subject who has been diagnosed or identified as having a disease (e.g., cancer) or who has been identified as being at risk (e.g., increased risk) of having or developing a disease (e.g., cancer) by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for identifying a treatment for a subject who has been diagnosed or identified as having a disease (e.g., cancer) or who has been identified as being at risk (e.g., increased risk) of having or developing a disease (e.g., cancer) include detecting the presence of one or more members of a single class of biomarkers in one or more samples obtained from a subject (e.g., genetic biomarkers or protein biomarkers). In some embodiments, methods provided herein for identifying a treatment for a subject who has been diagnosed or identified as having a disease (e.g., cancer) or who has been identified as being at risk (e.g., increased risk) of having or developing a disease (e.g., cancer) include detecting the presence of aneuploidy in one or more samples obtained from a subject (e.g., genetic biomarkers or protein biomarkers). In some embodiments, methods provided herein for identifying a treatment for a subject who has been diagnosed or identified as having a disease (e.g., cancer) or who has been identified as being at risk (e.g., increased risk) of having or developing a disease (e.g., cancer) include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein for identifying a treatment for a subject who has been diagnosed or identified as having a disease (e.g., cancer) or who has been identified as being at risk (e.g., increased risk) of having or developing a disease (e.g., cancer) include detecting the presence of one or more members of two or more classes of biomarkers in one or more samples obtained from a subject (e.g., genetic biomarkers and protein biomarkers). In some embodiments, methods provided herein for identifying a treatment for a subject who has been diagnosed or identified as having a disease (e.g., cancer) or who has been identified as being at risk (e.g., increased risk) of having or developing a disease (e.g., cancer) include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed or identified as having a disease (e.g., cancer) or as being at risk (e.g., increased risk) of having or developing a disease (e.g., cancer) and/or a treatment for the subject can be identified when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed or identified as being at risk (e.g., increased risk) of having or developing a disease (e.g., cancer) and/or a treatment for the subject can be identified when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed or identified as having a disease (e.g., cancer) or as being at risk (e.g., increased risk) of having or developing a disease (e.g., cancer) and/or a treatment for the subject is identified when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or a treatment for the subject is identified when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or a treatment for the subject is identified when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed or identified as having a disease (e.g., cancer) or as being at risk (e.g., increased risk) of having or developing a disease (e.g., cancer) and/or a treatment for the subject is identified when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of identifying a treatment for a subject who has been diagnosed or identified as having a disease or who has been identified as being at risk (e.g., increased risk) of having or developing a disease by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject, the identified treatment is any of the variety of therapeutic interventions disclosed herein including without limitation, chemotherapy, neoadjuvant chemotherapy, radiation therapy, hormone therapy, cytotoxic therapy, immunotherapy, adoptive T cell therapy (e.g., chimeric antigen receptors and/or T cells having wild-type or modified T cell receptors), targeted therapy such as administration of kinase inhibitors (e.g., kinase inhibitors that target a particular genetic lesion, such as a translocation or mutation), (e.g. a kinase inhibitor, an antibody, a bispecific antibody), signal transduction inhibitors, bispecific antibodies or antibody fragments (e.g., BiTEs), monoclonal antibodies, immune checkpoint inhibitors, surgery (e.g., surgical resection), or any combination of the above. In some embodiments in which the disease is cancer, an identified therapeutic intervention reduces the severity of the cancer, reduces a symptom of the cancer, and/or reduces the number of cancer cells present within the subject.

In some embodiments of identifying a treatment for a subject who has been diagnosed or identified as having a disease or who has been identified as being at risk (e.g., increased risk) of having or developing a disease (e.g., by any of the variety of methods described herein), the subject is also identified as a subject who will or is likely to respond to that treatment. In some embodiments of identifying a treatment for a subject who has been diagnosed or identified as having a disease or who has been identified as being at risk (e.g., increased risk) of having or developing a disease (e.g., by any of the variety of methods described herein), the subject is also identified as a candidate for further diagnostic testing. In some embodiments of identifying a treatment for a subject who has been diagnosed or identified as having a disease or who has been identified as being at risk (e.g., increased risk) of having or developing a disease (e.g., by any of the variety of methods described herein), the subject is also identified as a candidate for increased monitoring. In some embodiments of identifying a treatment for a subject who has been diagnosed or identified as having a disease or who has been identified as being at risk (e.g., increased risk) of having or developing a disease (e.g., by any of the variety of methods described herein), the subject is also administered a treatment (e.g., any of the variety of therapeutic interventions described herein).

Identifying a Subject Who Will or is Likely to Respond to a Treatment

Also provided herein are methods and materials for identifying a subject who will or is likely to respond to a treatment by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of identifying a subject who will or is likely to respond to a treatment, the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of identifying a subject who will or is likely to respond to a treatment, the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of identifying a subject who will or is likely to respond to a treatment that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include identifying a subject who will or is likely to respond to a treatment by detecting the presence of one or more members of one or more classes of biomarkers in a sample obtained from the subject further include detecting the presence of aneuploidy in a sample obtained from the subject. For example, methods that include identifying a subject who will or is likely to respond to a treatment by detecting the presence of one or more members of a class of genetic biomarkers in a sample obtained from the subject can further include detecting the presence of aneuploidy in a sample obtained from the subject (e.g., the same sample or two different samples from the subject). As another example, methods that include identifying a subject who will or is likely to respond to a treatment by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include identifying a subject who will or is likely to respond to a treatment by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for identifying a subject who will or is likely to respond to a treatment include detecting the presence of one or more members of a single class of biomarkers in one or more samples obtained from a subject (e.g., genetic biomarkers or protein biomarkers). In some embodiments, methods provided herein for identifying a subject who will or is likely to respond to a treatment include detecting the presence of aneuploidy in one or more samples obtained from a subject (e.g., genetic biomarkers or protein biomarkers). In some embodiments, methods provided herein for identifying a subject who will or is likely to respond to a treatment include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein for identifying a subject who will or is likely to respond to a treatment include detecting the presence of one or more members of two or more classes of biomarkers in one or more samples obtained from a subject (e.g., genetic biomarkers and protein biomarkers). In some embodiments, methods provided herein for identifying a subject who will or is likely to respond to a treatment include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed or identified as having a disease (e.g., cancer) or as being at risk (e.g., increased risk) of having or developing a disease (e.g., cancer) and/or the subject can be identified as a subject who will or is likely to respond to a treatment when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed or identified as being at risk (e.g., increased risk) of having or developing a disease (e.g., cancer) and/or the subject can be identified as a subject who will or is likely to respond to a treatment when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed or identified as having a disease (e.g., cancer) or as being at risk (e.g., increased risk) of having or developing a disease (e.g., cancer) and/or the subject is identified as a subject who will or is likely to respond to a treatment when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who will or is likely to respond to a treatment when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who will or is likely to respond to a treatment when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed or identified as having a disease (e.g., cancer) or as being at risk (e.g., increased risk) of having or developing a disease (e.g., cancer) and/or the subject is identified as a subject who will or is likely to respond to a treatment when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of identifying a subject who will or is likely to respond to a treatment by detecting of one or more members (e.g., increased risk) of having or developing a disease by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject, the subject is identified as a subject who will or is likely to respond to a treatment that is any of the variety of therapeutic interventions disclosed herein including without limitation, chemotherapy, neoadjuvant chemotherapy, radiation therapy, hormone therapy, cytotoxic therapy, immunotherapy, adoptive T cell therapy (e.g., chimeric antigen receptors and/or T cells having wild-type or modified T cell receptors), targeted therapy such as administration of kinase inhibitors (e.g., kinase inhibitors that target a particular genetic lesion, such as a translocation or mutation), (e.g. a kinase inhibitor, an antibody, a bispecific antibody), signal transduction inhibitors, bispecific antibodies or antibody fragments (e.g., BiTEs), monoclonal antibodies, immune checkpoint inhibitors, surgery (e.g., surgical resection), or any combination of the above. In some embodiments in which the disease is cancer, a subject that is identified as a subject who will or is likely to respond to an identified therapeutic intervention is identified as a subject in whom the therapeutic intervention will or is likely to reduce the severity of the cancer, reduce a symptom of the cancer, and/or reduce the number of cancer cells present within the subject.

In some embodiments, a subject identified as a subject who will or is likely to respond to a treatment (e.g., using any of the variety of methods described herein) is also identified for further diagnostic testing. In some embodiments, a subject identified as a subject who will or is likely to respond to a treatment (e.g., using any of the variety of methods described herein) is also identified for increased monitoring. Additionally or alternatively, a subject identified as a subject who will or is likely to respond to a treatment (e.g., using any of the variety of methods described herein) is also administered a treatment (e.g., any of the variety of therapeutic interventions described herein).

Methods of Identifying a Subject as a Candidate for Further Diagnostic Testing

Also provided herein are methods and materials for identifying a subject as a candidate for further diagnostic testing by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of identifying a subject as a candidate for further diagnostic testing, the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of identifying a subject as a candidate for further diagnostic testing, the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of identifying a subject as a candidate for further diagnostic testing that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include identifying a subject as a candidate for further diagnostic testing by detecting the presence of one or more members of one or more classes of biomarkers in a sample obtained from the subject further include detecting the presence of aneuploidy in a sample obtained from the subject. For example, methods that include identifying a subject as a candidate for further diagnostic testing by detecting the presence of one or more members of a class of genetic biomarkers in a sample obtained from the subject can further include detecting the presence of aneuploidy in a sample obtained from the subject (e.g., the same sample or two different samples from the subject). As another example, methods that include identifying a subject as a candidate for further diagnostic testing by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include identifying a subject as a candidate for further diagnostic testing by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for identifying a subject as a candidate for further diagnostic testing include detecting the presence of one or more members of a single class of biomarkers in one or more samples obtained from a subject (e.g., genetic biomarkers or protein biomarkers). In some embodiments, methods provided herein for identifying a subject as a candidate for further diagnostic testing include detecting the presence of aneuploidy in one or more samples obtained from a subject (e.g., genetic biomarkers or protein biomarkers). In some embodiments, methods provided herein for i identifying a subject as a candidate for further diagnostic testing include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein for identifying a subject as a candidate for further diagnostic testing include detecting the presence of one or more members of two or more classes of biomarkers in one or more samples obtained from a subject (e.g., genetic biomarkers and protein biomarkers). In some embodiments, methods provided herein for identifying a subject as a candidate for further diagnostic testing include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed or identified as having a disease (e.g., cancer) or as being at risk (e.g., increased risk) of having or developing a disease (e.g., cancer) and/or the subject can be identified as a subject who is a candidate for further diagnostic testing when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed or identified as being at risk (e.g., increased risk) of having or developing a disease (e.g., cancer) and/or the subject can be identified as a subject who is a candidate for further diagnostic testing when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed or identified as having a disease (e.g., cancer) or as being at risk (e.g., increased risk) of having or developing a disease (e.g., cancer) and/or the subject is identified as a subject who is a candidate for further diagnostic testing when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who is a candidate for further diagnostic testing when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who is a candidate for further diagnostic testing when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed or identified as having a disease (e.g., cancer) or as being at risk (e.g., increased risk) of having or developing a disease (e.g., cancer) and/or the subject is identified as a subject who is a candidate for further diagnostic testing when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments of identifying a subject identifying a subject as a candidate for further diagnostic testing by detecting of one or more members (e.g., increased risk) of having or developing a disease by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject, the subject is for any of the variety of types of further diagnostic testing disclosed herein including, without limitation, a scan (e.g., a computed tomography (CT), a CT angiography (CTA), a esophagram (a Barium swallom), a Barium enema, a magnetic resonance imaging (MRI), a PET scan, a positron emission tomography and computed tomography (PET-CT) scan, an ultrasound (e.g., an endobronchial ultrasound, an endoscopic ultrasound), an X-ray, or a DEXA scan) or a physical examination (e.g., an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, or a pelvic exam).

In some embodiments, a subject identified as a candidate for further diagnostic testing (e.g., using any of the variety of methods described herein) is also identified as a candidate for increased monitoring. Additionally or alternatively, a subject identified as a candidate for further diagnostic testing (e.g., using any of the variety of methods described herein) is also identified as a subject who will or is likely to respond to a treatment. Additionally or alternatively, a subject identified as a candidate for further diagnostic testing (e.g., using any of the variety of methods described herein) is also administered a treatment (e.g., any of the variety of therapeutic interventions described herein).

Methods of Identifying a Subject as a Candidate for Increased Monitoring

Also provided herein are methods and materials for identifying a subject as a candidate for increased monitoring by detecting of one or more members (e.g., 1, 2, 3, 4, 5, 6, 7, 8, 9, 10, 11, 12, 13, 14, 15, 16, 17, 18, 19, 20, or more members) of one or more classes of biomarkers and/or the presence of aneuploidy in a sample obtained from the subject. In some embodiments of identifying a subject as a candidate for increased monitoring, the presence of one or more members of one or more classes of biomarkers and/or the presence of aneuploidy are tested simultaneously (e.g., in one testing procedure, including embodiments in which the testing procedure itself may include multiple discrete test methods of systems). In some embodiments of identifying a subject as a candidate for increased monitoring, the presence of one or more members of one or more classes of biomarkers and/or the presence of aneuploidy are tested sequentially (e.g., in two or more different testing procedures conducted at two or more different time points, including embodiments in which the testing procedure itself may include multiple discrete test methods of systems). In some embodiments of identifying a subject as a candidate for increased monitoring that include either simultaneous or sequential testing (or both) for the presence of one or more members of one or more classes of biomarkers and/or the presence of aneuploidy, the testing may be performed on a single sample or may be performed on two or more different samples (e.g., two or more different samples obtained from the same subject).

Any of the variety of detection methods described herein (see, e.g., sections entitled "Detection of Genetic Biomarkers", "Detection of Protein Biomarkers", and "Detection of Aneuploidy") can be used to detect the presence of one or more members of one or more classes of biomarkers and/or the presence of aneuploidy in a sample obtained from a subject. In some embodiments, the one or more members of the one or more classes of biomarkers and/or the one or more classes of biomarkers are associated with a disease in a subject. In some embodiments, aneuploidy is associated with a disease in a subject. In some embodiments, the disease is cancer (e.g., any of the variety of types of cancer described herein). In some embodiments, the one or more members are members of a class of genetic biomarkers. In some embodiments, the one or more members are members of a class of protein biomarkers. In some embodiments, methods that include identifying a subject as a candidate for increased monitoring by detecting the presence of one or more members of one or more classes of biomarkers in a sample obtained from the subject further include detecting the presence of aneuploidy in a sample obtained from the subject. For example, methods that include identifying a subject as a candidate for increased monitoring by detecting the presence of one or more members of a class of genetic biomarkers in a sample obtained from the subject can further include detecting the presence of aneuploidy in a sample obtained from the subject (e.g., the same sample or two different samples from the subject). As another example, methods that include identifying a subject as a candidate for increased monitoring by detecting the presence of one or more members of a class of protein biomarkers in a sample obtained from the subject can further include detecting the presence of aneuploidy in a sample obtained from the subject (e.g., the same sample or two different samples from the subject). In some embodiments, methods that include identifying a subject as a candidate for increased monitoring by detecting both the presence of one or more members of a class of genetic biomarkers and detecting the presence of one or more members of a class of protein biomarkers in a sample obtained from the subject can further include detecting the presence of aneuploidy in a sample obtained from the subject (e.g., the same sample or two or more different samples from the subject).

In some embodiments, methods provided herein for identifying a subject as a candidate for increased monitoring include detecting the presence of one or more members of a single class of biomarkers in one or more samples obtained from a subject (e.g., genetic biomarkers or protein biomarkers). In some embodiments, methods provided herein for identifying a subject as a candidate for increased monitoring include detecting the presence of aneuploidy in one or more samples obtained from a subject (e.g., genetic biomarkers or protein biomarkers). In some embodiments, methods provided herein for i identifying a subject as a candidate for increased monitoring include detecting the presence of one or more members of a single class of biomarkers in one or more samples obtained from a subject (e.g., genetic biomarkers or protein biomarkers) and detecting the presence of aneuploidy in one or more samples obtained from the subject. In some embodiments, methods provided herein for identifying a subject as a candidate for increased monitoring include detecting the presence of one or more members of two or more classes of biomarkers in one or more samples obtained from a subject (e.g., genetic biomarkers and protein biomarkers). In some embodiments, methods provided herein for identifying a subject as a candidate for increased monitoring include detecting the presence of one or more members of two or more classes of biomarkers in one or more samples obtained from a subject (e.g., genetic biomarkers and protein biomarkers) and detecting the presence of aneuploidy in one or more samples obtained from the subject.

In some embodiments, a single sample obtained from a subject can be tested to detect the presence of one or more members of one or more classes of biomarkers and/or for the presence of aneuploidy, and the subject can be diagnosed or identified as having a disease (e.g., cancer) or as being at risk (e.g., increased risk) of having or developing a disease (e.g., cancer) and/or the subject can be identified as a subject who is a candidate for increased monitoring when the presence of the one or more members of the one or more classes of biomarkers and/or the presence of aneuploidy is detected. Alternatively, two or more samples can be obtained from a subject, and each of the two or more samples can be individually tested to detect the presence of one or more members of one or more classes of biomarkers and/or for the presence of aneuploidy, and the subject can be diagnosed or identified as being at risk (e.g., increased risk) of having or developing a disease (e.g., cancer) and/or the subject can be identified as a subject who is a candidate for increased monitoring when the presence of the one or more members of the one or more classes of biomarkers and/or the presence of aneuploidy is detected. As one non-limiting example, a first sample obtained from a subject can be tested to detect the presence of one or more members of a first class of biomarkers (e.g., genetic biomarkers), and a second sample obtained from the subject can be tested to detect the presence of one or more members of a second class of biomarkers (e.g., protein biomarkers), wherein the subject is diagnosed or identified as having a disease (e.g., cancer) or as being at risk (e.g., increased risk) of having or developing a disease (e.g., cancer) and/or the subject is identified as a subject who is a candidate for increased monitoring when the presence of the one or more members of the first class of biomarkers is detected and/or the presence of the one or more members of the second class of biomarkers is detected (e.g., when the presence of the one or more members of the class of biomarkers is detected and the presence of the one or more members of the second class of biomarkers are detected). As another non-limiting example, a first sample obtained from a subject can be tested to detect the presence of one or more members of a class of biomarkers (e.g., genetic biomarkers or protein biomarkers), and a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who is a candidate for increased monitoring when the presence of the one or more members of the class of biomarkers is detected and/or the presence aneuploidy is detected (e.g., when the presence of the one or more members of the class of biomarkers is detected and the presence aneuploidy are detected). As another non-limiting example, a first sample obtained from a subject can be tested to detect the presence of one or more members of a first class of biomarkers (e.g., genetic biomarkers) and to detect the presence of one or more members of a second class of biomarkers (e.g., protein biomarkers), while a second sample obtained from the subject can be tested to detect the presence of aneuploidy, wherein the subject is diagnosed or identified as having a disease (e.g., cancer) or as being at risk (e.g., increased risk) of having or developing a disease (e.g., cancer) and/or the subject is identified as a subject who is a candidate for increased monitoring when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected). As another non-limiting example, a first sample obtained from a subject can be tested to detect the presence of one or more members of a first class of biomarkers (e.g., genetic or protein biomarkers) and to detect the presence of aneuploidy, while a second sample obtained from the subject can be tested to detect the presence of one or more members of a second class of biomarkers (e.g., a class of biomarkers that is different from the first class that is tested for in the first sample), wherein the subject is diagnosed or identified as having a disease (e.g., cancer) or as being at risk (e.g., increased risk) of having or developing a disease (e.g., cancer) and/or the subject is identified as a subject who is a candidate for increased monitoring when the presence of the one or more members of the first class of biomarkers is detected, the presence of the one or more members of the second class of biomarkers is detected, and/or the presence of aneuploidy is detected (e.g., when the presence of the one or more members of the first class of biomarkers is detected, the presence of the one or more members of the second class of biomarkers is detected, and the presence of aneuploidy are detected).

In some embodiments, a subject identified as a candidate for increased monitoring (e.g., using any of the variety of methods described herein) is also identified as a candidate for further diagnostic testing. Additionally or alternatively, a subject identified as a candidate for increased monitoring (e.g., using any of the variety of methods described herein) is also identified as a subject who will or is likely to respond to a treatment. Additionally or alternatively, a subject identified as a candidate for increased monitoring (e.g., using any of the variety of methods described herein) is also administered a treatment (e.g., any of the variety of therapeutic interventions described herein).

Genetic Biomarkers in Combination with Protein Biomarkers

In one aspect, provided herein are methods and materials for detecting the presence of one or more members of a panel of genetic biomarkers and the presence of one or more members of a panel of protein biomarkers in one or more samples obtained from a subject. In another aspect, provided herein are methods and materials for diagnosing or identifying the presence of a disease in a subject (e.g., identifying the subject as having cancer) by detecting the presence of one or more members of a panel of genetic biomarkers and the presence of one or more members of a panel of protein biomarkers in one or more samples obtained from the subject. In another aspect, provided herein are methods and materials for identifying a subject as being at risk (e.g., increased risk) of having or developing a disease (e.g., cancer) by detecting the presence of one or more members of a panel of genetic biomarkers and the presence of one or more members of a panel of protein biomarkers in one or more samples obtained from the subject. In another aspect, provided herein are methods and materials for treating a subject who has been diagnosed or identified as having a disease (e.g., cancer) or who has been identified as being at risk (e.g., increased risk) of having or developing a disease (e.g., cancer) by detecting the presence of one or more members of a panel of genetic biomarkers and the presence of one or more members of a panel of protein biomarkers in one or more samples obtained from the subject. In another aspect, provided herein are methods and materials for identifying a treatment for a subject who has been diagnosed or identified as having a disease (e.g., cancer) or who has been identified as being at risk (e.g., increased risk) of having or developing a disease (e.g., cancer) by detecting the presence of one or more members of a panel of genetic biomarkers and the presence of one or more members of a panel of protein biomarkers in one or more samples obtained from the subject. In another aspect, provided herein are methods and materials for identifying a subject who will or is likely to respond to a treatment by detecting the presence of one or more members of a panel of genetic biomarkers and the presence of one or more members of a panel of protein biomarkers in one or more samples obtained from the subject. In another aspect, provided herein are methods and materials for identifying a subject as a candidate for further diagnostic testing by detecting the presence of one or more members of a panel of genetic biomarkers and the presence of one or more members of a panel of protein biomarkers in one or more samples obtained from the subject. In another aspect, provided herein are methods and materials for identifying a subject as a candidate for increased monitoring by detecting the presence of one or more members of a panel of genetic biomarkers and the presence of one or more members of a panel of protein biomarkers in one or more samples obtained from the subject.

In some embodiments, methods provided herein that include detecting the presence of one or more members of a panel of genetic biomarkers and the presence of one or more members of a panel of protein biomarkers in one or more samples obtained from a subject provide high sensitivity in the detection or diagnosis of cancer (e.g., a high frequency or incidence of correctly identifying a subject as having cancer). In some embodiments, methods provided herein that include detecting the presence of one or more members of a panel of genetic biomarkers and the presence of one or more members of a panel of protein biomarkers in one or more samples obtained from a subject provide a sensitivity in the detection or diagnosis of cancer (e.g., a high frequency or incidence of correctly identifying a subject as having cancer) that is higher than the sensitivity provided by separately detecting the presence of one or more members of a panel of genetic biomarkers or the presence of one or more members of a panel of protein biomarkers. In some embodiments, methods and materials provided herein that include detecting the presence of one or more members of a panel of genetic biomarkers and the presence of one or more members of a panel of protein biomarkers in one or more samples obtained from a subject provide a sensitivity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. In some embodiments, methods and materials provided herein that include detecting the presence of one or more members of a panel of genetic biomarkers and the presence of one or more members of a panel of protein biomarkers in one or more samples obtained from a subject provide high sensitivity in detecting a single type of cancer. In some embodiments, methods and materials provided herein that include detecting the presence of one or more members of a panel of genetic biomarkers and the presence of one or more members of a panel of protein biomarkers in one or more samples obtained from a subject provide high sensitivity in detecting two or more types of cancers. Any of a variety of cancer types can be detected using methods and materials provided herein (see, e.g., the section entitled "Cancers"). In some embodiments, cancers that can be detected using methods and materials that include detecting the presence of one or more members of a panel of genetic biomarkers and the presence of one or more members of a panel of protein biomarkers in one or more samples obtained from a subject include pancreatic cancer. In some embodiments, cancers that can be detected using methods and materials that include detecting the presence of one or more members of a panel of genetic biomarkers and the presence of one or more members of a panel of protein biomarkers in one or more samples obtained from a subject include liver cancer, ovarian cancer, esophageal cancer, stomach cancer, pancreatic cancer, colorectal cancer, lung cancer, or breast cancer. In some embodiments, cancers that can be detected using methods and materials that include detecting the presence of one or more members of a panel of genetic biomarkers and the presence of one or more members of a panel of protein biomarkers in one or more samples obtained from a subject include cancers of the female reproductive tract (e.g., cervical cancer, endometrial cancer, ovarian cancer, or fallopian tubal cancer). In some embodiments, cancers that can be detected using methods and materials that include detecting the presence of one or more members of a panel of genetic biomarkers and the presence of one or more members of a panel of protein biomarkers in one or more samples obtained from a subject include bladder cancer or upper-tract urothelial carcinomas.

In some embodiments, methods provided herein that include detecting the presence of one or more members of a panel of genetic biomarkers and the presence of one or more members of a panel of protein biomarkers in one or more samples obtained from a subject provide high specificity in the detection or diagnosis of cancer (e.g., a low frequency or incidence of incorrectly identifying a subject as having cancer when that subject does not have cancer). In some embodiments, methods provided herein that include detecting the presence of one or more members of a panel of genetic biomarkers and the presence of one or more members of a panel of protein biomarkers in one or more samples obtained from a subject provide a specificity in the detection or diagnosis of cancer (e.g., a high frequency or incidence of correctly identifying a subject as having cancer) that is higher than the specificity provided by separately detecting the presence of one or more members of a panel of genetic biomarkers or the presence of one or more members of a panel of protein biomarkers. In some embodiments, methods and materials provided herein that include that include detecting the presence of one or more members of a panel of genetic biomarkers and the presence of one or more members of a panel of protein biomarkers in one or more samples obtained from a subject provide a specificity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. As will be understood by those of ordinary skill in the art, a specificity of 99% means that only 1% of subjects that do not have cancer are incorrectly identified as having cancer. In some embodiments, methods and materials provided herein that include detecting the presence of one or more members of a panel of genetic biomarkers and the presence of one or more members of a panel of protein biomarkers in one or more samples obtained from a subject provide high specificity in detecting a single cancer (e.g., there is a low probability of incorrectly identifying that subject as having that single cancer type). In some embodiments, methods and materials provided herein that include detecting the presence of one or more members of a panel of genetic biomarkers and the presence of one or more members of a panel of protein biomarkers in one or more samples obtained from a subject provide high specificity in detecting two or more cancers (e.g., there is a low probability of incorrectly identifying that subject as having those two or more cancer types).

In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO). In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO). In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, prolactin, TIMP-1, and myeloperoxidase (MPO). In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, prolactin, TIMP-1, and/or myeloperoxidase (MPO). In some embodiments of methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, follistatin, G-CSF, and CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, follistatin, G-CSF, and/or CA15-3. In some embodiments of methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, or 8) of the following protein biomarkers: CA19-9, CEA, HGF, OPN, CA125, AFP, prolactin, TIMP-1, follistatin, G-CSF, and/or CA15-3, the subject is determined as having (e.g., diagnosed to have) or is determined to be (e.g. diagnosed as being) at elevated risk of having or developing cancer one of the following types of cancer: liver cancer, ovarian cancer, esophageal cancer, stomach cancer, pancreatic cancer, colorectal cancer, lung cancer, and/or breast cancer.

In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, and CA15-3. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) each of the following protein biomarkers: CA19-9, CEA, HGF, OPN, CA125, AFP, prolactin, TIMP-1, and CA15-3. In some embodiments of methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, or 8) of the following protein biomarkers: CA19-9, CEA, HGF, OPN, CA125, AFP, prolactin, TIMP-1, and/or CA15-3, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) one or more (e.g., 1, 2, 3, or 4) of the following protein biomarkers: CA19-9, CEA, HGF, and/or OPN. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: KRAS (e.g., genetic biomarkers in codons 12 and/or 61), TP53, CDKN2A, and SMAD4, and 2) one or more (e.g., 1, 2, 3, or 4) of the following protein biomarkers: CA19-9, CEA, HGF, and/or OPN. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) each of the following protein biomarkers: CA19-9, CEA, HGF, and OPN. In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in each of the following genes: KRAS (e.g., genetic biomarkers in codons 12 and/or 61), TP53, CDKN2A, and SMAD4, and 2) each of the following protein biomarkers: CA19-9, CEA, HGF, and OPN. In some embodiments of methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) one or more (e.g., 1, 2, 3, or 4) of the following protein biomarkers: CA19-9, CEA, HGF, and/or OPN, a subject is determined as having (e.g., diagnosed to have) or is determined to be (e.g. diagnosed as being) at elevated risk of having or developing pancreatic cancer.

A sample obtained from a subject can be any of the variety of samples described herein that contains cell-free DNA (e.g., ctDNA) and/or proteins. In some embodiments, cell-free DNA (e.g., ctDNA) and/or proteins in a sample obtained from the subject are derived from a tumor cell. In some embodiments, cell-free DNA (e.g., ctDNA) in a sample obtained from the subject includes one or more genetic biomarkers. In some embodiments, proteins in a sample obtained from the subject includes one or more protein biomarkers. Non-limiting examples of samples in which genetic biomarkers and/or protein biomarkers can be detected include blood, plasma, and serum. In some embodiments, the presence of one or more genetic biomarkers and the presence of one or more protein biomarkers is detected in a single sample obtained from the subject. In some embodiments, the presence of one or more genetic biomarkers is detected in a first sample obtained from a subject, and the presence of one or more protein biomarkers is detected in a second sample obtained from the subject.

In some embodiments, methods provided herein that include detecting the presence of one or more members of a panel of genetic biomarkers (e.g., each member of a panel of genetic biomarkers) and the presence of one or more members of a panel of protein biomarkers (e.g., each member of a panel of protein biomarkers) in one or more samples obtained from a subject, an elevated level of one or more members of the panel of protein biomarkers can be detected. For example, an elevated level of a protein biomarker can be a level that is higher that a reference level. A reference level can be any level of the protein biomarker that is not associated with the presence of cancer. For example, a reference level of a protein biomarker can be a level that is present in a reference subject that does not have cancer or does not harbor a cancer cell. A reference level of a protein biomarker can be the average level that is present in a plurality of reference subjects that do not have cancer or do not harbor a cancer cell. A reference level of a protein biomarker in a subject determined to have cancer can be the level that was presence in the subject prior to the onset of cancer. In some embodiments, a panel of protein biomarkers in which one or more members of the panel is present at an elevated level includes one or more of (e.g., 1, 2, 3, 4, 5, 6, 7, or each of): CA19-9, CEA, HGF, OPN, CA125, prolactin, TIMP-1, and/or myeloperoxidase (MPO). In some embodiments, a panel of protein biomarkers in which one or more members of the panel is present at an elevated level includes one or more of (e.g., 1, 2, 3, 4, 5, 6, 7, 8, 9, 10, or each of): CA19-9, CEA, HGF, OPN, CA125, AFP, prolactin, TIMP-1, follistatin, G-CSF, and/or CA15-3. In some embodiments, a panel of protein biomarkers in which one or more members of the panel is present at an elevated level includes one or more of (e.g., 1, 2, 3, 4, 5, 6, 7, 8, or each of): CA19-9, CEA, HGF, OPN, CA125, AFP, prolactin, TIMP-1, and/or CA15-3. In some embodiments, a panel of protein biomarkers in which one or more members of the panel is present at an elevated level includes one or more of (e.g., 1, 2, 3, or each of): CA19-9, CEA, HGF, and/or OPN.

In some embodiments, methods provided herein that include detecting the presence of one or more members of a panel of genetic biomarkers (e.g., each member of a panel of genetic biomarkers) and the presence of one or more members of a panel of protein biomarkers (e.g., each member of a panel of protein biomarkers) in one or more samples obtained from a subject, a decreased level of one or more members of the panel of protein biomarkers can be detected. For example, a decreased level of a protein biomarker can be a level that is lower that a reference level. A reference level can be any level of the protein biomarker that is not associated with the presence of cancer. For example, a reference level of a protein biomarker can be a level that is present in a reference subject that does not have cancer or does not harbor a cancer cell. A reference level of a protein biomarker can be the average level that is present in a plurality of reference subjects that do not have cancer or do not harbor a cancer cell. A reference level of a protein biomarker in a subject determined to have cancer can be the level that was presence in the subject prior to the onset of cancer. In some embodiments, a panel of protein biomarkers in which one or more members of the panel is present at a decreased level includes one or more of (e.g., 1, 2, 3, 4, 5, 6, 7, or each of): CA19-9, CEA, HGF, OPN, CA125, prolactin, TIMP-1, and/or myeloperoxidase (MPO). In some embodiments, a panel of protein biomarkers in which one or more members of the panel is present at a decreased level includes one or more of (e.g., 1, 2, 3, 4, 5, 6, 7, 8, 9, 10, or each of): CA19-9, CEA, HGF, OPN, CA125, AFP, prolactin, TIMP-1, follistatin, G-CSF, and/or CA15-3. In some embodiments, a panel of protein biomarkers in which one or more members of the panel is present at a decreased level includes one or more of (e.g., 1, 2, 3, 4, 5, 6, 7, 8, or each of): CA19-9, CEA, HGF, OPN, CA125, AFP, prolactin, TIMP-1, and/or CA15-3. In some embodiments, a panel of protein biomarkers in which one or more members of the panel is present at a decreased level includes one or more of (e.g., 1, 2, 3, or each of): CA19-9, CEA, HGF, and/or OPN.

In some embodiments, when a subject is determined as having (e.g., diagnosed to have) cancer or determined to be (e.g. diagnosed as being) at elevated risk of having or developing cancer (e.g., by detecting: 1) the presence of one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) the presence of one or more protein biomarkers in any of the panels described herein as being useful in conjunction with this genetic biomarker panel), the subject is selected as a candidate for (e.g., is selected for) further diagnostic testing (e.g., any of the variety of further diagnostic testing methods described herein), the subject is selected as a candidate for (e.g. is selected for) increased monitoring (e.g., any of the variety of increasing monitoring methods described herein), the subject is identified as a subject who will or is likely to respond to a treatment (e.g., any of the variety of therapeutic interventions described herein), the subject is selected as a candidate for (e.g., is selected for) a treatment, a treatment (e.g., any of the variety of therapeutic interventions described herein) is selected for the subject, and/or a treatment (e.g., any of the variety of therapeutic interventions described herein) is administered to the subject. For example, when a subject is determined as having (e.g., diagnosed to have) cancer or determined to be (e.g. diagnosed as being) at elevated risk of having or developing cancer, the subject can undergo further diagnostic testing, which further diagnostic testing can confirm the presence of cancer in the subject. Additionally or alternatively, the subject can be monitored at in increased frequency. In some embodiments of a subject determined as having (e.g., diagnosed to have) cancer or determined to be (e.g. diagnosed as being) at elevated risk of having or developing cancer in which the subject undergoes further diagnostic testing and/ or increased monitoring, the subject can additionally be administered a therapeutic intervention. In some embodiments, after a subject is administered a therapeutic intervention, the subject undergoes additional further diagnostic testing (e.g., the same type of further diagnostic testing as was performed previously and/or a different type of further diagnostic testing) and/or continued increased monitoring (e.g., increased monitoring at the same or at a different frequency as was previously done). In embodiments, after a subject is administered a therapeutic intervention and the subject undergoes additional further diagnostic testing and/ or additional increased monitoring, the subject is administered another therapeutic intervention (e.g., the same therapeutic intervention as was previously administered and/or a different therapeutic intervention). In some embodiments, after a subject is administered a therapeutic intervention, the subject is tested for the presence of one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) the presence of one or more protein biomarkers in any of the panels described herein as being useful in conjunction with this genetic biomarker panel.

In some embodiments, methods provided herein that include detecting the presence of one or more members of a panel of genetic biomarkers and the presence of one or more members of a panel of protein biomarkers in one or more samples obtained from a subject further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). The presence of aneuploidy in any chromosome or portion thereof (e.g., an arm of a chromosome) can be detected. In some embodiments of methods that include detecting the presence of genetic biomarkers, protein biomarkers, and aneuploidy, the presence of aneuploidy on one or more of chromosome arms 5q, 8q, and 9p is detected. In some embodiments of methods that include detecting the presence of genetic biomarkers, protein biomarkers, and aneuploidy, the presence of aneuploidy on one or more of chromosome arms 4p, 7q, 8q, and 9q is detected.

In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, prolactin, TIMP-1, and myeloperoxidase (MPO), the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, prolactin, TIMP-1, and/or myeloperoxidase (MPO), the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, 2) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), and 3) the presence of aneuploidy, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, follistatin, G-CSF, and CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that detecting in one or more samples obtained from a subject the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, follistatin, G-CSF, and/or CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, 2) one or more (e.g., 1, 2, 3, 4, 5, 6, 7, or 8) of the following protein biomarkers: CA19-9, CEA, HGF, OPN, CA125, AFP, prolactin, TIMP-1, follistatin, G-CSF, and/or CA15-3, and 3) the presence of aneuploidy, the subject is determined as having (e.g., diagnosed to have) or is determined to be (e.g. diagnosed as being) at elevated risk of having or developing cancer one of the following types of cancer: liver cancer, ovarian cancer, esophageal cancer, stomach cancer, pancreatic cancer, colorectal cancer, lung cancer, and/or breast cancer.

In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments or methods provided herein that include detecting in one or more samples obtained from a subject the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) each of the following protein biomarkers: CA19-9, CEA, HGF, OPN, CA125, AFP, prolactin, TIMP-1, and CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS, and 2) each of the following protein biomarkers: CA19-9, CEA, HGF, OPN, CA125, AFP, prolactin, TIMP-1, and CA15-3, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, 2) one or more (e.g., 1, 2, 3, 4, 5, 6, 7, or 8) of the following protein biomarkers: CA19-9, CEA, HGF, OPN, CA125, AFP, prolactin, TIMP-1, and/or CA15-3, and 3) the presence of aneuploidy, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments of methods provided herein that include detecting in one or more samples obtained from a subject the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) one or more (e.g., 1, 2, 3, or 4) of the following protein biomarkers: CA19-9, CEA, HGF, and/or OPN, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in each of the following genes: KRAS (e.g., genetic biomarkers in codons 12 and/or 61), TP53, CDKN2A, and SMAD4, and 2) one or more (e.g., 1, 2, 3, or 4) of the following protein biomarkers: CA19-9, CEA, HGF, and/or OPN, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) each of the following protein biomarkers: CA19-9, CEA, HGF, and OPN, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments or methods provided herein that include detecting in one or more samples obtained from a subject the presence of: 1) one or more genetic biomarkers in each of the following genes: KRAS (e.g., genetic biomarkers in codons 12 and/or 61), TP53, CDKN2A, and SMAD4, and 2) each of the following protein biomarkers: CA19-9, CEA, HGF, and OPN, the methods further include detecting the presence of aneuploidy in a sample obtained from the subject (e.g., the same sample use to detect either or both of the presence of one or more members of a panel of genetic biomarkers and the presence of one or more members of a panel of protein biomarkers, or a different sample). In some embodiments of methods provided herein that include detecting in one or more samples obtained from a subject the presence of: 1) one or more genetic biomarkers in one or more (e.g., 1, 2, 3, or 4) of the following genes: KRAS (e.g., genetic biomarkers in codons 12 and/or 61), TP53, CDKN2A, and/or SMAD4, and 2) one or more (e.g., 1, 2, 3, or 4) of the following protein biomarkers: CA19-9, CEA, HGF, and/or OPN, a subject is determined as having (e.g., diagnosed to have) or is determined to be (e.g. diagnosed as being) at elevated risk of having or developing pancreatic cancer.

In some embodiments, any of the variety of methods provided herein that include detecting the presence of one or more members of a panel of genetic biomarkers and the presence of one or more members of a panel of protein biomarkers in one or more samples obtained from a subject further include detecting the presence of one or more members of one or more additional classes of biomarkers. Non-limiting examples of such additional classes of biomarkers includes: copy number changes, DNA methylation changes, other nucleic acids (e.g., mRNAs, miRNAs, lncRNAs, circRNA, mtDNA, telomeric DNA, translocation and genomic rearrangements), peptides, and/or metabolites.

In some embodiments, the one or more additional classes of biomarkers include a metabolite biomarker. In some embodiments, a subject is determined to be at elevated risk of having or developing cancer if the biological sample contains one or more metabolites indicative of cancer. In some embodiments, a subject is determined as having cancer if the biological sample contains one or more metabolites indicative of cancer. Non-limiting examples of metabolites indicative of cancer include: 5-methylthioadenosine (MTA), Glutathione reduced (GSH), N-acetylglutamate, Lactose, N-acetylneuraminate, UDP-acetylglucosamine, UDP-Acetylgalactosamine, UDP-glucuronate, Pantothenate, Arachidonate (20:4n6), Choline, Cytidine 5'-diphosphocholine, Dihomo-linolenate (20:3n3), Docosapentaenoate (DPA 22:5n3), Eicosapentaenoate (EPA 20:5n3), Glycerophosphorylcholine (GPC), Docosahexaenoate (DHA 22:6n3), Linoleate (18:2n6), Cytidine 5'-monophosphate (5'-CMP), Gamma-glutamylglutamate, X-14577, X-11583, Isovalerylcarnitine, Phosphocreatine, 2-Aminoadipic acid, Gluconic acid, O-Acetylcarnitine, aspartic acid, Deamido-NAD+, glutamic acid, Isobutyrylcarnitine, Carnitine, Pyridoxal, Citric acid, Adenosine, ATP, valine, XC0061, Isoleucine, γ-Butyrobetaine, Lactic acid, alanine, phenylalanine, Gluconolactone, leucine, Glutathione (GSSG)_divalent, tyrosine, NAD+, XC0016, UTP, creatine, Theobromine, CTP, GTP, 3-Methylhistidine, Succinic acid, Glycerol 3-phosphate, glutamine, 5-Oxoproline, Thiamine, Butyrylcarnitine, 4-Acetamidobutanoic acid, UDP-Glucose, UDP-Galactose, threonine, N-Acetylglycine, proline, ADP, Choline, Malic acid, S-Adenosylmethionine, Pantothenic acid, Cysteinesulfinic acid, 6-Aminohexanoic acid, Homocysteic acid, Hydroxyproline, Methionine sulfoxide, 3-Guanidinopropionic acid, Glucose 6-phosphate, Phenaceturic acid, Threonic acid, tryptophan, Pyridoxine, N-Acetylaspartic acid, 4-Guanidinobutyric acid, serine, Citrulline, Betaine, N-Acetylasparagine, 2-Hydroxyglutaric acid, arginine, Glutathione (GSH), creatinine, Dihydroxyacetone phosphate, histidine, glycine, Glucose 1-phosphate, N-Formylglycine, Ketoprofen, lysine, beta-alanine, N-Acetylglutamic acid, 2-Amino-2-(hydroxymethyl)-1,3-propanediol, Ornithine, Phosphorylcholine, Glycerophosphocholine, Terephthalic acid, Glyceraldehyde 3-phosphate, Gly-Asp, Taurine, Fructose 1,6-diphosphate, 3-Aminoisobutyric acid, Spermidine, GABA, Triethanolamine, Glycerol, N-Acetylserine, N-Acetylornithine, Diethanolamine, AMP, Cysteine glutathione disulfide, Streptomycin sulfate+H2O divalent, trans-Glutaconic acid, Nicotinic acid, Isobutylamine, Betaine aldehyde+H2O, Urocanic acid, 1-Aminocyclopropane-1-carboxylic acid Homoserinelactone, 5-Aminovaleric acid, 3-Hydroxybutyric acid, Ethanolamine, Isovaleric acid, N-Methylglutamic acid, Cystathionine, Spermine, Carnosine, 1-Methylnicotinamide, N-Acetylneuraminic acid, Sarcosine, GDP, N-Methylalanine, palmitic acid, 1,2-dioleoyl-sn-glycero-3-phospho-rac-glycerolcholesterol 5α,6α epoxidelanosterol, lignoceric acid, loleoyl_rac_GL, cholesterol_epoxide, erucic acid, T-LCA, oleoyl-L-carnitine, oleanolic acid, 3-phosphoglycerate, 5-hydroxynorvaline, 5-methoxytryptamine, adenosine-5-monophosphate, alpha-ketoglutarate, asparagine, benzoic acid, hypoxanthine, maltose, maltotriose, methionine sulfoxide, nornicotine, phenol, Phosphoethanolamine, pyrophosphate, pyruvic acid, quinic acid, taurine, uric acid, inosine, lactamide, 5-hydroxynorvaline NIST, cholesterol, deoxypentitol, 2-hydroxyestrone, 2-hydroxyestradiol, 2-metholyestrone, 2-metholxyestradiol, 2-hydroxyestrone-3-methyl ether, 4-hydroxyestrone, 4-metholxyestrone, 4-methoxyestradiol, 16alpha-hydroxyestrone, 17-epiestriol, estriol, 16-Ketoestradiol, 16-epiestriol, acylcarnitine C18:1, amino acids citrulline and trans-4-hydroxyproline, glycerophospholipids PC aa C28:1, PC ae C30:0 and PC ae C30:2, and sphingolipid SM (OH) C14:1. See e.g., Halama et al., Nesting of colon and ovarian cancer cells in the endothelial niche is associated with alterations in glycan and lipid metabolism, Scientific Reports volume 7, Article number: 39999 (2017); Hur et al., Systems approach to characterize the metabolism of liver cancer stem cells expressing CD133, Sci Rep., 7:45557, doi: 10.1038/srep45557, (2017); Eliassen et al., Urinary Estrogens and Estrogen Metabolites and Subsequent Risk of Breast Cancer among Premenopausal Women, Cancer Res; 72(3); 696-706 (2011); Gangi et al., Metabolomic profile in pancreatic cancer patients: a consensus-based approach to identify highly discriminating metabolites, Oncotarget, February 2; 7(5): 5815-5829 (2016); Kumar et al., Serum and Plasma Metabolomic Biomarkers for Lung Cancer, Bioinformation, 13(6): 202-208, doi: 10.6026/97320630013202 (2017); Schmidt et al., Pre-diagnostic metabolite concentrations and prostate cancer risk in 1077 cases and 1077 matched controls in the European Prospective Investigation into Cancer and Nutrition, BMC Med., 15:122, doi: 10.1186/s12916-017-0885-6 (2017); each of which is incorporated herein by reference in its entirety.

In some embodiments, the one or more additional classes of biomarkers include a peptide (e.g., a peptide that is distinct from the various protein biomarkers described herein as being useful in one or more methods). In some embodiments, a subject is determined to be at elevated risk of having or developing cancer if the biological sample contains one or more peptides indicative of cancer. In some embodiments, a subject is determined as having cancer if the biological sample contains one or more peptides indicative of cancer. In some embodiments, a peptide is derived from a protein (e.g., the peptide includes an amino acid sequence present in a protein biomarker or a different protein). Non-limiting examples of peptides indicative of cancer include the following peptides and peptides derived from the following proteins: CEACAM, CYFRA21-1, CA125, PKLK, ProGRP, NSE, TPA 6, TPA 7, TPA 8, NRG, NRG 100, CNDP, APOB100, SCC, VEGF, EGFR, PIK3CA, HER2, BRAF, ROS, RET, NRAS, MET, MEK1, HER2, C4.4A, PSF3, FAM83B, ECD, CTNNB, VIM, S100A4, S100A7, COX2, MUC1, KLKB1, SAA, HP-β chain, C9, Pgrmc1, Ciz1, Transferrin, α-1 antitrypsin, apolipo protein 1, complement c3a, Caveolin-1, Kallikrein 6, Glucose regulated protein-8, α defensing-1,-2,-3, Serum C-peptide, Alpha-2-HS glycol protein, Tryptic KRT 8 peptide, Plasma glycol protein, Catenin, Defensin α 6, MMPs, Cyclin D, S100 P, Lamin A/C filament protein, Heat shock protein, aldehyde dehydrogenase, Tx1-2, (thioredoxin like protein-2), P53, nm23, u-PA, VEGF, Eph B4, CRABP2, WT-1, Rab-3D, Mesothelin, ERα, ANXA4, PSAT1, SPB5, CEA5, CEA6, A1AT, SLPI, APOA4, VDBP, HE4, IL-1, -6, -7, -8, -10, -11, -12, -16, -18, -21, -23, -28A, -33, LIF, TNFR1-2, HVEM (TNFRSF14), IL1R-a, IL1R-b, IL-2R, M-CSF, MIP-1a, TNF-α, CD40, RANTES, CD40L, MIF, IFN-β, MCP-4 (CCL13), MIG (CXCL9), MIP-1δ (CCL15), MIP3a (CCL20), MIP-4 (CCL18), MPIF-1, SDF-1a+b (CXCL12), CD137/4-1BB, lymphotactin (XCL1), eotaxin-1 (CCL11), eotaxin-2 (CCL24), 6Ckine/CCL21), BLC (CXCL13), CTACK (CCL27), BCA-1 (CXCL13), HCC4 (CCL16), CTAP-3 (CXCL7), IGF1, VEGF, VEGFR3, EGFR, ErbB2, CTGF, PDGF AA, BB, PDGFRb, bFGF, TGFbRIII, β-cellulin, IGFBP1-4, 6, BDNF, PEDF, angiopoietin-2, renin, lysophosphatidic acid, β2-microglobulin, sialyl TN, ACE, CA 19-9, CEA, CA 15-3, CA-50, CA 72-4, OVX1, mesothelin, sialyl TN, MMP-2, -3, -7, -9, VAP-1, TIMP1-2, tenascin C, VCAM-1, osteopontin, KIM-1, NCAM, tetranectin, nidogen-2, cathepsin L, prostasin, matriptase, kallikreins 2, 6, 10, cystatin C, claudin, spondin2, SLPI, bHCG, urinary gonadotropin peptide, inhibin, leptin, adiponectin, GH, TSH, ACTH, PRL, FSH, LH, cortisol, TTR, osteocalcin, insulin, ghrelin, GIP, GLP-1, amylin, glucagon, peptide YY, follistatin, hepcidin, CRP, Apo A1, CIII, H, transthyretin, SAA, SAP, complement C3,4, complement factor H, albumin, ceruloplasmin, haptoglobin, β-hemoglobin, transferrin, ferritin, fibrinogen, thrombin, von Willebrand factor, myoglobin, immunosuppressive acidic protein, lipid-associated sialic acid, S100A12 (EN-RAGE), fetuin A, clusterin, α1-antitrypsin, a2-macroglobulin, serpin1 (human plasminogen activator inhibitor-1), Cox-1, Hsp27, Hsp60, Hsp80, Hsp90, lectin-type oxidized LDL receptor 1, CD14, lipocalin 2, ITIH4, sFasL, Cyfra21-1, TPA, perforin, DcR3, AGRP, creatine kinase-MB, human milk fat globule 1-2, NT-Pro-BNP, neuron-specific enolase, CASA, NB/70K, AFP, afamin, collagen, prohibitin, keratin-6, PARC, B7-H4, YK-L40, AFP-L3, DCP, GPC3, OPN, GP73, CK19, MDK, A2, 5-HIAA, CA15-3, CA19-9, CA27.29, CA72-4, calcitonin, CGA, BRAF V600E, BAP, BCT-ABL fusion protein, KIT, KRAS, PSA, Lactate dehydrogenase, NMP22, PAI-1, uPA, fibrin D-dimer, S100, TPA, thyroglobulin, CD20, CD24, CD44, RS/DJ-1, p53, alpha-2-HS-glycoprotein, lipophilin B, beta-globin, hemopexin, UBE2N, PSMB6, PPP1CB, CPT2, COPA, MSK1/2, Pro-NPY, Secernin-1, Vinculin, NAAA, PTK7, TFG, MCCC2, TRAP1, IMPDH2, PTEN, POSTN, EPLIN, eIF4A3, DDAH1, ARG2, PRDX3&4, P4HB, YWHAG, Enoyl CoA-hydrase, PHB, TUBB, KRT2, DES, HSP71, ATP5B, CKB, HSPD1, LMNA, EZH2, AMACR, FABP5, PPA2, EZR, SLP2, SM22, Bax, Smac/Diablo phosphorylated Bcl2, STAT3 and Smac/Diablo expression, PHB, PAP, AMACR, PSMA, FKBP4, PRDX4, KRT7/8/18, GSTP1, NDPK1, MTX2, GDF15, PCa-24, Caveolin-2, Prothrombin, Antithrombin-III, Haptoglobin, Serum amyloid A-1 protein, ZAG, ORM2, APOC3, CALML5, IGFBP2, MUC5AC, PNLIP, PZP, TIMP1, AMBP, inter-alpha-trypsin inhibitor heavy chain H1, inter-alpha-trypsin inhibitor heavy chain H2, inter-alpha-trypsin inhibitor heavy chain H3, V-type proton ATPase subunit B, kidney isoform, Hepatocyte growth factor-like protein, Serum amyloid P-component, Acylglycerol kinase, Leucine-rich repeat-containing protein 9, Beta-2-glycoprotein 1, Plasma protease C1 inhibitor, Lipoxygenase homology domain-containing protein 1, Protocadherin alpha-13. See, e.g., Kuppusamy et al., Volume 24, Issue 6, September 2017, Pages 1212-1221; Elzek and Rodland, Cancer Metastasis Rev. 2015 March; 34(1): 83-96; Noel and Lokshin, Future Oncol. 2012 January; 8(1): 55-71; Tsuchiya et al., World J Gastroenterol. 2015 Oct. 7; 21(37): 10573-10583; Lou et al., Biomark Cancer. 2017; 9:1-9; Park et al., Oncotarget. 2017 Jun. 27; 8(26): 42761-42771; Saraswat et al., Cancer Med. 2017 July; 6(7): 1738-1751; Zamay et al., Cancers (Basel). 2017 November; 9(11): 155; Tanase et al., Oncotarget. 2017 Mar. 14; 8(11): 18497-18512, each of which is incorporated herein by reference in its entirety.

In some embodiments, the one or more additional classes of biomarkers include nucleic acid lesions or variations (e.g., a nucleic acid lesion or variation that is distinct from the various genetic biomarkers described herein as being useful in one or more methods). In some embodiments, a subject is determined to be at elevated risk of having or developing cancer if the biological sample contains one or more nucleic acid lesions or variations indicative of cancer. In some embodiments, a subject is determined as having cancer if the biological sample contains one or more nucleic acid lesions or variations indicative of cancer. Non-limiting examples of nucleic acid lesions or variations include copy number changes, DNA methylation changes, and/or other nucleic acids (e.g., mRNAs, miRNAs, lncRNAs, circRNA, mtDNA, telomeric DNA, translocation and genomic rearrangements).

Translocations and genomic rearrangements have been correlated with various cancers (e.g., prostate, glioma, lung cancer, non-small cell lung cancer, melanoma, and thyroid cancer) and used as biomarkers for years (e.g., Demeure et al., 2014, World J Surg., 38:1296-305; Hogenbirk et al., 2016, PNAS USA, 113:E3649-56; Gasi et al., 2011, PLoS One, 6:e16332; Ogiwara et al., 2008, Oncogene, 27:4788-97; U.S. Pat. Nos. 9,745,632; and 6,576,420). In addition, changes in copy number have been used as biomarkers for various cancers including, without limitation, head and neck squamous cell carcinoma, lymphoma (e.g., non-Hodgkin's lymphoma) and colorectal cancer (Kumar et al., 2017, Tumour Biol, 39:1010428317740296; Kumar et al., 2017, Tumour Biol., 39:1010428317736643; Henrique et al., 2014, Expert Rev. Mol. Diagn., 14:419-22; and U.S. Pat. No. 9,816,139). DNA methylation and changes in DNA methylation (e.g., hypomethylation, hypermethylation) also are used as biomarkers in cancer. For example, hypomethylation has been associated with hepatocellular carcinoma (see, for example, Henrique et al., 2014, Expert Rev. Mol. Diagn., 14:419-22), esophageal carcinogenesis (see, for example, Alvarez et al., 2011, PLoS Genet., 7:e1001356) and gastric and liver cancer (see, for example, U.S. Pat. No. 8,728,732), and hypermethylation has been associated with colorectal cancer (see, for example, U.S. Pat. No. 9,957,570;). In addition to genome-wide changes in methylation, specific methylation changes within particular genes can be indicative of specific cancers (see, for example, U.S. Pat. No. 8,150,626). Li et al. (2012, J. Epidemiol., 22:384-94) provides a review of the association between numerous cancers (e.g., breast, bladder, gastric, lung, prostate, head and neck squamous cell, and nasopharyngeal) and aberrant methylation. Additionally or alternatively, additional types of nucleic acids or features of nucleic acids have been associated with various cancers. Non-limiting examples of such nucleic acids or features of nucleic acids include the presence or absence of various microRNAs (miRNAs) have been used in the diagnosis of colon, prostate, colorectal, and ovarian cancers (see, for example, D'Souza et al., 2018, PLos One, 13:e0194268; Fukagawa et al., 2017, Cancer Sci., 108:886-96; Giraldez et al., 2018, Methods Mol. Biol., 1768:459-74; U.S. Pat. Nos. 8,343,718; 9,410,956; and 9,074,206). For a review on the specific association of miR-22 with cancer, see Wang et al. (2017, Int. J. Oncol., 50:345-55); the abnormal expression of long non-coding RNAs (lncRNAs) also have been used as a biomarker in cancers such as prostate cancer, colorectal cancer, cervical cancer, melanoma, non-small cell lung cancer, gastric cancer, endometrial carcinoma, and hepatocellular carcinoma (see, for example, Wang et al., 2017, Oncotarget, 8:58577086; Wang et al., 2018, Mol. Cancer, 17:110; Yu et al., 2018, Eur. Rev. Med. Pharmacol. Sci., 22:4812-9; Yu et al., 2018, Eur. Rev. Med. Pharmacol. Sci., 22:993-1002; Zhang et al., 2018, Eur. Rev. Med. Pharmacol. Sci., 22:4820-7; Zhang et al., 2018, Eur. Rev. Med. Pharmacol. Sci., 22:2304-9; Xie et al., 2018, EBioMedicine, 33:57-67; and U.S. Pat. No. 9,410,206); the presence or absence of circular RNA (circRNA) has been used as a biomarker in lung cancer, breast cancer, gastric cancer, colorectal cancer, and liver cancer (e.g., Geng et al., 2018, J. Hematol. Oncol., 11:98) and melanoma (e.g., Zhang et al., 2018, Oncol. Lett., 16:1219-25); changes in telomeric DNA (e.g., in length or in heterozygosity) or centromeric DNA (e.g., changes in expression of centromeric genes) also have been associated with cancers (e.g., prostate, breast, lung, lymphoma, and Ewing's sarcoma) (see, for example, Baretton et al., 1994, Cancer Res., 54:4472-80; Liscia et al., 1999, Br. J. Cancer, 80:821-6; Proctor et al., 2009, Biochim. Biophys. Acta, 1792:260-74; and Sun et al., 2016, Int. J. Cancer, 139:899-907); various mutations (e.g., deletions), rearrangements and/or copy number changes in mitochondrial DNA (mtDNA) have been used prognostically and diagnostically for various cancers (e.g., prostate cancer, melanoma, breast cancer, lung cancer, and colorectal cancer). See, for example, Maragh et al., 2015, Cancer Biomark., 15:763-73; Shen et al., 2010, Mitochondrion, 10:62-68; Hosgood et al., 2010, Carcinogen., 31:847-9; Thyagarajan et al., 2012, Cancer Epid. Biomarkers & Prev., 21:1574-81; and U.S. Pat. No. 9,745,632; and the abnormal presence, absence or amount of messenger RNAs (mRNAs) also have been correlated with various cancers including, without limitation, breast cancer, Wilms' tumors, and cervical cancer (see, for example, Guetschow et al., 2012, Anal. Bioanaly. Chem., 404:399-406; Schwienbacher et al., 2000, Cancer Res., 60:1521-5; and Ngan et al., 1997, Genitourin Med., 73:54-8). Each of these citations is incorporated herein by reference in its entirety.

This document provides methods and materials for assessing and/or treating mammals (e.g., humans) having, or suspected of having, cancer. In some embodiments, this document provides methods and materials for identifying a mammal as having cancer. For example, a sample (e.g., a blood sample) obtained from a mammal can be assessed to determine if the mammal has cancer based, at least in part, on the presence or absence of one or more first biomarkers (e.g., genetic biomarkers) and/or an elevated level of one or more second biomarkers (e.g., peptide biomarkers) in the sample. A biomarker panel (e.g., a set of one or more biomarkers) described herein can include the presence of two or more (e.g., three, five, nine, 10, 25, 100, 250, 500, 1000, 1500, 2000, 2500, or more) biomarkers (e.g., biomarkers associated with cancer). In some embodiments, a biomarker panel can include about 2,011 biomarkers (e.g., about 2,001 genomic biomarkers and about 10 peptide biomarkers). In some embodiments, methods and materials described herein also can include identifying the location (e.g., the anatomic site) of a cancer in a mammal. For example, a sample (e.g., a blood sample) obtained from a mammal can be assessed to determine the location of the cancer in the mammal based, at least in part, on the presence or absence of one or more first biomarkers (e.g., genetic biomarkers) and/or an elevated level of one or more second biomarkers (e.g., peptide biomarkers). In some embodiments, methods and materials described herein also can include treating a mammal having cancer (e.g., administering one or more cancer treatments to treat the mammal). For example, a sample (e.g., a blood sample) obtained from a mammal can be assessed to determine if the mammal has cancer based, at least in part, on the presence or absence of one or more first biomarkers (e.g., genetic biomarkers) and/or an elevated level of one or more second biomarkers (e.g., peptide biomarkers), and administering one or more cancer treatments to treat the mammal (e.g., to reduce the severity of the cancer, to reduce a symptom of the cancer, and/or to reduce the number of cancer cells present within the mammal).

The term "elevated level" as used herein with respect to a level of a peptide biomarker refers to any level that is greater than the reference level of the peptide typically observed in a sample (e.g., a reference sample) from one or more healthy mammals. In some embodiments, a reference sample can be a sample obtained from a mammal that does not have a cancer. For example, for a peptide biomarker associated with colorectal cancer, a reference sample can be a sample obtained from a subject that does not have colorectal cancer. In some embodiments, a reference sample can be a sample obtained from the same mammal in which the elevated level of a peptide biomarker is observed, where the reference sample was obtained prior to onset of the cancer. In some embodiments, such a reference sample obtained from the same mammal is frozen or otherwise preserved for future use as a reference sample. In some embodiments, when reference samples have undetectable levels of a peptide biomarker, an elevated level can be any detectable level of the peptide biomarker. It will be appreciated that levels from comparable samples are used when determining whether or not a particular level is an elevated level.

Any appropriate mammal can be assessed and/or treated as described herein. A mammal can be a mammal having cancer. A mammal can be a mammal suspected of having cancer. In some embodiments, humans or other primates such as monkeys can be assessed for the presence or absence of one or more first biomarkers (e.g., genetic biomarkers) and/or an elevated level of one or more second biomarkers (e.g., peptide biomarkers) as described herein. In some embodiments, dogs, cats, horses, cows, pigs, sheep, mice, and rats can be assessed for the presence or absence of one or more first biomarkers (e.g., genetic biomarkers) and/or an elevated level of one or more second biomarkers (e.g., peptide biomarkers) as described herein. For example, a human can be assessed for the presence or absence of one or more first biomarkers (e.g., genetic biomarkers) and/or an elevated level of one or more second biomarkers (e.g., peptide biomarkers) as described herein and, optionally, can be treated with one or more cancer treatments as described herein.

Any appropriate sample from a mammal can be assessed as described herein (e.g., assessed for the presence or absence of one or more first biomarkers (e.g., genetic biomarkers) and/or an elevated level of one or more second biomarkers (e.g., peptide biomarkers)). In some embodiments, a sample can include DNA (e.g., genomic DNA). In some embodiments, a sample can include cell-free DNA (e.g., circulating tumor DNA (ctDNA)). In some embodiments, a sample can include peptides. For example, a sample can include circulating peptides (e.g., cancer related peptides). As used herein a "circulating peptide" is a peptide that can be detected in any closed system (e.g., the circulatory system) within the body of a mammal. In some embodiments, a sample can be fluid sample (e.g., a liquid biopsy). Examples of samples that can contain DNA and/or peptides include, without limitation, blood (e.g., whole blood, serum, or plasma), amnion, tissue, urine, cerebrospinal fluid, saliva, sputum, broncho-alveolar lavage, bile, lymphatic fluid, cyst fluid, stool, ascites, pap smears, breast milk, and exhaled breath condensate. For example, a plasma sample can be assessed for the presence or absence of one or more first biomarkers (e.g., genetic biomarkers) and/or an elevated level of one or more second biomarkers (e.g., peptide biomarkers) as described herein.

In some embodiments, a sample can be processed (e.g., to isolate and/or purify DNA and/or peptides from the sample). For example, DNA isolation and/or purification can include cell lysis (e.g., using detergents and/or surfactants), protein removal (e.g., using a protease), and/or RNA removal (e.g., using an RNase). As another example, peptide isolation and/or purification can include cell lysis (e.g., using detergents and/or surfactants), DNA removal (e.g., using a DNase), and/or RNA removal (e.g., using an RNase).

Any appropriate biomarkers can be used as described herein (e.g., to determine if a mammal has cancer based, at least in part, on the presence or absence of one or more first biomarkers (e.g., genetic biomarkers) and/or an elevated level of one or more second biomarkers (e.g., peptide biomarkers) in the sample). Examples of biomarkers include, without limitation, genetic biomarkers, peptide biomarkers, metabolites, mRNA transcripts, miRNAs, methylation patterns (e.g., DNA methylation patterns), proteins (e.g., antibodies), and chromatin patterns. In some embodiments, the presence of one or more genetic biomarkers can be used to identify a mammal as having cancer. In some embodiments, an elevated level one or more peptide biomarkers can be used to identify a mammal as having cancer. In some embodiments, the presence of one or more genetic biomarkers and an elevated level of one or more peptide biomarkers in combination can be used to identify a mammal as having cancer. In some embodiments, detecting the presence of one or more genetic biomarkers and an elevated level of one or more peptide biomarkers in combination can increase the specificity and/or sensitivity of detection as compared to detecting either genetic biomarkers or peptide biomarkers alone.

A genetic biomarker can be any appropriate genetic biomarker. For example, a genetic biomarker can be a genetic biomarker associated with cancer. A genetic biomarker can include a modification in a gene. Examples of modifications include, without limitation, single base substitutions, insertions, deletions, indels, translocations, and copy number variations. A genetic biomarker can be in any appropriate gene. In some embodiments, a genetic biomarker can include a modification (e.g., an inactivating modification) in a tumor suppressor gene. In some embodiments, a genetic biomarker can include a modification (e.g., an activating modification) in an oncogene. Examples of genes that can include a genetic biomarker include, without limitation, NRAS, CTNNB1, PIK3CA, FBXW7, APC, EGFR, BRAF, CDKN2A, PTEN, FGFR2, HRAS, KRAS, AKT1, TP53, PPP2R1A, GNAS, JUN, ABCA7, ACVR1B, ACVR2A, AJUBA, AKT1, ALB, ALDOB, ALK, AMBRA1, AMER1, AMOT, ANKRD46, APC, AR, ARHGAP35, ARID1A, ARID1B, ARID2, ARID4B, ARL15, ARMCX1, ASXL1, ASXL2, ATAD2, ATG14, ATG5, ATM, ATRX, ATXN2, AXIN1, B2M, BAP1, BCL9, BCLAF1, BCOR, BIRC6, BIRC8, BLVRA, BRAF, BRCA1, BRCA2, BRD7, BRE, BRWD3, BTBD7, BTRC, C11orf70, C12orf57, C2CD5, C3orf62, C8orf34, CAMKV, CAPG, CASP8, CBFB, CBX4, CCAR1, CCDC117, CCDC88A, CCM2, CCNC, CCND1, CCR3, CD1D, CD79B, CDC73, CDCP1, CDH1, CDK12, CDK4, CDKN1A, CDKN1B, CDKN2A, CEBPA, CELF1, CENPB, CEP128, CHD2, CHD4, CHD8, CHEK2, CHRDL1, CHUK, CIC, CLEC4C, CMTR2, CNN2, CNOT1, CNOT4, COL11A1, COPS4, COX7B2, CREBBP, CSDE1, CSMD3, CTCF, CTDNEP1, CTNNB1, CUL1, CUL2, CYB5B, DACH1, DCHS1, DCUN1D1, DDX3X, DDX5, DHX15, DHX16, DICER1, DIRC2, DIS3, DIXDC1, DKK2, DNAJB5, DNER, DNM1L, DNMT3A, EED, EGFR, EIF1AX, EIF2AK3, EIF2S2, EIF4A1, EIF4A2, ELF3, EMG1, EMR3, EP300, EPB41L4A, EPHA2, EPS8, ERBB2, ERBB3, ERRFI1, EXO5, EZH2, F5, FANCM, FAT1, FBN2, FBXW7, FCER1G, FGFR1, FGFR2, FGFR3, FLT3, FN1, FOXA1, FUBP1, FUS, GALNTL5, GATA3, GGCT, GIGYF2, GK2, GLIPR2, GNPTAB, GNRHR, GOLM1, GOT2, GPS2, GPX7, GRK1, GSE1, GZMA, HDAC1, HERC1, HERC4, HGF, HIST1H2BO, HLA-A, HLA-B, HMCN1, HNRNPA1, HRAS, HSP90AB1, ID3, IDH1, IDH2, IFNGR2, IFT88, IKZF2, INO80C, INPP4A, INPPL1, IWS1, JAK1, JAK2, KANSL1, KAT8, KATNAL1, KBTBD7, KCNMB4, KDM5C, KDM6A, KEAP1, KIAA1467, KLF4, KMT2A, KMT2B, KMT2C, KMT2D, KMT2E, KRAS, KRT15, LAMTOR1, LARP4B, LPAR2, LYN, MAP2K1, MAP2K2, MAP2K4, MAP3K1, MAP4K3, MAPK1, MAX, MB21D2, MBD1, MBD6, MBNL1, MBNL3, MED12, MED23, MEN1, MGA, MKLN1, MLLT4, MOAP1, MORC4, MS4A1, MSI1, MTOR, MYC, MYCN, MYD88, MYL6, MYO1B, MYO6, NAA15, NAA25, NAPIL2, NAPIL4, NCOA2, NCOR1, NEK9, NF1, NF2, NFE2L2, NFE2L3, NIPBL, NIT1, NKX3-1, NME4, NOTCH1, NOTCH2, NPM1, NRAS, NSD1, PBRM1, PCBP1, PCOLCE2, PHF6, PIK3CA, PIK3CB, PIK3R1, POLA2, POT1, PPARD, PPM1D, PPP2R1A, PPP6C, PRKACA, PRKCI, PRPF40A, PSIP1, PTEN, PTH2, PTMS, PTN, PTPN11, RAB18, RAC1, RAF1, RANBP3L, RAPGEF6, RASA1, RB1, RBBP6, RBM10, RBM26, RC3H2, REL, RERE, RFC4, RHEB, RHOA, RIMS2, RIT1, RNF111, RNF43, RPL11, RPL5, RQCD1, RRAS2, RUNX1, RXRA, SARM1, SCAF11, SEC22A, SENP3, SENP8, SETD1B, SETD2, SF3A3, SF3B1, SFPQ, SIN3A, SKAP2, SMAD2, SMAD3, SMAD4, SMARCA4, SMARCB1, SMARCC2, SNCB, SOS1, SOX4, SOX9, SP3, SPEN, SPOP, SPSB2, STAG2, STK11, STK31, SUFU, TAF1A, TARDBP, TAS2R30, TBL1XR1, TBX3, TCF12, TCF7L2, TET2, TEX11, TFDP2, TGFBR2, THRAP3, TM9SF1, TMCO2, TMED10, TMEM107, TMEM30A, TMPO, TNFRSF9, TNRC6B, TP53, TP53BP1, TRAF3, TRIM8, TRIP12, TSC1, TTK, TTR, TUBA3C, U2AF1, UBE2D3, UBR5, UNC13C, UNKL, UPP1, USO1, USP28, USP9X, VHL, VN1R2, VPS33B, WAC, WDR33, WDR47, WT1, WWP1, XPO1, YOD1, ZC3H13, ZDHHC4, ZFHX3, ZFP36L1, ZFP36L2, ZGRF1, ZMYM3, ZMYM4, ZNF234, ZNF268, ZNF292, ZNF318, ZNF345, ZNF600, ZNF750, and ZNF800. For example, a genetic biomarker can be in one or more of NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. In some embodiments, methods and materials described herein can include detecting one or more genetic biomarkers (e.g., one or more modifications in one or more genes). For example, methods and materials described herein can include detecting mutations in one or more genes encoding any of the proteins set forth in Example 1, or in one or more of the genes set forth in Table 3 or Table 5. In some embodiments, methods and materials described herein can include detecting one or more of the modifications set forth in Table 3 or Table 5. In some embodiments, methods and materials described herein can include detecting the presence or absence of about 2,001 modifications in about 16 genes. For example, methods and materials described herein can include detecting the presence or absence about 2,001 genetic biomarkers in one or more of NRAS, CTNNB1, PIK3CA, FBXW7, APC, EGFR, BRAF, CDKN2A, PTEN, FGFR2, HRAS, KRAS, AKT1, TP53, PPP2R1A, and GNAS. In some embodiments, genetic biomarkers can be as described elsewhere (see, e.g., Bettegowda et al., 2014 *Science translational medicine* 6: 224ra224; Haber et al., 2014 *Cancer Discov* 4:650-661; Dawson et al., 2013 *N Engl J Med* 368:1199-1209; Wang et al., 2015 *Science translational medicine* 7: 293ra104; Forshew et al., 2012 *Science translational medicine* 4: 136ra168; Abbosh et al., 2017 *Nature* 545:446-451; Beddowes et al., 2017 *Breast* 34 (Suppl 1):S31-S35; and Phallen et al., 2017 *Science translational medicine* 9).

Any appropriate method can be used to detect the presence or absence of one or more biomarkers (e.g., genetic biomarkers) as described herein. In some embodiments, one or more genetic biomarkers can be detected independently (e.g., via singleplex peptide tools). In some embodiments, one or more genetic biomarkers can be detected simultaneously (e.g., via multiplex DNA tools such as "chips" or microarrays). Examples of methods for detecting genetic biomarkers include, without limitation, sequencing (e.g., PCR-based sequencing such as multiplex PCR-based sequencing), DNA hybridization methods (e.g., Southern blotting), restriction enzyme digestion methods, PCR-based multiplex methods, digital PCR methods, droplet digital PCR (ddPCR) methods, PCR-based singleplex PCR methods, Sanger sequencing methods, next-generation sequencing methods (e.g., single-molecule real-time sequencing, nanopore sequencing, and Polony sequencing), quantitative PCR methods, ligation methods, and microarray methods. In some embodiments, methods and materials described herein can include multiplex PCR-based sequencing. For example, methods and materials described herein can include multiplex PCR-based sequencing as set forth in Example 1. In some embodiments of methods provided herein, the presence of one or more mutations present in a sample obtained from a subject is detected using a method is performed that can increase the sensitivity of massively parallel sequencing instruments with an error reduction technique. For example, such techniques can permit the detection of rare mutant alleles in a range of 1 mutant template among 5,000 to 1,000,000 wild-type templates. In some embodiments, the presence of one or more mutations present in a sample obtained from a subject is detected by amplifying DNA (e.g., DNA obtained from cells in a sample or cell-free DNA) to form families of amplicons in which each member of a family is derived from a single template molecule in the cell-free DNA, wherein each member of a family is marked by a common oligonucleotide barcode, and wherein each family is marked by a distinct oligonucleotide barcode. For example, the presence of one or more mutations present in a sample obtained from a subject can be detected by assigning a unique identifier (UID) to each template molecule, amplifying each uniquely tagged template molecule to create UID-families, and redundantly sequencing the amplification products. In some embodiments, the oligonucleotide barcode is introduced into the template molecule by a step of amplifying with a population of primers that collectively contain a plurality of oligonucleotide barcodes. In some embodiments, the oligonucleotide barcode is endogenous to the template molecule, and an adapter comprising a DNA synthesis priming site is ligated to an end of the template molecule adjacent to the oligonucleotide barcode. See, e.g., Kinde et al., 2011 *Proc Natl Acad Sci USA* 108:9530-9535.

In some embodiments of methods provided herein, the presence of one or more mutations present in a sample obtained from a subject is detected using sequencing technology (e.g., a next-generation sequencing technology). A variety of sequencing technologies are known in the art. For example, methods for detection and characterization of circulating tumor DNA in cell-free DNA can be described elsewhere (see, e.g., Haber and Velculescu, 2014 Cancer Discov., 4:650-61). Non-limiting examples of such techniques include SafeSeqs (see, e.g., Kinde et al., 2011 *Proc Natl Acad Sci USA;* 108:9530-5), OnTarget (see, e.g., Forshew et al., 2012 *Sci Transl Med;* 4: 136ra68,), and TamSeq (see, e.g., Thompson et al., 2012 *PLoS ONE,* 7:e31597). In some embodiments, the presence of one or more mutations present in a sample obtained from a subject is detected using droplet digital PCR (ddPCR), a method that is known to be highly sensitive for mutation detection. In some embodiments, the presence of one or more mutations present in a sample obtained from a subject is detected using other sequencing technologies, including but not limited to, chain-termination techniques, shotgun techniques, sequencing-by-synthesis methods, methods that utilize microfluidics, other capture technologies, or any of the other sequencing techniques known in the art that are useful for detection of small amounts of DNA in a sample (e.g., ctDNA in a cell-free DNA sample).

In some embodiments, the presence of one or more mutations present in a sample obtained from a subject is detected using array-based methods. For example, the step of detecting a genetic alteration (e.g., one or more genetic alterations) in cell-free DNA is performed using a DNA microarray. In some embodiments, a DNA microarray can detect one more of a plurality of cancer cell mutations. In some embodiments, cell-free DNA is amplified prior to detecting the genetic alteration. Non-limiting examples of array-based methods that can be used in any of the methods described herein, include: a complementary DNA (cDNA) microarray (see, e.g., Kumar et al. 2012 *J. Pharm. Bioallied Sci.* 4(1): 21-26; Laere et al. 2009 *Methods Mol. Biol.* 512:71-98; Mackay et al. 2003 *Oncogene* 22:2680-2688; Alizadeh et al. 1996 *Nat. Genet.* 14:457-460), an oligonucleotide microarray (see, e.g., Kim et al. 2006 *Carcinogenesis* 27(3): 392-404; Lodes et al. 2009 *PLoS One* 4(7): e6229), a bacterial artificial chromosome (BAC) clone chip (see, e.g., Chung et al. 2004 *Genome Res.* 14(1): 188-196; Thomas et al. 2005 *Genome Res.* 15(12): 1831-1837), a single-nucleotide polymorphism (SNP) microarray (see, e.g., Mao et al. 2007 *Curr. Genomics* 8(4): 219-228; Jasmine et al. 2012 *PLoS One* 7(2): e31968), a microarray-based comparative genomic hybridization array (array-CGH) (see, e.g., Beers and Nederlof, 2006 *Breast Cancer Res.* 8(3): 210; Pinkel et al. 2005 *Nat. Genetics* 37:S11-S17; Michels et al. 2007 *Genet. Med.* 9:574-584), a molecular inversion probe (MIP) assay (see, e.g., Wang et al. 2012 *Cancer Genet* 205(7-8): 341-55; Lin et al. 2010 *BMC Genomics* 11:712). In some embodiments, the cDNA microarray is an Affymetrix microarray (see, e.g., Irizarry 2003 *Nucleic Acids Res* 31:e15; Dalma-Weiszhausz et al. 2006 *Methods Enzymol.* 410:3-28), a NimbleGen microarray (see, e.g., Wei et al. 2008 *Nucleic Acids Res* 36(9): 2926-2938; Albert et al. 2007 *Nat. Methods* 4:903-905), an Agilent microarray (see, e.g., Hughes et al. 2001 *Nat. Biotechnol.* 19(4): 342-347), or a BeadArray array (see, e.g., Liu et al. 2017 *Biosens Bioelectron* 92:596-601). In some embodiments, the oligonucleotide microarray is a DNA tiling array (see, e.g., Mockler and Ecker, 2005 *Genomics* 85(1): 1-15; Bertone et al. 2006 *Genome Res* 16(2): 271-281). Other suitable array-based methods are known in the art.

In some embodiments, multiplex PCR-based sequencing can include a number of amplicons that provides improved sensitivity of detection of one or more genetic biomarkers. For example, multiplex PCR-based sequencing can include about 60 amplicons (e.g., 50, 51, 52, 53, 54, 55, 56, 57, 58, 59, 60, 61, 62, 63, 64, 65, 66, 67, 68, 69, or 70 amplicons). In some embodiments, multiplex PCR-based sequencing can include 61 amplicons. Amplicons produced using multiplex PCR-based sequencing can include nucleic acids having a length from about 15 bp to about 1000 bp (e.g., from about 25 bp to about 1000 bp, from about 35 bp to about 1000 bp, from about 50 bp to about 1000 bp, from about 100 bp to about 1000 bp, from about 250 bp to about 1000 bp, from about 500 bp to about 1000 bp, from about 750 bp to about 1000 bp, from about 15 bp to about 750 bp, from about 15 bp to about 500 bp, from about 15 bp to about 300 bp, from about 15 bp to about 200 bp, from about 15 bp to about 100 bp, from about 15 bp to about 80 bp, from about 15 bp to about 75 bp, from about 15 bp to about 50 bp, from about 15 bp to about 40 bp, from about 15 bp to about 30 bp, from about 15 bp to about 20 bp, from about 20 bp to about 100 bp, from about 25 bp to about 50 bp, or from about 30 bp to about 40 bp). For example, amplicons produced using multiplex PCR-based sequencing can include nucleic acids having a length of about 33 bp.

A peptide biomarker can be any appropriate peptide biomarker. In some embodiments, a peptide biomarker can be a peptide biomarker associated with cancer. For example, a peptide biomarker can be a peptide having elevated levels in a cancer (e.g., as compared to a reference level of the peptide). Examples of peptide biomarkers include, without limitation, AFP, Angiopoietin-2, AXL, CA125, CA 15-3, CA19-9, CD44, CEA, CYFRA 21-1, DKK1, Endoglin, FGF2, Follistatin, Galectin-3, G-CSF, GDF15, HE4, HGF, IL-6, IL-8, Kallikrein-6, Leptin, LRG-1, Mesothelin, Midkine, Myeloperoxidase, NSE, OPG, OPN, PAR, Prolactin, sEGFR, sFas, SHBG, sHER2/sEGFR2/sErbB2, sPECAM-1, TGFa, Thrombospondin-2, TIMP-1, TIMP-2, and Vitronectin. For example, a peptide biomarker can include one or more of OPN, IL-6, CEA, CA125, HGF, Myeloperoxidase, CA19-9, Midkine and/or TIMP-1. In some embodiments, methods and materials described herein can include one or more peptide biomarkers (e.g., one or more peptides have elevated levels in a cancer). For example, methods and materials described herein can include one or more of the peptide biomarkers set forth in Example 1. For example, methods and materials described herein can include elevated levels one or more of the peptide biomarkers set forth in Table 4. In some embodiments, methods and materials described herein can include detecting the levels of about 10 peptides. For example, methods and materials described herein can include detecting the level of OPN, IL-6, CEA, CA125, HGF, Myeloperoxidase, CA19-9, Midkine, and/or TIMP-1. In some embodiments, peptide biomarkers can be as described elsewhere (see, e.g., Liotta et al., 2003 *Clin Adv Hematol Oncol* 1:460-462; Wang et al., 2016 *Expert Rev Proteomics* 13:99-114; and Patz, Jr. et al., 2007 *J Clin Oncol* 25:5578-5583).

Any appropriate method can be used to detect the level (e.g., an elevated level) of one or more biomarkers (e.g., peptide biomarkers) as described herein. In some embodiments, the levels of one or more peptide biomarkers can be detected independently (e.g., via singleplex peptide tools). In some embodiments, the levels of one or more peptide biomarkers can be detected simultaneously (e.g., via multiplex peptide tools such as "chips" or microarrays). Examples of methods for detecting peptide levels include, without limitation, spectrometry methods (e.g., high-performance liquid chromatography (HPLC) and liquid chromatography-mass spectrometry (LC/MS)), antibody dependent methods (e.g., enzyme-linked immunosorbent assay (ELISA), protein immunoprecipitation, immunoelectrophoresis, western blotting, and protein immunostaining), and aptamer dependent methods. In some embodiments, the level of one or more peptide biomarkers can be detected as described in the Examples. For example, the level of one or more peptide biomarkers can be detected by multiplex immunoassay.

Any appropriate cancer can be identified and/or treated as described herein. In some embodiments, a cancer can be a common cancer. In some embodiments, a cancer can be a cancer where no blood-based test is available. In some embodiments, a cancer can be a cancer where no test for early detection is available. In some embodiments, a cancer can be a Stage I cancer. In some embodiments, a cancer can be a Stage II cancer. In some embodiments, a cancer can be a Stage III cancer. In some embodiments, a cancer can be a Stage IV cancer. In some embodiments, a cancer can be a surgically resectable cancer. Examples of cancers that be identified as described herein (e.g., based at least in part on the presence or absence of one or more first biomarkers (e.g., genetic biomarkers) and/or an elevated level of one or more second biomarkers (e.g., peptide biomarkers)) include, without limitation, liver cancer, ovarian cancer, esophageal cancer, stomach cancer, pancreatic cancer, colorectal cancer, lung cancer, breast cancer, and prostate cancer.

Methods and materials provided herein also can identify the location of cancer (e.g., can determine the cancer site and/or type) in a mammal. The location of any cancer (e.g., the cancer site and/or type) that has mutations in one or more genetic biomarkers and/or one or more peptide biomarkers as described herein can be determined. In some embodiments, materials and methods provided herein can identify the presence of a colorectal cancer. For example, the presence of one or more genetic biomarkers in one or more of APC, KRAS, and/or TP53 gene mutations and an elevated level of CEA in a sample obtained from a mammal can be used to identify the presence of a colorectal cancer in the mammal. In some embodiments, materials and methods provided herein can identify the presence of a liver cancer. For example, the presence of one or more genetic biomarkers in one or more of TP53, CTNNB1, and/or TERT and an elevated level of AFP in a sample obtained from a mammal can be used to identify the presence of a liver cancer in the mammal. In some embodiments, materials and methods provided herein can identify the presence of an ovarian cancer. For example, the presence of one or more genetic biomarkers in TP53 and an elevated level CA125 in a sample obtained from a mammal can be used to identify the presence of an ovarian cancer in the mammal. In some embodiments, materials and methods provided herein can identify the presence of a pancreatic cancer. For example, the presence of one or more genetic biomarkers in KRAS (e.g., KRAS codon 12) and an elevated level of CA19-9 in a sample obtained from a mammal can be used to identify the presence of a pancreatic cancer in the mammal.

In some embodiments, a mammal identified as having cancer as described herein (e.g., based at least in part on the presence or absence of one or more first biomarkers (e.g., genetic biomarkers) and/or an elevated level of one or more second biomarkers (e.g., peptide biomarkers)) can have the cancer diagnosis confirmed using any appropriate method. Examples of methods that can be used to diagnose or confirm diagnosis of a cancer include, without limitation, physical examinations (e.g., pelvic examination), imaging tests (e.g., ultrasound or CT scans), cytology, and tissue tests (e.g., biopsy).

In some embodiments, any of the variety of methods disclosed herein can be performed on subjects who have previously undergone treatments for cancer. In some embodiments, methods provided herein can be used to determine the efficacy of the treatment. For example, a subject having cancer can be administered a treatment (also referred to herein as a "therapeutic intervention"), after which the continued presence of cancer or the amount of cancer (or lack thereof) is determined by detecting the presence of one or more mutations in one or more genes (e.g., NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS) and/or elevated levels of one or more peptide biomarkers (e.g., OPN, IL-6, CEA, CA125, HGF, Myeloperoxidase, CA19-9, Midkine, and/or TIMP-1).

In some embodiments, once a subject has been determined to have a cancer, the subject may be additionally monitored or selected for increased monitoring. In some embodiments, methods provided herein can be used to select a subject for increased monitoring at a time period prior to the time period when conventional techniques are capable of diagnosing the subject with an early-stage cancer. For example, methods provided herein for selecting a subject for increased monitoring can be used when a subject has not been diagnosed with cancer by conventional methods and/or when a subject is not known to harbor a cancer. In some embodiments, a subject selected for increased monitoring can be administered a diagnostic test (e.g., any of the diagnostic tests disclosed herein) at an increased frequency compared to a subject that has not been selected for increased monitoring. For example, a subject selected for increased monitoring can be administered a diagnostic test at a frequency of twice daily, daily, bi-weekly, weekly, bi-monthly, monthly, quarterly, semi-annually, annually, or any at frequency therein. In some embodiments, a subject selected for increased monitoring can be administered a one or more additional diagnostic tests compared to a subject that has not been selected for increased monitoring. For example, a subject selected for increased monitoring can be administered two diagnostic tests, whereas a subject that has not been selected for increased monitoring is administered only a single diagnostic test (or no diagnostic tests). In some embodiments, a subject that has been selected for increased monitoring can also be selected for further diagnostic testing. Once the presence of a cancer cell has been identified (e.g., by any of the variety of methods disclosed herein), it may be beneficial for the subject to undergo both increased monitoring (e.g., to assess the progression of the tumor or cancer in the subject and/or to assess the development of additional cancer cell mutations), and further diagnostic testing (e.g., to determine the size and/or exact location of the tumor harboring the cancer cell). In some embodiments, a therapeutic intervention is administered to the subject that is selected for increased monitoring after a cancer cell mutation is detected. Any of the therapeutic interventions disclosed herein or known in the art can be administered. For example, a subject that has been selected for increased monitoring can be further monitored, and a therapeutic intervention can be administered if the presence of the cancer cell is maintained throughout the increased monitoring period. Additionally or alternatively, a subject that has been selected for increased monitoring can be administered a therapeutic intervention, and further monitored as the therapeutic intervention progresses. In some embodiments, after a subject that has been selected for increased monitoring has been administered a therapeutic intervention, the increased monitoring will reveal one or more additional cancer cell mutations. In some embodiments, such one or more additional cancer cell mutations will provide cause to administer a different therapeutic intervention (e.g., a resistance mutation may arise in a cancer cell during the therapeutic intervention, which cancer cell harboring the resistance mutation is resistance to the original therapeutic intervention).

In some embodiments, once a subject has been determined to have a cancer, the subject may be administered further tests or selected for further diagnostic testing. In some embodiments, methods provided herein can be used to select a subject for further diagnostic testing at a time period prior to the time period when conventional techniques are capable of diagnosing the subject with an early-stage cancer. For example, methods provided herein for selecting a subject for further diagnostic testing can be used when a subject has not been diagnosed with cancer by conventional methods and/or when a subject is not known to harbor a cancer. In some embodiments, a subject selected for further diagnostic testing can be administered a diagnostic test (e.g., any of the diagnostic tests disclosed herein) at an increased frequency compared to a subject that has not been selected for further diagnostic testing. For example, a subject selected for further diagnostic testing can be administered a diagnostic test at a frequency of twice daily, daily, bi-weekly, weekly, bi-monthly, monthly, quarterly, semi-annually, annually, or any at frequency therein. In some embodiments, a subject selected for further diagnostic testing can be administered a one or more additional diagnostic tests compared to a subject that has not been selected for further diagnostic testing. For example, a subject selected for further diagnostic testing can be administered two diagnostic tests, whereas a subject that has not been selected for further diagnostic testing is administered only a single diagnostic test (or no diagnostic tests). In some embodiments, the diagnostic testing method can determine the presence of the same type of cancer as the cancer that was original detected. Additionally or alternatively, the diagnostic testing method can determine the presence of a different type of cancer as the cancer that was original detected. In some embodiments, the diagnostic testing method is a scan. In some embodiments, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan. In some embodiments, the diagnostic testing method is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, a pelvic exam, a positron emission tomography and computed tomography (PET-CT) scan. In some embodiments, a subject that has been selected for further diagnostic testing can also be selected for increased monitoring. Once the presence of a cancer cell has been identified (e.g., by any of the variety of methods disclosed herein), it may be beneficial for the subject to undergo both increased monitoring (e.g., to assess the progression of the tumor or cancer in the subject and/or to assess the development of additional cancer cell mutations), and further diagnostic testing (e.g., to determine the size and/or exact location of the tumor harboring the cancer cell). In some embodiments, a therapeutic intervention is administered to the subject that is selected for further diagnostic testing after a cancer cell mutation is detected. Any of the therapeutic interventions disclosed herein or known in the art can be administered. For example, a subject that has been selected for further diagnostic testing can be administered a further diagnostic test, and a therapeutic intervention can be administered if the presence of the cancer cell is confirmed. Additionally or alternatively, a subject that has been selected for further diagnostic testing can be administered a therapeutic intervention, and can be further monitored as the therapeutic intervention progresses. In some embodiments, after a subject that has been selected for further diagnostic testing has been administered a therapeutic intervention, the additional testing will reveal one or more additional cancer cell mutations. In some embodiments, such one or more additional cancer cell mutations will provide cause to administer a different therapeutic intervention (e.g., a resistance mutation may arise in a cancer cell during the therapeutic intervention, which cancer cell harboring the resistance mutation is resistance to the original therapeutic intervention).

Once identified as having a cancer as described herein (e.g., based at least in part on the presence or absence of one or more first biomarkers (e.g., genetic biomarkers) and/or an elevated level of one or more second biomarkers (e.g., peptide biomarkers) and/or the presence of aneuploidy), a mammal can be treated with one or more cancer treatments (also referred to herein as "therapeutic interventions").

In certain aspects, provided herein are state-of-the-art tests that can detect mutations in cancer cells that are released into the blood stream. In some embodiments, one or more cancer types can be detected. Assays as described herein can be used as a cancer screening test with improved sensitivity while retaining specificity. For example, such assays can combine detection of genetic biomarkers (e.g., mutations in circulating tumor DNA (ctDNA)) with detection of thresholded protein markers in plasma. In some embodiments, a genetic biomarker (e.g., a mutation in circulating tumor DNA (ctDNA)) is tested alone. In some embodiments, protein biomarkers are tested alone. In some embodiments, the combination of the genetic biomarker (e.g., a mutation in circulating tumor DNA (ctDNA)) and protein markers can be superior to any single marker. In an exemplary pilot study of 1,703 patients (1,240 cancer and 463 healthy controls), the ctDNA and protein biomarkers panel had a sensitivity of 64% and a specificity of 99.35%.

In some embodiments, assays as described herein may be applied to apparently healthy individuals. For example, assays as described herein may reduce deaths and suffering from cancer by detecting pre-symptomatic cancers through a blood test taken during routine office visits to physicians. Additionally, assays as described herein may be applied to patients with localized cancers, particularly those that have been or can be treated or resected. Assays as described herein may improve management and prognosis though the earlier detection of recurrence.

In some embodiments, genetic biomarkers (e.g., mutations in cell-free DNA (e.g., ctDNA)) may be tested from any of a variety of biological samples obtained from a subject (e.g., a human subject) including, but not limited to blood, plasma, serum, urine, cerebrospinal fluid, saliva, sputum, broncho-alveolar lavage, bile, lymphatic fluid, cyst fluid, stool, ascites, and combinations thereof.

In some embodiments, genetic biomarkers (e.g., mutations in ctDNA) in 10 exemplary genes (AKT1, APC, BRAF, CDKN2A, CTNNB1, FBXW7, FGF2, GNAS, HRAS, KRAS) and elevation of 11 exemplary protein markers in serum beyond a threshold (CA19-9 (>92 U/ml), CEA (>7,507 pg/ml), CA125 (>577 U/ml), AFP (>21,321 pg/ml), Prolactin (>145,345 pg/ml), HGF (>899 pg/ml), OPN (>157,772 pg/ml), TIMP-1 (>176,989 pg/ml), Follistatin (>1,970 pg/ml), G-CSF (>800 pg/ml), and CA15-3 (>98 U/ml)) may be tested in the assay. In some embodiments, genetic biomarkers (e.g., mutations in ctDNA) in 16 exemplary genes (KT1, APC, BRAF, CDKN2, CTNNB1, FBXW7, FGFR2, GNAS, HRAS, KRAS, PPP2R1A, TP53, PTEN, PIK3CA, EGFR and NRAS) and elevation of 11 exemplary protein biomarkers in serum beyond a threshold (CA19-9 (>92 U/ml), CEA (>7,507 pg/ml), CA125 (>577 U/ml), AFP (>21,321 pg/ml), Prolactin (>145,345 pg/ml), HGF (>899 pg/ml), OPN (>157,772 pg/ml), TIMP-1 (>176,989 pg/ml), Follistatin (>1,970 pg/ml), G-CSF (>800 pg/ml), and CA15-3 (>98 U/ml)) may be tested in the assay. In some embodiments, the presence of a genetic biomarker (e.g., a mutation) or an elevation beyond threshold of any one of the protein biomarkers constitutes a positive result (e.g., identification of cancer in a subject). In some embodiments, the presence of genetic biomarkers (e.g., mutations) or elevations in two or more protein biomarkers constitute a positive result. For example, the presence of genetic biomarkers (e.g., mutations) in two, three, four, five, six, seven, eight, nine, or ten exemplary genes and/or elevations in two, three, four, five, six, seven, eight, nine, ten, or eleven protein biomarkers constitute a positive result.

In some embodiments, proteins (e.g., protein biomarkers) may be tested from any of a variety of biological samples obtained from a subject (e.g., a human subject) including, but not limited to blood, plasma, serum, urine, cerebrospinal fluid, saliva, sputum, broncho-alveolar lavage, bile, lymphatic fluid, cyst fluid, stool, ascites, and combinations thereof. Proteins (e.g., protein biomarkers) that are found in high amounts in cancers can be tested for amounts of the proteins that do not occur in healthy human subjects. Examples of proteins (e.g., protein biomarkers), any one, two, three, four, five, six, seven, eight, nine, ten, or eleven of which may be tested, include, without limitation, carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3. Any protein biomarker known in the art may be used when a threshold value is obtained above which normal, healthy human subjects do not fall, but human subjects with cancer do fall.

In some embodiments, a threshold level of CA19-9 can be at least about 92 U/mL (e.g., about 92 U/mL). In some embodiments, a threshold level of CA19-9 can be 92 U/mL. In some embodiments, a threshold level of CEA can be at least about 7,507 pg/ml (e.g., about 7,507 pg/ml). In some embodiments, a threshold level of CEA can be 7.5 ng/mL. In some embodiments, a threshold level of HGF can be at least about 899 pg/ml (e.g., about 899 pg/ml). In some embodiments, a threshold level of HGF can be 0.92 ng/mL. In some embodiments, a threshold level of OPN can be at least about 157,772 pg/ml (e.g., about 157,772 pg/ml). In some embodiments, a threshold level of OPN can be 158 ng/ml. In some embodiments, a threshold level of CA125 can be at least about 577 U/ml (e.g., about 577 U/ml). In some embodiments, a threshold level of CA125 can be 577 U/mL. In some embodiments, a threshold level of AFP can be at least about 21,321 pg/ml (e.g., about 21,321 pg/ml). In some embodiments, a threshold level of AFP can be 21,321 pg/ml. In some embodiments, a threshold level of prolactin can be at least about 145,345 pg/ml (e.g., about 145,345 pg/ml). In some embodiments, a threshold level of prolactin can be 145,345 pg/ml. In some embodiments, a threshold level of TIMP-1 can be at least about 176,989 pg/ml (e.g., about 176,989 pg/ml). In some embodiments, a threshold level of TIMP-1 can be 176,989 pg/ml. In some embodiments, a threshold level of follistatin can be at least about 1,970 pg/ml (e.g., about 1,970 pg/ml). In some embodiments, a threshold level of follistatin can be 1,970 pg/ml. In some embodiments, a threshold level of G-CSF can be at least about 800 pg/ml (e.g., about 800 pg/ml). In some embodiments, a threshold level of G-CSF can be 800 pg/ml. In some embodiments, a threshold level of CA15-3 can be at least about 98 U/ml (e.g., about 98 U/ml). In some embodiments, a threshold level of CA15-3 can be 98 U/ml. In some embodiments, a threshold level of CA19-9, CEA, and/or OPN can be 5%, 10%, 15%, 20%, 25%, 30%, 35%, 40%, 45%, 50%, 55%, 60%, 65%, 70%, 75%, 80%, 85%, 90%, 95%, 100% or more greater than the threshold levels listed above (e.g., greater than a threshold level of 92 U/mL for CA-19-9, 7,507 pg/ml for CEA, 899 pg/ml for HGF, 157,772 pg/ml for OPN, 577 U/ml for CA125, 21,321 pg/ml for AFP, 145,345 pg/ml for prolactin, 176,989 pg/ml for TIMP-1, 1,970 pg/ml for follistatin, 800 pg/ml for G-CSF, and/or 98 U/ml for CA15-3).

In some embodiments, a threshold level of protein biomarker can be greater than the levels that are typically tested for diagnostic or clinical purposes. For example, the threshold level of CA19-9 can be greater than about 37 U/ml (e.g., greater than about 40, 45, 50, 55, 60, 65, 70, 75, 80, 85, 90, 95 or more U/mL). Additionally or alternatively, the threshold level of CEA can be greater than about 2.5 ug/L (e.g., greater than about 3.0, 3.5, 4.0, 4.5, 5.0, 5.5, 6.0, 6.5, 7.0, 7.5 or more ug/L). Additionally or alternatively, the threshold level of CA125 can be greater than about 35 U/mL (e.g., greater than about 40, 45, 50, 55, 60, 65, 70, 75, 80, 85, 90, 95, 100, 150, 200, 250, 300, 350, 400, 450, 500, 550 or more U/mL). Additionally or alternatively, the threshold level of AFP can be greater than about 21 ng/ml (e.g., greater than about 25, 30, 40, 50, 60, 70, 80, 90, 100, 150, 200, 250, 300, 350, 400 or more ng/L). Additionally or alternatively, the threshold level of TIMP-1 can be greater than about 2300 ng/ml (e.g., greater than about 2,500, 3,000, 4,000, 5,000, 6,000, 7,000, 8,000, 9,000, 10,000, 15,000, 20,000, 25,000, 30,000, 35,000, 40,000 or more ng/L). Additionally or alternatively, the threshold level of follistatin can be greater than about 2 ug/mL (e.g., greater than about 2.5, 3.0, 3.5, 4.0, 4.5, 5.0, 5.5, 6.0, 6.5, 7.0, 7.5 or more ug/L). Additionally or alternatively, the threshold level of CA15-3 can be greater than about 30 U/mL (e.g., greater than about 35, 40, 45, 50, 55, 60, 65, 70, 75, 80, 85, 90, 95 or more U/mL). In some embodiments, detecting one or more protein biomarkers at threshold levels that are higher than are typically tested for during traditional diagnostic or clinical assays can improve the sensitivity of cancer detection.

In some embodiments, an assay includes detection of thresholded protein biomarkers in a biological sample (e.g., any biological sample disclosed herein such as plasma) without detection of genetic biomarkers (e.g., mutations in circulating tumor DNA (ctDNA)). For example, an assay may include detection of one or more of CA19-9, CEA, HGF, OPN, CA125, AFP, prolactin, TIMP-1, follistatin, G-CSF, and/or CA15-3 in a biological sample. In some embodiments, an assay may include detection of one or more of CA19-9, CEA, HGF, OPN, CA125, AFP, prolactin, TIMP-1, follistatin, G-CSF, and/or CA15-3 in a biological sample at any of the threshold levels disclosed herein. In some embodiments, once an assay that includes detection of thresholded protein biomarkers in a biological sample is performed, subsequent testing or monitoring is performed (e.g., any of the variety of further diagnostic testing or increased monitoring techniques disclosed herein). In some embodiments, once an assay that includes detection of thresholded protein markers in a biological sample is performed, a second assay that includes detecting a genetic biomarker (e.g., a genetic biomarker present in cell-free DNA (e.g., ctDNA)) can be performed (e.g., detecting any of the variety of genetic alterations in genetic biomarkers that are present in cell-free DNA or ctDNA as described herein).

In some embodiments, an assay includes detection of a genetic biomarker in circulating tumor DNA (ctDNA) in a biological sample (e.g., any biological sample disclosed herein such as plasma) without detection of thresholded protein biomarkers. For example, an assay may include detection of genetic biomarkers (e.g., genetic alterations) in one or more of any of the genes disclosed herein including, without limitation, CDKN2A, FGF2, GNAS, ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, PLAG1, CDK6, NUP98, CBLC, JUN, PPARG, SMAD4, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, and/or TCF3. In some embodiments, an assay may include detection of genetic biomarkers (e.g., genetic alterations) in one or more of AKT1, APC, BRAF, CDKN2A, CTNNB1, FBXW7, FGF2, GNAS, HRAS, KRAS. In some embodiments, an assay may include detection of genetic biomarkers (e.g., genetic alterations) in one or more of KT1, APC, BRAF, CDKN2, CTNNB1, FBXW7, FGFR2, GNAS, HRAS, KRAS, PPP2R1A, TP53, PTEN, PIK3CA, EGFR and NRAS. In some embodiments, once an assay that includes detection of a genetic biomarker present in ctDNA in a biological sample is performed, subsequent testing or monitoring is performed (e.g., any of the variety of further diagnostic testing or increased monitoring techniques disclosed herein). In some embodiments, once an assay that includes detection of a genetic biomarker present in ctDNA in a biological sample is performed, a second assay that includes detecting protein biomarkers at high thresholds can be performed (e.g., detecting any of the variety of protein biomarkers described herein including, but not limited to, carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3 and combinations thereof).

In some embodiments, at least two codons or at least two amplicons of a tumor suppressor gene or an oncogene can be tested. In some embodiments, at least three, at least four, or at least five or more codons or amplicons of an individual tumor suppressor gene or oncogene can be assayed. In some embodiments, the more distributed the mutations are in a gene, the more codons or amplicons one may desirably test.

Exemplary codons of tumor suppressor genes and oncogenes which may be tested include, without limitation, one or more of the following codons and their surrounding splice sites: codons 16-18 of AKT1; codons 1304-1311, 1450-1459 of APC; codons 591-602 of BRAF; codons 51-58, 76-88 of CDKN2A; codons 31-39, 38-47 of CTNNB1; codons 856-868 of EGFR; codons 361-371, 464-473, 473-483, 498-507 of FBXW7; codons 250-256 of FGFR2; codons 199-208 of GNAS; codons 7-19 of HRAS; codons 7-14, 57-65, 143-148 of KRAS; codons 3-15, 54-63 of NRAS; codons 80-90, 343-348, 541-551, 1038-1050 of PIK3CA; codons 175-187 of PPP2R1A; codons 90-98, 125-132, 133-146, 145-154 of PTEN; and codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, 374-386 of TP53. All or some of these regions may be tested. In some embodiments, the mutation can be in KRAS, e.g., in codon 12 or 61. In other embodiments, the mutation may be in other codons of KRAS. In some embodiments, the mutation can be in CDKN2A (e.g., any of the CDKN2A mutations identified in Example 2), In some embodiments, the mutation may be in tumor suppressors or oncogenes, including but not limited to ABL1; EVI1; MYC; APC; IL2; TNFAIP3; ABL2; EWSR1; MYCL1; ARHGEF12; JAK2; TP53; AKT1; FEV; MYCN; ATM; MAP2K4; TSC1; AKT2; FGFR1; NCOA4; BCL11B; MDM4; TSC2; ATF1; FGFR1OP; NFKB2; BLM; MEN1; VHL; BCL11A; FGFR2; NRAS; BMPR1A; MLH1; WRN; BCL2; FUS; NTRK1; BRCA1; MSH2; WT1; BCL3; GOLGA5; NUP214; BRCA2; NF1; BCL6; GOPC; PAX8; CARS; NF2; BCR; HMGA1; PDGFB; CBFA2T3; NOTCH1; BRAF; HMGA2; PIK3CA; CDH1; NPM1; CARD11; HRAS; PIM1; CDH11; NR4A3; CBLB; IRF4; PLAG1; CDK6; NUP98; CBLC; JUN; PPARG; SMAD4; PALB2; CCND1; KIT; PTPN11; CEBPA; PML; CCND2; KRAS; RAF1; CHEK2; PTEN; CCND3; LCK; REL; CREB1; RB1; CDX2; LMO2; RET; CREBBP; RUNX1; CTNNB1; MAF; ROS1; CYLD; SDHB; DDB2; MAFB; SMO; DDX5; SDHD; DDIT3; MAML2; SS18; EXT1; SMARCA4; DDX6; MDM2; TCL1A; EXT2; SMARCB1; DEK; MET; TET2; FBXW7; SOCS1; EGFR; MITF; TFG; FH; STK11; ELK4; MLL; TLX1; FLT3; SUFU; ERBB2; MPL; TPR; FOXP1; SUZ12; ETV4; MYB; USP6; GPC3; SYK; ETV6; IDH1; and TCF3. Testing may include amplification and/or sequencing.

In some embodiments, sequence determination to a high degree of accuracy can be advantageous when analytes are present in low quantities and/or fractions. High accuracy sequence determination may employ oligonucleotide barcodes, whether endogenous or exogenous. These may be introduced into a template analyte by amplification, for example, in the case of an exogenous barcode. Alternatively, an endogenous oligonucleotide barcode may be used by attaching to it, for example, by means of ligation, an oligonucleotide adapter molecule. The adapter molecule may contain a priming site for DNA synthesis, and/or for hybridization to a solid surface. The adapter can be immediately adjacent to the endogenous barcode or a fixed number of nucleotides from the endogenous barcode.

In some embodiments, oligonucleotide barcodes permit the labeling of individual template molecules in the sample prior to processing, in particular amplification. For example, by demanding that all or a high proportion or a threshold proportion of family members (having the same oligonucleotide barcode) display a mutation, it is possible to filter out or minimize false positive mutations that arise during amplification and/or other DNA synthesis or processing. See, e.g., Kinde I, Wu J, Papadopoulos N, Kinzler K W, & Vogelstein B (2011) Detection and quantification of rare mutations with massively parallel sequencing. Proc Natl Acad Sci USA 108(23):9530-9535, the content of which is explicitly incorporated by reference. Additionally or alternatively, a threshold for mutation calling that a mutation occurs in two different families. Multiple filters of this nature may be applied.

In some embodiments, methods provided herein can be used to detect a genetic biomarker (e.g., a genetic alteration (e.g., one or more genetic alterations)) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein can be used to detect a genetic biomarker (e.g., a genetic alteration (e.g., one or more genetic alterations)) in circulating tumor DNA present in cell-free DNA, where the circulating tumor DNA represents 100% of the cell-free DNA. In some embodiments, methods provided herein can be used to detect a genetic biomarker (e.g., a genetic alteration (e.g., one or more genetic alterations)) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, one or more genetic biomarkers present in cell-free DNA (e.g., ctDNA) and/or one or more protein biomarkers can be tested from any of a variety of biological samples isolated or obtained from a subject (e.g., a human subject) including, but not limited to the blood, plasma, serum, urine, cerebrospinal fluid, saliva, sputum, broncho-alveolar lavage, bile, lymphatic fluid, cyst fluid, stool, ascites, and combinations thereof. In some embodiments, one or more genetic biomarkers present in cell-free DNA (e.g., ctDNA) and one or more protein biomarkers can be tested from the same sample. For example, a single sample can be isolated or obtained from a subject, which single sample can be tested for one or more genetic biomarkers present in cell-free DNA (e.g., ctDNA), one or more protein biomarkers, or both. One or more genetic biomarkers present in cell-free DNA (e.g., ctDNA) and one or more protein biomarkers can be tested from the sample at the same time or at different times. For example, the sample can be tested for one or more genetic biomarkers present in cell-free DNA (e.g., ctDNA)) at a first time, and for one or more protein biomarkers at a second time, or vice versa. In some embodiments, the sample can be refrigerated, frozen, or otherwise stored for future testing. In some embodiments, one or more genetic biomarkers present in cell-free DNA (e.g., ctDNA) and one or more protein biomarkers can be tested from different samples. For example, a first sample can be isolated or obtained from a subject and tested for one or more genetic biomarkers present in cell-free DNA (e.g., ctDNA), and a second sample can be isolated or obtained from the subject and tested for one or more protein biomarkers. The first and second samples can be of the same type (e.g., plasma or serum), or of different types. The first and/or second samples can be refrigerated, frozen, or otherwise stored for future testing.

In some embodiments, any of the variety of assays disclosed herein can be repeated to increase the accuracy of mutation detection. Assays may be done in duplicate or triplicate, for example. In some embodiments, positive assays can be repeated on the same initial sample from a patient. Additionally or alternatively, a second sample may be obtained from a patient at a later time, for example, when a positive results is found. Any of the variety of assays described herein, including ctDNA, and/or protein biomarkers, may be repeated or run in parallel replicates.

In some embodiments, a radiologic, sonographic, or other technique may be applied to any subject (e.g., a human subject) in which a mutation is detected. The technique may be applied to the whole body, to a single organ, or to a region of the body. The technique may be used, for example, to ascertain a particular type of cancer is present, to confirm a cancer is present, or to identify location of a cancer in the body. In some embodiments, the technique is a scan. In some embodiments, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan, or a positron emission tomography and computed tomography (PET-CT) scan. In some embodiments, the technique is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, or a pelvic exam, In some embodiments, the technique is a biopsy (e.g., a bone marrow aspiration, a tissue biopsy). In some embodiments, the biopsy is performed by fine needle aspiration or by surgical excision. In some embodiments, the technique further includes obtaining a biological sample (e.g., a tissue sample, a urine sample, a blood sample, a check swab, a saliva sample, a mucosal sample (e.g., sputum, bronchial secretion), a nipple aspirate, a secretion or an excretion). In some embodiments, the technique includes determining exosomal proteins (e.g., an exosomal surface protein (e.g., CD24, CD147, PCA-3)) (Soung et al. (2017) Cancers 9(1): pii:E8). In some embodiments, the diagnostic testing method is an oncotype DX® test (Bachner (2016) Ecancermedicalscience 10:675).

In some embodiments, various methods described herein can be used to detect cancers selected from the group consisting of: pancreatic cancer, colon cancer, esophageal cancer, stomach cancer, ovarian cancer, liver cancer, lung cancer, and breast cancer, and combinations thereof.

In some embodiments, methods provided herein (e.g., methods in which genetic biomarkers present in cell-free DNA (e.g., ctDNA) and high threshold protein biomarkers are detected in a biological sample isolated from the subject) can be used for selecting a treatment for a subject. For example, once a subject has been determined to have cancer (e.g., pancreatic cancer, colon cancer, esophageal cancer, stomach cancer, ovarian cancer, liver cancer, lung cancer, or breast cancer) by any of the variety of methods disclosed herein, an appropriate treatment can be selected (e.g., any of the variety of therapeutic interventions described herein). In some embodiments, methods provided herein (e.g., methods in which genetic biomarkers present in cell-free DNA (e.g., ctDNA) and high threshold protein biomarkers are detected in a biological sample isolated from the subject) can be used for selecting a subject for treatment. For example, once a subject has been determined to have cancer (e.g., pancreatic cancer, colon cancer, esophageal cancer, stomach cancer, ovarian cancer, liver cancer, lung cancer, or breast cancer) by any of the variety of methods disclosed herein, that subject can be identified as an appropriate subject to receive a treatment (e.g., any of the variety of therapeutic interventions described herein). In some embodiments, methods provided herein (e.g., methods in which genetic biomarkers present in cell-free DNA (e.g., ctDNA) and high threshold protein biomarkers are detected in a biological sample isolated from the subject) can be used for selecting a subject for increased monitoring. For example, once a subject has been determined to have cancer (e.g., pancreatic cancer, colon cancer, esophageal cancer, stomach cancer, ovarian cancer, liver cancer, lung cancer, or breast cancer) by any of the variety of methods disclosed herein, that subject can be identified as an appropriate subject to receive increased monitoring (e.g., any of the variety of monitoring techniques described herein). In some embodiments, methods provided herein (e.g., methods in which genetic biomarkers present in cell-free DNA (e.g., ctDNA) and high threshold protein biomarkers are detected in a biological sample isolated from the subject) can be used for selecting a subject for further diagnostic testing. For example, once a subject has been determined to have cancer (e.g., pancreatic cancer, colon cancer, esophageal cancer, stomach cancer, ovarian cancer, liver cancer, lung cancer, or breast cancer) by any of the variety of methods disclosed herein, that subject can be identified as an appropriate subject to receive further diagnostic testing (e.g., any of the variety of diagnostic techniques described herein).

In some embodiments, methods provided herein can be used to detect the presence of cancer (e.g., pancreatic cancer, colon cancer, esophageal cancer, stomach cancer, ovarian cancer, liver cancer, lung cancer, or breast cancer) at a time period prior to diagnosis of the subject with an early-stage cancer and/or at a time prior to the subject exhibiting symptoms associated with cancer. For example, methods provided herein can be used when a subject has not been diagnosed with cancer and/or when a subject is not known to harbor a cancer cell.

In some embodiments, certain protein biomarkers can be detected at high threshold levels to detect specific types of cancers. For example, high threshold levels of CA19-9 can be detected to indicate the presence of pancreatic cancer. Additionally or alternatively, high threshold levels of CEA can be detected to indicate the presence of, for example, colon, gastric, pancreatic, lung, and/or breast cancer. Additionally or alternatively, high threshold levels of CA-125 can be detected to indicate the presence of, for example, ovarian cancer. Additionally or alternatively, high threshold levels of AFP can be detected to indicate the presence of liver cancer. Additionally or alternatively, high threshold levels of prolactin can be detected to indicate the presence of, for example, ovarian, breast, and/or lung cancer. Additionally or alternatively, high threshold levels of HFG can be detected to indicate the presence of, for example, esophageal, gastric, and/or liver cancer. Additionally or alternatively, high threshold levels of OPN can be detected to indicate the presence of, for example, ovarian, breast, and/or lung cancer. Additionally or alternatively, high threshold levels of TIMP-1 can be detected to indicate the presence of, for example, colon and/or pancreatic cancer. Additionally or alternatively, high threshold levels of follistatin can be detected to indicate the presence of, for example, ovarian and/or lung cancer. Additionally or alternatively, high threshold levels of G-CSF can be detected to indicate the presence of, for example, ovarian cancer. Additionally or alternatively, high threshold levels of CA15-3 can be detected to indicate the presence of, for example, breast cancer. Exemplary protein biomarkers detected in various cancer types are shown in Example 2.

In some embodiments, assays for genetic biomarkers (e.g., genetic alterations) can be combined with assays for elevated protein biomarkers to increase the sensitivity of a blood test for low stage pancreatic cancers. In some embodiments, 50%, 55%, 60%, 65%, 70%, 75%, 80%, 85%, 90%, 95% or more of such cancers can be detected through this combination test, including some patients with a favorable prognosis. In some embodiments, 64% of such cancers can be detected through this combination test, including some patients with a favorable prognosis. One of the design features of certain studies presented herein was that only patients with resectable pancreatic cancers were included, and patients with advanced disease (i.e., Stage III or IV) were excluded. Though this exclusion reduced the sensitivity that could be otherwise be achieved by evaluating all pancreatic cancer patients, regardless of stage, the resectable cases are represent a promising group with advantageous clinical relevance with respect to evaluating a screening technology. In some embodiments, methods provided herein can be used to detect all pancreatic cancers in subjects (e.g., human subjects).

Whether combining genetic biomarkers present in ctDNA and protein markers could increase sensitivity over either alone was not known prior to the present disclosure. In fact, it was conceivable that the same patients with detectable circulating protein markers would largely overlap those releasing DNA into the circulation. This was of particular concern for early stage cancer patients, because both ctDNA and protein-based markers are known to be considerably higher in patients with advanced cancers compared to those with earlier stage cancers (Lennon A M & Goggins M (2010) Diagnostic and Therapeutic Response Markers. Pancreatic Cancer, (Springer New York, New York, NY), pp 675-701, Locker G Y, et al. (2006) ASCO 2006 update of recommendations for the use of tumor markers in gastrointestinal cancer. J Clin Oncol 24(33): 5313-5327, Bettegowda C, et al. (2014) Detection of circulating tumor DNA in early- and late-stage human malignancies. Science translational medicine 6(224): 224ra224).

In some embodiments of the methods provided herein, very high specificity (e.g., 99.5%: 95% CI 97-100%) can be achieved. For example, only one false positive among 182 healthy individuals of average age 64 was observed in the studies presented herein. Given the relative infrequency of cancer in the general population, the specificity of any potentially useful blood-based screening test for pancreatic cancer is preferably high, e.g., preferably >99%. Otherwise, the number of false positives would greatly exceed the number of true positives (i.e., have suboptimal positive predictive value) (Lennon A M, et al. (2014) The Early Detection of Pancreatic Cancer: What Will It Take to Diagnose and Treat Curable Pancreatic Neoplasia? Cancer Res 74(13): 3381-3389). Such stringency for screening tests is not typically required for tests to monitor disease in patients with known cancer. For monitoring, specificity can be relaxed somewhat in the interest of obtaining higher sensitivity. High specificity was achieved with various methods disclosed herein in at least two ways. First, ctDNA was used as one of the components of the test. KRAS mutations are exquisitely specific for neoplasia and their specificity has traditionally been limited by technical rather than biological factors. The incorporation of molecular barcoding into various assays described herein (e.g., using a Safe-SeqS technique) can minimize the false positive results from sequencing that have traditionally been major technical issues confronting any ctDNA-based assays. KRAS mutations are particularly suitable for early detection strategies because they are rarely found in clones arising during age-associated clonal hematopoiesis. Such clones, which may represent early forms of myelodysplasia, are a potential source of false positive ctDNA assays. The vast majority of such mutations occur within nine genes (DNMT3A, TET2, JAK2, ASXL1, TP53, GNAS, PPM1D, BCORL1 and SF3B1) (48-50), posing challenges for the use of these genes as biomarkers in ctDNA-based assays. Second, high thresholds were used for scoring the protein markers as positive. These thresholds were based on prior studies in the literature or on an independent set of controls, permitting avoidance of positive scores in the vast majority of healthy patients (Kim J E, et al. (2004) Clinical usefulness of carbohydrate antigen 19-9 as a screening test for pancreatic cancer in an asymptomatic population. J Gastroenterol Hepatol 19(2):182-186). In some embodiments, such high thresholds can be used without an overall reduction in sensitivity because the ctDNA assay added sensitivity on its own and the ctDNA-positive cases only partially overlapped the protein-biomarker-positive cases (See, e.g., FIG. 9, FIG. 10, and Example 2).

Protein biomarkers have been combined with each other in the past to achieve higher sensitivity (Dong T, Liu C C, Petricoin E F, & Tang L L (2014) Combining markers with and without the limit of detection. Stat Med 33(8): 1307-132). For example, it was shown that combining CA19-9 and TIMP-1 was more sensitive for the detection of PDAC than either biomarker alone (Zhou W, et al. (1998) Identifying markers for pancreatic cancer by gene expression analysis. Cancer Epidemiol Biomarkers Prev 7(2):109-112). More recently, it was shown that the combination of CA19-9, TIMP-1, and LRG-1 was more sensitive for the detection of early PDAC than CA19-9 alone (Dong T, Liu C C, Petricoin E F, & Tang L L (2014) Combining markers with and without the limit of detection. Stat Med 33(8):1307-1320). The combination of protein biomarkers with ultra-sensitive ctDNA, as disclosed herein, is different. A recent study evaluated a combination of ctDNA and CA19-9 for pancreatic cancer but found no benefit to combining the biomarkers over CA19-9 alone. Without being bound by theory, it is possible this conclusion was reached due to inadequate sensitivity of the test used in detecting KRAS mutations (Le Calvez-Kelm F, et al. (2016) KRAS mutations in blood circulating cell-free DNA: a pancreatic cancer case-control. Oncotarget 7(48):78827-78840). Furthermore, the specificity for ctDNA achieved in that study was relatively low, reducing its suitability for screening.

In some embodiments, methods provided herein can be used to detect resectable cancers through a non-invasive blood test in a majority of patients.

In some embodiments, results obtained using any of the variety of methods disclosed herein can underestimate the survival benefits of early detection. The majority of the patients that were studied herein, even though they had resectable cancers, were symptomatic and their cancers were discovered only by virtue of their symptoms. Accordingly, 77% of patients in the cohort described herein were Stage IIB and the median size of tumors in these patients was 3 cm. In some embodiments, in a screening study of asymptomatic individuals, a greater proportion of earlier stage patients, with smaller tumors, can be discovered using any of the variety of methods disclosed herein. In some embodiments, any of the variety of methods disclosed herein can be more sensitive for the detection of patients with larger tumors and with a poorer prognosis than for patients with smaller tumors, even though all tumors can be surgically resectable (See, e.g., FIG. 9B, and Example 2). In some embodiments, KRAS mutations can be found in the circulation of patients with cancer types other than those of the pancreas, primarily those of the lung (Herbst R S, Heymach J V, & Lippman S M (2008) Lung cancer. N Engl J Med 359(13):1367-1380), and CA19-9, CEA, HGF, and OPN expression can be elevated in several other cancer types (Kim J E, et al. (2004) Clinical usefulness of carbohydrate antigen 19-9 as a screening test for pancreatic cancer in an asymptomatic population. J Gastroenterol Hepatol 19(2):182-186; Thomas D S, et al. (2015) Evaluation of serum CEA, CYFRA21-1 and CA125 for the early detection of colorectal cancer using longitudinal preclinical samples. Br J Cancer 113(2):268-274; Di Renzo M F, et al. (1995) Overexpression and amplification of the met/HGF receptor gene during the progression of colorectal cancer. Clin Cancer Res 1(2):147-154; El-Tanani M K, et al. (2006) The regulation and role of osteopontin in malignant transformation and cancer. Cytokine Growth Factor Rev 17(6):463-474). Thus, in some embodiments, patients testing positive using any of the variety of methods disclosed herein can undergo additional appropriate imaging studies to identify tumor localization.

In some embodiments, methods provided herein lay a foundation for evaluation of patients at high risk for PDAC, and for implementation of early detection strategies (Kalinich M, et al. (2017) An RNA-based signature enables high specificity detection of circulating tumor cells in hepatocellular carcinoma. Proc Natl Acad Sci USA 114(5):1123-1128). As an example, new-onset diabetes is known to be associated with an increased risk for pancreatic cancer. Approximately 1% of diabetic patients aged 50 and older are diagnosed with pancreatic cancer within 3 years of first meeting criteria for diabetes (Chari S T, et al. (2005) Probability of pancreatic cancer following diabetes:a population-based study. Gastroenterology 129(2):504-511). With an incidence of 1%, the PPV/NPV of certain combination assays disclosed herein is expected to be 54% and 99.6%, respectively, in this population, which is well within the range of currently approved screening tests for cancers.

Available evidence indicates that many cancers have detectable genetic biomarkers present in ctDNA in their earliest stages, often more commonly than observed in pancreatic cancer (Bettegowda C, et al. (2014) Detection of circulating tumor DNA in early- and late-stage human malignancies. Science translational medicine 6(224): 224ra224). Similarly, a large number of protein biomarkers have already been described for the detection of numerous cancer types (Liotta L A & Petricoin E F, 3rd (2003) The promise of proteomics. Clin Adv Hematol Oncol 1(8):460-462). These protein biomarkers can be thresholded according to any of the variety of methods described herein, permitting the use ctDNA-protein combinations to detect a variety of cancer types (Bettegowda C, et al. (2014) Detection of circulating tumor DNA in early- and late-stage human malignancies. Science translational medicine 6(224): 224ra224).

In certain aspects, provided herein are assays that can be used as a cancer screening test with improved sensitivity while retaining specificity. In some embodiments, the assays combine detection of mutations in genetic biomarkers present in circulating tumor DNA (ctDNA) with detection of thresholded protein biomarkers in plasma. In some embodiments, ctDNA is tested for the presence of genetic biomarkers alone. In some embodiments, protein biomarkers are tested alone. In some embodiments, the combination of the genetic biomarkers present in ctDNA and protein markers can be superior to any single marker. For example, in some embodiments the combination can detect nearly two-thirds of pancreatic cancers that have no evidence of distant metastasis at the time of surgical resection. In some embodiments, sequence determination to a high degree of accuracy can be advantageous when analytes are present in low quantities and/or fractions. High accuracy sequence determination may employ oligonucleotide barcodes, whether endogenous or exogenous. These may be introduced into a template analyte by amplification, for example, in the case of an exogenous barcode. Alternatively, an endogenous oligonucleotide barcode may be used by attaching to it, for example, by means of ligation, an oligonucleotide adapter molecule. The adapter molecule may contain a priming site for DNA synthesis, and/or for hybridization to a solid surface. The adapter can be immediately adjacent to the endogenous barcode or a fixed number of nucleotides from the endogenous barcode.

In some embodiments, oligonucleotide barcodes permit the labeling of individual template molecules in the sample prior to processing, in particular amplification. For example, by demanding that all or a high proportion or a threshold proportion of family members (having the same oligonucleotide barcode) display a mutation, it is possible to filter out or minimize false positive mutations that arise during amplification and/or other DNA synthesis or processing. See, e.g., Kinde I, Wu J, Papadopoulos N, Kinzler K W, & Vogelstein B (2011) Detection and quantification of rare mutations with massively parallel sequencing. Proc Natl Acad Sci USA 108(23):9530-9535, the content of which is explicitly incorporated by reference. Additionally or alternatively, a threshold for mutation calling that a mutation occurs in two different families. Multiple filters of this nature may be applied.

In some embodiments, methods provided herein can be used to detect a genetic alteration (e.g., one or more genetic alterations) in circulating tumor DNA present in cell-free DNA, where the cell-free DNA is present in an amount less than about 1500 ng, e.g., less than about 1400 ng, less than about 1300 ng, less than about 1200 ng, less than about 1100 ng, less than about 1000 ng, less than about 900 ng, less than about 800 ng, less than about 700 ng, less than about 600 ng, less than about 500 ng, less than about 400 ng, less than about 300 ng, less than about 200 ng, less than about 150 ng, less than about 100 ng, less than about 95 ng, less than about 90 ng, less than about 85 ng, less than about 80 ng, less than about 75 ng, less than about 70 ng, less than about 65 ng, less than about 60 ng, less than about 55 ng, less than about 50 ng, less than about 45 ng, less than about 40 ng, less than about 35 ng, less than about 30 ng, less than about 25 ng, less than about 20 ng, less than about 15 ng, less than about 10 ng, or less than about 5 ng. In some embodiments, methods provided herein can be used to detect a genetic alteration (e.g., one or more genetic alterations) in circulating tumor DNA present in cell-free DNA, where the circulating tumor DNA represents 100% of the cell-free DNA. In some embodiments, methods provided herein can be used to detect a genetic alteration (e.g., one or more genetic alterations) in circulating tumor DNA present in cell-free DNA, where the circulating tumor DNA represents less than 100% of the cell-free DNA, e.g. about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, about 0.95%, about 0.90%, about 0.85%, about 0.80%, about 0.75%, about 0.70%, about 0.65%, about 0.60%, about 0.55%, about 0.50%, about 0.45%, about 0.40%, about 0.35%, about 0.30%, about 0.25%, about 0.20%, about 0.15%, about 0.10%, about 0.09%, about 0.08%, about 0.07%, about 0.06%, about 0.05% of the cell-free DNA, or less.

In some embodiments, the presence of genetic biomarkers (e.g., mutations in cell-free DNA (e.g., ctDNA)) may be tested from any of a variety of biological samples isolated or obtained from a subject (e.g., a human subject) including, but not limited to blood, plasma, serum, urine, cerebrospinal fluid, saliva, sputum, broncho-alveolar lavage, bile, lymphatic fluid, cyst fluid, stool, ascites, and combinations thereof. In some embodiments, one or more genetic biomarkers present in cell-free DNA (e.g., ctDNA) and one or more protein biomarkers can be tested from the same sample. For example, a single sample can be isolated or obtained from a subject, which single sample can be tested for genetic biomarkers present in cell-free DNA (e.g., ctDNA), one or more protein biomarkers, or both. The presence of one or more genetic biomarkers in cell-free DNA (e.g., ctDNA) and the presence of one or more protein biomarkers can be tested from the sample at the same time or at different times. For example, the sample can be tested for the presence of one or more genetic biomarkers in cell-free DNA (e.g., ctDNA) at a first time, and for the presence of one or more protein biomarkers at a second time, or vice versa. In some embodiments, the sample can be refrigerated, frozen, or otherwise stored for future testing. In some embodiments, the presence of genetic biomarkers in cell-free DNA (e.g., ctDNA) and the presence of one or more protein biomarkers can be tested from different samples. For example, a first sample can be isolated or obtained from a subject and tested for the presence of genetic biomarkers in cell-free DNA (e.g., ctDNA), and a second sample can be isolated or obtained from the subject and tested for the presence of one or more protein biomarkers. The first and second samples can be of the same type (e.g., plasma or serum), or of different types. The first and/or second samples can be refrigerated, frozen, or otherwise stored for future testing.

In some embodiments, any of the variety of assays disclosed herein can be repeated to increase the accuracy of mutation detection. Assays may be done in duplicate or triplicate, for example. In some embodiments, positive assays can be repeated on the same initial sample from a patient. Additionally or alternatively, a second sample may be obtained from a patient at a later time, for example, when a positive results is found. Any of the variety of assays described herein, including ctDNA and/or protein biomarkers, may be repeated or run in parallel replicates.

In some embodiments, a genetic biomarker (e.g., a mutation in cell-free DNA) may be in a tumor suppressor gene or an oncogene. For example, the genetic biomarkers (e.g., mutations) may be in hot spots for mutations, e.g., sites that are frequently muted in tumors or other cancers. In some embodiments, the mutation can be in KRAS, e.g., in codon 12 or 61. In other embodiments, the genetic biomarker (e.g., mutation) may be in other codons of KRAS. In some embodiments, the genetic biomarker (e.g., mutation) can be in CDKN2A (e.g., any of the CDKN2A mutations identified in Example 2), In some embodiments, the genetic biomarker (e.g., mutation) may be in tumor suppressor genes or oncogenes, including but not limited to ABL1; EVI1; MYC; APC; IL2; TNFAIP3; ABL2; EWSR1; MYCL1; ARHGEF12; JAK2; TP53; AKT1; FEV; MYCN; ATM; MAP2K4; TSC1; AKT2; FGFR1; NCOA4; BCL11B; MDM4; TSC2; ATF1; FGFR1OP; NFKB2; BLM; MEN1; VHL; BCL11A; FGFR2; NRAS; BMPR1A; MLH1; WRN; BCL2; FUS; NTRK1; BRCA1; MSH2; WT1; BCL3; GOLGA5; NUP214; BRCA2; NF1; BCL6; GOPC; PAX8; CARS; NF2; BCR; HMGA1; PDGFB; CBFA2T3; NOTCH1; BRAF; HMGA2; PIK3CA; CDH1; NPM1; CARD11; HRAS; PIM1; CDH11; NR4A3; CBLB; IRF4; PLAG1; CDK6; NUP98; CBLC; JUN; PPARG; SMAD4; PALB2; CCND1; KIT; PTPN11; CEBPA; PML; CCND2; KRAS; RAF1; CHEK2; PTEN; CCND3; LCK; REL; CREB1; RB1; CDX2; LMO2; RET; CREBBP; RUNX1; CTNNB1; MAF; ROS1; CYLD; SDHB; DDB2; MAFB; SMO; DDX5; SDHD; DDIT3; MAML2; SS18; EXT1; SMARCA4; DDX6; MDM2; TCL1A; EXT2; SMARCB1; DEK; MET; TET2; FBXW7; SOCS1; EGFR; MITF; TFG; FH; STK11; ELK4; MLL; TLX1; FLT3; SUFU; ERBB2; MPL; TPR; FOXP1; SUZ12; ETV4; MYB; USP6; GPC3; SYK; ETV6; IDH1; and TCF3. In some embodiments, protein biomarkers may be tested from any of a variety of biological samples isolated or obtained from a subject (e.g., a human subject) including, but not limited to blood, plasma, serum, urine, cerebrospinal fluid, saliva, sputum, broncho-alveolar lavage, bile, lymphatic fluid, cyst fluid, stool, ascites, and combinations thereof. Protein biomarkers that are found in high amounts in cancers can be tested for amounts of the protein biomarkers that do not occur in healthy human subjects. Examples of protein biomarkers, any one, two, three, or four of which may be tested, include, without limitation, carbohydrate antigen 19-9 (CA19-9), carcinoembryonic antigen (CEA), hepatocyte growth factor (HGF), and osteopontin (OPN). In some embodiments, a threshold level of CA19-9 can be at least about 100 U/mL (e.g., about 100 U/mL). In some embodiments, a threshold level of CA19-9 can be 100 U/mL. In some embodiments, a threshold level of CEA can be at least about 7.5 ng/mL (e.g., about 7.5 ng/ml). In some embodiments, a threshold level of CEA can be 7.5 ng/mL. In some embodiments, a threshold level of HGF can be at least about 0.92 ng/ml (e.g., about 0.92 ng/ml). In some embodiments, a threshold level of HGF can be 0.92 ng/mL. In some embodiments, a threshold level of OPN can be at least about 158 ng/ml (e.g., about 158 ng/ml). In some embodiments, a threshold level of OPN can be 158 ng/mL. In some embodiments, a threshold level of CA19-9, CEA, and/or OPN can be 5%, 10%, 15%, 20%, 25%, 30%, 35%, 40%, 45%, 50%, 55%, 60%, 65%, 70%, 75%, 80%, 85%, 90%, 95%, 100% or more greater than the threshold levels listed above (e.g., greater than a threshold level of 100 U/mL for CA-19-9, 7.5 ng/ml for CEA, 0.92 ng/mL for HGF, and/or 158 ng/mL for OPN).

Any protein biomarker known in the art may be used when a threshold value is obtained above which normal, healthy human subjects do not fall, but human subjects with cancer do fall. Non-limiting examples of such protein biomarkers include Translation elongation factor (EEF1A1); Glyceraldehyde-3-phosphate dehydrogenase (GAPDH); Actin gamma (ACTG1); Ferritin, heavy polypeptide 1 (FTH1); Eukaryotic translation elongation factor 1 gamma (EEF1G); Ribosomal protein, large subunit, P0 (RPLP0); Heat shock protein 90 kDa alpha (cytosolic), class B member 1 (HSP90AB1); Pyruvate kinase, muscle (PKM2); Ferritin, light polypeptide (FTL); and Ribosomal protein L3 (RPL3). Protein biomarkers known to be overexpressed in serum include but are not limited to Transferrin, α-1 antitrypsin, apolipo protein 1, complement c3a, Caveolin-1, Kallikrein 6, Glucose regulated protein-8, α defensing-1,-2,-3, Serum C-peptide, Alpha-2-HS glycol protein, Catenin, Defensin α 6, MMPs, Cyclin D, S100 P, Lamin A/C filament protein, and Txl-2, (thioredoxin like protein-2).

In some embodiments, an assay includes detection of thresholded protein biomarkers in a biological sample (e.g., any biological sample disclosed herein such as plasma) without detection of genetic biomarkers (e.g., mutations in circulating tumor DNA (ctDNA)). For example, an assay may include detection of one or more of CA19-9, CEA, HGF, and/or OPN in a biological sample. In some embodiments, an assay may include detection of one or more of CA19-9, CEA, HGF, and/or OPN in a biological sample at any of the threshold levels disclosed herein. In some embodiments, once an assay that includes detection of thresholded protein biomarkers in a biological sample is performed, subsequent testing or monitoring is performed (e.g., any of the variety of further diagnostic testing or increased monitoring techniques disclosed herein). In some embodiments, once an assay that includes detection of thresholded protein biomarkers in a biological sample is performed, a second assay that includes detecting one or more genetic biomarkers present in cell-free DNA (e.g., ctDNA) can be performed (e.g., detecting any of the variety of genetic alterations that are present in cell-free DNA or ctDNA as described herein).

In some embodiments, an assay includes detection of one or more genetic biomarkers present in circulating tumor DNA (ctDNA) in a biological sample (e.g., any biological sample disclosed herein such as plasma) without detection of thresholded protein biomarkers. For example, an assay may include detection of genetic biomarkers (e.g., genetic alterations) in one or more of any of the genes disclosed herein including, without limitation, CDKN2A, FGF2, GNAS, ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, PLAG1, CDK6, NUP98, CBLC, JUN, PPARG, SMAD4, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, and/or TCF3. In some embodiments, an assay may include detection of genetic alterations in KRAS (e.g., in codons 12 and/or 61 of KRAS). In some embodiments, once an assay that includes detection of one or more genetic biomarkers present in ctDNA in a biological sample is performed, subsequent testing or monitoring is performed (e.g., any of the variety of further diagnostic testing or increased monitoring techniques disclosed herein). In some embodiments, once an assay that includes detection of one or more genetic biomarkers present in ctDNA in a biological sample is performed, a second assay that includes detecting one or more protein biomarkers at high thresholds can be performed (e.g., detecting any of the variety of protein biomarkers described herein including, but not limited to, carbohydrate antigen 19-9 (CA19-9), carcinoembryonic antigen (CEA), hepatocyte growth factor (HGF), osteopontin (OPN), and combinations thereof).

In some embodiments, one or more genetic biomarkers present in cell-free DNA (e.g., ctDNA) and/or one or more protein biomarkers can be tested from any of a variety of biological samples isolated or obtained from a subject (e.g., a human subject) including, but not limited to, the blood, plasma, serum, urine, cerebrospinal fluid, saliva, sputum, broncho-alveolar lavage, bile, lymphatic fluid, cyst fluid, stool, ascites, and combinations thereof. In some embodiments, one or more genetic biomarkers present in cell-free DNA (e.g., ctDNA) and one or more protein biomarkers can be tested from the same sample. For example, a single sample can be isolated or obtained from a subject, which single sample can be tested for the presence of one or more genetic biomarkers in cell-free DNA (e.g., ctDNA), the presence of one or more protein biomarkers, or both. Genetic biomarkers present in cell-free DNA (e.g., ctDNA) and one or more protein biomarkers can be tested from the sample at the same time or at different times. For example, the sample can be tested for the presence of one or more genetic biomarkers in cell-free DNA (e.g., ctDNA) at a first time, and for one or more protein biomarkers at a second time, or vice versa. In some embodiments, the sample can be refrigerated, frozen, or otherwise stored for future testing. In some embodiments, the presence of one or more genetic biomarkers in cell-free DNA (e.g., ctDNA) and the presence of one or more protein biomarkers can be tested from different samples. For example, a first sample can be isolated or obtained from a subject and tested for the presence of one or more genetic biomarkers in cell-free DNA (e.g., ctDNA), and a second sample can be isolated or obtained from the subject and tested for the presence of one or more protein biomarkers. The first and second samples can be of the same type (e.g., plasma or serum), or of different types. The first and/or second samples can be refrigerated, frozen, or otherwise stored for future testing.

In some embodiments, multiple codons or gene regions in a tumor suppressor gene or oncogene may be tested to identify a genetic biomarker (e.g., a mutation). For example, at least two, at least three, at least four, at least five or more codons or gene regions may be tested in a gene. Additionally or alternatively, multiple genes may be tested for mutations to increase the scope of an assay for more types of cancers or more cancers within a single type.

In some embodiments, a radiologic, sonographic, or other technique may be applied to any subject (e.g., a human subject) in which genetic biomarker (e.g., a mutation) is detected. The technique may be applied to the whole body, to a single organ, or to a region of the body. The technique may be used, for example, to ascertain a particular type of cancer is present, to confirm a cancer is present, or to identify location of a cancer in the body. In some embodiments, the technique is a scan. In some embodiments, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan, or a positron emission tomography and computed tomography (PET-CT) scan. In some embodiments, the technique is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, or a pelvic exam, In some embodiments, the technique is a biopsy (e.g., a bone marrow aspiration, a tissue biopsy). In some embodiments, the biopsy is performed by fine needle aspiration or by surgical excision. In some embodiments, the technique further includes obtaining a biological sample (e.g., a tissue sample, a urine sample, a blood sample, a check swab, a saliva sample, a mucosal sample (e.g., sputum, bronchial secretion), a nipple aspirate, a secretion or an excretion). In some embodiments, the technique includes determining exosomal proteins (e.g., an exosomal surface protein (e.g., CD24, CD147, PCA-3)) (Soung et al. (2017) Cancers 9(1): pii:E8). In some embodiments, the diagnostic testing method is an oncotype DX® test (Bachner (2016) Ecancermedicalscience 10:675).

In some embodiments, cancers of organs other than pancreatic cancer may be detected according to any of the variety of methods described herein.

In some embodiments, methods provided herein (e.g., methods in which the presence of one or more genetic biomarkers in cell-free DNA (e.g., ctDNA) and the presence of one or more high threshold protein biomarkers are detected in a biological sample isolated from the subject) can be used for selecting a treatment for a subject. For example, once a subject has been determined to have cancer (e.g., pancreatic cancer) by any of the variety of methods disclosed herein, an appropriate treatment can be selected (e.g., any of the variety of therapeutic interventions described herein). In some embodiments, methods provided herein (e.g., methods in which the presence of one or more genetic biomarkers in cell-free DNA (e.g., ctDNA) and the presence of one or more high threshold protein biomarkers are detected in a biological sample isolated from the subject) can be used for selecting a subject for treatment. For example, once a subject has been determined to have cancer (e.g., pancreatic cancer) by any of the variety of methods disclosed herein, that subject can be identified as an appropriate subject to receive a treatment (e.g., any of the variety of therapeutic interventions described herein). In some embodiments, methods provided herein (e.g., methods in which the presence of one or more genetic biomarkers in cell-free DNA (e.g., ctDNA) and the presence of one or more high threshold protein biomarkers are detected in a biological sample isolated from the subject) can be used for selecting a subject for increased monitoring. For example, once a subject has been determined to have cancer (e.g., pancreatic cancer) by any of the variety of methods disclosed herein, that subject can be identified as an appropriate subject to receive increased monitoring (e.g., any of the variety of monitoring techniques described herein). In some embodiments, methods provided herein (e.g., methods in which the presence of one or more genetic biomarkers in cell-free DNA (e.g., ctDNA) and the presence of one or more high threshold protein biomarkers are detected in a biological sample isolated from the subject) can be used for selecting a subject for further diagnostic testing. For example, once a subject has been determined to have cancer (e.g., pancreatic cancer) by any of the variety of methods disclosed herein, that subject can be identified as an appropriate subject to receive further diagnostic testing (e.g., any of the variety of diagnostic techniques described herein).

In some embodiments, methods provided herein can be used to detect the presence of cancer (e.g., pancreatic cancer) at a time period prior to diagnosis of the subject with an early-stage cancer and/or at a time prior to the subject exhibiting symptoms associated with cancer. For example, methods provided herein can be used when a subject has not been diagnosed with cancer and/or when a subject is not known to harbor a cancer cell.

In some embodiments of any of the methods described herein, the subject can be administered a single or multiple doses (e.g., two, three, four, five, six, seven, eight, nine, or ten doses) of any of the therapeutic interventions described herein.

In some embodiments, assays for genetic biomarkers (e.g., genetic alterations) can be combined with assays for elevated protein biomarkers to increase the sensitivity of a blood test for low stage pancreatic cancers. In some embodiments, 50%, 55%, 60%, 65%, 70%, 75%, 80%, 85%, 90%, 95% or more of such cancers can be detected through this combination test, including some patients with a favorable prognosis. In some embodiments, 64% of such cancers can be detected through this combination test, including some patients with a favorable prognosis. One of the design features of certain studies presented herein was that only patients with resectable pancreatic cancers were included, and patients with advanced disease (i.e., Stage III or IV) were excluded. Though this exclusion reduced the sensitivity that could be otherwise be achieved by evaluating all pancreatic cancer patients, regardless of stage, the resectable cases are represent a promising group with advantageous clinical relevance with respect to evaluating a screening technology. In some embodiments, methods provided herein can be used to detect all pancreatic cancers in subjects (e.g., human subjects).

Whether combining genetic biomarkers present in ctDNA and protein marker biomarkers could increase sensitivity over either alone was not known prior to the present disclosure. In fact, it was conceivable that the same patients with detectable circulating protein biomarkers would largely overlap those releasing DNA into the circulation. This was of particular concern for early stage cancer patients, because both ctDNA and protein-based biomarkers are known to be considerably higher in patients with advanced cancers compared to those with earlier stage cancers (Lennon A M & Goggins M (2010) Diagnostic and Therapeutic Response Markers. Pancreatic Cancer, (Springer New York, New York, NY), pp 675-701; Locker G Y, et al. (2006) ASCO 2006 update of recommendations for the use of tumor markers in gastrointestinal cancer. J Clin Oncol 24(33): 5313-5327; Bettegowda C, et al. (2014) Detection of circulating tumor DNA in early- and late-stage human malignancies. Science translational medicine 6(224):224ra224).

In some embodiments of the methods provided herein, very high specificity (e.g., 99.5%: 95% CI 97-100%) can be achieved For example, only one false positive among 182 healthy individuals of average age 64 was observed in the studies presented herein. Given the relative infrequency of cancer in the general population, the specificity of any potentially useful blood-based screening test for pancreatic cancer is preferably high, e.g., preferably >99%. Otherwise, the number of false positives would greatly exceed the number of true positives (i.e., have suboptimal positive predictive value) (Lennon A M, et al. (2014) The Early Detection of Pancreatic Cancer: What Will It Take to Diagnose and Treat Curable Pancreatic Neoplasia? Cancer Res 74(13):3381-3389). Such stringency for screening tests is not typically required for tests to monitor disease in patients with known cancer. For monitoring, specificity can be relaxed somewhat in the interest of obtaining higher sensitivity. High specificity was achieved with methods disclosed herein in at least two ways. First, ctDNA was used as one of the components of the test. KRAS mutations are exquisitely specific for neoplasia and their specificity has traditionally been limited by technical rather than biological factors. The incorporation of molecular barcoding into various assays described herein (e.g., using a Safe-SeqS technique) can minimize the false positive results from sequencing that have traditionally been major technical issues confronting any ctDNA-based assays. KRAS mutations are particularly suitable for early detection strategies because they are rarely found in clones arising during age-associated clonal hematopoiesis. Such clones, which may represent early forms of myelodysplasia, are a potential source of false positive ctDNA assays. The vast majority of such mutations occur within nine genes (DNMT3A, TET2, JAK2, ASXL1, TP53, GNAS, PPM1D, BCORL1 and SF3B1) (48-50), posing challenges for the use of these genes as biomarkers in ctDNA-based assays. Second, high thresholds were used for scoring the protein biomarkers as positive. These thresholds were based on prior studies in the literature or on an independent set of controls, permitting avoidance of positive scores in the vast majority of healthy patients (Kim J E, et al. (2004) Clinical usefulness of carbohydrate antigen 19-9 as a screening test for pancreatic cancer in an asymptomatic population. J Gastroenterol Hepatol 19(2):182-186). In some embodiments, such high thresholds can be used without an overall reduction in sensitivity because the ctDNA assay added sensitivity on its own and the ctDNA-positive cases only partially overlapped the protein-biomarker-positive cases (See, e.g., FIG. 9, FIG. 10, and Example 2).

Protein biomarkers have been combined with each other in the past to achieve higher sensitivity (Dong T, Liu C C, Petricoin E F, & Tang L L (2014) Combining markers with and without the limit of detection. Stat Med 33(8):1307-1320). For example, it was shown that combining CA19-9 and TIMP-1 was more sensitive for the detection of PDAC than either biomarker alone (Zhou W, et al. (1998) Identifying markers for pancreatic cancer by gene expression analysis. Cancer Epidemiol Biomarkers Prev 7(2):109-112). More recently, it was shown that the combination of CA19-9, TIMP-1, and LRG-1 was more sensitive for the detection of early PDAC than CA19-9 alone (Capello M, et al. (2017) Sequential Validation of Blood-Based Protein Biomarker Candidates for Early-Stage Pancreatic Cancer. J Natl Cancer Inst 109(4)). The combination of protein biomarkers with ultrasensitive ctDNA, as disclosed herein, is different. A recent study evaluated a combination of ctDNA and CA19-9 for pancreatic cancer but found no benefit to combining the biomarkers over CA19-9 alone. Without being bound by theory, it is possible this conclusion was reached due to inadequate sensitivity of the test used in detecting KRAS mutations (Le Calvez-Kelm F, et al. (2016) KRAS mutations in blood circulating cell-free DNA: a pancreatic cancer case-control. Oncotarget 7(48):78827-78840). Furthermore, the specificity for ctDNA achieved in that study was relatively low, reducing its suitability for screening.

In some embodiments, methods provided herein can be used to detect resectable pancreatic cancers through a non-invasive blood test in a majority of patients.

In some embodiments, results obtained using any of the variety of methods disclosed herein can underestimate the survival benefits of early detection. The majority of the patients that were studied herein, even though they had resectable cancers, were symptomatic and their cancers were discovered only by virtue of their symptoms. Accordingly, 77% of patients in the cohort described herein were Stage IIB and the median size of tumors in these patients was 3 cm. In some embodiments, in a screening study of asymptomatic individuals, a greater proportion of earlier stage patients, with smaller tumors, can be discovered using any of the variety of methods disclosed herein. In some embodiments, any of the variety of methods disclosed herein can be more sensitive for the detection of patients with larger tumors and with a poorer prognosis than for patients with smaller tumors, even though all tumors can be surgically resectable (See, e.g., FIG. 9B and Example 2). In some embodiments, KRAS mutations can be found in the circulation of patients with cancer types other than those of the pancreas, primarily those of the lung (Herbst R S, Heymach J V, & Lippman S M (2008) Lung cancer. N Engl J Med 359(13):1367-1380), and CA19-9, CEA, HGF, and OPN expression can be elevated in several other cancer types (Kim J E, et al. (2004) Clinical usefulness of carbohydrate antigen 19-9 as a screening test for pancreatic cancer in an asymptomatic population. J Gastroenterol Hepatol 19(2):182-186; Thomas D S, et al. (2015) Evaluation of serum CEA, CYFRA21-1 and CA125 for the early detection of colorectal cancer using longitudinal preclinical samples. Br J Cancer 113(2):268-274; Di Renzo M F, et al. (1995) Overexpression and amplification of the met/HGF receptor gene during the progression of colorectal cancer. Clin Cancer Res 1(2):147-154; El-Tanani M K, et al. (2006) The regulation and role of osteopontin in malignant transformation and cancer. Cytokine Growth Factor Rev 17(6):463-474). Thus, in some embodiments, patients testing positive using any of the variety of methods disclosed herein can undergo additional appropriate imaging studies to identify tumor localization.

In some embodiments, methods provided herein lay a foundation for evaluation of patients at high risk for PDAC, and for implementation of early detection strategies (Kalinich M, et al. (2017) An RNA-based signature enables high specificity detection of circulating tumor cells in hepatocellular carcinoma. Proc Natl Acad Sci USA 114(5):1123-1128). As an example, new-onset diabetes is known to be associated with an increased risk for pancreatic cancer. Approximately 1% of diabetic patients aged 50 and older are diagnosed with pancreatic cancer within 3 years of first meeting criteria for diabetes (Chari S T, et al. (2005) Probability of pancreatic cancer following diabetes: a population-based study. Gastroenterology 129(2):504-511). With an incidence of 1%, the PPV/NPV of certain combination assays disclosed herein is expected to be 54% and 99.6%, respectively, in this population, which is well within the range of currently approved screening tests for cancers.

Available evidence indicates that many cancers have detectable ctDNA in their earliest stages, often more commonly than observed in pancreatic cancer (Bettegowda C, et al. (2014) Detection of circulating tumor DNA in early- and late-stage human malignancies. Science translational medicine 6(224):224ra224). Similarly, a large number of protein biomarkers have already been described for the detection of numerous cancer types (Liotta L A & Petricoin E F, 3rd (2003) The promise of proteomics. Clin Adv Hematol Oncol 1(8):460-462). These protein biomarkers can be thresholded according to any of the variety of methods described herein, permitting the use ctDNA-protein combinations to detect a variety of cancer types (Bettegowda C, et al. (2014) Detection of circulating tumor DNA in early- and late-stage human malignancies. Science translational medicine 6(224): 224ra224).

Genetic Biomarkers in Combination with Aneuploidy

In one aspect, provided herein are methods and materials for detecting the presence of one or more members of a panel of genetic biomarkers and the presence of aneuploidy in one or more samples obtained from a subject. In another aspect, provided herein are methods and materials for diagnosing or identifying the presence of a disease in a subject (e.g., identifying the subject as having cancer) by detecting the presence of one or more members of a panel of genetic biomarkers and the presence of aneuploidy in one or more samples obtained from the subject. In another aspect, provided herein are methods and materials for identifying a subject as being at risk (e.g., increased risk) of having or developing a disease (e.g., cancer) by detecting the presence of one or more members of a panel of genetic biomarkers and the presence of aneuploidy in one or more samples obtained from the subject. In another aspect, provided herein are methods and materials for treating a subject who has been diagnosed or identified as having a disease (e.g., cancer) or who has been identified as being at risk (e.g., increased risk) of having or developing a disease (e.g., cancer) by detecting the presence of one or more members of a panel of genetic biomarkers and the presence of aneuploidy in one or more samples obtained from the subject. In another aspect, provided herein are methods and materials for identifying a treatment for a subject who has been diagnosed or identified as having a disease (e.g., cancer) or who has been identified as being at risk (e.g., increased risk) of having or developing a disease (e.g., cancer) by detecting the presence of one or more members of a panel of genetic biomarkers and the presence of aneuploidy in one or more samples obtained from the subject. In another aspect, provided herein are methods and materials for identifying a subject who will or is likely to respond to a treatment by detecting the presence of one or more members of a panel of genetic biomarkers and the presence of aneuploidy in one or more samples obtained from the subject. In another aspect, provided herein are methods and materials for identifying a subject as a candidate for further diagnostic testing by detecting the presence of one or more members of a panel of genetic biomarkers and the presence of aneuploidy in one or more samples obtained from the subject. In another aspect, provided herein are methods and materials for identifying a subject as a candidate for increased monitoring by detecting the presence of one or more members of a panel of genetic biomarkers and the presence of aneuploidy in one or more samples obtained from the subject.

In some embodiments, methods provided herein that include detecting the presence of one or more members of a panel of genetic biomarkers and the presence of aneuploidy in one or more samples obtained from a subject provide high sensitivity in the detection or diagnosis of cancer (e.g., a high frequency or incidence of correctly identifying a subject as having cancer). In some embodiments, methods provided herein that include detecting the presence of one or more members of a panel of genetic biomarkers and the presence of aneuploidy in one or more samples obtained from a subject provide a sensitivity in the detection or diagnosis of cancer (e.g., a high frequency or incidence of correctly identifying a subject as having cancer) that is higher than the sensitivity provided by separately detecting the presence of one or more members of a panel of genetic biomarkers or the presence of aneuploidy. In some embodiments, methods and materials provided herein that include detecting the presence of one or more members of a panel of genetic biomarkers and the presence of aneuploidy in one or more samples obtained from a subject provide a sensitivity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. In some embodiments, methods and materials provided herein that include detecting the presence of one or more members of a panel of genetic biomarkers and the presence of aneuploidy in one or more samples obtained from a subject provide high sensitivity in detecting a single type of cancer. In some embodiments, methods and materials provided herein that include detecting the presence of one or more members of a panel of genetic biomarkers and the presence of aneuploidy in one or more samples obtained from a subject provide high sensitivity in detecting two or more types of cancers. Any of a variety of cancer types can be detected using methods and materials provided herein (see, e.g., the section entitled "Cancers"). In some embodiments, cancers that can be detected using methods and materials that include detecting the presence of one or more members of a panel of genetic biomarkers and the presence of aneuploidy in one or more samples obtained from a subject include pancreatic cancer. In some embodiments, cancers that can be detected using methods and materials that include detecting the presence of one or more members of a panel of genetic biomarkers and the presence of aneuploidy in one or more samples obtained from a subject include liver cancer, ovarian cancer, esophageal cancer, stomach cancer, pancreatic cancer, colorectal cancer, lung cancer, or breast cancer. In some embodiments, cancers that can be detected using methods and materials that include detecting the presence of one or more members of a panel of genetic biomarkers and the presence of aneuploidy in one or more samples obtained from a subject include cancers of the female reproductive tract (e.g., cervical cancer, endometrial cancer, ovarian cancer, or fallopian tubal cancer). In some embodiments, cancers that can be detected using methods and materials that include detecting the presence of one or more members of a panel of genetic biomarkers and the presence of aneuploidy in one or more samples obtained from a subject include bladder cancer or upper-tract urothelial carcinomas.

In some embodiments, methods provided herein that include detecting the presence of one or more members of a panel of genetic biomarkers and the presence of aneuploidy in one or more samples obtained from a subject provide high specificity in the detection or diagnosis of cancer (e.g., a low frequency or incidence of incorrectly identifying a subject as having cancer when that subject does not have cancer). In some embodiments, methods provided herein that include detecting the presence of one or more members of a panel of genetic biomarkers and the presence of aneuploidy in one or more samples obtained from a subject provide a specificity in the detection or diagnosis of cancer (e.g., a high frequency or incidence of correctly identifying a subject as having cancer) that is higher than the specificity provided by separately detecting the presence of one or more members of a panel of genetic biomarkers or the presence of aneuploidy. In some embodiments, methods and materials provided herein that include that include detecting the presence of one or more members of a panel of genetic biomarkers and the presence of aneuploidy in one or more samples obtained from a subject provide a specificity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. As will be understood by those of ordinary skill in the art, a specificity of 99% means that only 1% of subjects that do not have cancer are incorrectly identified as having cancer. In some embodiments, methods and materials provided herein that include detecting the presence of one or more members of a panel of genetic biomarkers and the presence of aneuploidy in one or more samples obtained from a subject provide high specificity in detecting a single cancer (e.g., there is a low probability of incorrectly identifying that subject as having that single cancer type). In some embodiments, methods and materials provided herein that include detecting the presence of one or more members of a panel of genetic biomarkers and the presence of aneuploidy in one or more samples obtained from a subject provide high specificity in detecting two or more cancers (e.g., there is a low probability of incorrectly identifying that subject as having those two or more cancer types).

In some embodiments, methods provided herein that include detecting the presence of one or more members of a panel of genetic biomarkers and the presence of aneuploidy in one or more samples obtained from a subject include detecting the presence of: 1) one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, and 2) the presence of aneuploidy. In some embodiments, methods provided herein that include detecting the presence of one or more members of a panel of genetic biomarkers and the presence of aneuploidy in one or more samples obtained from a subject include detecting the presence of: 1) one or more genetic biomarkers in each of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A, and 2) the presence of aneuploidy. In some embodiments of methods provided herein that include detecting the presence of one or more members of a panel of genetic biomarkers and the presence of aneuploidy in one or more samples obtained from a subject include detecting the presence of: 1) one or more one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, and 2) the presence of aneuploidy, the subject is determined as having (e.g., diagnosed to have) or is determined to be (e.g. diagnosed as being) at elevated risk of having or developing one of the following types of cancer: cervical cancer, endometrial cancer, ovarian cancer, or fallopian tubal cancer.

In some embodiments, methods provided herein that include detecting the presence of one or more members of a panel of genetic biomarkers and the presence of one or more members of a panel of protein biomarkers in one or more samples obtained from a subject include detecting the presence of: 1) one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), and 3) the presence of aneuploidy. In some embodiments, methods provided herein that include detecting the presence of one or more members of a panel of genetic biomarkers and the presence of aneuploidy in one or more samples obtained from a subject include detecting the presence of: 1) one or more genetic biomarkers in each of the following genes: TP53, PIK3CA, FGFR3, KRAS, ERBB2, CDKN2A, MLL, HRAS, MET, and VHL, 2) the presence of a TERT promoter mutation (e.g., a genetic biomarker in a TERT promoter), and 3) the presence of aneuploidy. In some embodiments of methods provided herein that include detecting the presence of one or more members of a panel of genetic biomarkers and the presence of aneuploidy in one or more samples obtained from a subject include detecting the presence of: 1) one or more one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), and 3) the presence of aneuploidy, the subject is determined as having (e.g., diagnosed to have) or is determined to be (e.g. diagnosed as being) at elevated risk of having or developing cancer one of the following types of cancer: bladder cancer or an upper-tract urothelial carcinoma.

A sample obtained from a subject can be any of the variety of samples described herein that contains DNA (e.g., ctDNA in the blood, or DNA present in bladder, cervical, endometrial, or uterine samples) and/or proteins. In some embodiments, DNA (e.g., cell-free DNA (e.g., ctDNA) or DNA present in bladder, cervical, endometrial, or uterine samples) and/or proteins in a sample obtained from the subject are derived from a tumor cell. In some embodiments, DNA (e.g., cell-free DNA (e.g., ctDNA) in a sample obtained from the subject includes one or more genetic biomarkers and or aneuploid DNA. In some embodiments, proteins in a sample obtained from the subject includes one or more protein biomarkers. Non-limiting examples of samples in which genetic biomarkers and/or protein biomarkers and/or aneuploidy can be detected include a blood sample, a plasma sample, a serum sample, a urine sample, an endometrial sample, a cervical sample, and a uterine sample. In some embodiments, the presence of one or more genetic biomarkers and the presence of aneuploidy in a single sample obtained from the subject. In some embodiments, the presence of one or more genetic biomarkers is detected in a first sample obtained from a subject, and the presence of aneuploidy is detected in a second sample obtained from the subject.

In some embodiments, when a subject is determined as having (e.g., diagnosed to have) cancer or determined to be (e.g. diagnosed as being) at elevated risk of having or developing cancer (e.g., by detecting the presence of: 1) one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, and 2) the presence of aneuploidy), the subject is selected as a candidate for (e.g., is selected for) further diagnostic testing (e.g., any of the variety of further diagnostic testing methods described herein), the subject is selected as a candidate for (e.g. is selected for) increased monitoring (e.g., any of the variety of increasing monitoring methods described herein), the subject is identified as a subject who will or is likely to respond to a treatment (e.g., any of the variety of therapeutic interventions described herein), the subject is selected as a candidate for (e.g., is selected for) a treatment, a treatment (e.g., any of the variety of therapeutic interventions described herein) is selected for the subject, and/or a treatment (e.g., any of the variety of therapeutic interventions described herein) is administered to the subject. In some embodiments, when a subject is determined as having (e.g., diagnosed to have) cancer or determined to be (e.g. diagnosed as being) at elevated risk of having or developing cancer (e.g., by detecting the presence of: 1) one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), and 3) the presence of aneuploidy), the subject is selected as a candidate for (e.g., is selected for) further diagnostic testing (e.g., any of the variety of further diagnostic testing methods described herein), the subject is selected as a candidate for (e.g. is selected for) increased monitoring (e.g., any of the variety of increasing monitoring methods described herein), the subject is identified as a subject who will or is likely to respond to a treatment (e.g., any of the variety of therapeutic interventions described herein), the subject is selected as a candidate for (e.g., is selected for) a treatment, a treatment (e.g., any of the variety of therapeutic interventions described herein) is selected for the subject, and/or a treatment (e.g., any of the variety of therapeutic interventions described herein) is administered to the subject. For example, when a subject is determined as having (e.g., diagnosed to have) cancer or determined to be (e.g. diagnosed as being) at elevated risk of having or developing cancer, the subject can undergo further diagnostic testing, which further diagnostic testing can confirm the presence of cancer in the subject. Additionally or alternatively, the subject can be monitored at in increased frequency. In some embodiments of a subject determined as having (e.g., diagnosed to have) cancer or determined to be (e.g. diagnosed as being) at elevated risk of having or developing cancer in which the subject undergoes further diagnostic testing and/or increased monitoring, the subject can additionally be administered a therapeutic intervention. In some embodiments, after a subject is administered a therapeutic intervention, the subject undergoes additional further diagnostic testing (e.g., the same type of further diagnostic testing as was performed previously and/or a different type of further diagnostic testing) and/or continued increased monitoring (e.g., increased monitoring at the same or at a different frequency as was previously done). In embodiments, after a subject is administered a therapeutic intervention and the subject undergoes additional further diagnostic testing and/or additional increased monitoring, the subject is administered another therapeutic intervention (e.g., the same therapeutic intervention as was previously administered and/or a different therapeutic intervention). In some embodiments, after a subject is administered a therapeutic intervention, the subject is tested for the presence of: 1) one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, and 2) the presence of aneuploidy. In some embodiments, after a subject is administered a therapeutic intervention, the subject is tested for the presence of: 1) one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), and 3) the presence of aneuploidy.

In some embodiments, methods provided herein that include detecting the presence of one or more members of a panel of genetic biomarkers and the presence of aneuploidy further include detecting the presence one or more members of a panel of protein biomarkers in one or more samples obtained from a subject (e.g., the same sample use to detect either or both of the presence of one or more members of a panel of genetic biomarkers and the presence of aneuploidy, or a different sample). Any of a variety of protein biomarkers can be detected (e.g., any of the variety of protein biomarkers and/or protein biomarker panels described herein).

In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, and 2) the presence of aneuploidy, the methods further include detecting the presence of one or more members of a panel of protein biomarkers in a sample obtained from the subject (e.g., the same sample use to detect either or both of the presence of one or more members of a panel of genetic biomarkers and the presence of aneuploidy, or a different sample). In some embodiments of methods provided herein that include detecting in one or more samples obtained from a subject the presence of: 1) one or more genetic biomarkers in each of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A, and 2) the presence of aneuploidy, the methods further include detecting the presence of one or more members of a panel of protein biomarkers in a sample obtained from the subject (e.g., the same sample use to detect either or both of the presence of one or more members of a panel of genetic biomarkers and the presence of aneuploidy, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, 2) the presence of aneuploidy, and 3) the presence of one or more members of a panel of protein biomarkers, the presence of one or more members of, the subject is determined as having (e.g., diagnosed to have) or is determined to be (e.g. diagnosed as being) at elevated risk of having or developing one of the following types of cancer: cervical cancer, endometrial cancer, ovarian cancer, or fallopian tubal cancer.

In some embodiments or methods provided herein that include detecting in one or more samples obtained from a subject the presence of: 1) one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), and 3) the presence of aneuploidy, the methods further include detecting the presence of one or more members of a panel of protein biomarkers in a sample obtained from the subject (e.g., the same sample use to detect either or both of the presence of one or more members of a panel of genetic biomarkers and the presence of aneuploidy, or a different sample). In some embodiments of methods provided herein that include detecting in one or more samples obtained from a subject the presence of: 1) one or more genetic biomarkers in each of the following genes: TP53, PIK3CA, FGFR3, KRAS, ERBB2, CDKN2A, MLL, HRAS, MET, and VHL, 2) the presence of a TERT promoter mutation (e.g., a genetic biomarker in a TERT promoter), and 3) the presence of aneuploidy, the methods further include detecting the presence of one or more members of a panel of protein biomarkers in a sample obtained from the subject (e.g., the same sample use to detect either or both of the presence of one or more members of a panel of genetic biomarkers and the presence of aneuploidy, or a different sample). In some embodiments of methods provided herein that include detecting in one or more samples obtained from a subject the presence of: 1) one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL, 2) the presence of a TERT promoter mutation (e.g., a genetic biomarker in a TERT promoter), 3) the presence of aneuploidy, and 4) the presence of one or more members of a panel of protein biomarkers, the subject is determined as having (e.g., diagnosed to have) or is determined to be (e.g. diagnosed as being) at elevated risk of having or developing cancer one of the following types of cancer: bladder cancer or an upper-tract urothelial carcinoma.

In some embodiments of methods provided herein that include detecting the presence of one or more members of a panel of genetic biomarkers and the presence of aneuploidy, one or more (e.g., 1, 2, 3, 4, 5, 6, 7, or 8) of the following protein biomarkers can further be detected: CA19-9, CEA, HGF, OPN, CA125, prolactin, TIMP-1, and/or myeloperoxidase (MPO). In some embodiments of methods provided herein that include detecting the presence of one or more members of a panel of genetic biomarkers and the presence of aneuploidy, each of the following protein biomarkers can further be detected: CA19-9, CEA, HGF, OPN, CA125, prolactin, TIMP-1, and myeloperoxidase (MPO).

In some embodiments of methods provided herein that include detecting the presence of one or more members of a panel of genetic biomarkers and the presence of aneuploidy, one or more (e.g., 1, 2, 3, 4, 5, 6, 7, 8, 9, 10, or 11) of the following protein biomarkers can further be detected: CA19-9, CEA, HGF, OPN, CA125, AFP, prolactin, TIMP-1, follistatin, G-CSF, and/or CA15-3. In some embodiments of methods provided herein that include detecting the presence of one or more members of a panel of genetic biomarkers and the presence of aneuploidy, each of the following protein biomarkers can further be detected: CA19-9, CEA, HGF, OPN, CA125, AFP, prolactin, TIMP-1, follistatin, G-CSF, and CA15-3.

In some embodiments of methods provided herein that include detecting the presence of one or more members of a panel of genetic biomarkers and the presence of aneuploidy, one or more (e.g., 1, 2, 3, 4, 5, 6, 7, 8, or 9) of the following protein biomarkers can further be detected: CA19-9, CEA, HGF, OPN, CA125, AFP, prolactin, TIMP-1, and/or CA15-3. In some embodiments of methods provided herein that include detecting the presence of one or more members of a panel of genetic biomarkers and the presence of aneuploidy, each of the following protein biomarkers can further be detected: CA19-9, CEA, HGF, OPN, CA125, AFP, prolactin, TIMP-1, and CA15-3.

In some embodiments of methods provided herein that include detecting the presence of one or more members of a panel of genetic biomarkers and the presence of aneuploidy, one or more (e.g., 1, 2, 3, or 4) of the following protein biomarkers can further be detected: CA19-9, CEA, HGF, and/or OPN. In some embodiments of methods provided herein that include detecting the presence of one or more members of a panel of genetic biomarkers and the presence of aneuploidy, each of the following protein biomarkers can further be detected: CA19-9, CEA, HGF, and OPN.

In some embodiments, any of the variety of methods provided herein that include detecting the presence of one or more members of a panel of genetic biomarkers and the presence of aneuploidy in one or more samples obtained from a subject further include detecting the presence of one or more members of one or more additional classes of biomarkers. Non-limiting examples of such additional classes of biomarkers includes: copy number changes, DNA methylation changes, other nucleic acids (e.g., mRNAs, miRNAs, lncRNAs, circRNA, mtDNA, telomeric DNA, translocation and genomic rearrangements), peptides, and/or metabolites.

In some embodiments, the one or more additional classes of biomarkers include a metabolite biomarker. In some embodiments, a subject is determined to be at elevated risk of having or developing cancer if the biological sample contains one or more metabolites indicative of cancer. In some embodiments, a subject is determined as having cancer if the biological sample contains one or more metabolites indicative of cancer. Non-limiting examples of metabolites indicative of cancer include: 5-methylthioadenosine (MTA), Glutathione reduced (GSH), N-acetylglutamate, Lactose, N-acetylneuraminate, UDP-acetylglucosamine, UDP-Acetylgalactosamine, UDP-glucuronate, Pantothenate, Arachidonate (20:4n6), Choline, Cytidine 5'-diphosphocholine, Dihomo-linolenate (20:3n3), Docosapentaenoate (DPA 22:5n3), Eicosapentaenoate (EPA 20:5n3), Glycerophosphorylcholine (GPC), Docosahexaenoate (DHA 22:6n3), Linoleate (18:2n6), Cytidine 5'-monophosphate (5'-CMP), Gamma-glutamylglutamate, X-14577, X-11583, Isovalerylcarnitine, Phosphocreatine, 2-Aminoadipic acid, Gluconic acid, O-Acetylcarnitine, aspartic acid, Deamido-NAD+, glutamic acid, Isobutyrylcarnitine, Carnitine, Pyridoxal, Citric acid, Adenosine, ATP, valine, XC0061, Isoleucine, γ-Butyrobetaine, Lactic acid, alanine, phenylalanine, Gluconolactone, leucine, Glutathione (GSSG)_divalent, tyrosine, NAD+, XC0016, UTP, creatine, Theobromine, CTP, GTP, 3-Methylhistidine, Succinic acid, Glycerol 3-phosphate, glutamine, 5-Oxoproline, Thiamine, Butyrylcarnitine, 4-Acetamidobutanoic acid, UDP-Glucose, UDP-Galactose, threonine, N-Acetylglycine, proline, ADP, Choline, Malic acid, S-Adenosylmethionine, Pantothenic acid, Cysteine-sulfinic acid, 6-Aminohexanoic acid, Homocysteic acid, Hydroxyproline, Methionine sulfoxide, 3-Guanidinopropionic acid, Glucose 6-phosphate, Phenaceturic acid, Threonic acid, tryptophan, Pyridoxine, N-Acetylaspartic acid, 4-Guanidinobutyric acid, serine, Citrulline, Betaine, N-Acetylasparagine, 2-Hydroxyglutaric acid, arginine, Glutathione (GSH), creatinine, Dihydroxyacetone phosphate, histidine, glycine, Glucose 1-phosphate, N-Formylglycine, Ketoprofen, lysine, beta-alanine, N-Acetylglutamic acid, 2-Amino-2-(hydroxymethyl)-1,3-propanediol, Ornithine, Phosphorylcholine, Glycerophosphocholine, Terephthalic acid, Glyceraldehyde 3-phosphate, Gly-Asp, Taurine, Fructose 1,6-diphosphate, 3-Aminoisobutyric acid, Spermidine, GABA, Triethanolamine, Glycerol, N-Acetylserine, N-Acetylornithine, Diethanolamine, AMP, Cysteine glutathione disulfide, Streptomycin sulfate+H2O divalent, trans-Glutaconic acid, Nicotinic acid, Isobutylamine, Betaine aldehyde+H2O, Urocanic acid, 1-Aminocyclopropane-1-carboxylic acid Homoserinelactone, 5-Aminovaleric acid, 3-Hydroxybutyric acid, Ethanolamine, Isovaleric acid, N-Methylglutamic acid, Cystathionine, Spermine, Carnosine, 1-Methylnicotinamide, N-Acetylneuraminic acid, Sarcosine, GDP, N-Methylalanine, palmitic acid, 1,2-diolcoyl-sn-glycero-3-phospho-rac-glycerolcholesterol 5α,6α epoxidelanosterol, lignoceric acid, loleoyl_rac_GL, cholesterol_epoxide, erucic acid, T-LCA, oleoyl-L-carnitine, oleanolic acid, 3-phosphoglycerate, 5-hydroxynorvaline, 5-methoxytryptamine, adenosine-5-monophosphate, alpha-ketoglutarate, asparagine, benzoic acid, hypoxanthine, maltose, maltotriose, methionine sulfoxide, nornicotine, phenol, Phosphoethanolamine, pyrophosphate, pyruvic acid, quinic acid, taurine, uric acid, inosine, lactamide, 5-hydroxynorvaline NIST, cholesterol, deoxypentitol, 2-hydroxyestrone, 2-hydroxyestradiol, 2-metholyestrone, 2-metholxyestradiol, 2-hydroxyestrone-3-methyl ether, 4-hydroxyestrone, 4-metholxyestrone, 4-methoxyestradiol, 16alpha-hydroxyestrone, 17-epiestriol, estriol, 16-Ketoestradiol, 16-epiestriol, acylcarnitine C18:1, amino acids citrulline and trans-4-hydroxyproline, glycerophospholipids PC aa C28:1, PC ae C30:0 and PC ae C30:2, and sphingolipid SM (OH) C14:1. See e.g., Halama et al., Nesting of colon and ovarian cancer cells in the endothelial niche is associated with alterations in glycan and lipid metabolism, Scientific Reports volume 7, Article number: 39999 (2017); Hur et al., Systems approach to characterize the metabolism of liver cancer stem cells expressing CD133, Sci Rep., 7:45557, doi: 10.1038/srep45557, (2017); Eliassen et al., Urinary Estrogens and Estrogen Metabolites and Subsequent Risk of Breast Cancer among Premenopausal Women, Cancer Res; 72(3); 696-706 (2011); Gangi et al., Metabolomic profile in pancreatic cancer patients: a consensus-based approach to identify highly discriminating metabolites, Oncotarget, February 2; 7(5): 5815-5829 (2016); Kumar et al., Serum and Plasma Metabolomic Biomarkers for Lung Cancer, Bioinformation, 13(6): 202-208, doi: 10.6026/97320630013202 (2017); Schmidt et al., Pre-diagnostic metabolite concentrations and prostate cancer risk in 1077 cases and 1077 matched controls in the European Prospective Investigation into Cancer and Nutrition, BMC Med., 15:122, doi: 10.1186/s12916-017-0885-6 (2017); each of which is incorporated herein by reference in its entirety.

In some embodiments, the one or more additional classes of biomarkers include a peptide (e.g., a peptide that is distinct from the various protein biomarkers described herein as being useful in one or more methods). In some embodiments, a subject is determined to be at elevated risk of having or developing cancer if the biological sample contains one or more peptides indicative of cancer. In some embodiments, a subject is determined as having cancer if the biological sample contains one or more peptides indicative of cancer. In some embodiments, a peptide is derived from a protein (e.g., the peptide includes an amino acid sequence present in a protein biomarker or a different protein). Non-limiting examples of peptides indicative of cancer include the following peptides and peptides derived from the following proteins: CEACAM, CYFRA21-1, CA125, PKLK, ProGRP, NSE, TPA 6, TPA 7, TPA 8, NRG, NRG 100, CNDP, APOB100, SCC, VEGF, EGFR, PIK3CA, HER2, BRAF, ROS, RET, NRAS, MET, MEK1, HER2, C4.4A, PSF3, FAM83B, ECD, CTNNB, VIM, S100A4, S100A7, COX2, MUC1, KLKB1, SAA, HP-β chain, C9, Pgrmc1, Ciz1, Transferrin, α-1 antitrypsin, apolipo protein 1, complement c3a, Caveolin-1, Kallikrein 6, Glucose regulated protein-8, α defensing-1,-2,-3, Serum C-peptide, Alpha-2-HS glycol protein, Tryptic KRT 8 peptide, Plasma glycol protein, Catenin, Defensin α 6, MMPs, Cyclin D, S100 P, Lamin A/C filament protein, Heat shock protein, aldehyde dehydrogenase, Tx1-2, (thioredoxin like protein-2), P53, nm23, u-PA, VEGF, Eph B4, CRABP2, WT-1, Rab-3D, Mesothelin, ERα, ANXA4, PSAT1, SPB5, CEA5, CEA6, A1AT, SLPI, APOA4, VDBP, HE4, IL-1, -6, -7, -8, -10, -11, -12, -16, -18, -21, -23, -28A, -33, LIF, TNFR1-2, HVEM (TNFRSF14), IL1R-a, IL1R-b, IL-2R, M-CSF, MIP-1a, TNF-α, CD40, RANTES, CD40L, MIF, IFN-β, MCP-4 (CCL13), MIG (CXCL9), MIP-1δ (CCL15), MIP3a (CCL20), MIP-4 (CCL18), MPIF-1, SDF-1a+b (CXCL12), CD137/4-1BB, lymphotactin (XCL1), eotaxin-1 (CCL11), eotaxin-2 (CCL24), 6Ckine/CCL21), BLC (CXCL13), CTACK (CCL27), BCA-1 (CXCL13), HCC4 (CCL16), CTAP-3 (CXCL7), IGF1, VEGF, VEGFR3, EGFR, ErbB2, CTGF, PDGF AA, BB, PDGFRb, bFGF, TGFbRIII, β-cellulin, IGFBP1-4, 6, BDNF, PEDF, angiopoietin-2, renin, lysophosphatidic acid, β2-microglobulin, sialyl TN, ACE, CA 19-9, CEA, CA 15-3, CA-50, CA 72-4, OVX1, mesothelin, sialyl TN, MMP-2, -3, -7, -9, VAP-1, TIMP1-2, tenascin C, VCAM-1, osteopontin, KIM-1, NCAM, tetranectin, nidogen-2, cathepsin L, prostasin, matriptase, kallikreins 2, 6, 10, cystatin C, claudin, spondin2, SLPI, bHCG, urinary gonadotropin peptide, inhibin, leptin, adiponectin, GH, TSH, ACTH, PRL, FSH, LH, cortisol, TTR, osteocalcin, insulin, ghrelin, GIP, GLP-1, amylin, glucagon, peptide YY, follistatin, hepcidin, CRP, Apo A1, CIII, H, transthyretin, SAA, SAP, complement C3,4, complement factor H, albumin, ceruloplasmin, haptoglobin, β-hemoglobin, transferrin, ferritin, fibrinogen, thrombin, von Willebrand factor, myoglobin, immunosuppressive acidic protein, lipid-associated sialic acid, S100A12 (EN-RAGE), fetuin A, clusterin, α1-antitrypsin, a2-macroglobulin, serpin1 (human plasminogen activator inhibitor-1), Cox-1, Hsp27, Hsp60, Hsp80, Hsp90, lectin-type oxidized LDL receptor 1, CD14, lipocalin 2, ITIH4, sFasL, Cyfra21-1, TPA, perforin, DcR3, AGRP, creatine kinase-MB, human milk fat globule 1-2, NT-Pro-BNP, neuron-specific enolase, CASA, NB/70K, AFP, afamin, collagen, prohibitin, keratin-6, PARC, B7-H4, YK-L40, AFP-L3, DCP, GPC3, OPN, GP73, CK19, MDK, A2, 5-HIAA, CA15-3, CA19-9, CA27.29, CA72-4, calcitonin, CGA, BRAF V600E, BAP, BCT-ABL fusion protein, KIT, KRAS, PSA, Lactate dehydrogenase, NMP22, PAI-1, uPA, fibrin D-dimer, S100, TPA, thyroglobulin, CD20, CD24, CD44, RS/DJ-1, p53, alpha-2-HS-glycoprotein, lipophilin B, beta-globin, hemopexin, UBE2N, PSMB6, PPP1CB, CPT2, COPA, MSK1/2, Pro-NPY, Secernin-1, Vinculin, NAAA, PTK7, TFG, MCCC2, TRAP1, IMPDH2, PTEN, POSTN, EPLIN, eIF4A3, DDAH1, ARG2, PRDX3&4, P4HB, YWHAG, Enoyl CoA-hydrase, PHB, TUBB, KRT2, DES, HSP71, ATP5B, CKB, HSPD1, LMNA, EZH2, AMACR, FABP5, PPA2, EZR, SLP2, SM22, Bax, Smac/Diablo phosphorylated Bcl2, STAT3 and Smac/Diablo expression, PHB, PAP, AMACR, PSMA, FKBP4, PRDX4, KRT7/8/18, GSTP1, NDPK1, MTX2, GDF15, PCa-24, Caveolin-2, Prothrombin, Antithrombin-III, Haptoglobin, Serum amyloid A-1 protein, ZAG, ORM2, APOC3, CALML5, IGFBP2, MUC5AC, PNLIP, PZP, TIMP1, AMBP, inter-alpha-trypsin inhibitor heavy chain H1, inter-alpha-trypsin inhibitor heavy chain H2, inter-alpha-trypsin inhibitor heavy chain H3, V-type proton ATPase subunit B, kidney isoform, Hepatocyte growth factor-like protein, Serum amyloid P-component, Acylglycerol kinase, Leucine-rich repeat-containing protein 9, Beta-2-glycoprotein 1, Plasma protease C1 inhibitor, Lipoxygenase homology domain-containing protein 1, Protocadherin alpha-13. See, e.g., Kuppusamy et al., Volume 24, Issue 6, September 2017, Pages 1212-1221; Elzek and Rodland, Cancer Metastasis Rev. 2015 March; 34(1): 83-96; Noel and Lokshin, Future Oncol. 2012 January; 8(1): 55-71; Tsuchiya et al., World J Gastroenterol. 2015 Oct. 7; 21(37): 10573-10583; Lou et al., Biomark Cancer. 2017; 9:1-9; Park et al., Oncotarget. 2017 Jun. 27; 8(26): 42761-42771; Saraswat et al., Cancer Med. 2017 July; 6(7): 1738-1751; Zamay et al., Cancers (Basel). 2017 November; 9(11): 155; Tanase et al., Oncotarget. 2017 Mar. 14; 8(11): 18497-18512, each of which is incorporated herein by reference in its entirety.

In some embodiments, the one or more additional classes of biomarkers include nucleic acid lesions or variations (e.g., a nucleic acid lesion or variation that is distinct from the various genetic biomarkers described herein as being useful in one or more methods). In some embodiments, a subject is determined to be at elevated risk of having or developing cancer if the biological sample contains one or more nucleic acid lesions or variations indicative of cancer. In some embodiments, a subject is determined as having cancer if the biological sample contains one or more nucleic acid lesions or variations indicative of cancer. Non-limiting examples of nucleic acid lesions or variations include copy number changes, DNA methylation changes, and/or other nucleic acids (e.g., mRNAs, miRNAs, lncRNAs, circRNA, mtDNA, telomeric DNA, translocation and genomic rearrangements).

Translocations and genomic rearrangements have been correlated with various cancers (e.g., prostate, glioma, lung cancer, non-small cell lung cancer, melanoma, and thyroid cancer) and used as biomarkers for years (e.g., Demeure et al., 2014, World J Surg., 38:1296-305; Hogenbirk et al., 2016, PNAS USA, 113:E3649-56; Gasi et al., 2011, PLoS One, 6:e16332; Ogiwara et al., 2008, Oncogene, 27:4788-97; U.S. Pat. Nos. 9,745,632; and 6,576,420). In addition, changes in copy number have been used as biomarkers for various cancers including, without limitation, head and neck squamous cell carcinoma, lymphoma (e.g., non-Hodgkin's lymphoma) and colorectal cancer (Kumar et al., 2017, Tumour Biol, 39:1010428317740296; Kumar et al., 2017, Tumour Biol., 39:1010428317736643; Henrique et al., 2014, Expert Rev. Mol. Diagn., 14:419-22; and U.S. Pat. No. 9,816,139). DNA methylation and changes in DNA methylation (e.g., hypomethylation, hypermethylation) also are used as biomarkers in cancer. For example, hypomethylation has been associated with hepatocellular carcinoma (see, for example, Henrique et al., 2014, Expert Rev. Mol. Diagn., 14:419-22), esophageal carcinogenesis (see, for example, Alvarez et al., 2011, PLoS Genet., 7:e1001356) and gastric and liver cancer (see, for example, U.S. Pat. No. 8,728,732), and hypermethylation has been associated with colorectal cancer (see, for example, U.S. Pat. No. 9,957,570;). In addition to genome-wide changes in methylation, specific methylation changes within particular genes can be indicative of specific cancers (see, for example, U.S. Pat. No. 8,150,626). Li et al. (2012, J. Epidemiol., 22:384-94) provides a review of the association between numerous cancers (e.g., breast, bladder, gastric, lung, prostate, head and neck squamous cell, and nasopharyngeal) and aberrant methylation. Additionally or alternatively, additional types of nucleic acids or features of nucleic acids have been associated with various cancers. Non-limiting examples of such nucleic acids or features of nucleic acids include the presence or absence of various microRNAs (miRNAs) have been used in the diagnosis of colon, prostate, colorectal, and ovarian cancers (see, for example, D'Souza et al., 2018, PLos One, 13:e0194268; Fukagawa et al., 2017, Cancer Sci., 108:886-96; Giraldez et al., 2018, Methods Mol. Biol., 1768:459-74; U.S. Pat. Nos. 8,343,718; 9,410,956; and 9,074,206). For a review on the specific association of miR-22 with cancer, see Wang et al. (2017, Int. J. Oncol., 50:345-55); the abnormal expression of long non-coding RNAs (lncRNAs) also have been used as a biomarker in cancers such as prostate cancer, colorectal cancer, cervical cancer, melanoma, non-small cell lung cancer, gastric cancer, endometrial carcinoma, and hepatocellular carcinoma (see, for example, Wang et al., 2017, Oncotarget, 8:58577086; Wang et al., 2018, Mol. Cancer, 17:110; Yu et al., 2018, Eur. Rev. Med. Pharmacol. Sci., 22:4812-9; Yu et al., 2018, Eur. Rev. Med. Pharmacol. Sci., 22:993-1002; Zhang et al., 2018, Eur. Rev. Med. Pharmacol. Sci., 22:4820-7; Zhang et al., 2018, Eur. Rev. Med. Pharmacol. Sci., 22:2304-9; Xie et al., 2018, EBioMedicine, 33:57-67; and U.S. Pat. No. 9,410,206); the presence or absence of circular RNA (circRNA) has been used as a biomarker in lung cancer, breast cancer, gastric cancer, colorectal cancer, and liver cancer (e.g., Geng et al., 2018, J. Hematol. Oncol., 11:98) and melanoma (e.g., Zhang et al., 2018, Oncol. Lett., 16:1219-25); changes in telomeric DNA (e.g., in length or in heterozygosity) or centromeric DNA (e.g., changes in expression of centromeric genes) also have been associated with cancers (e.g., prostate, breast, lung, lymphoma, and Ewing's sarcoma) (see, for example, Baretton et al., 1994, Cancer Res., 54:4472-80; Liscia et al., 1999, Br. J. Cancer, 80:821-6; Proctor et al., 2009, Biochim. Biophys. Acta, 1792:260-74; and Sun et al., 2016, Int. J. Cancer, 139:899-907); various mutations (e.g., deletions), rearrangements and/or copy number changes in mitochondrial DNA (mtDNA) have been used prognostically and diagnostically for various cancers (e.g., prostate cancer, melanoma, breast cancer, lung cancer, and colorectal cancer). See, for example, Maragh et al., 2015, Cancer Biomark., 15:763-73; Shen et al., 2010, Mitochondrion, 10:62-68; Hosgood et al., 2010, Carcinogen., 31:847-9; Thyagarajan et al., 2012, Cancer Epid. Biomarkers & Prev., 21:1574-81; and U.S. Pat. No. 9,745,632; and the abnormal presence, absence or amount of messenger RNAs (mRNAs) also have been correlated with various cancers including, without limitation, breast cancer, Wilms' tumors, and cervical cancer (see, for example, Guetschow et al., 2012, Anal. Bioanaly. Chem., 404:399-406; Schwienbacher et al., 2000, Cancer Res., 60:1521-5; and Ngan et al., 1997, Genitourin Med., 73:54-8). Each of these citations is incorporated herein by reference in its entirety.

In certain aspects, provided herein are methods of detecting diseases in a subject (e.g., a human). Various methods disclosed herein provide a broadly applicable approach for non-invasive detection of cancer in subjects (e.g., a cancer such as, without limitation, endometrial or ovarian cancer). Various methods disclosed herein provide a broadly applicable approach treatment of a subject having or suspected of having cancer after non-invasive detection of cancer in subjects (e.g., a cancer such as, without limitation, endometrial or ovarian cancer).

In some embodiments, methods provided herein include detecting genetic biomarkers (e.g., mutations) in one or more genes from cells present in a sample (e.g., a cervical or endometrial sample) obtained from a subject. For example, methods provided herein can be used to detect the presence of one or more genetic biomarkers (e.g., mutations) in one or more genes selected from the group consisting of: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A, wherein the presence of one or more genetic biomarkers (e.g., mutations) in one or more genes is indicative of the presence of ovarian or endometrial cancer in the subject. In some embodiments, the methods provided herein include detecting in a sample obtained from a subject the presence of aneuploidy (e.g., monosomy or trisomy), wherein the presence aneuploidy is indicative of the presence of ovarian or endometrial cancer in the subject. In some embodiments, methods provided herein include detecting in a sample obtained from a subject each of the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and the presence of aneuploidy (e.g., monosomy or trisomy). In some embodiments, methods which include detecting in a sample obtained from a subject each of the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and the presence of aneuploidy (e.g., monosomy or trisomy) provide a better indication that the subject has a cancer (e.g., a endometrial or ovarian cancer) than methods in which either aspect is tested individually.

In some embodiments, a sample for detecting the presence of a cancer (e.g. an ovarian or endometrial cancer) can be collected using a Pap brush. In some embodiments of any of the variety of methods provided herein, a sample for detecting the presence of a cancer (e.g. an ovarian or endometrial cancer) can be collected using a Tao brush.

In some embodiments, methods provided herein further include testing a sample obtained from a subject (e.g., a plasma sample) for genetic biomarkers in nucleic acids that are present as circulating tumor DNA (ctDNA). For example, a sample (e.g., a plasma sample) can be tested to detect genetic biomarkers in nucleic acids that harbor one or more mutations in one or more of the following genes: AKT1, APC, BRAF, CDKN2A, CTNNB1, EGFR, FBXW7, FGFR2, GNAS, HRAS, KRAS, NRAS, PIK3CA, PPP2R1A, PTEN, and/or TP53.

In various embodiments of methods provided herein in which one or more genetic biomarkers (e.g., mutations) in genes in cells present in a sample (e.g., a cervical or endometrial sample) obtained from a subject are detected, genetic biomarkers (e.g., mutations) in one or more of NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A can be detected. In some embodiments, one or more genetic biomarkers (e.g., mutations) in 1, 2, 3, 4, 5, 6, 7, 8, 9, 10, 11, 12, 13, 14, 15, 16, or 17 of these genes can be detected. In some embodiments, one or more genetic biomarkers (e.g., mutations) in all 18 of these genes can be detected. In some embodiments, the one or more genetic biomarkers (e.g., mutations) in these genes can be a mutation shown in Table 15. In some embodiments, the one or more genetic biomarkers (e.g., mutations) in these genes can be a mutation shown in Table 16. In some embodiments, the one or more genetic biomarkers (e.g., mutations) in these genes can be a mutation shown in Table 17. In some embodiments, the one or more genetic biomarkers (e.g., mutations) in these genes can be a mutation in a gene shown in Table 15. In some embodiments, the one or more genetic biomarkers (e.g., mutations) in these genes can be a mutation in a gene shown in Table 16. In some embodiments, the one or more genetic biomarkers (e.g., mutations) in these genes can be a mutation in a gene shown in Table 17. In some embodiments, methods provided herein to detect the presence of an ovarian or endometrial cancer by detecting the presence of one or more genetic biomarkers (e.g., mutations) in one or more of the following genes: NRAS, PTEN, FGFR2, KRAS, POLE, AKT1, TP53, RNF43, PPPF2R1A, MAPK1, CTNNB1, PIK3CA, FBXW7, PIK3R1, APC, EGFR, BRAF, and/or CDKN2A can be combined with the detection of aneuploidy, the detection of genetic biomarkers (e.g., mutations) present in ctDNA, or both. In some embodiments, combining with the detection of aneuploidy, the detection of genetic biomarkers (e.g., mutations) present in ctDNA, or both can increase the specificity and/or sensitivity of detecting ovarian or endometrial cancer. In some embodiments, the sample is collected using a Pap brush. In some embodiments, the sample is collected using a Tao brush.

In some embodiments, methods provided herein can be used to detect the presence of an endometrial cancer. For example, methods provided herein can be used to detect the presence of one or more genetic biomarkers (e.g., mutations) in one or more of the following genes: PTEN, TP53, PIK3CA, PIK3R1, CTNNB1, KRAS, FGFR2, POLE, APC, FBXW7, RNF43, and/or PPP2R1A, wherein the presence of one or more genetic biomarkers (e.g., mutations) in one or more genes is indicative of the presence of endometrial cancer in the subject. In some embodiments, one or more genetic biomarkers (e.g., mutations) in 1, 2, 3, 4, 5, 6, 7, 8, 9, 10, or 11 of these genes can be detected. In some embodiments, one or more genetic biomarkers (e.g., mutations) in all 12 of these genes can be detected. In some embodiments, the one or more genetic biomarkers (e.g., mutations) in these genes can be any mutation described herein (e.g., a mutation as shown in any one of Tables 15, 16, or 17). In some embodiments, methods provided herein to detect the presence of an endometrial cancer by detecting the presence of one or more genetic biomarkers (e.g., mutations) in one or more of the following genes: PTEN, TP53, PIK3CA, PIK3R1, CTNNB1, KRAS, FGFR2, POLE, APC, FBXW7, RNF43, and/or PPP2R1A can be combined with the detection of aneuploidy, the detection of genetic biomarkers (e.g., mutations) present in ctDNA, or both. In some embodiments, combining with the detection of aneuploidy, the detection of genetic biomarkers (e.g., mutations) present in ctDNA, or both can increase the specificity and/or sensitivity of detecting endometrial cancer. In some embodiments, the sample is collected using a Pap brush. In some embodiments, the sample is collected using a Tao brush.

In some embodiments, methods provided herein can be used to detect the presence of an ovarian cancer. For example, methods provided herein can be used to detect the presence of one or more genetic biomarkers (e.g., mutations) in TP53, wherein the presence of one or more genetic biomarkers (e.g., mutations) in one or more genes is indicative of the presence of ovarian cancer in the subject. In some embodiments, an ovarian cancer detected by detecting the presence of a genetic biomarker (e.g., mutation) in TP53 can be a high-grade ovarian cancer. In some embodiments, the one or more genetic biomarkers (e.g., mutations) in TP53 can be any TP53 mutation described herein (e.g., a TP53 mutation as shown in any one of Tables 15, 16, or 17). In some embodiments, methods provided herein to detect the presence of an endometrial cancer by detecting the presence of one or more genetic biomarkers (e.g., mutations) in TP53 can be combined with the detection of aneuploidy, the detection of genetic biomarkers (e.g., mutations) present in ctDNA, or both. In some embodiments, combining with the detection of aneuploidy, the detection of mutations present in ctDNA, or both can increase the specificity and/or sensitivity of detecting ovarian cancer. In some embodiments, the sample is collected using a Pap brush. In some embodiments, the sample is collected using a Tao brush.

Genetic biomarkers (e.g., mutations) in one or more of the genes described herein can be detected by any of the exemplary techniques for detecting mutations described herein. Moreover, those of ordinary skill in the art will be aware of other suitable methods for detecting genetic biomarkers (e.g., mutations) in these genes.

In some embodiments, methods provided herein (e.g., method including the detection of one or more genetic biomarkers (e.g., mutations) in any of the genes described herein, the detection of aneuploidy, or both) further include testing a sample obtained from a subject (e.g., a plasma sample) for genetic biomarkers in nucleic acids that are present as circulating tumor DNA (ctDNA). In some embodiments, the sample includes nucleic acids that harbor one or more of genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) which nucleic acids can be assayed according to any of the variety of methods disclosed herein. In some embodiments, the plasma sample includes nucleic acids that harbor one or more of genetic biomarkers (e.g., mutations) in one or more genes (e.g., AKT1, APC, BRAF, CDKN2A, CTNNB1, EGFR, FBXW7, FGFR2, GNAS, HRAS, KRAS, NRAS, PIK3CA, PPP2R1A, PTEN, and/or TP53) which nucleic acids can be assayed according to any of the variety of methods disclosed herein. In some embodiments, the presence of one or more genetic biomarkers (e.g., mutations) in a gene listed in Table 15 can be detected in a sample (e.g., a plasma sample). In some embodiments, the presence of one or more genetic biomarkers (e.g., mutations) listed in Table 15 can be detected in a sample (e.g., a plasma sample). In some embodiments, the presence of one or more genetic biomarkers (e.g., mutations) in a gene listed in Table 16 can be detected in a sample (e.g., a plasma sample). In some embodiments, the presence of one or more genetic biomarkers (e.g., mutations) listed in Table 16 can be detected in a sample (e.g., a plasma sample). In some embodiments, the presence of one or more genetic biomarkers (e.g., mutations) in a gene listed in Table 17 can be detected in a sample (e.g., a plasma sample). In some embodiments, the presence of one or more genetic biomarkers (e.g., mutations) listed in Table 17 can be detected in a sample (e.g., a plasma sample). As will be appreciated by those of ordinary skill in the art, such ctDNA can represent nucleic acids that are shed from cancer cells (e.g., cervical cancer, endometrial cancer cells, ovarian cancer cells, and/or fallopian tubal cancer cells) and as such, can be assayed using any of the variety of methods provided herein to determine the presence of a cancer in the subject. In some embodiments, the sample for detecting the presence of one or more mutations in ctDNA is, or can include, blood (e.g., whole blood, serum, or plasma), amnion, tissue, urine, cerebrospinal fluid, saliva, sputum, broncho-alveolar lavage, bile, lymphatic fluid, cyst fluid (e.g., ovarian cyst fluid), stool, ascites, pap smears, peritoneal fluid, peritoneal lavage, uterine lavage, and combinations thereof. Mutations in ctDNA can be detected by any of the exemplary techniques for detecting mutations described herein. Moreover, those of ordinary skill in the art will be aware of other suitable methods for detecting mutations in ctDNA.

In some embodiments, methods provided herein include detecting in a sample (e.g., a cervical or endometrial sample) obtained from a subject the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or aneuploidy (e.g., monosomy or trisomy). In some embodiments, the sample is a cervical sample. In some embodiments, the sample is an endometrial sample. In some embodiment, the sample comprises tissue or cells from each of the cervix and the endometrium. In some embodiments, a sample is obtained with a Pap brush. In some embodiments, a sample is obtained with a Tao brush. In some embodiments, methods include isolating cells from the rest of the sample. For example, cells can be completely isolated from other components of the sample, or can be isolated to a degree such that the isolated cells include only small amounts of other material from the sample. In some embodiments, nucleic acids present in cells isolated from a sample can be assayed using any of the variety of methods provided herein. For example, nucleic acids present in cells from the sample can be isolated and assayed.

In some embodiments, methods provided herein include detecting in a sample (e.g., a cervical or endometrial sample) obtained from a subject the presence of one or more genetic biomarkers (e.g., mutations) in one or more of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, wherein at least one of the genetic biomarker (e.g., at least one of the mutations) is present at a low frequency in the sample. For example, methods provided herein can detect a genetic biomarker (e.g., a mutation) when the genetic biomarker (e.g., the mutation) is present in 0.1%, 0.2%, 0.3%, 0.4%, 0.5%, 0.6%, 0.7%, 0.8%, 0.9%, 1% or fewer of the cells in the sample. In some embodiments, methods provided herein can detect a genetic biomarker (e.g., a mutation) when the genetic biomarker (e.g., the mutation) is present in less than 0.1%, 0.2%, 0.3%, 0.4%, 0.5%, 0.6%, 0.7%, 0.8%, 0.9%, or 1% of the total nucleic acid present in the sample.

In some embodiments of any of the variety of methods disclosed herein in which the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or the presence of aneuploidy (e.g., monosomy or trisomy), cytology may be performed in combination with or independently of the method. For example, cytology can be performed in combination with any of the variety of methods disclosed herein to improve the detection of a cancer (e.g., an ovarian or endometrial cancer) in the subject. In some embodiments, performing cytology in combination with detecting the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or the presence of aneuploidy (e.g., monosomy or trisomy) increases the sensitivity of the assay (e.g., by at least 10%, 20%, 30%, 40%, 50%, 60% or more). In some embodiments, performing cytology in combination with detecting the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or the presence of aneuploidy (e.g., monosomy or trisomy) increases the specificity of the assay (e.g., by at least 10%, 20%, 30%, 40%, 50%, 60% or more). In some embodiments, performing cytology in combination with detecting the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or the presence of aneuploidy (e.g., monosomy or trisomy) permits the detection of cancers that would otherwise be undetectable or only rarely detectable with cytology alone (e.g., low-grade tumors). As another example, cytology can be performed independently to confirm the presence of a cancer (e.g., an ovarian or endometrial cancer) once its presence is determined by detecting the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or aneuploidy (e.g., monosomy or trisomy). In some embodiments, methods provided herein include detecting each of the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and the presence of aneuploidy (e.g., monosomy or trisomy), and performing cytology.

In some embodiments, any of the variety of methods disclosed herein can be performed on subjects who have previously undergone treatments for cancer (e.g., an ovarian or endometrial cancer). In some embodiments, methods provided herein can be used to determine the efficacy of the treatment. For example, a subject having an ovarian or endometrial cancer can be administered a treatment (also referred to herein as a "therapeutic intervention"), after which the continued presence of cancer or the amount of cancer (or lack thereof) is determined by detecting the presence of one or more genetic biomarkers (e.g., mutations) in one or more genes (e.g., NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A) and/or the presence of aneuploidy (e.g., monosomy or trisomy).

In certain aspects, provided herein are methods of detecting diseases in a subject (e.g., a human). Various methods disclosed herein provide a broadly applicable approach for non-invasive detection of cancer (e.g., an early-stage cancer such as, without limitation, bladder cancer or upper tract urothelial carcinomas (UTUC)). In some embodiments, the disease detected is cancer. In some embodiments, the cancer detected is malignant. In some embodiments, the disease detected is related to urinary tract. In some embodiments, the disease detected is a cancer affecting the urinary tract. In some embodiments, the disease detected is bladder cancer. In some embodiments, the disease detected is related to renal pelvis. In some embodiments, the disease detected is a cancer affecting renal pelvis. In some embodiments, the disease detected is an UTUC.

In some embodiments, methods provided herein include detecting mutations in one or more genes in a sample (e.g., a urine sample) obtained from a subject. For example, methods provided herein can be used to detect the presence of one or more genetic biomarkers (e.g., one or more mutations) in one or more of the following genes: TP53, PIK3CA, FGFR3, KRAS, ERBB2, CDKN2A, MLL, HRAS, MET, and/or VHL. In some embodiments, methods provided herein include detecting the presence of at least one genetic biomarker (e.g., mutation) in a TERT promoter in a sample obtained from a subject. In some embodiments, the methods provided herein include detecting the presence of aneuploidy (e.g., monosomy or trisomy) in a sample obtained from a subject. In some embodiments, methods provided herein include detecting in a sample obtained from a subject two or more of: genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and the presence of at least one genetic biomarker (e.g., mutation) in a TERT promoter. In some embodiments, methods provided herein include detecting in a sample obtained from a subject each of the presence of one or more genetic biomarkers (e.g., one or more mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and the presence of at least one genetic biomarker (e.g., mutation) in a TERT promoter. In some embodiments, methods which include detecting in a sample obtained from a subject each of the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and the presence of at least one genetic biomarker (e.g., mutation) in a TERT promoter provide a better indication that the subject has a cancer (e.g., a bladder cancer or an UTUC) than methods in which fewer than all of these three parameters are tested. In some embodiments, methods which include detecting in a sample obtained from a subject each of the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and the presence of at least one genetic biomarker (e.g., mutation) in a TERT promoter can increase the specificity and/or sensitivity of detecting ovarian or endometrial cancer (e.g., a bladder cancer or an UTUC).

In various embodiments of methods provided herein in which one or more genetic biomarkers (e.g., one or more mutations) in genes in a sample (e.g., a urine sample) obtained from a subject are detected, genetic biomarkers (e.g., mutations) in one or more of TP53, PIK3CA, FGFR3, KRAS, ERBB2, CDKN2A, MLL, HRAS, MET, and/or VHL can be detected. In some embodiments, genetic biomarkers (e.g., mutations) in 1, 2, 3, 4, 5, 6, 7, 8, or 9 of these genes can be detected. In some embodiments, genetic biomarkers (e.g., mutations) in all 10 of these genes can be detected. In some embodiments, the one or more genetic biomarkers (e.g., mutations) in these genes can be any mutation disclosed herein. For example, the one or more genetic biomarkers (e.g., mutations) in these genes can be a mutation shown in Table 19 or Table 29. In some embodiments, at least one genetic biomarkers (e.g., mutations) in one of TR53 or FGFR3 are detected. In some embodiments, at least one genetic biomarker (e.g., at least one mutation) in each of TR53 or FGFR3 are detected.

In some embodiments, methods provided herein include detecting the presence of at least one genetic biomarker (e.g., mutation) in a TERT promoter in a sample (e.g., a urine sample) obtained from a subject. Any genetic biomarker (e.g., mutation) in a TERT promoter disclosed herein can be detected. For example, any of the variety of TERT promoter genetic biomarkers (e.g., mutations) shown in Table 26 or Table 30 can be detected using methods provided herein. In some embodiments, TERT promoter genetic biomarkers (e.g., mutations) that can be detected according to various methods provided herein include the g.1295228 C>T and/or g.1295250 C>T mutations. In some embodiments, TERT promoter genetic biomarkers (e.g., mutations) that can be detected according to various methods provided herein include mutations at positions hg1295228 and/or hg 1295250, which are 66 and 88 bp upstream of the transcription start site, respectively. In some embodiments, a genetic biomarker (e.g., a mutation) in a TERT promoter is identified using a singleplex PCR assay. In some embodiments, a genetic biomarker (e.g., a mutation) in a TERT promoter is identified using a multiplex PCR assay. In some embodiments, single amplification primer can be used to amplify a segment containing the region of the TERT promoter known to harbor genetic biomarkers (e.g., mutations) in cancer (e.g., bladder cancer or UTUC).

As used herein, the term "TERT" refers to the gene and/or the protein encoded by the gene, which is telomerase reverse transcriptase, a catalytic subunit of the enzyme telomerase, which, together with the telomerase RNA component (TERC), comprises the most important unit of the telomerase complex. High rates of activating mutations in the upstream promoter of the TERT gene are found in the majority of BC as well as in other cancer types. TERT promoter mutations commonly affect two hot spots: g.1295228 C>T and g.1295250 C>T. These mutations lead to the generation of CCGGAA/T or GGAA/T motifs altering binding site for ETS transcription factors and subsequently increased TERT promoter activity. TERT promoter mutations occur in up to 80% of invasive urothelial carcinomas of the bladder and upper urinary tract as well as in several of its histologic variants. Moreover, TERT promoter mutations occur in 60-80% of BC precursors, including Papillary Urothelial Neoplasms of Low Malignant Potential, non-invasive Low Grade Papillary Urothelial Carcinoma, non-invasive High Grade Papillary Urothelial Carcinoma and "flat" Carcinoma in Situ (CIS), as well as in urinary cells from a subset of these patients. TERT promoter mutations have thus been established as a common genetic alteration in BC. Human TERT promoter sequences are known in the art.

Genetic biomarkers (e.g., mutations) in one or more of the genes described herein can be detected by any of the exemplary techniques for detecting mutations described herein. Moreover, those of ordinary skill in the art will be aware of other suitable methods for detecting genetic biomarkers (e.g., mutations) in these genes.

In some embodiments, methods provided herein include detecting in a sample (e.g., a urine sample) obtained from a subject the presence of one or more genetic biomarkers (e.g., mutations) in one or more of the following genes: TP53, PIK3CA, FGFR3, KRAS, ERBB2, CDKN2A, MLL, HRAS, MET, and/or VHL, the presence of at least one genetic biomarker (e.g., at least one mutation) in a TERT promoter, or both. In some embodiments, the sample is a urine sample. In some embodiments provided herein, methods include isolating such cells from the rest of the sample. For example, cells can be completely isolated from other components of the sample, or can be isolated to a degree such that the isolated cells include only small amounts of other material(s) from the sample. In some embodiments, the presence of genetic biomarkers in nucleic acids present in cells isolated from a sample and/or the presence of aneuploidy in cells isolated from a sample can be assayed using any of the variety of methods provided herein. For example, nucleic acids present in cells from the sample can be isolated and assayed for the presence of one or more genetic biomarkers and/or the presence of aneuploidy. In some embodiments, cells are not isolated from the sample prior to isolating their nucleic acids for analysis. In some embodiments, the sample includes nucleic acids that harbor one or more genetic biomarkers (e.g., mutations) in one or more genes (e.g., TP53, PIK3CA, FGFR3, KRAS, ERBB2, CDKN2A, MLL, HRAS, MET, and/or VHL), at least one genetic biomarker (e.g., a mutation) in a TERT promoter, and/or aneuploidy (e.g., monosomy or trisomy), which nucleic acids are assayed according to any of the variety of methods disclosed herein. As will be appreciated by those of ordinary skill in the art, such nucleic acids can represent nucleic acids that are shed from cancer cells (e.g., bladder cancer cells or cells from UTUCs) and as such, can be assayed using any of the variety of methods provided herein to determine the presence of a cancer in the subject.

In some embodiments, methods provided herein include detecting in a sample (e.g., a urine sample) obtained from a subject the presence of one or more genetic biomarkers (e.g., mutations) in one or more of the following genes: TP53, PIK3CA, FGFR3, KRAS, ERBB2, CDKN2A, MLL, HRAS, MET, and/or VHL, the presence of at least one genetic biomarker (e.g., a mutation) in a TERT promoter, or both, wherein at least one of the genetic biomarkers (e.g., at least one of the mutations) is present at a low frequency in the sample. For example, methods provided herein can detect a genetic biomarker (e.g., a mutation) when the genetic biomarker (e.g., the mutation) is present in 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1% or fewer of the cells in the sample. In some embodiments, methods provided herein can detect a genetic biomarker (e.g., a mutation) when the genetic biomarker (e.g., the mutation) is present in 0.03% or fewer of the cells in the sample. In some embodiments, methods provided herein can detect a genetic biomarker (e.g., a mutation) when the genetic biomarker (e.g., the mutation) is present in less than 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% of the total nucleic acid present in the sample.

In some embodiments of any of the variety of methods disclosed herein in which the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and/or the presence of at least one genetic biomarker (e.g., a mutation) in a TERT promoter is detected, cytology may be performed in combination with or independently of the method. For example, cytology can be performed in combination with any of the variety of methods disclosed herein to improve the detection of a cancer (e.g., a bladder cancer or an UTUC) in the subject. In some embodiments, performing cytology in combination with detecting the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and/or the presence of at least one genetic biomarker (e.g., a mutation) in a TERT promoter increases the sensitivity of the assay as compared to cytology alone (e.g., by at least 10%, 20%, 30%, 40%, 50%, 60% or more). In some embodiments, performing cytology in combination with detecting the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and/or the presence of at least one mutation in a TERT promoter (e.g., a genetic biomarker in a TERT promoter) increases the specificity of the assay as compared to cytology alone (e.g., by at least 10%, 20%, 30%, 40%, 50%, 60% or more). In some embodiments, performing cytology in combination with detecting the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and/or the presence of at least one genetic biomarker (e.g., a mutation) in a TERT promoter permits the detection of cancers that would otherwise be undetectable or only rarely detectable with cytology alone (e.g., low-grade tumors). As another example, cytology can be performed independently to confirm the presence of a cancer (e.g., a bladder cancer or an UTUC) once its presence is determined by detecting the presence of one or more genetic biomarkers (e.g., mutations) in one or more genes (e.g., TP53, PIK3CA, FGFR3, KRAS, ERBB2, CDKN2A, MLL, HRAS, MET, and/or VHL), aneuploidy (e.g., monosomy or trisomy), and/or the presence of at least one genetic biomarker (e.g., a mutation) in a TERT promoter. In some embodiments, methods provided herein include detecting each of the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), the presence of at least one genetic biomarker (e.g., a mutation) in a TERT promoter, and performing cytology.

In some embodiments, any of the variety of methods disclosed herein can be performed on subjects who have previously undergone treatments for cancer (e.g., bladder cancer or UTUC). In some embodiments, methods provided herein can be used to determine the efficacy of the treatment. For example, a subject having bladder cancer or UTUC can be administered a treatment (also referred to herein as a "therapeutic intervention"), after which the continued presence of cancer or the amount of cancer (or lack thereof) is determined by detecting the presence of one or more genetic biomarkers (e.g., mutations) in one or more genes (e.g., TP53, PIK3CA, FGFR3, KRAS, ERBB2, CDKN2A, MLL, HRAS, MET, and/or VHL), the presence of aneuploidy (e.g., monosomy or trisomy), and/or the presence of at least one genetic biomarker (e.g., a mutation) in a TERT promoter.

Some embodiments of methods provided herein include testing cytological specimens for cancer. In some embodiments, one or more cytological tests are used for diagnosis or screening. In some embodiments, the one or more cytological tests are used for diagnosing cancer. In some embodiments, the one or more cytological tests are used for screening cancer. In some embodiments, one or more cytological tests are used for classifying a disease or condition. In some embodiments, one or more cytological tests are used for classifying a cancer.

Various methods may be used to collect a sample including, but not limited to, aspiration cytology (e.g. fine needle aspiration), exfolative cytology (e.g. impression smears and tissue scrapings), cystoscopy.

In some embodiments, the cytological test includes a gross examination. In some embodiments, the cytological test includes a histological examination. In some embodiments, the cytological test includes a frozen section exam. In some embodiments, the cytological test is administered in conjunction with another method or test. In some embodiments, the other method or test includes a histochemical stain. In some embodiments, the other method or test includes an immunohistochemical stain. In some embodiments, the other method or test includes electron microscopy. In some embodiments, the other method or test includes flow cytometry. In some embodiments, the other method or test includes image cytometry. In some embodiments, the other method or test includes genetic tests. For example, the genetic test may include, but is not limited to, a cytogenetic test, a fluorescent in situ hybridization (FISH) test, and/or a molecular genetic test.

In some embodiments, a molecular genetic test is used on a cytological sample (e.g., a sample on which cytology is also performed) to detect the presence of one or more genetic biomarkers (e.g., mutations) in PTEN, TP53, PIK3CA, PIK3R1, CTNNB1, KRAS, FGFR2, POLE, APC, FBXW7, RNF43, and/or PPP2R1A. In some embodiments, a molecular genetic test is used on a cytological sample (e.g., a sample on which cytology is also performed) to detect the presence of one or more genetic biomarkers (e.g., mutations) in TP53, PIK3CA, FGFR3, KRAS, ERBB2, CDKN2A, MLL, HRAS, MET, and/or VHL. In some embodiments, a molecular genetic test is used on a cytological sample (e.g., a sample on which cytology is also performed) to detect the presence of one or more genetic biomarkers (e.g., mutations) in NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A. In some embodiments, a molecular genetic test is used on a cytological sample (e.g., a sample on which cytology is also performed) to detect the presence of one or more genetic biomarkers (e.g., mutations) in TP53.

Protein Biomarkers in Combination with Aneuploidy

In one aspect, provided herein are methods and materials for detecting the presence of one or more members of a panel of protein biomarkers and the presence of aneuploidy in one or more samples obtained from a subject. In another aspect, provided herein are methods and materials for diagnosing or identifying the presence of a disease in a subject (e.g., identifying the subject as having cancer) by detecting the presence of one or more members of a panel of protein biomarkers and the presence of aneuploidy in one or more samples obtained from the subject. In another aspect, provided herein are methods and materials for identifying a subject as being at risk (e.g., increased risk) of having or developing a disease (e.g., cancer) by detecting the presence of one or more members of a panel of protein biomarkers and the presence of aneuploidy in one or more samples obtained from the subject. In another aspect, provided herein are methods and materials for treating a subject who has been diagnosed or identified as having a disease (e.g., cancer) or who has been identified as being at risk (e.g., increased risk) of having or developing a disease (e.g., cancer) by detecting the presence of one or more members of a panel of protein biomarkers and the presence of aneuploidy in one or more samples obtained from the subject. In another aspect, provided herein are methods and materials for identifying a treatment for a subject who has been diagnosed or identified as having a disease (e.g., cancer) or who has been identified as being at risk (e.g., increased risk) of having or developing a disease (e.g., cancer) by detecting the presence of one or more members of a panel of protein biomarkers and the presence of aneuploidy in one or more samples obtained from the subject. In another aspect, provided herein are methods and materials for identifying a subject who will or is likely to respond to a treatment by detecting the presence of one or more members of a panel of protein biomarkers and the presence of aneuploidy in one or more samples obtained from the subject. In another aspect, provided herein are methods and materials for identifying a subject as a candidate for further diagnostic testing by detecting the presence of one or more members of a panel of protein biomarkers and the presence of aneuploidy in one or more samples obtained from the subject. In another aspect, provided herein are methods and materials for identifying a subject as a candidate for increased monitoring by detecting the presence of one or more members of a panel of protein biomarkers and the presence of aneuploidy in one or more samples obtained from the subject.

In some embodiments, methods provided herein that include detecting the presence of one or more members of a panel of protein biomarkers and the presence of aneuploidy in one or more samples obtained from a subject provide high sensitivity in the detection or diagnosis of cancer (e.g., a high frequency or incidence of correctly identifying a subject as having cancer). In some embodiments, methods provided herein that include detecting the presence of one or more members of a panel of protein biomarkers and the presence of aneuploidy in one or more samples obtained from a subject provide a sensitivity in the detection or diagnosis of cancer (e.g., a high frequency or incidence of correctly identifying a subject as having cancer) that is higher than the sensitivity provided by separately detecting the presence of one or more members of a panel of protein biomarkers or the presence of aneuploidy. In some embodiments, methods and materials provided herein that include detecting the presence of one or more members of a panel of protein biomarkers and the presence of aneuploidy in one or more samples obtained from a subject provide a sensitivity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. In some embodiments, methods and materials provided herein that include detecting the presence of one or more members of a panel of protein biomarkers and the presence of aneuploidy in one or more samples obtained from a subject provide high sensitivity in detecting a single type of cancer. In some embodiments, methods and materials provided herein that include detecting the presence of one or more members of a panel of protein biomarkers and the presence of aneuploidy in one or more samples obtained from a subject provide high sensitivity in detecting two or more types of cancers. Any of a variety of cancer types can be detected using methods and materials provided herein (see, e.g., the section entitled "Cancers"). In some embodiments, cancers that can be detected using methods and materials that include detecting the presence of one or more members of a panel of protein biomarkers and the presence of aneuploidy in one or more samples obtained from a subject include pancreatic cancer. In some embodiments, cancers that can be detected using methods and materials that include detecting the presence of one or more members of a panel of protein biomarkers and the presence of aneuploidy in one or more samples obtained from a subject include liver cancer, ovarian cancer, esophageal cancer, stomach cancer, pancreatic cancer, colorectal cancer, lung cancer, or breast cancer. In some embodiments, cancers that can be detected using methods and materials that include detecting the presence of one or more members of a panel of protein biomarkers and the presence of aneuploidy in one or more samples obtained from a subject include cancers of the female reproductive tract (e.g., cervical cancer, endometrial cancer, ovarian cancer, or fallopian tubal cancer). In some embodiments, cancers that can be detected using methods and materials that include detecting the presence of one or more members of a panel of protein biomarkers and the presence of aneuploidy in one or more samples obtained from a subject include bladder cancer or upper-tract urothelial carcinomas.

In some embodiments, methods provided herein that include detecting the presence of one or more members of a panel of protein biomarkers and the presence of aneuploidy in one or more samples obtained from a subject provide high specificity in the detection or diagnosis of cancer (e.g., a low frequency or incidence of incorrectly identifying a subject as having cancer when that subject does not have cancer). In some embodiments, methods provided herein that include detecting the presence of one or more members of a panel of protein biomarkers and the presence of aneuploidy in one or more samples obtained from a subject provide a specificity in the detection or diagnosis of cancer (e.g., a high frequency or incidence of correctly identifying a subject as having cancer) that is higher than the specificity provided by separately detecting the presence of one or more members of a panel of protein biomarkers or the presence of aneuploidy. In some embodiments, methods and materials provided herein that include that include detecting the presence of one or more members of a panel of protein biomarkers and the presence of aneuploidy in one or more samples obtained from a subject provide a specificity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. As will be understood by those of ordinary skill in the art, a specificity of 99% means that only 1% of subjects that do not have cancer are incorrectly identified as having cancer. In some embodiments, methods and materials provided herein that include detecting the presence of one or more members of a panel of protein biomarkers and the presence of aneuploidy in one or more samples obtained from a subject provide high specificity in detecting a single cancer (e.g., there is a low probability of incorrectly identifying that subject as having that single cancer type). In some embodiments, methods and materials provided herein that include detecting the presence of one or more members of a panel of protein biomarkers and the presence of aneuploidy in one or more samples obtained from a subject provide high specificity in detecting two or more cancers (e.g., there is a low probability of incorrectly identifying that subject as having those two or more cancer types).

In some embodiments, methods provided herein that include detecting the presence of one or more members of a panel of protein biomarkers and the presence of aneuploidy in one or more samples obtained from a subject include detecting the presence of: 1) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), and 2) the presence of aneuploidy.

In some embodiments, methods provided herein that include detecting the presence of one or more members of a panel of protein biomarkers and the presence of aneuploidy in one or more samples obtained from a subject include detecting the presence of: 1) each of the following protein biomarkers: CA19-9, CEA, HGF, OPN, CA125, prolactin, TIMP-1, and myeloperoxidase (MPO), and the presence of aneuploidy. In some embodiments of methods provided herein that include detecting the presence of one or more members of a panel of protein biomarkers and the presence of aneuploidy in one or more samples obtained from a subject include detecting the presence of: 1) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), and 2) the presence of aneuploidy, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments, methods provided herein that include detecting the presence of one or more members of a panel of protein biomarkers and the presence of aneuploidy in one or more samples obtained from a subject include detecting the presence of: 1) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, and 2) the presence of aneuploidy. In some embodiments, methods provided herein that include detecting the presence of one or more members of a panel of protein biomarkers and the presence of aneuploidy in one or more samples obtained from a subject include detecting the presence of: 1) each of the following protein biomarkers: CA19-9, CEA, HGF, OPN, CA125, AFP, prolactin, TIMP-1, follistatin, G-CSF, and CA15-3, and 2) the presence of aneuploidy. In some embodiments of methods provided herein that include detecting the presence of one or more members of a panel of protein biomarkers and the presence of aneuploidy in one or more samples obtained from a subject include detecting the presence of: 1) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, and 2) the presence of aneuploidy, the subject is determined as having (e.g., diagnosed to have) or is determined to be (e.g. diagnosed as being) at elevated risk of having or developing cancer one of the following types of cancer: liver cancer, ovarian cancer, esophageal cancer, stomach cancer, pancreatic cancer, colorectal cancer, lung cancer, and/or breast cancer.

In some embodiments, methods provided herein that include the presence of one or more members of a panel of protein biomarkers and the presence of aneuploidy in one or more samples obtained from a subject include detecting the presence of: 1) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, and 2) the presence of aneuploidy. In some embodiments, methods provided herein that include detecting the presence of one or more members of a panel of genetic biomarkers and the presence of one or more members of a panel of protein biomarkers in one or more samples obtained from a subject include detecting the presence of: 1) each of the following protein biomarkers: CA19-9, CEA, HGF, OPN, CA125, AFP, prolactin, TIMP-1, and CA15-3, and 2) the presence of aneuploidy. In some embodiments of methods provided herein that include detecting the presence of one or more members of a panel of protein biomarkers and the presence of aneuploidy in one or more samples obtained from a subject include detecting the presence of: 1) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, and 2) the presence of aneuploidy, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments, methods provided herein that include detecting the presence of one or more members of a panel of protein biomarkers and the presence of aneuploidy in one or more samples obtained from a subject include detecting the presence of: 1) one or more (e.g., 1, 2, 3, or 4) of the following protein biomarkers: CA19-9, CEA, HGF, and/or OPN, and 2) the presence of aneuploidy. In some embodiments, methods provided herein that include detecting the presence of one or more members of a panel of protein biomarkers and the presence of aneuploidy in one or more samples obtained from a subject include detecting the presence of: 1) each of the following protein biomarkers: CA19-9, CEA, HGF, and OPN, and 2) the presence of aneuploidy. In some embodiments of methods provided herein that include detecting the presence of one or more members of a panel of protein biomarkers and the presence of aneuploidy in one or more samples obtained from a subject include detecting the presence of 1) one or more (e.g., 1, 2, 3, or 4) of the following protein biomarkers: CA19-9, CEA, HGF, and/or OPN, and 2) the presence of aneuploidy, a subject is determined as having (e.g., diagnosed to have) or is determined to be (e.g. diagnosed as being) at elevated risk of having or developing pancreatic cancer.

A sample obtained from a subject can be any of the variety of samples described herein that contains DNA (e.g., ctDNA in the blood, or DNA present in bladder, cervical, endometrial, or uterine samples) and/or proteins. In some embodiments, DNA (e.g., cell-free DNA (e.g., ctDNA) or DNA present in bladder, cervical, endometrial, or uterine samples) and/or proteins in a sample obtained from the subject are derived from a tumor cell. In some embodiments, DNA (e.g., cell-free DNA (e.g., ctDNA) in a sample obtained from the subject includes one or more genetic biomarkers and or aneuploid DNA. In some embodiments, proteins in a sample obtained from the subject includes one or more protein biomarkers. Non-limiting examples of samples in which genetic biomarkers and/or protein biomarkers and/or aneuploidy can be detected include a blood sample, a plasma sample, a serum sample, a urine sample, an endometrial sample, a cervical sample, and a uterine sample. In some embodiments, the presence of one or more protein biomarkers and the presence aneuploidy is detected in a single sample obtained from the subject. In some embodiments, the presence of one or more protein biomarkers is detected in a first sample obtained from a subject, and the presence of aneuploidy is detected in a second sample obtained from the subject.

In some embodiments, methods provided herein that include detecting the presence of one or more members of a panel of protein biomarkers (e.g., each member of a panel of protein biomarkers) and the presence of aneuploidy in one or more samples obtained from a subject, an elevated level of one or more members of the panel of protein biomarkers can be detected. For example, an elevated level of a protein biomarker can be a level that is higher that a reference level. A reference level can be any level of the protein biomarker that is not associated with the presence of cancer. For example, a reference level of a protein biomarker can be a level that is present in a reference subject that does not have cancer or does not harbor a cancer cell. A reference level of a protein biomarker can be the average level that is present in a plurality of reference subjects that do not have cancer or do not harbor a cancer cell. A reference level of a protein biomarker in a subject determined to have cancer can be the level that was presence in the subject prior to the onset of cancer. In some embodiments, a panel of protein biomarkers in which one or more members of the panel is present at an elevated level includes one or more of (e.g., 1, 2, 3, 4, 5, 6, 7, or each of): CA19-9, CEA, HGF, OPN, CA125, prolactin, TIMP-1, and/or myeloperoxidase (MPO). In some embodiments, a panel of protein biomarkers in which one or more members of the panel is present at an elevated level includes one or more of (e.g., 1, 2, 3, 4, 5, 6, 7, 8, 9, 10, or each of): CA19-9, CEA, HGF, OPN, CA125, AFP, prolactin, TIMP-1, follistatin, G-CSF, and/or CA15-3. In some embodiments, a panel of protein biomarkers in which one or more members of the panel is present at an elevated level includes one or more of (e.g., 1, 2, 3, 4, 5, 6, 7, 8, or each of): CA19-9, CEA, HGF, OPN, CA125, AFP, prolactin, TIMP-1, and/or CA15-3. In some embodiments, a panel of protein biomarkers in which one or more members of the panel is present at an elevated level includes one or more of (e.g., 1, 2, 3, or each of): CA19-9, CEA, HGF, and/or OPN.

In some embodiments, methods provided herein that include detecting the presence of one or more members of a panel of protein biomarkers (e.g., each member of a panel of protein biomarkers) and the presence of aneuploidy in one or more samples obtained from a subject, a decreased level of one or more members of the panel of protein biomarkers can be detected. For example, a decreased level of a protein biomarker can be a level that is lower that a reference level. A reference level can be any level of the protein biomarker that is not associated with the presence of cancer. For example, a reference level of a protein biomarker can be a level that is present in a reference subject that does not have cancer or does not harbor a cancer cell. A reference level of a protein biomarker can be the average level that is present in a plurality of reference subjects that do not have cancer or do not harbor a cancer cell. A reference level of a protein biomarker in a subject determined to have cancer can be the level that was presence in the subject prior to the onset of cancer. In some embodiments, a panel of protein biomarkers in which one or more members of the panel is present at a decreased level includes one or more of (e.g., 1, 2, 3, 4, 5, 6, 7, or each of): CA19-9, CEA, HGF, OPN, CA125, prolactin, TIMP-1, and/or myeloperoxidase (MPO). In some embodiments, a panel of protein biomarkers in which one or more members of the panel is present at a decreased level includes one or more of (e.g., 1, 2, 3, 4, 5, 6, 7, 8, 9, 10, or each of): CA19-9, CEA, HGF, OPN, CA125, AFP, prolactin, TIMP-1, follistatin, G-CSF, and/or CA15-3. In some embodiments, a panel of protein biomarkers in which one or more members of the panel is present at a decreased level includes one or more of (e.g., 1, 2, 3, 4, 5, 6, 7, 8, or each of): CA19-9, CEA, HGF, OPN, CA125, AFP, prolactin, TIMP-1, and/or CA15-3. In some embodiments, a panel of protein biomarkers in which one or more members of the panel is present at a decreased level includes one or more of (e.g., 1, 2, 3, or each of): CA19-9, CEA, HGF, and/or OPN.

In some embodiments, when a subject is determined as having (e.g., diagnosed to have) cancer or determined to be (e.g. diagnosed as being) at elevated risk of having or developing cancer (e.g., by detecting: 1) the presence of aneuploidy, and 2) the presence of one or more protein biomarkers in any of the panels described herein as being useful in conjunction with the presence of aneuploidy), the subject is selected as a candidate for (e.g., is selected for) further diagnostic testing (e.g., any of the variety of further diagnostic testing methods described herein), the subject is selected as a candidate for (e.g. is selected for) increased monitoring (e.g., any of the variety of increasing monitoring methods described herein), the subject is identified as a subject who will or is likely to respond to a treatment (e.g., any of the variety of therapeutic interventions described herein), the subject is selected as a candidate for (e.g., is selected for) a treatment, a treatment (e.g., any of the variety of therapeutic interventions described herein) is selected for the subject, and/or a treatment (e.g., any of the variety of therapeutic interventions described herein) is administered to the subject. For example, when a subject is determined as having (e.g., diagnosed to have) cancer or determined to be (e.g. diagnosed as being) at elevated risk of having or developing cancer, the subject can undergo further diagnostic testing, which further diagnostic testing can confirm the presence of cancer in the subject. Additionally or alternatively, the subject can be monitored at in increased frequency. In some embodiments of a subject determined as having (e.g., diagnosed to have) cancer or determined to be (e.g. diagnosed as being) at elevated risk of having or developing cancer in which the subject undergoes further diagnostic testing and/or increased monitoring, the subject can additionally be administered a therapeutic intervention. In some embodiments, after a subject is administered a therapeutic intervention, the subject undergoes additional further diagnostic testing (e.g., the same type of further diagnostic testing as was performed previously and/or a different type of further diagnostic testing) and/or continued increased monitoring (e.g., increased monitoring at the same or at a different frequency as was previously done). In embodiments, after a subject is administered a therapeutic intervention and the subject undergoes additional further diagnostic testing and/or additional increased monitoring, the subject is administered another therapeutic intervention (e.g., the same therapeutic intervention as was previously administered and/or a different therapeutic intervention). In some embodiments, after a subject is administered a therapeutic intervention, the subject is tested for 1) the presence of one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), and 2) the presence of aneuploidy. In some embodiments, after a subject is administered a therapeutic intervention, the subject is tested for 1) the presence of one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, and 2) the presence of aneuploidy. In some embodiments, after a subject is administered a therapeutic intervention, the subject is tested for 1) the presence of one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, and 2) the presence of aneuploidy. In some embodiments, after a subject is administered a therapeutic intervention, the subject is tested for 1) the presence of one or more (e.g., 1, 2, 3, or 4) of the following protein biomarkers: CA19-9, CEA, HGF, and/or OPN, and 2) the presence of aneuploidy.

In some embodiments of methods provided herein that include detecting the presence of one or more members of a panel of protein biomarkers and the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). Any of a variety of genetic biomarkers can be detected (e.g., any of the variety of genetic biomarkers and/or genetic biomarker panels described herein).

In some embodiments, methods provided herein that include detecting in one or more samples obtained from a subject the presence of: 1) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments, methods provided herein that include detecting in one or more samples obtained from a subject the presence of: 1) each of the following protein biomarkers: CA19-9, CEA, HGF, OPN, CA125, prolactin, TIMP-1, and myeloperoxidase (MPO), and the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments of methods provided herein that include detecting in one or more samples obtained from a subject the presence of: 1) one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO), 2) the presence of aneuploidy, and 3) the presence of one or more members of a panel of genetic biomarkers, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments of methods provided herein that include detecting in one or more samples obtained from a subject the presence of: 1) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments of methods provided herein that include detecting in one or more samples obtained from a subject the presence of: 1) each of the following protein biomarkers: CA19-9, CEA, HGF, OPN, CA125, AFP, prolactin, TIMP-1, follistatin, G-CSF, and CA15-3, and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments of methods provided herein that include detecting in one or more samples obtained from a subject the presence of: 1) one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3, 2) the presence of aneuploidy, and 3) the presence of one or more members of a panel of genetic biomarkers, the subject is determined as having (e.g., diagnosed to have) or is determined to be (e.g. diagnosed as being) at elevated risk of having or developing cancer one of the following types of cancer: liver cancer, ovarian cancer, esophageal cancer, stomach cancer, pancreatic cancer, colorectal cancer, lung cancer, and/or breast cancer.

In some embodiments of methods provided herein that detecting in one or more samples obtained from a subject the presence of: 1) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments or methods provided herein that include detecting in one or more samples obtained from a subject the presence of: 1) each of the following protein biomarkers: CA19-9, CEA, HGF, OPN, CA125, AFP, prolactin, TIMP-1, and CA15-3, and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments of methods provided herein that include in one or more samples obtained from a subject the presence of: 1) one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3, 2) the presence of aneuploidy, and 3) the presence of one or more members of a panel of genetic biomarkers, the subject is determined as having (e.g., diagnosed to have) or is determined to be (e.g. diagnosed as being) at elevated risk of having or developing one of the following types of cancer: liver cancer, ovarian cancer, esophageal cancer, stomach cancer, pancreatic cancer, colorectal cancer, lung cancer, and/or breast cancer.

In some embodiments of methods provided herein that include detecting in one or more samples obtained from a subject the presence of: 1) one or more (e.g., 1, 2, 3, or 4) of the following protein biomarkers: CA19-9, CEA, HGF, and/or OPN, and 2) the presence of aneuploidy, the methods further include detecting the presence one or more members of a panel of genetic biomarkers in one or more samples obtained from a subject (e.g., the same sample use to detect either or both of the presence of one or more members of a panel of protein biomarkers and the presence of aneuploidy, or a different sample). In some embodiments of methods provided herein that include detecting in one or more samples obtained from a subject the presence of: 1) each of the following protein biomarkers: CA19-9, CEA, HGF, and OPN, and 2) the presence of aneuploidy. In some embodiments of methods provided herein that include detecting in one or more samples obtained from a subject the presence of 1) one or more (e.g., 1, 2, 3, or 4) of the following protein biomarkers: CA19-9, CEA, HGF, and/or OPN, 2) the presence of aneuploidy, and 3) the presence of one or more members of a panel of genetic biomarkers, a subject is determined as having (e.g., diagnosed to have) or is determined to be (e.g. diagnosed as being) at elevated risk of having or developing pancreatic cancer.

In some embodiments of methods provided herein that include detecting the presence of one or more members of a panel of protein biomarkers and the presence of aneuploidy, one or more genetic biomarkers in one or more (e.g., 1, 2, 3, 4, 5, 6, 7, 8, 9, 10, 11, 12, 13, 14, 15, or 16) of the following genes can further be detected: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. In some embodiments of methods provided herein that include detecting the presence of one or more members of a panel of protein biomarkers and the presence of aneuploidy, one or more genetic biomarkers in each of the following genes can further be detected: NRAS, CTNNB1, PIK3CA, FBXW7, APC, EGFR, BRAF, CDKN2A, PTEN, FGFR2, HRAS, KRAS, AKT1, TP53, PPP2R1A, and GNAS.

In some embodiments of methods provided herein that include detecting the presence of one or more members of a panel of protein biomarkers and the presence of aneuploidy, one or more genetic biomarkers in one or more (e.g., 1, 2, 3, or 4) of the following genes can further be detected: KRAS (e.g., genetic biomarkers in codons 12 and/or 61), TP53, CDKN2A, and/or SMAD4. In some embodiments of methods provided herein that include detecting the presence of one or more members of a panel of protein biomarkers and the presence of aneuploidy, one or more genetic biomarkers in each of the following genes can further be detected: KRAS (e.g., genetic biomarkers in codons 12 and/or 61), TP53, CDKN2A, and SMAD4.

In some embodiments of methods provided herein that include detecting the presence of one or more members of a panel of protein biomarkers and the presence of aneuploidy, one or more genetic biomarkers in one or more (e.g., 1, 2, 3, 4, 5, 6, 7, 8, 9, or 10) of the following genes can further be detected: TP53, PIK3CA, FGFR3, KRAS, ERBB2, CDKN2A, MLL, HRAS, MET, and/or VHL. In some embodiments of methods provided herein that include detecting the presence of one or more members of a panel of protein biomarkers and the presence of aneuploidy, one or more genetic biomarkers in each of the following genes can further be detected: TP53, PIK3CA, FGFR3, KRAS, ERBB2, CDKN2A, MLL, HRAS, MET, and VHL.

In some embodiments of methods provided herein that include detecting the presence of one or more members of a panel of protein biomarkers and the presence of aneuploidy, one or more genetic biomarkers in one or more (e.g., 1, 2, 3, 4, 5, 6, 7, 8, 9, 10, 11, 12, 13, 14, 15, 16, 17, or 18) of the following genes can further be detected: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A. In some embodiments of methods provided herein that include detecting the presence of one or more members of a panel of protein biomarkers and the presence of aneuploidy, one or more genetic bio-markers in each of the following genes can further be detected: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A.

In some embodiments of methods provided herein that include detecting the presence of one or more members of a panel of protein biomarkers and the presence of aneuploidy, one or more genetic biomarkers in one or more (e.g., 1, 2, 3, 4, 5, 6, 7, 8, 9, 10, 11, or 12) of the following genes can further be detected: PTEN, TP53, PIK3CA, PIK3R1, CTNNB1, KRAS, FGFR2, POLE, APC, FBXW7, RNF43, and/or PPP2R1A. In some embodiments of methods provided herein that include detecting the presence of one or more members of a panel of protein biomarkers and the presence of aneuploidy, one or more genetic biomarkers in each of the following genes can further be detected: PTEN, TP53, PIK3CA, PIK3R1, CTNNB1, KRAS, FGFR2, POLE, APC, FBXW7, RNF43, and PPP2R1A.

In some embodiments of methods provided herein that include detecting the presence of one or more members of a panel of protein biomarkers and the presence of aneuploidy, one or more genetic biomarkers in one or more (e.g., 1, 2, 3, 4, 5, 6, 7, 8, 9, 10, 11, 12, 13, 14, 15, or 16) of the following genes can further be detected: AKT1, APC, BRAF, CDKN2A, CTNNB1, EGFR, FBXW7, FGFR2, GNAS, HRAS, KRAS, NRAS, PIK3CA, PPP2R1A, PTEN, and/or TP53. In some embodiments of methods provided herein that include detecting the presence of one or more members of a panel of genetic biomarkers and the presence of aneuploidy, one or more protein biomarkers in each of the following genes can further be detected: AKT1, APC, BRAF, CDKN2A, CTNNB1, EGFR, FBXW7, FGFR2, GNAS, HRAS, KRAS, NRAS, PIK3CA, PPP2R1A, PTEN, and TP53.

In some embodiments, any of the variety of methods provided herein that include detecting the presence of one or more members of a panel of protein biomarkers and the presence of aneuploidy in one or more samples obtained from a subject further include detecting the presence of one or more members of one or more additional classes of biomarkers. Non-limiting examples of such additional classes of biomarkers includes: copy number changes, DNA methylation changes, other nucleic acids (e.g., mRNAs, miRNAs, lncRNAs, circRNA, mtDNA, telomeric DNA, translocation and genomic rearrangements), peptides, and/or metabolites.

In some embodiments, the one or more additional classes of biomarkers include a metabolite biomarker. In some embodiments, a subject is determined to be at elevated risk of having or developing cancer if the biological sample contains one or more metabolites indicative of cancer. In some embodiments, a subject is determined as having cancer if the biological sample contains one or more metabolites indicative of cancer. Non-limiting examples of metabolites indicative of cancer include: 5-methylthioadenosine (MTA), Glutathione reduced (GSH), N-acetylglutamate, Lactose, N-acetylneuraminate, UDP-acetylglucosamine, UDP-Acetylgalactosamine, UDP-glucuronate, Pantothenate, Arachidonate (20:4n6), Choline, Cytidine 5'-diphosphocholine, Dihomo-linolenate (20:3n3), Docosapentaenoate (DPA 22:5n3), Eicosapentaenoate (EPA 20:5n3), Glycerophosphorylcholine (GPC), Docosahexaenoate (DHA 22:6n3), Linoleate (18:2n6), Cytidine 5'-monophosphate (5'-CMP), Gamma-glutamylglutamate, X-14577, X-11583, Isovalerylcarnitine, Phosphocreatine, 2-Aminoadipic acid, Gluconic acid, O-Acetylcarnitine, aspartic acid, Deamido-NAD+, glutamic acid, Isobutyrylcarnitine, Carnitine, Pyridoxal, Citric acid, Adenosine, ATP, valine, XC0061, Isoleucine, γ-Butyrobetaine, Lactic acid, alanine, phenylalanine, Gluconolactone, leucine, Glutathione (GSSG)_divalent, tyrosine, NAD+, XC0016, UTP, creatine, Theobromine, CTP, GTP, 3-Methylhistidine, Succinic acid, Glycerol 3-phosphate, glutamine, 5-Oxoproline, Thiamine, Butyrylcarnitine, 4-Acetamidobutanoic acid, UDP-Glucose, UDP-Galactose, threonine, N-Acetylglycine, proline, ADP, Choline, Malic acid, S-Adenosylmethionine, Pantothenic acid, Cysteinesulfinic acid, 6-Aminohexanoic acid, Homocysteic acid, Hydroxyproline, Methionine sulfoxide, 3-Guanidinopropionic acid, Glucose 6-phosphate, Phenaceturic acid, Threonic acid, tryptophan, Pyridoxine, N-Acetylaspartic acid, 4-Guanidinobutyric acid, serine, Citrulline, Betaine, N-Acetylasparagine, 2-Hydroxyglutaric acid, arginine, Glutathione (GSH), creatinine, Dihydroxyacetone phosphate, histidine, glycine, Glucose 1-phosphate, N-Formylglycine, Ketoprofen, lysine, beta-alanine, N-Acetylglutamic acid, 2-Amino-2-(hydroxymethyl)-1,3-propanediol, Ornithine, Phosphorylcholine, Glycerophosphocholine, Terephthalic acid, Glyceraldehyde 3-phosphate, Gly-Asp, Taurine, Fructose 1,6-diphosphate, 3-Aminoisobutyric acid, Spermidine, GABA, Triethanolamine, Glycerol, N-Acetylserine, N-Acetylornithine, Diethanolamine, AMP, Cysteine glutathione disulfide, Streptomycin sulfate+H2O divalent, trans-Glutaconic acid, Nicotinic acid, Isobutylamine, Betaine aldehyde+H2O, Urocanic acid, 1-Aminocyclopropane-1-carboxylic acid Homoserinelactone, 5-Aminovaleric acid, 3-Hydroxybutyric acid, Ethanolamine, Isovaleric acid, N-Methylglutamic acid, Cystathionine, Spermine, Carnosine, 1-Methylnicotinamide, N-Acetylneuraminic acid, Sarcosine, GDP, N-Methylalanine, palmitic acid, 1,2-dioleoyl-sn-glycero-3-phospho-rac-glycerolcholesterol 5α,6α epoxidelanosterol, lignoceric acid, loleoyl_rac_GL, cholesterol_epoxide, erucic acid, T-LCA, oleoyl-L-carnitine, oleanolic acid, 3-phosphoglycerate, 5-hydroxynorvaline, 5-methoxytryptamine, adenosine-5-monophosphate, alpha-ketoglutarate, asparagine, benzoic acid, hypoxanthine, maltose, maltotriose, methionine sulfoxide, nornicotine, phenol, Phosphoethanolamine, pyrophosphate, pyruvic acid, quinic acid, taurine, uric acid, inosine, lactamide, 5-hydroxynorvaline NIST, cholesterol, deoxypentitol, 2-hydroxyestrone, 2-hydroxyestradiol, 2-metholyestrone, 2-metholxyestradiol, 2-hydroxyestrone-3-methyl ether, 4-hydroxyestrone, 4-metholxyestrone, 4-methoxyestradiol, 16alpha-hydroxyestrone, 17-epiestriol, estriol, 16-Ketoestradiol, 16-epiestriol, acylcarnitine C18:1, amino acids citrulline and trans-4-hydroxyproline, glycerophospholipids PC aa C28:1, PC ae C30:0 and PC ae C30:2, and sphingolipid SM (OH) C14:1. See e.g., Halama et al., Nesting of colon and ovarian cancer cells in the endothelial niche is associated with alterations in glycan and lipid metabolism, Scientific Reports volume 7, Article number: 39999 (2017); Hur et al., Systems approach to characterize the metabolism of liver cancer stem cells expressing CD133, Sci Rep., 7:45557, doi: 10.1038/srep45557, (2017); Eliassen et al., Urinary Estrogens and Estrogen Metabolites and Subsequent Risk of Breast Cancer among Premenopausal Women, Cancer Res; 72(3); 696-706 (2011); Gangi et al., Metabolomic profile in pancreatic cancer patients: a consensus-based approach to identify highly discriminating metabolites, Oncotarget, February 2; 7(5): 5815-5829 (2016); Kumar et al., Serum and Plasma Metabolomic Biomarkers for Lung Cancer, Bioinformation, 13(6): 202-208, doi: 10.6026/97320630013202 (2017); Schmidt et al., Pre-diagnostic metabolite concentrations and prostate cancer risk in 1077 cases and 1077 matched controls in the European Prospective Investigation into Cancer and Nutrition, BMC Med., 15:122, doi: 10.1186/s12916-017-0885-6 (2017); each of which is incorporated herein by reference in its entirety.

In some embodiments, the one or more additional classes of biomarkers include a peptide (e.g., a peptide that is distinct from the various protein biomarkers described herein as being useful in one or more methods). In some embodiments, a subject is determined to be at elevated risk of having or developing cancer if the biological sample contains one or more peptides indicative of cancer. In some embodiments, a subject is determined as having cancer if the biological sample contains one or more peptides indicative of cancer. In some embodiments, a peptide is derived from a protein (e.g., the peptide includes an amino acid sequence present in a protein biomarker or a different protein). Non-limiting examples of peptides indicative of cancer include the following peptides and peptides derived from the following proteins: CEACAM, CYFRA21-1, CA125, PKLK, ProGRP, NSE, TPA 6, TPA 7, TPA 8, NRG, NRG 100, CNDP, APOB100, SCC, VEGF, EGFR, PIK3CA, HER2, BRAF, ROS, RET, NRAS, MET, MEK1, HER2, C4.4A, PSF3, FAM83B, ECD, CTNNB, VIM, S100A4, S100A7, COX2, MUC1, KLKB1, SAA, HP-β chain, C9, Pgrmc1, Ciz1, Transferrin, α-1 antitrypsin, apolipo protein 1, complement c3a, Caveolin-1, Kallikrein 6, Glucose regulated protein-8, α defensing-1,-2,-3, Serum C-peptide, Alpha-2-HS glycol protein, Tryptic KRT 8 peptide, Plasma glycol protein, Catenin, Defensin α 6, MMPs, Cyclin D, S100 P, Lamin A/C filament protein, Heat shock protein, aldehyde dehydrogenase, Txl-2, (thioredoxin like protein-2), P53, nm23, u-PA, VEGF, Eph B4, CRABP2, WT-1, Rab-3D, Mesothelin, ERα, ANXA4, PSAT1, SPB5, CEA5, CEA6, A1AT, SLPI, APOA4, VDBP, HE4, IL-1, -6, -7, -8, -10, -11, -12, -16, -18, -21, -23, -28A, -33, LIF, TNFR1-2, HVEM (TNFRSF14), IL1R-a, IL1R-b, IL-2R, M-CSF, MIP-1a, TNF-α, CD40, RANTES, CD40L, MIF, IFN-β, MCP-4 (CCL13), MIG (CXCL9), MIP-1δ (CCL15), MIP3a (CCL20), MIP-4 (CCL18), MPIF-1, SDF-1a+b (CXCL12), CD137/4-1BB, lymphotactin (XCL1), eotaxin-1 (CCL11), eotaxin-2 (CCL24), 6Ckine/CCL21), BLC (CXCL13), CTACK (CCL27), BCA-1 (CXCL13), HCC4 (CCL16), CTAP-3 (CXCL7), IGF1, VEGF, VEGFR3, EGFR, ErbB2, CTGF, PDGF AA, BB, PDGFRb, bFGF, TGFbRIII, β-cellulin, IGFBP1-4, 6, BDNF, PEDF, angiopoietin-2, renin, lysophosphatidic acid, β2-microglobulin, sialyl TN, ACE, CA 19-9, CEA, CA 15-3, CA-50, CA 72-4, OVX1, mesothelin, sialyl TN, MMP-2, -3, -7, -9, VAP-1, TIMP1-2, tenascin C, VCAM-1, osteopontin, KIM-1, NCAM, tetranectin, nidogen-2, cathepsin L, prostasin, matriptase, kallikreins 2, 6, 10, cystatin C, claudin, spondin2, SLPI, bHCG, urinary gonadotropin peptide, inhibin, leptin, adiponectin, GH, TSH, ACTH, PRL, FSH, LH, cortisol, TTR, osteocalcin, insulin, ghrelin, GIP, GLP-1, amylin, glucagon, peptide YY, follistatin, hepcidin, CRP, Apo A1, CIII, H, transthyretin, SAA, SAP, complement C3,4, complement factor H, albumin, ceruloplasmin, haptoglobin, β-hemoglobin, transferrin, ferritin, fibrinogen, thrombin, von Willebrand factor, myoglobin, immunosuppressive acidic protein, lipid-associated sialic acid, S100A12 (EN-RAGE), fetuin A, clusterin, a1-antitrypsin, a2-macroglobulin, serpin1 (human plasminogen activator inhibitor-1), Cox-1, Hsp27, Hsp60, Hsp80, Hsp90, lectin-type oxidized LDL receptor 1, CD14, lipocalin 2, ITIH4, sFasL, Cyfra21-1, TPA, perforin, DcR3, AGRP, creatine kinase-MB, human milk fat globule 1-2, NT-Pro-BNP, neuron-specific enolase, CASA, NB/70K, AFP, afamin, collagen, prohibitin, keratin-6, PARC, B7-H4, YK-L40, AFP-L3, DCP, GPC3, OPN, GP73, CK19, MDK, A2, 5-HIAA, CA15-3, CA19-9, CA27.29, CA72-4, calcitonin, CGA, BRAF V600E, BAP, BCT-ABL fusion protein, KIT, KRAS, PSA, Lactate dehydrogenase, NMP22, PAI-1, uPA, fibrin D-dimer, S100, TPA, thyroglobulin, CD20, CD24, CD44, RS/DJ-1, p53, alpha-2-HS-glycoprotein, lipophilin B, beta-globin, hemopexin, UBE2N, PSMB6, PPP1CB, CPT2, COPA, MSK1/2, Pro-NPY, Secernin-1, Vinculin, NAAA, PTK7, TFG, MCCC2, TRAP1, IMPDH2, PTEN, POSTN, EPLIN, cIF4A3, DDAH1, ARG2, PRDX3&4, P4HB, YWHAG, Enoyl CoA-hydrase, PHB, TUBB, KRT2, DES, HSP71, ATP5B, CKB, HSPD1, LMNA, EZH2, AMACR, FABP5, PPA2, EZR, SLP2, SM22, Bax, Smac/Diablo phosphorylated Bcl2, STAT3 and Smac/Diablo expression, PHB, PAP, AMACR, PSMA, FKBP4, PRDX4, KRT7/8/18, GSTP1, NDPK1, MTX2, GDF15, PCa-24, Caveolin-2, Prothrombin, Antithrombin-III, Haptoglobin, Serum amyloid A-1 protein, ZAG, ORM2, APOC3, CALML5, IGFBP2, MUC5AC, PNLIP, PZP, TIMP1, AMBP, inter-alpha-trypsin inhibitor heavy chain H1, inter-alpha-trypsin inhibitor heavy chain H2, inter-alpha-trypsin inhibitor heavy chain H3, V-type proton ATPase subunit B, kidney isoform, Hepatocyte growth factor-like protein, Serum amyloid P-component, Acylglycerol kinase, Leucine-rich repeat-containing protein 9, Beta-2-glycoprotein 1, Plasma protease C1 inhibitor, Lipoxygenase homology domain-containing protein 1, Protocadherin alpha-13. See, e.g., Kuppusamy et al., Volume 24, Issue 6, September 2017, Pages 1212-1221; Elzek and Rodland, Cancer Metastasis Rev. 2015 March; 34(1): 83-96; Noel and Lokshin, Future Oncol. 2012 January; 8(1): 55-71; Tsuchiya et al., World J Gastroenterol. 2015 Oct. 7; 21(37): 10573-10583; Lou et al., Biomark Cancer. 2017; 9:1-9; Park et al., Oncotarget. 2017 Jun. 27; 8(26): 42761-42771; Saraswat et al., Cancer Med. 2017 July; 6(7): 1738-1751; Zamay et al., Cancers (Basel). 2017 November; 9(11): 155; Tanase et al., Oncotarget. 2017 Mar. 14; 8(11): 18497-18512, each of which is incorporated herein by reference in its entirety.

In some embodiments, the one or more additional classes of biomarkers include nucleic acid lesions or variations (e.g., a nucleic acid lesion or variation that is distinct from the various genetic biomarkers described herein as being useful in one or more methods). In some embodiments, a subject is determined to be at elevated risk of having or developing cancer if the biological sample contains one or more nucleic acid lesions or variations indicative of cancer. In some embodiments, a subject is determined as having cancer if the biological sample contains one or more nucleic acid lesions or variations indicative of cancer. Non-limiting examples of nucleic acid lesions or variations include copy number changes, DNA methylation changes, and/or other nucleic acids (e.g., mRNAs, miRNAs, lncRNAs, circRNA, mtDNA, telomeric DNA, translocation and genomic rearrangements).

Translocations and genomic rearrangements have been correlated with various cancers (e.g., prostate, glioma, lung cancer, non-small cell lung cancer, melanoma, and thyroid cancer) and used as biomarkers for years (e.g., Demeure et al., 2014, World J Surg., 38:1296-305; Hogenbirk et al., 2016, PNAS USA, 113:E3649-56; Gasi et al., 2011, PLoS One, 6:e16332; Ogiwara et al., 2008, Oncogene, 27:4788-97; U.S. Pat. Nos. 9,745,632; and 6,576,420). In addition, changes in copy number have been used as biomarkers for various cancers including, without limitation, head and neck squamous cell carcinoma, lymphoma (e.g., non-Hodgkin's lymphoma) and colorectal cancer (Kumar et al., 2017, Tumour Biol, 39:1010428317740296; Kumar et al., 2017, Tumour Biol., 39:1010428317736643; Henrique et al., 2014, Expert Rev. Mol. Diagn., 14:419-22; and U.S. Pat. No. 9,816,139). DNA methylation and changes in DNA methylation (e.g., hypomethylation, hypermethylation) also are used as biomarkers in cancer. For example, hypomethylation has been associated with hepatocellular carcinoma (see, for example, Henrique et al., 2014, Expert Rev. Mol. Diagn., 14:419-22), esophageal carcinogenesis (see, for example, Alvarez et al., 2011, PLoS Genet., 7:e1001356) and gastric and liver cancer (see, for example, U.S. Pat. No. 8,728,732), and hypermethylation has been associated with colorectal cancer (see, for example, U.S. Pat. No. 9,957,570;). In addition to genome-wide changes in methylation, specific methylation changes within particular genes can be indicative of specific cancers (see, for example, U.S. Pat. No. 8,150,626). Li et al. (2012, J. Epidemiol., 22:384-94) provides a review of the association between numerous cancers (e.g., breast, bladder, gastric, lung, prostate, head and neck squamous cell, and nasopharyngeal) and aberrant methylation. Additionally or alternatively, additional types of nucleic acids or features of nucleic acids have been associated with various cancers. Non-limiting examples of such nucleic acids or features of nucleic acids include the presence or absence of various microRNAs (miRNAs) have been used in the diagnosis of colon, prostate, colorectal, and ovarian cancers (see, for example, D'Souza et al., 2018, PLos One, 13:e0194268; Fukagawa et al., 2017, Cancer Sci., 108:886-96; Giraldez et al., 2018, Methods Mol. Biol., 1768:459-74; U.S. Pat. Nos. 8,343,718; 9,410,956; and 9,074,206). For a review on the specific association of miR-22 with cancer, see Wang et al. (2017, Int. J. Oncol., 50:345-55); the abnormal expression of long non-coding RNAs (lncRNAs) also have been used as a biomarker in cancers such as prostate cancer, colorectal cancer, cervical cancer, melanoma, non-small cell lung cancer, gastric cancer, endometrial carcinoma, and hepatocellular carcinoma (see, for example, Wang et al., 2017, Oncotarget, 8:58577086; Wang et al., 2018, Mol. Cancer, 17:110; Yu et al., 2018, Eur. Rev. Med. Pharmacol. Sci., 22:4812-9; Yu et al., 2018, Eur. Rev. Med. Pharmacol. Sci., 22:993-1002; Zhang et al., 2018, Eur. Rev. Med. Pharmacol. Sci., 22:4820-7; Zhang et al., 2018, Eur. Rev. Med. Pharmacol. Sci., 22:2304-9; Xie et al., 2018, EBioMedicine, 33:57-67; and U.S. Pat. No. 9,410,206); the presence or absence of circular RNA (circRNA) has been used as a biomarker in lung cancer, breast cancer, gastric cancer, colorectal cancer, and liver cancer (e.g., Geng et al., 2018, J. Hematol. Oncol., 11:98) and melanoma (e.g., Zhang et al., 2018, Oncol. Lett., 16:1219-25); changes in telomeric DNA (e.g., in length or in heterozygosity) or centromeric DNA (e.g., changes in expression of centromeric genes) also have been associated with cancers (e.g., prostate, breast, lung, lymphoma, and Ewing's sarcoma) (see, for example, Baretton et al., 1994, Cancer Res., 54:4472-80; Liscia et al., 1999, Br. J. Cancer, 80:821-6; Proctor et al., 2009, Biochim. Biophys. Acta, 1792:260-74; and Sun et al., 2016, Int. J. Cancer, 139:899-907); various mutations (e.g., deletions), rearrangements and/or copy number changes in mitochondrial DNA (mtDNA) have been used prognostically and diagnostically for various cancers (e.g., prostate cancer, melanoma, breast cancer, lung cancer, and colorectal cancer). See, for example, Maragh et al., 2015, Cancer Biomark., 15:763-73; Shen et al., 2010, Mitochondrion, 10:62-68; Hosgood et al., 2010, Carcinogen., 31:847-9; Thyagarajan et al., 2012, Cancer Epid. Biomarkers & Prev., 21:1574-81; and U.S. Pat. No. 9,745,632; and the abnormal presence, absence or amount of messenger RNAs (mRNAs) also have been correlated with various cancers including, without limitation, breast cancer, Wilms' tumors, and cervical cancer (see, for example, Guetschow et al., 2012, Anal. Bioanaly. Chem., 404:399-406; Schwienbacher et al., 2000, Cancer Res., 60:1521-5; and Ngan et al., 1997, Genitourin Med., 73:54-8). Each of these citations is incorporated herein by reference in its entirety.

Single Class of Biomarkers or Aneuploidy

In one aspect, provided herein are methods and materials for detecting the presence of one or more members of a single class of biomarkers (e.g., genetic biomarkers or protein biomarkers) or the presence of aneuploidy in one or more samples obtained from a subject. In another aspect, provided herein are methods and materials for diagnosing or identifying the presence of a disease in a subject (e.g., identifying the subject as having cancer) by detecting the presence of one or more members of a single class of biomarkers (e.g., genetic biomarkers or protein biomarkers) or the presence of aneuploidy in one or more samples obtained from a subject. In another aspect, provided herein are methods and materials for identifying a subject as being at risk (e.g., increased risk) of having or developing a disease (e.g., cancer) by detecting the presence of one or more members of a single class of biomarkers (e.g., genetic biomarkers or protein biomarkers) or the presence of aneuploidy in one or more samples obtained from a subject. In another aspect, provided herein are methods and materials for treating a subject who has been diagnosed or identified as having a disease (e.g., cancer) or who has been identified as being at risk (e.g., increased risk) of having or developing a disease (e.g., cancer) by detecting the presence of one or more members of a single class of biomarkers (e.g., genetic biomarkers or protein biomarkers) or the presence of aneuploidy in one or more samples obtained from a subject. In another aspect, provided herein are methods and materials for identifying a treatment for a subject who has been diagnosed or identified as having a disease (e.g., cancer) or who has been identified as being at risk (e.g., increased risk) of having or developing a disease (e.g., cancer) by detecting the presence of one or more members of a single class of biomarkers (e.g., genetic biomarkers or protein biomarkers) or the presence of aneuploidy in one or more samples obtained from a subject. In another aspect, provided herein are methods and materials for identifying a subject who will or is likely to respond to a treatment by detecting the presence of one or more members of a single class of biomarkers (e.g., genetic biomarkers or protein biomarkers) or the presence of aneuploidy in one or more samples obtained from a subject. In another aspect, provided herein are methods and materials for identifying a subject as a candidate for further diagnostic testing by detecting the presence of one or more members of a single class of biomarkers (e.g., genetic biomarkers or protein biomarkers) or the presence of aneuploidy in one or more samples obtained from a subject. In another aspect, provided herein are methods and materials for identifying a subject as a candidate for increased monitoring by detecting the presence of one or more members of a single class of biomarkers (e.g., genetic biomarkers or protein biomarkers) or the presence of aneuploidy in one or more samples obtained from a subject.

In some embodiments, methods provided herein that include detecting the presence of one or more members of a single class of biomarkers (e.g., genetic biomarkers or protein biomarkers) or the presence of aneuploidy in one or more samples obtained from a subject provide high sensitivity in the detection or diagnosis of cancer (e.g., a high frequency or incidence of correctly identifying a subject as having cancer). In some embodiments, methods provided herein that include detecting the presence of one or more members of a single class of biomarkers (e.g., genetic biomarkers or protein biomarkers) or the presence of aneuploidy in one or more samples obtained from a subject provide a sensitivity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. In some embodiments, methods provided herein that include detecting the presence of one or more members of a single class of biomarkers (e.g., genetic biomarkers or protein biomarkers) or the presence of aneuploidy in one or more samples obtained from a subject provide high sensitivity in detecting a single type of cancer. In some embodiments, methods provided herein that include detecting the presence of one or more members of a single class of biomarkers (e.g., genetic biomarkers or protein biomarkers) or the presence of aneuploidy in one or more samples obtained from a subject provide high sensitivity in detecting two or more types of cancers. Any of a variety of cancer types can be detected using methods and materials provided herein (see, e.g., the section entitled "Cancers"). In some embodiments, cancers that can be detected using methods and materials that include detecting the presence of one or more members of a single class of biomarkers (e.g., genetic biomarkers or protein biomarkers) or the presence of aneuploidy in one or more samples obtained from a subject include liver cancer, ovarian cancer, esophageal cancer, stomach cancer, pancreatic cancer, colorectal cancer, lung cancer, or breast cancer. In some embodiments, cancers that can be detected using methods and materials that include detecting the presence of one or more members of a single class of biomarkers (e.g., genetic biomarkers or protein biomarkers) or the presence of aneuploidy in one or more samples obtained from a subject include pancreatic cancer. In some embodiments, cancers that can be detected using methods and materials that include detecting the presence of one or more members of a single class of biomarkers (e.g., genetic biomarkers or protein biomarkers) or the presence of aneuploidy in one or more samples obtained from a subject include cancers of the female reproductive tract (e.g., cervical cancer, endometrial cancer, ovarian cancer, or fallopian tubal cancer). In some embodiments, cancers that can be detected using methods and materials that include detecting the presence of one or more members of a single class of biomarkers (e.g., genetic biomarkers or protein biomarkers) or the presence of aneuploidy in one or more samples obtained from a subject include bladder cancer or upper-tract urothelial carcinomas.

In some embodiments, methods provided herein that include detecting the presence of one or more members of a single class of biomarkers (e.g., genetic biomarkers or protein biomarkers) or the presence of aneuploidy in one or more samples obtained from a subject In some embodiments, methods provided herein that include detecting the presence of one or more members of a single class of biomarkers (e.g., genetic biomarkers or protein biomarkers) or the presence of aneuploidy in one or more samples obtained from a subject provide high specificity in the detection or diagnosis of cancer (e.g., a low frequency or incidence of incorrectly identifying a subject as having cancer when that subject does not have cancer). In some embodiments, methods provided herein that include detecting the presence of one or more members of a single class of biomarkers (e.g., genetic biomarkers or protein biomarkers) or the presence of aneuploidy in one or more samples obtained from a subject provide a specificity of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher. As will be understood by those of ordinary skill in the art, a specificity of 99% means that only 1% of subjects that do not have cancer are incorrectly identified as having cancer. In some embodiments, methods provided herein that include detecting the presence of one or more members of a single class of biomarkers (e.g., genetic biomarkers or protein biomarkers) or the presence of aneuploidy in one or more samples obtained from a subject provide high specificity in detecting a single cancer (e.g., there is a low probability of incorrectly identifying that subject as having that single cancer type). In some embodiments, methods provided herein that include detecting the presence of one or more members of a single class of biomarkers (e.g., genetic biomarkers or protein biomarkers) or the presence of aneuploidy in one or more samples obtained from a subject provide high specificity in detecting two or more cancers (e.g., there is a low probability of incorrectly identifying that subject as having those two or more cancer types).

In some embodiments, methods provided herein that include detecting the presence of one or more members of a single class of biomarkers include detecting the presence of one or more members of a panel of genetic biomarkers.

In some embodiments, methods provided herein that include detecting the presence of one or more members of a panel of genetic biomarkers include detecting one or more genetic biomarkers in one or more (e.g., 1, 2, 3, 4, 5, 6, 7, 8, 9, 10, 11, 12, 13, 14, 15, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. In some embodiments, methods provided herein that include detecting the presence of one or more members of a panel of genetic biomarkers include detecting one or more genetic biomarkers in each of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and GNAS.

In some embodiments, methods provided herein that include detecting the presence of one or more members of a panel of genetic biomarkers include detecting one or more genetic biomarkers in one or more (e.g., 1, 2, 3, or 4) of the following genes: KRAS (e.g., genetic biomarkers in codons 12 and/or 61), TP53, CDKN2A, and/or SMAD4. In some embodiments, methods provided herein that include detecting the presence of one or more members of a panel of genetic biomarkers include detecting one or more genetic biomarkers in each of the following genes: KRAS (e.g., genetic biomarkers in codons 12 and/or 61), TP53, CDKN2A, and SMAD4.

In some embodiments, methods provided herein that include detecting the presence of one or more members of a panel of genetic biomarkers include detecting one or more genetic biomarkers in one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A. In some embodiments, methods provided herein that include detecting the presence of one or more members of a panel of genetic biomarkers include detecting one or more genetic biomarkers in each of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A. In some embodiments, methods provided herein that include detecting the presence of one or more members of a panel of genetic biomarkers include detecting one or more genetic biomarkers in one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A. In some embodiments, methods provided herein that include detecting the presence of one or more members of a panel of genetic biomarkers include detecting one or more genetic biomarkers in each of the following genes: PTEN, TP53, PIK3CA, PIK3R1, CTNNB1, KRAS, FGFR2, POLE, APC, FBXW7, RNF43, and PPP2R1A. In some embodiments, methods provided herein that include detecting the presence of one or more members of a panel of genetic biomarkers include detecting one or more genetic biomarkers in TP53

In some embodiments, methods provided herein that include detecting the presence of one or more members of a panel of genetic biomarkers include detecting one or more genetic biomarkers in one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL. In some embodiments, methods provided herein that include detecting the presence of one or more members of a panel of genetic biomarkers include detecting one or more genetic biomarkers in each of the following genes: TP53, PIK3CA, FGFR3, KRAS, ERBB2, CDKN2A, MLL, HRAS, MET, and VHL.

In some embodiments, methods provided herein that include detecting the presence of one or more members of a panel of protein biomarkers include detecting one or more (e.g., 1, 2, 3, 4, 5, 6, 7, or 8) of the following protein biomarkers: CA19-9, CEA, HGF, OPN, CA125, prolactin, TIMP-1, and/or myeloperoxidase (MPO). In some embodiments, methods provided herein that include detecting the presence of one or more members of a panel of protein biomarkers include detecting each of the following protein biomarkers: CA19-9, CEA, HGF, OPN, CA125, prolactin, TIMP-1, and myeloperoxidase (MPO). In some embodiments, methods provided herein that include detecting the presence of one or more members of a panel of protein biomarkers include detecting one or more (e.g., 1, 2, 3, 4, 5, 6, 7, 8, 9, 10, or 11) of the following protein biomarkers: CA19-9, CEA, HGF, OPN, CA125, AFP, prolactin, TIMP-1, follistatin, G-CSF, and/or CA15-3. In some embodiments, methods provided herein that include detecting the presence of one or more members of a panel of protein biomarkers include detecting each of the following protein biomarkers: CA19-9, CEA, HGF, OPN, CA125, AFP, prolactin, TIMP-1, follistatin, G-CSF, and CA15-3. In some embodiments, methods provided herein that include detecting the presence of one or more members of a panel of protein biomarkers include detecting one or more (e.g., 1, 2, 3, 4, 5, 6, 7, 8, or 9) of the following protein biomarkers: CA19-9, CEA, HGF, OPN, CA125, AFP, prolactin, TIMP-1, and/or CA15-3. In some embodiments, methods provided herein that include detecting the presence of one or more members of a panel of protein biomarkers include detecting each of the following protein biomarkers: CA19-9, CEA, HGF, OPN, CA125, AFP, prolactin, TIMP-1, and CA15-3. In some embodiments, methods provided herein that include detecting the presence of one or more members of a panel of protein biomarkers include detecting one or more (e.g., 1, 2, 3, or 4) of the following protein biomarkers: CA19-9, CEA, HGF, and/or OPN. In some embodiments, methods provided herein that include detecting the presence of one or more members of a panel of protein biomarkers include detecting each of the following protein biomarkers: CA19-9, CEA, HGF, and OPN.

In some embodiments, methods provided herein that include detecting the presence of aneuploidy include detecting aneuploidy on one or more of chromosome arms 5q, 8q, and/or 9p. In some embodiments, methods provided herein that include detecting the presence of aneuploidy include detecting aneuploidy on one or more of chromosome arms 4p, 7q, 8q, and/or 9q.

In some embodiments, methods provided herein that include detecting the presence of one or more members of a single class of biomarkers include detecting the presence of one or more members of a class of biomarkers including, without limitation: copy number changes, DNA methylation changes, other nucleic acids (e.g., mRNAs, miRNAs, lncRNAs, circRNA, mtDNA, telomeric DNA, translocation and genomic rearrangements), peptides, or metabolites.

In some embodiments, methods provided herein include detecting the presence of one or more metabolites. In some embodiments, a subject is determined to be at elevated risk of having or developing cancer if the biological sample contains one or more metabolites indicative of cancer. In some embodiments, a subject is determined as having cancer if the biological sample contains one or more metabolites indicative of cancer. Non-limiting examples of metabolites indicative of cancer include: 5-methylthioadenosine (MTA), Glutathione reduced (GSH), N-acetylglutamate, Lactose, N-acetylneuraminate, UDP-acetylglucosamine, UDP-Acetylgalactosamine, UDP-glucuronate, Pantothenate, Arachidonate (20:4n6), Choline, Cytidine 5'-diphosphocholine, Dihomo-linolenate (20:3n3), Docosapentaenoate (DPA 22:5n3), Eicosapentaenoate (EPA 20:5n3), Glycerophosphorylcholine (GPC), Docosahexaenoate (DHA 22:6n3), Linoleate (18:2n6), Cytidine 5'-monophosphate (5'-CMP), Gamma-glutamylglutamate, X-14577, X-11583, Isovalerylcarnitine, Phosphocreatine, 2-Aminoadipic acid, Gluconic acid, O-Acetylcarnitine, aspartic acid, Deamido-NAD+, glutamic acid, Isobutyrylcarnitine, Carnitine, Pyridoxal, Citric acid, Adenosine, ATP, valine, XC0061, Isoleucine, γ-Butyrobetaine, Lactic acid, alanine, phenylalanine, Gluconolactone, leucine, Glutathione (GSSG)_divalent, tyrosine, NAD+, XC0016, UTP, creatine, Theobromine, CTP, GTP, 3-Methylhistidine, Succinic acid, Glycerol 3-phosphate, glutamine, 5-Oxoproline, Thiamine, Butyrylcarnitine, 4-Acetamidobutanoic acid, UDP-Glucose, UDP-Galactose, threonine, N-Acetylglycine, proline, ADP, Choline, Malic acid, S-Adenosylmethionine, Pantothenic acid, Cysteinesulfinic acid, 6-Aminohexanoic acid, Homocysteic acid, Hydroxyproline, Methionine sulfoxide, 3-Guanidinopropionic acid, Glucose 6-phosphate, Phenaceturic acid, Threonic acid, tryptophan, Pyridoxine, N-Acetylaspartic acid, 4-Guanidinobutyric acid, serine, Citrulline, Betaine, N-Acetylasparagine, 2-Hydroxyglutaric acid, arginine, Glutathione (GSH), creatinine, Dihydroxyacetone phosphate, histidine, glycine, Glucose 1-phosphate, N-Formylglycine, Ketoprofen, lysine, beta-alanine, N-Acetylglutamic acid, 2-Amino-2-(hydroxymethyl)-1,3-propanediol, Ornithine, Phosphorylcholine, Glycerophosphocholine, Terephthalic acid, Glyceraldehyde 3-phosphate, Gly-Asp, Taurine, Fructose 1,6-diphosphate, 3-Aminoisobutyric acid, Spermidine, GABA, Triethanolamine, Glycerol, N-Acetylserine, N-Acetylornithine, Diethanolamine, AMP, Cysteine glutathione disulfide, Streptomycin sulfate+H2O divalent, trans-Glutaconic acid, Nicotinic acid, Isobutylamine, Betaine aldehyde+H2O, Urocanic acid, 1-Aminocyclopropane-1-carboxylic acid Homoserinelactone, 5-Aminovaleric acid, 3-Hydroxybutyric acid, Ethanolamine, Isovaleric acid, N-Methylglutamic acid, Cystathionine, Spermine, Carnosine, 1-Methylnicotinamide, N-Acetylneuraminic acid, Sarcosine, GDP, N-Methylalanine, palmitic acid, 1,2-dioleoyl-sn-glycero-3-phospho-rac-glycerolcholesterol 5α,6α epoxidelanosterol, lignoceric acid, loleoyl_rac_GL, cholesterol_epoxide, erucic acid, T-LCA, oleoyl-L-carnitine, oleanolic acid, 3-phosphoglycerate, 5-hydroxynorvaline, 5-methoxytryptamine, adenosine-5-monophosphate, alpha-ketoglutarate, asparagine, benzoic acid, hypoxanthine, maltose, maltotriose, methionine sulfoxide, nornicotine, phenol, Phosphoethanolamine, pyrophosphate, pyruvic acid, quinic acid, taurine, uric acid, inosine, lactamide, 5-hydroxynorvaline NIST, cholesterol, deoxypentitol, 2-hydroxyestrone, 2-hydroxyestradiol, 2-metholyestrone, 2-metholxyestradiol, 2-hydroxyestrone-3-methyl ether, 4-hydroxyestrone, 4-metholxyestrone, 4-methoxyestradiol, 16alpha-hydroxyestrone, 17-epiestriol, estriol, 16-Ketoestradiol, 16-epiestriol, acylcarnitine C18:1, amino acids citrulline and trans-4-hydroxyproline, glycerophospholipids PC aa C28:1, PC ae C30:0 and PC ae C30:2, and sphingolipid SM (OH) C14:1. See e.g., Halama et al., Nesting of colon and ovarian cancer cells in the endothelial niche is associated with alterations in glycan and lipid metabolism, Scientific Reports volume 7, Article number: 39999 (2017); Hur et al., Systems approach to characterize the metabolism of liver cancer stem cells expressing CD133, Sci Rep., 7:45557, doi: 10.1038/srep45557, (2017); Eliassen et al., Urinary Estrogens and Estrogen Metabolites and Subsequent Risk of Breast Cancer among Premenopausal Women, Cancer Res; 72(3); 696-706 (2011); Gangi et al., Metabolomic profile in pancreatic cancer patients: a consensus-based approach to identify highly discriminating metabolites, Oncotarget, February 2; 7(5): 5815-5829 (2016); Kumar et al., Serum and Plasma Metabolomic Biomarkers for Lung Cancer, Bioinformation, 13(6): 202-208, doi: 10.6026/97320630013202 (2017); Schmidt et al., Pre-diagnostic metabolite concentrations and prostate cancer risk in 1077 cases and 1077 matched controls in the European Prospective Investigation into Cancer and Nutrition, BMC Med., 15:122, doi: 10.1186/s12916-017-0885-6 (2017); each of which is incorporated herein by reference in its entirety.

In some embodiments, methods provided herein include detecting the presence of one or more peptides (e.g., one or more peptides that are distinct from the various protein biomarkers described herein as being useful in one or more methods). In some embodiments, a subject is determined to be at elevated risk of having or developing cancer if the biological sample contains one or more peptides indicative of cancer. In some embodiments, a subject is determined as having cancer if the biological sample contains one or more peptides indicative of cancer. In some embodiments, a peptide is derived from a protein (e.g., the peptide includes an amino acid sequence present in a protein biomarker or a different protein). Non-limiting examples of peptides indicative of cancer include the following peptides and peptides derived from the following proteins: CEACAM, CYFRA21-1, CA125, PKLK, ProGRP, NSE, TPA 6, TPA 7, TPA 8, NRG, NRG 100, CNDP, APOB100, SCC, VEGF, EGFR, PIK3CA, HER2, BRAF, ROS, RET, NRAS, MET, MEK1, HER2, C4.4A, PSF3, FAM83B, ECD, CTNNB, VIM, S100A4, S100A7, COX2, MUC1, KLKB1, SAA, HP-β chain, C9, Pgrmc1, Ciz1, Transferrin, α-1 antitrypsin, apo-lipo protein 1, complement c3a, Caveolin-1, Kallikrein 6, Glucose regulated protein-8, α defensing-1,-2,-3, Serum C-peptide, Alpha-2-HS glycol protein, Tryptic KRT 8 peptide, Plasma glycol protein, Catenin, Defensin α 6, MMPs, Cyclin D, S100 P, Lamin A/C filament protein, Heat shock protein, aldehyde dehydrogenase, Tx1-2, (thioredoxin like protein-2), P53, nm23, u-PA, VEGF, Eph B4, CRABP2, WT-1, Rab-3D, Mesothelin, ERα, ANXA4, PSAT1, SPB5, CEA5, CEA6, A1AT, SLPI, APOA4, VDBP, HE4, IL-1, -6, -7, -8, -10, -11, -12, -16, -18, -21, -23, -28A, -33, LIF, TNFR1-2, HVEM (TNFRSF14), IL1R-a, IL1R-b, IL-2R, M-CSF, MIP-1a, TNF-α, CD40, RANTES, CD40L, MIF, IFN-β, MCP-4 (CCL13), MIG (CXCL9), MIP-1δ (CCL15), MIP3a (CCL20), MIP-4 (CCL18), MPIF-1, SDF-1a+b (CXCL12), CD137/4-1BB, lymphotactin (XCL1), eotaxin-1 (CCL11), eotaxin-2 (CCL24), 6Ckine/CCL21), BLC (CXCL13), CTACK (CCL27), BCA-1 (CXCL13), HCC4 (CCL16), CTAP-3 (CXCL7), IGF1, VEGF, VEGFR3, EGFR, ErbB2, CTGF, PDGF AA, BB, PDGFRb, bFGF, TGFbRIII, β-cellulin, IGFBP1-4, 6, BDNF, PEDF, angiopoietin-2, renin, lysophosphatidic acid, β2-microglobulin, sialyl TN, ACE, CA 19-9, CEA, CA 15-3, CA-50, CA 72-4, OVX1, mesothelin, sialyl TN, MMP-2, -3, -7, -9, VAP-1, TIMP1-2, tenascin C, VCAM-1, osteopontin, KIM-1, NCAM, tetranectin, nidogen-2, cathepsin L, prostasin, matriptase, kallikreins 2, 6, 10, cystatin C, claudin, spondin2, SLPI, bHCG, urinary gonadotropin peptide, inhibin, leptin, adiponectin, GH, TSH, ACTH, PRL, FSH, LH, cortisol, TTR, osteocalcin, insulin, ghrelin, GIP, GLP-1, amylin, glucagon, peptide YY, follistatin, hepcidin, CRP, Apo A1, CIII, H, transthyretin, SAA, SAP, complement C3,4, complement factor H, albumin, ceruloplasmin, haptoglobin, β-hemoglobin, transferrin, ferritin, fibrinogen, thrombin, von Willebrand factor, myoglobin, immunosuppressive acidic protein, lipid-associated sialic acid, S100A12 (EN-RAGE), fetuin A, clusterin, a1-antitrypsin, a2-macroglobulin, serpin1 (human plasminogen activator inhibitor-1), Cox-1, Hsp27, Hsp60, Hsp80, Hsp90, lectin-type oxidized LDL receptor 1, CD14, lipocalin 2, ITIH4, sFasL, Cyfra21-1, TPA, perforin, DcR3, AGRP, creatine kinase-MB, human milk fat globule 1-2, NT-Pro-BNP, neuron-specific enolase, CASA, NB/70K, AFP, afamin, collagen, prohibitin, keratin-6, PARC, B7-H4, YK-L40, AFP-L3, DCP, GPC3, OPN, GP73, CK19, MDK, A2, 5-HIAA, CA15-3, CA19-9, CA27.29, CA72-4, calcitonin, CGA, BRAF V600E, BAP, BCT-ABL fusion protein, KIT, KRAS, PSA, Lactate dehydrogenase, NMP22, PAI-1, uPA, fibrin D-dimer, S100, TPA, thyroglobulin, CD20, CD24, CD44, RS/DJ-1, p53, alpha-2-HS-glycoprotein, lipophilin B, beta-globin, hemopexin, UBE2N, PSMB6, PPP1CB, CPT2, COPA, MSK1/2, Pro-NPY, Secernin-1, Vinculin, NAAA, PTK7, TFG, MCCC2, TRAP1, IMPDH2, PTEN, POSTN, EPLIN, eIF4A3, DDAH1, ARG2, PRDX3&4, P4HB, YWHAG, Enoyl CoA-hydrase, PHB, TUBB, KRT2, DES, HSP71, ATP5B, CKB, HSPD1, LMNA, EZH2, AMACR, FABP5, PPA2, EZR, SLP2, SM22, Bax, Smac/Diablo phosphorylated Bcl2, STAT3 and Smac/Diablo expression, PHB, PAP, AMACR, PSMA, FKBP4, PRDX4, KRT7/8/18, GSTP1, NDPK1, MTX2, GDF15, PCa-24, Caveolin-2, Prothrombin, Antithrombin-III, Haptoglobin, Serum amyloid A-1 protein, ZAG, ORM2, APOC3, CALML5, IGFBP2, MUC5AC, PNLIP, PZP, TIMP1, AMBP, inter-alpha-trypsin inhibitor heavy chain H1, inter-alpha-trypsin inhibitor heavy chain H2, inter-alpha-trypsin inhibitor heavy chain H3, V-type proton ATPase subunit B, kidney isoform, Hepatocyte growth factor-like protein, Serum amyloid P-component, Acylglycerol kinase, Leucine-rich repeat-containing protein 9, Beta-2-glycoprotein 1, Plasma protease C1 inhibitor, Lipoxygenase homology domain-containing protein 1, Protocadherin alpha-13. See, e.g., Kuppusamy et al., Volume 24, Issue 6, September 2017, Pages 1212-1221; Elzek and Rodland, Cancer Metastasis Rev. 2015 March; 34(1): 83-96; Noel and Lokshin, Future Oncol. 2012 January; 8(1): 55-71; Tsuchiya et al., World J Gastroenterol. 2015 Oct. 7; 21(37): 10573-10583; Lou et al., Biomark Cancer. 2017; 9:1-9; Park et al., Oncotarget. 2017 Jun. 27; 8(26): 42761-42771; Saraswat et al., Cancer Med. 2017 July; 6(7): 1738-1751; Zamay et al., Cancers (Basel). 2017 November; 9(11): 155; Tanase et al., Oncotarget. 2017 Mar. 14; 8(11): 18497-18512, each of which is incorporated herein by reference in its entirety.

In some embodiments, methods provided herein include detecting the presence of one or more nucleic acid lesions or variations (e.g., one or more nucleic acid lesions or variations that are distinct from the various genetic biomarkers described herein as being useful in one or more methods). In some embodiments, a subject is determined to be at elevated risk of having or developing cancer if the biological sample contains one or more nucleic acid lesions or variations indicative of cancer. In some embodiments, a subject is determined as having cancer if the biological sample contains one or more nucleic acid lesions or variations indicative of cancer. Non-limiting examples of nucleic acid lesions or variations include copy number changes, DNA methylation changes, and/or other nucleic acids (e.g., mRNAs, miRNAs, lncRNAs, circRNA, mtDNA, telomeric DNA, translocation and genomic rearrangements). Translocations and genomic rearrangements have been correlated with various cancers (e.g., prostate, glioma, lung cancer, non-small cell lung cancer, melanoma, and thyroid cancer) and used as biomarkers for years (e.g., Demeure et al., 2014, World J Surg., 38:1296-305; Hogenbirk et al., 2016, PNAS USA, 113:E3649-56; Gasi et al., 2011, PLoS One, 6:e16332; Ogiwara et al., 2008, Oncogene, 27:4788-97; U.S. Pat. Nos. 9,745,632; and 6,576,420). In addition, changes in copy number have been used as biomarkers for various cancers including, without limitation, head and neck squamous cell carcinoma, lymphoma (e.g., non-Hodgkin's lymphoma) and colorectal cancer (Kumar et al., 2017, Tumour Biol, 39:1010428317740296; Kumar et al., 2017, Tumour Biol., 39:1010428317736643; Henrique et al., 2014, Expert Rev. Mol. Diagn., 14:419-22; and U.S. Pat. No. 9,816,139). DNA methylation and changes in DNA methylation (e.g., hypomethylation, hypermethylation) also are used as biomarkers in cancer. For example, hypomethylation has been associated with hepatocellular carcinoma (see, for example, Henrique et al., 2014, Expert Rev. Mol. Diagn., 14:419-22), esophageal carcinogenesis (see, for example, Alvarez et al., 2011, PLoS Genet., 7:e1001356) and gastric and liver cancer (see, for example, U.S. Pat. No. 8,728,732), and hypermethylation has been associated with colorectal cancer (see, for example, U.S. Pat. No. 9,957,570;). In addition to genome-wide changes in methylation, specific methylation changes within particular genes can be indicative of specific cancers (see, for example, U.S. Pat. No. 8,150,626). Li et al. (2012, J. Epidemiol., 22:384-94) provides a review of the association between numerous cancers (e.g., breast, bladder, gastric, lung, prostate, head and neck squamous cell, and nasopharyngeal) and aberrant methylation. Additionally or alternatively, additional types of nucleic acids or features of nucleic acids have been associated with various cancers. Non-limiting examples of such nucleic acids or features of nucleic acids include the presence or absence of various microRNAs (miRNAs) have been used in the diagnosis of colon, prostate, colorectal, and ovarian cancers (see, for example, D'Souza et al., 2018, PLos One, 13:e0194268; Fukagawa et al., 2017, Cancer Sci., 108:886-96; Giraldez et al., 2018, Methods Mol. Biol., 1768:459-74; U.S. Pat. Nos.

8,343,718; 9,410,956; and 9,074,206). For a review on the specific association of miR-22 with cancer, see Wang et al. (2017, Int. J. Oncol., 50:345-55); the abnormal expression of long non-coding RNAs (lncRNAs) also have been used as a biomarker in cancers such as prostate cancer, colorectal cancer, cervical cancer, melanoma, non-small cell lung cancer, gastric cancer, endometrial carcinoma, and hepatocellular carcinoma (see, for example, Wang et al., 2017, Oncotarget, 8:58577086; Wang et al., 2018, Mol. Cancer, 17:110; Yu et al., 2018, Eur. Rev. Med. Pharmacol. Sci., 22:4812-9; Yu et al., 2018, Eur. Rev. Med. Pharmacol. Sci., 22:993-1002; Zhang et al., 2018, Eur. Rev. Med. Pharmacol. Sci., 22:4820-7; Zhang et al., 2018, Eur. Rev. Med. Pharmacol. Sci., 22:2304-9; Xie et al., 2018, EBioMedicine, 33:57-67; and U.S. Pat. No. 9,410,206); the presence or absence of circular RNA (circRNA) has been used as a biomarker in lung cancer, breast cancer, gastric cancer, colorectal cancer, and liver cancer (e.g., Geng et al., 2018, J. Hematol. Oncol., 11:98) and melanoma (e.g., Zhang et al., 2018, Oncol. Lett., 16:1219-25); changes in telomeric DNA (e.g., in length or in heterozygosity) or centromeric DNA (e.g., changes in expression of centromeric genes) also have been associated with cancers (e.g., prostate, breast, lung, lymphoma, and Ewing's sarcoma) (see, for example, Baretton et al., 1994, Cancer Res., 54:4472-80; Liscia et al., 1999, Br. J. Cancer, 80:821-6; Proctor et al., 2009, Biochim. Biophys. Acta, 1792:260-74; and Sun et al., 2016, Int. J. Cancer, 139:899-907); various mutations (e.g., deletions), rearrangements and/or copy number changes in mitochondrial DNA (mtDNA) have been used prognostically and diagnostically for various cancers (e.g., prostate cancer, melanoma, breast cancer, lung cancer, and colorectal cancer). See, for example, Maragh et al., 2015, Cancer Biomark., 15:763-73; Shen et al., 2010, Mitochondrion, 10:62-68; Hosgood et al., 2010, Carcinogen., 31:847-9; Thyagarajan et al., 2012, Cancer Epid. Biomarkers & Prev., 21:1574-81; and U.S. Pat. No. 9,745,632; and the abnormal presence, absence or amount of messenger RNAs (mRNAs) also have been correlated with various cancers including, without limitation, breast cancer, Wilms' tumors, and cervical cancer (see, for example, Guetschow et al., 2012, Anal. Bioanaly. Chem., 404:399-406; Schwienbacher et al., 2000, Cancer Res., 60:1521-5; and Ngan et al., 1997, Genitourin Med., 73:54-8). Each of these citations is incorporated herein by reference in its entirety.

Validation of Detected Genetic Biomarkers

In some embodiments, methods provided herein can be used to verify that a genetic biomarker detected in circulating tumor DNA present in cell-free DNA indicates the presence of a cancer cell in the subject. In some embodiments, methods provided herein can be used to verify that a genetic alteration (e.g., one or more genetic alterations) detected in circulating tumor DNA present in cell-free DNA indicates the presence of a cancer cell in the subject. For example, certain genetic biomarkers (e.g., genetic alterations) that are present in cancer cells also occur in other non-cancer cells in the body. Such non-cancer cells include, without limitation, white blood cell clones arising during age-associated clonal hematopoiesis (e.g., clonal hematopoietic expansion (also known as clonal hematopoiesis of indeterminate potential or CHIP) or myelodysplasia). As a result, such clones, which may represent early forms of myelodysplasia, are a potential source of false positives in ctDNA-based assays. In such cases, detecting a genetic biomarker (e.g., a genetic alteration) in cell-free DNA can lead to a false diagnosis of cancer since the genetic biomarker (e.g., genetic alteration) arises from hematopoietic white blood cells, rather than from a cancer (e.g., a solid tumor). Methods provided herein can reduce or eliminate such false cancer diagnoses.

Methods provided herein can be used to reduce or eliminate false cancer diagnoses by determining whether one or more genetic biomarkers (e.g., genetic alterations) detected in cell-free DNA originate from hematopoietic white blood cells rather than from a cancer cell. For example, DNA can be isolated or obtained from white blood cells of a subject, which DNA can be tested to determine the presence or absence of a genetic biomarker (e.g., a genetic alteration) that was identified in cell-free DNA from the subject, which genetic biomarker (e.g., genetic alteration) is associated with cancer. In some embodiments, if the genetic biomarker (e.g., genetic alteration) is identified in the DNA from a white blood cell, it is indicative that the genetic biomarker (e.g., genetic alteration) identified in cell-free DNA originated from the white blood cells, and not from a cancer cell present in the subject. In some embodiments, if the genetic biomarker (e.g., genetic alteration) is not identified in the DNA from the white blood cells, it is indicative that the genetic biomarker (e.g., genetic alteration) identified in cell-free DNA originated from a cancer cell present in the subject, and not from a white blood cell. Methods of testing DNA isolated or obtained from white blood cells for the presence or absence of a genetic biomarker (e.g., a genetic mutation) that is associated with cancer in order to determine whether that genetic biomarker (e.g., genetic alteration) originates from a cancer cell in the subject are generically described herein as "verifying a genetic alteration against white blood cells", "verifying a genetic alteration against DNA from white blood cells", "white blood cell verification", and similar phrases.

Any genetic biomarker (e.g., genetic alteration) that is associated with cancer can be verified using methods described herein. Examples of genetic biomarkers (e.g., genes having genetic alterations) associated with cancer include, without limitation, ABCA7, ABL1, ABL2, ACVR1B, ACVR2A, AJUBA, AKT1, AKT2, ALB, ALDOB, ALK, AMBRA1, AMER1, AMOT, ANKRD46, APC, AR, ARHGAP35, ARHGEF12, ARID1A, ARID1B, ARID2, ARID4B, ARL15, ARMCX1, ASXL1, ASXL2, ATAD2, ATF1, ATG14, ATG5, ATM, ATRX, ATXN2, AXIN1, B2M, BAP1, BCL11A, BCL11B, BCL2, BCL3, BCL6, BCL9, BCLAF1, BCOR, BCR, BIRC6, BIRC8, BLM, BLVRA, BMPR1A, BRAF, BRCA1, BRCA2, BRD7, BRE, BRWD3, BTBD7, BTRC, C11orf70, C12orf57, C2CD5, C3orf62, C8orf34, CAMKV, CAPG, CARD11, CARS, CASP8, CBFA2T3, CBFB, CBLC, CBX4, CCAR1, CCDC117, CCDC88A, CCM2, CCNC, CCND1, CCND2, CCND3, CCR3, CD1D, CD79B, CDC73, CDCP1, CDH1, CDH11, CDK12, CDK4, CDK6, CDKN1A, CDKN1B, CDKN2A, CDX2, CEBPA, CELF1, CENPB, CEP128, CHD2, CHD4, CHD8, CHEK2, CHRDL1, CHUK, CIC, CLEC4C, CMTR2, CNN2, CNOT1, CNOT4, COL11A1, COPS4, COX7B2, CREB1, CREBBP, CSDE1, CSMD3, CTCF, CTDNEP1, CTNNB1, CUL1, CUL2, CYB5B, CYLD, DACH1, DCHS1, DCUN1D1, DDB2, DDIT3, DDX3X, DDX5, DDX6, DEK, DHX15, DHX16, DICER1, DIRC2, DIS3, DIXDC1, DKK2, DNAJB5, DNER, DNM1L, DNMT3A, EED, EGFR, EIF1AX, EIF2AK3, EIF2S2, EIF4A1, EIF4A2, ELF3, ELK4, EMG1, EMR3, EP300, EPB41L4A, EPHA2, EPS8, ERBB2, ERBB3, ERRFI1, ETV4, ETV6, EVI1, EWSR1, EXO5, EXT1, EXT2, EZH2, F5, FANCM, FAT1, FBN2, FBXW7, FCER1G, FEV, FGF2, FGFR1, FGFR1OP, FGFR2, FGFR3, FH, FLT3, FN1, FOXA1, FOXP1, FUBP1, FUS, GAL- NTL5, GATA3, GGCT, GIGYF2, GK2, GLIPR2, GNAS, GNPTAB, GNRHR, GOLGA5, GOLM1, GOPC, GOT2, GPC3, GPS2, GPX7, GRK1, GSE1, GZMA, HDAC1, HERC1, HERC4, HGF, HIST1H2BO, HLA-A, HLA-B, HMCN1, HMGA1, HMGA2, HNRNPA1, HRAS, HSP90AB1, ID3, IDH1, IDH2, IFNGR2, IFT88, IKZF2, IL2, INO80C, INPP4A, INPPL1, IRF4, IWS1, JAK1, JAK2, JUN, KANSL1, KAT8, KATNAL1, KBTBD7, KCNMB4, KDM5C, KDM6A, KEAP1, KIAA1467, KIT, KLF4, KMT2A, KMT2B, KMT2C, KMT2D, KMT2E, KRAS, KRT15, LAMTOR1, LARP4B, LCK, LMO2, LPAR2, LYN, MAF, MAFB, MAML2, MAP2K1, MAP2K2, MAP2K4, MAP3K1, MAP4K3, MAPK1, MAX, MB21D2, MBD1, MBD6, MBNL1, MBNL3, MDM2, MDM4, MED12, MED23, MEN1, MET, MGA, MITF, MKLN1, MLH1, MLL, MLLT4, MOAP1, MORC4, MPL, MS4A1, MSH2, MSI1, MTOR, MYB, MYC, MYCL1, MYCN, MYD88, MYL6, MYO1B, MYO6, NAA15, NAA25, NAPIL2, NAPIL4, NCOA2, NCOA4, NCOR1, NEK9, NF1, NF2, NFE2L2, NFE2L3, NFKB2, NIPBL, NIT1, NKX3-1, NME4, NOTCH1, NOTCH2, NPM1, NR4A3, NRAS, NSD1, NTRK1, NUP214, NUP98, PALB2, PAX8, PBRM1, PCBP1, PCOLCE2, PDGFB, PHF6, PIK3CA, PIK3CB, PIK3R1, PIM1, PLAG1, PML, POLA2, POT1, PPARD, PPARG, PPM1D, PPP2R1A, PPP6C, PRKACA, PRKCI, PRPF40A, PSIP1, PTEN, PTH2, PTMS, PTN, PTPN11, RAB18, RAC1, RAF1, RANBP3L, RAPGEF6, RASA1, RB1, RBBP6, RBM10, RBM26, RC3H2, REL, RERE, RET, RFC4, RHEB, RHOA, RIMS2, RIT1, RNF111, RNF43, ROS1, RPL11, RPL5, RQCD1, RRAS2, RUNX1, RXRA, SARM1, SCAF11, SDHB, SDHD, SEC22A, SENP3, SENP8, SETD1B, SETD2, SF3A3, SF3B1, SFPQ, SIN3A, SKAP2, SMAD2, SMAD3, SMAD4, SMARCA4, SMARCB1, SMARCC2, SMO, SNCB, SOCS1, SOS1, SOX4, SOX9, SP3, SPEN, SPOP, SPSB2, SS18, STAG2, STK11, STK31, SUFU, SUFU, SUZ12, SYK, TAF1A, TARDBP, TAS2R30, TBL1XR1, TBX3, TCF12, TCF3, TCF7L2, TCL1A, TET2, TEX11, TFDP2, TFG, TGFBR2, THRAP3, TLX1, TM9SF1, TMCO2, TMED10, TMEM107, TMEM30A, TMPO, TNFAIP3, TNFRSF9, TNRC6B, TP53, TP53BP1, TPR, TRAF3, TRIM8, TRIP12, TSC1, TSC2, TTK, TTR, TUBA3C, U2AF1, UBE2D3, UBR5, UNC13C, UNKL, UPP1, USO1, USP28, USP6, USP9X, VHL, VN1R2, VPS33B, WAC, WDR33, WDR47, WRN, WT1, WWP1, XPO1, YOD1, ZC3H13, ZDHHC4, ZFHX3, ZFP36L1, ZFP36L2, ZGRF1, ZMYM3, ZMYM4, ZNF234, ZNF268, ZNF292, ZNF318, ZNF345, ZNF600, ZNF750, and/or ZNF800. In some embodiments, genetic biomarkers (e.g., genes having genetic alterations) associated with cancer that can be verified against white blood cell DNA isolated or obtained from a subject include tumor suppressor genes or oncogenes. In some embodiments, one or more codons and/or their surrounding splice sites can be tested according to methods disclosed herein. Exemplary codons of tumor suppressor genes and oncogenes which may be tested include, without limitation, one or more of the following codons and their surrounding splice sites: codons 16-18 of AKT1; codons 1304-1311, 1450-1459 of APC; codons 591-602 of BRAF; codons 51-58, 76-88 of CDKN2A; codons 31-39, 38-47 of CTNNB1; codons 856-868 of EGFR; codons 361-371, 464-473, 473-483, 498-507 of FBXW7; codons 250-256 of FGFR2; codons 199-208 of GNAS; codons 7-19 of HRAS; codons 7-14, 57-65, 143-148 of KRAS; codons 3-15, 54-63 of NRAS; codons 80-90, 343-348, 541-551, 1038-1050 of PIK3CA; codons 175-187 of PPP2R1A; codons 90-98, 125-132, 133-146, 145-154 of PTEN; and codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, 374-386 of TP53. In some embodiments, genetic biomarkers (e.g., genes having genetic alterations) associated with cancer that can be verified against white blood cell DNA isolated or obtained from a subject include one or more of the genetic biomarkers (e.g., genetic alterations) identified in Table 11 or Table 12. Testing DNA isolated or obtained from white blood cells may include amplification and/or sequencing of such DNA (e.g., using any of the methods described herein including, without limitation, Safe-SeqS methods). Using a technique such as Safe-SeqS provides corresponding advantages when testing DNA isolated or obtained from white blood cells as it does when testing cell-free DNA from the subject.

In some embodiments, a single genetic biomarker (e.g., genetic alteration) is verified against DNA isolated or obtained from white blood cells. In some embodiments, more than one genetic biomarkers (e.g., genetic alterations) are verified against DNA isolated or obtained from white blood cells. For example, 2, 3, 4, 5, 6, 7, 8, 9, 10 or more genetic biomarkers (e.g., genetic alterations) can be verified against DNA isolated or obtained from white blood cells using methods described herein. In some embodiments, one or more genetic biomarkers (e.g., genetic alterations) are verified against DNA isolated or obtained from white blood cells using a plurality of samples that are isolated or obtained from white blood cells. For example, one or more genetic biomarkers (e.g., genetic alterations) can be verified against DNA isolated or obtained from white blood cells by isolating DNA from two white blood cell samples isolated or obtained from the subject. Verifying genetic biomarkers (e.g., genetic alterations) against DNA isolated or obtained from white blood cells using a plurality of samples can increase the sensitivity of the testing, thus leading to a more accurate diagnosis.

In some embodiments, one or more genetic biomarkers (e.g., genetic alterations) can be determined to originate from a cancer cell in the subject (or not) by verifying the genetic biomarker(s) (e.g., genetic alteration(s)) against DNA isolated or obtained from white blood cells in the absence of additional diagnostic testing methods. In some embodiments, one or more genetic biomarkers (e.g., genetic alterations) can be determined to originate from a cancer cell in the subject (or not) by verifying the genetic biomarker(s) (e.g., genetic alteration(s)) against DNA isolated or obtained from white blood cells in combination with additional diagnostic testing methods. In some embodiments, such additional diagnostic testing methods can include one or more of the diagnostic testing methods described herein. In some embodiments, such additional diagnostic testing methods can include testing a protein biomarker (e.g., one or more of the protein biomarkers disclosed herein). In some embodiments, such additional diagnostic testing methods can include testing a protein biomarker (e.g., one or more of the protein biomarkers disclosed herein) at a certain threshold level. Examples of protein biomarkers that can be combined with white blood cell verification include, without limitation, carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3. Any of the variety of threshold levels for such protein biomarkers disclosed herein can be used in combination with white blood cell verification of genetic biomarker(s) (e.g., genetic alteration(s)) found in cell-free DNA. Exemplary and non-limiting threshold levels for certain protein biomarkers include: CA19-9 (>92 U/ml), CEA (>7,507 pg/ml), CA125 (>577 U/ml), AFP (>21,321 pg/ml), Prolactin (>145,345 pg/ml), HGF (>899 pg/ml), OPN (>157,772 pg/ml), TIMP-1 (>176,989 pg/ml), Follistatin (>1,970 pg/ml), G-CSF (>800 pg/ml), and CA15-3 (>98 U/ml). In some embodiments, threshold levels for protein biomarkers can be higher (e.g., about 10%, about 20%, about 30%, about 40%, about 50%, about 60%, about 70%, about 80%, about 90%, about 100%, or higher) than the exemplary threshold levels described herein. In some embodiments, threshold levels for protein biomarkers can be lower (e.g., about 10%, about 20%, about 30%, about 40%, about 50%, or lower) than the exemplary threshold levels described herein. In certain embodiments, a testing a single protein biomarker is combined with white blood cell verification of genetic biomarker(s) (e.g., genetic alteration(s))) found in cell-free DNA. In certain embodiments, testing more than one protein biomarker (two, three, four, five, six, seven, eight, nine, ten, eleven, or more protein biomarkers) is combined with white blood cell verification of genetic biomarker(s) (e.g., genetic alteration(s)) found in cell-free DNA.

In some embodiments, a plurality of genetic biomarkers (e.g., a panel of genetic biomarkers) is verified against DNA isolated or obtained from white blood cells. In some embodiments, a plurality of genetic biomarkers that is verified against DNA isolated or obtained from white blood cells includes one or more of NRAS, CTNNB1, PIK3CA, FBXW7, APC, EGFR, BRAF, CDKN2A, PTEN, FGFR2, HRAS, KRAS, AKT1, TP53, PPP2R1A, or GNAS. In some embodiments, a plurality of genetic biomarkers that is verified against DNA isolated or obtained from white blood cells includes each of NRAS, CTNNB1, PIK3CA, FBXW7, APC, EGFR, BRAF, CDKN2A, PTEN, FGFR2, HRAS, KRAS, AKT1, TP53, PPP2R1A, and GNAS. In some embodiments, one or more genetic biomarkers (e.g., genetic alterations) that include one or more of (e.g., each of) NRAS, CTNNB1, PIK3CA, FBXW7, APC, EGFR, BRAF, CDKN2A, PTEN, FGFR2, HRAS, KRAS, AKT1, TP53, PPP2R1A, or GNAS can be determined to originate from a cancer cell in the subject (or not) by verifying the genetic biomarker(s) against DNA isolated or obtained from white blood cells in combination with additional diagnostic testing methods. Such additional diagnostic testing methods include, without limitation, testing for the presence of one or more protein biomarkers and/or for the presence of aneuploidy. In some embodiments, the one or more protein biomarkers can be one or more of (e.g., each of) CA19-9, CEA, HGF, OPN, CA125, prolactin, TIMP-1, or myeloperoxidase (MPO). In some embodiments, the one or more protein biomarkers can be one or more of (e.g., each of) CA19-9, CEA, HGF, OPN, CA125, AFP, prolactin, TIMP-1, or CA15-3. In some embodiments, the one or more protein biomarkers can be one or more of (e.g., each of) CA19-9, CEA, HGF, OPN, CA125, AFP, prolactin, TIMP-1, follistatin, G-CSF, or CA15-3.

In some embodiments, a plurality of genetic biomarkers that is verified against DNA isolated or obtained from white blood cells includes one or more of KRAS, TP53, CDKN2A, or SMAD4. In some embodiments, a plurality of genetic biomarkers that is verified against DNA isolated or obtained from white blood cells includes each of KRAS, TP53, CDKN2A, and SMAD4. In some embodiments, one or more genetic biomarkers (e.g., genetic alterations) that include one or more of (e.g., each of) KRAS, TP53, CDKN2A, or SMAD4 can be determined to originate from a cancer cell in the subject (or not) by verifying the genetic biomarker(s) against DNA isolated or obtained from white blood cells in combination with additional diagnostic testing methods. Such additional diagnostic testing methods include, without limitation, testing for the presence of one or more protein biomarkers and/or for the presence of aneuploidy. In some embodiments, the one or more protein biomarkers can be one or more of (e.g., each of) CA19-9, CEA, HGF, or OPN.

In some embodiments, a plurality of genetic biomarkers that is verified against DNA isolated or obtained from white blood cells includes one or more of NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A. In some embodiments, a plurality of genetic biomarkers that is verified against DNA isolated or obtained from white blood cells includes each of NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A. In some embodiments, one or more genetic biomarkers (e.g., genetic alterations) that include one or more of (e.g., each of) NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A can be determined to originate from a cancer cell in the subject (or not) by verifying the genetic biomarker(s) against DNA isolated or obtained from white blood cells in combination with additional diagnostic testing methods. Such additional diagnostic testing methods include, without limitation, testing for the presence of one or more protein biomarkers and/or for the presence of aneuploidy (e.g., aneuploidy in one or more chromosomes or chromosomal arms that are associated with the presence of cancer). In some embodiments, the presence of aneuploidy can be detected on one or more of chromosomal arms 4p, 7q, 8q, or 9q.

In some embodiments, a plurality of genetic biomarkers that is verified against DNA isolated or obtained from white blood cells includes one or more of TP53, PIK3CA, FGFR3, KRAS, ERBB2, CDKN2A, MLL, HRAS, MET, or VHL. In some embodiments, a plurality of genetic biomarkers that is verified against DNA isolated or obtained from white blood cells includes each of TP53, PIK3CA, FGFR3, KRAS, ERBB2, CDKN2A, MLL, HRAS, MET, and VHL. In some embodiments, one or more genetic biomarkers (e.g., genetic alterations) that include one or more of (e.g., each of) TP53, PIK3CA, FGFR3, KRAS, ERBB2, CDKN2A, MLL, HRAS, MET, or VHL CDKN2A can be determined to originate from a cancer cell in the subject (or not) by verifying the genetic biomarker(s) against DNA isolated or obtained from white blood cells in combination with additional diagnostic testing methods. Such additional diagnostic testing methods include, without limitation, testing for the presence of one or more protein biomarkers and/or for the presence of aneuploidy (e.g., aneuploidy in one or more chromosomes or chromosomal arms that are associated with the presence of cancer). In some embodiments, the presence of aneuploidy can be detected on one or more of chromosomal arms 5q, 8q, or 9p.

In some embodiments, a sample isolated or obtained from the subject that is used to isolate or obtain white blood cell DNA can be the same as the sample isolated or obtained from the subject that is used for testing genetic biomarkers in cell-free DNA and/or protein biomarkers. For example, the sample can be a blood sample (e.g., whole blood), which blood sample is subsequently separated into a plasma fraction and a white blood cell fraction. Such separation can be achieved, for example, by density gradient centrifugation in which plasma is separated from white blood cells, which are typically found in the buffy coat. After such separation, DNA from the white blood cells in the buffy coat can be isolated and tested, while genetic biomarkers in cell-free DNA from the plasma fraction can also be isolated and tested. In some embodiments, the plasma fraction is allowed to clot in order to obtain a serum fraction. In some embodiments the sample is frozen, refrigerated, or otherwise stored prior to and/or after testing and/or fractionation. In some embodiments, one or more fractions from the sample are frozen, refrigerated, or otherwise stored prior to and/or after testing.

In some embodiments, a sample isolated or obtained from the subject that is used to isolate or obtain white blood cell DNA can be different from the sample isolated or obtained from the subject that is used for testing genetic biomarkers in cell-free DNA and/or protein biomarkers. For example, a first sample can be isolated or obtained from the subject, which first sample is used for testing genetic biomarkers in cell-free DNA and/or protein biomarkers. Prior to, simultaneously, or after the first sample is isolated or obtained, a second sample can be isolated or obtained from the subject, which second sample is used to isolate or obtain DNA from white blood cells for verifying one or more genetic biomarkers (e.g., genetic alterations) identified in cell-free DNA. The second sample can be fractionated as described herein (e.g., by density gradient centrifugation). In some embodiments the first and/or second sample (or fractions thereof) can be frozen, refrigerated, or otherwise stored prior to and/or after testing and/or fractionation.

In some embodiments, once a genetic biomarker (e.g., a genetic alteration) has been verified against DNA isolated or obtained from white blood cells and the genetic biomarker (e.g., a genetic alteration) is determined not to be present in DNA isolated from white blood cells (e.g., the genetic biomarker (e.g., a genetic alteration) is determined to originate from a cancer cell in the subject), the subject can undergo further diagnostic testing or increased monitoring (e.g., using one or more of the diagnostic testing and/or monitoring methods disclosed herein). In some embodiments, once a genetic biomarker (e.g., a genetic alteration) has been verified against DNA isolated or obtained from white blood cells and the genetic biomarker (e.g., a genetic alteration) is determined not to be present in DNA isolated from white blood cells (e.g., the genetic biomarker (e.g., a genetic alteration) is determined to originate from a cancer cell in the subject), the subject can be administered a therapeutic intervention (e.g., one or more of the therapeutic interventions disclosed herein).

Sample Classification

The present disclosure provides methods of identifying the presence of cancer in a subject based on one or more protein biomarkers (e.g., protein concentrations in whole blood or plasma). Various methods can be used to determine whether the subject has cancer and/or the likelihood that the subject has cancer. These methods involve various types of statistical techniques and methods described herein, including, e.g., a regression model, a logistic regression model, a neural network, a clustering model, principal component analysis, correlated component analysis, nearest neighbor classifier analysis, linear discriminant analysis, quadratic discriminant analysis, a support vector machine, a decision tree, Random Forest, a genetic algorithm, classifier optimization using bagging, classifier optimization using boosting, classifier optimization using the Random Subspace Method, a projection pursuit, and genetic programming and weighted voting, etc.

In some embodiments, a regression analysis can be used to determine whether a subject has cancer. The regression analysis can be performed on a panel of protein biomarkers, a panel of genetic biomarkers (e.g., mutations), and/or a panel includes both protein biomarkers and genetic biomarkers. In some embodiments, the regression analysis is performed on the $\Omega$ score for one or more mutations (e.g., top mutation) and/or a panel of protein biomarkers.

In some embodiments, the regression analysis is performed based on a mathematic model has the form:

$$V = \alpha + \Sigma \beta_i f(X_i)$$

In this form of the model, V is a value indicating the likelihood score that a subject has cancer. In some embodiments, the likelihood score is indicative of the probability that a test subject has cancer. $X_i$ represents the value of each biomarker (e.g., $\Omega$ score, protein concentrations in plasma etc.). $\beta_i$ is a coefficient for $f(X_i)$, which is a variable corresponds to value of the biomarker. The function $f(x)$ is a function that gives a corresponding value of x. In some embodiments, $f(x)=x$. Thus, the mathematic model can have the form $V=\alpha+\Sigma\beta_i X_i$. In some other embodiments, $f(x)$ may be a function for normalization or standardization. In some embodiments, the formula may include additional parameters to account for age, sex, and race category.

In some embodiments, V is a value indicating the likelihood score for a subject has cancer. In some embodiments, V is an actual probability (a number varying between 0 and 1). In other embodiments, V is a value from which a probability can be derived.

In some embodiments, the mathematical model is a regression model, for example, a logistic regression model or a linear regression model. The regression model can be used to test various sets of biomarkers.

In the case of linear regression models, the model can be used to analyze expression data from a test subject and to provide a result indicative of a quantitative measure of the test subject, for example, the likelihood that the subject has cancer.

In general, a linear regression equation is expressed as $$Y = \alpha + \beta_1 X_1 + \beta_2 X_2 + \ldots + \beta_k X_k + \varepsilon$$

Y, the dependent variable, indicates a quantitative measure of a biological feature (e.g., likelihood of having cancer or not having cancer). The dependent variable Y depends on k explanatory variables (the measured characteristic values for the biomarkers), plus an error term that encompasses various unspecified omitted factors. In the above-identified model, the parameter $\beta_1$ gauges the effect of the first explanatory variable $X_1$ on the dependent variable Y. $\beta_2$ gives the effect of the explanatory variable $X_2$ on Y.

A logistic regression model is a non-linear transformation of the linear regression. The logistic regression model is often referred to as the "logit" model and can be expressed as $$\ln[p/(1-p)] = \alpha + \beta_1 X_1 + \beta_2 X_2 + \ldots + \beta_k X_k + \varepsilon$$

where, $\alpha$ is a constant;

$\varepsilon$ is an error term;

ln is the natural logarithm, $\log_{(e)}$, where $e = 2.71828 \ldots$, p is the probability that the event Y occurs, p/(1-p) is the "odds,"

ln[p/(1-p)] is the log odds, or "logit."

It will be appreciated by those of skill in the art that α and ε can be folded into a single constant, and expressed as α. In some embodiments, a single term α is used, and ε is omitted. The "logistic" distribution is an S-shaped distribution function. The logit distribution constrains the estimated probabilities (p) to lie between 0 and 1.

In some embodiments, the logistic regression model is expressed as $$Y = \alpha + \Sigma \beta_i X_i$$

Here, Y is a value (e.g., a likelihood score) indicating whether the set of biomarkers for a given subject should classify with the case group (e.g., groups of subjects with cancer), as opposed to the control group (e.g., groups of subjects without cancer). The probability that the set of biomarkers classifies with the case group, as opposed to the control group, thus, the probability that the subject has cancer can be derived from Y. The higher the score, the higher the probability that the subject has cancer.

$X_i$ is the value of ith biomarker. In some embodiments, it can be the protein concentrations in plasma, gender, age, or a score derived from genetic markers (e.g., Ω score). $\beta_i$ is a logistic regression equation coefficient for the biomarker, α is a logistic regression equation constant that can be zero, and $\beta_i$ and α are the result of applying logistic regression analysis to the case group and the control group.

In some embodiments, the logistic regression model is fit by maximum likelihood estimation (MLE). The coefficients (e.g., α, β1, β2, . . . ) are determined by maximum likelihood. A likelihood is a conditional probability (e.g., P(Y|X), the probability of Y given X). The likelihood function (L) measures the probability of observing the particular set of dependent variable values (Y1, Y2, . . . , Yn) that occur in the sample data set. In some embodiments, it is written as the product of the probability of observing Y1, Y2, . . . , Yn:

$$L = \text{Prob}(Y1, Y2, \ldots, Yn) = \text{Prob}(Y1) * \text{Prob}(Y2) * \ldots \text{Prob}(Yn)$$

The higher the likelihood function, the higher the probability of observing the Ys in the sample. MLE involves finding the coefficients (α, β1, β2, . . . ) that make the log of the likelihood function (LL<0) as large as possible or −2 times the log of the likelihood function (−2LL) as small as possible. In MLE, some initial estimates of the parameters α, β1, β2, and so forth are made. Then, the likelihood of the data given these parameter estimates is computed. The parameter estimates are improved, the likelihood of the data is recalculated. This process is repeated until the parameter estimates remain substantially unchanged (for example, a change of less than 0.01 or 0.001). Examples of logistic regression and fitting logistic regression models are found in Hastie, The Elements of Statistical Learning, Springer, N.Y., 2001, pp. 95-100.

Once the logistic regression equation coefficients and the logistic regression equation constant are determined, the model can be readily applied to a test subject to obtain Y. In some embodiments, Y can be used to calculate probability (p) by solving the function $Y = \ln(p/(1-p))$.

In some embodiments, explanatory variables are normalized or standardized before fitting into the model. Standardized coefficients (or beta coefficients) are the estimates resulting from a regression analysis that have been standardized so that the variances of dependent and explanatory variables are 1. Therefore, standardized coefficients represent how many standard deviations a dependent variable will change, per standard deviation increase in the explanatory variable. For univariate regression, the absolute value of the standardized coefficient equals the correlation coefficient. Standardization of the coefficient is usually performed to identify which of the explanatory variables have a greater effect on the dependent variable in a multiple regression analysis. In some embodiments, variables are standardized or normalized before fitting into a logistic regression model. Standardized logistic regression coefficients (or standardized beta coefficients) are the estimates resulting from performing a logistic regression analysis on variables that have been standardized. In some embodiments, only explanatory variables are standardized, and in some other embodiments, only dependent variables are standardized. Further, in some embodiments, both explanatory variables and dependent variables are standardized. In some embodiments, the standardized regression coefficient equals the corresponding unstandardized coefficient multiplied by the ratio $\text{std}(X_i)/\text{std}(Y)$, where "std" denotes standard deviation.

In some embodiments, the omega score (e.g., the omega score for the top mutation) can be used as an explanatory variable in a logistic regression. In some embodiments, the logistic regression can include one or more other explanatory variables (e.g., concentrations of proteins). In some embodiments, the protein biomarkers can be selected based on Mann-Whitney-Wilcoxon test. In some embodiments, the selected protein biomarkers have higher median values in cancer samples than in normal samples. In some embodiments, a forward selection is used to select explanatory variables from all biomarkers (including genetic biomarkers and protein biomarkers).

Applying a mathematical model to the data can generate one or more classifiers. The classifiers are mathematical model with appropriate parameters (e.g., β coefficient in regression model). These parameters can be determined by applying a mathematical model to a training data set, e.g., a data set that includes both control subjects and a group of subjects that have cancer.

A classifier can be evaluated for its ability to properly characterize each subject in a dataset (e.g., a training dataset or a validation dataset) using methods known to a person of ordinary skill in the art. Various statistical criteria can be used, for example, area under the curve (AUC), percentage of correct predictions, sensitivity, and/or specificity. In some embodiments, the classifier is evaluated by cross validation, Leave One OUT Cross Validation (LOOCV), n-fold cross validation, and jackknife analysis. In some embodiments, each classifier is evaluated for its ability to properly characterize those subjects in a dataset not used to generate the classifier (a "test dataset").

In some embodiments, the method used to evaluate the classifier for its ability to properly characterize each subject in a dataset is a method that evaluates the classifier's sensitivity (true positive fraction) and 1-specificity (true negative fraction). In some embodiments, the method used to test the classifier is a Receiver Operating Characteristic (ROC), which provides several parameters to evaluate both the sensitivity and the specificity of the result of the equation generated. In some embodiments, the ROC area (area under the curve) is used to evaluate the equations. A ROC area greater than 0.5, 0.6, 0.7, 0.8, 0.9 is preferred. A perfect ROC area score of 1.0 is indicative of both 100% sensitivity and 100% specificity. In some embodiments, classifiers are selected on the basis of the evaluation score. In some embodiments, the evaluation scoring system used is a receiver operating characteristic (ROC) curve score determined by the area under the ROC curve. In some embodiments, classifiers with scores of greater than 0.95, 0.9, 0.85, 0.8, 0.7, 0.65, 0.6, 0.55, or 0.5 are chosen. In some embodiments, where specificity is important to the use of the classifier, a sensitivity threshold can be set, and classifiers ranked on the basis of the specificity are chosen. For example, classifiers with a cutoff for specificity of greater than 0.95, 0.9, 0.85, 0.8, 0.7, 0.65, 0.6, 0.55 0.5 or 0.45 can be chosen. Similarly, the specificity threshold can be set, and classifiers ranked on the basis of sensitivity (e.g., greater than 0.95, 0.9, 0.85, 0.8, 0.7, 0.65, 0.6, 0.55 0.5 or 0.45) can be chosen. Thus, in some embodiments, only the top ten ranking classifiers, the top twenty ranking classifiers, or the top one hundred ranking classifiers are selected. The ROC curve can be calculated by various statistical tools, including, but not limited to, Statistical Analysis System (SAS®), R, and COR Express® statistical analysis software.

As would be understood by a person of ordinary skill in the art, the utility of the combinations and classifiers determined by a mathematical model will depend upon some characteristics (e.g., race, age group, gender, medical history) of the population used to generate the data for input into the model. One can select the individually identified biomarkers or subsets of the individually identified genes, and test all possible combinations of the selected biomarkers to identify useful combinations of biomarker sets.

In some embodiment, a subject's likelihood score (e.g., the Y value in a logistic regression) can be used to determine whether a subject is likely to have cancer. Thus, if the likelihood score is greater than a pre-determined reference threshold, the subject is likely to have cancer. In some embodiment, if the likelihood s score is less than a reference threshold, the subject is not likely to have cancer. A person skilled in the art will appreciate that the appropriate reference threshold for each classifier can be different, and can be optimized for various statistical measures (e.g., sensitivity, specificity, percentage of correct predictions). In some embodiments, the reference threshold is determined by experiments or in a clinical trial.

In some embodiments, multiple classifiers are created that are satisfactory for the given purpose (e.g., all have sufficient AUC and/or sensitivity and/or specificity). In some embodiments, a formula is generated that utilizes more than one classifier. For example, a formula can be generated that utilizes classifiers in series. Other possible combinations and weightings of classifiers would be understood and are encompassed herein.

In some embodiments, the probability that a subject has cancer can be derived from the likelihood score. Thus, if the probability is greater than a pre-determined threshold, for example, 0.1, 0.2, 0.3, 0.4, 0.5, 0.6, 0.7, 0.8, 0.9, the subject will be administered with a treatment for cancer. In some embodiments, if the probability is less than a pre-determined threshold, for example, 0.1, 0.2, 0.3, 0.4, 0.5, 0.6, 0.7, 0.8, 0.9, the subject will not be administered with a treatment for cancer. In some embodiments, the pre-determined threshold for treatment is 0.4, 0.5, or 0.6, and the pre-determined threshold for not treating, or for discontinuation of treatment, is 0.4, 0.5, or 0.6. In some embodiments, the pre-determined threshold is determined by experiments or in a clinical trial.

A person skilled in the art will also appreciate that the sensitivity and the specificity of the method depend on the reference threshold (or the cut-off point). When the reference threshold is raised, the sensitivity will decrease, but the specificity will increase. In some embodiments, the reference threshold can be optimized for the sensitivity, the specificity, or the percentage of correct predictions.

Determining Tissue of Origin

The present disclosure provides methods of determining cancer type, or the origin of a cancer cell or a tumor cell. Mathematical models can be applied to various biomarkers as described herein (e.g., protein concentrations for various biomarkers, genetic mutations in various biomarkers).

Mathematical models useful in accordance with the disclosure include those using both supervised and unsupervised learning techniques. In some embodiments, the mathematical model chosen uses supervised learning in conjunction with a training dataset to evaluate each possible combination of biomarkers. Various mathematical models can be used, for example, a regression model, a logistic regression model, a neural network, a clustering model, principal component analysis, correlated component analysis, nearest neighbor classifier analysis, linear discriminant analysis, quadratic discriminant analysis, a support vector machine, a decision tree, Random Forest, a genetic algorithm, classifier optimization using bagging, classifier optimization using boosting, classifier optimization using the Random Subspace Method, a projection pursuit, and genetic programming and weighted voting, etc.

In some embodiments, a supervised learning model is used to determine the origin of a cancer cell or a tumor cell. The supervised learning model refers to a model that learns a function that maps an input to an output based on example input-output pairs. It can infer a function from labeled training data consisting of a set of training examples. In supervised learning, each example is a pair consisting of an input object (typically a vector, e.g., a vector of protein biomarkers) and a desired output value (also called the supervisory signal, e.g., cancer type or tissue of origin). A supervised learning algorithm analyzes the training data and produces an inferred function, which can be used for mapping the biomarkers obtained from a test subject. Many supervised machine learning methods can be used. The methods include, but are not limited to, Support Vector Machines, regression analysis, linear regression, logistic regression, naive Bayes, linear discriminant analysis, decision trees, k-nearest neighbor algorithm, neural networks (e.g., Multilayer perceptron).

In some embodiments, an unsupervised learning model is used to determine the origin of a cancer cell or a tumor cell. The unsupervised machine learning refers to the machine learning task of inferring a function that describes the structure of "unlabeled" data (i.e. data that has not been classified or categorized). This is performed under the assumption that relevant biomarkers will have more similarity if the samples have the same origin. The unsupervised machine learning can identify these shared characteristics and apply these models to biomarkers obtained from a test subject, thereby determining the origin of a cancer cell or a tumor cell in the subject. Many unsupervised machine learning methods can be used. The methods include, but are not limited to, clustering (e.g., k-means clustering, mixture model clustering, and hierarchical clustering, etc.), anomaly detection, unsupervised neural networks (e.g., autoencoders, deep belief nets, Hebbian learning, generative adversarial networks, and self-organizing map, etc.).

In some embodiments, Random Forest is used. Random Forest refers to a learning method for classification, regression and other tasks, that operate by constructing a multitude of decision trees at training time and outputting the class that is the mode of the classes (classification) or mean prediction (regression) of the individual trees. Random Forest can be implemented by various programs, e.g., by the Random Forest package (Liaw, Andy, and Matthew Wiener. "Classification and regression by randomForest." R news 2.3

(2002): 18-22). In some embodiments, Random Forest identifies the presence of cancer in a subject based on one or more protein biomarkers (e.g., protein concentrations in whole blood or plasma). In some embodiments, more than ten rounds of 10-fold cross validation can be performed.

In some embodiments, support vector machines (SVM) can be used to determine tissue of origin. SVM starts with a set of training examples, each marked as belonging to one or the other of two categories (e.g., cancer type). The SVM training algorithm builds a model that assigns new examples to one category or the other, making it a non-probabilistic binary linear classifier (e.g., cancer from a particular origin, and cancer that is not from the particular origin). An SVM model is a representation of the examples as points in space, mapped so that the examples of the separate categories are divided by a clear gap that is as wide as possible.

These mathematical models can be applied to various biomarkers, or panels of biomarkers (e.g., protein biomarkers) as described herein to determine the origin of the cancer cell. In some embodiments, these methods are only applied to subjects who have been predicted to have cancer.

In some embodiments, once a subject is determined to have or is determined as being likely to have cancer, a tissue of origin for the cancer is determined as shown in FIG. 68. For example, a decision can be made at each branch of the tree shown in FIG. 68, and once a terminus is reached (e.g. there are no more decisions to be made), the tissue of origin can be predicted or determined as shown. The tree shown in FIG. 68 provides a framework for a practitioner to predict or determine the tissue of origin of a cancer (e.g., breast cancer, colorectal cancer, liver cancer, lung cancer, ovarian cancer, pancreatic cancer, and gastrointestinal cancer).

The tree shown in FIG. 68 is exemplary and non-limiting. For example, at some decision points, the level of a protein biomarker (e.g. one or more protein biomarkers) can be determined (e.g., the level of a protein biomarker present in a sample obtained from a subject), and the level of that protein biomarker(s) can be compared to the level indicated on the tree shown in FIG. 68. In some embodiments, the level of a protein biomarker is determined (e.g., the level of a protein biomarker present in a sample obtained from a subject), and the level of that protein biomarker is compared to the level that differs from the level indicated on the tree shown in FIG. 68. In some embodiments, the different level of a protein biomarker (e.g. one or more of the protein biomarkers) on the tree shown in FIG. 68 is about 10% different from (e.g., about 10% greater than or 10% less than), about 15% different from (e.g., about 15% greater than or 15% less than), about 20% different from (e.g., about 20% greater than or 20% less than), about 25% different from (e.g., about 25% greater than or 25% less than), about 30% different from (e.g., about 30% greater than or 30% less than), about 35% different from (e.g., about 35% greater than or 35% less than), about 40% different from (e.g., about 40% greater than or 40% less than), about 45% different from (e.g., about 45% greater than or 45% less than), about 50% different from (e.g., about 50% greater than or 50% less than) the level of that protein biomarker shown at one or more decision points on the tree shown in FIG. 68. At some decision points, the gender (e.g., the biological gender) of the subject is determined and compared to the gender at one or more decision points indicated on the tree shown in FIG. 68. At some decision points, the subject can be determined to be a woman. At some decision points, the subject can be determined to be a man.

In some embodiments, once a subject is determined to have or is determined as being likely to have cancer, a tissue of origin for the cancer is determined according to the list of rules shown in FIG. 69 and the table below. For example, the level of a protein biomarker (e.g. one or more protein biomarkers) can be determined (e.g., the level of a protein biomarker present in a sample obtained from a subject), and the level of that protein biomarker(s) can be compared to the level indicated in the rules shown in FIG. 69 and the table below. As one non-limiting example, the rule [condition=CA125>102.76 & sFas<=830.345 & gender % in % c('F'), prediction=ovarian] means that if a woman (% in % c('F')) has CA125>102.76, and sFas<=830.345, then the woman has or is predicted to have ovarian cancer. A person skilled in the art will be able to detect the level of one or more protein biomarkers in a subject and/or determine the gender (e.g., biological gender) of a subject, and determine that the subject has or is likely to have a cancer type listed on FIG. 69. In some embodiments, once a subject is determined to have or is determined as being likely to have cancer, a tissue of origin for the cancer is determined to be colorectal when the level of one or more protein biomarkers in a subject and/or the gender (e.g., biological gender) of a subject does not follow any of the specific rules shown in FIG. 69 and the table below. In some embodiments, the level of a protein biomarker is determined (e.g., the level of a protein biomarker present in a sample obtained from a subject), and the level of that protein biomarker is compared to the level that differs from the level indicated in the rules shown in FIG. 69 and the table below. In some embodiments, the different level of a protein biomarker (e.g. one or more of the protein biomarkers) in the rules shown in FIG. 69 is about 10% different from (e.g., about 10% greater than or 10% less than), about 15% different from (e.g., about 15% greater than or 15% less than), about 20% different from (e.g., about 20% greater than or 20% less than), about 25% different from (e.g., about 25% greater than or 25% less than), about 30% different from (e.g., about 30% greater than or 30% less than), about 35% different from (e.g., about 35% greater than or 35% less than), about 40% different from (e.g., about 40% greater than or 40% less than), about 45% different from (e.g., about 45% greater than or 45% less than), about 50% different from (e.g., about 50% greater than or 50% less than) the level of that protein biomarker shown at one or more decision points in the rules shown in FIG. 69 and the table below. In some embodiments, the gender (e.g., the biological gender) of the subject is determined and compared to the gender in one or more of the rules shown in FIG. 69 and the table below. In some embodiments, the subject can be determined to be a woman (e.g., "gender % in % c('F')"). In some embodiments, the subject can be determined to be a man (e.g., "gender % in % c('M')"). For the table below, exemplary and non-limiting rules and cancer type predictions are indicated. "Else" indicates that if none of the other exemplary rules are met, the cancer can be predicted to be colorectal.

| Exemplary Rules | Prediction |
| --- | --- |
| CA125 > 102.76 & sFas <= 830.345 & gender % in % c('F') | Ovarian |
| CA199 > 37.65 & CYFRA211 <= 14640.67 & CD44 > 15.67 & Midkine > 289.485 & PAR > 4580.45 & sHER2 > 6935.375 | Pancreatic |
| AFP > 17774.49 & TIMP2 <= 61777.34 & Galectin3 <= 16.72 & Mesothelin <= 27.71 | Liver |
| CA199 <= 71.53 & Leptin > 12927.9 & sFas > 411.525 & TIMP1 <= 59700.835 & TIMP2 <= 37667.97 & gender % in % c('F') | Breast |

| Exemplary Rules | Prediction |
|---|---|
| CA125 <= 104.41 & CA153 <= 16.22 & CA199 <= 117.275 & HGF <= 465.81 & Leptin <= 7244.265 & SHBG > 29.53 | CRC |
| Prolactin > 37214.25 & sFas > 1046.435 & TIMP 1 <= 93517.645 & DKK1 <= 1.095 & sHER2 <= 6054.825 & gender % in % c('M') | Lung |
| CA153 <= 15.285 & IL8 > 39.235 & IL8 <= 163.64 & sFas <= 1098.015 & Myeloperoxidase > 19.325 & sHER2 <= 5172.43 | Stomach/ Esophageal |
| AFP <= 2867.07 & CA153 > 9.505 & Prolactin > 37962.925 & sFas > 688.47 & Myeloperoxidase <= 11.935 & Thrombospondin2 <= 3273.685 | Lung |
| AFP <= 36492.58 & CA125 <= 10.475 & Prolactin <= 275955.405 & sFas <= 1351.39 & AXL > 1999.77 & sHER2 <= 10172.47 | CRC |
| CEA <= 1892.955 & sFas <= 1076.05 & TIMP2 > 40306.87 & CD44 <= 26.915 & sHER2 <= 9959.43 & gender % in % c('F') | Ovarian |
| Leptin <= 5186.325 & OPN > 94670.57 & TIMP1 > 75617.725 & SHBG <= 141.115 & sHER2 <= 8369.265 & Thrombospondin2 <= 17040.89 | Stomach/ Esophageal |
| AFP <= 40375.115 & CA153 <= 20.835 & CEA > 3057.27 & Leptin <= 237948.935 & OPN <= 250628.405 & TIMP2 <= 68136.905 | CRC |
| AFP <= 299906.424 & sFas > 1100.55 & TIMP1 <= 85064.65 & TIMP2 <= 53195.905 & DKK1 <= 1.285 & gender % in % c('F') | Breast |
| Leptin > 8839.01 & sFas <= 1745.34 & TIMP1 > 63205.505 & CD44 <= 19.735 & Mesothelin <= 39.705 & gender % in % c('F') | CRC |
| AFP <= 5369.16 & CA153 <= 16.21 & CEA > 1374.755 & Myeloperoxidase <= 368.56 & Midkine <= 4401.495 & sHER2 <= 10713.16 | CRC |
| TIMP2 <= 61631.2 & Myeloperoxidase > 23.725 & SHBG <= 96.985 & DKK1 <= 1.335 & Midkine <= 348.515 & sHER2 <= 5523.84 | Stomach/ Esophageal |
| CA125 <= 56.21 & HGF <= 928.54 & Prolactin > 65977.55 & sFas <= 2849.195 & Mesothelin > 13.68 & AXL <= 2093.75 | Lung |
| CA199 <= 36.795 & CEA <= 115717.2 & HE4 <= 15657.71 & Leptin > 15287.95 & sFas > 716.205 & gender % in % c('F') | Breast |
| Else | CRC |

For FIGS. 68 and 69 and the table shown above, the units of certain protein biomarkers are indicated in the key below:

| | |
|---|---|
| CA19-9 | U/ml |
| CEA | pg/ml |
| CA125 | U/ml |
| AFP | pg/ml |
| Prolactin | Ppg/ml |
| HGF | pg/ml |
| OPN | pg/ml |
| TIMP-1 | pg/ml |
| TIMP-2 | pg/ml |
| Mesothelin | ng/ml |
| Midkine | pg/ml |
| Kallikrein-6 | pg/ml |
| CD44 | ng/ml |
| Angiopoietin-2 | pg/ml |
| Endoglin | pg/ml |
| Follistatin | pg/ml |
| G-CSF | pg/ml |
| GDF15 | ng/ml |
| DKK1 | ng/ml |
| NSE | ng/ml |
| OPG | ng/ml |
| AXL | pg/ml |
| sHER2/sEGFR2/sErbB2 | pg/ml |
| Thrombospondin-2 | pg/ml |
| sEGFR | pg/ml |
| PAR | pg/ml |
| sPECAM-1 | pg/ml |
| CA 15-3 | U/ml |
| Leptin | pg/ml |
| IL-6 | pg/ml |
| IL-8 | pg/ml |
| sFas | pg/ml |
| FGF2 | pg/ml |
| CYFRA 21-1 | pg/ml |
| HE4 | pg/ml |
| TGFa | pg/ml |
| Galectin-3 | ng/ml |
| Myeloperoxidase | ng/ml |
| SHBG | nM |

Detecting Genetic Biomarkers

Any of a variety of techniques can be used to detect the presence of one or more genetic biomarkers (e.g., mutations) present in a sample (e.g., a cervical, endometrial, urine, saliva, ctDNA, blood, serum, and/or plasma sample) obtained from a subject. Non-limiting examples of such techniques include a PCR-based multiplex assay, a digital PCR assay, a droplet digital PCR (ddPCR) assay, a PCR-based singleplex PCR assay, a Sanger sequencing assay, a next-generation sequencing assay, a quantitative PCR assay, a ligation assay, and a microarray assay. Those of ordinary skill in the art will be aware of other suitable techniques for detecting the presence of one or more genetic biomarkers (e.g., mutations) present in a sample obtained from a subject.

In some embodiments of methods provided herein, the presence of one or more genetic biomarkers (e.g., mutations) present in a sample (e.g., a cervical, endometrial, urine, saliva, ctDNA, blood, serum, and/or plasma sample) obtained from a subject is detected using a method that can increase the sensitivity of massively parallel sequencing instruments with an error reduction technique. For example, such techniques can permit the detection of rare mutant alleles in a range of 1 mutant template among 100 to 1,000,000 wild-type templates (e.g., 500 to 1,000,000 wild-type templates). In some embodiments, such techniques can permit the detection of rare mutant alleles when they are present as a low fraction of the total number of templates (e.g., when rare mutant alleles when are present at a fraction of less than about 1%, less than about 0.1%, less than about 0.01%, less than about 0.001%, less than about 0.00001% of total templates, or lower, or any fraction between these exemplary fractions). In some embodiments, the presence of one or more genetic biomarkers (e.g., mutations) present in a sample obtained from a subject is detected by amplifying DNA (e.g., DNA obtained from cells in a sample or cell-free DNA) to form families of amplicons in which each member of a family is derived from a single template molecule in the cell-free DNA, wherein each member of a family is marked by a common oligonucleotide barcode, and wherein each family is marked by a distinct oligonucleotide barcode. For example, the presence of one or more genetic biomarkers (e.g., mutations) present in a sample obtained from a subject can be detected by molecularly assigning a unique identifier (UID) to each template molecule, amplifying each uniquely tagged template molecule to create UID-families, and redundantly sequencing the amplification products. In some embodiments, the oligonucleotide barcode is introduced into the template molecule by a step of amplifying with a population of primers that collectively contain a plurality of oligonucleotide barcodes. In some embodiments, the oligonucleotide barcode is endogenous to the template molecule, and an adapter including a DNA synthesis priming site is ligated to an end of the template molecule adjacent to the oligonucleotide barcode. See, e.g., Kinde I, Wu J, Papadopoulos N, Kinzler K W, Vogelstein B (2011) Detection and quantification of rare mutations with massively parallel sequencing. Proc Natl Acad Sci USA 108:9530-9535, the contents of which are incorporated herein by reference in their entirety.

In some embodiments of methods provided herein, the presence of one or more genetic biomarkers (e.g., mutations) present in a sample (e.g., a cervical, endometrial, or plasma sample) obtained from a subject is detected using sequencing technology (e.g., a next-generation sequencing technology). A variety of sequencing technologies are known in the art. For example, a variety of technologies for detection and characterization of circulating tumor DNA in cell-free DNA is described in Haber and Velculescu, Blood-Based Analyses of Cancer: Circulating Tumor Cells and Circulating Tumor DNA, Cancer Discov., June; 4(6):650-61. doi: 10.1158/2159-8290.CD-13-1014, 2014, incorporated herein by reference in its entirety. Non-limiting examples of such techniques include SafeSeqs (Kinde et. al, Detection and quantification of rare mutations with massively parallel sequencing, Proc Natl Acad Sci USA; 108, 9530-5, 2011), OnTarget (Forshew et al., Noninvasive identification and monitoring of cancer mutations by targeted deep sequencing of plasma DNA, Sci Transl Med; 4:136ra68, 2012), and TamSeq (Thompson et al., Winnowing DNA for rare sequences: highly specific sequence and methylation based enrichment. PLoS ONE, 7:e31597, 2012), each of which is incorporated herein by reference in its entirety. In some embodiments, the presence of one or more mutations present in a sample obtained from a subject is detected using droplet digital PCR (ddPCR), a method that is known to be highly sensitive for mutation detection. In some embodiments, the presence of one or more mutations present in a sample obtained from a subject is detected using other sequencing technologies, including but not limited to, chain-termination techniques, shotgun techniques, sequencing-by-synthesis methods, methods that utilize microfluidics, other capture technologies, or any of the other sequencing techniques known in the art that are useful for detection of small amounts of DNA in a sample (e.g., ctDNA in a cell-free DNA sample).

In some embodiments, the presence of one or more genetic biomarkers (e.g., mutations) present in a sample (e.g., a cervical, endometrial, urine, saliva, ctDNA, blood, serum, and/or plasma sample) obtained from a subject is detected using array-based methods. For example, the step of detecting a genetic alteration (e.g., one or more genetic alterations) in cell-free DNA can be performed using a DNA microarray. In some embodiments, a DNA microarray can detect one more of a plurality of genetic biomarkers (e.g., cancer cell mutations). In some embodiments, cell-free DNA is amplified prior to detecting the genetic biomarker (e.g., the genetic alteration). Non-limiting examples of array-based methods that can be used in any of the methods described herein, include: a complementary DNA (cDNA) microarray (Kumar et al. (2012) J. Pharm. Bioallied Sci. 4(1): 21-26; Laere et al. (2009) Methods Mol. Biol. 512: 71-98; Mackay et al. (2003) Oncogene 22:2680-2688; Alizadeh et al. (1996) Nat. Genet. 14:457-460), an oligonucleotide microarray (Kim et al. (2006) Carcinogenesis 27(3): 392-404; Lodes et al. (2009) PLoS One 4(7): e6229), a bacterial artificial chromosome (BAC) clone chip (Chung et al. (2004) Genome Res. 14(1): 188-196; Thomas et al. (2005) Genome Res. 15(12): 1831-1837), a single-nucleotide polymorphism (SNP) microarray (Mao et al. (2007) Curr. Genomics 8(4): 219-228; Jasmine et al. (2012) PLoS One 7(2): e31968), a microarray-based comparative genomic hybridization array (array-CGH) (Beers and Nederlof (2006) Breast Cancer Res. 8(3): 210; Pinkel et al. (2005) Nat. Genetics 37:S11-S17; Michels et al. (2007) Genet. Med. 9:574-584), a molecular inversion probe (MIP) assay (Wang et al. (2012) Cancer Genet 205(7-8): 341-55; Lin et al. (2010) BMC Genomics 11:712). In some embodiments, the cDNA microarray is an Affymetrix microarray (Irizarry (2003) Nucleic Acids Res 31:e15; Dalma-Weiszhausz et al. (2006) Methods Enzymol. 410:3-28), a NimbleGen microarray (Wei et al. (2008) Nucleic Acids Res 36(9): 2926-2938; Albert et al. (2007) Nat. Methods 4:903-905), an Agilent microarray (Hughes et al. (2001) Nat. Biotechnol. 19(4): 342-347), or a BeadArray array (Liu et al. (2017) Biosens Bioelectron 92: 596-601). In some embodiments, the oligonucleotide microarray is a DNA tiling array (Mockler and Ecker (2005) Genomics 85(1): 1-15; Bertone et al. (2006) Genome Res 16(2): 271-281). Other suitable array-based methods are known in the art.

In some embodiments, once a subject has been determined to have a cancer (e.g., an ovarian cancer, an endometrial cancer, a bladder cancer, or an UTUC), the subject may be additionally monitored or selected for increased monitoring. In some embodiments, methods provided herein can be used to select a subject for increased monitoring at a time period prior to the time period when conventional techniques are capable of diagnosing the subject with an early-stage cancer. For example, methods provided herein for selecting a subject for increased monitoring can be used when a subject has not been diagnosed with cancer by conventional methods and/or when a subject is not known to harbor a cancer. In some embodiments, a subject selected for increased monitoring can be administered a diagnostic test (e.g., any of the diagnostic tests disclosed herein) at an increased frequency compared to a subject that has not been selected for increased monitoring. For example, a subject selected for increased monitoring can be administered a diagnostic test at a frequency of twice daily, daily, bi-weekly, weekly, bi-monthly, monthly, quarterly, semi-annually, annually, or any at frequency therein. In some embodiments, a subject selected for increased monitoring can be administered a one or more additional diagnostic tests compared to a subject that has not been selected for increased monitoring. For example, a subject selected for increased monitoring can be administered two diagnostic tests, whereas a subject that has not been selected for increased monitoring is administered only a single diagnostic test (or no diagnostic tests). In some embodiments, a subject that has been selected for increased monitoring can also be selected for further diagnostic testing. Once the presence of a cancer cell has been identified (e.g., by any of the variety of methods disclosed herein), it may be beneficial for the subject to undergo both increased monitoring (e.g., to assess the progression of the tumor or cancer in the subject and/or to assess the development of additional genetic biomarkers (e.g., cancer cell mutations) and/or aneuploidy), and further diagnostic testing (e.g., to determine the size and/or exact location of the tumor harboring the cancer cell). In some embodiments, a therapeutic intervention is administered to the subject that is selected for increased monitoring after a genetic biomarker (e.g., a cancer cell mutation) and/or aneuploidy is detected. Any of the therapeutic interventions disclosed herein or known in the art can be administered. For example, a subject that has been selected for increased monitoring can be further monitored, and a therapeutic intervention can be administered if the presence of the cancer cell is maintained throughout the increased monitoring period. Additionally or alternatively, a subject that has been selected for increased monitoring can be administered a therapeutic intervention, and further monitored as the therapeutic intervention progresses. In some embodiments, after a subject that has been selected for increased monitoring has been administered a therapeutic intervention, the increased monitoring will reveal one or more genetic biomarkers (e.g., one or more additional cancer cell mutations) and/or aneuploidy. In some embodiments, such one or more genetic biomarkers (e.g., one or more additional cancer cell mutations) and/or aneuploidy will provide cause to administer a different therapeutic intervention (e.g., a resistance mutation may arise in a cancer cell during the therapeutic intervention, which cancer cell harboring the resistance mutation is resistance to the original therapeutic intervention).

In some embodiments, once a subject has been determined to have a cancer (e.g., an ovarian cancer, an endometrial cancer, a bladder cancer, or an UTUC), the subject may be administered further tests or selected for further diagnostic testing. In some embodiments, methods provided herein can be used to select a subject for further diagnostic testing at a time period prior to the time period when conventional techniques are capable of diagnosing the subject with an early-stage cancer. For example, methods provided herein for selecting a subject for further diagnostic testing can be used when a subject has not been diagnosed with cancer by conventional methods and/or when a subject is not known to harbor a cancer. In some embodiments, a subject selected for further diagnostic testing can be administered a diagnostic test (e.g., any of the diagnostic tests disclosed herein) at an increased frequency compared to a subject that has not been selected for further diagnostic testing. For example, a subject selected for further diagnostic testing can be administered a diagnostic test at a frequency of twice daily, daily, bi-weekly, weekly, bi-monthly, monthly, quarterly, semi-annually, annually, or any at frequency therein. In some embodiments, a subject selected for further diagnostic testing can be administered a one or more additional diagnostic tests compared to a subject that has not been selected for further diagnostic testing. For example, a subject selected for further diagnostic testing can be administered two diagnostic tests, whereas a subject that has not been selected for further diagnostic testing is administered only a single diagnostic test (or no diagnostic tests). In some embodiments, the diagnostic testing method can determine the presence of the same type of cancer as the cancer that was original detected. Additionally or alternatively, the diagnostic testing method can determine the presence of a different type of cancer as the cancer that was original detected. In some embodiments, the diagnostic testing method is a scan. In some embodiments, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan. In some embodiments, the diagnostic testing method is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, a pelvic exam, a positron emission tomography and computed tomography (PET-CT) scan. In some embodiments, a subject that has been selected for further diagnostic testing can also be selected for increased monitoring. Once the presence of a cancer cell has been identified (e.g., by any of the variety of methods disclosed herein), it may be beneficial for the subject to undergo both increased monitoring (e.g., to assess the progression of the tumor or cancer in the subject and/or to assess the development of additional genetic biomarkers (e.g., additional cancer cell mutations) and/or aneuploidy), and further diagnostic testing (e.g., to determine the size and/or exact location of the tumor harboring the cancer cell). In some embodiments, a therapeutic intervention is administered to the subject that is selected for further diagnostic testing after a genetic biomarker (e.g., a cancer cell mutation) and/or aneuploidy is detected. Any of the therapeutic interventions disclosed herein or known in the art can be administered. For example, a subject that has been selected for further diagnostic testing can be administered a further diagnostic test, and a therapeutic intervention can be administered if the presence of the cancer cell is confirmed. Additionally or alternatively, a subject that has been selected for further diagnostic testing can be administered a therapeutic intervention, and can be further monitored as the therapeutic intervention progresses. In some embodiments, after a subject that has been selected for further diagnostic testing has been administered a therapeutic intervention, the additional testing will reveal one or more additional genetic biomarkers (e.g., cancer cell mutations) and/or aneuploidy. In some embodiments, such one or more additional genetic biomarkers (e.g., cancer cell mutations) and/or aneuploidy will provide cause to administer a different therapeutic intervention (e.g., a resistance mutation may arise in a cancer cell during the therapeutic intervention, which cancer cell harboring the resistance mutation is resistance to the original therapeutic intervention).

In some embodiments, the presence of one or more genetic biomarkers (e.g., mutations) present in a sample (e.g., a cervical, endometrial, urine, saliva, ctDNA, blood, serum, and/or plasma sample) obtained from a subject is detected using any of the variety of bottleneck sequencing system methods described in International Patent Application Publication Number WO 2017/132438, the contents of which are incorporated by reference herein in their entirety. Bottleneck Sequencing System (BotSeqS) is a next-generation sequencing method that simultaneously quantifies rare somatic point mutations across the mitochondrial and nuclear genomes. BotSeqS combines molecular barcoding with a simple dilution step immediately prior to library amplification. BotSeqS can be used to show age and tissue-dependent accumulations of rare mutations and demonstrate that somatic mutational burden in normal tissues can vary by several orders of magnitude, depending on biologic and environmental factors. BotSeqS has been used to show major differences between the mutational patterns of the mitochondrial and nuclear genomes in normal tissues. BotSeqS has shown that the mutation spectra of normal tissues were different from each other, but similar to those of the cancers that arose in them.

According to some embodiments of BotSeqS, a method is provided for obtaining the sequence of a DNA. Adaptors are ligated to ends of random fragments of a DNA population to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment.

According to some embodiments of BotSeqS, a method is provided for sequencing DNA. Adaptors are ligated to ends of a population of fragmented double-stranded DNA molecules to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment. Nucleotide sequence of a member of a first family is aligned to a reference sequence. A difference between the member of the first family and the reference sequence is identified. The difference is identified as a potential rare or potential non-clonal mutation if it is found in a second family from an opposite strand of the single strand of the adaptor-ligated fragment.

According to some embodiments of BotSeqS, a method is provided for sequencing DNA. A double-stranded DNA population from a sample is randomly fragmented to form a library of fragments. Adaptors are ligated to ends of the fragments to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment. Nucleotide sequence of a member of a first family is aligned to a reference sequence. A difference between the member of the first family and the reference sequence is identified. The difference is identified as a potential rare or potential non-clonal mutation if it is found in a second family from an opposite strand of the single strand of the adaptor-ligated fragment.

In some embodiments of detecting the presence of one or more genetic biomarkers (e.g., mutations) present in a sample (e.g., a cervical, endometrial, urine, saliva, ctDNA, blood, serum, and/or plasma sample) obtained from a subject, rare somatic point mutations are quantified across the mitochondrial and nuclear genomes. One or more embodiments of such methods are referred to informally as Bot-SeqS, which is short for Bottleneck Sequencing System. Using molecular barcoding (exogenous or endogenous) and a simple dilution step immediately prior to library amplification, the method permits, for example, determining mutational burden based on age or tissue type of normal tissues. Various BotSeqS methods described herein can also be used to demonstrate the effect of mutagens and environmental insults on mutation rate. Various BotSeqS methods described herein are designed to accurately detect rare point mutations in any molecularly-barcoded library in a completely unbiased fashion.

BotSeqS was can be used with any molecular barcoding strategy, such as endogenous position-demarcated barcodes, described in Kinde, I, et al., Detection and quantification of rare mutations with massively parallel sequencing. Proceedings of the National Academy of Sciences of the United States of America 108, 9530-9535 (2011), and exogenously added matched barcodes (Kinde, I, et al., Detection and quantification of rare mutations with massively parallel sequencing. Proceedings of the National Academy of Sciences of the United States of America 108, 9530-9535 (2011); Jabara et al., Accurate sampling and deep sequencing of the HIV-1 protease gene using a Primer ID. Proceedings of the National Academy of Sciences of the United States of America 108, 20166-20171 (2011); Schmitt, M. W. et al. Detection of ultra-rare mutations by next-generation sequencing. Proceedings of the National Academy of Sciences of the United States of America 109, 14508-14513 (2012); Hiatt et al., Single molecule molecular inversion probes for targeted, high-accuracy detection of low-frequency variation. Genome research 23, 843-854 (2013); Kivioja, T. et al. Counting absolute numbers of molecules using unique molecular identifiers. Nature methods 9, 72-74 (2012); Kinde, I. et al. Evaluation of DNA from the Papanicolaou test to detect ovarian and endometrial cancers. Science translational medicine 5, 167ra164 (2013); Kumar, A. et al. Deep sequencing of multiple regions of glial tumors reveals spatial heterogeneity for mutations in clinically relevant genes. Genome biology 15, 530 (2014); Keys, J. R. et al. Primer ID Informs Next-Generation Sequencing Platforms and Reveals Preexisting Drug Resistance Mutations in the HIV-1 Reverse Transcriptase Coding Domain. AIDS Res Hum Retroviruses 31, 658-668 (2015)). In some embodiments, BotSeqS measures very rare mutations, genome-wide in a completely unbiased fashion, whereas SafeSeqS measures relatively frequent but not clonal mutations (i.e., "sub-clonal") at pre-defined targeted loci.

Conceptually, BotSeqS can be envisioned as achieving low coverage of randomly sampled genomic loci, whereas Safe-SeqS works through ultra-high coverage of a targeted locus.

Low genomic coverage which can be seen as a feature of various BotSeqS methods described herein, permits rare mutations to constitute a major portion of the signal at that genomic position, contributing to the sensitivity of the method. The applications of such methods are varied. They can be used to measure very rare somatic mutations. They can be used to assess somatic mosaicism, cell lineage development, theories on aging, environmental carcinogen exposure, and cancer risk assessment. Many of these applications are demonstrated in the examples herein.

Various filters can be applied to the data that are generated with various BotSeqS sequencing methods. One filter that can be applied is for mtDNA only; Watson AND Crick duplicate families only, excluding templates that include high frequency mutations (i.e., homopolymers, >1 mutation per template) and excluding templates that map to repeat-Masker. Another filter that can be applied is for nuclear DNA only; Watson AND Crick duplicate families only, excluding templates that include high frequency mutations (i.e., homopolymers, >1 mutation per template) and excluding templates that map to repetitive DNA or structural variants. Another filter that can be applied is for mtDNA only, single-base substation only, average quality score of greater than or equal to 30, Read 1>=2 Watson duplicates with >=90% mutation fraction only, Read 2>=2 Crick duplicates with >=90% mutation fraction only, Exclude all variants called in WGS, Exclude all variants in dbSNP142, Exclude calls that map to repeatMasker, Exclude visual artifacts and high frequency mutations (i.e., homopolymers, cycle 6 and 7, >1 change per template >1 template per change). Yet another filter that can be applied is Nuclear DNA only, Single-base substitution only, Average quality score >=30, Read 1>=2 PCR duplicates with >=90% mutation fraction only, Read 2>=2 PCR duplicates with >=90% mutation fraction only, Exclude all variants called in WGS, Exclude all variants in dbSNP130 and dbSNP142, Exclude calls that map to repetitive DNA or structural variants, Exclude visual artifacts and high frequency mutations (i.e., homopolymers, cycle 6 and 7, >1 change per template).

Various databases were used to align and filter the data, including: dbSNP build 130, Database of Genome Variants, Segmental Duplications, Fragments of Interrupted Repeats, Simple Tandem Repeats, Repeat Masker, dbSNP build 142, updated Database of Genome Variants, updated Database of Genome Variants, updated Segmental Duplications, updated Fragments of Interrupted Repeats, updated Simple Tandem Repeats, updated Repeat Masker. The GRCh37/hg19 genome assembly from the USCS Human genome Browser was used.

Fragments of double stranded DNA can be made from longer chain polymers, using any technique known in the art, including but not limited to enzyme digestion, sonication, and shearing. Alternately, some sources of DNA are already fragmented at suitable sizes. Such sources include without limitation saliva, sputum, urine, plasma, and stool. If the source of DNA is already appropriately sized, then the fragments do not need be further fragmented. Desirably, the fragmentation process, whether endogenous or by human action, is random. The desirable size of fragments may depend on the length of sequencing reads. Fragments may be less than 2 kbp, less than 1500 bp, less than 1 kbp, less than 500 bp, less than 400 bp, less than 200 bp, or less than 100 bp. Fragments may desirably be greater than twice the read length, for example. Fragments may be at least 50 bp, at least 100 bp, at least 150 bp, at least 200 bp, at least 300 bp, at least 400 bp, at least 500 bp, for example.

In some embodiments, fragments are ligated to adaptors. In some embodiments, each end of a fragment has different adaptors. This can be a laborious process, that may involve much screening and processing to obtain fragments with two distinct adaptors on each end. One way to accomplish this goal is to use Y, U, or hairpin shaped adaptors which contain or can be processed to contain sequence non-complementary sequences on the Watson and Crick strands. If there is a non-complementary region in an adaptor, amplification of the adaptor-ligated fragment will generate double stranded fragments with different adaptor orientation on fragments derived from each strand, when amplified.

Figure 55:
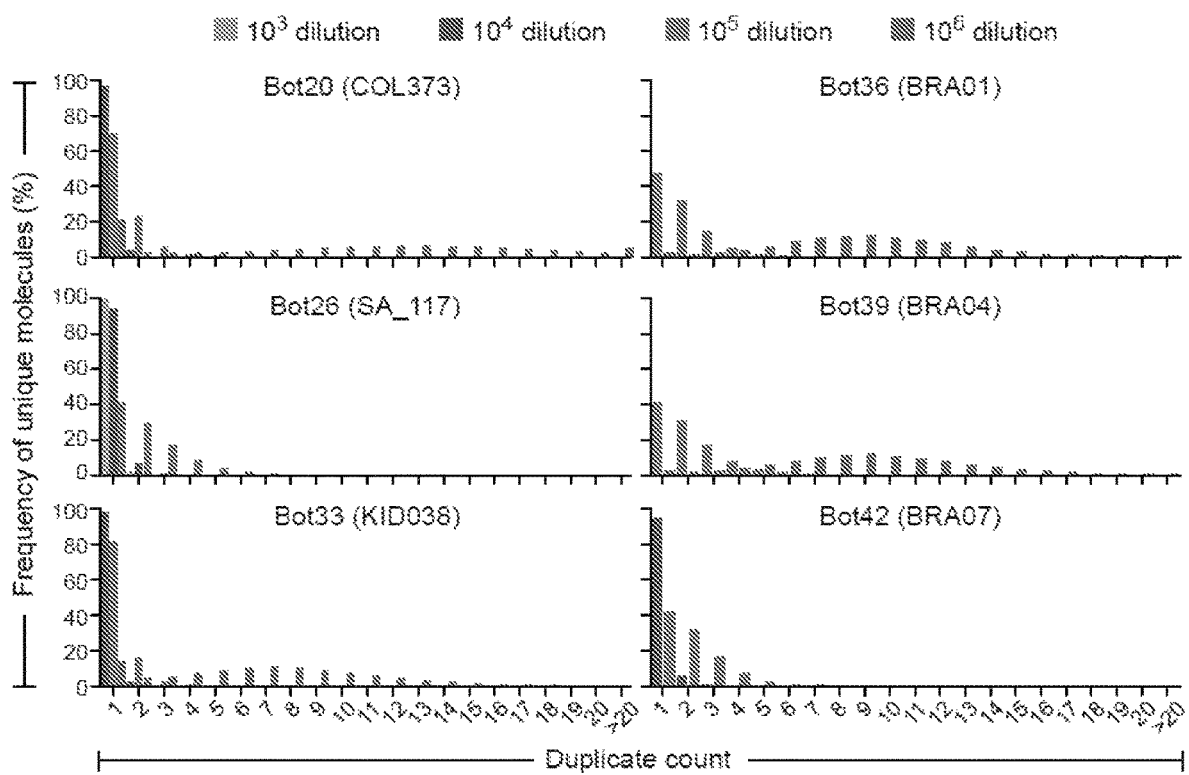
FIG. 55 contains an assessment of duplicate counts with MiSeq™ prerun. Histograms showing the distribution of family members (PCR duplicates from individual template molecules, shown on the x-axis). Either two or three serial dilutions ($10^3$, $10^4$, $10^5$, or $10^6$) were evaluated on the MiSeq™ for six samples (COL373, SA_117, KID038, BRA01, BRA04, BRA07) to generate ~5 M properly paired reads per library. Family member counts were determined here using Picard's Estimate Library Complexity program. Libraries generated from the $10^5$ dilution (blue) were subsequently used for the final HiSeq™ run reported in this study. Note that the HiSeq™ distribution is expected to shift to the right compared to the MiSeq™ distribution due to the increase of clusters sequenced per library (~5 M clusters scaled to ~70 M clusters). For example, the BotSeqS libraries from the 106 dilution (red) were not used because the members per family would be too high on a HiSeq™ run, limiting the number of different families that could be evaluated with a given amount of sequencing.

Dilution of libraries of adaptor-ligated fragments can be done using any level of dilution that is appropriate for the source. Less concentrated samples can undergo less dilution and more concentrated samples can undergo more dilution. Complexity of a sample will also factor into the desired degree of dilution. Any dilution series may be used as is convenient, such as two-fold dilutions, five-fold dilutions, ten-fold dilutions, etc. In some embodiments, a dilution level is chosen that will yield ~5-10 members of a family per adapter-ligated fragment. This is influenced by how many fragments are sequenced. For example, at one specific dilution, sequencing-20 million clusters will yield 1-4 members, but sequencing 75 million clusters yield 5-10 (see FIG. 55). The more molecules that are sequenced, the higher the number of members that will be found per family. Upon sequencing family members derived from the diluted, adaptor-ligated fragments, one desirably obtains nucleotide sequence of 4-100 family members of an adaptor-ligated fragment.

Dilution may beneficially achieve a relatively low level of coverage of the genome. That is, the genome may be sampled rather than exhaustively and repetitively sequenced. In some embodiments, the dilution is sufficient so that fewer than 10 families from nuclear DNA include 20 or more overlapping nucleotides in the non-adaptor portion. In some embodiments, the dilution is sufficient so that fewer than 5 families from nuclear DNA include 20 or more overlapping nucleotides in the non-adaptor portion. In some embodiments, the dilution is sufficient so that fewer than 10 families comprise the potential rare or potential non-clonal difference detected between a test sequence and a reference sequence. In some embodiments, the dilution is sufficient so that fewer than 5 families comprise the potential rare or potential non-clonal difference detected between a test sequence and a reference sequence.

In some embodiments, dilution accomplishes three features. First, dilution can achieve lower coverage of representative loci to one or a few molecules to "uncover" rare mutations. Second, dilution can increase the chances that both strands of the initial molecules will be sequenced redundantly. Third, dilution can facilitate the random sampling of the genome with minimal amount of sequencing.

Amplification can be performed by any technique known in the art. Typically, polymerase chain reaction will be used. Other techniques, whether linear or logarithmic may be used.

Typically, primers will be used in the amplification that are complementary to adaptor sequences.

Sequencing can be accomplished by any known technique in the art. A next generation sequencing method may be used. The sequences of the fragments can be aligned to a reference sequence. They can be grouped into families on the basis of an endogenous or an exogenous barcode. An endogenous barcode typically comprises the N nucleotides that are adjacent to the adaptor. The value of N can be chosen as is convenient and provides sufficient diversity/complexity. Exogenous barcodes can be added in a separate ligation step, by amplification primers, or they can be part of the adaptors. In some embodiments, the barcodes are random. In some embodiments, from 2 to 1000 family members are sequenced. In some embodiments, fewer than 100 family members are sequenced. In some embodiments, at least 4 family members are sequenced. In some embodiments, 4 to 10 family members are sequenced.

According to various method described herein, one need not separate physically or analyze separately the nuclear and mitochondrial genomes. This permits one to compare rates in the two genomes in the same cells.

Exogenous barcoding may be used to identify individual fragments, samples, tissues, patients, etc. Although the examples provided herein employed endogenous barcoding, this may be supplemented with or replaced by exogenous barcoding. In some embodiments, the complexity of the barcode population is greater than the complexity of the population of fragments to be barcoded such that the barcode represents a particular fragment. Barcodes can be added to a population of fragments using any technique known in the art, including without limitation, by amplification or ligation, or as part of adaptor molecules that are added by ligation. Differences that can be detected between a determined nucleotide sequence and a reference nucleotide sequence include without limitation mutations, such as point mutations, indels (e.g., insertions or deletions of 1-6 bases), and/or substitutions. If the same mutation is found in two different families, then a higher degree of certainty is attached to it (e.g., it is more likely that it arose in the biological sample, rather than in the experimental processing). The two families can have identical sequences deriving from the double stranded fragments, but can have a different orientation with respect to the adaptor sequences. To achieve a higher degree of certainty, one can require that at least two members of each of two families have the sequence difference. To achieve a higher degree of certainty, one can require that 90% or more of the members of a family have the sequence difference.

As a means of filtering out germline or clonal mutations, libraries of fragments that have not been amplified and which are from the same sample can be sequenced. Germline and clonal mutations will be evident from inspection because of their repeated occurrences.

BotSeqS methods are simply-implemented NGS-based approaches that can accurately measure rare point mutations in an unbiased, genome-wide manner. Using BotSeqS, several important goals were achieved: (i) estimates of rare mutation frequencies across the whole genome were defined; (ii) rare mutations in both the nuclear and mitochondrial genomes of the same population of cells were simultaneously evaluated; (iii) rare mutation frequencies among various normal tissues of individuals of different age, DNA repair capacity, or exposure histories were compared; and (iv) the spectra of rare mutations in normal tissues was identified, allowing their comparison to those of clonal mutations in cancers.

Data presented herein show that mutations increase with age, a result that is broadly consistent with the literature (Kennedy, S. R., Loeb, L. A. & Herr, A. J. Somatic mutations in aging, cancer and neurodegeneration. Mech Ageing Dev 133, 118-126 (2012); Vijg, J. Somatic mutations, genome mosaicism, cancer and aging. Current opinion in genetics & development 26, 141-149 (2014). The rate of increase of mutations is not as great in brain as it is in colon or kidney, presumably because the colon and kidney are both self-renewing tissues throughout adult life while the brain is not. On the other hand, the fact that the mutation frequency increased at all after childhood was surprising, given that the major cell types in pre-frontal cortex are generally thought to be post-mitotic (Spalding et al., Retrospective birth dating of cells in humans. Cell 122, 133-143 (2005)). Without being bound by theory, there are several potential explanations for this increase. A small number of cells that are replicating more actively than neurons or glia could be responsible for the increase. Such cells could include microglia or infiltrating lymphocytes or other inflammatory cells. Alternatively, these mutations could represent the results of spontaneous DNA damage independent of DNA replication. A recent single-cell sequencing study of human neurons suggested that spontaneous damage occurs during transcription (Lodato, M. A. et al. Somatic mutation in single human neurons tracks developmental and transcriptional history. Science 350, 94-98 (2015)). However, in contrast to single-cell sequencing, BotSeqS measures mutations that are found on both strands. Thus for the explanation of spontaneous DNA damage to be plausible, the mutations identified by BotSeqS would have to have been subject to DNA repair. Consistent with this possibility, DNA repair processes are known to be active in post-mitotic neurons and glia (Madabhushi, R., Pan, L. & Tsai, L. H. DNA damage and its links to neurodegeneration. Neuron 83, 266-282 (2014)).

A third possibility is that these mutations are artifacts of the procedure we used to detect them. It is fascinating that this formal possibility is essentially impossible to exclude because the mutations that were are likely found in only one cell of the tissue studied, and the DNA from that cell is no longer available for subsequent evaluation. Additionally, there is no other technique available to observe such mutations with the sensitivity achieved by various BotSeqS methods described herein. The sensitivity is currently limited only by the amount of sequencing devoted to the project. It is easy to detect mutations occurring at $6 \times 10^{-8}$ per bp using a small fraction of a HiSeq™ 2500 flow cell. It is estimated that mutations could be detected at $<10^{-9}$ per bp using an entire flow cell. The only other method that approaches this sensitivity has been described by Loeb and colleagues (Schmitt, M. W. et al. Detection of ultra-rare mutations by next-generation sequencing. Proceedings of the National Academy of Sciences of the United States of America 109, 14508-14513 (2012); Kennedy, S. R. et al. Detecting ultralow-frequency mutations by Duplex Sequencing. Nature protocols 9, 2586-2606 (2014)), but this is applicable only to pre-defined regions (~0.001%) of the genome. In the absence of direct confirmation, one is forced to use correlations and other approaches to support the accuracy of the technology described herein. These correlations include the following, as detailed in Table 51: similar mutation frequencies and spectra identified in different DNA aliquots of the same samples; similar mutation frequencies and spectra identified in the same tissues of different individuals of similar age; expected increases in mutation frequencies with age; tissue-specific differences in age-dependent increases in mutation frequencies; higher mutation frequencies in normal tissues deficient in mismatch repair or exposed to environmental mutagens; and mutation spectra in normal tissues consistent with those previously observed in cancers from the same tissues. Other in silico and experimental approaches used to evaluate the accuracy of BotSeqS are described in the Example 7.

It was also possible to compare mutation frequencies in the mitochondrial and nuclear genomes of the same tissues. In normal individuals in the absence of exposure to mutagens, the mutation frequency was much higher in the mitochondria than in the nuclear genome (median ratio of 26.2). This is consistent with the relatively poor efficiency of DNA repair in the mitochondria compared to the nuclear genome. Equally important, however, is that the ratio of mitochondrial to nuclear mutation frequencies was vastly lower (median of 1.3) in the normal kidneys of individuals exposed to either cigarette smoke or AA. This finding is not consistent with the known, less efficient repair of DNA in mitochondria. Moreover, there was a shift towards the AA mutational signature, A:T to T:A transversions, in the nuclear DNA of normal kidneys in individuals exposed to AA, but virtually none in the mtDNA. Without being bound by theory, one possibility is that the higher mutation prevalence in the mtDNA could be masking the effect of environmental mutagens on the mitochondrial genome compared to its effect on the nuclear genome. Another possibility is that there are unexpected and pronounced differences in the ways through which these mutagens cause DNA damage in these two organelles.

Another novel finding of the data presented herein is the finding that mutation spectra differed among normal tissues, even in the absence of exposures to known mutagens. Whether such differences reflect varying exposures to as yet unidentified commonly encountered mutagens, or tissue-specific repair processes, is not known. In some embodiments, the rare mutation spectra in normal tissues were found to be similar to the clonal mutations found in cancers. Though varying mutation spectra in cancers has often been attributed to cancer-specific processes, the data presented herein suggest that at least a subset of these mutations actually reflect tissue-specific processes. This concept is consistent with the idea that a substantial fraction of the mutations found in cancers occur in normal stem cells (Tomasetti, C. & Vogelstein, B. Cancer etiology. Variation in cancer risk among tissues can be explained by the number of stem cell divisions. Science 347, 78-81 (2015); Tomasetti, C, Vogelstein, B. & Parmigiani, G. Half or more of the somatic mutations in cancers of self-renewing tissues originate prior to tumor initiation. Proceedings of the National Academy of Sciences of the United States of America 110, 1999-2004 (2013). Various BotSeqS approaches described herein, which can easily measure very rare mutations in any tissue or cell type of interest, will be applicable to questions of broad biomedical interest.

In some embodiments, the presence of one or more genetic biomarkers (e.g., mutations) present in a sample (e.g., a cervical, endometrial, urine, saliva, ctDNA, blood, serum, and/or plasma sample) obtained from a subject is detected using any of the variety of methods described in U.S. Pat. No. 9,476,095, the contents of which are incorporated by reference herein in their entirety. The identification of mutations that are present in a small fraction of DNA templates is advantageous for progress in several areas of biomedical research. Though massively parallel sequencing instruments are in principle well-suited to this task, the error rates in such instruments are generally too high to allow confident identification of rare variants. Provided herein is an approach that can substantially increase the sensitivity of massively parallel sequencing instruments for this purpose. One example of this approach, called "Safe-SeqS" for (Safe-Sequencing System) includes (i) assignment of a unique identifier (UID) to each template molecule; (ii) amplification of each uniquely tagged template molecule to create UID-families; and (iii) redundant sequencing of the amplification products. PCR fragments with the same UID are truly mutant ("super-mutants") if ≥95% of them contain the identical mutation. This approach is useful for, e.g., determining the fidelity of a polymerase, the accuracy of oligonucleotides synthesized in vitro, and the prevalence of mutations in the nuclear and mitochondrial genomes of normal cells.

In some embodiments of methods provided herein, the presence of one or more genetic biomarkers (e.g., mutations) present in a sample (e.g., a cervical, endometrial, urine, saliva, ctDNA, blood, serum, and/or plasma sample) obtained from a subject is detected using a unique identifier (UID) nucleic acid sequence attached to a first end of each of a plurality of analyte nucleic acid fragments to form uniquely identified analyte nucleic acid fragments, the nucleotide sequence of a uniquely identified analyte nucleic acid fragment is redundantly determined, wherein determined nucleotide sequences which share a UID form a family of members, and a nucleotide sequence is identified as accurately representing an analyte nucleic acid fragment when at least 1% of members of the family contain the sequence.

In some embodiments of methods provided herein, the presence of one or more genetic biomarkers (e.g., mutations) present in a sample (e.g., a cervical, endometrial, urine, saliva, ctDNA, blood, serum, and/or plasma sample) obtained from a subject is detected using a unique identifier sequence (UID) attached to a first end of each of a plurality of analyte DNA fragments using at least two cycles of amplification with first and second primers to form uniquely identified analyte DNA fragments. In such embodiments, the UIDs can be in excess of the analyte DNA fragments during amplification, the first primers can include a first segment complementary to a desired amplicon; a second segment containing the UID; and a third segment containing a universal priming site for subsequent amplification, the second primers can include a universal priming site for subsequent amplification, each cycle of amplification can attach one universal priming site to a strand, the uniquely identified analyte DNA fragments can be amplified to form a family of uniquely identified analyte DNA fragments from each uniquely identified analyte DNA fragment, and nucleotide sequences of a plurality of members of the family can be determined.

In some embodiments of methods provided herein, the presence of one or more genetic biomarkers (e.g., mutations) present in a sample (e.g., a cervical, endometrial, urine, saliva, ctDNA, blood, serum, and/or plasma sample) obtained from a subject is detected using endogenous unique identifier sequences (UIDs). For example, fragmented analyte DNA can be obtained that includes fragments of 30 to 2000 bases, inclusive. Each end of a fragment can form an endogenous UID for the fragment. Adapter oligonucleotides can be attached to ends of the fragments to form adapted fragments. Fragments representing one or more selected genes can optionally be enriched by means of capturing a subset of the fragments using capture oligonucleotides complementary to selected genes in the analyte DNA or by amplifying fragments complementary to selected genes. The adapted fragments can be amplified using primers complementary to the adapter oligonucleotides to form families of adapted fragments. Nucleotide sequences can be determined for a plurality of members of a family. Nucleotide sequences of the plurality of members of the family can be compared. A nucleotide sequence can be identified as accurately representing an analyte DNA fragment when at least a 1% of members of the family contain the sequence.

In some embodiments, provided herein are compositions including populations of primer pairs, wherein each pair includes a first and second primer for amplifying and identifying a gene or gene portion. The first primer can include a first portion (e.g., of 10-100 nucleotides) complementary to the gene or gene portion and a second portion of (e.g., of 10 to 100 nucleotides) including a site for hybridization to a third primer. The second primer can include a first portion of (e.g., of 10-100 nucleotides) complementary to the gene or gene portion and a second portion (e.g., of 10 to 100 nucleotides) including a site for hybridization to a fourth primer. In some embodiments, interposed between the first portion and the second portion of the second primer is a third portion consisting of 2 to 4000 nucleotides forming a unique identifier (UID). The unique identifiers in the population can have at least 4 different sequences. The first and second primers can be complementary to opposite strands of the gene or gene portion. A kit may include the population of primers and the third and fourth primers complementary to the second portions of each of the first and second primers.

In some embodiments of methods provided herein, the presence of one or more genetic biomarkers (e.g., mutations) present in a sample (e.g., a cervical, endometrial, urine, saliva, ctDNA, blood, serum, and/or plasma sample) obtained from a subject is detected using an approach called "Safe-SeqS" (from Safe-Sequencing System). In one embodiment, Safe-SeqS involves two basic steps (FIG. 61): the first step is assignment of a Unique Identifier (UID) to each nucleic acid template molecule to be analyzed, and the second step is the amplification of each uniquely tagged template, so that many daughter molecules with the identical sequence are generated (defined as a UID-family). If a mutation pre-existed in the template molecule used for amplification, that mutation should be present in a certain proportion, or even all, of daughter molecules containing that UID (barring any subsequent replication or sequencing errors). A UID-family in which every family member (or a certain predetermined proportion) has an identical mutation is called a "super-mutant." Mutations not occurring in the original templates, such as those occurring during the amplification steps or through errors in base-calling, should not give rise to super-mutants (e.g., will not be present at the pre-determined frequency in a UID family.) In some embodiments, amplification is not necessary.

Any of the variety of Safe-SeqS approaches can be employed for any purpose where a very high level of accuracy and sensitivity is desired to be obtained from sequence data. As described herein, the approach can be used to assess the fidelity of a polymerase, the accuracy of in vitro synthesized nucleic acid synthesis, and the prevalence of mutations in nuclear or mitochondrial nucleic acids of normal cells. The approach may be used to detect and/or quantify mosaics and somatic mutations.

In some embodiments of Safe-SeqS approaches provided herein, fragments of nucleic acids may be obtained using a random fragment forming technique such as mechanical shearing, sonicating, or subjecting nucleic acids to other physical or chemical stresses. Fragments may not be strictly random, as some sites may be more susceptible to stresses than others. Endonucleases that randomly or specifically fragment may also be used to generate fragments. In some embodiments of any of the variety of Safe-SeqS approaches, fragments of nucleic acids may be obtained using a technique that does not result in random fragments. Size of fragments may vary, but desirably will be in ranges between 30 and 5,000 basepairs, between 100 and 2,000, between 150 and 1,000, or within ranges with different combinations of these endpoints. Nucleic acids may be, for example, RNA or DNA. Modified forms of RNA or DNA may also be used.

In some embodiments of Safe-SeqS approaches provided herein, attachment of an exogenous UID to an analyte nucleic acids fragment may be performed by any means known in the art, including enzymatic, chemical, or biologic. One means employs a polymerase chain reaction. Another means employs a ligase enzyme. The enzyme may be mammalian or bacterial, for example. Ends of fragments may be repaired prior to joining using other enzymes such as Klenow Fragment of T4 DNA Polymerase. Other enzymes which may be used for attaching are other polymerase enzymes. An UID may be added to one or both ends of the fragments. A UID may be contained within a nucleic acid molecule that contains other regions for other intended functionality. For example, a universal priming site may be added to permit later amplification. Another additional site may be a region of complementarity to a particular region or gene in the analyte nucleic acids. A UID may be from 2 to 4,000, from 100 to 1000, from 4 to 400, bases in length, for example. In some embodiments, a UID is 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 600, 700, 800, 900, 1000 nucleotides or more in length, or can be of any length between these lengths. In embodiments in which two or more UIDs are used, the UIDs can be of the same or different lengths.

In some embodiments of Safe-SeqS approaches provided herein, UIDs may be made using random addition of nucleotides to form a short sequence to be used as an identifier. At each position of addition, a selection from one of four deoxyribonucleotides may be used. Alternatively, a selection from one of three, two, or one deoxyribonucleotides may be used. Thus, the UID may be fully random, somewhat random, or non-random in certain positions. Another manner of making UIDs utilizes pre-determined nucleotides assembled on a chip. In this manner of making, complexity is attained in a planned manner. In some embodiments, it may be advantageous to attach a UID to each end of a fragment, increasing the complexity of the UID population on fragments.

A cycle of polymerase chain reaction for adding exogenous UID refers to the thermal denaturation of a double stranded molecule, the hybridization of a first primer to a resulting single strand, the extension of the primer to form a new second strand hybridized to the original single strand. A second cycle refers to the denaturation of the new second strand from the original single strand, the hybridization of a second primer to the new second strand, and the extension of the second primer to form a new third strand, hybridized to the new second strand. Multiple cycles may be employed to increase efficiency, for example, when the analyte is dilute or inhibitors are present.

In the case of endogenous UIDs, adapters can be added to the ends of fragments by any of a variety of methods including, without limitation, ligation. In some embodiments, complexity of the analyte fragments can be decreased by a capture step, either on a solid phase or in liquid step. In some embodiments, the capture step employs hybridization to probes representing a gene or set of genes of interest. In some embodiments, if on a solid phase, non-binding fragments are separated from binding fragments. Suitable solid phases known in the art include filters, membranes, beads, columns, etc. In some embodiments, if in a liquid phase, a capture reagent can be added which binds to the probes, for example through a biotin-avidin type interaction. After capture, desired fragments can be eluted for further processing. The order of adding adapters and capturing is not critical. Another non-limiting means of reducing the complexity of the analyte fragments involves amplification of one or more specific genes or regions. One exemplary way to accomplish this is to use inverse PCR. Primers can be used which are gene-specific, thus enriching while forming libraries. Optionally, the gene-specific primers can contain grafting sequences for subsequent attachment to a massively parallel sequencing platform.

Because In some embodiments, endogenous UIDs provide a limited number of unique possibilities, depending on the fragment size and sequencing read length, combinations of both endogenous and exogenous UIDs can be used. In some embodiments, introducing additional sequences when amplifying increase the available UIDs and thereby increase sensitivity. For example, before amplification, the template can be split into 96 wells, and 96 different primers can be used during the amplification; this would effectively increase the available UIDs 96-fold, because up to 96 templates with the same endogenous UID could be distinguished. This technique can also be used with exogenous UIDs, such that each well's primers adds a unique, well-specific sequence to the amplification products, which can also improve the specificity of detection of rare templates.

In some embodiments of Safe-SeqS approaches provided herein, amplification of fragments containing a UID can be performed according to known techniques to generate families of fragments. Polymerase chain reaction can be used. Other amplification methods can also be used, as is convenient. Inverse PCR may be used, as can rolling circle amplification. Amplification of fragments typically is done using primers that are complementary to priming sites that are attached to the fragments at the same time as the UIDs. In some embodiments, priming sites are distal to the UIDs, so that amplification includes the UIDs. In some embodiments, amplification forms a family of fragments, each member of the family sharing the same UID. Because the diversity of UIDs is typically greatly in excess of the diversity of the fragments, each family should derive from a single fragment molecule in the analyte. Primers used for the amplification may be chemically modified to render them more resistant to exonucleases. Non-limiting examples of such modifications include the use of phosphorothioate linkages between one or more 3' nucleotides, and boranophosphates.

In some embodiments of Safe-SeqS approaches provided herein, family members are sequenced and compared to identify any divergencies within a family. In some embodiments, sequencing is performed on a massively parallel sequencing platform, many of which are commercially available. If the sequencing platform employs a sequence for "grafting," i.e., attachment to the sequencing device, such a sequence can be added during addition of UIDs or adapters or separately. A grafting sequence may be part of a UID primer, a universal primer, a gene target-specific primer, the amplification primers used for making a family, or separate. Redundant sequencing refers to the sequencing of a plurality of members of a single family.

A threshold can be set for identifying a genetic biomarker (e.g., a mutation) in an analyte. If the "mutation" appears in all members of a family, then it derives from the analyte. If it appears in less than all members, then it may have been introduced during the analysis. Thresholds for calling a mutation may be set, for example, at 1%, 5%, 10%, 20%, 30%, 40%, 50%, 60%, 70%, 80%, 90%, 95%, 97%, 98%, or 100%. Thresholds can be set based on the number of members of a family that are sequenced and the particular purpose and situation.

In some embodiments of Safe-SeqS approaches provided herein, populations of primer pairs are used to attach exogenous UIDs. For example, the first primer can include a first portion (e.g., of 10-100 nucleotides) complementary to the gene or gene portion and a second portion (e.g., of 10 to 100 nucleotides) including a site for hybridization to a third primer. In some embodiments the first portion and/or the second portion of the first primer is 10, 15, 20, 25, 30, 35, 40, 45, 50, 55, 60, 65, 70, 75, 80, 85, 90, 95, or 100 nucleotides in length, or any length in between. The second primer can include a first portion (e.g., of 10-100 nucleotides) complementary to the gene or gene portion and a second portion (e.g., of 10 to 100 nucleotides) including a site for hybridization to a fourth primer. In some embodiments the first portion and/or the second portion of the second primer is 10, 15, 20, 25, 30, 35, 40, 45, 50, 55, 60, 65, 70, 75, 80, 85, 90, 95, or 100 nucleotides in length, or any length in between. In some embodiments, interposed between the first portion and the second portion of the second primer is a third portion (e.g., of 2 to 4,000 nucleotides, e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 600, 700, 800, 900, 1000 nucleotides, or any number of nucleotides between these values) forming a unique identifier (UID) . . . . In some embodiments, interposed between the first portion and the second portion of both the first and second primer is a third portion (e.g., of 2 to 4,000 nucleotides, e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 600, 700, 800, 900, 1000 nucleotides, or any number of nucleotides between these values), each of which forms a unique identifier (UID). In some embodiments, the third portion of the first primer is the same length as the third portion of the second primer. In some embodiments, the third portion of the first primer is a different length than the third portion of the second primer. In some embodiments, the unique identifiers in the population have at least 4, at least 16, at least 64, at least 256, at least 1,024, at least 4,096, at least 16,384, at least 65,536, at least 262,144, at least 1,048,576, at least 4,194,304 at least 16,777,216, or at least 67,108,864 different sequences. In some embodiments, the first and second primers are complementary to opposite strands of the gene or gene portion. A kit can be made containing both the primers for attaching exogenous UIDs as well as amplification primers, i.e., the third and fourth primers complementary to the second portions of each of the first and second primers. The third and fourth primers can optionally contain additional grafting or indexing sequences. The UID may include randomly selected sequences, pre-defined nucleotide sequences, or both randomly selected sequences and pre-defined nucleotides. If both, these can be joined together in blocks or interspersed.

In some embodiments of Safe-SeqS approaches provided herein, the methods of analysis can be used to quantitate as well as to determine a sequence. For example, the relative abundance of two analyte DNA fragments may be compared using methods described herein.

The results described herein demonstrate that the Safe-SeqS approach can substantially improve the accuracy of massively parallel sequencing (Tables 52 and 53). Safe-SeqS can be implemented through either endogenous or exogenously introduced UIDs (or both), and can be applied to virtually any sample preparation workflow or sequencing platform. As demonstrated herein, Safe-SeqS can easily be used to identify rare mutants in a population of DNA templates, to measure polymerase error rates, and to judge the reliability of oligonucleotide syntheses. One of the advantages of the strategy is that it yields the number of templates analyzed as well as the fraction of templates containing variant bases. Previously described in vitro methods for the detection of small numbers of template molecules (e.g., Dressman D, Yan H, Traverso G, Kinzler K W, & Vogelstein B (2003) Transforming single DNA molecules into fluorescent magnetic particles for detection and enumeration of genetic variations. Proc Natl Acad Sci USA 100:8817-8822; Li J, et al. (2008) Replacing PCR with COLD-PCR enriches variant DNA sequences and redefines the sensitivity of genetic testing. Nat Med 14:579-584) allow the fraction of mutant templates to be determined but cannot determine the number of mutant and normal templates in the original sample.

It is of interest to compare Safe-SeqS to other approaches for reducing errors in next generation sequencing. Sophisticated algorithms to increase the accuracy of base-calling have been developed (e.g., (Erlich Y, Mitra P, delaBastide M, McCombie W R, & Hannon G J (2008) Alta-Cyclic: a self-optimizing base caller for next-generation sequencing. Nat Methods 5:679-682; Rougemont J, et al. (2008) Probabilistic base calling of Solexa sequencing data. BMC Bioinformatics 9:431; Druley T E, et al. (2009) Quantification of rare allelic variants from pooled genomic DNA, Nat Methods 6:263-265; Vallania F L, et al. (2010) High-throughput discovery of rare insertions and deletions in large cohorts. Genome Res 20:1711-1718)). These can certainly reduce false positive calls, but their sensitivity is still limited by artifactual mutations occurring during the PCR steps required for library preparation as well as by (a reduced number of) base-calling errors. For example, the algorithm employed in the current study used very stringent criteria for base-calling and was applied to short read-lengths, but was still unable to reduce the error rate to less than an average of $2.0 \times 10^{-4}$ errors/bp. This error frequency is at least as low as those reported with other algorithms. To improve sensitivity further, these base-calling improvements can be used together with Safe-SeqS. Travers et al. have described another powerful strategy for reducing errors (Eid J, et al. (2009) Real-time DNA sequencing from single polymerase molecules. Science 323:133-138). With this technology, both strands of each template molecule are sequenced redundantly after a number of preparative enzymatic steps. However, this approach can only be performed on a specific instrument. Moreover, for many clinical applications, there are relatively few template molecules in the initial sample and evaluation of nearly all of them is required to obtain the requisite sensitivity. In some embodiments, approaches described herein that employ exogenously introduced UIDs (FIG. 63) address this concern by coupling the UID assignment step with a subsequent amplification in which few molecules are lost.

Strong evidence supporting the fact that mutations identified by conventional analyses in the current study represent artifacts rather than true mutations in the original templates is provided by the observation that the mutation prevalence in all but one experiment was similar—$2.0 \times 10^{-4}$ to $2.4 \times 10^{-4}$ mutations/bp (Tables 52 and 53). The exception was the experiment with oligonucleotides synthesized from phosphoramidites, in which the error of the synthetic process was apparently higher than the error rate of conventional Illumina analysis when used with stringent base-calling criteria. In contrast, the mutation prevalence of Safe-SeqS varied much more, from 0.0 to $1.4 \times 10^{-5}$ mutations/bp, depending on the template and experiment. Moreover, the mutation prevalence measured by Safe-SeqS in the most controlled experiment, in which polymerase fidelity was measured (Table 53A), was almost identical to that predicted from previous experiments in which polymerase fidelity was measured by biological assays. Measurements of mutation prevalence in the DNA from normal cells provided herein are consistent with some previous experimental data. However, estimates of these prevalences vary widely and may depend on cell type and sequence analyzed (see SI text). It therefore cannot be said with certainty that the few mutations revealed by Safe-SeqS represented errors occurring during the sequencing process rather than true mutations present in the original DNA templates. Potential sources of error in the Safe-SeqS process are described in the SI text.

Another potential application of Safe-SeqS is the minimization of PCR contamination, a serious problem for clinical laboratories. With endogenous or exogenous UID assignment, the UIDs of mutant templates can simply be compared to those identified in prior experiments; the probability that the same mutation from two independent samples would have the same UID in different experiments is negligible when mutations are infrequent. Additionally, with exogenous UIDs, a control experiment with the same template but without the UID assigning PCR cycles (FIG. 63) can ensure that no DNA contamination is present in that template preparation; no template should be amplified in the absence of UID assignment cycles and thus no PCR product of the proper size should be observed.

It was demonstrated that the exogenous UIDs strategy can be used to analyze a single amplicon in depth. This technology may not be applicable to situations wherein multiple amplicons must be analyzed from a sample containing a limited number of templates. Multiplexing in the UID assignment cycles (FIG. 63) may provide a solution to this challenge. A second potential concern is that clinical samples may contain inhibitors that reduce the efficiency of this step. This problem can presumably be overcome by performing more than two cycles in UID assignment PCR step (FIG. 63), though this has the potential to complicate the determination of the number of templates analyzed. The specificity of Safe-SeqS is currently limited by the fidelity of the polymerase used in the UID assignment PCR step, i.e., $8.8 \times 10^{-7}$ mutations/bp in its current implementation with two cycles. Increasing the number of cycles in the UID assignment PCR step to five would decrease the overall specificity to $^{[<]BEGINITAL_m}2 \times 10^{-6}$ mutations/bp. However, this specificity can be increased by requiring more than one super-mutant for mutation identification—the probability of introducing the same artifactual mutation twice or three times would be exceedingly low ($[2 \times 10^{-6}]^2$ or $[2 \times 10^{-6}]^3$, respectively). In sum, there are several simple ways to perform Safe-SeqS variations and analysis variations to realize the needs of specific experiments.

Luria and Delbrück, in their classic paper in 1943, wrote that their "prediction cannot be verified directly, because what we observe, when we count the number of resistant bacteria in a culture, is not the number of mutations which have occurred but the number of resistant bacteria which have arisen by multiplication of those which mutated, the amount of multiplication depending on how far back the mutation occurred." Various Safe-SeqS procedures described here can verify such predictions because the number as well as the time of occurrence of each mutation can be estimated from the data, as noted in the experiments on polymerase fidelity. In addition to templates generated by polymerases in vitro, the same approach can be applied to DNA from bacteria, viruses, and mammalian cells. It is therefore expected that this strategy will provide definitive answers to a variety of important biomedical questions.

In some embodiments, a genetic biomarker (e.g., one or more genetic biomarkers) is detected using any of the variety of methods described in U.S. Patent Application Publication No. 2018/0208999, which is hereby incorporated by reference in its entirety. For example, detection of a genetic biomarker can include analysis of the count, the fragmentation patterns, and size of cell-free nucleic acids, e.g., plasma DNA and serum DNA, including nucleic acids from pathogens, such as viruses. Various embodiments are directed to applications (e.g., classification of biological samples) of the analysis of the count, the fragmentation patterns, and size of cell-free nucleic acids, e.g., plasma DNA and serum DNA, including nucleic acids from pathogens, such as viruses. Some embodiments, of the application can determine if a subject has a particular condition. For example, a method can determine if a subject has cancer or a tumor, or other pathology. Embodiments of another application can be used to assess the stage of a condition, or the progression of a condition over time. For example, a method may be used to determine a stage of cancer in a subject, or the progression of cancer in a subject over time (e.g., using samples obtained from a subject at different times). According to one embodiment, sequence reads obtained from a sequencing of the mixture of cell free nucleic acid molecules can be used to determine an amount of the sequence reads aligning to a reference genome corresponding to the virus. The amount of sequence reads aligning to the reference genome can be compared to a cutoff value to screen for the pathology. According to another embodiment, sizes of viral nucleic acid molecules (e.g., those aligning to a reference genome corresponding to the virus) can be used. A statistical value of a size distribution of the nucleic acid molecules from the virus can be determined. A level of pathology in the subject can be determined by processing the statistical value against a cutoff value. According to another embodiment, a first amount of cell-free nucleic acid molecules that end within one or more first windows of a reference genome corresponding to the virus is determined. Each first window comprising at least one of a first set of genomic positions at which ends of cell-free nucleic acid molecules are present at a rate above a first threshold in subjects with a cancer (or other pathology) associated with the virus. A relative abundance can be computed by normalizing the first amount using a second amount of cell-free nucleic acid molecules, which includes cell-free nucleic acid molecules ending at a second set of genomic positions outside of the one or more first windows including the first set of genomic positions. A level of cancer in the subject can be determined by processing the relative abundance against a cutoff value. Embodiments can combine various techniques. For example, a first assay can be count-based, size-based, or fragmentation-based. A second assay can be one of the other techniques. As examples a majority voting can be used, or cutoff values can be determined for both techniques, thereby determining a set of data points from the two techniques that correspond to a particular level of pathology.

In some embodiments, detection of a genetic biomarker (e.g., one or more genetic biomarkers) can include any of the variety of methods described in U.S. Patent Application Publication No. 2018/0203974, which is hereby incorporated by reference in its entirety. For example, detection of a genetic biomarker can include a computer-implemented method, involving receiving a data set in a computer comprising a processor and a computer-readable medium, where the computer-readable medium comprises instructions that, when executed by the processor, cause the computer to e.g. identify somatic mutations in the biological test sample; and generate a somatic mutational profile that comprises the somatic mutations; and detecting the presence of the cancer in the patient based on the exposure weights of the mutational signatures. Additionally or alternatively, detection of a genetic biomarker can include using a non-negative matrix factorization (NMF) approach to construct a signature matrix that can be used to identify latent signatures in a patient. In other embodiments, the methods may use principal components analysis (PCA) or vector quantization (VQ) approaches to construct a signature matrix. In one example, the patient sample is a cell-free nucleic acid sample (e.g., cell-free DNA (cfDNA) and/or cell-free RNA (cfRNA)). The construction of a signature matrix using non-negative matrix factorization can be generalized to multiple features relevant to cancer detection and/or classification. In some embodiments, a signature matrix comprises a plurality of signatures where the probability of the occurrence for each of a plurality of features are represented. Examples of relevant features include, but are not limited to, an upstream sequence context of a base substitution mutation, a downstream sequence context of a base substitution mutation, an insertion, a deletion, a somatic copy number alteration (SCNA), a translocation, a genomic methylation status, a chromatin state, a sequencing depth of coverage, an early versus late replicating region, a sense versus antisense strand, an inter mutation distance, a variant allele frequency, a fragment start/stop, a fragment length, and a gene expression status, or any combination thereof. In one embodiment, the upstream and/or downstream sequence context can comprise a region of a nucleic acid that ranges in length from about 2 to about 40 bp, such as from about 3 to about 30 bp, such as from about 3 to about 20 bp, or such as from about 2 to about 10 bp of sequence context of a base substitution mutation. In one embodiment, the upstream and/or downstream sequence context may be a triplet sequence context, a quadruplet sequence context, a quintuplet sequence context, a sextuplet sequence context, or a septuplet sequence context of base substitution mutations. In some embodiments, the upstream and/or downstream sequence context can be the triplet sequence context of a base substitution mutation. In one embodiment, the methods are used to identify latent somatic mutational signatures in a subject's (e.g., an asymptomatic subject) cfDNA sample for early detection of cancer. In another embodiment, the methods are used to infer tissue of origin for a patient's cancer based on latent mutational signatures identified in the patient's cfDNA sample. In yet another embodiment, the methods are used to identify latent mutational signatures in a patient's cfDNA sample that can be used to classify the patient for different types of therapies. In yet another embodiment, non-negative matrix factorization is applied to learn error modes in a somatic variant (mutation) calling assay. For example, systematic errors (e.g., errors contributed during library preparation, PCR, hybridization capture, and/or sequencing) that underlie the assay can be identified and assigned unique signatures that can be used to distinguish between the contribution from true somatic variants and artifactual variants arising from the technical processes in the assay. In yet another embodiment, non-negative matrix factorization can be used to identify mutational signatures that are associated with healthy aging. Mutation processes that are associated with aging are assigned mutational signatures that can be used to distinguish between healthy somatic mutations associated with patient age and somatic mutations contributed from, and indicative of, a cancer process in the patient. In another embodiment, one or more mutational signatures can be monitored over time and used for diagnosing, monitoring, and/or classifying cancer. For example, the observed mutational profile in cfDNA from patient samples at two or more time points can be evaluated. In some embodiments, two or more mutational signature processes can be evaluated as a combination of different mutational signatures. In still another embodiment, one or more mutational signatures can be monitored over time (e.g., at a plurality of time points) to monitor the effectiveness of a therapeutic regimen or other cancer treatment. Somatic mutations (i.e., driver mutations and passenger mutations) in a cancer genome are typically the cumulative consequence of one or more mutational processes of DNA damage and repair. Although not wishing to be bound by theory, it is believed that the strength and duration of exposure to each mutational process (e.g., environmental factors and DNA repair processes) results in a unique profile of somatic mutations in a subject (e.g., a cancer patient).

These unique combinations of mutation types form a unique "mutational signature" for the cancer patient. Furthermore, as is well known in the art, a somatic mutation, or mutational profile can depend on the particular sequence context of the mutation. For example, UV damage typically results in a base change of C to T, when the base change occurs within a sequence context of (−T|C|−)C(A|T|C|G). In this example, C is the mutated base and the bases upstream (T or C) and downstream (A, T, C, or G) of C affect the probability of a mutation under UV radiation. In another example, spontaneous deamination of 5-methylcytosine typically results in a base change of C to T, when the base change occurs within a sequence context of (A|T|C|G)C(−|−|−|G). Accordingly, in one embodiment, the sequence context of identified mutations can be utilized as a feature for analyzing somatic mutations in the detection and/or classification of cancer.

In some embodiments, detection of a genetic biomarker (e.g., one or more genetic biomarkers) can include any of the variety of methods described in P.C.T. Publication No. WO 2018/119399, which is hereby incorporated by reference in its entirety. For example, detection of a genetic biomarker can include methods for preparing a sequencing library from a DNA-containing test sample, including methods for rescuing one or more partially ligated DNA fragments to enhance library preparation conversion efficiencies. The methods can further be used to improve recovery of duplex sequence information from double-stranded DNA. Additionally or alternatively, detection of a genetic biomarker can include a method for preparing a double-stranded DNA sequencing library, the method comprising the following steps: (a) obtaining a test sample comprising a plurality of double-stranded DNA (dsDNA) fragments, wherein the dsDNA fragments comprise a forward strand and a reverse strand; (b) ligating double-strand DNA adapters to both ends of the dsDNA fragments; and (c) extending unligated 3'-ends of the dsDNA fragments with a DNA polymerase to create dsDNA fragment-adapter templates to prepare a sequencing library. In some embodiments, the dsDNA fragment-adapter templates are further amplified prior to sequencing. In other embodiments, one or more steps of the method may be carried out in a single reaction step. For example, steps (b) through (c) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA oligonucleotides or primers (e.g., including sequencing adapters and/or a universal primer). Optionally, the dsDNA molecules can be purified, and optionally fragmented, from test sample prior to ligation step (b). Additionally or alternatively, detection of a genetic biomarker can include a method for preparing a double-stranded DNA sequencing library, the method comprising the following steps: (a) obtaining a test sample comprising a plurality of double-stranded DNA (dsDNA) fragments, the dsDNA fragments comprising a forward strand and a reverse strand; (b) adding double-stranded adapters to the dsDNA fragments and ligating the double-strand adapters to both ends of the dsDNA fragments; (c) extending unligated 3'-ends of the dsDNA fragments with a polymerase to create dsDNA fragment-adapter templates, wherein the polymerase further comprises strand displacement activity; (d) adding a poly-adenine tail to the 3'-ends of the dsDNA fragment-adapter templates; (e) adding a set of ssDNA oligonucleotides (or primers) and hybridizing the ssDNA oligonucleotides to the dsDNA fragment-adapter templates; and (f) extending the set of ssDNA oligonucleotides to create a dsDNA sequencing library. In some embodiments, one or more steps of the method may be carried out in a single reaction step. For example, steps (b) through (f) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA oligonucleotides or primers (e.g., including sequencing adapters and/or a universal primer). Optionally, the dsDNA molecules can be purified, and optionally fragmented, from test sample prior to ligation step (b).

In some embodiments, detection of a genetic biomarker (e.g., one or more genetic biomarkers) can include any of the variety of methods described in P.C.T. Publication No. WO 2018/119438, which is hereby incorporated by reference in its entirety. For example, detection of a genetic biomarker can include methods of analyzing sequencing data to detect CNVs in a nucleic acid sample. Detecting CNVs in a nucleic acid sample obtained from a human subject can be informative for determining a presence of cancer in the subject. In one embodiment, detecting CNVs in a nucleic acid sample obtained from a human subject can be used for early detection of cancer in the subject. In various embodiments, the methods determine coverage at individual nucleotide bases determined from targeted sequencing reads. Sources of coverage variation can be corrected at the base level. For each gene of a targeted gene panel, the determined base level coverage across bases of the gene can be considered to more effectively detect CNVs of each gene. Generally, baseline coverage biases that exist at each base position can be modeled using training data gathered from healthy individuals. Therefore, when analyzing a test sample obtained from a subject, the base level coverage can be determined for each base position in view of the expected coverage biases obtained through modeling. Specifically, if the coverage bias at a base position for a test sample obtained from the subject differs from the expected coverage bias obtained through modeling, coverage biases can be normalized and removed. For a gene in a targeted gene panel, base level coverages across the base positions of the gene are analyzed to determine whether the coverage for the gene differs from an expected level of coverage for the gene as previously determined using training data gathered from healthy individuals. If so, a CNV can be called. The calling of a CNV can indicate a presence of cancer in the subject or that the subject is susceptible to an increased likelihood of developing cancer.

In some embodiments, detection of a genetic biomarker (e.g., one or more genetic biomarkers) can include any of the variety of methods described in P.C.T. Publication No. WO 2018/111872, which is hereby incorporated by reference in its entirety. For example, detection of a genetic biomarker can include preparing sequencing libraries based on a plurality of RNA molecules which are tagged and amplified by tagging the molecule with an oligonucleotide hybridising to a polyC tail introduced by the terminal transferase activity of the reverse transcriptase, e.g. MMLV RT, and ligating the oligonucleotide to the RNA molecule using a ligase, e.g. T4 RNA ligase, and producing cDNA molecules based on mRNA and strand displacing reverse transcriptases, e.g. MMLV RT, and producing a second cDNA strand in order to produce a dsDNA library for sequencing. In some embodiments, the methods comprise sequencing at least a portion of a sequencing library to obtain sequencing data or sequence reads from a test sample (e.g., a biological sample from a subject). In one embodiment, the method for preparing a sequencing library from a test sample comprising RNA comprises the steps: (a) obtaining a test sample comprising RNA sequences, and purifying the RNA sequences from the test sample; (b) synthesizing first complementary DNA (cDNA) strands based on the RNA sequences and C-tailing 3'-ends of cDNA strands; (c) annealing a complementary template switching oligonucleotide to the C-tail of the cDNA and ligating the complementary template switching oligonucleotide to the 5'-ends of the RNA sequences to produce RNA templates; and (d) synthesizing a plurality of cDNA strands from the RNA templates using a strand-displacement reverse transcriptase. In some embodiments, one or more steps of the method may be carried out in a single reaction step. For example, steps (b) through (d) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase). In some embodiments, the method for preparing a sequencing library from a test sample comprising RNA, comprises the steps: (a) obtaining a test sample comprising one or more RNA sequences, and purifying the one or more RNA sequences from the test sample; (b) annealing a first RNA primer to the one or more RNA sequences; (c) extending the first RNA primer in a first nucleic acid extension reaction using reverse transcriptase, wherein the reverse transcriptase comprises reverse transcription and terminal transferase activities, to generate a plurality of DNA sequences complementary to the one or more RNA templates, and wherein the complementary DNA (cDNA) sequences further comprise a plurality of non-templated bases at the 3'-end of the cDNA sequences; (d) annealing a complementary nucleic acid sequence to the non-templated bases at the 3'-end of the cDNA sequence, wherein the complementary nucleic acid sequence further comprises a unique molecular identifier (UMI) or a unique sequence tag; (e) ligating the complementary nucleic acid sequence to the 5'-end of the one or more RNA sequences to generate one or more RNA templates, wherein the one or more RNA templates comprise the original one or more RNA sequences covalently linked to the complementary nucleic acid sequence comprising the UMI or unique sequence tag; (f) annealing one or more second RNA primers to the one or more RNA template; and (g) extending the one or more second RNA primers in a second nucleic acid extension reaction using a strand-displacement reverse transcriptase to generate a plurality of DNA sequence complementary to the one or more RNA templates, wherein the plurality of complementary DNA (cDNA) sequences each comprise the complementary DNA sequence and a UMI or unique sequence tag. In some embodiments, one or more steps of the method may be carried out in a single reaction step. For example, in some embodiments, steps (b) through (g) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase). In one embodiment, the method involves preparing a sequencing library from a test sample comprising RNA molecules, the method comprising the steps: (a) obtaining a test sample comprising one or more RNA sequences, and purifying the one or more RNA sequences from the test sample; (b) annealing a first RNA primer to the one or more RNA sequences; (c) extending the first RNA primer in a first nucleic acid extension reaction using a reverse transcriptase, wherein the reverse transcriptase comprises reverse transcription and terminal transferase activities, to generate a plurality of DNA sequences complementary to the one or more RNA sequences, wherein the terminal transferase activity adds a cytosine (C) tail to the 3'-end of the complementary DNA (cDNA) sequences; (d) annealing a template switching oligonucleotide to the 3'-cytosine tail of the cDNA sequence, wherein the template switching oligonucleotide comprises a unique molecular identifier (UMI) or a unique sequence tag; (e) ligating the template switching oligonucleotide to the 5'-end of the one or more RNA sequences with T4 RNA ligase to generate one or more RNA templates, wherein the one or more RNA templates comprise the original one or more RNA sequences covalently linked to the template switching oligonucleotide and the UMI or unique sequence tag; (f) annealing a plurality of second RNA primers to the one or more RNA templates; and (g) extending the plurality of second RNA primers in a second nucleic acid extension reaction using a strand-displacement reverse transcriptase to generate a plurality of DNA sequence complementary to the one or more RNA templates, wherein the plurality of complementary DNA (cDNA) each comprise the complementary DNA sequence and a UMI or unique sequence tag. In some embodiments, one or more steps of a method can be carried out in a single reaction step. For example, steps (b) through (g) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase).

In some embodiments, detection of a genetic biomarker (e.g., one or more genetic biomarkers) can include any of the variety of methods described in P.C.T. Publication No. WO 2018/085862, which is hereby incorporated by reference in its entirety. For example, detection of a genetic biomarker can include methods and systems for identifying somatic mutational signatures for detecting, diagnosing, monitoring and/or classifying cancer in a patient known to have, or suspected of having cancer. In various embodiments, the methods use a non-negative matrix factorization (NMF) approach to construct a signature matrix that can be used to identify latent signatures in a patient sample for detection and classification of cancer. In other embodiments, the methods may use principal components analysis (PCA) or vector quantization (VQ) approaches to construct a signature matrix. In one example, the patient sample is a cell-free nucleic acid sample (e.g., cell-free DNA (cfDNA) and/or cell-free RNA (cfRNA)). The construction of a signature matrix using non-negative matrix factorization can be generalized to multiple features relevant to cancer detection and/or classification. In some embodiments, a signature matrix comprises a plurality of signatures where the probability of the occurrence for each of a plurality of features are represented. Examples of relevant features include, but are not limited to, an upstream sequence context of a base substitution mutation, a downstream sequence context of a base substitution mutation, an insertion, a deletion, a somatic copy number alteration (SCNA), a translocation, a genomic methylation status, a chromatin state, a sequencing depth of coverage, an early versus late replicating region, a sense versus antisense strand, an inter mutation distance, a variant allele frequency, a fragment start/stop, a fragment length, and a gene expression status, or any combination thereof. In one embodiment, the upstream and/or downstream sequence context can comprise a region of a nucleic acid that ranges in length from about 2 to about 40 bp, such as from about 3 to about 30 bp, such as from about 3 to about 20 bp, or such as from about 2 to about 10 bp of sequence context of a base substitution mutation. In one embodiment, the upstream and/or downstream sequence context may be a triplet sequence context, a quadruplet sequence context, a quintuplet sequence context, a sextuplet sequence context, or a septuplet sequence context of base substitution mutations. In some embodiments, the upstream and/or downstream sequence context can be the triplet sequence context of a base substitution mutation. In one embodiment, the methods are used to identify latent somatic mutational signatures in a subject's (e.g., an asymptomatic subject) cfDNA sample for early detection of cancer. In another embodiment, the methods are used to infer tissue of origin for a patient's cancer based on latent mutational signatures identified in the patient's cfDNA sample. In yet another embodiment, the methods are used to identify latent mutational signatures in a patient's cfDNA sample that can be used to classify the patient for different types of therapies. In yet another embodiment, non-negative matrix factorization is applied to learn error modes in a somatic variant (mutation) calling assay. For example, systematic errors (e.g., errors contributed during library preparation, PCR, hybridization capture, and/or sequencing) that underlie the assay can be identified and assigned unique signatures that can be used to distinguish between the contribution from true somatic variants and artifactual variants arising from the technical processes in the assay. In yet another embodiment, non-negative matrix factorization can be used to identify mutational signatures that are associated with healthy aging. Mutation processes that are associated with aging are assigned mutational signatures that can be used to distinguish between healthy somatic mutations associated with patient age and somatic mutations contributed from, and indicative of, a cancer process in the patient. In another embodiment, one or more mutational signatures can be monitored over time and used for diagnosing, monitoring, and/or classifying cancer. For example, the observed mutational profile in cfDNA from patient samples at two or more time points can be evaluated. In some embodiments, two or more mutational signature processes can be evaluated as a combination of different mutational signatures. In still another embodiment, one or more mutational signatures can be monitored over time (e.g., at a plurality of time points) to monitor the effectiveness of a therapeutic regimen or other cancer treatment. In one embodiment, the sequence context of identified mutations can be utilized as a feature for analyzing somatic mutations in the detection and/or classification of cancer.

In some embodiments, detection of a genetic biomarker (e.g., one or more genetic biomarkers) can include any of the variety of methods described in U.S. Patent Application Publication No. 2018/0163201, which is hereby incorporated by reference in its entirety. For example, detection of a genetic biomarker can include methods for preparing sequencing libraries comprising a plurality of RNA molecules. In one embodiment, the method for preparing a sequencing library from a test sample comprising RNA, comprises the steps: (a) obtaining a test sample comprising RNA sequences, and purifying the RNA sequences from the test sample; (b) synthesizing first complementary DNA (cDNA) strands based on the RNA sequences and C-tailing 3'-ends of cDNA strands; (c) annealing a complementary template switching oligonucleotide to the C-tail of the cDNA and ligating the complementary template switching oligonucleotide to the 5'-ends of the RNA sequences to produce RNA templates; and (d) synthesizing a plurality of cDNA strands from the RNA templates using a strand-displacement reverse transcriptase. In some embodiments, one or more steps of the method may be carried out in a single reaction step. For example, steps (b) through (d) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase). In one embodiment, the method comprises the steps: (a) obtaining a test sample comprising one or more RNA sequences, and purifying the one or more RNA sequences from the test sample; (b) annealing a first RNA primer to the one or more RNA sequences; (c) extending the first RNA primer in a first nucleic acid extension reaction using reverse transcriptase, wherein the reverse transcriptase comprises reverse transcription and terminal transferase activities, to generate a plurality of DNA sequences complementary to the one or more RNA templates, and wherein the complementary DNA (cDNA) sequences further comprise a plurality of non-templated bases at the 3'-end of the cDNA sequences; (d) annealing a complementary nucleic acid sequence to the non-templated bases at the 3'-end of the cDNA sequence, wherein the complementary nucleic acid sequence further comprises a unique molecular identifier (UMI) or a unique sequence tag; (e) ligating the complementary nucleic acid sequence to the 5'-end of the one or more RNA sequences to generate one or more RNA templates, wherein the one or more RNA templates comprise the original one or more RNA sequences covalently linked to the complementary nucleic acid sequence comprising the UMI or unique sequence tag; (f) annealing one or more second RNA primers to the one or more RNA template; and (g) extending the one or more second RNA primers in a second nucleic acid extension reaction using a strand-displacement reverse transcriptase to generate a plurality of DNA sequence complementary to the one or more RNA templates, wherein the plurality of complementary DNA (cDNA) sequences each comprise the complementary DNA sequence and a UMI or unique sequence tag. In some embodiments, one or more steps of the method may be carried out in a single reaction step. For example, in some embodiments, steps (b) through (g) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase). In one embodiment, a method involves preparing a sequencing library from a test sample comprising RNA molecules, the method comprising the steps: (a) obtaining a test sample comprising one or more RNA sequences, and purifying the one or more RNA sequences from the test sample; (b) annealing a first RNA primer to the one or more RNA sequences; (c) extending the first RNA primer in a first nucleic acid extension reaction using a reverse transcriptase, wherein the reverse transcriptase comprises reverse transcription and terminal transferase activities, to generate a plurality of DNA sequences complementary to the one or more RNA sequences, wherein the terminal transferase activity adds a cytosine (C) tail to the 3'-end of the complementary DNA (cDNA) sequences; (d) annealing a template switching oligonucleotide to the 3'-cytosine tail of the cDNA sequence, wherein the template switching oligonucleotide comprises a unique molecular identifier (UMI) or a unique sequence tag; (e) ligating the template switching oligonucleotide to the 5'-end of the one or more RNA sequences with T4 RNA ligase to generate one or more RNA templates, wherein the one or more RNA templates comprise the original one or more RNA sequences covalently linked to the template switching oligonucleotide and the UMI or unique sequence tag; (f) annealing a plurality of second RNA primers to the one or more RNA templates; and (g) extending the plurality of second RNA primers in a second nucleic acid extension reaction using a strand-displacement reverse transcriptase to generate a plurality of DNA sequence complementary to the one or more RNA templates, wherein the plurality of complementary DNA (cDNA) each comprise the complementary DNA sequence and a UMI or unique sequence tag. In some embodiments, one or more steps of a method can be carried out in a single reaction step. For example, steps (b) through (g) may be carried out in a single reaction tube utilizing a reaction mixture comprising RNA primers (e.g., random hexamer RNA primers, polyT primers, or a combination thereof), a strand-displacement reverse transcriptase (e.g., MMLV reverse transcriptase), an RNA ligase (e.g., T4 RNA ligase), and optionally, a polynucleotide kinase (e.g., T4 polynucleotide kinase).

In some embodiments, detection of a genetic biomarker (e.g., one or more genetic biomarkers) can include any of the variety of methods described in P.C.T. Publication No. WO 2018/081130, which is hereby incorporated by reference in its entirety. For example, detection of a genetic biomarker can include a method comprising obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample. In some embodiments, the method comprises obtaining a second biological sample from the subject, wherein the second biological sample comprises cell-free nucleic acid from the subject and potentially cell-free nucleic acid from a pathogen. In some embodiments, the method comprises performing a second assay comprising massively parallel sequencing of the cell-free nucleic acid in the second biological sample to generate sequence reads. In some embodiments, the method comprises determining an amount of the sequence reads that align to a reference genome of the pathogen. In some embodiments, the method comprises determining an amount of the cell-free nucleic acid molecules that have a size within a given range and align to a reference genome of the pathogen based on the massively parallel sequencing. In some embodiments, the method comprises screening for the tumor based on performing a first assay comprising measuring a copy number of the cell-free nucleic acid from the pathogen in the first biological sample, and performing a second assay comprising massively parallel sequencing of the cell-free nucleic acid in the second biological sample to generate sequence reads. In some embodiments, the first biological sample and the second biological sample are the same. In some embodiments, the method further comprises determining a percentage of the sequence reads that align to a reference genome of the pathogen. In some embodiments, the method further comprises comparing the percentage of the sequence reads that align to a reference genome of the pathogen to a cutoff value. In some embodiments, the method further comprises determining a size ratio of a first proportion of the cell-free nucleic acid molecules from the second biological sample that align to the reference genome of the pathogen with a size within the given range and a second proportion of the cell-free nucleic acid molecules from the second biological sample that align to a reference genome of the subject with a size within the given range. In some embodiments, the method further comprises determining a size index, wherein the size index is an inverse of the size ratio, and comparing the size index to a second cutoff value. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the first biological sample and the second biological sample are plasma. In some embodiments, the method comprises obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample, wherein the first assay comprises a positive predictive value for a presence of the tumor in the subject. In some embodiments, the method comprises performing a second assay on a second biological sample from the subject, wherein the second biological sample comprises cell-free nucleic acid from the subject and potentially cell-free nucleic acid from the pathogen, and wherein a positive predictive value for a presence of the tumor in the subject of the first assay and the second assay is at least 5-fold greater than the positive predictive value of the first assay. In some embodiments, the positive predictive value for a presence of the tumor in the subject of the first assay and the second assay is at least 7.5-fold greater than the positive predictive value of the first assay. In some embodiments, the positive predictive value for a presence of the tumor in the subject of the first assay and the second assay is at least 15%. In some embodiments, the positive predictive value for a presence of the tumor in the subject of the first assay and the second assay is at least 25%. In some embodiments, the first biological sample and the second biological sample are the same. In some embodiments, the first biological sample and the second biological sample are plasma. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the second assay comprises massively parallel sequencing of the cell-free nucleic acid in the second biological sample to generate sequence reads. In some embodiments, the second assay comprises of determining an amount of the sequence reads that align to a reference genome of the pathogen. In some embodiments, the second assay comprises determining an amount of the cell-free nucleic acid molecules in the second biological sample that have a size within a given range and align to a reference genome of the pathogen. In some embodiments, the method comprises obtaining a first biological sample from the subject, wherein the first biological sample comprises cell-free nucleic acid from the subject and potentially cell-free nucleic acid from a pathogen. In some embodiments, the method comprises performing a first assay comprising measuring a copy number of the cell-free nucleic acid from the pathogen in the first biological sample, wherein the first assay has a false positive rate for a presence of the tumor in the subject. In some embodiments, the method comprises performing a second assay on a second biological sample from the subject, wherein the second biological sample comprises cell-free nucleic acid from the subject and potentially cell-free nucleic acid from the pathogen, wherein a false positive rate for a presence of the tumor in the subject of the first assay and the second assay is at least 5-fold lower than the false positive rate of the first assay. In some embodiments, the false positive rate for a presence of the tumor in the subject of the first assay and the second assay is at least 10-fold lower than the false positive rate of the first assay. In some embodiments, the false positive rate for a presence of the tumor in the subject of the first assay and the second assay is less than 1%. In some embodiments, the first biological sample and the second biological sample are the same. In some embodiments, the first biological sample and the second biological sample are plasma. In some embodiments, the tumor is nasopharyngeal cancer. In some embodiments, the pathogen is Epstein-Barr Virus (EBV). In some embodiments, measuring a copy number of the cell-free nucleic acid from the pathogen in the first biological sample comprises amplification. In some embodiments, the amplification comprises polymerase chain reaction (PCR). In some embodiments, the PCR comprises quantitative PCR (qPCR). In some embodiments, the second assay comprises massively parallel sequencing of the cell-free nucleic acid in the second biological sample to generate sequence reads. In some embodiments, the second assay comprises of determining an amount of the sequence reads that align to a reference genome of the pathogen. In some embodiments, the second assay comprises determining an amount of the cell-free nucleic acid molecules in the second biological sample that have a size within a given range and align to a reference genome of the pathogen. In some embodiments, the method comprises analyzing a biological sample, including a mixture of cell-free nucleic acid molecules, to determine a level of pathology in a subject from which the biological sample is obtained, the mixture including nucleic acid molecules from the subject and potentially nucleic acid molecules from a pathogen. In some embodiments, the method comprises analyzing a first plurality of cell-free nucleic acid molecules from a biological sample of the subject, wherein the analyzing comprises determining a genomic position in a reference genome corresponding to at least one end of the first plurality of cell-free nucleic acid molecules, the reference genome corresponding to the pathogen. In some embodiments, the method comprises determining a first amount of the first plurality of cell-free nucleic acid molecules that end within one of first windows, each first window comprising at least one of a first set of genomic positions at which ends of cell-free nucleic acid molecules are present at a rate above a first threshold in subjects with a pathology associated with the pathogen. In some embodiments, the method comprises computing a relative abundance of the first plurality of cell-free nucleic acid molecules ending within one of the first windows by normalizing the first amount using a second amount of the first plurality of cell-free nucleic acid molecules from the biological sample, wherein the second amount of the first plurality of cell-free nucleic acid molecules includes cell-free nucleic acid molecules ending at a second set of genomic positions outside of the first windows including the first set of genomic positions. In some embodiments, the method comprises determining the level of pathology in the subject by processing the relative abundance against one or more cutoff values. In some embodiments, the relative abundance against one or more cutoff values includes determining whether the relative abundance is greater than the one or more cutoff values. In some embodiments, the method further comprises determining the second amount of the first plurality of cell-free nucleic acid molecules that end within one of second windows, each second window comprising at least one of the second set of genomic positions at which ends of cell-free nucleic acid molecules are present at a rate above a second threshold in subjects without a pathology resulting from pathogen, wherein normalizing the first amount includes computing the relative abundance using the first amount and the second amount. In some embodiments, the method further comprises identifying the second set of genomic positions. In some embodiments, the identifying comprises analyzing, by a computer system, the cell-free nucleic acid molecules of a reference sample from a reference subject that does not have the pathology. In some embodiments, analyzing each of the plurality of cell-free nucleic acid molecules comprises determining a genomic position in the reference genome corresponding to at least one end of the cell-free nucleic acid molecule. In some embodiments, the reference subject is healthy. In some embodiments, the relative abundance comprises a ratio of the first amount and the second amount. In some embodiments, the method further comprises identifying the first set of genomic positions at which ends of cell-free nucleic acid molecules occur at the rate above a first threshold. In some embodiments, identifying the first set of genomic positions comprises analyzing, by a computer system, a second plurality of cell-free nucleic acid molecules from at least one first additional sample to identify ending positions of the second plurality of cell-free nucleic acid molecules, wherein the at least one first additional sample is known to have the pathology associated with the pathogen and is of a same sample type as the biological sample. In some embodiments, the method further comprises, for each genomic window of a plurality of genomic windows, computing a corresponding number of the second plurality of cell-free nucleic acid molecules ending on the genomic window, and comparing the corresponding number to a reference value to determine whether the rate of cell-free nucleic acid molecules ending on one or more genomic positions within the genomic window is above the first threshold. In some embodiments, a first genomic window of the plurality of genomic windows has a width of at least one genomic position, and wherein each of the genomic positions within the first genomic window are identified as having the rate of cell-free nucleic acid molecules ending on the genomic position be above the first threshold when the corresponding number exceeds the reference value. In some embodiments, the first set of genomic positions have the highest N values for the corresponding numbers, wherein N is at least 100.

In some embodiments, detection of a genetic biomarker (e.g., one or more genetic biomarkers) can include any of the variety of methods described in U.S. Patent Application Publication No. 20180119216, which is hereby incorporated by reference in its entirety. For example, detection of a genetic biomarker can include methods for preparing and analyzing a single-stranded sequencing library from a double-stranded DNA (e.g., double-stranded cfDNA) sample. In some embodiments, the sample includes double-stranded DNA (dsDNA) molecules, and damaged dsDNA (e.g., nicked dsDNA) molecules. In some embodiments, the sample includes single-stranded DNA (ssDNA) molecules. The methods facilitate the collection of information, including strand-pairing and connectivity information, from dsDNA, ssDNA and damaged DNA (e.g., nicked DNA) molecules in a sample, thereby providing enhanced diagnostic information as compared to sequencing libraries that are prepared using conventional methods. Additionally or alternatively, detection of a genetic biomarker can include preparing a single stranded DNA (ssDNA) library for sequencing. For example, detection of a genetic biomarker can include using a ssDNA library preparation wherein both the forward (sense) and reverse (antisense) strands of a double stranded DNA fragment are tagged with an identical, or substantially identical, unique sequence tag (e.g., a partition-specific barcode or UMI) that allows for the complementary strands from a dsDNA molecule to be identified and analyzed. In one embodiment, the method comprises preparing a single-stranded DNA library for sequencing, the method comprising the following steps: (a) obtaining a test sample comprising double stranded DNA (dsDNA) and isolating dsDNA from the test sample; (b) partitioning the dsDNA sample into a plurality of individual reaction compartments; (c) adding a reaction mixture to each of said individual reaction compartments, said reaction mixture including a plurality of oligonucleotide comprising a unique sequence tag; (d) denaturing dsDNA to produce single-strand DNA (ssDNA) fragments; and (e) ligating unique sequence tags to the ssDNA fragments. In another embodiment, a method is provided for preparing a cell-free DNA library for sequencing, the method comprising the following steps: (a) obtaining a test sample comprising cell-free double stranded DNA (dsDNA) and isolating dsDNA from the test sample; (b) partitioning the dsDNA sample into a plurality of individual reaction droplets; (c) adding a reaction mixture to each of said individual droplets, said reaction mixture including a plurality of DNA capture beads, wherein each of said DNA capture beads includes a plurality of attached oligonucleotides comprising unique sequence tag; (d) heating the droplets to denature the dsDNA or chemically denaturing the dsDNA to produce single-strand DNA (ssDNA) fragments and to release the unique sequence tags from the beads; and (e) ligating the unique sequence tags to 3' ends of the ssDNA fragments. In some embodiments, said beads are selected from the group comprising streptavidin-coated beads, solid phase reversible immobilization (SPRI) bead, and magnetic beads. In another embodiment, a method is provided for preparing a single-stranded DNA library for sequencing, the method comprising the following steps: (a) providing a plurality of partitions, wherein individual partitions of the plurality comprise: (i) a portion of a test sample comprising, e.g., damaged and/or undamaged, double stranded DNA (dsDNA) isolated from one or more individuals; and (ii) a plurality of oligonucleotides, wherein the plurality of oligonucleotides comprise a partition-specific barcode; (b) incubating the partitions under conditions suitable to denature the double-stranded DNA into single-stranded DNA; and (c) ligating the single-stranded DNA to the oligonucleotides, wherein the ligating covalently links the partition-specific barcode to the single-stranded DNA and produces partition-specific barcoded single-stranded DNA. In some embodiments, the method further comprises combining the plurality of partitions. In some embodiments, the method further comprises hybridizing oligonucleotide primer to the partition-specific barcoded single-stranded DNA and extending the primer, thereby producing partition-specific barcoded double-stranded DNA. In some embodiments, the method comprises amplifying the partition-specific barcoded single-stranded DNA and/or the partition-specific barcoded double-stranded DNA. In some embodiments, the method further comprises dephosphorylating the double stranded DNA isolated from one or more individuals. In some embodiments, the method comprises dephosphorylating the double stranded DNA isolated from one or more individuals and then partitioning the double stranded DNA isolated from one or more individuals, thereby providing the plurality of partitions.

In some embodiments, detection of a genetic biomarker (e.g., one or more genetic biomarkers) can include any of the variety of methods described in U.S. Patent Application Publication No. 2018/0087105, which is hereby incorporated by reference in its entirety. For example, detection of a genetic biomarker can include methods for preparing and analyzing a sequencing library from a mixed cell-free DNA (cfDNA) sample, wherein the mixed sample includes double-stranded DNA (dsDNA), damaged dsDNA (e.g., nicked dsDNA), and single-stranded DNA (ssDNA) molecules. The subject methods facilitate the collection of information from dsDNA, ssDNA and damaged DNA (e.g., nicked DNA) molecules in a sample, thereby providing enhanced diagnostic information as compared to sequencing libraries that are prepared from dsDNA alone. In some embodiments, the method comprise preparing a combined cell-free DNA (cfDNA) sequencing library from a mixed cfDNA sample by: ligating a universal adapter comprising a unique sequence tag to at least one single-stranded DNA (ssDNA) molecule in the mixed cfDNA sample; extending the universal adapter to generate an ssDNA-derived double-stranded DNA (dsDNA) molecule; and generating a combined cfDNA sequencing library from the ssDNA-derived dsDNA molecule. In some embodiments, a method further comprises ligating a sequencing Y-adapter to the ssDNA-derived dsDNA molecule before generating the combined cfDNA sequencing library. In some embodiments, the sequencing Y-adapter comprises a unique sequence tag. In some embodiments, the first and second unique sequence tags are different. In some embodiments, the method further comprises: extending the second sequencing Y-adapter to generate a second nick-derived dsDNA molecule; ligating a third sequencing Y-adapter to the second nick-derived dsDNA molecule; and generating a combined cfDNA sequencing library from the first and the second nick-derived dsDNA molecules. In some embodiments, the method for preparing a combined cfDNA sequencing library from a mixed cfDNA sample comprises: ligating a first sequencing Y-adapter to a first end of a nicked dsDNA molecule in the mixed cfDNA sample, wherein the nicked dsDNA molecule comprises a nicked strand and an unnicked strand; ligating a second sequencing Y-adapter to a second end of the nicked dsDNA molecule in the mixed cfDNA sample; denaturing the sequencing Y-adapter-ligated nicked dsDNA molecule to generate a first ssDNA molecule derived from the unnicked strand, a second ssDNA molecule derived from the nicked strand, and a third ssDNA molecule derived from the nicked strand; extending the second sequencing Y-adapter to generate a first nick-derived dsDNA molecule; ligating a third sequencing Y-adapter to the first nick-derived dsDNA molecule; and generating a combined cfDNA sequencing library from the first nick-derived dsDNA molecule. In some embodiments, the first sequencing Y-adapter comprises a first unique sequence tag, the second sequencing Y-adapter comprises a second unique sequence tag, and the third sequencing Y-adapter comprises a third unique sequence tag. In some embodiments, the first, second and third unique sequence tags are the same. In some embodiments, the first, second and third unique sequence tags are different. In some embodiments, the first and second unique sequence tags are the same, and the third unique sequence tag is different. In some embodiments, the first and third unique sequence tags are the same, and the second unique sequence tag is different. In some embodiments, the second and third unique sequence tags are the same, and the first unique sequence tag is different.

In some embodiments, detection of a genetic biomarker (e.g., one or more genetic biomarkers) can include any of the variety of methods described in U.S. Patent Application Publication No. 2018/0002749, which is hereby incorporated by reference in its entirety. For example, detection of a genetic biomarker can include methods, compositions, reactions mixtures, kits, and systems for sequencing both RNA and DNA from a single source sample. In some embodiments, RNA is treated so as to differentiate RNA sequences from DNA sequences derived from the same sample. In some embodiments, the RNA and DNA are cell-free polynucleotides. In some embodiments, the methods improve the sensitivity and/or base calling accuracy of sequencing methodologies in the identification of mutations (e.g. rare sequence variants). In some embodiments, the method comprises: (a) obtaining a sample comprising both RNA and DNA; (b) reverse transcribing the RNA to produce cDNA/RNA hybrid molecules; (c) degrading the RNA of the hybrid molecules to produce single-stranded cDNA; (d) preferentially joining a tag oligonucleotide comprising a tag sequence to the single-stranded cDNA in a reaction comprising a single-stranded DNA ligase to produce tagged cDNA; and (e) sequencing the DNA and the tagged cDNA; wherein the reverse transcribing, preferentially joining, and sequencing are performed in the presence of the DNA. In some embodiments, the RNA and DNA are cell-free nucleic acids. Nucleic acids (including cell-free nucleic acids) can be isolated from any of a variety of sources, such as blood, a blood fraction (e.g. serum or plasma), urine, and other bodily fluids. In some embodiments, the reverse transcribing comprises extension of primers comprising a random sequence (e.g. one or more nucleotides selected at random from a set of two or more different nucleotides at one or more positions, with each of the different nucleotides selected at one or more positions represented in a pool of oligonucleotides comprising the random sequence). In some embodiments, the reverse transcribing comprises extension of the cDNA of the hybrid along a template-switch oligonucleotide (TSO), which may comprise a universal switch primer sequence. In some embodiments, the tag oligonucleotide is joined to a 3' end of the single-stranded cDNA. In some embodiments, the tag oligonucleotide comprises a primer binding sequence. In some embodiments, the sequencing comprises amplifying the tagged cDNA to produce double-stranded tagged cDNA. In some embodiments, amplifying the tagged cDNA comprises extending a primer hybridized to the primer binding sequence. In some embodiments, the sequencing comprises joining sequencing adapters to the tagged cDNA and the DNA. In some embodiments, the tag oligonucleotide comprises a unique molecular identifier (UMI), wherein each of a plurality of tagged cDNA molecules is distinguishable from others in the plurality of tagged cDNA molecules based on the UMI (e.g. as determined by the sequence of the UMI, optionally in combination with the sequence of the cDNA). In some embodiments, the sample is blood, a blood fraction, plasma, serum, saliva, sputum, urine, semen, transvaginal fluid, cerebrospinal fluid, or stool. In some embodiments, the sample is blood or a blood fraction (e.g. serum or plasma). In some embodiments, the method further comprises using a processor to group RNA-derived sequences separately from DNA-derived sequences based on the presence or absence of the tag sequence, or a complement of the tag sequence. In some embodiments, the method further comprises identifying presence or absence of a condition of a subject (e.g. cancer) based on the RNA-derived sequences and the DNA-derived sequences. In some embodiments, the method further comprises treating the subject based on the RNA-derived sequences and the DNA-derived sequences. In some embodiments, the method comprises: (a) obtaining a sample comprising both RNA and DNA; (b) joining a tag oligonucleotide comprising a tag sequence to the RNA in a reaction comprising an RNA ligase to produce tagged RNA; (c) reverse transcribing the tagged RNA to produce tagged cDNA; and (d) sequencing the DNA and the tagged cDNA; wherein the joining, reverse transcribing, and sequencing are performed in the presence of the DNA. In some embodiments, the RNA and DNA are cell-free nucleic acids. In some embodiments, the method further comprises fragmenting the RNA to produce fragmented RNA prior to joining the tag sequence. In some embodiments, the fragmented RNA have an average size within a pre-defined range (e.g. an average or median length from about 10 to about 1,000 nucleotides in length, such as between 10-800, 10-500, 50-500, 90-200, or 50-150 nucleotides; or an average or median length of less than 1500, 1000, 750, 500, 400, 300, 250, or fewer nucleotides in length). In some embodiments, fragmenting the RNA comprises subjecting the RNA and DNA to conditions that preferentially fragment the RNA. In some embodiments, fragmenting the RNA comprises sonication, chemical fragmentation, or heating. In some embodiments, the method further comprises dephosphorylating 3' ends of fragmented RNA. In some embodiments, the tag oligonucleotide is joined to a 3' end of the RNA. In some embodiments, the tag oligonucleotide comprises a primer binding sequence. In some embodiments, the reverse transcribing comprises extending a primer hybridized to the primer binding sequence. In some embodiments, the reverse transcribing comprises extension of the tagged cDNA along a template-switch oligonucleotide (TSO), which may comprise a universal switch primer sequence. In some embodiments, the sequencing comprises amplifying the tagged cDNA to produce double-stranded tagged cDNA. In some embodiments, the sequencing comprises joining sequencing adapters to the tagged cDNA and the DNA. In some embodiments, the tag oligonucleotide comprises a unique molecular identifier (UMI), wherein each of a plurality of tagged cDNA molecules is distinguishable from others in the plurality of tagged cDNA molecules based on the UMI (e.g. as determined by the sequence of the UMI, optionally in combination with the sequence of the cDNA). In some embodiments, the sample is blood, a blood fraction, plasma, serum, saliva, sputum, urine, semen, transvaginal fluid, cerebrospinal fluid, or stool. In some embodiments, the sample is blood or a blood fraction (e.g. serum or plasma). In some embodiments, the reverse transcribing comprises extension of primers comprising a random sequence. In some embodiments, the method further comprises using a processor to group RNA-derived sequences separately from DNA-derived sequences based on the presence or absence of the tag sequence, or a complement of the tag sequence. In some embodiments, the method further comprises identifying presence or absence of a condition of a subject (e.g. cancer) based on the RNA-derived sequences and the DNA-derived sequences. In some embodiments, the method further comprises treating the subject based on the RNA-derived sequences and the DNA-derived sequences.

In some embodiments, detection of a genetic biomarker (e.g., one or more genetic biomarkers) can include any of the variety of methods described in P.C.T. Publication No. WO 2017/218512, which is hereby incorporated by reference in its entirety. For example, detection of a genetic biomarker can include methods for enriching a plurality of target nucleic acids in a sample, the methods comprising providing an endonuclease system, wherein each of the plurality of target nucleic acids comprises a first variant and a second variant, wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid, wherein the first variant of each target nucleic acid comprises a PAM site adjacent to a region complementary to a crRNA targeting sequence, and wherein the second variant does not comprise the PAM site or does not comprise the region complementary to the crRNA targeting sequence adjacent to the PAM site, and contacting the sample with the endonuclease system, thereby depleting the first variant and enriching the second variant of each of the plurality of target nucleic acids in the sample. In some embodiments, the first variant of each target nucleic acid comprises a PAM site adjacent to a region complementary to a crRNA targeting sequence, and the second variant does not comprise the PAM site. In some embodiments, the first variant of each target nucleic acid comprises a PAM site adjacent to a region complementary to a crRNA targeting sequence, and the second variant does not comprise the region complementary to the crRNA targeting sequence adjacent to the PAM site. In some embodiments, the first variant of each target nucleic acid comprises a PAM site adjacent to a region complementary to a crRNA targeting sequence, and the second variant does not comprise the region complementary to the crRNA targeting sequence. In some embodiments, the methods comprise amplifying the enriched second variants of the plurality of target nucleic acids to produce an enriched sequencing library. In some embodiments, the methods comprise sequencing the enriched sequencing library to detect structural rearrangements or mutations in the target nucleic acids in the sample.

In some embodiments, detection of a genetic biomarker (e.g., one or more genetic biomarkers) can include any of the variety of methods described in P.C.T. Publication No. WO 2017/127741, which is hereby incorporated by reference in its entirety. For example, detection of a genetic biomarker can include methods and systems for high fidelity sequencing and identification of rare nucleic acid variants. The systems and methods may be used to identify rare variants in cell-free nucleic acid samples such as tumor specific mutations among a sample comprising a normal genomic nucleic acid majority. The systems and methods allow for the confident identification of mutations occurring at frequencies below 1:10,000 in a sample. Identification of such rare variants results from optimization of several steps in the sequencing process followed by analysis of sequencing reads based on aligned read pairs referred to as ensembles. The systems and methods may find applications outside of rare variant identification such as sequencing optimization for a desired level of performance or sensitivity. The methods include sequencing nucleic acid. Steps of the method may include obtaining sequencing reads of a nucleic acid, identifying an ensemble comprising two or more sequencing reads with shared start coordinates and read lengths, determining a number of sequenced molecules comprised by the ensemble, identifying a candidate variant in the ensemble, and determining a likelihood of the candidate variant being a true variant using a likelihood estimation model and the determined number of sequenced molecules. In certain embodiments, the step of obtaining sequencing reads may further comprise preparing a sequencing library from the nucleic acid, amplifying the sequencing library, and sequencing the sequencing library using next generation sequencing (NGS). In certain embodiments, adapters may be ligated to the nucleic acid under conditions configured to allow adapter stacking. The preparation of the sequencing library may comprise ligating adapters to the nucleic acid at a temperature of about 16 degrees Celsius using a reaction time of about 16 hours. The amplification step may comprise PCR amplification and the methods may further comprise selecting an over-amplification factor and a PCR cycle number required to detect variants at a specified concentration in a sample using an in-silico model. In various embodiments, the methods include designing a hybrid capture panel to target a genomic region based on factors comprising, guanine-cytosine (GC) content, mutation frequency in a target population, and sequence uniqueness and capturing the amplified nucleic acid using the hybrid capture panel before the sequencing step. The capturing step may include using a first hybrid capture panel targeting a sense strand of a target loci and a second hybrid capture panel targeting an antisense strand of the target loci. In certain embodiments, a synthetic nucleic acid control, also referred to as control sequence, control spike-in, or positive control, may be added to the nucleic acid before amplification of the sequencing library and error rate may then be determined using sequencing reads of the synthetic nucleic acid control. The synthetic nucleic acid control may comprise a known sequence having low diversity across a species from which the nucleic acid is derived and having a plurality of non-naturally occurring mismatches to the known sequence and, in certain embodiments, the plurality of non-naturally occurring mismatches can be 4. The synthetic nucleic acid control may include a guanine-cytosine (GC) content distribution that is representative of the target loci of the hybrid capture panel or may include a plurality of nucleic acids comprising varying overlaps with a pull down probe of the hybrid capture panel. Error rate or candidate variant frequency may be determined using sequencing reads of the synthetic nucleic acid control.

In some embodiments, detection of a genetic biomarker (e.g., one or more genetic biomarkers) can include any of the variety of methods described in U.S. Pat. No. 9,902,992, which is hereby incorporated by reference in its entirety. For example, detection of a genetic biomarker can include a method for detecting copy number variation comprising: a) sequencing extracellular polynucleotides from a bodily sample from a subject, wherein each of the extracellular polynucleotide are optionally attached to unique barcodes; b) filtering out reads that fail to meet a set threshold; c) mapping sequence reads obtained from step (a) to a reference sequence; d) quantifying/counting mapped reads in two or more predefined regions of the reference sequence; e) determining a copy number variation in one or more of the predefined regions by (i) normalizing the number of reads in the predefined regions to each other and/or the number of unique barcodes in the predefined regions to each other; and (ii) comparing the normalized numbers obtained in step (i) to normalized numbers obtained from a control sample. Additionally or alternatively, detection of a genetic biomarker can include a method for detecting a rare mutation in a cell-free or substantially cell free sample obtained from a subject comprising: a) sequencing extracellular polynucleotides from a bodily sample from a subject, wherein each of the extracellular polynucleotide generate a plurality of sequencing reads; b) sequencing extracellular polynucleotides from a bodily sample from a subject, wherein each of the extracellular polynucleotide generate a plurality of sequencing reads; sequencing extracellular polynucleotides from a bodily sample from a subject, wherein each of the extracellular polynucleotide generate a plurality of sequencing reads; c) filtering out reads that fail to meet a set threshold; d) mapping sequence reads derived from the sequencing onto a reference sequence; e) identifying a subset of mapped sequence reads that align with a variant of the reference sequence at each mappable base position; f) for each mappable base position, calculating a ratio of (a) a number of mapped sequence reads that include a variant as compared to the reference sequence, to (b) a number of total sequence reads for each mappable base position; g) normalizing the ratios or frequency of variance for each mappable base position and determining potential rare variant(s) or mutation(s); h) and comparing the resulting number for each of the regions with potential rare variant(s) or mutation(s) to similarly derived numbers from a reference sample. Additionally or alternatively, detection of a genetic biomarker can include a method of characterizing the heterogeneity of an abnormal condition in a subject, the method comprising generating a genetic profile of extracellular polynucleotides in the subject, wherein the genetic profile comprises a plurality of data resulting from copy number variation and/or other rare mutation (e.g., genetic alteration) analyses. In some embodiments, the prevalence/concentration of each rare variant identified in the subject is reported and quantified simultaneously. In other embodiments, a confidence score, regarding the prevalence/concentrations of rare variants in the subject, is reported. In some embodiments, extracellular polynucleotides comprise DNA. In other embodiments, extracellular polynucleotides comprise RNA. Polynucleotides may be fragments or fragmented after isolation. Additionally or alternatively, detection of a genetic biomarker can include a method for circulating nucleic acid isolation and extraction. In some embodiments, extracellular polynucleotides are isolated from a bodily sample that may be selected from a group consisting of blood, plasma, serum, urine, saliva, mucosal excretions, sputum, stool and tears. In some embodiments, the methods also comprise a step of determining the percent of sequences having copy number variation or other rare genetic alteration (e.g., sequence variants) in said bodily sample. In some embodiments, the percent of sequences having copy number variation in said bodily sample is determined by calculating the percentage of predefined regions with an amount of polynucleotides above or below a predetermined threshold. Additionally or alternatively, detection of a genetic biomarker can include a method for detecting a rare mutation in a cell-free or a substantially cell free sample obtained from a subject comprising: a) sequencing extracellular polynucleotides from a bodily sample from a subject, wherein each of the extracellular polynucleotides generate a plurality of sequencing reads; b) filtering out reads that fail to meet a set threshold; c) mapping sequence reads derived from the sequencing onto a reference sequence; d) identifying a subset of mapped sequence reads that align with a variant of the reference sequence at each mappable base position; e) for each mappable base position, calculating a ratio of (a) a number of mapped sequence reads that include a variant as compared to the reference sequence, to (b) a number of total sequence reads for each mappable base position; f) normalizing the ratios or frequency of variance for each mappable base position and determining potential rare variant(s) or other genetic alteration(s); and g) comparing the resulting number for each of the regions. Additionally or alternatively, detection of a genetic biomarker can include a method comprising: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; and d. collapsing the set of sequencing reads to generate a set of consensus sequences, each consensus sequence corresponding to a unique polynucleotide among the set of tagged parent polynucleotides. In certain embodiments, the method further comprises: e. analyzing the set of consensus sequences for each set of tagged parent molecules.

In some embodiments, detection of a genetic biomarker (e.g., one or more genetic biomarkers) can include any of the variety of methods described in P.C.T. Publication No. WO 2018/064629, which is hereby incorporated by reference in its entirety. For example, detection of a genetic biomarker can include a bait set panel comprising one or more bait sets that selectively enrich for one or more nucleosome-associated regions of a genome, said nucleosome-associated regions comprising genomic regions having one or more genomic base positions with differential nucleosomal occupancy, wherein the differential nucleosomal occupancy is characteristic of a cell or a tissue type of origin or a disease state. In some embodiments, each of the one or more nucleosome-associated regions of a bait set panel comprise at least one of: (i) significant structural variation, comprising a variation in nucleosomal positioning, said structural variation selected from the group consisting of: an insertion, a deletion, a translocation, a gene rearrangement, methylation status, a micro-satellite, a copy number variation, a copy number-related structural variation, or any other variation which indicates differentiation; and (ii) instability, comprising one or more significant fluctuations or peaks in a genome partitioning map indicating one or more locations of nucleosomal map disruptions in a genome. In some embodiments, the one or more bait sets of a bait set panel are configured to capture nucleosome-associated regions of the genome based on a function of a plurality of reference nucleosomal occupancy profiles (i) associated with one or more disease states and one or more non-disease states; (ii) associated with a known somatic mutation, such as SNV, CNV, indel, or re-arrangement; and/or (iii) associated with differential expression patterns. In an embodiment, the one or more bait sets of a bait set panel selectively enrich for one or more nucleosome-associated regions in a cell-free deoxyribonucleic acid (cfDNA) sample. Additionally or alternatively, detection of a genetic biomarker can include a method for enriching a nucleic acid sample for nucleosome-associated regions of a genome comprising (a) bringing a nucleic acid sample in contact with a bait set panel, said bait set panel comprising one or more bait sets that selectively enrich for one or more nucleosome-associated regions of a genome; and (b) enriching the nucleic acid sample for one or more nucleosome-associated regions of a genome. Additionally or alternatively, detection of a genetic biomarker can include a method for generating a bait set comprising (a) identifying one or more regions of a genome, said regions associated with a nucleosome profile, and (b) selecting a bait set to selectively capture said regions. In an embodiment, a bait set in a bait set panel selectively enriches for one or more nucleosome-associated regions in a cell-free deoxyribonucleic acid sample. Additionally or alternatively, detection of a genetic biomarker can include a method for enriching for multiple genomic regions comprising bringing a predetermined amount of a nucleic acid sample in contact with a bait panel comprising (i) a first bait set that selectively hybridizes to a first set of genomic regions of the nucleic acid sample, provided at a first concentration ratio that is less than a saturation point of the first bait set, and (ii) a second bait set that selectively hybridizes to a second set of genomic regions of the nucleic acid sample, provided at a second concentration ratio that is associated with a saturation point of the second bait set; and enriching the nucleic acid sample for the first set of genomic regions and the second set of genomic regions. Additionally or alternatively, detection of a genetic biomarker can include a method for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing, comprising (a) for each of the plurality of sequence reads associated with the cell-free DNA molecules, providing: a predetermined expectation of an indel being detected in one or more sequence reads of the plurality of sequence reads; a predetermined expectation that a detected indel is a true indel present in a given cell-free DNA molecule of the cell-free DNA molecules, given that an indel has been detected in the one or more of the sequence reads; and a predetermined expectation that a detected indel is introduced by non-biological error, given that an indel has been detected in the one or more of the sequence reads; (b) providing quantitative measures of one or more model parameters characteristic of sequence reads generated by nucleic acid sequencing; (c) detecting one or more candidate indels in the plurality of sequence reads associated with the cell-free DNA molecules; and (d) for each candidate indel, performing a hypothesis test using one or more of the model parameters to classify said candidate indel as a true indel or an introduced indel, thereby improving accuracy of detecting an indel. Additionally or alternatively, detection of a genetic biomarker can include a kit comprising (a) a sample comprising a predetermined amount of DNA; and (b) a bait set panel comprising (i) a first bait set that selectively hybridizes to a first set of genomic regions of a nucleic acid sample comprising a predetermined amount of DNA, provided at a first concentration ratio that is less than a saturation point of the first bait set and (ii) a second bait set that selectively hybridizes to a second set of genomic regions of the nucleic acid sample, provided at a second concentration ratio that is associated with a saturation point of the second bait set. Additionally or alternatively, detection of a genetic biomarker can include a method for enriching for multiple genomic regions, comprising: (a) bringing a predetermined amount of nucleic acid from a sample in contact with a bait mixture comprising (i) a first bait set that selectively hybridizes to a first set of genomic regions of the nucleic acid from the sample, which first bait set is provided at a first concentration that is less than a saturation point of the first bait set, and (ii) a second bait set that selectively hybridizes to a second set of genomic regions of the nucleic acid sample, which second bait set is provided at a second concentration that is associated with a saturation point of the second bait set; and (b) enriching the nucleic acid sample for the first set of genomic regions and the second set of genomic regions. Additionally or alternatively, detection of a genetic biomarker can include a method for enriching multiple genomic regions, comprising: (a) bringing a predetermined amount of nucleic acid from a sample in contact with a bait mixture comprising: (i) a first bait set that selectively hybridizes to a first set of genomic regions of the nucleic acid from the sample, which first bait set is provided at a first concentration that is less than a saturation point of the first bait set, and (ii) a second bait set that selectively hybridizes to a second set of genomic regions of the nucleic acid from the sample, which second bait set is provided at a second concentration that is at or above a saturation point of the second bait set; and (b) enriching the nucleic acid from the sample for the first set of genomic regions and the second set of genomic regions, thereby producing an enriched nucleic acid.

In some embodiments, detection of a genetic biomarker (e.g., one or more genetic biomarkers) can include any of the variety of methods described in U.S. Pat. No. 9,790,559, which is hereby incorporated by reference in its entirety. For example, detection of a genetic biomarker can include a method for detecting copy number variation comprising: a) sequencing extracellular polynucleotides from a bodily sample from a subject, wherein each of the extracellular polynucleotide are optionally attached to unique barcodes; b) filtering out reads that fail to meet a set threshold; c) mapping sequence reads obtained from step (a) to a reference sequence; d) quantifying/counting mapped reads in two or more predefined regions of the reference sequence; e) determining a copy number variation in one or more of the predefined regions by (i) normalizing the number of reads in the predefined regions to each other and/or the number of unique barcodes in the predefined regions to each other; and (ii) comparing the normalized numbers obtained in step (i) to normalized numbers obtained from a control sample. Additionally or alternatively, detection of a genetic biomarker can include a method for detecting a rare mutation in a cell-free or substantially cell free sample obtained from a subject comprising: a) sequencing extracellular polynucleotides from a bodily sample from a subject, wherein each of the extracellular polynucleotides generate a plurality of sequencing reads; b) sequencing extracellular polynucleotides from a bodily sample from a subject, wherein each of the extracellular polynucleotide generate a plurality of sequencing reads; sequencing extracellular polynucleotides from a bodily sample from a subject, wherein each of the extracellular polynucleotide generate a plurality of sequencing reads; c) filtering out reads that fail to meet a set threshold; d) mapping sequence reads derived from the sequencing onto a reference sequence; e) identifying a subset of mapped sequence reads that align with a variant of the reference sequence at each mappable base position; f) for each mappable base portion, calculating a ratio of (a) a number of mapped sequence reads that include a variant as compared to the reference sequence, to (b) a number of total sequence reads for each mappable base position, g) normalizing the ratios or frequency of variance for each mappable base position and determining potential rare variant(s) or mutation(s); h) and comparing the resulting number for each of the regions with potential rare variant(s) or mutation(s) to similarly derived numbers from a reference sample. Additionally or alternatively, detection of a genetic biomarker can include a method of characterizing the heterogeneity of an abnormal condition in a subject, the method comprising generating a genetic profile of extracellular polynucleotides in the subject, wherein the genetic profile comprises a plurality of data resulting from copy number variation and/or other rare mutation (e.g., genetic alteration) analyses. Additionally or alternatively, detection of a genetic biomarker can include a system comprising a computer readable medium for performing the following steps: selecting predefined regions in a genome; enumerating number of sequence reads in the predefined regions; normalizing the number of sequence reads across the predefined regions, and determining percent of copy number variation in the predefined regions. In some embodiments, the entirety of the genome or at least 10%, 20%, 30%, 40%, 50%, 60%, 70%, 80%, or 90% of the genome is analyzed. In some embodiments, computer readable medium provides data in percent cancer DNA or RNA in plasma or serum to the end user. Additionally or alternatively, detection of a genetic biomarker can include a method for detecting a rare mutation in a cell-free or a substantially cell free sample obtained from a subject comprising: a) sequencing extracellular polynucleotides from a bodily sample from a subject, wherein each of the extracellular polynucleotides generate a plurality of sequencing reads; b) filtering out reads that fail to meet a set threshold; c) mapping sequence reads derived from the sequencing onto a reference sequence; d) identifying a subset of mapped sequence reads that align with a variant of the reference sequence at each mappable base position; e) for each mappable base position, calculating a ratio of (a) a number of mapped sequence reads that include a variant as compared to the reference sequence, to (b) a number of total sequence reads tor each mappable base position; f) normalizing the ratios or frequency of variance for each mappable base position and determining potential rare variant(s) or other genetic alteration(s); and g) comparing the resulting number for each of the regions. Additionally or alternatively, detection of a genetic biomarker can include a method comprising: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; and d. collapsing the set of sequencing reads to generate a set of consensus sequences, each consensus sequence corresponding to a unique polynucleotide among the set of tagged parent polynucleotides. In certain embodiments, the method further comprises; e. analyzing the set of consensus sequences for each set of tagged parent molecules. Additionally or alternatively, detection of a genetic biomarker can include a method comprising: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; d. collapsing the set of sequencing reads to generate a set of consensus sequences, each consensus sequence corresponding to a unique polynucleotide among the set of tagged parent polynucleotides; and e. filtering out from among the consensus sequences those that fail to meet a quality threshold. In one embodiment, the quality threshold considers a number of sequence reads from amplified progeny polynucleotides collapsed into a consensus sequence. In another embodiment, the quality threshold considers a number of sequence reads from amplified progeny polynucleotides collapsed into a consensus sequence. Additionally or alternatively, detection of a genetic biomarker can include a method comprising: a. providing at least one set of tagged parent polynucleotides, wherein each set maps to a different reference sequence in one or more genomes, and, for each set of tagged parent polynucleotides; i. amplifying the first polynucleotides to produce a set of amplified polynucleotides; ii. sequencing a subset of the set of amplified polynucleotides, to produce a set of sequencing reads; and iii. collapsing the sequence reads by: 1. grouping sequences reads sequenced from amplified progeny polynucleotides into families, each family amplified from the same tagged parent polynucleotide. In one embodiment collapsing further comprises: 2. determining a quantitative measure of sequence reads in each family. In another embodiment the method further comprises (including a) including a): b. determining a quantitative measure of unique families; and c. based on (1) the quantitative measure of unique families and (2) the quantitative measure of sequence read in each group, inferring a measure of unique tagged parent polynucleotides in the set. In another embodiment, inferring is performed using statistical or probabilistic models. In another embodiment, the method further comprises using a control or set of control samples to correct for amplification or representation biases between the two sets. In another embodiment, the method further comprises determining copy number variation between the sets. In another embodiment the method further comprises (including a, b, c): d. determining a quantitative measure of polymorphic forms among the families; and e. based on the determined quantitative measure of polymorphic forms, inferring a quantitative measure of polymorphic forms in the number of inferred unique tagged parent polynucleotides. In another embodiment wherein polymorphic forms include but are not limited to: substitutions, insertions, deletions, inversions, microsatellite changes, transversions, translocations, fusions, methylation, hypermethylation, hydroxymethylation, acetylation, epigenetic variants, regulatory-associated variants or protein binding sites. In another embodiment wherein the sets derive from a common sample, the method further comprising: a. inferring copy number variation for the plurality of sets based on a comparison of the inferred number of tagged parent polynucleotides in each set mapping to each of a plurality of reference sequences. In another embodiment, the original number of polynucleotides in each set is further inferred. Additionally or alternatively, detection of a genetic biomarker can include a system comprising a computer readable medium for performing the aforesaid methods. Additionally or alternatively, detection of a genetic biomarker can include a method of communicating sequence information about at least one individual polynucleotide molecule comprising: a. providing at least one individual polynucleotide molecule; b. encoding sequence information in the at least one individual polynucleotide molecule to produce a signal; c. passing at least part of the signal through a channel to produce a received signal comprising nucleotide sequence information about the at least one individual polynucleotide molecule, wherein the received signal comprises noise and/or distortion; d. decoding the received signal to produce a message comprising sequence information about the at least one individual polynucleotide molecule, wherein decoding reduces noise and/or distortion in the message; and e. providing the message to a recipient. In one embodiment, the noise comprises incorrect nucleotide cells. In another embodiment, distortion comprises uneven amplification of the individual polynucleotide molecule compared with other individual polynucleotide molecules. In another embodiment distortion results from amplification or sequencing bias. Additionally or alternatively, detection of a genetic biomarker can include a method for detecting a rare mutation in a cell-free or substantially cell free sample obtained from a subject comprising: a) sequencing extracellular polynucleotides from a bodily sample from a subject, wherein each of the extracellular polynucleotide generate a plurality of sequencing reads; b) performing multiplex sequencing on regions or whole-genome sequencing if enrichment is not performed; c) filtering out reads that fail to meet a set threshold; d) mapping sequence reads derived from the sequencing onto a reference sequence; e) identifying a subset of mapped sequence reads that align with a variant of the reference sequence at each mappable base position; f) for each mappable base position, calculating a ratio of (a) a number of mapped sequence reads that include a variant as compared to the reference sequence, to (b) a number of total sequence reads for each mappable base position; g) normalizing the ratios or frequency of variance for each mappable base position and determining potential rare variant(s) or mutation(s); and h) and comparing the resulting number for each of the regions with potential rare variant(s) or mutation(s) to similarly derived numbers from a reference sample. Additionally or alternatively, detection of a genetic biomarker can include a method of characterizing the heterogeneity of an abnormal condition in a subject, the method comprising generating a genetic profile of extracellular polynucleotides in the subject, wherein the genetic profile comprises a plurality data resulting from copy number variation and rare mutation analyses. Additionally or alternatively, detection of a genetic biomarker can include a method comprising determining copy number variation or performing rare mutation analysis in a cell-free or substantially cell free sample obtained from a subject using multiplex sequencing. Additionally or alternatively, detection of a genetic biomarker can include a method comprising: a) providing at least one set of tagged parent polynucleotides, and for each set of tagged parent polynucleotides; b) amplifying the tagged parent polynucleotides in the set to produce a corresponding set of amplified progeny polynucleotides; c) sequencing a subset (including a proper subset) of the set of amplified progeny polynucleotides, to produce a set of sequencing reads; d) collapsing the set of sequencing reads to generate a set of consensus sequences, each consensus sequence corresponding to a unique polynucleotide among the set of tagged parent polynucleotides; and e) filtering out from among the consensus sequences those that fail to meet a quality threshold.

In some embodiments, detection of a genetic biomarker (e.g., one or more genetic biomarkers) can include any of the variety of methods described in U.S. Pat. No. 7,700,286, which is hereby incorporated by reference in its entirety. For example, detection of a genetic biomarker can include a cancer detection assay in plasma/serum measuring by adding and comparing the amount of DNA and RNA of certain genes in the plasma/serum of cancer patients that are the reflection of a gene amplification and a gene over expression. Thus, gene amplification (seen by more DNA) and gene over expression (more RNA) are linked.

Additionally or alternatively, detection of a genetic biomarker can include a method for the diagnosis or the follow up of the evolution of cancers which comprises measuring together gene over expression (RNA) and gene amplification (DNA) in the bodily fluids of patients suspected to harbor cancer on any gene that is both amplified and over expressed in cancer cells and comparing to healthy controls. More particularly, RNA and DNA are extracted from a bodily fluid, such as plasma, serum, sputum, saliva, etc., purified and amplified, and the over expressed RNA and amplified DNA are analyzed and compared to a unique house keeping gene. In some embodiments, the nucleic acids are amplified by reversed transcriptase chain reaction (RT-PCR) and are analyzed by gel coloration, by radioactive immunological technique (RIA), by enzyme linked immunosorbant test (ELISA) or by a microchip test (gene array), and possibly quantified by any method for nucleic acid quantification. In some embodiments, the quantification of RNA and DNA is carried out by real time PCR, such as "TAQMAN™", or on capillaries "LIGHTCYCLER™", or real time PCR and RT PCR of any company. In some embodiments, the genes analyzed may be compared to a reference nucleic acid extract (DNA and RNA) corresponding to the expression (RNA) and quantity (DNA) of a unique house keeping gene, or to a reference RNA corresponding to the expression of a house keeping coding gene, or to a reference DNA corresponding to a unique gene, or may be estimated in reference to a standard curve obtained with nucleic acids of a cell line.

In some embodiments, detection of a genetic biomarker (e.g., one or more genetic biomarkers) can include any of the variety of methods described in U.S. Patent Application Publication No. 2018/0195131, which is hereby incorporated by reference in its entirety. For example, detection of a genetic biomarker can include methods to detect fusion genes, which may be used to detect a disease, such as cancer. Additionally or alternatively, detection of a genetic biomarker can include methods for enrichment of breakpoint fragments, such as to detect and characterize fusion genes, which may be associated with a disease, such as cancer. Additionally or alternatively, detection of a genetic biomarker can include a method for providing a diagnostic or therapeutic intervention to a subject having or suspected of having cancer, comprising (a) providing a biological sample comprising cell-free nucleic acid molecules from a subject; (b) contacting the cell-free nucleic acid molecules from the biological sample with a probe set under hybridization conditions sufficient to produce probe-captured polynucleotides, which probe set comprises a plurality of polynucleotide probes, wherein each of the plurality of polynucleotide probes has (i) sequence complementarity with a fusion gene and (ii) affinity for the fusion gene that is greater than a polynucleotide having sequence complementary with the fusion gene and containing only unmodified nucleotides; (c) isolating the probe-captured polynucleotides from the mixture, to produce a sample enriched with isolated polynucleotides comprising breakpoint fragments of the fusion gene; (d) sequencing the isolated polynucleotides to produce sequences; (e) detecting polynucleotides comprising breakpoints of fusion genes based on the sequences; and (f) providing the diagnostic or therapeutic intervention based on the detection of breakpoint fragments. Additionally or alternatively, detection of a genetic biomarker can include a method for capturing a breakpoint fragment of a fusion gene, comprising (a) providing a biological sample containing or suspected of containing a cell-free nucleic acid molecule comprising the breakpoint fragment of the fusion gene; and (b) contacting the biological sample with a polynucleotide probe under conditions sufficient to (i) permit hybridization between the polynucleotide probe and the breakpoint fragment to provide a probe-captured polynucleotide in a mixture, which polynucleotide probe has sequence complementarity with the breakpoint fragment and has affinity for the fusion gene that is greater than a polynucleotide having sequence complementary with the fusion gene and containing only unmodified nucleotides; and (ii) enrichment or isolation of the probe-captured polynucleotide from the mixture, wherein the polynucleotide probe has sequence complementarity with the breakpoint fragment. Additionally or alternatively, detection of a genetic biomarker can include a probe set comprising a plurality of polynucleotide probes, wherein each of the polynucleotide probes has (i) sequence complementarity with a fusion gene as part of a cell-free nucleic acid molecule and (ii) affinity for the fusion gene that is greater than a polynucleotide having sequence complementary with the fusion gene and containing only unmodified nucleotides. Additionally or alternatively, detection of a genetic biomarker can includes a high affinity polynucleotide, comprising a sequence that is configured to specifically hybridize to a nucleic acid sequence associated with a fusion gene in a cell-free nucleic acid molecule. Additionally or alternatively, detection of a genetic biomarker can include a high affinity polynucleotide configured to specifically hybridize to a fusion gene. In one embodiment, the high affinity polynucleotide comprises one or more locked nucleic acid nucleotides. In another embodiment the high affinity polynucleotide has a melting temperature that is at least any of 1° C., 2° C., 3° C., 4° C., 5° C., 10° C., 15° C. or 20° C. higher than a polynucleotide with the same sequence comprising only natural nucleotides. In another embodiment, the high affinity polynucleotide has a melting temperature that is at least any of 2%, 4%, 6%, 8%, or 10% higher than a polynucleotide with the same sequence comprising only natural nucleotides. In another embodiment, the high affinity polynucleotide is configured to specifically hybridize to a cancer fusion gene. Additionally or alternatively, detection of a genetic biomarker can include a high affinity polynucleotide probe comprising a high affinity polynucleotide configured to specifically hybridize to a fusion gene. In one embodiment, the high affinity polynucleotide comprises one or more locked nucleic acid nucleotides. In another embodiment, the probe comprises a functionality selected from a detectable label, a binding moiety or a solid support. In another embodiment, the probe is configured to hybridize to a breakpoint fragment of a fusion gene. In another embodiment, the breakpoint fragment has a length between about 140 nucleotides and about 180 nucleotides. In another embodiment the fragment is cell-free deoxyribonucleic acid (DNA) or genomic DNA. In another embodiment, the high affinity polynucleotide is bound to a solid support. Additionally or alternatively, detection of a genetic biomarker can include a method for capturing a breakpoint fragment of a fusion gene comprising contacting the breakpoint fragment with a high affinity polynucleotide probe under stringent hybridization conditions and allowing hybridization, wherein the polynucleotide probe is bound to a solid support and wherein the polynucleotide probe has a nucleotide sequence that is substantially or perfectly complementary to a nucleotide sequence of the breakpoint fragment. In one embodiment, the high affinity polynucleotide comprises one or more locked nucleic acid nucleotides. Additionally or alternatively, detection of a genetic biomarker can include a method for enriching a sample for polynucleotides comprising a breakpoint of a fusion gene, comprising: a) contacting a probe set with a mixture of polynucleotides under hybridization conditions to produce probe-captured polynucleotides; and b) isolating the probe-captured polynucleotides from the mixture, to produce a sample enriched with polynucleotides comprising breakpoint fragments of the fusion gene. In one embodiment, the high affinity polynucleotide comprises one or more locked nucleic acid nucleotides. In another embodiment, the polynucleotides comprise cell-free DNA or fragmented genomic DNA. In another embodiment, the method further comprises isolating captured polynucleotides from the probes. In another embodiment, the method further comprises sequencing the isolated polynucleotides. Additionally or alternatively, detection of a genetic biomarker can include a method of diagnosing cancer in a subject comprising: a) providing a sample comprising polynucleotides from a subject; b) contacting the cell-free DNA (cfDNA) from the sample with a probe set under hybridization conditions to produce probe-captured polynucleotides; c) isolating the probe-captured polynucleotides from the mixture, to produce a sample enriched with polynucleotides comprising breakpoint fragments of the fusion gene; d) sequencing the isolated polynucleotides to produce sequences; e) detecting polynucleotides comprising breakpoints of fusion genes based on the sequences; and f) diagnosing cancer based on the detection of breakpoint fragments. In one embodiment, the high affinity polynucleotide comprises one or more locked nucleic acid nucleotides.

In some embodiments, detection of a genetic biomarker (e.g., one or more genetic biomarkers) can include any of the variety of methods described in U.S. Patent Application Publication No. 2018/0120291, which is hereby incorporated by reference in its entirety. For example, detection of a genetic biomarker can include a method for analyzing a disease state of a subject, comprising (a) using a genetic analyzer to generate genetic data from nucleic acid molecules in biological samples of the subject obtained at (i) two or more time points or (ii) substantially the same time point, wherein the genetic data relates to genetic information of the subject, and wherein the biological samples include a cell-free biological sample; (b) receiving the genetic data from the genetic analyzer; (c) with one or more programmed computer processors, using the genetic data to produce an adjusted test result in a characterization of the genetic information of the subject; and (d) outputting the adjusted test result into computer memory. In some embodiments, the genetic data comprises current sequence reads and prior sequence reads, and wherein (c) comprises comparing the current sequence reads with the prior sequence reads and updating a diagnostic confidence indication accordingly with respect to the characterization of the genetic information of the subject, which diagnostic confidence indication is indicative of a probability of identifying one or more genetic variations in a biological sample of the subject. In some embodiments, the method further comprises obtaining a subsequent characterization and leaving as is a diagnostic confidence indication in the subsequent characterization for de novo information. In some embodiments, the method further comprises determining a frequency of one or more genetic variants detected in a collection of sequence reads included in the genetic data and producing the adjusted test result at least in part by comparing the frequency of the one or more genetic variants at the two or more time points. In some embodiments, the method further comprises determining an amount of copy number variation at one or more genetic loci detected in a collection of sequence reads included in the genetic data and producing the adjusted test result at least in part by comparing the amount at the two or more time points. In some embodiments, the method further comprises using the adjusted test result to provide (i) a therapeutic intervention or (ii) a diagnosis of a health or disease to the subject. In some embodiments, the genetic data comprises a first set of genetic data and a second set of genetic data, wherein the first set of genetic data is at or below a detection threshold and the second set of genetic data is above the detection threshold. In some embodiments, the detection threshold is a noise threshold. In some embodiments, the method further comprises, in (c), adjusting a diagnosis of the subject from negative or uncertain to positive when the same genetic variants are detected in the first set of genetic data and the second set of genetic data in a plurality of sampling instances or time points. In some embodiments, the method further comprises, in (c), adjusting a diagnosis of the subject from negative or uncertain to positive in a characterization from an earlier time point when the same genetic variants are detected in the first set of genetic data at an earlier time point and in the second set of genetic data at a later time point. Additionally or alternatively, detection of a genetic biomarker can include a method of detecting a trend in the amount of cancer polynucleotides in a biological sample from a subject over time, comprising determining, using or more programmed computer processors, a frequency of the cancer polynucleotides at each of a plurality of time points; determining an error range for the frequency at each of the plurality of time points to provide at least a first error range at a first time point and a second error range at a second time point subsequent to the first time point; and determining whether (1) the first error range overlaps with the second error range, which overlap is indicative of stability of frequency of the cancer polynucleotides at a plurality of time points, (2) the second error range is greater than the first error range, thereby indicating an increase in frequency of the cancer polynucleotides at a plurality of time points, or (3) the second error range is less than the first error range, thereby indicating a decrease in frequency of the cancer polynucleotides at a plurality of time points. Additionally or alternatively, detection of a genetic biomarker can include a method to detect one or more genetic variations and/or amount of genetic variation in a subject, comprising sequencing nucleic acid molecules in a cell-free nucleic acid sample of the subject with a genetic analyzer to generate a first set of sequence reads at a first time point; comparing the first set of sequence reads with at least a second set of sequence reads obtained at least at a second time point before the first time point to yield a comparison of first set of sequence reads and the at least the second set of sequence reads; using the comparison to update a diagnostic confidence indication accordingly, which diagnostic confidence indication is indicative of a probability of identifying one or more genetic variations in a cell-free nucleic acid sample of the subject; and detecting a presence or absence of the one or more genetic variations and/or amount of genetic variation in nucleic acid molecules in a cell-free nucleic acid sample of the subject based on the diagnostic confidence indication. In some embodiments, the method further comprises obtaining the cell-free nucleic acid Additionally or alternatively, detection of a genetic biomarker can include a method for detecting a mutation in a cell-free nucleic acid sample of a subject, comprising: (a) determining consensus sequences by comparing current sequence reads obtained from a genetic analyzer with prior sequence reads from a prior time period to yield a comparison, and updating a diagnostic confidence indication based on the comparison, wherein each consensus sequence corresponds to a unique polynucleotide among a set of tagged parent polynucleotides derived from the cell-free nucleic acid sample, and (b) based on the diagnostic confidence, generating a genetic profile of extracellular polynucleotides in the subject, wherein the genetic profile comprises data resulting from copy number variation or mutation analyses. Additionally or alternatively, detection of a genetic biomarker can include a method to detect abnormal cellular activity, comprising: providing at least one set of tagged parent polynucleotides derived from a biological sample of a subject; amplifying the tagged parent polynucleotides in the set to produce a corresponding set of amplified progeny polynucleotides; using a genetic analyzer to sequence a subset of the set of amplified progeny polynucleotides to produce a set of sequencing reads; and collapsing the set of sequencing reads to generate a set of consensus sequences by comparing current sequence reads with prior sequence reads from at least one prior time period and updating a diagnostic confidence indication accordingly, which diagnostic confidence indication is indicative of a probability of identifying one or more genetic variations in a biological sample of the subject, wherein each consensus sequence corresponds to a unique polynucleotide among the set of tagged parent polynucleotides. Additionally or alternatively, detection of a genetic biomarker can include a method for detecting a mutation in a cell-free or substantially cell free sample of a subject comprising: (a) sequencing extracellular polynucleotides from a bodily sample of the subject with a genetic analyzer; (b) for each of the extracellular polynucleotides, generating a plurality of sequencing reads; (c) filtering out reads that fail to meet a set threshold; (d) mapping sequence reads derived from the sequencing onto a reference sequence; (e) identifying a subset of mapped sequence reads that align with a variant of the reference sequence at each mappable base position; (f) for each mappable base position, calculating a ratio of (i) a number of mapped sequence reads that include a variant as compared to the reference sequence, to (ii) a number of total sequence reads for each mappable base position; and (g) using one or more programmed computer processors to compare the sequence reads with other sequence reads from at least one previous time point and updating a diagnostic confidence indication accordingly, which diagnostic confidence indication is indicative of a probability of identifying the variant. Additionally or alternatively, detection of a genetic biomarker can include a method for operating a genetic test equipment, comprising: providing initial starting genetic material obtained from a bodily sample obtained from a subject; converting double stranded polynucleotide molecules from the initial starting genetic material into at least one set of non-uniquely tagged parent polynucleotides, wherein each polynucleotide in a set is mappable to a reference sequence; and for each set of tagged parent polynucleotides: (i) amplifying the tagged parent polynucleotides in the set to produce a corresponding set of amplified progeny polynucleotides; (ii) sequencing the set of amplified progeny polynucleotides to produce a set of sequencing reads; (iii) collapsing the set of sequencing reads to generate a set of consensus sequences, wherein collapsing uses sequence information from a tag and at least one of: (1) sequence information at a beginning region of a sequence read, (2) an end region of the sequence read and (3) length of the sequence read, wherein each consensus sequence of the set of consensus sequences corresponds to a polynucleotide molecule among the set of tagged parent polynucleotides; and (iv) analyzing the set of consensus sequences for each set of tagged parent molecules; (v) comparing current sequence reads with prior sequence reads from at least one other time point; and (vi) updating a diagnostic confidence indication accordingly, which diagnostic confidence indication is indicative of a probability of identifying one or more genetic variations in a bodily sample of the subject. Additionally or alternatively, detection of a genetic biomarker can include a method for detecting one or more genetic variants in a subject, comprising: (a) obtaining nucleic acid molecules from one or more cell-free biological samples of said subject; (b) assaying said nucleic acid molecules to produce a first set of genetic data and a second set of genetic data, wherein said first set of genetic data and/or said second set of genetic data is within a detection threshold; (c) comparing said first set of genetic data to said second set of genetic data to identify said one or more genetic variants in said first set of genetic data or said second set of genetic data; and (d) based on said one or more genetic variants identified in (c), using one or more programmed computer processors to update a diagnostic confidence indication for identifying said one or more genetic variants in a cell-free biological sample of said subject. Additionally or alternatively, detection of a genetic biomarker can include a method for calling a genetic variant in cell-free deoxyribose nucleic acids (cfDNA) from a subject comprising: (a) using a DNA sequencing system to sequence cfDNA from a sample taken at a first time point from a subject; (b) detecting a genetic variant in the sequenced cfDNA from the first time point, wherein the genetic variant is detected at a level below a diagnostic limit; (c) using the DNA sequencing system to sequence cfDNA from a sample taken from the subject at one or more subsequent time points; (d) detecting the genetic variant in the sequenced cfDNA from the one or more subsequent time points, wherein the genetic variant is detected at level below the diagnostic limit; (e) calling the samples as positive for the genetic variant based on detecting the genetic variant below the diagnostic limit in samples taken at a plurality of the time points. Additionally or alternatively, detection of a genetic biomarker can include a method for calling a genetic variant in cell-free deoxyribose nucleic acids (cfDNA) from a subject comprising: (a) using a deoxyribonucleic acid (DNA) sequencing system to sequence cfDNA from a sample from a subject; (b) detecting a genetic variant in the sequenced cfDNA, wherein the genetic variant is detected at a level below a diagnostic limit; (c) using the DNA sequencing system to sequence cfDNA from the sample taken from the subject, wherein the sample is re-sequenced one or more times; (d) detecting the genetic variant in the sequenced cfDNA from the one or more re-sequenced samples, wherein the genetic variant is detected at level below the diagnostic limit; and (e) calling the samples as positive for the genetic variant based on detecting the genetic variant below the diagnostic limit in re-sequenced samples.

In some embodiments, detection of a genetic biomarker (e.g., one or more genetic biomarkers) can include any of the variety of methods described in U.S. Patent Application Publication No. 2017/0240972, which is hereby incorporated by reference in its entirety. For example, detection of a genetic biomarker can include systems and methods for determining gene fusion by determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion. Additionally or alternatively, detection of a genetic biomarker can include a method for processing genetic sequence read data from a sample, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion. In some embodiments, the method comprises assigning a unique molecule or read identifier (read ID) to each read. In some embodiments, the method comprises clipping each mapped portion of the reads from one or both sides. In some embodiments, the breakpoints are independent of the reads in identity and are identified by a sign, a chromosome and a position. In some embodiments, the breakpoints keep statistics including a number of reads and molecules that are clipped or split at the breakpoint, and a number of wild-type reads and molecules that pass over the breakpoint. In some embodiments, the method comprises selecting every two mapped read portions with common read IDs that belong to two breakpoints with appropriate signs as a potential fusion candidate. In some embodiments, the potential fusion candidate location in the original read before mapping shows the read portion as originally located next to each other. In some embodiments, the method comprises checking if read portions are mapped on one strand for differences in the breakpoints' signs. In some embodiments, the method comprises tracking fusion set statistics Additionally or alternatively, detection of a genetic biomarker can include a system to analyze genetic information, comprising a DNA sequencer; a processor coupled to the DNA sequencer, the processor running computer code to process genetic sequence read data from a sample, the computer code comprising instructions for: determining a fused read containing sequencing data of a portion of a fused chromosome DNA molecule; determining at least a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion. Additionally or alternatively, detection of a genetic biomarker can include a method comprising: sequencing DNA molecules with a DNA sequencer to generate a collection of sequences; mapping the collection of sequences to a reference genome; identifying fused reads from the mapped collection, wherein a fused read contains sub-sequences, wherein a first sub-sequence maps to a first genetic locus and a second sub-sequence maps to a second, distinct genetic locus; for each fused read, identifying a first breakpoint at the first genetic locus and a second breakpoint at the second genetic locus, wherein a breakpoint is a point on the reference genome where a sequence of a fused read is clipped, and wherein the first and second breakpoints form a breakpoint pair; generating sets of fused reads, each set comprising fused reads having the same breakpoint pair; clustering sets of fused reads, wherein each cluster is formed from sets of fused reads having first breakpoints within a first predetermined nucleotide distance and second breakpoints within a second predetermined nucleotide distance; and determining a gene fusion for one or more clusters, wherein a gene fusion for a cluster has, as a first fusion gene breakpoint, a breakpoint selected from the first breakpoints in the cluster and, as a second fusion gene breakpoint, a breakpoint selected from the second breakpoints in the cluster, and wherein the first and second fusion gene breakpoints are each selected based on selection criteria. Additionally or alternatively, detection of a genetic biomarker can include a method comprising: sequencing a plurality of DNA molecules with a DNA sequencer; tagging each of the plurality of sequences molecules with an identifier; mapping each tagged sequence to a reference genome; identifying clipped reads from the mapped tagged sequences, wherein a clipped read is a tagged sequence containing a mapped portion and a clipped portion, wherein the mapped portion maps to a genetic locus and the clipped portion does not map to the genetic locus; determining a breakpoint of each clipped read, wherein a breakpoint is a point on the reference genome where a sequence of a clipped read is clipped; creating breakpoint sets, each breakpoint set comprising identifiers of clipped reads having the same breakpoint; creating sets of breakpoint pairs by comparing pairs of breakpoint sets, each set of breakpoint pairs including identifiers present in both members of a compared pair of breakpoint sets; clustering sets of breakpoint pairs, wherein each cluster includes sets of breakpoint pairs having a first breakpoint of the pair within a first predetermined genetic distance and a second breakpoint of the pair within a second predetermined genetic distance; and determining a gene fusion for one or more of the clusters, wherein a gene fusion for a cluster has, as a first fusion gene breakpoint, a breakpoint selected from the first breakpoints in the cluster and, as a second fusion gene breakpoint, a breakpoint selected from the second breakpoints in the cluster, and wherein the first and second fusion gene breakpoints are each selected based on a selection criteria. In some embodiments, the selection criteria include the breakpoint having the most fused reads in the cluster. Additionally or alternatively, detection of a genetic biomarker can include a method for identifying a fusion gene breakpoint, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; identifying each fusion cluster meeting a predetermined criterion as a gene fusion, and identifying a breakpoint of the gene fusion as the fusion gene breakpoint. Additionally or alternatively, detection of a genetic biomarker can include a method for diagnosing a condition in a subject, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion, wherein said gene fusion is indicative of the condition.

In some embodiments, detection of a genetic biomarker (e.g., one or more genetic biomarkers) can include any of the variety of methods described in U.S. Patent Application Publication No. 2017/0240973, which is hereby incorporated by reference in its entirety. For example, detection of a genetic biomarker can include a method comprising: (a) obtaining sequencing reads of deoxyribonucleic acid (DNA) molecules of a cell-free bodily fluid sample of a subject; (b) generating from the sequence reads a first data set comprising for each genetic locus in a plurality of genetic loci a quantitative measure related to sequencing read coverage ("read coverage"); (c) correcting the first data set by performing saturation equilibrium correction and probe efficiency correction; (d) determining a baseline read coverage for the first data set, wherein the baseline read coverage relates to saturation equilibrium and probe efficiency; and (e) determining a copy number state for each genetic locus in the plurality of genetic loci relative to the baseline read coverage. In some embodiments, the first data set comprises, for each genetic locus in a plurality of genetic loci, a quantitative measure related to (i) guanine-cytosine content ("GC content") of the genetic locus. In some embodiments, the method comprises, prior to (c), removing from the first data set genetic loci that are high-variance genetic loci, wherein removing comprises: (i) fitting a model relating the quantitative measures related to guanine-cytosine content and the quantitative measures of sequencing read coverage of the genetic loci; and (ii) removing from the genetic loci at least 10% of the genetic loci, wherein the removing the genetic loci comprises removing genetic loci that most differ from the model, thereby providing the first data set of baselining genetic loci. In some embodiments, the method comprises removing at least 45% of the genetic loci. In some embodiments, determining a copy number state comprises comparing the read coverage of the genetic loci to the baseline read coverage. In some embodiments, the cell-free bodily fluid is selected from the group consisting of serum, plasma, urine, and cerebrospinal fluid. In some embodiments, the read coverage is determined by mapping the sequencing reads to a reference genome. In some embodiments, obtaining the sequencing reads comprises ligating adaptors to the DNA molecules from the cell-free bodily fluid from the subject. In some embodiments, the DNA molecules are duplex DNA molecules and the adaptors are ligated to the duplex DNA molecules such that each adaptor differently tags complementary strands of the DNA molecule to provide tagged strands. In some embodiments, determining the quantitative measure related to the probability that a strand of DNA derived from the genetic locus is represented within the sequencing reads comprises sorting sequencing reads into paired reads and unpaired reads, wherein (i) each paired read corresponds to sequence reads generated from a first tagged strand and a second differently tagged complementary strand derived from a double-stranded polynucleotide molecule in said set, and (ii) each unpaired read represents a first tagged strand having no second differently tagged complementary strand derived from a double-stranded polynucleotide molecule represented among said sequence reads in said set of sequence reads. In some embodiments, the method further comprises determining quantitative measures of (i) said paired reads and (ii) said unpaired reads that map to each of one or more genetic loci to determine a quantitative measure related to total double-stranded DNA molecules in said sample that map to each of said one or more genetic loci based on said quantitative measure related to paired reads and unpaired reads mapping to each locus. In some embodiments, the adaptors comprise barcode sequences. In some embodiments, determining the read coverage comprises collapsing the sequencing reads based on position of the mapping of the sequencing reads to the reference genome and the barcode sequences. In some embodiments, the genetic loci comprise one or more oncogenes. In some embodiments, a method comprises determining that at least a subset of the baselining genetic loci has undergone copy number alteration in the tumor cells of the subject by determining relative quantities of variants within the baselining genetic loci for which the germline genome of the subject is heterozygous. In some embodiments, the relative quantities of the variants are not approximately equal. In some embodiments, baselining genetic loci for which the relative quantities of the variants are not approximately equal are removed from the baselining genetic loci, thereby providing allelic-frequency corrected baselining genetic loci. In some embodiments, the allelic-frequency corrected baselining genetic loci are used as the baselining loci in the methods of any one of the preceding claims. Additionally or alternatively, detection of a genetic biomarker can include a method comprising: receiving into memory sequencing reads of deoxyribonucleic acid (DNA) molecules of a cell-free bodily fluid sample of a subject; executing code with a computer processor to perform the following steps: generating from the sequence reads a first data set comprising for each genetic locus in a plurality of genetic loci a quantitative measure related to sequencing read coverage ("read coverage"); correcting the first data set by performing saturation equilibrium correction and probe efficiency correction; determining a baseline read coverage for the first data set, wherein the baseline read coverage relates to saturation equilibrium and probe efficiency; and determining a copy number state for each genetic locus in the plurality of genetic loci relative to the baseline read coverage. Additionally or alternatively, detection of a genetic biomarker can include a system comprising: a network; a database comprising computer memory configured to store nucleic acid (e.g., DNA) sequence data which are connected to the network; a bioinformatics computer comprising a computer memory and one or more computer processors, which computer is connected to the network; wherein the computer further comprises machine-executable code which, when executed by the one or more computer processors, copies nucleic acid (e.g., DNA) sequence data stored on the database, writes the copied data to memory in the bioinformatics computer and performs steps including: generating from the nucleic acid (e.g., DNA) sequence data a first data set comprising for each genetic locus in a plurality of genetic loci a quantitative measure related to sequencing read coverage ("read coverage"); correcting the first data set by performing saturation equilibrium correction and probe efficiency correction; determining a baseline read coverage for the first data set, wherein the baseline read coverage relates to saturation equilibrium and probe efficiency; and determining a copy number state for each genetic locus in the plurality of genetic loci relative to the baseline read coverage. In some embodiments, the database is connected to a DNA sequencer.

In some embodiments, detection of a genetic biomarker (e.g., one or more genetic biomarkers) can include any of the variety of methods described in U.S. Patent Application Publication No. 2017/0260590, which is hereby incorporated by reference in its entirety. For example, detection of a genetic biomarker can include a method comprising: (a) sequencing polynucleotides from cancer cells from a biological sample of a subject; (b) identifying and quantifying somatic mutations in the polynucleotides; (c) developing a profile of tumor heterogeneity in the subject indicating the presence and relative quantity of a plurality of the somatic mutations in the polynucleotides, wherein different relative quantities indicates tumor heterogeneity; and (d) determining a therapeutic intervention for a cancer exhibiting the tumor heterogeneity, wherein the therapeutic intervention is effective against a cancer having the profile of tumor heterogeneity determined. In some embodiments, the cancer cells are spatially distinct. In some embodiments, the therapeutic intervention is more effective against a cancer presenting with the plurality of somatic mutations than it is against a cancer presenting with any one, but not all, of the somatic mutations. In some embodiments, the method further comprises: (e) monitoring changes in tumor heterogeneity in the subject over time and determining different therapeutic interventions over time based on the changes. In some embodiments, the method further comprises: (e) displaying the therapeutic intervention. In some embodiments, the method further comprises: (e) implementing the therapeutic intervention. In some embodiments, the method further comprises: (e) generating a phylogeny of tumor evolution based on the tumor profile; wherein determining the therapeutic intervention takes into account the phylogeny. In some embodiments, determining is performed with the aid of computer-executed algorithm. In some embodiments, sequence reads generated by sequencing are subject to noise reduction before identifying and quantifying. In some embodiments, noise reduction comprises molecular tracking of sequences generated from a single polynucleotide in the sample. In some embodiments, determining a therapeutic intervention takes into account the relative frequencies of the tumor-related genetic alterations. In some embodiments, the therapeutic intervention comprises administering, in combination or in series, a plurality of drugs, wherein each drug is relatively more effective against a cancer presenting with a different one of somatic mutations that occur at different relative frequency. In some embodiments, a drug that is relatively more effective against a cancer presenting with a somatic mutation occurring at higher relative frequency is administered in higher amount. In some embodiments, the drugs are delivered at doses that are stratified to reflect the relative amounts of the variants in the DNA. In some embodiments, cancers presenting with at least one of the genetic variants is resistant to at least one of the drugs. In some embodiments, determining a therapeutic intervention takes into account the tissue of origin of the cancer. In some embodiments, the therapeutic intervention is determined based on a database of interventions shown to be therapeutic for cancers having tumor heterogeneity characterized by each of the somatic mutations. Additionally or alternatively, detection of a genetic biomarker can include a method comprising providing a therapeutic intervention for a subject having a cancer having a tumor profile from which tumor heterogeneity can be inferred, wherein the therapeutic intervention is effective against cancers with the tumor profile. In some embodiments, the tumor profile indicates relative frequency of a plurality of more somatic mutations. In some embodiments, the method further comprises monitoring changes in the relative frequencies in the subject over time and determining different therapeutic interventions over time based on the changes. In some embodiments, the therapeutic intervention is more effective against a cancer presenting with each of the somatic mutations than it is against a cancer presenting with any one, but not all, of the somatic mutations. In some embodiments, the therapeutic intervention comprises administering, in combination or in series, a plurality of drugs, wherein each drug is relatively more effective against a cancer presenting with a different one of somatic mutations that occur at different relative frequency. In some embodiments, a drug that is relatively more effective against a cancer presenting with a somatic mutation occurring at higher relative frequency is administered in higher amount. In some embodiments, the drugs are delivered at doses that are stratified to reflect the relative amounts of the variants in the DNA. In some embodiments, cancers presenting with at least one of the genetic variants is resistant to at least one of the drugs. Additionally or alternatively, detection of a genetic biomarker can include a system comprising a computer readable medium comprising machine-executable code that, upon execution by a computer processor, implements a method comprising: (a)

receiving into memory sequence reads of polynucleotides mapping to a genetic locus; (b) determining, among said sequence reads, identity of bases that are different than a base of a reference sequence at the locus of the total number of sequence reads mapping to a locus; (c) reporting the identity and relative quantity of the determined bases and their location in the genome; and (d) inferring heterogeneity of a given sample based on information in (c). In some embodiments, the method implemented further comprises receiving into memory sequence reads derived from samples at a plurality of different times and calculating a difference in relative amount and identity of a plurality of bases between the two samples. Additionally or alternatively, detection of a genetic biomarker can include a method comprising: (a) performing biomolecular analysis of biomolecular polymers from disease cells (e.g., spatially distinct disease cells) from a subject; (b) identifying and quantifying biomolecular variants in the biomolecular macromolecules; (c) developing a profile of disease cell heterogeneity in the subject indicating the presence and relative quantity of a plurality of the variants in the biomolecular macromolecules, wherein different relative quantities indicates disease cell heterogeneity; and (d) determining a therapeutic intervention for a disease exhibiting the disease cell heterogeneity, wherein the therapeutic intervention is effective against a disease having the profile of disease cell heterogeneity determined. In some embodiments, the disease cells are spatially distinct disease cells. In some embodiments, the therapeutic intervention is determined based on a database of interventions shown to be therapeutic for cancers having tumor heterogeneity characterized by each of the somatic mutations. Additionally or alternatively, detection of a genetic biomarker can include a method of detecting disease cell heterogeneity in a subject comprising: a) quantifying polynucleotides that bear a sequence variant at each of a plurality of genetic loci in polynucleotides from a sample from the subject, wherein the sample comprises polynucleotides from somatic cells and from disease cells; b) determining for each locus a measure of copy number variation (CNV) for polynucleotides bearing the sequence variant; c) determining for each locus a weighted measure of quantity of polynucleotides bearing a sequence variant at the locus as a function of CNV at the locus; and d) comparing the weighted measures at each of the plurality of loci, wherein different weighted measures indicate disease cell heterogeneity. In some embodiments, the disease cells are tumor cells. In some embodiments, polynucleotides comprise cfDNA. Additionally or alternatively, detection of a genetic biomarker can include a method of inferring a measure of burden of DNA from cells undergoing cell division in a sample comprising measuring copy number variation induced by proximity of one or more genomic loci to cells' origins of replication, wherein increased CNV indicates cells undergoing cell division. In some embodiments, the burden is measured in cell-free DNA. In some embodiments, the measure of burden relates to the fraction of tumor cells or genome-equivalents of DNA from tumor cells in the sample. In some embodiments, CNV due to proximity to origins of replication is inferred from a set of control samples or cell-lines. In some embodiments, a hidden-markov model, regression model, principal component analysis-based model, or genotype-modified model is used to approximate variations due to origins of replications. In some embodiments, the measure of burden is presence or absence of cells undergoing cell division. In some embodiments, proximity is within 1 kb of an origin of replication. Additionally or alternatively, detection of a genetic biomarker can include a method of increasing sensitivity and/or specificity of determining gene-related copy-number variations by ameliorating the effect of variations due to proximity to origins of replications. In some embodiments, the method comprises measuring CNV at a locus, determining amount of CNV due to proximity of the locus to an origin of replication, and correcting the measured CNV to reflect genomic CNV, e.g., by subtracting amount of CNV attributable to cell division. In some embodiments, the genomic data is obtained from cell-free DNA. In some embodiments, the measure of burden relates to the fraction of tumor cells or genome-equivalents of DNA in a sample. In some embodiments, variations due to origins of replication are inferred from a set of control samples or cell-lines. In some embodiments, a hidden-markov model, regression model, principal component analysis-based model, or genotype-modified model is used to approximate variations due to origins of replications.

In some embodiments, detection of a genetic biomarker (e.g., one or more genetic biomarkers) can include any of the variety of methods described in U.S. Patent Application Publication No. 2017/0061072, which is hereby incorporated by reference in its entirety. For example, detection of a genetic biomarker can include methods and systems for detection of single-nucleotide variations (SNVs) from somatic sources in a cell-free biological sample of a subject, such as in a mixture of nucleic acid molecules from somatic and germline sources. In some embodiments, the systems and methods detect single-nucleotide variations (SNVs) from somatic sources in a cell-free biological sample of a subject by generating training data with class labels; forming a machine learning unit having one output for each of adenine (A), cytosine (C), guanine (G), and thymine (T) base calls, respectively; training the machine learning unit with a training set of biological samples; and applying the machine learning unit to detect the SNVs from somatic sources in the cell-free biological sample, wherein the cell-free biological sample may comprise a mixture of nucleic acid molecules (e.g., deoxyribonucleic acid (DNA)) from somatic and germline sources, e.g., cells comprising somatic mutations and germline DNA.

In some embodiments, detection of a genetic biomarker (e.g., one or more genetic biomarkers) can include any of the variety of methods described in U.S. Patent Application Publication No. 2017/0058332, which is hereby incorporated by reference in its entirety. For example, detection of a genetic biomarker can include a method to detect a somatic or germline variant, comprising providing a predetermined genomic DNA (gDNA) to an assay mixture, capturing a sample of a subject's genetic information using a gene analyzer, and detecting genetic variants from the genetic information; and classifying a variant as from a germ line source if present in gDNA derived molecules having lengths longer than cell-free DNA (cfDNA) derived molecules. In some embodiments, the gDNA has a fragment length of more than about 200 bases. In some embodiments, the gDNA has a fragment length of at least 400 bases or at least 500 bases. In some embodiments, gDNA fragment length is higher than the cfDNA fragment length distribution. In some embodiments, the gDNA is added to the assay mixture. In some embodiments, the gDNA is left in the assay mixture after a filtering operation. In some embodiments, the gDNA is left in the assay mixture after a centrifugation operation. In some embodiments, approximately 1% to 5% gDNA is added to the assay mixture. In some embodiments, at least 1% gDNA is added to the assay mixture. Additionally or alternatively, detection of a genetic biomarker can include a method comprising providing a sample comprising both genomic DNA (gDNA) and cell-free DNA (cfDNA) from a subject; determining subject germline genotype at least one genetic locus from the gDNA; determining a quantitative measure of at least one genetic variant at each genetic locus in the cfDNA; determining whether the quantitative measure of the genetic variant is or is not consistent with germline genotype; and calling the genetic variant as a germline variant if the quantitative measure is consistent with germline genotype, or as a somatic mutant if the quantitative measure is not consistent with the germline genotype. Additionally or alternatively, detection of a genetic biomarker can include a method comprising determining a quantitative measure of a genetic variant detected in cell-free DNA (cfDNA) from a subject; determining that the measure is consistent with a heterozygous genotype in the subject; determining a probable genotype of the subject at the locus from genomic DNA (gDNA); comparing the genotype at the locus from gDNA with the variant detected in the cfDNA; and calling the variant as a somatic mutation if the variant detected in the cfDNA is not consistent with the genotype at the locus from gDNA. In some embodiments, calling the variant as a somatic mutation if the genotype at the locus from gDNA is determined to be homozygous. In some embodiments, calling the variant as a somatic mutation if the genotype at the locus from gDNA is determined to be heterozygous with a confidence selected from the group consisting of: at least 70%, at least 80%, at least 90%, at least 95%, or at least 99%. In some embodiments, determining a quantitative measure of a genetic variant comprises sequencing the cfDNA. In some embodiments, determining the probable genotype of the subject comprises sequencing genomic DNA from the subject. In some embodiments, the sequencing is selected from the group consisting of: targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof.

In some embodiments, detection of a genetic biomarker (e.g., one or more genetic biomarkers) can include any of the variety of methods described in P.C.T. Publication No. WO 2018/119452, which is hereby incorporated by reference in its entirety. For example, detection of a genetic biomarker can include methods, compositions and systems for analyzing a nucleic acid population comprising at least two forms of nucleic acid selected from double-stranded DNA, single-stranded DNA and single-stranded RNA. In some embodiments the method comprises (a) linking at least one of the forms of nucleic acid with at least one tag nucleic acid to distinguish the forms from one another, (b) amplifying the forms of nucleic acid at least one of which is linked to at least one nucleic acid tag, wherein the nucleic acids and linked nucleic acid tag, if present, are amplified, to produce amplified nucleic acids, of which those amplified from the at least one form are tagged; (c) assaying sequence data of the amplified nucleic acids at least some of which are tagged; and (d) decoding tag nucleic acid molecules of the amplified nucleic acids to reveal the forms of nucleic acids in the population providing an original template for the amplified nucleic acids linked to the tag nucleic acid molecules for which sequence data has been assayed. In some embodiments, the method further comprises enriching for at least one of the forms relative to one or more of the other forms. In some embodiments, at least 70% of the molecules of each form of nucleic acid in the population are amplified in step (b). In some embodiments, at least three forms of nucleic acid are present in the population and at least two of the forms are linked to different tag nucleic acid forms distinguishing each of the three forms from one another. In some embodiments each of the at least three forms of nucleic acid in the population is linked to a different tag. In some embodiments, each molecule of the same form is linked to a tag comprising the same identifying information tag (e.g., a tag with the same or comprising the same sequence). In some embodiments, molecules of the same form are linked to different types of tags. In some embodiments step (a) comprises: subjecting the population to reverse transcription with a tagged primer, wherein the tagged primer is incorporated into cDNA generated from RNA in the population. In some embodiments, the reverse transcription is sequence-specific. In some embodiments, the reverse transcription is random. In some embodiments, the method further comprises degrading RNA duplexed to the cDNA. In some embodiments, the method further comprises separating single-stranded DNA from double-stranded DNA and ligating nucleic acid tags to the double-stranded DNA. In some embodiments, the single-stranded DNA is separated by hybridization to one or more capture probes. In some embodiments, the method further comprises differentially tagging single-stranded DNA with a single-stranded tag using a ligase that functions on single stranded nucleic acids, and double-stranded DNA with double-stranded adapters using ligase that functions on double-stranded nucleic acids. In some embodiments, the method further comprises before assaying, pooling tagged nucleic acids comprising different forms of nucleic acid. In some embodiments, the method further comprises analyzing the pools of partitioned DNA separately in individual assays. The assays can be the same, substantially similar, equivalent, or different. In any of the above methods, the sequence data can indicate presence of a somatic or germline variant, or a copy number variation or a single nucleotide variation, or an indel or gene fusion. Additionally or alternatively, detection of a genetic biomarker can include a method of analyzing a nucleic acid population comprising nucleic acids with different extents of modification. Additionally or alternatively, detection of a genetic biomarker can include methods for screening for characteristics (e.g., 5' methylcytosine) associated with a disease. The method comprises contacting the nucleic acid population with an agent (such as a methyl binding domain or protein) that preferentially binds to nucleic acids bearing the modification; separating a first pool of nucleic acids bound to the agent from a second pool of nucleic acids unbound to the agent, wherein the first pool of nucleic acids are overrepresented for the modification, and the nucleic acids in the second pool are underrepresented for the modification; linking the nucleic acids in the first pool and/or second pool to one or more nucleic acid tags that distinguish the nucleic acids in the first pool and the second pool to produce a population of tagged nucleic acids; amplifying the tagged nucleic acids, wherein the nucleic acids and the linked tags are amplified; assaying sequence data of the amplified nucleic acids and linked tags; decoding the tags to reveal whether the nucleic acids for which sequence data has been assayed were amplified from templates in the first or second pool. Additionally or alternatively, detection of a genetic biomarker can include a method for analyzing a nucleic acid population in which at least some of the nucleic acids include one or more modified cytosine residues. The method comprises linking capture moieties, e.g., biotin, to nucleic acids in the population to serve as templates for amplification; performing an amplification reaction to produce amplification products from the templates; separating the templates linked to capture moieties from amplification products; assaying sequence data of the templates linked to capture moieties by bisulfite sequencing; and assaying sequence data of the amplification products. Additionally or alternatively, detection of a genetic biomarker can include a method of analyzing a nucleic acid population comprising nucleic acids with different extents of 5-methylcytosine. The method comprises (a) contacting the nucleic acid population with an agent that preferentially binds to 5-methylated nucleic acids; (b) separating a first pool of nucleic acids bound to the agent from a second pool of nucleic acids unbound to the agent, wherein the first pool of nucleic acids are overrepresented for 5-methylcytosine, and the nucleic acids in the second pool are underrepresented for 5-methylation; (c) linking the nucleic acids in the first pool and/or second pool to one or more nucleic acid tags that distinguish the nucleic acids in the first pool and the second pool, wherein the nucleic acid tags linked to nucleic acids in the first pool comprise a capture moiety (e.g., biotin); (d) amplifying the labelled nucleic acids, wherein the nucleic acids and the linked tags are amplified; (e) separating amplified nucleic acids bearing the capture moiety from amplified nucleic acids that do not bear the capture moiety; and (f) assaying sequence data of the separated, amplified nucleic acids. Additionally or alternatively, detection of a genetic biomarker can include a method of analyzing a nucleic acid population comprising at least two forms of nucleic acid selected from double-stranded DNA, single-stranded DNA and single-stranded RNA, the method, wherein each of the at least two forms comprises a plurality of molecules, comprising: linking at least one of the forms of nucleic acid with at least one tag nucleic acid to distinguish the forms from one another, amplifying the forms of nucleic acid at least one of which is linked to at least one nucleic acid tag, wherein the nucleic acids and linked nucleic acid tag, are amplified, to produce amplified nucleic acids, of which those amplified from the at least one form are tagged; assaying sequence data of the amplified nucleic acids at least some of which are tagged; wherein the assaying obtains sequence information sufficient to decode the tag nucleic acid molecules of the amplified nucleic acids to reveal the forms of nucleic acids in the population providing an original template for the amplified nucleic acids linked to the tag nucleic acid molecules for which sequence data has been assayed. In one embodiment the method further comprises the step of decoding the tag nucleic acid molecules of the amplified nucleic acids to reveal the forms of nucleic acids in the population providing an original template for the amplified nucleic acids linked to the tag nucleic acid molecules for which sequence data has been assayed. In another embodiment, the method further comprises enriching for at least one of the forms relative to one or more of the other forms. In another embodiment, at least 70% of the molecules of each form of nucleic acid in the population are amplified. In another embodiment, at least three forms of nucleic acid are present in the population and at least two of the forms are linked to different tag nucleic acid forms distinguishing each of the three forms from one another. In another embodiment each of the at least three forms of nucleic acid in the population is linked to a different tag. In another embodiment, each molecule of the same form is linked to a tag comprising the same tag information. In another embodiment, molecules of the same form are linked to different types of tags. In another embodiment, the method further comprises subjecting the population to reverse transcription with a tagged primer, wherein the tagged primer is incorporated into cDNA generated from RNA in the population. In another embodiment, the reverse transcription is sequence-specific. In another embodiment wherein the reverse transcription is random. In another embodiment, the method further comprises degrading RNA duplexed to the cDNA. In another embodiment, the method further comprises separating single-stranded DNA from double-stranded DNA and ligating nucleic acid tags to the double-stranded DNA. In another embodiment, the single-stranded DNA is separated by hybridization to one or more capture probes. In another embodiment, the method further comprises circularizing single-stranded DNA with a circligase and ligating nucleic acid tags to the double-stranded DNA. In another embodiment, the method comprises, before assaying, pooling tagged nucleic acids comprising different forms of nucleic acid. In another embodiment, the nucleic acid population is from a bodily fluid sample. In another embodiment, the bodily fluid sample is blood, serum, or plasma. In another embodiment, the nucleic acid population is a cell free nucleic acid population. In another embodiment, the bodily fluid sample is from a subject suspected of having a cancer. In another embodiment the sequence data indicates presence of a somatic or germline variant. In another embodiment, the sequence data indicates presence of a copy number variation. In another embodiment, the sequence data indicates presence of a single nucleotide variation (SNV), indel or gene fusion. In another embodiment, the sequence data indicates presence of a single nucleotide variation (SNV), indel or gene fusion. Additionally or alternatively, detection of a genetic biomarker can include a method, comprising: providing a population of nucleic acid molecules obtained from a bodily sample of a subject; fractionating the population of nucleic acid molecules based on one or more characteristics to generate plurality of groups of nucleic acid molecules, wherein the nucleic acid molecules of each of the plurality of groups comprise distinct identifiers; pooling the plurality of groups of nucleic acid molecules; sequencing the pooled plurality of groups of nucleic acid molecules to generate plurality of sets sequence reads; and fractionating the sequence reads based on the identifiers. Additionally or alternatively, detection of a genetic biomarker can include a method for analyzing the fragmentation pattern of cell-free DNA comprising: providing a population of cell-free DNA from a biological sample; fractionating the population of cell-free DNA, thereby generating subpopulations of cell-free DNA; sequencing at least one subpopulation of cell-free DNA, thereby generating sequence reads; aligning the sequence reads to a reference genome; and, determining the fragmentation pattern of the cell-free DNA in each subpopulation by analyzing any number of the: length of each sequence read mapping to each base position in the reference genome; number of sequence reads mapping to the base position in the reference genome as a function of length of the sequence reads;

number of sequence reads starting at each base position in the reference genome; or, number of sequence reads ending at each base position in the reference genome. In another embodiment, the one or more characteristics comprise a chemical modification selected from the group consisting of: methylation, hydroxymethylation, formylation, acetylation, and glycosylation.

In some embodiments, detection of a genetic biomarker (e.g., one or more genetic biomarkers) can include any of the variety of methods described in P.C.T. Publication No. WO 2018/009723, which is hereby incorporated by reference in its entirety. For example, detection of a genetic biomarker can include methods, systems, and compositions for performing nucleosome profiling using cell-free nucleic acids (e.g., cfDNA). This can be used to identify new driver genes, determine copy number variation (CNV), identify somatic mutations and structural variations such as fusions and indels, as well as identify regions that can be used in a multiplexed assay to detect any of the above variations. Additionally or alternatively, detection of a genetic biomarker can include various uses of cell-free nucleic acids (e.g., DNA or RNA). Such uses include detecting, monitoring and determining treatment for a subject having or suspected of having a health condition, such as a disease (e.g., cancer). The methods provided may use sequence information in a macroscale and global manner, with or without somatic variant information, to assess a fragmentome profile that can be representative of a tissue of origin, disease, progression, etc. Additionally or alternatively, detection of a genetic biomarker can include a computer-implemented method for determining a presence or absence of a genetic aberration in deoxyribonucleic acid (DNA) fragments from cell-free DNA obtained from a subject, the method comprising: (a) constructing, by a computer, a multi-parametric distribution of the DNA fragments over a plurality of base positions in a genome; and (b) without taking into account a base identity of each base position in a first locus, using the multi-parametric distribution to determine the presence or absence of the genetic aberration in the first locus in the subject. In some embodiments, the genetic aberration comprises a sequence aberration. In some embodiments, the sequence aberration comprises a single nucleotide variant (SNV). In some embodiments, the sequence aberration comprises an insertion or deletion (indel), or a gene fusion. In some embodiments, the sequence aberration comprises two or more different members selected from the group consisting of (i) a single nucleotide variant (SNV), (ii) an insertion or deletion (indel), and (iii) a gene fusion. In some embodiments, the genetic aberration comprises a copy number variation (CNV). In some embodiments, the multi-parametric distribution comprises a parameter indicative of a length of the DNA fragments that align with each of the plurality of base positions in the genome. In some embodiments, the multi-parametric distribution comprises a parameter indicative of a number of the DNA fragments that align with each of the plurality of base positions in the genome. In some embodiments, the multi-parametric distribution comprises a parameter indicative of a number of the DNA fragments that start or end at each of the plurality of base positions in the genome. In some embodiments, n the multi-parametric distribution comprises parameters indicative of two or more of: (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome. In some embodiments, the multi-parametric distribution comprises parameters indicative of (i) a length of the DNA fragments that align with each of the plurality of base positions in the genome, (ii) a number of the DNA fragments that align with each of the plurality of base positions in the genome, and (iii) a number of the DNA fragments that start or end at each of the plurality of base positions in the genome. Additionally or alternatively, detection of a genetic biomarker can include a method of generating a classifier for determining a likelihood that a subject belongs to one or more classes of clinical significance, the method comprising: a) providing a training set comprising, for each of the one or more classes of clinical significance, populations of cell-free DNA from each of a plurality of subjects of a species belonging to the class of clinical significance and from each of a plurality of subjects of the species not belonging to the class of clinical significance; b) sequencing cell-free DNA fragments from the populations of cell-free DNA to produce a plurality of DNA sequences; c) for each population of cell-free DNA, mapping the plurality of DNA sequences to each of one or more genomic regions in a reference genome of the species, each genomic region comprising a plurality of genetic loci; d) preparing, for each population of cell-free DNA, a dataset comprising, for each of a plurality of the genetic loci, values indicating a quantitative measure of at least one characteristic selected from: (i) DNA sequences mapping to the genetic locus, (ii) DNA sequences starting at the locus, and (iii) DNA sequences ending at the genetic locus, to yield a training set; and e) training a computer-based machine learning system on the training set, thereby generating a classifier for determining a likelihood that the subject belongs to one or more classes of clinical significance. Additionally or alternatively, detection of a genetic biomarker can include a method of determining an abnormal biological state in a subject, the method comprising: a) sequencing cell-free DNA fragments from cell-free DNA from the subject to produce DNA sequences; b) mapping the DNA sequences to each of one or more genomic regions in a reference genome of a species of the subject, each genomic region comprising a plurality of genetic loci; c) preparing a dataset comprising, for each of a plurality of the genetic loci, values indicating a quantitative measure of at least one feature selected from: (i) DNA sequences mapping to the genetic locus, (ii) DNA sequences starting at the locus, and (iii) DNA sequences ending at the genetic locus; and d) based on the dataset, determining a likelihood of the abnormal biological state. Additionally or alternatively, detection of a genetic biomarker can include a computer-implemented method for generating an output indicative of a presence or absence of a genetic aberration in deoxyribonucleic acid (DNA) fragments from cell-free DNA obtained from a subject, the method comprising: (a) constructing, by a computer, a distribution of the DNA fragments from the cell-free DNA over a plurality of base positions in a genome; and (b) for each of one or more genetic loci, calculating, by a computer, a quantitative measure indicative of a ratio of (1) a number of the DNA fragments with dinucleosomal protection associated with a genetic locus from the one or more genetic loci, and (2) a number of the DNA fragments with mononucleosomal protection associated with the genetic locus, or vice versa; and (c) determining, using the quantitative measure for each of the one or more genetic loci, said output indicative of a presence or absence of the genetic aberration in the one or more genetic loci in the subject. In some embodiments, the distribution comprises one or more multi-parametric distributions. Additionally or alternatively, detection of a genetic biomarker can include a computer-implemented method for deconvolving a distribution of deoxyribonucleic acid (DNA) fragments from cell-free DNA obtained from a subject, the method comprising: (a) constructing, by a computer, a distribution of a coverage of the DNA fragments from the cell-free DNA over a plurality of base positions in a genome; and (b) for each of one or more genetic loci, deconvolving, by a computer, the distribution of the coverage, thereby generating fractional contributions associated with one or more members selected from the group consisting of a copy number (CN) component, a cell clearance component, and a gene expression component. Additionally or alternatively, detection of a genetic biomarker can include a computer-implemented classifier for determining genetic aberrations in a test subject using deoxyribonucleic acid (DNA) fragments from cell-free DNA obtained from the test subject, comprising: (a) an input of a set of distribution scores for each of one or more populations of cell-free DNA obtained from each of a plurality of subjects, wherein each distribution score is generated based at least on one or more of: (i) a length of the DNA fragments that align with each of a plurality of base positions in a genome, (ii) a number of the DNA fragments that align with each of a plurality of base positions in a genome, and (iii) a number of the DNA fragments that start or end at each of a plurality of base positions in a genome; and (b) an output of classifications of one or more genetic aberrations in the test subject. Additionally or alternatively, detection of a genetic biomarker can include a computer-implemented method for creating a trained classifier, comprising: (a) providing a plurality of different classes, wherein each class represents a set of subjects with a shared characteristic; (b) for each of a plurality of populations of cell-free DNA obtained from each of the classes, providing a multi-parametric model representative of cell-free deoxyribonucleic acid (DNA) fragments from the populations of cell-free DNA, thereby providing a training data set; and (c) training, by a computer, a learning algorithm on the training data set to create one or more trained classifiers, wherein each trained classifier is configured to classify a test population of cell-free DNA from a test subject into one or more of the plurality of different classes. Additionally or alternatively, detection of a genetic biomarker can include a method of classifying a test sample from a subject, comprising: (a) providing a multi-parametric model representative of cell-free deoxyribonucleic acid (DNA) fragments from a test population of cell-free DNA from the subject; and (b) classifying the test population of cell-free DNA using a trained classifier. Additionally or alternatively, detection of a genetic biomarker can include a computer-implemented method comprising: (a) generating, by a computer, sequence information from cell-free DNA fragments from a subject; (b) mapping, by a computer, the cell-free DNA fragments to a reference genome based on the sequence information; and (c) analyzing, by a computer, the mapped cell-free DNA fragments to determine, at each of a plurality of base positions in the reference genome, a plurality of measures selected from the group consisting of: (i) number of cell-free DNA fragments mapping to the base position, (ii) length of each cell-free DNA fragment mapping to the base position, (iii) number of cell-free DNA fragments mapping to the base position as a function of length of the cell-free DNA fragment; (iv) number of cell-free DNA fragments starting at the base position; (v) number of cell-free DNA fragments ending at the base position; (vi) number of cell-free DNA fragments starting at the base position as a function of length, and (vii) number of cell-free DNA fragments ending at the base position as a function of length. Additionally or alternatively, detection of a genetic biomarker can include a computer-implemented method for deconvolving a distribution of deoxyribonucleic acid (DNA) fragments from cell-free DNA obtained from a subject, the method comprising: (a) constructing, by a computer, a distribution of a coverage of the DNA fragments from the cell-free DNA over a plurality of base positions in a genome; and (b) for each of one or more genetic loci, deconvolving, by a computer, the distribution of the coverage, thereby generating fractional contributions associated with one or more members selected from the group consisting of a copy number (CN) component, a cell clearance component, and a gene expression component. In some embodiments, the method further comprises comprising generating an output indicative of a presence or absence of a genetic aberration based at least on a portion of the fractional contributions.

In some embodiments, detection of a genetic biomarker (e.g., one or more genetic biomarkers) can include any of the variety of methods described in P.C.T. Publication No. WO 2017/181146, which is hereby incorporated by reference in its entirety. For example, detection of a genetic biomarker can include methods and systems that may be used for early cancer detection. In some embodiments, the method comprises (a) providing a sample comprising cfDNA from a subject, wherein the subject does not detectably exhibit a cancer; (b) capturing from the sample cfDNA molecules covered by a sequencing panel, wherein the sequencing panel comprises one or more regions from each of a plurality of different genes, wherein: (i) the sequencing panel is no greater than 50,000 nucleotides; (ii) the presence of a tumor marker in any one of the different genes indicates that the subject has the cancer; and (iii) at least 80% of subjects having the cancer have a tumor marker present in at least one of the plurality of different genes; and (c) sequencing the captured cfDNA molecules to a read depth sufficient to detect the tumor markers at a frequency in the sample as low as 0.01%. In some embodiments, a tumor marker is selected from the group consisting of a single base substitution, a copy number variation, an indel, a gene fusion, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns and abnormal changes in nucleic acid methylation. In some embodiments, at least 85%, at least 90%, at least 93%, at least 95%, at least 97%), at least 98% or at least 99% of subjects having the cancer have a tumor marker present in at least one of the plurality of different genes. Some embodiments comprise sequencing the captured cfDNA molecules to a read depth sufficient to detect the tumor markers at a frequency in the sample as low as 0.005%, 0.001% or 0.0005%. Additionally or alternatively, detection of a genetic biomarker can include a method comprising: a. providing a sample comprising cell-free nucleic acid (cfNA) molecules from a subject, wherein the subject does not detectably exhibit a cancer; b. capturing from the sample cfNA molecules covered by a sequencing panel, wherein the sequencing panel comprises one or more regions from each of a plurality of different genes, wherein: i. the sequencing panel is no greater than 50,000 nucleotides; ii. a presence of a tumor marker in any one of the different genes indicates that the subject has the cancer; and iii. at least 80% of subjects having the cancer have a tumor marker present in at least one of the plurality of different genes; and c. sequencing the captured cfNA molecules to a read depth sufficient to detect the tumor markers at a frequency in the sample as low as 1.0%, 0.75%, 0.5%, 0.25%, 0.1%, 0.075%, 0.05%, 0.025%, 0.01%, or 0.005%. Additionally or alternatively, detection of a genetic biomarker can include a method for detecting cancer in a subject comprising: sequencing circulating cell-free DNA (cfDNA) from the subject at a depth of at least 50,000 reads per base to detect one or more genetic variants associated with cancer. In some embodiments, the sequencing is at a depth of at least 100,000 reads per base. In some embodiments, the sequencing is at a depth of about 120,000 reads per base. In some embodiments, the sequencing is at a depth of about 150,000 reads per base. In some embodiments, the sequencing is at a depth of about 200,000 reads per base. In some embodiments, the reads per base represent at least 5,000 original nucleic acid molecules, at least 10,000 original nucleic acid molecules, at least 20,000 original nucleic acid molecules, at least 30,000 original nucleic acid molecules, at least 40,000 original nucleic acid molecules, or at least 50,000 original nucleic acid molecules. In some embodiments, the method further comprises comparing sequence information from the cfDNA to sequence information obtained from a cohort of healthy individuals, a cohort of cancer patients, or germline DNA from the subject. In some embodiments, the method further comprises amplifying the cfDNA prior to sequencing, and determining a consensus sequence from sequence reads obtained from the sequencing to reduce errors from amplification or sequencing. In some embodiments, determining the consensus sequence is performed on a molecule-by-molecule basis. In some embodiments, determining the consensus sequence is performed on a base by base basis. In some embodiments, detection of consensus sequence is based on assessing probabilities of each of the potential nucleotides based on the observed sequencing output, as well as sequencing and amplification error profile characteristics of an individual sample, a batch of samples, or a reference set of samples. In some embodiments, determining the consensus sequence is performed using molecular barcodes that tag individual cfDNA molecules derived from the subject. In some embodiments, a set of molecules with a consensus sequence deviant from the human reference is compared to those observed in other samples processed in the laboratory to determine and exclude any potential contaminating event. In some embodiments, determining the consensus sequence is optimized by comparing the consensus sequence to those obtained from the cohort of healthy individuals, the cohort of cancer patients, or the germline DNA from the subject. In some embodiments, the method further comprises tagging the cfDNA molecules with a barcode such that at least 20% of the cfDNA in a sample derived from the subject are tagged. In some embodiments, the tagging is performed by attaching adaptors comprising a barcode. In some embodiments, the adaptors comprise any or all of blunt end adaptors, restriction enzyme overhang adaptors, or adaptors with a single nucleotide overhang. In some embodiments, the adaptors with a single nucleotide overhang comprise C-tail adaptors, A-tail adaptors, T-tail adaptors, and/or G-tail adaptors. In some embodiments, the tagging is performed by PCR amplification using primers with barcodes. In some embodiments, the barcode is single stranded. In some embodiments, the barcode is double stranded. In some embodiments, the method further comprises dividing the cfDNA into partitions. In some embodiments, the cfDNA in each partition is uniquely tagged with respect to each other partition. In some embodiments, the cfDNA in each partition is non-uniquely tagged with respect to each other partition. In some embodiments, the cfDNA in each partition is not tagged. Additionally or alternatively, detection of a genetic biomarker can include a method for detecting a tumor in a subject suspected of having cancer or having cancer, comprising: (a) sequencing cell-free DNA (cfDNA) molecules derived from a cell-free DNA (cfDNA) sample obtained from the subject; (b) analyzing sequence reads derived from the sequencing to identify (i) circulating tumor DNA (ctDNA) among the cfDNA molecules and (ii) one or more driver mutations in the cfDNA; and (c) using information about the presence, absence, or amount of the one or more driver mutations in the ctDNA molecules to identify (i) the tumor in the subject and (ii) actions for treatment of the tumor to be taken by the subject, wherein the method detects the tumor in the subject with a sensitivity of at least 85%, a specificity of at least 99%, and a diagnostic accuracy of at least 99%.

In some embodiments, detection of a genetic biomarker (e.g., one or more genetic biomarkers) can include any of the variety of methods described in P.C.T. Publication No. WO 2017/136603, which is hereby incorporated by reference in its entirety. For example, detection of a genetic biomarker can include methods and systems for detecting or monitoring cancer evolution. Additionally or alternatively, detection of a genetic biomarker can include a computer-implemented method, comprising: (a) obtaining information about a plurality of subjects with cancer at a first time point, wherein the information comprises for each subject of the plurality of subjects at least a genetic profile of a tumor obtained by genotyping nucleic acids from a cell-free bodily fluid and any treatment provided to the subject before the first time point, and determining a first state of each of the plurality of subjects based on the information at the first time point to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state. In some embodiments, the method further comprises (d) for the given first state among a set of states at an earlier time point, determining the probability that the given first state will result in the second state among the set of states at the later time point; and (e) generating an electronic output indicative of the probability determined in (d). Additionally or alternatively, detection of a genetic biomarker can include a computer-implemented method, comprising: (a) obtaining information about a plurality of subjects with cancer at a first time point, wherein the information comprises, for each subject of the plurality of subjects, at least a genetic profile of a tumor obtained by genotyping at least 50 genes and any treatment provided to the subject before the first time point, and determining a first state of each of the plurality of subjects based on the information at the first time point, to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state. In some embodiments, the method further comprises (d) for the given first state among a set of states at an earlier time point, determining the probability that the given first state will result in the second state among the set of states at the later time point; and (e) generating an electronic output indicative of the probability determined in (d). In some embodiments, obtaining the information comprises sequencing cell-free deoxyribonucleic acid (cfDNA) from the plurality of subjects and, optionally, performing a medical interview of each of the plurality of subjects. In some embodiments, treatment was provided to the subject before the first time point. In some embodiments, the methods comprise generating one or more decision trees, each decision tree comprising a root node, one or more decision branches, one or more decision nodes, and one or more terminal nodes, wherein a state at the root node represents the first time point, the one or more decision branches represent alternative treatments, and the one or more decision nodes and the one or more terminal nodes represent subsequent states. In some embodiments, the one or more decision branches comprise a plurality of decision branches. In some embodiments, the subsequent states comprise a viability state(s) of the subjects indicative of the subjects being alive or deceased. In some embodiments, the subsequent states comprise a subject survival rate. In some embodiments, each of the first states comprises a common set of one or more somatic mutations. In some embodiments, the information further comprises a subject profile. Additionally or alternatively, detection of a genetic biomarker can include a method, comprising: (a) obtaining information about a subject with a cancer at a first time point, wherein the information comprises at least one characteristic of the subject from a patient profile, a tumor profile, or a treatment; (b) determining an initial state of the subject based on the information at the first time point; (c) determining a probability for each of a plurality of subsequent states at each of one or more subsequent time points based on the initial state of the subject, thereby providing a set of probabilities with regards to state outcomes; (d) generating a recommendation of a treatment for the cancer based at least in part on the set of probabilities with regards to state outcomes that optimizes for a probability that subject obtains a particular outcome; and (e) generating an electronic output indicative of the recommendation generated in (d). In some embodiments, the probability is at least in part a function of a treatment choice from among a plurality of treatment choices. In some embodiments, the one or more subsequent time points comprises a plurality of subsequent time points. In some embodiments, the method further comprises determining the probability at a plurality of subsequent time points. In some embodiments, the time points comprise at least three time points. In some embodiments, the time points comprise at least four time points. In some embodiments, the first time point is prior to the subject receiving the treatment and the subsequent time point is after the subject receiving the treatment. In some embodiments, a second treatment is administered after the subsequent time point based on the subsequent state at the subsequent time point. In some embodiments, the at least one characteristic of the subject is from the patient profile and is selected from the group consisting of: age, gender, genetic profile, enzyme levels, organ function, quality of life, frequency of medical interventions, remission status, and patient outcome. Additionally or alternatively, detection of a genetic biomarker can include a method, comprising: (a) establishing one or more communications links over a communication network with one or more medical service providers; (b) receiving over the communications network from the one or more medical service providers medical information about one or more subjects; (c) receiving from the medical service provider one or more samples comprising cell-free deoxyribonucleic acid (cfDNA) from each of the one or more subjects; (d) sequencing the cfDNA and identifying one or more genetic variants present in the cfDNA; (e) creating or supplementing a database with information for each of the one or more subjects, the information comprising both identified genetic variants and received medical information; and (f) using the database and a computer implemented algorithm, generating at least one predictive model that predicts, based on an initial state of a subject, the probability of a subsequent state for each of a plurality of different therapeutic interventions. Additionally or alternatively, detection of a genetic biomarker can include a non-transitory computer-readable medium comprising machine executable code that, upon execution by one or more computer processors, implements a method comprising: (a) obtaining information about a plurality of subjects with cancer at a first time point, wherein the information comprises, for each subject of the plurality of subjects, at least a genetic profile of a tumor obtained by genotyping nucleic acids from a cell-free bodily fluid and any treatment provided to the subject before the first time point, and determining a first state of each of the plurality of subjects based on the information at the first time point, to produce a set of first states; (b) obtaining the information about the plurality of subjects at one or more second time points subsequent to the first time point, and determining a second state of each of the plurality of subjects at each of the one or more second time points based on the information at a given one of the one or more second time points, to produce a set of subsequent states; and (c) using the set of first states from (a) and the set of subsequent states from (b) to generate a predictive algorithm that is configured to determine a probability that a given first state will result in a second state among a set of states at a later time point subsequent to the given first state. Additionally or alternatively, detection of a genetic biomarker can include a method, comprising: (a) obtaining information about a subject comprising at least a genetic profile of a tumor and a treatment previously or currently provided to the subject, if any, and determining an initial state of the subject based on the information; (b) providing a decision tree, wherein a root node represents an initial subject state, decision branches represent alternative treatments available to the subject, chance nodes represent points of uncertainty, and decision nodes or terminal nodes represent subsequent states; (c) providing a course of treatment for the subject that maximizes a probability of the subject achieving a living state at a terminal node; and (d) administering the course of treatment to the subject. In some embodiments, the method further comprises: (e) at a second time point subsequent to the initial state, obtaining information about a subject comprising at least a genetic profile of a tumor and a treatment previously or currently provided to the subject, if any, and determining an second state of the subject among a plurality of subsequent states based on the information; (f) based on the second state, providing a subsequent course of treatment for the subject that maximizes probability of the subject achieving a living state at a terminal node; and (g) administering the subsequent course of treatment to the subject. In some embodiments, the method further comprises: (e) at a second time point subsequent to the initial state, obtaining information about a subject comprising at least a genetic profile of a tumor and a treatment previously or currently provided to the subject, if any, and determining an second state of the subject among a plurality of subsequent states based on the information; (f) based on the second state, providing a subsequent course of treatment for the subject that maximizes probability of the subject achieving a living state at a terminal node; and (g) administering the subsequent course of treatment to the subject.

In some embodiments, detection of a genetic biomarker (e.g., one or more genetic biomarkers) can include any of the variety of methods described in U.S. Pat. No. 10,017,759, which is hereby incorporated by reference in its entirety. For example, detection of a genetic biomarker can include methods for preparing a library of nucleic acid fragments, and more specifically to methods for preparing a library of nucleic acid fragments in a single tube using proteases for a variety of applications including, e.g., next generation DNA sequencing. Additionally, a method of preparing a library of tagged nucleic acid fragments including (a) contacting a population of cells directly with a lysis reagent to generate a cell lysate, wherein the lysis reagent has one or more proteases, and wherein the cell lysate contains a target nucleic acid; (b) inactivating the one or more proteases to form an inactivated cell lysate, and (c) directly applying at least one transposase and at least one transposon end composition containing a transferred strand to the inactivated cell lysate under conditions where the target nucleic acid and the transposon end composition undergo a transposition reaction to generate a mixture, wherein (i) the target nucleic acid is fragmented to generate a plurality of target nucleic acid fragments, and (ii) the transferred strand of the transposon end composition is joined to 5' ends of each of a plurality of the target nucleic acid fragments to generate a plurality of 5' tagged target nucleic acid fragments. In some embodiments, steps (a), (b), and (c) are performed in a single reaction mixture, e.g., in a tube. In some embodiments, the population of cells is a minimal population of cells. In some embodiments, the minimal population of cells contains one, two, three, four, or five cells. In some embodiments, the target nucleic acid is a double-stranded DNA, and wherein the target nucleic acid remains the double-stranded DNA prior to applying a transposase and a transposon end composition in step (c). In some embodiments, the target nucleic acid is genomic DNA. In some embodiments, the target nucleic acid contains chromosomal DNA or a fragment thereof. In some embodiments, the target nucleic acid includes a genome or a partial genome. In some embodiments, the method further includes (d) incubating the mixture from step (c) directly with at least one nucleic acid modifying enzyme under conditions wherein a 3' tag is joined to the 5' tagged target nucleic acid fragments to generate a plurality of di-tagged target nucleic acid fragments. In some embodiments, steps (a), (b), (c), and (d) are performed in a single reaction tube. In some embodiments, the method further includes (e) amplifying one or more di-tagged target nucleic acid fragments to generate a library of tagged nucleic acid fragments with additional sequence at 5' end and/or 3' end of the di-tagged nucleic acid fragments. In some embodiments, steps (a), (b), (c), (d), and (e) are performed in a single reaction tube. In some embodiments, the amplifying includes use of one or more of a polymerase chain reaction (PCR), a strand-displacement amplification reaction, a rolling circle amplification reaction, a ligase chain reaction, a transcription-mediated amplification reaction, or a loop-mediated amplification reaction. In some embodiments, the amplifying includes a PCR using a single primer that is complementary to the 3' tag of the di-tagged target DNA fragments. In some embodiments, the amplifying includes a PCR using a first and a second primer, wherein at least a 3' end portion of the first primer is complementary to at least a portion of the 3' tag of the di-tagged target nucleic acid fragments, and wherein at least a 3' end portion of the second primer exhibits the sequence of at least a portion of the 5' tag of the di-tagged target nucleic acid fragments. In some embodiments, a 5' end portion of the first primer is non-complementary to the 3' tag of the di-tagged target nucleic acid fragments, and a 5' end portion of the second primer does not exhibit the sequence of at least a portion of the 5' tag of the di-tagged target nucleic acid fragments. In some embodiments, the first primer includes a first universal sequence, and/or wherein the second primer includes a second universal sequence. In some embodiments, the method further includes sequencing the tagged nucleic acid fragments. In some embodiments, the sequencing of the tagged nucleic acid fragments includes use of one or more of sequencing by synthesis, bridge PCR, chain termination sequencing, sequencing by hybridization, nanopore sequencing, and sequencing by ligation. In some embodiments, the sequencing of the tagged nucleic acid fragments includes use of next generation sequencing. In some embodiments, the method further includes analyzing copy number variation. In some embodiments, the method further includes analyzing single nucleotide variation.

In some embodiments, detection of a genetic biomarker (e.g., one or more genetic biomarkers) can include any of the variety of methods described in U.S. Pat. No. 9,944,924, which is hereby incorporated by reference in its entirety. For example, detection of a genetic biomarker can include the use of application-specific capture primers in next generation sequencing. A method of modifying an immobilized capture primer can include: a) providing a solid support having an immobilized application-specific capture primer, the application-specific capture primer including: i) a 3' portion including an application-specific capture region, and ii) a 5' portion including a universal capture region; b) contacting an application-specific polynucleotide with the application-specific capture primer under conditions sufficient for hybridization to produce an immobilized application-specific polynucleotide, and c) removing the application-specific capture region of an application-specific capture primer not hybridized to an application-specific polynucleotide to convert the unhybridized application-specific capture primer to a universal capture primer. In some embodiments, a portion of the application-specific capture region is removed. In some embodiments, the application-specific capture primer comprises a plurality of different immobilized application-specific capture primers. In some embodiments, the application-specific polynucleotide comprises a plurality of different application-specific polynucleotides. In some embodiments, the application-specific capture region includes a target-specific capture region and the application-specific polynucleotide includes a target polynucleotide. In some embodiments, the application-specific capture region includes a transposon end (TE) region and the application-specific polynucleotide includes a TE oligonucleotide. In some embodiments, the method further includes applying an oligonucleotide before execution of step c) under conditions sufficient for oligonucleotide hybridization with the universal capture region of an application-specific capture primer to produce a double-stranded DNA region. In certain embodiments, the oligonucleotide is a P5 or P7 oligonucleotide. In some embodiments, the method further includes applying an oligonucleotide before execution of step c) under conditions sufficient for oligonucleotide hybridization with the application-specific capture region of an application-specific capture primer to produce a double-stranded DNA region. In some embodiments, the method further includes contacting the application-specific capture primer with a nuclease, wherein the application-specific capture region of an application specific capture primer not hybridized with an application-specific polynucleotide to is removed by the nuclease. In some embodiments, the nuclease is an exonuclease. In some embodiments, the exonuclease is exonuclease I. In some embodiments, the exonuclease is exonuclease III. In some embodiments, the nuclease is an endonuclease.

In some embodiments, detection of a genetic biomarker (e.g., one or more genetic biomarkers) can include any of the variety of methods described in U.S. Pat. No. 9,992,598, which is hereby incorporated by reference in its entirety. For example, detection of a genetic biomarker can include a method for amplicon preparation. The method includes: (a) contacting a nucleic acid sample including a plurality of target polynucleotides with at least one primer under conditions sufficient for hybridization, the at least one primer containing an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized amplicons, the solid support further including a plurality of universal capture primers; (d) extending the plurality of target specific capture primers to produce a plurality of immobilized extension products complementary to the target polynucleotides; (e) annealing the plurality of universal capture primers to the plurality of the immobilized extension products, and (f) amplifying by PCR the plurality of immobilized extension products to produce a second plurality of immobilized amplicons, wherein the population of immobilized amplicons includes a uniformity of 85% or more. The method can be used with 10 ng or less input nucleic acid and can further include sequencing the second plurality of immobilized amplicons. The method also can be used for determining the presence of a gene associated with a disorder or disease, including a cancer associated gene. Cell free DNA also can be employed in the method. Additionally, detection of a genetic biomarker can include a method for increasing detection sensitivity of a nucleic acid sequence variant, which includes: (a) contacting a nucleic acid sample including a plurality of target polynucleotides with gene specific forward and reverse primers under conditions sufficient for hybridization, each species of the gene specific forward primer including a unique sequence index and an adapter; (b) amplifying by polymerase chain reaction (PCR) the plurality of target polynucleotides to produce a plurality of amplicons; (c) directly contacting a plurality of target specific capture primers immobilized on a solid support with the plurality of amplicons under conditions sufficient for hybridization to produce a first plurality of immobilized of amplicons, the solid support further including a plurality of universal capture primers; (d) extending the plurality of target specific capture primers to produce a plurality of immobilized extension products complementary to the target polynucleotides; (e) annealing the plurality of universal capture primers to the plurality of the immobilized extension products; (f) amplifying by PCR the plurality of immobilized extension products to produce a second plurality of immobilized amplicons, wherein the second plurality of immobilized amplicons includes a uniformity of 85% or more; (g) sequencing the second plurality of immobilized amplicons, and (h) eliminating random sequence errors for one or more target polynucleotide by comparing three or more nucleotide sequences at a variant position for a target polynucleotide species, wherein the target polynucleotide species are identified by the unique sequence index to thereby determine a true nucleotide sequence variant in the one or more target polynucleotides. The method can detect a mismatch rate of 0.3% or less for a variant nucleotide position.

In some embodiments, detection of a genetic biomarker (e.g., one or more genetic biomarkers) can include any of the variety of methods described in U.S. Pat. No. 9,879,312, which is hereby incorporated by reference in its entirety. For example, detection of a genetic biomarker can include methods for the selective enrichment of nucleic acids. Some embodiments include the selective enrichment of long nucleic acids comprising a target nucleic acid. Some embodiments include the selective enrichment of PCR products. Some embodiments of the methods comprise (a) contacting the population of nucleic acids with a nickase, thereby producing a population of nicked nucleic acids; (b) contacting the population of nicked nucleic acids with an exonuclease, thereby generating a nucleic acid having a single-stranded portion, wherein the single-strand portion comprises at least a portion of the target; (c) contacting a capture probe to the at least a portion of the target, wherein the probe hybridizes to the target; and (d) separating a nucleic acid hybridized to the capture probe from a nucleic acid not bound to the capture probe. In other embodiments, the methods comprise (a) obtaining a population of nucleic acids, wherein at least some of the nucleic acids in the population comprise a target; (b) contacting the population of nucleic acids with a nickase, thereby producing a population of nicked nucleic acids; (c) contacting the population of nicked nucleic acids with an exonuclease, thereby generating a nucleic acid having a single-stranded portion, wherein the single-strand portion comprises at least a portion of the target; (d) contacting a capture probe to the at least a portion of the target, wherein the probe hybridizes to the target; and (e) separating a nucleic acid hybridized to the capture probe from a nucleic acid not bound to the capture probe. Some embodiments of the methods also include a step of releasing the hybridized nucleic acid from the capture probe. Other embodiments also include amplifying the target. Still further embodiments additionally include sequencing at least a portion of the target. In some embodiments, one or more process steps, for example step (a), can also include contacting the population of double stranded nucleic acids with a type II restriction endonuclease that includes an isoschizomer of the nickase; and recircularizing the cut double stranded nucleic acids under conditions that favor intramolecular recircularization of individual nucleic acids. In such embodiments, various type II restriction endonucleases, or combinations of type II restriction endonucleases, can be used. In some embodiments, for example, the restriction endonuclease includes BbvCI. In other embodiments, the nickase includes Nb.BbvCI and Nt.BbvCI. In some embodiments of the methods, the probe includes a capture moiety. In some such embodiments, the capture moiety includes biotin or streptavidin. In some embodiments, the step of separating a nucleic acid hybridized to the capture probe from a nucleic acid not bound to the capture probe also includes contacting the hybridized target and probe to a binding moiety. In some embodiments, the binding moiety includes avidin, and streptavidin. In some embodiments, the binding moiety also includes a bead, microsphere or other particle. Embodiments of the methods also include repeating one or more steps of the process. In certain embodiments, all of the method steps are repeated. In some embodiments of the methods, the target includes a first capture moiety, and the probe includes a second capture moiety. Some such embodiments also include contacting the first capture moiety to a first binding moiety, thereby providing for enrichment of the target, and contacting the second capture moiety to a second binding moiety, thereby providing for enrichment of the probe. In addition to the foregoing, some embodiments of the methods also provide for the selective enrichment of a nucleic acid that comprise the steps of (a) providing a population of nucleic acids, wherein at least some of the nucleic acids in the population include a target hybridized with a capture probe; (b) locking the hybridized probe to the target; and (c) separating a nucleic acid locked to a probe from a nucleic acid that is not locked to a probe. In other embodiments, the methods comprise (a) obtaining a population of nucleic acids, wherein at least some of the nucleic acids in the population include a target; (b) hybridizing the target with a capture probe; (c) locking the probe hybridized probe to the target; and (d) separating a nucleic acid locked to a probe from a nucleic acid that is not locked to a probe. In addition to the foregoing, some embodiments of the methods, also include methods for selective enrichment of a nucleic acid that comprise (a) providing a population of nucleic acids, wherein at least some of the nucleic acids in the population include a target that comprises a portion of the 5' end of a nucleic acid and a portion of the 3' end of the nucleic acid, said target being hybridized to a selector probe that comprises a first and second oligonucleotide annealed together, wherein the first oligonucleotide is complementary to at least a portion of the 5' end of the nucleic acid and complementary to at least a portion of the second oligonucleotide, and the second oligonucleotide is complementary to at least a portion of the 3' end of the nucleic acid; (b) joining the selector probe to the target; and (c) separating a nucleic acid joined to the selector probe from a nucleic acid not joined to the selector probe. Other embodiments of the enrichment methods comprise the steps of (a) obtaining a population of nucleic acids, wherein at least some of the nucleic acids in the population include a target, the target including a portion of the 5' end of a nucleic acid and a portion of the 3' end of the nucleic acid; (b) obtaining a selector probe that comprises a first and second oligonucleotide annealed together, wherein the first oligonucleotide is complementary to at least a portion of the 5' end of the nucleic acid and complementary to at least a portion of the second oligonucleotide, and the second oligonucleotide is complementary to at least a portion of the 3' end of the nucleic acid; (c) contacting the selector probe to the target, wherein the probe hybridizes to the target; (d) joining the selector probe to the target; and (e) separating a nucleic acid joined to the selector probe from a nucleic acid not joined to the selector probe. In addition to the foregoing, some embodiments of the methods also include methods for selective enrichment of a nucleic acid that comprise (a) providing a population of single-stranded nucleic acids, wherein at least some of the nucleic acids in the population include a target, the target comprising the 5' end of a nucleic acid and the 3' end of the nucleic acid, said target being hybridized to a selector probe that comprises a first and second oligonucleotide annealed together, wherein the first oligonucleotide comprises a 5' portion complementary to the 3' end of the nucleic acid, a spacer portion, and a 3' portion complementary to the 5' end of the nucleic acid, the second oligonucleotide being complementary to the spacer portion; (b) joining the selector probe to the target; and (c) separating a nucleic acid joined to the selector probe from a nucleic acid not joined to the selector probe. Other embodiments of the methods comprise (a) obtaining a population of single-stranded nucleic acids, wherein at least some of the nucleic acids in the population include a target, the target comprising the 5' end of a nucleic acid and the 3' end of the nucleic acid; (b) obtaining a selector probe that includes a first and second oligonucleotide annealed together, wherein the first oligonucleotide comprises a 5' portion complementary to the 3' end of the nucleic acid, a spacer portion, and a 3' portion complementary to the 5' end of the nucleic acid, the second oligonucleotide being complementary to the spacer portion; (c) contacting the selector probe to the target, wherein the probe hybridizes to the target; (d) joining the selector probe to the target; and (e) separating a nucleic acid joined to the selector probe from a nucleic acid not joined to the selector probe. Some embodiments also include methods for normalizing amplified nucleic acids that include selecting a first population of oligonucleotides having a ratio of oligonucleotides that includes capture moieties to oligonucleotides lacking capture moieties for a first population of oligonucleotides; obtaining a second population of oligonucleotides; amplifying target nucleic acids with the first and second populations of oligonucleotides; and separating amplified targets having incorporated oligonucleotide comprising capture moieties from amplified targets lacking incorporated oligonucleotide capture moieties. In some embodiments, the step of separating further comprises contacting the hybridized target and probe to a binding moiety. In some embodiments, the binding moiety includes avidin and streptavidin. In some embodiments, the binding moiety also includes a bead, microsphere or other particle.

In some embodiments, detection of a genetic biomarker (e.g., one or more genetic biomarkers) can include any of the variety of methods described in U.S. Pat. No. 9,828,672, which is hereby incorporated by reference in its entirety. For example, detection of a genetic biomarker can include reagents for nucleic acid preparation comprising a siderophore. In some embodiments, the siderophore is a bacterial siderophore. In some embodiments, the siderophore is a desferrioxamine B (DFO-B) mesylate salt. In some embodiments, the reagents may comprise a DNA polymerase. In some embodiments, the reagents may comprise dNTPs. In some embodiments, the reagents do not contain EDTA. Some embodiments provide methods for preparing a nucleic acid library, which comprise: providing a plurality of nucleic acid molecules from a sample; and manipulating the plurality of nucleic acid molecules in a reagent for nucleic acid preparation comprising a siderophore. In some embodiments, manipulating the plurality of nucleic acid molecules comprises hybridizing the plurality of nucleic acid molecules to a plurality of oligonucleotide probes. In some embodiments, the plurality of nucleic acid molecules and/or the plurality of oligonucleotide probes are immobilized on a support. In some embodiments, the plurality of nucleic acid molecules and/or the plurality of oligonucleotide probes are immobilized on the support through a binding partner pair to the support. In some embodiments, the support is a magnetic bead. In some embodiments, manipulating the plurality of nucleic acid molecules comprises removing oligonucleotide probes not specifically bound to the plurality of nucleic acid molecules. In some embodiments, the methods comprise modifying the oligonucleotide probes specifically bound to the plurality of nucleic acid molecules. In some embodiments, the methods comprise fragmenting the plurality of nucleic acid molecules. In some embodiments, the methods comprise adding adapters to the plurality of nucleic acid molecules. In some embodiments, the adapters are added to the plurality of nucleic acid molecules by amplification. Some embodiments provide methods for reducing oxidative damage to a nucleic acid molecule, which methods comprise preparing the nucleic acid molecule in the absence of EDTA. In some embodiments, preparing the nucleic acid molecule comprises preparing the nucleic acid molecule in the presence of a siderophore. In some embodiments, the siderophore is a bacterial siderophore. In some embodiments, the siderophore is a desferrioxamine B (DFO-B) mesylate salt. In some embodiments, preparing the nucleic acid molecule comprises exposing the nucleic acid molecule to Fe(III). In some embodiments, preparing the nucleic acid molecule comprises exposing the nucleic acid molecule to a magnetic bead. In some embodiments, the oxidative damage comprises a point mutation in the nucleic acid molecule. In some embodiments, the point mutation is a C to A transversion. Some embodiments provide methods for increasing the Q (phred) score of a sequencing reaction, which methods comprise preparing a nucleic acid molecule in the absence of EDTA. In some embodiments, preparing the nucleic acid molecule comprises preparing the nucleic acid molecule in the presence of a siderophore. In some embodiments, the siderophore is a bacterial siderophore. In some embodiments, the siderophore is a desferrioxamine B (DFO-B) mesylate salt. In some embodiments, the Q score is greater than about 34. In some embodiments, the Q score is greater than about 38. In some embodiments, the Q score is greater than about 42. In some embodiments, the sequencing reaction is a deep sequencing application. In some embodiments, the deep sequencing application is cancer-related deep sequencing application. In some embodiments, the methods comprise sequencing the nucleic acid molecule in the absence of EDTA. Some embodiments provide kits comprising at least one container means, wherein the at least one container means comprises a reagent for nucleic acid preparation comprising a siderophore. In some embodiments, the siderophore is a desferrioxamine B (DFO-B) mesylate salt. In some embodiments, the reagent does not contain EDTA.

In some embodiments, detection of a genetic biomarker (e.g., one or more genetic biomarkers) can include any of the variety of methods described in U.S. Pat. No. 9,708,655, which is hereby incorporated by reference in its entirety. For example, detection of a genetic biomarker can include compositions, systems, and methods for detecting events using tethers anchored to or adjacent to nanopores. In some embodiments, a composition includes a nanopore including a first side, a second side, and an aperture extending through the first and second sides; and a permanent tether including a head region, a tail region, and an elongated body disposed therebetween. The head region can be anchored to or adjacent to the first side or second side of the nanopore. The elongated body including a reporter region can be movable within the aperture responsive to a first event occurring adjacent to the first side of the nanopore. In one non-limiting example, the head region can be anchored to a molecule, such as a protein, disposed on the first side or second side of the nanopore. In some embodiments, a method includes providing a nanopore including a first side, a second side, and an aperture extending through the first and second sides; and providing a permanent tether including a head region, a tail region, and an elongated body disposed therebetween. The head region can be anchored to or adjacent to the first or second side of the nanopore, and the elongated body can include a reporter region. The method can include moving the reporter within the aperture responsive to a first event occurring adjacent to the first side of the nanopore. In some embodiments, the reporter region is translationally movable within the aperture responsive to the first event. Additionally, or alternatively, the reporter region can be rotationally movable within the aperture responsive to the first event. Additionally, or alternatively, the reporter region can be conformationally movable within the aperture responsive to the first event. In some embodiments, the head region is anchored to or adjacent to the first side or second side of the nanopore via a covalent bond. The head region can be anchored to the first side of the nanopore. The tail region can extend freely toward the second side of the nanopore. In some embodiments, the reporter region is translationally movable toward the first side of the nanopore responsive to the first event. The reporter region can be translationally movable toward the second side after the first event. The reporter region further can be translationally movable toward the first side responsive to a second event occurring adjacent to the first side of the nanopore, the second event being after the first event. The reporter region further can be translationally movable toward the second side after the second event. In some embodiments, the first event includes adding a first nucleotide to a polynucleotide. In embodiments that include a second event, the second event can include adding a second nucleotide to the polynucleotide. An electrical or flux blockade characteristic of the reporter region can be different than an electrical or flux blockade characteristic of another region of the elongated body. In some embodiments, a system can include a composition and measurement circuitry configured to measure a first current or flux through the aperture or to measure a first optical signal while the reporter region is moved responsive to the first event.

In some embodiments, detection of a genetic biomarker (e.g., one or more genetic biomarkers) can include any of the variety of methods described in U.S. Pat. No. 9,670,530, which is hereby incorporated by reference in its entirety. For example, detection of a genetic biomarker can include methods of determining a haplotype or partial haplotype of a DNA sample containing high molecular weight segments of genomic DNA. Such methods may be characterized by the following operations: (a) processing the DNA sample to produce an enriched DNA sample enriched for DNA from a first high molecular weight segment having a plurality of alleles from a first haplotype; (b) sequencing DNA in the enriched DNA sample to produce a plurality of sequence reads, which are shorter in length than the first high molecular weight segment, where some of the sequence reads contain a first allele of the first haplotype and other of the sequence reads contain a second allele of the first haplotype; (c) aligning the sequence reads to a reference genome to produce aligned reads, where aligned reads from the first high molecular weight segment tend to cluster into islands on the reference genome; (d) determining distances separating adjacent ones of the aligned reads on the reference genome, where the separation distances between adjacent aligned reads fall into at least two groups distinguishable by the magnitude of their separation distances; (e) selecting a first group of the aligned reads having separation distances to adjacent aligned reads that are smaller than a cutoff value, thereby excluding aligned reads having greater separation distances, where at least a portion of the first group of the aligned reads belong to the same island on the reference genome; and (f) using alleles from the first group of aligned reads to define a first haplotype or first partial haplotype. In some embodiments, the methods have an additional operation of determining a complete haplotype from the first partial haplotype and other partial haplotypes. In some embodiments, selecting a first group of the aligned reads includes determining the cutoff value. As an example, the determining the cutoff value includes: (i) generating a mixture model from the separation distances between adjacent aligned reads, wherein the mixture model fits two distributions to the separation distances; and (ii) determining the cutoff value from a property of at least one of the two distributions. In some cases, each of the two distributions comprises its own central tendency (e.g., the mean of a Gaussian distribution). In certain embodiments, selecting a first group of the aligned reads includes determining the cutoff value. As an example, the determining the cutoff value includes: (i) generating a mixture model from the separation distances between adjacent aligned reads, wherein the mixture model fits two distributions to the separation distances; and (ii) determining the cutoff value from a property of at least one of the two distributions. In some cases, each of the two distributions comprises its own central tendency (e.g., the mean of a Gaussian distribution). In certain embodiments, generating a mixture model involves applying an expectation maximization procedure to the separation distances between adjacent aligned reads. In some implementations, determining the cutoff value includes an operation of identifying a fraction of the probability mass of the distribution containing the shorter separation distances. For example, the fraction of the probability mass of the distribution containing the shorter separation distances may be about 80% or greater.

In some embodiments, detection of a genetic biomarker (e.g., one or more genetic biomarkers) can include any of the variety of methods described in U.S. Pat. No. 9,587,273, which is hereby incorporated by reference in its entirety. For example, detection of a genetic biomarker can include a method of selecting a representational sample of nucleic acid sequences from a complex mixture. The method includes: (a) contacting a complex mixture of nucleic acids under conditions sufficient for hybridization with a population of capture probes complementary to one or more nucleic acids comprising a predetermined portion of the sequence collectively present in the complex mixture to form hybridization complexes of the one or more nucleic acids with the population of probes, the population of capture probes being attached to a solid support, and (b) removing unhybridized nucleic acids to select a representational sample of nucleic acids having a complexity of less than 10% but more than 0.001% of the complex mixture, wherein the representational sample comprises a nucleic acid copy having a proportion of each sequence in the copy relative to all other sequences in the copy substantially the same as the proportions of the sequences in the predetermined portion of one or more nucleic acids within the complex mixture. Additionally or alternatively, detection of a genetic biomarker can include a method of selecting a representational sample of genomic sequences from a complete genome. In some embodiments, the method further provides a nucleic acid population that includes a representational sample having a complexity of less than 10% but more than 0.001% of a complex mixture, the representational sample comprising a nucleic acid copy having a proportion of each sequence in the copy relative to all other sequences in the copy substantially the same as the proportions of sequences in a predetermined portion of a sequence collectively present in one or more nucleic acids within the complex mixture.

In some embodiments, detection of a genetic biomarker (e.g., one or more genetic biomarkers) can include any of the variety of methods described in U.S. Pat. No. 9,574,234, which is hereby incorporated by reference in its entirety. For example, detection of a genetic biomarker can include methods and compositions for analyzing nucleic acid sequences. In some embodiments, the methods utilize clonal objects, such as DNA balls, that have been captured on beads. Some embodiments provide compositions having a bead and one clonal object, wherein the clonal object is affinity bound or hybridized to the bead, for example, through patch on the surface of the bead, such as an affinity binding patch or a hybridization patch. In some aspects, the patch includes a plurality of polynucleotides attached to a single region on the surface of the bead. Some embodiments also provide a population of beads having affinity bound or hybridized clonal objects. In particular embodiments, each of the clonal objects are affinity bound or hybridized to the beads through a patch on the surface of each bead, such as an affinity binding patch or a hybridization patch. The ratio of beads to bound or hybridized clonal objects in the population can be 1:1. In particular embodiments, no more than one clonal object is bound or hybridized to any given bead in the population. Using these methods, compositions can be fabricated wherein a bead and one clonal object are affinity bound or hybridized to each other through attachment to a patch on the surface of the bead. Some embodiments can provide a method of fabricating an affinity binding patch on a bead by providing a bead having a plurality of capture moieties; providing a solid surface having a plurality of capture-complement moieties, wherein the capture-complement moieties further comprise a cleavable moiety and an affinity ligand; specifically binding the capture moieties to the capture-complement moieties, thereby forming an immobilized bead on the solid surface; and cleaving the cleavable moiety so as to retain the affinity ligand on the bead, thereby fabricating an affinity binding patch on the bead. In particular embodiments, the capture moieties or the capture-complement moieties or both include capture sequences of polynucleotides. Accordingly, Some embodiments can provide a method of fabricating an affinity binding patch on a bead by providing a bead having a plurality of first polynucleotides attached to the surface of the bead, wherein the first polynucleotides each have a capture sequence; providing a solid surface having a plurality of second polynucleotides attached to the solid surface, wherein the second polynucleotides each have a capture-complement sequence, a cleavable moiety and an affinity ligand; hybridizing the capture sequences of the first polynucleotides to the capture-complement sequences of the second polynucleotides, thereby forming an immobilized bead on the solid surface; and cleaving the second polynucleotides at the cleavable moiety so as to retain the affinity ligand on the second plurality of polynucleotides, thereby fabricating an affinity binding patch on the bead. In some aspects, the method further includes fabricating one clonal object bound to the affinity binding patch by contacting the affinity ligand with a binding agent, wherein the binding agent has two or more binding sites, and binding one clonal object to the binding agent through a second affinity ligand on the clonal object, wherein the one clonal object has a single tandemly repeated target nucleic acid molecule, thereby fabricating one clonal object bound to the affinity binding patch. Some embodiments can provide a method of fabricating a bead having one clonal object by providing a bead having a plurality of first capture moieties; providing a solid surface having a plurality of second capture moieties patterned into patches on the surface, wherein the second capture moieties each have a cleavable moiety, wherein one clonal object is bound to one patch on the surface via one or more of the second capture moieties, wherein the one clonal object has a single tandemly repeated target nucleic acid molecule; specifically binding the first capture moiety to the clonal object, thereby forming an immobilized bead on the solid surface, and cleaving the cleavable moiety so as to retain the clonal object, thereby fabricating a bead having one clonal object. In particular embodiments, the capture moieties comprise polynucleotides. Accordingly, Some embodiments can provide a method of fabricating a bead having one clonal object by providing a bead having a plurality of first polynucleotides; providing a solid surface having a plurality of second polynucleotides patterned into patches on the surface, wherein the second polynucleotides each have a cleavable moiety, wherein one clonal object is hybridized to one polynucleotide patch on the surface, wherein the one clonal object has a single tandemly repeated target nucleic acid molecule; hybridizing the first polynucleotides to the clonal object, thereby forming an immobilized bead on the solid surface, and cleaving the second polynucleotides at the cleavable moiety so as to retain the clonal object, thereby fabricating a bead having one clonal object. Some embodiments can provide a method of fabricating a hybridization patch on a bead by providing a bead having a plurality of first polynucleotides attached to the surface of the bead, wherein the first polynucleotides each have a first capture sequence, providing a solid surface having a plurality of second polynucleotides attached to the solid surface, wherein the second polynucleotides each have a first capture-complement sequence and a second capture-complement sequence, hybridizing the first capture sequences of the first polynucleotides to the first capture-complement sequence of the second polynucleotides, thereby forming an immobilized bead on the solid surface, and extending the first polynucleotides of the immobilized bead using the second capture-complement sequence as a template, thereby fabricating a hybridization patch of extended first polynucleotides on the bead, the extended first polynucleotides having a second capture sequence. In some aspects, the method further includes fabricating one clonal object bound to the patch on the bead by providing a clonal object having the second capture-complement sequence, and hybridizing the second capture-complement sequence of the clonal object to the second capture sequences of the bead, thereby fabricating one clonal object bound to the patch on the bead. In some aspects of the method, extending the first polynucleotides includes the addition of one or more nucleoside triphosphates having an affinity ligand, thereby fabricating an affinity binding patch on the bead. Some embodiments include methods of amplifying a target nucleic acid molecule. Some embodiments provide a method of amplifying a target nucleic acid molecule by placing the compositions or populations of beads having affinity bound or hybridized clonal objects onto a solid surface having microwells, wherein only one bead can spatially fit into one microwell and amplifying the target nucleic acid molecules in the microwells, thereby forming amplicons. In some aspects, the method further includes sequencing the amplified target nucleic acid molecules using methods such as sequencing by synthesis, sequencing by ligation or sequencing by hybridization, thereby determining the nucleic acid sequence of the target nucleic acid molecule.

In some embodiments, detection of a genetic biomarker (e.g., one or more genetic biomarkers) can include any of the variety of methods described in U.S. Pat. No. 9,453,258, which is hereby incorporated by reference in its entirety. For example, detection of a genetic biomarker can include determination of a sequence, for example a nucleic acid sequence, using a minimal dye set, minimal excitation light sources, and minimal optical emission filters while still allowing for differentiation of the incorporation of all four nucleotides in a sequencing reaction. Additionally or alternatively, detection of a genetic biomarker can include methods for determining the sequence of a polynucleotide comprising detecting in a sequencing reaction the incorporation of three different types of detectable nucleotide conjugates into a polynucleotide and determining the incorporation of a fourth type of nucleotide based on the detection pattern of the three different types of detectable nucleotides into the polynucleotide thereby determining the sequence of a polynucleotide, wherein the incorporation of three different types of detectable nucleotide conjugates is detected from a signal state and wherein the incorporation of the fourth type of nucleotide is determined from a dark state. Additionally or alternatively, detection of a genetic biomarker can include methods for determining the sequence of a polynucleotide comprising applying to a polynucleotide sample for sequencing a solution comprising four modified nucleotide types wherein three modified nucleotide types are conjugated to one or more detection moieties and one or more linkers positioned between the nucleotide and the one or more detection moieties, and wherein a fourth nucleotide type lacks a detection moiety, detecting a pattern of incorporation of said modified nucleotides in a sequencing reaction thereby capturing a first detectable pattern, applying one or more compositions to the sequencing reaction thereby changing the first detectable pattern, detecting a second detectable pattern, and determining the sequence of the polynucleotide sample based on the detectable patterns. In some embodiments, the polynucleotide for sequencing comprises one or more of deoxyribonucleic acids, modified deoxyribonucleic acids, ribonucleic acids and modified ribonucleic acids. In some embodiments, the polynucleotide for sequencing is a genomic DNA library preparation. In some embodiments, the nucleotide conjugate comprises nucleotide types selected from the group consisting of dATP, dTTP, dUTP, dCTP, dGTP or non-natural nucleotide analogs thereof. In some embodiments, the non-natural nucleotide analog comprises a reversible terminator moiety and is selected from the group consisting of rbATP, rbTTP, rbCTP, rbUTP and rbGTP. In some embodiments, the nucleotide incorporation is sequence by synthesis, sequence by ligation, and sequence by hybridization or a combination thereof. In some embodiments, the three nucleotide type conjugates are detected by detecting a fluorescent moiety. In some embodiments, the fluorescent moiety is the same for the three nucleotide conjugates whereas in other embodiments the fluorescent moiety is one or more different fluorescent moieties. In some embodiments, the one or more different fluorescent moieties are detected by the same emission filter. In some embodiments, the fluorescent moiety comprises a fluorescent resonance energy transfer system moiety. In some embodiments, the incorporation of the fourth nucleotide is determined by lack of detection. In some embodiments, the detectable nucleic acid conjugates are detected by fluorescence. In some embodiments, the fluorescence is detected by a first and a second imaging event, in further embodiments the first and second imaging events are separated in time. In some embodiments, the first imaging event detects a pattern of fluorescence that is different from the pattern of fluorescence detected by the second imaging event. In some embodiments, the incorporation of one or more nucleotides is determined by the difference in the pattern of fluorescence between the first and second imaging events. In some embodiments, the one or more nucleotide type conjugates further comprise one or more linker sequences, in further embodiments the one or more linker sequences comprise one or more of a cleavable linker and a spacer linker. In some embodiments, the cleavable linker comprises one or more cleavable linkage groups selected from the group consisting of a disulfide, a diol, a diazo, an ester, a sulfone, an azide, an alyl and a silyl ether, whereas in preferred embodiments the cleavable linkage group is a disulfide. In some embodiments, the spacer linker is one or more of polyethylene glycol or concatamers thereof and 2-{2-[3-(2-amino-ethylcarbornyl)-phenoxy]-1-azido-ethoxy}-ethoxy-acetic acid. In some embodiments, the one or more spacer linkers further comprise one or more cleavable linkage groups wherein the cleavable linkage group is selected from the group consisting of a disulfide, a diol, a diazo, an ester, a sulfone, an azide, an alyl and a silyl ether. In some embodiments, the spacer linker is polyethylene glycol or concatamers thereof whereas in other embodiments the spacer linker is 2-{2-[3-(2-amino-ethylcarbornyl)-phenoxy]-1-azido-ethoxy}-ethoxy-acetic acid. In some embodiments, the one or more nucleotide conjugates comprise a polyethylene glycol linker and a 2-{2-[3-(2-amino-ethylcarbornyl)-phenoxy]-1-azido-ethoxy}-ethoxy-acetic acid linker which may or may not further comprise a hapten and a fluorescent moiety. In some embodiments, the hapten is selected from the group consisting of biotin, digoxigenin and dinitrophenol. In some embodiments, the one or more nucleotide conjugates comprises a streptavidin-fluorescent moiety conjugate whereas in other embodiments, the one or more nucleotide conjugates comprises an anti-hapten antibody-fluorescent moiety conjugate selected from the group consisting of anti-digoxigenin and anti-dinitrophenol. In some embodiments the nucleotide conjugate comprising a polyethylene glycol linker and a 2-{2-[3-(2-amino-ethylcarbornyl)-phenoxy]-1-azido-ethoxy}-ethoxy-acetic acid linker further comprises two fluorescent moieties. In some embodiments, the two fluorescent moieties constitute a fluorescence resonance energy transfer system.

In some embodiments, detection of a genetic biomarker (e.g., one or more genetic biomarkers) can include any of the variety of methods described in U.S. Pat. No. 9,441,267, which is hereby incorporated by reference in its entirety. For example, detection of a genetic biomarker can include methods of determining the identity of a nucleotide at a detection position in a target sequence. The methods comprise providing a hybridization complex comprising the target sequence and a capture probe covalently attached to a microsphere on a surface of a substrate. The methods comprise determining the nucleotide at the detection position. The hybridization complex can comprise the capture probe, a capture extender probe, and the target sequence. In addition, the target sequence may comprise exogenous adapter sequences. In an additional aspect, the method comprises contacting the micro spheres with a plurality of detection probes each comprising a unique nucleotide at the readout position and a unique detectable label. The signal from at least one of the detectable labels is detected to identify the nucleotide at the detection position. In an additional aspect, the detection probe does not contain detection label, but rather is identified based on its characteristic mass, for example via mass spectrometry. In addition, the detection probe comprises a unique label that is detected based on its characteristic mass. Additionally or alternatively, detection of a genetic biomarker can include methods wherein the target sequence comprises a first target domain directly 5' adjacent to the detection position. The hybridization complex comprises the target sequence, a capture probe and an extension primer hybridized to the first target domain of the target sequence. The determination step comprises contacting the micro spheres with a polymerase enzyme, and a plurality of NTPs each comprising a covalently attached detectable label, under conditions whereby if one of the NTPs basepairs with the base at the detection position, the extension primer is extended by the enzyme to incorporate the label. As is known to those in the art, dNTPs and ddNTPs are the preferred substrates for DNA polymerases. NTPs are the preferred substrates for RNA polymerases. The base at the detection position is then identified. Additionally or alternatively, detection of a genetic biomarker can include methods wherein the target sequence comprises a first target domain directly 5' adjacent to the detection position, wherein the capture probe serves as an extension primer and is hybridized to the first target domain of the target sequence. The determination step comprises contacting the micro spheres with a polymerase enzyme, and a plurality of NTPs each comprising a covalently attached detectable label, under conditions whereby if one of the NTPs basepairs with the base at the detection position, the extension primer is extended by the enzyme to incorporate the label. The base at the detection position is thus identified. Additionally or alternatively, detection of a genetic biomarker can include methods wherein the target sequence comprises (5' to 3'), a first target domain comprising an overlap domain comprising at least a nucleotide in the detection position and a second target domain contiguous with the detection position. The hybridization complex comprises a first probe hybridized to the first target domain, and a second probe hybridized to the second target domain. The second probe comprises a detection sequence that does not hybridize with the target sequence, and a detectable label. If the second probe comprises a base that is perfectly complementary to the detection position a cleavage structure is formed. The method further comprises contacting the hybridization complex with a cleavage enzyme that will cleave the detection sequence from the signalling probe and then forming an assay complex with the detection sequence, a capture probe covalently attached to a microsphere on a surface of a substrate, and at least one label. The base at the detection position is thus identified.

In some embodiments, detection of a genetic biomarker (e.g., one or more genetic biomarkers) can include any of the variety of methods described in U.S. Pat. No. 7,060,431, which is hereby incorporated by reference in its entirety. For example, detection of a genetic biomarker can include array compositions comprising a substrate with a surface comprising discrete sites. The composition can further comprise a population of microspheres comprising at least a first and a second subpopulation; each subpopulation comprises a bioactive agent; and an identifier binding ligand that will bind a decoder binding ligand such that the identity of the bioactive agent can be elucidated. The microspheres are distributed on the surface. Some embodiments provide array compositions comprising a substrate with a surface comprising discrete sites, and a population of microspheres comprising at least a first and a second subpopulation. Each subpopulation comprises a bioactive agent and does not comprise an optical signature. Some embodiments provide methods of making an array composition as outlined above. The methods comprise forming a surface comprising individual sites on a substrate and distributing microspheres on said surface such that said individual sites contain microspheres. The microspheres comprise at least a first and a second subpopulation each comprising a bioactive agent and do not comprise an optical signature. Some embodiments provide methods of making a composition comprising forming a surface comprising individual sites on a substrate and distributing microspheres on the surface such that the individual sites contain microspheres. The microspheres comprise at least a first and a second subpopulation each comprising a bioactive agent and an identifier binding ligand that will bind a decoder binding ligand such that the identification of the bioactive agent can be elucidated. Additionally or alternatively, detection of a genetic biomarker can include methods of decoding an array composition comprising providing an array composition as outlined above, and adding a plurality of decoding binding ligands to the array composition to identify the location of at least a plurality of the bioactive agents. Additionally or alternatively, detection of a genetic biomarker can include methods of determining the presence of a target analyte in a sample. The methods comprise contacting the sample with an array composition as outlined above, and determining the presence or absence of the target analyte. Additionally or alternatively, detection of a genetic biomarker can include a method comprising providing an array composition comprising a population of microspheres comprising at least a first and a second subpopulation, wherein each subpopulation comprises a bioactive agent and at least a first and a second decoding attribute, and detecting each of said first and second decoding attributes to identify each of said bioactive agents. Additionally or alternatively, detection of a genetic biomarker can include a method of increasing the information obtained in a decoding step. The method includes the use of degenerate probes as DBL-IBL combinations. Additionally or alternatively, detection of a genetic biomarker can include the use of multiple decoding attributes on a bead. Additionally or alternatively, detection of a genetic biomarker can include a method of increasing the confidence of decoding. The method includes using the decoding as a quality control measure. Additionally or alternatively, detection of a genetic biomarker can include a method of decoding an array composition comprising providing an array composition comprising a population of microspheres comprising at least 50 subpopulations, wherein each subpopulation comprises a bioactive agent adding a plurality of decoding binding ligands to said population of microspheres to identify at least 50 of the bioactive agents. Additionally or alternatively, detection of a genetic biomarker can include a method of determining the presence of a target analyte in a sample comprising contacting said sample with a composition comprising a population of microspheres comprising at least 50 subpopulations, wherein each subpopulation comprises a bioactive agent adding a plurality of decoding binding ligands to said population of microspheres to identify at least 50 of the bioactive agents and determining the presence or absence of said target analyte.

In some embodiments, detection of a genetic biomarker (e.g., one or more genetic biomarkers) can include any of the variety of methods described in U.S. Pat. No. 7,060,431, which is hereby incorporated by reference in its entirety. For example, detection of a genetic biomarker can include microfluidic devices for the detection of a target analyte in a sample. The devices comprise a solid support that has any number of modules, including a sample inlet port and at least one sample handling well comprising a well inlet port and a well outlet port. The device generally further comprises a first microchannel to allow fluid contact between the sample inlet port and the sample handling well. The device also comprises a detection module comprising a substrate with a surface comprising discrete sites, and a population of microspheres comprising at least a first and a second subpopulation, wherein each subpopulation comprises a bioactive agent. The microspheres are distributed on said surface. The detection module also comprises a detection inlet port to receive the sample. The device also comprises a second microchannel to allow fluid contact between the sample handling well and the detection inlet port. Additionally or alternatively, detection of a genetic biomarker can include a method of assembling a detector in a microfluidic device. The method includes providing a microfluidic device comprising a first microchannel to allow fluid contact between a sample inlet port and a sample handling well, a second microchannel to allow fluid contact between said sample handling well and a detection inlet port, and a detection module comprising a substrate with a surface comprising discrete sites. The method further includes flowing a fluid across the substrate. The fluid comprises a population of microspheres comprising at least a first and a second subpopulation, wherein each subpopulation comprises a bioactive agent, whereby the beads flow across the discrete sites, and are deposited randomly in the discrete sites. The method additionally includes reversing the flow of the fluid. Additionally or alternatively, detection of a genetic biomarker can include a method of assembling a detector in a microfluidic device. The method includes providing a microfluidic device comprising a plurality of first micro channels, and a population of microspheres in microchannels. The device further includes a receiving chamber connected to said microchannels. The method further includes flowing said microspheres through said microchannels into said receiving chamber.

In some embodiments, detection of a genetic biomarker (e.g., one or more genetic biomarkers) can include any of the variety of methods described in U.S. Pat. No. 9,222,134, which is hereby incorporated by reference in its entirety. For example, detection of a genetic biomarker can include methods, systems and compositions for detecting molecules. In particular, methods, systems and compositions for detecting multiple types of molecules on a solid support. Some embodiments relate to methods for detecting molecules. In some embodiments, such methods comprise the steps of (a) providing a solid support comprising molecules associated with a site on the solid support such that the molecules are detected in aggregate during a detection step, wherein the site comprises at least two different types of molecules; (b) detecting a signal corresponding to the aggregate of molecules at the site; (c) estimating the fraction of different types of molecules at the site or estimating the amount of signal corresponding to different types of molecules at the site; (d) calculating the amount of signal corresponding to different types of molecules at the site using the fraction estimate, thereby obtaining a signal estimate or calculating the fraction of different types of molecules at the site using the signal estimate, thereby obtaining a fraction estimate; and (e) iteratively updating the fraction estimate and signal estimate until the estimates converge, thereby detecting molecules associated with the site. In some embodiments of the above-described methods, the providing step further comprises providing a mixture of molecules to the solid support. In other embodiments, the providing step further comprises associating the molecules with the site. In still other embodiments, the providing step further comprises attaching the molecules at the site. In some embodiments of the above-described methods, the estimating step is performed by guessing the fraction of different types of molecules at the site or guessing the amount of signal corresponding to different types of molecules at the site. In other embodiments, the estimating step comprises performing a principal component analysis (PCA). In some embodiments of the above-described methods, the updating step comprises performing a numerical optimization algorithm. In some such methods, the numerical optimization algorithm is based on an iterative map search. In some such embodiments, the numerical optimization algorithm is based on Fienup's iteration map. In some embodiments of the above-described methods, sequence data is obtained for one or more molecules. In some such methods, sequence data is obtained by a sequencing-by-synthesis process. In certain embodiments, the sequencing-by-synthesis process comprises a pyrosequencing process. In some embodiments of the above-described methods, the solid support comprises a bead. In some other embodiments, the solid support comprises a flow-cell. In preferred embodiments of the above-described methods, the molecules comprise nucleic acids. In some such methods, the nucleic acids are attached at the site. In some embodiments, the nucleic acids comprise a first subpopulation of nucleic acids and a second subpopulation of nucleic acids, wherein the nucleic acids of the first subpopulation each have an identical target region and the nucleic acids of the second subpopulation each have an identical region that is a variant of the target region. In some embodiments, the nucleotide sequence of the target region of the nucleic acids of the first subpopulation has at least 1 nucleotide that is different as compared to the nucleotide sequence of the variant of the target region of the nucleic acids of the second subpopulation. In some embodiments, the nucleotide sequence of the target region of the nucleic acids of the first subpopulation has at least 3 nucleotides that are different as compared to the nucleotide sequence of the variant of the target region of the nucleic acids of the second subpopulation. In some embodiments, a nucleotide sequence difference between the target region in the nucleic acids of the first subpopulation and the variant of the target region in the nucleic acids of the second subpopulation comprises at least one difference selected from the group consisting of a mutation, a polymorphism, an insertion, a deletion, a substitution, a simple tandem repeat polymorphism, and a single nucleotide polymorphism (SNP). In some embodiments, the nucleic acids comprise alleles of a genetic locus from a polyploid organism. In some other embodiments, the nucleic acids comprise alternative splicing forms of a nucleic acid. In yet other embodiments, the nucleic acids comprise alleles of a genetic locus from a diploid organism. Also described are molecule detection systems. The molecule detection systems can comprise a solid support comprising molecules associated with a site on the solid support such that the molecules are detected in aggregate, wherein the molecules comprise at least two different types of molecules, and a detector configured to detect the molecules associated with the site. In some embodiments, the molecules are attached at the site. In a preferred embodiment, the molecules comprise nucleic acids. In some embodiments of the molecule detection systems, a site comprises about 2 to about 1011 molecules, about 2 to about 1010 molecules, about 2 to about 109 molecules, about 2 to about 108 molecules, about 2 to about 107 molecules, about 2 to about 106 molecules, about 2 to about 105 molecules, about 2 to about 104 molecules. In some embodiments, the molecules are associated with the site. In other embodiments, the molecules are attached at the site. In certain embodiments, the molecules comprise nucleic acids. Some embodiments of the above-described molecule detection systems can further comprise a fluid handling system configured to apply fluid to the site. Other embodiments of the above-described molecule detection systems can further comprise a light source configured to provide an excitation beam to the site. Some embodiments of the above-described molecule detection systems can further comprise a first data processing module configured to estimate the fraction of different types of molecules at the site or the amount of signal corresponding to different types of molecules at the site. In some embodiments, the first data processing module is also used for determining the variation associated with the estimate. In other embodiments, the determining step is performed using a separate data processing module. In some embodiments of such systems, the systems can further comprise a second data processing module configured to calculate the amount of signal corresponding to different types of molecules at the site using the fraction estimate or to calculate the fraction of different types of molecules at the site using the signal estimate. In other embodiments of such systems, the systems can further comprise a third data processing module configured to iteratively update the fraction estimate and signal estimate. In some embodiments of the above-described molecule detection systems, the systems are configured to identify the nucleotide sequence of a target region of a nucleic acid. Additionally or alternatively, detection of a genetic biomarker can include methods of identifying a target region of a nucleic acid. The methods can comprise (a) associating a first subpopulation of nucleic acids with a site on a solid support, wherein nucleic acids of the first subpopulation comprise an identical target region; (b) associating a second subpopulation of nucleic acids with the site on the solid support, wherein nucleic acids of the second subpopulation comprise an identical target region that is a variant of the target region of the nucleic acids of the first subpopulation; (c) detecting a signal corresponding to one or more nucleotides of the target region of first subpopulation nucleic acids and one or more nucleotides of the variant of the target region of second subpopulation nucleic acids; (d) estimating the fraction of first subpopulation nucleic acids and second subpopulation nucleic acids associated with the site or estimating the amount of signal corresponding to first subpopulation nucleic acids and second subpopulation nucleic acids associated with the site; (e) calculating the amount of signal corresponding to first subpopulation nucleic acids and second subpopulation nucleic acids associated with the site using the fraction estimate, or calculating the fraction of first subpopulation nucleic acids and second subpopulation nucleic acids associated with the site using the signal estimate; and (f) iteratively updating the fraction estimate and signal estimate until the estimates converge, thereby identifying a target region of a nucleic acid. In some embodiments of the above-described methods, step (a) comprises attaching first subpopulation nucleic acids and second subpopulation nucleic acids to the solid support. In some embodiments of the above-described methods, step (d) comprises performing a principal component analysis (PCA). In some embodiments of the above-described methods, step (f) comprises performing a numerical optimization algorithm. In some such embodiments, the numerical optimization algorithm is based on iterative map search. In some other embodiments, the numerical optimization algorithm is based on Fienup's iteration map. In some embodiments of the above-described methods, sequence data is obtained from both first and second subpopulation nucleic acids. In some such embodiments, sequence data is obtained by a sequencing-by-synthesis process. In some embodiments, the sequencing-by-synthesis process comprises a pyrosequencing process. Additionally or alternatively, detection of a genetic biomarker can include methods for identifying a biosignature. The methods can comprise the steps of (a) providing samples obtained from a plurality of subjects, wherein the samples comprise molecules; (b) tagging molecules from the samples so as to identify the subject from which each sample originated; (c) associating molecules from the samples with a site on a solid support such that the molecules are detected in aggregate during a detection step, wherein the site comprises at least two different types of molecules; (d) obtaining a biosignature for molecules associated with the site by: i) detecting a signal corresponding to the aggregate of the molecules at the site, ii) estimating the fraction of different types of molecules at the site or the amount of signal corresponding to different types of molecules at the site, iii) calculating the amount of signal corresponding to different types of molecules at the site using the fraction estimate, or calculating the fraction of different types of molecules at the site using the signal estimate, and iv) iteratively updating the fraction estimate and signal estimate until the estimates converge, thereby obtaining a biosignature for molecules at the site; and (e) comparing the biosignature obtained in step (d) to a reference biosignature, thereby identifying the biosignature. In a preferred embodiment, the molecules are attached at the site. In a preferred embodiment of the above-described methods, the molecules comprise nucleic acids. In some such embodiments, the nucleic acids comprise a marker from a pathogen. In certain embodiments, the pathogen comprises a pathogen selected from the group consisting of a virus, a bacterium and a eukaryotic cell. In some embodiments, the eukaryotic cell can be a cancer cell. In some embodiments of the above-described methods, the sample comprises an abnormal cell type. In some embodiments of the above-described methods, the sample is obtained from a cancer patient. Also described is a solid support including a population of nucleic acids associated with a site on the solid support such that nucleic acids of the population of nucleic acids are detected in aggregate, the population of nucleic acids comprising a first subpopulation and a second subpopulation, wherein nucleic acids of the first subpopulation comprise an identical target region and nucleic acids of the second subpopulation comprise an identical region that is a variant of the target region. Additionally or alternatively, detection of a genetic biomarker can include beads comprising a first subpopulation of capture nucleic acids having a competitor molecule hybridized thereto and a second subpopulation of capture nucleic acids comprising a region that permits hybridization of a complementary molecule. Additionally or alternatively, detection of a genetic biomarker can include beads comprising capture nucleic acids hybridized with an amplified nucleic acid comprising a degenerate tag, the degenerate tag being hybridized to a capture nucleic acid. In some embodiments, the bead is present in a channel of a substrate. In other embodiments, the bead is present in a well of a multiwell substrate. In a preferred embodiment, the well is configured to hold a single bead having the amplified nucleic acids hybridized thereto.

In some embodiments, detection of a genetic biomarker (e.g., one or more genetic biomarkers) can include any of the variety of methods described in U.S. Pat. No. 9,163,283, which is hereby incorporated by reference in its entirety. For example, detection of a genetic biomarker can include compositions comprising a plurality of nucleic acids, each nucleic acid comprising an invariant sequence, a variable sequence and a label. Additionally or alternatively, detection of a genetic biomarker can include a method for decoding an array composition. The method includes providing an array composition comprising a substrate with a surface comprising discrete sites and a population of microspheres comprising first and second subpopulations, each subpopulation comprising an identifier nucleic acid sequence comprising a primer sequence and a decoder sequence. The method further comprises adding to the array a first set of combinatorial decoding probes comprising a priming sequence, at least one decoding nucleotide and a label, and detecting the presence of the label.

In some embodiments, detection of a genetic biomarker (e.g., one or more genetic biomarkers) can include any of the variety of methods described in U.S. Pat. No. 9,045,796, which is hereby incorporated by reference in its entirety. For example, detection of a genetic biomarker can include a method of detecting one or several typable loci contained within a given genome, where the method includes the steps of providing an amplified representative population of genome fragments having such typable loci, contacting the genome fragments with a plurality of nucleic acid probes having sequences corresponding to the typable loci under conditions wherein probe-fragment hybrids are formed; and detecting typable loci of the probe-fragment hybrids. In particular embodiments these nucleic acid probes are at most 125 nucleotides in length. However, probes having any of a variety of lengths or sequences can be used as set forth in more detail below. Additionally or alternatively, detection of a genetic biomarker can include a method of detecting typable loci of a genome including the steps of providing an amplified representative population of genome fragments that has such typable loci, contacting the genome fragments with a plurality of nucleic acid probes having sequences corresponding to the typable loci under conditions wherein probe-fragment hybrids are formed; and directly detecting typable loci of the probe-fragment hybrids. Additionally or alternatively, detection of a genetic biomarker can include a method of detecting typable loci of a genome including the steps of providing an amplified representative population of genome fragments having the typable loci; contacting the genome fragments with a plurality of immobilized nucleic acid probes having sequences corresponding to the typable loci under conditions wherein immobilized probe-fragment hybrids are formed; modifying the immobilized probe-fragment hybrids; and detecting a probe or fragment that has been modified, thereby detecting the typable loci of the genome. Additionally or alternatively, detection of a genetic biomarker can include a method, including the steps of (a) providing a plurality of genome fragments, wherein the plurality of genome fragments has at least 100 ug of DNA having a complexity of at least 1 Gigabases; (b) contacting the plurality of genome fragments with a plurality of different immobilized nucleic acid probes, wherein at least 500 of the different nucleic acid probes hybridize with genome fragments to form probe-fragment hybrids; and (c) detecting typable loci of the probe-fragment hybrids. Additionally or alternatively, detection of a genetic biomarker can include a method can also include the steps of (a) providing a plurality of genome fragments, wherein the plurality of genome fragments has a concentration of at least 1 ug/ul of DNA having a complexity of at least 1 Gigabases; (b) contacting the plurality of genome fragments with a plurality of different immobilized nucleic acid probes, wherein at least 500 of the different nucleic acid probes hybridize with genome fragments to form probe-fragment hybrids; and (c) detecting typable loci of the probe-fragment hybrids. Additionally or alternatively, detection of a genetic biomarker can include a method of amplifying genomic DNA, including the steps of providing isolated double stranded genomic DNA, producing nicked DNA by contacting the double stranded genomic DNA with a nicking agent, contacting this nicked DNA with a strand displacing polymerase and a plurality of primers, so as to amplify the genomic DNA. Additionally or alternatively, detection of a genetic biomarker can include a method for detecting typable loci of a genome. The method includes the steps of (a) in vitro transcribing a plurality of amplified gDNA fragments, thereby obtaining genomic RNA (gRNA) fragments; (b) hybridizing the gRNA fragments with a plurality of nucleic acid probes having sequences corresponding to the typable loci; and (c) detecting typable loci of the gRNA fragments that hybridize to the probes. Additionally or alternatively, detection of a genetic biomarker can include a method of producing a reduced complexity, locus-specific, amplified representative population of genome fragments. The method includes the steps of (a) replicating a native genome with a plurality of random primers, thereby producing an amplified representative population of genome fragments; (b) replicating a sub-population of the amplified representative population of genome fragments with a plurality of different locus-specific primers, thereby producing a locus-specific, amplified representative population of genome fragments; and (c) isolating the sub-population, thereby producing a reduced complexity, locus-specific, amplified representative population of genome fragments. Additionally or alternatively, detection of a genetic biomarker can include a method for inhibiting ectopic extension of probes in a primer extension assay. The method includes the steps of (a) contacting a plurality of probe nucleic acids with a plurality of target nucleic acids under conditions wherein probe-target hybrids are formed; (b) contacting the plurality of probe nucleic acids with an ectopic extension inhibitor under conditions wherein probe-ectopic extension inhibitor hybrids are formed; and (c) selectively modifying probes in the probe-target hybrids compared to probes in the probe-ectopic extension inhibitor hybrids. Additionally or alternatively, detection of a genetic biomarker can include a method including the steps of (a) contacting a plurality of genome fragments with a plurality of different immobilized nucleic acid probes under conditions wherein immobilized probe-fragment hybrids are formed; (b) modifying the immobilized probes while hybridized to the genome fragments, thereby forming modified immobilized probes; (c) removing said genome fragments from said probe-fragment hybrids; and (d) detecting the modified immobilized probes after removing the genome fragments, thereby detecting typable loci of the genome fragments. Additionally or alternatively, detection of a genetic biomarker can include a method including the steps of (a) representationally amplifying a native genome, wherein an amplified representative population of genome fragments having the typable loci is produced under isothermal conditions; (b) contacting the genome fragments with a plurality of nucleic acid probes having sequences corresponding to the typable loci under conditions wherein probe-fragment hybrids are formed; and (c) detecting typable loci of the probe-fragment hybrids.

In some embodiments, detection of a genetic biomarker (e.g., one or more genetic biomarkers) can include any of the variety of methods described in U.S. Pat. No. 8,765,419, which is hereby incorporated by reference in its entirety. For example, detection of a genetic biomarker can include methods and systems for detection of pyrophosphate, which can either be used alone or in connection with other technologies, such as pyrosequencing. In some embodiments, such methods and systems permit the detection of pyrophosphate with reduced background. Additionally or alternatively, detection of a genetic biomarker can include methods and systems for pyrosequencing of nucleic acids with reduced background. Additionally or alternatively, detection of a genetic biomarker can include methods of delaying pyrophosphate detection. The methods can include the steps of providing a pyrophosphate sequestering agent, generating pyrophosphate in the presence of the sequestering agent, whereby the pyrophosphate is reversibly sequestered, releasing the pyrophosphate from the sequestering agent and detecting the pyrophosphate. Additionally or alternatively, detection of a genetic biomarker can include methods for sequencing a nucleic acid. The method can include the steps of providing nucleotides or nucleotide analogs in the presence of a pyrophosphate sequestering agent and a pyrophosphate detecting agent, incorporating one or more of the nucleotides or nucleotide analogs into a polynucleotide so as to extend the polynucleotide in the presence of the pyrophosphate sequestering agent, thereby generating sequestered pyrophosphate, removing the unincorporated nucleotides or nucleotide analogs from the presence of the pyrophosphate detecting agent, releasing the pyrophosphate from the sequestering agent in the presence of the pyrophosphate detecting agent and detecting released pyrophosphate, wherein released pyrophosphate indicates that one or more nucleotides or nucleotide analogs have been incorporated into the polynucleotide. Additionally or alternatively, detection of a genetic biomarker can include methods of modulating the availability of free pyrophosphate during sequencing of a nucleic acid molecule. These methods can include the steps of combining nucleotides or nucleotide analogs with a nucleic acid template; incubating the nucleic acid template and the nucleotides or nucleotide analogs together with a polymerase and a pyrophosphate sequestering agent under conditions sufficient to form a polynucleotide complementary to all or a portion of the nucleic acid template, wherein pyrophosphate generated during the incubating is reversibly sequestered by the sequestering agent, removing from the nucleic acid template the nucleotides or nucleotide analogs that have not been incorporated into the polynucleotide and releasing the pyrophosphate from the pyrophosphate sequestering agent by providing a release reagent. Additionally or alternatively, detection of a genetic biomarker can include arrays comprising a solid support having a plurality of sites distributed thereon, wherein at least a portion of the sites comprise a template nucleic acid and a pyrophosphate sequestering agent capable of reversibly sequestering pyrophosphate. In certain aspects, the sites comprise wells. In certain aspects, the template nucleic acid is attached to a particle or bead within the wells. In certain aspects, the wells further comprise beads having a pyrophosphate detecting agent attached thereto. In certain aspects, the pyrophosphate sequestering agent is disposed between the template nucleic acid and the pyrophosphate detecting agent. In certain aspects, the pyrophosphate detecting agent comprises ATP sulfurylase and luciferase. In certain aspects, the wells further comprise packing beads. In some embodiments, pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or TiO2. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads. In addition to the foregoing, in some embodiments of the methods and arrays, pyrophosphate can be released from the sequestering agent by providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects, the release reagent comprises phosphate. In other aspects, the release reagent comprises a bisphosphonate. In certain aspects, the release reagent is the enzyme ATP sulfurylase. In this particular aspect, the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate. In some aspects, arrays can include sites that further comprise a polymerase and nucleotides or nucleotide analogs. In some embodiments, arrays can further comprises at least one electrode capable of producing an electric field in the presence of the sites. Additionally or alternatively, detection of a genetic biomarker can include methods of making an array. The methods can include the steps of providing a solid support having a plurality of sites distributed thereon and providing a template nucleic acid and a pyrophosphate sequestering agent capable of reversibly sequestering pyrophosphate to at least a portion of the sites. In certain aspects, the step of providing the template nucleic acid to the plurality of sites occurs prior to providing the pyrophosphate sequestering agent. In certain aspects, the step of providing the template nucleic acid to the plurality of sites occurs subsequent to providing the pyrophosphate sequestering agent. In certain aspects, the step of providing the template nucleic acid to the plurality of sites occurs at the same time as providing the pyrophosphate sequestering agent. In some embodiments, arrays manufactured according to the methods above can be employed in the sequencing and/or pyrophosphate sequestering and release processes. For example, in some embodiments, the pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or TiO2. In other aspects, the pyrophosphate sequestering agent comprises hydroxyapatite. In other aspects, the sequestering agent comprises an ammonium or substituted ammonium salt, or a resin or bead that contains such groups. In certain aspects of the above embodiments, the pyrophosphate sequestering agent comprises particles or beads. In addition to the foregoing, in some embodiments, arrays manufactured according to the above methods can be utilized in processes in which pyrophosphate can be released from the sequestering agent by providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects, the release reagent comprises phosphate. In other aspects, the release reagent comprises a bisphosphonate. In certain aspects, the release reagent is the enzyme ATP sulfurylase. In this particular aspect, the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

In some embodiments, detection of a genetic biomarker (e.g., one or more genetic biomarkers) can include any of the variety of methods described in U.S. Pat. No. 8,741,630, which is hereby incorporated by reference in its entirety. For example, detection of a genetic biomarker can include methods of detecting a target analyte in a biological sample, comprising providing a composite array comprising a substrate having a surface; a first and a second assay location on said surface, wherein said assay locations comprise a population of microspheres, and wherein said microspheres comprise bioactive agents; a physical partition separating said first assay location from said second assay location; adding said biological sample to said first assay location under conditions sufficient to allow said target analyte to bind to said bioactive agents; and detecting the binding of said bioactive agents to said target analyte. In more specific embodiments, the binding of the bioactive agents to the target analyte can be detected by a change in an optical signature of the microspheres. Target analytes and bioactive agents can include a nucleic acid, for example. In some embodiments, the methods can further comprise detecting a target analyte in a second biological sample by adding said second biological sample to said second assay location and thereafter detecting the binding of said bioactive agents to said target analyte. In certain aspects, the substrate can include a microscope slide. Further methods include detecting a target nucleic acid in a biological sample, wherein said target nucleic acid includes one or more single nucleotide polymorphisms (SNPs) at one or more predetermined positions, comprising providing a composite array comprising a substrate having a surface; a population of microspheres, wherein said microspheres are linked to capture probes configured to bind to said target nucleic acid at said one or more predetermined positions; a first and second assay location on said surface, wherein said assay locations comprise said population of microspheres; a physical partition separating said first assay location from said second assay location; adding said biological sample to said first assay location under conditions sufficient to allow said target nucleic acid to bind to said capture probes; and detecting the binding of said target nucleic acid to said capture probes. Additionally or alternatively, detection of a genetic biomarker can include array compositions comprising a rigid support; a molded layer with at least a first assay location comprising discrete sites, where the molded layer is adhered to the rigid support; a layer of bonding agent adhering the rigid support to the molded layer; and a population of microspheres comprising at least a first and a second subpopulation, where the first subpopulation comprises a first bioactive agent and the second subpopulation comprises a second bioactive agent where the microspheres are randomly distributed on the sites. Additionally or alternatively, detection of a genetic biomarker can include a method for making an array composition containing at least a first assay location having discrete sites comprising the steps of contacting a surface of a template structure, the surface comprising one or more sets of projections, with a moldable material; removing the moldable material from the surface of the template structure, whereby the removed moldable material forms a molded layer with at least a first assay location comprising discrete sites; adhering the molded layer to a rigid support; and randomly distributing microspheres on the molded layer such that individual discrete sites comprise microspheres, where the microspheres comprise at least a first and a second subpopulation, where the first subpopulation comprises a first bioactive agent and the second subpopulation comprises a second bioactive agent.

In some embodiments, detection of a genetic biomarker (e.g., one or more genetic biomarkers) can include any of the variety of methods described in U.S. Pat. No. 7,901,897, which is hereby incorporated by reference in its entirety. For example, detection of a genetic biomarker can include composite array compositions comprising a first substrate with a surface comprising a plurality of assay locations, each assay location comprising a plurality of discrete sites. The substrate further comprises a population of microspheres comprising at least a first and a second subpopulation, wherein each subpopulation comprises a bioactive agent. The microspheres are distributed on each of the assay locations. Additionally or alternatively, detection of a genetic biomarker can include composite array compositions comprising a first substrate with a surface comprising a plurality of assay locations and a second substrate comprising a plurality of array locations, each array location comprising discrete sites. The compositions further comprise a population of microspheres comprising at least a first and a second subpopulation, wherein each subpopulation comprises a bioactive agent. The microspheres are distributed on each of the array locations. Additionally or alternatively, detection of a genetic biomarker can include methods of decoding an array composition comprising providing an array composition as outlined above, and adding a plurality of decoding binding ligands to the composite array composition to identify the location of at least a plurality of the bioactive agents. Additionally or alternatively, detection of a genetic biomarker can include methods of determining the presence of one or more target analytes in one or more samples comprising contacting the sample with the composition, and determining the presence or absence of said target analyte. Additionally or alternatively, detection of a genetic biomarker can include a hybridization chamber. The hybridization chamber includes a base plate and a lid. A sealant is localized between the lid and base plate to provide for an airtight seal. When a two-component array system is used, the chamber also includes component ports in the lid to immobilize the array components. That is, array components are inserted through the port in the lid. The ports may include seals so that an airtight seal is maintained. The chamber also may include clamps and alignment pins. Additionally or alternatively, detection of a genetic biomarker can include a hybridization chamber wherein the base plate contains holes. The holes may be in a microplate array format. In one embodiment, at least two holes are joined by a channel. In one embodiment, a flexible membrane is placed on the base plate. When pressure i.e. a vacuum, is applied to the membrane, wells form in the membrane at the location of the holes in the base plate. The apparatus also includes a pneumatic device for the delivery of a vacuum or positive pressure to the membrane. Additionally or alternatively, detection of a genetic biomarker can include a method of mixing samples in an array formal. The method includes providing a vacuum to the membrane such that wells are formed. A solution is then applied to the membrane such that at least one of the wells is filled with liquid. Subsequently, the vacuum is applied intermittently to the membrane, which results in mixing of the liquid. Additionally or alternatively, detection of a genetic biomarker can include an apparatus comprising a hybridization chamber and any of the composite array compositions. Additionally or alternatively, detection of a genetic biomarker can include performing methods of decoding an array composition in a hybridization chamber. Additionally or alternatively, detection of a genetic biomarker can include performing methods of determining the presence of one or more target analytes in one or more samples in a hybridization chamber.

In some embodiments, detection of a genetic biomarker (e.g., one or more genetic biomarkers) can include any of the variety of methods described in U.S. Pat. No. 8,288,103, which is hereby incorporated by reference in its entirety. For example, detection of a genetic biomarker can include a method of detecting target sequences in a sample comprising providing a first solid support comprising at least a first and a second target sequence, contacting the first and second target sequences with first and second probes, respectively, wherein each of the first and second probes comprise a first universal priming site, a target specific domain substantially complementary to at least a portion of the target sequence, to form first and second hybridization complexes, respectively, removing unhybridized probes, contacting the first and second hybridization complexes with a first enzyme to form modified first and second probes, respectively contacting the modified first and second probes with at least a first primer that hybridizes to the universal priming site NTPs, and an extension enzyme, wherein the first and second modified probes are amplified to form first and second amplicons, respectively, and detecting the amplicons. Additionally or alternatively, detection of a genetic biomarker can include a method of detecting target sequences in a sample comprising providing a first solid support comprising at least a first and a second target sequence, contacting the first and second target sequences with first and second probes, respectively, wherein each of the first and second probes comprise a first universal priming site, a target specific domain substantially complementary to at least a portion of the target sequence, to form first and second hybridization complexes, respectively, removing unhybridized probes, contacting the first and second probes with at least a first universal primer that hybridizes to the universal priming site, NTPs and an extension enzyme, wherein the first and second probes are extended to form first and second modified probes, respectively, contacting the first and second modified probes with at least third and fourth probes, respectively, wherein the modified first and second probes comprise a detection position, the third and fourth probes each comprise an interrogation position, and a second enzyme, wherein the second enzyme only modifies the third and fourth probes if there is perfect complementarity between the bases at the interrogation position and the detection position, forming third and fourth modified probes, and detecting the third and fourth modified probes. Additionally or alternatively, detection of a genetic biomarker can include a method comprising providing a plurality of target nucleic acid sequences each comprising from 3' to 5' a first, second and third target domain, the first target domain comprising a detection position, the second target domain being at least one nucleotide contacting the target nucleic acid sequences with sets of probes for each target sequence, each set comprising a first probe comprising from 5' to 3' a first domain comprising a first universal priming sequence, and a second domain comprising a sequence substantially complementary to the first target domain of a target sequence, and an interrogation position within the 3' four terminal bases, a second probe comprising a first domain comprising a sequence substantially complementary to the third target domain of a target sequence, to form a set of first hybridization complexes, contacting the first hybridization complexes with an extension enzyme and dNTPs, under conditions whereby if the base at the interrogation positions is perfectly complementary with the bases at the detection positions, extension of the first probes occurs through the second target domains to form second hybridization complexes, contacting the second hybridization complexes with a ligase to ligate the extended first probes to the second probes to form amplification templates. Additionally or alternatively, detection of a genetic biomarker can include a multiplex reaction method comprising providing a sample comprising at least first and second targets hybridizing the first and second targets with first and second probes, respectively forming first and second hybridization complexes, respectively, immobilizing the first and second hybridization complexes, washing to remove unhybridized nucleic acids, contacting the first and second hybridization complexes with an enzyme, whereby the first and second probes are modified forming modified first and second probes, respectively, whereby the modified first and second probes are modified to contain first and second interrogation nucleotides that are complementary to first and second detection nucleotides in the first and second targets, respectively, contacting the modified first and second probes with first and second allele specific primers, respectively, whereby the first and second allele specific primers hybridize to the modified first and second probes, respectively, 5' to the first and second interrogation nucleotides, dNTPs, polymerase, whereby the first and second allele specific primers are modified when a target domain of the allele specific primers is perfectly complementary to the modified target probes to form modified first and second allele specific probes, amplifying the modified first and second allele specific probes to form first and second amplicons, and detecting the first and second amplicons. Additionally or alternatively, detection of a genetic biomarker can include a method comprising providing a plurality of target nucleic acid sequences each comprising from 3' to 5' a first, second and third target domain, the first target domain comprising a detection position, the second target domain being at least one nucleotide, contacting the target nucleic acid sequences with sets of probes for each target sequence, each set comprising: a first probe comprising from 5' to 3', a first domain comprising a first universal priming sequence, and a second domain comprising a sequence substantially complementary to the first target domain of a target sequence, and an interrogation position within the 3' four terminal bases, a second probe comprising a first domain comprising a sequence substantially complementary to the third target domain of a target sequence, to form a set of first hybridization complexes, contacting the first hybridization complexes with at least a first universal primer that hybridize to the first universal priming sequence, an extension enzyme and dNTPs, under conditions whereby if the base at the interrogation positions are perfectly complementary with the bases at the detection positions, extension of the first probes occurs through the second target domains to form second hybridization complexes, contacting the second hybridization complexes with a ligase to ligate the extended first probes to the second probes to form amplification templates.

In some embodiments, detection of a genetic biomarker (e.g., one or more genetic biomarkers) can include any of the variety of methods described in U.S. Pat. No. 7,899,626, which is hereby incorporated by reference in its entirety. For example, detection of a genetic biomarker can include a method of measuring the methylation level of DNA. The method can include the steps of providing data representing the standard deviation of methylation measurements of DNA, determining the methylation level of at least one locus in a sample DNA and comparing the methylation level of the at least one locus to the data to determine the standard deviation of the measurement. Additionally or alternatively, detection of a genetic biomarker can include a method of comparing the methylation level of DNA samples. The method can include the steps of providing data representing the standard deviation of methylation measurements of DNA; determining the methylation level of at least one locus in a first sample DNA; determining the methylation level of the at least one locus in a second sample DNA; identifying the standard deviations of the methylation level of the at least one locus in the first sample DNA and in the second sample DNA from the data; and determining whether the methylation level of the at least one locus in the first sample DNA and in the second sample DNA are the same or different based on the standard deviations. Additionally or alternatively, detection of a genetic biomarker can include a DNA methylation level detection system, including a scanner for reading methylation levels for a plurality of loci in a sample DNA and a first module configured to compare the methylation levels against data representing the standard deviation of methylation measurements of DNA. Some embodiments relate to a method of measuring the methylation level of DNA including providing data representing the standard deviation of methylation measurements of DNA; determining the methylation level of at least one locus in a sample DNA; and comparing the methylation level of said at least one locus to said data to determine the standard deviation of said measurement. In some embodiments, at least one locus comprises a plurality of loci. In some embodiments, the methylation levels are determined using an array. In some embodiments, the plurality of loci comprises at least 100 loci measured simultaneously on said array. In some embodiments, the data correlates standard deviation of methylation level as a function of methylation level. In some embodiments, the data comprises different standard deviation values for different methylation levels. In some embodiments, the data comprises said different standard deviation values occurring along a parabola when correlated to said different methylation levels. In some embodiments, the data is produced by creating a training set comprising mixtures of DNA with varying methylation levels, wherein said training set comprises replicates of said mixtures; determining the methylation level of at least one locus in said mixtures of said training set; determining standard deviation values for said methylation levels determined for said replicates of said training set; and correlating said standard deviation values and said methylation levels determined for said training set. In some embodiments, the mixtures of the training set comprise different ratios of genomic DNA from a cell population with highly methylated DNA and a cell population with minimally methylated DNA. In some embodiments, the methylation levels for the mixtures of said training set vary from 0 to 1. Some embodiments further include identifying at least three regions from 0 to 1, determining the median of the methylation levels for each of the regions and fitting a parabola to said median for each of said regions. In some embodiments, the standard deviation values comprise the 95th percentile standard deviation values. Some embodiments further include the steps of determining the methylation level of said at least one locus in a second sample DNA; identifying the standard deviations of said methylation level of said at least one locus in said sample DNA and in said second sample DNA from said data; and determining whether said methylation level of said at least one locus in said first sample DNA and in said second sample DNA are the same or different based on said standard deviations. Some embodiments relate to a DNA methylation level detection system including a scanner for reading methylation levels for a plurality of loci in a sample DNA; and a first module configured to compare said methylation levels against data representing the standard deviation of methylation measurements of DNA. In some embodiments, the methylation levels are determined using an array. In some embodiments, the plurality of loci comprises at least 100 loci measured simultaneously on said array. In some embodiments, the data correlates standard deviation of methylation level as a function of methylation level. In some embodiments, the data comprises different standard deviation values for different methylation levels. In some embodiments, the data comprises said different standard deviation values occurring along a parabola when correlated to said different methylation levels. In some embodiments, the data is produced by creating a training set comprising mixtures of DNA with varying methylation levels, wherein said training set comprises replicates of said mixtures; determining the methylation level of at least one locus in said mixtures of said training set; determining standard deviation values for said methylation levels determined for said replicates of said training set; and correlating said standard deviation values and said methylation levels determined for said training set. Some embodiments relate to a method of comparing the methylation level of DNA samples including providing data representing the standard deviation of methylation measurements of DNA; determining the methylation level of at least one locus in a first sample DNA; determining the methylation level of said at least one locus in a second sample DNA; identifying the standard deviations of said methylation level of said at least one locus in said first sample DNA and in said second sample DNA from said data; and determining whether said methylation level of said at least one locus in said first sample DNA and in said second sample DNA are the same or different based on said standard deviations.

In some embodiments, detection of a genetic biomarker (e.g., one or more genetic biomarkers) can include any of the variety of methods described in U.S. Pat. No. 7,776,531, which is hereby incorporated by reference in its entirety. For example, detection of a genetic biomarker can include a probe composition, including (a) a substrate; (b) a probe molecule attached to the substrate; and (c) a stabilization polymer layer on the substrate, wherein said stabilization polymer layer coats the probe molecule. Additionally or alternatively, detection of a genetic biomarker can include a method of making a probe composition. The method includes the steps of (a) providing a substrate having an attached biopolymer probe; and (b) contacting the substrate with a stabilization polymer. Additionally or alternatively, detection of a genetic biomarker can include a method of shipping a solid-phase probe. The method includes the steps of (a) providing a substrate having an attached probe molecule, and further having a stabilization polymer layer; (b) placing the substrate in a package; and (c) shipping the package to a remote location.

In some embodiments, detection of a genetic biomarker (e.g., one or more genetic biomarkers) can include any of the variety of methods described in U.S. Pat. No. 7,499,806, which is hereby incorporated by reference in its entirety. For example, detection of a genetic biomarker can include array compositions comprising a substrate with a surface comprising discrete sites, at least one fiducial, and a population of microspheres comprising at least a first and a second subpopulation. Each subpopulation comprises a bioactive agent, and the microspheres are distributed on said surface. Each subpopulation may optionally comprise a unique optical signature, an identifier binding ligand that will bind a decoder binding ligand such that the identification of the bioactive agent can be elucidated, or both. Additionally or alternatively, detection of a genetic biomarker can include compositions comprising a computer readable memory to direct a computer to function in a specified manner. The computer readable memory comprises an acquisition module for receiving a data image of a random array comprising a plurality of discrete sites, a registration module for registering a data image, and a comparison module for comparing registered data images. Each module comprises computer code for carrying out its function. The registration module may utilize any number of fiducials, including a fiducial fiber when the substrate comprises a fiber optic bundle, a fiducial microsphere, or a fiducial template generated from the random array. Additionally or alternatively, detection of a genetic biomarker can include methods of making the array compositions comprising forming a surface comprising individual sites on a substrate, distributing microspheres on the surface such that the individual sites contain microspheres, and incorporating at least one fiducial onto the surface. When the array has complete rotational freedom, at least two fiducials are preferred in the array to allow for correction of rotation. Additionally or alternatively, detection of a genetic biomarker can include methods for comparing separate data images of a random array. The methods comprise using a computer system to register a first data image of the random array to produce a registered first data image, using the computer system to register a second data image of the random array to produce a registered second data image, and comparing the first and the second registered data images to determine any differences between them. Additionally or alternatively, detection of a genetic biomarker can include methods of decoding a random array composition comprising providing a random array composition. A first plurality of decoding binding ligands is added to the array composition and a first data image is created. A fiducial is used to generate a first registered data image. A second plurality of decoding binding ligands is added to the array composition and a second data image is created. The fiducial is used to generate a second registered data image. A computer system is used to compare the first and the second registered data image to identify the location of at least two bioactive agents. Additionally or alternatively, detection of a genetic biomarker can include methods of determining the presence of a target analyte in a sample. The methods comprise acquiring a first data image of a random array composition, and registering the first data image to create a registered first data image. The sample is then added to the random array and a second data image is acquired from the array. The second data image is registered to create a registered second data image. Then the first and the second registered data images are compared to determine the presence or absence of the target analyte. Optionally, the data acquisition may be at different wavelengths. Additionally or alternatively, detection of a genetic biomarker can include methods for preprocessing or prefiltering signal data comprising acquiring a data image from an array, and determining the similarity of a first signal from at least one array site to a reference signal to determine whether the site comprises a candidate bead. Additionally or alternatively, detection of a genetic biomarker can include methods for registering an analytical image of a microsphere array comprising providing a hybridization intensity image. After the microsphere array is decoded, a registration grid is computed based on known locations of bioactive agents on the microspheres obtained from the decoding step. The sample is added to the microsphere array and a hybridization intensity image is acquired from the array. Bright bead types are distributed throughout the array to serve as fiducials. The registration grid is overlaid on to the image and then the registration grid is aligned so that the identity of the signal intensity at each grid location for each bead type within the array is ascertained. Once the correct position of the grid is obtained, each core is assigned a number so that the correct placement of the grid can be made for further sequential images.

In some embodiments, detection of a genetic biomarker (e.g., one or more genetic biomarkers) can include any of the variety of methods described in U.S. Pat. No. 6,942,968, which is hereby incorporated by reference in its entirety. For example, detection of a genetic biomarker can include a composition that includes a substrate with a surface comprising discrete sites, a reflective coating on the surface, and a population of microspheres distributed on the substrate. The microspheres comprise at least a first and a second subpopulation. Generally, at least one subpopulation comprises a bioactive agent. Additionally or alternatively, detection of a genetic biomarker can include a composition wherein the substrate comprises a first and a second surface, wherein the first surface comprises the discrete sites, and the reflective coating is on the second surface. The population of microspheres are distributed on the first surface. Additionally or alternatively, detection of a genetic biomarker can include a method of making a reflective array. The method includes providing a substrate with a surface comprising discrete sites, applying to the surface a coating of reflective material and distributing microspheres on the surface. Additionally or alternatively, detection of a genetic biomarker can include a method, wherein the substrate comprises a first and a second surface, wherein the first surface comprises discrete sites, the reflective material is on the second surface and the microspheres are distributed on the first surface. Additionally or alternatively, detection of a genetic biomarker can include a method comprising providing a preformed unitary fiber optic bundle comprising a proximal and a distal end, the distal end comprising plurality of discrete sites comprising a population of microspheres, the population comprising at least first and second subpopulations, and imaging the fiber optic bundle from the distal end. A reflective coating may be applied to either the distal end or the proximal end of the fiber optic bundle. Additionally or alternatively, detection of a genetic biomarker can include an array composition comprising a substrate with a surface comprising discrete sites comprising alternatively shaped wells. The wells may contain a cross section that is shaped as a square, a hexagon, a star, a triangle, a pentagon or an octagon. Additionally or alternatively, detection of a genetic biomarker can include method comprising providing a substrate with a plurality of discrete sites, the sites comprising alternatively shaped wells and a population of microspheres, the population comprising at least first and second subpopulations, and imaging the substrate. Additionally or alternatively, detection of a genetic biomarker can include an array composition comprising a substrate with a surface comprising discrete sites and a population of microspheres distributed on the substrate, wherein the microspheres comprise a bioactive agent and a signal transducer element. Additionally or alternatively, detection of a genetic biomarker can include a method of detecting a non-labeled target analyte in a sample comprising providing a substrate with a plurality of discrete sites, distributing on the sites a population of microspheres comprising a bioactive agent and a signal transducer element, contacting the substrate with the sample, whereby upon binding of the target analyte to the bioactive agent, a signal from the signal transducer element is altered as an indication of the presence of the target analyte. Additionally or alternatively, detection of a genetic biomarker can include a method of detecting a chiral molecule in a sample comprising providing a substrate with a surface comprising at least first and second discrete sites at least first and second bioactive agents attached to the first and second discrete sites respectively, contacting the substrate with the sample, illuminating the substrate with polarized light, and detecting rotation of the light in at least one of the first and second discrete sites as an indication of the presence of the chiral molecule. Additionally or alternatively, detection of a genetic biomarker can include a method of determining the location of a microsphere in an array comprising providing a substrate with a first surface comprising at least a first and a second discrete site, wherein the first discrete site comprises a microsphere, but the second discrete site does not comprising a microsphere, illuminating the substrate and detecting illumination of the substrate, whereby reduced illumination at the first discrete site relative to the second discrete site provides an indication of the presence of the first microsphere in the first discrete site. Additionally or alternatively, detection of a genetic biomarker can include a method of increasing signal output from an array comprising providing a substrate with a surface comprising at least first and second discrete sites and at least first and second labels attached to the first and second discrete sites respectively, cooling the substrate to at least below room temperature and detecting a signal from the first and second labels, whereby the signal is increased relative to a signal obtained from a substrate that is not cooled. Additionally or alternatively, detection of a genetic biomarker can include a method for background signal subtraction in an array comprising providing a substrate with a surface comprising at least first and second discrete sites and at least first and second labels attached to the first and second discrete sites respectively, detecting the signal from the first and second discrete sites in a plurality of different emissions, and subtracting the lowest signal from each of the first and second discrete sites from the remaining signals from the first and second discrete sites, respectively. Additionally or alternatively, detection of a genetic biomarker can include a method of correcting image non-uniformity comprising providing a substrate with a surface comprising at least first and second discrete sites, at least first and second labels attached to the first and second discrete sites respectively and at least a first internal reference point of known signal intensity, detecting a first and second signal from the first and second labels, respectively, detecting a signal from the internal reference point, and determining the variation between the signal from the internal reference point and the known signal intensity of the internal reference point as an indication of said image non-uniformity. Additionally or alternatively, detection of a genetic biomarker can include a method of detecting a target analyte in a sample comprising providing an array comprising a substrate with a surface comprising discrete sites, a reflective coating on said surface, and a population of microspheres distributed on the substrate. The microspheres comprise at least a first and a second subpopulation each comprising a different bioactive agent. The method further includes contacting the array with the sample, such that the target analyte binds to at least one of the bioactive agents and detecting the presence of the target analyte. In a preferred embodiment, the target analyte is labeled. Additionally or alternatively, detection of a genetic biomarker can include a method of detecting a target analyte in a sample comprising providing an array comprising a substrate with a surface comprising discrete sites comprising alternatively shaped wells and a population of microspheres distributed on the substrate. The microspheres comprise at least a first and a second subpopulation each comprising a different bioactive agent. The method further includes contacting the array with the sample, such that the target analyte binds to at least one of the bioactive agents and detecting the presence of the target analyte. Additionally or alternatively, detection of a genetic biomarker can include a method of detecting a target analyte in a sample comprising providing a substrate with a surface comprising at least first and second discrete sites and a population of microspheres distributed on the substrate, wherein the microspheres comprise at least a first and a second subpopulation each comprising a different bioactive agent, contacting the substrate with the sample, such that the target analyte binds to at least one of the bioactive agents. In some embodiments, the method includes cooling the substrate to at least below room temperature and detecting a signal, whereby the signal is increased relative to a signal obtained from a substrate that is not cooled.

In some embodiments, detection of a genetic biomarker (e.g., one or more genetic biomarkers) can include any of the variety of methods described in U.S. Pat. No. 6,890,764, which is hereby incorporated by reference in its entirety. For example, detection of a genetic biomarker can include compositions comprising a substrate with a surface comprising discrete sites, and a population of microspheres distributed on the sites. At least one of the microspheres comprises a nanocrystal. The nanocrystal can be embedded in the microsphere, for example using the sol-gel polymerization process, or it can be attached to the microsphere. The microspheres optionally comprise bioactive agents and/or identifier binding ligands. In an additional aspect, the population of microspheres comprises at least a first and a second subpopulation comprising a first and a second bioactive agent, respectively, and a first and a second optical signature, respectively, capable of identifying each bioactive agent. At least one of the optical signatures comprises a nanocrystal. Additionally or alternatively, detection of a genetic biomarker can include methods of making a composition comprising forming a surface comprising individual sites on a substrate and distributing microspheres on the surface such that the individual sites contain microspheres. The microspheres comprise an optical signature, and at least one optical signature comprises at least one nanocrystal. Additionally or alternatively, detection of a genetic biomarker can include a method of determining the presence of a target analyte in a sample comprising contacting the sample with a composition. The composition comprises a substrate with a surface comprising discrete sites and a population of microspheres comprising at least a first and a second subpopulation each comprising a bioactive agent and an optical signature capable of identifying the bioactive agent. The microspheres are distributed on the surface such that the discrete sites contain microspheres and wherein at least one of the optical signatures comprises at least one nanocrystal. The presence or absence of the target analyte is then determined. Additionally or alternatively, detection of a genetic biomarker can include methods of making a composition comprising adhering nanocrystals to porous silica, and sealing the pores of the silica using the sol-gel polymerization process.

In some embodiments, detection of a genetic biomarker (e.g., one or more genetic biomarkers) can include any of the variety of methods described in U.S. Patent Application Publication No. 2018/0201992, which is hereby incorporated by reference in its entirety. For example, detection of a genetic biomarker can include methods, apparatus, systems, and computer program products for determining nucleic acid fragment sequences using unique molecular indices (UMIs). In some implementations, the UMIs includes nonrandom UMIs (NRUMIs) or variable-length, nonrandom unique molecular indices (vNRUMIs). Additionally or alternatively, detection of a genetic biomarker can include methods for sequencing nucleic acid molecules from a sample. The method includes: (a) applying adapters to DNA fragments in the sample to obtain DNA-adapter products, wherein each adapter includes a nonrandom unique molecular index, and wherein nonrandom unique molecular indices of the adapters have at least two different molecular lengths and form a set of variable-length, nonrandom unique molecular indices (vNRUMIs); (b) amplifying the DNA-adapter products to obtain a plurality of amplified polynucleotides; (c) sequencing the plurality of amplified polynucleotides, thereby obtaining a plurality of reads associated with the set of vNRUMIs; (d) identifying, among the plurality of reads, reads associated with a same variable-length, nonrandom unique molecular index (vNRUMI); and (e) determining a sequence of a DNA fragment in the sample using the reads associated with the same vNRUMI. In some implementations, identifying the reads associated with the same vNRUMI includes obtaining, for each read of the plurality of reads, alignment scores with respect to the set of vNRUMIs, each alignment score indicating similarity between a subsequence of a read and a vNRUMI, wherein the subsequence is in a region of the read in which nucleotides derived from the vNRUMI are likely located. In some implementations, the alignment scores are based on matches of nucleotides and edits of nucleotides between the subsequence of the read and the vNRUMI. In some implementations, the edits of nucleotides include substitutions, additions, and deletions of nucleotides. In some implementations, each alignment score penalizes mismatches at the beginning of a sequence but does not penalize mismatches at the end of the sequence. In some implementations, obtaining an alignment score between a read and a vNRUMI includes: (a) calculating an alignment score between the vNRUMI and each one of all possible prefix sequences of the subsequence of the read; (b) calculating an alignment score between the subsequence of the read and each one of all possible prefix sequences of the vNRUMI; and (c) obtaining a largest alignment score among the alignment scores calculated in (a) and (b) as the alignment score between the read and the vNRUMI. In some implementations, the subsequence has a length that equals to a length of the longest vNRUMI in the set of vNRUMIs. In some implementations, identifying the reads associated with the same vNRUMI in (d) further includes: selecting, for each read of the plurality of reads, at least one vNRUMI from the set of vNRUMIs based on the alignment scores; and associating each read of the plurality of reads with the at least one vNRUMI selected for the read. In some implementations, selecting the at least one vNRUMI from the set of vNRUMIs includes selecting a vNRUMI having a highest alignment score among the set of vNRUMIs. In some implementations, the at least one vNRUMI includes two or more vNRUMIs. In some implementations, the method further includes selecting one of the two or more vNRUMI as the same vNRUMI of (d) and (e). In some implementations, the adapters applied in (a) are obtained by: (i) providing a set of oligonucleotide sequences having at least two different molecular lengths; (ii) selecting a subset of oligonucleotide sequences from the set of oligonucleotide sequences, all edit distances between oligonucleotide sequences of the subset of oligonucleotide sequences meeting a threshold value, the subset of oligonucleotide sequences forming the set of vNRUMIs; and (iii) synthesizing the adapters each including a double-stranded hybridized region, a single-stranded 5' arm, a single-stranded 3' arm, and at least one vNRUMI of the set of vNRUMIs. In some implementations, the threshold value is 3. In some implementations, the set of vNRUMIs include vNRUMIs of 6 nucleotides and vNRUMIs of 7 nucleotides. In some implementations, the determining of (e) includes collapsing reads associated with the same vNRUMI into a group to obtain a consensus nucleotide sequence for the sequence of the DNA fragment in the sample. In some implementations, the consensus nucleotide sequence is obtained based partly on quality scores of the reads. In some implementations, the determining of (e) includes: identifying, among the reads associated with the same vNRUMI, reads having a same read position or similar read positions in a reference sequence, and determining the sequence of the DNA fragment using reads that (i) are associated with the same vNRUMI and (ii) have the same read position or similar read positions in the reference sequence. In some implementations, the set of vNRUMIs includes no more than about 10,000 different vNRUMIs. In some implementations, the set of vNRUMIs includes no more than about 1,000 different vNRUMIs. In some implementations, the set of vNRUMIs includes no more than about 200 different vNRUMIs. In some implementations, applying adapters to the DNA fragments in the sample includes applying adapters to both ends of the DNA fragments in the sample. Additionally or alternatively, detection of a genetic biomarker can include methods for preparing sequencing adapters, the methods including: (a) providing a set of oligonucleotide sequences having at least two different molecular lengths; (b) selecting a subset of oligonucleotide sequences from the set of oligonucleotide sequences, all edit distances between oligonucleotide sequences of the subset of oligonucleotide sequences meeting a threshold value, the subset of oligonucleotide sequences forming a set of variable-length, nonrandom unique molecular indexes (vNRUMIs); and (c) synthesizing a plurality of sequencing adapters, wherein each sequencing adapter includes a double-stranded hybridized region, a single-stranded 5' arm, a single-stranded 3' arm, and at least one vNRUMI of the set of vNRUMIs. In some implementations, (b) includes: (i) selecting an oligonucleotide sequence from the set of oligonucleotide sequences; (ii) adding the selected oligonucleotide to an expanding set of oligonucleotide sequences and removing the selected oligonucleotide from the set of oligonucleotide sequences to obtain a reduced set of oligonucleotide sequences; (iii) selecting an instant oligonucleotide sequence from the reduced set that maximizes a distance function, wherein the distance function is a minimal edit distance between the instant oligonucleotide sequence and any oligonucleotide sequences in the expanding set, and wherein the distance function meeting the threshold value; (iv) adding the instant oligonucleotide to the expanding set and removing the instant oligonucleotide from the reduced set; (v) repeating (iii) and (iv) one or more times; and (vi) providing the expanding set as the subset of oligonucleotide sequences forming the set of vNRUMIs. Additionally or alternatively, detection of a genetic biomarker can include a method for sequencing nucleic acid molecules from a sample, including (a) applying adapters to DNA fragments in the sample to obtain DNA-adapter products, wherein each adapter includes a nonrandom unique molecular index, and wherein nonrandom unique molecular indices of the adapters have at least two different molecular lengths and form a set of variable-length, nonrandom unique molecular indices (vNRUMIs); (b) amplifying the DNA-adapter products to obtain a plurality of amplified polynucleotides; (c) sequencing the plurality of amplified polynucleotides, thereby obtaining a plurality of reads associated with the set of vNRUMIs; and (d) identifying, among the plurality of reads, reads associated with a same variable-length, nonrandom unique molecular index (vNRUMI). Additionally or alternatively, detection of a genetic biomarker can include a method for sequencing nucleic acid molecules from a sample, including (a) applying adapters to DNA fragments in the sample to obtain DNA-adapter products, wherein each adapter includes a unique molecular index (UMI), and wherein unique molecular indices (UMIs) of the adapters have at least two different molecular lengths and form a set of variable-length unique molecular indices (vUMIs); (b) amplifying the DNA-adapter products to obtain a plurality of amplified polynucleotides; (c) sequencing the plurality of amplified polynucleotides, thereby obtaining a plurality of reads associated with the set of vUMIs; and (d) identifying, among the plurality of reads, reads associated with a same variable-length unique molecular index (vUMI). Additionally or alternatively, detection of a genetic biomarker can include a method for sequencing nucleic acid molecules from a sample, including (a) applying adapters to DNA fragments in the sample to obtain DNA-adapter products, wherein each adapter includes a unique molecular index (UMI) in a set of unique molecular indices (UMIs); (b) amplifying the DNA-adapter products to obtain a plurality of amplified polynucleotides; (c) sequencing the plurality of amplified polynucleotides, thereby obtaining a plurality of reads associated with the set of UMIs; (d) obtaining, for each read of the plurality of reads, alignment scores with respect to the set of UMIs, each alignment score indicating similarity between a subsequence of a read and a UMI; (e) identifying, among the plurality of reads, reads associated with a same UMI using the alignment scores; and (e) determining a sequence of a DNA fragment in the sample using the reads associated with the same UMI. Additionally or alternatively, detection of a genetic biomarker can include a system, apparatus, and computer program products for determining DNA fragment sequences implementing the methods. Additionally or alternatively, detection of a genetic biomarker can include a computer program product including a non-transitory machine readable medium storing program code that, when executed by one or more processors of a computer system, causes the computer system to implement a method for determining sequence information of a sequence of interest in a sample using unique molecular indices (UMIs). The program code includes instructions to perform the methods above.

In some embodiments, detection of a genetic biomarker (e.g., one or more genetic biomarkers) can include any of the variety of methods described in U.S. Patent Application Publication No. 2018/0201974, which is hereby incorporated by reference in its entirety. For example, detection of a genetic biomarker can include methods and compositions for targeted amplification of DNA and sample identification. Additionally or alternatively, detection of a genetic biomarker can include methods for obtaining nucleic acid sequence information from a biological sample comprising: (a) providing a biological sample comprising different target nucleic acids; (b) contacting the biological sample with a plurality of different probe sets to form hybridization complexes with the different target nucleic acids; (c) amplifying the nucleic acid from the biological samples to produce amplicons; wherein there is no purification of the nucleic acid from the biological sample prior to the contacting step (b); and (d) obtaining nucleic acid sequence information for a plurality of portions of the amplified sample. Additionally or alternatively, detection of a genetic biomarker can include a method of obtaining nucleic acid sequence information from a FFPE sample comprising: (a) providing a FFPE sample comprising different target nucleic acids embedded within a preserved tissue; (b) contacting the FFPE sample with a plurality of different probe sets to form hybridization complexes with the different target nucleic acids; (c) amplifying the nucleic acid from the FFPE samples to produce amplicons; wherein there is no purification of the nucleic acid from the FFPE sample prior to the contacting step (b); and (d) obtaining nucleic acid sequence information for a plurality of the amplicons. In particular embodiments, there is no purification of the nucleic acid from the FFPE sample prior to the amplifying in step (c). Additionally or alternatively, detection of a genetic biomarker can include methods for amplification of nucleic acid from a FFPE sample comprising: (a) providing a FFPE sample comprising nucleic acid embedded within a preserved tissue, the nucleic acid having, from 3' to 5': contiguous first, second, and third target domains; (b) contacting the FFPE sample with a plurality of different probe sets to form hybridization complexes with the different target nucleic acids, wherein each probe set comprises: (i) a first probe comprising, from 5' to 3': a first priming sequence and a sequence that is substantially complementary to the first target domain; and (ii) a second probe comprising 5' to 3': a sequence substantially complementary to the third target domain, and a second priming sequence; (c) contacting the hybridization complexes with an extension enzyme and nucleotides, wherein the first probes are extended along the second target domains of hybridization complexes formed in (b); (d) ligating the extended first probes to the second probes to form amplification templates; and (e) amplifying the amplification templates with first and second primers that are complementary to the first priming sequence and the second priming sequence to produce amplicons and obtaining nucleic acid sequence information for a plurality of the amplicons. Additionally or alternatively, detection of a genetic biomarker can include a method for nucleic acid sample identification comprising: (a) providing a nucleic acid-containing cellular sample; (b) lysing cells of the sample with a lysis reagent to liberate nucleic acid from within the cells of the cellular sample, thereby forming a lysate; (c) amplifying the nucleic acid from the lysed samples; wherein there is no purification of the nucleic acid from the lysate prior to beginning the amplification step (c); and (d) obtaining nucleic acid sequence information for a plurality of portions of the amplified sample, and comparing the sequence information to a second set of sequence information. In certain aspects, the nucleic acid is DNA. In certain aspects, the sample is a blood sample. In certain aspects, the sample comprises dried blood. In certain aspects, the sample comprises a FFPE tissue sample. In certain aspects, the second set of sequence information comprises a whole genome sequence. In certain aspects, the second set of sequence information comprises exome sequence information. In certain aspects, the amplifying comprises a targeted amplification reaction. In certain aspects, the targeted amplification reaction comprises extension and ligation of two probes. In certain aspects, the targeted amplification reaction comprises polymerase chain reaction using at least two amplification primers that are specific for a portion of the sample genome. Additionally or alternatively, detection of a genetic biomarker can include a method of tracking the identity of a biological sample during different stages of sample processing, comprising: (a) providing a nucleic acid-containing cellular sample; (b) separating a portion of the sample into a first portion and a second portion and obtaining a first set of nucleic acid sequence information from the first portion the biological sample according to the above embodiments, wherein the first set of nucleic acid sequence information comprises identity informative sequence information; (c) purifying nucleic acid from the second portion and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same source. Additionally or alternatively, detection of a genetic biomarker can include a method of confirming the source of two different biological samples comprising: (a) providing a first nucleic acid-containing cellular sample; (b) obtaining a first set of nucleic acid sequence information from the first portion the biological sample according to some of the above embodiments, wherein the first set of nucleic acid sequence information comprises identity informative sequence information; (c) providing a second nucleic acid sample comprising purified nucleic acid and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same individual.

In some embodiments, detection of a genetic biomarker (e.g., one or more genetic biomarkers) can include any of the variety of methods described in U.S. Patent Application Publication No. 2018/0155774, which is hereby incorporated by reference in its entirety. For example, detection of a genetic biomarker can include compositions, systems, and methods for sequencing polynucleotides using tethers anchored to polymerases adjacent to nanopores. Under one aspect, a composition includes a nanopore including a first side, a second side, and an aperture extending through the first and second sides. The composition also can include a plurality of nucleotides, wherein each of the nucleotides includes an elongated tag. The composition also can include first and second polynucleotides, the first polynucleotide being complementary to the second polynucleotide. The composition also can include a polymerase disposed adjacent to the first side of the nanopore, the polymerase configured to add nucleotides of the plurality of nucleotides to the first polynucleotide based on a sequence of the second polynucleotide. The composition also can include a permanent tether including a head region, a tail region, and an elongated body disposed therebetween, the head region being anchored to the polymerase, wherein the elongated body occurs in the aperture of the nanopore. The composition also can include a first moiety disposed on the elongated body, wherein the first moiety is configured to bind to the elongated tag of a first nucleotide upon which the polymerase is acting, as well as a reporter region disposed on the elongated body, wherein the reporter region is configured to indicate when the first nucleotide is complementary or is not complementary to a next nucleotide in the sequence of the second polynucleotide. Under another aspect, a method can include providing a nanopore including a first side, a second side, and an aperture extending through the first and second sides. The method further can include providing a plurality of nucleotides, wherein each of the nucleotides includes an elongated tag. The method further can include providing first and second polynucleotides, the first polynucleotide being complementary to the second polynucleotide. The method further can include providing a polymerase disposed adjacent to the first side of the nanopore, the polymerase configured to add nucleotides of the plurality of nucleotides to the first polynucleotide based on a sequence of the second polynucleotide, wherein the polymerase is anchored to a permanent tether including a head region, a tail region, and an elongated body disposed therebetween, the elongated body occurring in the aperture of the nanopore. The method further can include determining that a first nucleotide is being acted upon by the polymerase based on binding of the elongated tag to a first moiety disposed on the elongated body. The method further can include, with a reporter region disposed on the elongated body, indicating when the first nucleotide is complementary or is not complementary to a next nucleotide in the sequence of the second polynucleotide.

In some embodiments, detection of a genetic biomarker (e.g., one or more genetic biomarkers) can include any of the variety of methods described in U.S. Patent Application Publication No. 2018/0141020, which is hereby incorporated by reference in its entirety. For example, detection of a genetic biomarker can include substrates and methods useful for placing a single molecule onto a target area. In a first aspect is a substrate that includes a plurality of first and second capture primers immobilized to a feature on the substrate. At least one target polynucleotide, one end attached to one of the capture primers and the other end linked to a target molecule, wherein the target polynucleotide includes a target region flanked by first and second capture primer binding regions complementary to the first and second capture primers, the second capture primer binding region includes a base pair mismatch to the second capture primer, and a plurality of clonal amplicons complementary to the target polynucleotide immobilized to the feature. In some embodiments, the base pair mismatch is a 1, 2, 3, 4, 5, 6, 7, 8, 9, or 10 base pair mismatch. In some embodiments, the base pair mismatch is a three base pair mismatch. In some embodiments, the substrate further includes a plurality of features. In some embodiments, the feature includes a single target molecule. In some embodiments, the feature is filled to capacity with the plurality of clonal amplicons. In some embodiments, the plurality of features includes a single target molecule. In some embodiments, two or more of the features include different single target molecules. In some embodiments, the features are filled to capacity with the plurality of clonal amplicons. Additionally or alternatively, detection of a genetic biomarker can include methods of placing a single target molecule on a feature of a substrate. In one aspect, the method is a method of placing a single target molecule on a feature of a substrate by hybridizing a plurality of first and second capture primers immobilized to a feature on a substrate with at least one target polynucleotide, where the target polynucleotide includes a target region flanked by first and second capture primer binding regions complementary to the first and second capture primers, and the second capture primer binding region includes a base pair mismatch to the second capture primer and being linked to a target molecule. The method further includes amplifying the at least one target polynucleotide at an average amplification rate that exceeds an average transport rate of a target polynucleotide to a feature to produce a plurality of clonal amplicons complementary to the target polynucleotide. In some embodiments of the methods, the base pair mismatch is a 1, 2, 3, 4, 5, 6, 7, 8, 9, or 10 base pair mismatch. In some embodiments of the methods, the base pair mismatch is a three base pair mismatch. In some embodiments of the methods, the substrate comprises a plurality of features. In some embodiments of the methods, the feature includes a single target molecule. In some embodiments of the methods, the feature is filled to capacity with the plurality of clonal amplicons. In some embodiments of the methods, the plurality of features includes a single target molecule. In some embodiments of the methods, the two or more of the features include different single target molecules. In some embodiments of the methods, the features are filled to capacity with the plurality of clonal amplicons. In some embodiments of the methods, the average amplification rate of subsequent amplicons produced at the feature exceeds the average amplification rate of a first amplicon. In some embodiments, the target polynucleotide includes one or more polynucleotides selected from the group consisting of RNA, DNA, and PNA. In some embodiments, the target polynucleotides include double stranded DNA (dsDNA). In some embodiments, the target polynucleotide comprises less than 1,000 nucleotides. In some embodiments, the target polynucleotide comprises between 10 to 25, 26 to 50, 51 to 100, 101 to 200, 201 to 300, 301 to 400, 401 to 500, 501 to 600, 601 to 700, 701 to 800, 801 to 900, or 901 to 1000 base pairs in length. In some embodiments, the target molecule includes a polypeptide, polynucleotide, carbohydrate, amino acid, nucleotide, monosaccharide, hapten, ligand, antigen, analyte, small molecule organic compound or inorganic compound. In some embodiments, the target molecule includes a polypeptide. In some embodiments, the polypeptide is selected from the group consisting of a nanopore, binding polypeptide and enzyme. In some embodiments, the nanopore pore is selected from the group consisting of MspA, OmpF, OmpG, NalP, WZA, ClyA toxin, α-hemolysin, anthrax toxin, leukocidins and DNA origami nanopore. In some embodiments, the binding polypeptide is selected from the group consisting of an antibody, a Fab, a Fab', a F(ab')2, a scFV, a diabody, a triabody, a minibody and a single-domain antibody (sdAB), T cell receptor, microcins, Neuropeptides, G-protein coupled receptors, antibody, epidermal growth factor receptor and HER2.

In some embodiments, detection of a genetic biomarker (e.g., one or more genetic biomarkers) can include any of the variety of methods described in U.S. Patent Application Publication No. 2018/0095969, which is hereby incorporated by reference in its entirety. For example, detection of a genetic biomarker can include methods, systems and apparatus for capturing, integrating, organizing, navigating and querying large-scale data from high-throughput biological and chemical assay platforms. Some embodiments provide methods, systems and interfaces for associating experimental data, features and groups of data related by structure and/or function with chemical, medical and/or biological terms in an ontology or taxonomy. Some embodiments also provide methods, systems and interfaces for filtering data by data source information, allowing dynamic navigation through large amounts of data to find the most relevant results for a particular query. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the operations including: (a) selecting, by the one or more processors, a plurality of gene sets from a database, wherein each gene set of the plurality of gene sets includes a plurality of genes and a plurality of experimental values associated with the plurality of genes, and wherein the plurality of experimental values are correlated with the biological, chemical or medical concept of interest in at least one experiment; (b) determining, for each gene set and by the one or more processors, one or more experimental gene scores for first one or more genes among the plurality of genes using one or more experimental values of the first one or more genes; (c) determining, for each gene set and by the one or more processors, one or more in silico gene scores for second one or more genes among the plurality of genes based at least in part on the first one or more genes' correlations with the second one or more genes, wherein the first one or more genes' correlations with the second one or more genes are indicated in other gene sets in the database beside the plurality of gene sets; (d) obtaining, by the one or more processors, summary scores for the first and second one or more genes based at least in part on the one or more experimental gene scores for the first one or more genes determined in (b) and the one or more in silico gene scores for the second one or more genes determined in (c), wherein each summary score is aggregated across the plurality of gene sets; and (e) identifying, by the one or more processors, the genes that are potentially associated with the biological, chemical or medical concept of interest using the summary scores of the first and second one or more genes. Implementations may include one or more of the following features. In some implementations, (c) includes, for each gene set of the plurality of gene sets: (i) identifying a second plurality of gene sets from the database, each gene set of the second plurality of gene sets including a second plurality of genes and a second plurality of experimental values associated with the second plurality of genes, and where the second plurality of experimental values are correlated with a first gene among the first one or more genes. The method may also include (ii) aggregating the experimental values across the second plurality of gene sets to obtain a vector of aggregated values for the first gene among the first one or more genes. The method may also include (iii) applying (i) and (ii) to one or more other genes among the first one or more genes, thereby obtaining one or more vectors of experimental values for the one or more other genes among the first one or more genes. The method may also include (iv) aggregating vectors of aggregated values for the first gene and the one or more other genes among the first one or more genes, thereby obtaining one compressed vector including the one or more in silico gene scores for the second one or more genes. Additionally or alternatively, detection of a genetic biomarker can include a method where each of the aggregated vectors of (iv) for a particular gene among the first one or more genes is weighted in proportion to an experimental value of the particular gene. The method where each of the aggregated vectors of (iv) for a particular gene among the first one or more genes is weighted in proportion to a number of gene sets of the second plurality of gene sets identified for the particular gene. Some implementations provide the method further including, determining, before (d), one or more gene-group scores for third one or more genes. Some implementations provide the method where each gene-group score for a particular gene is determined using (i) gene memberships of one or more gene groups that each include a group of genes related to a group label, where the group of genes includes the particular gene, and (ii) at least some of the one or more experimental values of the first one or more genes. Some implementations provide the method where (d) includes obtaining the summary scores for the first and second one or more genes based at least in part on the gene-group scores for at least some of the third one or more genes, as well as the one or more experimental scores for the first one or more genes determined in (b) and the one or more in silico scores for the second one or more genes determined in (c). Some implementations provide the method where determining the one or more gene-group scores for the third one or more genes includes: identifying, for a particular gene among the third one or more genes, the one or more gene groups that each include the particular gene. The method may also include determining, for each gene group, a percentage of members of the gene group that are among the first one or more genes. The method may also include aggregating, for each gene group, one or more experimental values of at least some of the first one or more genes that are members of the gene group, thereby obtaining a sum experimental value for the gene group. The method may also include determining, for the particular gene among the third one or more genes, a gene-group score using the percentage of members of the gene group that are among the first one or more genes and the sum experimental value for the gene group. Some implementations provide the method where determining the gene-group score using the percentage of members of the gene group that are among the first one or more genes and the sum experimental value for the gene group includes: obtaining, for each gene group, a product of the percentage of members and the sum experimental value, thereby obtaining one or more products for the one or more gene groups. The method may also include summing, across the one or more gene groups, the one or more products, thereby obtaining a summed product. The method may also include determining, for the particular gene among the third one or more genes, a gene-group score based on the summed product. In some implementations, the method further includes, before (d), determining interactome scores respectively for fourth one or more genes. In some implementations, each interactome score for a particular gene is determined using (i) connections between the particular gene and other genes connected to the particular gene in a network of genes and (ii) at least some of the one or more experimental values of the first one or more genes. In some implementations, (d) includes obtaining the summary scores for at least the first one or more genes and the second one or more genes based at least in part on the interactome scores for at least some of the fourth one or more genes, as well as the one or more experimental gene scores for the first one or more genes determined in (b) and the one or more in silico gene scores for the second one or more genes determined in (c). In some implementations, the network of genes are based on interactions and relations among genes, proteins, and/or phospholipids. In some implementations, calculating the interactome score includes calculating the interactome score as Ni':

$$Ni'=Ni+\Sigma((Ni+Nn)*\text{edge\_weight}n)$$

wherein Ni is the summary score of the particular gene i, Nn is a summary score of gene n connected to the particular gene, and edge_weightn is the weight of the edge connecting the particular gene i and gene n. In some implementations, calculating the interactome score further includes: saving Ni' that are smaller than a second threshold in a first pass dictionary; and repeating the calculation for all genes in the first pass dictionary, thereby updating the interactome scores. In some implementations, the method further includes training the model by optimizing an objective function. In some implementations, training the model includes applying a bootstrap technique to bootstrap samples. In some implementations, the objective function relates to at least one summary score distribution after bootstrapping. In some implementations, optimizing the objective function includes minimizing differences of summary scores between a training set and a validation set. In some implementations, optimizing the objective function includes maximizing a distance between a summary score distribution obtained from the plurality of gene sets and a summary score distribution obtained from random gene sets. In some implementations, summary scores are ranked and binned in buckets of a defined size, wherein penalty scores are assigned to the buckets, the penalty scores favoring higher ranked summary scores. In some implementations, the objective function is based only on top ranked summary scores. In some implementations, training the model includes using the objective function in an unsupervised machine learning approach to learn parameters of the model. In some implementations, the model has the form:

$$F(\theta)=k1*c1+k2*c2+\ldots+kn*cn$$

wherein θ are parameters of the model, ci are components of the model, and ki are weight factors for the components. In some implementations, the method further includes partitioning one or more of the components of the model into sub-components based on sample weights of experimental data types. In some implementations, the summary scores of the first and second one or more genes are penalized based on how likely experimental values of the first and second one or more genes in one or more random gene sets are correlated with the biological, chemical or medical concept of interest. In some implementations, each summary score of a particular gene is penalized by a penalty value that is inversely proportional to a p value of a rank product, wherein the rank product includes a product of ranks of the particular gene across the one or more random gene sets. One general aspect includes a computer program product including a non-transitory machine readable medium storing program code that, when executed by one or more processors of a computer system, causes the computer system to implement a method for identifying genes that are potentially associated with a biological, chemical or medical concept of interest, said program code including: (a) code for selecting a plurality of gene sets from a database, where each gene set of the plurality of gene sets includes a plurality of genes and a plurality of experimental values associated with the plurality of genes, and where the plurality of experimental values are correlated with the biological, chemical or medical concept of interest in at least one experiment. The program code also includes (b) code for determining, for each gene set, one or more experimental gene scores for first one or more genes among the plurality of genes using one or more experimental values of the first one or more genes. The program code also includes (c) code for determining, for each gene set, one or more in silico gene scores for second one or more genes among the plurality of genes based at least in part on the first one or more genes' correlations with the second one or more genes, where the first one or more genes' correlations with the second one or more genes are indicated in other gene sets in the database beside the plurality of gene sets. The program code also includes (d) code for obtaining summary scores for the first and second one or more genes based at least in part on the one or more experimental gene scores for the first one or more genes determined in (b) and the one or more in silico gene scores for the second one or more genes determined in (c), where each summary score is aggregated across the plurality of gene sets. The program code also includes (e) code for identifying the genes that are potentially associated with the biological, chemical or medical concept of interest using the summary scores of the first and second one or more genes.

In some embodiments, detection of a genetic biomarker (e.g., one or more genetic biomarkers) can include any of the variety of methods described in U.S. Patent Application Publication No. 2018/0023119, which is hereby incorporated by reference in its entirety. For example, detection of a genetic biomarker can include methods for preparing a sequencing library that includes nucleic acids from a plurality of single cells. In one embodiment, the method includes providing isolated nuclei from a plurality of cells; subjecting the isolated nuclei to a chemical treatment to generate nucleosome-depleted nuclei while maintaining integrity of the isolated nuclei; distributing subsets of the nucleosome-depleted nuclei into a first plurality of compartments and contacting each subset with a transposome complex, where the transposome complex in each compartment includes a transposase and a first index sequence that is different from first index sequences in the other compartments; fragmenting nucleic acids in the subsets of nucleosome-depleted nuclei into a plurality of nucleic acid fragments and incorporating the first index sequences into at least one strand of the nucleic acid fragments to generate indexed nuclei that include indexed nucleic acid fragments, where the indexed nucleic acid fragments remain attached to the transposases; combining the indexed nuclei to generate pooled indexed nuclei; distributing subsets of the pooled indexed nuclei into a second plurality of compartments; incorporating into the indexed nucleic acid fragments in each compartment a second index sequence to generate dual-index fragments, where the second index sequence in each compartment is different from second index sequences in the other compartments; and combining the dual-index fragments, thereby producing a sequencing library that includes whole genome nucleic acids from the plurality of single cells. In one embodiment, the chemical treatment includes a treatment with a chaotropic agent capable of disrupting nucleic acid-protein interactions, such as lithium 3,5-diiodosalicylic acid. In one embodiment, the chemical treatment includes a treatment with a detergent capable of disrupting nucleic acid-protein interactions, such as sodium dodecyl sulfate (SDS). In one embodiment, the nuclei are treated with a cross-linking agent before subjecting the isolated nuclei to the chemical treatment, such as formaldehyde. The cross-linking agent can be at a concentration from about 0.2% to about 2%, and in one embodiment is about 1.5%. In one embodiment, the cross-linking by formaldehyde is reversed after distributing subsets of the pooled indexed nuclei and before incorporating into the indexed nucleic acid fragments in each compartment a second index sequence. In one embodiment, the reversal of the cross-linking includes incubation at about 55° C. to about 72° C. In one embodiment, the transposases are disassociated from the indexed nucleic acid fragments prior to the reversal of the cross-linking. In one embodiment, the transposases are disassociated from the indexed nucleic acid fragments using sodium dodecyl sulfate (SDS). In one embodiment, the nuclei are treated with a restriction enzyme prior to fragmenting nucleic acids in the subsets of nucleosome-depleted nuclei into a plurality of nucleic acid fragments and incorporating the first index sequences. In one embodiment, the nuclei are treated with a ligase after treatment with the restriction enzyme. In one embodiment, the distributing subsets of the nucleosome-depleted nuclei, the distributing subsets of the pooled indexed nuclei, or the combination thereof, is performed by fluorescence-activated nuclei sorting. In one embodiment, the subsets of the nucleosome-depleted nuclei include approximately equal numbers of nuclei, and in one embodiment, the subsets of the nucleosome-depleted nuclei include from 1 to about 2000 nuclei. In one embodiment, the subsets of the pooled indexed nuclei include approximately equal numbers of nuclei, and in one embodiment, the subsets of the pooled indexed nuclei include from 1 to about 25 nuclei. In one embodiment, the subsets of the pooled indexed nuclei include at least 10 times fewer nuclei than the subsets of the nucleosome-depleted nuclei, or at least 100 times fewer nuclei than the subsets of the nucleosome-depleted nuclei. In one embodiment, the first plurality of compartments, the second plurality of compartments, or the combination thereof, is a multi-well plate, such as a 96-well plate or a 384-well plate. In one embodiment, the transposome complex is added to the compartments after the subsets of nucleosome-depleted nuclei are distributed into the compartments. In one embodiment, each of the transposome complexes includes a transposon, and each of the transposons includes a transferred strand. In one embodiment, the transferred strand includes the first index sequence and a first universal sequence. In one embodiment, the incorporation of the second index sequence into the indexed nucleic acid fragments includes contacting the indexed nucleic acid fragments in each compartment with a first universal primer and a second universal primer, each including an index sequence and each including a sequence identical to or complementary to a portion of the first universal sequence, and performing an exponential amplification reaction. In one embodiment, the exponential amplification reaction can be a polymerase chain reaction (PCR), and in one embodiment, the PCR can include 15 to 30 cycles.

In some embodiments, detection of a genetic biomarker (e.g., one or more genetic biomarkers) can include any of the variety of methods described in U.S. Patent Application Publication No. 2018/0037950, which is hereby incorporated by reference in its entirety. For example, detection of a genetic biomarker can include microarrays and methods of modifying immobilized capture primers. In one aspect, is a microarray including: a) a substrate including at least one well, a surface surrounding the well and an inner well surface; b) a first layer covering the inner well surface and including at least one first capture primer pair; and c) a second layer covering the first layer and the surface surrounding the well. In another aspect, is a microarray including: a) a substrate including at least one well, a surface surrounding the well and an inner well surface; and b) a layer covering the inner well surface and including at least one first capture primer pair and at least one second capture primer pair. In another aspect, is a method for amplifying a nucleic acid, including: a) producing a first layer on a substrate, wherein the substrate includes at least one well, a surface surrounding the well and an inner well surface, wherein the first layer covers the inner well surface; b) depositing at least one first capture primer pair in the first layer; c) producing a second layer on the substrate covering the first layer and the surface surrounding the well; d) contacting a sample including a plurality of target polynucleotides with the substrate under conditions sufficient for a target polynucleotide to hybridize with a capture primer of the at least one first capture primer pair, and e) performing a first kinetic exclusion assay (KEA) to produce a clonal population of amplicons from the target polynucleotide inside the well, thereby amplifying the target polynucleotide. Additionally or alternatively, detection of a genetic biomarker can include a method for amplifying a nucleic acid, including: a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of first capture primers including a 3' portion including an Illumina® P5 primer nucleotide sequence and a plurality of second capture primers including a 3' portion including an Illumina® P7 primer nucleotide sequence; c) producing a second layer on the substrate covering the first layer and the surface surrounding the well; d) depositing at least one second capture primer pair in the second layer, wherein the second capture primer pair is 3' phosphate-terminated and includes a plurality of first capture primers including a 3' portion including an Illumina® P5 primer nucleotide sequence and a plurality of second capture primers including a 3' portion including an Illumina® P7 primer nucleotide sequence; e) contacting a sample including a plurality of target polynucleotides with the substrate under conditions sufficient for a single target polynucleotide per well to hybridize with a primer of the at least one first capture primer pair, wherein the target polynucleotides are flanked by complementary universal primer regions each including a complementary Illumina® P5' primer nucleotide sequence or a complementary Illumina® P7' primer nucleotide sequence; f) performing a first KEA to produce a monoclonal population of amplicons from the single target polynucleotide inside the at least one well, thereby amplifying the target polynucleotide; g) contacting the substrate with a T4-kinase to deblock the primers of the second primer pair, and h) performing bridge amplification or a second KEA to enlarge the monoclonal population of amplicons of the single target polynucleotide beyond the well. Additionally or alternatively, detection of a genetic biomarker can include a method for amplifying a nucleic acid, including: a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of at least one first capture primers including a 3' portion including an Illumina® P5 primer nucleotide sequence and an Illumina® SBS3 primer nucleotide sequence and a plurality of at least one second capture primers including a 3' portion including an Illumina® P7 primer nucleotide sequence and an Illumina® SBS8 primer nucleotide sequence; c) producing a second layer on the substrate covering the first layer and the surface surrounding the well; d) depositing at least one second capture primer pair in the second layer, wherein the at least one second capture primer pair includes a plurality of first capture primers including a 3' portion including an Illumina® P5 primer nucleotide sequence and a plurality of second capture primers including an 3' portion including an Illumina® P7 nucleotide sequence; e) contacting a sample including a plurality of target polynucleotides with the substrate under conditions sufficient for a single target polynucleotide per well to hybridize with a primer of the at least one first capture primer pair, wherein the plurality of target polynucleotides are flanked by a complementary SBS each including a complementary Illumina® SBS3' primer nucleotide sequence or a complementary Illumina® SBS8' nucleotide sequence, and f) performing a KEA for an extended time to produce a monoclonal population of amplicons from the single target polynucleotide inside and outside the at least one well, thereby amplifying the single target polynucleotide inside the well and enlarging the monoclonal population of target polynucleotides beyond the at least one well. Additionally or alternatively, detection of a genetic biomarker can include a method for amplifying a nucleic acid, including: a) producing a first layer on a substrate, wherein the substrate includes at least one well, a surface surrounding the well, and an inner well surface, wherein the first layer at least partially covers the inner well surface; b) depositing at least one first capture primer pair in the first layer, wherein the first primer pair includes a plurality of first capture primers including a 3' portion including an Illumina® P5 primer nucleotide sequence and a plurality of second capture primers including a 3' portion including an Illumina® P7 primer nucleotide sequence; c) producing a second layer on the substrate covering the first layer and the surface surrounding the well; d) contacting a sample including a plurality of target polynucleotides with the substrate under conditions sufficient for a single target polynucleotide per well to hybridize with a primer of the at least one first capture primer pair, wherein the plurality of polynucleotides are flanked by complementary universal primer regions each including a complementary Illumina® P5' primer nucleotide sequence or a complementary Illumina® P7' nucleotide sequence; e) performing a first KEA to produce a monoclonal population of amplicons from the single target polynucleotide inside the at least one well, thereby amplifying the target polynucleotide; f) depositing at least one second capture primer pair in the second layer, wherein the at least one second capture primer pair includes a plurality of first capture primers including a 3' portion including an Illumina® P5 primer nucleotide sequence and a plurality of second capture primers including a 3' portion including an Illumina® P7 primer nucleotide sequence, and g) performing bridge amplification or a second KEA to enlarge the monoclonal population of amplicons of the single target polynucleotide. Additionally or alternatively, detection of a genetic biomarker can include a method for amplifying a nucleic acid, including: a) producing a layer on a substrate, wherein the substrate includes at least one well, a surface surrounding the well and an inner well surface, wherein the well has a diameter of about 1 µm or more and wherein the layer at least partially covers the inner well surface; b) depositing at least one first capture primer pair and at least one second capture primer pair in the layer, wherein the primer density of the at least one first capture primer pair is higher than the primer density of the at least second primer pair; c) contacting a sample including a plurality of target polynucleotides with the substrate under conditions sufficient for a single target polynucleotide per well to hybridize with the second primer, and d) performing a KEA to produce a monoclonal population of amplicons from the single target polynucleotide hybridized to the second primer inside the well, thereby amplifying the single target polynucleotide. Additionally or alternatively, detection of a genetic biomarker can include a method for modifying an immobilized capture primer including: a) contacting a substrate including a plurality of immobilized capture primers with a plurality of template nucleic acids under conditions sufficient for hybridization to produce one or more immobilized template nucleic acids, wherein the plurality of immobilized capture primers includes a first plurality of primers including a 5'-terminal universal capture region Y and a second plurality of primers including a 3'-terminal universal capture region Z, and wherein each template nucleic acid is flanked by 5'-terminal and a 3'-terminal universal capture regions Y or Z and includes one or more restriction sites and the target-specific capture region between the 5'-terminal universal capture region and the one or more restriction sites or between the 3'-terminal universal capture region and the one or more restriction sites, and b) extending one or more immobilized capture primers to produce one or more immobilized extension products complementary to the one or more template nucleic acid. Additionally or alternatively, detection of a genetic biomarker can include a method for modifying an immobilized capture primer including: a) contacting a substrate including a plurality of immobilized capture primers with a plurality of template nucleic acids under conditions sufficient for hybridization to produce one or more immobilized template nucleic acid, wherein the plurality of immobilized capture primers includes a first plurality of primers including a 3'-terminal Illumina® P5 primer nucleotide sequence and a second plurality of primers including a 3'-terminal Illumina® P7 primer nucleotide sequence, and wherein each template nucleic acid is flanked by a 3'-terminal complementary Illumina® P5' primer nucleotide sequence and a 5'-terminal complementary Illumina® P7' primer nucleotide sequence, and includes two SapI restriction sites, a spacer region between the SapI restriction sites, and a target-specific capture region between the 3' terminal complementary Illumina® P5' primer nucleotide sequence and the SapI restriction sites; and b) extending one or more immobilized capture primers to produce one or more immobilized extension products complementary to the one or more template nucleic acids. c) amplifying the one or more immobilized extension products by bridge amplification or KEA to produce one or more monoclonal clusters of immobilized double-stranded template nucleic acids; d) contacting the one or more monoclonal cluster of immobilized double-stranded template nucleic acids with SapI to cut the two restriction sites in a plurality of immobilized double-stranded template nucleic acids to produce a plurality of immobilized double-stranded chimeric capture primers including the Illumina® P5 primer nucleotide sequence and the target-specific capture region and a plurality of immobilized double-stranded regenerated universal capture primers including the Illumina® P7 primer nucleotide sequence, and e) optionally, contacting the plurality of immobilized double-stranded chimeric capture primers and immobilized double-stranded regenerated universal capture primers with a 5'-3' dsDNA-exonuclease to produce a plurality of immobilized single-stranded chimeric capture primers and a plurality of immobilized single-stranded regenerated universal capture primers.

In some embodiments, detection of a genetic biomarker (e.g., one or more genetic biomarkers) can include any of the variety of methods described in U.S. Patent Application Publication No. 2017/0356030, which is hereby incorporated by reference in its entirety. For example, detection of a genetic biomarker can include compositions, systems, and methods for detecting the presence of polymer subunits using chemiluminescence. Under one aspect, a composition includes a substrate; a first polynucleotide coupled to the substrate; a second polynucleotide hybridized to the first polynucleotide; and a catalyst coupled to a first nucleotide of the second polynucleotide, the catalyst being operable to cause a chemiluminogenic molecule to emit a photon. In some embodiments, the composition further includes a plurality of the chemiluminogenic molecules. The catalyst can cause each of the chemiluminogenic molecules to emit a corresponding photon. The composition further can include a plurality of reagent molecules, the catalyst causing each of the chemiluminogenic molecules to emit a corresponding photon by oxidizing that chemiluminogenic molecule using a reagent molecule. The oxidized chemiluminogenic molecule can have an excited state that decays by emitting the corresponding photon. A system can include any of the foregoing compositions and circuitry configured to detect the photon emitted by the chemiluminogenic molecule. In some embodiments, the circuitry further is configured to detect the presence of the first nucleotide based on detection of the photon. Under another aspect, a method can include providing a substrate; providing a first polynucleotide coupled to the substrate; hybridizing a second polynucleotide to the first polynucleotide; coupling a first catalyst to a first nucleotide of the second polynucleotide; and causing, by the first catalyst, a first chemiluminogenic molecule to emit a photon. Under another aspect, a method of sequencing a first polynucleotide includes providing the first polynucleotide to be sequenced and coupled to a substrate; b) hybridizing a second polynucleotide to the first polynucleotide; and contacting the second polynucleotide with a polymerase and a plurality of nucleotides. A first subset of the plurality of nucleotides includes a first moiety, a second subset of the plurality of nucleotides includes a second moiety, a third subset of the plurality of nucleotides includes a third moiety, and a fourth subset of the plurality of nucleotides includes a fourth moiety or no moiety. The method further can include adding a nucleotide of the plurality of nucleotides to the second polynucleotide based on a sequence of the first polynucleotide. The method further can include exposing the nucleotide to a catalyst coupled to a fifth moiety; exposing the nucleotide to chemiluminogenic molecules; and detecting emission of photons or an absence of photons from the chemiluminogenic molecules. The method further can include exposing the nucleotide to a catalyst coupled to a sixth moiety; exposing the nucleotide to chemiluminogenic molecules; and detecting emission of photons or an absence of photons from the chemiluminogenic molecules. The method further can include exposing the nucleotide to a cleaver molecule; exposing the nucleotide to chemiluminogenic molecules; and detecting emission of photons or an absence of photons from the chemiluminogenic molecules. The method further can include detecting the added nucleotide based on the detection of emission of photons or absence of photons from the chemiluminogenic molecules at one or more of the detection steps or a combination thereof. Under another aspect, a composition includes a catalyst operable to cause a chemiluminogenic molecule to emit a photon; a substrate; a first polynucleotide coupled to the substrate; a second polynucleotide hybridized to the first polynucleotide; and a quencher coupled to a first nucleotide of the second polynucleotide, the quencher operable to inhibit photon emission by the chemiluminogenic molecule. Under another aspect, a method includes providing a catalyst operable to cause a first chemiluminogenic molecule to emit a photon; providing a substrate; providing a first polynucleotide coupled to the substrate; hybridizing a second polynucleotide to the first polynucleotide; coupling a first quencher to a first nucleotide of the second polynucleotide; and inhibiting, by the first quencher, photon emission by the first chemiluminogenic molecule. Under another aspect, a method of sequencing a first polynucleotide includes providing the first polynucleotide to be sequenced and coupled to a substrate; hybridizing a second polynucleotide to the first polynucleotide; and providing a catalyst coupled sufficiently close to the second polynucleotide that a quencher coupled to the second polynucleotide can inhibit photon emission from chemiluminescent molecules that interact with the catalyst. The method further can include contacting the second polynucleotide with a polymerase and a plurality of nucleotides. A first subset of the plurality of nucleotides includes a first moiety, a second subset of the plurality of nucleotides includes a second moiety, a third subset of the plurality of nucleotides includes a third moiety, and a fourth subset of the plurality of nucleotides includes a fourth moiety or no moiety.

In some embodiments, detection of a genetic biomarker (e.g., one or more genetic biomarkers) can include any of the variety of methods described in U.S. Patent Application Publication No. 2017/0137876, which is hereby incorporated by reference in its entirety. For example, detection of a genetic biomarker can include a method that may be used to substantially reduce or eliminate high quality errors that may be generated during first extension. In another embodiment, the methods may also be used to reduce errors caused by mis-incorporation of nucleotides during the first few cycles of amplification. Additionally or alternatively, detection of a genetic biomarker can include a method of sequencing with improved accuracy comprising; providing a nucleic acid template; producing, by linear amplification directly from the template nucleic acid, a population comprising a plurality of complementary strands retained in close proximity to each other or identifiable as being obtained from the same template nucleic acid; and performing a sequencing reaction on said proximity retained (e.g. surface bound) oligonucleotides. In some embodiments, the method further comprises the step of carrying out further (exponential) amplification of the population of complementary strands after the rounds of linear amplification and prior to performing the sequencing reaction. Optionally the linear amplification (directly from the nucleic acid template) includes the steps of; hybridising said nucleic acid template to a first primer; extending the first primer to produce a complementary strand to the template; denaturing to release the complementary strand which remains in close proximity (e.g. it remains bound to the surface and thus does not travel at all or does not diffuse far before re-hybridising nearby); and repeating the hybridisation and amplification steps to produce a population of surface bound complementary strands obtained directly from the template nucleic acid.

In some embodiments, detection of a genetic biomarker (e.g., one or more genetic biomarkers) can include any of the variety of methods described in U.S. Patent Application Publication No. 2017/0101676, which is hereby incorporated by reference in its entirety. For example, detection of a genetic biomarker can include techniques for enrichment of target sequences in a nucleic acid library and reducing the capture of off-target sequences by a set of target hybridization probes. Because target hybridization probes have imperfect specificity for their nucleic acid targets, a sequencing run using a set of target hybridization probes may also include a certain percentage of reads that represent sequences that are off-target. For example, in an exome sequencing reaction, certain hybridization probes may pull down intronic or intergenic sequences from a nucleic acid library along with target sequences. These off-target fragments, once pulled down, are then present in the pool of nucleic acid fragments that are sequenced. While the sequencing information representative of the off-target reads is typically discarded, the present techniques use acquired sequencing information of these off-target reads to design hybridization probes that are specific for the off-target sequences and that are used to separate and/or remove fragments that include these sequences from the pool of fragments captured by the target-specific hybridization probes. The off-target hybridization probes are designed based on analysis of the off-target reads of a hybrid capture sequencing run that is performed with a set of target hybridization probes. In certain embodiments, the on-target probe design may also be based on systematic off-target analysis across samples to improve the specificity of the target hybridization probes for their desired targets. Additionally or alternatively, detection of a genetic biomarker can include a method of reducing off-target capture in a targeted sequencing reaction. The method includes the steps of providing a set of off-target hybridization probes that specifically bind to a plurality of off-target sequences present in a nucleic acid library generated from a sample, the nucleic acid library comprising a plurality of nucleic acid fragments and providing a set of target-specific hybridization probes that specifically bind to a plurality of target sequences present in the nucleic acid library. The method also includes the steps of contacting the off-target hybridization probes with the nucleic acid library under conditions whereby the off-target hybridization probes hybridize to the off-target sequences and contacting the target-specific hybridization probes with the nucleic acid library under conditions whereby the target-specific hybridization probes hybridize to the target sequences. The method also includes the steps of selecting a group of nucleic acid fragments from the nucleic acid library bound to the target-specific hybridization probes; and sequencing the group of nucleic acid fragments bound to the target-specific hybridization probes. Additionally or alternatively, detection of a genetic biomarker can include a method of providing probes for off-target sequence capture in a targeted sequencing reaction. The method includes the steps of receiving a request for a set of target-specific hybridization probes. The method also includes the steps of contacting the target-specific hybridization probes with a reference nucleic acid library generated from a reference sample, the nucleic acid library comprising a plurality of nucleic acid fragments, to generate a reference group of target-specific and off-target nucleic acid fragments bound to the target-specific hybridization probes and separating the reference group of nucleic acid fragments bound to the target-specific hybridization probes from unbound nucleic acid fragments. The method also includes the steps of sequencing the reference group of nucleic acid fragments to generate reference sequencing data; identifying off-target sequences in the reference sequencing data; and providing a set of off-target hybridization probes based on the identified off-target sequences. Additionally or alternatively, detection of a genetic biomarker can include a sequencing kit for reducing off-target capture in a targeted sequencing reaction that includes a set of off-target hybridization probes that specifically bind to a plurality of off-target sequences present in a nucleic acid library generated from a sample, the nucleic acid library comprising a plurality of nucleic acid fragments and a set of target-specific hybridization probes that specifically bind to a plurality of target sequences present in the nucleic acid library.

In some embodiments, detection of a genetic biomarker (e.g., one or more genetic biomarkers) can include any of the variety of methods described in U.S. Patent Application Publication No. 2016/0319345, which is hereby incorporated by reference in its entirety. For example, detection of a genetic biomarker can include methods, apparatus, systems, and computer program products for determining nucleic acid fragment sequences using unique molecular indices (UMIs). In various implementations, sequencing methods determine the sequences of nucleic acid fragments from both strands of the nucleic acid fragments. In some implementations, the methods employ physical UMIs located on one or both strands of sequencing adapters. In some implementations, the methods also employ virtual UMIs located on both strands of the nucleic acid fragments. One aspect relates to a method for sequencing nucleic acid molecules from a sample using unique molecular indices (UMIs). Each unique molecular index (UMI) is an oligonucleotide sequence that can be used to identify an individual molecule of a double-stranded DNA fragment in the sample. The method include: (a) applying adapters to both ends of double-stranded DNA fragments in the sample, wherein the adapters each include a double-stranded hybridized region, a single-stranded 5' arm, a single-stranded 3' arm, and a physical UMI on one strand or each strand of the adapters, thereby obtaining DNA-adapter products; (b) amplifying both strands of the DNA-adapter products to obtain a plurality of amplified polynucleotides; (c) sequencing the plurality of amplified polynucleotides, thereby obtaining a plurality of reads each associated with a physical UMI; (d) identifying a plurality of physical UMIs associated with the plurality of reads; (e) identifying a plurality of virtual UMIs associated with the plurality of reads, wherein each virtual UMI is a sequence found in a DNA fragment in the sample; and (f) determining sequences of the double-stranded DNA fragments in the sample using the plurality of reads obtained in (c), the plurality of physical UMIs identified in (d), and the plurality of virtual UMIs identified in (e). In some implementations, the method include operation (f) includes: (i) combining, for each of one or more of the double-stranded DNA fragments in the sample, (1) reads having a first physical UMI and at least one virtual UMI in the 5' to 3' direction and (2) reads having a second physical UMI and the at least one virtual UMI in the 5' to 3' direction to determine a consensus nucleotide sequence; and (ii) determining, for each of the one or more of the double-stranded DNA fragments in the sample, a sequence using the consensus nucleotide sequence. In some implementations, the adapters each include a physical UMI on only one strand of the adapters on the single-stranded 5' arm or the single-stranded 3' arm. In some of these implementation, (f) includes: (i) collapsing reads having a same first physical UMI into a first group to obtain a first consensus nucleotide sequence; (ii) collapsing reads having a same second physical UMI into a second group to obtain a second consensus nucleotide sequence; and (iii) determining, using the first and second consensus nucleotide sequences, a sequence of one of the double-stranded DNA fragments in the sample. In some implementations, (iii) includes: (1) obtaining, using localization information and sequence information of the first and second consensus nucleotide sequences, a third consensus nucleotide sequence, and (2) determining, using the third consensus nucleotide sequence, the sequence of one of the double-stranded DNA fragments. In some implementations, operation (e) includes identifying the plurality of virtual UMIs, while the adapters each include the physical UMI on only one strand of the adapters in the single-stranded 5' arm region or the single-stranded 3' arm region. In some implementations, (f) includes: (i) combining reads having a first physical UMI and at least one virtual UMI in the 5' to 3' direction and reads having a second physical UMI and the at least one virtual UMI in the 5' to 3' direction to determine a consensus nucleotide sequence; and (ii) determining a sequence of one of the double-stranded DNA fragments in the sample using the consensus nucleotide sequence. In some implementations of the methods above, obtaining the plurality of reads in operation (c) includes: obtaining two pair-end reads from each of the amplified polynucleotides, where in the two pair-end reads include a long read and a short read, the long read being longer than the short read. In some of these implementations, operation (f) includes: combining read pairs associated with a first physical UMI into a first group and combining read pairs associated with a second physical UMI into a second group, wherein the first and the second physical UMIs are uniquely associated with a double-stranded fragment in the sample; and determining the sequence of the double-stranded fragment in the sample using sequence information of long reads in the first group and sequence information of long reads in the second group. Another aspect adapters to both ends of double-stranded DNA fragments in the sample, wherein the adapters each include a double-stranded hybridized region, a single-stranded 5' arm, a single-stranded 3' arm, and a physical unique molecular index (UMI) on the single-stranded 5' arm or the single-stranded 3' arm; (b) amplifying both strands of ligation products from (a), thereby obtaining a plurality of single-stranded, amplified polynucleotides; (c) sequencing the plurality of amplified polynucleotides, thereby obtaining a plurality of reads each associated with a physical UMI; (d) identifying a plurality of physical UMIs associated with the plurality of reads; and (e) determining sequences of the double-stranded DNA fragments in the sample using the plurality of sequences obtained in (c) and the plurality of physical UMIs identified in (d). An additional aspect relates to a method for sequencing nucleic acid molecules from a sample. The method includes: (a) attaching adapters to both ends of double-stranded DNA fragments in the sample, wherein the adapters each include a double-stranded hybridized region, a single-stranded 5' arm, a single-stranded 3' arm, and a physical unique molecular index (UMI) shorter than 12 nucleotides on one strand or each strand of the adapters; (b) amplifying both strands of ligation products from (a), thereby obtaining a plurality of single-stranded, amplified polynucleotides each including a physical UMI; (c) sequencing the plurality of amplified polynucleotides, thereby obtaining a plurality of reads each associated with a physical UMI; (d) identifying a plurality of physical UMIs associated with the plurality of reads; and (e) determining sequences of the double-stranded DNA fragments in the sample using the plurality of reads obtained in (c) and the plurality of physical UMIs identified in (d). Another aspect relates a method for making a duplex sequencing adapter having a physical UMI on each strand. The method includes: providing a preliminary sequencing adapter including a double-stranded hybridized region, two single-stranded arms, and an overhang including 5'-CCANNNNANNNNTGG-3' at an end of the double-stranded hybridized region that is further away from the two single stranded arms; extending one strand of the double-stranded hybridized region using the overhang as a template, thereby producing an extension product; and applying restriction enzyme Xcm1 to digest a double-stranded end of the extension product, thereby producing the duplex sequencing adapter having a physical UMI on each strand. In some implementations, the preliminary sequencing adapter includes a read primer sequence on each strand. A further aspect relates to a computer program product including a non-transitory machine readable medium storing program code that, when executed by one or more processors of a computer system, causes the computer system to implement a method for determining sequence information of a sequence of interest in a sample using unique molecular indices (UMIs). The program code includes: (a) code for obtaining reads of a plurality of amplified polynucleotides, wherein the plurality of amplified polynucleotides are obtained by amplifying double-stranded DNA fragments in the sample including the sequence of interest and attaching adapters to the double-stranded DNA fragments; (b) code for identifying a plurality of physical UMIs in the reads of the plurality of amplified polynucleotides, wherein each physical UMI is found in an adapter attached to one of the double-stranded DNA fragments; (c) code for identifying a plurality of virtual UMIs in the received reads of the plurality of amplified polynucleotides, wherein each virtual UMI is found in an individual molecule of one of the double-stranded DNA fragments; and (c) code for determining sequences of the double-stranded DNA fragments using the reads of the plurality of amplified polynucleotides, the plurality of physical UMIs, and the plurality of virtual UMIs, thereby reducing errors in the determined sequences of the double-stranded DNA fragments. In some implementations, the adapters each include a double-stranded hybridized region, a single-stranded 5' arm, a single-stranded 3' arm, and a physical unique molecular index (UMI) on one strand or each strand of the adapters. An additional aspect relates to a computer system, including: one or more processors; system memory; and one or more computer-readable storage media. The media has stored thereon computer-executable instructions that causes the computer system to implement a method to determine sequence information of a sequence of interest in a sample using unique molecular indices (UMIs), which are oligonucleotide sequences that can be used to identify individual molecules of double-stranded DNA fragments in the sample. The instructions includes: (a) receiving reads of a plurality of amplified polynucleotides, wherein the plurality of amplified polynucleotides are obtained by amplifying double-stranded DNA fragments in the sample including the sequence of interest and attaching adapters to the double-stranded DNA fragments; (b) identifying a plurality of physical UMIs in the received reads of the plurality of amplified polynucleotides, wherein each physical UMI is found in an adapter attached to one of the double-stranded DNA fragments; (c) identifying a plurality of virtual UMIs in the received reads of the plurality of amplified polynucleotides, wherein each virtual UMI is found in an individual molecule of one of the double-stranded DNA fragments; and (d) determining sequences of the double-stranded DNA fragments using the sequences of the plurality of amplified polynucleotides, the plurality of physical UMIs, and the plurality of virtual UMIs, thereby reducing errors in the determined sequences of the double-stranded DNA fragments. One aspect provides methods for sequencing nucleic acid molecules from a sample using nonrandom unique molecular indices (UMIs). The methods involve: (a) applying adapters to both ends of DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products; (b) amplifying the DNA-adapter products to obtain a plurality of amplified polynucleotides; (c) sequencing the plurality of amplified polynucleotides, thereby obtaining a plurality of reads associated with a plurality of nonrandom UMIs; (d) from the plurality of reads, identifying reads sharing a common nonrandom UMI; and (e) from the identified reads sharing the common nonrandom UMI, determining the sequence of at least a portion of a DNA fragment, from the sample, having an applied adaptor with the common non-random UMI. Another aspect relates to methods for sequencing nucleic acid molecules from a sample using nonrandom unique molecular indices (UMIs). In some implementations, a method involves: (a) applying adapters to both ends of double-stranded DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products, wherein the non-random UMI can be combined with other information to uniquely identify an individual molecule of the double-stranded DNA fragments; (b) amplifying both strands of the DNA-adapter products to obtain a plurality of amplified polynucleotides; (c) sequencing the plurality of amplified polynucleotides, thereby obtaining a plurality of reads each associated with a nonrandom UMI; (d) identifying a plurality of nonrandom UMIs associated with the plurality of reads; and (e) using the plurality of reads and the plurality of nonrandom UMIs to determine sequences of the double-stranded DNA fragments in the sample. Additionally or alternatively, detection of a genetic biomarker can include a system, apparatus, and computer program products for determining DNA fragment sequences implementing the methods disclosed. One aspect provides a computer program product including a non-transitory machine readable medium storing program code that, when executed by one or more processors of a computer system, causes the computer system to implement a method to determine sequence information of a sequence of interest in a sample using unique molecular indices (UMIs). The program code includes instructions to perform the methods above.

In some embodiments, detection of a genetic biomarker (e.g., one or more genetic biomarkers) can include any of the variety of methods described in U.S. Patent Application Publication No. 2015/0360193, which is hereby incorporated by reference in its entirety. For example, detection of a genetic biomarker can include methods, compositions and kits for the amplification of nucleic acid samples to generate nucleic acid libraries. Additionally or alternatively, detection of a genetic biomarker can include a method of creating a nucleic acid library from a nucleic acid sample, the method comprising: a) providing a set of amplification primers to a nucleic acid sample, the set of amplification primers comprising a plurality of random primers and a plurality of locus specific primers, wherein the locus specific primers are configured to amplify a plurality of predetermined regions of the nucleic acid library, and wherein the random primers are in greater abundance compared to the locus specific primers; and b) amplifying the nucleic acid library using the set of amplification primers, thereby creating a nucleic acid library. Also presented is a kit for amplifying a nucleic acid sample, wherein the kit comprises a plurality of random primers and a plurality of locus specific primers configured to amplify a plurality of predetermined regions of a nucleic acid library. In certain aspects, the kit further comprises a set of instructions for using the random primers and the locus specific primers in an amplification reaction set, wherein the random primers are in greater abundance compared to the locus specific primers. In certain aspects, the kit further comprises a set of instructions for combining the set of amplification primers with a nucleic acid library and amplifying the nucleic acid library. In addition to the foregoing method, also presented is a method of creating a nucleic acid library from a nucleic acid sample, the method comprising: a) amplifying a nucleic acid sample with an AT-rich set of random amplification primers. In certain aspects, the AT-rich set of random amplification primers is a mixture of primers. Also presented is a kit for amplifying a nucleic acid sample, wherein the kit comprises an AT-rich set of random amplification primers. In certain aspects, the kit further comprises a set of instructions for combining the set of amplification primers with a nucleic acid library and amplifying the nucleic acid library. In certain other aspects, the kit further comprises a DNA polymerase. In still other aspects, the AT-rich set of random amplification primers is a mixture of primers. Additionally or alternatively, detection of a genetic biomarker can include a method of creating a nucleic acid library from a nucleic acid sample, the method comprising: a) amplifying a nucleic acid sample with a set of random amplification primers, the random amplification primers comprising AT-rich 5' tails. In certain aspects, the set of random amplification primers is a mixture of primers. Also presented is a method of creating a nucleic acid library from a nucleic acid sample, the method comprising: amplifying a nucleic acid sample with a set of variable-length random amplification primers, wherein each variable-length random amplification primer comprises a random 3' portion and a degenerate 5' tail, the degenerate 5' tail being proportional in length to the A/T content of the random 3' portion of the primer. In certain aspects, the set of variable-length random amplification primers is a mixture of primers. Also presented is a method of creating a nucleic acid library from a nucleic acid sample, the method comprising: a) amplifying a nucleic acid sample with a set of random amplification primers, wherein each primer comprises a random 3' portion and a constant 5' priming portion, thereby producing amplification products, wherein each amplification product comprises the constant 5' priming portion; b) circularizing the amplification products; and c) amplifying the circularized amplification products using primers which hybridize to the constant 5' priming portion. In certain aspects, the amplifying in step (c) comprises performing multiple displacement amplification. In certain aspects, the set of random amplification primers is a mixture of primers.

In some embodiments, detection of a genetic biomarker (e.g., one or more genetic biomarkers) can include any of the variety of methods described in U.S. Patent Application Publication No. 2015/0176071, which is hereby incorporated by reference in its entirety. For example, detection of a genetic biomarker can include determining proximity of sequence fragments with respect to a larger target nucleic acid from which the fragments were derived. For example, the methods can be used to determine phasing and to identify haplotypes for a relatively long target nucleic acid sequence when individual sequence reads are shorter than the length of the target nucleic acid under evaluation. Additionally or alternatively, detection of a genetic biomarker can include a method of sequencing a target nucleic acid polymer. The method can include the steps of (a) modifying a target nucleic acid polymer to produce a modified nucleic acid polymer, wherein the modified nucleic acid polymer includes a plurality of sequence regions from the target nucleic acid polymer; (b) producing fragments of the modified nucleic acid polymer in a vessel having a solid support surface, each fragment comprising one of the sequence regions; (c) capturing the fragments randomly at locations in a region of the solid support surface; (d) determining nucleotide sequences of the sequence regions by detecting the fragments at the locations; and (e) producing a representation of the nucleotide sequence for the target nucleic acid polymer based on the nucleotide sequences from the fragments and the relative distances between the locations on the solid support surface. Additionally or alternatively, detection of a genetic biomarker can include a method of sequencing a target nucleic acid polymer that includes the steps of (a) adding inserts into a target nucleic acid polymer to form a modified nucleic acid polymer including a plurality of internal inserts; (b) producing fragments of the modified nucleic acid polymer in a fluid that is in contact with a solid support surface, thereby releasing fragments that each include at least a portion of the inserts; (c) capturing the fragments from the fluid randomly at locations on a solid support surface; (d) determining nucleotide sequences from the fragments by detecting the fragments at the locations; and (e) producing a representation of the nucleotide sequence for the target nucleic acid polymer based on the nucleotide sequences from the fragments and the relative distances between the locations on the solid support surface. Additionally or alternatively, detection of a genetic biomarker can include a method of sequencing a target nucleic acid polymer, that includes the steps of (a) modifying a target nucleic acid polymer to produce a modified nucleic acid polymer, wherein the modified nucleic acid polymer includes a plurality of sequence regions from the target nucleic acid polymer; (b) attaching the modified nucleic acid polymer to a region on a solid support surface; (c) producing fragments of the modified nucleic acid polymer that is attached to the solid support surface, wherein the fragments are attached to locations at the region of the solid support surface; (d) determining nucleotide sequences from the fragments by detecting the fragments at the locations; and (e) producing a representation of the nucleotide sequence for the target nucleic acid polymers based on the nucleotide sequences from the fragments and the relative distances between the locations on the solid support surface. Additionally or alternatively, detection of a genetic biomarker can include a method of determining the source for individual sequences in a mixture of sequences from different sources. The method can include the steps of (a) providing a mixture of target nucleic acid polymers from a plurality of different sources; (b) modifying the mixture of target nucleic acid polymers to produce a mixture of modified nucleic acid polymers, wherein the mixture of modified nucleic acid polymers includes a plurality of sequence regions from the different sources; (c) producing fragments of the modified nucleic acid polymers in a vessel having a solid support surface, each fragment comprising a sequence region from a single one of the different sources; (d) capturing the fragments randomly at locations of the solid support surface, under conditions wherein fragments from a common target nucleic acid polymer preferentially localize to proximal locations on the solid support surface; (e) determining nucleotide sequences of the fragments at the locations; and (f) identifying the nucleotide sequences that are derived from a common source in the plurality of different sources based on the nucleotide sequences from the fragments and the relative distances between the locations on the solid support surface.

In some embodiments, detection of a genetic biomarker (e.g., one or more genetic biomarkers) can include any of the variety of methods described in U.S. Patent Application Publication No. 2014/0364323, which is hereby incorporated by reference in its entirety. For example, detection of a genetic biomarker can include methods for determining the presence of a plurality of nucleotide sequences of interest in a plurality of samples, while preserving the identity of each sample. The method can be used in many applications, including genotyping, expression analysis, and identification of individual species in complex samples. In one embodiment, each sample is contacted with a plurality of probe sets. A first probe has a first identification sequence and a first hybridization sequence complementary to a first portion of the sequence of interest. A second probe has a second hybridization sequence complementary to a second portion of the same sequence of interest and a second identification sequence. If the first hybridization sequence is hybridized to the first portion of the sequence of interest, and the second hybridization sequence is hybridized to the second portion of the same sequence of interest, then the first and second probes are joined. This can also be performed using ligation and/or extension methods, such as with a GoldenGate® assay design. The presence of the sequence of interest and the identity of the sample containing the sequence of interest are determined, based on identification sequence codes present in the joined probes.

In some embodiments, detection of a genetic biomarker (e.g., one or more genetic biomarkers) can include any of the variety of methods described in U.S. Patent Application Publication No. 2013/0059741, which is hereby incorporated by reference in its entirety. For example, detection of a genetic biomarker can include compositions and methods for assaying the presence of a target analyte in a sample using a solid support. Additionally or alternatively, detection of a genetic biomarker can include a solid support having a binding protein, such as an antibody, antibody fragment or protein receptor, immobilized to the solid support and at least two separate nucleic acid primers immobilized near the binding protein. Additionally or alternatively, detection of a genetic biomarker can include a solid support wherein a binding complex is formed between the binding protein immobilized to the solid support, a target analyte and a second binding protein. In some embodiments, a solid support is provided wherein such a binding complex further forms a hybridization complex between one nucleic acid primer immobilized on the solid support and an oligonucleotide tag linked to the second binding protein. Additionally or alternatively, detection of a genetic biomarker can include an array that in includes a plurality of these solid supports. In some embodiments, solid supports can be used in a method for detecting numerous target analytes. In one embodiment, the method for detecting a target analyte includes providing a solid support having a binding protein immobilized to the solid support and a second binding protein provided in solution, wherein the first binding protein recognizes and is capable of binding a target analyte in the presence of the second binding protein, which also recognizes and binds the same target analyte, contacting the solid support with target analyte and the second binding protein under sufficient conditions to allow formation of a binding complex between the target analyte and both the first and second binding proteins, hybridizing the oligonucleotide tag linked to the second binding protein to a first nucleic acid primer immobilized on the solid support, extending this first primer whereby a complement of the oligonucleotide tag is generated, amplifying the newly generated complement using a second nucleic acid primer immobilized to the solid support and detecting the presence of the amplicon, wherein the presence of the amplicon indicates the presence of the target analyte. Additionally or alternatively, detection of a genetic biomarker can include a method for detecting a target analyte, wherein the method described above alternatively proceeds following the extension step by hybridizing the complement of the oligonucleotide tag that is generated, to a second nucleic acid primer immobilized on the solid support forming a second hybridization complex, then extending the second nucleic acid primer with at least one labeled nucleic acid residue, using methods such as single base extension or sequencing by synthesis, wherein the nucleic acid residue added to the primer is dependent on the nucleic acid sequence of the oligonucleotide tag, followed by detecting the presence of the labeled nucleic acid residue on the solid surface, wherein the presence of the labeled nucleic acid residue indicates the presence of the target analyte.

In some embodiments, detection of a genetic biomarker (e.g., one or more genetic biomarkers) can include any of the variety of methods described in U.S. Patent Application Publication No. 2012/0156753, which is hereby incorporated by reference in its entirety. For example, detection of a genetic biomarker can include methods for 5' ligation tagging of uncapped RNA in a sample that has a 5' polyphosphate group, comprising: (A) providing: (i) a sample that contains uncapped RNA that has a 5' polyphosphate group, including wherein the sample additionally contains RNA that has a 5' monophosphate group and/or capped RNA and/or RNA that has a 5' hydroxyl group; (ii) RNA 5' polyphosphatase; (iii) an acceptor oligonucleotide that exhibits a tag; and (iv) RNA ligase; (B) contacting the sample with the RNA 5' polyphosphatase under conditions and for sufficient time wherein the uncapped RNA that has a 5' polyphosphate group is converted to RNA that has a 5' monophosphate group; and (C) contacting the sample from step (B) with the acceptor oligonucleotide and the RNA ligase under conditions and for sufficient time wherein the 3' end of the acceptor oligonucleotide is ligated to RNA that has a 5' monophosphate group but not to the capped RNA and 5'-ligation-tagged RNA is generated. In other embodiments, the sample provided in step (A) additionally contains RNA that has a 5' monophosphate group but the acceptor oligonucleotide is only ligated to the RNA that has a 5' monophosphate group which was converted from the uncapped RNA that has a 5' polyphosphate group in step (B) and is not ligated to the RNA that has a 5' monophosphate group already in the sample provided in step (A), wherein the method additionally comprises the substeps of: providing an RNA 5' monophosphatase; and, prior to step (B), contacting the sample with the RNA 5' monophosphatase under conditions and for sufficient time wherein RNA in the sample that has a 5' monophosphate group is converted to RNA that has a 5' hydroxyl group; and inactivating or removing the RNA 5' monophosphatase. In other embodiments, the method additionally comprises 5' ligation tagging of the capped RNA in the sample, wherein the method additionally comprises the substeps of: providing a nucleic acid pyrophosphatase or decapping enzyme; and, prior to step (C), contacting the sample from step (B) with the nucleic acid pyrophosphatase or the decapping enzyme under conditions and for sufficient time wherein capped RNA in the sample is converted to RNA that has a 5' monophosphate group, whereby the capped RNA contained in the sample provided in step (A) is also 5'-ligation tagged in step (C).

In some embodiments, detection of a genetic biomarker (e.g., one or more genetic biomarkers) can include any of the variety of methods described in U.S. Patent Application Publication No. 2012/0010091, which is hereby incorporated by reference in its entirety. For example, detection of a genetic biomarker can include a method for preparing a cDNA library from a plurality of single cells. In one aspect, the method includes the steps of releasing mRNA from each single cell to provide a plurality of individual mRNA samples, synthesizing a first strand of cDNA from the mRNA in each individual mRNA sample and incorporating a tag into the cDNA to provide a plurality of tagged cDNA samples, pooling the tagged cDNA samples and amplifying the pooled cDNA samples to generate a cDNA library having double-stranded cDNA. In some embodiments, a cDNA library can be produced by the above methods. Additionally or alternatively, detection of a genetic biomarker can include methods for analyzing gene expression in a plurality of cells by preparing a cDNA library as described above and sequencing the library.

In some embodiments, detection of a genetic biomarker (e.g., one or more genetic biomarkers) can include any of the variety of methods described in U.S. Patent Application Publication No. 2011/0152111, which is hereby incorporated by reference in its entirety. For example, detection of a genetic biomarker can include a method of detecting a target nucleic acid sequence in an archived tissue sample comprising providing a nucleic acid sample prepared from an archived tissue sample, hybridizing a first set of ligation probes to said target sequence to form a ligation structure, ligating said probes using a ligase to form a ligated probe, amplifying said ligated probe to form amplicons, and detecting said amplicons. Additionally or alternatively, detection of a genetic biomarker can include a method of detecting a plurality of target nucleic acid sequences in an archived tissue sample comprising providing a nucleic acid sample prepared from an archived tissue sample, said sample comprising a plurality of target nucleic acid sequences, adding a plurality of detection probes, each substantially complementary to one of said target nucleic acid sequences, providing an enzyme to form modified detection probes, amplifying said modified detection probes to form amplicons and detecting said amplicons. Additionally or alternatively, detection of a genetic biomarker can include a method of detecting a plurality of target nucleic acid sequences in an archived tissue sample comprising providing a nucleic acid sample prepared from an archived tissue sample, said sample comprising a plurality of target nucleic acid sequences, hybridizing a plurality of sets of ligation probes to said target sequence to form a plurality of ligation structures, ligating each of said plurality of ligation structures using a ligase to form a plurality of ligated probes, amplifying said ligated probes to form a plurality of amplicons and detecting said amplicons as an indication of the presence of said plurality of target nucleic acid sequences.

In some embodiments, detection of a genetic biomarker (e.g., one or more genetic biomarkers) can include any of the variety of methods described in P.C.T. Publication No. WO 2017/019456, which is hereby incorporated by reference in its entirety. For example, detection of a genetic biomarker can include methods and compositions that facilitate the characterization of transcriptomes and/or genomic variation in tissues while preserving spatial information related to the origin of target nucleic acids in the tissue. For example, the methods can enable the identification of the location of a cell or a cell cluster in a tissue biopsy that carries an aberrant mutation. The methods can therefore be useful for diagnostic purposes, e.g., for the diagnosis of cancer, and possibly aid in the selection of targeted therapies. Additionally or alternatively, detection of a genetic biomarker can include a capture array for spatial detection and analysis of nucleic acids in a tissue sample, comprising a capture site comprising a pair of capture probes immobilized on a surface, wherein a first capture probe of the pair of capture probes comprises a first primer binding region and a spatial address region, and wherein a second capture probe of the pair of capture probes comprises a second primer binding region and a capture region. Additionally or alternatively, detection of a genetic biomarker can include a method for spatial detection and analysis of nucleic acids in a tissue sample that includes (a) providing a capture array, comprising a capture site comprising a pair of capture probes immobilized on a surface, wherein a first capture probe of the pair of capture probes comprises a first primer binding region and a spatial address region, and wherein a second capture probe of the pair of capture probes comprises a second primer binding region and a capture region. Additionally or alternatively, detection of a genetic biomarker can include a method for spatial detection and analysis of nucleic acids in a tissue sample that includes providing a magnetic nanoparticle comprising an immobilized capture probe comprising a capture region. Additionally or alternatively, detection of a genetic biomarker can include a capture array for spatial detection and analysis of nucleic acids in a tissue sample, comprising a capture site comprising a capture probe comprising a spatial address region, and a transposon end (TE) region.

In some embodiments, detection of a genetic biomarker (e.g., one or more genetic biomarkers) can include any of the variety of methods described in P.C.T. Publication No. WO 2016/130704, which is hereby incorporated by reference in its entirety. For example, detection of a genetic biomarker can include to methods and compositions relating to evaluating components of a single cell preserved or embedded or contained within a contiguity preserving elements (CE). In one aspect are methods for analyzing plurality of analyte types from a single cell. In some embodiments, a plurality of contiguity preserving elements (CE) are provided, each CE comprises a single cell. The cells are lysed within the CE such that the plurality of analytes within the single cell are released within the CE. In some embodiments, plurality of types of reporter moieties are provided such that each type of reporter moiety is specific for each type of analyte. In some embodiments, the reporter moiety identify a single cell. The plurality of analytes are modified such that each type of analyte comprise a reporter moiety specific for the analyte type. In some embodiments, the CE comprising the analytes comprising said reporter moieties are combined. In some embodiments, the combined CE comprising the analytes comprising said reporter moieties are compartmentalized. In some embodiments, additional reporter moieties are provided and combined with the analytes comprising analytes such that the analytes comprise two or more different reporter moieties. The analytes comprising the reporter moieties are analyzed such that the identity of the analyte is detected and the reporter moiety identifies the source of the analyte from a single cell. In some embodiments, the exemplary plurality of analytes include but are not limited to DNA, RNA, cDNA, protein, lipids, carbohydrates, cellular organelles, (e.g., nucleus, Golgi apparatus, ribosomes, mitochondria, endoplasmic reticulum, chloroplast, cell membrane, etc.), cellular metabolites, tissue sections, cells, single cell, contents from cells or from a single cell, nucleic acid isolated from cells or from a single cell, or nucleic acid isolated from cells or from a single cell and further modified, or cell free DNA (e.g., from placental fluid or plasma). In some embodiments, the plurality of analytes include genomic DNA and mRNA. In some embodiments, the mRNA have poly A tail. In some embodiments, the genomic DNA and the mRNA are immobilized on a solid support within the CE simultaneously. In some embodiments, the immobilization of the genomic DNA is sequential to the immobilization of the mRNA to the solid support. In some embodiments, the genomic DNA is combined with transposome complexes and the transposon ends are immobilized on a solid support and the mRNA are immobilized to the solid by hybridization of oligo (dT) probes immobilized on a solid support. In some embodiments, the genomic DNA is combined with transposome complexes and, optionally, the transposon ends hybridize to complementary sequences immobilized on a solid support such that the mRNA are immobilized to the solid by hybridization of oligo (dT) probes immobilized on a solid support. Other methods can be used to immobilize the mRNA as well. In some embodiments, the solid support is a bead. In some embodiments, the solid support is a flow cell surface. In some embodiments, the solid surface is the wall of a reaction vessel. In some embodiments, the methods include sequencing nucleic acids preserved or embedded or contained within CE. Some embodiments relate to preparing DNA within CE to obtain phasing and sequence assembly information from a target nucleic acid, and obtaining phasing and sequence assembly sequence information from such templates. Particular embodiments relate to the use of integrases, for example transposases, to maintain physical proximity of associated ends of fragmented nucleic acids; and to the use of combinatoric indexing to create individual libraries from each CE. Obtaining haplotype information from CE includes distinguishing between different alleles (e.g., SNPs, genetic anomalies, etc.) in a target nucleic acid. Such methods are useful to characterize different alleles in a target nucleic acid, and to reduce the error rate in sequence information.

In some embodiments, detection of a genetic biomarker (e.g., one or more genetic biomarkers) can include any of the variety of methods described in P.C.T. Publication No. WO 2002/012897, which is hereby incorporated by reference in its entirety. For example, detection of a genetic biomarker can include array compositions comprising a substrate with a surface comprising discrete sites, at least one fiducial, and a population of microspheres comprising at least a first and a second subpopulation. Each subpopulation comprises a bioactive agent, and the microspheres are distributed on said surface. Each subpopulation may optionally comprise a unique optical signature, an identifier binding ligand that will bind a decoder binding ligand such that the identification of the bioactive agent can be elucidated, or both. In an additional aspect, compositions comprising a computer readable memory to direct a computer to function in a specified manner are provided. The computer readable memory comprises an acquisition module for receiving a data image of a random array comprising a plurality of discrete sites, a registration module for registering a data image, and a comparison module for comparing registered data images. Each module comprises computer code for carrying out its function. The registration module may utilize any number of fiducials, including a fiducial, fiber when the substrate comprises a fiber optic bundle, a fiducial microsphere, or a fiducial template generated from the random array. In some embodiments, methods of making the array compositions comprise forming a surface comprising individual sites on a substrate, distributing microspheres on the surface such that the individual sites contain microspheres, and incorporating at least one fiducial onto the surface are provided. When the array has complete rotational freedom, at least two fiducials are preferred in the array to allow for correction of rotation. Additionally or alternatively, detection of a genetic biomarker can include methods for comparing separate data images of a random array. The methods comprise using a computer system to register a first data image of the random array to produce a registered first data image, using the computer system to register a second data image of the random array to produce a registered second data image, and comparing the first and the second registered data images to determine any differences between them. Some embodiments provide methods of decoding a random array composition comprising providing a random array composition. A first plurality of decoding binding ligands is added to the array composition and a first data image is created. A fiducial is used to generate a first registered data image. A second plurality of decoding binding ligands is added to the array composition and a second data image is created. The fiducial is used to generate a second registered data image. A computer system is used to compare the first and the second registered data image to identify the location of at least two bioactive agents. Some embodiments provide methods of determining the presence of a target analyte in a sample. The methods comprise acquiring a first data image of a random array composition, and registering the first data image to create a registered first data image. The sample is then added to the random array and a second data image is acquired from the array. The second data image is registered to create a registered second data image. Then the first and the second registered data images are compared to determine the presence or absence of the target analyte. Optionally, the data acquisition may be at different wavelengths. Some embodiments provide methods for preprocessing or prefiltering signal data comprising acquiring a data image from an array, and determining the similarity of a first signal from at least one array site to a reference signal to determine whether the site comprises a candidate bead.

In some embodiments, detection of a genetic biomarker (e.g., one or more genetic biomarkers) can include any of the variety of methods described in P.C.T. Publication No. WO 2018/136416, which is hereby incorporated by reference in its entirety. For example, detection of a genetic biomarker can include methods and systems for identifying splice variants. In one implementation, a method comprises: determining one or more sample splice junctions from a plurality of RNA sequence reads from a single biological sample; retrieving, a set of baseline splice junctions determined from a plurality of healthy RNA samples; comparing the one or more sample splice junctions to the set of baseline splice junctions; and identifying one or more filtered sample splice junctions, the filtered sample splice junctions comprising sample splice junctions that do not overlap with the baseline splice junctions, wherein the one or more filtered sample splice junctions are candidate oncogenic events. Some embodiments further comprise outputting the list of candidate oncogenic events. In some embodiments, the plurality of healthy RNA samples comprises healthy RNA samples taken from a cross section of one or more of: geographical regions, ages, genders, ethnic groups, tissue types, or sample preservation qualities type. In some embodiments, the plurality of healthy RNA samples comprises samples from one or more tissue types selected from the group consisting of: lung, adrenal gland, bladder, breast, ovary, liver, prostate, skin, and spleen. In some embodiments, the plurality of healthy RNA samples comprises samples from donors across a range of ages. In some embodiments, the baseline splice junctions from the plurality of healthy RNA samples are determined prior to the determining the sample junctions from the single sample. In some embodiments, the plurality of healthy RNA samples for the base line splice junctions are not obtained from the same biological object as the single biological sample. In some embodiments, the baseline junctions are from a same genomic region as the sample junctions. In some embodiments, the single biological sample is from a tumor sample. In some embodiments, the sample splice junctions and the baseline splice junctions are both determined using a common assay. In some embodiments, determining the one or more sample junctions comprises: determining the plurality of RNA sequence reads from the single biological sample; retrieving, a DNA reference sequence aligned with the RNA sequence reads from the single biological sample; and determining one or more sample junctions as missing contiguous locations in the RNA read compared with the DNA reference. In some embodiments, the filtered sample splice junctions do not overlap with third party junctions, the third party junctions determined from a splice graph that captures multiple alternate combinations of exons for a given gene. In some embodiments, the set of baseline splice junctions are determined without determining a splice graph that captures multiple alternate combinations of exons for a given gene. Some embodiments provide a system for identifying splice variants. The system includes a memory, at least one processor; and at least one non-transitory computer-readable medium containing instructions that, when executed by the at least one processor, cause the at least one processor to perform operations comprising determining one or more sample splice junctions from a plurality of RNA sequence reads from a single biological sample; retrieving, a set of baseline splice junctions determined from a plurality of healthy RNA samples; comparing the one or more sample splice junctions to the set of baseline splice junctions; and identifying one or more filtered sample splice junctions, the filtered sample splice junctions comprising sample splice junctions that do not overlap with the set of baseline splice junctions, wherein the filtered sample splice junctions are candidate oncogenic events.

In some embodiments, detection of a genetic biomarker (e.g., one or more genetic biomarkers) can include any of the variety of methods described in P.C.T. Publication No. WO 2018/093780, which is hereby incorporated by reference in its entirety. For example, detection of a genetic biomarker can include a computer implemented method for validating variant calls. The method operates under control of one or more processors executing program instructions for, receiving sequencing data including a sample read that has a corresponding sequence of nucleotides along the genomic sequence of interest, receiving an indication of a potential variant call at a designated position within the sequence of nucleotides along the genomic sequence of interest, and obtaining baseline variant frequencies at the designated position within one or more baseline genomic sequences. The method obtains a sample variant frequency at the designated position for the genomic sequence of interest.

The method analyzes the baseline and sample variant frequencies at the designated position to obtain a quality score; and validates the potential variant call for the genomic sequence of interest based on the quality score. Optionally, the analyzing operation includes obtaining a relation between the sample variant frequency and a distribution of the baseline variant frequencies, the quality score based on the relation. Optionally, the analyzing operation comprises indexing the sample variant frequency with respect to a distribution of the baseline variant frequencies. The relation may be based on a non-parametric Wilcoxon rank sum test. The baseline variant frequencies indicate a degree of background noise at corresponding positions along the baseline genomic sequence. Optionally, the validating further comprises comparing the quality score to a threshold; and declaring the potential variant call to be a valid variant call when the quality score exceeds the threshold. The baseline variant frequencies may be derived from multiple baseline genomic sequences that are associated with more than one type of allele. Optionally, the method further comprises receiving sequencing data that includes a plurality of reference reads of a sequence of nucleotides along the baseline genomic sequence, and determining the baseline variant frequencies for the reference reads at the designated positions. The determining of the baseline variant frequencies may further comprise receiving the sequencing data from the reference reads for a set of positions within a current base pair window; identifying a candidate variant frequency for one or more positions in the set of positions within the current base pair window; selecting one of the candidate variant frequencies as the baseline variant frequency for a designated position within the reference read; and shifting the base pair window along the baseline genomic sequence and repeating the operations. In accordance with the above embodiments, systems and methods are described to reduce false positive variant calling from systematic errors. Systematic errors may arise due to various factors such as FFPE artifacts, sequencing errors, library preparation errors, PCR errors and the like. Variant calls are statically subjected to a locus specific background error distribution that may be compiled from a panel of FFPE normal samples with varied DNA quality from various tissues sequenced by the NGS-based assay. The same sequencing data of the FFPE normal samples may also be utilized to normalize systematic bias in read coverage caused by PCR, DNA quality, probe pulldown efficiency, or sequence GC content to reveal the true copy number alterations in a test sample. To further enlarge the signal to noise ratio in CNV calling, additional enhancer probes may be added in the hybrid capture to provide robust estimation of gene amplification. Additionally or alternatively, detection of a genetic biomarker can include methods and systems that address noise problems and prevent systematic errors from contributing to false positive variant calls. In connection there with, a set of normal samples is used to identify systematic bias in order for the system to increase the calling stringency in tumor samples in regions with high background noise. For FFPE samples, normal FFPE samples may be used to construct the baseline. For ctDNA samples, normal genomic DNA data may be used to construct the baseline.

In some embodiments, detection of a genetic biomarker (e.g., one or more genetic biomarkers) can include any of the variety of methods described in P.C.T. Publication No. WO 2018/068014, which is hereby incorporated by reference in its entirety. For example, detection of a genetic biomarker can include systems and methods for sequencing polynucleotides. In one embodiment, the system comprises: a memory comprising a reference nucleotide sequence; a processor configured to execute instructions that perform a method comprising: receiving a first nucleotide subsequence of a read from a sequencing system; processing the first nucleotide subsequence using a first alignment path to determine a first plurality of candidate locations of the read on the reference sequence; determining whether the first nucleotide subsequence aligns to the reference sequence based on the determined candidate locations; receiving a second nucleotide subsequence from the sequencing system; processing the second nucleotide subsequence to determine a second plurality of candidate locations of the read that align to the reference sequence using: a second alignment path if the read is aligned to the reference sequence, and the first alignment path if otherwise, wherein the second alignment path is more computationally efficient than the first alignment path to determine the second plurality of candidate locations of the read. In one embodiment, the method comprises: receiving a first nucleotide subsequence from a sequencing system during a sequencing run; and performing a secondary analysis of the first nucleotide subsequence of a read based on a reference sequence using a first analysis path or a second analysis path, wherein the second analysis path is more computationally efficient than the first processing path in performing the secondary analysis.

In some embodiments, detection of a genetic biomarker (e.g., one or more genetic biomarkers) can include any of the variety of methods described in P.C.T. Publication No. WO 2018/057770, which is hereby incorporated by reference in its entirety. For example, detection of a genetic biomarker can include detection of copy number variations in a biological sample. In one embodiment, copy number variants may be at least a single gene in size. In another embodiment, copy number variants may be at least 140 bp, 140-280 bp, or at least 500 bp. In one embodiment, a "copy number variant" refers to the sequence of nucleic acid in which copy-number differences are found by comparison of a sequence of interest in test sample with an expected level of the sequence of interest. In some embodiments, a reference sample is derived from a set of sequencing data of unmatched samples to generate normalization information that permits an individual test sample to be normalized such that deviations from expected copy numbers may be determined on normalized sequencing data. The normalization data is generated using the techniques provided and permits normalization to a hypothetical most representative sample matched to the test sample. By normalizing the test sample, noise introduced by sequencing or other bias is removed. In certain embodiments, the raw sequencing data coverage from a targeted sequencing run is normalized to reduce technical and biological noise to improve CNV detection. In one embodiment, samples of interest (e.g., fixed formalin paraffin embedded samples) are sequenced according to a desired sequencing technique, such as a targeted sequencing technique that uses a sequencing panel of probes to target regions of interest. Once the sequencing data is collected, the sequencing data is normalized to remove noise, and the normalized data is subsequently analyzed to detect CNVs. In some embodiments, a method of normalizing copy number is provided that includes the steps of receiving a sequencing request from a user to sequence one or more regions of interest in a biological sample; acquiring baseline sequencing data from the one or more regions of interest from a plurality of baseline biological samples that are not matched to the biological sample; determining copy number normalization information using the baseline sequencing data, wherein the copy number normalization information comprises at least one copy number baseline for a region of interest of the one or more regions of interest; and providing the copy number normalization information to the user. In another embodiment, a method of detecting copy number variation is provided that includes the steps of acquiring sequencing data from a biological sample, wherein the sequencing data comprises a plurality of raw sequencing read counts for a respective plurality of regions of interest; and normalizing the sequencing data to remove region-dependent coverage. The normalizing comprises: for each region of interest, comparing a raw sequencing read count of one or bins in a region of interest of the biological sample to a baseline median sequencing read count to generate a baseline-corrected sequencing read count for the one or more bins in the region of interest, wherein the baseline median sequencing read count for one or more bins in the region of interest is derived from a plurality of baseline samples that are not matched to the biological sample and is determined from only the most representative portions of the baseline sequencing data for each region of interest; and removing GC bias from the baseline-corrected sequencing read count to generate a normalized sequencing read count for each region of interest. The method also includes determining copy number variation in each region of interest based on the normalized sequencing read count of the one or more bins in each region of interest. In another embodiment, a method of assessing a targeted sequencing panel is provided that includes the steps of identifying a first plurality of targets in a genome for a targeted sequencing panel, wherein the first plurality of targets corresponds to portions of a respective plurality of genes; determining a GC content of each of the first plurality of targets; eliminating targets of the first plurality of targets with GC content outside of a predetermined range to yield a second plurality of targets smaller than the first plurality of targets; when, after the eliminating, the an individual gene has fewer than a predetermined number of targets corresponding portions to the individual gene, identifying additional targets in the individual gene; adding the additional targets to the second plurality to yield a third plurality of targets; and providing a sequencing panel comprising probes specific for the third plurality of targets.

In some embodiments, detection of a genetic biomarker (e.g., one or more genetic biomarkers) can include any of the variety of methods described in P.C.T. Publication No. WO 2017/197027, which is hereby incorporated by reference in its entirety. For example, detection of a genetic biomarker can include methods for enriching or amplifying polynucleotides, and more specifically to methods for enriching or amplifying a target DNA sequence using endonuclease systems, e.g., CRISPR-Cas systems or Argonaute systems, and applications thereof. Additionally or alternatively, detection of a genetic biomarker can include methods for amplifying a target double-stranded nucleic acid using CRISPR-Cas systems. Additionally or alternatively, detection of a genetic biomarker can include a method for amplifying a target double-stranded nucleic acid including: (a) providing a system having: a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; (b) contacting the target double-stranded nucleic acid with the system to form a complex; (c) hybridizing a primer to a second strand of the target double-stranded nucleic acid, the primer containing a sequence complementary to a region of the second strand of the target double-stranded nucleic acid, and (d) extending a nucleic acid complementary to the second strand of the target double-stranded nucleic acid from the primer using a polymerase. Additionally or alternatively, detection of a genetic biomarker can include a method for amplifying a target double-stranded nucleic acid comprising: (a) providing a first system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a target-specific nucleotide region complementary to a region of a first strand of the target double-stranded nucleic acid; (b) providing second system having: a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, the method further includes repeating step (a) and step (e) for one or more times, e.g., until a desired degree of amplification is reached. Additionally or alternatively, detection of a genetic biomarker can include a method for amplifying a target double-stranded nucleic acid including: (a) providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of a first strand of the target double-stranded nucleic acid; (b) contacting the target double-stranded nucleic acid with the system to form a complex; (c) hybridizing a primer to a second strand of the target double-stranded nucleic acid, the primer containing a sequence complementary to a region of the second strand of the target double-stranded nucleic acid, and (d) extending a nucleic acid complementary to the second strand of the target double-stranded nucleic acid from the primer using a polymerase. Additionally or alternatively, detection of a genetic biomarker can include a method for enriching a target nucleic acid including: obtaining a population of cell free DNA (cfDNA) from a subject's plasma or serum, the population of cell free DNA containing the target nucleic acid; providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of the target nucleic acid; contacting the target nucleic acid with the endonuclease system to form a complex, and separating the complex and thereby enriching for the target nucleic acid. Additionally or alternatively, detection of a genetic biomarker can include a method for detecting single nucleotide variant (SNV)

including: obtaining a population of cell free DNA from a subject's plasma or serum; providing a first system having: a first 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a region of a first target nucleic acid, and wherein the first Argonaute protein has nuclease activity; cleaving the first target nucleic acid using the first endonuclease system, and amplifying a second target nucleic acid using Polymerase Chain Reaction (PCR), wherein the second target nucleic acid contains a single nucleotide variant version of the first target nucleic acid. Additionally or alternatively, detection of a genetic biomarker can include a method for labeling a target nucleic including providing a first system having: a 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a first region of the target nucleic acid, and wherein the first Argonaute protein is capable of generating a single-stranded nick; contacting a double-stranded nucleic acid containing the target nucleic acid with the first nuclease system to generate a first single-stranded nick at the first region of the target nucleic acid, and labeling the target nucleic acid. In some embodiments, the method further includes separating the target nucleic acid through the labeling and thereby enriching the target nucleic acid. In some embodiments, the method further includes amplifying the target nucleic acid. In some embodiments, the method further includes providing a second system having: a second 5' phosphorylated single-stranded nucleic acid or a derivative thereof, and a second Argonaute protein or a variant thereof, wherein the second 5' phosphorylated single-stranded nucleic acid or the derivative thereof contains a second target-specific nucleotide region complementary to a second region of the target nucleic acid, and wherein the second Argonaute protein is capable of generating a single-stranded nick, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid. Additionally or alternatively, detection of a genetic biomarker can include a method for enriching a target nucleic acid including: providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions of the target nucleic acid; contacting the target nucleic acid with the population of Argonaute proteins programmed with the set of 5' phosphorylated single-stranded nucleic acids to generate a series of nucleic acid fragments, and ligating adaptors to at least one of nucleic acid fragments, wherein the Argonaute proteins are capable of generating double-stranded DNA breaks. Additionally or alternatively, detection of a genetic biomarker can include a method for sequencing a target nucleic acid including: providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions across the target nucleic acid; contacting the target nucleic acid with the population of Argonaute proteins programmed with the set of 5' phosphorylated single-stranded nucleic acids to generate a series of nucleic acid fragments, and sequencing the series of nucleic acid fragments. Additionally or alternatively, detection of a genetic biomarker can include a method for sequencing a target nucleic acids including: providing a plurality of populations of Argonaute proteins, each population of Argonaute proteins being programmed with a different set of 5' phosphorylated single-stranded nucleic acids, wherein each set of 5' phosphorylated single-stranded nucleic acids contains 5' phosphorylated single-stranded nucleic acids complementary to a different series of regions across the target nucleic acid, contacting the target nucleic acid with each of the plurality of populations of Argonaute proteins in a separate reaction to generate a different series of nucleic acid fragments, and sequencing the nucleic acid fragments.

In some embodiments, detection of a genetic biomarker (e.g., one or more genetic biomarkers) can include any of the variety of methods described in P.C.T. Publication No. WO 2015/198074, which is hereby incorporated by reference in its entirety. For example, detection of a genetic biomarker can include methods, apparatus, systems and computer program products for presenting sequence information. In some embodiments, this includes obtaining a first sequence and a second sequence, determining a similarity between the first sequence and the second sequence, wherein the similarity is based upon distance between the first sequence and the second sequence, and displaying a block at an intersection point on a matrix plot based on the similarity between the first sequence and the second sequence.

In some embodiments, detection of a genetic biomarker (e.g., one or more genetic biomarkers) can include any of the variety of methods described in P.C.T. Publication No. WO 2002/099982, which is hereby incorporated by reference in its entirety. For example, detection of a genetic biomarker can include a composition that includes a substrate with a surface comprising discrete sites, a reflective coating on the surface, and a population of microspheres distributed on the substrate. The microspheres comprise at least a first and a second subpopulation. Generally, at least one subpopulation comprises a bioactive agent. Additionally or alternatively, detection of a genetic biomarker can include a composition wherein the substrate comprises a first and a second surface, wherein the first surface comprises the discrete sites, and the reflective coating is on the second surface. The population of microspheres are distributed on the first surface. Additionally or alternatively, detection of a genetic biomarker can include a method of making a reflective array. The method includes providing a substrate with a surface comprising discrete sites, applying to the surface a coating of reflective material and distributing microspheres on the surface. Additionally or alternatively, detection of a genetic biomarker can include a method of detecting a non-labeled target analyte in a sample comprising providing a substrate with a plurality of discrete sites, distributing on the sites a population of microspheres comprising a bioactive agent and a signal transducer element, contacting the substrate with the sample, whereby upon binding of the target analyte to the bioactive agent, a signal from the signal transducer element is altered as an indication of the presence of the target analyte.

In some embodiments, detection of a genetic biomarker (e.g., one or more genetic biomarkers) can include any of the variety of methods described in P.C.T. Publication No. WO 2002/016649, which is hereby incorporated by reference in its entirety. For example, detection of a genetic biomarker can include a method of detecting a target nucleic acid. The method comprises contacting the target nucleic acid with an adapter sequence such that the target nucleic acid is joined to the adapter sequence to form a modified target nucleic acid. In addition, the method comprises contacting the modified target nucleic acid with an array comprising a substrate with a surface comprising discrete sites and a population of microspheres comprising at least a first subpopulation comprising a first capture probe, such that the first capture probe and the modified target nucleic acid form a complex, wherein the microspheres are distributed on the surface, and detecting the presence of the target nucleic acid. In addition, the method comprises adding at least one decoding binding ligand to the array such that the identity of the target nucleic acid is determined.

In some embodiments, detection of a genetic biomarker (e.g., one or more genetic biomarkers) can include any of the variety of methods described in U.S. Pat. No. 9,914,973, which is hereby incorporated by reference in its entirety. For example, detection of a genetic biomarker can include methods, compositions, and kits for detecting gene dysregulations such as those arising from gene fusions and chromosomal translocations. The methods, compositions and kits are useful for detecting mutations that cause the differential expression of a 5' region of a target gene relative to the 3' region of the target gene. Additionally or alternatively, detection of a genetic biomarker can include a method for detecting the presence or absence of a dysregulation in a target gene in a test sample. In one embodiment, the method includes: (a) amplifying portions of a 5' region of a transcript of the target gene or a cDNA derived therefrom, if present in a test sample, with two or more different 5' target primer pairs that are directed to the portions of the 5' region of the target gene; (b) amplifying portions of a 3' region of a transcript of the target gene or a cDNA derived therefrom, if present in the test sample, with two or more different 3' target primer pairs that are directed to the portions of 3' region of the target gene; (c) detecting the amplification products produced by the two or more 5' target primer pairs and the two or more 3' target primer pairs; (d) determining the average cycle threshold (Ct) among the two or more 5' target primer pairs and the average Ct among the two or more 3' target primer pairs, (e) calculating an IDE Score as the difference between the average cycle threshold among the 5' target primer pairs and the average cycle threshold among the 3' target primer pairs, and (f) identifying the test sample as (i) having a target gene dysregulation if the IDE Score is significantly different than a cutoff value and the difference indicates the presence of a target gene dysregulation, or (ii) not having a target gene dysregulation if the IDE Score in the test sample does not differ significantly from the cutoff value. Additionally or alternatively, detection of a genetic biomarker can include a method for diagnosing the presence or absence of cancer or a susceptibility to cancer in a subject. In one embodiment, the method includes: (a) obtaining a test sample that comprises nucleic acid from the subject; (b) amplifying portions of a 5' region of a transcript of a target gene or a cDNA derived therefrom, if present in the test sample, with two or more different 5' target primer pairs that are directed to the portions of the 5' region of the target gene; (c) amplifying portions of a 3' region of a transcript of the target gene or a cDNA derived therefrom, if present in the test sample, with two or more different 3' target primer pairs that are directed to the portions of the 3' region of the target gene; (d) detecting the amplification products produced by the two or more 5' target primer pairs and the two or more 3' target primer pairs; (e) determining the average cycle threshold (Ct) among the two or more 5' target primer pairs and the average Ct among the two or more 3' target primer pairs; (f) calculating an IDE Score as the difference between the average cycle threshold among the 5' target primer pairs and the average cycle threshold among the 3' target primer pairs, and (g) diagnosing the subject as (i) having cancer or a susceptibility to cancer when the IDE Score is significantly different than a cutoff value and the difference indicates the presence of cancer or a susceptibility to cancer, or (ii) not having cancer or a susceptibility to cancer resulting from dysregulation of the target gene if the IDE Score in the test sample does not differ significantly from the cutoff value. In some embodiments, the expression level of the 5' region of a target gene is determined by amplification using two, three, four, five or six different primer pairs directed to various portions of the 5' region of the target gene. Similarly, two, three, four, five or six different primer pairs directed to various portions of the 3' region of the target gene may be used to determine the expression level of the 3' region of the target gene. The amounts of amplification products each may be normalized to the amount of an endogenous control gene transcript ("Control") such as, for example, ABL. In some embodiments, the expression level or relative amount of transcript can be determined using real-time PCR and comparing the threshold cycle (Ct) for each amplicon. The average Ct values for each of the 3' (avgCt3') and 5' (avgCt5') regions of a target gene are used to calculate an IDE Score, which may be calculated as IDE=(avgCt5'−avgCt3'), or IDE= (avgCt5')/(Ctcontrol)−(avgCt3')/(Ctcontrol), or IDE-[Ln ((avgCt5')/Ctcontrol)]−[Ln((avgCt3')/Ctcontrol)]. In some embodiments, the Ct values are normalized to a reference sample.

In some embodiments, detection of a genetic biomarker (e.g., one or more genetic biomarkers) can include any of the variety of methods described in U.S. Pat. No. 9,783,854, which is hereby incorporated by reference in its entirety. For example, detection of a genetic biomarker can include methods and compositions for detecting target nucleic acids at very low levels and in the presence of large amounts of non-target nucleic acids. Generally, a target and non-target nucleic acid are distinguished by the presence or absence of a fragmentation site, such as a restriction enzyme recognition site. By differentiating the target and non-target by a fragmentation site, the methods and compositions can be used with various nucleic acid detection methods known in the art, such as PCR. Additionally or alternatively, detection of a genetic biomarker can include a method for detecting the presence or absence of a target nucleic acid by testing a sample that potentially contains the target nucleic acid in the presence of non-target nucleic acid, the method includes: a) fragmenting the sample nucleic acid under conditions such that a subsequent amplification directed to the target nucleic acid results in an increased detection of the target nucleic acid over the non-target nucleic acid as compared to amplification without fragmentation; b) amplifying the target nucleic acid with a pair of primers, where a first primer is specific for the target nucleic acid; and c) detecting the presence or absence of an amplification product, which indicates the presence or absence of the target nucleic acid in the sample. Additionally or alternatively, detection of a genetic biomarker can include a method for diagnosing a cancer or detecting the presence of a tumor cell by determining if an individual has a mutant sequence associated with the cancer or tumor cell type, the method includes: a) obtaining a sample including nucleic acid from the individual; b) fragmenting the sample nucleic acid under conditions such that a subsequent amplification directed to the target nucleic acid results in an increased detection of the target nucleic acid over the non-target nucleic acid as compared to amplification without fragmentation; c) amplifying the target nucleic acid with a pair of primers, where a first primer is specific for the target nucleic acid; and d) detecting the presence or absence of an amplification product containing the mutant sequence, where diagnosis of cancer is determined by the presence absence or amount of amplification product containing the mutant sequence. Additionally or alternatively, detection of a genetic biomarker can include a method for determining prognosis with cancer by determining if an individual has a mutant sequence associated with the cancer, the method includes: a) obtaining a sample containing nucleic acid from the individual; b) fragmenting the mutant nucleic acid under conditions such that a subsequent amplification directed to the mutant nucleic acid results in an increased detection of the mutant nucleic acid over the non-mutant nucleic acid as compared to amplification without fragmentation; c) amplifying the mutant nucleic acid with a pair of primers, where a first primer is specific for the mutant nucleic acid; and d) detecting the presence, absence and/or amount of an amplification product containing the mutant sequence, where the likelihood of an outcome in the individual is associated with the presence and or amount of mutant nucleic acid sequence. Additionally or alternatively, detection of a genetic biomarker can include a method for determining drug sensitivity of an individual diagnosed with cancer, the method includes: a) obtaining a sample comprising nucleic acid from the individual; b) fragmenting the mutant nucleic acid under conditions such that a subsequent amplification directed to the mutant nucleic acid results in an increased detection of the mutant nucleic acid over the non-mutant nucleic acid as compared to amplification without fragmentation; c) amplifying the mutant nucleic acid with a pair of primers, where a first primer is specific for the mutant nucleic acid; d) detecting the presence, absence and/or amount of an amplification product containing the mutant sequence; and e) relating the presence, absence and/or amount of an amplification product containing the mutant sequence to cancer drug sensitivity. In some embodiments, the mutated nucleic acid sequence is due to a deletion, insertion, substitution and/or translocation or combinations thereof. In preferred embodiments, fragmentation of nucleic acid sequence in which cleavage of wild-type sequence is with a restriction enzyme, Such pre-amplification digestion treatment allows for fragmentation to destroy or substantially decrease the number of wild-type sequences that might be amplified. In yet more preferred embodiments, the fragmentation using a restriction enzyme is combined with the use of a mutation specific primer (or mutated sequence primer). In preferred embodiments, a mutated sequence destroys or disrupts a restriction enzyme recognition site present in the corresponding wild-type sequence and that a mutation specific primer can be designed to bind to the mutated version of the sequence and not its wild-type counterpart. For example, a mutation specific primer can overlap a border region, which is a region that contains portions of both a wild-type sequence adjacent to a portion of the mutated sequence. In one approach, a sample is assayed for the presence or absence of a mutated sequence by amplification and detection of the resulting amplification products. In a preferred embodiment, amplification of target nucleic acids is accomplished by polymerase chain reaction (PCR). Single or multiple mutant sequences can be assayed. Amplification of multiple mutant sequences can be performed simultaneously in a single reaction vessel, e.g., multiplex PCR. In this case, probes may be distinguishably labeled and/or amplicons may be distinguishable by size differentiation. Alternatively, the assay could be performed in parallel in separate reaction vessels. In such later case, the probes could have the same label. In some embodiments, the methods further comprise a nucleic acid extraction step. In some embodiments, at least one primer of each primer pair in the amplification reaction is labeled with a detectable moiety. Thus, following amplification, the various target segments can be identified by size and color. The detectable moiety is preferably a fluorescent dye. In some embodiments, different pairs of primers in a multiplex PCR may be labeled with different distinguishable detectable moieties. Thus, for example, HEX and FAM fluorescent dyes may be present on different primers in multiplex PCR and associated with the resulting amplicons. In other embodiments, the forward primer is be labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length. Thus, in certain embodiments, at least two different fluorescent dyes are used to label different primers used in a single amplification. In still another embodiment, control primers can be labeled with one moiety, while the patient (or test sample) primers can be labeled with a different moiety, to allow for mixing of both samples (post PCR) and the simultaneous detection and comparison of signals of normal and test sample. In a modification of this embodiment, the primers used for control samples and patient samples can be switched to allow for further confirmation of results.

Analysis of amplified products from amplification reactions, such as multiplex PCR, can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label.

In some embodiments, detection of a genetic biomarker (e.g., one or more genetic biomarkers) can include any of the variety of methods described in U.S. Pat. No. 9,546,404, which is hereby incorporated by reference in its entirety. For example, detection of a genetic biomarker can include methods, compositions, and kits directed to the detection of gene dysregulations such as those arising from gene fusions and chromosomal abnormalities, e.g., translocations, insertions, inversions and deletions. In some embodiments, the methods, compositions and kits are useful for detecting mutations that cause the differential expression of a 5' region of a target gene relative to the 3' region of the target gene. Additionally or alternatively, detection of a genetic biomarker can include a method for detecting a dysregulation in a target gene. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the target gene is dysregulated. Additionally or alternatively, detection of a genetic biomarker can include a method for detecting the presence or absence of a dysregulation in a target gene in a sample. The method may include: (a) measuring the amount of transcription of a 5' region of the target gene and a 3' region of the target gene in the test sample; and (b) comparing the relative expression of the 5' region to the 3' region of the target gene in the test sample to the relative expression of the 5' region to the 3' region of the target gene in a reference sample. The method may also provide that a difference in the relative expression in the test sample compared to the reference sample is indicative of the presence of a gene dysregulation. In an embodiment, the relative amount of transcript can be determined using real-time PCR and comparing the threshold cycle, or Ct, value, for each amplicon. The Ct value can be normalized to a reference sample. Additionally or alternatively, detection of a genetic biomarker can include a method for diagnosing cancer or a susceptibility to cancer in a subject. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the subject has cancer or is susceptible to cancer resulting from a gene dysregulation. Additionally or alternatively, detection of a genetic biomarker can include a method for diagnosing prostate cancer or a susceptibility to prostate cancer in a subject. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the target gene is dysregulated. Optionally, the nucleic acid sample containing the target gene of interest may be subjected to another analysis to determine the nature of the gene dysregulation. Suitable analyses include, for example, comparative hybridization (e.g., comparative genomic hybridization). Comparative hybridization techniques such as comparative genomic hybridization (CGH) is limited by the fact that this technique is only able to detect unbalanced rearrangements (rearrangements that lead to gain or loss of genetic material). Comparative hybridization cannot adequately detect chromosomal abnormalities such as balanced translocations. Thus, any of the methods may be used in combination with a comparative hybridization technique. The combination of the methods with comparative hybridization (e.g., CGH) will be able to detect both balanced and unbalanced rearrangements and provide a more accurate diagnosis than if the comparative hybridization technique was used alone. In the case of unbalanced rearrangements, the comparative hybridization technique may be used as a confirmatory assay. In some embodiments, target gene dysregulations may arise from gene fusions and chromosomal abnormalities including, for example, translocations, deletions, inversions, and insertions. In some embodiments, the biological sample is contacted with the one or more 5' target primer pairs and the one or more 3' target primer in a multiplex amplification reaction. In one embodiment, the detecting is accomplished using a labeled oligonucleotide probe complementary to each amplification product. For example, each oligonucleotide probe may include a different detectable label, such as a donor fluorophore and quencher moiety. In another embodiment, at least one of the primers for the 5' region and/or at least one of the primers for the 3' region is detectably labeled, preferably with different detectable labels. In illustrative embodiments, the amplifying is performed using quantitative RT-PCR, e.g., real-time RT-PCR. In some embodiments, the chromosomal abnormality is selected from the group consisting of: a translocation, a deletion, an inversion, and an insertion. In one embodiment, the biological sample is a sample from a subject to be tested for a chromosomal abnormality. In some embodiments, the methods further include amplifying a region of an endogenous control gene transcript present in the biological sample with a primer pair complementary to the endogenous control gene and detecting the amplification of the region of the endogenous control gene. In some embodiments, the amount of amplified target gene transcripts (i.e., the 5' region and the 3' region) may be normalized to the amount of amplified endogenous control gene transcript. In some embodiments, the method further includes: (a) measuring the amount of transcription of a 5' region of a second target gene and a 3' region of the second target gene in the test sample; and (b) comparing the relative expression of the 5' region to the 3' region of the second target gene in the test sample to the relative expression of the 5' region to the 3' region of the second target gene in a reference sample. The method may also provide that a difference in the relative expression of both the target gene and the second target gene in the test sample compared to the reference sample is indicative of the presence of a target gene: second target gene translocation. Suitable biological samples include, for example, whole blood, isolated blood cells, plasma, serum, and urine.

In some embodiments, detection of a genetic biomarker (e.g., one or more genetic biomarkers) can include any of the variety of methods described in U.S. Pat. No. 8,911,942, which is hereby incorporated by reference in its entirety. For example, detection of a genetic biomarker can include a method of performing comparative hybridization by comparing the amount of test and reference nucleic acids hybridized to a nucleic acid array, the amounts determined by detecting a signal from the hybridized nucleic acids which are labeled with the same detectable label. This method is applicable to comparative hybridization methods in general and to comparative genomic hybridization (CGH) in particular. Accordingly, reference to CGH where the test and reference nucleic acid is genomic nucleic acid should be understood to encompass methods where the test and reference nucleic acids are other than genomic nucleic acids. In a preferred embodiment, CGH is performed using two samples of genomic nucleic acids; a test sample containing genomic nucleic acids, and a reference or control sample containing genomic nucleic acids with no known chromosomal or genetic abnormalities. The test sample and the reference sample are co-hybridized to a nucleic acid array that contains a plurality of nucleic acids or nucleic acid segments spotted onto a surface (such as a glass slide) at discrete locations. The array may contain target nucleic acid markers for certain known genetic mutations or disease states, or may represent (in aggregate) an entire chromosome, or the full chromosomal complement to obtain a genetic profile similar to karyotyping. In these approaches, the detectable label may be attached to the test and reference nucleic acids before hybridization or after hybridization. In another approach, the detectable label may be attached to one of the test or reference nucleic acids before hybridization while the label is attached to the other of the test or reference nucleic acid after hybridization. The detectable label may be attached covalently or non-covalently such as by a ligand-receptor interaction or by hybridization between complementary nucleotide sequences. In some embodiments, the comparative hybridization can be done using the same detectable label by another approach that may be referred to as an "additive" approach. In accordance with this approach, the test sample nucleic acids comprise a first tag; and the reference sample nucleic acids comprise a second tag. Following hybridization, the surface is contacted with a first complex containing a detectable label and a first entity, such that the first complex selectively binds with the first tag. The next step comprises determining the location and amount of the detectable label bound to the array surface (i.e., to "read" the array). Once the array is read to determine the amount of detectable label associated with nucleic acid that comprises the first tag, the surface is then contacted with a second complex containing the same detectable label as present in the first complex and containing a second entity, such that the second complex selectively binds with the second tag. The array is then read a second time to determine the location and amount of the total detectable label representing both nucleic acids hybridized to the surface. The last step comprises using the results of the two reads to determine the amount of the hybridized nucleic acid that is associated with the second tag. In a preferred approach, the first read is subtracted from the second read to obtain the signal representing the nucleic acid that is linked to the second tag. The signal from the two samples thus determined can be used to identify differences between the test sample genomic nucleic acids and the reference sample genomic nucleic acids so as to detect any chromosomal or genetic abnormalities associated with the test sample nucleic acid. In some embodiments, the amount of the hybridized nucleic acid that is associated with the second tag can be determined using a duplicate of the hybridized array but which has not been contacted with the first complex. Thus, the duplicate array is contacted with the second complex and not the first complex. The signal from this second array directly represents the amount of hybridized nucleic acid with the second tag, which can be compared to the amount of signal from the first array that was contacted only with the first complex and represents the amount of hybridized nucleic acid associated with the first tag. Because the two analyses are independent of each other, each array may be processed in any order or simultaneously. In some embodiments, one may first hybridize the array with the test and reference nucleic acids wherein one of the test and reference nucleic acids has already been labeled (e.g. by random priming). The array is then read after hybridization to determine signal corresponding with the particular labeled nucleic acid sample. The array is then contacted with a complex comprising a detectable label and an entity, wherein the complex selectively reacts with the other of the test or reference nucleic acid via a tag attached to said other of the test or reference nucleic acid. The assay is read again to measure the total signal for both hybridized nucleic acids. The next step comprises using the results of the two reads to determine the amount of the hybridized nucleic acid that is associated with the tag. In a preferred approach, the first read is subtracted from the second read to obtain the signal representing the nucleic acid that was linked to the tag. The signal from the two samples thus determined can be used to identify differences between the test sample genomic nucleic acids and the reference sample genomic nucleic acids so as to detect any chromosomal or genetic abnormalities associated with the test sample nucleic acid. In some embodiments, the hybridized nucleic acid that is associated with the second tag can be determined using a duplicate of the hybridized array except that the duplicate is prepared by hybridizing to test and reference nucleic acids that do not contain a detectable label. In this case, the duplicate array is contacted with a complex comprising a detectable label and an entity, wherein the complex selectively reacts with the other of the test or reference nucleic acid via a tag attached to said other of the test or reference nucleic acid. The signal from this second array directly represents the amount of hybridized nucleic acid with the second tag, which can be compared to the amount of signal from the first array that was contacted only with the first complex and represents the amount of hybridized nucleic acid associated with the first tag. Because the two analyses are independent of each other, each array may be processed in any order or simultaneously. Additionally or alternatively, detection of a genetic biomarker can include a method of comparing the expression of genes in a test sample versus that of reference sample. The first step of the method includes contacting under hybridization conditions cDNA prepared from mRNA of a test sample and cDNA prepared from mRNA of a reference sample to a surface containing a plurality of nucleic acid segments each immobilized at discrete locations on the surface. In this case, the test sample cDNA and the reference sample cDNA are labeled before or after hybridization with the same detectable label which is linked to the cDNA of the test sample via a first linkage, and to the cDNA of the reference sample via a second linkage. Either the first linkage or the second linkage is susceptible to selective removal and the detectable label linked to nucleic acids hybridized to the surface determined. The location and amount of detectable label linked to nucleic acids hybridized the surface of the support is determined. The label is then selectively removed from either the hybridized test sample cDNA or the hybridized reference sample cDNA. The location and amount of the detectable label remaining on the support is then determined and represents one of the samples. The difference between the location and amount remaining after removal compared and the location and amount prior to removal represents the other of the samples. The relative amount of each sample nucleic acid hybridized to the array reflects the expression of genes in the test sample compared to the reference sample.

In some embodiments, detection of a genetic biomarker (e.g., one or more genetic biomarkers) can include any of the variety of methods described in U.S. Pat. No. 8,871,687, which is hereby incorporated by reference in its entirety. For example, detection of a genetic biomarker can include a method for determining a sequence of contiguous bases within a polynucleotide, the method relying on single-base primer extension using labeled dideoxynucleotide terminators. The primers are immobilized to solid supports (e.g. microspheres or two-dimensional arrays), allowing for the identification of the labeled terminator incorporated into each primer. Data on the incorporated terminators is used to determine the base identity of a contiguous sequence of nucleotides in a target nucleic acid. Additionally or alternatively, detection of a genetic biomarker can include a method for determining a contiguous sequence comprising at least four bases of a target nucleic acid comprising: (a) preparing one or more reaction mixtures containing the target nucleic acid and four or more primers complementary to a portion of the target nucleic acid such that the primers each have a 3' end located 5' to each nucleotide position of the sequence to be determined, wherein each reaction contains from one to all of said primers in any combination and is under conditions where the primers anneal to the target nucleic acid; (b) extending the one or more primers from step (a) with a polymerase in the presence of one or more labeled dideoxynucleotides; (c) immobilizing said primers to a solid support; and (d) detecting the label of the dideoxynucleotide incorporated into each primer and utilizing this information to determine said contiguous sequence of at least four bases of the target nucleic acid. The primers may extended before immobilization to the solid support, i.e. step (b) occurs before step (c) or extended after immobilization on the solid support, i.e. step (c) occurs before step (a). In one embodiment, at least two differently-labeled dideoxynucleotides are provided in the same reaction mixture. In another embodiment, four differently-labeled dideoxynucleotides are provided in the same reaction mixture. Additionally or alternatively, detection of a genetic biomarker can include methods for determining a contiguous sequence of four or more bases of a target nucleic acid by performing singleplex single-base primer extension reactions or multiplex single-base primer extension reactions. In one embodiment, the four or more primers corresponding to the entire portion of the target nucleic acid to be sequenced are combined in a single reaction mixture. In another embodiment, two or more primers are combined in one reaction mixture, and two or more primers are combined in an additional reaction mixture or mixtures. Alternatively, the four or more primers are each added to a separate reaction mixture. In one embodiment, the primers comprise a tag sequence and are immobilized to the solid support via hybridization to a complementary capture oligonucleotide conjugated to the solid support. In another embodiment, the primers are immobilized to the solid support via a covalent attachment. In one embodiment, the solid support is a labeled microsphere. For example, the microspheres may be made of polystyrene. In one embodiment, the label of each microsphere is optically-detected, based upon varying concentrations of at least two dyes. In certain embodiments, the labeled microspheres and the labeled dideoxynucleotide are detected by flow cytometry. In another embodiment, the solid support is a two-dimensional array and the immobilized primers are positionally defined on the array. The primers may be immobilized to the array via a covalent attachment or via a linker sequence. In certain embodiments, the extended primers with labeled dideoxynucleotides are detected by scanning the array.

In some embodiments, detection of a genetic biomarker (e.g., one or more genetic biomarkers) can include any of the variety of methods described in U.S. Pat. No. 8,492,089, which is hereby incorporated by reference in its entirety. For example, detection of a genetic biomarker can include a method of performing comparative hybridization by comparing the amount of test and reference nucleic acids hybridized to a nucleic acid array, the amounts determined by detecting a signal from the hybridized nucleic acids which are labeled with the same detectable label. This method is applicable to comparative hybridization methods in general and to CGH in particular. Accordingly, reference to CGH where the test and reference nucleic acid is genomic nucleic acid should be understood to encompass methods where the test and reference nucleic acids are other than genomic nucleic acids. In a preferred embodiment, CGH is performed using two samples of genomic nucleic acids: a test sample containing genomic nucleic acids, and a reference or control sample containing genomic nucleic acids with no known chromosomal or genetic abnormalities. The test sample and the reference sample are co-hybridized to a nucleic acid array that contains a plurality of nucleic acids or nucleic acid segments spotted onto a surface (such as a glass slide) at discrete locations. The array may contain target nucleic acid markers for certain known genetic mutations or disease states, or may represent (in aggregate) an entire chromosome, or the full chromosomal complement to obtain a genetic profile similar to karyotyping. In these approaches, the detectable label may be attached to the test and reference nucleic acids before hybridization or after hybridization. In another approach, the detectable label may be attached to one of the test or reference nucleic acids before hybridization while the label is attached to the other of the test or reference nucleic acid after hybridization. The detectable label may be attached covalently or non-covalently such as by a ligand-receptor interaction or by hybridization between complementary nucleotide sequences. In some embodiments, the test and reference samples are labeled with a detectable label; preferably the test and reference samples are labeled with the same detectable label; preferably the detectable label is a flourochrome; preferably the detectable label is dCTP-Cy3. In certain aspects, methods are provided that allow for the use of a single label to determine the relative amount of test and reference nucleic acids hybridized to the array. Additionally or alternatively, detection of a genetic biomarker can include a method of determining differences between nucleic acid in a test sample and a reference sample, wherein the method involves amplifying nucleic acid sequence from the test sample nucleic acid and amplifying nucleic acid sequence from the reference sample nucleic acid, where one of the amplification reactions is conducted using dUTP and not dTTP and the other is conducted using dTTP and not dUTP; hybridizing to a nucleic acid array a solution comprising the amplified test sample and amplified reference sample; and determining the relative amount of hybridized test and reference nucleic acids bound to the array. In certain embodiments, determining the relative amount of hybridized test and reference nucleic acids includes a) determining a signal for the detectable label hybridized to the array representing the total of hybridized test and reference nucleic acid; b) treating the hybridized nucleic acids with an enzyme that selectively degrades DNA having uracil residues; and c) determining a signal for the detectable label hybridized to the array following step b), which signal represents one of the hybridized test or reference nucleic acid. In particularly preferred embodiments, the enzyme that selectively degrades DNA having uracil residues is uracil-DNA N-glycosylase (UNG). Additionally or alternatively, detection of a genetic biomarker can include a method of determining differences between nucleic acid in a test sample and a reference sample is provided, where the method involves: (a) contacting under hybridization conditions a test sample containing nucleic acids and a reference sample containing nucleic acids to a surface containing a plurality of nucleic acid segments each immobilized at discrete locations on the surface, where the test sample and the reference sample are labeled before or after hybridization with the same detectable label; (b) determining the location and amount of the detectable label linked to nucleic acids hybridized to the surface; (c) selectively removing either the hybridized test sample nucleic acids or the hybridized reference sample nucleic acids; (d) determining the location and amount of the detectable label linked to nucleic acids hybridized to the surface following step (c); and (e) comparing the results of step (b) to the results of step (d) to detect differences in the nucleic acids of the test sample and reference sample. In some preferred embodiments, the step of selectively removing hybridized test nucleic acids or reference nucleic acids is performed by subjecting the nucleic acids to an enzyme that selectively degrades DNA having certain properties; preferably an enzyme that degrades DNA having uracil residues; more preferably the enzyme that selectively degrades DNA having uracil residues is uracil-DNA N-glycosylase (UNG). In some embodiments, the step of selectively removing hybridized test nucleic acids or reference nucleic acids by subjecting nucleic acids to an enzyme that selectively degrades DNA having uracil residues is achieved by (1) amplifying sequence from a test sample and amplifying sequence from a reference sample nucleic acid, where one of the amplification reactions is conducted using dUTP and not dTTP and the other is conducted using dTTP and not dUTP; (2) hybridizing the amplified nucleic acids; and (3) treating the hybridized nucleic acids with an enzyme that selectively degrades DNA having uracil residues. In some embodiments, the methods may be used to detect any differences between nucleic acids in a test sample and a reference sample, including differences in the amount of nucleic acids having a particular sequence or differences in nucleic acid sequences. In particularly preferred embodiments, the methods are used to detect genetic abnormalities in the test sample. The methods may be applied to CGH using a chromosomal spread or array-based CGH. In some preferred embodiments, the methods provided may be used to compare the expression of genes in a test sample versus that of a reference sample. Additionally or alternatively, detection of a genetic biomarker can include a method of performing comparative hybridization. The method includes comparing the amount of test and reference nucleic acids hybridized to a nucleic acid array, wherein the amount of hybridized test and reference nucleic acids is determined by detecting a signal from the hybridized nucleic acids which are labeled with the same detectable label. In one embodiment, the amount of hybridized test and reference nucleic acids are determined by: a) determining a signal for the detectable label hybridized to the array representing the total of hybridized test and reference nucleic acid; b) treating the hybridized nucleic acids to selectively remove one of the test or reference nucleic acids; c) determining a signal for the detectable label hybridized to the array following step b), which represents one of the hybridized test or reference nucleic acid; and d) determining a signal for the other of the hybridized test or reference by using the signal from c) and b). In certain preferred embodiments, the step of amplifying sequence from a test sample and amplifying sequence from a reference sample involves amplifying genomic DNA in the samples is conducted using random priming such as is well known in the art. Alternatively, the step of amplifying sequence from a test sample and amplifying sequence from a reference sample may involve using RNA to generate cDNA and amplifying the cDNA using random priming and or amplifying specific sequences using particular primers. In certain preferred embodiments, the amplification reaction may be performed using one or more labeled nucleotides as a means to label the amplified nucleic acids with a detectable label; preferably both test and reference sample nucleic acids are amplified with the same labeled nucleotide; preferably the labeled nucleotide is dCTP-Cy3. Additionally or alternatively, detection of a genetic biomarker can include a method of comparing the expression of genes in a test sample versus that of a reference sample is provided. The method includes comparing the amount of cDNA prepared from mRNA of a test sample and cDNA prepared from mRNA of a reference sample hybridized to a nucleic acid array, the amount of hybridized test and reference cDNA determined by detecting a signal from the hybridized cDNA which is labeled with the same detectable label. The method involves amplifying nucleic acid sequence from cDNA prepared from RNA of the test sample and amplifying nucleic acid sequence from cDNA prepared from RNA of the reference sample, where one of the amplification reactions is conducted using dUTP and not dTTP and the other is conducted using dTTP and not dUTP; hybridizing to the nucleic acid array a solution comprising the amplified test sample and amplified reference sample; and determining the relative amount of hybridized test and reference nucleic acids bound to the array. In certain embodiments, determining the relative amount of hybridized test and reference nucleic acids includes a) determining a signal for the detectable label hybridized to the array representing the total of hybridized test and reference nucleic acid; b) treating the hybridized nucleic acids with an enzyme that selectively degrades DNA having uracil residues; and c) determining a signal for the detectable label hybridized to the array following step b), which signal represents one of the hybridized test or reference nucleic acid.

In some embodiments, detection of a genetic biomarker (e.g., one or more genetic biomarkers) can include any of the variety of methods described in U.S. Pat. No. 8,093,063, which is hereby incorporated by reference in its entirety. For example, detection of a genetic biomarker can methods for detecting a genomic nucleic acid of interest in a test sample without amplification and without the need for intact cells or nuclei. Generally, a genomic nucleic acid is hybridized to a labeled probe and anchored to a solid support through means other than nucleic acid hybridization. The genomic nucleic acid is detected by detecting the label in the hybridized complex on the solid support. The method may be used to detect a genetic abnormality e.g., point mutation, gene duplication or deletion, and chromosomal translocation. The method may also be used for diagnosis or prognosis of a disease. Additionally or alternatively, detection of a genetic biomarker can include a method for detecting a target sequence in genomic nucleic acid, by: a. contacting a sample of genomic nucleic acid containing the target sequence with a probe specific for the target sequence and forming on a solid support a complex consisting of the genomic nucleic acid and the probe hybridized to the target sequence, wherein the probe contains a detectable label, the genomic nucleic acid is anchored to the solid support through means other than nucleic acid hybridization and the target sequence of the genomic nucleic acid has not been amplified; and b. detecting the presence of the target sequence in the genomic nucleic acid by detecting association of the label with the solid support. Additionally or alternatively, detection of a genetic biomarker can include a method for detecting the presence or absence of a genetic abnormality in genomic nucleic acid, by: a. contacting a sample of genomic nucleic acid with a probe specific for the genetic abnormality and forming on a solid support a complex consisting of the genomic nucleic acid and the probe if the genetic abnormality is present in the genomic nucleic acid, the genomic nucleic acid is anchored to the solid support through means other than nucleic acid hybridization and the target sequence of the genomic nucleic acid has not been amplified; b. detecting the presence of the genetic abnormality by detecting association of the label with the solid support. Additionally or alternatively, detection of a genetic biomarker can include a method for detecting genetic abnormality in a genomic nucleic acid, by: a. contacting a sample of genomic nucleic acid containing the genetic abnormality with a first probe specific for the genetic abnormality and forming a first complex on a solid support consisting of the genomic nucleic acid and the first probe, wherein the probe contains a detectable label, the genomic nucleic acid is anchored to the solid support through means other than nucleic acid hybridization and the target sequence of the genomic nucleic acid has not been amplified; b. contacting a sample of genomic nucleic acid with a second probe specific for the reference nucleic acid and forming a second complex on a solid support consisting of the reference nucleic acid and the second probe, wherein the second probe contains a detectable label; and c. measuring the amount of the first complex formed by detecting the detectable label of the first probe associated with the complex and measuring the amount of second complex formed by detecting the detectable label of the second probe associated with the complex; and d. comparing the amount of the first complex to the amount of the second complex, wherein a difference in the amount of two complexes is an indicative of genetic abnormality. In some embodiments, the genomic nucleic acid and reference nucleic acid are from the same sample. In another embodiment of any of the foregoing aspects, the genomic nucleic acid and the reference nucleic acid are from a different sample, which may be from the same or different individuals. In another embodiment, the amount of first complex and the second complex are determined using the same solid support, and the detectable labels of the first probe and the second probe are different. Additionally or alternatively, detection of a genetic biomarker can include a method for detecting genetic abnormality in a genomic nucleic acid, by: a. contacting a sample of genomic nucleic acid containing the genetic abnormality with a first probe specific for the genetic abnormality and forming a first complex on a solid support consisting of the genomic nucleic acid and the first probe, wherein the probe contains a detectable label, the genomic nucleic acid is anchored to the solid support through means other than nucleic acid hybridization and the target sequence of the genomic nucleic acid has not been amplified; b. contacting a sample of genomic nucleic acid with a second probe specific for the reference nucleic acid and forming a second complex on a solid support consisting of the reference nucleic acid and the second probe, wherein the second probe contains a detectable label; and c. measuring the amount of the first complex formed by detecting the detectable label of the first probe associated with the complex and measuring the amount of second complex formed by detecting the detectable label of the second probe associated with the complex; and d. obtaining a ratio of the amount of the first and the second complex; and e. comparing the ratio obtained to a ratio similarly obtained using genomic nucleic acid from a reference sample, wherein a difference in the ratios is indicative of genetic abnormality. In preferred embodiments, the genomic nucleic acid and the reference nucleic acid are anchored to the solid support through interaction of biotin and avidin. In another preferred embodiment, the solid support is a bead. In another preferred embodiment, the first and second complexes are detected by flow cytometry. Additionally or alternatively, detection of a genetic biomarker can include a method for diagnosis in an individual by: a. contacting a sample of genomic nucleic acid from the individual with a probe complementary to nucleic acid sequence specific for the disease and forming on a solid support a complex consisting of the genomic nucleic acid and the probe if the genomic nucleic acid contains the nucleic acid sequence specific for the disease, wherein the probe contains a detectable label, the genomic nucleic acid is anchored to the solid support through means other than nucleic acid hybridization and the target sequence of the genomic nucleic acid has not been amplified; and b. measuring the amount of the complex formed on the solid support by detecting the amount of detectable label associated with the support; and c. comparing the amount of complex formed to the amount of complex formed using genomic nucleic acid from a reference sample assayed under similar conditions, wherein a difference in amount of complex formed from the individual as compared to the reference sample is diagnostic for the disease. In one embodiment, the reference sample may be obtained from an individual assumed to be free of the disease. In another embodiment, the reference sample may be obtained from an individual known to have the disease. In another embodiment, the reference sample is obtained from the same individual after obtaining the first sample. In one embodiment, the method may be used for measuring tumor burden in an individual suspected of having cancer. In another embodiment, the method may be used for prognosis of a disease. The genomic nucleic acid may be anchored covalently or non-covalently to the solid support. In some embodiments, the genomic nucleic acid may be anchored non-covalently to the solid support via a "binding pair," which refers to two molecules which form a complex through a specific interaction. Thus, the genomic nucleic acid can be captured on the solid support through an interaction between one member of the binding pair linked to the genomic nucleic acid and the other member of the binding pair coupled to the solid support. In a preferred embodiment, the binding pair is biotin and avidin, or variants of avidin e.g. streptavidin, and NeutrAvidin™. In other embodiments, the binding pair may be a ligand-receptor, a hormone-receptor, an antigen-antibody. In some embodiments, the genomic nucleic acid may be anchored to the solid support through covalent linking. In one embodiment, the covalent linking of the genomic nucleic acid to the solid support is achieved through photoactive groups e.g. azido, azidophenacyl, 4-nitrophenyl 3-diazopyruvate, psolarens, psolaren derivatives. In another embodiment, the genomic nucleic acid can be cross-linked to variety of solid surfaces by UV cross linking. In another embodiment, the genomic nucleic acid may be anchored to the solid support though chemical coupling using chemical linkers. In another preferred embodiment, the genomic nucleic acid is genomic DNA. In another embodiment, the reference nucleic acid is a house keeping gene or a single copy sequence in a chromosome. In some embodiments, the test sample or the reference sample containing genomic nucleic acid and reference nucleic acid, respectively, can be obtained from or accessed within cells, tissues, body fluids, plasma, serum, urine, central nervous system fluid, stool, bile duct, paraffin-embedded tissue, cell lysates, tissue lysates and the like. The test and reference nucleic acid may be obtained from any number of sources and by any method.

In some embodiments, detection of a genetic biomarker (e.g., one or more genetic biomarkers) can include any of the variety of methods described in U.S. Pat. No. 8,076,074, which is hereby incorporated by reference in its entirety. For example, detection of a genetic biomarker can include methods for detecting chromosomal abnormalities including balanced translocations, wherein the method involves performing array-based CGH in conjunction with probes for detecting the translocations. In one aspect, the methods involve hybridizing to a genomic nucleic acid array a test sample of genomic nucleic acid, a reference sample of nucleic acid, and at least one probe for detecting a balanced translocation; and determining the relative amount of hybridized test and reference nucleic acids hybridized to the array as well as determining hybridization to the array of the probe or probes for detecting the translocation. In a preferred embodiment, the methods are performed using two samples of genomic nucleic acid; a test sample containing genomic nucleic acid, and a reference or a control sample containing genomic nucleic acid the latter with no known chromosomal or genetic abnormalities. The test and reference samples are co-hybridized to a nucleic acid array containing a plurality of nucleic acids or nucleic acid segments spotted onto a surface (such as a glass side) at discrete locations. The array may contain target nucleic acid markers for certain known genetic mutations or disease states, or may represent (in aggregate) an entire chromosome, or the full chromosomal complement to obtain a genetic profile. In these approaches, the detectable label may be attached to the test and reference nucleic acids before or after hybridization and in any order. The detectable label may be attached covalently or non-covalently such as by a ligand-receptor interaction or by hybridization between complementary nucleotide sequences. In addition, a probe for detecting translocations is hybridized to the genomic DNA. In one approach, the probe is complementary to a moving segment of the genome which is translocated. The moving segment may be upstream or 5' of the translocation break point or downstream or 3' of the translocation breakpoint. If the test sample does not contain the balanced translocation, then the probe will hybridize to the array where the moving segment is located in the wildtype. If the test sample does contain the balanced translocation, then the probe will again hybridize to the array where the moving segment is located in the wildtype and to the area of array which contains the nucleic acid which now contains the moving segment. Additionally, multiple probes all complementary to the moving segment being translocated can be used in a single hybridization.

In some embodiments, detection of a genetic biomarker (e.g., one or more genetic biomarkers) can include any of the variety of methods described in U.S. Pat. No. 8,021,888, which is hereby incorporated by reference in its entirety. For example, detection of a genetic biomarker can include a method for performing a rapid hybridization assay. The method can be used to reduce the time to complete nucleic acid hybridization between nucleic acids in solution and nucleic acid immobilized to a solid support. The method applies acoustic surface waves during any of prehybridization to non-specific nucleic acid, hybridization to target nucleic acid or during any washing steps following hybridization. In one approach, nucleic acid hybridization to immobilized nucleic acid includes the following steps: a) contacting a solid support comprising one or more immobilized nucleic acid probe molecules under hybridization conditions with a non-specific blocking nucleic acid wherein the one or more immobilized nucleic acid probe molecules are capable of hybridizing with a sequence complementary thereto; b) contacting the solid support under hybridization conditions with a test sample containing nucleic acid target molecules; c) applying acoustic surface waves to the hybridization of step a) or step b) or both; and d) determining whether the one or more nucleic acid probes of the solid support have hybridized to test sample nucleic acid target molecules. In another approach, nucleic acid hybridization to immobilized nucleic acid includes the following steps: a) contacting a solid support containing one or more immobilized nucleic acid probe molecules under hybridization conditions with a nucleic acid test sample containing one or more nucleic acid target molecules, the one or more immobilized nucleic acid probe molecules capable of hybridizing with a sequence complementary thereto; b) applying acoustic surface waves to the hybridization of step a); and c) determining whether the one or more nucleic acid probes of the solid support has hybridized to test sample nucleic acid target molecules. This method also may include a prehybridization step with non-specific nucleic acid such as described for the method further above. One or more washing steps may be applied after the prehybridization step or the hybridization step. One or more washing steps may include application of acoustic surface waves. With the application of acoustic waves, the prehybridization step may be limited to less than about 7 hours, more preferably less than about 5 hours and even more preferably less than about 3 hours. The hybridization step to target nucleic acid may be less than about 3 hours, more preferably less than about 2 hours and even more preferably less than about 1 hours. The washing steps are performed for less than about 1 hour, more preferably less than about 30 minutes. In a preferred embodiment, the method is performed in less than about 9 hours, more preferably less than about 7 hours and even more preferably less than about 5 hours. The method of hybridization to a test nucleic acid target molecule may further include one or more reference nucleic acid target molecules. The test and/or reference nucleic acid target molecules may be labeled with a detectable agent. In some embodiments, the solid support may contain an array of immobilized nucleic acid probe molecules. In some embodiments, the immobilized nucleic acid probe molecules may include the sequence of a bacterial artificial chromosome.

In some embodiments, detection of a genetic biomarker (e.g., one or more genetic biomarkers) can include any of the variety of methods described in U.S. Patent Application Publication No. 2018/0142304, which is hereby incorporated by reference in its entirety. For example, detection of a genetic biomarker can include methods and compositions for the detection of mutations that are predictive of the responsiveness of a subject diagnosed with breast cancer, colorectal cancer, melanoma, or lung cancer to a particular therapeutic regimen. In some embodiments, the methods allow for rapid and sensitive detection of mutations in the target nucleic acid sequences of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. Additionally or alternatively, detection of a genetic biomarker can include a method for detecting at least one mutation in a plurality of cancer-related genes in a subject comprising (a) extracting genomic DNA from a formalin fixed paraffin-embedded tumor sample obtained from the subject; (b) generating a library comprising amplicons corresponding to each of the plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library occurs without the use of a bait set comprising nucleic acid sequences that are complementary to at least one of the plurality of amplicons; and (ii) the quality of the genomic DNA extracted from the formalin fixed paraffin-embedded tumor sample is not assessed using quantitative PCR prior to generating the library; (c) ligating an adapter sequence to the ends of the plurality of amplicons; and (d) detecting at least one mutation in at least one of the plurality of amplicons using high throughput massive parallel sequencing. In some embodiments of the method, the at least one mutation detected is a mutation in EGFR, KRAS, BRAF, NRAS, ERBB2 or PIK3CA. In one embodiment, the at least one mutation detected is selected from the group consisting of BRAF V600E, BRAF V600K, BRAF K483Q, BRAF G466V, BRAF G464V, BRAF E501V, BRAF E501K, EGFR ΔE746_A750, EGFR R680Q, EGFR G598E, KRAS A146T, KRAS R68M, KRAS L19F, KRAS G12V, KRAS G12D, KRAS G12C, KRAS G13D, KRAS G13C, KRAS G12A, KRAS G12S, KRAS Q22K, NRAS Q61K, NRAS Q61R, NRAS G12R, NRAS G12D, PIK3CA C420R, PIK3CA G106R, PIK3CA R38H, PIK3CA E453K, PIK3CA H1044R, PIK3CA N1044K, PIK3CA E545K, PIK3CA Q546H, PIK3CA H1047R, PIK3CA H1043L, PIK3CA M1043V, PIK3CA E542K, PIK3CA E542Q, PIK3CA T1053A, PIK3CA I121V, PIK3CA H1047L, ERBB2 L755S, ERBB2 S310Y, ERBB2 D769Y, ERBB2 S255R, DDR2 H92Y, DDR2 R31L, DDR2 L34P, DDR2 P381R and DDR2 K392N. In some embodiments of the method, the library comprising amplicons corresponding to each of the plurality of cancer-related genes is generated using no more than 10 ng of extracted genomic DNA from the formalin fixed paraffin-embedded tumor sample. In some embodiments of the method, the library comprising amplicons corresponding to each of the plurality of cancer-related genes is generated using 11-25 ng of extracted genomic DNA from the formalin fixed paraffin-embedded tumor sample. In certain embodiments, the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In some embodiments of the method, the adapter sequence is a P5 adapter, P7 adapter, P1 adapter, A adapter, or Ion Xpress™ barcode adapter. Additionally or alternatively, in some embodiments, the plurality of amplicons further comprises a unique index sequence. In some embodiments, the formalin fixed paraffin-embedded tumor sample is a heterogeneous tumor. In certain embodiments, 5% of the cells of the heterogeneous tumor harbor at least one mutation in at least one of the plurality of amplicons.

In some embodiments, detection of a genetic biomarker (e.g., one or more genetic biomarkers) can include any of the variety of methods described in U.S. Patent Application Publication No. 2018/0051329, which is hereby incorporated by reference in its entirety. For example, detection of a genetic biomarker can methods for determining the presence of a variant in one or more genes in a subject comprising: (a) providing raw sequencing data generated from a nucleic acid sequencing reaction on a nucleic acid sample from the subject using a nucleic acid sequencer; (b) removing low quality reads from the raw sequencing data that fail a quality filter; (c) trimming adapter and/or molecular identification (MID) sequences from the filtered raw sequencing data; (d) mapping the filtered raw sequencing data to a genomic reference sequence to generate mapped reads; (e) sorting and indexing the mapped reads; (f) adding read groups to a data file to generate a processed sequence file; (g) creating realigner targets; (h) performing local realignment of the processed sequence file to generate a re-aligned sequence file; (i) removing of duplicate reads from the re-aligned sequence file; (j) analyzing coding regions of interest; and (k) generating a report that identifies whether the variant is present based on the analysis in step (j), wherein steps (g) and (j) are performed using a modified genomic alignment utility limited to nucleic acid regions containing the one or more genes of interest. In some embodiments, the method comprises performing the nucleic acid sequencing reaction on the nucleic acid sample from the subject using a nucleic acid sequencer to generate the raw sequencing data of step (a). In some embodiments, analyzing coding regions of interest comprises calling variants at every position in the regions of interest. In some embodiments, the regions of interest are padded by an additional 150 bases. In some embodiments, variant calling is performed with a modified GATK variant caller. In some embodiments, mapping the reads to a genomic reference sequence is performed with a Burrows Wheeler Aligner (BWA). In some embodiments, mapping the reads to a genomic reference sequence does not comprise soft clipping. In some embodiments, the genomic reference sequence is GRCh37.1 human genome reference. In some embodiments, the sequencing method comprises emulsion PCR (emPCR), rolling circle amplification, or solid-phase amplification. In some embodiments, the solid-phase amplification is clonal bridge amplification. In some embodiments, the nucleic acid for sequence analysis is extracted from a biological sample from a subject. In some embodiments, the biological sample is a fluid or tissue sample. In some embodiments, the biological sample is a blood sample. In some embodiments, the nucleic acid is genomic DNA. In some embodiments, the nucleic acid is cDNA reversed transcribed from mRNA. In some embodiments, wherein the nucleic acid samples is prepared prior to sequencing by performing one or more of the following methods: (a) shearing the nucleic acid; (b) concentrating the nucleic acid sample; (c) size selecting the nucleic acid molecule in a sheared nucleic acid sample; (d) repairing ends of the nucleic acid molecules in the sample using a DNA polymerase; (e) attaching one or more adapter sequences; (f) amplifying nucleic acids to increase the proportion of nucleic acids having an attached adapter sequence; (g) enriching the nucleic acid sample for one or more genes of interest; and/or (h) quantification of the nucleic acid sample primer immediately prior to sequencing. In some embodiments, the one or more adapter sequences comprises nucleic acid sequences for priming the sequencing reaction and/or a nucleic acid amplification reaction. In some embodiments, the one or more adapter sequences comprises a molecular identification (MID) tag. In some embodiments, enriching the nucleic acid sample for one or more genes of interest comprises exon capture using one or more biotinylated RNA baits. In some embodiments, the nucleic acid for sequence analysis is obtained from a subject that is a mammal. In some embodiments, the subject is a human patient. In some embodiments, the subject is a human suspected of having cancer or suspected of being at risk of developing a cancer. In some embodiments, the methods provided further comprise confirming the presence of the one or more variants by sequencing. Additionally or alternatively, detection of a genetic biomarker can include systems comprising one or more electronic processors configured to: (a) remove low quality reads from the raw sequencing data that fail a quality filter; (b) trim adapter and/or molecular identification (MID) sequences from the filtered raw sequencing data; (c) map the filtered raw sequencing data to a genomic reference sequence to generate mapped reads; (d) sort and index the mapped reads; (e) add read groups to a data file to generate a processed sequence file; (f) create realigner targets; (g)

perform local realignment of the processed sequence file to generate a re-aligned sequence file; (h) remove of duplicate reads from the re-aligned sequence file; and (i) analyze coding regions of interest. In some embodiments, analyzing coding regions of interest comprises calling variants at every position in the regions of interest. In some embodiments, the regions of interest are padded by an additional 150 bases. In some embodiments, variant calling is performed with a modified GATK variant caller. In some embodiments, mapping the reads to a genomic reference sequence is performed with a Burrows Wheeler Aligner (BWA). In some embodiments, mapping the reads to a genomic reference sequence does not comprise soft clipping. In some embodiments, the genomic reference sequence is GRCh37.1 human genome reference. Additionally or alternatively, detection of a genetic biomarker can include non-transitory computer-readable media having instructions stored thereon, the instructions comprising: (a) instructions to remove low quality reads that fail a quality filter; (b) instructions to trim adapter and MID sequences from the filtered raw sequencing data; (c) instructions to map the filtered raw sequencing data to a genomic reference sequence to generate mapped reads; (d) instructions to sort and index the mapped reads; (e) instructions to add read groups to a data file to generate a processed sequence file; (f) instructions to create realigner targets; (g) instructions to perform local realignment of the processed sequence file to generate a re-aligned sequence file; (h) instructions to remove duplicate reads from the re-aligned sequence file; and (i) instructions to analyze coding regions of interest. In some embodiments, analyzing coding regions of interest comprises calling variants at every position in the regions of interest. In some embodiments, the regions of interest are padded by an additional 150 bases. In some embodiments, variant calling is performed with a modified GATK variant caller. In some embodiments, mapping the reads to a genomic reference sequence is performed with a Burrows Wheeler Aligner (BWA). In some embodiments, mapping the reads to a genomic reference sequence does not comprise soft clipping. In some embodiments, the genomic reference sequence is GRCh37.1 human genome reference.

In some embodiments, detection of a genetic biomarker (e.g., one or more genetic biomarkers) can include any of the variety of methods described in U.S. Patent Application Publication No. 2017/0316149, which is hereby incorporated by reference in its entirety. For example, detection of a genetic biomarker can include apparatus, systems, and methods for classifying genetic variants. In some embodiments, a standardized, rules-based process may provide a variant pathogenicity risk score based on clinical grade information in a CLIA-certified laboratory. Such a standardized system may provide reliable pathogenicity scores for DNA variants encountered in a clinical laboratory setting. In some embodiments, a sample of DNA may be obtained from a patient, who may or may not have been diagnosed with a disease or other medical condition. From the sample, the patient's genome may be sequenced in whole or in part. The result of sequencing may then be compared, e.g., to one or more reference genomes to identify variants in the patient's genome. One or more of the variants may be compared to databases of known variants. The result of that comparison may be identification of one or more previously unknown variants, one or more variants that are known but unclassified, or both. In some embodiments, an unclassified variant may be evaluated against one or more objective criteria. For example, in an embodiment, an embodiment may be assigned a starting score. Application of one or more objective criteria may cause additions and subtractions from the score, leading to a final score that may be used to classify the variant. In some embodiments, classification of one or more previously-classified variants may be revisited, e.g., periodically, to reevaluate the variants in light of new information gained since the previous evaluation. Additionally or alternatively, detection of a genetic biomarker can include a method of assigning a score to a genetic variant is based on multiple scoring criteria and reflects an estimate of pathogenicity of the variant. The method comprises identifying the variant in sequenced DNA obtained from a patient and assigning a starting score to the variant, where the starting score is a single numeric value that is associated with variants of unknown significance. In some embodiments, the method also comprises: calculating a first score adjustment that is based on objective evaluation of minor evidence and splicing predictions; calculating a second score adjustment that is based on objective evidence of the frequency with which the variant occurs in a general population; calculating a third score adjustment that is based on objective evidence of the frequency with which the variant occurs in clinically characterized patients; calculating a fourth score adjustment that is based on objective evidence of the frequency with which the variant has been observed to co-occur with one or more other variants that are known to be pathogenic; calculating a fifth score adjustment that is based on objective evidence of a degree to which the variant exhibits segregation within one or more families; calculating a sixth score adjustment that is based on objective evidence of association between the variant and one or more disease phenotypes within data describing one or more families; and calculating a seventh score adjustment based on objective evidence regarding whether the variant affects functions of one or more proteins that are known to be associated with disease. In some embodiments, the method also comprises calculating a variant score based on the starting value, the first score adjustment, the second score adjustment, the third score adjustment, the fourth score adjustment, the fifth score adjustment, the sixth score adjustment, and the seventh score adjustment, the variant score being a single numeric value. And the method comprises assigning the variant to an assigned classification based solely on the variant score, where the assigned classification is one of a group that consists of a plurality of classifications, each classification in the plurality being associated with a respective different evaluation of variant pathogenicity.

In some embodiments, detection of a genetic biomarker (e.g., one or more genetic biomarkers) can include any of the variety of methods described in U.S. Patent Application Publication No. 2017/0009287, which is hereby incorporated by reference in its entirety. For example, detection of a genetic biomarker can include apparatus, systems, and methods of detecting variations in the number of copies of genetic subsequences within the genome of an organism. According to some embodiments, samples of genetic material, including DNA, may be taken from several patients. Sections of the patients' DNA may then be sequenced, e.g., through a process that includes, for each patient, purifying, concentrating, and fragmenting that patient's DNA. Each fragment may receive a molecular label that identifies the patient from whom the DNA was received and the DNA may otherwise be modified in preparation for sequencing (e.g., through one or more steps that may include one or more of: filtration, amplification, and modification such as to attach primers to the fragments). The fragments from several patients may be pooled, and the pool may include, e.g., one or more controls that comprise known genetic material. The fragments in the pool may then be sequenced, and the results of the sequencing may be stored, e.g., as one or more computer files. The results may then be processed, e.g., by one or more computer systems, to identify possible copy number variations in the patients from whom the samples were taken. For example, in some embodiments, the sequences may be demultiplexed to identify the respective patients whose DNA each sequence represents. Each patient's samples may then be aligned to a reference genome, and coverage for each base pair in each region of interest on the patient's genome may then determined. From the base pair coverage, the coverage of one or more subunits of the patient's genome may then be determined. For example, in some embodiments, the coverage of multiple exons may be determined. In some embodiments, the measurements of the coverage may then go through one or more steps of normalization. For example, the mean coverage of one or more amplicons known to be on autosomes may be compared to the mean coverage of one or more amplicons known to be on the X chromosome to provide a rough estimate of the number of X chromosomes (viz., one or two) in the patient's karyotype. If the patient is determined to have only one X chromosome, normalization may include doubling the coverage of all amplicons known to come from the X chromosome. Following normalization, reference values may be calculated for each amplicon, and CNV may be detected by comparing actual coverage values for each patient's amplicons with the calculated reference values. Additionally or alternatively, detection of a genetic biomarker can include a method is provided of detecting copy number variation (CNV) in the DNA of a plurality of patients. The method comprises receiving a plurality of samples, each sample containing DNA from a single patient, and from each sample, generating a plurality of fragments of DNA. The method also comprises barcoding each of the fragments with an identifier that uniquely identifies the respective patient from whom the DNA was received, pooling the plurality of samples into a DNA library, and subjecting the DNA library to one or more stages of filtering to increase the relative concentration of fragments within a plurality of selected regions of interest. In some embodiments, the method further comprises producing sequencing data for the plurality of patients by sequencing the filtered DNA library, demultiplexing the sequencing data, and, for each patient, generating coverage data by identifying, for each of the regions of interest, coverage of each region of interest in the sequencing data. In some embodiments, the method comprises generating normalized coverage data from the coverage data and generating reference coverage, common to all samples, for each region of interest, the generation of the reference coverage being based upon the normalized coverage data. In some embodiments, the method also comprises automatically detecting CNV for at least one subsequence of at least one of the regions of interest of at least one of the patients based upon comparing the reference coverage to the normalized coverage data and providing output that identifies the patient, the subsequence, and the CNV. In some embodiments, generating normalized coverage data from the coverage data comprises generating raw coverage data for each patient by at least generating an estimate of the number of the patient's X chromosomes based on the coverage data and scaling the patient's coverage of at least one region of interest that is known to be X-linked and further comprises generating normalized coverage data from the raw coverage data. In some embodiments, generating the estimate of the number of each patient's X chromosomes occurs without reference to any demographic information about the respective patient and without reference to any information about the respective patient's phenotype. Alternatively, in some embodiments, the method comprises, for each patient, generating a second estimate of the number of the patient's X chromosomes based on the normalized coverage data and also comprises revising the normalized coverage data based on the second estimates. In some embodiments, generating the second estimate of the number of each patient's X chromosomes occurs without reference to any demographic information about the respective patient and without reference to any information about the respective patient's phenotype. In some embodiments, the coverage data comprises per-base coverage for each region of interest within the sequencing data; generating raw coverage data comprises scaling the patient's per-base coverage of the at least one region of interest that is known to be X-linked; the normalized coverage data comprises per-base coverage; the reference coverage comprises per-base coverage for each position within each region of interest; and automatically detecting CNV is based upon the per-base reference coverage and the normalized coverage data. In some embodiments, each region of interest corresponds respectively to exactly one exon and contains that exon. In some embodiments, the method comprises automatically detecting CNV for a plurality of adjacent exons within a gene of a patient, each of the adjacent exons having the same CNV and automatically rolling up the CNV of the adjacent exons. Further, in an embodiment, the method comprises automatically detecting CNV for all exons within a gene of a patient, each of the exons within the gene having the same CNV, and automatically rolling up the CNV of the exons within the gene into a single CNV for the gene. In some embodiments, the method comprises subjecting the DNA library to one or more stages of amplification, such that each region of interest is an amplicon. In some embodiments, the coverage data comprises per-base coverage for each region of interest within the sequencing data; the normalized coverage data comprises per-base coverage; the reference coverage comprises per-base coverage for each position within each region of interest; and automatically detecting CNV is based upon the per-base reference coverage and the normalized coverage data.

In some embodiments, detection of a genetic biomarker (e.g., one or more genetic biomarkers) can include any of the variety of methods described in U.S. Patent Application Publication No. 2009/0088328, which is hereby incorporated by reference in its entirety. For example, detection of a genetic biomarker can include a method of determining the printing quality of nucleic acid arrays and to provide methods to determine the efficiency of procedures to block non-specific binding on nucleic acid arrays. Additionally or alternatively, detection of a genetic biomarker can include utilizing fluorescence detection to evaluate the quality of a printed nucleic acid array without the need to add or otherwise link a fluorescent compound or dye to the nucleic acid. Nucleic acid arrays suitable for this analysis are those where the spots of the array are formed by printing a solution that contains the nucleic acid and one or more ions. Thus, the array is formed from nucleic acid in an ionic solution and the printing quality is evaluated by the fluorescence associated with each printed spot. Printing quality may be evaluated by measuring the intensity of fluorescence at the location of each printed sample, and/or by measuring the "morphology" (i.e. shape) of the printed sample. Printed spots can be "imaged" by measuring fluorescence across a spotted sample in two dimensions. The resulting image of a printed spot can be compared with a reference printed image expected for the printing equipment and solid phase used. The methods can be used to determine the quality the quality of specific spots on an array, to determine the quality of specific regions of an array, or to determine the quality of an array as a whole. Spot quality and/or array quality can be detected immediately following array printing or after the array is subject to processing steps prior to hybridization. Such steps may include exposing the array to heat, humidity, UV irradiation, a blocking procedure, and/or washing. In the case where the quality of a blocking step for non-specific binding is performed, the quality of blocking can be determined by measuring fluorescence at each loaded sample prior to and following a blocking procedure. A decrease in the fluorescence after the washing and/or blocking procedure indicates the efficiency of the blocking and/or washing step. Additionally or alternatively, detection of a genetic biomarker can include a method for determining the printing quality of a nucleic acid array prior to hybridization, said method comprising: (a) printing an array of nucleic acid samples onto a solid support, each sample comprising nucleic acid in an ionic solution; and (b) detecting fluorescence of printed samples to determine the quality of printing.

In some embodiments, detection of a genetic biomarker (e.g., one or more genetic biomarkers) can include any of the variety of methods described in U.S. Patent Application Publication No. 2006/0292576, which is hereby incorporated by reference in its entirety. For example, detection of a genetic biomarker can include methods of detecting and analyzing chromosomal abnormalities of interest in a test sample. In preferred embodiments, nucleic acids from a test sample are hybridized to two probes complementary to different segments of a gene of interest or different segments to a chromosomal fragment of interest. One probe is anchored to the solid support while the second probe comprises a detectable label which is used for detection. This method provides for the capture and detection of target nucleic acids hybridizing to both probes simultaneously. Hybridization of both the first and second probes to the same target nucleic acid indicates detection of a chromosomal abnormality in the target nucleic acid, while hybridization of only one of the probes to the same target nucleic acid indicates the absence of a genetic abnormality in the target nucleic acid. The anchored probe may be anchored covalently or non-covalently to the support. If non-covalent attachment is used, a preferred method is via a "binding pair," which refers to two molecules which form a complex through a specific interaction. Thus, the nucleic acid probe can be captured on the solid support through an interaction between one member of the binding pair linked to the probe and the other member of the binding pair coupled to the solid support. A binding pair member also can be used to link the detectable label to the other nucleic acid probe. In a preferred embodiment, the binding pair is biotin and avidin or streptavidin. In other embodiments, the binding pair is comprised of a ligand-receptor, a hormone-receptor, an antigen-antibody, or an oligonucleotide-complement. In some embodiments, the two probes may be hybridized to the target nucleic acid in a liquid and then the complex can be captured by a solid support. The anchored probe in this approach is preferably anchored non-covalently and preferably via a binding pair. In other variants, the solid support may first comprise the anchored probe, which is then contacted for hybridization with the target nucleic acid, alone or together with the labeled probe. Additionally or alternatively, detection of a genetic biomarker can include methods of detecting the presence or absence of a genetic abnormality in a target nucleic acid in a test sample. The method includes forming on a solid support a complex comprising the target nucleic acid, a first nucleic acid probe hybridizing to a first segment of the target nucleic acid, the first nucleic acid probe labeled with a detectable label, and a second nucleic acid probe hybridizing to a second segment of the target nucleic acid, the second nucleic acid probe anchored to the solid support. The complex is detected by detecting incorporated detectable label, wherein hybridization of both the first and second probes to the same target nucleic acid indicates the presence of genetic abnormality in the target nucleic acid, while hybridization of only one of the probes to the same target nucleic acid indicates the absence of a genetic abnormality in the target nucleic acid. Additionally or alternatively, detection of a genetic biomarker can include methods of detecting a chromosomal translocation in the nucleic acid of a test sample. The method includes the hybridization of two nucleic acid probes, one complementary to a sequence of the donor chromosome segment and the other complementary to a sequence of the recipient chromosome which adjoins or is near to the inserted donor chromosome segment. One probe is anchored to the support and the other probe is labeled with a detectable label. A test sample of genomic DNA hybridizing to both probes will form a complex on the support or such a complex is preformed and then captured on a solid support and detected via the detectable label. The quantity of captured, labeled complex from the test sample represents the test value. If the test value shows that label is associated with captured hybridization complexes, the test sample is determined to contain the chromosomal translocation. In one embodiment, one can compare the test value for the test sample with a test value from a reference sample which contains the target gene but lacking the translocation. Additionally or alternatively, detection of a genetic biomarker can include methods of detecting a duplication or deletion in a particular target chromosomal region or gene in an individual. The method includes forming on a solid support a complex comprising the nucleic acid associated with the particular chromosomal region or gene which is obtained from the sample, a labeled nucleic acid probe hybridizing to a first segment of the particular chromosomal region or gene, and a second nucleic acid probe hybridizing to a second segment of the particular chromosomal region or gene, wherein the second nucleic acid probe is anchored to the solid support. In a preferred embodiment, the target nucleic acid is genomic DNA which has been fragmented. The quantity of captured, labeled complex from the test sample represents the test value. The test value may be compared to a control value which may be obtained from the quantity of complex obtained from a different target gene or chromosomal region preferably from the same sample. A higher test value as compared to the control value is indicative of duplication or amplification, whereas a lower test value as compared to control value is indicative of a chromosomal or gene deletion. In another approach, one can determine a ratio of the test value of the test sample to the control value in that sample and compare to a similar ratio representing the test value and control value of a reference sample which contains nucleic acid that does not contain a deletion, duplication, or amplification in the chromosomal region or gene of interest. Additionally or alternatively, detection of a genetic biomarker can include methods of determining the diagnosis, predicting response to therapy, detecting minimal residual disease or prognosis of a disease in an individual. In this method, a complex is formed between a target nucleic acid from a test sample, a probe comprising a detectable label and hybridizing to one segment of a target nucleic acid and a second probe anchored to the support and hybridizing to a second segment of the target nucleic acid. The amount of complex on the solid support is measured through detection of incorporated detectable label of the first probe. The amount of complex formed is compared to the amount of complex formed in a similar manner from a sample obtained from a reference sample. The reference sample may be obtained from a normal individual, wherein a difference between the measurements from the test and reference samples is correlated with diagnosis or prognosis of a disease. Additionally or alternatively, detection of a genetic biomarker can include methods of monitoring treatment or progression of a disease. In this method samples are obtained from a patient at different points in time (e.g., before and after a regimen of treatment of the disease). A complex is formed between a target nucleic acid from the first sample, a probe comprising a detectable label and hybridizing to one segment of a target nucleic acid and a second probe anchored to the support and hybridizing to a second segment of a target nucleic acid. The amount of complex on the support from the first sample is compared to the amount of complex formed using the same probes and target nucleic acid from the second sample. A difference in amount of complex formed can be correlated to progression of the disease or success of the treatment regimen. Additionally or alternatively, detection of a genetic biomarker can include methods of measuring tumor burden in an individual. In this method, a complex is formed on a solid support between a target nucleic acid from a test sample, a probe comprising a detectable label and hybridizing to one segment of a target nucleic acid and a second probe anchored to the support and hybridizing to a second segment of the target nucleic acid. The amount of complex on the solid support is measured through detection of incorporated detectable label of the first probe. The amount of complex formed is compared to a reference value or set of values of the amount of complex formed in a similar manner from a sample obtained from a reference sample, from a patient whose tumor burden is known, to determine tumor burden of the test sample. In some embodiments, methods of determining tumor burden include the formation of two complexes on solid support. The first complex comprises a first target nucleic acid from a test sample from the individual and two nucleic acid probes; one containing a detectable label and the other anchored to the support. The second complex comprises a second or control target nucleic acid from the test sample and two different nucleic acid probes, one containing a detectable label, distinguishable from the label of the first complex, and the other probe anchored to the solid support. The amount of each of the two complexes is measured and a test ratio determined. This ratio is then compared to a reference ratio or set of ratios that correlate the test ratio to tumor burden.

In some embodiments, detection of a genetic biomarker (e.g., one or more genetic biomarkers) can include any of the variety of methods described in U.S. Patent Application Publication No. 2006/0127918, which is hereby incorporated by reference in its entirety. For example, detection of a genetic biomarker can include a nucleic-containing substrate that includes: (a) an organosilane-pretreated surface; (b) a polymer film cross-linked to the organosilane-pretreated surface; and (c) a nucleic acid molecule bound to one or more of the polymer film and the organosilane-pretreated surface. In preferred embodiments, the polymer film is formed from a polymer comprising reactive groups, and the nucleic acid molecule has not been covalently modified to facilitate covalent attachment at the reactive groups. The nucleic acid molecule may be associated with or bound to one or more of the polymer film and the organosilane-pretreated surface through covalent and/or noncovalent interactions. In preferred embodiments, the nucleic acid molecule is at least about 250 nucleotides in length, and more preferably at least about 500 nucleotides in length. In one embodiment, the nucleic acid molecule is a DNA molecule present in the form of a bacterial artificial chromosome (BAC) or another suitable cloning vector (e.g., an E. coli P1 based artificial chromosome, a plasmid, a cosmid, and the like). In some embodiments, the bound nucleic acid molecule is present on the surface of the substrate at a concentration sufficient to detect a nucleic acid target molecule by nucleic acid hybridization methodology. For example, the nucleic acid molecule may be present at a concentration of at least about 500 copies/cm2 on the surface of the substrate. More suitably the nucleic molecule is present on the surface of the substrate at a concentration of at least about 1000 copies/cm2 and/or at least about 5000 copies/cm2. The nucleic acid molecule preferably remains substantially attached to the substrate when subjected to washing under high stringency conditions (e.g., when the slide is washed with a low salt buffer optionally including a non-ionic detergent at a relatively high temperature). In some embodiments, the organosilane is a modified silane molecule that includes alkyl groups. In one embodiment, the organosilane includes alkyl groups with six or more carbon atoms and preferably ten or more carbon atoms. The organosilane may include alkoxy groups. The organosilane may also include halide groups. In some embodiments, the polymer comprises reactive groups. Suitable reactive groups include electrophilic groups that react with nucleophilic groups under suitable conditions. For example, reactive groups may include amino-reactive groups (i.e., groups that react with the nitrogen atom of an amino group), thiol-reactive groups (i.e., groups that react with the sulfur atom of a thiol-group), hydroxyl-reactive groups (i.e., groups that react with the oxygen atom of a hydroxyl-group), and combinations thereof. In some embodiments, the polymer may include activated esters, epoxides, azlactones, activated hydroxyls, aldehydes, isocyanates, thioisocyanates, carboxylic acid chlorides, alkyl halides, maleimide, α-iodoacetamides, or combinations thereof. In one embodiment, the reactive group is an activated ester, and in particular, the activated ester may include an N-hydroxylsuccinimide ester. In some embodiments, the nucleic acid-containing substrate is configured as a nucleic acid microarray. The nucleic acid microarray may be suitable for performing comparative genomic hybridization analysis. In one embodiment, the nucleic acid microarray comprises genomic DNA cloned in bacterial artificial chromosomes (BACs). Additionally or alternatively, detection of a genetic biomarker can include a method for preparing a nucleic acid-containing substrate as described above. The method typically includes: (a) pre-treating a surface of the substrate with a composition that includes an organosilane; (b) coupling a polymer to the organo-silane pretreated surface to form a polymer film; and (c) binding a nucleic acid molecule to one or both of the organosilane-pretreated surface and the polymer film. In preferred embodiments, the polymer film is formed from a polymer comprising reactive groups, and the nucleic acid has not been covalently modified to facilitate covalent attachment at the reactive groups. The nucleic acid molecule may be associated with and/or bound to one or more of the polymer film and the organosilane-pretreated surface through covalent and/or noncovalent interactions. Additionally or alternatively, detection of a genetic biomarker can include a method for detecting the presence and/or amount of a target nucleic acid molecule in a sample that includes: a) contacting the target molecule with a nucleic acid-containing substrate, which is prepared as described above, under suitable conditions for hybridizing the target to the nucleic acid of the substrate; and b) detecting the presence of the target molecule bound to the substrate. In preferred embodiments, the nucleic acid-containing substrate is a nucleic acid microarray, and detection of the presence and/or amount of the nucleic acid target is performed using comparative genomic hybridization analysis.

In some embodiments, detection of a genetic biomarker (e.g., one or more genetic biomarkers) can include any of the variety of methods described in P.C.T. Publication No. WO 2018/125892, which is hereby incorporated by reference in its entirety. For example, detection of a genetic biomarker can include methods and polynucleotide adapter compositions related to the detection of mutations in ctDNA present in samples derived from a subject diagnosed as having, or suspected of having cancer. In some embodiments, the methods allow for rapid and sensitive detection and profiling of ctDNA mutations in various target nucleic acid sequences in the exons and/or introns of one or more cancer-related genes including, but not limited to ALK, BRAF, EGFR, ERBB2, KIT, KRAS, MET, NRAS, NTRK1, PIK3CA, ROS1, and RET The methods provide for a framework for ultrasensitive ctDNA profiling achieved using accurate analytical models of detection limits. These qualities improve detection limits over previous methods for samples with limited DNA content. Additionally or alternatively, detection of a genetic biomarker can include a nucleic acid adapter comprising a first oligonucleotide strand and a second oligonucleotide strand, wherein (a) the first oligonucleotide strand (i) comprises a first proximal region and a first distal region, wherein the first proximal region comprises a first unique molecular identifier sequence and a first spacer sequence having the sequence 5' TGACT 3' (SEQ ID NO:), wherein the first spacer sequence is located 3' to the first unique molecular identifier sequence; and (ii) does not comprise a degenerate or semi-degenerate sequence; (b) the second oligonucleotide strand (i) comprises a second proximal region and a second distal region, wherein the second proximal region comprises a second unique molecular identifier sequence and a second spacer sequence having the sequence 5' GTCA 3' (SEQ ID NO:), wherein the spacer sequence is located 5' to the second unique molecular identifier; and (ii) does not comprise a degenerate or semi-degenerate sequence; (c) the first proximal region of the first oligonucleotide strand hybridizes with the second proximal region of the second oligonucleotide strand; and (d) the first distal region of the first oligonucleotide strand does not hybridize with the second distal region of the second oligonucleotide strand. In some embodiments of the nucleic acid adapter, the "T" nucleotide located at the 3' end of the first spacer sequence contains a phosphorothioate bond. In some embodiments of the nucleic acid adapter, the 5' end of the first oligonucleotide strand is labelled with biotin. In other embodiments of the nucleic acid adapter, the 3' end of the second oligonucleotide strand is labelled with biotin. In some embodiments, the nucleic acid adapter is used to sequence a double-stranded target nucleic acid molecule selected from the group consisting of double-stranded DNA or double-stranded RNA. The double-stranded DNA may be sheared genomic DNA, or cell-free DNA. In some embodiments, the nucleic acid adapter of the present technology further comprises at least two PCR primer binding sites, at least two sequencing primer binding sites, or any combination thereof. Additionally or alternatively, in some embodiments, the nucleic acid adapter of the present technology further comprises a sample-specific barcode sequence, wherein the sample-specific barcode sequence comprises 2-20 nucleotides. Additionally or alternatively, detection of a genetic biomarker can include a method for detecting at least one mutation in a double-stranded circulating tumor DNA (ctDNA) molecule present in a sample obtained from a patient comprising (a) ligating a plurality of Y-shaped adapters to both ends of the double-stranded ctDNA molecule to form a double-stranded adapter-ctDNA complex, each Y-shaped adapter comprising a first oligonucleotide strand and a second oligonucleotide strand; (b) amplifying both strands of the adapter-ctDNA complex to produce first amplicons and second amplicons, wherein the first amplicons are derived from the first oligonucleotide strand, and the second amplicons are derived from the second oligonucleotide strand; (c) sequencing the first and second amplicons; (d) detecting at least one mutation in the double-stranded ctDNA molecule, when a mutation detected in the first amplicons is consistent with a mutation detected in the second amplicons. In some embodiments of the method, the patient is diagnosed with ovarian cancer, breast cancer, colon cancer, lung cancer, prostate cancer, gastric cancer, pancreatic cancer, cervical cancer, liver cancer, bladder cancer, cancer of the urinary tract, thyroid cancer, renal cancer, carcinoma, melanoma, head and neck cancer, or brain cancer. In some embodiments, the method further comprises enriching the first amplicons and second amplicons with a plurality of bait sequences, wherein the plurality of bait sequences comprises at least one gene region that corresponds to each of a plurality of cancer-related genes. The plurality of cancer-related genes may comprise ALK, BRAF, EGFR, ERBB2, KIT, KRAS, MET, NRAS, NTRK1, PIK3CA, ROS1, and RET. Additionally or alternatively, in some embodiments of the method, the plurality of bait sequences are RNA baits, DNA baits, or a mixture of RNA baits and DNA baits. In certain embodiments, the plurality of bait sequences comprises a 1:1 mixture of RNA baits and DNA baits. In other embodiments, the plurality of bait sequences comprises a mixture of RNA baits and DNA baits having a ratio of 2:1, 1.5:1, 0.75:1 or 0.5:1. In certain embodiments of the method, both of the 3' ends of the double-stranded ctDNA molecule further comprise an "A"-overhang. In any of the above embodiments, each Y-shaped adapter further comprises at least two sequencing primer binding sites. Additionally or alternatively, in some embodiments, each Y-shaped adapter further comprises a patient-specific barcode sequence, wherein the patient-specific barcode sequence comprises 2-20 nucleotides. Each Y-shaped adapter of the present technology may be labelled with biotin. In some embodiments of the method, the sample comprises no more than 5 ng of cell-free DNA. In other embodiments, the sample comprises at least 6-30 ng of cell-free DNA. In certain embodiments, the sample is whole blood, serum, plasma, synovial fluid, lymphatic fluid, ascites fluid, or interstitial fluid.

In some embodiments, detection of a genetic biomarker (e.g., one or more genetic biomarkers) can include any of the variety of methods described in U.S. Pat. No. 9,389,234, which is hereby incorporated by reference in its entirety. For example, detection of a genetic biomarker can include methods and system for molecular profiling and using the results from molecular profiling to identify treatments for individuals. In some embodiments, the treatments were not identified initially as a treatment for the disease. Additionally or alternatively, detection of a genetic biomarker can include a method of identifying a candidate treatment for a subject in need thereof, comprising: performing an immunohistochemistry (IHC) analysis on a sample from the subject to determine an IHC expression profile on at least five proteins; performing a microarray analysis on the sample to determine a microarray expression profile on at least ten genes; performing a fluorescent in-situ hybridization (FISH) analysis on the sample to determine a FISH mutation profile on at least one gene; performing DNA sequencing on the sample to determine a sequencing mutation profile on at least one gene; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have no mutations, or one or more mutations in one or more genes included in the FISH mutation profile; and/or iv. have no mutations, or one or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer. In some embodiments, the IHC expression profiling comprises assaying one or more of SPARC, PGP, Her2/neu, ER, PR, c-kit, AR, CD52, PDGFR, TOP2A, TS, ERCC1, RRM1, BCRP, TOPO1, PTEN, MGMT, and MRP1. In some embodiments, the microarray expression profiling comprise assaying one or more of ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70. In some embodiments, the FISH mutation profiling comprises assaying EGFR and/or HER2. In some embodiments, the sequencing mutation profiling comprises assaying one or more of KRAS, BRAF, c-KIT and EGFR. Additionally or alternatively, detection of a genetic biomarker can include a method of identifying a candidate treatment for a subject in need thereof, comprising: performing an immunohistochemistry (IHC) analysis on a sample from the subject to determine an IHC expression profile on at least five of: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least five of: ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on EGFR and/or HER2; performing DNA sequencing on the sample to determine a sequencing mutation profile on at least one of KRAS, BRAF, c-KIT and EGFR; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have no mutations, or one or more mutations in one or more genes included in the FISH mutation profile; and/or iv. have no mutations, or one or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer. In some embodiments, the IHC expression profiling is performed on at least 50%, 60%, 70%, 80% or 90% of the biomarkers listed. In some embodiments, the microarray expression profiling is performed on at least 50%, 60%, 70%, 80% or 90% of the biomarkers listed. Additionally or alternatively, detection of a genetic biomarker can include a method of identifying a candidate treatment for a cancer in a subject in need thereof, comprising: performing an immunohistochemistry (IHC) analysis on a sample from the subject to determine an IHC expression profile on at least the group of proteins consisting of: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least the group of genes consisting of ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on at least the group of genes consisting of EGFR and HER2; performing DNA sequencing on the sample to determine a sequencing mutation profile on at least the group of genes consisting of KRAS, BRAF, c-KIT and EGFR; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have zero or more mutations in one or more genes included in the FISH mutation profile; and/or iv. have zero or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer. In some embodiments, the microarray expression profiling is performed using a low density microarray, an expression microarray, a comparative genomic hybridization (CGH) microarray, a single nucleotide polymorphism (SNP) microarray, a proteomic array or an antibody array.

In some embodiments, detection of a genetic biomarker (e.g., one or more genetic biomarkers) can include any of the variety of methods described in U.S. Patent Application Publication No. 2018/0171337, which is hereby incorporated by reference in its entirety. For example, detection of a genetic biomarker can include a method, comprising: a) determining a molecular profile for at least one sample from the subject by assessing a plurality of genes and/or gene products; and b) identifying, based on the molecular profile, at least one of: i) at least one treatment that is associated with benefit for treatment of the cancer; ii) at least one treatment that is associated with lack of benefit for treatment of the cancer; and iii) at least one treatment associated with a clinical trial. The plurality of genes and/or gene products can be chosen from amongst genes and or gene products (e.g., transcripts and proteins) with efficacy known to be related to various chemotherapeutic agents. Additionally or alternatively, detection of a genetic biomarker can include mutational analysis performed on any desired panel of genes. In an embodiment, assessing the plurality of genes and/or gene products further comprises mutational analysis of at least one, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46, of ABL1, AKT1, ALK, APC, ATM, BRAF, BRCA1, BRCA2, CDH1, CSF1R, CTNNB1, EGFR, ERBB2 (HER2), ERBB4 (HER4), FBXW7, FGFR1, FGFR2, FLT3, GNA11, GNAQ, GNAS, HNF1A, HRAS, IDH1, JAK2, JAK3, KDR (VEGFR2), KIT (cKIT), KRAS, MET (cMET), MPL, NOTCH1, NPM1, NRAS, PDGFRA, PIK3CA, PTEN, PTPN11, RB1, RET, SMAD4, SMARCB1, SMO, STK11, TP53 and VHL. The mutational analysis may comprise any useful combination of these genes. The mutational analysis can be used to assess at least one, e.g., at least 1, 2, 3, 4, 5, 6, 7, 8, 9, 10, 11, 12, 13, 14 of a mutation, a polymorphism, a deletion, an insertion, a substitution, a translocation, a fusion, a break, a duplication, an amplification, a repeat, a copy number variation, a transcript variant, and a splice variant. The mutational analysis can be performed using any useful laboratory method or combination of methods. For example, the mutational analysis can be performed using at least one of ISH, amplification, PCR, RT-PCR, hybridization, microarray, sequencing, pyrosequencing, Sanger sequencing, high throughput or Next Generation sequencing (NGS), fragment analysis or RFLP. In some embodiments, the mutational analysis comprises Next Generation Sequencing.

In some embodiments, detection of a genetic biomarker (e.g., one or more genetic biomarkers) can include any of the variety of methods described in U.S. Patent Application Publication Nos. 2017/0175197, 2017/0039328, and 2015/0307947 and P.C.T. Publication No. WO 2012/092336, which are hereby incorporated by reference in its entirety.

In some embodiments, detection of a genetic biomarker (e.g., one or more genetic biomarkers) can include any of the variety of methods described in P.C.T. Publication No. WO 2017/053915, which is hereby incorporated by reference in its entirety. For example, detection of a genetic biomarker can include systems, methods, apparatuses, and computer program products for providing a user interface for an application for analyzing biological data. Additionally or alternatively, detection of a genetic biomarker can include a method of analyzing biological data, the method comprising: receiving, at a computing device comprising a processor and memory, patient data for a plurality of patients, the patient data corresponding to at least one of a biological sampling event, a biological processing event, at least one therapeutic regime, at least one biomarker status, and a patient status; determining at least one interrelationship between any one of the biological sampling event, the biological processing event, the at least one therapeutic regime, the at least one biomarker status, and the patient status; performing a therapeutic regime analysis to determine an interrelationship status for the interrelationship between at least one therapeutic regime and at least one of the patient status and the at least one biomarker status; and displaying at least one graphical interface on a user interface in communication with the computing device, the graphical interface including a plurality of visual elements, each visual element of the plurality of visual elements being associated with the patient data, at least one visual element being associated with the at least one interrelationship, at least one visual element including an indicium corresponding to at least one of the interrelationship status and the biomarker status. Additionally or alternatively, detection of a genetic biomarker can include a method of analyzing biological data associated with a biological sample from a target patient, the method comprising: receiving, at a computing device comprising a processor and memory, patient data associated with the target patient, the patient data corresponding to a biological sampling event, a biological processing event, a therapeutic regime, a marker status, and a patient status; receiving reference data associated with a plurality of patients, the reference data corresponding to a plurality of biological sampling events, biological processing events, therapeutic regimes, marker statuses, and patient statuses; determining at least one interrelationship between any one of the biological sampling events, the biological processing events, the therapeutic regimes, the marker statuses, and the patient statuses; performing a therapeutic regime analysis to determine the interrelationship between at least one therapeutic regime and at least one of the at least one patient status and the at least one marker status; displaying at least one graphical user interface, the graphical user interface configured to: i) display a plurality of graphical user interface objects associated with the reference data, ii) display a plurality of graphical user interface objects associated with the patient data, iii) display, on at least one graphical interface on a user interface in communication with the computing device, a primary graphical user interface object configured to, upon receiving an indication of a user input defining a selection of the primary graphical user interface object, cause the graphical user interface to display a secondary graphical user interface object; and assisting in providing patient care based on the one or more interrelationships displayed on the user interface. In some embodiments, the method may further comprise manipulating a primary visual element to display a secondary visual element including additional information corresponding to the patient data upon selection thereof. The method may further comprise displaying the secondary visual element such that the secondary visual element overlays the primary visual element or the primary visual element is resized such that the secondary visual element is displayed adjacent to the primary visual element. In some embodiments, the method may further comprise assisting in providing patient care based on the one or more interrelationships displayed on the user interface. In some embodiments, assisting in providing the patient care comprises assisting in at least one of providing a diagnosis, providing a prognosis, selecting a recommended therapeutic regime, generating a hypothesis, and evaluating an efficiency of the therapeutic regime, based on the one or more interrelationships. In some embodiments, assisting in providing the patient care comprises selectively manipulating the graphical interface and one or more of the plurality of visual elements displayed thereon to visually compare a target patient against a set of reference patients. Visually comparing the target patient against the set of reference patients can be based on various desired attributes, including without limitation shared patient attributes, the at least one therapeutic regime, and/or the at least one biomarker status. Additionally or alternatively, detection of a genetic biomarker can include a computer-readable storage medium that is non-transitory and has computer-readable program code portions stored therein that, in response to execution by a processor, cause an apparatus to at least: receive, at a computing device comprising the processor and memory, patient data for a plurality of patients, the patient data corresponding to at least one of a biological sampling event, a biological processing event, at least one therapeutic regime, at least one biomarker status, and a patient status; determine at least one interrelationship between any one of the biological sampling event, the biological processing event, the at least one therapeutic regime, the at least one biomarker status, and the patient status; perform a therapeutic regime analysis to determine an interrelationship status for the interrelationship between at least one therapeutic regime and at least one of the patient status and the at least one biomarker status; and display at least one graphical interface on a user interface in communication with the computing device, the graphical interface including a plurality of visual elements, each visual element of the plurality of visual elements being associated with the patient data, at least one visual element being associated with the at least one interrelationship, at least one visual element including an indicium corresponding to at least one of the interrelationship status and the biomarker status. Additionally or alternatively, detection of a genetic biomarker can include an apparatus for analyzing biological data, the apparatus including a user interface, and a computing device in communication with the user interface, the computing device comprising a processor and memory including computer-readable program code stored therein, the computer-readable code configured, upon the execution thereof by the processor, to cause the apparatus to: receive patient data for a plurality of patients, the patient data corresponding to at least one of a biological sampling event, a biological processing event, at least one therapeutic regime, at least one biomarker status, and a patient status; determine at least one interrelationship between any one of the biological sampling event, the biological processing event, the at least one therapeutic regime, the at least one biomarker status, and the patient status; perform a therapeutic regime analysis to determine an interrelationship status for the interrelationship between at least one therapeutic regime and at least one of the patient status and the at least one biomarker status; and display at least one graphical interface on the user interface, the graphical interface including a plurality of visual elements, each visual element of the plurality of visual elements being associated with the patient data, at least one visual element being associated with the at least one interrelationship, at least one visual element including an indicium corresponding to at least one of the interrelationship status and the biomarker status.

In some embodiments, detection of a genetic biomarker (e.g., one or more genetic biomarkers) can include any of the variety of methods described in P.C.T. Publication No. WO 2018/064229, which is hereby incorporated by reference in its entirety. For example, detection of a genetic biomarker can include aptamers that bind biomarkers of interest. In some embodiments, oligonucleotide probes are used to detect the presence or levels of biomarkers or other biological entity in a biological sample.

In some embodiments, detection of a genetic biomarker (e.g., one or more genetic biomarkers) can include any of the variety of methods described in P.C.T. Publication No. WO 2017/205686, which is hereby incorporated by reference in its entirety. For example, detection of a genetic biomarker can include oligonucleotide probes that recognize tissues having phenotypes of interest. In various embodiments, the oligonucleotide probes are used in diagnostic, prognostic or theranostic processes to characterize a phenotype of that sample. The diagnosis may be related to a cancer. Additionally or alternatively, detection of a genetic biomarker can include a method of enriching an oligonucleotide library comprising a plurality of oligonucleotides, comprising: (a) providing a support arrayed with a plurality of samples; (b) contacting the support with the plurality of oligonucleotides; and (c) recovering members of the oligonucleotide probe library that bound to members of the plurality of samples, thereby enriching the oligonucleotide probe library. Additionally or alternatively, detection of a genetic biomarker can include a method of enriching an oligonucleotide library comprising a plurality of oligonucleotides, the method comprising: (a) performing at least one round of positive selection, wherein the positive selection comprises: (i) simultaneously contacting a plurality of samples with the plurality of oligonucleotides; and (ii) recovering members of the plurality of oligonucleotides that associated with the plurality of samples; (iii) optionally performing at least one round of negative selection, wherein the negative selection comprises: (i) simultaneously contacting a plurality of control samples with the plurality of oligonucleotides; (ii) recovering members of the plurality of oligonucleotides that did not associate with the plurality of control samples. In embodiments of the methods of enrichment, the plurality of samples is chosen to be representative of a phenotype of interest. Additionally or alternatively, detection of a genetic biomarker can include a method of characterizing a phenotype in a sample comprising: (a) arraying at least one sample on a substrate; (b) contacting the substrate with a plurality of oligonucleotides; and (b) measuring a presence or level of a complex formed between members of the plurality of oligonucleotides and the samples arrayed on the substrate, wherein the presence or level is used to characterize the phenotype. Additionally or alternatively, detection of a genetic biomarker can include a kit comprising at least one reagent for carrying out the methods, including methods of enrichment and characterizing. Additionally or alternatively, detection of a genetic biomarker can include use of at least one reagent for carrying out the methods. The at least one reagent can be any useful reagent, including without limitation at least one of a support, a plurality of nucleotides, a filtration unit, and PEG.

In some embodiments, detection of a genetic biomarker (e.g., one or more genetic biomarkers) can include any of the variety of methods described in U.S. Pat. No. 10,011,826, which is hereby incorporated by reference in its entirety. For example, detection of a genetic biomarker can include a method of isolating/extracting in parallel various biomolecules, in particular nucleic acids and proteins, from the same fixed biological samples. In some embodiments, the methods also comprise quantifying and analyzing the biomolecules isolated by the method, a kit for isolating/extracting in parallel various biomolecules from a fixed sample, and using said kit for diagnosing, prognosing, deciding the therapy of and monitoring the therapy of a disease. In some embodiments, a method of parallel purification of various kinds of biomolecules from the same biological starting material fixed by crosslinking, comprises: a) a step of dissolving said crosslinking of the starting material, b) a step of separating the different biomolecules present in the starting material into at least one fraction (A) and at least one fraction (B), and c) isolating or detecting, or isolating and detecting different biomolecules from at least one of said fractions (A) and (B) of step b), and a kit for performing said method.

In some embodiments, detection of a genetic biomarker (e.g., one or more genetic biomarkers) can include any of the variety of methods described in U.S. Pat. No. 9,797,000, which is hereby incorporated by reference in its entirety. For example, detection of a genetic biomarker can include a method of detecting the presence of a target RNA, the method comprising: a) providing at least one DNA capture probe, wherein the at least one DNA capture probe is bound to a support; b) hybridizing the target RNA to said at least one DNA capture probe, yielding a target RNA:DNA capture probe complex; c) isolating the target RNA:DNA capture probe complex; d) providing at least one DNA amplification probe, and hybridizing said at least one DNA amplification probe to said target RNA:DNA capture probe complex, yielding a target RNA:DNA capture/amplification probe complex; e) providing an anti-RNA: DNA hybrid antibody, and incubating said target RNA:DNA capture/amplification probe complex with said antibody, yielding a target RNA:DNA:antibody complex; f) detecting said antibody, wherein said detecting indicates the presence of said target RNA. In some embodiments, the antibody is conjugated to a detectable marker, and the step of detecting comprises detecting the marker. In one aspect, the detectable marker is selected from the group consisting of alkaline phosphatase and horseradish peroxidase. In some embodiments, the step of detecting comprises providing a second antibody that binds to said anti-RNA:DNA hybrid antibody, wherein said second antibody is conjugated to a detectable marker, and wherein said detecting further comprises detecting the marker. In some embodiments, the support comprises a magnetic bead. In one aspect, the magnetic bead is conjugated to at least one streptavidin molecule, and the at least one DNA capture probe is conjugated to a biotin molecule. Additionally or alternatively, detection of a genetic biomarker can include a method of providing target RNA for detection, the method comprising: incubating a biological sample containing the target RNA with carboxyl beads; isolating the beads; lysing the biological sample attached to the isolated beads; and isolating the beads from the lysed biological sample, wherein the resulting supernatant contains the target RNA for detection.

In some embodiments, detection of a genetic biomarker (e.g., one or more genetic biomarkers) can include any of the variety of methods described in U.S. Pat. No. 9,689,047, which is hereby incorporated by reference in its entirety. For example, detection of a genetic biomarker can include a method of detecting a target nucleic acid in a sample comprising non-target nucleic acids is provided, said method comprising: (a) purifying the target nucleic acid from the sample by a method comprising: (i) contacting the sample with at least one purification probe, wherein at least a portion of the nucleic acid probe hybridizes to the at least one target nucleic acid to form a DNA:RNA hybrid; (ii) immobilizing the DNA:RNA hybrid to a first solid support by a method comprising contacting the DNA:RNA hybrid with at least a first antibody capable of binding to the DNA:RNA hybrid, wherein the antibody is bound to or adapted to be bound to the first solid support; and (iii) separating the first solid support from the sample to generate at least one purified target nucleic acid; b. genotyping the purified target nucleic acid by a method comprising: (i) amplifying at least a portion of the purified target nucleic acid to generate an amplicon, such as by an isothermal amplification, such as whole genome amplification; (ii) immobilizing the amplicon to a second solid support by a method comprising contacting the amplicon with at least one immobilization probe, wherein: (a) the immobilization probe is bound to or adapted to be bound to the second solid support; and (B) at least a portion of the immobilization probe hybridizes the at least one target nucleic acid; (iii) contacting the immobilized amplicon with at least one detection probe, wherein the at least a portion of the detection probe hybridizes to the at least one target nucleic acid to generate a detection complex; and (iv) detecting at least a first detectable signal generated by the detection complex, wherein the detectable signal indicates the genotype of the target nucleic acid. In some embodiments, the plurality of purified target nucleic acids is contacted with a plurality of immobilization probes, wherein each of the plurality of immobilization probes is specific for a distinct purified target nucleic acid. Additionally or alternatively, detection of a genetic biomarker can include a method is provided comprising: a. a purifying step comprising: generating a double-stranded nucleic acid hybrid of the at least one target nucleic acid by hybridizing the at least one target nucleic acid to a hybrid probe set comprising at least a first nucleic acid probe specific for the at least one target nucleic acid; immobilizing the double-stranded nucleic acid hybrid to a first solid support through by contacting the double-stranded nucleic acid hybrid with at least a first antibody capable of binding to the double-stranded nucleic acid hybrid and binding the at least a first antibody to the first solid support; and separating the double-stranded nucleic acid hybrid from the sample to generate at least one purified nucleic acid; b. an amplifying step, wherein at least a portion of the at least one purified nucleic acid is amplified to generate amplified nucleic acids; and c. a genotyping step comprising: immobilizing the amplified nucleic acids to at least a second solid support by hybridizing the amplified nucleic acids to an immobilization probe set comprising at least one polynucleotide probe specific for the at least one target nucleic acid; and detecting the presence of the at least one target nucleic acid with a detection probe set comprising at least one polynucleotide probe specific for the at least one target nucleic acid.

In some embodiments, detection of a genetic biomarker (e.g., one or more genetic biomarkers) can include any of the variety of methods described in U.S. Pat. No. 9,422,593, which is hereby incorporated by reference in its entirety. For example, detection of a genetic biomarker can include a method of detecting at least one target nucleic acid comprising: (1) sequence-specific isolation of a target nucleic acid from a sample; (2) amplifying the isolated target nucleic acid; and (3) detecting the target nucleic acid using a plurality of detectably labeled nucleic acid detection probes, wherein each (a) bears a different detectable label from the other detection probes, and/or (b) has a different melting temperature from probes bearing the same detectable label. In some embodiments, the method comprises: A. purifying the at least one target nucleic acid by a method comprising: A1. generating a double-stranded nucleic acid hybrid of the at least one target nucleic acid by hybridizing the at least one target nucleic acid to a hybrid probe set comprising at least a first nucleic acid probe specific for the at least one target nucleic acid; A2. separating the double-stranded nucleic acid hybrid from the sample to generate at least one purified nucleic acid; B. amplifying at least a portion of the at least one purified nucleic acid; and C. detecting the target nucleic acid by a method comprising: C1. contacting the amplified nucleic acid with at least one detection probe set, wherein: C1(a). each of the detection probes of the detection probe set bears a detectable label; C1(b). at least two of the detection probes of the detection probe set carry the same detectable label; and C1(c). each of the probes carrying the same detectable label has a melting temperature (Tm) which differs from the other probes with the same label; C2. detecting the amplified nucleic acid by determining whether the labeled probe has hybridized to its nucleic acid sequence; and C3. detecting the temperature at which each detection probe dissociates from the nucleic acid sequence to which it has bound. In some embodiments, the double-stranded nucleic acid hybrid is separated from the sample by a method comprising contacting the double stranded nucleic acid hybrid with a molecule that binds specifically to double-stranded nucleic acid hybrids, preferably an anti-DNA:RNA hybrid antibody.

In some embodiments, detection of a genetic biomarker (e.g., one or more genetic biomarkers) can include any of the variety of methods described in U.S. Pat. No. 9,593,366, which is hereby incorporated by reference in its entirety. For example, detection of a genetic biomarker can include a method of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands. Additionally or alternatively, detection of a genetic biomarker can include a method of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein nucleic acids in the target sample are not separated from other material in the target sample. Additionally or alternatively, detection of a genetic biomarker can include a method of randomly amplifying messenger RNA, the method comprising, reverse transcribing messenger RNA to produce a first strand cDNA, bringing into contact a set of random G-deficient primers, DNA polymerase, and the first strand cDNA, and incubating under conditions that promote replication of the first strand cDNA, wherein replication of the first strand cDNA results in replicated strands, wherein during replication at least one of the replicated strands is displaced from the first strand cDNA by strand displacement replication of another replicated strand. Additionally or alternatively, detection of a genetic biomarker can include a method of randomly amplifying a target nucleic acid sequence, the method comprising: (a) mixing a set of random G-deficient primers with a target sample, to produce a primer-target sample mixture, and incubating the primer-target sample mixture under conditions that promote hybridization between the random G-deficient primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity. Additionally or alternatively, detection of a genetic biomarker can include a method of randomly amplifying a whole genome, the method comprising, bringing into contact a set of random G-deficient primers, DNA polymerase, and a target sample, and incubating the target sample under conditions that promote replication of the target sequence.

In some embodiments, detection of a genetic biomarker (e.g., one or more genetic biomarkers) can include any of the variety of methods described in U.S. Pat. No. 9,487,823, which is hereby incorporated by reference in its entirety. For example, detection of a genetic biomarker can include compositions and a method for amplification of nucleic acid sequences of interest. In some embodiments, the method is based on strand displacement replication of the nucleic acid sequences by primers. In some embodiments, the method is a form of multiple displacement amplification (MDA) useful for amplifying genomic nucleic acid samples and other nucleic acid samples of high complexity. The method can be used to amplify such highly complex nucleic acid samples using only one or a limited number of primers. It has been discovered that one or a small number of primers can effectively amplify whole genomes and other nucleic acid samples of high sequence complexity. The primers are specially selected or designed to be able to prime and efficiently amplify the broad range of sequences present in highly complex nucleic acid samples despite the limited amount of primer sequence represented in the primers. The method generally involves bringing into contact one, a few, or more primers having specific nucleic acid sequences, DNA polymerase, and a nucleic acid sample, and incubating the nucleic acid sample under conditions that promote replication of nucleic acid molecules in the nucleic acid sample. Replication of the nucleic acid molecules results in replicated strands such that, during replication, the replicated strands are displaced from the nucleic acid molecules by strand displacement replication of another replicated strand. The replication can result in amplification of all or a substantial fraction of the nucleic acid molecules in the nucleic acid sample. In some embodiments, the method, which uses a form of whole genome strand displacement amplification (WGSDA), one, a few, or more primers are used to prime a sample of genomic nucleic acid (or another sample of nucleic acid of high complexity). Additionally or alternatively, detection of a genetic biomarker can include a method of amplifying human genomes, the method comprising: bringing in to contact a single DNA primer of at least 6 nucleotides in length which is non-degenerate and non-random, a non-human, strand displacement DNA polymerase, and a human genomic nucleic acid sample to form a mixture, and incubating the mixture under conditions that promote replication of nucleic acid molecules in the human genomic nucleic acid sample; wherein the primer hybridizes to nucleic acid molecules in the genomic nucleic acid sample, and wherein the primer has a specific nucleotide sequence, wherein the genomic nucleic acid sample comprises all or a substantial portion of a human genome; and replicating the nucleic acid molecules in the human genomic nucleic acid sample under isothermal conditions, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample.

In some embodiments, detection of a genetic biomarker (e.g., one or more genetic biomarkers) can include any of the variety of methods described in U.S. Pat. No. 9,115,410, which is hereby incorporated by reference in its entirety. For example, detection of a genetic biomarker can include a nucleic acid detection method, referred to as target-specific HYBRID CAPTURE ("TSHC"). Additionally or alternatively, detection of a genetic biomarker can include a method of detecting and/or quantifying one or more target nucleic acids, comprising the steps of target enrichment, amplification, and detection for the rapid and sensitive detection of the target nucleic acid sequences. In some embodiments, one or more target nucleic acids are detected by: capturing the target nucleic acids to a solid support by mixing the target nucleic acids, nucleic acid probes complementary to the target nucleic acids, wherein one is RNA and the other is DNA, and a solid support; removing unbound target nucleic acids and nucleic acid probes; amplifying the captured target nucleic acids or nucleic acid probes, forming a plurality of amplicons, where the presence of the amplicons is indicative of the presence of the target nucleic acids; and detecting the target nucleic acids by mixing the target nucleic acids with selectable and distinguishable oligonucleotides which hybridize to a portion of the target nucleic acids, (i.e., capture sequence probes; CSPs) and nucleic acid probes complementary to a different portion of the target nucleic acids (i.e., signal sequence probes; SSPs), wherein either the probe or target is an RNA and the other is DNA, where DNA:RNA hybrids are detected by DNA:RNA hybrid-specific binding agents, which are directly or indirectly labeled, thereby detecting the target nucleic acids. The SSPs are not limited to serving as only a means for producing a signal for detection; but may be used in the target enrichment step by hybridizing to the target nucleic acid, enabling capture with a DNA:RNA hybrid-specific binding agent. In some embodiments, a plurality of target nucleic acids are detected by: hybridizing a plurality of target nucleic acids to nucleic acid probes which are complementary to the target nucleic acids, forming DNA:RNA hybrids; capturing the DNA:RNA hybrids with DNA:RNA hybrid-specific antibodies conjugated to solid supports; removing unbound target nucleic acids and nucleic acid probes; amplifying the captured target nucleic acids or nucleic acid probes, forming a plurality of amplicons, using random primers and DNA polymerase, where the presence of the plurality of amplicons is indicative of the presence of the target nucleic acids; hybridizing nucleic acid probes complementary to a portion of the target nucleic acid sequences, forming DNA:RNA hybrids between targets and probes; hybridizing oligonucleotides conjugated to a solid support to a different portion of the target nucleic acids, wherein the solid support is selectable; selecting the oligonucleotide complexes; and detecting the plurality of target nucleic acids by binding DNA:RNA hybrid-specific binding agents to the DNA:RNA hybrids. In some embodiments, one or more target DNAs are detected by a multiplex method having the steps of: hybridizing a plurality of target DNAs to RNA probes which are complementary to the target DNAs, forming DNA:RNA hybrids; capturing the DNA:RNA hybrids with DNA:RNA hybrid-specific antibodies which are conjugated to beads; removing unbound nucleic acids and nucleic acid probes by washing excess nucleic acids and probes; isothermally amplifying the target DNAs using random primers and DNA polymerase, forming a plurality of amplicons; hybridizing RNA probes complementary to a portion of the target DNAs (i.e., SSPs), forming DNA:RNA hybrids; hybridizing specific DNA oligonucleotides to a different portion of the target DNAs, wherein the DNA oligonucleotides are conjugated to selectable beads; and detecting the plurality of target DNAs by binding detectably labeled DNA:RNA hybrid-specific antibodies to the DNA:RNA hybrids and selecting target DNA using selectable oligonucleotide-conjugated beads (i.e., CSPs), wherein the DNA:RNA hybrid-specific antibodies are detectably and distinguishably labeled. The presence of each target is detected by the labeled DNA:RNA antibody through SSPs which form DNA:RNA hybrids with the target, while the various targets are separated or selected based on the oligonucleotide-conjugated bead (i.e., CSP). The presence of amplicon and DNA:RNA hybrids is indicative of the presence of the target DNAs.

In some embodiments, detection of a genetic biomarker (e.g., one or more genetic biomarkers) can include any of the variety of methods described in U.S. Pat. No. 9,051,606, which is hereby incorporated by reference in its entirety. For example, detection of a genetic biomarker can include methods for making and using multicomponent Nucleic Acid Enzymes (MNAzymes). Additionally or alternatively, detection of a genetic biomarker can include a composition comprising at least two or more oligonucleotide components wherein at least a first oligonucleotide component and a second oligonucleotide component self-assemble in the presence of an MNAzyme assembly facilitator to form a catalytically active multi-component nucleic acid enzyme (MNAzyme), wherein each of said at least first and said second oligonucleotide components comprise a substrate arm portion, a catalytic core portion, and a sensor arm portion; wherein upon self-assembly, the sensor arm portion of said first and second oligonucleotide components act as sensor arms of the MNAzyme, the substrate arm portion of the first and second oligonucleotide components act as substrate arms of the MNAzyme, and the catalytic core portion of the first and second oligonucleotide components act as a catalytic core of the MNAzyme; and wherein the sensor arms of the MNAzyme interact with said MNAzyme assembly facilitator so as to maintain the first and second oligonucleotide components in proximity for association of their respective catalytic core portions to form the catalytic core of the MNAzyme, said catalytic core capable of modifying at least one substrate, and wherein said substrate arms of said MNAzyme engage a substrate so that said catalytic core of said MNAzyme can modify said substrate. In some embodiments, the composition may further comprise at least a third oligonucleotide component which acts to stabilize at least one of said substrate arm portions or sensor arm portions. In some embodiments, the method may further comprise at least a third oligonucleotide component and a fourth oligonucleotide component that self-assemble in the presence of at least one additional assembly facilitator to form at least one additional catalytically active MNAzyme, wherein each of said at least third and fourth oligonucleotide components comprise a substrate arm portion, a catalytic core portion, and a sensor arm portion; wherein upon self-assembly of said at least a third oligonucleotide component and a fourth oligonucleotide component, the sensor arm portion of said at least third and said at least fourth oligonucleotide components form sensor arms of said at least one additional catalytically active MNAzyme, the substrate arm portion of said at least third and said at least fourth oligonucleotide components form substrate arms of said at least one additional catalytically active MNAzyme, and the catalytic core portion of said at least third and said at least fourth oligonucleotide components form a catalytic core of said at least one additional catalytically active MNAzyme; and wherein the sensor arms of said at least one additional MNAzyme interact with said at least one additional assembly facilitator so as to maintain said at least third and said at least fourth oligonucleotide components in proximity for association of their respective catalytic core portions to form the catalytic core of said at least one additional MNAzyme, said catalytic core capable of acting on at least one additional substrate, and wherein the substrate arms of said at least one additional MNAzyme engage at least one additional substrate so that the catalytic core of said at least one additional MNAzyme can act on said at least one additional substrate. Additionally or alternatively, detection of a genetic biomarker can include a method for detecting the presence of at least one assembly facilitator comprising: (a) providing two or more oligonucleotide components, wherein at least a first oligonucleotide component and a second oligonucleotide component self-assemble in the presence of an assembly facilitator to form at least one catalytically active multi-component nucleic acid enzyme (MNAzyme); (b) contacting the two or more oligonucleotide components with a sample putatively containing the assembly facilitator under conditions permitting: (1) the self-assembly of said at least one catalytically active MNAzyme, and (2) the catalytic activity of said MNAzyme; and (c) determining the presence of the catalytic activity of said at least one MNAzyme, wherein the presence of the catalytic activity is indicative of the presence of said at least one assembly facilitator. In some embodiments, the method may further comprise a step of amplifying the assembly facilitator. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). Additionally or alternatively, detection of a genetic biomarker can include a method for detecting the presence of at least one assembly facilitator comprising: (a) providing two or more oligonucleotide components, wherein at least a first oligonucleotide component and a second oligonucleotide component self-assemble in the presence of at least a first assembly facilitator to form at least a first catalytically active multi-component nucleic acid enzyme (MNAzyme); (b) providing at least a first substrate, said first substrate capable of being modified by said first MNAzyme, wherein said modification of said substrate by said MNAzyme provides a detectable effect; (c) contacting said two or more oligonucleotide components with a sample putatively containing said at least first assembly facilitator under conditions permitting: (1) the self-assembly of said at least first MNAzyme, and (2) the catalytic activity of said at least first MNAzyme; and (d) detecting said detectable effect. In some embodiments, the method may further comprise the step of amplifying the nucleic acid. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). Additionally or alternatively, detection of a genetic biomarker can include a method for detecting the presence of at least one target comprising: (a) providing two or more oligonucleotide components wherein at least a first oligonucleotide component and at least a second oligonucleotide component are capable of self-assembly in the presence of said target to form a catalytically active multi-component nucleic acid enzyme (MNAzyme); and wherein at least one of said first and said second oligonucleotide components further comprises at least one aptamer portion; (b) contacting said oligonucleotide components with a sample putatively containing said at least one target under conditions permitting: (1) binding of said target to said aptamer portions and (2) catalytic activity of the MNAzyme; and (c) determining the presence of the catalytic activity of the MNAzyme, wherein the presence of the catalytic activity is indicative of the presence of said target. Additionally or alternatively, detection of a genetic biomarker can include a method for detecting a target using an MNAzyme mediated signal amplification cascade comprising: (a) providing a first oligonucleotide component and a second oligonucleotide component that self assemble in the presence of said target to form a first catalytically active multi-component nucleic acid enzyme (MNAzyme); (b) providing an insoluble support having a first and a second substrate attached thereto, said first and second substrates are capable of being modified by said first MNAzyme, wherein said first and second substrates comprise at least a third and a fourth oligonucleotide component respectively, capable of forming a second catalytically active MNAzyme, wherein said third and fourth oligonucleotide components are released upon modification of said first and second substrates by said first MNAzyme; (c) providing said insoluble support having a third and a fourth substrate attached thereto, said third and fourth substrates are capable of being modified by said second MNAzyme, wherein said third and fourth substrates comprise at least a fifth and a sixth oligonucleotide component respectively, capable of forming a third catalytically active MNAzyme, wherein said fifth and said sixth oligonucleotide components are released upon modification of said third and fourth substrates by said second MNAzyme, and; (d) providing an assembly facilitator capable of facilitating the assembly of said second and said third MNAzyme, and; (e) providing a fifth substrate which is capable of being modified by said second MNAzyme to provide a detectable effect; (f) contacting said first and second oligonucleotide components with a sample putatively containing said target, in the presence of said assembly facilitator, and in the presence of said insoluble support having said first, second, third and fourth substrates attached thereto under conditions permitting: (1) self-assembly of said first, second and third, MNAzymes, and (2) catalytic activity of said first, second and third, MNAzymes; and (g) wherein said third MNAzyme modifies said first and second substrates thereby further providing said second MNAzyme wherein said second MNAzyme further modifies at least one of said third, fourth and fifth substrates thereby further providing said third MNAzyme thereby further providing said detectable effect, and; (h) wherein detection of said detectable effect is indicative of the presence of said target.

In some embodiments, detection of a genetic biomarker (e.g., one or more genetic biomarkers) can include any of the variety of methods described in U.S. Pat. No. 9,012,149, which is hereby incorporated by reference in its entirety. For example, detection of a genetic biomarker can include a method for synthesis of a cDNA that contains the sequence of an miRNA or other small RNA that can be amplified using standard nucleic acid amplification methods such as the Polymerase Chain Reaction. The method can provide higher specificity of cDNA synthesis from small RNAs, while simultaneously permitting experimenters to carry out the two key enzymatic reactions necessary for this synthesis under substantially the same reaction conditions, conditions that include the presence of divalent cations at concentrations from 10 millimolar and 80 millimolar. When these reactions conditions are used as part of an assay for a small RNA, especially for an miRNA, greater specificity and sensitivity results. In some embodiments, the method for preparing a cDNA copy of a small RNA molecule, comprises: (a) providing a small RNA from a biological sample, wherein said RNA is from 18 to 28 nucleotides in length; (b) incubating the small RNA with an enzyme capable of catalyzing the addition of nucleotides at the 3' end of the small RNA in the presence of a single ribonucleotide triphosphate selected from the group consisting of ATP, GTP, UTP, and CTP and at a final concentration of divalent magnesium cation between 20 millimolar and 80 millimolar in a reaction to add nucleotides to the small RNA to generate a tailed small RNA; (c) annealing a DNA primer to the tailed small RNA whereby the DNA template extends from the 3' end of the tailed small RNA, thereby providing a single stranded region of DNA that may be used to direct polymerization of deoxyribonucleotide triphosphates; and (d) incubating the annealed tailed small RNA and DNA primer in the presence of reverse transcriptase and deoxyribonucleotide triphosphates and at a final concentration of divalent magnesium cation between 20 millimolar and 80 millimolar under conditions allowing reverse transcription into cDNA and amplification of the annealed tailed small RNA to produce an amplification product.

In some embodiments, detection of a genetic biomarker (e.g., one or more genetic biomarkers) can include any of the variety of methods described in U.S. Pat. No. 8,962,250, which is hereby incorporated by reference in its entirety. For example, detection of a genetic biomarker can include methods of nucleic acid amplification and quantification such as a method of amplifying a plurality of selected nucleic acid molecules from a pool of nucleic acid molecules comprising: (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and (b) further amplifying the selected nucleic acid molecules in a plurality of second round amplification reactions, each including a portion of the completed multiplex reaction as a template and at least one pair of inner primers each pair being specific for one of the selected nucleic acid sequences such that each second round reaction further amplifies a subset of the plurality of selected nucleic acid molecules respectively. Additionally or alternatively, detection of a genetic biomarker can include a method of amplifying a plurality of selected nucleic acid molecules from a pool of nucleic acid molecules comprising: (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and (b) further amplifying the selected nucleic acid molecules in a plurality of second round amplification reactions, each including a portion of the completed multiplex reaction as a template and at least one pair of primers each pair comprising an inner primer and one of the outer primers and being specific for one of the selected nucleic acid sequences such that each second round reaction further amplifies a subset of the plurality of selected nucleic acid molecules respectively. Additionally or alternatively, detection of a genetic biomarker can include a method of estimating the number of selected nucleic acid molecules from a pool of nucleic acid molecules comprising: (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; (b) further amplifying the selected nucleic acid molecules in a plurality of second round amplification reactions, each including a detectible reporter, a portion of the completed multiplex reaction as a template and at least one pair of inner primers each pair being specific for one of the selected nucleic acid sequences whereby each second round reaction further amplifies a subset of the plurality of selected nucleic acid molecules respectively; and (c) monitoring each second round amplification reaction by means of the detectible reporter such that the number of selected nucleic acid molecules of each selected sequence is estimated. Additionally or alternatively, detection of a genetic biomarker can include a method of estimating the number of selected nucleic acid molecules from a pool of nucleic acid molecules comprising: (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and (b) further amplifying the selected nucleic acid molecules in a plurality of second round amplification reactions, each including a detectible reporter, a portion of the completed multiplex reaction as a template and at least one pair of primers each pair comprising an inner primer and one of the outer primers and being specific for one of the selected nucleic acid sequences such that each second round reaction further amplifies a subset of the plurality of selected nucleic acid molecules respectively; and (c) monitoring each second round amplification reaction by means of the detectible reporter such that the number of selected nucleic acid molecules of each selected sequence is estimated. In some embodiments, the fully nested form of the Multiplex Tandem-Polymerase Chain Reaction (MT-PCR) method is used according to the first and third aspects, whereby each selected nucleic acid molecule is amplified using a pair of outer primers in the first round of amplification and two inner primers in the second round of amplification. In some embodiments, the hemi-nested MT-PCR method is used according to the second and fourth aspects, whereby each selected nucleic acid molecule is amplified using a pair of outer primers in the first round of amplification and the selected nucleic acid sequence is amplified further in the second round of amplification using a pair of primers comprising one of the outer primers used in the first round of amplification paired with one inner primer. In some embodiments, the second round amplification reaction includes a plurality of primer pairs and a plurality of fluorescent probes such that a plurality of selected nucleic acid molecules of each selected sequence are amplified and quantified by means of the fluorescent probes each being specific for a selected nucleic acid sequence. In some embodiments, at least one of the outer primers includes UTP nucleotides whereby the primer is amenable to digestion by a UNG enzyme and the outer primers are removed at the end of the first round of amplification by digestion with a UNG enzyme thereby substantially preventing contamination of the second round amplification reaction by the first round primers. In some embodiments, the methods are used in a method of detecting polymorphisms, mutations, insertions and deletions. Additionally or alternatively, detection of a genetic biomarker can include a method of identifying and/or quantifying at least one selected nucleic acid sequence including the steps of: (i) mixing one or more selected nucleic acid sequences with one or more detectible reporters; (ii) generating a melting curve by measuring the signal generated by said one or more detectible reporters; (iii) identifying and/or quantifying said one or more selected nucleic acid sequences from said melting curve.

In some embodiments, detection of a genetic biomarker (e.g., one or more genetic biomarkers) can include any of the variety of methods described in U.S. Pat. No. 8,877,436, which is hereby incorporated by reference in its entirety. For example, detection of a genetic biomarker can include a method for determining the presence of a target nucleic acid molecule in a sample containing biological material. In some embodiments, the method for determining the presence of a target nucleic acid molecule in a sample comprises: a) suspending the sample in a collection medium; b) releasing target nucleic acid molecules from the sample into the collection medium; c) converting double-stranded target nucleic acid molecules to single-stranded target nucleic acid molecules; d) contacting one or more probes with the single-stranded target nucleic acid molecules under conditions that allow the probes and target single-stranded target nucleic acid molecules to hybridize forming double-stranded nucleic acid hybrids; e) capturing the double-stranded nucleic acid hybrids; f) separating the double-stranded nucleic acid hybrids from un-bound single-stranded target nucleic acid molecules; and g) detecting the double-stranded nucleic acid hybrids, thereby indicating the presence of the target nucleic acid. In some embodiments, the detection method may be automated, either fully automated, or partially automated—in other words requiring some human input. In some embodiments, the detection of target nucleic acid molecules in multiple samples at the same time or within a very short period of time, for example in a machine or a series of machines. Additionally or alternatively, detection of a genetic biomarker can include a collection medium into which a sample containing a target nucleic acid molecule are collected. The target nucleic acid molecule can be kept in the collection medium with minimal degradation of the target nucleic acid molecule over a time period of weeks or months. In some embodiments, DNA-based target sample material can be kept in the collection medium with minimal degradation of the target nucleic acid molecule over a time period of weeks or months. In some embodiments, the detergent-based collection medium allows for the rapid analysis and processing of a sample. In some embodiments, the collection medium comprises about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide.

In some embodiments, detection of a genetic biomarker (e.g., one or more genetic biomarkers) can include any of the variety of methods described in U.S. Pat. No. 8,372,637, which is hereby incorporated by reference in its entirety. For example, detection of a genetic biomarker can include a method of stabilizing a biological sample that has the following steps:
a) preparation of a biological sample, and b) contacting the biological sample with a composition having a substance according to the following structural formula:

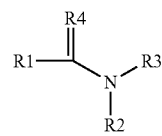

in which R1 is a hydrogen residue or a methyl residue, R2 and R3 are identical or different hydrocarbon residues with a length of the carbon chain of 1-20, and R4 is an oxygen, sulfur or selenium residue. The hydrocarbon residues R2 and/or R3 can be selected independently of one another from the group comprising alkyl, long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. In some embodiments, the chain length n on R2 and/or R3 can have the values 1, 2, 3, 4, 5, 6, 7, 8, 9, 10, 11, 12, 13, 14, 15, 16, 17, 18, 19 and 20. In some embodiments, R2 and R3 have lengths of the carbon chain of 1-10. In some embodiments, R2 and R3 have lengths of the carbon chain of 1-5. In this case the chain length n can in particular have the values 1, 2, 3, 4 and 5. In some embodiments, methyl and ethyl residues are used on R2 and/or R3. The chain length n then has values of 1 and 2. In some embodiments, the substance used in the composition can be used as the sole agent for preservation. In some embodiments, the substance can also be used in conjunction with other preserving substances or even only as an additive to other preserving substances in the composition. In some embodiments, the volume ratio or weight ratio between the substance and one or more other preserving substances in the composition can be in the range from 0.01:100 to 100:0. Preferably it is in the range from 0.1:100 to 100:0 and especially preferably it is in the range from 1:100 to 100:0 and particularly preferably it is in the range from 5:100 to 100:0. In some embodiments, the class of substances used is for example dialkylacetamides (if R1 is a methyl residue) or dialkylformamides (if R1 is a hydrogen residue). In some embodiments, the biological sample is a material selected from the group comprising sample material, plasma, body fluids, blood, serum, cells, leukocyte fractions, crusta phlogistica, sputum, saliva, urine, semen, feces, forensic samples, smears, aspirates, biopsies, tissue samples, tissue parts and organs, food samples, environmental samples, plants and plant parts, bacteria, viruses, viroids, prions, yeasts and fungi, and fragments or constituents of the aforementioned materials, and/or isolated, synthetic or modified proteins, nucleic acids, lipids, carbohydrates, metabolic products and/or metabolites. In some embodiments, the substance is a substance selected from the group comprising N,N-dimethylacetamide, N,N-diethylacetamide, N,N-dimethylformamide, N,N-diethylformamide, N,N-dimethylthioformamide and N,N-diethylthioformamide. Their structural formulas are as follows:

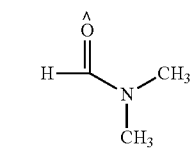
N,N-dimethylformamide

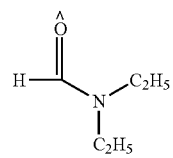
N,N-diethylformamide

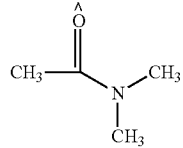
N,N-dimethylacetamide

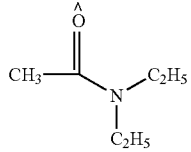
N,N-diethylacetamide

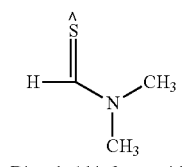
Dimethylthioformamide

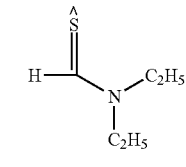
Diethylthioformamide.

In some embodiments, detection of a genetic biomarker (e.g., one or more genetic biomarkers) can include any of the variety of methods described in U.S. Pat. No. 8,043,834, which is hereby incorporated by reference in its entirety. For example, detection of a genetic biomarker can include compositions and methods useful for labeling and detection of analytes. In some embodiments, the compositions are associations of three components: reporter binding agents, amplification target circles, and DNA polymerase. The compositions are assembled prior to their use in a rolling circle amplification reaction and can be stored and transported prior to use without substantial loss of activity. In some embodiments, the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, and wherein the composition is not in an assay or reaction. In some embodiments, the composition can be used as universal reagents of rolling circle amplification. For this purpose, the compositions can have specific binding molecules that can interact with particular moieties or molecules that are present on, or are used to label any target molecule of interest. For example, the specific binding molecule in the reagent composition can be streptavidin or another biotin-specific molecule (such as an anti-biotin antibody). Any target molecule labeled with biotin can then be associated with the reagent composition and labeled and/or detected via rolling circle amplification mediated by the composition. This reagent composition can be used with any biotinylated target molecule. Similarly, use of an antibody specific to a class of antibodies (for example, and anti-mouse antibody) as the specific binding molecule in reagent compositions. Such reagent compositions can be used to label and detect a class of antibodies in an assay. For example, the reagent composition can be used to label and detect all mouse antibodies bound to antigen in immunoassays regardless of the specificity of the individual mouse antibodies. This is analogous to the use of antibodies specific to a class of antibodies in sandwich immunoassays. The reagents compositions provide greater signal amplification and tighter localization of the signal than in traditional immunoassays.

In some embodiments, detection of a genetic biomarker (e.g., one or more genetic biomarkers) can include any of the variety of methods described in U.S. Pat. No. 7,682,790, which is hereby incorporated by reference in its entirety. For example, detection of a genetic biomarker can include compositions for the isolation and/or stabilisation of nucleic acids in materials of biological origin. The compositions contain as an essential ingredient a cationic compound of general formula

wherein

Y may denote nitrogen or phosphorus;

R1, R2, R3 and R4 independently of one another may denote a branched or unbranched C1-C20-alkyl group and/or a C6-C20-aryl group as well as a C6-C26-aralkyl group; and X— may represent an anion of an inorganic or organic, mono- or polybasic acid and at least one proton donor as additive. In some embodiments, the cationic compounds consist of an ammonium salt wherein R1 denotes a higher alkyl group, preferably with 12, 14 or 16 carbon atoms, and R2, R3 and R4 in each case denote a methyl group. In some embodiments, R1 denotes an aralkyl group, preferably a benzyl group, R2 denotes a higher alkyl group—preferably with 12, 14 or 16 carbon atoms—and R3 and R4 denote a methyl group. In some embodiments, the anion is bromide, chloride, phosphate, sulphate, formate, acetate, propionate, oxalate or succinate. In some embodiments, aliphatic hydroxy-di- and -tricarboxylic acids, e.g., tartronic acid, D-(+), L-(−) or DL-malic acid, (2R, 3R)-(+)-tartaric acid, (2S,3S)-(−)-tartaric acid, meso-tartaric acid and citric acid, are used. In some embodiments, aliphatic ketodicarboxylic acids may also be used as additives, such as e.g. mesoxalic acid and oxaloacetic acid, of which oxaloacetic acid is most particularly preferred. In some embodiments, amino acids may be used, of which α-amino acids—such as e.g. aminoacetic acid (glycine), α-aminopropionic acid (alanine), α-amino-iso-valeric acid (valine), α-amino-iso-caproic acid (leucine) and α-amino-β-methylvaleric acid (isoleucine) are preferred. As further additives, mineral acids and their salts may also be used. Preferably, the salts of mineral acids—such as phosphoric acid or sulphuric acid—with alkali metals or the ammonium salts thereof are used. Phosphoric acid and ammonium sulphate are most preferably used. Additionally or alternatively, detection of a genetic biomarker can include a method of stabilizing nucleic acids in a biological sample, the method comprising: mixing a storage stabilization composition with a solution containing the nucleic acids, wherein the composition comprises a cationic compound of the general formula

Y+R1R2R3R4X— wherein Y represents nitrogen or phosphorus;
R1, R2, R3 and R4, independently, represent a branched or unbranched C1-C20-alkyl group and/or a C6-C20-aryl group as well as a C6-C26-aralkyl group;
X-represents an anion of an inorganic or organic, mono- or polybasic acid; and
at least one proton donor
wherein the proton donor is present in the composition in a concentration of above 50 mM to saturation and wherein the proton donor is selected from the group consisting of saturated aliphatic monocarboxylic acids, unsaturated alkenyl-carboxylic acids, saturated and/or unsaturated aliphatic C2-C6-dicarboxylic acids, aliphatic hydroxyl-di- and tricarboxylic acids, aliphatic ketocarboxylic acids, amino acids or the inorganic acids or the salts thereof, on their own or in combination; stabilizing the nucleic acids, wherein the nucleic acids are stabilized by forming an ionic complex with the cationic compound; optionally separating the insoluble ionic complex from the solution; and optionally releasing the nucleic acids from the insoluble ionic complex.

In some embodiments, detection of a genetic biomarker (e.g., one or more genetic biomarkers) can include any of the variety of methods described in U.S. Pat. No. 7,683,035, which is hereby incorporated by reference in its entirety. For example, detection of a genetic biomarker can include (1) a method of stabilizing and/or isolating nucleic acids from a biological sample, comprising the following step: contacting the biological sample with at least one cationic compound of formula (I):

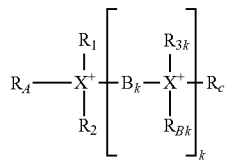

wherein conjugated bases of strong and/or weak inorganic and/or organic acids are used as anion (A), and wherein the substance consisting of (I) and the anion is neutral in charge on the whole, and wherein
X represents nitrogen (N) or phosphorus (P),
k represents the integer 1, 2, 3, 4, 5, 6, 7, 8, 9, 10, 11, 12, 13, 14, 15, 16, 17, 18, 19, 20, 21, 22, 23, or 24,
$B_k$ represents aliphatic alkanediyl bridges, which may be substituted on none, on one or more carbon atoms, and wherein one or more non-adjacent carbon atoms may be replaced by oxygen, and which have the structure —(CH2)$_n$—(OCH2)$_m$- wherein n and m independently represent the integer 0, 1, 2, 3, 4, 5, or 6, with n+m>0; alternatively,
$B_k$ represents a substituted phenyl, naphthyl or biphenyl bridge, which, in addition, may be substituted on one or more carbon atoms and has the structure

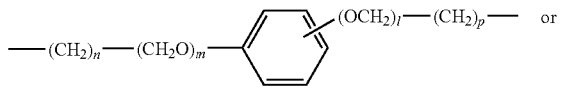

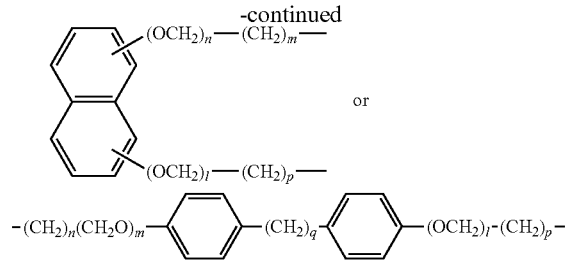

wherein n, m, l, p, q independently represent the integer 0, 1, 2, 3, 4, 5, or 6;
R1, R2, R3k, which may be identical or different and which may be unsubstituted or substituted on one or more carbon atoms, represent hydrogen, linear or branched C1-C6 alkyl, linear or branched C1-C6 alkenyl, linear or branched C1-C6 alkynyl, phenyl, benzyl, and phenoxyethyl having the structure

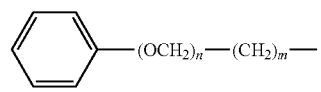

wherein n, m independently represent the integer 0, 1, 2, 3, 4, 5, or 6, and
Z represents one of the structures —O—, —CO—, —CO2-, —OCO—, —CO—N—, —N—CO—, —O—CO—N—, —N—CO—O—, —S—, or —S—S—;
or R1, R2, R3k represent phenyl, benzyl, phenoxyethyl having the structure
wherein n, m independently represent the integer 0, 1, 2, 3, 4, 5, or 6;
RA, RBK, RC, which may be identical or different and which may be unsubstituted or substituted on one or more carbon atoms, represent hydrogen, linear or branched C1-C21 alkyl, linear or branched C1-C21 alkenyl, linear or branched C1-C21 alkynyl, and a structure

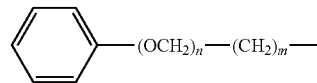

wherein n, m independently represent the integer 0, 1, 2, 3, 4, 5, 6, 7, 8, 9, 10, 11, 12, 13, 14, 15, 16, 17, 18, 19, 20, 21, 22, 23, or 24, and
Z represents —O—, —CO—, —CO2-, —OCO—, —CO—N—, —N—CO—, —O—CO—N—, —N—CO—O—, —S—, or —S—S—;
alternatively, RA and RC together form a residue RAC having a cyclic structure

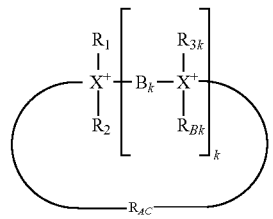

wherein the residue RAC, which may be unsubstituted or substituted on one or more carbon atoms, represents linear or branched C1-C8 alkyl, linear or branched C1-C8 alkenyl, or linear or branched C1-C8 alkynyl, and if k>1, the bridging groups Bk and the groups RBk and R3k are the same or different;

(2) A kit for stabilizing and/or isolating nucleic acids, comprising at least one cationic compound as defined above by formula (I); (3) A complex, comprising a nucleic acid and at least one cationic compound, formed as the result of the method in (1); (4) A composition of matter, comprising at least one cationic compound as defined above by formula (I); (5) A pharmaceutical composition, comprising the composition of matter in (4); (6) A diagnostic composition, comprising the composition of matter in (4); and (7) A composition for research, comprising the composition of matter in (4).

In some embodiments, detection of a genetic biomarker (e.g., one or more genetic biomarkers) can include any of the variety of methods described in U.S. Pat. No. 7,323,310, which is hereby incorporated by reference in its entirety. For example, detection of a genetic biomarker can include an amplification reaction mixture for selectively amplifying RNA from a target RNA template comprising: a cellular RNA-dependent RNA-polymerase and at least two primers complementary to said target RNA template. In some embodiments, the RNA-dependent RNA-polymerase (RdRp) is a tomato or other cellular RdRp. In some embodiments, the RdRp is a cellular RdRp, and in a particularly preferred embodiment, the RdRp is selected from the group consisting of tomato RdRp, Tobacco RdRp, cucumber RdRp, and wheat RdRp. In some embodiments, the amplification reaction mixture comprises a cellular RdRp and at least two primers complementary to a target RNA template. In a preferred embodiment, the reaction mixtures further comprise an RNA helicase, an energy source and optionally a divalent cation such as, e.g., Mg2+, Mn2+ or Co2+. The amplification reaction mixtures may further include RNase inhibitors, RNA stabilizing agents, single-stranded binding proteins, rNTPs and analogs of rNTPs, for the amplification of target RNA into product RNA. An amplification buffer is also provided which is supportive of both RdRp and RNA helicase activity. Additionally or alternatively, detection of a genetic biomarker can include a method for selectively amplifying RNA from an RNA template, comprising: contacting the template RNA with an amplification reaction mixture according to claim 1; and incubating said amplification reaction mixture to produce amplified RNA product, wherein said incubation step comprises at least one denaturation condition.

In some embodiments, detection of a genetic biomarker (e.g., one or more genetic biomarkers) can include any of the variety of methods described in U.S. Pat. No. 6,977,153, which is hereby incorporated by reference in its entirety. For example, detection of a genetic biomarker can include a method involving synthesizing first strand cDNA molecules from RNA molecules, circularizing the first strand cDNA molecules and replicating the circularized first strand cDNA molecules using rolling circle replication. Additionally or alternatively, detection of a genetic biomarker can include a method of amplifying RNA sequences, the method comprising: incubating a cDNA primer and an RNA sample comprising RNA molecules under conditions that promote synthesis of first strand cDNA molecules from the RNA molecules; incubating a circularization probe and the first strand cDNA molecules under conditions that promote circularization of the first strand cDNA molecules; and incubating the circularized first strand cDNA molecules under conditions that promote rolling circle replication of the circularized first strand cDNA molecules, thereby amplifying RNA sequences. Additionally or alternatively, detection of a genetic biomarker can include a method of amplifying RNA sequences, the method comprising: incubating a cDNA primer and an RNA sample comprising RNA molecules under conditions that promote synthesis of first strand cDNA molecules from the RNA molecules, wherein the conditions that promote synthesis of first strand cDNA molecules comprise incubating the cDNA primer and the RNA sample in the presence of a reverse transcriptase; incubating the first strand cDNA molecules in the presence of an RNAse H activity; incubating the first strand cDNA molecules under alkaline conditions; neutralizing the first strand cDNA molecules; purifying the first strand cDNA molecules; incubating a circularization probe and the first strand cDNA molecules under conditions that promote circularization of the first strand cDNA molecules, wherein the conditions that promote circularization of the first strand cDNA molecules comprise incubating the circularization probe and the first strand cDNA molecules in the presence of ligase; incubating the circularized first strand cDNA molecules under conditions that promote rolling circle replication of the circularized first strand cDNA molecules, thereby amplifying RNA sequences, wherein the conditions that promote rolling circle replication of the circularized first strand cDNA molecules comprise incubating the circularized first strand cDNA molecules in the presence of a DNA polymerase. Additionally or alternatively, detection of a genetic biomarker can include a method of amplifying RNA sequences, the method comprising: incubating a cDNA primer and an RNA sample comprising RNA molecules under conditions that promote synthesis of first strand cDNA molecules from the RNA molecules; incubating a circularization probe and the first strand cDNA molecules under conditions that promote ligation of the first strand cDNA molecules to each other to form first strand cDNA concatemers; and incubating the first strand cDNA concatemers under conditions that promote strand displacement replication of the first strand cDNA concatemers, thereby amplifying RNA sequences.

In some embodiments, detection of a genetic biomarker (e.g., one or more genetic biomarkers) can include any of the variety of methods described in U.S. Pat. No. 6,815,212, which is hereby incorporated by reference in its entirety. For example, detection of a genetic biomarker can include methods provided for detecting the binding of a first member to a second member of a ligand pair, comprising the steps of (a) combining a set of first tagged members with a biological sample which may contain one or more second members, under conditions, and for a time sufficient to permit binding of a first member to a second member, wherein said tag is correlative with a particular first member and detectable by non-fluorescent spectrometry, or potentiometry, (b) separating bound first and second members from unbound members, (c) cleaving the tag from the tagged first member, and (d) detecting the tag by non-fluorescent spectrometry, or potentiometry, and therefrom detecting the binding of the first member to the second member. A wide variety of first and second member pairs may be utilized, including for example, nucleic acid molecules (e.g., DNA, RNA, nucleic acid analogues such as PNA, or any combination of these), proteins or polypeptides (e.g., an antibody or antibody fragment (e.g., monoclonal antibody, polyclonal antibody, or a binding partner such as a CDR), oligosaccharides, hormones, organic molecules and other substrates (e.g., xenobiotics such as glucuronidase—drug molecule), or any other ligand pair. In some embodiments, the first and second members may be the same type of molecule or of different types. For example, representative first member second member ligand pairs include: nucleic acid molecule/nucleic acid molecule; antibody/nucleic acid molecule; antibody/hormone; antibody/xenobiotic; and antibody/protein. Additionally or alternatively, detection of a genetic biomarker can include methods for analyzing the pattern of gene expression from a selected biological sample, comprising the steps of (a) exposing nucleic acids from a biological sample, (b) combining the exposed nucleic acids with one or more selected tagged nucleic acid probes, under conditions and for a time sufficient for said probes to hybridize to said nucleic acids, wherein the tag is correlative with a particular nucleic acid probe and detectable by non-fluorescent spectrometry, or potentiometry, (c) separating hybridized probes from unhybridized probes, (d) cleaving the tag from the tagged fragment, and (e) detecting the tag by non-fluorescent spectrometry, or potentiometry, and therefrom determining the patter of gene expression of the biological sample. Within one embodiment, the biological sample may be stimulated with a selected molecule prior to the step of exposing the nucleic acids. Representative examples of "stimulants" include nucleic acid molecules, recombinant gene delivery vehicles, organic molecules, hormones, proteins, inflammatory factors, cytokines, drugs, drug candidates, paracrine and autocrine factors, and the like. Within further embodiments, the tag(s) may be detected by fluorometry, mass spectrometry, infrared spectrometry, ultraviolet spectrometry, or, potentiostatic amperometry (e.g., utilizing coulometric or amperometric detectors). Representative examples of suitable spectrometric techniques include time-of-flight mass spectrometry, quadrupole mass spectrometry, magnetic sector mass spectrometry and electric sector mass spectrometry. Specific embodiments of such techniques include ion-trap mass spectrometry, electrospray ionization mass spectrometry, ion-spray mass spectrometry, liquid ionization mass spectrometry, atmospheric pressure ionization mass spectrometry, electron ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nano-spray mass spectrometry, nebulised spray ionization mass spectrometry, chemical ionization mass spectrometry, resonance ionization mass spectrometry, secondary ionization mass spectrometry and thermospray mass spectrometry.

In some embodiments, detection of a genetic biomarker (e.g., one or more genetic biomarkers) can include any of the variety of methods described in U.S. Pat. No. 6,361,940, which is hereby incorporated by reference in its entirety. For example, detection of a genetic biomarker can include compositions and methods to increase the specificity of hybridization of nucleic acids and priming of nucleic acids in PCR. In some embodiments, the composition comprises a nucleic acid and a salt, the salt comprising an anion and a cation, the anion selected from halogenated acetate, propionate and halogenated propionate, the cation selected from primary, secondary and tertiary ammonium comprising 1-36 carbon atoms, and quaternary ammonium comprising 4-48 carbon atoms. In some embodiments, the composition is non-flowing and comprises an oligonucleotide of 6-100 nucleotides and a salt, the salt comprising an anion and a cation, the anion selected from acetate, halogenated acetate, propionate, and halogenated propionate, the cation selected from primary, secondary and tertiary ammonium comprising 1-36 carbon atoms, and quaternary ammonium comprising 4-48 carbon atoms. In some embodiments, the composition is free from organic solvent and comprises an oligonucleotide of 6-100 nucleotides and a salt, the salt comprising an anion and a cation, the anion selected from acetate, halogenated acetate, propionate, and halogenated propionate, the cation selected from primary, secondary and tertiary ammonium comprising 1-36 carbon atoms, and quaternary ammonium comprising 4-48 carbon atoms. In some embodiments, the composition comprises a nucleic acid and a salt, the nucleic acid immobilized on a solid support, the salt.comprising an anion and a cation, the anion selected from acetate, halogenated acetate, propionate and halogenated propionate, the cation selected from primary, secondary and tertiary ammonium comprising 1-36 carbons, and quaternary ammonium comprising 4-48 carbons. Additionally or alternatively, detection of a genetic biomarker can include a salt selected from the group: (a) an acetate salt of a cation of the formula HN(CH3)2Ra wherein Ra is a C4-C7 hydrocarbyl; (b) a halogenated acetate salt of a cation of the formula HN(CH3)2Rb wherein Rb is a C7-C12 hydrocarbyl; (c) acetate and halogenated acetate salts of a cation of the formula H2N(C5-C7cycloalkyl) Rc where R c is a C1-C12 hydrocarbyl; and (d) acetate and halogenated acetate salts of N-substituted piperdine, wherein the nitrogen of piperidine is substituted with C1-C12 hydrocarbyl. Additionally or alternatively, detection of a genetic biomarker can include an oligonucleotide in solution, where the oligonucleotide is formed from constituents including a plurality of fragments, each fragment shown schematically by structure (1)

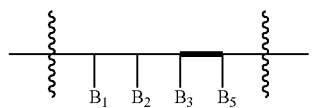

wherein,

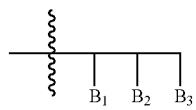

represents a sequence of at least three nucleotides as found in wild-type DNA, where "B" represents a base independently selected at each location; — represents a series of covalent chemical bonds termed a "specificity spacer," which separates and connects two bases B 3 and B 5; the specificity spacer having steric and chemical properties such that (a) it does not prevent hybridization between a fragment of structure (1) and an oligonucleotide fragment having a complementary base sequence, as shown schematically as structure (2)

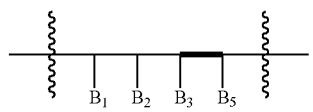

-continued

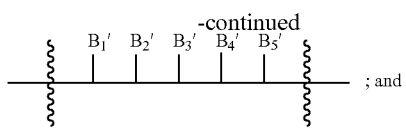

; and and (b) it cannot enter into hydrogen bonding with a base positioned opposite itself in a hybridized complementary base sequence of structure (2). Additionally or alternatively, detection of a genetic biomarker can include an array which includes a plurality of oligonucleotides immobilized in an array format to a solid support, each oligonucleotide of the plurality formed from components which include a plurality of fragments, each fragment shown schematically by structure (1)

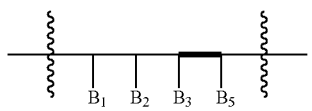

wherein,

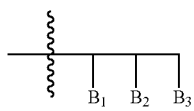

represents a sequence of at least three nucleotides as found in wild-type DNA, where "B" represents a base independently selected at each location; — represents a series of covalent chemical bonds termed a "specificity spacer," which separates and connects two bases B 3 and B 5; the specificity spacer having steric and chemical properties such that (a) it does not prevent hybridization between a fragment of structure (1) and an oligonucleotide fragment having a complementary base sequence, as shown schematically as structure (2)

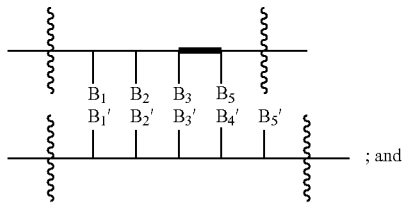

; and and (b) it cannot enter into hydrogen bonding with a base positioned opposite itself in a hybridized complementary base sequence of structure (2). Additionally or alternatively, detection of a genetic biomarker can include a method of distinguishing between hybridization of a complementary nucleic acid target and a nucleic acid probe in which the probe and target are perfectly complementary and in which the probe and target have one or more base mismatches, comprising: (a) mixing the nucleic acid target with the nucleic acid probe in a solution comprising a hybotrope; (b) hybridizing at a discriminating temperature; and (c) detecting probe hybridized to target, thereby determining whether the nucleic acid probe and target are perfectly complementary or mismatched. In a preferred embodiment, the nucleic acid probe is labeled with a radioactive molecule, fluorescent molecule, mass-spectrometry tag or enzyme. In preferred embodiments, the nucleic acid probe and/or the target nucleic acid is from 6 to 40 bases. Preferably, the hybotrope is an ammonium salt. Specific preferred ammonium salt hybotropes include, without limitation, bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate. Other suitable hybotropes include LiTCA, RbTCA, GuSCN, NaSCN, NaClO 4, KI, TMATCA TEATCA, TMATBA, TMTCA, TMTBA, TBATCA and TBATBA. Preferably, the hybotrope is present at a molarity of from about 0.005 M to about 6 M. Preferably, the probe nucleic acid is DNA or RNA, and the target nucleic acid is DNA or RNA. Preferably, the target nucleic acid is affixed to a solid substrate. Preferably, the method further comprises polymerase chain reaction. Additionally or alternatively, detection of a genetic biomarker can include a method of distinguishing between hybridization of a complementary nucleic acid target and a nucleic acid probe in which the probe and target are perfectly complementary and in which the probe and target have one or more base mismatches, comprising: (a) mixing a nucleic acid target with a nucleic acid probe containing at least one abasic or deoxyNebularine substitution; (b) hybridizing at a discriminating temperature; and (c) detecting probe bound to the target, thereby determining whether the nucleic acid probe and target are perfectly complementary or mismatched. Additionally or alternatively, detection of a genetic biomarker can include a method of increasing discrimination in a nucleic acid synthesis procedure, comprising: (a) mixing a single-stranded nucleic acid target with an oligonucleotide primer in a solution comprising a hybotrope and a polymerase; (b) annealing the primer to the target at a discriminating temperature; and (c) synthesizing a complementary strand to the target to form a duplex. Additionally or alternatively, detection of a genetic biomarker can include a method of distinguishing a single base change in a nucleic acid molecule from a wild-type sequence, comprising: (a) mixing a single-stranded nucleic acid target with an oligonucleotide primer in a solution comprising an amine-based salt and a polymerase, wherein the oligonucleotide primer has a 3'-most base complementary to the wild-type sequence or the single base change; (b) annealing the primer to the target at a discriminating temperature; (c) extending the primer, wherein a complementary strand to the target is synthesized when the 3'-most base of the primer is complementary to the target; and (d) detecting the extension of the primer.

In some embodiments, detection of a genetic biomarker (e.g., one or more genetic biomarkers) can include any of the variety of methods described in U.S. Pat. No. 6,248,521, which is hereby incorporated by reference in its entirety. For example, detection of a genetic biomarker can include methods of amplifying nucleic acid molecules from a template comprising (a) mixing single-stranded nucleic acid templates on a solid substrate with a solution comprising an oligonucleotide primer that hybridizes to the templates and a DNA polymerase, wherein the mixing occurs in discrete areas on the substrate, and wherein the solution remains in the discrete areas; (b) synthesizing a complementary strand to the template to form a duplex; (c) denaturing the duplex; and (d) synthesizing complementary strands to the template, therefrom amplifying nucleic acid molecules; wherein mixing, synthesizing, and denaturing are conducted at dew point. The solid substrate may be a silicon wafer or glass slide. The templates may be covalently attached to the solid substrate or deposited on the surface of the substrate. The template may be uniformly applied to the entire array prior to mixing or applied individually to each discrete area on the substrate. When applied individually, preferably the applying is performed using spring probes. In a most preferred embodiment, an apparatus is used to control the dew point. Additionally or alternatively, detection of a genetic biomarker can include a method of performing single nucleotide extension assay is provided, comprising (a) mixing oligonucleotides on a solid substrate with a solution comprising single-stranded nucleic acid molecules that hybridize to the oligonucleotides, a single nucleotide, and a DNA polymerase, wherein the mixing occurs in discrete areas of the substrate, and wherein the solution remains in discrete areas; and (b) detecting an extension product of the oligonucleotide; wherein the oligonucleotide will be extended only when the single nucleotide is complementary to the nucleotide adjacent to the hybridized oligonucleotide, wherein mixing is performed at dew point.

In some embodiments, detection of a genetic biomarker (e.g., one or more genetic biomarkers) can include any of the variety of methods described in U.S. Patent Application Publication No. 2018/0155705, which is hereby incorporated by reference in its entirety. For example, detection of a genetic biomarker can include a method for isolating extracellular nucleic acids from a biological sample, comprising (a) preparing from the sample a binding mixture comprising: i) extracellular nucleic acids; ii) particles providing an anion exchange surface; iii) at least one non-ionic detergent which is a polyoxyalkylene fatty alcohol ether; iv) optionally at least one salt, wherein the binding mixture has a pH so that extracellular nucleic acids bind to the particles, (b) separating the particles with the bound extracellular nucleic acids from the remaining binding mixture; (c) optionally washing the bound extracellular nucleic acids; and (d) optionally eluting bound extracellular nucleic acids. In some embodiments, the binding mixture is prepared by forming a suspension by contacting the particles with a lysis and/or binding composition which comprises the at least one polyoxyalkylene fatty alcohol ether and which optionally comprises a salt and/or a buffer; contacting the suspension with the sample comprising extracellular nucleic acids; and optionally adding a proteolytic enzyme prior to, at the same time or after the sample was contacted with the suspension. Additionally or alternatively, detection of a genetic biomarker can include a kit for performing the method, which comprises (a) a lysis and/or binding composition comprising: i) at least one non-ionic detergent which is a polyoxyalkylene fatty alcohol ether; ii) optionally at least one salt; iii) at least one buffer; wherein said composition has an acidic pH; (b) particles providing an anion exchange surface; (c) optionally a proteolytic enzyme; (d) optionally one or more wash solutions and (e) optionally one or more elution solutions.

In some embodiments, detection of a genetic biomarker (e.g., one or more genetic biomarkers) can include any of the variety of methods described in U.S. Patent Application Publication No. 2018/0148716, which is hereby incorporated by reference in its entirety. For example, detection of a genetic biomarker can include methods of generating a circular double-stranded DNA (dsDNA) or a sequencing library, wherein the method comprises circulating a dsDNA or ligating a first and a second dsDNA in the presence of a DNA ligase and a single-stranded DNA binding protein or a double-stranded DNA-binding protein. In some embodiments, the method of generating a sequencing library comprises further steps, preceding the ligation, of: (i) providing DNA fragments; (ii) end-repairing the DNA fragments by a polynucleotide kinase enzyme and an enzyme with polymerase and exonuclease activities; and (iii) optionally adding a terminal adenine to the end of the end-repaired DNA fragments by a deoxynucleotidyl transferase enzyme. In some embodiments, said method further comprises the subsequent steps of purification and size-selection of the ligated fragments for sequencing. In some embodiments, the adapter-ligated fragments are amplified prior to sequencing. Additionally or alternatively, detection of a genetic biomarker can include a kit comprising: (i) a DNA ligase; and (ii) a single-stranded DNA (ssDNA) binding protein or a double-stranded DNA (dsDNA)-binding protein. In some embodiments, the kit comprises: (i) a polynucleotide kinase and an enzyme with polymerase and exonuclease activities; (ii) optionally a deoxynucleotidyl transferase; (iii) a DNA ligase; (iv) a single-stranded or a double-stranded DNA binding protein; and (v) optionally a reaction buffer. In preferred embodiments, any of the kits comprises a mixture of a ligase, a single-stranded DNA (ssDNA) binding protein or a double-stranded DNA (dsDNA) binding protein, and optionally a reaction buffer. In a preferred embodiment, the enzyme with polymerase and exonuclease activities is a DNA polymerase. In the methods or kits referenced above, the polynucleotide kinase enzyme is the T4 Polynucleotide Kinase (PNK), the enzyme with polymerase and exonuclease activities is T4 DNA Polymerase, and/or the deoxynucleotidyl transferase enzyme is a Taq polymerase or a Klenow Fragment exo-. In some embodiments, ligation methods are referred to, wherein both the first and the second dsDNAs comprise two ssDNA ends, whereby each of the ssDNA ends of the first dsDNA ligates with each of the complementary ss ends of the second dsDNA to provide ligated circular dsDNA. In some embodiments, the first or the second DNA is capable of conferring the ability to auto-replicate within competent cells. In the methods or kits referenced above, the DNA binding protein is a viral, bacterial, archaeal, or eukaryotic single-stranded DNA binding protein or double-stranded DNA binding protein. In some embodiments, the DNA ligase in any of the above methods or kits is a T3 DNA ligase or a T4 DNA ligase. In other embodiments, the ligase is a T7 DNA ligase or an Ampligase®. In some embodiments of the above methods, each of the first and the second dsDNA have one or two single stranded DNA (ssDNA) end(s). This/these ssDNA end(s) is/are less than 20 nucleotides (nt) in length.

In some embodiments, detection of a genetic biomarker (e.g., one or more genetic biomarkers) can include any of the variety of methods described in U.S. Patent Application Publication No. 2018/0002738, which is hereby incorporated by reference in its entirety. For example, detection of a genetic biomarker can include methods for amplifying target nucleic acids in a nucleic acid sample and kits useful in such methods. In some embodiments, the method for amplifying target nucleic acids in a nucleic acid sample, comprises: (a) extending each of a plurality of barcode primers (BC primers) to obtain extension products using the target nucleic acids as templates, wherein (i) each barcode primer comprises, from 5' to 3', a 1st universal primer sequence (US1), a molecular tag sequence (MT), and a 1st target-specific sequence (TS1), (ii) a plurality of barcode primers comprise at least 20 different barcode primers, and (iii) among the plurality of barcode primers (BC primers), the 1st universal primer sequences (US1) are the same, but the 1st target-specific sequences (TS1) are different; (b) separating the plurality of barcode primers that have not been extended in step (a) from the extension products; and (c) amplifying the extension products of step (b) in the presence of a plurality of limited amplification primers (LA primers) to obtain a plurality of 1st amplification products, wherein (i) each limited amplification primer comprises, from 5' to 3', a 2nd universal primer sequence (US2) and a 2nd target-specific sequence (TS2), and (ii) among the plurality of limited amplification primers, the 2nd universal primer sequences (US2) are the same, but the 2nd target-specific sequences (TS2) are different. Additionally or alternatively, detection of a genetic biomarker can include a kit comprising: (1) a plurality of barcode primers (BC primers), wherein (i) each barcode primer comprises, from 5' to 3', a 1st universal primer sequence (US1), a molecular tag sequence (MT), and a 1st target-specific sequence (TS1), (ii) a plurality of barcode primers comprise at least 20 different barcode primers, and (iii) among the plurality of barcode primers, the 1st universal primer sequence (US1) are the same, the molecular tag sequences (MT) are different, and the 1st target-specific sequence (TS1) are different; and (2) a plurality of limited amplification primers (LA primers), wherein (i) each limited amplification primer comprises, from 5' to 3', a 2nd universal primer sequence (US2) and a 2nd target-specific sequence (TS2), and (ii) among the plurality of limited amplification primers, the 2nd universal primer sequences (US2) are the same, but the 2nd target-specific sequence (TS2) are different.

In some embodiments, detection of a genetic biomarker (e.g., one or more genetic biomarkers) can include any of the variety of methods described in U.S. Patent Application Publication No. 2016/0374330, which is hereby incorporated by reference in its entirety. For example, detection of a genetic biomarker can include a method suitable for stabilizing an extracellular nucleic acid population comprised in a cell-containing biological sample is provided, comprising contacting the cell-containing sample with at least one poly(oxyethylene) polymer as stabilizing agent or with mono-ethylene glycol as stabilizing agent. Additionally or alternatively, detection of a genetic biomarker can include a method for isolating extracellular nucleic acids from a cell-containing biological sample is provided, wherein said method comprises: a) stabilizing the cell-containing biological sample according to the method defined above; and b) isolating extracellular nucleic acids from the stabilized sample. Additionally or alternatively, detection of a genetic biomarker can include a composition suitable for stabilizing a cell-containing biological sample is provided comprising: i) a poly(oxyethylene) polymer as stabilizing agent or ii) mono-ethylene glycol as stabilizing agent and one or more, preferably two or more further additives selected from the group consisting of: one or more primary, secondary or tertiary amides; a caspase inhibitor; an anticoagulant and/or a chelating agent. Preferably, the composition comprises a poly(oxyethylene) polymer, which preferably is a high molecular weight poly(oxyethylene) polymer having a molecular weight of at least 1500, as stabilizing agent and furthermore comprises one or more, preferably two or more further additives selected from the group consisting of at least one further poly(oxyethylene) polymer having a molecular weight that is at least 100, preferably at least 200, at least 300 or at least 400 below the molecular weight of the first poly(oxyethylene) polymer, which preferably is a high molecular weight poly(oxyethylene) polymer, wherein said further poly(oxyethylene) polymer preferably is a low molecular weight poly(oxyethylene) polymer having a molecular weight of 1000 or less; one or more primary, secondary or tertiary amides; a caspase inhibitor; an anticoagulant and/or a chelating agent. Additionally or alternatively, detection of a genetic biomarker can include a collection device for collecting a cell-containing biological sample is provided, wherein the collection device comprises i) a poly(oxyethylene) polymer as stabilizing agent or ii) mono-ethylene glycol as stabilizing agent and one or more further additives selected from the group consisting of: one or more primary, secondary or tertiary amides; a caspase inhibitor; an anticoagulant and/or a chelating agent. Preferably, the collection device according to the fifth aspect comprises a poly(oxyethylene) polymer, which preferably is a high molecular weight poly(oxyethylene) polymer having a molecular weight of at least 1500, as stabilizing agent and furthermore comprises one or more, preferably two or more further additives selected from the group consisting of at least one further poly(oxyethylene) polymer having a molecular weight that is at least 100, preferably at least 200, at least 300 or at least 400 below the molecular weight of the first poly(oxyethylene) polymer which preferably is a high molecular weight poly(oxyethylene) polymer, wherein said further poly(oxyethylene) polymer preferably is a low molecular weight poly(oxyethylene) polymer having a molecular weight of 1000 or less; one or more primary, secondary or tertiary amides; a caspase inhibitor; an anticoagulant and/or a chelating agent.

In some embodiments, detection of a genetic biomarker (e.g., one or more genetic biomarkers) can include any of the variety of methods described in U.S. Patent Application Publication No. 2016/0048564, which is hereby incorporated by reference in its entirety. For example, detection of a genetic biomarker can include a method for building a community database of variant observations, comprising: receiving human variant datasets derived from samples generated by a plurality of distinct users, wherein the users consented to share pooled variant observations with other users; storing the received human variant datasets in a knowledge base of genomic information; searching the knowledge base to identify a plurality of variant observations that meet inclusion criteria for a pool; adding each identified variant observation to the pool; and calculating one or more anonymized allele statistics from the pool, wherein at least one of the receiving, storing, searching, adding, or calculating are performed by one or more computers. Additionally or alternatively, detection of a genetic biomarker can include a method for determining a candidate for a clinical trial, comprising: receiving clinical trial enrollment criteria from a user including genetic targeting criteria;

searching a knowledge base of patient test information received from a plurality of independent entities for patients that match the clinical trial enrollment criteria; and providing to the user search results for consented patients that match the clinical trial enrollment criteria; wherein at least one of the receiving, searching, or providing are performed by one or more computers.

In some embodiments, detection of a genetic biomarker (e.g., one or more genetic biomarkers) can include any of the variety of methods described in U.S. Patent Application Publication No. 2016/0017320, which is hereby incorporated by reference in its entirety. For example, detection of a genetic biomarker can include methods for reducing errors in sequencing and thus improving accuracy in mutation detection and transcriptome profiling including methods that use semi-random barcodes to tag sequencing fragments before amplification to reduce bias and sequencing errors. Additionally or alternatively, detection of a genetic biomarker can include oligonucleotides that comprise semi-random barcode sequences, including sequencing adapters, reverse transcription primers and PCR primers. The term "semi-random barcode sequences," "semi-random sequences," or "semi-random barcodes" refers to a population of semi-random nucleotide sequences each consisting of (Xmer)n, wherein Xmer is 3-mer (i.e., a 3-nucleotide oligonucleotide, also referred to as "trimer"), 4-mer (i.e., a 4-nucleotide oligonucleotide, also refers to as "tetramer")), 5-mer (i.e., a 5-nucleotide oligonucleotide, also refers to as "pentamer"), or 6-mer (i.e., a 6-nucleotide oligonucleotide, also refers to as "hexamer"), and n is an integer from 2 to 10. Each nucleotide sequence in the population is referred to as "semi-random barcode sequence," "semi-random barcode," or "semi-random sequence." In certain embodiments, the semi-random sequence consist of (Xmer)n, wherein Xmer is 3-mer, and n is 2, 3, 4, 5, 6, 7, 8, 9, or 10, preferably 4, 5, 6, 7, 8 or 9. In certain embodiments, Xmer is 4-mer, and n is 2, 3, 4, 5, 6, 7, 8, or 9, preferably 2, 3, 4, 5, 6, or 7. In certain embodiments, Xmer is 5-mer, and n is 2, 3, 4, 5, 6, 7, or 8, preferably 2, 3, 4, 5, or 6. In certain embodiments, Xmer is 6-mer, and n is 2, 3, 4, 5, 6, or 7 preferably 2, 3, 4, or 5. The semi-random barcode sequences may be synthesized from a mixture of Xmers with defined sequences. For example, in certain embodiments, the semi-random barcodes consist of (Xmer)n, wherein Xmer is 3-mer and n is 7. In other words, the semi-random barcodes are a population of 21 bp oligonucleotides that consist of 7 trimers. Such semi-random barcodes may be synthesized with 7 successive steps during each of which steps, a random trimer from a defined trimer mixture may be incorporated. A defined Xmer mixture for synthesizing semi-random barcodes may have 2, 3, 4, 5, 6, 7, 8, 9, 10, 11, 12, 13, 14, 15, 16, 17, 18, 19, 20, 21, 22, 23, 24, or 25, or at least 2, 3, 4, 5, 6, 7, 8, 9, 10, 11, 12, 13, 14, 15, 16, 17, 18, 19, 20, 21, 22, 23, 24, or 25, different Xmers. The number of different semi-random barcode sequences synthesized from a defined Xmer mixture may be at least 100, 200, 300, 400, 500, 1,000, 2,000, 3,000, 4,000, 5,000, 10,000, 50,000, 100,000, 50,000, 100,000, 500,000, or 1,000,000. Preferably, each Xmer (e.g., trimer, tetramer, pentamer, and hexamer) has at least 2 bases different from another Xmer in a defined Xmer mixture so that any single-base variant within each Xmer block in sequencing reads can be identified as errors, not a different barcode. In certain embodiments, each Xmer (e.g., tetramer, pentamer, and hexamer) has at least 3 bases different from another Xmer in a defined Xmer mixture so that any single- or 2-base variant within each Xmer block in sequencing reads can be identified as errors, not a different barcode. In certain embodiments, each Xmer (e.g., pentamer and hexamer) has at least 4 bases different from another Xmer in a defined Xmer mixture so that any 1-, 2-, or 3-base variant within each Xmer block in sequencing reads can be identified as errors, not a different barcode. Additionally or alternatively, detection of a genetic biomarker can include a plurality of single-stranded (ss) oligonucleotides, wherein each oligonucleotide comprises from the 5' to 3' direction a 1st sequence and a 2nd sequence; (a) the 1st sequence is a semi-random sequence consisting of (Xmer)n, wherein Xmer is 3-mer, 4-mer, 5-mer, or 6-mer, and n is an integer from 2 to 8, and (b) the 2nd sequence is (i) at least 10 nucleotides in length, (ii) fully or substantially complementary to a target sequence, and (iii) the same among the plurality of oligonucleotides. Additionally or alternatively, detection of a genetic biomarker can include a plurality of double-stranded (ds) sequencing adapters, wherein each sequencing adapter comprises: (a) an oligonucleotide ("1st oligonucleotide") from above, and (b) a 2nd ss oligonucleotide that comprises from the 3' to 5' direction (i) a sequence ("Sequence A") that is fully complementary to the 1st sequence of the 1st oligonucleotide of the sequencing adapter, and (ii) the target sequence ("Sequence B"), and wherein the 1st oligonucleotide anneals to the 2nd ss oligonucleotide. Additionally or alternatively, detection of a genetic biomarker can include a plurality of sets of double-stranded (ds) sequencing adapters, wherein (A) each set comprises a plurality of single-stranded (ss) sequencing adapters, wherein each sequencing adapter in each set comprises: (a) an oligonucleotide ("1st oligonucleotide") of the plurality of ss oligonucleotides from above, and (b) a 2nd ss oligonucleotide that comprises: (i) a sequence ("Sequence A") that is fully complementary to the 1st sequence of the 1st oligonucleotide of the sequence adapter, and (ii) the target sequence ("Sequence B") located 5' to Sequence A, and (iii) a sequence ("Sequence C") that is located 3' to Sequence B and is fully complementary to the 3rd sequence of the 1st oligonucleotide, and wherein the 1st oligonucleotide anneals to the 2nd oligonucleotide; and (B) wherein the plurality of ds sequencing adapters in different sets are identical to each other except in the 3rd sequence of the 1st oligonucleotide and in Sequence C of the 2nd oligonucleotide. Additionally or alternatively, detection of a genetic biomarker can include a method for preparing a sequencing library that comprises (1) ligating the plurality of ds sequencing adapters that comprise a semi-random barcode sequence (i.e., the 1st sequence of the 1st oligonucleotide) to dsDNA molecules or fragments of a sample.

In some embodiments, detection of a genetic biomarker (e.g., one or more genetic biomarkers) can include any of the variety of methods described in U.S. Patent Application Publication No. 2015/0275267, which is hereby incorporated by reference in its entirety. For example, detection of a genetic biomarker can include a method is provided for preparing a target RNA depleted composition from an initial RNA containing composition, comprising: a) contacting the initial RNA containing composition with one or more groups of probe molecules, wherein a group of probe molecules has the following characteristics: i) the group comprises two or more different probe molecules having a length of 100 nt or less; ii) the probe molecules comprised in said group are complementary to a target region present in a target RNA; iii) when hybridized to said target region, the two or more different probe molecules are located adjacent to each other in the formed double-stranded hybrid; and generating a double-stranded hybrid between the target RNA and the probe molecules; b) capturing the double-stranded hybrid by using a binding agent which binds the double-stranded hybrid, thereby forming a hybrid/binding agent complex; c) separating the hybrid/binding agent complexes from the composition, thereby providing a target RNA depleted composition. Additionally or alternatively, detection of a genetic biomarker can include specifically designed groups of probe molecules which hybridize to and thus mark unwanted target RNA, such as e.g. different rRNA species, for depletion. Each group of probe molecules targets a specific region in a target RNA, also referred to as target region, and comprises two or more different short probe molecules which hybridize to said target region. When hybridized to their target region, the short probe molecules of one group are located adjacent to each other in the formed double-stranded hybrid and thus are located in close proximity. The formed double-stranded hybrid spans and thus covers the target region. The formed double-stranded hybrid which comprises the short probe molecules of one group is then bound by an anti-hybrid binding agent, whereby a hybrid/binding agent complex is formed. Said complexes can be easily separated from the remaining composition, thereby removing unwanted target RNA and thus providing a target RNA depleted composition. Additionally or alternatively, detection of a genetic biomarker can include a method for sequencing RNA molecules of interest comprised in a sample, comprising: a) obtaining a RNA containing composition, preferably by isolating total RNA from the sample; b) depleting unwanted target RNA from the RNA containing composition, which preferably is total RNA, using the method according to the first aspect, thereby providing a target RNA depleted composition; c) optionally removing unbound probe molecules; d) sequencing RNA molecules comprised in the target RNA depleted composition.

In some embodiments, detection of a genetic biomarker (e.g., one or more genetic biomarkers) can include any of the variety of methods described in U.S. Patent Application Publication No. 2015/0225775, which is hereby incorporated by reference in its entirety. For example, detection of a genetic biomarker can include a method for performing polymerase chain reaction (PCR), comprising: a) amplifying one or more different target nucleic acids in the presence of one or more different primer pairs specific to the one or more different target nucleic acids in a single reaction mixture via PCR, wherein each primer of the one or more different primer pairs contains one or more cleavable bases, and wherein in substantially all of the primers of the one or more different primer pairs, each of the one or more cleavable bases is at least 4 nucleotides away from the 3' terminus of the primer that comprises the one or more cleavable bases. In certain embodiments, in substantially all of the primers of the one or more different primer pairs, each of the one or more cleavable bases is at least 5 nucleotides away from the 3' terminus of the primer that comprises the one or more cleavable bases. In certain other embodiments, in substantially all of the primers of the one or more different primer pairs, each of the one or more cleavable bases is at least 6 nucleotides away from the 3' terminus of the primer that comprises the one or more cleavable bases. In certain other embodiments, in substantially all of the primers of the one or more different primer pairs, each of the one or more cleavable bases is at least 7 nucleotides away from the 3' terminus of the primer that comprises the one or more cleavable bases. In certain other embodiments, in substantially all of the primers of the one or more different primer pairs, each of the one or more cleavable bases is at least 8 nucleotides away from the 3' terminus of the primer that comprises the one or more cleavable bases. Step a) may comprise amplifying a single target nucleic acid in the presence of a primer pair specific to the single target nucleic acid in the single reaction mixture. Alternatively, step a) may comprise amplifying a plurality of different primer pairs specific to the plurality of different target nucleic acids in the single reaction mixture. In certain embodiments, in all of the primers of the one or more different primer pairs, each of one or more cleavable bases is at least 4 nucleotides away from the 3' terminus of the primer that comprises the one or more cleavable bases. In certain other embodiments, in all of the primers of the one or more different primer pairs, each of one or more cleavable bases is at least 5 nucleotides away from the 3' terminus of the primer that comprises the one or more cleavable bases. In certain other embodiments, in all of the primers of the one or more different primer pairs, each of one or more cleavable bases is at least 6 nucleotides away from the 3' terminus of the primer that comprises the one or more cleavable bases. In certain other embodiments, in all of the primers of the one or more different primer pairs, each of one or more cleavable bases is at least 7 nucleotides away from the 3' terminus of the primer that comprises the one or more cleavable bases. In certain other embodiments, in all of the primers of the one or more different primer pairs, each of one or more cleavable bases is at least 8 nucleotides away from the 3' terminus of the primer that comprises the one or more cleavable bases. Preferably, the cleavable base is uracil. Alternatively, the cleavable base is inosine, an oxidized pyrimidine, an oxidized purine, 5-hydroxyuracil, 5-hydroxylmethyluracil, or 5-formyluracil. The one or more different primer pairs may comprise at least 100 different primer pairs. In some embodiments, the method may further comprise one or more: b) cleaving the one or more cleavable bases in the amplification product(s) of step a) to produce single-stranded DNA overhangs in the amplification product(s), c) digesting the single stranded DNA overhangs obtained in step b) to generate trimmed amplification product(s), d) ligating adapters to the trimmed amplification product(s) to produce adapter-linked trimmed amplification product(s), and e) sequencing the adapter-linked trimmed amplification product(s) of step d). Additionally or alternatively, detection of a genetic biomarker can include a primer pair set, comprising: one or more of different primer pairs specific for one or more different target nucleic acids, wherein each primer of the one or more different primer pairs contains one or more cleavable bases, and wherein in substantially all of the primers of the one or more different primer pairs, each of the one or more cleavable bases is at least 4 nucleotides away from the 3' terminus of the primer that comprises the one or more cleavable bases. In certain embodiments, in substantially all of the primers of the one or more different primer pairs, each of the one or more cleavable bases is at least 5 nucleotides away from the 3' terminus of the primer that comprises the one or more cleavable bases. In certain other embodiments, in substantially all of the primers of the one or more different primer pairs, each of the one or more cleavable bases is at least 6 nucleotides away from the 3' terminus of the primer that comprises the one or more cleavable bases. In certain other embodiments, in substantially all of the primers of the one or more different primer pairs, each of the one or more cleavable bases is at least 7 nucleotides away from the 3' terminus of the primer that comprises the one or more cleavable bases. In certain other embodiments, in substantially all of the primers of the one or more different primer pairs, each of the one or more cleavable bases is at least 8 nucleotides away from the 3' terminus of the primer that comprises the one or more cleavable bases. Additionally or alternatively, detection of a genetic biomarker can include a PCR reaction mixture, comprising: the primer pair set, a DNA polymerase, dNTPs, and a PCR reaction buffer.

In some embodiments, detection of a genetic biomarker (e.g., one or more genetic biomarkers) can include any of the variety of methods described in U.S. Patent Application Publication No. 2015/0197787, which is hereby incorporated by reference in its entirety. For example, detection of a genetic biomarker can include a method is provided for enriching target sequences from a sequencing library to provide a target enriched sequencing library, wherein the sequencing library is suitable for massive parallel sequencing and comprises a plurality of double-stranded nucleic acid molecules, wherein the method comprises: a) providing nucleoprotein filaments comprising (i) a single stranded invasion probe, wherein the invasion probe has a region of substantial complementarity to one strand of a double-stranded target sequence, (ii) a recombinase; b) forming a complex between the invasion probe and a complementary portion of the target sequence wherein complex formation is mediated by the recombinase; c) separating the complexes from the remaining sequencing library, thereby enriching the target sequences. Additionally or alternatively, detection of a genetic biomarker can include a method is provided for sequencing a target region of interest, comprising: a) providing a sequencing library suitable for massive parallel sequencing and comprising a plurality of double stranded nucleic acid molecules, wherein a portion of the double stranded nucleic acid molecules comprised in the sequencing library, the target sequences, comprise a sequence which lies in the target region of interest; b) enriching target sequences corresponding to the target region of interest according to the method above, thereby providing a target enriched sequencing library; c) sequencing the enriched target sequences in parallel. Additionally or alternatively, detection of a genetic biomarker can include use of the method for sequencing for exome sequencing, exon sequencing, targeted genomic resequencing, gene panel orientated targeted genomic resequencing, transcriptome sequencing and/or molecular diagnostics. Additionally or alternatively, detection of a genetic biomarker can include a kit for performing a method according to first aspect, which comprises a) adaptors for creating a sequencing library suitable for massive parallel sequencing; b) optionally one or more ligation reagents for coupling the adaptors to a nucleic acid fragment; c) a recombinase, preferably a RecA like recombinase; d) a non-hydrolyzable co-factor for the recombinase, preferably adenosine 5'-(gamma-thio)triphosphate; e) a plurality of different invasion probes wherein the invasion probes differ in their region of complementarity to a target region of interest; f) a plurality of different stabilization probes being at least partially complementary to the plurality of invasion probes; and g) a solid support suitable for capturing synaptic complexes formed between the invasion probes and target sequences.

In some embodiments, detection of a genetic biomarker (e.g., one or more genetic biomarkers) can include any of the variety of methods described in U.S. Patent Application Publication No. 2015/0093756, which is hereby incorporated by reference in its entirety. For example, detection of a genetic biomarker can include methods of amplifying a target nucleic acid in a helicase-dependent reaction. Additionally or alternatively, detection of a genetic biomarker can include methods of amplifying and detecting a target nucleic acid in a helicase-dependent reaction as well as modified detection labels to assist in the detection. In some embodiments, the method for amplifying a target nucleic acid in a helicase-dependent reaction, the method comprises: (a) providing target nucleic acid to be amplified; wherein the target nucleic acid is double stranded and is denatured by heating at 65° C. for 10 minutes in the presence of 50 mM NaOH prior to step (b); (b) adding oligonucleotide primers for hybridizing to the target nucleic acid of step (a); (c) synthesizing an extension product of the oligonucleotide primers which are complementary to the templates, by means of a DNA polymerase to form a duplex; (d) contacting the duplex of step (c) with a helicase preparation for unwinding the duplex such that the helicase preparation comprises a helicase and a single strand binding protein (SSB) unless the helicase preparation comprises a thermostable helicase wherein the single strand binding protein is optional; and (e) repeating steps (b) (d) to exponentially and selectively amplify the target nucleic acid in a helicase-dependent reaction. Additionally or alternatively, detection of a genetic biomarker can include a method amplifying a target nucleic acid in a helicase-dependent reaction where the target nucleic acid is subjected to a "pre" step involving RNA probes and RNA-DNA hybrid capture antibodies. This method comprises: (a) providing target nucleic acid to be amplified; wherein the target nucleic acid is single stranded DNA and wherein an RNA probes that is complementary is added to the single stranded DNA to bind to the DNA to form a target nucleic acid RNA-DNA hybrid; and wherein a hybrid capture antibodies that recognizes RNA-DNA hybrids bound to a magnetic bead is added to the RNA-DNA hybrid to be used in step (b) (b) adding oligonucleotide primers for hybridizing to the target nucleic acid RNA-DNA hybrid of step (a); (c) synthesizing an extension product of the oligonucleotide primers which are complementary to the templates, by means of a DNA polymerase to form a duplex; (d) contacting the duplex of step (c) with a helicase preparation for unwinding the duplex such that the helicase preparation comprises a helicase and a single strand binding protein (SSB) unless the helicase preparation comprises a thermostable helicase wherein the single strand binding protein is optional; and (e) repeating steps (b)-(d) to exponentially and selectively amplify the target nucleic acid in a helicase-dependent reaction. Additionally or alternatively, detection of a genetic biomarker can include a modified TaqMan probe (and method using this probe). The probe has a short tail at the 3'- or 5'-end complementary to the 5'- or 3'-end, and wherein the TaqMan probe is complementary to the target nucleic acid except for this short tail, and wherein the short tail sequence forms a stem loop structure.

In some embodiments, detection of a genetic biomarker (e.g., one or more genetic biomarkers) can include any of the variety of methods described in U.S. Patent Application Publication No. 2015/0011416, which is hereby incorporated by reference in its entirety. For example, detection of a genetic biomarker can include a method for determining the presence of one or more target polynucleotides, the method comprising; performing a PCR amplification regimen comprising cycles of strand separation, primer annealing, and primer extension on a reaction mixture comprising a nucleic acid sample and a set of oligonucleotide primers specific for each target polynucleotide; wherein each set of oligonucleotide primers comprises a first subset of at least one truncated dual domain forward primer and a second subset of at least one reverse primer; wherein each truncated dual domain primer of a set comprises a 5' tail region that differs from the 5' tail region on other truncated dual domain primers in the set and a 3' core region complementary to a sequence on one strand of a double-stranded nucleic acid comprising the target; wherein for each truncated dual domain primer, the 3' core substantially anneals to its complementary target site sequence at a first annealing temperature, and the sequence comprised by the 5' tail and 3' core region substantially anneals to its complement at a second annealing temperature, the second annealing temperature being higher than the first annealing temperature, such that at the second annealing temperature the 3' core of the truncated dual domain primer cannot substantially anneal to a template molecule that does not also have the complement of the truncated dual domain primer's 5' tail sequence; wherein for each truncated dual domain primer of a primer set: the 5' tail sequence does not have any homology to the target sequence; and the 5' tail sequence has 6 or fewer contiguous homologous bases relative to any other 5' tail sequence of the truncated dual domain primer set; wherein the PCR amplification regimen comprises first and second phases, the first phase comprising annealing at the first annealing temperature for a first set of cycles, and; the second phase comprising annealing at the second annealing temperature for a second set of cycles; and detecting an amplified product for each target polynucleotide, wherein the detecting indicates the presence of the target polynucleotide. In some embodiments, a reverse primer comprises a dual domain primer. In some embodiments, a reverse primer comprises a truncated dual domain primer. In some embodiments, a reverse primer comprises an amplifying primer. In some embodiments, the set of primers comprises at least one dual domain forward primer; wherein each dual domain primer of a set comprises a 5' tail region that differs from the 5' tail region of other dual domain primers in the set, a 3' core region complementary to a sequence on one strand of a double-stranded nucleic acid comprising said target, and a terminal nucleotide complementary to one of the variant nucleotides occurring at said target site; wherein for each dual domain primer, the 3' core substantially anneals to its complementary target site sequence at a first annealing temperature, and the sequence comprised by the 5' tail and 3' core region substantially anneals to its complement at a second annealing temperature, the second annealing temperature being higher than the first annealing temperature, such that at said second annealing temperature said 3' core of said dual domain primer cannot substantially anneal to a template molecule that does not also have the complement of the dual domain primer's 5' tail sequence; and wherein for each truncated dual domain primer of a primer set: the 5' tail sequence does not have any homology to the target sequence; and the 5' tail sequence has 6 or fewer contiguous homologous bases relative to any other 5' tail sequence of the dual domain or truncated dual domain primer set. Additionally or alternatively, detection of a genetic biomarker can include a composition for determining the presence of one or more target polynucleotides, comprising; at least one set of oligonucleotide primers specific for each target polynucleotide; wherein each set of oligonucleotide primers comprises a first subset of at least one truncated dual domain forward primer and a second subset of at least one reverse primer; wherein each truncated dual domain primer of a set comprises a 5' tail region that differs from the 5' tail region on other truncated dual domain primers in the set and a 3' core region complementary to a sequence on one strand of a double-stranded nucleic acid comprising the target; wherein for each truncated dual domain primer, the 3' core substantially anneals to its complementary target site sequence at a first annealing temperature, and the sequence comprised by the 5' tail and 3' core region substantially anneals to its complement at a second annealing temperature, the second annealing temperature being higher than the first annealing temperature, such that at the second annealing temperature the 3' core of the truncated dual domain primer cannot substantially anneal to a template molecule that does not also have the complement of the primer's 5' tail sequence; wherein for each member of the truncated dual domain primer set: the 5' tail sequence does not have any homology to the target sequence; and the 5' tail sequence has 6 or fewer contiguous homologous bases relative to the other 5' tail sequences of the truncated dual domain primer set. In some embodiments, the composition can further comprise a nucleic acid sample. Additionally or alternatively, detection of a genetic biomarker can a method for determining the presence of one or more target polynucleotides, the method comprising; performing a PCR amplification regimen comprising cycles of strand separation, primer annealing, and primer extension on a reaction mixture comprising a nucleic acid sample and a set of oligonucleotide primers specific for each target polynucleotide; wherein each set of oligonucleotide primers comprises a first subset of at least one truncated dual domain forward primer and a second subset of at least one reverse primer; wherein each truncated dual domain primer of a set comprises a 5' tail region that differs from the 5' tail region on other truncated dual domain primers in the set and a 3' core region complementary to a sequence on one strand of a double-stranded nucleic acid comprising the target; wherein for each truncated dual domain primer, the 3' core substantially anneals to its complementary target site sequence at a first annealing temperature, and the sequence comprised by the 5' tail and 3' core region substantially anneals to its complement at a second annealing temperature, the second annealing temperature being higher than the first annealing temperature, such that at the second annealing temperature the 3' core of the truncated dual domain primer cannot substantially anneal to a template molecule that does not also have the complement of the truncated dual domain primer's 5' tail sequence; wherein for each truncated dual domain primer of a primer set: the 5' tail sequence does not have any homology to the target sequence; and the 5' tail sequence has 6 or fewer contiguous homologous bases relative to any other 5' tail sequence of the truncated dual domain primer set; wherein the PCR amplification regimen comprises first and second phases, the first phase comprising annealing at the first annealing temperature for a first set of cycles, and; the second phase comprising annealing at the second annealing temperature for a second set of cycles; and detecting an amplified product for each target polynucleotide, wherein the detecting indicates the presence of the target polynucleotide. Additionally or alternatively, detection of a genetic biomarker can include a composition for determining the presence of one or more target polynucleotides, comprising; at least one set of oligonucleotide primers specific for each target polynucleotide; wherein each set of oligonucleotide primers comprises a first subset of at least one truncated dual domain forward primer and a second subset of at least one reverse primer; wherein each truncated dual domain primer of a set comprises a 5' tail region that differs from the 5' tail region on other truncated dual domain primers in the set and a 3' core region complementary to a sequence on one strand of a double-stranded nucleic acid comprising the target; wherein for each truncated dual domain primer, the 3' core substantially anneals to its complementary target site sequence at a first annealing temperature, and the sequence comprised by the 5' tail and 3' core region substantially anneals to its complement at a second annealing temperature, the second annealing temperature being higher than the first annealing temperature, such that at the second annealing temperature the 3' core of the truncated dual domain primer cannot substantially anneal to a template molecule that does not also have the complement of the primer's 5' tail sequence; wherein for each member of the truncated dual domain primer set: the 5' tail sequence does not have any homology to the target sequence; and the 5' tail sequence has 6 or fewer contiguous homologous bases relative to the other 5' tail sequences of the truncated dual domain primer set.

In some embodiments, detection of a genetic biomarker (e.g., one or more genetic biomarkers) can include any of the variety of methods described in U.S. Patent Application Publication No. 2010/0113758, which is hereby incorporated by reference in its entirety. For example, detection of a genetic biomarker can include a process for the purification of biomolecules from a sample which comprises the following steps: a) arrangement of a reaction vessel with a binding matrix in a centrifuge, wherein a solution or suspension of a sample containing biomolecules is prepared in the reaction vessel or introduced into the reaction vessel before or after this step; and b) inclusion of at least one multi-stage centrifugation step comprising at least a first centrifugation step at a first acceleration value and at least a second centrifugation step at a second acceleration value which is higher than the first acceleration value; wherein c) step b) can be a binding step, a washing step and/or an elution step. Preferably, the multi-stage step b) is a binding step in which the biomolecules are bound to the binding matrix by centrifugation. Particularly preferably, it is envisaged that the biomolecules are substances chosen from the group containing nucleic acids, amino acids, oligopeptides, polypeptides, monosaccharides, oligosaccharides, polysaccharides, fats, fatty acids and/or lipids. In some embodiments, the binding matrix comprises a silicate substrate, and that furthermore the sample containing biomolecules is mixed with at least one chaotropic salt before the centrifugation. The embodiment is suitable in particular for nucleic acids. Preferably, the following steps are envisaged in this embodiment: a) arrangement of a column-like reaction vessel with a binding matrix comprising a silicate substrate in a centrifuge, wherein a solution or suspension of a nucleic acid-containing sample and at least one chaotropic salt is prepared in the reaction vessel or introduced into the reaction vessel before or after this step; b) inclusion of a first centrifugation step at a first acceleration value; c) inclusion of a second centrifugation step at a second acceleration value which is higher than the first acceleration value; d) optionally inclusion of further centrifugation steps between step c) and step d) or after step d); e) optionally inclusion of one or more washing steps; and f) elution of the nucleic acids bound to the silicate substrate with an elution solution. In this embodiment, the multi-step centrifugation step is a binding step in which the nucleic acids are bound to the silicate matrix.

In some embodiments, detection of a genetic biomarker (e.g., one or more genetic biomarkers) can include any of the variety of methods described in U.S. Patent Application Publication No. 2009/0298187, which is hereby incorporated by reference in its entirety. For example, detection of a genetic biomarker can include a method for determining the presence of a target nucleic acid in a sample. The method comprises: a) contacting one or more polynucleotide probes with the sample under a hybridization condition sufficient for the one or more polynucleotide probes to hybridize to the target nucleic acid in the sample to form double-stranded nucleic acid hybrids, wherein the one or more polynucleotide probes does not hybridize to a variant of the target nucleic acid; and b) detecting the double-stranded nucleic acid hybrids, wherein detecting comprises contacting the double-stranded nucleic acid hybrids with a first anti-hybrid antibody that is immunospecific to double-stranded nucleic acid hybrids, whereby detection of the double-stranded nucleic acid hybrids determines the target nucleic acid in the sample. In some embodiments, the hybridization of the nucleic acids and detection of the double-stranded nucleic acid hybrids are performed at the same time. In some embodiments, after the double-stranded nucleic acid hybrids are contacted with a first anti-hybrid antibody that is immunospecific to double-stranded nucleic acid hybrids, a second anti-hybrid antibody is added to detect the double-stranded nucleic acid hybrids whereby detection of the double-stranded nucleic acid hybrids by these second anti-hybrid antibodies determines the presence of target nucleic acid in the sample.

In some embodiments, detection of a genetic biomarker (e.g., one or more genetic biomarkers) can include any of the variety of methods described in U.S. Pat. No. 6,686,157, which is hereby incorporated by reference in its entirety. For example, detection of a genetic biomarker can include a method and compositions for the sensitive detection of the amount and location of specific nucleic acid sequences. In some embodiments, the method makes use of a branched oligomer, referred to as a lollipop oligomer, that has a tail portion, a right arm portion, and a left arm portion. These three components are joined at a common junction making a three-tailed structure. The two arms each end with sequences complementary to adjacent sequences in a target sequence. This allows the right and left arms to be ligated together when the oligomer is hybridized to the target sequence, thus topologically linking the oligomer to the target sequence. The tail portion can then be detected at the location of the target sequence. By using the tail of the oligomer to prime rolling circle replication of a DNA circle, a long tandem repeat DNA is associated with the target sequence. Rolling circle replication does not disturb association of the arms and the target sequence, thus maintaining close association of the tandem repeat DNA and the target sequence. Additionally or alternatively, detection of a genetic biomarker can include a method of amplifying nucleic acid sequences, the method comprising: (a) mixing one or more different lollipop oligomers with one or more target samples each comprising one or more target sequences, and incubating under conditions that promote hybridization between the oligomers and the target sequences, wherein the lollipop oligomers each comprise a branched oligomer comprising a tail portion, wherein the tail portion comprises a rolling circle replication primer, wherein the rolling circle replication primer comprises a complementary portion that is complementary to a primer complement portion of an amplification target circle, (b) prior to, simultaneous with, or following step (a), mixing one or more amplification target circles with the oligomers, and incubating under conditions that promote hybridization between the amplification target circles and the rolling circle replication primer portions of the oligomers, and (c) mixing DNA polymerase with the oligomers and amplification target circles, and incubating under conditions that promote replication of the amplification target circles, wherein replication of the amplification target circles results in the formation of tandem sequence DNA.

In some embodiments, detection of a genetic biomarker (e.g., one or more genetic biomarkers) can include any of the variety of methods described in U.S. Pat. No. 6,090,935, which is hereby incorporated by reference in its entirety. For example, detection of a genetic biomarker can include a method for isolating nucleic acid from a sample, said method comprising boiling said sample, cooling the boiled sample, allowing the nucleic acid in the liquid phase of the cooled sample to directly bind to a solid support comprising magnetic particles, and separating the solid support with the nucleic acid bound thereto from the remainder of said liquid phase. Additionally or alternatively, detection of a genetic biomarker can include a method for isolating nucleic acid from a sample that is fixed or aged, said method comprising boiling the fixed or aged sample, cooling the boiled sample allowing the nucleic acid in the cooled sample to directly bind to a solid support having a high surface area comprising magnetic particles, and separating the solid support with the nucleic acid bound thereto from the remainder of the cooled sample.

In some embodiments, detection of a genetic biomarker (e.g., one or more genetic biomarkers) can include any of the variety of methods described in P.C.T. Publication No. WO 2017/032808, which is hereby incorporated by reference in its entirety. For example, detection of a genetic biomarker can include a method of RNA sequencing, whereby said method comprises: (i) providing RNA; (ii) generating (a) single-stranded first DNA strand(s) (cDNA), which is/are complementary to the RNA, by subjecting the RNA to reverse transcription by using a reverse transcriptase, a first set of oligonucleotide primers, and the RNA of step (i), and (iii) generating a second DNA strand by using a DNA polymerase, a second set of oligonucleotide primers, and the single-stranded cDNA of (ii), wherein a) the first set of oligonucleotide primers comprises a covalently coupled moiety at its/their 5' terminal nucleotide, which blocks ligation at the 5' terminus of the generated first DNA strand; or b) the second set of oligonucleotide primers comprises a covalently coupled moiety at its/their 5' terminal nucleotide, which blocks ligation at the 5' terminus of the generated second DNA strand. In some embodiments, the method further comprises the subsequent steps of: (iv) optionally end-repairing the double-stranded DNA strands using a polynucleotide kinase and an enzyme with polymerase and exonuclease activities to obtain end-repaired DNA strands; (v) optionally adding a terminal adenine to the 3' termini of the DNA strands using a deoxynucleotidyl transferase enzyme; and (vi) ligation of adapters, which optionally comprise terminal thymines, to the DNA strands, which optionally comprise 3' terminal adenines. Said methods may further comprise sequence analysis of the generated DNA. In some embodiments, said method comprises: (i) providing RNA; (ii) generating (a) single-stranded first DNA strand(s) (cDNA), which is/are complementary to the RNA, by subjecting the RNA to reverse transcription by using a reverse transcriptase, a first set of oligonucleotide primers, and the RNA of step (i); (iii) generating a second DNA strand by using a DNA polymerase, a second set of oligonucleotide primers, and the single-stranded cDNA of (ii); (iv) ligating adapters to the double-stranded DNA; of step (iii) and (v) sequencing the generated DNA, wherein a) the first set of oligonucleotide primers comprises a covalently coupled moiety at its/their 5' terminal nucleotide, which blocks ligation at the 5' terminus of the generated first DNA strand; or b) the second set of oligonucleotide primers comprises a covalently coupled moiety at its/their 5' terminal nucleotide, which blocks ligation at the 5' terminus of the generated second DNA strand. By generating the second DNA strand, a double-stranded DNA is generated. In some embodiments of the above-mentioned method, prior to step (iv), the method comprises the step of: (iii) (a) end-repairing the double-stranded DNA strands using a polynucleotide kinase and an enzyme with polymerase and exonuclease, activities to obtain end-repaired DNA strands. In some embodiments, step (iii) (a) is followed by step (iii) (b) comprising adding a terminal adenine to the 3' termini of the DNA strands by using a deoxynucleotidyl transferase enzyme, wherein the adapters comprise 3' terminal thymines, which in step (iv) ligate to the DNA strands comprising 3' terminal adenines. In some embodiments, the oligonucleotide primers, which are covalently coupled to a blocking moiety and/or unmodified oligonucleotide primers, are random oligonucleotide primers. In some embodiments, said methods comprise the initial step of extracting and optionally enriching the RNA of interest. In some embodiments, the extracted RNA is fragmented to an average size of 19-510 bp. In some embodiments of the above methods, the molecules may be attached to a solid support for paired-end sequencing. In some embodiments a "moiety, which blocks ligation", or a "blocking moiety" refers to a specific part of a larger molecule, which is more than one atom, herein the part of a modified oligonucleotide, which is covalently coupled to the 5' nucleotide of a modified primer oligonucleotide. Said moiety preferably blocks any ligation at the site, where the moiety is located, preferably at the 5' terminal nucleotide of the 5' terminus of an oligonucleotide. In some embodiments of the above methods, the oligonucleotide primer comprising a blocking moiety is characterized in that (i) the oligonucleotide comprises at the 5' terminal nucleotide a 5' phosphate that is not free, wherein optionally a 5' OH group or a 5' phosphate group at the 5' terminal nucleotide is covalently coupled to the moiety, which blocks ligation; (ii) the base of the 5' terminal nucleotide is not any one of thymine, adenine, cytosine, guanine and uracil; (iii) one or both 2' hydrogen(s) of the deoxyribose of the 5' terminal nucleotide is/are replaced by another atom or a blocking moiety; and/or (iv) the oligonucleotide comprises a 5' terminal nucleotide having a pentose in a sterical conformation, which is not the sterical conformation of ribose or deoxyribose in RNA or DNA. In some embodiments of the above methods, the oligonucleotide primers comprising a covalently coupled moiety, which blocks ligation, comprise a 5' OH or a free 5' phosphate group at the 5' terminal nucleotide before being covalently coupled to a moiety, which confers the property of ligation-blocking.

In some embodiments, detection of a genetic biomarker (e.g., one or more genetic biomarkers) can include any of the variety of methods described in P.C.T. Publication No. WO 2016/193490, which is hereby incorporated by reference in its entirety. For example, detection of a genetic biomarker can include a poly(alkylene oxide) polymer based size selective DNA isolation method for isolating DNA molecules having a size above a certain cut-off value from a DNA containing sample is provided, comprising (a) preparing a binding mixture comprising the DNA containing sample, at least one poly(alkylene oxide) polymer and at least one divalent cation, wherein said binding mixture has a pH that lies in the range of 8 to 10 and binding precipitated DNA molecules to a solid phase having an unmodified silicon containing surface, thereby providing a solid phase having bound thereto DNA molecules having a size above the cut-off value, wherein under the used binding conditions DNA molecules having a size which is less than the cut-off value substantially do not bind to the solid phase; (b) separating the bound DNA molecules from the remaining sample; optionally washing the bound DNA molecules; and optionally eluting the bound DNA molecules from the solid phase. In some embodiments, DNA molecules having a size above the desired cut-off value efficiently bind to the solid phase with high yield while DNA molecules having a size below said cut-off value are predominantly not bound and thus are not recovered in step (a). The cut-off value can be adjusted by modifying the concentration of the poly(alkylene oxide) polymer in the binding mixture as it is known from the prior art and also demonstrated by the examples. The presence of the divalent cation and the alkaline pH value as specified ensures efficient binding of the DNA molecules having a size above the cut-off value, even though a solid phase having an unmodified silicon containing surface is used. The method is particularly suitable for isolating adapter ligated DNA molecules as target DNA molecules from an adapter ligation sample and for removing adapter monomers and adapter-adapter ligation products.

In some embodiments, detection of a genetic biomarker (e.g., one or more genetic biomarkers) can include any of the variety of methods described in U.S. Pat. No. 7,811,759, which is hereby incorporated by reference in its entirety. For example, detection of a genetic biomarker can include a method for creating a signature ncRNA profile for a disease state or condition, said method comprising: a. determining a first ncRNA profile from a first source, said first source being characterized as being free from said disease state or condition; b. determining a second ncRNA profile from a second source, said second source characterized as being positive for said disease state or condition, said first and second ncRNA profile being obtained according to a method for determining a profile of a plurality of target ncRNA molecules in a RNA sample, said method comprising the steps of: i. providing said RNA sample from a subject, said sample containing said plurality of target ncRNAs; ii. contacting said sample with a first oligonucleotide specific for each of said target ncRNAs to be detected under conditions appropriate to faun a complex between said first oligonucleotides and said target ncRNAs, each of said first oligonucleotides comprising a first signal generator to generate a first detectable signal and each of said first oligonucleotides having a first Tm for binding each of said target ncRNAs that is substantially the same; iii. contacting said sample with a second oligonucleotide capable of binding each of said target ncRNAs to be detected under conditions appropriate to form a complex between said second oligonucleotides and said target ncRNAs, said second oligonucleotide comprising a second signal generator to generate a second detectable signal and each of said second oligonucleotides having a second Tm for binding each of said target ncRNAs that is substantially the same; iv. determining the presence of said plurality of target ncRNA in said sample by measuring the first and second detectable signals; and v. generating a profile of the sample based on the target ncRNAs detected c. comparing said first and second ncRNA profiles and identifying those ncRNA molecules that are altered in said second ncRNA profile to create a signature ncRNA profile for said disease state or condition.

In some embodiments, detection of a genetic biomarker (e.g., one or more genetic biomarkers) can include any of the variety of methods described in U.S. Patent Application Publication No. 2005/0244847, which is hereby incorporated by reference in its entirety. For example, detection of a genetic biomarker can include methods for amplifying a circular nucleic acid template, comprising contacting the template with a reaction mixture comprising a thermostable polymerase, individual nucleotides and forward and reverse primers complementary to a common region within the template, wherein the common region is preferably from about 80 to 150 base pairs in length. In one embodiment, the 5' ends of the primers hybridize to opposite strands of the template about 10 to 50 base pairs apart, still more preferably from zero to twenty-five base pairs apart. In some embodiments, the 5' end of the forward primer will generally be proximal to the 5' end of the reverse primer and distal to the 3' end of the reverse primer when the primers are hybridized to the template. In a particularly preferred embodiment, the common region is a conserved region, e.g., an origin of replication, within an extrachromosomal nucleic acid. The reaction mixture may further include a reaction buffer comprising a weak organic base and a weak organic acid. Additionally or alternatively, detection of a genetic biomarker can include reagents for performing in vitro amplification of extrachromosomal DNA, including solutions supporting amplification and subsequent ligation reactions and solutions supporting a combined amplification and ligation reaction, i.e., which provide the appropriate environment for simultaneous polymerase and ligase enzyme activity.

In some embodiments, detection of a genetic biomarker (e.g., one or more genetic biomarkers) can include any of the variety of methods described in P.C.T. Publication No. WO 2018/137826, which is hereby incorporated by reference in its entirety. For example, detection of a genetic biomarker can include methods for enriching template nucleic acids and to methods for generating a sequencing library. In some embodiments, the method for enriching template nucleic acids or for generating a sequencing library comprises: a) hybridizing template nucleic acids to oligonucleotides bound to a solid surface and initially comprising at least two functional sequence elements; b) extending the surface bound oligonucleotides hybridized to the template nucleic acids to form a double strand; c) optionally modifying the double-stranded nucleic acids generated in step b); d) 3' truncation of the surface bound oligonucleotides that have not been used in the template nucleic acid hybridization of step a); and e) optionally modifying the single-stranded surface bound oligonucleotides generated in step d). In some embodiments, the further comprises the additional step of: f) hybridizing further template nucleic acids to the surface bound oligonucleotides or using functional sequence elements within surface bound oligonucleotides for a downstream application. In some embodiments, the downstream application is nucleic acid amplification on the solid surface, de-coupling from solid surface, in-vitro transcription by the use of an RNA polymerase promotor within the oligonucleotide, labeling of immobilized nucleic acid by the use of a primer binding site or a molecular barcode region for identification within the oligonucleotide, sequencing, or a combination thereof. In some embodiments, at least one of the functional sequence elements is a hybridization site or preferably a sequence useful for a downstream application. In another embodiment, the functional sequence elements are consecutive or overlapping. In certain embodiments, the functional sequence elements are separated by predefined cleavage sites or generated by hybridization of protecting oligonucleotides to the surface bound oligonucleotides. In some embodiments, steps a) to c) are repeated at least once with template nucleic acids from different samples. In other embodiments, steps a) to e) are repeated at least once with template nucleic acids from the same sample or from different samples, optionally wherein the repetition(s) is (are) performed in parallel. In some embodiments, the density of the surface bound oligonucleotides is between 500-500000 oligonucleotides/$\mu m^2$, more preferably 750-200000 oligonucleotides/$\mu m^2$, most preferably 1000-100000 oligonucleotides/$\mu m^2$. In other embodiments, the surface bound oligonucleotides comprise 2 to 20 functional sequence elements, more preferably 2 to 10, most preferably 2 to 5. In certain embodiments, the length of the surface bound oligonucleotides is within the range of 4-200 nt, preferably 10-200 nt, more preferably 6-180 nt, more preferably 8-160 nt, more preferably 10-140 nt, most preferably 20-100 nt. In some embodiments, the length of the surface bound oligonucleotides is 10 nt, preferably 20 nt. In some embodiments, all functional sequence elements of the same position within a surface bound oligonucleotide have a unique sequence or comprise 2-100000, preferably 2-50000, more preferably 2-25000, more preferably 2-10000, more preferably 2-5000, more preferably 2-2500, most preferably 2-1000 different sequences. In certain embodiments, the 3' truncation is achieved enzymatically or chemically. In some embodiments, the double-stranded nucleic acids bound to the surface are modified by introducing barcode sequences, adding sequencing adaptors, adding a fluorophore at the terminus, incorporation of modified bases, or other modifications. In other embodiments, the single-stranded oligonucleotides bound to the surface are modified by adding biotin, labeling moieties, blocking moieties, or other modifications.

In some embodiments, detection of a genetic biomarker (e.g., one or more genetic biomarkers) can include any of the variety of methods described in P.C.T. Publication No. WO 2018/013598, which is hereby incorporated by reference in its entirety. For example, detection of a genetic biomarker can include methods, adapters and kits for performing single end duplex DNA sequencing. In some embodiments, the method for performing DNA sequencing, comprises: (a) performing a ligation reaction in the presence of a plurality of double-stranded target nucleic acids and a first set of substantially complementary double-stranded adapters to generate ligation products, wherein each adapter of the first set comprises a first strand and a second strand, the first strand comprises, from 5' to 3', a 5' region that is 10 or more nucleotides in length, a molecular tag sequence, and an optional 3' region, the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region, at least one mismatch between the first and second strands is located in the 3' region of the first strand if the 3' region is present, and/or in the 5' region that is 3' to the 10-nucleotide or longer portion of the 5' region of the first strand, and different adapters of the first set comprise different molecular tag sequences in their first strands and corresponding fully complementary sequences of the different molecular tag sequences in their second strands, but are otherwise identical to each other, (b) performing an amplification reaction using the ligation products of step (a) as templates to generate amplification products, wherein the amplification products comprise one or more locations that do not form complementary base pairs in the first and second strands of the substantially complementary double-stranded adapters, and (c) performing sequencing reactions using amplification products of step (b) or their further amplification products as templates to obtain sequence reads that comprise the one or more locations where a complementary base pair is not formed in the first and second strands of the double-stranded adapters. Additionally or alternatively, detection of a genetic biomarker can include a set of substantially complementary double-stranded adapters, comprising at least 16 different adapters, wherein each adapter of the set comprises a first strand and a second strand, the first strand comprises, from 5' to 3', a 5' region, a molecular tag sequence, and an optional 3' region, the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region, at least one mismatch between the first and second strands is located in the 3' region of the first strand if the 3' region is present, and/or in the 5' region that is 3' to the 10-nucleotide or longer portion of the 5' region of the first strand, and different adapters comprise different molecular tag sequences in their first strands and corresponding fully complementary sequences of the different molecular tag sequences in their second strands, but are otherwise identical to each other. Additionally or alternatively, detection of a genetic biomarker can include a kit, comprising: (1) a set of substantially complementary double-stranded adapters, and (2) a ligase.

In some embodiments, detection of a genetic biomarker (e.g., one or more genetic biomarkers) can include any of the variety of methods described in U.S. Patent Application Publication No. 2017/165289, which is hereby incorporated by reference in its entirety. For example, detection of a genetic biomarker can include primers, primer sets, kits and methods for multiple displacement amplification (MDA). In some embodiments, the method for amplifying nucleic acids by multiple displacement amplification, comprises: performing one or more separate multiple displacement amplification reactions, wherein each reaction is performed in the presence of: (1) a primer set, wherein each primer of the primer set comprises a self-complementary sequence at its 5' terminus and a random sequence or a semi-random sequence at its 3' terminus, and wherein the self-complementary sequences in each primer set are the same, but different from the self-complementary sequences in another primer set, (2) a DNA polymerase having a strand displacement activity, and (3) target nucleic acids. In certain embodiments, the self-complementary sequences in one or more primer sets are each 6 to 20 nucleotides in length. In certain embodiments, the random sequences or the semi-random sequences in one or more primer sets are 4 to 20 nucleotides in length. Preferably, the primers are resistant to 3'-5' exonuclease proofreading activity. In certain embodiments, the DNA polymerase having a strand displacement activity is Phi29 polymerase. In certain embodiments, at least 2 separate multiple displacement amplification reactions are performed. In certain embodiments, the target nucleic acids used in one or more separate multiple displacement amplification reactions are genomic DNA from one or more different single cells, such as human cells. In certain embodiments, the multiple displacement amplification is performed at a temperature from about 20° C. to about 40° C., such as cycling between two temperatures within the above-noted range or under an isothermal condition. In certain embodiments where a plurality of separate multiple displacement amplification reactions are performed, the method further comprises: pooling the nucleic acids amplified from the plurality of multiple displacement amplification reactions together, generating a sequencing library using the pooled amplified nucleic acids, and sequencing the pooled amplified nucleic acids. Additionally or alternatively, detection of a genetic biomarker can include a primer set, wherein each primer in the primer set comprises a self-complementary sequence at its 5' terminus and a random sequence or a semi-random sequence at its 3' terminus, and wherein the self-complementary sequences of the primers are identical to each other. Additionally or alternatively, detection of a genetic biomarker can include a plurality of primer sets, wherein each primer comprises a self-complementary sequence at its 5' terminus and a random sequence or a semi-random sequence at its 3' terminus, wherein the self-complementary sequences of primers in each primer set are the same, but different from the self-complementary sequences of primers in another primer set. In certain embodiments, the plurality of primer sets comprises at least 3 different primer sets.

In some embodiments, detection of a genetic biomarker (e.g., one or more genetic biomarkers) can include any of the variety of methods described in P.C.T. Publication No. WO 2017/085321, which is hereby incorporated by reference in its entirety. For example, detection of a genetic biomarker can include a method for producing a sterilized composition suitable for stabilizing an extracellular nucleic acid population of a biological sample, the method comprising: a) providing a composition comprising: i. at least one caspase inhibitor, and ii. at least one compound selected from a thioalcohol (preferably N-acetyl-cysteine or glutathione), a water-soluble vitamin, and vitamin E or a derivative thereof; and b) irradiating the composition for sterilization. Additionally or alternatively, detection of a genetic biomarker can include a method for stabilizing an extracellular nucleic acid population comprised in a cell-containing biological sample comprising: a) obtaining i) a sterilized composition suitable for stabilizing an extracellular nucleic acid population of a biological sample, or ii) a composition above in sterilized form; and b) contacting the cell-containing biological sample with the sterilized composition for stabilization. Additionally or alternatively, detection of a genetic biomarker can include a method for isolating extracellular nucleic acids from a stabilized cell-containing biological sample comprising: a) stabilizing the cell-containing biological sample according to the method; and b) isolating extracellular nucleic acids. Additionally or alternatively, detection of a genetic biomarker can include a method for processing and/or analyzing extracellular nucleic acids comprising: a) isolating extracellular nucleic acids from a stabilized cell-containing biological sample according to the method; and b) processing and/or analyzing the isolated extracellular nucleic acids. Additionally or alternatively, detection of a genetic biomarker can include a method for producing a sterilizable composition, wherein the composition in sterilized form is suitable for stabilizing an extracellular nucleic acid population of a biological sample, the method comprising: a) preparing a composition comprising: i. at least one caspase inhibitor, and ii. at least one compound selected from a thioalcohol (preferably N-acetyl-cysteine or glutathione), a water-soluble vitamin, and vitamin E or a derivative thereof, and optionally b) sterilizing the composition. Additionally or alternatively, detection of a genetic biomarker can include a sterilizable composition, wherein the composition in sterilized form is suitable for stabilizing an extracellular nucleic acid population of a biological sample, wherein the composition is a composition as provided in step a) of the method. It comprises i. at least one caspase inhibitor, and ii. at least one compound selected from a thioalcohol (preferably N-acetyl-cysteine or glutathione), a water-soluble vitamin, and vitamin E or a derivative thereof. The sterilizable composition according to the sixth aspect, which can be a composition as provided in step a) of the method, in embodiments can be sterilized to provide a sterilized composition. Additionally or alternatively, detection of a genetic biomarker can include a sample collection device such as a container, preferably a sample collection tube, comprising the sterilizable composition above. Additionally or alternatively, detection of a genetic biomarker can include the use of at least one compound selected from the group consisting of a thioalcohol (preferably N-acetyl-cysteine or glutathione), a water-soluble vitamin, and vitamin E or a derivative thereof, for protecting a composition suitable for stabilizing an extracellular nucleic acid population of a biological sample or components thereof during sterilization by irradiation.

In some embodiments, detection of a genetic biomarker (e.g., one or more genetic biomarkers) can include any of the variety of methods described in P.C.T. Publication No. WO 2016/170147, which is hereby incorporated by reference in its entirety. For example, detection of a genetic biomarker can include methods of generating dsDNA, wherein the method comprises ligating a first and a second dsDNA, both optionally having one or two single-stranded end(s), in the presence of a DNA ligase and an agent, which modulates the melting temperature of dsDNA. Additionally or alternatively, detection of a genetic biomarker can include a method for ligating a first and a second dsDNA, wherein both the first and the second dsDNAs comprise two ssDNA regions, whereby each of the ssDNA region ends of the first dsDNA ligates with each of the complementary ss region ends of the second dsDNA to provide ligated circular dsDNA in the presence of a an agent, which modifies the melting temperature of dsDNA. In some embodiments, the first or the second DNA is capable of conferring the ability to auto-replicate within competent cells. Additionally or alternatively, detection of a genetic biomarker can include a method for generation of a sequencing library, wherein the method comprises the steps of: (i) providing DNA fragments; (ii) end-repairing the DNA fragments by a polynucleotide kinase enzyme and an enzyme with polymerase and exonuclease activities to obtain blunt-ended, 5' phosphorylated DNA fragments; (iii) optionally adding a terminal adenine to the end of the end-repaired DNA fragments by a deoxynucleotidyl transferase enzyme; and (iv) ligating the DNA fragments, optionally having the terminal adenine, with sequencing adapters wherein preferably the adapters have a terminal thymidine if the fragments have a terminal adenine. In some embodiments, said method further comprises step (v), wherein the ligated fragments of step (iv) are purified and size-selected for sequencing. In some embodiments, said method further comprises step (vi), wherein the adapter-ligated fragments are amplified and the amplification product is optionally purified prior to sequencing. In another embodiment, the fragments of step (v) or (vi) are subjected to sequencing. Additionally or alternatively, detection of a genetic biomarker can include a kit comprising: (i) a DNA ligase; and (ii) an agent, which modulates the melting temperature of dsDNA. In another embodiment, the agent which modulates the melting temperature of dsDNA is selected from any one of tetramethylammonium chloride (TMAC), piperazinium chloride, tetramethylpiperazinium chloride, tetraethylammonium chloride (TEAC), trimethylamine N-oxide (TMANO), 2-methyl-4-carboxy-5-hydroxy-3,4,5,6-tetrahydropyrimidine THP (A), 2-methyl-4-carboxy-3,4,5,6-tetrahydropyrimidine THP (B), non-ionic detergents, such as NP-40, and TritonRX-100, and mixtures thereof. In a preferred embodiment, the agent which modulates the melting temperature of dsDNA is selected from any one of f tetramethylammonium chloride (TMAC), piperazinium chloride, tetramethylpiperazinium chloride, tetraethylammonium chloride (TEAC), trimethylamine N-oxide (TMANO), 2-methyl-4-carboxy-5-hydroxy-3, 4,5,6-tetrahydropyrimidine THP (A), 2-methyl-4-carboxy-3,4,5,6-tetrahydropyrimidine THP (B), and mixtures thereof. In some embodiments, the agent which modulates the melting temperature of dsDNA is in a ligation buffer. In some embodiments, the ligase and the agent which modulates the melting temperature of dsDNA are in separate containers.

In some embodiments, detection of a genetic biomarker (e.g., one or more genetic biomarkers) can include any of the variety of methods described in P.C.T. Publication No. WO 2016/135300, which is hereby incorporated by reference in its entirety. For example, detection of a genetic biomarker can include methods and kits for specific inhibition of enzymes involved in the DNA preparation for NGS library construction protocols. Additionally or alternatively, detection of a genetic biomarker can include a method of generating a sequencing library, wherein the method comprises the steps of: (i) providing DNA fragments; (ii) end-repairing the DNA fragments by a polynucleotide kinase enzyme and an enzyme with polymerase and exonuclease activities to obtain blunt-ended, 5' phosphorylated DNA fragments; (iii) optionally adding a terminal adenine to the end of the end-repaired DNA fragments by a deoxynucleotidyl transferase enzyme; and (iv) ligating the DNA fragments, optionally having the terminal adenine base, with sequencing adaptors by a DNA ligase; whereby after completion of step (ii) and/or the optional step (iii) the enzyme or enzymes used in that/those step/s is/are inactivated by the addition of (a) specific inhibitor(s). None of the inhibitors of the above method inhibits the enzyme activity of a/the subsequent step(s). In some embodiments, the steps of the above method, which comprise enzyme inactivation by a specific inhibitor, do not comprise heat-inactivation of said enzyme(s). In some embodiments, the steps of the above method, which comprise enzyme inactivation by a specific inhibitor, do not comprise a subsequent purification step from said enzyme(s). In some alternative embodiments, the steps of the above method, which comprise addition of (a) specific inhibitor(s), comprise an upstream heat-inactivation of said enzyme(s), but do not comprise a purification step from said enzyme(s). In some embodiments, the above method may further comprise step (v), wherein the ligated fragments of step (iv) are purified and size-selected for sequencing.

In some embodiments, detection of a genetic biomarker (e.g., one or more genetic biomarkers) can include any of the variety of methods described in P.C.T. Publication No. WO 2001/023618, which is hereby incorporated by reference in its entirety. For example, detection of a genetic biomarker can include a composition comprising an oligonucleotide and an annealing promoting compound (APC). The composition may be used, for example, to reduce the specificity of a hybridization reaction involving the oligonucleotide. The oligonucleotide may optionally be immobilized on a solid surface, where suitable solid surfaces include a nylon tip, a nylon bead, and a nylon membrane. In a preferred embodiment, the APC is an aminoalcohol, where the aminoalcohol comprises at least one amine group and at least one hydroxyl group. The composition may further comprise an acid and/or a buffer, so that the aminoalcohol may be present in the composition, either entirely or in part, as a salt of the aminoalcohol. The composition is preferably aqueous, and has a pH of between 4 and 10. Exemplary aminoalcohol APCs are 4-hydroxypiperidine, 1-methyl-3-piperidinemethanol, 4,4'-trimethylenebis(1-piperidineethanol), 3-piperidinemethanol, 1-ethyl-4-hydroxy-piperidine, 2-piperidineethanol, 3-hydroxy-1-methylpiperidine, 1-ethyl-3-hydroxy-piperidine, 4-hydroxy-1-methylpiperidine, 1-methyl-2-piperidinemethanol, 2-piperidine-methanol, 2,2,6,6-tetramethyl-4-piperidinol, 1,4-bis(2-hydroxyethyl)piperazine and 1-(2-hydroxyethyl)piperazine. Additionally or alternatively, detection of a genetic biomarker can include a method of decreasing the specificity of a hybridization reaction between two oligonucleotides. The method comprises adding an annealing promoting compound (APC) to a hybridization reaction between two oligonucleotides. Additionally or alternatively, detection of a genetic biomarker can include a method of decreasing the specificity of a hybridization reaction between two oligonucleotides. The method comprises mixing a first oligonucleotide, a second oligonucleotide, and an annealing promoting compound (APC) under conditions suitable for the formation of an oligonucleotide duplex. Additionally or alternatively, detection of a genetic biomarker can include a method of identifying a target oligonucleotide. The method comprises: (a) mixing a first oligonucleotide having a sequence complementary to the target oligonucleotide, a second oligonucleotide having a sequence complementary to the complement of the target oligonucleotide, an annealing promoting compound (APC), a polymerase, a buffer compatible with polymerase activity, and a target oligonucleotide; (b) heating the mixture of (a) to a temperature above the melting temperature of the first oligonucleotide and the second oligonucleotide and their respective complementary sequences; (c) reducing the temperature of the mixture of (b) to below the melting temperature, to thereby allow hybridization between the first oligonucleotide, the second oligonucleotide, and the target oligonucleotide; (d) raising the temperature of the mixture of (c) to a temperature compatible with polymerase activity; and (e) detecting a product of polymerization.

In some embodiments, detection of a genetic biomarker (e.g., one or more genetic biomarkers) can include any of the variety of methods described in U.S. Pat. No. 9,792,403, which is hereby incorporated by reference in its entirety. For example, detection of a genetic biomarker can include a system for generating a characterization model (including, e.g., variant type and/or zygosity) for a variant (e.g., a mutation) in a tissue or sample, e.g., a tumor, or tumor sample, from a subject, e.g., a human subject, e.g., a cancer patient. The system comprises: at least one processor operatively connected to a memory, the at least one processor when executing is configured to: a) acquire: i) a sequence coverage input (SCI), which comprises, for each of a plurality of selected subgenomic intervals (e.g., exons) a value for sequence coverage at the selected subgenomic intervals (including, e.g., a normalized sequence coverage value); ii) an SNP allele frequency input (SAFI), which comprises, for each of a plurality of selected germline SNPs, a value for the allele frequency, in the tissue or sample, e.g., tumor sample; iii) a variant allele frequency input (VAFI), which comprises the allele frequency for said variant, e.g., mutation, in the tissue or sample, e.g., tumor sample; b) acquire values, determined as a function of SCI and SAFI, for: a genomic segment total copy number (C), for each of a plurality of genomic segments; a genomic segment minor allele copy number (M), for each of a plurality of genomic segments; and sample purity (p); and c) calculate one or both, of: i) a value for variant type, e.g., mutation type, e.g., g, which is indicative of the variant being somatic, germline, subclonal somatic, or not-distinguishable, wherein the at least one processor when executing is configured calculate the value for variant type, e.g., mutation type, as a function of VAFI, p, C, and M; ii) an indication of the zygosity (e.g., homozygous, heterozygous, and absent) of the variant, e.g., mutation, in the tissue or sample, e.g., tumor sample, as function of C and M. In an embodiment, the system is configured such that the analysis can be performed without the need for analyzing non-tumor tissue from the subject. In an embodiment, the system is configured to determine for at least one of the tumor sample, the selected subgenomic intervals, and the selected germline SNPs that the variant type, e.g., mutation type, cannot be determined for analyzed values. In an embodiment, at least one processor when executing acquires the SCI calculated as a function (e.g., the log of the ratio) of the number of reads for a subgenomic interval and the number or reads for a control (e.g., a process-matched control). In an embodiment, at least one processor when executing is configured to calculate SCI as a function (e.g., the log of the ratio) of the number of reads for a subgenomic interval and the number or reads for a control (e.g., a process-matched control). In an embodiment, the at least one processor when executing is configured to validate a minimum number of subgenomic intervals have been selected or analyzed. In an embodiment, at least one processor when executing is configured to validate a minimum number of a plurality of germline SNPs have been selected or analyzed. In an embodiment, the minimum number of germline SNPs comprises at least 10, 25, 50, 100, 150, 200, 250, 300, 350, 400, 450, 500, 1,000, 2,000, 3,000, 4,000, 5000, 6000, 7000, 8000, 9000, 10,000, or 15,000 germline SNPs. In an embodiment, the SAFI is based, at least in part, on a minor allele frequency in the tumor sample. In an embodiment, the at least one processor when executing is configured to calculate, or acquire, SAFI based, at least in part, on a minor allele frequency in the tumor sample. In an embodiment, the SAFI is based, at least in part, on an alternative allele frequency (e.g., an allele frequency other than a standard allele in a human genome reference database). In an embodiment, the at least one processor when executing is configured to calculate, or acquire, SAFI based, at least in part, on an alternative allele frequency (e.g., an allele frequency other than a standard allele in a human genome reference database). In an embodiment, the at least one processor when executing is configured to access values of C, M, and p calculated from fitting a genome-wide copy number model to the SCI and the SAFI. In an embodiment, the at least one processor when executing is configured to calculate C, M, and p. In an embodiment, the at least one processor when executing generates a best fit between the genome-wide copy number model and the SCI and the SAFI to calculate C, M, and p. In an embodiment, values of C, M, and p fit a plurality of genome-wide copy number model inputs of the SCI and the SAFI. In an embodiment, the at least one processor when executing is configured to generate a user interface. In an embodiment, the user interface is configured to accept as input any one or more of: a sequence coverage input (SCI), which comprises, for each of a plurality of selected subgenomic intervals, e.g., exons, a value for sequence coverage at the selected subgenomic intervals (including, e.g., a normalized sequence coverage value); an SNP allele frequency input (SAFI), which comprises, for each of a plurality of selected germline SNPs, a value for the allele frequency, in the tumor sample; a variant allele frequency input (VAFI), which comprises the allele frequency for said variant, e.g., mutation, in the tumor sample; a genomic segment total copy number (C), for each of a plurality of genomic segments; a genomic segment minor allele copy number (M), for each of a plurality of genomic segments; and sample purity (p). In an embodiment, responsive to the user interface input, e.g., for one or more (e.g., 2, 3, 4, 5 or all) of SCI, SAFI, VAFI, C, M, or p, the system generates a characterization model, e.g., a characterization model for a variant. Additionally or alternatively, detection of a genetic biomarker can include a method of characterizing a variant, e.g., a mutation, in a tissue or sample, e.g., a tumor, or tumor sample, from a subject, e.g., a human, e.g., a cancer patient, comprising: a) acquiring: i) a sequence coverage input (SCI), which comprises, for each of a plurality of selected subgenomic intervals, e.g., exons, a value for normalized sequence coverage at the selected subgenomic intervals; ii) an SNP allele frequency input (SAFI), which comprises, for each of a plurality of selected germline SNPs, a value for the allele frequency, in the tumor or sample, e.g., tumor sample; iii) a variant allele frequency input (VAFI), which comprises the allele frequency for said variant, e.g., mutation, in the tumor or sample, e.g., tumor sample; b) acquiring values, as a function of SCI and SAFI, for: C, for each of a plurality of genomic segments, wherein C is a genomic segment total copy number; M, for each of a plurality of genomic segments, wherein M is a genomic segment minor allele copy number; and p, wherein p is sample purity; and c) acquiring one or both of: i) a value for variant type, e.g. mutation type, e.g., g, which is indicative of the variant, e.g., a mutation, being somatic, a subclonal somatic variant, germline, or not-distinguishable, and is a function of VAFI, p, C, and M; ii) an indication of the zygosity of the variant, e.g., mutation, in the tumor or sample, e.g., tumor sample, as function of C and M. In an embodiment, the analysis can be performed without the need for analyzing non-tumor tissue from the subject. In an embodiment, the analysis is performed without analyzing non-tumor tissue from the subject, e.g., non-tumor tissue from the same subject is not sequenced. In an embodiment, the SCI comprises values that are a function, e.g., the log of the ratio, of the number of reads for a subgenomic interval, e.g., from the sample, and the number or reads for a control, e.g., a process-matched control. In an embodiment, the SCI comprises values, e.g., log r values, for at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subgenomic intervals, e.g., exons. In an embodiment, the SCI comprises values, e.g., log r values, for at least 100 subgenomic intervals, e.g., exons. In an embodiment, the SCI comprises values, e.g., log r values, for 1,000 to 10,000, 2,000 to 9,000, 3,000 to 8,000, 3,000 to 7,000, 3,000 to 6,000, or 4,000 to 5,000, subgenomic intervals, e.g., exons. In an embodiment, the SCI comprises values, e.g., log r values, for subgenomic intervals, e.g., exons, from at least 10, 25, 50, 100, 150, 200, 250, 300, 350, 400, 450, 500, 1,000, 2,000, 3,000, or 4,000, genes. In an embodiment, at least one, a plurality, or substantially all of the values comprised in the SCI are corrected for correlation with GC content. In an embodiment, a subgenomic interval, e.g., an exon, from the sample has at least 10, 20, 30, 40, 50, 100, 150, 200, 250, 300, 350, 400, 450, 500, 600, 700, 800, 900, or 1,000 reads. In an embodiment, a plurality, e.g., at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subgenomic intervals, e.g., exons, from the sample has a predetermined number of reads. In an embodiment, the predetermined number of reads is at least 10, 20, 30, 40, 50, 100, 150, 200, 250, 300, 350, 400, 450, 500, 600, 700, 800, 900, or 1,000. In an embodiment, the plurality of germline SNPs comprise at least 10, 25, 50, 100, 150, 200, 250, 300, 350, 400, 450, 500, 1,000, 2,000, 3,000, 4,000, 5000, 6000, 7000, 8000, 9000, 10,000, or 15,000 germline SNPs. In an embodiment, the plurality of germline SNPs comprise at least 100 germline SNPs. In an embodiment, the plurality of germline SNPs comprises 500 to 5,000, 1,000 to 4,000, or 2,000 to 3,000 germline SNPs. In an embodiment, the allele frequency is a minor allele frequency. In an embodiment, the allele frequency is an alternative allele, e.g., an allele other than a standard allele in a human genome reference database. In an embodiment, the method comprises characterizing a plurality of variants, e.g., mutants, in the tumor sample. In an embodiment, the method comprises characterizing at least 2, 3, 4, 5, 6, 7, 8 9, 10, 25, 50, 100, 150, 200, 250, 300, 350, 400, 450, or 500 variants, e.g., mutants. In an embodiment, the method comprises characterizing variants, e.g., mutants, in at least 2, 3, 4, 5, 6, 7, 8 9, 10, 25, 50, 100, 150, 200, 250, 300, 350, 400, 450, or 500 different genes. In an embodiment, the method comprises acquiring a VAFI for at least 2, 3, 4, 5, 6, 7, 8 9, 10, 25, 50, 100, 150, 200, 250, 300, 350, 400, 450, or 500 variants, e.g., mutants. In an embodiment, the method comprises performing one, two or all, of steps a), b), and c) for at least 2, 3, 4, 5, 6, 7, 8 9, 10, 25, 50, 100, 150, 200, 250, 300, 350, 400, 450, or 500 variants, e.g., mutants. In an embodiment, values of C, M, and p are, have, or can be obtained by, fitting a genome-wide copy number model to one or both of the SCI and the SAFI. In an embodiment, values of C, M, and p fit a plurality of genome-wide copy number model inputs of the SCI and the SAFI. In an embodiment, a genomic segment comprises a plurality of subgenomic intervals, e.g., exons, e.g., subgenomic intervals which have been assigned a SCI value. In an embodiment, a genomic segment comprises at least 10, 20, 30, 40, 50, 60, 70, 80, 90, 100, 125, 150, 175, 200, 225, 250, 275, 300, 400, or 500 subgenomic intervals, e.g., exons. In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100, subgenomic intervals, e.g., exons. In an embodiment, a genomic segment comprises between 100 and 10,000, 100 and 5,000, 100 and 4,000, 100 and 3,000, 100 and 2,000, or 100 and 1,000, subgenomic intervals, e.g., exons. In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100 genomic SNPs, which have been assigned a SAFI value. In an embodiment, a genomic segment comprises between 100 and 10,000, 100 and 5,000, 100 and 4,000, 100 and 3,000, 100 and 2,000, or 100 and 1,000, genomic SNPs which have been assigned a SAFI value. In an embodiment, each of a plurality of genomic segments are characterized by having one or both of: a measure of normalized sequence coverage, e.g., log r, that differ by no more than a preselected amount, e.g., the values for log 2 r for subgenomic intervals, e.g., exons, within the boundaries of the genomic segment differ by no more than a reference value, or are substantially constant; and SNP allele frequencies for germline SNPs that differ by no more than a preselected amount, e.g., the values for germline SNP allele frequencies for subgenomic intervals, e.g., exons, within the boundaries of the genomic segment differ by no more than a reference value, or are substantially constant. In an embodiment, the number of subgenomic intervals, e.g., exons, that are contained in, or are combined to form, a genomic segment is at least 2, 5, 10, 15, 20, 50, or 100 times the number of genomic segments. In an embodiment, the number of subgenomic intervals, e.g., exons, is at least 3, 4, 5, 6, 7, 8, 9, 10, 11, 12, 13, 14, or 15 times the number of genomic segments. In an embodiment, a boundary for a genomic segment is provided. In an embodiment, the method comprises assembling sequences for subgenomic intervals, e.g., exons, into genetic segments. In an embodiment, the method comprises assembling sequences for subgenomic intervals, with a method, e.g., a method comprising a circular binary segmentation (CBS), an HMM based method, a Wavelet based method, or a Cluster along Chromosomes method. In an embodiment, fitting the genome-wide copy number model to the SCI comprises using the equation of:

$$logRatio_i = \log_2 \frac{pC_i + 2(1-p)}{p\psi + 2(1-p)},$$

where $\psi$ is tumor ploidy. In an embodiment, $\psi = (\Sigma l_i C_i)/\Sigma l_i$, let $l_i$ be the length of a genomic segment. In an embodiment, fitting the genome-wide copy number model to the SAFI comprises using the equation of:

$$AF = \frac{pM + 1(1-p)}{pC + 2(1-p)},$$

where AF is allele frequency. In an embodiment, the fitting comprises using Gibbs sampling. In an embodiment, fitting comprises using e.g., Markov chain Monte Carlo (MCMC) algorithm, e.g., ASCAT (Allele-Specific Copy Number Analysis of Tumors), OncoSNP, or PICNIC (Predicting Integral Copy Numbers In Cancer). In an embodiment, fitting comprises using Metropolis-Hastings MCMC. In an embodiment, fitting comprises using a non-Bayesian approach, e.g., a frequentist approach, e.g., using least squares fitting. In an embodiment, g is determined by determining the fit of values for VAFI, p, C, and M to a model for somatic/germline status. In an embodiment, the method comprises acquiring an indication of heterozygosity for said variant, e.g., mutation. In an embodiment, sample purity (p) is global purity, e.g., is the same for all genomic segments. In an embodiment, the value of g is acquired by:

$$AF = \frac{pM + g(1-p)}{pC + 2(1-p)},$$

where AF is allele frequency. In an embodiment, a value of g that is close to 0, e.g., does not differ significantly from 0, indicates the variant is a somatic variant. In an embodiment, a value of g that is 0, or close to 0, e.g., within a predetermined distance from 0, e.g., a value of g of less than 0.4, indicates the variant is a somatic variant. In an embodiment, a value of g that is close to 1, e.g., does not differ significantly from 1, indicates the variant is a germline variant. In an embodiment, a value of g that is 1, or close to 1, e.g., within a predetermined distance from 1, e.g., a value of g of more than 0.6, indicates the variant is a germline variant. In an embodiment, a value of g is less than 1 but more than 0, e.g., if it is less than 1 by a predetermined amount and more than 0 by a predetermined amount, e.g., if g is between 0.4 and 0.6, it indicates an indistinguishable result. In an embodiment, a value of g that is significantly less than 0, is indicative of a subclonal somatic variant. In an embodiment, the value of g is acquired by:

$$AF = \frac{pM' + g(1-p)}{pC + 2(1-p)},$$

where AF is allele frequency, and M'=C−M (e.g., when M is a non-minor allele frequency), e.g., the variant is a germline polymorphism if g=1 and the variant is a somatic mutation if g=0.

In an embodiment, the somatic/germline status is determined, e.g., when the sample purity is below about 40%, e.g., between about 10% and 30%, e.g., between about 10% and 20%, or between about 20% and 30%. In an embodiment, when: a value of M equal to 0 not equal to C is indicative of absence of the variant, e.g., mutation, e.g., not existent in the tumor;

a non-zero value of M equal to C is indicative of homozygosity of the variant, e.g., mutation, e.g., with loss of heterozygosity (LOH); a value of M equal to 0 equal to C indicates a homozygous deletion of the variant, e.g., mutation, e.g., not existent in the tumor; and a non-zero value of M not equal to C is indicative of heterozygosity of the variant, e.g., mutation. In an embodiment, the method comprises acquiring an indication of zygosity for said variant, e.g., mutation. In an embodiment, the mutation status is determined as homozygous (e.g., LOH) if M=C≠0. In an embodiment, the mutation status is determined as homozygous deletion if M=C=0. In an embodiment, the mutation status is determined as heterozygous is 0<M<C. In an embodiment, the mutation is absent from the tumor if M=0 and C≠0. In an embodiment, the zygosity is determined, e.g., when the sample purity is greater than about 80%, e.g., between about 90% and 100%, e.g., between about 90% and 95%, or between about 95% and 100%. In an embodiment, the control is a sample of euploid (e.g., diploid) tissue from a subject other than the subject from which the tumor sample is from, or a sample of mixed euploid (e.g., diploid) tissues from one or more (e.g., at least 2, 3, 4, or 5) subjects other than the subject from which the tumor sample is from. In an embodiment, the method comprises sequencing each of the selected subgenomic intervals and each of the selected germline SNPs, e.g., by next generation sequencing (NGS). In an embodiment, the sequence coverage prior to normalization is at least about 10×, 20×, 30×, 50×, 100×, 250×, 500×, 750×, or 1000× the depth of the sequencing.

In some embodiments, detection of a genetic biomarker (e.g., one or more genetic biomarkers) can include any of the variety of methods described in P.C.T. Publication No. WO 2018/0218113, which is hereby incorporated by reference in its entirety.

In some embodiments, detection of a genetic biomarker (e.g., one or more genetic biomarkers) can include any of the variety of methods described in U.S. Patent Application Publication No. 2017/0356053, which is hereby incorporated by reference in its entirety. For example, detection of a genetic biomarker can include the use of hybridization of a sample nucleic acid to a bait set to evaluate a region of interest, e.g., to evaluate the clonal profile of a region of interest, in the sample. Additionally or alternatively, detection of a genetic biomarker can include a method of evaluating or providing a clonal profile of a subject interval, e.g., a subgenomic interval, or an expressed subgenomic interval (or of a cell containing the same), in a subject, comprising: (a) acquiring a nucleic acid library comprising a plurality of members, each member of the plurality comprising a nucleic acid from the subject, e.g., a plurality of tumor members from a solid tumor or hematologic malignancy (or premalignancy) sample; (b) contacting the library with a bait set to provide a plurality of selected members, each of which comprises the subject interval, or a portion thereof (sometimes referred to herein as a library catch); optionally, (c) amplifying each member of the plurality of selected members, e.g., to provide an amplified sequence of the subject interval; (d) acquiring the sequence of one or more occurrences of the subject interval; thereby providing or evaluating the clonal profile of a subject interval. In an embodiment, the method comprises evaluating the clonal profile of a subgenomic interval and of an expressed subgenomic interval. In an embodiment, the method comprises comparing the sequence of a first allele or signature (e.g., a first V segment) at the subject interval with a comparison value, e.g., a preselected value, e.g., a value that is a function of the sequence of a second allele or signature (e.g., a second V segment). In an embodiment, the method further comprises: (e) acquiring: (i) a value for the distribution, expression (the occurrence or level of transcribed copies of a subgenomic signature), abundance, or identity, of a sequence, signature or allele at the subject interval, e.g., the relative abundance, of a sequence, a signature, or an allele, or the relative abundance of each of a plurality of sequences, signatures, or alleles, at the subject interval; or (ii) a value for variability, e.g., sequence variability arising from a somatic hypermutation, sequence variability arising from a VD, DJ, or VJ junction, e.g., by the formation of an indel at the junction, or a CDR, e.g., heavy chain CDR3, sequence variability, within a signature or subject interval, e.g., wherein a value for variability is a function of the number of different variants present for the subject interval in a subject or sample. In an embodiment, the method comprises providing the clonal profile of a sequence, allele or signature, e.g., a V segment, or VDJ or VJ rearrangement, at a first subject interval; and i) a phenotype, e.g., disease state, of the subject; or ii) the genotype at a second subject interval. In an embodiment, step (d): (i) comprises acquiring the sequence of each of a plurality of occurrences of the subject interval, e.g., acquiring the sequence of first occurrence of a subject interval comprising a V segment and of a second occurrence of the interval comprising the V segment, wherein the first and second occurrences differ by the diversity at a VD, DJ, or VJ junction; or (ii) comprises acquiring the sequence of a first subject interval and of a second different subject interval, e.g., wherein the first subject interval comprises a sequence from a first gene and the second subject interval comprises sequence from a second gene. In an embodiment, step (d) comprises acquiring the sequence of each of a plurality of occurrences of the subject interval, e.g., a plurality of occurrences of a subject interval comprising a VDJ sequence, e.g., a plurality of occurrences of a subject interval comprising a VDJ sequence comprising a specific V segment, a specific D segment, and a specific J segment. In an embodiment, the method comprises acquiring a value for e(i). In an embodiment, the value of (e)(i) comprises a value for the abundance of a sequence, signature, or allele (e.g., a first V segment) in a subject interval relative to a comparison value, e.g., a preselected value, e.g., a value that is a function of the abundance of a second sequence, signature, or allele (e.g., a second V segment). In an embodiment, the value of (e)(i) comprises a value for the abundance of an event, e.g., a sequence, allele, or signature, e.g., a mutation or rearrangement, in a subject interval, relative to a comparison value, e.g., a preselected value, e.g., a value that is a function of the abundance of a sequence lacking the event, e.g., an unmutated or unrearranged sequence in the subject interval. In an embodiment, the value of (e)(i) comprises a value of relative abundance for each of X unique (i.e., different from one another) sequences, signatures, or alleles, at a subject interval. Additionally or alternatively, detection of a genetic biomarker can include a method of evaluating a subject for the occurrence of a whole arm or large rearrangement, e.g., a rearrangement, e.g., a translocation, duplication, insertion, or deletion, comprising, e.g., at least 5%, 10%, 20%, 30%, 40%, 50%, 60%, 70%, 80%, or 90%, or all of a chromosome arm, comprising: (a) acquiring a nucleic acid library comprising a plurality of members, each member of the plurality comprising nucleic acid from the subject; (b) contacting the library with a bait set, e.g., under conditions of solution hybridization, to provide a plurality of selected members, each of which comprises a subject interval, or a portion thereof (sometimes referred to herein as a library catch); (c) amplifying each member of the plurality, e.g., by a method that does not rely on a sequence specific interaction with target/subject nucleic acid in the member, e.g., by amplifying each member of the plurality with a primer that does not bind to target/subject nucleic acid in the member; and (d) acquiring the sequence of a plurality of subject intervals, wherein said plurality of subject intervals is disposed on a chromosome such as to allow determination of a whole arm or large rearrangement. Additionally or alternatively, detection of a genetic biomarker can include a method of evaluating a subject, comprising: (a) acquiring a nucleic acid library comprising a plurality of members, each member of the plurality comprising nucleic acid from the subject, e.g., a plurality of tumor members from a hematological-cancer sample; (b) contacting the library with a bait set, e.g., under conditions of solution hybridization, to provide a plurality of selected members, each of which comprises the subject interval, or a portion thereof (sometimes referred to herein as a library catch); (c) amplifying each member of the plurality of selected members, e.g., by a method that does not rely on a sequence specific interaction with target/subject nucleic acid in the member, e.g., by amplifying each member of the plurality of selected members with a primer that does not bind to target/subject nucleic acid in the member; (d) acquiring the sequence of a subgenomic interval and an expressed subgenomic interval; thereby evaluating the subject, wherein: (i) the method comprises contacting the library with a bait set that provides both a subgenomic interval and an expressed subgenomic interval; (ii) the method comprises contacting the library with a first bait set that provides a subgenomic interval and a second bait set that provides an expressed subgenomic interval; (iii) wherein the library comprises genomic DNA and is contacted with a bait set that provides a subgenomic interval and the method further comprises a second library which comprises cDNA which is contacted with the bait set to provide an expressed subgenomic interval; (iv) wherein the library comprises genomic DNA and is contacted with a bait set that provides a subgenomic interval and the method further comprises a second library which comprises cDNA which is contacted with a second bait set to provide an expressed subgenomic interval; or (v) the method comprises performing one of steps (a), (b) and (c) in a first reaction mix to provide a first subject interval, e.g., a subgenomic interval, and on a second reaction mix to provide a second subject interval, e.g., an expressed subgenomic interval, e.g., that corresponds to the subgenomic interval. Additionally or alternatively, detection of a genetic biomarker can include a method of analyzing a sample, e.g., a tumor sample from a hematologic malignancy (or premalignancy), e.g., a hematologic malignancy (or premalignancy). The method comprises: (a) acquiring one or a plurality of libraries comprising a plurality members from a sample, e.g., a plurality of tumor members from a tumor sample; (b) optionally, enriching the one or a plurality of libraries for preselected sequences, e.g., by contacting the one or a plurality of libraries with a bait set (or plurality of bait sets) to provide selected members (sometimes referred to herein as library catch); (c) acquiring a read for a subject interval, e.g., a subgenomic interval or an expressed subgenomic interal, from a member, e.g., a tumor member from a library or library catch, e.g., by a method comprising sequencing, e.g., with a next generation sequencing method; (d) aligning said read by an alignment method; and (e) assigning a nucleotide value (e.g., calling a mutation, e.g., with a Bayesian method) from said read for the preselected nucleotide position, thereby analyzing said tumor sample, optionally wherein: a read from each of X unique subject intervals (e.g., subgenomic intervals, expressed subgenomic intervals, or both) is aligned with a unique alignment method, wherein unique subject interval (e.g., subgenomic interval or expressed subgenomic interval) means different from the other X-1 subject intervals (e.g., subgenoime intervals, expressed subgenomic intervals, or both), and wherein unique alignment method means different from the other X-1 alignment methods, and X is at least 2. Additionally or alternatively, detection of a genetic biomarker can include a method of analyzing a sample, e.g., a tumor sample from a hematologic malignancy (or premalignancy), e.g., a hematologic malignancy (or premalignancy). The method comprises: (a) acquiring one or a plurality of libraries comprising a plurality members from a sample, e.g., a plurality of tumor members from the sample, e.g., the tumor sample; (b) optionally, enriching the one or a plurality of libraries for preselected sequences, e.g., by contacting the library with a bait set (or plurality of bait sets) to provide selected members, e.g., a library catch; (c) acquiring a read for a subject interval (e.g., a subgenomic interval or an expressed subgenomic interval) from a member, e.g., a tumor member from said library or library catch, e.g., by a method comprising sequencing, e.g., with a next generation sequencing method; (d) aligning said read by an alignment method; and (e) assigning a nucleotide value (e.g., calling a mutation, e.g., with a Bayesian method or a calling method) from said read for the preselected nucleotide position, thereby analyzing said tumor sample. optionally wherein a nucleotide value is assigned for a nucleotide position in each of X unique subject intervals (subgenomic intervals, expressed subgenomic intervals, or both) is assigned by a unique calling method, wherein unique subject interval (e.g., subgenomic interval or expressed subgenomic interval) means different from the other X-1 subject intervals (e.g., subgenoime intervals, expressed subgenomic intervals, or both), and wherein unique calling method means different from the other X-1 calling methods, and X is at least 2. The calling methods can differ, and thereby be unique, e.g., by relying on different Bayesian prior values.

In some embodiments, detection of a genetic biomarker (e.g., one or more genetic biomarkers) can include any of the variety of methods described in U.S. Patent Application Publication No. 2015/0324519, which is hereby incorporated by reference in its entirety. For example, detection of a genetic biomarker can include methods, systems, and apparatuses for making more accurate variant calls based on sequencing reads of a sample, e.g., obtained from a targeted sequencing. For example, once sequence reads are received and aligned to a reference sequence, sequence reads having a variant at a location can be counted. A first variant frequency of a particular variant measured at one location of a sample can be compared to one or more second variant frequencies of the particular variant measured at other positions and/or from other samples. The second variant frequency can correspond to an expected value for sequencing errors for a sequencing run. In some embodiments, a probability value indicating the confidence level that a variant is a true positive at a location can be calculated based on variant counts and total read counts at a plurality of locations in the target region in one or more samples. The probability value can then be compared with a threshold level to determine whether the detected variant is a true positive. In other embodiments, a difference in variant counts and total reads counts at a same location in a test sample and a reference sample (e.g., assumed to only have sequencing errors at the location) can be used to determine whether a variant is a true positive in a test sample. According to one embodiment, a method can detect true positives for rare variants in a target region of a test sample. For each sample, variant frequencies for variants of a same variant class at locations where a reference allele exists on a reference sequence can be calculated using variant counts and total read counts. A distribution of the variant frequencies for variants of the same class can be used to determine the probability value of a variant at a location in the test sample with a determined variant frequency. Based on the probability value, the variant at the location in the test sample is classified as either a true positive (mutation) or a false positive. In other embodiments, a method can detect true positives for rate variants in a target region of a test sample by using a comparison with one or more reference samples. A variant count and a wild type count for a specific variant at a specific location in the test sample can be determined from the aligned sequence reads, and compared with a variant count and a wild type count for the specific variant at the specific location in the one or more reference samples to determine a probability value. Based on the probability value, the specific variant at the specific location in the test sample is classified as either a true positive or false positive. In one embodiment, a computer-implemented method of detecting low frequency variants in a target region in a first sample is provided. In some embodiments, the method comprises (at a computer system) receiving a plurality of sequence reads obtained from sequencing DNA fragments from one or more samples, the one or more samples including the first sample, wherein the sequencing includes targeting the target region in the DNA fragments; aligning the plurality of sequence reads to the target region of a reference sequence; identifying a first candidate variant having a first allele at a first location of the target region based on sequence reads of the first sample differing from a reference allele at the first location of the reference sequence; determining a first variant frequency for the first allele at the first location based on sequence reads of the first sample that align to the first location of the reference sequence; identifying the first candidate variant as corresponding to a first variant class selected from a plurality of variant classes, each variant class of the plurality of variant classes corresponding to a different type of variant; identifying a set of second locations in the target region of the reference sequence that have the reference allele, wherein at least 50% of the other locations in the one or more samples exhibit a false positive for the first allele, and wherein the set of second locations includes the first location; at each of the set of second locations and for each of the one or more samples: determining a second variant frequency of the first allele based on sequence reads of the sample that align to the second location of the reference sequence, the second variant frequencies forming a statistical distribution; comparing the first variant frequency to a statistical value of the statistical distribution to determine a probability value of the first variant frequency relative to the statistical value of the statistical distribution; and comparing the probability value to a threshold value as part of determining whether the first candidate variant is a true positive in the first sample for the first allele, the threshold value differentiating between false positives and true positives for the first allele. In certain embodiments, the reference sequence corresponds to a consensus sequence as determined from normal cells. In some embodiments, the one or more samples are derived from cell-free DNA fragments. In some embodiments, the one or more samples are derived from RNA of a biological sample. In some embodiments, the plurality of samples are sequenced in a single sequencing run. In other embodiments, the statistical value of the statistical distribution includes a mean value. In other embodiments, the probability value is a z-score, modified z-score, cumulative probability, Phred quality score, or modified Phred quality score. In other embodiments, the statistical distribution is the statistical distribution of logarithmic transformations of the second variant frequencies. In other embodiments, the threshold is determined using support vector machines classifier based on training data obtained from one or more sequencing runs. In other embodiments, the threshold is a function of variant frequency. In another embodiment, a computer-implemented method of detecting a variant having a first allele at a first location in a target region in a first sample is provided. In some embodiments, the method comprises (at a computer system): receiving a plurality of sequence reads obtained from sequencing DNA fragments from at least two samples, the at least two samples including the first sample, wherein the sequencing includes targeting the target region in the DNA fragments; aligning the plurality of sequence reads to the target region of a reference sequence; identifying whether the first allele exists at the first location in each sample of the at least two samples based on aligned sequence reads of each sample at the first location differing from a reference allele at the first location of the reference sequence; determining a variant count of the first allele at the first location and a wild type count of the reference allele at the first location for each sample of the at least two samples; selecting, from the at least two samples, at least one sample as a reference sample; comparing a first variant count of the first allele at the first location and a first wild type count of the reference allele at the first location for the first sample to a second variant count of the first allele at the first location and a second wild type count of the reference allele at the first location for the reference sample to determine a probability value of the variant having the first allele at the first location for the first sample; and comparing the probability value to a threshold value as part of determining whether the first allele at the first location in the first sample is a true positive for the first allele, the threshold value differentiating between false positives and true positives for the first allele at the first location. In certain embodiments, the reference sample comprises two samples with lowest variant frequencies for the first allele at the first location among the at least two samples other than the first sample. In some embodiments, the probability value is determined using chi-squared cumulative distribution function. In some embodiments, the probability value is determined using Pearson proportion test. In some embodiments, the probability value is one or more of z-score, modified z-score, p-value, chi-squared value, cumulative probability value, and quality score. In some embodiments, the quality score is determined using a look-up table. In some embodiments, the threshold is determined using support vector machines classifier based on training data obtained from one or more sequencing runs. In some embodiments, the threshold is a function of variant frequency. In another embodiment, a computer product comprising a non-transitory computer readable medium storing a plurality of instructions that when executed control a computer system to detect true variants in a target region of a first sample is provided. In some embodiments, the instructions comprise receiving a plurality of sequence reads obtained from sequencing DNA fragments from one or more samples, the one or more samples including the first sample, wherein the sequencing includes targeting the target region in the DNA fragments; aligning the plurality of sequence reads to the target region of a reference sequence; identifying a set of sequence locations in the target region of the reference sequence that have a reference allele of variants in a variant class, wherein at least 50% of the sequence locations in the one or more samples exhibit a false positive for the variants in the variant class in the sequence reads, and wherein the set of sequence locations includes a first location; at each location of the set of sequence locations and for each sample of the one or more samples: determining a read count at each location for each sample; identifying candidate variants having variant alleles for the variants in the variant class based on sequence reads of each sample differing from the reference allele at the same location of the reference sequence, a total number of the candidate variants at each location in each sample being the variant count in each location for each sample; determining a variant frequency of variants in the variant class based on the read count and the variant count, the variant frequency for each location in each sample forming a statistical distribution, wherein the variant frequency at a first location in the set of sequence locations for the first sample is a first variant frequency; comparing the first variant frequency to a value of the statistical distribution to determine a probability value of the first variant frequency relative to the value of the statistical distribution; and comparing the probability value to a threshold value as part of determining whether candidate variants in the first sample are true positives, the threshold value differentiating between false positives and true positives for the variants in the variant class. In certain embodiments, the statistical distribution is the statistical distribution of a logarithmic transformation of the variant frequency at each location for each sample.

In some embodiments, detection of a genetic biomarker (e.g., one or more genetic biomarkers) can include any of the variety of methods described in U.S. Pat. No. 9,340,830, which is hereby incorporated by reference in its entirety. For example, detection of a genetic biomarker can include a method of analyzing a tumor sample. The method comprises: (a) acquiring a library comprising a plurality of target members, e.g., tumor members, from a sample, e.g., a tumor sample; (b) optionally, contacting the library with a bait set (or plurality of bait sets) to provide selected members (sometimes referred to herein as "library catch"); (c) acquiring a read for a subgenomic interval from a tumor member from said library or library catch, e.g., by sequencing, e.g., with a next generation sequencing method; (d) aligning said read; and (e) assigning a nucleotide value (e.g., calling a mutation, e.g., with a Bayeisan method) from said read for a preselected nucleotide position, e.g., for a preselected nucleotide position in each of a plurality of subgenomic intervals, e.g., each of a plurality genes, thereby analyzing said sample, wherein: (i) each of X nucleotide positions is analyzed under a unique set of conditions for one or a combination of steps (b), (c), (d), or (e)(wherein unique means different from the other X-1 sets of conditions and wherein X is at least 2, 5, 10, 20, 30, 40, 50, 100, 200, 300 or 500). E.g., a first set of conditions, is used for a first nucleotide position, e.g., in a first subgenomic interval or gene, and a second set of conditions, e.g., a second set of conditions, is used for a second nucleotide position, e.g., in a second subgenomic interval or gene; (ii) for each of X nucleotide positions, responsive to a characteristic of a preselected alteration, e.g., mutation, that can occur at the nucleotide position, the nucleotide position is analyzed under a unique set of conditions (wherein unique means different from the other X-1 sets of conditions and wherein X is at least 2, 5, 10, 20, 30, 40, 50, 100, 200, 300 or 500). E.g., responsive to a characteristic, e.g., a characteristic, of a preselected alteration, e.g., mutation, that can occur at a nucleotide position in a first subgenomic interval, the nucleotide position is analyzed under a first set of conditions, and responsive to a characteristic, e.g., a characteristic, of a preselected alteration, e.g., mutation, that can occur at a nucleotide position in a second subgenomic interval, the nucleotide position is analyzed under second set of conditions; (iii) wherein said method is performed on a sample, e.g., a preserved tumor sample, under conditions that allow for 95, 98, or 99% sensitivity or specificity for nucleotide positions in at least 2, 5, 10, 20, 50 or 100 subgenomic intervals, e.g., genes; or (iv) wherein the method comprises one or more or all of: a) sequencing a first subgenomic interval to provide for about 500× or higher sequencing depth, e.g., to sequence a mutation present in no more than 5% of the cells from the sample; b) sequencing a second subgenomic interval to provide for about 200× or higher, e.g., about 200×-about 500×, sequencing depth, e.g., to sequence a mutation present in no more than 10% of the cells from the sample; c) sequencing a third subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient; d) sequencing a fourth subgenomic interval to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) sequencing a fifth subgenomic interval to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Additionally or alternatively, detection of a genetic biomarker can include a method of analyzing a sample, e.g., a tumor sample. The method comprises: (a) acquiring a library comprising a plurality members from a sample, e.g., a plurality of tumor members from a tumor sample; (b) optionally, enriching the library for preselected sequences, e.g., by contacting the library with a bait set (or plurality of bait sets) to provide selected members (sometimes referred to herein as library catch); (c) acquiring a read for a subgenomic interval from a member, e.g., a tumor member from said library or library catch, e.g., by a method comprising sequencing, e.g., with a next generation sequencing method; (d) aligning said read by an alignment method; and (e) assigning a nucleotide value (e.g., calling a mutation, e.g., with a Bayesian method) from said read for the preselected nucleotide position, thereby analyzing said tumor sample, wherein a read from each of X unique subgenomic intervals is aligned with a unique alignment method, wherein unique subgenomic interval means different from the other X-1 subgenoime intervals, and wherein unique alignment method means different from the other X-1 alignment methods, and X is at least 2. In an embodiment, step (b) is present. In an embodiment step (b) is absent. In an embodiment, X is at least 3, 4, 5, 10, 15, 20, 30, 50, 100, 500, or 1,000. In an embodiment, a method (e.g., element (d) of the method recited above) comprises selecting or using an alignment method for analyzing, e.g., aligning, a read, wherein said alignment method is a function of, is selected responsive to, or is optimized for, one or more or all of: (i) tumor type, e.g., the tumor type in said sample; (ii) the gene, or type of gene, in which said subgenomic interval being sequenced is located, e.g., a gene or type of gene characterized by a preselected or variant or type of variant, e.g., a mutation, or by a mutation of a preselected frequency; (iii) the site (e.g., nucleotide position) being analyzed; (iv) the type of variant, e.g., a substitution, within the subgenomic interval being evaluated; (v) the type of sample, e.g., an FFPE sample; and (vi) sequence in or near said subgenomic interval being evaluated, e.g., the expected propensity for misalignment for said subgenomic interval, e.g., the presence of repeated sequences in or near said subgenomic interval. Additionally or alternatively, detection of a genetic biomarker can include a method of analyzing a sample, e.g., a tumor sample. The method comprises: (a) acquiring a library comprising a plurality members from a sample, e.g., a plurality of tumor members from the sample, e.g., the tumor sample; (b) optionally, enriching the library for preselected sequences, e.g., by contacting the library with a bait set (or plurality of bait sets) to provide selected members, e.g., a library catch; (c) acquiring a read for a subgenomic interval from a member, e.g., a tumor member from said library or library catch, e.g., by a method comprising sequencing, e.g., with a next generation sequencing method; (d) aligning said read by an alignment method; and (e) assigning a nucleotide value (e.g., calling a mutation, e.g., with a Bayesian method or a calling method) from said read for the preselected nucleotide position, thereby analyzing said tumor sample, wherein a nucleotide value is assigned for a nucleotide position in each of X unique subgenomic intervals is assigned by a unique calling method, wherein unique subgenomic interval means different from the other X-1 subgenoime intervals, and wherein unique calling method means different from the other X-1 calling methods, and X is at least 2. The calling methods can differ, and thereby be unique, e.g., by relying on different Bayesian prior values. In an embodiment, step (b) is present. In an embodiment, step (b) is absent. Additionally or alternatively, detection of a genetic biomarker can include a method of analyzing a sample, e.g., a tumor sample. The method comprises: (a) acquiring a library comprising a plurality of members (e.g., target members) from a sample, e.g., a plurality of tumor members from a tumor sample; (b) contacting the library with a bait set to provide selected members (e.g., a library catch); (c) acquiring a read for a subgenomic interval from a member, e.g., a tumor member from said library or library catch, e.g., by a method comprising sequencing, e.g., with a next generation sequencing method; (d) aligning said read by an alignment method; and (e) assigning a nucleotide value (e.g., calling a mutation, e.g., with a Bayesian method or a method) from said read for the preselected nucleotide position, thereby analyzing said tumor sample, wherein the method comprises contacting the library with a plurality, e.g., at least two, three, four, or five, of baits or bait sets, wherein each bait or bait set of said plurality has a unique (as opposed to the other bait sets in the plurality), preselected efficiency for selection. E.g., each unique bait or bait set provides for a unique depth of sequencing. In an embodiment, the efficiency of selection of a first bait set in the plurality differs from the efficiency of a second bait set in the plurality by at least 2 fold. In an embodiment, the first and second bait sets provide for a depth of sequencing that differs by at least 2 fold. In an embodiment, the method comprises contacting one, or a plurality of the following bait sets with the library: a) a bait set that selects sufficient members comprising a subgenomic interval to provide for about 500× or higher sequencing depth, e.g., to sequence a mutation present in no more than 5% of the cells from the sample; b) a bait set that selects sufficient members comprising a subgenomic interval to provide for about 200× or higher, e.g., about 200×-about 500×, sequencing depth, e.g., to sequence a mutation present in no more than 10% of the cells from the sample; c) a bait set that selects sufficient members comprising a subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient; d) a bait set that selects sufficient members comprising a subgenomic interval to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) a bait set that selects sufficient members comprising a subgenomic interval to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Such bait sets can be used to detect, for example, amplification/deletion-prone cancer genes. Additionally or alternatively, detection of a genetic biomarker can include a sample, e.g., a tumor sample. The method comprises: (a) acquiring a library comprising a plurality members from a sample, e.g., a plurality of tumor members from a tumor sample; (b) optionally, enriching the library for preselected sequences, e.g., by contacting the library with a bait set (or plurality of bait sets) to provide selected members (e.g., a library catch); (c) acquiring a read for a subgenomic interval from a member, e.g., a tumor member from said library or library catch, e.g., by a method comprising sequencing, e.g., with a next generation sequencing method; (d) aligning said read by an alignment method; and (e) assigning a nucleotide value (e.g., calling a mutation, e.g., with a Bayesian method or a method) from said read for the preselected nucleotide position, thereby analyzing said tumor sample, wherein the method comprises sequencing, e.g., by a next generation sequencing method, a subgenomic interval from at least five, six, seven, eight, nine, ten, fifteen, twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53. In an embodiment, step (b) is present. In an embodiment, step (b) is absent.

In some embodiments, detection of a genetic biomarker (e.g., one or more genetic biomarkers) can include any of the variety of methods described in P.C.T. Publication No. WO 2017/151524, which is hereby incorporated by reference in its entirety. For example, detection of a genetic biomarker can include methods of evaluating the mutation load in a sample, by providing a sequence of a set of subgenomic intervals from the sample; and determining a value for the mutational load, wherein the value is a function of the number of alterations in the set of subgenomic intervals. In certain embodiments, the set of subgenomic intervals are from a predetermined set of genes, for example, a predetermined set of genes that does not include the entire genome or exome. In certain embodiments, the set of subgenomic intervals is a set of coding subgenomic intervals. In other embodiments, the set of subgenomic intervals contains both a coding subgenomic interval and a non-coding subgenomic interval. In certain embodiments, the value for the mutation load is a function of the number of an alteration (e.g., a somatic alteration) in the set of subgenomic intervals. In certain embodiments, the number of an alteration excludes a functional alteration, a germline alteration, or both. In some embodiments, the sample is a tumor sample or a sample derived from a tumor. Additionally or alternatively, detection of a genetic biomarker can include methods comprising, e.g., one or more of: acquiring a library comprising a plurality of tumor members from the sample; contacting the library with a bait set to provide selected tumor members by hybridization, thereby providing a library catch; acquiring a read for a subgenomic interval comprising an alteration from the tumor member from the library catch; aligning the read by an alignment method; assigning a nucleotide value from the read for a preselected nucleotide position; and selecting a set of subgenomic intervals from a set of the assigned nucleotide positions, wherein the set of subgenomic intervals are from a predetermined set of genes. Additionally or alternatively, detection of a genetic biomarker can include a method of evaluating the mutation load in a sample, e.g., a tumor sample (e.g., a sample acquired from a tumor), the method includes: a) providing a sequence, e.g., a nucleotide sequence, of a set of subgenomic intervals (e.g., coding subgenomic intervals) from the sample, wherein the set of subgenomic intervals are from a predetermined set of genes; and b) determining a value for the mutation load, wherein the value is a function of the number of an alteration (e.g., one or more alterations), e.g., a somatic alteration (e.g., one or more somatic alterations), in the set of subgenomic intervals. In certain embodiments, the number of an alteration excludes a functional alteration in a subgenomic interval. In other embodiments, the number of an alteration excludes a germline alteration in a subgenomic interval. In certain embodiments, the number of an alteration excludes a functional alteration in a subgenomic interval and a germline alteration in a subgenomic interval. In certain embodiments, the set of subgenomic intervals comprises coding subgenomic intervals. In other embodiments, the set of subgenomic intervals comprises non-coding subgenomic intervals. In certain embodiments, the set of subgenomic intervals comprises coding subgenomic intervals. In other embodiments, the set of subgenomic intervals comprises one or more coding subgenomic intervals and one or more non-coding subgenomic intervals. In certain embodiments, about 5% or more, about 10% or more, about 20% or more, about 30% or more, about 40% or more, about 50% or more, about 60% or more, about 70% or more, about 80% or more, about 90% or more, or about 95% or more, of the subgenomic intervals in the set of subgenomic intervals are coding subgenomic intervals. In other embodiments, about 90% or less, about 80% or less, about 70% or less, about 60% or less, about 50% or less, about 40% or less, about 30% or less, about 20% or less, about 10% or less, or about 5% or less, of the subgenomic intervals in the set of subgenomic intervals are non-coding subgenomic intervals. In other embodiments, the set of subgenomic intervals does not comprise the entire genome or the entire exome. In other embodiments, the set of coding subgenomic intervals does not comprise the entire exome. In certain embodiments, the mutation load is expressed as a percentile, e.g., among the mutation loads in samples from a reference population. In certain embodiments, the reference population includes patients having the same type of cancer as the subject. In other embodiments, the reference population includes patients who are receiving, or have received, the same type of therapy, as the subject. Additionally or alternatively, detection of a genetic biomarker can include a method of evaluating the mutation load in a sample, e.g., a tumor sample or a sample derived from a tumor. The method includes: (i) acquiring a library comprising a plurality of tumor members from the sample; (ii) contacting the library with a bait set to provide selected tumor members, wherein said bait set hybridizes with the tumor member, thereby providing a library catch; (iii) acquiring a read for a subgenomic interval comprising an alteration (e.g., a somatic alteration) from a tumor member from said library catch, e.g., by a next-generation sequencing method; (iv) aligning said read by an alignment method; (v) assigning a nucleotide value from said read for a preselected nucleotide position; (vi) selecting a set of subgenomic intervals (e.g., coding subgenomic intervals) from a set of the assigned nucleotide positions, wherein the set of subgenomic intervals are from a predetermined set of genes; and (vii) determining a value for the mutational load, wherein the value is a function of the number of an alteration (e.g., one or more alterations), e.g., a somatic alteration (e.g., one or more somatic alterations), in the set of subgenomic intervals. In certain embodiments, the number of an alteration (e.g., a somatic alteration) excludes a functional alteration in a subgenomic interval. In other embodiments, the number of an alteration excludes a germline alteration in a subgenomic interval. In certain embodiments, the number of an alteration (e.g., a somatic alteration) excludes a functional alteration in a subgenomic interval and a germline alteration in a subgenomic interval. In certain embodiments, the predetermined set of genes comprises a plurality of genes, which in mutant form, are associated with an effect on cell division, growth or survival, or are associated with a cancer. In certain embodiments, the method further comprises acquiring a library comprising a plurality of tumor members from the sample. In certain embodiments, the method further comprises contacting a library with a bait set to provide selected tumor members, wherein said bait set hybridizes with a tumor member from the library, thereby providing a library catch. In certain embodiments, the method further comprises acquiring a read for a subgenomic interval comprising the alteration (e.g., somatic alteration) from a tumor member from a library or library catch, thereby acquiring a read for the subgenomic interval, e.g., by a next-generation sequencing method. In certain embodiments, the method further comprises aligning a read for the subgenomic interval by an alignment method. In certain embodiments, the method further comprises assigning a nucleotide value for a preselected nucleotide position from a read for the subgenomic interval, e.g., by a mutation calling method. In certain embodiments, the method further comprises one, two, three, four, or all of: (a) acquiring a library comprising a plurality of tumor members from the sample; (b) contacting the library with a bait set to provide selected tumor members, wherein said bait set hybridizes with the tumor member, thereby providing a library catch; (c) acquiring a read for a subgenomic interval comprising the alteration (e.g., somatic alteration) from a tumor member from said library catch, thereby acquiring a read for the subgenomic interval, e.g., by a next-generation sequencing method; (d) aligning said read by an alignment method; or (e) assigning a nucleotide value from said read for a preselected nucleotide position, e.g., by a mutation calling method. In certain embodiments, the germline alteration is excluded by a method or system comprising the use of an SGZ algorithm. In certain embodiments, the method further comprises characterizing a variant, e.g., an alteration, in the tumor sample by: a) acquiring: i) a sequence coverage input (SCI), which comprises, for each of a plurality of selected subgenomic intervals, a value for normalized sequence coverage at the selected subgenomic intervals, wherein SCI is a function of the number of reads for a subgenomic interval and the number of reads for a process-matched control; ii) an SNP allele frequency input (SAFI), which comprises, for each of a plurality of selected germline SNPs, a value for the allele frequency in the tumor sample, wherein SAFI is based, at least in part, on a minor or alternative allele frequency in the tumor sample; and iii) a variant allele frequency input (VAFI), which comprises the allele frequency for said variant in the tumor sample; b) acquiring values, as a function of SCI and SAFI, for: i) a genomic segment total copy number (C) for each of a plurality of genomic segments; ii) a genomic segment minor allele copy number (M) for each of a plurality of genomic segments; and iii) sample purity (p), wherein the values of C, M, and p are obtained by fitting a genome-wide copy number model to SCI and SAFI; and c) acquiring: a value for mutation type, g, for which is indicative of the variant, being somatic, a subclonal somatic variant, germline, or not-distinguishable, and is a function of VAFI, p, C, and M. The SGZ algorithm is described in International Application Publication No. WO 2014/183078 and U.S. Application Publication No. 2014/0336996, the contents of which are incorporated by reference in their entirety. Additionally or alternatively, detection of a genetic biomarker can include a system for evaluating the mutation load in a sample (e.g., a tumor sample or a sample derived from a tumor). The system includes at least one processor operatively connected to a memory, the at least one processor when executing is configured to: a) acquire a sequence, e.g., a nucleotide sequence, of a set of subgenomic intervals (e.g., coding subgenomic intervals) from the sample, wherein the set of coding subgenomic intervals are from a predetermined set of genes; and b) determine a value for the mutational load, wherein the value is a function of the number of an alteration (e.g., a somatic alteration) in the set of subgenomic intervals. Additionally or alternatively, detection of a genetic biomarker can include a method of analyzing a sample, e.g., a tumor sample from a hematologic malignancy (or premalignancy). The method comprises: (a) acquiring one or a plurality of libraries comprising a plurality members from a sample, e.g., a plurality of tumor members from a tumor sample; (b) optionally, enriching the one or a plurality of libraries for preselected sequences, e.g., by contacting the one or a plurality of libraries with a bait set (or plurality of bait sets) to provide selected members (sometimes referred to herein as library catch); (c) acquiring a read for a subject interval, e.g., a subgenomic interval or an expressed subgenomic interval, from a member, e.g., a tumor member from a library or library catch, e.g., by a method comprising sequencing, e.g., with a next-generation sequencing method; (d) aligning said read by an alignment method, and (e) assigning a nucleotide value (e.g., calling a mutation, e.g., with a Bayesian method) from said read for the preselected nucleotide position, thereby analyzing said tumor sample, optionally wherein: a read from each of X unique subject intervals (e.g., subgenomic intervals, expressed subgenomic intervals, or both) is aligned with a unique alignment method, wherein unique subject interval (e.g., subgenomic interval or expressed subgenomic interval) means different from the other X-1 subject intervals (e.g., subgenomic intervals, expressed subgenomic intervals, or both), and wherein unique alignment method means different from the other X-1 alignment methods, and X is at least 2. In an embodiment, a method (e.g., element (d) of the method recited above) comprises selecting or using an alignment method for analyzing, e.g., aligning, a read, wherein said alignment method is a function of, is selected responsive to, or is optimized for, one or more or all of: (i) tumor type, e.g., the tumor type in said sample; (ii) the gene, or type of gene, in which said subject interval (e.g., subgenomic interval or expressed subgenomic interval) being sequenced is located, e.g., a gene or type of gene characterized by a preselected or variant or type of variant, e.g., a mutation, or by a mutation of a preselected frequency; (iii) the site (e.g., nucleotide position) being analyzed; (iv) the type of variant, e.g., a substitution, within the subject interval (e.g., subgenomic interval or expressed subgenomic interval) being evaluated; (v) the type of sample, e.g., an FFPE sample, a blood sample, or a bone marrow aspirate sample; and (vi) sequence in or near said subgenomic interval being evaluated, e.g., the expected propensity for misalignment for said subject interval (e.g., subgenomic interval or expressed subgenomic interval), e.g., the presence of repeated sequences in or near said subject interval (e.g., subgenomic interval or expressed subgenomic interval). In some embodiments, the method can comprise using an alignment method that is appropriately tuned and that includes: selecting a rearrangement reference sequence for alignment with a read, wherein said rearrangement reference sequence is preselected to align with a preselected rearrangement (in embodiments the reference sequence is not identical to the genomic rearrangement); comparing, e.g., aligning, a read with said preselected rearrangement reference sequence. In embodiments, other methods are used to align troublesome reads. These methods are particularly effective when the alignment of reads for a relatively large number of diverse subgenomic intervals is optimized. By way of example, a method of analyzing a tumor sample can comprise: performing a comparison, e.g., an alignment comparison, of a read under a first set of parameters (e.g., a first mapping algorithm or with a first reference sequence), and determining if said read meets a first predetermined alignment criterion (e.g., the read can be aligned with said first reference sequence, e.g., with less than a preselected number of mismatches); if said read fails to meet the first predetermined alignment criterion, performing a second alignment comparison under a second set of parameters, (e.g., a second mapping algorithm or with a second reference sequence); and, optionally, determining if said read meets said second predetermined criterion (e.g., the read can be aligned with said second reference sequence with less than a preselected number of mismatches), wherein said second set of parameters comprises use of a set of parameters, e.g., said second reference sequence, which, compared with said first set of parameters, is more likely to result in an alignment with a read for a preselected variant, e.g., a rearrangement, e.g., an insertion, deletion, or translocation.

In some embodiments, detection of a genetic biomarker (e.g., one or more genetic biomarkers) can include any of the variety of methods described in U.S. Patent Application Publication No. 2013/0266938, which is hereby incorporated by reference in its entirety. For example, detection of a genetic biomarker can include methods of detecting the presence or absence of a target nucleic acid sequence in a biological sample. In some embodiments, the method comprises: a. contacting a detectably-labeled probe comprising an anchor nucleic acid domain and a reporter nucleic acid domain with the sample; and b. detecting the presence or absence of binding of the probe to the target nucleic acid, wherein the anchor and reporter domains are linked by a non-nucleoside linker, and neither the anchor nor the reporter domain forms a stem loop in the absence of the target nucleic acid; and wherein (i) the probe is not extendible by a polymerase; (ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label; and/or (iii) the anchor domain and the reporter domain each comprise a contiguous sequence of at least 6 nucleotides complementary to the same strand of the target nucleic acid. In some embodiments, the probe is not extendible by a polymerase In some embodiments, the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label. In some embodiments, the anchor domain and the reporter domain each comprise a contiguous sequence of at least 10 nucleotides complementary to one strand of the target nucleic acid. In some embodiments, the detecting step comprises measuring the melting temperature of a complex formed between the reporter domain and the target nucleic acid. In some embodiments, the length of the reporter domain is between 4 to 20 nucleotides. In some embodiments, the length of the reporter domain is between 6 to 12 nucleotides. Additionally or alternatively, detection of a genetic biomarker can include reaction mixtures for detecting the presence or absence of a target sequence. In some embodiments, the reaction mixture comprises: a. a target nucleic acid comprising an anchor binding region and a reporter binding region, and b. a detectably-labeled probe comprising an anchor nucleic acid domain and a reporter nucleic acid domain, wherein the anchor and reporter domains are linked by a non-nucleoside linker, and neither the anchor nor the reporter domain forms a stem loop in the absence of the target nucleic acid, and wherein (i) the probe is not extendible by a polymerase; (ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label; and/or (iii) the anchor domain and the reporter domain each comprise a contiguous sequence of at least 6 nucleotides complementary to the same strand of the target nucleic acid. In some embodiments, the reaction mixture further comprises nucleoside triphosphates, a DNA polymerase, and/or an oligonucleotide primer. In some embodiments, the probe is not extendible by a polymerase.

Additionally or alternatively, detection of a genetic biomarker can include a detectably-labeled probe comprising an anchor nucleic acid domain and a reporter nucleic acid domain, wherein: the anchor and reporter domains are linked by a non-nucleoside linker; neither the anchor nor the reporter domain forms a stem loop in the absence of the target nucleic acid; and wherein: (i) the probe is not extendible by a polymerase; and/or (ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label. In some embodiments, the probe is not extendible by a polymerase. In some embodiments, the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label. In some embodiments, the length of the reporter domain is between 4 to 20 nucleotides. In some embodiments, the length of the reporter domain is between 6 to 12 nucleotides. In some embodiments, the anchor domain is between 6-40 nucleotides. In some embodiments, the label is a fluorescent label. In some embodiments, the probe comprises at least one non-natural nucleotide, wherein the non-natural nucleotide increases the melting temperature of the reporter domain compared to a corresponding natural nucleotide in the place of the non-natural nucleotide. In some embodiments, the linker is polyethylene glycol. In some embodiments, the linker is hexa-ethylene glycol.

In some embodiments, detection of a genetic biomarker (e.g., one or more genetic biomarkers) can include any of the variety of methods described in U.S. Patent Application Publication No. 2012/0225428, which is hereby incorporated by reference in its entirety. For example, detection of a genetic biomarker can include a set of probes comprising DNA and LNA nucleotides. In some embodiments, at the 5' end of the probes, the nucleobases are determined, whereas at the 3' end, there are one or more (for example, two or three) random nucleotides (also referred to as "wobble" positions). An embodiment consists of a short nucleic acid strand that can be used universally for the detection of various target sequences. The short nucleic acid sequence is also allele specific and enables the detection of a specific mutation, such as a single nucleotide polymorphism (SNP). Some embodiments include a composition comprising a first probe and a second probe. According to such embodiments, the first probe has a 5' end opposite a 3' end and at least eight nucleotides, the at least eight nucleotides comprising at least one DNA nucleotide and at least five locked nucleic acid nucleotides and a first discriminating position; and a second probe having a 5' end opposite a 3' end and a same number of nucleotides as the first probe. The nucleotides of the second probe comprise a same number of DNA nucleotides and locked nucleic acid nucleotides as the first probe and a second discriminating position located at a position corresponding to the first discriminating position in the first probe. Also, according to such embodiments, the nucleotides of the first and second probes comprise one of an adenine nucleobase, a cytosine nucleobase, a guanine nucleobase, a thymine nucleobase, a uracil nucleobase, and a methyl cytosine nucleobase, and the first and second probes comprise differing nucleobases at the first and second discriminating positions. However, according to such embodiments, the first and second probes comprise the same nucleobases at all other nucleotide positions of the probes. Other embodiments comprise a composition including a first and second set of probes. Each probe of the first and second sets have a 5' end opposite a 3' end and eight nucleotides. The nucleotides of each probe of the first set have at least one DNA nucleotide, at least five locked nucleic acid nucleotides, and a first discriminatory position, at least one locked nucleic acid nucleotide being a random locked nucleic acid nucleotide, whereas each probe of the second set of probes have a corresponding number of DNA nucleotides, locked nucleic acid nucleotides, and random locked nucleic acid nucleotides as a probe in the first set, and each probe of the second set has a second discriminating position located at a same nucleotide location as a first discriminating position of a probe in the first set. Also, according to some such embodiments, all probes of the first and second sets have a same nucleobase sequences with the exception of (i) the nucleobase at the random locked nucleic acid nucleotides; and (ii) the nucleobase at the first and second discriminating positions. Also, the nucleobase of the second discriminating position differs from the nucleobase of the first discriminating position at the same nucleotide location, and the at least one random locked nucleic acid nucleotide of each probe of the second set comprises a same nucleobase located at a same nucleotide location of the at least one random locked nucleic acid nucleotide of a probe of the first set. According to such embodiments, the nucleobase of the random locked nucleic acid nucleotide is selected from one of adenine, cytosine, guanine, and thymine, and any possible nucleobase sequence resulting from nucleobase variations at the one or more random locked nucleic acid nucleobase position(s) is represented by at least one probe in both the first and second set of probes. Additionally or alternatively, detection of a genetic biomarker can include a method of determining a genotype at a locus of interest in a sample comprising genetic material is provided. The method includes the steps of contacting the genetic material with a first probe and a second probe and detecting the binding of the first or second probe to the genetic material, thereby determining the genotype at the locus. According to such embodiments, the first and second probes each have a 5' end opposite a 3' end and eight nucleotides comprising at least one DNA nucleotide and at least five locked nucleic acid nucleotides. The nucleotides of the first probe comprise a first discriminating position and the nucleotides of the second probe comprise a second discriminating position at a same nucleotide location in the second probe as the first discriminating position in the first probe. Also, the first discriminating position comprises a different nucleobase than the second discriminating position, wherein the nucleobases at the other nucleotides of the first and second probes are the same. Additionally or alternatively, detection of a genetic biomarker can include a composition including a first set of probes and a second set of probes, each of the probes having eight nucleotides being composed of one to three DNA nucleotides and five to seven LNA (locked nucleic acid) nucleotides. According to such embodiments, all probes of the first and the second set of probes have identical nucleotide sequences with the exception of (i) the base(s) at one, two or three LNA random position(s); and (ii) the base at a discriminating position, wherein the one, two or three LNA random position(s) and the discriminating position are located at identical positions in all probes of the first and the second set. Further, according to such embodiments at each LNA random position the base is independently selected from adenine, cytosine, guanine and thymine and any possible sequence resulting from the base variation(s) at the one, two or three LNA random position(s) is represented by at least one probe in each set of probes. Additionally, according to such embodiments, the base at the discriminating position is identical within each set of probes, but differs between the first and the second set of probes. Additionally or alternatively, detection of a genetic biomarker can include a library of at least two sets of probes. According to such embodiments the library comprises a plurality of sets of probes each of the probes having eight nucleotides with the general structure 5'-D-L-L-L-L-X-X-3' or 5'-D-L-L-L-L-X-X-X-3' (where D is a DNA nucleotide; each L is a LNA nucleotide; and each X is a LNA random nucleotide). Also, within one set of probes, all probes have identical nucleotide sequences with the exception of the two and/or three LNA random nucleotides (with each position of a LNA random nucleotide base being independently selected from adenine, cytosine, guanine and thymine). Also, according to such embodiments, any possible sequence resulting from the base variation(s) at the two positions is represented by a probe in each set of probes and one set of probes differing from the other set of probes in the sequence of at least the DNA nucleotide D or an LNA nucleotide L. Additionally or alternatively, detection of a genetic biomarker can include a method of determining the genotype at a locus of interest in a sample obtained from a subject is provided. The method includes the steps of contacting the sample comprising the genetic material with any of the compositions of the composition embodiments above, and detecting the binding of a probe of the first or the second set of probes to the genetic material, thereby determining the genotype at the locus.

In some embodiments, detection of a genetic biomarker (e.g., one or more genetic biomarkers) can include any of the variety of methods described in U.S. Patent Application Publication No. 2010/0248991, which is hereby incorporated by reference in its entirety. For example, detection of a genetic biomarker can include a solid support comprising at least two sequence specific amplification primers wherein at least one primer is bound to said support with an inducible cleavable linker. Preferably, said cleavable linker is a photocleavable linker. In a first major embodiment, said solid support is a bead. Such a bead is composed of a material selected from the group consisting of silicon, titanium-dioxide, aluminum oxide, lanthanide oxide, glass, silicates, polystyrene, cellulose, sepharose and polyamide. A bead is either of one pure material or composed of two or more materials, whereas the two or more materials are mixed or assembled in a ordered manner like in core shell particles. The surface of a bead is functionalized in such a manner that oligonucleotides can be attached. Additionally or alternatively, detection of a genetic biomarker can include a library of beads as disclosed above. Preferably, each member of the plurality of primers which are bound to the bead via a cleavable linker carries a different detectable label or a unique mixture of multiple labels. In some embodiments, the solid support is a microtiter or picotiter (PTP) plate comprising a plurality of wells, characterized in that a plurality of said wells comprises a surface with at least two sequence specific amplification primers wherein at least one primer is bound to said support with a cleavable linker. Additionally or alternatively, detection of a genetic biomarker can include a method for preparing a solid support and preferably a bead comprising at least two sequence specific primers, further characterized in that at least one of said primers is cleavable, said method comprising the steps of providing a solid support carrying at least one or more functional groups, and reacting said one or more functional groups with the reactive group or groups of two sequence specific primers, wherein a cleavable reactive moiety is present either within one of the spacers connecting said solid support with its functional group or one of its functional groups or said cleavable moiety is present within one of the spacers connecting one of said sequence specific primers with its reactive group. Additionally or alternatively, detection of a genetic biomarker can include a method comprising the steps of providing a solid support comprising two functional groups each carrying a different protecting group, deprotecting a first functional group and reacting said group with the reactive group of a first primer, and deprotecting the second functional group and reacting said group of said bead with the reactive group of a second primer. Said two functional groups are connected to the bead via two separate linkers, but in a particular embodiment, said two functional groups are connected to the bead via a two arm linker. In some embodiments, the method comprises the steps of providing a solid support carrying exactly one functional group, deprotecting said functional group, and reacting said group with a mixture of a first and a second sequence specific primer, said first and second primers comprising identical reactive groups, characterized in that at least one of said primers is connected to its reactive group via a cleavable moiety. In some embodiments, the method comprises the steps of providing a bead carrying exactly one functional group, and deprotecting said functional group and reacting said group with an oligonucleotide representing a first and a second amplification primer which are connected by a cleavable moiety. In some embodiments, the method comprises the steps of providing a bead carrying protected OH groups, protected with two different orthogonal protecting groups, cleaving off one of said orthogonal protecting groups and synthesizing the first primer on the bead, and cleaving off the second of said orthogonal protecting group and synthesizing the second primer on the bead.

Figure 1:
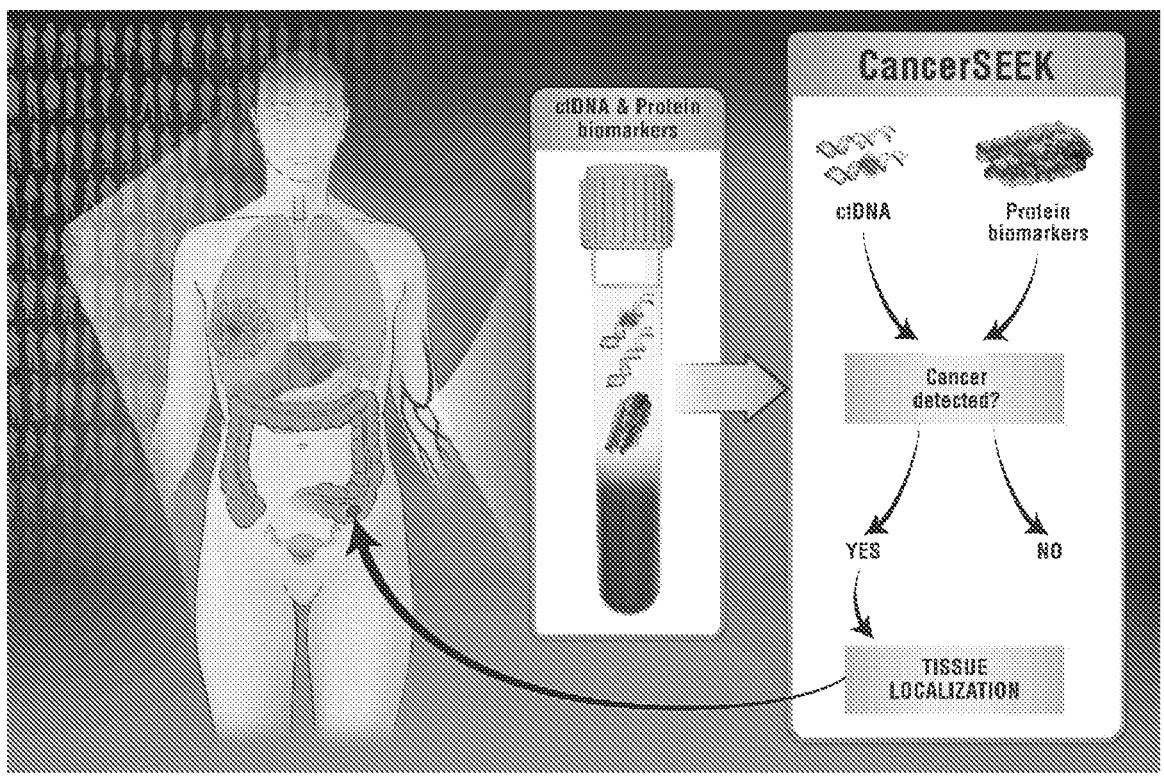
FIG. 1 contains a schematic overview showing a CancerSEEK test for the detection and localization of cancers.

In some embodiments, detection of a genetic biomarker (e.g., one or more genetic biomarkers) can include any of the variety of methods described in U.S. Patent Application Publication No. 2009/0105081, which is hereby incorporated by reference in its entirety. For example, detection of a genetic biomarker can include methods and systems for the capture and enrichment of target nucleic acids and analysis of the enriched target nucleic acids. Additionally or alternatively, detection of a genetic biomarker can include the enrichment of targeted sequences in a solution based format. In some embodiments, solution based capture methods comprise probe derived amplicons wherein said probes for amplification are affixed to a solid support. The solid support comprises support-immobilized nucleic acid probes to capture specific nucleic acid sequences (e.g., target nucleic acids) from, for example, a genomic sample. Probe amplification provides probe amplicons in solution which are hybridized to target sequences. Following hybridization of probe amplicons to target sequences, target nucleic acid sequences present in the sample are enriched by capturing (e.g., via linker chemistry such as biotin, digoxigenin, etc.) and washing the probes and eluting the hybridized target nucleic acids from the captured probes (FIG. 1). The target nucleic acid sequence(s), may be further amplified using, for example, non-specific ligation-mediated PCR (LM-PCR), resulting in an amplified pool of PCR products of reduced complexity compared to the original target sample. In some embodiments, hybridization between the probes and target nucleic acids is performed under preferably stringent conditions sufficient to support hybridization between the solution based probe amplicons, wherein said probes comprise linker chemistry and complementary regions of the target nucleic acid sample to provide probe/target hybridization complexes. The complexes are subsequently captured via the linker chemistry and washed under conditions sufficient to remove non-specifically bound nucleic acids and the hybridized target nucleic acid sequences are eluted from the captured probe/target complexes. Additionally or alternatively, detection of a genetic biomarker can include methods of isolating and reducing the genetic complexity of a plurality of nucleic acid molecules, the method comprising the steps of exposing fragmented, denatured nucleic acid molecules of said population to multiple, different oligonucleotide probes that are bound on a solid support under hybridizing conditions to capture nucleic acid molecules that specifically hybridize to said probes, or exposing fragmented, denatured nucleic acid molecules of said population to multiple, different oligonucleotide probes under hybridizing conditions followed by binding the complexes of hybridized molecules to a solid support to capture nucleic acid molecules that specifically hybridize to said probes, wherein in both cases said fragmented, denatured nucleic acid molecules have an average size of about 100 to about 1000 nucleotide residues, preferably about 250 to about 800 nucleotide residues and most preferably about 400 to about 600 nucleotide residues, separating unbound and non-specifically hybridized nucleic acids from the captured molecules, eluting the captured molecules, and optionally repeating the aforementioned processes for at least one further cycle with the eluted captured molecules. Additionally or alternatively, detection of a genetic biomarker can include an enrichment method for target nucleic acid sequences in a genomic sample, such as exons or variants, preferably SNP sites. This can be accomplished by synthesizing genomic probes specific for a region of the genome to capture complementary target nucleic acid sequences contained in a complex genomic sample. In some embodiments, the method further comprises determining the nucleic acid sequence of the captured and eluted target molecules, in particular by means of performing sequencing by synthesis reactions. Additionally or alternatively, detection of a genetic biomarker can include a method for detecting coding region variation relative to a reference genome, in particular relative to a reference genome that comprises fragmented, denatured genomic nucleic acid molecules, the method as previously described further comprising determining the nucleic acid sequence of the captured and eluted target molecules, in particular by means of performing sequencing by synthesis reactions and comparing the determined sequence to a sequence in a database, in particular to a sequence in a database of polymorphisms in the reference genome to identify variants from the reference genome. In embodiments, nucleic acid (pre-selected) capture probes are immobilized onto a solid support (e.g., slide, chip, bead, etc.) using any number of recognized methods (e.g., spotting, photolithography, in situ synthesis, etc.). In preferred embodiments, the probes are synthesized in situ by maskless array synthesis on a substrate and subsequently amplified by, for example, PCR resulting in probe derived amplicons in solution. In some embodiments, the probe sequences as synthesized comprise primer binding sites for amplification at one or both the 3' and 5' termini (e.g., at or near the ends) of the probes. In some embodiments, the sequence of the primer binding sites on the probes are the same at both the 3' and 5' prime ends or the probes, whereas in other embodiments the sequence of the primer binding sites is different at the 3' prime end then the sequence at the 5' prime end. In some embodiments, amplification primers for probe amplification further comprise a restriction endonuclease site, for example an MlyI site for easy removal of primer sequences from the final captured target, wherein one of the primers (e.g., forward or reverse primer) further comprises linker chemistry such as a binding moiety or sequence (e.g., biotin, digoxigenin, HIS tag, etc.) and are deposited onto the support with the immobilized probes along with reagents necessary for exponential PCR amplification (e.g., PCR procedures for exponential amplification of targets as known to a skilled artisan). PCR is performed thereby creating amplicons of probe capture sequences such that one of the strands comprises linker chemistry, such as a binding moiety or sequence. The amplicon containing solution is transferred to a vessel (e.g., tube, well of a 96 well plate, etc.) and, in some embodiments, purified from reaction components. An additional round of amplification is preferentially performed on the probe derived amplicons using asymmetric PCR, wherein the linker chemistry labeled primer is in abundance compared to the non-labeled primer to preferentially synthesize single stranded binding moiety/sequence labeled amplicons. The amplicons are purified away from reaction components and transferred to a vessel, denatured nucleic acid sample is added, and hybridization is allowed to occur. Following hybridization, labeled amplicon/target nucleic acid complexes are captured. For example, when biotin is the binding moiety a streptavidin (SA) coated substrate such as SA coated beads (e.g., paramagnetic beads/particles) are used to capture the biotin labeled amplicon/target complex. The SA bound complex is washed and the hybridized target nucleic acids are eluted from the complex and utilized in downstream applications, such as sequencing applications. Additionally or alternatively, detection of a genetic biomarker can include methods for isolating and reducing the complexity of a plurality of nucleic acid sequences comprising providing a solid support wherein said solid support comprises hybridization probes hybridizable to target nucleic acid sequences and providing a fragmented nucleic acid sample comprising target nucleic acid sequences, amplifying the hybridization probes wherein the amplification products comprise a binding moiety and wherein the amplification products are in solution, hybridizing the nucleic acid sample to the amplification products in solution under conditions such that hybridization between the amplification products and target nucleic acid sequences is allowed to occur, separating the hybridized target nucleic acid sequences/amplification product complexes from non-specifically hybridized nucleic acids by said binding moiety, and eluting the hybridized target nucleic acid sequences from the complex thereby isolation and reducing the complexity of a plurality of nucleic acid sequences. In some embodiments, the solid support is a microarray slide. In some embodiments, the target nucleic acid sample is fragmented genomic DNA with or without adaptor molecules at one or both ends of the fragments. In some embodiments, the hybridization probes comprise a restriction endonuclease site, for example a MlyI site. In some embodiments, probe amplification comprises exponential polymerase chain reaction, and may further comprise asymmetric non-exponential amplification. In some embodiments, the binding moiety is biotin and the capture substrate, such as a bead for example a paramagnetic particle, is coated with streptavidin for separation of the target nucleic acid/amplification product complex from non-specifically hybridized target nucleic acids. In some embodiments, the captured target nucleic acid/amplification product complexes are washed prior to elution of the bound target nucleic acids are sequenced. Additionally or alternatively, detection of a genetic biomarker can include methods for isolating and reducing the complexity of a plurality of nucleic acid sequences comprising providing a solid support wherein said solid support comprises hybridization probes hybridizable to target nucleic acid sequences and providing a fragmented nucleic acid sample comprising target nucleic acid sequences, amplifying the hybridization probes wherein the amplification products comprise a binding moiety and wherein the amplification products are in solution, hybridizing the nucleic acid sample to the amplification products in solution under conditions such that hybridization between the amplification products and target nucleic acid sequences is allowed to occur, separating the hybridized target nucleic acid sequences/amplification product complexes from non-specifically hybridized nucleic acids by said binding moiety, eluting the hybridized target nucleic acid sequences from the complex thereby isolation and reducing the complexity of a plurality of nucleic acid sequences, and sequencing the eluted target nucleic acid sequences. In some embodiments, the solid support is a microarray slide. In some embodiments, the target nucleic acid sample is fragmented genomic DNA with or without adaptor molecules at one or both ends of the fragments. In some embodiments, the hybridization probes comprise a restriction endonuclease site, for example a MlyI site. In some embodiments, probe amplification comprises exponential polymerase chain reaction, and may further comprise asymmetric non-exponential amplification. In some embodiments, the binding moiety is biotin and the capture substrate, such as a bead for example a paramagnetic particle, is coated with streptavidin for separation of the target nucleic acid/amplification product complex from non-specifically hybridized target nucleic acids. In some embodiments, the captured target nucleic acid/amplification product complexes are washed prior to elution of the bound target nucleic acids.

In some embodiments, detection of a genetic biomarker (e.g., one or more genetic biomarkers) can include any of the variety of methods described in P.C.T. Publication No. WO 2018/077847, which is hereby incorporated by reference in its entirety. For example, detection of a genetic biomarker can include a method of making a library of target nucleic acid molecules from a sample comprising a plurality of target molecules, the method comprising for substantially each target molecule: ligating a single adaptor to a target molecule forming a circular molecule, wherein the adaptor comprises two barcodes, two primer binding sites situated between the two barcodes, wherein the primers annealing to the binding sites are facing away from each other, and at least one modified nucleotide effecting a strand synthesis termination by a nucleic acid polymerase situated between the two primer binding sites; annealing a forward primer complementary to the adaptor to one strand of the target molecule; extending the forward primer up to the modified nucleotide, thereby producing a first strand; annealing a reverse primer complementary to the adaptor to the first strand; extending the first primer, thereby producing the second strand and a double-stranded molecule comprising the first strand sand the second strand wherein the two barcodes are flanking the target sequence. In some embodiments, at least one of the forward and the reverse primer comprises a 5'-flap sequence not complementary to the adaptor and comprising an additional primer binding site. Then the method further comprises a step of annealing an additional primer to the sequence complementary to the flap sequence in the forward primer and extending the additional primer thereby producing a double-stranded molecule comprising two additional primer sites and the two barcodes flanking the target sequence. In some embodiments, the target molecule and the adaptor are single-stranded. In other embodiments, the target molecule and the adaptor are double-stranded and the circular molecule is at least partially denatured primer to annealing of the primer. In some embodiments the barcode is a nucleotide sequence 4-20 bases long. The modified nucleotide effecting a strand synthesis termination by a nucleic acid polymerase may be selected from abasic nucleotides, nucleotides with protein side groups, synthetic nucleotide AraC (cytarabine) or deoxyuracil, isoguanine, 5-methylisocytosine, ethylene glycol spacers, nucleotides with bulky analogues such as fiuorophores, or unnatural base pair (UBP) "d5SICS-dNaM" nucleic acid analogues. The ligation may be selected from overhang ligation, T-A ligation, blunt-end ligation and topoisomerase catalyzed ligation. In some embodiments, the adaptor has a photocleavable linker on one end. In these embodiments, the linker is ligated on one end and exposed to UV light to enable ligation on the other end. In some embodiments, the additional primers are sequencing primers. Additionally or alternatively, detection of a genetic biomarker can include a library of target nucleic acid molecules wherein each molecule is a circular molecule comprising a target sequence and an adaptor linking the ends of the target sequence, the adaptor comprising: two barcodes; two primer binding sites situated between the two barcodes, wherein the primers annealing to the binding sites are facing away from each other; at least one modified nucleotide effecting a strand synthesis termination by a nucleic acid polymerase situated between the two primer binding sites. In some embodiments, the barcode is a nucleotide sequence 4-20 bases long. The modified nucleotide effecting a strand synthesis termination by a nucleic acid polymerase may be selected from abasic nucleotides, nucleotides with protein side groups, synthetic nucleotide AraC (cytarabine) or deoxyuracil, isoguanine, 5-methylisocytosine, ethylene glycol spacers, nucleotides with bulky analogues such as fiuorophores, or unnatural base pair (UBP) "d5SICS-dNaM" nucleic acid analogues. Additionally or alternatively, detection of a genetic biomarker can include a method of sequencing target nucleic acids in a sample comprising a plurality of target molecules, the method comprising: creating a library of target nucleic acid molecules from the sample by ligating a single double-stranded adaptor to substantially each double-stranded target molecule forming a double stranded circular molecule, wherein the adaptor comprises two barcodes, two primer binding sites situated between the two barcodes, wherein the primers annealing to the binding sites are facing away from each other, and at least one modified nucleotide effecting a strand synthesis termination by a nucleic acid polymerase situated between the two primer binding sites; denaturing at least a portion of the double-stranded circular target molecule; annealing a forward primer complementary to the adaptor to one strand of the target molecule; extending the forward primer up to the modified nucleotide, thereby producing a first strand; annealing a reverse primer complementary to the adaptor to the first strand; extending the first primer, thereby producing the second strand and a double-stranded molecule comprising the first strand and the second strand wherein the two barcodes are flanking the target sequence; amplifying the double stranded molecule; and sequencing the amplified products of the double-stranded molecule. In some embodiments, at least one of the forward and the reverse primer comprises a 5'-flap sequence not complementary to the adaptor and comprising an additional primer binding site. In some embodiments, the method further comprises after extending the first primer, annealing an additional primer to the sequence complementary to the flap sequence in the forward primer and extending the additional primer thereby producing a double-stranded molecule comprising two additional primer sites and the two barcodes flanking the target sequence. In some embodiments, amplifying or sequencing may be performed with the additional primers.

In some embodiments, detection of a genetic biomarker (e.g., one or more genetic biomarkers) can include any of the variety of methods described in P.C.T. Publication No. WO 2017/123316, which is hereby incorporated by reference in its entirety. For example, detection of a genetic biomarker can include a targeted sequencing workflow where an input sample comprising a sufficient quantity of genomic material is provided such that minimal or no amplification processes are required prior to sequencing. In some embodiments, the input sample is derived from an intact tumor or from lymph nodes. In some embodiments, the input sample is obtained through homogenization of an intact tumor sample (whole or partial) and/or one or more lymph nodes obtained from a patient or mammalian subject. In some embodiments, the input sample is derived from a sufficient quantity of blood, including whole blood or any fraction thereof. In some embodiments, the input sample is derived from cancerous tissue. In some embodiments, the input sample is derived from precancerous tissue. In some embodiments, the targeted sequencing workflow comprises one or more amplification steps (e.g. a pre-capture amplification step, an amplification step post-capture) prior to sequencing, where each amplification step prior to sequencing comprises from 0 to 3 amplification cycles, and wherein an aggregate of amplification cycles prior to sequencing does not exceed 4. In other embodiments, the targeted sequencing workflow comprises one or more amplification steps (e.g. a pre-capture amplification step, an amplification step post-capture) prior to sequencing, where each amplification step prior to sequencing comprises from 0 to 2 amplification cycles, and wherein an aggregate of amplification cycles prior to sequencing does not exceed 3. In yet other embodiments, the targeted sequencing workflow comprises one amplification step prior to sequencing (e.g. either a pre-capture amplification step or an amplification step post-capture), where the single amplification step prior to sequencing comprises from 0 to 3 amplification cycles. In further embodiments, the targeted sequencing workflow comprises one amplification step prior to sequencing, where the single amplification step prior to sequencing comprises from 1 to 3 cycles. In yet further embodiments, the targeted sequencing workflow comprises one amplification step prior to sequencing, where the single amplification step prior to sequencing comprises 1 cycle. In even further embodiments, the targeted sequencing workflow comprises one amplification step prior to sequencing, where the single amplification step prior to sequencing comprises 2 cycles. In some embodiments, either or both of the pre-capture amplification step or the amplification step post-capture but prior to sequencing utilizes LM-PCR. Additionally or alternatively, detection of a genetic biomarker can include a method of sequencing genomic material within a sample comprising: homogenizing a tumor sample and/or lymph node sample to provide a homogenized sample; isolating at least 0.5 micrograms of genomic material from the homogenized sample; preparing the at least 0.5 micrograms of isolated genomic material for sequencing; and sequencing the prepared genomic material. In some embodiments, the method does not comprise any amplification steps prior to sequencing. In some embodiments, the method comprises at least one pre-capture or post-capture amplification step, wherein an aggregate number of amplification cycles conducted during the at least one pre-capture or post-capture amplification step is at most 4 cycles. In some embodiments, the aggregate number of amplification cycles is 3. In some embodiments, the aggregate number of amplification cycles is 2. In some embodiments, the preparing of the at least 0.5 micrograms of isolated genomic material for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, the homogenized sample comprises a representative sampling of cells. In some embodiments, at least 1 microgram of genomic material is isolated from the homogenized samples. In some embodiments, at least 5 micrograms of genomic material is isolated from the homogenized samples. In some embodiments, at least 10 micrograms of genomic material is isolated from the homogenized samples. Additionally or alternatively, detection of a genetic biomarker can include a method of sequencing DNA within a sample comprising isolating at least 0.5 micrograms of DNA from a blood sample; preparing the at least 0.5 micrograms of isolated DNA for sequencing, and sequencing the prepared DNA. In some embodiments, the method comprises 0 amplification steps prior to sequencing. In some embodiments, the preparing of the at least 0.5 micrograms of isolated DNA for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, at least 1 microgram of DNA is isolated from the blood sample. Additionally or alternatively, detection of a genetic biomarker can include a method of targeted representational sequencing comprising: (i) homogenizing at least a portion of a tumor, one or more whole or partial lymph nodes, or any combination thereof to provide a homogenized sample; (ii) extracting genomic material from the homogenized sample; (iii) capturing the extracted genomic material onto beads; and (iv) sequencing the captured genomic material; wherein the targeted representational sequencing comprises performing at most 4 amplification cycles prior to sequencing of the captured genomic material. In some embodiments, the at most 3 amplification cycles may be conducted prior to capture of the extracted genomic material or after capture of the extracted genomic material, or any combination thereof. In some embodiments, no pre-capture amplification cycles are conducted. In some embodiments, an amount of captured genomic material ranges from about 90 ng to about 900 ng. In some embodiments, from 1 to 3 amplification cycles are performed following capture of the extracted genomic material, but prior to sequencing. In some embodiments, at least 0.5 micrograms of genomic material is extracted from the homogenized sample. In some embodiments, at least 100 times more genomic material is derived from the homogenized sample as compared with an amount of input material used in a sequencing method requiring more than 4 amplification cycles. Additionally or alternatively, detection of a genetic biomarker can include a method of sequencing DNA within a sample comprising: providing at least 0.5 micrograms of input genomic material, the at least 0.5 micrograms of genomic material derived from a tumor sample, a lymph node sample, or a blood sample, isolating DNA from the input genomic sample, preparing the isolated DNA for sequencing, and sequencing the prepared DNA, wherein the method does not comprise any amplification steps. In some embodiments, the at least 0.5 micrograms of input genomic material is derived from multiple histological and/or biopsy specimens. In some embodiments, the at least 0.5 micrograms of input genomic material is derived from a homogenized tumor sample. In some embodiments, the at least 0.5 micrograms of input genomic material is derived from a homogenized lymph node sample. In some embodiments, the at least 0.5 micrograms of input genomic material is a representative sampling of the tumor sample, lymph node sample, or blood sample from which it is derived. In some embodiments, the sequencing is performed using a next-generation sequencing method. In some embodiments, sequencing is performed using a synthesis sequencing methodology. Additionally or alternatively, detection of a genetic biomarker can include a method of reducing PCR-introduced mutations during sequencing comprising isolating DNA from a sample comprising a sufficient amount of genomic material; preparing the isolated DNA for sequencing; and sequencing the prepared DNA, wherein the method comprises at most 3 amplification cycles prior to sequencing. In some embodiments, the method comprises 1 or 2 amplification cycles prior to sequencing. In some embodiments, sufficient amount of input genomic material is an amount such that no pre-capture amplification cycles are utilized. In some embodiments, the sample is derived from a patient suspected of having cancer. In some embodiments, the sample is derived from a patient diagnosed with cancer. In some embodiments, the sample is derived from a patient at risk of developing cancer. In some embodiments, the sample is derived from healthy tissue samples. In some embodiments, 0.5 micrograms of DNA is isolated from the sample. In some embodiments, at least 1 microgram of genomic material is isolated from the sample. In some embodiments, at least 5 micrograms of genomic material is isolated from the sample. In some embodiments, at least 10 micrograms of genomic material is isolated from the sample. Additionally or alternatively, detection of a genetic biomarker can include a sequencing method where PCR-introduced mutations are reduced, the sequencing method comprising capturing at least 0.05 micrograms of genomic material, and performing between 0 and 2 amplification cycles prior to sequencing. In some embodiments, 0 amplification cycles are conducted. In other embodiments, 1 amplification cycle is conducted. In yet other embodiments, 2 amplification cycles are conducted. Additionally or alternatively, detection of a genetic biomarker can include a sequence capture method where PCR-introduced biases in the proportional representation of genome content are reduced, the sequencing method comprising providing an input sample comprising at least 0.5 micrograms of genomic material, and where the sequence capture method comprises performing between 0 and 2 amplification cycles prior to sequencing. In some embodiments, 0 amplification cycles are conducted. In other embodiments, 1 amplification cycle is conducted. In yet other embodiments, 2 amplification cycles are conducted. In some embodiments, the input sample comprises at least 1 microgram of genomic material. In some embodiments, the input sample comprises at least 5 micrograms of genomic material. In some embodiments, the input sample comprises at least 10 micrograms of genomic material. Additionally or alternatively, detection of a genetic biomarker can include a sequence capture method where PCR-introduced mutations are eliminated, the sequence capture method comprising preparing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material. In another aspect is a sequence capture method where a step of removing PCR-duplicate reads prior to sequencing is eliminated, the sequence capture method comprising providing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material. Additionally or alternatively, detection of a genetic biomarker can include a sequencing method where PCR-introduced mutations are virtually eliminated, the sequencing method comprising capturing at least 0.05 micrograms of genomic material. In some embodiments, about 0.05 micrograms of genomic material are provided after capture of the genomic material. In some embodiments, 1 or 2 post-capture amplification cycles are performed prior to sequencing.

In some embodiments, detection of a genetic biomarker (e.g., one or more genetic biomarkers) can include any of the variety of methods described in P.C.T. Publication No. WO 2017/132276, which is hereby incorporated by reference in its entirety. For example, detection of a genetic biomarker can include methods in which regions of a tumor sample predicted not to respond to a first therapeutic agent are excised from the sample with an automated dissection tool, mutations correlated with predictive biomarkers are detected in the excised region using NGS, and additional samples of the tumor are stained for one or more predictive biomarker(s) identified by NGS. Additionally or alternatively, detection of a genetic biomarker can include a method comprising: obtaining a first sample of a tumor, wherein the first sample is histochemically stained for a first predictive biomarker for a first therapeutic agent; excising one or more region(s) from the first sample with an automated dissection tool, wherein the excised region has a staining pattern for the first predictive biomarker indicating that the region is unlikely to respond to the first therapeutic agent; detecting with a next generation sequencer one or more one or more mutations predictive of a response to one or more additional therapeutic agents in a nucleic acid sample derived from the excised region(s) of the first sample; staining one or more additional samples of the tumor for one or more additional predictive biomarker(s) correlating to the one or more mutations identified in the samples, the one or more additional predictive biomarkers being predictive of a response to one or more of the additional therapeutic agent(s). Additionally or alternatively, detection of a genetic biomarker can include a system comprising: (a) a nucleic acid sample derived from one or more regions excised from a first sample of a tumor, wherein the first sample of the tumor is stained for a first predictive biomarker, and further wherein the one or more regions excised from the section have a staining pattern of the first predictive biomarker indicating that at least a portion of the tumor is unlikely to respond to a first therapeutic agent; (b) a next generation sequencer adapted to identify the presence or absence of mutations correlating to one or more additional predictive biomarkers; (c) a laboratory information system (LIS) comprising a database, the database containing: (cl) mutation analysis of a nucleic acid sample by next generation sequencing, wherein the mutation analysis indicates at least the presence or absence of mutations in the nucleic acid sample, the mutations correlating to one or more additional predictive biomarker(s) for one or more additional therapeutic agent(s); and (c2) instructions for directing an automated slide stainer to stain a second sample of the tumor with the one or more additional predictive biomarkers identified by the mutation analysis.

In some embodiments, detection of a genetic biomarker (e.g., one or more genetic biomarkers) can include any of the variety of methods described in U.S. Pat. No. 10,023,917, which is hereby incorporated by reference in its entirety. For example, detection of a genetic biomarker can include High Resolution Melting (HRM) assays as a prescreening diagnostic method to diagnose mutations in the hot spot regions of the most common genes (KRAS, BRAF, PIK3CA, AKT1) concerning the RAS/RAF/MAPK and PI3K/PTEN/AKT pathway. Additionally or alternatively, detection of a genetic biomarker can include pairs of amplification primers, which are useful for HRM analysis of genes which are important for predicting responsiveness to cancer therapeutic agents. Additionally or alternatively, detection of a genetic biomarker can include the following pairs of amplification primers for amplification and analysis of KRAS, exons 2 and 3, BRAF, exon 15, PIK3CA, exons 7, 9 and 20, and AKT1, exon 2. Additionally or alternatively, detection of a genetic biomarker can include a composition or reaction mixture comprising at least one pair of amplification primers as disclosed above. The composition may be used for PCR amplification of nucleic acids during a nucleic acid amplification reaction, and also PCR amplification and monitoring in real time. According to some embodiments, a mixture comprises at least: a pair of amplification primers as disclosed above; a thermostable DNA Polymerase; a mix of deoxynucleoside triphosphates which is usually dA, dG, dC and dT, or dA, dG, dC and dU; and a buffer. In some further embodiments, when suitable for amplification and detection in real time, of one or more specific nucleic acid target sequence(s) such a composition additionally comprises a nucleic acid detecting entity such as a fluorescent hybridization probe, or a fluorescent, double stranded DNA binding dye. In some embodiments, such a DNA double stranded Dye is a dye which can be used to perform HRM curve analysis. In some embodiments, the pair of amplification primers is designed to amplify a specific sequence of interest according to standard methods known in the art of molecular biology. In some embodiments, when brought into contact with a sample that shall be analyzed, such a PCR reaction mixture additionally comprises an at least partially purified DNA or other nucleic acid which putatively comprises a specific sequence of interest. Also, in some such embodiments, the concentrations of all reagents included are generally as known to persons skilled in the art and can be optimized for specific adaptations according to standard protocols. In some such embodiments, the concentration of the fluorescent, double stranded DNA binding dye is between approximately 0.1 to 10.0 µg/ml. In some embodiments, a kit is provided. Some illustrative embodiments of kits include at least one pair of amplification primers. Some embodiments of kits may further comprise one, several, or all of the following additional ingredients; a thermostable DNA Polymerase; a mix of deoxynucleoside triphosphates which is usually dA, dG, dC and dT, or dA, dG, dC and dU, and a buffer, and a fluorescent, double stranded DNA binding dye, which may be suited to be used for HRM. Additionally or alternatively, detection of a genetic biomarker can include a method for determining the increased likelihood of a response to a targeted treatment of a cancer disease, comprising the steps of: a) isolating genomic DNA from a patient sample; b) amplifying at least one fragment of said DNA by means of PCR with a specific pair of amplification primers; c) determining, whether said amplified fragment has a wildtype sequence or comprises a mutation by means of a High Resolution Melting Analysis (HRM); and d) correlating the presence or absence of a mutation with an increased likelihood of success of said targeted treatment. In some embodiments, the mutation is identified by means of a hybridization analysis or by means of sequencing. For example, the patient sample may be Formalin Fixed Paraffin Embedded (FFPE) tissue. In some such cases, HRM Analysis may be performed without any spiking of DNA.

In some embodiments, detection of a genetic biomarker (e.g., one or more genetic biomarkers) can include any of the variety of methods described in U.S. Pat. No. 9,873,908, which is hereby incorporated by reference in its entirety. For example, detection of a genetic biomarker can include methods for enriching low abundance alleles (e.g. mutant DNA) in a sample that allows subsequent detection of such alleles. Additionally or alternatively, detection of a genetic biomarker can include a method of enriching a variant of a target nucleic acid in a mixture of nucleic acids from a sample, the target nucleic acid existing in the form of two variant sequences, wherein said variants differ at a single nucleotide position, the method comprising, providing the sample that includes the target nucleic acid wherein the variant to be enriched is present in the sample in low abundance amongst a large excess of the other variant; providing an oligonucleotide that is complementary to one strand of the target nucleic acid at a concentration that is in molar excess to the target nucleic acid, wherein the oligonucleotide is attached with an affinity label and is perfectly matched at the single nucleotide position with the variant to be enriched and has a mismatch at the single nucleotide position with the other variant; providing conditions suitable for hybridization of the oligonucleotide to the target nucleic acid to generate duplex polynucleotides consisting of the oligonucleotide and one strand of either variant of the target nucleic acid; contacting the duplex polynucleotides with a mismatch intercalating compound that preferentially binds to only the duplex polynucleotides that contain a mismatch wherein said compound is further capable of catalyzing cleavage of one strand of the duplex polynucleotide at the mismatch site with light; subjecting the duplex polynucleotides to light resulting in both cleaved and uncleaved duplex polynucleotides; applying both cleaved and uncleaved duplex polynucleotides to an affinity matrix that recognizes and binds to the affinity label on the oligonucleotide; providing conditions whereby only the cleaved duplex polynucleotide is denatured and removing the denatured single strand from the affinity matrix; and providing a buffer under conditions to denature the uncleaved polynucleotide duplex; and collecting the buffer which contains one strand of the enriched variant of the target nucleic acid. In one embodiment, the mismatch intercalating compound is Rh(bpy)2(chrysi)3+ or Rh(bpy)2(phzi)3+ or their respective analogs. Additionally or alternatively, detection of a genetic biomarker can include a further step of amplifying and detecting the enriched variant of the target nucleic acid. Additionally or alternatively, detection of a genetic biomarker can include a method for detecting a mutant allele of a target nucleic acid in a mixture of nucleic acids from a sample wherein the mutant allele differs from a wild-type allele at a single nucleotide position and is present in the sample in low abundance amongst a large excess of the wild-type allele, the method comprising enriching the mutant allele in the sample wherein the enrichment is performed by providing an oligonucleotide that is complementary to one strand of the target nucleic acid at a concentration that is in molar excess to the target nucleic acid, wherein the oligonucleotide is attached with an affinity label and is perfectly matched at the single nucleotide position with the mutant allele and has a mismatch at the single nucleotide position with the wild-type allele; providing conditions suitable for hybridization of the oligonucleotide to the target nucleic acid to generate duplex polynucleotides consisting of the oligonucleotide and one strand of either the mutant allele or the wild-type allele; contacting the duplex polynucleotides with a mismatch intercalating compound that preferentially binds to only the duplex polynucleotides that contain a mismatch wherein said compound is further capable of catalyzing cleavage of one strand of the duplex polynucleotide at the mismatch site with light; subjecting the duplex polynucleotides to light resulting in both cleaved and uncleaved duplex polynucleotides; applying both cleaved and uncleaved duplex polynucleotides to an affinity matrix that recognizes and binds to the affinity label on the oligonucleotide; providing conditions whereby only the cleaved duplex polynucleotide is denatured and removing the denatured single strand of the wild-type allele from the affinity matrix; providing a buffer under conditions to denature the uncleaved polynucleotide duplex; and collecting the buffer which contains one strand of the enriched mutant allele of the target nucleic acid; amplifying the enriched mutant allele; and detecting the product of the enriched amplified mutant allele or the signal generated from the enriched amplified mutant allele. In one embodiment, the mismatch intercalating compound is Rh(bpy)2(chrysi)3+ or Rh(bpy)2(phzi)3+ or their respective analogs.

In some embodiments, detection of a genetic biomarker (e.g., one or more genetic biomarkers) can include any of the variety of methods described in U.S. Pat. No. 9,399,794, which is hereby incorporated by reference in its entirety. For example, detection of a genetic biomarker can include a method of detecting the presence or absence of a target nucleic acid in a test sample comprising: inputting into a learning statistical classifier system data from a training set of samples where the amount of the target nucleic acid and a control nucleic acid is known, using the learning statistical classifier system, calculating a plurality of weights for a general linear classifier; building a general linear classifier with the plurality of weights calculated by the learning statistical classifier system; contacting the test sample with a reaction mixture containing reagents necessary to amplify the target and the control nucleic acids by polymerase chain reaction (PCR) under conditions enabling PCR; measuring at least one amplification-dependent parameter for the target and the control nucleic acids to obtain a test set of data; applying the general linear classifier to the test set of data to classify the test sample as containing or not containing the target nucleic acid, thereby detecting the presence or absence of the target nucleic acid in the test sample. In variations of this embodiment, the learning statistical classifier system is selected from SVM, LDA and QDA. In further variations of this embodiment, the amplification-dependent parameter is fluorescence detected during each cycle of amplification. In further variations of this embodiment, the data is cycle-to-threshold (Ct) value. In further variations of this embodiment, the general linear classifier is a piece-wise linear classier. In further variations of this embodiment, a piece-wise function determined by constraints placed upon the amplification-dependent parameter for the control nucleic acid is input into the piece-wise linear classifier. In further variations of this embodiment, the target nucleic acid is a nucleic acid variant of a human sequence. Additionally or alternatively, detection of a genetic biomarker can include a method of detecting the presence or absence of a target nucleic acid in a test sample comprising: inputting into a learning statistical classifier system data from a training set of samples where the amount of the target nucleic acid and a control nucleic acid is known; using the learning statistical classifier system, calculating a plurality of weights for a general linear classifier; building a general linear classifier with the plurality of weights calculated by the learning statistical classifier system; subjecting the sample to polymerase chain reaction (PCR); measuring at least one amplification-dependent parameter for the target and the control nucleic acids to obtain a test set of data; applying the general linear classifier to the test set of data; classifying the test sample as containing or not containing the target nucleic acid, thereby detecting the presence or absence of the target nucleic acid in the test sample. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold (Ct) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment, the target nucleic acid is a nucleic acid variant of a human sequence. Additionally or alternatively, detection of a genetic biomarker can include a method of determining whether a target nucleic acid is present in a test sample comprising: subjecting a training set of samples wherein the amount of the target nucleic acid and a control nucleic acid is known to polymerase chain reaction (PCR) and measuring at least one amplification-dependent parameter for the target and the control nucleic acids to obtain a training set of data; inputting the data into a learning statistical classifier system; using the learning statistical classifier system, calculating a plurality of weights for a general linear classifier; building a general linear classifier with the plurality of weights determined by the learning statistical classifier system; subjecting the test sample to PCR and measuring at least one amplification-dependent parameter for the target and the control nucleic acids to obtain a test set of data; applying the general linear classifier to the test set of data; classifying the test sample as containing or not containing the target nucleic acid. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold (Ct) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment, the target nucleic acid is a nucleic acid variant of a human sequence. Additionally or alternatively, detection of a genetic biomarker can include a method of determining whether a target nucleic acid is present in a test sample comprising: subjecting a training set of samples wherein the amount of the target nucleic acid and a control nucleic acid is known to polymerase chain reaction (PCR) and measuring at least one amplification-dependent parameter for the target and the control nucleic acids to obtain a training set of data; inputting the data into a learning statistical classifier system; using the learning statistical classifier system, calculating a plurality of weights for a general linear classifier; building a general linear classifier with the plurality of weights determined by the learning statistical classifier system; subjecting the test sample to PCR and measuring at least one amplification-dependent parameter for the target and the control nucleic acids to obtain the test set of data; applying the general linear classifier to the test set of data obtained; classifying the test sample as containing or not containing the target nucleic acid. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold (Ct) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment, the target nucleic acid is a nucleic acid variant of a human sequence. Additionally or alternatively, detection of a genetic biomarker can include a computer readable medium including code for controlling one or more processors to classify whether a test sample contains a target nucleic acid, the code including instructions to: apply a learning statistical classifier system to a training data set where the amount of the target nucleic acid and a control nucleic acid is known, in order to build a general linear classifier of Formula I; apply the general linear classifier to a testing data set comprising the data from the test sample to produce a statistically derived decision classifying the test sample as containing or not containing the target nucleic acid. In variations of this embodiment, the learning statistical classifier system is selected from SVM, LDA and QDA. In further variations of this embodiment, the data in the datasets is cycle-to-threshold (Ct) value. In further variations of this embodiment, the general linear classifier is a piece-wise linear classifier. In further variations of this embodiment, the target nucleic acid is a nucleic acid variant of a human sequence. Additionally or alternatively, detection of a genetic biomarker can include a system for detecting a target nucleic acid in a test sample comprising: a data acquisition module configured to produce a data set from a training set of samples and one or more test samples, the data set indicating presence and amount of the target nucleic acid and a control nucleic acid; a data processing unit configured to process the data acquired by the acquisition module by applying a learning statistical classifier system to the training data set in order to build a general linear classifier of Formula I, and then apply the general linear classifier of Formula I to the test data set comprising the data from the test sample, to produce a statistically derived decision classifying the test sample as containing or not containing the target nucleic acid; a display module configured to display the data produced by the data processing unit. In variations of this embodiment, the learning statistical classifier system is selected from SVM, LDA and QDA. In further variations of this embodiment, the general linear classifier is a piece-wise linear classifier.

In some embodiments, detection of a genetic biomarker (e.g., one or more genetic biomarkers) can include any of the variety of methods described in U.S. Pat. No. 9,382,581, which is hereby incorporated by reference in its entirety. For example, detection of a genetic biomarker can include a method of allele-specific amplification of a variant of a target sequence, the target existing in the form of several variant sequences, the method comprising, (a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

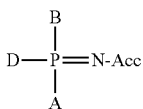

wherein A and B represents a nucleotide chain, D is OH or CH3, and Acc is an electron acceptor or an electron acceptor substituted with a residue R wherein R is an organic substituent, wherein Acc is selected from the group consisting of CN, SO2-R', in which R' comprises at least one amino-substituted alkyl, an optionally substituted aryl or an optionally substituted heterocycle, and a six membered N+ heterocycle with at least one alkylated N-atom in ortho- or para-position, said heterocycle selected from the group consisting of pyridinium, pyrimidinium, and quinolinium; (b) providing conditions suitable for oligonucleotide extension by a nucleic acid polymerase; (c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide. Additionally or alternatively, detection of a genetic biomarker can include a method of detecting a variant of a target sequence, the target existing in the form of several variant sequences, the method comprising, (a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

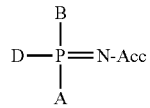

herein A and B represents a nucleotide chain, D is OH or CH3, and Acc is an electron acceptor or an electron acceptor substituted with a residue R wherein R is an organic substituent, wherein Acc is selected from the group consisting of CN, SO2-R', in which R' comprises at least one amino-substituted alkyl, an optionally substituted aryl or an optionally substituted heterocycle, and a six membered N+ heterocycle with at least one alkylated N-atom in ortho- or para-position, said heterocycle selected from the group consisting of pyridinium, pyrimidinium, and quinolinium; (b) providing conditions suitable for oligonucleotide extension by a nucleic acid polymerase; (c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide; (d) detecting products of said oligonucleotide extension, wherein said extension signifies the presence of the variant of said target sequence to which said second oligonucleotide has a complementary selective nucleotide. Additionally or alternatively, detection of a genetic biomarker can include an oligonucleotide for performing an allele-specific amplification of a target sequence, the target existing in the form of several variant sequences, the oligonucleotide comprising, (a) a sequence at least partially complementary to a portion of one or more variants of said target sequence; (b) at least one selective nucleotide complementary to only one variant of the target sequence; (c) a nucleotide with a base covalently modified at the exocyclic amino group; (d) a modified phosphate having a structure:

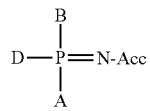

wherein A and B represents a nucleotide chain, D is OH or CH3, and Acc is an electron acceptor or an electron acceptor substituted with a residue R wherein R is an organic substituent, wherein Acc is selected from the group consisting of CN, SO2-R', in which R' comprises at least one amino-substituted alkyl, an optionally substituted aryl or an optionally substituted heterocycle, and a six membered N+ heterocycle with at least one alkylated N-atom in ortho- or para-position, said heterocycle selected from the group consisting of pyridinium, pyrimidinium, and quinolinium. Additionally or alternatively, detection of a genetic biomarker can include a reaction mixture for allele-specific amplification of a target sequence, the target existing in the form of several variant sequences, the mixture comprising, (a) a first oligonucleotide, at least partially complementary to one or more variant of the target sequence; and (b) a second oligonucleotide, at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

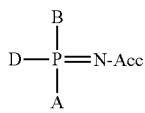

wherein A and B represents a nucleotide chain, D is OH or CH3, and Acc is an electron acceptor or an electron acceptor substituted with a residue R wherein R is an organic substituent, wherein Acc is selected from the group consisting of CN, SO2-R', in which R' comprises at least one amino-substituted alkyl, an optionally substituted aryl or an optionally substituted heterocycle, and a six membered N+ heterocycle with at least one alkylated N-atom in ortho- or para-position, said heterocycle selected from the group consisting of pyridinium, pyrimidinium, and quinolinium; (c) a nucleic acid polymerase; (d) nucleoside triphosphates; and (e) a buffer suitable for the extension of nucleic acids by the nucleic acid polymerase.

In some embodiments, detection of a genetic biomarker (e.g., one or more genetic biomarkers) can include any of the variety of methods described in U.S. Pat. No. 9,279,146, which is hereby incorporated by reference in its entirety. For example, detection of a genetic biomarker can include methods and compositions for enriching low abundance alleles (e.g. mutant DNA) in a sample that allows subsequent detection of such alleles. Additionally or alternatively, detection of a genetic biomarker can include a method of enriching a variant of a target nucleic acid sequence in a mixture of nucleic acids from a sample, the target nucleic acid existing in the form of two variant sequences, wherein said variants differ at a single nucleotide position, the method comprising, providing the sample that includes the target nucleic acid sequence wherein the variant to be enriched is present in the sample in low abundance amongst a large excess of the other variant; providing an oligonucleotide that is complementary to one strand of the target nucleic acid sequence, wherein the oligonucleotide has a mismatch at the single nucleotide position with the variant to be enriched and is perfectly matched at the single nucleotide position with the other variant; providing conditions suitable for hybridization of the oligonucleotide to the target nucleic acid to generate duplex polynucleotides consisting of the oligonucleotide and one strand of either variant of the target nucleic acid sequence; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence. Additionally or alternatively, detection of a genetic biomarker can include a method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising, enriching the mutant allele in the sample wherein the enrichment is performed by providing an oligonucleotide that is complementary to one strand of the target nucleic acid sequence, wherein the oligonucleotide has a mismatch at the single nucleotide position with the mutant allele and is perfectly matched at the single nucleotide position with the wild-type allele; providing conditions suitable for hybridization of the oligonucleotide to the target nucleic acid to generate duplex polynucleotides consisting of the oligonucleotide and one strand of either the mutant allele or the wild-type allele; contacting the duplex polynucleotides with a mismatch intercalating compound that is attached with an affinity label to generate a reaction mixture, wherein the mismatch intercalating compound is capable of binding to the duplex polynucleotides that contain a mismatch and is not capable of binding to the duplex polynucleotides that do not contain a mismatch; subjecting the reaction mixture to a affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched mutant allele; amplifying the enriched mutant allele; and detecting the product of the enriched amplified mutant allele or the signal generated from the enriched amplified mutant allele. Additionally or alternatively, detection of a genetic biomarker can include a method of enriching a variant of a target nucleic acid sequence in a mixture of nucleic acids from a sample, the target nucleic acid existing in the form of two variant sequences, wherein said variants differ at a single nucleotide position, the method comprising: providing the sample that includes the target nucleic acid sequence wherein the variant to be enriched is present in the sample in low abundance amongst a large excess of the other variant; heating the sample such that the mixture of nucleic acid is denatured; providing conditions suitable for the reannealing of the target nucleic acid, wherein duplex polynucleotides can be formed between one strand of one variant sequence and one strand of the other variant sequence to generate a mismatch at the single nucleotide position where the variants differ; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence. Additionally or alternatively, detection of a genetic biomarker can include a method for detecting a mutant allele of a target nucleic acid sequence in a mixture of nucleic acids from a sample wherein the mutant allele differs from a wild-type allele at a single nucleotide position and is present in the sample in low abundance amongst a large excess of the wild-type allele, the method comprising: enriching the mutant allele in the sample wherein the enrichment is performed by: heating the sample such that the mixture of nucleic acid is denatured; providing conditions suitable for the reannealing of the target nucleic acid, wherein duplex polynucleotides can be formed between one strand of the mutant allele and one strand of the wild-type allele to generate a mismatch at the single nucleotide position where the alleles differ; contacting the duplex polynucleotides with a mismatch intercalating compound that is attached with an affinity label to generate a reaction mixture, wherein said mismatch intercalating compound is capable of binding to the duplex polynucleotides that contain a mismatch and is not capable of binding to the duplex polynucleotides that do not contain a mismatch; subjecting the reaction mixture to an affinity matrix that recognizes and binds to the affinity label on the mismatch intercalating compound; washing the reaction mixture and separating the affinity matrix from all material that is not bound to the affinity matrix; and providing a buffer to elute nucleic acid from the affinity matrix, and collecting the eluted buffer which contains the enriched variant of the target nucleic acid sequence; amplifying the enriched mutant allele; and detecting the product of the enriched amplified mutant allele or the signal generated from the enriched amplified mutant allele.

In some embodiments, detection of a genetic biomarker (e.g., one or more genetic biomarkers) can include any of the variety of methods described in U.S. Pat. No. 9,238,832, which is hereby incorporated by reference in its entirety. For example, detection of a genetic biomarker can include a method of allele-specific amplification of a variant of a target sequence, the target existing in the form of several variant sequences, the method comprising (a) hybridizing a first and a second oligonucleotides to at least one variant of the target sequence; wherein the first oligonucleotide is at least partially complementary to one or more variants of the target sequence, and the second oligonucleotide is at least partially complementary to one or more variants of the target sequence, and has at least one internal selective nucleotide complementary to only one variant of the target sequence; (b) extending the second oligonucleotide with a nucleic acid polymerase, wherein said polymerase is capable of extending said second oligonucleotide preferentially when said selective nucleotide forms a base pair with the target, and substantially less when said selective nucleotide does not form a base pair with the target. Additionally or alternatively, detection of a genetic biomarker can include a method of detecting a variant of a target sequence, the target existing in the form of several variant sequences, the method comprising (a) hybridizing a first and second oligonucleotides to at least one variant of the target sequence; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence; (b) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and (c) detecting the products of said oligonucleotide extension, wherein the extension signifies the presence of the variant of a target sequence to which the oligonucleotide has a complementary selective nucleotide. Additionally or alternatively, detection of a genetic biomarker can include an oligonucleotide for performing an allele-specific amplification of a target sequence, said target existing in the form of several variant sequences, the oligonucleotide comprising (a) a sequence at least partially complementary to a portion of one or more variants of said target sequence; (b) at least one internal selective nucleotide complementary to only one variant of the target sequence. Additionally or alternatively, detection of a genetic biomarker can include a reaction mixture for allele-specific amplification of a target sequence, said target existing in the form of several variant sequences, the mixture comprising (a) a first oligonucleotide, at least partially complementary to one or more variant of the target sequence; and (b) a second oligonucleotide, at least partially complementary to one or more variants of the target sequence but having at least one internal selective nucleotide complementary to only one variant of the target sequence.

In some embodiments, detection of a genetic biomarker (e.g., one or more genetic biomarkers) can include any of the variety of methods described in U.S. Patent Application Publication No. 2016/0092630, which is hereby incorporated by reference in its entirety. For example, detection of a genetic biomarker can include accurate and fast mapping of sequencing reads obtained from a targeted sequencing. For example, once a target region is selected, alternate regions of the genome that are sufficiently similar to the target region can be identified. If a sequencing read is more similar to the target region than to an alternate region, then the read can be determined as aligning to the target region. The reads aligning to the target region can then be analyzed to determine whether a mutation exists in the target region. Accordingly, a sequencing read can then be compared to the target region and the corresponding alternate regions, and not to the entire genome, thereby providing computational efficiency. Additionally or alternatively, detection of a genetic biomarker can include a method detects variants in a target region of a sample genome of an organism. A plurality of sequence reads are received. The sequence reads are obtained from sequencing genomic segments in a sample obtained from the organism, where the sequencing includes targeting genomic segments from the target region. One or more alternate regions that have a respective first number of variations from the target region of a reference genome are identified. Each respective first number is greater than one and less than a first threshold number. A computer system performs an alignment of the plurality of sequence reads to the target region of the reference genome to identify a set of sequence reads that align to the target region of the reference genome with less than a second threshold number of variations. Sequence reads that align to one of the alternate regions with a second number of variations that is less than a third threshold number can be removed from the set. The remaining sequence reads of the set are analyzed to determine variants in the target region of the sample genome.

In some embodiments, detection of a genetic biomarker (e.g., one or more genetic biomarkers) can include any of the variety of methods described in U.S. Pat. No. 7,977,108, which is hereby incorporated by reference in its entirety. For example, detection of a genetic biomarker can include approaches for rapidly and reliably detecting and differentiating between mutant and non-mutant forms of nucleic acids that comprise repetitive nucleotide sequences. In certain embodiments, for example, the methods are used to assess microsatellite instability in patients as part of diagnostic or prognostic applications. In many embodiments, various polymorphisms of a given repetitive nucleotide sequence are detected using a single probe nucleic acid. Additionally or alternatively, detection of a genetic biomarker can include a method of detecting a mutant form of a target nucleic acid. The method includes providing at least one target nucleic acid and/or an amplicon of the target nucleic acid. The target nucleic acid includes at least one repetitive nucleotide sequence. The method also includes binding (e.g., hybridizing, etc.) at least one probe nucleic acid to the target nucleic acid and/or to the amplicon of the target nucleic acid. The probe nucleic acid includes at least a first nucleotide sequence that is at least substantially complementary to at least a portion of a non-mutant form of the repetitive nucleotide sequence. In addition, the method also includes detecting a bimodal dissociation of the probe nucleic acid from the target nucleic acid and/or from the amplicon of the target nucleic acid. In some embodiments, the detected bimodal dissociation comprises a bimodal distribution of melting peaks. Further, the detected bimodal dissociation generally correlates with at least one mutant form of the repetitive nucleotide sequence. In some embodiments, a detected non-bimodal (e.g., a single mode, etc.) dissociation correlates with a non-mutant form the repetitive nucleotide sequence. Typically, the probe nucleic acid, the target nucleic acid, and/or the amplicon of the target nucleic acid includes or is associated with at least one labeling moiety and/or at least one quencher moiety. In these embodiments, the detecting step generally includes detecting a detectable signal produced by the labeling moiety. Moreover, the bimodal dissociation of the probe nucleic acid from the target nucleic acid and/or from the amplicon of the target nucleic acid is typically detected under at least one varied condition, such as a varied temperature or the like. Additionally or alternatively, detection of a genetic biomarker can include a reaction mixture. The reaction mixture includes at least one target nucleic acid and/or an amplicon of the target nucleic acid. The target nucleic acid includes at least one repetitive nucleotide sequence. The reaction mixture also includes at least one probe nucleic acid that includes at least a first nucleotide sequence that is at least substantially complementary to at least a portion of a non-mutant form of the repetitive nucleotide sequence. Further, the probe nucleic acid dissociates bimodally from a bound target nucleic acid that includes at least one mutant form of the repetitive nucleotide sequence under at least one varied condition. In certain embodiments, the reaction mixture also includes various other components. For example, the reaction mixture optionally includes at least one salt (e.g., NaCl, KCl, and/or the like). In some embodiments, the reaction mixture also includes at least one buffer. The buffer typically maintains a pH of the reaction mixture between about 5.5 and about 10.0. The reaction mixture also optionally includes at least one cofactor, such as Mg2+ (e.g., MgSO4, MgCl2, etc.), Mn2+ (e.g., MnSO4, MnC12, etc.), and/or the like. Additionally or alternatively, detection of a genetic biomarker can include a probe nucleic acid. The probe nucleic acid includes at least a first nucleotide sequence that is at least substantially complementary to at least a portion of a non-mutant form of a repetitive nucleotide sequence. In addition, the probe nucleic acid dissociates bimodally from a bound target nucleic acid that includes at least one mutant form of the repetitive nucleotide sequence under at least one varied condition. Additionally or alternatively, detection of a genetic biomarker can include a system for detecting mutant forms of target nucleic acids. The system includes at least one probe nucleic acid that includes at least a first nucleotide sequence that is at least substantially complementary to a non-mutant form of a repetitive nucleotide sequence. The probe nucleic acid dissociates bimodally from a bound target nucleic acid that comprises at least one mutant form of the repetitive nucleotide sequence under at least one varied condition. Typically, at least one container comprises the probe nucleic acid, e.g., in solution. The system also includes at least one detector that detects dissociation of the probe nucleic acid from a target nucleic acid and/or from an amplicon of the target nucleic acid when the probe nucleic acid is bound to the target nucleic acid and/or to the amplicon of the target nucleic acid and subjected to one or more varied conditions. In some embodiments, the system also includes at least one thermal modulator that modulates temperatures to which the probe nucleic acid is exposed when the probe nucleic acid is bound to the target nucleic acid and/or to the amplicon of the target nucleic acid to effect the varied conditions. In certain embodiments, the system also includes at least one controller operably connected at least to the detector, which controller correlates detected bimodal dissociations of the probe nucleic acid from bound target nucleic acids and/or bound amplicons of target nucleic acids with diagnoses of at least one genetic disorder and/or at least one disease state for subjects from which the target nucleic acids were obtained. In some embodiments, the target nucleic acid typically comprises a DNA or an RNA, and is generally obtained from at least one subject. Mutant forms of the target nucleic acid typically correlate with a diagnosis of at least one genetic disorder (e.g., Fragile X Syndrome, etc.) and/or at least one disease state (e.g., at least one form of cancer, etc.) for a subject comprising the mutant form of the target nucleic acid. Further, the mutant form of the repetitive nucleotide sequence typically comprises at least one deletion relative to the non-mutant form of the repetitive nucleotide sequence. In some embodiments, for example, the repetitive nucleotide sequence corresponds to a microsatellite marker, a mononucleotide repeat, and/or the like. In some embodiments, the repetitive nucleotide sequence comprises at least one mononucleotide repeat (e.g., An, Tn, Gn, Cn, Un, etc., where n is an integer greater than 1). For example, the mononucleotide repeat optionally comprises a BAT-25 repeat, a BAT-26 repeat, among many others. In certain embodiments, detected mutant forms of the mononucleotide repeat comprise 22 or fewer adenine nucleotides. To further illustrate, the repetitive nucleotide sequence of the target nucleic acid includes at least one AT repeat, at least one GC repeat, at least one CGG repeat, at least one CGC repeat, at least one TAT repeat, at least one ATT repeat, and/or at least one complementary repeat thereof in certain embodiments. In some embodiments, for example, the first nucleotide sequence is longer than the non-mutant form of the repetitive nucleotide sequence. In these embodiments, the portion of the first nucleotide sequence that extends beyond the length of the non-mutant form of the repetitive nucleotide sequence is typically not substantially complementary to nucleotide sequences of the target nucleic acid that are adjacent to the repetitive nucleotide sequence. While not being constrained to a particular theory, in these embodiments it is thought that at least one segment of the probe nucleic acid forms a triple helix when the probe nucleic acid is bound to the mutant form of the target nucleic acid or to an amplicon of the mutant form of the target nucleic acid under at least one selected condition. In certain embodiments, the probe nucleic acid comprises at least one modified nucleotide. The probe nucleic acids, target nucleic acids, and/or amplicons of the target nucleic acids (e.g., via primer nucleic acids used to produce the amplicons, etc.) optionally comprise or are associated with at least one labeling moiety and/or at least one quencher moiety. To illustrate, the labeling moiety optionally comprises one or more of, e.g., a fluorescent dye, a weakly fluorescent label, a non-fluorescent label, a colorimetric label, a chemiluminescent label, a bioluminescent label, an antibody, an antigen, biotin, a hapten, an enzyme, or the like. To further exemplify, the fluorescent dye is optionally selected from the group consisting of, e.g., Cy3, Cy3.5, Cy5, Cy5.5, JOE, VIC, TET, HEX, FAM, R6G, R110, TAMRA, ROX, SYBR-Green, EtBr, and the like.

In some embodiments, detection of a genetic biomarker (e.g., one or more genetic biomarkers) can include any of the variety of methods described in U.S. Pat. No. 7,745,125, which is hereby incorporated by reference in its entirety. For example, detection of a genetic biomarker can include methods relating to nucleic acid polymerization and amplification. In certain embodiments, for example, the pyrophosphorolysis activated polymerization (PAP)-related methods involve the serial coupling of pyrophosphorolysis and polymerization. These methods can be used, e.g., for SNP analysis and rare somatic mutation detection, among many other applications. In some embodiments, the methods enhance the general specificity of oligonucleotide-mediated synthesis reactions. For example, analogous to other "hot start" methods (e.g., reversible, chemically-modified enzymes, aptamer- or antibody-mediated "hot start"), "zeroth cycle extension" (pre-PCR) is reduced or eliminated. Unlike these other methods, primer activation is effected at each and every new oligonucleotide-mediated synthesis step. This improves the overall specificity of the reaction, minimizing the generation of unwanted side products. Accordingly, the detection of low copy and even single copy sequences is improved. In addition, the performance in multiplex (where several or many different target are being amplified) amplification reactions is also improved by reducing or eliminating the generation of unintended and undesired, non-specific synthesis products, e.g., primer dimers in the case of PCR. Additionally or alternatively, detection of a genetic biomarker can include a reaction mixture that includes at least one oligonucleotide (e.g., a primer nucleic acid, a probe nucleic acid, etc.) comprising a 2'-terminator nucleotide (e.g., at a 3'-terminus). In certain embodiments, the oligonucleotide comprises the formula:

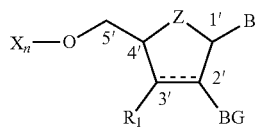

where Z is O or CH2; B is at least one homocyclic ring, at least one heterocyclic ring, at least one aryl group, or combinations thereof; BG is a blocking group; R1 is H, OH, a hydrophilic group, or a hydrophobic group; X is a nucleotide or a nucleotide analog; n is an integer greater than 0; and, represents a single or double bond. Optionally, the oligonucleotide comprises at least one label. In certain embodiments, at least one nucleotide position in the oligonucleotide corresponds to a polymorphic nucleotide position in a target nucleic acid. In some of these embodiments, for example, the 2'-terminator nucleotide corresponds to the polymorphic nucleotide position in the target nucleic acid. The reaction mixture typically includes additional reagents according to the particular application in which the reaction mixture is utilized. In some embodiments, for example, additional reagents are selected from, e.g., a first biocatalyst comprising a nucleotide removing activity (e.g., a pyrophosphorolysis activity and/or a nuclease activity), a second biocatalyst comprising a nucleotide incorporating activity, a target nucleic acid comprising at least a subsequence that is at least partially complementary to the oligonucleotide, an amplicon, a primer nucleic acid, a probe nucleic acid (e.g., a hybridization probe, a 5'-nuclease probe, a hairpin probe, etc.), an additional nucleotide (e.g., an extendible nucleotide, a terminator nucleotide, a ribonucleoside triphosphate, a deoxyribonucleoside triphosphate, etc.), an additional oligonucleotide (e.g., a primer nucleic acid, a probe nucleic acid, etc.), a soluble light emission modifier, a cosolvent, an intercalating agent, a clinical specimen, a sample, a buffer, a salt, a metal ion, pyrophosphate, glycerol, dimethyl sulfoxide, poly rA, and the like. In some embodiments, the target nucleic acid, the amplicon, the primer nucleic acid, the probe nucleic acid, the additional nucleotide, and/or the additional oligonucleotide comprises at least one label. In certain embodiments, the buffer comprises N-[Tris(hydroxymethyl)methyl]glycine at a concentration of at least 90 mM (e.g., about 95 mM, about 100 mM, about 105 mM, etc.). In some embodiments, the first biocatalyst comprises a nucleotide incorporating activity (i.e., in addition to the nucleotide removing activity). The nucleotide incorporating activity of the first and/or the second biocatalyst typically comprises a polymerase activity and/or a ligase activity. Optionally, the first and/or the second biocatalyst comprises a nuclease activity. To further illustrate, the first and/or second biocatalyst optionally comprises an enzyme selected from, e.g., a polymerase, a terminal transferase, a reverse transcriptase, a polynucleotide phosphorylase, a ligase, an AP endonuclease, and a telomerase. In certain embodiments, the first and/or second biocatalyst comprises a CS5 DNA polymerase that includes one or more mutations at amino acid positions selected from the group consisting of: G46, L329, Q601, D640, I669, S671, and E678. In some of these embodiments, for example, the mutations comprise a G46E mutation, an L329A mutation, a Q601R mutation, a D640G mutation, an I669F mutation, an S671F mutation, and/or an E678G mutation. In some embodiments, for example, the 2'-terminator nucleotide comprises a 2'-monophosphate-3'-hydroxyl nucleoside. Additionally or alternatively, detection of a genetic biomarker can include a method of removing a nucleotide from an oligonucleotide. The method includes incubating at least one target nucleic acid with: at least a first biocatalyst comprising a nucleotide removing activity (e.g., a pyrophosphorolysis activity and/or a nuclease activity), and at least one oligonucleotide (e.g., a primer nucleic, a probe nucleic acid, etc.) comprising a 2'-terminator nucleotide (e.g., at a 3'-terminus), which oligonucleotide is at least partially complementary to at least a first subsequence of the target nucleic acid, under conditions whereby the first biocatalyst removes at least the 2'-terminator nucleotide from the oligonucleotide to produce a removed 2'-terminator nucleotide and a shortened oligonucleotide, thereby removing the nucleotide from the oligonucleotide. In some embodiments, the method includes incubating the target nucleic acid with the first biocatalyst, the oligonucleotide, and pyrophosphate, which pyrophosphate is added to the removed 2'-terminator nucleotide. In some exemplary embodiments, the target nucleic acid comprises at least one polymorphic nucleotide position, and the method comprises detecting removal of the 2'-terminator nucleotide from the oligonucleotide, which removal correlates with the oligonucleotide comprising at least one nucleotide position that corresponds to the polymorphic nucleotide position. In these embodiments, the 2'-terminator nucleotide typically corresponds to the polymorphic nucleotide position. In certain embodiments, the oligonucleotide comprises at least one label, and the method comprises detecting a detectable signal emitted from the label. In some of these embodiments, the label comprises a donor moiety and/or an acceptor moiety and the detectable signal comprises light emission, and the method comprises incubating the target nucleic acid with the first biocatalyst, the oligonucleotide, and at least one soluble light emission modifier and detecting the light emission from the donor moiety and/or the acceptor moiety. Optionally, the 2'-terminator nucleotide comprises the donor moiety and/or the acceptor moiety. In some embodiments, the first biocatalyst comprises a nucleotide incorporating activity (i.e., in addition to the nucleotide removing activity), and the method comprises incubating the target nucleic acid with the first biocatalyst, the shortened oligonucleotide, and at least one additional nucleotide under conditions whereby the first biocatalyst incorporates the additional nucleotide at a terminus of the shortened oligonucleotide to produce an extended oligonucleotide. Optionally, the method comprises incubating the target nucleic acid with at least a second biocatalyst comprising a nucleotide incorporating activity, the shortened oligonucleotide, and at least one additional nucleotide under conditions whereby the second biocatalyst incorporates the additional nucleotide at a terminus of the shortened oligonucleotide to produce an extended oligonucleotide. To illustrate, the nucleotide incorporating activity typically includes a polymerase activity and/or a ligase activity. The first and/or second biocatalyst typically comprises an enzyme selected from, e.g., a polymerase, a terminal transferase, a reverse transcriptase, a polynucleotide phosphorylase, a ligase, an AP endonuclease, a telomerase, and the like. In certain embodiments, the first and/or second biocatalyst comprises a CS5 DNA polymerase comprising one or more mutations at amino acid positions selected from, e.g., G46, L329, Q601, D640, I669, S671, and E678. In some of these embodiments, the mutations comprise a G46E mutation, an L329A mutation, a Q601R mutation, a D640G mutation, an I669F mutation, an S671F mutation, and/or an E678G mutation. In some embodiments, one or more nucleotides of the oligonucleotide extend beyond a terminus of the target nucleic acid when the oligonucleotide and the target nucleic acid hybridize to form a hybridized nucleic acid. In some embodiments, at least one additional oligonucleotide comprises the additional nucleotide. The additional nucleotide comprises an extendible nucleotide and/or a terminator nucleotide. In certain embodiments, the additional nucleotide comprises at least one label, and the method comprises detecting a detectable signal emitted from the label. For example, the label optionally comprises a donor moiety and/or an acceptor moiety and the detectable signal comprises light emission, and the method comprises incubating the target nucleic acid with at least one soluble light emission modifier and detecting the light emission from the label. Additionally or alternatively, detection of a genetic biomarker can include incubating the target nucleic acid with at least one probe nucleic acid that comprises at least one label, which probe nucleic acid is at least partially complementary to at least a second subsequence of the target nucleic acid, and detecting a detectable signal emitted from the label of the probe nucleic acid or a fragment thereof. In some embodiments, the detectable signal comprises light emission, and the method further comprises incubating the target nucleic acid with at least one soluble light emission modifier and detecting the light emission from the label. For example, the probe nucleic acid optionally comprises a 5'-nuclease probe and the first and/or second biocatalyst extends the shortened oligonucleotide in a 5' to 3' direction and comprises a 5' to 3' exonuclease activity. Optionally, the probe nucleic acid comprises a hybridization probe and/or a hairpin probe. In certain embodiments, the target nucleic acid comprises at least one polymorphic nucleotide position, and the method comprises detecting extension of the shortened oligonucleotide, which extension correlates with the extended oligonucleotide comprising at least one nucleotide position that corresponds to the polymorphic nucleotide position. In some of these embodiments, the 2'-terminator nucleotide corresponds to the polymorphic nucleotide position. Additionally or alternatively, detection of a genetic biomarker can include a system that includes (a) at least one container or support comprising an oligonucleotide that comprises a 2'-terminator nucleotide. The system also includes at least one of: (b) at least one thermal modulator configured to thermally communicate with the container or the support to modulate temperature in the container or on the support; (c) at least one fluid transfer component that transfers fluid to and/or from the container or the support; and, (d) at least one detector configured to detect detectable signals produced in the container or on the support. In some embodiments, the system includes at least one controller operably connected to: the thermal modulator to effect modulation of the temperature in the container or on the support, the fluid transfer component to effect transfer of the fluid to and/or from the container or on the support, and/or the detector to effect detection of the detectable signals produced in the container or on the support.

In some embodiments, detection of a genetic biomarker (e.g., one or more genetic biomarkers) can include any of the variety of methods described in U.S. Patent Application Publication No. 2018/0135103, which is hereby incorporated by reference in its entirety. For example, detection of a genetic biomarker can include methods based on digital polymerase chain reaction (dPCR) in combination with a reference sample which is used in a double function. First, it is added to a dPCR run as an external standard. Secondly, the same reference sample is used as an internal standard, preferably by adding it to the primary sample. It runs through the whole sample preparation process in the same way as the nucleic acid of interest (target nucleic acid). Both the internal and the external reference are quantified using dPCR. The ratio of internal vs external reference quantification gives the yield of the sample preparation prior to the dPCR. Knowing this yield, the initial target concentration in the primary sample can be calculated. The reference used with dPCR leads to a full understanding of standards used in dPCR and helps preventing miscalculation due to pipetting and dilution errors. Even with non-precise standards, the absolute accuracy of dPCR is further improved and standards may be re-calibrated as a bonus. Additionally or alternatively, detection of a genetic biomarker can include a method for determining the amount or concentration of a nucleic acid of interest in an unprocessed sample, the method comprising the steps of: a) providing an unprocessed sample suspected of containing the nucleic acid of interest and a reference sample known to contain a reference nucleic acid, which is different from the nucleic acid of interest; b) combining the unprocessed sample with a defined amount of the reference sample, thereby obtaining a combined sample; c) processing the combined sample, thereby obtaining a processed sample suitable for digital polymerase chain reaction (dPCR); d) performing dPCR with the processed sample, thereby determining the amount or concentration of the nucleic acid of interest and the amount or concentration of the reference nucleic acid in the processed sample; e) performing the dPCR with a defined amount of the reference sample, thereby determining the amount or concentration of the reference nucleic acid in the defined amount of the reference sample;

f) comparing the amount or concentration of the reference nucleic acid determined in step d) to that determined in step e), thereby determining the yield of the nucleic acid in step c); and g) determining the amount or concentration of the nucleic acid of interest in the unprocessed sample based on the amount or concentration of the nucleic acid of interest in the processed sample determined in step d) and the yield determined in step f). Additionally or alternatively, detection of a genetic biomarker can include a method for determining the amount or concentration of a nucleic acid of interest in an unprocessed sample, the method comprising the steps of: a) providing an unprocessed sample suspected of containing the nucleic acid of interest;

b) providing a reference sample known to contain a reference nucleic acid, which is different from the nucleic acid of interest; c) processing the reference sample, thereby obtaining a processed reference sample suitable for dPCR; d) performing the dPCR with the processed reference sample, thereby determining the amount or concentration of the reference nucleic acid in the processed reference sample; e) performing the dPCR with a defined amount of unprocessed reference sample, thereby determining the amount or concentration of the reference nucleic acid in the defined amount of the unprocessed reference sample; f) comparing the amount or concentration of the reference nucleic acid determined in step d) to that determined in step e), thereby determining the yield of the nucleic acid in step c); g) processing the unprocessed sample, thereby obtaining a processed sample suitable for dPCR, wherein the processing steps c) and g) are identical; h) performing the dPCR with the processed sample, thereby determining the amount or concentration of the nucleic acid of interest; and i) determining the amount or concentration of the nucleic acid of interest in the unprocessed sample based on the amount or concentration of the nucleic acid of interest in the processed sample determined in step i) and the yield determined in step f). In some embodiments, (i) the amount or concentration of the reference nucleic acid in the reference sample is compared to a reference value, thereby controlling the reference sample; (ii) the amount or concentration of the reference nucleic acid in the reference sample is unknown or not predetermined; and/or (iii) the amount or concentration of the reference sample in step e) is identical to that in step b). In addition, the reference nucleic acid has one or more of the following characteristics: (i) is a nucleic acid selected from the group consisting of DNA, cDNA, RNA and a mixture thereof; (ii) has the same primer binding site as the nucleic acid of interest; (iii) has a primer binding site different from that of the nucleic acid of interest; (iv) has a length in nucleic acids that differs from that of the nucleic acid of interest by at most 50%, at most 25%, at most 10% or at most 5%; (v) has a sequence that is at least 50% identical, at least 60%, at least 70% or at least 80% identical to that of the nucleic acid of interest; (vi) has a content of G and C that differs from that of the nucleic acid of interest by at most 50%, at most 25%, at most 10% or at most 5%; and (vii) comprises a part that is not part of the nucleic acid of interest and that is used for detecting the reference nucleic acid. Moreover, the nucleic acid of interest has one or more of the following characteristics: (i) is a nucleic acid selected from the group consisting of DNA, cDNA, RNA and a mixture thereof; (ii) comprises a part that is not part of the reference nucleic acid and that is used for detecting the nucleic acid of interest; and (iii) is indicative of a microorganism, a cell, a virus, a bacterium, a fungus, a mammal species, a genetic status or a disease. Still further, the unprocessed sample has one or more of the following characteristics: (i) has been obtained from a cell culture, a source suspected of being contaminated or a subject, particularly wherein the subject is selected from the group consisting of a human, an animal and a plant, especially a human; and (ii) is selected from the group consisting of a body fluid, blood, blood plasma, blood serum, urine, bile, cerebrospinal fluid, a swab, a clinical specimen, an organ sample and a tissue sample. The processing step can include one or more of the following processes: dilution, lysis, centrifugation, extraction, precipitation, filtration, and purification. In some embodiments, dPCR, is characterized by one or more of the following: (i) is carried out in a liquid, in a gel, in an emulsion, in a droplet, in a microarray of miniaturized chambers, in a chamber of a microfluidic device, in a microwell plate, on a chip, in a capillary, on a nucleic acid binding surface or on a bead, especially in a microarray or on a chip; (ii) is carried out identically in at least 100 reaction areas, particularly at least 1,000 reaction areas, especially at least 5,000 reaction areas; and (iii) is carried out identically in at least 10,000 reaction areas, particularly at least 50,000 reaction areas, especially at least 100,000 reaction areas. More specifically, steps d) and e) are carried out in the same dPCR run and/or on the same dPCR device. In a further embodiment, dPCR, comprises using one or more fluorescent probes, alone or in combination with a quencher, to detect the nucleic acid of interest and/or the reference nucleic acid. In a specific embodiment, the fluorescent probe comprises fluorescein, rhodamine, or cyanine. In this embodiment, the determining step comprises detecting a fluorescent signal. In some embodiments, an external control is used. In a specific embodiment, the method is used to diagnose the presence or absence of a disease, a pathogen, a rare genetic sequence, a rare mutation, a copy number variation or relative gene expression. Optionally, the method is used to monitor disease progression, therapeutic response, and combinations thereof.

In some embodiments, detection of a genetic biomarker (e.g., one or more genetic biomarkers) can include any of the variety of methods described in U.S. Patent Application Publication No. 2014/0128270, which is hereby incorporated by reference in its entirety. For example, detection of a genetic biomarker can include a method of interrogating a sequence of a target nucleic acid having a sense and an anti-sense strands by a microarray analysis comprising a sequence determination computation, comprising omitting from the computation a signal from one of the sense and anti-sense strands for one or more nucleotide positions in the target nucleic acid sequence. In variations of this embodiment, omitting the signal from one of the sense and anti-sense strands at a nucleotide position comprises the steps of using a plurality of microarrays, measuring hybridization signals at the nucleotide position using one or more probe sets for each of the sense and the anti-sense strands; for each probe set, determining base discrimination ability by comparing the hybridization signals within each probe set; for each nucleotide position, computing discrimination ability for sense and antisense strand separately using the computed discrimination ability from each of the probe sets; for each nucleotide position, comparing the computed discrimination ability between the sense and the anti-sense strands; omitting the signal from the strand with lower base discrimination ability. In variations of this embodiment, the base discrimination is measured using Formula 1. In further variations of this embodiment, the discrimination ability for sense and antisense strand is computed as a percentile of the discrimination ability for probe sets in the strand at the base position. In yet further variations of this embodiment, the discrimination ability between sense and antisense strand is compared using Formula 3:

Formula 3

$$Q_{75i} < Q_{75j} - T, \text{for } Q_{75i} < PT \quad (1)$$

$$Q_{75i} < A(Q_{75j} - B)^2 + PT, \text{for } Q_{75i} \geq PT \quad (2)$$

Additionally or alternatively, detection of a genetic biomarker can include a method of detecting the presence or absence of a target nucleic acid having a sense and an anti-sense strands in a test sample using a microarray analysis including a sequence determination or mutation detection computation, comprising omitting from the computation a signal from one of the sense and anti-sense strands for one or more nucleotide positions in the target nucleic acid sequence. In variations of this embodiment, omitting the signal from one of the sense and anti-sense strands at a nucleotide position comprises the steps of: using a plurality of microarrays, measuring hybridization signals at the nucleotide position using one or more probe sets for each of the sense and the anti-sense strands; for each probe set, determining base discrimination by comparing the hybridization signals within each probe set; for each nucleotide position, computing discrimination ability for sense and antisense strand separately using discrimination ability from each of the probe sets; for each nucleotide position, comparing discrimination ability between the sense and the anti-sense strands; omitting the signal from a strand with lower base discrimination ability. In variations of this embodiment, the base discrimination is measured using Formula 1. In further variations of this embodiment, the discrimination ability of the sense and anti-sense strand is computed as a percentile of the discrimination ability for probe sets in the strand at the base position measured using a plurality of microarrays. Additionally or alternatively, detection of a genetic biomarker can include a computer readable medium including code for controlling one or more processors to detect the presence or absence of a target nucleic acid having a sense and an anti-sense strands in a test sample using a microarray analysis that includes a sequence determination or mutation detection computation, comprising omitting from the computation a signal from one of the sense and anti-sense strands for one or more nucleotide positions in the target nucleic acid sequence. In variations of this embodiment, the computer readable medium comprises a code controlling the steps of: using a plurality of microarrays, measuring hybridization signals at the nucleotide position using one or more probe sets for each of the sense and the anti-sense strands; for each probe set, determining base discrimination ability by comparing the hybridization signals within each probe set; for each nucleotide position, computing discrimination ability for sense and antisense strand separately using discrimination ability from each of the probe sets; for each nucleotide position, comparing discrimination ability between the sense and the anti-sense strands; omitting the signal from a strand with lower base discrimination ability. Additionally or alternatively, detection of a genetic biomarker can include a system for detecting a target nucleic acid in a test sample comprising: a data acquisition module configured to acquire hybridization data from a microarray; a data processing unit configured to process the data to determine a target nucleotide sequence by omitting the signal from one of the sense and anti-sense strands at one or more nucleotide positions in the target sequence via the steps of: using a plurality of microarrays, measuring hybridization signals at the nucleotide position using one or more probe sets for each of the sense and the anti-sense strands; for each probe set, determining base discrimination ability by comparing the hybridization signals within each probe set; for each nucleotide position, computing discrimination ability for sense and antisense strand separately using discrimination ability from each of the probe sets; for each nucleotide position, comparing discrimination ability between the sense and the anti-sense strands; omitting the signal from a strand with lower base discrimination ability; and a display module configured to display the data produced by the data processing unit.

In some embodiments, detection of a genetic biomarker (e.g., one or more genetic biomarkers) can include any of the variety of methods described in U.S. Patent Application Publication No. 2002/0160404, which is hereby incorporated by reference in its entirety. For example, detection of a genetic biomarker can include a method for the amplification of nucleic acid fragments from a sample comprising two or three thermocyclic amplification reactions in which completely randomized primers are used in the first amplification reaction and specific primers are used in the second amplification reaction, characterized in that, to amplify the DNA, a mixture of at least two DNA polymerases is used, at least one of which possesses 3'-5' exonuclease activity. An amplification reaction can comprise about 20 to 60 thermal cycles. The first amplification reaction preferably comprises at least 40 thermal cycles and, most preferably, at least 50 thermal cycles. The second amplification reaction preferably comprises at least 30 thermal cycles, and most preferably, at least 40 thermal cycles. Each thermal cycle comprises a denaturing phase, an annealing phase, and at least one elongation phase. Denaturation into single strands preferably takes place at temperatures of between 90° C. and 96° C. The annealing phase to hybridize the primers with the target nucleic acid preferably takes place at temperatures of between 30° C. and 50° C. Most preferably, the annealing phase takes place at temperatures of between 35° C. and 45° C. During the first amplification reaction, the annealing phase most preferably takes place at about 37° C. The elongation phase is carried out at temperatures of between 50° C. and 75° C. In a preferred embodiment, the elongation phase of the first amplification reaction takes place at temperatures of between 50° C. and 60° C. A temperature of about 55° C. is especially preferred. It is advantageous for the elongation to be carried out during the first amplification reaction in the majority of cycles using two or more elongation steps, with one elongation carried out at a lower temperature and then continuing the elongation at a higher temperature. Using this approach, populations of especially long amplicons are created during the first amplification reaction. In this embodiment, the first amplification reaction preferably takes place at about 55° C., and the second amplification reaction takes place at about 65° C. to 72° C. A temperature of about 68° C. is optimal. The primers used in the first amplification reaction are completely randomized, i.e., a population of single-stranded oligonucleotides is used in which every single nucleotide on every single position can comprise one of four nucleotide components A, T, G, or C. These primers are preferably 10-20 nucleotides long. Most preferably, the primers are about 15 nucleotides long. The specific primers used in the second amplification reaction are characterized in that they have a sequence that is identical to a sequence of the target nucleic acid or its complementary sequence over a range of at least 10 nucleotides. The specific primers used to carry out a "nested PCR" in a potential third amplification reaction are selected according to the same criteria as the primers used in the second amplification reaction. The sequences of the primers used that are identical to the target nucleic acid or its complement must be a component of the sequence amplified in the second amplification reaction. The mixture of DNA polymerases preferably contains a thermostable DNA polymerase without 3'-5' exonuclease activity such as Taq DNA polymerase, for instance, and another thermostable DNA polymerase with 3'-5' exonuclease activity, such as Pwo DNA polymerase obtained from Pyrokokkus woesii (Boehringer Mannheim order no. 1644947). Other DNA polymerases without 3'-5' exonuclease activity can also be used as a component of the polymerase mixture. Additionally or alternatively, detection of a genetic biomarker can include a method for DNA amplification. To ensure the sensitivity of detecting certain sequences, it is advantageous to carry out the cell analysis of the material to be analyzed using enzymatic protease digestion to obtain the sample DNA. Proteinase K can be used, for instance. Additionally or alternatively, detection of a genetic biomarker can include a method in which RNA is first isolated from the physical material to be analyzed. The sample of physical material can comprise one cell, fewer than 10 cells, or fewer than 100 cells. To obtain RNA, it is preferable to use chemical lysis using buffers that contain guanidinum isothiocynate. A corresponding cDNA is then created using a reverse transcriptase reaction. This cDNA is then used as the starting material for the primer-extension preamplification. The cDNA is preferably obtained via reverse transcription of poly-A RNA. The use of polymerase mixtures in the primer-extension preamplification PCR leads to a surprisingly high sensitivity of DNA detection that cannot be achieved using the methods known from the prior art. Additionally or alternatively, detection of a genetic biomarker can include a method for the amplification of nucleic acid fragments comprising two or three thermocyclic amplification reactions. Completely randomized primers are used in the first amplification reaction and specific primers are used in the second amplification reaction. In addition, the sample contains a quantity of nucleic acid corresponding to an equivalent of no more than 100 cells. In some embodiments, the likelihood of the amplificates forming is greater than 90%. In some embodiments, the likelihood is greater than 90% that amplificates will form from an equivalent of no more than 5-10 cells. In a special embodiment, the likelihood of amplificates forming from the equivalent of one cell is greater than 50%. The method is suitable for use in the amplification of nucleic acid fragments having a length between 100 and 1000 base pairs. The method is especially suited for use in the amplification of nucleic acid fragments having a length between 150 and 550 base pairs.

In some embodiments, detection of a genetic biomarker (e.g., one or more genetic biomarkers) can include any of the variety of methods described in U.S. Pat. No. 8,658,572, which is hereby incorporated by reference in its entirety. For example, detection of a genetic biomarker can include a microarray with high density of oligopeptide features, thereby allowing for the detection of protein interactions across an organism's proteome. An embodiment is a microarray comprising at least 50,000 oligopeptide features per cm2. Another embodiment is a microarray having oligopeptide features representing at least 50%, at least 60%, at least 70%, at least 80%, at least 90%, at least 95%, at least 99%, or 100% of the proteome of a target selected from a virus or organism. Additionally or alternatively, detection of a genetic biomarker can include a microarray comprising at least 50,000 oligopeptide features per cm2 wherein the features represent between about 90% and 100% of a target proteome, the target selected from a virus and an organism, and wherein at least a portion of the features comprise oligopeptides having a terminal 2-(2-nitro-4-benzoyl-phenyl)-propoxycarbonyl(benzoyl-NPPOC)-protected tyrosine residue.

In some embodiments, detection of a genetic biomarker (e.g., one or more genetic biomarkers) can include any of the variety of methods described in U.S. Pat. No. 8,822,158, which is hereby incorporated by reference in its entirety. For example, detection of a genetic biomarker can include a method for treating multiple nucleic acid molecules of interest comprising in the steps of: (a) providing a plurality of beads, characterized in that each bead comprises at least one pair of sequence specific amplification primers, further characterized in that at least one of said primers is bound to the bead via a photo-cleavable linker, (b) capturing the nucleic acid molecules of interest from a sample, (c) clonally isolating said plurality of beads, (d) photo-cleaving said at least one primer, (e) clonally amplifying said nucleic acid thereby creating multiple amplification products, and (f) analyzing said amplification products. In a first major embodiment, step c) comprises the generation of an emulsion wherein each bead is encapsulated in a single micelle. Preferably, step f) comprises the distribution of said plurality of beads into the cavities of a micro- or picotiter plate and detecting said amplification products. In a first particular embodiment, step f) further comprises a sequencing reaction of said amplification products. Preferably, said sequencing reaction is a sequencing by synthesis reaction, for example a pyrosequencing reaction. In case the multiple nucleic acid molecules are variants of the same type of nucleic acid, such a method may be used for quantitative mutational analysis.

In case the plurality of molecules corresponds to a plurality of different cellular RNAs or their corresponding cDNAs, such a method may be used for monitoring gene expression. In a second particular embodiment, the generation of said amplification products for example by means of PCR is monitored. Preferably, said amplification products are detected by means of a specifically double-stranded DNA binding fluorescent entity, a sequence specific hybridization probe: Furthermore, said amplification products may be analyzed by means of subjecting said amplification products to a thermal gradient. In a second major embodiment, step c) comprises the distribution of said plurality of beads into the cavities of a micro- or picotiter plate. Preferably, steps e) and f) are performed simultaneously by means of Real Time PCR. Subsequent to PCR, a melting curve analysis may be performed. In some embodiments, at least one primer which is bound to the bead via a cleavable linker carries a detectable tag. Preferably, said detectable tag is selected from a group consisting of mass-tag, color label, e-tag and a hapten which is detectable by an antibody. Highly preferred is a fluorescent label which is preferably quenched as long as said labeled primer has not been elongated. Alternatively; the cleavable primer carries a detectable tag. In this case, said amplification products are detected using labeled primers or labeled dNTPs. For example, the detectable tag may be a hapten such as Biotin or Digoxygenin. In a particular embodiment, each member of the plurality of primers which are bound to the bead via a cleavable linker carries a different detectable label.

In some embodiments, detection of a genetic biomarker (e.g., one or more genetic biomarkers) can include any of the variety of methods described in U.S. Patent Application Publication No. 2015/0024948, which is hereby incorporated by reference in its entirety. For example, detection of a genetic biomarker can include a system and methods for the enrichment and analysis of nucleic acid sequences. Additionally or alternatively, detection of a genetic biomarker can include the enrichment of targeted sequences in a format by representing one fusion partner gene on a capturing platform and allowing subsequent sequencing of chimeric nucleic acids such as nucleic acid strands that carry information on different DNA regions of a genome. Additionally or alternatively, detection of a genetic biomarker can include a method for detecting balanced chromosomal aberrations in a genome is provided. The method comprises the steps of: (a) exposing fragmented, denatured nucleic acid molecules of said genome to multiple, different oligonucleotide probes located on multiple, different sites of a solid support under hybridizing conditions to capture nucleic acid molecules that specifically hybridize to said probes, wherein said fragmented, denatured nucleic acid molecules have an average size of about 100 to about 1000 nucleotide residues, preferably about 250 to about 800 nucleotide residues and most preferably about 400 to about 600 nucleotide residues, in particular about 500 nucleotide residues, wherein said oligonucleotide probes have an average size of about 20 to about 100 nucleotides, preferably about 40 to about 85 nucleotides, more preferred about 45 to about 75 nucleotides, in particular about 55 to about 65 nucleotide residues or about 60 nucleotide residues, (b) separating unbound and non-specifically hybridized nucleic acids from the captured molecules; (c) eluting the captured molecules from the solid support, (d) optionally repeating steps (a) to (c) for at least one further cycle with the eluted captured molecules, (e) determining the nucleic acid sequence of the captured molecules, in particular by means of performing sequencing by synthesis reactions, (f) comparing the determined sequence to sequences in a database of the reference genome, (g) identifying sequences in the determined sequence which only partially match or do not match with sequences of the reference genome, (h) detecting at least one balanced chromosomal aberration. Additionally or alternatively, detection of a genetic biomarker can include pre-selected, immobilized nucleic acid probes for capturing target nucleic acid sequences from, for example, a genomic sample by hybridizing the sample to probes on a solid support is provided. According to some embodiments, the captured target nucleic acids may be washed and eluted off of the probes. In some cases, the eluted genomic sequences may be more amenable to detailed genetic analysis than a sample that has not been subjected to the methods. Additionally or alternatively, detection of a genetic biomarker can include the solution based capture method comprising probe derived amplicons wherein said probes for amplification are affixed to a solid support. The solid support comprises support-immobilized nucleic acid probes to capture specific nucleic acid sequences from a genomic sample. Probe amplification provides probe amplicons in solution which are hybridized to target sequences. Following hybridization of probe amplicons to target sequences, target nucleic acid sequences present in the sample are enriched by capturing and washing the probes and eluting the hybridized target nucleic acids from the captured probes. The target nucleic acid sequence(s) may be further amplified using, for example, non-specific ligation-mediated PCR (LM-PCR), resulting in an amplified pool of PCR products of reduced complexity compared to the original target sample which is further analysed by sequencing as described above. Additionally or alternatively, detection of a genetic biomarker can include a method for detecting balanced chromosomal aberrations in a genome of an organism is provided. The method comprises the steps of exposing fragmented, denatured nucleic acid molecules of the genome to a plurality of oligonucleotide probes bound to different positions of a solid support. The nucleic acid molecules have an average size of about 100 to about 1000 nucleotide residues and the oligonucleotide probes have an average size of about 20 to about 100 nucleotide residues. The method also includes the step of separating nucleic acid molecules bound to one or more of the oligonucleotide probes from nucleic acid molecules not bound to one or more of the oligonucleotide probes and then eluting the nucleic acid molecules bound to one or more of the oligonucleotide probes from the solid support. Thereafter, the nucleic acid molecules which were eluted in the step of eluting are sequenced, thereby getting a determined sequence for the nucleic acid molecules. Also, the method includes the step of comparing the determined sequence to a database comprising a reference genome sequence and identifying sequences in the determined sequence which only partially match or do not match with sequences of the reference genome, thereby detecting at least one balanced chromosomal aberration. In some embodiments, the oligonucleotide probes include a linker for binding to the solid support. In various embodiments, the linker may comprise a chemical linker. In some embodiments, the method may further include the steps of ligating at least one adaptor molecule to at least one end of the nucleic acid molecules prior to step exposing and amplifying the nucleic acid molecules which bound to one or more of the oligonucleotide probes with at least one primer comprising a sequence which specifically hybridizes to the adaptor molecule, whereby the step of amplifying is carried out after the step of eluting. Further, according to some embodiments, the solid support is either a nucleic acid microarray or a population of beads. In some embodiments, the method of detecting balanced chromosomal aberrations in a genome. The method includes the steps of providing a solid support comprising a plurality of different oligonucleotide probes bound to different positions of the solid support, wherein the oligonucleotide probes have an average size of about 20 to about 100 nucleotides, and providing a plurality of fragmented and denatured nucleic acid molecules having an average size of about 100 to about 1000 nucleotide residues. The method also includes the step of amplifying the oligonucleotide probes, thereby generating amplification products including a binding moiety and being maintained in solution. Thereafter, the method includes the steps of hybridizing the target nucleic acid molecules to the amplification products in solution under specific hybridizing conditions, thereby generating a plurality of hybridization complexes, and separating the hybridization complexes from nucleic acid molecules not hybridized to the amplification products. Next, according to the method, the hybridized target nucleic acid molecules are separated from the amplification product comprising the hybridization complex and sequenced, whereby a determined sequence for the nucleic acid molecules is obtained. According to the method, the determined sequence is compared to a database comprising a reference genome and sequences in the determined sequence which only partially match or do not match with sequences of the reference genome are determined in order for detecting at least one balanced chromosomal aberration. In some embodiments, the binding moiety is a biotin moiety. According to some embodiments, oligonucleotide probes having highly repetitive sequences are not used. Further, in some embodiments, the balanced chromosomal aberrations identified may include translocations or inversions.

In some embodiments, detection of a genetic biomarker (e.g., one or more genetic biomarkers) can include any of the variety of methods described in U.S. Pat. No. 6,514,736, which is hereby incorporated by reference in its entirety. For example, detection of a genetic biomarker can include a process for amplifying one or more specific nucleic acid sequences present in a nucleic acid or mixture thereof using primers and a thermostable enzyme. The extension product of one primer when hybridized to the other becomes a template for the production of the desired specific nucleic acid sequence, and vice versa, and the process is repeated as often as is necessary to produce the desired amount of the sequence. The method improves the specificity of the amplification reaction, resulting in a very distinct signal of amplified nucleic acid. In addition, the method eliminates the need for transferring reagents from one vessel to another after each amplification cycle. Such transferring is not required because the thermostable enzyme will withstand the high temperatures required to denature the nucleic acid strands and therefore does not need replacement. The temperature cycling may, in addition, be automated for further reduction in manpower and steps required to effectuate the amplification reaction. Additionally or alternatively, detection of a genetic biomarker can include a process for amplifying at least one specific nucleic acid sequence contained in a nucleic acid or a mixture of nucleic acids, wherein if the nucleic acid is double-stranded, it consists of two separated complementary strands of equal or unequal length, which process comprises: (a) contacting each nucleic acid strand with four different nucleoside triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand; (b) contacting each nucleic acid strand, at the same time as or after step (a), with a thermostable enzyme which enables combination of the; nucleoside triphosphates to form primer extension products complementary to each strand of each nucleic acid; (c) maintaining the mixture from step (b) at an effective temperature for an effective time to activate the enzyme, and to synthesize, for each different sequence being amplified, an extension product of each primer which is complementary to each nucleic acid strand template, but not so high (a temperature) as to separate each extension product from its complementary strand template; (d) heating the mixture from step (c) for an effective time and at an effective temperature to separate the primer extension products from the templates on which they were synthesized to produce single-stranded molecules, but not so high (a temperature) as to denature irreversibly the enzyme; (e) cooling the mixture from step (d) at an effective temperature for an effective time to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high (a temperature) as to separate each extension product from its complementary strand template, wherein steps (e) and (f) are carried out simultaneously or sequentially. The steps (d), (e) and (f) may be repeated until the desired level of sequence amplification is obtained. The preferred thermostable enzyme is a polymerase extracted from *Thermus aquaticus* (Taq polymerase). Most preferably, if the enzyme is Taq polymerase, in step (a) the nucleic acid strands are contacted with a buffer comprising about 1.5-2 mM of a magnesium salt, 150-200 µM each of the nucleotides, and 1 M of each primer, steps (a), (e) and (f) are carried out at about 45-58° C., and step (d) is carried out at about 90-100° C. In a preferred embodiment, the nucleic acid(s) are double-stranded and step (a) is accomplished by (i) heating each nucleic acid in the presence of four different nucleoside triphosphates and one oligonucleotide primer for each different specific sequence being amplified, for an effective time and at an effective temperature to denature each nucleic acid, wherein each primer is selected to be substantially complementary to different strands of each specific sequence, such that the extension product synthesized from one primer, when it is separated from its complement, can serve as a template for synthesis of the extension product of the other primer; and (ii) cooling the denatured nucleic acids to a temperature which promotes hybridization of each primer to its complementary nucleic acid strand. Additionally or alternatively, detection of a genetic biomarker can include a process for detecting the presence or absence of at least one specific nucleic acid sequence in a sample containing a nucleic acid or mixture of nucleic acids, or distinguishing between two different sequences in said sample, wherein the sample is suspected of containing said sequence or sequences, and wherein if the nucleic acid(s) are double-stranded, they each consist of two separated complementary strands of equal or unequal length, which process comprises steps (a) to (f) mentioned above, resulting in amplification in quantity of the specific nucleic acid sequence(s), if present; (g) adding to the product of step (f) a labeled oligonucleotide probe, for each sequence being detected, capable of hybridizing to said sequence or to a mutation thereof; and (h) determining whether said hybridization has occurred. Additionally or alternatively, detection of a genetic biomarker can include a process for detecting the presence or absence of at least one nucleotide variation in sequence in one or more nucleic acids contained in a sample, wherein if the nucleic acid is double-stranded it consists of two separated complementary strands of equal or unequal length, which process comprises steps (a)-(f) mentioned above, wherein steps (d), (e) and (f) are repeated a sufficient number of times to result in detectable amplification of the nucleic acid containing the sequence, if present; (g) affixing the product of step (f) to a membrane; (h) treating the membrane under hybridization conditions with a labeled sequence-specific oligonucleotide probe capable of hybridizing with the amplified nucleic acid sequence only if a sequence of the probe is complementary to a region of the amplified sequence; and (i) detecting whether the probe has hybridized to an amplified sequence in the nucleic acid sample. If the sample comprises cells, preferably they are heated before step (a) to expose the nucleic acids therein to the reagents. This step avoids extraction of the nucleic acids prior to reagent addition. In a variation of this process, the primer(s) and/or nucleoside triphosphates are labeled so that the resulting amplified sequence is labeled. The labeled primer(s) and/or nucleoside triphosphate(s) can be present in the reaction mixture initially or added during a later cycle. The sequence-specific oligonucleotide (unlabeled) is affixed to a membrane and treated under hybridization conditions with the labeled amplification product so that hybridization will occur only if the membrane-bound sequence is present in the amplification product. Additionally or alternatively, detection of a genetic biomarker can include a process for cloning into a cloning vector one or more specific nucleic acid sequences contained in a nucleic acid or a mixture of nucleic acids, which nucleic acid(s) when double-stranded consist of two separated complementary strands, and which nucleic acid(s) are amplified in quantity before cloning, which process comprises steps (a)-(f) mentioned above, with steps (d), (e) and (f) being repeated a sufficient number of times to result in detectable amplification of the nucleic acid(s) containing the sequence(s); (g) adding to the product of step (f) a restriction enzyme for each of said restriction sites to obtain cleaved products in a restriction digest; and (h) ligating the cleaved product(s) of step (g) containing the specific sequencels) to be cloned into one or more cloning vectors containing a promoter and a selectable marker. Additionally or alternatively, detection of a genetic biomarker can include a process for cloning into a cloning vector one or more specific nucleic acid sequences contained in a nucleic acid or mixture of nucleic acids, which nucleic acid(s), when double-stranded, consist of two separated complementary strands of equal or unequal length which nucleic acid(s) are amplified in quantity before cloning, which process comprises steps (a)-(f) mentioned above, with steps (d), (e) and (f) being repeated a sufficient number of times to result in effective amplification of the nucleic acid(s) containing the sequence(s) for blunt-end ligation into one or more cloning vectors; and (g) ligating the amplified specific sequence(s) to be cloned obtained from step (f) into one or more of said cloning vectors in the presence of a ligase, said amplified sequence(s) and vector(s) being present in sufficient amounts to effect the ligation. Additionally or alternatively, detection of a genetic biomarker can include a composition of matter useful in amplifying at least one specific nucleic acid sequence contained in a nucleic acid or a mixture of nucleic acids, comprising four different nucleoside triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer. Additionally or alternatively, detection of a genetic biomarker can include a sample of one or more nucleic acids comprising multiple strands of a specific nucleic acid sequence contained in the nucleic acid(s). The sample may comprise about 10-100 of the strands, about 100-1000 of the strands, or over about 1000 of the strands. Additionally or alternatively, detection of a genetic biomarker can include an amplified nucleic acid sequence from a nucleic acid or mixture of nucleic acids comprising multiple copies of the sequence produced by the amplification above processes.

In some embodiments, detection of a genetic biomarker (e.g., one or more genetic biomarkers) can include any of the variety of methods described in P.C.T. Publication No. WO 2017/181134, which is hereby incorporated by reference in its entirety. For example, detection of a genetic biomarker can include techniques for identifying driver genes, mutations, and/or pathways for various types of cancer. For example, the identified driver genes may be used for diagnosis by identifying mutations occurring on the identified driver genes, or for treatment by targeting the identified driver genes. In some embodiments, a driver gene may be identified by determining a gene-specific background mutation rate. In some embodiments, a statistical model for gene-specific background mutation rate may be determined by optimizing parameters estimated from single-gene and cross-genes modeling. In one example, the gene-specific background mutation can be statistically determined by recursively optimizing a gene-specific mean and a gene-specific dispersion using negative binomial regression and Bayesian inference. Genes, mutations, and/or pathways that have significantly more mutations than the expected background mutations across samples may be identified as candidate driver genes, mutations, and/or pathways. Additionally or alternatively, detection of a genetic biomarker can include a method comprising: for each sample of a plurality of samples from different subjects having a same type of cancer, receiving a set of one or more mutations in DNA measured in the sample, the DNA including a plurality of genes; for each sample of the plurality of samples, determining a sample mutation rate based on a total number of mutations measured in the sample; for each mutation context of a plurality of mutation contexts, determining a context mutation rate based on a first number of mutations identified in the sets of mutations for the mutation context, wherein a mutation context corresponds to a type of substitution or deletion; for each gene of the plurality of genes, determining, for each sample of the plurality of samples, a second number of silent mutations measured in the gene in the sample; determining an expected silent mutation rate using a sum of context mutation rates of silent mutations in the gene, wherein a silent mutation does not cause a change to an amino acid sequence of a translated protein for the gene; determining a probability distribution of gene-specific background mutation rate across the plurality of samples for the gene based on the expected silent mutation rate for the gene and the sample mutation rates of the plurality of samples, wherein determining the probability distribution of gene-specific background mutation rate for the gene includes: optimizing one or more parameters of the probability distribution of gene-specific background mutation rate for the gene to increase a fit of the probability distribution to the second number of silent mutations; determining an expected non-silent mutation rate using a sum of context mutation rates of a subset of non-silent mutations in the gene; determining an expected number of samples having at least one non-silent mutation using the expected non-silent mutation rate and the probability distribution of the gene-specific background mutation rate for the gene; and comparing the expected number to the measured number of samples having at least one non-silent mutation to obtain a likelihood value for the measured number; and identifying a group of genes having likelihood values above a threshold as candidate driver genes.

In some embodiments, detection of a genetic biomarker (e.g., one or more genetic biomarkers) can include any of the variety of methods described in P.C.T. Publication No. WO 2017/201315, which is hereby incorporated by reference in its entirety. For example, detection of a genetic biomarker can include an automated nucleic acid amplification method which may comprise the following steps: (a) providing at least two droplets, wherein each droplet comprises primers that anneal to a target nucleic acid; (b) amplifying the target nucleic acid in each said droplet in parallel; (c) quantitating the amplified target nucleic acid in at least one droplet; and (d) after a desired amount of the target nucleic acid has been obtained, recovering at least one droplet for further analyzing or processing of said at least one droplet. Additionally or alternatively, detection of a genetic biomarker can include an automated nucleic acid amplification method which may comprise the following steps: (a) providing at least two droplets, wherein each droplet comprises a target nucleic acid; (b) amplifying the target nucleic acid in each said droplet in parallel; (c) quantitating the amplified target nucleic acid in at least one droplet; and (d) after a desired amount of the target nucleic acid has been obtained, recovering at least one droplet for further analyzing or processing of said at least one droplet. In an embodiment, said droplets may be provided on an electrowetting-based device. Additionally or alternatively, detection of a genetic biomarker can include an automated nucleic acid amplification method which comprises the following steps: (a) providing an electrowetting-based device; (b) providing at least two droplets on said electrowetting-based device, wherein each droplet comprises primers that anneal to a target nucleic acid; (c) amplifying the target nucleic acid in each said droplet in parallel; (d) quantitating the amplified target nucleic acid in at least one droplet; and (e) after a desired amount of the target nucleic acid has been obtained, recovering at least one droplet using for further analyzing or processing of said at least one droplet. Additionally or alternatively, detection of a genetic biomarker can include an automated nucleic acid amplification method which comprises the following steps: (a) providing an electrowetting-based device; (b) providing at least two droplets on said electrowetting-based device, wherein each droplet comprises a target nucleic acid; (c) amplifying the target nucleic acid in each said droplet in parallel; (d) quantitating the amplified target nucleic acid in at least one droplet; and (e) after a desired amount of the target nucleic acid has been obtained, recovering at least one droplet using for further analyzing or processing of said at least one droplet. In some embodiments, said droplets may each may comprise a different target nucleic acid. Additionally or alternatively, detection of a genetic biomarker can include a method wherein said droplets each may comprise the same target nucleic acid. Additionally or alternatively, detection of a genetic biomarker can include to a method wherein said droplet may comprise a mixture of droplets that contain the same target nucleic acid and different target nucleic acids. Additionally or alternatively, detection of a genetic biomarker can include a method wherein the electrowetting-based device may comprise a biplanar configuration of parallel arrays of electrodes to effect electrowetting-mediated droplet manipulations. Some embodiments relate to a method wherein the electrowetting-based device may comprise a planar configuration of electrodes that effects electrowetting-mediated droplet manipulations. Some embodiments relate to a method wherein the electrowetting-based device may comprise square electrodes, optionally wherein said electrodes are about 5 mm by 5 mm. Some embodiments relate to a method wherein the electrowetting-based device may comprise electrodes, wherein said electrodes are square, triangular, rectangular, circular, trapezoidal, and/or irregularly shaped. Some embodiments relate to a method wherein the electrowetting-based device may comprise electrodes wherein said electrodes may comprise electrode dimensions ranging from about 100μηι by 100μηι to about 10 cm by 10 cm. Some embodiments relate to a method wherein the electrowetting-based device may comprise interdigitated electrodes. Some embodiments relate to a method wherein the electrowetting-based device may comprise electrodes, wherein said electrodes may comprise indium tin oxide ("ITO"), transparent conductive oxides ("TCOs"), conductive polymers, carbon nanotubes ("CNT"), graphene, nanowire meshes and/or ultra thin metal films, e.g., ITO. Additionally or alternatively, detection of a genetic biomarker can include a method wherein the detection zone may detect electrochemical and/or fluorescent signals. Additionally or alternatively, detection of a genetic biomarker can include a method wherein said detection zone may detect capacitance of a droplet. An additional embodiment pertains to a method wherein said detection zone may be a fixed location. Another embodiment relates to a method wherein said detection zone may comprise any location within the electrowetting-based device. Yet another embodiment generally pertains to a method wherein the method of amplification may comprise hot start PCR. Additionally or alternatively, detection of a genetic biomarker can include a method wherein said amplification may comprise isothermal amplification. Additionally or alternatively, detection of a genetic biomarker can include a method wherein said amplification may comprise thermocycling. Said thermocycling may comprise temperatures ranging from about 50° C. to about 98° C., e.g., about 50° C., about 60° C., about 65° C., about 72° C., about 95° C., or about 98° C. Said thermocycling may comprise times ranging from about 1 s to about 5 min., e.g., about 1 sec, about 5 sec, about 10 sec, about 20 sec, about 30 sec, about 45 sec, about 1 min, and/or about 5 min. Furthermore, said thermocycling may comprise three thermocycle steps, and said three thermocycle steps may be completed in one minute or less. In some embodiments, each droplet may further comprise a detection agent. Additionally or alternatively, detection of a genetic biomarker can include a method wherein each droplet may contain the same detection agent. Additionally or alternatively, detection of a genetic biomarker can include a method wherein each droplet may contain a different detection agent. Another embodiment generally relates to a method wherein the droplets may comprise a labeled subset of droplets wherein each droplet within the subset contains an agent for detecting the target nucleic acid, and an unlabeled subset of droplets wherein each droplet within the subset does not contain said agent for detecting the target nucleic acid. An additional embodiment generally encompasses a method wherein each droplet within the subset containing a detection agent may comprise a different detection agent. Additionally or alternatively, detection of a genetic biomarker can include a method wherein each droplet within the subset containing a detection agent may comprise the same detection agent. In some embodiments, the nucleic acid polymerase may be a modified naturally occurring Type A polymerase. A further embodiment generally relates to a method wherein the modified Type A polymerase may be selected from any species of the genus *Meiothermus, Thermotoga*, or *Thermomicrobium*. Another embodiment generally pertains to a method wherein the polymerase may be isolated from any of *Thermus aquaticus* (Taq), *Thermus thermophilus, Thermus caldophilus*, or *Thermus filiformis*. A further embodiment generally encompasses a method wherein the modified Type A polymerase may be isolated from *Bacillus stearothermophilus, Sphaerobacter thermophilus, Dictoglomus thermophilum*, or *Escherichia coli*. Additionally or alternatively, detection of a genetic biomarker can include a method wherein the modified Type A polymerase may be a mutant 7α-E507K polymerase. Another embodiment generally pertains to a method wherein a thermostable polymerase may be used to effect amplification of the target nucleic acid. A further embodiment generally relates to a method wherein the thermostable polymerase may be selected from the following: *Thermotoga maritima, Thermus aquaticus, Thermus thermophilus, Thermus flavus, Thermus filiformis, Thermus* species Sps 1 7. *Thermus* species Z05, *Thermus caldophilus, Bacillus caldotenax, Thermotoga neopolitana*, and *Thermosipho africanus*. Additionally or alternatively, detection of a genetic biomarker can include a method wherein a modified polymerase may be used to effect amplification of the target nucleic acid, e.g., wherein said modified polymerase may be selected from the following: G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, AZ05 polymerase, AZ05-Gold polymerase, AZ05R polymerase, E615G Taq DNA polymerase, E678G TMA-25 polymerase, and E678G TMA-30 polymerase. Additionally or alternatively, detection of a genetic biomarker can include a method wherein detection of the detection agent may occur at the end of an amplification cycle. In some embodiments, the method may detect a single nucleotide polymorphism. An additional embodiment generally relates to a method wherein the method may be used for amplicon generation. In some embodiments, the method may be used for a melting curve analysis. In some embodiments, the method may be used for target nucleic acid enrichment. In some embodiments, the method may be used for primer extension target enrichment ("PETE"). In some embodiments, the method may be used to for library amplification In some embodiments, the method may be used quantitate the number of adapter-ligated target nucleic acid molecules during library preparation. Additionally or alternatively, detection of a genetic biomarker can include a method wherein said quantitation of the number of adapter-ligated target nucleic acid molecules may occur (a) after adapter ligation to determine the amount of input material converted to adapter-ligated molecules (conversion rate) and/or the quantity of template used for library amplification; (b) after library amplification, to determine whether a sufficient amount of each library has been generated and/or to ensure equal representation of indexed libraries pooled for target capture or cluster amplification; and/or (c) prior to cluster amplification, to confirm that individual libraries or sample pools are diluted to the optimal concentration for NGS flow cell loading. Additionally, said quantitation of the number of adapter-ligated target nucleic acid molecules may occur after post-ligation cleanup steps (prior to library amplification). In some embodiments, after recovering at least one droplet, said further analyzing or processing of said at least one droplet may comprise a nucleic acid sequencing reaction, a next generation sequencing reaction, whole-genome shotgun sequencing, whole exome or targeted sequencing, amplicon sequencing, mate pair sequencing, RIP-seq/CLIP-seq, ChIP-seq, RNA-seq, transcriptome analysis, and/or methyl-seq. Additionally or alternatively, detection of a genetic biomarker can include a method wherein the droplets may be surrounded by a filler fluid, e.g., wherein said filler fluid may be an oil. In some embodiments, said oil may comprise a transparent oil. In some embodiments, said oil may comprise liquid polymerized siloxane, silicone oil mineral oil, and/or paraffin oil. Another embodiment generally relates to method wherein the droplets may be surrounded by a gas, e.g., wherein said gas may be air. Yet another embodiment generally relates to a method wherein the method may be used to avoid over-amplification bias. Another embodiment generally relates to a method wherein the method may be used to produce a representative sample of a population of mutations. Additionally or alternatively, detection of a genetic biomarker can include a method wherein the method may be used to determine the number of amplification cycles necessary to generate the desired concentration of a target nucleic acid. Additionally or alternatively, detection of a genetic biomarker can include a method wherein the method may be controlled through a computer in communication with the electrowetting-based device. Some embodiments generally relate to a method wherein said method comprises a master mix. In some embodiments, said master mix may comprise a polymerase, dNTP(s), MgCl2, and/or oligonucleotide primer(s). In some embodiments, said master mix may comprise dNTP(s) at a concentration comprising from about 1 mM to about 100 mM, e.g., about 1 mM, about 10 mM, or about 100 mM; MgCl2 at a concentration comprising from about 1 mM to about 100 mM, e.g., about 1 mM, about 10 mM, or about 100 mM; and/or a oligonucleotide primer(s) at a concentration comprising from about 1 nM to about 1 mM, e.g., about 1 nM, about 1 uM, or about 1 mM. Additionally or alternatively, detection of a genetic biomarker can include a device for amplification of a target nucleic acid, wherein said device may (a) comprise a biplanar configuration of parallel arrays of electrodes to effect electrowetting-mediated droplet manipulations; (b) comprise or be in contact with at least one heating element; and (c) comprise or be in contact with at least one detection zone. In an embodiment, said heating element may comprise an inductive heating element. Another aspect generally pertains to a device for amplification of a target nucleic acid, wherein said device may (a) comprise a planar configuration of electrodes to effect electrowetting-mediated droplet manipulations; (b) comprise or be in contact with at least one heating element; and (c) comprise or be in contact with at least one detection zone. In an embodiment, said heating element may comprise an inductive heating element. In some embodiments, said electrodes may comprise square shapes, optionally about 5 mm by 5 mm. In some embodiments, said electrodes may comprise square, triangular, rectangular, circular, trapezoidal, and/or irregularly shapes. In some embodiments, said electrodes may comprise electrode dimensions ranging from about 100μτι by 100μτι to about 10 cm by 10 cm. In some embodiments, said electrodes may be interdigitated. In some embodiments, said electrodes may comprise indium tin oxide ("ITO"), transparent conductive oxides ("TCOs"), conductive polymers, carbon nanotubes ("CNT"), graphene, nanowire meshes and/or ultra thin metal films, e.g., ITO. In some embodiments, said device may comprise droplets that range in volume from about 1 picoliter to about 5 mL, e.g., about 12.5 ut. In some embodiments, said device may comprise a gap between a top plate and a bottom plate of about 0.5 mm. In some embodiments, said device may comprise a plurality of inlet/outlet ports. In some embodiments, said device may comprise between 1 to about 400 inlet/outlet ports for loading and removal of the same sample or of different samples, and/or said device further comprises between 1 to about 100 inlet/out ports for the introduction and removal of filler fluid(s). In some embodiments, said device may comprise inlet/outlet ports wherein the spacing between adjacent ports ranges from about 5 mm to about 500 mm. In a further embodiment, said heating element may comprise a contact heater. An additional aspect relates to an embodiment wherein said amplification comprises thermocycling. Said thermocycling may comprise three thermocycle steps, and said three thermocycle steps may be completed in one minute or less. In another embodiment, said amplification may comprise isothermal amplification. In a further embodiment, said amplification may comprise hot start PCR. In yet another embodiment, the detection zone may detect electrochemical and/or fluorescent signals. An additional embodiment pertains to a detection zone that may detect capacitance of a droplet. In a further embodiment, said detection zone may be a fixed location. In another embodiment, said detection zone may comprise any location within the electrowetting-based device. In another embodiment, the target nucleic acid may be provided on the device within at least three droplets. In a further embodiment, said droplets may each comprise the same target nucleic acid. In yet another embodiment, said droplets may comprise a mixture of droplets that contain the same target nucleic acid and different target nucleic acids. In another embodiment, each droplet may further comprise a detection agent. In an additional embodiment, each droplet may contain the same detection agent. In another embodiment, each droplet may contain a different detection agent. Additionally, in another embodiment, the droplets may comprise a labeled subset of droplets that each contain an agent for detecting the target nucleic acid, and an unlabeled subset of droplets that each do not contain said agent for detecting the target nucleic acid. In an additional embodiment, each droplet within the subset containing a detection agent may comprise a different detection agent. In another embodiment, each droplet within the subset containing a detection agent may comprise the same detection agent. In a further embodiment, each subset of droplets may comprise 1 or more, 2 or more, 10 or more, 100 or more, 1,000 or more, or 10,000 or more droplets. In some embodiments, the device may detect a single nucleotide polymorphism. In yet another embodiment, the device may effect amplicon generation. In an additional embodiment, the device may effect a melting curve analysis. In yet another embodiment, the device may effect target nucleic acid enrichment. In yet another embodiment, the device may effect PETE. In an additional embodiment, the device may effect library amplification. In a further embodiment, the device may quantitate the number of adapter-ligated target nucleic acid molecules during library preparation. For example, said quantitation may occur (a) after adapter ligation to determine the amount of input material converted to adapter-ligated molecules (conversion rate) and/or the quantity of template used for library amplification; (b) after library amplification, to determine whether a sufficient amount of each library has been generated and/or to ensure equal representation of indexed libraries pooled for target capture or cluster amplification; and/or (c) prior to cluster amplification, to confirm that individual libraries or sample pools are diluted to the optimal concentration for NGS flow cell loading. Also, said quantitation may occur after post-ligation cleanup steps (prior to library amplification). In yet another embodiment, after a desired amount of the target nucleic acid has been obtained, at least one droplet may be recovered from said device prior to further analysis or processing of said droplet. For example, said further analyzing or processing of said at least one droplet may comprise a nucleic acid sequencing reaction, a next generation sequencing reaction, whole-genome shotgun sequencing, whole exome or targeted sequencing, amplicon sequencing, mate pair sequencing, RIP-seq/CLIP-seq, ChIP-seq, RNA-seq, transcriptome analysis, and/or methyl-seq. Additionally or alternatively, detection of a genetic biomarker can include a system for automated amplification of a target nucleic acid which may comprise: (a) an electrowetting-based device; (b) at least one heating element that comprises or is in contact with the electrowetting-based device; (c) at least one detection zone that comprises or is in contact with the electrowetting-based device. In an embodiment, said heating element may comprise an inductive heating element. In a further embodiment, said heating element may comprise a contact heater. An additional aspect relates to an embodiment wherein said amplification comprises thermocycling. Said thermocycling may comprise three thermocycle steps, and said three thermocycle steps may be completed in one minute or less. In another embodiment, said amplification may comprise isothermal amplification. In a further embodiment, said amplification may comprise hot start PCR. In yet another embodiment, the detection zone may detect electrochemical and/or fluorescent signals. An additional embodiment pertains to a detection zone that may detect capacitance of a droplet. In a further embodiment, said detection zone may be a fixed location. In another embodiment, said detection zone may comprise any location within the system. In another embodiment, the target nucleic acid may be provided on the system within at least three droplets. In a further embodiment, said droplets may each comprise the same target nucleic acid. In yet another embodiment, said droplets may comprise a mixture of droplets that contain the same target nucleic acid and different target nucleic acids. In another embodiment, each droplet may further comprise a detection agent. In an additional embodiment, each droplet may contain the same detection agent. In another embodiment, each droplet may contain a different detection agent. Additionally, in another embodiment, the droplets may comprise a labeled subset of droplets that each contain an agent for detecting the target nucleic acid, and an unlabeled subset of droplets that each do not contain said agent for detecting the target nucleic acid. In an additional embodiment, each droplet within the subset containing a detection agent may comprise a different detection agent. In another embodiment, each droplet within the subset containing a detection agent may comprise the same detection agent. In a further embodiment, each subset of droplets may comprise 1 or more, 2 or more, 10 or more, 100 or more, 1,000 or more, or 10,000 or more droplets. Additionally or alternatively, detection of a genetic biomarker can include an automated amplification method which may comprise (a) providing an electrowetting-based device with a biplanar configuration of parallel arrays of electrodes to effect electrowetting-mediated droplet manipulations, and further wherein said device contains at least one inductive heating element and at least one detection zone; (b) providing on said device droplets comprising a target nucleic acid, wherein said droplets comprise a subset of droplets that contains an agent for target nucleic acid detection and a subset of droplets that does not contain said agent for target nucleic acid detection; (c) amplifying the target nucleic acid in each said droplet in parallel; (d) quantitating the amplified target nucleic acid in said subset of droplets containing said agent through detection of said agent; and (e) after a desired amount of said target nucleic acid has been obtained in said subset of droplets containing an agent, recovering at least one droplet from said subset of droplets not containing an agent for further analyzing or processing.

In some embodiments, detection of a genetic biomarker (e.g., one or more genetic biomarkers) can include any of the variety of methods described in P.C.T. Publication No. WO 2017/123316, which is hereby incorporated by reference in its entirety. For example, detection of a genetic biomarker can include a targeted sequencing workflow where an input sample comprising a sufficient quantity of genomic material is provided such that minimal or no amplification processes are required prior to sequencing. In some embodiments, the input sample is derived from an intact tumor or from lymph nodes. In some embodiments, the input sample is obtained through homogenization of an intact tumor sample (whole or partial) and/or one or more lymph nodes obtained from a patient or mammalian subject. In some embodiments, the input sample is derived from a sufficient quantity of blood, including whole blood or any fraction thereof. In some embodiments, the input sample is derived from cancerous tissue. In some embodiments, the input sample is derived from precancerous tissue. In some embodiments, the targeted sequencing workflow comprises one or more amplification steps (e.g. a pre-capture amplification step, an amplification step post-capture) prior to sequencing, where each amplification step prior to sequencing comprises from 0 to 3 amplification cycles, and wherein an aggregate of amplification cycles prior to sequencing does not exceed 4. In other embodiments, the targeted sequencing workflow comprises one or more amplification steps (e.g. a pre-capture amplification step, an amplification step post-capture) prior to sequencing, where each amplification step prior to sequencing comprises from 0 to 2 amplification cycles, and wherein an aggregate of amplification cycles prior to sequencing does not exceed 3. In yet other embodiments, the targeted sequencing workflow comprises one amplification step prior to sequencing (e.g. either a pre-capture amplification step or an amplification step post-capture), where the single amplification step prior to sequencing comprises from 0 to 3 amplification cycles. In further embodiments, the targeted sequencing workflow comprises one amplification step prior to sequencing, where the single amplification step prior to sequencing comprises from 1 to 3 cycles. In yet further embodiments, the targeted sequencing workflow comprises one amplification step prior to sequencing, where the single amplification step prior to sequencing comprises 1 cycle. In even further embodiments, the targeted sequencing workflow comprises one amplification step prior to sequencing, where the single amplification step prior to sequencing comprises 2 cycles. In some embodiments, either or both of the pre-capture amplification step or the amplification step post-capture but prior to sequencing utilizes LM-PCR. Additionally or alternatively, detection of a genetic biomarker can include a method of sequencing genomic material within a sample comprising: homogenizing a tumor sample and/or lymph node sample to provide a homogenized sample; isolating at least 0.5 micrograms of genomic material from the homogenized sample; preparing the at least 0.5 micrograms of isolated genomic material for sequencing; and sequencing the prepared genomic material. In some embodiments, the method does not comprise any amplification steps prior to sequencing. In some embodiments, the method comprises at least one pre-capture or post-capture amplification step, wherein an aggregate number of amplification cycles conducted during the at least one pre-capture or post-capture amplification step is at most 4 cycles. In some embodiments, the aggregate number of amplification cycles is 3. In some embodiments, the aggregate number of amplification cycles is 2. In some embodiments, the preparing of the at least 0.5 micrograms of isolated genomic material for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, the homogenized sample comprises a representative sampling of cells. In some embodiments, at least 1 microgram of genomic material is isolated from the homogenized samples. In some embodiments, at least 5 micrograms of genomic material is isolated from the homogenized samples. In some embodiments, at least 10 micrograms of genomic material is isolated from the homogenized samples. Additionally or alternatively, detection of a genetic biomarker can include a method of sequencing DNA within a sample comprising isolating at least 0.5 micrograms of DNA from a blood sample; preparing the at least 0.5 micrograms of isolated DNA for sequencing, and sequencing the prepared DNA. In some embodiments, the method comprises 0 amplification steps prior to sequencing. In some embodiments, the preparing of the at least 0.5 micrograms of isolated DNA for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, at least 1 microgram of DNA is isolated from the blood sample. Additionally or alternatively, detection of a genetic biomarker can include a method of targeted representational sequencing comprising: (i) homogenizing at least a portion of a tumor, one or more whole or partial lymph nodes, or any combination thereof to provide a homogenized sample; (ii) extracting genomic material from the homogenized sample; (iii) capturing the extracted genomic material onto beads; and (iv) sequencing the captured genomic material; wherein the targeted representational sequencing comprises performing at most 4 amplification cycles prior to sequencing of the captured genomic material. In some embodiments, the at most 3 amplification cycles may be conducted prior to capture of the extracted genomic material or after capture of the extracted genomic material, or any combination thereof. In some embodiments, no pre-capture amplification cycles are conducted. In some embodiments, an amount of captured genomic material ranges from about 90 ng to about 900 ng. In some embodiments, from 1 to 3 amplification cycles are performed following capture of the extracted genomic material, but prior to sequencing. In some embodiments, at least 0.5 micrograms of genomic material is extracted from the homogenized sample. In some embodiments, at least 100 times more genomic material is derived from the homogenized sample as compared with an amount of input material used in a sequencing method requiring more than 4 amplification cycles. Additionally or alternatively, detection of a genetic biomarker can include a method of sequencing DNA within a sample comprising: providing at least 0.5 micrograms of input genomic material, the at least 0.5 micrograms of genomic material derived from a tumor sample, a lymph node sample, or a blood sample, isolating DNA from the input genomic sample, preparing the isolated DNA for sequencing, and sequencing the prepared DNA, wherein the method does not comprise any amplification steps. In some embodiments, the at least 0.5 micrograms of input genomic material is derived from multiple histological and/or biopsy specimens. In some embodiments, the at least 0.5 micrograms of input genomic material is derived from a homogenized tumor sample. In some embodiments, the at least 0.5 micrograms of input genomic material is derived from a homogenized lymph node sample. In some embodiments, the at least 0.5 micrograms of input genomic material is a representative sampling of the tumor sample, lymph node sample, or blood sample from which it is derived. In some embodiments, the sequencing is performed using a next-generation sequencing method. In some embodiments, sequencing is performed using a synthesis sequencing methodology. Additionally or alternatively, detection of a genetic biomarker can include a method of reducing PCR-introduced mutations during sequencing comprising isolating DNA from a sample comprising a sufficient amount of genomic material; preparing the isolated DNA for sequencing; and sequencing the prepared DNA, wherein the method comprises at most 3 amplification cycles prior to sequencing. In some embodiments, the method comprises 1 or 2 amplification cycles prior to sequencing. In some embodiments, sufficient amount of input genomic material is an amount such that no pre-capture amplification cycles are utilized. In some embodiments, the sample is derived from a patient suspected of having cancer. In some embodiments, the sample is derived from a patient diagnosed with cancer. In some embodiments, the sample is derived from a patient at risk of developing cancer. In some embodiments, the sample is derived from healthy tissue samples. In some embodiments, 0.5 micrograms of DNA is isolated from the sample. In some embodiments, at least 1 microgram of genomic material is isolated from the sample. In some embodiments, at least 5 micrograms of genomic material is isolated from the sample. In some embodiments, at least 10 micrograms of genomic material is isolated from the sample. Additionally or alternatively, detection of a genetic biomarker can include a sequencing method where PCR-introduced mutations are reduced, the sequencing method comprising capturing at least 0.05 micrograms of genomic material, and performing between 0 and 2 amplification cycles prior to sequencing. In some embodiments, 0 amplification cycles are conducted. In other embodiments, 1 amplification cycle is conducted. In yet other embodiments, 2 amplification cycles are conducted. Additionally or alternatively, detection of a genetic biomarker can include a sequence capture method where PCR-introduced biases in the proportional representation of genome content are reduced, the sequencing method comprising providing an input sample comprising at least 0.5 micrograms of genomic material, and where the sequence capture method comprises performing between 0 and 2 amplification cycles prior to sequencing. In some embodiments, 0 amplification cycles are conducted. In other embodiments, 1 amplification cycle is conducted. In yet other embodiments, 2 amplification cycles are conducted. In some embodiments, the input sample comprises at least 1 microgram of genomic material. In some embodiments, the input sample comprises at least 5 micrograms of genomic material. In some embodiments, the input sample comprises at least 10 micrograms of genomic material. Additionally or alternatively, detection of a genetic biomarker can include a sequence capture method where PCR-introduced mutations are eliminated, the sequence capture method comprising preparing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material. Additionally or alternatively, detection of a genetic biomarker can include a sequence capture method where a step of removing PCR-duplicate reads prior to sequencing is eliminated, the sequence capture method comprising providing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material. Additionally or alternatively, detection of a genetic biomarker can include a sequencing method where PCR-introduced mutations are virtually eliminated, the sequencing method comprising capturing at least 0.05 micrograms of genomic material. In some embodiments, about 0.05 micrograms of genomic material are provided after capture of the genomic material. In some embodiments, 1 or 2 post-capture amplification cycles are performed prior to sequencing.

Examples of genetic biomarkers that can be detected using any of the variety of techniques described herein include, without limitation, ABCA7, ABL1, ABL2, ACVR1B, ACVR2A, AJUBA, AKT1, AKT2, ALB, ALDOB, ALK, AMBRA1, AMER1, AMOT, ANKRD46, APC, AR, ARHGAP35, ARHGEF12, ARID1A, ARID1B, ARID2, ARID4B, ARL15, ARMCX1, ASXL1, ASXL2, ATAD2, ATF1, ATG14, ATG5, ATM, ATRX, ATXN2, AXIN1, B2M, BAP1, BCL11A, BCL11B, BCL2, BCL3, BCL6, BCL9, BCLAF1, BCOR, BCR, BIRC6, BIRC8, BLM, BLVRA, BMPR1A, BRAF, BRCA1, BRCA2, BRD7, BRE, BRWD3, BTBD7, BTRC, C11orf70, C12orf57, C2CD5, C3orf62, C8orf34, CAMKV, CAPG, CARD11, CARS, CASP8, CBFA2T3, CBFB, CBLC, CBX4, CCAR1, CCDC117, CCDC88A, CCM2, CCNC, CCND1, CCND2, CCND3, CCR3, CD1D, CD79B, CDC73, CDCP1, CDH1, CDH11, CDK12, CDK4, CDK6, CDKN1A, CDKN1B, CDKN2A, CDX2, CEBPA, CELF1, CENPB, CEP128, CHD2, CHD4, CHD8, CHEK2, CHRDL1, CHUK, CIC, CLEC4C, CMTR2, CNN2, CNOT1, CNOT4, COL11A1, COPS4, COX7B2, CREB1, CREBBP, CSDE1, CSMD3, CTCF, CTDNEP1, CTNNB1, CUL1, CUL2, CYB5B, CYLD, DACH1, DCHS1, DCUN1D1, DDB2, DDIT3, DDX3X, DDX5, DDX6, DEK, DHX15, DHX16, DICER1, DIRC2, DIS3, DIXDC1, DKK2, DNAJB5, DNER, DNM1L, DNMT3A, EED, EGFR, EIF1AX, EIF2AK3, EIF2S2, EIF4A1, EIF4A2, ELF3, ELK4, EMG1, EMR3, EP300, EPB41L4A, EPHA2, EPS8, ERBB2, ERBB3, ERRFI1, ETV4, ETV6, EVI1, EWSR1, EXO5, EXT1, EXT2, EZH2, F5, FANCM, FAT1, FBN2, FBXW7, FCER1G, FEV, FGF2, FGFR1, FGFR1OP, FGFR2, FGFR3, FH, FLT3, FN1, FOXA1, FOXP1, FUBP1, FUS, GALNTL5, GATA3, GGCT, GIGYF2, GK2, GLIPR2, GNAS, GNPTAB, GNRHR, GOLGA5, GOLM1, GOPC, GOT2, GPC3, GPS2, GPX7, GRK1, GSE1, GZMA, HDAC1, HERC1, HERC4, HGF, HIST1H2BO, HLA-A, HLA-B, HMCN1, HMGA1, HMGA2, HNRNPA1, HRAS, HSP90AB1, ID3, IDH1, IDH2, IFNGR2, IFT88, IKZF2, IL2, INO80C, INPP4A, INPPL1, IRF4, IWS1, JAK1, JAK2, JUN, KANSL1, KAT8, KATNAL1, KBTBD7, KCNMB4, KDM5C, KDM6A, KEAP1, KIAA1467, KIT, KLF4, KMT2A, KMT2B, KMT2C, KMT2D, KMT2E, KRAS, KRT15, LAMTOR1, LARP4B, LCK, LMO2, LPAR2, LYN, MAF, MAFB, MAML2, MAP2K1, MAP2K2, MAP2K4, MAP3K1, MAP4K3, MAPK1, MAX, MB21D2, MBD1, MBD6, MBNL1, MBNL3, MDM2, MDM4, MED12, MED23, MEN1, MET, MGA, MITF, MKLN1, MLH1, MLL, MLLT4, MOAP1, MORC4, MPL, MS4A1, MSH2, MSI1, MTOR, MYB, MYC, MYCL1, MYCN, MYD88, MYL6, MYO1B, MYO6, NAA15, NAA25, NAPIL2, NAPIL4, NCOA2, NCOA4, NCOR1, NEK9, NF1, NF2, NFE2L2, NFE2L3, NFKB2, NIPBL, NIT1, NKX3-1, NME4, NOTCH1, NOTCH2, NPM1, NR4A3, NRAS, NSD1, NTRK1, NUP214, NUP98, PALB2, PAX8, PBRM1, PCBP1, PCOLCE2, PDGFB, PHF6, PIK3CA, PIK3CB, PIK3R1, PIM1, PLAG1, PML, POLA2, POT1, PPARD, PPARG, PPM1D, PPP2R1A, PPP6C, PRKACA, PRKCI, PRPF40A, PSIP1, PTEN, PTH2, PTMS, PTN, PTPN11, RAB18, RAC1, RAF1, RANBP3L, RAPGEF6, RASA1, RB1, RBBP6, RBM10, RBM26, RC3H2, REL, RERE, RET, RFC4, RHEB, RHOA, RIMS2, RIT1, RNF111, RNF43, ROS1, RPL11, RPL5, RQCD1, RRAS2, RUNX1, RXRA, SARM1, SCAF11, SDHB, SDHD, SEC22A, SENP3, SENP8, SETD1B, SETD2, SF3A3, SF3B1, SFPQ, SIN3A, SKAP2, SMAD2, SMAD3, SMAD4, SMARCA4, SMARCB1, SMARCC2, SMO, SNCB, SOCS1, SOS1, SOX4, SOX9, SP3, SPEN, SPOP, SPSB2, SS18, STAG2, STK11, STK31, SUFU, SUFU, SUZ12, SYK, TAF1A, TARDBP, TAS2R30, TBL1XR1, TBX3, TCF12, TCF3, TCF7L2, TCL1A, TET2, TEX11, TFDP2, TFG, TGFBR2, THRAP3, TLX1, TM9SF1, TMCO2, TMED10, TMEM107, TMEM30A, TMPO, TNFAIP3, TNFRSF9, TNRC6B, TP53, TP53BP1, TPR, TRAF3, TRIM8, TRIP12, TSC1, TSC2, TTK, TTR, TUBA3C, U2AF1, UBE2D3, UBR5, UNC13C, UNKL, UPP1, USO1, USP28, USP6, USP9X, VHL, VN1R2, VPS33B, WAC, WDR33, WDR47, WRN, WT1, WWP1, XPO1, YOD1, ZC3H13, ZDHHC4, ZFHX3, ZFP36L1, ZFP36L2, ZGRF1, ZMYM3, ZMYM4, ZNF234, ZNF268, ZNF292, ZNF318, ZNF345, ZNF600, ZNF750, and/or ZNF800.

As used herein, "TP53" refers to the gene and/or the protein encoded by the gene, which is tumor suppressor protein p53 involved in the regulation of cell proliferation. TP53 gene plays a crucial role in preventing cancer formation. TP53 gene encodes proteins that bind to DNA and regulate gene expression to prevent mutations of the genome. Human TP53 sequences are known in the art (e.g., GenBank accession numbers NM_001276761, NM_000546, NM_001126112, NM_001126113, and NM_001126114). One of ordinary skill in the art can identify additional TP53 sequences and variants thereof.

As used herein, "PIK3CA" refers to the gene and/or the protein encoded by the gene, which is the catalytic subunit of Phosphoinositol-3 kinase (PI3K), isoform alpha, also referred to as p110alpha. PIK3CA has been found to be oncogenic and has been implicated in a variety of cancers. Human PIK3CA sequences are known in the art (e.g., GenBank accession number NM_006218). One of ordinary skill in the art can identify additional PIK3CA sequences and variants thereof.

As used herein, the term "FGFR3" refers to the gene and/or the protein encoded by the gene, which is fibroblast growth factor receptor 3 (FGFR3) which belongs to a family of structurally related tyrosine kinase receptors (FGFRs 1-4) encoded by four different genes. The extracellular portion of the protein interacts with fibroblast growth factors, setting in motion a cascade of downstream signals which ultimately influencing cell mitogenesis and differentiation. Human FGFR3 sequences are known in the art (e.g., GenBank accession numbers NM_000142, NM_001163213, NM_022965, NM_001354809, and NM_001354810). One of ordinary skill in the art can identify additional FGFR3 sequences and variants thereof.

As used herein, the term "KRAS" refers to the gene and/or the protein encoded by the gene known as K-ras or Ki-ras, which is proto-oncogene corresponding to the oncogene first identified in Kirsten rat sarcoma virus and the gene product was first found as a p21 GTPase. Human KRAS sequences are known in the art (e.g., GenBank accession numbers NM_004985 and NM_033360). One of ordinary skill in the art can identify additional KRAS sequences and variants thereof.

As used herein, the term "ErbB2" refers to the gene and/or the protein encoded by the gene, which is also known as v-erb-b2 avian erythroblastic leukemia viral oncogene homolog 2, c-erbB2/neu, her2/neu, or Her2. ErbB2 is a member of the epidermal growth factor receptor family of tyrosine kinases. It is amplified and/or overexpressed in several cancers, including breast and ovarian cancer. Human ErbB2 sequences are known in the art (e.g., GenBank accession numbers NM_001005862, NM_001289936, NM_001289937, NM_001289938, and NM_004448). One of ordinary skill in the art can identify additional ErbB2 sequences and variants thereof.

As used herein, "CDKN2A" refers to the gene and/or the protein encoded by the gene, which is known as cyclin-dependent kinase Inhibitor 2A, act as tumor suppressors by regulating the cell cycle. Human CDKN2A sequences are known in the art (e.g., GenBank accession numbers NM_000077, NM_001195132, NM_058195, NM_058196, and NM_058197). One of ordinary skill in the art can identify additional CDKN2A sequences and variants thereof.

As used herein, the term "MLL" refers to the gene and/or the protein encoded by the gene, which is lymphoid or mixed-lineage leukemia 2. MLL is a major mammalian histone H3 lysine 4 (H3K4) mono-methyltransferase. MLL protein co-localizes with lineage determining transcription factors on transcriptional enhancers and is essential for cell differentiation and embryonic development. MLL also plays critical roles in regulating cell fate transition, metabolism, and tumor suppression. Mutations in MLL have been associated with Kabuki Syndrome, congenital heart disease, and various forms of cancer. Human MLL sequences are known in the art (e.g., GenBank accession number NM_003482). One of ordinary skill in the art can identify additional MLL sequences and variants thereof.

As used herein, the term "HRAS" refers to the gene and/or the protein encoded by the gene, which is harvey rat sarcoma viral oncogene homolog, is a small G protein, activating the MAP kinase pathway. HRAS is involved in regulating cell division in response to growth factor stimulation. HRAS has been shown to be a proto-oncogene. When mutated, proto-oncogenes have the potential to cause normal cells to become cancerous. Human HRAS sequences are known in the art (e.g., GenBank accession numbers NM_001130442, NM_005343, NM_176795, and NM_001318054). One of ordinary skill in the art can identify additional HRAS sequences and variants thereof.

As used herein, the term "MET" refers to the gene and/or the protein encoded by the gene. MET gene encodes c-Met, also called tyrosine-protein kinase Met or hepatocyte growth factor receptor (HGFR). MET is a single pass tyrosine kinase receptor essential for embryonic development, organogenesis and wound healing. Hepatocyte growth factor/Scatter Factor (HGF/SF) and its splicing isoform (NK1, NK2) are the only known ligands of the MET receptor. MET is normally expressed by cells of epithelial origin, while expression of HGF/SF is restricted to cells of mesenchymal origin. When HGF/SF binds its cognate receptor MET it induces its dimerization through a not yet completely understood mechanism leading to its activation. Human MET sequences are known in the art (e.g., GenBank accession numbers NM_000245, NM_001127500, NM_001324401, and NM_001324402). One of ordinary skill in the art can identify additional MET sequences and variants thereof.

As used herein, the term "VHL" refers to the gene and/or the protein encoded by the gene. VHL gene is Von Hippel Lindau tumor suppressor gene. A germline mutation of the VHL gene is the basis of familial inheritance of Von Hippel-Lindau syndrome, a dominantly inherited hereditary cancer syndrome predisposing to a variety of malignant and benign tumors of the eye, brain, spinal cord, kidney, pancreas, and adrenal glands. Human VHL sequences are known in the art (e.g., GenBank accession numbers NM_000551, NM_198156, and NM_001354723). One of ordinary skill in the art can identify additional VHL sequences and variants thereof.

Scoring for Genetic Mutations

The present disclosure provides methods of identifying the presence of cancer in a subject with high sensitivity and specificity based at least in part on the presence of one or more genetic biomarkers. Various methods are provided herein to determine whether the subject has cancer and/or the likelihood that the subject has cancer. In some embodiments, these methods involve various types of statistical techniques and methods, including, e.g., scoring methods, regression analysis, clustering, principal component analysis, nearest neighbor classifier analysis (e.g., k-nearest neighbors algorithm), linear discriminant analysis, neural networks, and support vector machines, etc.

In some embodiments, one or more genetic biomarkers can be used to generate a score. The score can indicate that the likelihood that the subject has a cancer or does not have a cancer. In some embodiments, the likelihood is generated by comparing the mutation allele frequency of each mutation in one or more genetic biomarkers to a reference distribution of mutation allele frequency. As described herein, genomic segments containing one or more biomarkers can be amplified by a set of primers. The set of primers can have one or more pairs of primers that amplify one or more non-overlapping genomic segments. The same set of primers can be used to amplify template DNA collected from a subject in one or more wells (e.g., equal to, or more than 1, 2, 3, 4, 5, 6, 7, 8, 9, 10, 11, 12, 20, or 30 wells), thus the amplification process can provide duplicate signals for mutants (e.g., rare mutations) that are detectable in multiple wells. In some embodiments, the PCR products can be subject to one or more rounds of additional amplification before sequencing. In some embodiments, reads from a common template molecule can be then grouped, e.g., based on the unique identifier sequences (UIDs) that are incorporated as molecular barcodes. In some embodiments, artifactual mutations that are introduced during the sample preparation or sequencing steps can be reduced by requiring a mutation to be present in e.g., greater than 80%, 85%, 90%, 91%, 92%, 93%, 94%, 95%, 96%, 97%, 98%, or 99% of reads in each UID family. In some embodiments, redundant reads arising from optical duplication can be eliminated by requiring reads with the same UID and sample index to be at least 1000, 2000, 3000, 4000, 5000, 6000, 7000, 8000, or 9000 pixels apart when located on the same tile.

In some embodiments, mutations that meet one or two of the two following criteria are considered (i) present in the Catalogue of Somatic Mutations in Cancer (COSMIC) database, or (ii) predicted to be inactivating in tumor suppressor genes (nonsense mutations, out-of-frame insertions or deletions, canonical splice site mutations). In some embodiments, synonymous mutations, except those at exon ends, and intronic mutations, except for those at splice sites, are excluded. These selected mutations are referred as supermutants. Thus, in some embodiments, supermutants include e.g., mutations present in the Catalogue of Somatic Mutations in Cancer (COSMIC) database, mutations predicted to be inactivating in tumor suppressor genes (nonsense mutations, out-of-frame insertions or deletions, canonical splice site mutations), non-synonymous mutations, mutations that can affect splicing, and/or mutations that can affect expression, etc.

Thus, as used herein, the term "mutant allele frequency" or "MAF" within a sample (e.g., a well, a test sample) refers to the proportion of UIDs in the sample that have such a mutation. The MAF reflects the mutant fraction within each sample (e.g., each well) and represents an independent sampling of the mutant allele frequency in the sample of interest. In some embodiments, the MAF of a mutation in a sample (rather than the well) can be calculated by the total number of mutants present in all wells for the sample (e.g., a sample collected from a subject) divided by the total number of UIDs.

In some embodiments, MAF normalization is performed. In some embodiments, all mutations that do not have at least one supermutant in at least one well are excluded from the analysis. For example, the mutant allele frequency (MAF) can reflect the ratio between the total number of supermutants in each well from that sample and the total number of UIDs in the same well from that sample. In some embodiments, the MAF is first normalized based on the observed MAFs for each mutation in a set of normal controls comprising the normal plasmas in the training set. In some embodiments, mutations with <100 UIDs are excluded. The normalization can be performed by standard normalization (i.e. subtracting the mean and dividing by the standard deviation) or multiplying the MAF with a predetermined ratio. In some embodiments, the normalization is performed by first calculating the average MAF (ave_i) for each mutation i=1, . . . n, found among the normal controls. Using the 25th percentile of the distribution generated by these averages as the reference value (ave_ref), each MAF can be normalized multiplying it by the ratio ave_ref/ave_i. For example, if the observed average MAF of a mutation in a set of controls is 10 times higher than ave_ref, then each MAF for that mutation can be multiplied by ⅒.

The classification of a sample's genetic biomarker status can be obtained, e.g., from a statistical test by comparing the MAF of one or more mutations in the selected genetic biomarkers to a reference distribution of mutation allele frequency for the mutations in a group of control samples, by comparing the mutation allele frequency of one or more mutations in the selected genetic biomarkers to a first reference distribution of mutation allele frequency in control samples and a second reference distribution of mutation allele frequency in samples collected from subjects having a cancer, or by comparing the mutation allele frequency of one or more mutations in the selected genetic biomarkers to the maximum mutation allele frequency of the mutation in control samples.

The control reference distribution and the maximum mutation allele frequency of the mutation can be determined from controls samples. In some embodiments, the group of control samples has at least 1, 2, 3, 4, 5, 6, 7, 8, 9, 10, 20, 30, 40, 50, 60, 70, 80, 90, 100, 110, 120, 130, 140, 150, 160, 170, 180, 190, 200, or more control subjects. In some embodiments, the control subjects are healthy subjects, or at least do not have cancer, or are not suspected to have cancer. The control samples collected from these control subjects can be amplified and sequenced. The mutations in one or more selected genetic biomarkers can be determined. Thus, a MAF for a particular mutation in one subject can be determined, and the distribution of MAF in control samples can be determined from the group of control subjects. Similarly, the maximum mutation allele frequency of the mutation can also be determined in control samples.

In some embodiments, the MAF of one or more mutations in the selected genetic biomarkers can be compared against the reference distribution, thereby obtaining a score indicates that the likelihood or the probability that the subject has cancer. In some embodiments, if the score (e.g., likelihood or probability) is equal to or greater than a reference threshold, it can be determined that the subject is likely to have cancer, otherwise, it can be determined that the subject is not likely to have cancer. In some embodiments, the comparison can provide a score that indicates the likelihood or probability that the subject does not have cancer. In some embodiments, if the score (e.g., likelihood or probability) is equal to or less than a reference threshold, thus it can be determined that the subject is likely to have cancer, otherwise, it can be determined that the subject is not likely to have cancer.

In some embodiments, the MAF is first normalized based on the observed MAFs in a set of normal controls for each mutation. Following this mutation-specific normalization, the MAF of each mutation in each well is compared to a reference distribution of MAFs built from normal controls with all mutations included, and a p-value is calculated from this distribution. In some embodiments, the lowest p-value among all mutations detected in a given sample was deemed the "top mutation". The classification of a sample's ctDNA status is based on whether the p-value of this top mutation was below or above a given threshold. The threshold can be selected based on a desired specificity observed among an independent set of normal controls.

In some embodiments, the Stouffer's Z-score is used to combine hypothesis test results from two or more independent tests (e.g., test results from 2, 3, 4, 5, 6, 7, 8, 9, 10, 11, or 12 wells). For example, the results of MAF for two or mutations can be combined into one single test. In some embodiments, a sample is scored as positive when Stouffer's Z-score is greater than a reference threshold. In some embodiments, a sample is scored positive if the ratio of the Stouffer's Z-score to the average of the first few (e.g., 2, 3, 4, 5, 6 7, 8, 9, or 10) highest Stouffer's Z-scores in the controls is greater than a reference threshold.

In some embodiments, the MAF of one or more mutations in the selected genetic biomarkers is compared to maximum mutation allele frequency of the mutation in control samples. If one or more mutations (e.g., equal to or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200) have a MAF that is greater than the maximum mutation allele frequency of the mutation in control samples, the subject can be determined to have cancer. In some embodiments, a score can be obtained from the comparison. In some embodiments, the score is the total number of mutations that have a MAF that is greater than the maximum mutation allele frequency of the mutation in control samples. If the score is greater than a reference threshold, then it can be determined that the subject is likely to have cancer. In some embodiments, the average MAF of one or more mutations in the selected genetic biomarkers is calculated.

In some embodiments, the MAF of one or more mutations in the selected genetic biomarkers can be compared to a first reference distribution of mutation allele frequency in control samples and a second reference distribution of mutation allele frequency in samples collected from subjects having cancer. In some embodiments, a score is obtained by comparing the mutation frequencies of the sample of interest to the distributions of the mutation frequencies of, respectively, normal and cancer samples in the training set.

In some embodiments, the UID range for each mutation is split in 10 intervals (e.g., <1,000, 1,000-2,000, . . . , 8,000-9,000, >9,000). Depending on the number of UIDs, the MAF of each mutation in each well can be compared to two reference distributions of MAFs built from samples in the corresponding UID range: 1) a distribution built from all the normal control samples in the training set; and 2) a distribution built from the samples from cancer patients in the training set. In some embodiments, the cancer training set includes only those in which the same mutation is present in the sample (e.g., plasma) and in the corresponding primary tumor, with an MAF >5% in the tumor. Corresponding p-values, pN and pC, can be obtained. The reference distributions for both the normal and cancer samples can be built independently, from the training sets, in each round and each iteration of 10-fold cross-validation, i.e., 90% of the samples in each iteration are used for training and 10% of the samples are used for testing.

For each mutation, an omega score can be obtained. The log ratio of these two p values, pC/pN can then be calculated. In some embodiments, the minimum and maximum of these log ratios across the replicate wells can be eliminated so that the results will be less sensitive to outliers. In some embodiments, a log-likelihood ratio is used. As compared to the log-likelihood ratio, the log ratio of the p-values can provide some additional advantages, because the relatively low number of data points available do not allow a robust estimation of the densities of the MAF distributions (particularly for pC). Thus, in some embodiments, an "omega" score was then determined according to the following formula:

$$\Omega = \sum_{i=1} w_i * \ln\frac{p_i^C}{p_i^N}$$

where wi is the number of UIDs in well i divided by the total number of UIDs for that mutation in the wells that are included in the analysis. In some embodiments, the total number of wells that are included in the analysis is 1, 2, 3, 4, 5, 6, 7, 8, 9, 10, 11, 12, 20, 30, or more. In some embodiments, the wells with the maximum log ratio and the minimum log ratio can be excluded from the analysis. In some embodiments, the total number of wells are that are included for analysis is 1, thus, the omega score can be obtained by the following formula instead:

$$\Omega = \ln \frac{p_i^C}{p_i^N}$$

The log ratio of p-values can be weighted so that those wells containing more template molecules would have a greater impact on the final statistic (the omega score). The rationale for this weighting was that the larger the number of template molecules in a well, the more confidence in the result.

In some embodiments, an $\Omega$ score for each mutation can be determined. In some embodiments, mutations with $\Omega$ scores greater than a reference score (e.g., 1, 2, 3, 4, 5, 6, 7, 8, 9, or 10) are selected. The total number of mutations with $\Omega$ scores greater than a reference score reflects the mutation burden in a subject. In some embodiments, if the total number of mutations with $\Omega$ scores that is greater than a reference score is greater than a reference threshold, it is determined that the subject is likely to have cancer; otherwise, it can be determined that the subject is not likely to have a cancer.

In some embodiments, the mutation with the greatest $\Omega$ score is deemed the "top mutation". The $\Omega$ score for top mutation can be used to determine whether a subject is likely to have cancer. For example, the $\Omega$ score for the top mutation can be compared against a reference threshold, or be combined with some other information (e.g., protein biomarkers) in various methods (e.g., regression analysis) to determine the likelihood that a subject has cancer. In some embodiments, if the $\Omega$ score for the top mutation is greater than a reference threshold, it is determined that the subject is likely to have cancer; otherwise, it can be determined that the subject is not likely to have a cancer. In some embodiments, the $\Omega$ score is used in a regression analysis (e.g., logistic regression).

Detecting Protein Biomarkers

In some embodiments, the presence of a protein biomarker may be detected in any of a variety of biological samples isolated or obtained from a subject (e.g., a human subject) including, but not limited to blood, plasma, serum, urine, cerebrospinal fluid, saliva, sputum, broncho-alveolar lavage, bile, lymphatic fluid, cyst fluid, stool, ascites, and combinations thereof. Any protein biomarker known in the art may be detected when a threshold value is obtained above which normal, healthy human subjects do not fall, but human subjects with cancer do fall.

Any appropriate method can be used to detect the level of one or more protein biomarkers as described herein. In some embodiments, the level of one or more protein biomarkers is compared to a predetermined threshold. In some embodiments, the predetermined threshold is a general or global threshold. In other cases, the predetermined threshold is a threshold that is relevant to a particular protein biomarker. In some embodiments, the level of the one or more protein biomarkers is compared to an absolute amount of a reference protein biomarker. In some embodiments, the level of the one or more protein biomarkers is relative to an amount of a reference protein biomarker. In some embodiments, the level of the one or more protein biomarkers is an elevated level. In some embodiments, the level of the one or more protein biomarkers is above a predetermined threshold. In other cases, the level of the one or more protein biomarkers is within a predetermined threshold range. In some embodiments, the level of the one or more protein biomarkers is or approximates a predetermined threshold. In some embodiments, the level of the one or more protein biomarkers is below a predetermined threshold. In some embodiments, the level of the one or more protein biomarkers from a biological sample is lower than a particular threshold. In some embodiments, the level of the one or more protein biomarkers from a biological sample is depressed compared to a predetermined threshold.

In some embodiments, methods provided herein for selecting a subject for further diagnostic testing and/or increased monitoring include detecting a protein biomarker in the biological sample and comparing the amount of protein biomarker in the biological sample to a reference level in a reference sample. In some embodiments, methods for selecting a subject for further diagnostic testing and/or increased monitoring include detecting a protein biomarker in the biological sample and comparing the amount of protein biomarker in the biological sample to a reference level, wherein the reference level is a composite number derived from multiple reference samples. In some embodiments, the protein biomarker in the biological sample is at least 5% higher than a reference level. In some embodiments, the protein biomarker in the biological sample is at least 10% higher than a reference level. In some embodiments, the protein biomarker in the biological sample is at least 15% higher than a reference level. In some embodiments, the protein biomarker in the biological sample is at least 20% higher than a reference level. In some embodiments, the protein biomarker in the biological sample is at least 25% higher than a reference level. In some embodiments, the protein biomarker in the biological sample is at least 30% higher than a reference level. In some embodiments, the protein biomarker in the biological sample is at least 40% higher than a reference level. In some embodiments, the protein biomarker in the biological sample is at least 50% higher than a reference level. In some embodiments, the protein biomarker in the biological sample is at least 60% higher than a reference level. In some embodiments, the protein biomarker in the biological sample is at least 70% higher than a reference level. In some embodiments, the protein biomarker in the biological sample is at least 80% higher than a reference level. In some embodiments, the protein biomarker in the biological sample is at least 90% higher than a reference level. In some embodiments, the protein biomarker in the biological sample is at least 100% higher than a reference level. In some embodiments, the protein biomarker in the biological sample is at least 200% higher than a reference level. In some embodiments, the protein biomarker in the biological sample is at least 300% higher than a reference level. In some embodiments, the protein biomarker in the biological sample is at least 400% higher than a reference level. In some embodiments, the protein biomarker in the biological sample is at least 500% higher than a reference level. In some embodiments, the protein biomarker in the biological sample is at least 600% higher than a reference level. In some embodiments, the protein biomarker in the biological sample is at least 700% higher than a reference level. In some embodiments, the protein biomarker in the biological sample is at least 800% higher than a reference level. In some embodiments, the protein biomarker in the biological sample is at least 900% higher than a reference level. In some embodiments, the protein biomarker in the biological sample is at least 1000% higher than a reference level. In some embodiments, the protein biomarker in the biological sample is between about 5% to about 1000% higher than a reference level. In some embodiments, the protein biomarker in the biological sample is between about 10% to about 1000% higher than a reference level. In some embodiments, the protein biomarker in the biological sample is between about 15% to about 1000% higher than a reference level. In some embodiments, the protein biomarker in the biological sample is between about 20% to about 1000% higher than a reference level. In some embodiments, the protein biomarker in the biological sample is between about 25% to about 1000% higher than a reference level. In some embodiments, the protein biomarker in the biological sample is between about 30% to about 1000% higher than a reference level. In some embodiments, the protein biomarker in the biological sample is between about 10% to about 100% higher than a reference level. In some embodiments, the protein biomarker in the biological sample is between about 15% to about 100% higher than a reference level. In some embodiments, the protein biomarker in the biological sample is between about 20% to about 100% higher than a reference level. In some embodiments, the protein biomarker in the biological sample is between about 25% to about 100% higher than a reference level. In some embodiments, the protein biomarker in the biological sample is between about 30% to about 100% higher than a reference level.

In some embodiments, the protein biomarker is at least 5% lower than a reference level. In some embodiments, the protein biomarker is at least 10% lower than a reference level. In some embodiments, the protein biomarker is at least 15% lower than a reference level. In some embodiments, the protein biomarker is at least 20% lower than a reference level. In some embodiments, the protein biomarker is at least 25% lower than a reference level. In some embodiments, the protein biomarker is at least 30% lower than a reference level. In some embodiments, the protein biomarker in the biological sample is at least 40% lower than a reference level. In some embodiments, the protein biomarker in the biological sample is at least 50% lower than a reference level. In some embodiments, the protein biomarker in the biological sample is at least 60% lower than a reference level. In some embodiments, the protein biomarker in the biological sample is at least 70% lower than a reference level. In some embodiments, the protein biomarker in the biological sample is at least 80% lower than a reference level. In some embodiments, the protein biomarker in the biological sample is at least 90% lower than a reference level. In some embodiments, the protein biomarker in the biological sample is between about 5% to about 100% lower than a reference level. In some embodiments, the protein biomarker in the biological sample is between about 10% to about 100% lower than a reference level. In some embodiments, the protein biomarker in the biological sample is between about 15% to about 100% lower than a reference level. In some embodiments, the protein biomarker in the biological sample is between about 20% to about 100% lower than a reference level. In some embodiments, the protein biomarker in the biological sample is between about 25% to about 100% lower than a reference level. In some embodiments, the protein biomarker in the biological sample is between about 30% to about 100% lower than a reference level.

In some embodiments, the protein biomarker is a cytokine biomarker. In some embodiments, the protein biomarker is a chemokine biomarker. In some embodiments, the protein biomarker is a growth factor biomarker. In some embodiments, the protein biomarker is associated with inflammation. In some embodiments, the protein biomarker is associated with cancer. In some embodiments, the protein biomarker is associated with a particular type of cancer. Any appropriate cancer can be identified and/or treated as described herein. In some embodiments, the cancer is a common cancer. In some embodiments, the cancer is a cancer where no blood-based test is available. In some embodiments, the cancer is a cancer where no test for early detection is available. In some embodiments, the cancer is a Stage I cancer. In some embodiments, the cancer is a Stage II cancer. In some embodiments, the cancer is a Stage III cancer. In some embodiments, the cancer is a Stage IV cancer. In some embodiments, the cancer is a surgically resectable cancer. In some embodiments, the cancer is a surgically unresectable cancer. Examples of cancers that be identified as described herein (e.g., based at least in part on the presence or absence of one or more first biomarkers (e.g., genetic biomarkers) and/or an elevated level of one or more second biomarkers (e.g., peptide biomarkers)) and/or the presence of aneuploidy include, without limitation, liver cancer, ovarian cancer, esophageal cancer, stomach cancer, pancreatic cancer, colorectal cancer, lung cancer, breast cancer, and prostate cancer.

In some embodiments, the levels of one or more protein biomarkers can be detected independently (e.g., via singleplex peptide tools). Examples of methods for detecting protein levels include, without limitation, spectrometry methods (e.g., high-performance liquid chromatography (HPLC) and liquid chromatography-mass spectrometry (LC/MS)), antibody dependent methods (e.g., enzyme-linked immunosorbent assay (ELISA), protein immunoprecipitation, immunoelectrophoresis, western blotting, and protein immunostaining), and aptamer dependent methods. In some embodiments, the level of one or more protein biomarkers can be detected as described in the Examples.

Many of the singleplex peptide tools, such as, but not limited to ELISAs or western blotting, can be used sequentially or concurrently to analyze multiple peptide biomarkers. Multiplex peptide tools can include combining singleplex peptide tools or elements of singleplex peptide tools. Additionally or alternatively, detecting the levels of one or more peptide biomarkers can occur via multiplex peptide tools such as "chips," microarrays, or immunoassay systems. In one non-limiting example, multiple analytes can be probed by multiple capture antibodies spotted on microarrays and analyzed via horseradish peroxidase (HRP)-conjugated antibody/chemiluminescence system. In this method, each spot captures a specific target protein, and a second, target-specific detector antibody is used for quantification. In addition to membrane antibody arrays, glass slides may be used for quantitative antibody arrays. Commercial embodiments of multiplexed ELISAs include, but are not limited to, Q-Plex available from Quansys Biosciences, Mosaic™ available from R&D Systems, Ciraplex® available from Aushon Biosystems, MULTI-ARRAY available from Meso Scale Discovery, FAST Quant available from Whatman Schleicher & Schuell BioScience, A2 available from Beckman Coulter, and Quantibody® available from RayBiotech. Additionally or alternatively, multiplex assays can be utilize beads or particles to detect one or more protein biomarkers simultaneously. In one non-limiting example, polystyrene or paramagnetic beads are impregnated with dyes of differing wavelengths are used to detect multiple target antibodies simultaneously, wherein each dye or dye combination corresponds with a different target antibody. Sandwich assays are used to measure protein levels. Commercial embodiments of this technique utilize the Luminex® and FirePlex® technology platforms, e.g., BioPlex® Multiplex Immunoassay System available from Bio-Rad, FlowCytomix available from eBioscience, ProcartaPlex Immunoassay System available from ThermoFisher Scientific, Novex® Multiplex Assays available from Invitrogen.

In some embodiments, an assay includes detection of thresholded protein biomarkers in a biological sample (e.g., any biological sample described herein such as, without limitation, blood or plasma) without detection of genetic biomarkers (e.g., mutations in circulating tumor DNA (ctDNA)) and/or aneuploidy and/or an additional class of biomarker. In some embodiments, an assay includes detection of thresholded protein biomarkers in a biological sample (e.g., any biological sample described herein such as, without limitation, blood or plasma) with detection of genetic biomarkers (e.g., mutations in circulating tumor DNA (ctDNA)) and/or aneuploidy and/or an additional class of biomarker. For example, an assay may include detection of one or more of (e.g., each of) CA19-9, CEA, HGF, OPN, CA125, prolactin, TIMP-1, and/or myeloperoxidase (MPO) in a biological sample. In some embodiments, an assay may include detection of one or more of (e.g., each of) CA19-9, CEA, HGF, OPN, CA125, prolactin, TIMP-1, and/or myeloperoxidase (MPO) in a biological sample at any of the threshold levels disclosed herein. As another example, an assay may include detection of one or more of (e.g., each of) CA19-9, CEA, HGF, OPN, CA125, AFP, prolactin, TIMP-1, follistatin, G-CSF, and/or CA15-3 in a biological sample. In some embodiments, an assay may include detection of one or more of (e.g., each of) CA19-9, CEA, HGF, OPN, CA125, AFP, prolactin, TIMP-1, follistatin, G-CSF, and/or CA15-3 in a biological sample at any of the threshold levels disclosed herein. As another example, an assay may include detection of one or more of (e.g., each of) CA19-9, CEA, HGF, OPN, CA125, AFP, prolactin, TIMP-1, and/or CA15-3 in a biological sample. In some embodiments, an assay may include detection of one or more of (e.g., each of) CA19-9, CEA, HGF, OPN, CA125, AFP, prolactin, TIMP-1, and/or CA15-3 in a biological sample at any of the threshold levels disclosed herein. As another example, an assay may include detection of one or more of (e.g., each of) KRAS (e.g., codons 12 and 61), TP53, CDKN2A, and/or SMAD4 in a biological sample. In some embodiments, an assay may include detection of one or more of (e.g., each of) KRAS (e.g., codons 12 and 61), TP53, CDKN2A, and/or SMAD4 in a biological sample at any of the threshold levels disclosed herein. In some embodiments, once an assay that includes detection of thresholded protein biomarkers in a biological sample is performed, subsequent testing or monitoring is performed (e.g., any of the variety of further diagnostic testing or increased monitoring techniques disclosed herein). In some embodiments, once an assay that includes detection of thresholded protein biomarkers in a biological sample is performed, a second assay that includes detecting the presence of one or more genetic biomarkers present in cell-free DNA (e.g., ctDNA, e.g., any of the variety of genetic alterations that are present in cell-free DNA or ctDNA as described herein), the presence of one or more protein biomarkers (e.g., any of the variety of protein biomarkers described herein), the presence of aneuploidy, and/or the presence of one or more additional classes of biomarkers can be performed.

Examples of protein biomarkers that can be detected using any of the variety of techniques described herein include, without limitation, Actin gamma (ACTG1), AFP, Alpha-2-HS glycol protein, Angiopoietin-2, apolipo protein 1, AXL, CA125, CA15-3, carbohydrate antigen 19-9 (CA19-9), carcinoembryonic antigen (CEA), Catenin, Caveolin-1, CD44, class B member 1 (HSP90AB1), complement c3a, Cyclin D, CYFRA 21-1, Defensin α 6, DKK1, EAFP, Endoglin, Eukaryotic translation elongation factor 1 gamma (EEF1G), Ferritin, FGF2, follistatin, Galectin-3, G-CSF, GDF15, Glucose regulated protein-8, Glyceraldehyde-3-phosphate dehydrogenase (GAPDH), HE4, Heat shock protein 90 kDa alpha (cytosolic), heavy polypeptide 1 (FTH1), hepatocyte growth factor (HGF), IL-6, IL-8, Kallikrein 6, Lamin A/C filament protein, large subunit, Leptin, light polypeptide (FTL), LRG-1, Mesothelin, Midkine, MMPs, muscle (PKM2), Myeloperoxidase, NSE, OPG, osteopontin (OPN), P0 (RPLP0), PAR, prolactin, Pyruvate kinase, Ribosomal protein, Ribosomal protein L3 (RPL3), Ribosomal protein large subunit P0 (RPLP0), S100 P, sEGFR, Serum C-peptide, sFas, SHBG, sHER2/sEGFR2/sErbB2, sPECAM-1, TGFa, thioredoxin like protein-2, Thrombospondin-2, TIMP-1, TIMP-2, Transferrin, Translation elongation factor (EEF1A1), Txl-2 (thioredoxin like protein-2), Vitronectin, α defensing-1,-2,-3, and/or α-1 antitrypsin. Exemplary protein biomarkers detected in various cancer types are shown in Example 2.

Detecting Aneuploidy

Aneuploidy is the presence of an abnormal number of chromosomes in a cell. Aneuploidy usually originates during cell division when the chromosomes do not separate properly between the two cells. Aneuploidy occurs as the result of a weakened mitotic checkpoint, as these checkpoints tend to arrest or delay cell division until all components of the cell are ready to enter the next phase. If a checkpoint is weakened, the cell may fail to notice that a chromosome pair is not lined up on the mitotic plate. In such a case, most chromosomes would separate normally (with one chromatid ending up in each cell), while others could fail to separate at all. This would generate a daughter cell lacking a copy and a daughter cell with an extra copy. Aneuploidy has been consistently observed in many cancers.

Aneuploidy can be detected through karyotyping, a process in which a sample of cells is fixed and stained to create the typical light and dark chromosomal banding pattern and a picture of the chromosomes is analyzed. Other non-limiting techniques for detecting aneuploidy include e.g., Fluorescence In Situ Hybridization (FISH), quantitative PCR of Short Tandem Repeats, quantitative fluorescence PCR (QF-PCR), quantitative PCR dosage analysis, Quantitative Mass Spectrometry of Single Nucleotide Polymorphisms, Comparative Genomic Hybridization (CGH), microarrays, Sanger sequencing, and massively parallel sequencing methods, etc.

The present disclosure provides methods to detect aneuploidy. For example, the present disclosure provides methods and materials for evaluating sequencing data to identify a mammal as having a disease associated with one or more chromosomal anomalies (e.g., cancer). The sequencing data can be processed to identify significant single chromosomal arm gains or losses, as well as allelic imbalance on chromosome arms, using Within-Sample AneupLoidy DetectiOn (WALDO) method. WALDO incorporates a support vector machine (SVM) to discriminate between aneuploid and euploid samples. The SVM can be trained using aneuploid samples (e.g., synthetic aneuploid samples) and euploid samples (e.g., peripheral white blood cell (WBC)). A sample can be scored as positive (aneuploid), if the SVM discriminant score exceeded a given threshold. In some embodiments, a single primer pair is used to amplify ~38,000 loci of long interspersed nucleotide elements (LINEs) throughout the genome. Massively parallel sequencing is then performed. In some embodiments, one of the primers include an UID to as a molecular barcode, which can be used to reduce error rates associated with PCR and sequencing.

Overview of WALDO

In euploid samples, the number of LINE reads within each 500-kb genomic interval should track with the number of reads in certain other genomic regions. Genomic intervals that track together do so because the amplicons within them amplify to similar extents. Here, these genomic regions that track together are called "clusters." Clusters can be from sequencing data on euploid samples. In a test sample, whether the number of reads in each genomic interval in each predefined cluster is within the expected bound of the other clusters from that same sample is determined. If the reads within a genomic interval are outside the statistically expected bound, and there are many such outsiders on the same chromosome arm, then that chromosome arm is classified as aneuploidy In brief, while the number of reads at each LINE is not randomly distributed across the genome, the distribution of scaled reads within each cluster is approximately normal. A convenient property of normal distributions is that the sum of multiple normal distributions is also a normal distribution. The theoretical mean and variance of the summed reads on each chromosome arm can be computed simply by summing the means and variances of all of the clusters represented on that chromosome arm.

WALDO employs several methods that make it applicable to the analysis of PCR-generated amplicons from clinical samples. One of these methods is controlling amplification bias stemming from the strong dependence of the data on the size of the initial template. Another is the use of a Support Vector Machine (SVM) to enable the detection of aneuploidy in samples containing low neoplastic fractions.

Figure 36:
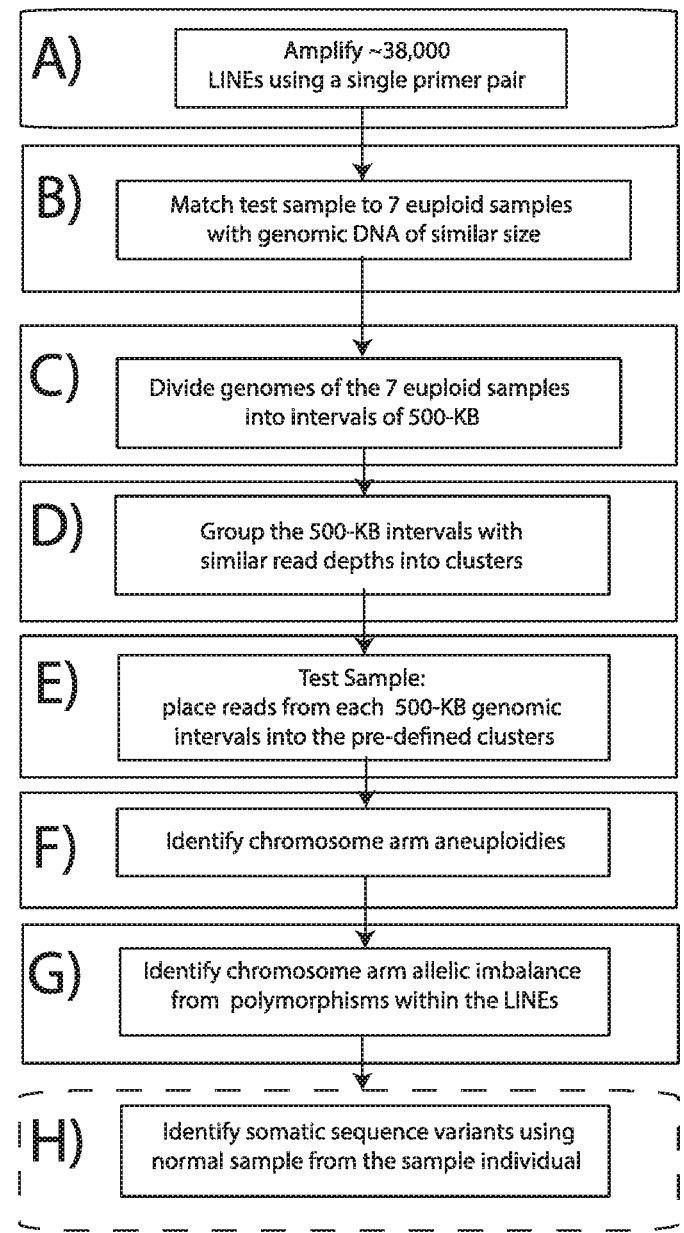
FIG. 36 contains a schematic showing an overview of an exemplary WALDO approach. (A) A single primer pair amplifies ~38,000 long interspersed nucleotide elements (LINEs). (B) A test sample is matched to seven euploid samples with genomic DNA of similar size. (C) The genome is divided into 4361 intervals, each of 500-kb in size. (D) The reads within these 500-kb genomic intervals in the euploid samples are grouped into 4361 clusters. All the 500-kb genomic intervals in the clusters have similar read depths. (E) The reads from each of the 500-kb genomic intervals in the test sample are placed into the pre-defined clusters. (F) Statistical tests, including a Support Vector Machine (SVM)-based algorithm, are used to determine whether the total reads from all the 500-kb genomic intervals on each chromosome arm are distributed as expected if the sample was euploid. The statistical tests are based on the observed distribution of reads within the clusters of the test sample, not by comparison to the reads in euploid samples. (G) Germline sequence variants at sites of known common polymorphisms within the LINEs provide information about arm-level allelic imbalance that can also be used to assess aneuploidy of individual chromosome arms. These same polymorphisms can be used to determine whether any two samples are derived from the same individual. (H) When there is a matched normal sample from the same individual available, WALDO can detect the number and nature of single base substitutions and insertions and deletions within the LINEs.

As shown in FIG. 36, a single primer pair is used to amplify LINEs. A test sample is then matched to several euploid samples with genomic DNA of similar size. The genome is divided into multiple intervals, and each interval has a similar size (e.g., 100, 200, 300, 400, 500, 600, 700, 800, 900 Kb, or 1 Mb, 2 Mb, 3 Mb, 4 Mb, or 5 Mb). The reads within these genomic intervals in the euploid samples are grouped into clusters. All of the genomic intervals in the clusters have similar read depths. The reads from each of the genomic intervals in the test sample are placed into the predefined clusters. Statistical tests, e.g., an SVM-based algorithm, are used to determine whether the total reads from all of the genomic intervals on each chromosome arm are distributed as expected if the sample is euploid. The statistical tests are based on the observed distribution of reads within the clusters of the test sample, not by comparison with the reads in euploid samples. Germline sequence variants at sites of known common polymorphisms within the LINEs provide information about arm-level allelic imbalance that can also be used to assess aneuploidy of individual chromosome arms. These same polymorphisms can be used to determine whether any two samples are derived from the same individual. When there is a matched normal sample from the same individual available, the methods described herein can detect the number and nature of single base substitutions and insertions and deletions within the LINEs.

Fast-SeqS

For each DNA sample evaluated, FAST-SeqS can be used to amplify approximately 38,000 amplicons with a single primer pair (Kinde I, Papadopoulos N, Kinzler K W, & Vogelstein B (2012) FAST-SeqS: a simple and efficient method for the detection of aneuploidy by massively parallel sequencing. PloS ONE 7 (7): e41162). Massively parallel sequencing can be performed. In some embodiments, degenerate bases at the 5' end of the primer are used as molecular barcodes to uniquely label each DNA template molecule. Thus, each DNA template molecule will be counted only once. In some embodiments, each unique read can be sequenced between 1 and 20 times (e.g., about 1, 2, 3, 4, 5, 6, 7, 8, 9, 10, 11, 12, 13, 14, 15, 16, 17, 18, 19, or 20 times)

Sample Alignment and Genomic Interval Grouping

Alignment programs (e.g., Bowtie2) can be used to align reads to human reference genome assembly (e.g., GRC37). Exact matches to the reference genome can be identified. These exact matches allow inclusion of common polymorphisms. In light of experimental and stochastic variation, the number of reads that mapped to each genomic region of any euploid sample is expected to be variable. In some embodiments, to minimize this variability, clusters of genomic intervals with similar read depth across all chromosomes in multiple euploid samples are identified. This step can estimate the expected variability in read depth in a sample when no aneuploidy is present. In some embodiments, the genomic interval has a size of 100, 200, 300, 400, 500, 600, 700, 800, 900 Kb, or 1 Mb, 2 Mb, 3 Mb, 4 Mb, or 5 Mb. In some embodiments, the genomic interval has a size of 500 kb.

Clustering of the genomic intervals can be performed as follows. Each test sample is matched to euploid samples that have similar amplicon sizes. This is important because smaller amplicons can be over-represented in the amplicons generated from DNA that is of small size prior to amplification. The euploid samples can be derived from WBC or plasma DNA from normal individuals, collectively termed the "euploid reference set". The euploid samples can include at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 samples. In some embodiments, the euploid samples does not include more than 5, 6, 7, 8, 9, or 10 samples.

For each test sample p, the samples with the smallest Euclidean distance to p, defined as $$D(p,q) = \sqrt{\Sigma_n (q_n - p_n)^2}$$

where, pn and qn are the fraction of amplicons of size n in samples p and q, and the sum is over all amplicon sizes in the two samples. In some embodiments, before calculating the Euclidian distances between the test samples from the samples in the euploid reference set, the following amplicons are excluded: (i) Using maximum likelihood estimates, the amplicons are ranked by variance among the euploid samples and the top 1% excluded. (ii), any amplicons with <10 reads in one sample but >50 reads in any of the other samples are removed. In each sample, the genomic intervals are scaled by subtracting the mean and dividing by the standard deviation of reads in each sample.

The scaled genomic intervals are then clustered across the selected normal samples. First, each genomic interval i is assigned to a primary cluster $C_i$. Next, the reads in genomic interval i across all samples is compared to the average number of read in the samples in all other genomic intervals i' that occurred on the remaining autosomal chromosomes. If the average number of reads in genomic interval i' is not significantly different from the number of reads in genomic interval i, it is added to cluster $C_i$. This process is repeated for each genomic interval, yielding multiple clusters (e.g., more than 1000, 2000, 3000, 4000, or 5000 clusters). Every interval i belongs to its primary cluster but the same interval can also belong to some other clusters. In some embodiments, there are about 4300 clusters.

In some embodiments, scaled reads are not randomly distributed. In some embodiments, the distribution of scaled reads within the genomic intervals in each cluster follows an approximately normal distribution.

Identifying Chromosome Arm Gains or Losses in a Test Sample

The methods described herein can use just a few euploid samples (e.g., about 2, 3, 4, 5 6, 7, 8, 9, or 10 samples) to define clusters of genomic intervals with similar amplification properties. The statistical tests for aneuploidy are based on the read distributions within the test sample and independently of the read distributions in any euploid sample. In some embodiments, maximum likelihood is used to estimate the means $\mu$ and variances $\delta^2$ of the genomic intervals in each cluster. In some embodiments, the robustness of these estimates can be improved by iteratively removing outlying genomic intervals within the test sample from the clusters. In some embodiments, clusters containing fewer than 10 genomic intervals are not included in the analysis. In some embodiments, for each cluster, any genomic interval meeting the criteria $$\min(2*CDF(\mu,\sigma_i^2), 2*(1-CDF(\mu,\sigma_i^2))) < 0.01.$$

is removed from all clusters. Next, the $\mu$ and the variances $\delta^2$ parameters of each cluster is re-estimated by maximum likelihood. The two steps are repeated until no outlying genomic intervals remained. The statistical significance of the total reads from all genomic intervals on the arm is estimated. Because sums of normally distributed random variables are also normally distributed random variables, the calculation is straightforward. For each chromosome arm, it can be calculated $$\Sigma_1^I R_i \sim N(\Sigma_1^I \mu_i, \Sigma_1^I \sigma_i^2)$$

wherein $R_i$ is the scaled reads and i is the number of clusters on the arm. Z-scores can be produced using the quantile function $$1-CDF(\Sigma_1^I \mu_i, \Sigma_1^I \sigma_i^2)$$

Positive Z-scores>$\alpha$ represents gains and negative Z-scores<–$\alpha$ represents losses. The $\alpha$ value is the selected significance threshold.

Arm Level Allelic Imbalance

Common polymorphisms from 1000 Genomes (including e.g., 24,720 single nucleotide and 1,500 indels, MAF>1%) can be used as candidate heterozygous sites. For each of the normal samples, polymorphic sites can be confidently called as heterozygous and diploid. Polymorphisms can be defined as those with variant-allele frequencies (VAF) (0.4<VAF<0.6), where VAF=#non-reference reads/total reads. VAFs can be modeled at these sites as random variables taken from a normal distribution with $\mu$=0.5; and the variances $\delta^2$ can be estimated by maximum likelihood as a function of read depth.

To determine whether the alleles on a chromosome arm in a test sample is unbalanced, the subset of polymorphic sites at which both alleles are present and in which the sum of the reads on both alleles is >25 are identified.

The observed VAF with the normal distribution, using the expected variance for the observed read depth, yielding a two-sided P-value. All p-values on a chromosome arm can be Z-transformed and combined with a weighted Stouffer's method, with the observed read depth at each site used as its weight. The formula used for this calculation is $$Z \sim \frac{\sum_{i=1}^{k} w_i Z_i}{\sqrt{\sum_{i=1}^{k} w_i^2}}$$

where $w_i$ is UID depth at variant i, $Z_i$ is the Z-score of variant i, and k is the number of variants observed on the chromosome arm. A chromosome arm is scored as having an allelic imbalance if the resulting Z score is greater than the selected statistical significance threshold $\alpha$ (e.g., by one-sided test).

Generation of Synthetic Aneuploid Samples

Synthetic aneuploid samples can be created by adding (or subtracting) reads from several chromosome arms to the reads from these normal DNA samples. The reads from 1, 5, 10, 15, 20, or 25 randomly selected chromosome arms are added or subtracted to each sample. The additions and subtractions are designed to represent neoplastic cell fractions ranging from 0.5% to 10% and result in synthetic samples containing exactly nine million reads. The reads from each chromosome arm can be added or subtracted uniformly. These synthetically generated samples in which reads from only a single chromosome arm are added or subtracted can be used estimate the performance of WALDO.

Genome-Wide Aneuploidy Detection

The present disclosure provides genome-wide aneuploidy detections. In some embodiments, a two-class support vector machine (SVM) can be trained to discriminate between euploid samples and the synthetic samples. The training set can contain white blood cells (WBC) samples and samples with aneuploidy (e.g., all synthetic samples).

SVM training can be done by various statistical software (e.g., in R, using radial basis kernel and default parameters).

The number of reads from the data on experimental samples can vary widely, particularly when the samples are derived from sources with limited amounts of DNA such as plasma. In some embodiments, samples with low reads can generate artificially high SVM scores if read depth is not taken into account. Thus, read depth can be controlled by modeling the change in SVM scores as a function of read depth in the normal samples. The average ratio r at each depth decreased monotonically as a function of increasing read depth. The relation between read depth and SVM score can be modeled using the following equation. Thus, raw SVM scores can be corrected by dividing by the ratio r, using the formula $$\log\left(1 - \frac{1}{r}\right) = Ax + B.$$

To score a sample as aneuploid, whether any single chromosome arm in it is lost or gained in a statistically significant manner is determined. A statistically significant gain of a single chromosome arm is defined as one whose Z-score is above the maximum Z-score observed in the normal samples (e.g., 1$\sigma$, 2$\sigma$, 3$\sigma$, 4$\sigma$, or 5$\sigma$ above). Similarly, a statistically significant loss of a single chromosome arm is defined as one whose Z-score is below the minimum Z-score observed in the normal samples (e.g., 1 $\sigma$, 2 $\sigma$, 3 $\sigma$, 4$\sigma$, or 5 $\sigma$ below). Allelic imbalance based on SNPs can be defined for a chromosome arm whose Z-score is above the maximum Z-score observed in normal samples (e.g., 1$\sigma$, 2$\sigma$, 3$\sigma$, 4$\sigma$, or 5$\sigma$ above). Only samples in which no single chromosome arm is gained or lost when defined in this way are subjected to SVM analysis. The rationale for this process is that the SVM is designed to identify samples with large numbers of chromosome arm gains or losses but relatively low neoplastic cell fractions. In some embodiments, the SVM is not designed to detect aneuploidy in samples with neoplastic cell fractions >10%, which are easily identified through evaluation of their Z-scores and comparison to the normal samples.

Somatic Sequence Mutations and Microsatellite Instability (MSI)

The present disclosure also provides methods to detect somatic sequence mutations and microsatellite instability. When matched normal samples are available, somatic single base substitution (SBS), insertion and deletion (indel) mutations can be detected based on LINE amplicon sequences and alignments. In some embodiments, the molecular barcoding approach for error reduction is used. In some embodiments, the SBS mutations can be identified by directly comparing amplicons from the test sample with amplicons from the matched normal, and do not require any alignment to the reference genome.

Indels can be called in a similar way. Amplicons are aligned from the test sample and matched normal sample to the reference genome (GRc37). In some embodiments, a somatic indel can be at least ten reads from the test sample differed from any normal read by virtue of the same insertion or deletion.

Microsatellite instability in a test sample can determined by counting the number of somatic indels in mononucleotide tracts of >3 nucleotides. Somatic indels in monotracts can be rare in a normal sample. Therefore, the null distribution of counts can be modeled as Poisson ($\lambda=1$), where $\lambda$ is the mean number of somatic indels in a monotract in a normal sample. A sample is determined as harboring MSI if the number of somatic indels is statistically significant. To evaluate how often normal samples can be scored as MSI using this process, the total reads in normal samples can be randomly split into two equal partitions. The first partition can be used as the reference sample and the second partition can be used as a test sample.

This document provides methods and materials for identifying one or more chromosomal anomalies (e.g., aneuploidies) in a sample. For example, a mammal (e.g., a sample obtained from a mammal) can be assessed for the presence or absence of one or more chromosomal anomalies. In some cases, this document provides methods and materials for using amplicon-based sequencing data to identify a mammal as having a disease associated with one or more chromosomal anomalies (e.g., cancer). For example, the methods and materials described herein can be applied to a sample obtained from a mammal to identify the mammal as having one or more chromosomal anomalies. For example, methods and materials described herein can be applied to a sample obtained from a mammal to identify the mammal as having a disease associated with one or more chromosomal anomalies (e.g., cancer). This document also provides methods and materials for identifying and/or treating a disease or disorder associated with one or more chromosomal anomalies (e.g., one or more chromosomal anomalies identified as described herein). In some cases, the one or more chromosomal anomalies can be identified in DNA (e.g., genomic DNA) obtained from a sample obtained from a mammal. For example, a prenatal mammal (e.g., prenatal human) can be identified as having a disease or disorder based, at least in part, on the presence of one or more chromosomal anomalies, and, optionally, can be treated with one or more treatments for the disease or disorder. For example, a mammal identified as having cancer based, at least in part, on the presence of one or more chromosomal anomalies can be treated with one or more cancer treatments.

Any appropriate mammal can be assessed and/or treated as described herein. A mammal can be a prenatal mammal (e.g., prenatal human). A mammal can be a mammal suspected of having a disease associated with one or more chromosomal anomalies (e.g., cancer). In some cases, humans or other primates such as monkeys can be assessed for the presence of one or more chromosomal anomalies as described herein. In some cases, dogs, cats, horses, cows, pigs, sheep, mice, and rats can be assessed for the presence of one or more chromosomal anomalies as described herein. For example, a human can be assessed for the presence of one or more chromosomal anomalies as described herein and, optionally, can be treated with one or more cancer treatments as described herein.

Any appropriate sample from a mammal can be assessed as described herein (e.g., assessed for the presence of one or more chromosomal anomalies). A sample can include genomic DNA. In some cases, a sample can include cell-free circulating DNA (e.g., cell-free circulating fetal DNA). In some cases, a sample can include circulating tumor DNA (ctDNA). Examples of samples that can contain DNA include, without limitation, blood (e.g., whole blood, serum, or plasma), amnion, tissue, urine, cerebrospinal fluid, saliva, sputum, broncho-alveolar lavage, bile, lymphatic fluid, cyst fluid, stool, ascites, pap smears, cerebral spinal fluid, endocervical, endometrial, and fallopian samples. For example, a sample can be a plasma sample. For example, a sample can be a urine sample. For example, a sample can be a saliva sample. For example, a sample can be a cyst fluid sample. For example, a sample can be a sputum sample. In some cases, a sample can include a neoplastic cell fraction (e.g., a low neoplastic cell fraction). In cases where a sample includes a low neoplastic cell fraction, the neoplastic cell fraction can be from about 0.01% to about 10% (e.g., from about 0.05% to about 10%, from about 0.5% to about 10%, from about 1% to about 10%, from about 3% to about 10%, from about 5% to about 10%, from about 7% to about 10%, from about 0.01% to about 8%, from about 0.01% to about 5%, from about 0.01% to about 2%, from about 0.01% to about 1%, from about 0.01% to about 0.5%, from about 0.05% to about 8%, from about 0.1% to about 4%, or from about 0.5% to about 1%) of the cell content of the entire sample. For example, a sample that includes a low neoplastic cell fraction can be about 1% neoplastic cells. For example, a sample that includes a low neoplastic cell fraction can be about 0.5% neoplastic cells.

In some cases, a sample can be processed to isolate and/or purify DNA from the sample. In some cases, DNA isolation and/or purification can include cell lysis (e.g., using detergents and/or surfactants). In some cases, DNA isolation and/or purification can include removing proteins (e.g., using a protease). In some cases, DNA isolation and/or purification can include removing RNA (e.g., using an RNase).

Methods and materials for identifying one or more chromosomal anomalies can include assessing a genome (e.g., a genome of a mammal) for the presence or absence of one or more chromosomal anomalies (e.g., aneuploidies). The presence or absence of one or more chromosomal anomalies in the genome of a mammal can, for example, be determined by sequencing a plurality of amplicons obtained from a sample obtained from the mammal to obtain sequencing reads, and grouping the sequencing reads into clusters of genomic intervals. In some cases, read counts of genomic intervals can be compared to read counts of other genomic intervals within the same sample. In some cases where read counts of genomic intervals are compared to read counts of other genomic intervals within the same sample, a second (e.g., control or reference) sample is not assayed. For example, when using methods and materials described herein to identify numerical disorders (e.g., aneuploidy) and/or structural abnormalities, genomic intervals can be compared to read counts of other genomic intervals within the same sample. In some cases, read counts of genomic intervals can be compared to read counts of genomic intervals in another sample. For example, when using the methods and materials described herein to identify genetic relatedness, polymorphisms (e.g., somatic mutations), and/or microsatellite instability, genomic intervals can be compared to read counts of genomic intervals in a reference sample. A reference sample can be a synthetic sample. A reference sample can be from a database. In some cases where the methods and materials described herein are used to identify genetic relatedness, a reference sample can be a forensic sample. In some cases where methods and materials described herein are used to identify genetic relatedness, a reference sample can be obtained from suspected relation. In some cases where the methods and materials described herein are used to identify, anomalies (e.g., aneuploidies), one or more polymorphisms (e.g., somatic mutations), and/or microsatellite instability, a reference sample can be a normal sample obtained from the same cancer patient (e.g., a sample from the cancer patient that does not harbor cancer cells) or a normal sample from another source (e.g., a patient that does not have cancer).

In some cases, methods and materials described herein can be used for detecting aneuploidy in a genome of mammal. For example, a plurality of amplicons obtained from a sample obtained from a mammal can be sequenced, the sequencing reads can be grouped into clusters of genomic intervals, the sums of the distributions of the sequencing reads in each genomic interval can be calculated, a Z-score of a chromosome arm can be calculated, and the presence or absence of an aneuploidy in the genome of the mammal can be identified. The distributions of the sequencing reads in each genomic interval can be summed. For example, sums of distributions of the sequencing reads in each genomic interval can be calculated using the equation $\Sigma_1^I R_i \sim N(\Sigma_1^I \mu_i, \Sigma_1^I \sigma_i^2)$, where $R_i$ is the number of sequencing reads, I is the number of clusters on a chromosome arm, N is a Gaussian distribution with parameters $\mu_i$ and $\sigma_i^2$, $\mu_i$ is the mean number of sequencing reads in each genomic interval, and $\sigma_i^2$ is the variance of sequencing reads in each genomic interval. a Z-score of a chromosome arm can be calculated using any appropriate technique. For example, a Z-score of a chromosome arm can be calculated using the quantile function $1-\text{CDF}(\Sigma_1^I \mu_i, \Sigma_1^I \sigma_i^2)$. The presence of an aneuploidy in the genome of the mammal can be identified in the genome of the mammal when the Z-score is outside a predetermined significance threshold, and the absence of an aneuploidy in the genome of the mammal can be identified in the genome of the mammal when the Z-score is within a predetermined significance threshold. The predetermined threshold can correspond to the confidence in the test and the acceptable number of false positives. For example, a significance threshold can be ±1.96, ±3, or ±5.

In some cases, methods and materials described herein can be used for detecting one or more polymorphisms in a genome of a mammal. For example, a plurality of amplicons obtained from a sample obtained from a first mammal (e.g., a test mammal or a mammal suspected of harboring one or more polymorphisms) can be sequenced, a plurality of amplicons obtained from a sample obtained from a second mammal (e.g., a reference mammal) can be sequenced, variant sequencing reads from the sample obtained from the first mammal can be grouped into clusters of genomic intervals, reference sequencing reads from the sample obtained from the second mammal can be grouped into clusters of genomic intervals, a chromosome arm having a sum of the variant sequencing reads and the reference sequencing reads on both alleles that is greater than about 3 (e.g., greater than about 4, greater than about 5, greater than about 6, greater than about 7, greater than about 8, greater than about 9, greater than about 10, greater than about 12, greater than about 15, greater than about 18, greater than about 20, greater than about 22, greater than about 25, or greater than about 30) can be selected, a variant-allele frequency (VAF) of the selected chromosome arm can be determined, and the presence or absence of one or more polymorphisms on the selected chromosome arm can be identified. A VAF of the selected chromosome arm can be determined using any appropriate technique. For example, a VAF of the selected chromosome arm can be the number of variant sequencing reads/total number of sequencing reads. The presence of one or more polymorphisms in the genome of the mammal can be identified in the genome of the mammal when the VAF is between about 0.2 and about 0.8 (e.g., between about 0.3 and about 0.8, between about 0.4 and about 0.8, between about 0.5 and about 0.8, between about 0.6 and about 0.8, between about 0.2 and about 0.7, between about 0.2 and about 0.6, between about 0.2 and about 0.5, or between about 0.2 and about 0.4), and the absence of one or more polymorphisms in the genome of the mammal can be identified in the genome of the mammal when the VAF is within a predetermined significance threshold. As one non-limiting example, the presence of one or more polymorphisms in the genome of the mammal can be identified in the genome of the mammal when the VAF is between about 0.4 and 0.6.

Methods and materials for identifying one or more chromosomal anomalies as described herein can include using amplicon-based sequencing reads. For example, a plurality of amplicons (e.g., amplicons obtained from a sample obtained from the mammal) can be sequenced. In some cases, each amplicon can be sequenced between about 1 and about 20 (e.g., between about 1 and about 15, between about 1 and about 12, between about 1 and about 10, between about 1 and about 8, between about 1 and about 5, between about 5 and about 20, between about 7 and about 20, between about 10 and about 20, between about 13 and about 20, between about 3 and about 18, between about 5 and about 16, or between about 8 and about 12) times. In some cases, amplicon-based sequencing reads can include continuous sequencing reads. In some cases, amplicons can include long interspersed nucleotide elements (LINEs). In some cases, amplicon-based sequencing reads can include from about 100,000 to about 25 million (e.g., from about 100,000 to about 20 million, from about 100,000 to about 15 million, from about 100,000 to about 12 million, from about 100,000 to about 10 million, from about 100,000 to about 5 million, from about 100,000 to about 1 million, from about 100,000 to about 750,000, from about 100,000 to about 500,000, from about 100,000 to about 250,000, from about 250,000 to about 25 million, from about 500,000 to about 25 million, from about 750,000 to about 25 million, from about 1 million to about 25 million, from about 5 million to about 25 million, from about 10 million to about 25 million, from about 15 million to about 25 million, from about 200,000 to about 20 million, from about 250,000 to about 15 million, from about 500,000 to about 10 million, from about 750,000 to about 5 million, or from about 1 million to about 2 million) sequencing reads. In some cases, methods of sequencing amplicons include, without limitation, a Fast Aneuploidy Screening Test-Sequencing System (FAST-SeqS). For example, sequencing a plurality of amplicons can include assigning a unique identifier (UID) to each template molecule (e.g., to each amplicon), amplifying each uniquely tagged template molecule to create UID-families, and redundantly sequencing the amplification products. For example, sequencing a plurality of amplicons can include calculating a Z-score of a variant on said selected chromosome arm using the equation $$Z \sim \frac{\sum_{i=1}^{k} w_i Z_i}{\sqrt{\sum_{i=1}^{k} w_i^2}},$$

where $w_i$ is UID depth at a variant i, $Z_i$ is the Z-score of variant i, and k is the number of variants observed on the chromosome arm. In some cases, methods of sequencing amplicons can be as described in Example 6. In some cases, methods of sequencing amplicons can be as described elsewhere (see, e.g., US 2015/0051085; and Kinde et al. 2012 *PloS ONE* 7:e41162).

In some cases, methods and materials for identifying one or more chromosomal anomalies (e.g., aneuploidies) as described herein can include amplification of a plurality of amplicons. For example, amplification of a plurality of amplicons can be performed using a single primer pair. Methods of amplifying a plurality amplicons include, without limitation, polymerase chain reaction (PCR) assays.

A plurality of amplicons can include any appropriate number of amplicons. In some cases, a plurality of amplicons can include from about 10,000 to about 1,000,000 (e.g., from about 15,000 to about 1,000,000, from about 25,000 to about 1,000,000, from about 35,000 to about 1,000,000, from about 50,000 to about 1,000,000, from about 75,000 to about 1,000,000, from about 100,000 to about 1,000,000, from about 125,000 to about 1,000,000, from about 160,000 to about 1,000,000, from about 180,000 to about 1,000,000, from about 200,000 to about 1,000,000, from about 300,000 to about 1,000,000, from about 500,000 to about 1,000,000, from about 750,000 to about 1,000,000, from about 10,000 to about 800,000, from about 10,000 to about 500,000, from about 10,000 to about 250,000, from about 10,000 to about 150,000, from about 10,000 to about 100,000, from about 10,000 to about 75,000, from about 10,000 to about 50,000, from about 10,000 to about 40,000, from about 10,000 to about 30,000, or from about 10,000 to about 20,000) amplicons. As one non-limiting example, a plurality of amplicons can include about 38,000 amplicons. Amplicons in a plurality of amplicons can be any appropriate length. In some cases, an amplicon can include from about 50 to about 140 (e.g., from about 60 to about 140, from about 76 to about 140, from about 90 to about 140, from about 100 to about 140, from about 130 to about 140, from about 50 to about 130, from about 50 to about 120, from about 50 to about 110, from about 50 to about 100, from about 50 to about 90, from about 50 to about 80, from about 60 to about 130, from about 70 to about 125, from about 80 to about 120, or from about 90 to about 100) nucleotides. As one non-limiting example, an amplicon can include about 100 nucleotides.

Methods and materials for identifying one or more chromosomal anomalies as described herein can include grouping sequencing reads (e.g., from a plurality of amplicons) into clusters (e.g., unique clusters) of genomic intervals. A genomic interval can be included in one or more clusters. In some cases, a genomic interval can belong to from about 100 to about 252 (e.g., from about 125 to about 252, from about 150 to about 252, from about 175 to about 252, from about 200 to about 252, from about 225 to about 252, from about 100 to about 250, from about 100 to about 225, from about 100 to about 200, from about 100 to about 175, from about 100 to about 150, from about 125 to about 225, from about 150 to about 200, or from about 160 to about 180) clusters. As one non-limiting example, a genomic interval can belong to about 176 clusters. Each cluster can include any appropriate number of genomic intervals. In some cases, each cluster can include the same number of genomic intervals. In some cases, cluster can include varying numbers of genomic clusters. As one non-limiting example, each cluster can include about 200 genomic intervals.

A cluster of genomic intervals can include any appropriate number of genomic intervals. In some cases, a cluster of genomic intervals can include from about 4000 to about 4500 (e.g., from about 4100 to about 4500, from about 4200 to about 4500, from about 4300 to about 4500, from about 4400 to about 4500, from about 4000 to about 4400, from about 4000 to about 4300, from about 4000 to about 4200, from about 4000 to about 4100, from about 4100 to about 4400, or from about 4200 to about 4300) genomic intervals. As one non-limiting example, a cluster of genomic intervals can include about 4361 genomic intervals. A genomic interval can be any appropriate length. For example, a genomic interval can be the length of an amplicon sequenced as described herein. For example, a genomic interval can be the length of a chromosome arm. In some cases, a genomic interval can include from about 100 to about 125,000,000 (e.g., from about 250 to about 125,000,000, from about 500 to about 125,000,000, from about 750 to about 125,000,000, from about 1,000 to about 125,000,000, from about 1,500 to about 125,000,000, from about 2,000 to about 125,000,000, from about 5,000 to about 125,000,000, from about 7,500 to about 125,000,000, from about 10,000 to about 125,000,000, from about 25,000 to about 125,000,000, from about 50,000 to about 125,000,000, from about 100,000 to about 125,000,000, from about 250,000 to about 125,000,000, from about 500,000 to about 125,000,000, from about 100 to about 1,000,000, from about 100 to about 750,000, from about 100 to about 500,000, from about 100 to about 250,000, from about 100 to about 100,000, from about 100 to about 50,000, from about 100 to about 25,000, from about 100 to about 10,000, from about 100 to about 5,000, from about 100 to about 2,500, from about 100 to about 1,000, from about 100 to about 750, from about 100 to about 500, from about 100 to about 250, from about 500 to about 1,000,000, from about 5000 to about 900,000, from about 50,000 to about 800,000, or from about 100,000 to about 750,000) nucleotides. As one non-limiting example, a genomic interval can include about 500,000 nucleotides. Clusters of genomic intervals can be formed using any appropriate method. For example, amplicons of similar size can be clustered. In some cases, clusters of genomic intervals can be formed as described in Example 6.

Methods and materials described herein also can employ supervised machine learning. In some cases, supervised machine learning can detect small changes in one or more chromosome arms. For example, supervised machine learning can detect changes such as chromosome arm gains or losses that are often present in a disease or disorder associated with chromosomal anomalies, such as cancer. In some cases, supervised machine learning can be used to classify samples according to aneuploidy status. For example, supervised machine learning can be employed to make genome-wide aneuploidy calls. In some cases, a support vector machine model can include obtaining an SVM score. An SVM score can be obtained using any appropriate technique. In some cases, an SVM score can be obtained as described elsewhere (see, e.g., Cortes 1995 *Machine learning* 20:273-297; and Meyer et al. 2015 *R package version:* 1.6-3). At lower read depths, a sample will typically have a higher raw SVM score. Thus, in some cases, raw SVM probabilities can be corrected based on the read depth of a sample using the equation $$\log\left(1 - \frac{1}{r}\right) = Ax + B,$$

where r is the ratio of the SVM score at a particular read depth/minimum SVM score of a particular sample given sufficient read depth. A and B can be determined as described in Example 6. For example, A=−7.076*10^−7, x=the number of unique template molecules for the given sample, and B=−1.946*10^−1.

Methods and materials described herein can be used to identify any appropriate chromosomal anomaly. Examples of chromosomal anomalies include, without limitation, numerical disorders, structural abnormalities, allelic imbalances, and microsatellite instabilities. A chromosomal anomaly can include a numerical disorder. For example, a chromosomal anomaly can include an aneuploidy (e.g., an abnormal number of chromosomes). In some cases, an aneuploidy can include an entire chromosome. In some cases, an aneuploidy can include part of a chromosome (e.g., a chromosome arm gain or a chromosome arm loss). Examples of aneuploidies include, without limitation, monosomy, trisomy, tetrasomy, and pentasomy. A chromosomal anomaly can include a structural abnormality. Examples of structural abnormalities include, without limitation, deletions, duplications, translocations (e.g., reciprocal translocations and Robertsonian translocations), inversions, insertions, rings, and isochromosomes. Chromosomal anomalies can occur on any chromosome pair (e.g., chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, chromosome 20, chromosome 21, chromosome 22, and/or one of the sex chromosomes (e.g., an X chromosome or a Y chromosome). For example, aneuploidy can occur, without limitation, in chromosome 13 (e.g., trisomy 13), chromosome 16 (e.g., trisomy 16), chromosome 18 (e.g., trisomy 18), chromosome 21 (e.g., trisomy 21), and/or the sex chromosomes (e.g., X chromosome monosomy; sex chromosome trisomy such as XXX, XXY, and XYY; sex chromosome tetrasomy such as XXXX and XXYY; and sex chromosome pentasomy such as XXXXX, XXXXY, and XYYYY). For example, structural abnormalities can occur, without limitation, in chromosome 4 (e.g., partial deletion of the short arm of chromosome 4), chromosome 11 (e.g., a terminal 11q deletion), chromosome 13 (e.g., Robertsonian translocation at chromosome 13), chromosome 14 (e.g., Robertsonian translocation at chromosome 14), chromosome 15 (e.g., Robertsonian translocation at chromosome 15), chromosome 17 (e.g., duplication of the gene encoding peripheral myelin protein 22), chromosome 21 (e.g., Robertsonian translocation at chromosome 21), and chromosome 22 (e.g., Robertsonian translocation at chromosome 22).

Methods and materials described herein can be used for identifying and/or treating a disease associated with one or more chromosomal anomalies (e.g., one or more chromosomal anomalies identified as described herein, such as, without limitation, an aneuploidy). In some cases, a DNA sample (e.g., a genomic DNA sample) obtained from a mammal can be assessed for the presence or absence of one or more chromosomal anomalies. For example, a prenatal mammal (e.g., prenatal human) can be identified as having a disease based, at least in part, on the presence of one or more chromosomal anomalies can be treated with one or more cancer treatments. As another example, a mammal identified as having cancer based, at least in part, on the presence of one or more chromosomal anomalies can be treated with one or more cancer treatments.

In some cases, a mammal identified as having a disease associated with one or more chromosomal anomalies as described herein (e.g., based at least in part on the presence of one or more chromosomal anomalies, such as, without limitation, an aneuploidy) can have the disease diagnosis confirmed using any appropriate method. Examples of methods that can be used to confirm the presence of one or more chromosomal anomalies include, without limitation, karyotyping, fluorescence in situ hybridization (FISH), quantitative PCR of short tandem repeats, quantitative fluorescence PCR (QF-PCR), quantitative PCR dosage analysis, quantitative mass spectrometry of SNPs, comparative genomic hybridization (CGH), whole genome sequencing, and exome sequencing.

Once identified as having a disease associated with one or more chromosomal anomalies as described herein (e.g., based at least in part on the presence of one or more chromosomal anomalies, such as, without limitation, an aneuploidy), a mammal can be treated accordingly. For example, when a mammal is identified as having a cancer associated with one or more chromosomal anomalies as described herein, the mammal can be treated with one or more cancer treatments. The one or more cancer treatments can include any appropriate cancer treatments. A cancer treatment can include surgery. A cancer treatment can include radiation therapy. A cancer treatment can include administration of a pharmacotherapy such chemotherapy, hormone therapy, targeted therapy, and/or cytotoxic therapy. Examples of cancer treatments include, without limitation, platinum compounds (such as cisplatin or carboplatin), taxanes (such as paclitaxel or docetaxel), albumin bound paclitaxel (nab-paclitaxel), altretamine, capecitabine, cyclophosphamide, etoposide (vp-16), gemcitabine, ifosfamide, irinotecan (cpt-11), liposomal doxorubicin, melphalan, pemetrexed, topotecan, vinorelbine, luteinizing-hormone-releasing hormone (LHRH) agonists (such as goserelin and leuprolide), anti-estrogen therapy (such as tamoxifen), aromatase inhibitors (such as letrozole, anastrozole, and exemestane), angiogenesis inhibitors (such as bevacizumab), poly(ADP)-ribose polymerase (PARP) inhibitors (such as olaparib, rucaparib, and niraparib), external beam radiation therapy, brachytherapy, radioactive phosphorus, and any combinations thereof.

Any appropriate disease associated with one or more chromosomal anomalies as described herein (e.g., based at least in part on the presence of one or more chromosomal anomalies, such as, without limitation, an aneuploidy) can be identified and/or treated as described herein. Examples of diseases and conditions that can be associated with one or more chromosomal anomalies include, without limitation, lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer, acute lymphoblastic leukemia (ALL), acute myeloid leukemia (AML), cancer in adolescents, adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, hepatobiliary cancer, upper urinary tract cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, Waldenstrom Macroglobulinemia, Wilms' tumor, 1p36 deletion syndrome, 1q21.1 deletion syndrome, 2q37 deletion syndrome, Wolf-Hirschhorn syndrome, Cri du chat, 5q deletion syndrome, Williams syndrome, Monosomy 8p, Monosomy 8q, Alfi's syndrome, Kleefstra syndrome, Monosomy 10p, Monosomy 10q, Jacobsen syndrome, Patau syndrome, Angelman syndrome, Prader-Willi syndrome, Miller-Dieker syndrome, Smith-Magenis syndrome, Edwards syndrome, Down syndrome, DiGeorge syndrome, Phelan-McDermid syndrome, 22q11.2 distal deletion syndrome, Cat eye syndrome, XYY syndrome, Triple X syndrome, Klinefelter syndrome, Wolf-Hirschhorn syndrome, Jacobsen syndrome, Charcot-Marie-Tooth disease type 1A, and Lynch Syndrome.

In some embodiments, methods provided herein can be used to detect aneuploidy (e.g., monosomy or trisomy) in a sample (e.g., a cervical sample, an endometrial sample, or a urine sample) obtained from a subject. Aneuploidy can be detected in any region of the genome that is known to be associated with cancer (e.g., endometrial or ovarian cancer). In some embodiments, aneuploidy can be detected in arms 4p, 7q, 8q, and/or 9q. Each of these arms harbors oncogenes and tumor suppressor genes that have been shown to undergo copy number alterations in many cancers, including endometrial or ovarian cancer. In some embodiments, aneuploidy can be detected in arms 5q, 8q, and/or 9p. Each of these arms harbors oncogenes and tumor suppressor genes that have been shown to undergo copy number alterations in many cancers, including bladder cancer. Other appropriate regions for aneuploidy detection, which aneuploidy regions(s) are associated with the presence of cancer in a subject, will be known to those of ordinary skill in the art.

In some embodiments, aneuploidy can be detected by amplifying interspersed nucleotide elements. For example, aneuploidy can be detected by amplifying long interspersed nucleotide elements (LINEs). Additionally or alternatively, aneuploidy can be detected by amplifying short interspersed nucleotide elements (SINEs). In some embodiments, aneuploidy can be detected using a technique in which a single PCR is used to co-amplify a plurality of members (e.g., ~38,000) of a subfamily of long interspersed nucleotide element-1 (L1 retrotransposons, also called LINEs). L1 retrotransposons, like other human repeats, have spread throughout the genome via retrotransposition and are found on all 39 non-acrocentric autosomal arms. In some embodiments, aneuploidy can be detected by any of the variety of methods disclosed in Patent Cooperation Treaty application publication number WO2013148496, the contents of which are incorporated herein by reference in their entirety. Those of ordinary skill in the art will be aware of other suitable methods for detecting aneuploidy. In some embodiments, the sample for detecting aneuploidy is collected using a Pap brush. In some embodiments, the sample for detecting aneuploidy is collected using a Tao brush.

In some embodiments, methods provided herein to detect aneuploidy can be combined with methods to detect the presence of one or more genetic biomarkers (e.g., mutations) in one or more genes selected from the group consisting of: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and the detection of genetic biomarkers (e.g., mutations) present in ctDNA, or both (e.g., to determine the presence of an ovarian or endometrial cancer). In some embodiments, methods provided herein to detect aneuploidy can be combined with methods to detect the presence of one or more genetic biomarkers (e.g., mutations) in one or more genes selected from the group consisting of: PTEN, TP53, PIK3CA, PIK3R1, CTNNB1, KRAS, FGFR2, POLE, APC, FBXW7, RNF43, and PPP2R1A, and the detection of genetic biomarkers (e.g., mutations) present in ctDNA, or both (e.g., to determine the presence of an endometrial cancer). In some embodiments, methods provided herein to detect aneuploidy can be combined with methods to detect the presence of one or more genetic biomarkers (e.g., mutations) in TP53, and the detection of genetic biomarkers (e.g., mutations) present in ctDNA, or both (e.g., to determine the presence of an ovarian cancer). In some embodiments, combining the detection of aneuploidy with the detection of one or more genetic biomarkers (e.g., mutations) in any of the genes described herein, the detection of genetic biomarkers (e.g., mutations) present in ctDNA, or both can increase the specificity and/or sensitivity of detecting ovarian or endometrial cancer. In some embodiments, the sample is collected using a Pap brush. In some embodiments, the sample is collected using a Tao brush.

Cancers

In some embodiments, methods provided herein can be used to detect the presence of cancer (e.g., the presence of a cancer cell) in a subject. In some embodiments, methods provided herein can be used to detect the presence of cancer at an early stage. In some embodiments, methods provided herein for identifying the presence of cancer in a subject with high sensitivity and specificity are performed prior to having determined that the subject already suffers from cancer, prior to having determined that the subject harbors a cancer cell, and/or prior to the subject exhibiting symptoms associated with cancer. In some embodiments, methods provided herein can be used to detect the presence of a genetic biomarker, a protein biomarker, and/or aneuploidy, which genetic biomarker, a protein biomarker, and/or aneuploidy is indicative that the subject has cancer (e.g., harbors a cancer cell).

Cancer types that can be detected by any of the variety of methods described herein include, without limitation, acute lymphoblastic leukemia (ALL), acute myeloid leukemia (AML), adrenal cancer, adrenocortical carcinoma, AIDS-related cancers, AIDS-related lymphoma, amyotrophic lateral sclerosis or ALS, anal cancer, appendix cancer, astrocytoma, astrocytoma, childhood cerebellar or cerebral, atypical teratoid/rhabdoid tumor, basal cell carcinoma, bile duct cancer, bile duct cancer, extrahepatic (see cholangiocarcinoma), bladder cancer, bone cancer, bone tumor, osteosarcoma/malignant fibrous histiocytoma, brain cancer, brain stem glioma, brain tumor, brain tumor, cerebellar astrocytoma, brain tumor, cerebral astrocytoma/malignant glioma, brain tumor, ependymoma, brain tumor, medulloblastoma, brain tumor, supratentorial primitive neuroectodermal tumors, brain tumor, visual pathway and hypothalamic glioma, brainstem glioma, breast cancer, bronchial adenomas/carcinoids, bronchial tumor, bronchioles lung cell carcinoma, Burkitt lymphoma, cancer in adolescents, carcinoid tumor, carcinoid tumor, childhood, carcinoid tumor, gastrointestinal, carcinoma of unknown primary, cardiac tumors, central nervous system lymphoma, primary, cerebellar astrocytoma, childhood, cerebral astrocytoma/malignant glioma, childhood, cervical cancer, childhood cancers, chondrosarcoma, chordoma, chronic lymphocytic leukemia (CLL), chronic myelogenous leukemia (CML), chronic myeloproliferative disorders, chronic myeloproliferative neoplasms, colon cancer, colorectal cancer, colorectal cancer (e.g., metastatic colorectal cancer), craniopharyngioma, cutaneous t-cell lymphoma, desmoplastic small round cell tumor, differentiated thyroid cancer, ductal carcinoma in situ, embryonal tumors, endometrial cancer, ependymoma, epithelioid hemangioendothelioma (EHE), esophageal cancer, esthesioneuroblastoma, Ewing's sarcoma in the Ewing family of tumors, extracranial germ cell tumor, extracranial germ cell tumor, childhood, extragonadal germ cell tumor, extrahepatic bile duct cancer, eye cancer, eye cancer, intraocular melanoma, eye cancer, retinoblastoma, fallopian tube cancer, fibrous histiocytoma of bone, gallbladder cancer, ganglioneuromatosis of the gastroenteric mucosa, gastric (stomach) cancer, gastric (stomach) cancer, gastric carcinoid, gastrointestinal carcinoid tumor, gastrointestinal stromal tumors (GIST), germ cell tumor, germ cell tumor: extracranial, extragonadal, or ovarian, gestational trophoblastic disease, gestational trophoblastic tumor, glioma, glioma of the brain stem, glioma, childhood cerebral astrocytoma, glioma, childhood visual pathway and hypothalamic, hairy cell leukemia, hairy cell tumor, head and neck cancer, heart cancer, hepatocellular (liver) cancer, histiocytosis, Hodgkin's lymphoma, hypopharyngeal cancer, hypothalamic and visual pathway glioma, childhood, inflammatory myofibroblastic tumor, intraocular melanoma, intraocular melanoma, Islet cell carcinoma (endocrine pancreas), islet cell tumors, Kaposi sarcoma, kidney cancer (renal cell cancer), Langerhans cell histiocytosis, laryngeal cancer, leukaemia, acute lymphoblastic (also called acute lymphocytic leukaemia), leukaemia, acute myeloid (also called acute myelogenous leukemia), leukaemia, chronic lymphocytic (also called chronic lymphocytic leukemia), leukemia, leukemia, chronic myelogenous (also called chronic myeloid leukemia), leukemia, hairy cell, lip and oral cavity cancer, liposarcoma, liver cancer (e.g., primary), lung adenocarcinoma, lung cancer, lung cancer (e.g., small cell lung carcinoma or non-small cell lung carcinoma), lymphoma, lymphoma, AIDS-related, lymphoma, Burkitt, lymphoma, cutaneous T-Cell, lymphoma, Hodgkin, lymphoma, primary central nervous system, lymphomas, Non-Hodgkin (an old classification of all lymphomas except Hodgkin's), macroglobulinemia, male breast cancer, malignant fibrous histiocytoma of bone, malignant fibrous histiocytoma of bone/osteosarcoma, medullary thyroid cancer, medulloblastoma, childhood, melanoma, melanoma, intraocular (eye), melanoma, intraocular (eye), Merkel cell cancer, Merkel cell carcinoma, mesothelioma, mesothelioma, adult malignant, mesothelioma, childhood, metastatic squamous neck cancer, metastatic squamous neck cancer with occult primary, midline tract carcinoma, mouth cancer, multiple endocrine neoplasia syndrome, childhood, multiple endocrine neoplasia syndromes, multiple endocrine neoplasia type 2A or 2B (MEN2A or MEN2B, respectively), multiple myeloma, multiple myeloma/plasma cell neoplasm, mycosis fungoides, myelodysplastic syndromes, myelodysplastic/myeloproliferative diseases, myelodysplastic/myeloproliferative neoplasms, myelogenous leukemia, myelogenous leukemia, chronic, myeloid leukemia, myeloid leukemia, adult acute, myeloid leukemia, childhood acute, myeloma, multiple (cancer of the bone-marrow), myeloproliferative disorders, chronic, myeloproliferative neoplasms, myxoma, nasal cavity and paranasal sinus cancer, nasopharyngeal cancer, nasopharyngeal carcinoma, neuroblastoma, oligodendroglioma, oral cancer, oral cavity cancer, oropharyngeal cancer, osteocarcinoma, osteosarcoma, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer, islet cell, pancreatic neuroendocrine tumors, papillary renal cell carcinoma, papillary thyroid cancer, papillomatosis, paraganglioma, paranasal sinus and nasal cavity cancer, parathyroid cancer, parathyroid hyperplasia, penile cancer, pharyngeal cancer, pheochromocytoma, Phyllodes breast tumors, pineal astrocytoma, pineal germinoma, pineoblastoma and supratentorial primitive neuroectodermal tumors, childhood, pituitary adenoma, pituitary cancer, plasma cell neoplasia/multiple myeloma, plasma cell neoplasm, pleuropulmonary blastoma, pregnancy and breast cancer, primary central nervous system lymphoma, primary peritoneal cancer, prostate cancer, rectal cancer, recurrent thyroid cancer, refractory differentiated thyroid cancer, renal cell cancer, renal cell carcinoma (kidney cancer), renal pelvis and ureter, transitional cell cancer, retinoblastoma, rhabdomyosarcoma, rhabdomyosarcoma, childhood, salivary gland cancer, sarcoma, sarcoma, Ewing family of tumors, Sarcoma, Kaposi, Sezary syndrome, skin cancer, skin cancer (melanoma), skin cancer (non-melanoma), skin carcinoma, Merkel cell, small intestine cancer, soft tissue sarcoma, squamous cell carcinoma, squamous cell carcinoma-see skin cancer (non-melanoma), squamous neck cancer, squamous neck cancer with occult primary, metastatic, stomach cancer, supratentorial primitive neuroectodermal tumor, childhood, T-cell lymphoma, T-cell lymphoma, cutaneous, testicular cancer, throat cancer, thymoma and thymic carcinoma, Thymoma, childhood, thyroid cancer, thyroid cancer, childhood, transitional cell cancer of the renal pelvis and ureter, trophoblastic tumor, gestational, unknown primary carcinoma, unknown primary site, cancer of, childhood, unknown primary site, carcinoma of, adult, ureter and renal pelvis, transitional cell cancer, urethral cancer, uterine cancer, uterine cancer, endometrial, uterine sarcoma, vaginal cancer, visual pathway and hypothalamic glioma, childhood, vulvar cancer, Waldenstrom macroglobulinemia, and Wilms tumor (kidney cancer).

In some embodiments, methods described herein are used to detect the presence of a single type of cancer. In some embodiments, methods described herein are capable of detecting two or more (e.g., 2, 3, 4, 5, 6, 7, 8, or more) types of cancer. For example, methods described herein can be used to detect the presence of liver cancer, ovarian cancer, esophageal cancer, stomach cancer, pancreatic cancer, colorectal cancer, lung cancer, or breast cancer. As another example, methods described herein can be capable of detecting the presence of each of liver cancer, ovarian cancer, esophageal cancer, stomach cancer, pancreatic cancer, colorectal cancer, lung cancer, and breast cancer (e.g., methods described herein are capable of detecting the presence of each of these types of cancers in a subject, although only one type of cancer may be present in the subject). In some embodiments, various methods described herein can be used to detect cancers selected from the group consisting of: pancreatic cancer, colon cancer, esophageal cancer, stomach cancer, ovarian cancer, liver cancer, lung cancer, and breast cancer, and combinations thereof. As another example, methods described herein can be used to detect the presence of cervical, endometrial, ovarian, or fallopian tubal cancers. As another example, methods described herein can be capable of detecting the presence of each of cervical, endometrial, ovarian, and fallopian tubal cancers (e.g., methods described herein are capable of detecting the presence of each of these types of cancers in a subject, although only one type of cancer may be present in the subject). As another example, methods described herein can be used to detect the presence of bladder cancer or an upper-tract urothelial carcinoma (UTUC). As another example, methods described herein can be capable of detecting the presence of each of bladder cancer and an upper-tract urothelial carcinoma (UTUC) (e.g., methods described herein are capable of detecting the presence of each of these types of cancers in a subject, although only one type of cancer may be present in the subject).

Further Diagnostic Testing

In some embodiments of diagnosing or identifying the presence of a disease (e.g., cancer) in a subject (e.g., using any of the variety of methods described herein), the subject is also identified as a candidate for further diagnostic testing. Provided herein are methods for selecting a subject for further diagnostic testing. In some embodiments, methods for selecting a subject for further diagnostic testing include detecting the presence of one or more genetic biomarkers in a biological sample isolated from the subject, detecting the presence of one or more protein biomarkers in a biological sample isolated from the subject, and/or detecting the presence of aneuploidy in a biological sample isolated from the subject and selecting a subject for further diagnostic testing when the presence of one or more genetic biomarkers, one or more protein biomarkers, or aneuploidy is identified. In some embodiments, methods for selecting a subject for further diagnostic testing further include detecting the presence of one or more member of one or more other classes of biomarkers. In some embodiments, the step of detecting is performed prior to having determined that the subject already suffers from cancer (e.g., when the subject is not known to harbor a cancer cell).

In some embodiments, the biological sample is isolated from a subject. Any suitable biological sample that contains one or more genetic biomarkers, protein biomarkers, and/or aneuploidy can be used in accordance with any of the variety of methods described herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, the subject may be selected for further diagnostic testing. In some embodiments, methods provided herein can be used to select a subject for further diagnostic testing at a time period prior to the time period when conventional techniques are capable of diagnosing the subject with an early-stage cancer. For example, methods provided herein for selecting a subject for further diagnostic testing can be used when a subject has not been diagnosed with cancer by conventional methods and/or when a subject is not known to harbor a cancer. In some embodiments, a subject selected for further diagnostic testing can be administered a diagnostic test (e.g., any of the diagnostic tests described herein) at an increased frequency compared to a subject that has not been selected for further diagnostic testing. For example, a subject selected for further diagnostic testing can be administered a diagnostic test at a frequency of twice daily, daily, bi-weekly, weekly, bi-monthly, monthly, quarterly, semi-annually, annually, or any at frequency therein. In some embodiments, a subject selected for further diagnostic testing can be administered one or more additional diagnostic tests compared to a subject that has not been selected for further diagnostic testing. For example, a subject selected for further diagnostic testing can be administered two diagnostic tests or more, whereas a subject that has not been selected for further diagnostic testing is administered only a single diagnostic test (or no diagnostic tests). In some embodiments, the diagnostic testing method can determine the presence of the same type of cancer as the originally detected cancer. Additionally or alternatively, the diagnostic testing method can determine the presence of a different type of cancer from the originally detected cancer.

In some embodiments, the diagnostic testing method is a scan. In some embodiments, the scan is a bone scan, a computed tomography (CT), a CT angiography (CTA), an esophagram (a Barium swallow), a Barium enema, a gallium scan, a magnetic resonance imaging (MRI), a mammography, a monoclonal antibody scan (e.g., ProstaScint® scan for prostate cancer, OncoScint® scan for ovarian cancer, and CEA-Scan® for colon cancer), a multigated acquisition (MUGA) scan, a PET scan, a PET/CT scan, a thyroid scan, an ultrasound (e.g., a breast ultrasound, an endobronchial ultrasound, an endoscopic ultrasound, a transvaginal ultrasound), an X-ray, a DEXA scan.

In some embodiments, the diagnostic testing method is a physical examination, such as, without limitation, an anoscopy, a biopsy, a bronchoscopy (e.g., an autofluorescence bronchoscopy, a white-light bronchoscopy, a navigational bronchoscopy), a digital breast tomosynthesis, a digital rectal exam, an endoscopy, including but not limited to a capsule endoscopy, virtual endoscopy, an arthroscopy, a bronchoscopy, a colonoscopy, a colposcopy, a cystoscopy, an esophagoscopy, a gastroscopy, a laparoscopy, a laryngoscopy, a neuroendoscopy, a proctoscopy, a sigmoidoscopy, a skin cancer exam, a thoracoscopy, an endoscopic retrograde cholangiopancreatography (ERCP), an ensophagogastroduodenoscopy, a pelvic exam.

In some embodiments, the diagnostic testing method is a biopsy (e.g., a bone marrow aspiration, a tissue biopsy). In some embodiments, the biopsy is performed by fine needle aspiration or by surgical excision. In some embodiments, the diagnostic testing method(s) further include obtaining a biological sample (e.g., a tissue sample, a urine sample, a blood sample, a check swab, a saliva sample, a mucosal sample (e.g., sputum, bronchial secretion), a nipple aspirate, a secretion or an excretion). In some embodiments, the diagnostic testing method(s) include determining exosomal proteins (e.g., an exosomal surface protein (e.g., CD24, CD147, PCA-3)) (Soung et al. (2017) Cancers 9(1):pii:E8). In some embodiments, the diagnostic testing method is an oncotype DX® test (Baehner (2016) Ecancermedicalscience 10:675).

In some embodiments, the diagnostic testing method is a test, such as without limitation, an alpha-fetoprotein blood test, a bone marrow test, a fecal occult blood test, a human papillomavirus test, low-dose helical computed tomography, a lumbar puncture, a prostate specific antigen (PSA) test, a pap smear, or a tumor marker test.

In some embodiments, the diagnostic testing method includes determining the level of a known protein biomarker (e.g., CA-125 or prostate specific antigen (PSA)). For example, a high amount of CA-125 can be found in subject's blood, which subject has ovarian cancer, endometrial cancer, fallopian tube cancer, pancreatic cancer, stomach cancer, esophageal cancer, colon cancer, liver cancer, breast cancer, or lung cancer. The term "biomarker" as used herein refers to "a biological molecule found in blood, other bodily fluids, or tissues that is a sign of a normal or abnormal process, or of a condition or disease", e.g., as defined by the National Cancer Institute. (see, e.g., the URL www.cancer.gov/publications/dictionaries/cancer-terms?CdrID=45618). A biomarker can include a genetic biomarker such as, without limitation, a nucleic acid (e.g., a DNA molecule, a RNA molecule (e.g., a microRNA, a long non-coding RNA (lncRNA) or other non-coding RNA) A biomarker can include a protein biomarker such as, without limitation, a peptide, a protein, or a fragment thereof.

In some embodiments, the biomarker is FLT3, NPM1, CEBPA, PRAM1, ALK, BRAF, KRAS, EGFR, Kit, NRAS, JAK2, KRAS, HPV virus, ERBB2, BCR-ABL, BRCA1, BRCA2, CEA, AFP, and/or LDH. See e.g., Easton et al. (1995) Am. J. Hum. Genet. 56:265-271, Hall et al. (1990) Science 250:1684-1689, Lin et al. (2008) Ann. Intern. Med. 149:192-199, Allegra et al. (2009) (2009) J. Clin. Oncol. 27:2091-2096, Paik et al. (2004) N. Engl. J. Med. 351:2817-2826, Bang et al. (2010) Lancet 376:687-697, Piccart-Gebhart et al. (2005) N. Engl. J. Med. 353:1659-1672, Romond et al. (2005) N. Engl. J. Med. 353:1673-1684, Locker et al. (2006) J. Clin. Oncol. 24:5313-5327, Giligan et al. (2010) J. Clin. Oncol. 28:3388-3404, Harris et al. (2007) J. Clin. Oncol. 25:5287-5312; Henry and Hayes (2012) Mol. Oncol. 6:140-146. In some embodiments, the biomarker is a biomarker for detection of breast cancer in a subject, such as, without limitation, MUC-1, CEA, p53, urokinase plasminogen activator, BRCA1, BRCA2, and/or HER2 (Gam (2012) World J. Exp. Med. 2 (5): 86-91). In some embodiments, the biomarker is a biomarker for detection of lung cancer in a subject, such as, without limitation, KRAS, EGFR, ALK, MET, and/or ROS1 (Mao (2002) Oncogene 21:6960-6969; Korpanty et al. (2014) Front Oncol. 4:204). In some embodiments, the biomarker is a biomarker for detection of ovarian cancer in a subject, such as, without limitation, HPV, CA-125, HE4, CEA, VCAM-1, KLK6/7, GST1, PRSS8, FOLR1, ALDH1 (Nolen and Lokshin (2012) Future Oncol. 8(1): 55-71; Sarojini et al. (2012) J. Oncol. 2012:709049). In some embodiments, the biomarker is a biomarker for detection of colorectal cancer in a subject, such as, without limitation, MLH1, MSH2, MSH6, PMS2, KRAS, and BRAF (Gonzalez-Pons and Cruz-Correa (2015) Biomed. Res. Int. 2015:149014; Alvarez-Chaver et al. (2014) World J. Gastroenterol. 20 (14): 3804-3824). In some embodiments, the diagnostic testing method determines the presence and/or expression level of a nucleic acid (e.g., microRNA (Sethi et al. (2011) J. Carcinog. Mutag. S1-005), RNA, a SNP (Hosein et al. (2013) Lab. Invest doi: 10.1038/labinvest.2013.54; Falzoi et al. (2010) Pharmacogenomics 11:559-571), methylation status (Castelo-Branco et al. (2013) Lancet Oncol 14:534-542), a hotspot cancer mutation (Yousem et al. (2013) Chest 143:1679-1684)). Non-limiting examples of methods of detecting a nucleic acid in a sample include: PCR, RT-PCR, sequencing (e.g., next generation sequencing methods, deep sequencing), a DNA microarray, a microRNA microarray, a SNP microarray, fluorescent in situ hybridization (FISH), restriction fragment length polymorphism (RFLP), gel electrophoresis, Northern blot analysis, Southern blot analysis, chromogenic in situ hybridization (CISH), chromatin immunoprecipitation (ChIP), SNP genotyping, and DNA methylation assay. See, e.g., Meldrum et al. (2011) Clin. Biochem. Rev. 32 (4): 177-195; Sidranksy (1997) Science 278 (5340): 1054-9.

In some embodiments, the diagnostic testing method includes determining the presence of a protein biomarker in a sample (e.g., a plasma biomarker (Mirus et al. (2015) Clin. Cancer Res. 21 (7): 1764-1771)). Non-limiting examples of methods of determining the presence of a protein biomarker include: western blot analysis, immunohistochemistry (IHC), immunofluorescence, mass spectrometry (MS) (e.g., matrix assisted laser desorption/ionization (MALDI)-MS, surface enhanced laser desorption/ionization time-of-flight (SELDI-TOF)-MS), enzyme-linked immunosorbent assay (ELISA), flow cytometry, proximity assay (e.g., VeraTag proximity assay (Shi et al. (2009) Diagnostic molecular pathology: the American journal of surgical pathology, part B: 18: 11-21, Huang et al. (2010) AM. J. Clin. Pathol. 134:303-11)), a protein microarray (e.g., an antibody microarray (Ingvarsson et al. (2008) Proteomics 8:2211-9, Woodbury et al. (2002) J. Proteome Res. 1:233-237), an IHC-based microarray (Stromberg et al. (2007) Proteomics 7:2142-50), a microarray ELISA (Schroder et al. (2010) Mol. Cell. Proteomics 9:1271-80). In some embodiments, the method of determining the presence of a protein biomarker is a functional assay. In some embodiments, the functional assay is a kinase assay (Ghosh et al. (2010) Biosensors & Bioelectronics 26:424-31, Mizutani et al. (2010) Clin. Cancer Res. 16:3964-75, Lee et al. (2012) Biomed. Microdevices 14:247-57), a protease assay (Lowe et al. (2012) ACS nano. 6:851-7, Fujiwara et al. (2006) Breast cancer 13:272-8, Darragh et al. (2010) Cancer Res 70:1505-12). See, e.g., Powers and Palecek (2015) J. Heathc Eng. 3 (4): 503-534, for a review of protein analytical assays for diagnosing cancer patients.

In some embodiments, the diagnostic testing method includes detecting the presence of aneuploidy in a biological sample (e.g. detecting whether the biological sample contains cells with an abnormal number of chromosomes). Non-limiting examples of methods of detecting the presence of aneuploidy include karyotyping, digital karyotyping, fluorescence in situ hybridization (FISH), quantitative PCR of short tandem repeats, quantitative fluorescence PCR (QF-PCR), quantitative PCR dosage analysis, quantitative mass spectrometry of single nucleotide polymorphisms, and comparative genomic hybridization (CGH).

In some embodiments, a subject that has been selected for further diagnostic testing can also be selected for increased monitoring. Once the presence of a cancer cell has been identified (e.g., by any of the variety of methods described herein), it may be beneficial for the subject to undergo both increased monitoring (e.g., to assess the progression of the tumor or cancer in the subject and/or to assess the development of additional cancer cell mutations), and further diagnostic testing (e.g., to determine the size and/or exact location of the tumor harboring the cancer cell).

In some embodiments, a subject that is selected for further diagnostic testing can also be selected for a therapeutic intervention. Any of the therapeutic interventions described herein or known in the art can be administered. For example, a subject that has been selected for further diagnostic testing can be administered a further diagnostic test, and a therapeutic intervention can be administered if the presence of the cancer cell is confirmed. Additionally or alternatively, a subject that has been selected for further diagnostic testing can be administered a therapeutic intervention, and can be further monitored as the therapeutic intervention progresses. In some embodiments, after a subject that has been selected for further diagnostic testing has been administered a therapeutic intervention, the additional testing will reveal the presence of one or more additional genetic biomarkers, the presence of one or more additional protein biomarkers, and/or the presence of aneuploidy. In some embodiments, the presence of one or more additional genetic biomarkers, the presence of one or more additional protein biomarkers, and/or the presence of aneuploidy will provide cause to administer a different therapeutic intervention (e.g., a resistance mutation may arise in a cancer cell during the therapeutic intervention, which cancer cell harboring the resistance mutation is resistance to the original therapeutic intervention).

Increased Monitoring

Also provided herein are methods for selecting a subject for increased monitoring. In some embodiments, methods for selecting a subject for increased monitoring include detecting the presence of one or more genetic biomarkers in a biological sample isolated from the subject, detecting the presence of one or more protein biomarkers in a biological sample isolated from the subject, and/or detecting the presence of aneuploidy in a biological sample isolated from the subject, and selecting a subject for increased monitoring when the presence of one or more genetic biomarkers, one or more protein biomarkers, or aneuploidy is identified. In some embodiments, methods for selecting a subject for increased monitoring further include detecting the presence of one or more member of one or more other classes of biomarkers. In some embodiments, the step of detecting is performed when the subject is not known to harbor a cancer cell (e.g., when the subject is not known to harbor a cancer cell).

In some embodiments, the biological sample is isolated from a subject. Any suitable biological sample that contains one or more genetic biomarkers, protein biomarkers, and/or aneuploidy can be used in accordance with any of the variety of methods disclosed herein. For example, the biological sample can include blood, plasma, urine, cerebrospinal fluid, saliva, sputum, broncho-alveolar lavage, bile, lymphatic fluid, cyst fluid, stool, ascites, and combinations thereof. Methods of isolating biological samples from a subject are known to those of ordinary skill in the art.

In some embodiments, once a subject has been determined to have a cancer, the subject may be selected for increased or additional monitoring. In some embodiments, methods provided herein can be used to select a subject for increased monitoring at a time period prior to the time period when conventional techniques are capable of diagnosing the subject with an early-stage cancer. For example, methods provided herein for selecting a subject for increased monitoring can be used when a subject has not been diagnosed with cancer by conventional methods and/or when a subject is not known to harbor a cancer. In some embodiments, a subject selected for increased monitoring can be administered a diagnostic test (e.g., any of the diagnostic tests disclosed herein) at an increased frequency compared to a subject that has not been selected for increased monitoring. For example, a subject selected for increased monitoring can be administered a diagnostic test at a frequency of twice daily, daily, bi-weekly, weekly, bi-monthly, monthly, quarterly, semi-annually, annually, or any at frequency therein. In some embodiments, a subject selected for increased monitoring can be administered one or more additional diagnostic tests compared to a subject that has not been selected for increased monitoring. For example, a subject selected for increased monitoring can be administered two diagnostic tests, whereas a subject that has not been selected for increased monitoring is administered only a single diagnostic test (or no diagnostic tests).

In some embodiments, a subject that has been selected for increased monitoring can also be selected for further diagnostic testing. Once the presence of a cancer cell has been identified (e.g., by any of the variety of methods described herein), it may be beneficial for the subject to undergo both increased monitoring (e.g., to assess the progression of the tumor or cancer in the subject and/or to assess the development of additional cancer cell mutations), and further diagnostic testing (e.g., to determine the size and/or exact location of the tumor harboring the cancer cell).

In some embodiments, a subject that is selected for increased monitoring can also be selected for a therapeutic intervention. Any of the therapeutic interventions described herein or known in the art can be administered. For example, a subject that has been selected for increased monitoring can be further monitored, and a therapeutic intervention can be administered if the presence of the cancer cell is maintained throughout the increased monitoring period. Additionally or alternatively, a subject that has been selected for increased monitoring can be administered a therapeutic intervention, and further monitored as the therapeutic intervention progresses. In some embodiments, after a subject that has been selected for increased monitoring has been administered a therapeutic intervention, the increased monitoring will reveal the presence of one or more additional genetic biomarkers, the presence of one or more additional protein biomarkers, and/or the presence of aneuploidy. In some embodiments, the presence of one or more additional genetic biomarkers, the presence of one or more additional protein biomarkers, and/or the presence of aneuploidy will provide cause to administer a different therapeutic intervention (e.g., a resistance mutation may arise in a cancer cell during the therapeutic intervention, which cancer cell harboring the resistance mutation is resistance to the original therapeutic intervention).

Therapeutic Interventions

In some embodiments, once a subject has been determined to have a cancer (e.g., ancercical, endometrial, ovarian, or fallopian tubal cancer), or is suspected of having cancer, the subject may be administered a therapeutic intervention or selected for therapeutic intervention. In some embodiments, wherein the presence of cancer (e.g., a cervical, endometrial, ovarian, or fallopian tubal cancer) been detected in a subject, the subject is administered a therapeutic intervention that specifically targets the subject's cancer (e.g. genetic modifications present in the cervical, endometrial, ovarian, or fallopian tubal cancer). For example, when a subject is determined to have ovarian cancer, a therapeutic intervention appropriate for ovarian cancer can be administered. As another example, when a subject is determined to have endometrial cancer, a therapeutic intervention appropriate for endometrial cancer can be administered. In some embodiments the therapeutic intervention is chemotherapy (e.g., any of the platinum-based chemotherapeutic agents described herein (e.g., cisplatin, carboplatin), or a taxane (e.g., placitaxel (Taxol®) or docetaxel (Taxotere®). In some embodiments, the chemotherapeutic agent is an albumin-bound paclitaxel (nap-paclitaxel, Abraxane®), altretamine (Hexalen®), capecitabine (Xeloda®), cyclophosphamide (Cytoxan®), etoposide (VP-16), gemcitabine (Gemzar®), ifosfamide (Ifex®), irinotecan (CPT-11, Camptosar®), liposomal doxorubicin (Doxil®), melphalan, pemetrexed (Alimta®), topotecan, or vinorelbine (Navelbine®). In some embodiments, the therapeutic intervention is a combination of chemotherapeutic agents (e.g., paclitaxel, ifosfamide, and cisplatin; vinblastine, ifosfamide and cisplatin; etoposide, ifosfamide and cisplatin). In some embodiments, the therapeutic intervention is an epigenetic therapy (see, e.g., Smith et al. (2017) Gynecol. Oncol. Rep. 20:81-86). In some embodiments, the epigenetic therapy is a DNA methyltransferase (DNMT) inhibitor (e.g., 5-azacytidine (5-AZA), decitabine (5-aza-2'-deoxycytidine) (Fu et al. (2011) Cancer 117(8): 1661-1669; Falchook et al. (2013) Investig. New Drugs 31(5): 1192-1200; Matei et al. (2012) Cancer Res. 72(9): 2197-2205). In some embodiments, the DNMT1 inhibitor is NY-ESO-1 (Odunsi et al. (2014) Cancer Immunol. Res. 2(1): 37-49). In some embodiments, the epigenetic therapy is a histone deacetylase (HDAC) inhibitor. In some embodiments, the HDAC inhibitor is vorinostat (Modesitt (2008) 109(2): 182-186) or belinostat (Mackay et al. (2010) Eur. J. Cancer 46(9): 1573-1579). In some embodiments, the HDAC inhibitor is given in combination with a chemotherapeutic agent (e.g., carboplatin (paraplatin), cisplatin, paclitaxel or docetaxel (taxotere)) (Mendivil (2013) Int. J. Gynecol. Cancer 23(3): 533-539; Dizon (2012) Gynecol. Oncol. 125(2): 367-371; Dizon (2012) Int J. Gynecol. Cancer 23(3): 533-539). In some embodiments, the therapeutic intervention is an anti-angiogenic agent (e.g., bevacizumab). In some embodiments, the therapeutic intervention is a poly(ADP-ribose) polymerase (PARP)-1 and/or PARP-2 inhibitor. In some embodiments, the PARP-1 and PARP-2 inhibitor is niraparib (zejula) (Scott (2017) Drugs doiL10.1007/s40265-017-0752). In some embodiments, the PARP inhibitor is olaparib (lynparza) or rucaparib (rubraca). In some embodiments, the therapeutic intervention is a hormone (e.g., a luteinizing-hormone-releasing hormone (LHRH) agonist). In some embodiments, the LHRH agonist is goserelin (Zoladex®) or leuprolide (Lupron®). In some embodiments, the therapeutic intervention is an anti-estrogen compound (e.g., tamoxifen). In some embodiments, the therapeutic intervention is an aromatase inhibitor (e.g., letrozole (Femara®), anastrozole (Arimidex®) or exemestane (Aromasin®). In some embodiments, the therapeutic intervention is surgery (e.g., debulking of the tumor mass, a hysterectomy, a bilateral salpingo-oophorectomy, an omentectomy). The term "debulking" refers to surgical removal of almost the entire tumor ("optimally debulked"). In some embodiments, debulking can include removing a portion of the bladder, the spleen, the gallbladder, the stomach, the liver, and/or pancreas. In some embodiments, adjuvant chemotherapy is further administered to the subject after surgery (e.g., debulking of the tumor mass, a hysterectomy, a bilateral salpingo-oophorectomy, an omentectomy). In some embodiments, adjuvant chemotherapy is administered intra-abdominally (intraperitoneally). In some embodiments, the therapeutic intervention is a prophylactic surgery (e.g., a hysterectomy). In some embodiments, a paracentesis is performed to remove ascites.

In some embodiments, once a subject has been determined to have a cancer (e.g., a bladder cancer or an UTUC) according to any of the variety of methods provided herein, the subject may be administered a therapeutic intervention or selected for therapeutic intervention. For example, when a subject is determined to have bladder cancer, a therapeutic intervention appropriate for bladder cancer can be administered. Examples of such therapeutic interventions that are appropriate for bladder cancer include, without limitation, transuretral resection of the bladder (TURB), intravesical BCG (Bacillus Calmette-Guerin), intravesical chemotherapy, adjuvant chemotherapy, neoadjuvant chemotherapy, cystectomy or cystoprostatectomy, radiation therapy, immunotherapy, immune checkpoint inhibitors, or any combination of the above. As another example, when a subject is determined to have an UTUC, a therapeutic intervention appropriate for an UTUC can be administered. Examples of such therapeutic interventions that are appropriate for an UTUC include, without limitation, transurethral resection, intravesical BCG (Bacillus Calmette-Guerin), intravesical chemotherapy, adjuvant chemotherapy, neoadjuvant chemotherapy, ureterectomy or nephroureterectomy, radiation therapy, immunotherapy, immune checkpoint inhibitors, or any combination of the above.

In some embodiments, the detected cancer is a low-grade tumor (e.g., a neoplasm of low malignant potential (PUNLMP) or a non-invasive low grade papillary urothelial carcinoma). In some embodiments, once a subject has been determined to have a low-grade tumor, the subject may be administered a therapeutic intervention or selected for therapeutic intervention that includes transuretral resection of the bladder (TURB).

In some embodiments, wherein the presence of colorectal cancer been detected in a subject, the subject is administered a therapeutic intervention that specifically targets the subject's colorectal cancer (e.g. genetic modifications present in the colorectal cancer). In some embodiments, the subject is administered an anti-EGFR monoclonal antibody (e.g., cetuximab or panitumumab) (Cunningham et al. (2004) N. Engl. J. Med. 351(4): 337-345). In some embodiments, the therapeutic invention is an antiangiogenic agent. In some embodiments, the antiangiogenic agent is bevacizumab (Avastin) (Hurwitz et al. (2004) N. Engl. J. Med. 350:2335-2342). In some embodiments, the antiangiogenic agent is a VEGF inhibitor (e.g., aflibercept (Tang et al. (2008) J. Clin. Oncol 26 (May 20 suppl; abstr 4027); vatalanib (PTK/ZK222584; Hecht et al. (2005) ASCO Annual Meeting Proceedings J. Clin. Oncol. 23: 16S (abstr. LBA3)); sunitinib (Saltz et al. (2007) J. Clin. Oncol. 25:4793-4799); AZD2171 (Rosen et al. (2007) J. Clin. Oncol. 25:2369-76); AMG 706 (Drevis et al. (2007) 25:3045-2054)). In some embodiments, bevacizumb is administered with a chemotherapy treatment (see, e.g., Hurwitz et al. (2004) N. Engl. J. Med. 350:2335-2342; Gruenberger et al. (2008) J. Clin. Oncol. 26:1830-1835). Non-limiting examples of chemotherapy treatments that can be used in a subject with colorectal cancer include: 5-FU, leucovorin, oxaliplatin (Eloxatin), capecitabine, celecoxib and sulindac. In some embodiments, a combination of chemotherapeutic agents is used, e.g., FOLFOX (5-FU, leucovorin and oxaliplatin), FOLFIRI (leucovorin, 5-FU and irinotecan (Camptosar), CapeOx (capecitabine (Xeloda) and oxaliplatin). In some embodiments, the therapeutic intervention is a mammalian target of rapamycin (mTOR) inhibitor (e.g., a rapamycin analog (Kesmodel et al. (2007) Gastrointestinal Cancers Symposium (abstr 234)); RAD-001 (Tabernero et al. (2008) J. Clin. Oncol. 26:1603-1610). In some embodiments, the therapeutic intervention is a protein kinase C antagonist (e.g., enzastaurin (Camidge et al. (2008) Anticancer Drugs 19:77-84, Resta et al. (2008) J. Clin. Oncol. 26 (May 20 suppl) (abstr 3529)). In some embodiments, the therapeutic intervention is an inhibitor of nonreceptor tyrosine kinase Src (e.g., AZ0530 (Tabernero et al. (2007) J. Clin. Oncol. 25: 18S (abstr 3520))). In some embodiments, the therapeutic intervention is an inhibitor of kinesin spindle protein (KSP) (e.g., ispinesib (SB-715992) (Chu et al. (2004) J. Clin. Oncol. 22:14S (abstr 2078), Burris et al. (2004) J. Clin. Oncol. 22:128 (abstr 2004))).

In some embodiments, wherein the presence of lung cancer been detected in a subject, the subject is administered a therapeutic intervention that specifically targets the subject's lung cancer (e.g. genetic modifications present in the lung cancer). In some embodiments the therapeutic intervention is chemotherapy (e.g., any of the platinum-based chemotherapeutic agents described herein (e.g., cisplatin, carboplatin), or a taxane (e.g., placitaxel (Taxol®) or docetaxel (Taxotere®). In some embodiments, the chemotherapeutic agent is an albumin-bound paclitaxel (nap-paclitaxel, Abraxane®), altretamine (Hexalen®), capecitabine (Xeloda®), cyclophosphamide (Cytoxan®), etoposide (VP-16), gemcitabine (Gemzar®), ifosfamide (Ifex®), irinotecan (CPT-11, Camptosar®), liposomal doxorubicin (Doxil®), melphalan, pemetrexed (Alimta®), topotecan, or vinorelbine (Navelbine®). In some embodiments, the therapeutic intervention is a combination of chemotherapeutic agents (e.g., paclitaxel, ifosfamide, and cisplatin; vinblastine, ifosfamide and cisplatin; etoposide, ifosfamide and cisplatin). In some embodiments, the therapeutic intervention is an epigenetic therapy (see, e.g., Smith et al. (2017) Gynecol. Oncol. Rep. 20:81-86). In some embodiments, the epigenetic therapy is a DNA methyltransferase (DNMT) inhibitor (e.g., 5-azacytidine (5-AZA), decitabine (5-aza-2'-deoxycytidine) (Fu et al. (2011) Cancer 117(8): 1661-1669; Falchook et al. (2013) Investig. New Drugs 31(5): 1192-1200; Matei et al. (2012) Cancer Res. 72(9): 2197-2205). In some embodiments, the DNMT1 inhibitor is NY-ESO-1 (Odunsi et al. (2014) Cancer Immunol. Res. 2(1): 37-49). In some embodiments, the epigenetic therapy is a histone deacetylase (HDAC) inhibitor. In some embodiments, the HDAC inhibitor is vorinostat (Modesitt (2008) 109(2): 182-186) or belinostat (Mackay et al. (2010) Eur. J. Cancer 46(9): 1573-1579). In some embodiments, the HDAC inhibitor is given in combination with a chemotherapeutic agent (e.g., carboplatin (paraplatin), cisplatin, paclitaxel or docetaxel (taxotere)) (Mendivil (2013) Int. J. Gynecol. Cancer 23(3): 533-539; Dizon (2012) Gynecol. Oncol. 125(2): 367-371; Dizon (2012) Int J. Gynecol. Cancer 23(3): 533-539). In some embodiments, the therapeutic intervention is an antiangiogenic agent (e.g., bevacizumab). In some embodiments, the therapeutic intervention is a poly(ADP-ribose) polymerase (PARP)-1 and/or PARP-2 inhibitor. In some embodiments, the PARP-1 and PARP-2 inhibitor is niraparib (zejula) (Scott (2017) Drugs doiL10.1007/s40265-017-0752). In some embodiments, the PARP inhibitor is olaparib (lynparza) or rucaparib (rubraca). In some embodiments, the therapeutic intervention is a hormone (e.g., a luteinizing-hormone-releasing hormone (LHRH) agonist). In some embodiments, the LHRH agonist is goserelin (Zoladex®) or leuprolide (Lupron®). In some embodiments, the therapeutic intervention is an anti-estrogen compound (e.g., tamoxifen). In some embodiments, the therapeutic intervention is an aromatase inhibitor (e.g., letrozole (Femara®), anastrozole (Arimidex®) or exemestane (Aromasin®). In some embodiments, the therapeutic intervention is surgery (e.g., debulking of the tumor mass, a hysterectomy, a bilateral salpingo-oophorectomy, an omentectomy). The term "debulking" refers to surgical removal of almost the entire tumor ("optimally debulked"). In some embodiments, debulking can include removing a portion of the bladder, the spleen, the gallbladder, the stomach, the liver, and/or pancreas. In some embodiments, adjuvant chemotherapy is further administered to the subject after surgery (e.g., debulking of the tumor mass, a hysterectomy, a bilateral salpingo-oophorectomy, an omentectomy). In some embodiments, adjuvant chemotherapy is administered intra-abdominally (intraperitoneally). In some embodiments, the therapeutic intervention is a prophylactic surgery (e.g., a hysterectomy). In some embodiments, a paracentesis is performed to remove ascites.

In some embodiments, wherein the presence of breast cancer been detected in a subject, the subject is administered a therapeutic intervention that specifically targets the subject's breast cancer (e.g. genetic modifications present in the breast cancer). In some embodiments, the targeted drug therapy is a HER2 inhibitor (e.g., trastuzumab (Herceptin), pertuzumab (perjeta); ado-trastuzumab emtansine (T-DM1; Kadcyla); lapatinib (Tykerb), neratinib). See, e.g., Baselga et al. (2012) N Engl J Med 366:109-119; Konecny et al. (2006) Cancer Res 66:1630-1639, Xia et al. (2007) Cancer Res. 67:1170-1175; Gomez et al. (2008) J Clin Oncol 26:2999-30005; Wong et al. (2009) Clin. Cancer Res. 15:2552-2558; Agus et al. (2002) Cancer Cell 2:127-137; Lewis Philips et al. (2008) Cancer Res 68:9280-9290. In some embodiments, the targeted drug therapy is a cyclin-dependent kinase inhibitor (e.g., a CDK4/6 inhibitor (e.g., palbociclib (Ibrance®), ribociclin (Kisqali®), abemaciclib) (Turner et al. (2015) N Engl J Med 373:209-219; Finn et al. (2016) N Eng J Med 375:1925-1936; Ehab and Elbaz (2016) Breast Cancer 8:83-91; Xu et al. (2017) J Hematol. Oncol. 10 (1): 97; Corona et al. (2017) Cri Rev Oncol Hematol 112:208-214; Barroso-Sousa et al. (2016) Breast Care 11(3): 167-173)). In some embodiments, the targeted drug therapy is a PARP inhibitor (e.g., olaparib (AZD2281), veliparib (ABT-888), niraparib (MK-4827), talazoparib (BMN-673), rucaparib (AG-14699), CEP-9722) See, e.g., Audeh et al. (2010) Lancet 376:245-251; Fong et al. (2009) N Engl J Med 361:123-134; Livrahi and Garber (2015) BMC Medicine 13:188; Kaufamn et al. (2015) J Clin. Oncol. 33:244-250; Gelmon et al. (2011) Lancet Oncol. 12:852-61; Isakoff et al. (2011) Cancer Res 71: P3-16-05; Sandhu et al. (2013) Lancet Oncol 14:882-92; Tutt et al. (2010) Lancet 376:235-44; Somlo et al. (2013) J. Clin. Oncol. 31:1024; Shen et al. (2013) CLin. Cancer Res. 19(18): 5003-15; Awada et al. (2016) Anticancer Drugs 27(4): 342-8. In some embodiments, the targeted drug therapy is a mTOR inhibitor (e.g., everolimus (afinitor)). See, e.g., Gong et al. (2017) Oncotarget doi: 10.18632/oncotarget.16336; Louseberg et al. (2017) Breast Cancer 10:239-252; Hare and Harvey (2017) Am J Cancer Res 7 (3): 383-404. In some embodiments, the targeted drug therapy is a heat shock protein 90 inhibitor (e.g., tanespimycin) (Modi et al. (2008) J. Clin Oncol. 26:s1027; Miller et al. (2007) J. Clin. Oncol. 25:s1115; Schulz et al. (2012) J Exp Med 209(2): 275-89). In some embodiments, the targeted drug therapy further includes a bone-modifying drug (e.g., a bisphosphonate or denosumab (Xgeva)). See, e.g., Ethier et al. (2017) Curr Oncol Rep 19(3): 15; Abdel-Rahman (2016) Expert Rev Anticancer Ther 16(8): 885-91. In some embodiments, the therapeutic intervention is a hormone (e.g., a luteinizing-hormone-releasing hormone (LHRH) agonist). In some embodiments, the LHRH agonist is goserelin (Zoladex®) or leuprolide (Lupron®). In some embodiments, the therapeutic intervention is an anti-estrogen compound (e.g., tamoxifen, fulvestrant (faslodex)). In some embodiments, the therapeutic intervention is an aromatase inhibitor (e.g., letrozole (Femara®), anastrozole (Arimidex®) or exemestane (Aromasin®). In some embodiments, the therapeutic intervention is surgery (e.g., a lumpectomy, a single mastectomy, a double mastectomy, a total mastectomy, a modified radical mastectomy, a sentinel lymph node biopsy, an axillary lymph node dissection; breast-conserving surgery). The extent of surgical removal will depend on the stage of breast cancer and overall prognosis. In some embodiments, the therapeutic intervention is radiation therapy. In some embodiments, the radiation therapy is partial breast irradiation or intensity-modulated radiation therapy. In some embodiments, the therapeutic intervention is chemotherapy (e.g., capecitabine (xeloda), carboplatin (paraplatin), cisplatin (platinol), cyclophosphamide (neosar), docetaxel (docefrez, taxotere), doxorubicin (Adriamycin), pegylated liposomal doxorubicin (doxil), epirubicin (ellence), fluorouracil (5-FU, adrucil), gemcitabine (gemzar), methotrexate, paclitaxel (taxol), protein-bound paclitaxel (abraxane), vinorelbine (navelbine), eribulin (halaven), or ixabepilone (ixempra)). In some embodiments, the therapeutic intervention is a combination of at least two chemotherapeutic agents (e.g., doxorubicin and cyclophosphamide (AC); epirubicin and cyclophosphamide (EC); cyclophosphamide, doxorubicin and 5-FU (CAF); cyclophosphamide, epirubicin and 5-FU (CEF); cyclophosphamide, methotrexate and 5-FU (CMF); epirubicin and cyclophosphamide (EC); docetaxel, doxorubicin and cyclophosphamide (TAC); docetaxel and cyclophosphamide (TC).

In some embodiments, a therapeutic intervention is administered to the subject after a cancer is detected or identified. Any of the therapeutic interventions disclosed herein or known in the art can be administered. Exemplary therapeutic interventions include, without limitation, a kinase inhibitor, an immune checkpoint inhibitor (e.g., a PD-1, a PD-L1, and/or a CTLA-4 immune checkpoint inhibitor), a chemotherapeutic agent, adoptive T cell therapy (e.g., chimeric antigen receptors and/or T cells having wild-type or modified T cell receptors), an antibody, a bispecific antibody or fragments thereof (e.g., BiTEs), chemotherapy, adjuvant chemotherapy, neoadjuvant chemotherapy, cytotoxic therapy, hormone therapy, immunotherapy, a monoclonal antibody, radiation therapy, signal transduction inhibitors, surgery (e.g., surgical resection), a targeted therapy such as administration of kinase inhibitors (e.g., kinase inhibitors that target a particular genetic lesion, such as a translocation or mutation), or any combination of thereof. Such therapeutic interventions can be administered alone or in combination. In some embodiments of any of the methods described herein, the one or more therapeutic interventions are administered sequentially or simultaneously to the subject after the cancer cell has been detected. In some embodiments, the therapeutic intervention can be administered at a time when the subject has an early-stage cancer, and wherein the therapeutic intervention is more effective that if the therapeutic intervention were to be administered to a subject at a later time. In some embodiments, a therapeutic intervention can reduce the severity of the cancer, reduce a symptom of the cancer, and/or to reduce the number of cancer cells present within the subject.

In some embodiments, the therapeutic intervention can include an immune checkpoint inhibitor. Non-limiting examples of immune checkpoint inhibitors include nivolumab (Opdivo), pembrolizumab (Keytruda), atezolizumab (tecentriq), avelumab (bavencio), durvalumab (imfinzi), ipilimumab (yervoy). See, e.g., Pardoll (2012) Nat. Rev Cancer 12:252-264; Sun et al. (2017) Eur Rev Med Pharmacol Sci 21(6):1198-1205; Hamanishi et al. (2015) J. Clin. Oncol. 33(34):4015-22; Brahmer et al. (2012) N Engl J Med 366(26):2455-65; Ricciuti et al. (2017) J. Thorac Oncol. 12(5):e51-e55; Ellis et al. (2017) Clin Lung Cancer pii:S1525-7304(17) 30043-8; Zou and Awad (2017) Ann Oncol 28(4): 685-687; Sorscher (2017) N Engl J Med 376(10: 996-7; Hui et al. (2017) Ann Oncol 28(4): 874-881; Vansteenkiste et al. (2017) Expert Opin Biol Ther 17(6): 781-789; Hellmann et al. (2017) Lancet Oncol. 18(1): 31-41; Chen (2017) J. Chin Med Assoc 80 (1): 7-14.

In some embodiments, the therapeutic intervention is adoptive T cell therapy (e.g., chimeric antigen receptors and/or T cells having wild-type or modified T cell receptors). See, e.g., Rosenberg and Restifo (2015) Science 348(6230): 62-68; Chang and Chen (2017) Trends Mol Med 23(5):430-450; Yee and Lizee (2016) Cancer J. 23(2):144-148; Chen et al. (2016) Oncoimmunology 6(2):e1273302; US 2016/0194404; US 2014/0050788; US 2014/0271635; U.S. Pat. No. 9,233,125; incorporated by reference in their entirety herein.

In some embodiments, a therapeutic intervention is a chemotherapeutic agent. Non-limiting examples of chemotherapeutic agents include: amsacrine, azacitidine, axathioprine, bevacizumab (or an antigen-binding fragment thereof), bleomycin, busulfan, carboplatin, capecitabine, chlorambucil, cisplatin, cyclophosphamide, cytarabine, dacarbazine, daunorubicin, docetaxel, doxifluridine, doxorubicin, epirubicin, erlotinib hydrochlorides, etoposide, fiudarabine, floxuridine, fludarabine, fluorouracil, gemcitabine, hydroxyurea, idarubicin, ifosfamide, irinotecan, lomustine, mechlorethamine, melphalan, mercaptopurine, methotrxate, mitomycin, mitoxantrone, oxaliplatin, paclitaxel, pemetrexed, procarbazine, all-trans retinoic acid, streptozocin, tafluposide, temozolomide, teniposide, tioguanine, topotecan, uramustine, valrubicin, vinblastine, vincristine, vindesine, vinorelbine, and combinations thereof. Additional examples of anti-cancer therapies are known in the art; see, e.g. the guidelines for therapy from the American Society of Clinical Oncology (ASCO), European Society for Medical Oncology (ESMO), or National Comprehensive Cancer Network (NCCN).

In some embodiments, when a subject is identified as having a genetic biomarker (e.g., a mutation) in NRAS, the subject is administered a therapeutic intervention. In some embodiments, a subject identified as having a genetic biomarker (e.g., a mutation) in NRAS is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in NRAS is one or more of a RAS-targeted therapeutic, a receptor tyrosine kinase inhibitor, a Ras-Raf-MEK-ERK pathway inhibitor, a PI3K-Akt-mTOR pathway inhibitor, and a farnesyl transferase inhibitor. In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201. In some embodiments, the PI3K-Akt-mTOR pathway inhibitor is one or more of a PI3K inhibitor, an AKT inhibitor, and an mTOR inhibitor. In some embodiments, the PI3K inhibitor is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the AKT inhibitor is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the farnesyl transferase inhibitor is one or more of lonafarnib, tipifarnib, BMS-214662, L778123, L744832 and FTI-277. In some embodiments, the therapeutic intervention administered to the subject having a genetic biomarker in NRAS is a MEK inhibitor and a PI3K inhibitor. In some embodiments, the therapeutic intervention administered to the subject having a genetic biomarker in NRAS is a MEK inhibitor and an ERK inhibitor. Other therapeutic interventions effective for treating a subject having a genetic biomarker in NRAS are known in the art. In some embodiments, a therapeutic intervention administered to the subject having a genetic biomarker in NRAS is effective in treating a cancer in the subject. For example, after administration of a therapeutic intervention that is effective in treating a subject having a genetic biomarker in NRAS, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in CTNNB1, the subject is administered a therapeutic intervention. In some embodiments, a subject identified as having a genetic biomarker (e.g., a mutation) in CTNNB1 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in CTNNB1 is one or more of a β-catenin inhibitor, a WNT/β-catenin signaling inhibitor, and a spindle assembly checkpoint kinase TTK (MPS1) inhibitor. In some embodiments, the β-catenin inhibitor is one or more of PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, and iCRT14. In some embodiments, the WNT/β-catenin signaling inhibitor is one or more of PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, iCRT14, SM04554, LGK 974, XAV939, curcumin (e.g., Meriva®), quercetin, epigallocatechin gallate (EGCC), resveratrol, DIF, genistein, celecoxib (CELEBREX®), CWP232291, NSC668036, FJ9, BML-286 (3289-8625), IWP, IWP-1, IWP-2, JW55, G007-LK, pyrvinium, foxy-5, Wnt-5a, ipafricept (OMP-54F28), vantictumab (OMP-18R5), OTSA 101, OTSA101-DTPA-90Y, SM04690, SM04755, nutlin-3a, XAV939, IWR1, JW74, okadaic acid, tautomycin, SB239063, SB203580, adenosine diphosphate (hydroxymethyl)pyrrolidinediol (ADP-HPD), 2-[4-(4-fluorophenyl)piperazin-1-yl]-6-methylpyrimidin-4 (3H)-one, PJ34, niclosamide (NICLOCIDE™), cambinol, sulindac (CLINORIL®, Aflodac), J01-017a, NSC668036, filipin, IC261, PF670462, bosutinib (BOSULIF®), PHA665752, imatinib (GLEEVEC®), ICG-001, ethacrynic acid, ethacryinic acid derivatives, pictilisib (GDC-0941), Rp-8-Br-CAMP, SDX-308, WNT974, CGX1321, ETC-1922159, AD-REIC/Dkk3, WIKI4, and windorphen. In some embodiments, the spindle assembly checkpoint kinase TTK (MPS1) inhibitor is one or more of NTRC 0066-0, CFI-402257, a (5,6-dihydro)pyrimido[4,5-e]indolizine, and BOS172722. Other therapeutic interventions effective for treating a subject having a genetic biomarker in CTNNB1 are known in the art. In some embodiments, a therapeutic intervention administered to the subject having a genetic biomarker in CTNNB1 is effective in treating a cancer in the subject. For example, after administration of a therapeutic intervention that is effective in treating a subject having a genetic biomarker in CTNNB1, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in PIK3CA, the subject is administered a therapeutic intervention. In some embodiments, a subject identified as having a genetic biomarker (e.g., a mutation) in PIK3CA is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in PIK3CA is one or more of a PI3K-alpha inhibitor, a panPI3K inhibitor, and a dual PI3K and mTOR inhibitor. In some embodiments, the PI3K alpha inhibitor is taselisib (GDC-0032, RG7604), GDC-0077, serabelisib (TAK-117, MLN1117, INK 1117), alpelisib (BYL719), and CH5132799. In some embodiments, the panPI3K inhibitor is buparlisib (BKM120), copanlisib (ALIQOPA™, BAY80-6946), sonolisib (PX-866), ZSTK474, pictilisib (GDC-0941), pilaralisib (XL147, SAR245408), AMG 511, PKI-402, wortmannin, LY294002, and WX-037. In some embodiments, the PI3K and mTOR dual inhibitor is dactolisib (NVP-BEZ235, BEZ-235), PQR309, SF1126, gedatolisib (PF-05212384, PKI-587), BGT-226 (NVP-BGT226), PF-04691502, apitolisib (GDC-0980), omipalisib (GSK2126458, GSK458), voxtalisib (XL756, SAR245409), GSK1059615, GDC-0084 (RG7666), VS-5584 (SB2343), and PI-103. In some embodiments, the therapeutic intervention administered to the subject having a genetic biomarker in PIK3CA is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. Other therapeutic interventions effective for treating a subject having a genetic biomarker in PIK3CA are known in the art. In some embodiments, a therapeutic intervention administered to the subject having a genetic biomarker in PIK3CA is effective in treating a cancer in the subject. For example, after administration of a therapeutic intervention that is effective in treating a subject having a genetic biomarker in PIK3CA, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in FBXW7, the subject is administered a therapeutic intervention. In some embodiments, a subject identified as having a genetic biomarker (e.g., a mutation) in FBXW7 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in FBXW7 is one or more of an mTOR inhibitor and a MCL-1 inhibitor. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the MCL-1 inhibitor is S63845, AZD5991, AMG 176, 483-LM, and MIK665. Other therapeutic interventions effective for treating a subject having a genetic biomarker in FBXW7 are known in the art. In some embodiments, a therapeutic intervention administered to the subject having a genetic biomarker in FBXW7 is effective in treating a cancer in the subject. For example, after administration of a therapeutic intervention that is effective in treating a subject having a genetic biomarker in FBXW7, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in APC, the subject is administered a therapeutic intervention. In some embodiments, a subject identified as having a genetic biomarker (e.g., a mutation) in APC is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in APC is one or more of TASIN-1 (Truncated APC Selective INhibitor) and a WNT/β-catenin signaling inhibitor. In some embodiments, the WNT/β-catenin signaling inhibitor is one or more of PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, iCRT14, PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, iCRT14, SM04554, LGK 974, XAV939, curcumin (e.g., Meriva®), quercetin, epigallocatechin gallate (EGCC), resveratrol, DIF, genistein, celecoxib (CELEBREX®), CWP232291, NSC668036, FJ9, BML-286 (3289-8625), IWP, IWP-1, IWP-2, JW55, G007-LK, pyrvinium, foxy-5, Wnt-5a, ipafricept (OMP-54F28), vantictumab (OMP-18R5), OTSA 101, OTSA101-DTPA-90Y, SM04690, SM04755, nutlin-3a, XAV939, IWR1, JW74, okadaic acid, tautomycin, SB239063, SB203580, adenosine diphosphate (hydroxymethyl)pyrrolidinediol (ADP-HPD), 2-[4-(4-fluorophenyl)piperazin-1-yl]-6-methylpyrimidin-4 (3H)-one, PJ34, niclosamide (NICLOCIDE™), cambinol, sulindac (CLINORIL®, Aflodac), J01-017a, NSC668036, filipin, IC261, PF670462, bosutinib (BOSULIF®), PHA665752, imatinib (GLEEVEC®), ICG-001, ethacrynic acid, ethacryinic acid derivatives, pictilisib (GDC-0941), Rp-8-Br-cAMP, SDX-308, WNT974, CGX1321, ETC-1922159, AD-REIC/Dkk3, WIKI4, and windorphen. Other therapeutic interventions effective for treating a subject having a genetic biomarker in APC are known in the art. In some embodiments, a therapeutic intervention administered to the subject having a genetic biomarker in APC is effective in treating a cancer in the subject. For example, after administration of a therapeutic intervention that is effective in treating a subject having a genetic biomarker in APC, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in EGFR, the subject is administered a therapeutic intervention. In some embodiments, a subject identified as having a genetic biomarker (e.g., a mutation) in EGFR is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in EGFR is one or more of an EGFR-selective inhibitor, a panHER inhibitor, and an anti-EGFR antibody. In some embodiments, the EGFR inhibitor is a covalent inhibitor. In some embodiments, the EGFR inhibitor is a non-covalent inhibitor. In some embodiments, the therapeutic intervention administered to the subject having a genetic biomarker in EGFR is one or more of osimertinib (AZD9291, merelectinib, TAGRISSO™), erlotinib (TARCEVA®), gefitinib (IRESSA®), cetuximab (ERBITUX®), necitumumab (PORTRAZZA™, IMC-11F8), neratinib (HKI-272, NERLYNX®), lapatinib (TYKERB®), panitumumab (ABX-EGF, VECTIBIX®), vandetanib (CAPRELSA®), rociletinib (CO-1686), olmutinib (OLITA™, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC0010), AC0010MA EAI045, matuzumab (EMD-7200), nimotuzumab (h-R3, BIOMAb EGFR®), zalutumab, MDX447, depatuxizumab (humanized mAb 806, ABT-806), depatuxizumab mafodotin (ABT-414), ABT-806, mAb 806, canertinib (CI-1033), shikonin, shikonin derivatives (e.g., deoxyshikonin, isobutyryl-shikonin, acetylshikonin, β,β-dimethylacrylshikonin and acetylalkannin), poziotinib (NOV120101, HM781-36B), AV-412, ibrutinib, WZ4002, brigatinib (AP26113, ALUNBRIG®), pelitinib (EKB-569), tarloxotinib (TH-4000, PR610), BPI-15086, Hemay022, ZN-e4, tesevatinib (KD019, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, avitinib, GW572016, pyrotinib (SHR1258), SCT200, CPGJ602, Sym004, MAb-425, Modotuximab (TAB-H49), futuximab (992 DS), zalutumumab, KL-140, RO5083945, IMGN289, JNJ-61186372, LY3164530, Sym013, AMG 595, EGFRBi-Armed Autologous T Cells, and EGFR CAR-T Therapy. Other therapeutic interventions effective for treating a subject having a genetic biomarker in EGFR are known in the art. In some embodiments, a therapeutic intervention administered to the subject having a genetic biomarker in EGFR is effective in treating a cancer in the subject. For example, after administration of a therapeutic intervention that is effective in treating a subject having a genetic biomarker in EGFR, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in BRAF, the subject is administered a therapeutic intervention. In some embodiments, a subject identified as having a genetic biomarker (e.g., a mutation) in BRAF is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in BRAF is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the therapeutic intervention administered to the subject having a genetic biomarker in BRAF is a BRAF inhibitor and a MEK inhibitor. In some embodiments, the BRAF inhibitor is vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, or LXH254 and the MEK inhibitor is trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), or hypothemycin. In some embodiments, the therapeutic intervention administered to the subject having a genetic biomarker in BRAF is a BRAF inhibitor and an ERK inhibitor. In some embodiments, the BRAF inhibitor is vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, or LXH254 and the ERK inhibitor is FRI-20 (ON-01060), VTX-11e, 25-OH-D3-3-BE (B3CD, bromoacetoxycalcidiol), FR-180204, AEZ-131 (AEZS-131), AEZS-131, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, or ONC201. Other therapeutic interventions effective for treating a subject having a genetic biomarker in BRAF are known in the art. In some embodiments, a therapeutic intervention administered to the subject having a genetic biomarker in BRAF is effective in treating a cancer in the subject. For example, after administration of a therapeutic intervention that is effective in treating a subject having a genetic biomarker in BRAF, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in CDNK2A, the subject is administered a therapeutic intervention. In some embodiments, a subject identified as having a genetic biomarker (e.g., a mutation) in CDNK2A is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in CDNK2A is a CDK4/6 inhibitor. In some embodiments, the CDK4/6 inhibitor is one or more of palbociclib, ribociclib, and abemaciclib. Other therapeutic interventions effective for treating a subject having a genetic biomarker in CDNK2A are known in the art. In some embodiments, a therapeutic intervention administered to the subject having a genetic biomarker in CDNK2A is effective in treating a cancer in the subject. For example, after administration of a therapeutic intervention that is effective in treating a subject having a genetic biomarker in CDNK2A, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in CDKN2, the subject is administered a therapeutic intervention. In some embodiments, a subject identified as having a genetic biomarker (e.g., a mutation) in CDKN2 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in CDKN2 is a CDK4/6 inhibitor. In some embodiments, the CDK4/6 inhibitor is one or more of palbociclib, ribociclib, and abemaciclib Other therapeutic interventions effective for treating a subject having a genetic biomarker in CDKN2 are known in the art. In some embodiments, a therapeutic intervention administered to the subject having a genetic biomarker in CDKN2 is effective in treating a cancer in the subject. For example, after administration of a therapeutic intervention that is effective in treating a subject having a genetic biomarker in CDKN2, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in PTEN, the subject is administered a therapeutic intervention. In some embodiments, a subject identified as having a genetic biomarker (e.g., a mutation) in PTEN is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in PTEN is one or more of a PI3K/AKT/mTOR signaling pathway inhibitor and a PARP inhibitor. In some embodiments, the PI3K-Akt-mTOR pathway inhibitor is one or more of a PI3K inhibitor, an AKT inhibitor, and an mTOR inhibitor. In some embodiments, the PI3K inhibitor is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the AKT inhibitor is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the farnesyl transferase inhibitor is one or more of lonafarnib, tipifarnib, BMS-214662, L778123, L744832 and FTI-277. In some embodiments, the PARP inhibitor is one or more of olaparib, veliparib, iniparib, rucaparib, CEP-9722, E7016, or E7449. Other therapeutic interventions effective for treating a subject having a genetic biomarker in PTEN are known in the art. In some embodiments, a therapeutic intervention administered to the subject having a genetic biomarker in PTEN is effective in treating a cancer in the subject. For example, after administration of a therapeutic intervention that is effective in treating a subject having a genetic biomarker in PTEN, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in FGFR2, the subject is administered a therapeutic intervention. In some embodiments, a subject identified as having a genetic biomarker (e.g., a mutation) in FGFR2 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in FGFR2 is one or more of an anti-FGFR2 antibody, an FGFR2 selective inhibitor and a pan-FGFR inhibitor. In some embodiments, the therapeutic intervention is a covalent FGFR2 inhibitor (e.g., PRN1371, BLU9931, FIIN-4, H3B-6527, and FIIN-2). In some embodiments, the therapeutic interventions is a non-covalent FGFR2 inhibitor (e.g., AZD4547, BGJ398, Debio-1347, dovitinib, JNJ-42756493 and LY2874455). In some embodiments, the anti-FGFR2 antibody is GP369, BAY1187982, or FPA144 (bemarituzumab). In some embodiments, the therapeutic intervention is one or more of PRN1371, BLU9931, FIIN-4, H3B-6527, NVP-BGJ398, ARQ087, TAS-120, JNJ-42756493, CH5183284/Debio 1347, INCB054828, GP369, BAY1187982, or FPA144 (bemarituzumab), NVP-BGJ398, JNJ-42756493 (erdafitinib), rogaratinib (BAY1163877), FIIN-2, JNJ-42756493, LY2874455, lenvatinib (E7080), ponatinib (AP2534), regorafenib (BAY 73-4506), dovitinib (TKI258), lucitanib (E3810), cediranib (AZD2171), intedanib (BIBF 1120), brivanib (BMS-540215), ASP5878, AZD4547, BGJ398 (infigratinib), E7090, HMPL-453, nintedanib (OFEV®, BIBF 1120), MAX-40279, XL999, orantinib (SU6668), pazopanib (VOTRIENT®), anlotinib, AL3818. Other therapeutic interventions effective for treating a subject having a genetic biomarker in FGFR2 are known in the art. In some embodiments, a therapeutic intervention administered to the subject having a genetic biomarker in FGFR2 is effective in treating a cancer in the subject. For example, after administration of a therapeutic intervention that is effective in treating a subject having a genetic biomarker in FGFR2, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in HRAS, the subject is administered a therapeutic intervention. In some embodiments, a subject identified as having a genetic biomarker (e.g., a mutation) in HRAS is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in HRAS is one or more of a RAS-targeted therapeutic, a receptor tyrosine kinase inhibitor, a Ras-Raf-MEK-ERK pathway inhibitor, a PI3K-Akt-mTOR pathway inhibitor, and a farnesyl transferase inhibitor. In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201. In some embodiments, the PI3K-Akt-mTOR pathway inhibitor is one or more of a PI3K inhibitor, an AKT inhibitor, and a mTOR inhibitor. In some embodiments, the PI3K inhibitor is one or more of buparlisib (BKM120), alpelisib (BYL719), WX-037, copanlisib (AL-IQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP- BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the AKT inhibitor is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the farnesyl transferase inhibitor is one or more of lonafarnib, tipifarnib, BMS-214662, L778123, L744832 and FTI-277. In some embodiments, the therapeutic intervention administered to the subject having a genetic biomarker in HRAS is a MEK inhibitor and a PI3K inhibitor. In some embodiments, the therapeutic intervention administered to the subject having a genetic biomarker in HRAS is a MEK inhibitor and an ERK inhibitor. Other therapeutic interventions effective for treating a subject having a genetic biomarker in HRAS are known in the art. In some embodiments, a therapeutic intervention administered to the subject having a genetic biomarker in HRAS is effective in treating a cancer in the subject. For example, after administration of a therapeutic intervention that is effective in treating a subject having a genetic biomarker in HRAS, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in KRAS, the subject is administered a therapeutic intervention. In some embodiments, a subject identified as having a genetic biomarker (e.g., a mutation) in KRAS is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in KRAS is one or more of a RAS-targeted therapeutic, a receptor tyrosine kinase inhibitor, a Ras-Raf-MEK-ERK pathway inhibitor, a PI3K-Akt-mTOR pathway inhibitor, and a farnesyl transferase inhibitor. In some embodiments, the RAS-targeted therapeutic is one or more of SML-10-70-4 and AA12. In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201. In some embodiments, the PI3K-Akt-mTOR pathway inhibitor is one or more of a PI3K inhibitor, an AKT inhibitor, and a mTOR inhibitor. In some embodiments, the PI3K inhibitor is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the AKT inhibitor is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, crucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the farnesyl transferase inhibitor is one or more of lonafarnib, tipifarnib, BMS-214662, L778123, L744832 and FTI-277. In some embodiments, the therapeutic intervention administered to the subject having a genetic biomarker in KRAS is a MEK inhibitor and a PI3K inhibitor. In some embodiments, the therapeutic intervention administered to the subject having a genetic biomarker in KRAS is a MEK inhibitor and an ERK inhibitor. Other therapeutic interventions effective for treating a subject having a genetic biomarker in KRAS are known in the art. In some embodiments, a therapeutic intervention administered to the subject having a genetic biomarker in KRAS is effective in treating a cancer in the subject. For example, after administration of a therapeutic intervention that is effective in treating a subject having a genetic biomarker in KRAS, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in AKT1, the subject is administered a therapeutic intervention. In some embodiments, a subject identified as having a genetic biomarker (e.g., a mutation) in AKT1 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in AKT1 is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. Other therapeutic interventions effective for treating a subject having a genetic biomarker in AKT1 are known in the art. In some embodiments, a therapeutic intervention administered to the subject having a genetic biomarker in AKT1 is effective in treating a cancer in the subject. For example, after administration of a therapeutic intervention that is effective in treating a subject having a genetic biomarker in AKT1, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in TP53, the subject is administered a therapeutic intervention. In some embodiments, a subject identified as having a genetic biomarker (e.g., a mutation) in TP53 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in TP53 is one or more of p53 reactivation and induction of massive apoptosis-1 (PRIMA-1), APR-246 (PRIMA-1$^{MET}$), 2-sulfonylpyrimidines such as PK11007, pyrazoles such as PK7088, zinc metallochaperone-1 (ZMC1; NSC319726/ZMC 1), a thiosemicarbazone (e.g., COTI-2), CP-31398, STIMA-1 (SH Group-Targeting Compound That Induces Massive Apoptosis), MIRA-1 (NSC19630) and its analogs MIRA-2 and -3, RITA (NSC652287), Chetomin (CTM), PK7088, Stictic acid (NSC87511), p53R3, SCH529074, WR-1065, Hsp90 inhibitors (e.g., 17-AAG, geldanamycin, ganetespib, AUY922, IPI-504), HDAC inhibitors (e.g., vorinostat/SAHA, romidepsin/depsipeptide, HBI-8000), arsenic compounds, gambogic acid, spautin-1, YK-3-237, NSC59984, disulfiram (DSF), gentamicin, G418, and amikamicin, reactivate transcriptional activity (RETRA), PD0166285, inhibitors of MDM2 (e.g., RG7112 (RO5045337), RO5503781, MI-773 (SAR405838), DS-3032b, AM-8553, AMG 232, MI-219, MI-713, MI-888, TDP521252, NSC279287, PXN822, SAH-8 (stapled peptides), ATSP-7041, spiroligomer, PK083, PK5174, PK5196, PK7088, nutlin 3a, RG7388, Ro-2443, stictic acid, and NSC319726), and inhibitors of MDM4. Other therapeutic interventions effective for treating a subject having a genetic biomarker in TP53 are known in the art. In some embodiments, a therapeutic intervention administered to the subject having a genetic biomarker in TP53 is effective in treating a cancer in the subject. For example, after administration of a therapeutic intervention that is effective in treating a subject having a genetic biomarker in TP53, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in PPP2R1A, the subject is administered a therapeutic intervention. In some embodiments, a subject identified as having a genetic biomarker (e.g., a mutation) in PPP2R1A is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in PPP2R1A is one or more of activators of PP2A such as SET inhibitors (e.g., FTY-720, ceramide, and OP449). Other therapeutic interventions effective for treating a subject having a genetic biomarker in PPP2R1A are known in the art. In some embodiments, a therapeutic intervention administered to the subject having a genetic biomarker in PPP2R1A is effective in treating a cancer in the subject. For example, after administration of a therapeutic intervention that is effective in treating a subject having a genetic biomarker in PPP2R1A, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in GNAS, the subject is administered a therapeutic intervention. In some embodiments, a subject identified as having a genetic biomarker (e.g., a mutation) in GNAS is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in GNAS is one or more of a Ras-Raf-MEK-ERK pathway inhibitor and a WNT/β-catenin signaling inhibitor. In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201. In some embodiments, the WNT/β-catenin signaling inhibitor is one or more of PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, iCRT14, PRI-724, CWP232291, PNU74654, 2,4 diamino-quinazoline, PKF115-584, PKF118-744, PKF118-310, PFK222-815, CGP 049090, ZTM000990, BC21, vitamin D, retinoid acid, aspirin, sulindac (CLINORIL®, Aflodac), 2,4 diamino-quinazoline derivatives, methyl 3-{[(4-methylphenyl)sulfonyl]amino}benzoate (MSAB), AV65, iCRT3, iCRT5, iCRT14, SM04554, LGK 974, XAV939, curcumin (e.g., Meriva®), quercetin, epigallocatechin gallate (EGCC), resveratrol, DIF, genistein, celecoxib (CELEBREX®), CWP232291, NSC668036, FJ9, BML-286 (3289-8625), IWP, IWP-1, IWP-2, JW55, G007-LK, pyrvinium, foxy-5, Wnt-5a, ipafricept (OMP-54F28), vanticumab (OMP-18R5), OTSA 101, OTSA101-DTPA-90Y, SM04690, SM04755, nutlin-3a, XAV939, IWR1, JW74, okadaic acid, tautomycin, SB239063, SB203580, adenosine diphosphate (hydroxymethyl)pyrrolidinediol (ADP-HPD), 2-[4-(4-fluorophenyl)piperazin-1-yl]-6-methylpyrimidin-4 (3H)-one, PJ34, niclosamide (NICLOCIDE™), cambinol, sulindac (CLINORIL®, Aflodac), J01-017a, NSC668036, filipin, IC261, PF670462, bosutinib (BOSULIF®), PHA665752, imatinib (GLEEVEC®), ICG-001, ethacrynic acid, ethacryinic acid derivatives, pictilisib (GDC-0941), Rp-8-Br-CAMP, SDX-308, WNT974, CGX1321, ETC-1922159, AD-REIC/Dkk3, WIKI4, and windorphen. Other therapeutic interventions effective for treating a subject having a genetic biomarker in GNAS are known in the art. In some embodiments, a therapeutic intervention administered to the subject having a genetic biomarker in GNAS is effective in treating a cancer in the subject. For example, after administration of a therapeutic intervention that is effective in treating a subject having a genetic biomarker in GNAS, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in SMAD4, the subject is administered a therapeutic intervention. In some embodiments, a subject identified as having a genetic biomarker (e.g., a mutation) in SMAD4 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in SMAD4 is one or more of a PI3K inhibitor, antiangiogenic therapy, and 5-FU-based chemotherapy. In some embodiments, the PI3K inhibitor is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the antiangiogenic therapy is an inhibitor of one or more of VEGFR1, VEGFR, VEGFR2, VEGFA, CDH5, EDNRA, ANGPT2, CD34, and ANGPT. In some embodiments, the antiangiogenic therapy is one or more of vatalanib (PTK787/ZK222584), TKI-538, sunitinib (SU11248, SUTENT®), pazopanib (VOTRIENT®), bevacizumab (AVASTIN®), thalidomide, lenalidomide (REVLIMID®), ranibizumab, EYE001, and axitinib (AG013736, INLYTA®). Other therapeutic interventions effective for treating a subject having a genetic biomarker in SMAD4 are known in the art. In some embodiments, a therapeutic intervention administered to the subject having a genetic biomarker in SMAD4 is effective in treating a cancer in the subject. For example, after administration of a therapeutic intervention that is effective in treating a subject having a genetic biomarker in SMAD4, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in POLE, the subject is administered a therapeutic intervention. In some embodiments, a subject identified as having a genetic biomarker (e.g., a mutation) in POLE is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in POLE is one or more of immunotherapy and an immune checkpoint inhibitor. Other therapeutic interventions effective for treating a subject having a genetic biomarker in POLE are known in the art. In some embodiments, a therapeutic intervention administered to the subject having a genetic biomarker in POLE is effective in treating a cancer in the subject. For example, after administration of a therapeutic intervention that is effective in treating a subject having a genetic biomarker in POLE, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in RNF43, the subject is administered a therapeutic intervention. In some embodiments, a subject identified as having a genetic biomarker (e.g., a mutation) in RNF43 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in RNF43 is one or more of autologous RNF43 peptide-pulsed dendritic cells (DCs), RNF43 peptide-pulsed DCs, systemic low dose interleukin-2, and PORCN inhibitors. In some embodiments, the PORCN inhibitor is one or more of RXC0004, ETC-1922159, ETC-159, IWP-2, LGK974, and WNT-C59. Other therapeutic interventions effective for treating a subject having a genetic biomarker in RNF43 are known in the art. In some embodiments, a therapeutic intervention administered to the subject having a genetic biomarker in RNF43 is effective in treating a cancer in the subject. For example, after administration of a therapeutic intervention that is effective in treating a subject having a genetic biomarker in RNF43, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in MAPK1, the subject is administered a therapeutic intervention. In some embodiments, a subject identified as having a genetic biomarker (e.g., a mutation) in MAPK1 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in MAPK1 is one or more of an ERK inhibitor, a MEK inhibitor, an ERBB-receptor inhibitor (e.g., an EGFR inhibitor or a HER2 inhibitor), or PI3K-Akt-mTOR pathway inhibitor. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, ONC201. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the PI3K-Akt-mTOR pathway inhibitor is one or more of a PI3K inhibitor, an AKT inhibitor, and an mTOR inhibitor. In some embodiments, the PI3K inhibitor is one or more of buparlisib (BKM120), alpelisib (BYL719), WX-037, copanlisib (AL-IQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the AKT inhibitor is one or more of miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b]pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the mTOR inhibitor is one or more of MLN0128, AZD-2014, CC-223, AZD2014, CC-115, everolimus (RAD001), temsirolimus (CCI-779), ridaforolimus (AP-23573), and sirolimus (rapamycin). In some embodiments, the HER2 inhibitor is one or more of AZD8931, AST1306, AEE788, CP724714, CUDC101, TAK285, dacomitinib, pelitinib, AC480, trastuzumab (HERCEPTIN®), pertuzumab (PERJETA®), trastuzumab-dkst (OGIVRI®), DXL-702, E-75, PX-104.1, ZW25, CP-724714, irbinitinib (ARRY-380, ONT-380), TAS0728, lapatinib (TYKERB®, TYVERB®), AST-1306, AEE-788, perlitinib (EKB-569), afatinib (BIBW 2992, GILOTRIF®), neratinib (HKI-272, NERLYNX®, PKI-166, D-69491, HKI-357, AP32788, GW572016, canertinib (CI-1033), AC-480 (BMS-599626), dacomitinib (PF299804, PF299), RB-200h, ARRY-334543 (ARRY-543, ASLAN001), poziotinib (NOV120101), CUDC-101, emodin, IDM-1, ado-trastuzumab emtansine (KADCYLA®), Zemab, DS-8201a, T-DM1, anti-HER2 CAR-T therapy, HER2-Peptid-Vakzine, and HER2Bi-Armed Activated T Cells. In some embodiments, the EGFR inhibitor is osimertinib (AZD9291, merelectinib, TAG-RISSO™), erlotinib (TARCEVA®), gefitinib (IRESSA®), cetuximab (ERBITUX®), necitumumab (PORTRAZZA™, IMC-11F8), neratinib (HKI-272, NERLYNX®), lapatinib (TYKERB®), panitumumab (ABX-EGF, VECTIBIX®), vandetanib (CAPRELSA®), rociletinib (CO-1686), olmutinib (OLITA™, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC0010), AC0010MA EAI045, matuzumab (EMD-7200), nimotuzumab (h-R3, BIOMAb EGFR®), zalutumab, MDX447, depatuxizumab (humanized mAb 806, ABT-806), depatuxizumab mafodotin (ABT-414), ABT-806, mAb 806, canertinib (CI-1033), shikonin, shikonin derivatives (e.g., deoxyshikonin, isobutyrylshikonin, acetylshikonin, β,β-dimethylacrylshikonin and acetylalkannin), poziotinib (NOV120101, HM781-36B), AV-412, ibrutinib, WZ4002, brigatinib (AP26113, ALUNBRIG®), pelitinib (EKB-569), tarloxotinib (TH-4000, PR610), BPI-15086, Hemay022, ZN-e4, tesevatinib (KD019, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, avitinib, GW572016, pyrotinib (SHR1258), SCT200, CPGJ602, Sym004, MAb-425, Modotuximab (TAB-H49), futuximab (992 DS), zalutumumab, KL-140, RO5083945, IMGN289, JNJ-61186372, LY3164530, Sym013, AMG 595, EGFRBi-Armed Autologous T Cells, and EGFR CAR-T Therapy. Other therapeutic interventions effective for treating a subject having a genetic biomarker in MAPK1 are known in the art. In some embodiments, a therapeutic intervention administered to the subject having a genetic biomarker in MAPK1 is effective in treating a cancer in the subject. For example, after administration of a therapeutic intervention that is effective in treating a subject having a genetic biomarker in MAPK1, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in PI3KR1, the subject is administered a therapeutic intervention. In some embodiments, a subject identified as having a genetic biomarker (e.g., a mutation) in PI3KR1 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in PI3KR1 is one or more of one or more of a panPI3K inhibitor, a dual PI3K and mTOR inhibitor, and a Ras-Raf-MEK-ERK pathway inhibitor. In some embodiments, the panPI3K inhibitor is buparlisib (BKM120), copanlisib (ALIQOPA™, BAY80-6946), sonolisib (PX-866), ZSTK474, pictilisib (GDC-0941), pilaralisib (XL147, SAR245408), AMG 511, PKI-402, wortmannin, LY294002, and WX-037. In some embodiments, the PI3K and mTOR dual inhibitor is dactolisib (NVP-BEZ235, BEZ-235), PQR309, SF1126, gedatolisib (PF-05212384, PKI-587), BGT-226 (NVP-BGT226), PF-04691502, apitolisib (GDC-0980), omipalisib (GSK2126458, GSK458), voxtalisib (XL756, SAR245409), GSK1059615, GDC-0084 (RG7666), VS-5584 (SB2343), and PI-103. In some embodiments, the therapeutic intervention administered to the subject having a genetic biomarker in PIK3CA is one or more of buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, RO5126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozcaenol, 5-iodotubercidin, GDC0994, and ONC201. Other therapeutic interventions effective for treating a subject having a genetic biomarker in PI3KR1 are known in the art. In some embodiments, a therapeutic intervention administered to the subject having a genetic biomarker in PI3KR1 is effective in treating a cancer in the subject. For example, after administration of a therapeutic intervention that is effective in treating a subject having a genetic biomarker in PI3KR1, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in FGFR3, the subject is administered a therapeutic intervention. In some embodiments, a subject identified as having a genetic biomarker (e.g., a mutation) in FGFR3 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in FGFR3 is one or more of an anti-FGFR3 antibody, an FGFR3 selective inhibitor and a pan-FGFR inhibitor. In some embodiments, the therapeutic intervention is a covalent FGFR inhibitor (e.g., PRN1371, BLU9931, FIIN-4, H3B-6527, and FIIN-2). In some embodiments, the therapeutic interventions is a non-covalent FGFR inhibitor (e.g., AZD4547, BGJ398, Debio-1347, dovitinib, JNJ-42756493 and LY2874455). In some embodiments, the anti-FGFR3 antibody is), MFGR1877S or B-701. In some embodiments, the therapeutic intervention is one or more of MFGR1877S, B-701, FP-1039 (GSK230), NVP-BGJ398, JNJ-42756493 (erdafitinib), rogaratinib (BAY1163877), FIIN-2, JNJ-42756493, LY2874455, lenvatinib (E7080), ponatinib (AP24534), regorafenib (BAY 73-4506), dovitinib (TKI258), lucitanib (E3810), cediranib (AZD2171), intedanib (BIBF 1120), brivanib (BMS-540215), ASP5878, AZD4547, BGJ398 (infigratinib), Debio-1347, dovitinib, E7090, HMPL-453, nintedanib (OFEV®, BIBF 1120), MAX-40279, XL999, orantinib (SU6668), pazopanib (VOTRIENT®), anlotinib, and AL3818. Other therapeutic interventions effective for treating a subject having a genetic biomarker in FGFR3 are known in the art. In some embodiments, a therapeutic intervention administered to the subject having a genetic biomarker in FGFR3 is effective in treating a cancer in the subject. For example, after administration of a therapeutic intervention that is effective in treating a subject having a genetic biomarker in FGFR3, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in ERBB2, the subject is administered a therapeutic intervention. In some embodiments, a subject identified as having a genetic biomarker (e.g., a mutation) in ERBB2 is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in ERBB2 is one or more of an anti-ERBB2 antibody, a selective ERBB2 inhibitor, and a pan-ERBB inhibitor. In some embodiments, the therapeutic intervention is a covalent ERBB2 inhibitor. In some embodiments, the therapeutic intervention is a non-covalent ERBB2 inhibitor. In some embodiments, the therapeutic intervention administered to the subject having a genetic biomarker in ERBB2 is one or more of AZD8931, AST1306, AEE788, CP724714, CUDC101, TAK285, dacomitinib, pelitinib, AC480, trastuzumab (HERCEPTIN®), pertuzumab (PERJETA®), trastuzumab-dkst (OGIVRI®), DXL-702, E-75, PX-104.1, ZW25, CP-724714, irbinitinib (ARRY-380, ONT-380), TAS0728, lapatinib (TYKERB®, TYVERB®), AST-1306, AEE-788, perlitinib (EKB-569), afatinib (BIBW 2992, GILOTRIF®), neratinib (HKI-272, NERLYNX®, PKI-166, D-69491, HKI-357, AP32788, GW572016, canertinib (CI-1033), AC-480 (BMS-599626), dacomitinib (PF299804, PF299), RB-200h, ARRY-334543 (ARRY-543, ASLAN001), poziotinib (NOV120101), CUDC-101, emodin, IDM-1, ado-trastuzumab emtansine (KADCYLA®), Zemab, DS-8201a, T-DM1, anti-HER2 CAR-T therapy, HER2-Peptid-Vakzine, and HER2Bi-Armed Activated T Cells. Other therapeutic interventions effective for treating a subject having a genetic biomarker in ERBB2 are known in the art. In some embodiments, a therapeutic intervention administered to the subject having a genetic biomarker in ERBB2 is effective in treating a cancer in the subject. For example, after administration of a therapeutic intervention that is effective in treating a subject having a genetic biomarker in ERBB2, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in MLL, the subject is administered a therapeutic intervention. In some embodiments, a subject identified as having a genetic biomarker (e.g., a mutation) in MLL is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in MLL is one or more of cytosine arabinoside, all-trans retinoic acid (ATRA), an HDAC inhibitor (e.g., valproic acid and HBI-8000), a DNA methyltransferase inhibitor (e.g., decitabine), an LSD1 inhibitor (e.g., ORY1001 (RG6016), ORY1001 (RG6016), GSK2879552, GSK2879552, INCB059872, IMG7289, and CC90011), menin 1 inhibitors (e.g., MI1, MI2, MI3, Mi2-2 (MI-2-2), MI463, MI503, MIV-6R), DOLT1 (histone-lysine KMT) inhibitors (e.g., EPZ004777, EPZ-5676, SGC0946, CN-SAH, SYC-522, SAH, and SYC-534), and WDR5-MLL antagonists (e.g., MM-101, MM-102, MM-103, MM-401, WDR5-0101, WDR5-0102, WDR5-0103, and OICR-9429). Other therapeutic interventions effective for treating a subject having a genetic biomarker in MLL are known in the art. In some embodiments, a therapeutic intervention administered to the subject having a genetic biomarker in MLL is effective in treating a cancer in the subject. For example, after administration of a therapeutic intervention that is effective in treating a subject having a genetic biomarker in MLL, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in MET, the subject is administered a therapeutic intervention. In some embodiments, a subject identified as having a genetic biomarker (e.g., a mutation) in MET is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in MET is a MET inhibitor, an HGF antagonist, an anti-HGF antibody (e.g., rilotumumab (AMG102), ficlatuzumab (AV-299), and TAK701, YYB101), and a multikinase inhibitor (e.g., tivantinib (ARQ 197), golvatinib (E7050), cabozantinib (XL 184, BMS-907351), foretinib (GSK1363089), crizotinib (PF-02341066), MK-2461, BPI-9016M, BPI-9016M, TQ-B3139, MGCD265, and MK-8033). In some embodiments, the MET inhibitor is one or more of capmatinib (INC280, INCB28060), onartuzumab (MetMAb), Savolitinib, tepotinib (MSC2156119J, EMD1214063), CE-35562, AMG-337, AMG-458, Foretinib, PHA-665725, MK-2461, PF-04217903 and SU11274, SU11274 and PHA-665752, SAIT301, HS-10241, ARGX-111, MSC2156119J, glumetinib (SCC244), EMD 1204831, AZD6094 (savolitinib, volitinib, HMPL-504), PLB1001, ABT-700, AMG 208, INCB028060, AL2846, and PF-04217903. In some embodiments, the therapeutic intervention administered to the subject having a genetic biomarker in MET is one or more of capmatinib (INC280, INCB28060), onartuzumab (MetMAb), Savolitinib, tepotinib (MSC2156119J, EMD1214063), CE-35562, AMG-337, AMG-458, Foretinib, PHA-665725, MK-2461, PF-04217903 and SU11274, SU11274 and PHA-665752, SAIT301, HS-10241, ARGX-111, MSC2156119J, glumetinib (SCC244), EMD 1204831, AZD6094 (savolitinib, volitinib, HMPL-504), PLB1001, ABT-700, AMG 208, INCB028060, AL2846, PF-04217903, rilotumumab (AMG102), ficlatuzumab (AV-299), and TAK701, YYB101, tivantinib (ARQ 197), Golvatinib (E7050), Cabozantinib (XL 184, BMS-907351), Foretinib (GSK1363089), Crizotinib (PF-02341066), MK-2461, BPI-9016M, BPI-9016M, TQ-B3139, MGCD265, MK-8033, ABBV-399, HTI-1066, and JNJ-61186372. Other therapeutic interventions effective for treating a subject having a genetic biomarker in MET are known in the art. In some embodiments, a therapeutic intervention administered to the subject having a genetic biomarker in MET is effective in treating a cancer in the subject. For example, after administration of a therapeutic intervention that is effective in treating a subject having a genetic biomarker in MET, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in VHL, the subject is administered a therapeutic intervention. In some embodiments, a subject identified as having a genetic biomarker (e.g., a mutation) in VHL is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in VHL is one or more of an antiangiogenic therapy (e.g., inhibitors of one or more of VEGFR1, VEGFR, VEGFR2, VEGFA, CDH5, EDNRA, ANGPT2, CD34, and ANGPT) vatalanib (PTK787/ZK222584), TKI-538, sunitinib (SU11248, SUTENT®), pazopanib (VOTRIENT®), bevacizumab (AVASTIN®), thalidomide, lenalidomide (REVLIMID®), ranibizumab, EYE001, axitinib (AG013736, INLYTA®), a c-KIT inhibitor (e.g., dovitinib (TKI258)), an HDAC inhibitor (e.g., vorinostat and HBI-8000), a HIF-2alpha inhibitor (e.g., PT2385 and PT2977), a Hsp90 inhibitor (e.g., 17 allylamino-17-demethoxygeldanamycin, AUY922, and IPI-504), and growth factor and receptor inhibitors (e.g, E10030). Other therapeutic interventions effective for treating a subject having a genetic biomarker in VHL are known in the art. In some embodiments, a therapeutic intervention administered to the subject having a genetic biomarker in VHL is effective in treating a cancer in the subject. For example, after administration of a therapeutic intervention that is effective in treating a subject having a genetic biomarker in VHL, the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as having a genetic biomarker (e.g., a mutation) in TERT (e.g., in a TERT promoter), the subject is administered a therapeutic intervention. In some embodiments, a subject identified as having a genetic biomarker (e.g., a mutation) in TERT (e.g., in a TERT promoter) is identified as having a cancer (e.g., based on the presence of the genetic biomarker, either alone or in combination with the presence of other genetic biomarkers and/or the presence of one or more members of other classes of biomarkers and/or the presence of aneuploidy as described herein). In some embodiments, the therapeutic intervention administered to the subject having a genetic biomarker in TERT (e.g., in a TERT promoter) is one or more of eribulin, an hTERT mRNA transfected dendritic cell vaccine (e.g., AST-VACI (hTERT-DC, GRNVAC1)), INO-1400, INO-1401, GX301, dendritic cells transfected with hTERT-, survivin- and tumor cell derived mRNA, and arsenic trioxide. Other therapeutic interventions effective for treating a subject having a genetic biomarker in TERT (e.g., in a TERT promoter) are known in the art. In some embodiments, a therapeutic intervention administered to the subject having a genetic biomarker in TERT (e.g., in a TERT promoter) is effective in treating a cancer in the subject. For example, after administration of a therapeutic intervention that is effective in treating a subject having a genetic biomarker in TERT (e.g., in a TERT promoter), the number of cancer cells in the subject can be reduced, the size of one or more tumors in the subject can be reduced, the rate or extent of metastasis can be reduced, symptoms associated with the disease or disorder or condition can be wholly or partly alleviated, the state of the disease can be stabilized (i.e., not worsened), and/or survival can be prolonged as compared to expected survival if not receiving treatment.

In some embodiments, when a subject is identified as being at risk (e.g., increased risk) of developing a disease (e.g., using any of the variety of methods described herein), the subject is administered a therapeutic intervention. In some embodiments, a subject identified as being at risk (e.g., increased risk) of developing a disease (e.g., using any of the variety of methods described herein) is identified as being at risk of developing cancer (e.g., based on the presence of one or more genetic biomarkers, the presence of one or more protein biomarkers, the presence of one or more other biomarkers, and/or the presence of aneuploidy as described herein). In some embodiments, the therapeutic intervention administered to the subject identified as being at risk of developing cancer is a chemopreventive. Non-limiting examples of chemopreventives include a non-steroidal anti-inflammatory drug (e.g., aspirin, tolfenamic acid, indomethacin, celecoxib, sulindac sulfide, diclofenac, indomethacin, ibuprofen, flurbiprofen, piroxicam, diflunisal, etodolac, ketoprofen, ketorolac, nabumetone, naproxen, oxaprozin, salsalate, and tolmetin), a selective estrogen receptor modulator (e.g., tamoxifen (NOLVADEX®, SOLTAMOX™) and raloxifene (EVISTA®)), instillational BCG, valrubicin, finasteride, dutasteride, curcumin, bisdemethoxycurcumin, metformin, an aromatase inhibitor (e.g., exemestane), resveratrol, lunasin, vitamin A, isothiocyanate, green tea, luteolin, genistein, lycopene, bitter melon, withaferin A, guggulsterone, selenides, diselenides, crocetin, piperine, a statin (a 3-hydroxy-3-methylglutaryl coenzyme A reductase inhibitor), a carotenoid, vitamin A, a retinoid, folic acid, vitamin C, vitamin D, vitamin E, calcium, a flavonoid, and an anti-cancer vaccine. In some embodiments, tamoxifen and/or raloxifene is administered to a subject identified as being at risk of developing breast cancer. In some embodiments, instillational BCG and/or valrubicin is administered to a subject identified as being at risk of developing bladder cancer. In some embodiments, finasteride and/or dutasteride is administered to a subject identified as being at risk of developing prostate cancer. In some embodiments, celecoxib is administered to a subject identified as being at risk of developing colorectal neoplasia.

In some embodiments, the therapeutic intervention can result in an early onset of remission of a cancer in a subject. In some embodiments, the therapeutic intervention can result in an increase in the time of remission of a cancer in a subject. In some embodiments, the therapeutic intervention can result in an increase in the time of survival of a subject. In some embodiments, the therapeutic intervention can result in decreasing the size of a solid primary tumor in a subject. In some embodiments, the therapeutic intervention can result in decreasing the volume of a solid primary tumor in a subject. In some embodiments, the therapeutic intervention can result in decreasing the size of a metastasis in a subject. In some embodiments, the therapeutic intervention can result in decreasing the volume of a metastasis in a subject. In some embodiments, the therapeutic intervention can result in decreasing the tumor burden in a subject.

In some embodiments, the therapeutic intervention can result in improving the prognosis of a subject. In some embodiments, the therapeutic intervention can result in decreasing the risk of developing a metastasis in a subject. In some embodiments, the therapeutic intervention can result in decreasing the risk of developing an additional metastasis in a subject. In some embodiments, the therapeutic intervention can result in decreasing cancer cell migration in a subject. In some embodiments, the therapeutic intervention can result in decreasing cancer cell invasion in a subject. In some embodiments, the therapeutic intervention can result in a decrease in the time of hospitalization of a subject. In some embodiments, the therapeutic intervention can result in a decrease of the presence of cancer stem cells within a tumor in a subject.

In some embodiments, the therapeutic intervention can result in an increase in immune cell infiltration within the tumor microenvironment in a subject. In some embodiments, the therapeutic intervention can result in altering the immune cell composition within the tumor microenvironment of a tumor in a subject. In some embodiments, the therapeutic intervention can result in modulating a previously immunosuppressive tumor microenvironment into an immunogenic, inflammatory tumor microenvironment. In some embodiments, the therapeutic intervention can result in a reversal of the immunosuppressive tumor microenvironment in a subject.

In some embodiments, the therapeutic intervention can halt tumor progression in a subject. In some embodiments, the therapeutic intervention can delay tumor progression in a subject. In some embodiments, the therapeutic intervention can inhibit tumor progression in a subject. In some embodiments, the therapeutic intervention can inhibit immune checkpoint pathways of a tumor in a subject. In some embodiments, the therapeutic intervention can immuno-modulate the tumor microenvironment of a tumor in a subject. In some embodiments, the therapeutic intervention can immuno-modulate the tumor macroenvironment of a tumor in a subject.

In some embodiments, a therapeutic intervention can reduce the number of cancer cells present in a subject. For example, a therapeutic intervention can reduce the number of cancer cells present in a subject by 10%, 20%, 30%, 40%, 50%, 60%, 70%, 80%, 90%, 95%, or more. In some embodiments, a therapeutic intervention can reduce the number of cancer cells present in a subject such that no cancer cells are observable. In some embodiments, a therapeutic intervention can reduce the observable tumors present in a subject.

In some embodiments, one or more therapeutic interventions (e.g., a chemotherapy or any of the other appropriate therapeutic interventions discloses herein) can be administered to a subject once or multiple times over a period of time ranging from days to weeks. In some embodiments, one or more therapeutic interventions can be formulated into a pharmaceutically acceptable composition for administration to a subject having cancer. For example, a therapeutically effective amount of a therapeutic intervention (e.g. a chemotherapeutic or immunotherapeutic agent) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more therapeutic interventions can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some embodiments, a pharmaceutically acceptable composition including one or more therapeutic interventions can be administered locally or systemically. For example, a composition provided herein can be administered locally by injection into tumors. In some embodiments, a composition provided herein can be administered systemically, orally, or by injection to a subject (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more therapeutic interventions can be any amount that reduces the number of cancer cells present within the subject without producing significant toxicity to the subject. If a particular subject fails to respond to a particular amount, then the amount of a therapeutic intervention can be increased by, for example, two fold. After receiving this higher amount, the subject can be monitored for both responsiveness to the treatment and toxicity symptoms, and adjustments made accordingly. The effective amount can remain constant or can be adjusted as a sliding scale or variable dose depending on the subject response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more therapeutic interventions can be any amount that reduces the number of cancer cells present within the subject without producing significant toxicity to the subject. For example, the frequency of administration of one or more therapeutic interventions can be from about two to about three times a week to about two to about three times a month. The frequency of administration of one or more therapeutic interventions can remain constant or can be variable during the duration of treatment. A course of treatment with a composition containing one or more therapeutic interventions can include rest periods. For example, a composition containing one or more therapeutic interventions can be administered daily over a two-week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more therapeutic interventions can be any duration that reduces the number of cancer cells present within the subject without producing significant toxicity to the subject. In some embodiments, the effective duration can vary from several days to several weeks. In general, the effective duration for reducing the number of cancer cells present within the subject can range in duration from about one week to about four weeks. Multiple factors can influence the actual effective duration used for a particular treatment. For example, an effective duration can vary with the frequency of administration, effective amount, use of multiple treatment agents, route of administration, and severity of the condition being treated.

EXEMPLARY EMBODIMENTS

In some embodiments, provided herein are methods of detecting biomarkers, which methods include detecting the presence of one or more members of a first class of biomarkers in a sample obtained from the subject and detecting the presence of one or more members of a second class of biomarkers in the sample obtained from the subject. In some embodiments of methods of detecting biomarkers, the methods further include detecting the presence of aneuploidy in the sample obtained from the subject. In some embodiments of methods of detecting biomarkers, the first class of biomarkers includes genetic biomarkers. In some embodiments of methods of detecting biomarkers, members of the first class of biomarkers are associated with the presence of cancer. In some embodiments of methods of detecting biomarkers, the second class of biomarkers includes protein biomarkers. In some embodiments of methods of detecting biomarkers, members of the second class of biomarkers are associated with the presence of cancer.

In some embodiments, provided herein are methods of detecting biomarkers, which methods include: detecting the presence of one or more members of a first class of biomarkers in a sample obtained from the subject; detecting the presence of aneuploidy in the sample obtained from the subject. In some embodiments of methods of detecting biomarkers, the methods further include detecting the presence of one or more members of a second class of biomarkers in the sample obtained from the subject. In some embodiments of methods of id detecting biomarkers, the first class of biomarkers comprises genetic biomarkers. In some embodiments of methods of detecting biomarkers, the first class of biomarkers comprises protein biomarkers. In some embodiments of methods of detecting biomarkers, members of the first class of biomarkers are associated with the presence of cancer. In some embodiments of methods of detecting biomarkers in which the first class of biomarkers comprises protein biomarkers, the second class of biomarkers comprises genetic biomarkers. In some embodiments of methods of detecting biomarkers in which the first class of biomarkers comprises protein biomarkers, members of the second class of biomarkers are associated with the presence of cancer.

In some embodiments, provided herein are methods of identifying a subject as having cancer, which methods include: detecting the presence of one or more members of a first class of biomarkers in a sample obtained from the subject; detecting the presence of one or more members of a second class of biomarkers in the sample obtained from the subject; and identifying the subject as having cancer when the presence of one or more members of the first class of biomarkers are detected in the sample, the presence of one or more members of the second class of biomarkers are detected in the sample, or both. In some embodiments of methods of identifying a subject as having cancer, the methods further include detecting the presence of aneuploidy in the sample obtained from the subject; wherein the subject is identified as having cancer when the presence of one or more members of the first class of biomarkers are detected in the sample, the presence of one or more members of the second class of biomarkers are detected in the sample, the presence aneuploidy is detected in the sample, or combinations thereof. In some embodiments of methods of identifying a subject as having cancer, the first class of biomarkers includes genetic biomarkers. In some embodiments of methods of identifying a subject as having cancer, members of the first class of biomarkers are associated with the presence of cancer. In some embodiments of methods of identifying a subject as having cancer, the second class of biomarkers includes protein biomarkers. In some embodiments of methods of identifying a subject as having cancer, members of the second class of biomarkers are associated with the presence of cancer.

In some embodiments, provided herein are methods of identifying a subject as having cancer, which methods include: detecting the presence of one or more members of a first class of biomarkers in a sample obtained from the subject; detecting the presence of aneuploidy in the sample obtained from the subject; and identifying the subject as having cancer when the presence of one or more members of the first class of biomarkers are detected in the sample, the presence of aneuploidy is detected in the sample, or both. In some embodiments of methods of identifying a subject as having cancer, the methods further include detecting the presence of one or more members of a second class of biomarkers in the sample obtained from the subject; wherein the subject is identified as having cancer when the presence of one or more members of the first class of biomarkers are detected in the sample, the presence of one or more members of the second class of biomarkers are detected in the sample, the presence aneuploidy is detected in the sample, or combinations thereof. In some embodiments of methods of identifying a subject as having cancer, the first class of biomarkers comprises genetic biomarkers. In some embodiments of methods of identifying a subject as having cancer, the first class of biomarkers comprises protein biomarkers. In some embodiments of methods of identifying a subject as having cancer, members of the first class of biomarkers are associated with the presence of cancer. In some embodiments of methods of identifying a subject as having cancer in which the first class of biomarkers comprises protein biomarkers, the second class of biomarkers comprises genetic biomarkers. In some embodiments of methods of identifying a subject as having cancer in which the first class of biomarkers comprises protein biomarkers, members of the second class of biomarkers are associated with the presence of cancer.

In some embodiments of methods of identifying a subject as having cancer that include detecting the presence of one or more members of a first class of biomarkers in a sample obtained from the subject and detecting the presence of one or more members of a second class of biomarkers in the sample obtained from the subject, the sensitivity of detecting the presence of cancer is increased as compared to methods which include detecting the presence of one or more members of only a single class of biomarkers. In some embodiments of methods of identifying a subject as having cancer that include detecting the presence of one or more members of a first class of biomarkers in a sample obtained from the subject and detecting the presence of one or more members of a second class of biomarkers in the sample obtained from the subject, the specificity of detecting the presence of cancer is increased as compared to methods which include detecting the presence of one or more members of only a single class of biomarkers. In some embodiments of methods of identifying a subject as having cancer that include detecting the presence of one or more members of a first class of biomarkers in a sample obtained from the subject and detecting the presence of aneuploidy in the sample obtained from the subject, the sensitivity of detecting the presence of cancer is increased as compared to methods which include detecting only one or more members of the class of biomarkers or only the presence of aneuploidy. In some embodiments of methods of identifying a subject as having cancer that include detecting the presence of one or more members of a first class of biomarkers in a sample obtained from the subject and detecting the presence of aneuploidy in the sample obtained from the subject, the specificity of detecting the presence of cancer is increased as compared to methods in which include detecting only one or more members of the class of biomarkers or only the presence of aneuploidy.

In some embodiments, provided herein are methods of treating a subject identified as having cancer, which methods include: detecting the presence of one or more members of a first class of biomarkers in a sample obtained from the subject; detecting the presence of one or more members of a second class of biomarkers in the sample obtained from the subject; identifying the subject as having cancer when the presence of one or more members of the first class of biomarkers are detected in the sample, the presence of one or more members of the second class of biomarkers are detected in the sample, or both; and administering to the subject a therapeutic intervention. In some embodiments of methods of treating a subject identified as having cancer, the methods further include detecting the presence of aneuploidy in the sample obtained from the subject; wherein the subject is identified as having cancer when the presence of one or more members of the first class of biomarkers are detected in the sample, the presence of one or more members of the second class of biomarkers are detected in the sample, the presence aneuploidy is detected in the sample, or combinations thereof. In some embodiments of methods of treating a subject identified as having cancer, the first class of biomarkers includes genetic biomarkers. In some embodiments of methods of treating a subject identified as having cancer, members of the first class of biomarkers are associated with the presence of cancer. In some embodiments of methods of treating a subject identified as having cancer, the second class of biomarkers includes protein biomarkers. In some embodiments of methods of treating a subject identified as having cancer, members of the second class of biomarkers are associated with the presence of cancer.

In some embodiments, provided herein are methods of treating a subject identified as having cancer, which methods include: detecting the presence of one or more members of a first class of biomarkers in a sample obtained from the subject; detecting the presence of aneuploidy in the sample obtained from the subject; identifying the subject as having cancer when the presence of one or more members of the first class of biomarkers are detected in the sample, the presence of aneuploidy is detected in the sample, or both; and administering to the subject a therapeutic intervention. In some embodiments of methods of treating a subject identified as having cancer, the methods further include detecting the presence of one or more members of a second class of biomarkers in the sample obtained from the subject; wherein the subject is identified as having cancer when the presence of one or more members of the first class of biomarkers are detected in the sample, the presence of one or more members of the second class of biomarkers are detected in the sample, the presence aneuploidy is detected in the sample, or combinations thereof. In some embodiments of methods of treating a subject identified as having cancer, the first class of biomarkers comprises genetic biomarkers. In some embodiments of methods of treating a subject identified as having cancer, the first class of biomarkers comprises protein biomarkers. In some embodiments of methods of treating a subject identified as having cancer, members of the first class of biomarkers are associated with the presence of cancer. In some embodiments of methods of treating a subject identified as having cancer in which the first class of biomarkers comprises protein biomarkers, the second class of biomarkers comprises genetic biomarkers. In some embodiments of methods of treating a subject identified as having cancer in which the first class of biomarkers comprises protein biomarkers, members of the second class of biomarkers are associated with the presence of cancer.

In some embodiments of methods of treating a subject identified as having cancer that include detecting the presence of one or more members of a first class of biomarkers in a sample obtained from the subject and detecting the presence of one or more members of a second class of biomarkers in the sample obtained from the subject, the sensitivity of detecting the presence of cancer is increased as compared to methods which include detecting the presence of one or more members of only a single class of biomarkers. In some embodiments of methods of treating a subject identified as having cancer that include detecting the presence of one or more members of a first class of biomarkers in a sample obtained from the subject and detecting the presence of one or more members of a second class of biomarkers in the sample obtained from the subject, the specificity of detecting the presence of cancer is increased as compared to methods which include detecting the presence of one or more members of only a single class of biomarkers. In some embodiments of methods of treating a subject identified as having cancer that include detecting the presence of one or more members of a first class of biomarkers in a sample obtained from the subject and detecting the presence of aneuploidy in the sample obtained from the subject, the sensitivity of detecting the presence of cancer is increased as compared to methods which include detecting only one or more members of the class of biomarkers or only the presence of aneuploidy. In some embodiments of methods of treating a subject identified as having cancer that include detecting the presence of one or more members of a first class of biomarkers in a sample obtained from the subject and detecting the presence of aneuploidy in the sample obtained from the subject, the specificity of detecting the presence of cancer is increased as compared to methods in which include detecting only one or more members of the class of biomarkers or only the presence of aneuploidy.

In some embodiments of methods of treating a subject identified as having cancer, any of the variety of therapeutic interventions described herein (e.g., surgery, chemotherapy, hormone therapy, targeted therapy, radiation therapy, and combinations thereof) can be administered to the subject.

In some embodiments, provided herein are methods of identifying a subject as having cancer that include: detecting the presence of one or more genetic biomarkers in circulating DNA in a blood sample obtained from said subject; detecting the presence of an elevated level of one or more peptide biomarkers in the blood sample obtained from a subject; and identifying the subject as having cancer when the presence of one or more genetic biomarkers is detected in circulating DNA in said blood sample, when an elevated level of one or more peptide biomarkers is detected in said blood sample, or both. In some embodiments, provided herein are methods of treating a subject having cancer that include: detecting the presence of one or more genetic biomarkers in circulating DNA in a blood sample obtained from said subject; detecting the presence of an elevated level of one or more peptide biomarkers in the blood sample obtained from a subject; and administering one or more therapeutic interventions (e.g., one or more of surgery, chemotherapy, hormone therapy, targeted therapy, and radiation therapy) to said subject when the presence of one or more genetic biomarkers is detected in circulating DNA in said blood sample, when an elevated level of one or more peptide biomarkers is detected in said blood sample, or both. In some embodiments, provided herein are methods of identifying the location of a cancer in a subject, said method comprising: detecting the presence of one or more genetic biomarkers in circulating DNA in a blood sample obtained from said subject; detecting the presence of an elevated level of one or more peptide biomarkers in the blood sample obtained from a subject; and identifying the location of the cancer in the subject when the presence of one or more genetic biomarkers is detected in circulating DNA in said blood sample, when an elevated level of one or more peptide biomarkers is detected in said blood sample, or both.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the subject is a human. In some embodiments of identifying a subject as having cancer, treating a subject having cancer, or identifying the location of a cancer in a subject, said blood sample is a plasma sample. In some embodiments of identifying a subject as having cancer, treating a subject having cancer, or identifying the location of a cancer in a subject, the cancer is a Stage I cancer. In some embodiments of identifying a subject as having cancer, treating a subject having cancer, or identifying the location of a cancer in a subject, the one or more genetic biomarkers comprise one or more modifications in one or more genes. In some embodiments of identifying a subject as having cancer, treating a subject having cancer, or identifying the location of a cancer in a subject, the one or more modifications comprise inactivating modifications, and wherein said one or more genes comprise tumor suppressor genes. In some embodiments of identifying a subject as having cancer, treating a subject having cancer, or identifying the location of a cancer in a subject, the one or more modifications include a modification independently selected from single base substitutions, insertions, or deletions, translocations, fusions, breaks, duplications, or amplifications.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the cancer is liver cancer, ovary cancer, esophageal cancer, stomach cancer, pancreatic cancer, colorectal cancer, lung cancer, breast cancer, or prostate cancer. In some embodiments of identifying a subject as having cancer, treating a subject having cancer, or identifying the location of a cancer in a subject in which the cancer is liver cancer, ovary cancer, esophageal cancer, stomach cancer, pancreatic cancer, colorectal cancer, lung cancer, breast cancer, or prostate cancer and in which the one or more genetic biomarkers are genes, the one or more genes are one or more of: NRAS, CTNNB1, PIK3CA, FBXW7, APC, EGFR, BRAF, CDKN2A, PTEN, FGFR2, HRAS, KRAS, AKT1, TP53, PPP2R1A, or GNAS. In some embodiments of identifying a subject as having cancer, treating a subject having cancer, or identifying the location of a cancer in a subject in which the one or more genes one or more of: NRAS, CTNNB1, PIK3CA, FBXW7, APC, EGFR, BRAF, CDKN2A, PTEN, FGFR2, HRAS, KRAS, AKT1, TP53, PPP2R1A, or GNAS, the one or more protein biomarkers are one or more of CA19-9, CEA, HGF, OPN, CA125, prolactin, TIMP-1, or myeloperoxidase (MPO). In some embodiments of identifying a subject as having cancer, treating a subject having cancer, or identifying the location of a cancer in a subject in which the one or more genes one or more of: NRAS, CTNNB1, PIK3CA, FBXW7, APC, EGFR, BRAF, CDKN2A, PTEN, FGFR2, HRAS, KRAS, AKT1, TP53, PPP2R1A, or GNAS, the one or more protein biomarkers are one or more of CA19-9, CEA, HGF, OPN, CA125, AFP, prolactin, TIMP-1, follistatin, G-CSF, or CA15-3. In some embodiments of identifying a subject as having cancer, treating a subject having cancer, or identifying the location of a cancer in a subject in which the one or more genes one or more of: NRAS, CTNNB1, PIK3CA, FBXW7, APC, EGFR, BRAF, CDKN2A, PTEN, FGFR2, HRAS, KRAS, AKT1, TP53, PPP2R1A, or GNAS, the one or more protein biomarkers are one or more of CA19-9, CEA, HGF, OPN, CA125, AFP, prolactin, TIMP-1, or CA15-3. In some embodiments of identifying a subject as having cancer, treating a subject having cancer, or identifying the location of a cancer in a subject in which the one or more genes one or more of: NRAS, CTNNB1, PIK3CA, FBXW7, APC, EGFR, BRAF, CDKN2A, PTEN, FGFR2, HRAS, KRAS, AKT1, TP53, PPP2R1A, or GNAS, the one or more modifications are independently selected from the modifications set forth in Table 3.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the cancer is pancreatic cancer. In some embodiments of identifying a subject as having cancer, treating a subject having cancer, or identifying the location of a cancer in a subject in which the cancer is pancreatic cancer and in which the one or more genetic biomarkers are genes, the one or more genes are one or more of KRAS, TP53, CDKN2A, or SMAD4. In some embodiments of identifying a subject as having cancer, treating a subject having cancer, or identifying the location of a cancer in a subject in which the one or more genes one or more of: KRAS, TP53, CDKN2A, or SMAD4, the one or more protein biomarkers are one or more of CA19-9, CEA, HGF, or OPN.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the step of detecting the presence of one or more genetic biomarkers is performed using a method that includes a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments, the multiplex PCR-based sequencing assay includes: a. assigning a unique identifier (UID) to each of a plurality of template molecules present in the sample; b. amplifying each uniquely tagged template molecule to create UID-families; and c. redundantly sequencing the amplification products.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the step of elevated level of one or more protein biomarkers is performed using a multiplex immunoassay system.

In some embodiments of identifying a subject as having cancer, the methods further include identifying a location of the cancer. In some embodiments of identifying a subject as having cancer, the methods further include administering to the subject one or more therapeutic interventions. In some embodiments, the one or more therapeutic interventions are one or more of: surgery, chemotherapy, hormone therapy, targeted therapy, or radiation therapy.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the methods further include: a) determining a mutation allele frequency in the blood sample for two or more of the genetic biomarkers; b) obtaining a score that indicates the likelihood that the subject has a cancer by comparing the mutation allele frequency of each mutation in the selected genetic biomarkers to a first reference distribution of mutation allele frequency in control samples and a second reference distribution of mutation allele frequency in samples collected from subjects having a cancer; and c) identifying the subject as having a cancer when the score is higher than a reference value for the score. In some embodiments, obtaining the score includes calculating the ratio of the probability of the mutation allele frequency in the first reference distribution to the probability of the mutation allele frequency in the second reference distribution for each mutation in the selected genetic biomarkers. In some embodiments, the score is determined by calculating the weighted average of the log ratio of the probability of the mutation allele frequency in the first reference distribution to the probability of the mutation allele frequency in the second reference distribution for each mutation in the selected genetic biomarkers. In some embodiments, detecting the presence of one or more genetic biomarkers is performed in two or more test samples using an assay comprising: a. assigning a unique identifier (UID) to each of a plurality of template molecules present in the sample; b. amplifying each uniquely tagged template molecule to create UID-families; and c. redundantly sequencing the amplification products. In some embodiments, the score is calculated by the following formula:

$$\Omega = \sum_{i=1} w_i * \ln\frac{p_i^C}{p_i^N},$$

wherein $w_i$ is the number of unique identifier sequences (UIDs) in a test sample i divided by the total number of UIDs for that mutation in all test samples, $pi^N$ is the probability of the mutation allele frequency in the first reference distribution, and $pi^C$ is the probability of the mutation allele frequency in the second reference distribution.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the sensitivity of identifying a subject as having cancer is increased as compared to: 1) the sensitivity obtained when the presence of one or more members of only a single class of biomarkers in the sample obtained from the subject is detected. In some embodiments of identifying a subject as having cancer, treating a subject having cancer, or identifying the location of a cancer in a subject, the specificity of identifying a subject as having cancer is increased as compared to: 1) the specificity obtained when the presence of one or more members of only a single class of biomarkers in the sample obtained from the subject is detected.

In some embodiments of identifying a subject as having cancer, treating a subject having cancer, or identifying the location of a cancer in a subject (e.g., based on the presence of one or more genetic biomarkers in circulating DNA in a blood sample obtained from said subject and/or presence of an elevated level of one or more peptide biomarkers in the blood sample obtained from a subject), the methods further include: detecting the presence of aneuploidy in the sample obtained from the subject, wherein the subject is identified as having cancer when the presence of one or more members of the first class of biomarkers are detected in the sample, the presence of one or more members of the second class of biomarkers are detected in the sample, the presence aneuploidy is detected in the sample, or combinations thereof.

In some embodiments, provided herein are method of identifying a patient as having a cancer that include: a) determining a mutation allele frequency in a sample collected from the patient for each mutation in one or more of the following genes: NRAS, CTNNB1, PIK3CA, FBXW7, APC, EGFR, BRAF, CDKN2A, PTEN, FGFR2, HRAS, KRAS, AKT1, TP53, PPP2R1A, or GNAS; b) obtaining a score that indicates the likelihood that the patient has a cancer by comparing the mutation allele frequency of each mutation in the selected genes to a first reference distribution of mutation allele frequency in control samples and a second reference distribution of mutation allele frequency in samples collected from patients having a cancer; and c) identifying the patient as having a cancer when the score is higher than a reference value for the score is higher than a reference value for the score. In some embodiments, such methods further include measuring the concentration of one or more of the following proteins: CA19-9, CEA, HGF, OPN, CA125, prolactin, TIMP-1, or myeloperoxidase (MPO) and determining that the concentration of at least one protein is higher than a reference value. In some embodiments, such methods further include measuring the concentration of one or more of the following proteins: CA19-9, CEA, HGF, OPN, CA125, AFP, prolactin, TIMP-1, follistatin, G-CSF, or CA15-3 and determining that the concentration of at least one protein is higher than a reference value. In some embodiments, such methods further include measuring the concentration of one or more of the following proteins: CA19-9, CEA, HGF, OPN, CA125, AFP, prolactin, TIMP-1, or CA15-3 and determining that the concentration of at least one protein is higher than a reference value. In some embodiments, obtaining the score comprises calculating the ratio of the probability of the mutation allele frequency in the first reference distribution to the probability of the mutation allele frequency in the second reference distribution for each mutation in the selected genes. In some embodiments, the score is determined by calculating the weighted average of the log ratio of the probability of the mutation allele frequency in the first reference distribution to the probability of the mutation allele frequency in the second reference distribution for each mutation in the selected genes. In some embodiments, the sample is assayed in two or more test samples using a method that includes: a. assigning a unique identifier (UID) to each of a plurality of template molecules present in the sample; b. amplifying each uniquely tagged template molecule to create UID-families; and c. redundantly sequencing the amplification products. In some embodiments, the score is calculated by the following formula:

$$\Omega = \sum_{i=1} w_i * \ln\frac{p_i^C}{p_i^N},$$

wherein $w_i$ is the number of unique identifier sequences (UIDs) in a test sample i divided by the total number of UIDs for that mutation in all test samples, $pi^N$ is the probability of the mutation allele frequency in the first reference distribution, and $pi^C$ is the probability of the mutation allele frequency in the second reference distribution. In some embodiments, the blood sample is a plasma sample. In some embodiments, the cancer is a Stage I cancer. In some embodiments, the cancer is liver cancer, ovary cancer, esophageal cancer, stomach cancer, pancreatic cancer, colorectal cancer, lung cancer, breast cancer, or prostate cancer. In some embodiments, the at least one mutation comprises an inactivating modifications, and wherein the at least one mutation is in a tumor suppressor gene. In some embodiments, the at least one mutation comprises a mutation that is a single base substitution, an insertion, or a deletion. In some embodiments, the at least one mutation is a mutation set forth in Table 3. In some embodiments, the step of detecting the level of one or more proteins is performed using a multiplex immunoassay system. In some embodiments, the methods further include identifying a location of the cancer. In some embodiments, the methods further include comprising administering to the mammal one or more therapeutic interventions. In some embodiments, the one or more therapeutic interventions are one or more of: surgery, chemotherapy, hormone therapy, targeted therapy, or radiation therapy.

In some embodiments, provided herein are method of identifying a patient as having a cancer that include: a) determining a mutation allele frequency in a sample collected from the patient for each mutation in one or more of the following genes: KRAS, TP53, CDKN2A, or SMAD4; b) obtaining a score that indicates the likelihood that the patient has a cancer by comparing the mutation allele frequency of each mutation in the selected genes to a first reference distribution of mutation allele frequency in control samples and a second reference distribution of mutation allele frequency in samples collected from patients having a cancer; and c) identifying the patient as having a cancer when the score is higher than a reference value for the score is higher than a reference value for the score. In some embodiments, such methods further include measuring the concentration of one or more of the following proteins: CA19-9, CEA, HGF, or OPN and determining that the concentration of at least one protein is higher than a reference value. In some embodiments, obtaining the score comprises calculating the ratio of the probability of the mutation allele frequency in the first reference distribution to the probability of the mutation allele frequency in the second reference distribution for each mutation in the selected genes. In some embodiments, the score is determined by calculating the weighted average of the log ratio of the probability of the mutation allele frequency in the first reference distribution to the probability of the mutation allele frequency in the second reference distribution for each mutation in the selected genes. In some embodiments, the sample is assayed in two or more test samples using a method that includes: a. assigning a unique identifier (UID) to each of a plurality of template molecules present in the sample; b. amplifying each uniquely tagged template molecule to create UID-families; and c. redundantly sequencing the amplification products. In some embodiments, the score is calculated by the following formula:

$$\Omega = \sum_{i=1} w_i * \ln \frac{p_i^C}{p_i^N},$$

wherein $w_i$ is the number of unique identifier sequences (UIDs) in a test sample i divided by the total number of UIDs for that mutation in all test samples, $pi^N$ is the probability of the mutation allele frequency in the first reference distribution, and $pi^C$ is the probability of the mutation allele frequency in the second reference distribution. In some embodiments, the blood sample is a plasma sample. In some embodiments, the cancer is a Stage I cancer. In some embodiments, the cancer is liver cancer, ovary cancer, esophageal cancer, stomach cancer, pancreatic cancer, colorectal cancer, lung cancer, breast cancer, or prostate cancer. In some embodiments, the at least one mutation comprises an inactivating modifications, and wherein the at least one mutation is in a tumor suppressor gene. In some embodiments, the at least one mutation comprises a mutation that is a single base substitution, an insertion, or a deletion. In some embodiments, the step of detecting the level of one or more proteins is performed using a multiplex immunoassay system. In some embodiments, the methods further include identifying a location of the cancer. In some embodiments, the methods further include comprising administering to the mammal one or more therapeutic interventions. In some embodiments, the one or more therapeutic interventions are one or more of: surgery, chemotherapy, hormone therapy, targeted therapy, or radiation therapy.

In some embodiments, provided herein are systems for generating a report for a patient that include: at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS; b) at least one computer database including: i) a first reference distribution of mutation allele frequency in control samples for each mutation in the set of genes; and ii) a second reference distribution of mutation allele frequency in samples collected from patients having a cancer for each mutation in the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value.

In some embodiments, provided herein are systems for generating a report for a patient that include: at least one device configured to assay a set of genes in a biological sample to determine mutation allele frequency of each mutation in the set of genes in a sample collected from the patient, wherein the set of genes comprises one or more (e.g., 1, 2, 3, or 4) of the following genes: KRAS, TP53, CDKN2A, and/or SMAD4; b) at least one computer database including: i) a first reference distribution of mutation allele frequency in control samples for each mutation in the set of genes; and ii) a second reference distribution of mutation allele frequency in samples collected from patients having a cancer for each mutation in the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value.

In some embodiments, provided herein are systems for generating a report to identify a cancer treatment for a patient that include: a) at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments, provided herein are systems for generating a report to identify a cancer treatment for a patient that include: a) at least one device configured to assay a set of genes in a biological sample to determine mutation allele frequency of each mutation in the set of genes in a sample collected from the patient, wherein the set of genes comprises one or more (e.g., 1, 2, 3, or 4) of the following genes: KRAS, TP53, CDKN2A, and/or SMAD4; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments, provided herein are systems for generating a report for a patient to identify the patient as a candidate for increased monitoring, further diagnostic testing, or both that include: a) at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments, provided herein are systems for generating a report for a patient to identify the patient as a candidate for increased monitoring, further diagnostic testing, or both that include: a) at least one device configured to assay a set of genes in a biological sample to determine mutation allele frequency of each mutation in the set of genes in a sample collected from the patient, wherein the set of genes comprises one or more (e.g., 1, 2, 3, or 4) of the following genes: KRAS, TP53, CDKN2A, and/or SMAD4; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments of systems for generating a report for a patient, systems for generating a report to identify a cancer treatment for a patient, or systems for generating a report for a patient to identify the patient as a candidate for increased monitoring, further diagnostic testing, or both, calculating the score comprises calculating the ratio of the probability of the mutation allele frequency in the first reference distribution to the probability of the mutation allele frequency in the second reference distribution for each mutation in the selected genes. In some embodiments of systems for generating a report for a patient, systems for generating a report to identify a cancer treatment for a patient, or systems for generating a report for a patient to identify the patient as a candidate for increased monitoring, further diagnostic testing, or both, the score is calculated by calculating the weighted average of the log ratio of the probability of the mutation allele frequency in the first reference distribution to the probability of the mutation allele frequency in the second reference distribution for each mutation in the selected genes. In some embodiments of systems for generating a report for a patient, systems for generating a report to identify a cancer treatment for a patient, or systems for generating a report for a patient to identify the patient as a candidate for increased monitoring, further diagnostic testing, or both, the computer database comprises test sample data, the test sample data includes assignment of a unique identifier (UID) to each of a plurality of template molecules present in the sample. In some embodiments of systems for generating a report for a patient, systems for generating a report to identify a cancer treatment for a patient, or systems for generating a report for a patient to identify the patient as a candidate for increased monitoring, further diagnostic testing, or both, the score is calculated by the following formula:

$$\Omega = \sum_{i=1} w_i * \ln \frac{p_i^C}{p_i^N},$$

wherein $w_i$ is the number of unique identifier sequences (UIDs) in a test sample i divided by the total number of UIDs for that mutation in all test samples, $pi^N$ is the probability of the mutation allele frequency in the first reference distribution, and $pi^C$ is the probability of the mutation allele frequency in the second reference distribution. In some embodiments of systems for generating a report for a patient, systems for generating a report to identify a cancer treatment for a patient, or systems for generating a report for a patient to identify the patient as a candidate for increased monitoring, further diagnostic testing, or both, the device configured to assay a set of genes comprises a device that employs a includes a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments of systems for generating a report for a patient, systems for generating a report to identify a cancer treatment for a patient, or systems for generating a report for a patient to identify the patient as a candidate for increased monitoring, further diagnostic testing, or both, the multiplex PCR-based sequencing assay comprises: a. assigning a unique identifier (UID) to each of a plurality of template molecules present in the sample; b. amplifying each uniquely tagged template molecule to create UID-families; and c. redundantly sequencing the amplification products. In some embodiments of systems for generating a report for a patient, systems for generating a report to identify a cancer treatment for a patient, or systems for generating a report for a patient to identify the patient as a candidate for increased monitoring, further diagnostic testing, or both, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, or 8) of: CA19-9, CEA, HGF, OPN, CA125, prolactin, TIMP-1, and/or myeloperoxidase (MPO). In some embodiments of systems for generating a report for a patient, systems for generating a report to identify a cancer treatment for a patient, or systems for generating a report for a patient to identify the patient as a candidate for increased monitoring, further diagnostic testing, or both, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, 9, 10, or 11) of: CA19-9, CEA, HGF, OPN, CA125, AFP, prolactin, TIMP-1, follistatin, G-CSF, and/or CA15-3. In some embodiments of systems for generating a report for a patient, systems for generating a report to identify a cancer treatment for a patient, or systems for generating a report for a patient to identify the patient as a candidate for increased monitoring, further diagnostic testing, or both, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, or 9) of: CA19-9, CEA, HGF, OPN, CA125, AFP, prolactin, TIMP-1, and/or CA15-3. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, or 8) of: CA19-9, CEA, HGF, OPN, CA125, prolactin, TIMP-1, and/or myeloperoxidase (MPO). In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, 9, 10, or 11) of: CA19-9, CEA, HGF, OPN, CA125, AFP, prolactin, TIMP-1, follistatin, G-CSF, and/or CA15-3. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, the system further includes a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, or 9) of: CA19-9, CEA, HGF, OPN, CA125, AFP, prolactin, TIMP-1, and/or CA15-3. In some embodiments of systems for generating a report for a patient, systems for generating a report to identify a cancer treatment for a patient, or systems for generating a report for a patient to identify the patient as a candidate for increased monitoring, further diagnostic testing, or both, the system further includes a device (e.g., a device that includes a multiplex immunoassay system) configured to detect a level of one or more protein biomarkers in a biological sample, wherein the protein biomarkers are one or more (e.g., 1, 2, 3, or 4) of: CA19-9, CEA, HGF, and/or OPN. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, or 4) of the following genes: KRAS, TP53, CDKN2A, and/or SMAD4, the system further includes a device (e.g., a device that includes a multiplex immunoassay system) configured to detect a level of one or more protein biomarkers in a biological sample, wherein the protein biomarkers are one or more (e.g., 1, 2, 3, or 4) of: CA19-9, CEA, HGF, and/or OPN. In some embodiments of systems for generating a report for a patient, systems for generating a report to identify a cancer treatment for a patient, or systems for generating a report for a patient to identify the patient as a candidate for increased monitoring, further diagnostic testing, or both, the sensitivity of the system in identifying a subject as having cancer is improved as compared to conventional systems for generating a report for a patient. In some embodiments of systems for generating a report for a patient, systems for generating a report to identify a cancer treatment for a patient, or systems for generating a report for a patient to identify the patient as a candidate for increased monitoring, further diagnostic testing, or both, the specificity of the system in identifying a subject as having cancer is improved as compared to conventional systems for generating a report for a patient. In some embodiments of systems for generating a report for a patient, systems for generating a report to identify a cancer treatment for a patient, or systems for generating a report for a patient to identify the patient as a candidate for increased monitoring, further diagnostic testing, or both, the first and second reference distribution of mutation allele frequency values are input into the system from a location that is remote from the at least one computer database. In some embodiments of systems for generating a report for a patient, systems for generating a report to identify a cancer treatment for a patient, or systems for generating a report for a patient to identify the patient as a candidate for increased monitoring, further diagnostic testing, or both, first and second reference distribution of mutation allele frequency values are input into the system over an internet connection. In some embodiments of systems for generating a report for a patient, systems for generating a report to identify a cancer treatment for a patient, or systems for generating a report for a patient to identify the patient as a candidate for increased monitoring, further diagnostic testing, or both, the report is in electronic or paper format. In some embodiments of systems for generating a report for a patient, systems for generating a report to identify a cancer treatment for a patient, or systems for generating a report for a patient to identify the patient as a candidate for increased monitoring, further diagnostic testing, or both, the cancer is any of the variety of cancer types described herein (see, e.g., section entitled "Cancers"). In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS and at least one a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, or 8) of: CA19-9, CEA, HGF, OPN, CA125, prolactin, TIMP-1, and/or myeloperoxidase (MPO), the cancer is liver cancer, ovary cancer, esophageal cancer, stomach cancer, pancreatic cancer, colorectal cancer, lung cancer, breast cancer, or prostate cancer. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS and at least one a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, 9, 10, or 11) of: CA19-9, CEA, HGF, OPN, CA125, AFP, prolactin, TIMP-1, follistatin, G-CSF, and/or CA15-3, the cancer is liver cancer, ovary cancer, esophageal cancer, stomach cancer, pancreatic cancer, colorectal cancer, lung cancer, breast cancer, or prostate cancer. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS and at least one a device (e.g., a device that includes a multiplex immunoassay system) configured to detect a level of one or more protein biomarkers in a biological sample, wherein the protein biomarkers are one or more (e.g., 1, 2, 3, 4, 5, 6, 7, 8, or 9) of: CA19-9, CEA, HGF, OPN, CA125, AFP, prolactin, TIMP-1, and/or CA15-3, the cancer is liver cancer, ovary cancer, esophageal cancer, stomach cancer, pancreatic cancer, colorectal cancer, lung cancer, breast cancer, or prostate cancer. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, or 4) of the following genes: KRAS, TP53, CDKN2A, and/or SMAD4 and at least one a device (e.g., a device that includes a multiplex immunoassay system) configured to detect a level of one or more protein biomarkers in a biological sample, wherein the protein biomarkers are one or more (e.g., 1, 2, 3, or 4) of: CA19-9, CEA, HGF, and/or OPN, the cancer is pancreatic cancer. In some embodiments of systems for generating a report for a patient or systems for generating a report to identify a cancer treatment for a patient, the patient is identified as a candidate for increased monitoring, further diagnostic testing, or both (e.g. any of the variety of increased monitoring or further diagnostic methods described herein).

In some embodiments, provided herein are methods of identifying a subject as having cancer that include: detecting the presence of one or more genetic biomarkers in a first sample obtained from said subject; detecting the presence of aneuploidy in a second sample obtained from said subject; and identifying the subject as having cancer when the presence of one or more genetic biomarkers is detected in the first sample, when the presence of aneuploidy is detected in the second sample, or both. In some embodiments, provided herein are methods of treating a subject having cancer that include: detecting the presence of one or more genetic biomarkers in a first sample obtained from said subject; detecting the presence of aneuploidy in a second sample obtained from said subject; and administering one or more therapeutic interventions to said subject when the presence of one or more genetic biomarkers is detected in the first sample, when the presence of aneuploidy is detected in the second sample, or both.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the step of detecting the presence of one or more genetic biomarkers comprises a method that includes a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments, the step of detecting the presence of one or more genetic biomarkers comprises a method that increases the sensitivity of massively parallel sequencing instruments with an error reduction technique comprising: a. assigning a unique identifier (UID) to each of a plurality of template molecules present in the sample; b. amplifying each uniquely tagged template molecule to create UID-families; and c. redundantly sequencing the amplification products.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the step of detecting the presence of aneuploidy includes: amplifying long interspersed nucleotide elements (LINEs) across the genome of the second sample, thereby obtaining a plurality of amplicons; sequencing the plurality of amplicons to obtain sequencing reads; placing the sequencing reads into pre-defined clusters of genomic intervals; and determining the presence of aneuploidy in the second sample when the number of sequencing reads of a genomic region within a pre-defined cluster is significantly different from the expected number of sequencing reads of the genomic region within the pre-defined cluster. In some embodiments, the pre-defined clusters of genomic intervals are created by grouping genomic intervals based on read depths of sequencing reads of two or more euploid samples. In some embodiments, determining that the number of sequencing reads of a genomic region within a pre-defined cluster is significantly different from the expected number of sequencing reads of the genomic region within the pre-defined cluster includes: calculating the distribution of sequencing reads of all genomic intervals in the pre-defined cluster, wherein the sequence reads of all genomic intervals in the pre-defined cluster are obtained by sequencing the amplicons derived from the second sample; and determining the number of sequencing reads of the genomic region is outside a significance threshold of the distribution. In some embodiments, determining that the number of sequencing reads of a genomic region within a pre-defined cluster is significantly different from the expected number of sequencing reads of the genomic region within the pre-defined cluster includes: calculating sums of distributions of the sequencing reads in each genomic interval using the equation $\Sigma_1^I R_i \sim N(\Sigma_1^I \mu_i, \Sigma_1^I \sigma_i^2)$, wherein $R_i$ is the number of sequencing reads, I is the number of clusters on a chromosome arm, N is a Gaussian distribution with parameters $\mu_i$ and $\sigma_i^2$, where $\mu_i$ is the mean number of sequencing reads in each genomic interval, and where $\sigma_i^2$ is the variance of sequencing reads in each genomic interval; calculating a Z-score of a chromosome arm using the quantile function $1\text{-}CDF(\Sigma_1^I \mu_i, \Sigma_1^I \sigma_i^2)$; and identifying the presence of an aneuploidy in the tissue of the mammal when the Z-score is outside a significance threshold.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the step of detecting the presence of aneuploidy includes: sequencing a plurality of amplicons obtained from a second sample to obtain variant sequencing reads for a plurality of polymorphic sites; selecting a chromosome arm having the variant sequencing reads and the reference sequencing reads on both alleles that is greater than about 3; determining a variant-allele frequency (VAF) of each polymorphic site in the selected chromosome arm, wherein said VAF is the number of variant sequencing reads/total number of sequencing reads; and identifying the presence of aneuploidy on the selected chromosome arm if the VAF of one or more polymorphic sites is outside a significance threshold of a normal distribution, wherein the expected VAF is 0.5. In some embodiments, the step of sequencing includes: a. assigning a unique identifier (UID) to each of a plurality of amplicons, b. amplifying each uniquely tagged amplicon to create UID-families, and c. redundantly sequencing the amplification products. In some embodiments, the step of identifying the presence of aneuploidy on the selected chromosome arm includes: calculating a Z-score for one or more polymorphic sites on said selected chromosome arm using the equation $$Z \sim \frac{\Sigma_{i=1}^{k} w_i Z_i}{\sqrt{\Sigma_{i=1}^{k} w_i^2}},$$

where $w_i$ is UID depth at a variant i, $Z_i$ is the Z-score of VAF for variant i, and k is the number of variants observed on the chromosome arm.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the methods further include performing cytology on the first sample, the second sample, or both, and identifying the subject as having cancer when the presence of one or more genetic biomarkers is detected in the first sample, when the presence of aneuploidy is detected in the second sample, a positive cytology indicates that the subject has cancer, or combinations thereof.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the cancer is a bladder cancer or an upper tract urothelial carcinoma; the one or more genetic biomarkers are one or more of: TP53, PIK3CA, FGFR3, KRAS, ERBB2, CDKN2A, MLL, HRAS, MET, or VHL; the method further includes detecting the presence of at least one genetic biomarker (e.g., a mutation) in a TERT promoter; and the presence of one or more genetic biomarkers in one or more of TP53, PIK3CA, FGFR3, KRAS, ERBB2, CDKN2A, MLL, HRAS, MET, and VHL, the presence of the at least one genetic biomarker (e.g., a mutation) in the TERT promoter, or the presence of aneuploidy indicates that the subject has bladder cancer. In some embodiments, the presence of one or more genetic biomarkers in one or more of TP53, PIK3CA, FGFR3, KRAS, ERBB2, CDKN2A, MLL, HRAS, MET, and VHL, the presence of the at least one genetic biomarker (e.g., a mutation) in the TERT promoter, and the presence of aneuploidy indicates that the subject has bladder cancer. In some embodiments, the one or more genetic biomarkers are TP53, FGFR3, or both. In some embodiments, the step of detecting the presence of aneuploidy comprises detecting the presence of aneuploidy on one or more of chromosome arms 5q, 8q, and 9p. In some embodiments, the one or more genetic biomarkers, the one or more genetic biomarkers (e.g., a mutations) in the TERT promoter, or both, are present in 0.03% or fewer of the urinary cells in the sample. In some embodiments, the step of detecting the presence of at least one genetic biomarker (e.g., a mutation) in the TERT promoter is performed using a PCR based multiplex assay, a Sanger Sequencing assay, or a next generation sequencing assay. In some embodiments, the step of detecting the presence of at least one genetic biomarker (e.g., a mutation) in the TERT promoter is performed by increasing the sensitivity of massively parallel sequencing instruments with an error reduction technique including: a. assigning a unique identifier (UID) to each of a plurality of template molecules present in the sample; b. amplifying each uniquely tagged template molecule to create UID-families; and c. redundantly sequencing the amplification products.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the method includes detecting bladder cancer and further includes administering transuretral resection of the bladder (TURB), intravesical BCG (Bacillus Calmette-Guerin), intravesical chemotherapy, adjuvant chemotherapy, neoadjuvant chemotherapy, cystectomy or cystoprostatectomy, radiation therapy, immunotherapy, immune checkpoint inhibitors, or any combination thereof.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the method includes detecting an upper tract urothelial carcinoma and further includes administering transurethral resection, intravesical BCG (Bacillus Calmette-Guerin), intravesical chemotherapy, adjuvant chemotherapy, neoadjuvant chemotherapy, ureterectomy or nephroureterectomy, radiation therapy, immunotherapy, immune checkpoint inhibitors, or any combination thereof.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the cancer is an ovarian or endometrial cancer; the one or more genetic biomarkers are one or more of NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A; and the presence of one or more mutations in one or more of NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A, the presence of aneuploidy, or both indicates that the subject has ovarian or endometrial cancer. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the cancer is an endometrial cancer; the one or more genetic biomarkers are one or more of PTEN, TP53, PIK3CA, PIK3R1, CTNNB1, KRAS, FGFR2, POLE, APC, FBXW7, RNF43, or PPP2R1A; and the presence of one or more mutations in one or more of PTEN, TP53, PIK3CA, PIK3R1, CTNNB1, KRAS, FGFR2, POLE, APC, FBXW7, RNF43, or PPP2R1A, the presence of aneuploidy, or both indicates that the subject has endometrial cancer. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the cancer is a high-grade serous carcinoma; the one or more genetic biomarkers in TP53; and the presence of one or more genetic biomarkers in TP53, the presence of aneuploidy, or both indicates that the subject has a high-grade serous carcinoma. In some embodiments, the step of detecting the presence of aneuploidy includes detecting the presence of aneuploidy on one or more of chromosome arms 4p, 7q, 8q, and 9q. In some embodiments, the first sample, the second sample, or both are collected via intrauterine sampling. In some embodiments, the first sample, the second sample, or both are collected with a Tao brush. In some embodiments, the methods further include detecting in a circulating tumor DNA (ctDNA) sample obtained from the subject the presence of at least one genetic biomarker in one or more of the following genes: AKT1, APC, BRAF, CDKN2A, CTNNB1, EGFR, FBXW7, FGFR2, GNAS, HRAS, KRAS, NRAS, PIK3CA, PPP2R1A, PTEN, or TP53. In some embodiments, the methods further include administering to the subject a therapy, wherein the therapy includes: surgery, adjuvant chemotherapy, neoadjuvant chemotherapy, radiation therapy, immunotherapy, targeted therapy, immune checkpoint inhibitors, or combinations thereof.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the genetic biomarker is a mutation in a gene.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the first sample and the second sample are the same. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the first sample and the second sample are different. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the first sample is a blood sample.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the methods further include a) determining a mutation allele frequency in the sample for two or more of the genetic biomarkers; b) obtaining a score that indicates the likelihood that the subject has a cancer by comparing the mutation allele frequency of each mutation in the selected genetic biomarkers against a reference distribution of mutation allele frequency for each mutation in control samples; and c) identifying the subject as having a cancer when the score is higher than a reference value for the score. In some embodiments, the methods further include selecting one genetic biomarker with the highest score that indicates the probability that the subject has a cancer from the two or more genetic biomarkers; and comparing the score for the selected genetic biomarker to the reference value. In some embodiments, the score is Stouffer's Z-score.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the methods further include a) determining a mutation allele frequency in the sample for two or more of the genetic biomarkers; and b) comparing the mutation allele frequency of each mutation in the selected genetic biomarkers to the maximum mutation allele frequency of each mutation for each mutation in control samples.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the sensitivity of identifying a subject as having cancer is increased as compared to: 1) the sensitivity obtained when only the presence of one or more genetic biomarkers in the sample obtained from the subject is detected, or 2) the sensitivity obtained when the presence of only aneuploidy in the sample obtained from the subject is detected. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the specificity of identifying a subject as having cancer is increased as compared to: 1) the specificity obtained when only the presence of one or more genetic biomarkers in the sample obtained from the subject is detected, or 2) the specificity obtained when the presence of only aneuploidy in the sample obtained from the subject is detected.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the methods further include detecting the presence of a detecting one or more protein biomarkers in a sample obtained from the subject, wherein the sample is the first sample, the second sample, or a third sample. In some embodiments of identifying a subject as having cancer or treating a subject having cancer (e.g., based on the presence of one or more genetic biomarkers in a first sample obtained from said subject and/or the presence of aneuploidy in a second sample obtained from the subject), subject is a human. In some embodiments of identifying a subject as having cancer or treating a subject having cancer (e.g., based on the presence of one or more genetic biomarkers in a first sample obtained from said subject and/or the presence of aneuploidy in a second sample obtained from the subject), the cancer is a Stage I cancer.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), the one or more genetic biomarkers comprise one or more modifications in one or more genes. In some embodiments, the one or more modifications comprise inactivating modifications, and wherein said one or more genes comprise tumor suppressor genes. In some embodiments, the one or more modifications include a modification independently selected from single base substitutions, insertions, or deletions, translocations, fusions, breaks, duplications, or amplifications.

In some embodiments of identifying a subject as having cancer or treating a subject having cancer (e.g., based on the presence of one or more genetic biomarkers in a first sample obtained from said subject and/or the presence of aneuploidy in a second sample obtained from the subject), In some embodiments, provided herein are methods of identifying a patient as having a cancer that include: a) determining a mutation allele frequency in a sample collected from the patient for each mutation in one or more of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A; b) obtaining a score that indicates the likelihood that the subject has a cancer by comparing the mutation allele frequency of each mutation in the selected genetic biomarkers against a reference distribution of mutation allele frequency for each mutation in control samples; and c) identifying the subject as having a cancer when the score is higher than a reference value for the score. In some embodiments, provided herein are methods of identifying a patient as having a cancer that include: a) determining a mutation allele frequency in a sample collected from the patient for each mutation in one or more of the following genes: PTEN, TP53, PIK3CA, PIK3R1, CTNNB1, KRAS, FGFR2, POLE, APC, FBXW7, RNF43, or PPP2R1A; b) obtaining a score that indicates the likelihood that the subject has a cancer by comparing the mutation allele frequency of each mutation in the selected genetic biomarkers against a reference distribution of mutation allele frequency for each mutation in control samples; and c) identifying the subject as having a cancer when the score is higher than a reference value for the score. In some embodiments, the methods further include selecting one genetic biomarker with the highest score that indicates the probability that the subject has a cancer from the two or more genetic biomarkers; and comparing the score for the selected genetic biomarker to the reference value. In some embodiments, provided herein are methods of identifying a patient as having a cancer that include: a) determining a mutation allele frequency in the sample for one or more of the genetic biomarkers; b) obtaining a score that indicates the probability that the subject does not have a cancer by comparing the mutation allele frequency of each mutation in the selected genetic biomarkers against a reference distribution of mutation allele frequency for each mutation in control samples; and c) identifying the subject as not having a cancer when the score is lower than a reference value for the score. In some embodiments, the methods further include selecting one genetic biomarker with the lowest score that indicates the probability that the subject does not have a cancer; and comparing the score for the selected genetic biomarker to the reference value. In some embodiments, the score is Stouffer's Z-score. In some embodiments, provided herein are methods of identifying a patient as having a cancer that include: a) determining a mutation allele frequency in the blood sample for two or more of the genetic biomarkers; and b) comparing the mutation allele frequency of each mutation in the selected genetic biomarkers to the maximum mutation allele frequency of each mutation for each mutation in control samples. In some embodiments, provided herein are methods of identifying a patient as having a cancer described in the preceding paragraph, the sample is assayed in two or more test samples using a method comprising: a. assigning a unique identifier (UID) to each of a plurality of template molecules present in the sample; b. amplifying each uniquely tagged template molecule to create UID-families; and c. redundantly sequencing the amplification products. In some embodiments of identifying a patient as having a cancer, the methods further include detecting the presence of aneuploidy in the sample (e.g., the presence of aneuploidy on one or more of chromosome arms 4p, 7q, 8q, and 9q). In some embodiments of identifying a patient as having a cancer, the methods further include detecting in a circulating tumor DNA (ctDNA) sample obtained from the subject the presence of at least one genetic biomarker in one or more of the following genes: AKT1, APC, BRAF, CDKN2A, CTNNB1, EGFR, FBXW7, FGFR2, GNAS, HRAS, KRAS, NRAS, PIK3CA, PPP2R1A, PTEN, or TP53. In some embodiments, the cancer is a Stage I cancer. In some embodiments, the cancer is cervical cancer, endometrial cancer, ovarian cancer, or fallopian tubal cancer. In some embodiments, the at least one mutation comprises an inactivating modification, and wherein the at least one mutation is in a tumor suppressor gene. In some embodiments, the modifications are independently selected from single base substitutions, insertions, deletions, translocations, fusions, breaks, duplications, or amplifications. In some embodiments, the methods further include administering to the subject one or more therapeutic interventions (e.g., one or more of: surgery, adjuvant chemotherapy, neoadjuvant chemotherapy, radiation therapy, immunotherapy, targeted therapy, immune checkpoint inhibitors, or combinations thereof).

In some embodiments, provided herein are methods of identifying a patient as having a cancer that include: a) determining a mutation allele frequency in a sample collected from the patient for each mutation in one or more of the following genes: TP53, PIK3CA, FGFR3, KRAS, ERBB2, CDKN2A, MLL, HRAS, MET, or VHL; b) obtaining a score that indicates the likelihood that the subject has a cancer by comparing the mutation allele frequency of each mutation in the selected genetic biomarkers against a reference distribution of mutation allele frequency for each mutation in control samples; and c) identifying the subject as having a cancer when the score is higher than a reference value for the score. In some embodiments, the methods further include selecting one genetic biomarker with the highest score that indicates the probability that the subject has a cancer from the two or more genetic biomarkers; and comparing the score for the selected genetic biomarker to the reference value. In some embodiments, provided herein are methods of identifying a patient as having a cancer that include: a) determining a mutation allele frequency in the sample for one or more of the genetic biomarkers; b) obtaining a score that indicates the probability that the subject does not have a cancer by comparing the mutation allele frequency of each mutation in the selected genetic biomarkers against a reference distribution of mutation allele frequency for each mutation in control samples; and c) identifying the subject as not having a cancer when the score is lower than a reference value for the score. In some embodiments, the methods further include selecting one genetic biomarker with the lowest score that indicates the probability that the subject does not have a cancer; and comparing the score for the selected genetic biomarker to the reference value. In some embodiments, the score is Stouffer's Z-score. In some embodiments, provided herein are methods of identifying a patient as having a cancer that include: a) determining a mutation allele frequency in the blood sample for two or more of the genetic biomarkers; and b) comparing the mutation allele frequency of each mutation in the selected genetic biomarkers to the maximum mutation allele frequency of each mutation for each mutation in control samples. In some embodiments, provided herein are methods of identifying a patient as having a cancer described in the preceding paragraph, the sample is assayed in two or more test samples using a method comprising: a. assigning a unique identifier (UID) to each of a plurality of template molecules present in the sample; b. amplifying each uniquely tagged template molecule to create UID-families; and c. redundantly sequencing the amplification products. In some embodiments, the methods further include detecting the presence of at least one genetic biomarker (e.g., a mutation) in a TERT promoter in the sample. In some embodiments of identifying a patient as having a cancer, the methods further include detecting the presence of aneuploidy in the sample (e.g., the presence of aneuploidy on one or more of chromosome arms 5q, 8q, and 9p). In some embodiments of identifying a patient as having a cancer, the methods further include detecting in a circulating tumor DNA (ctDNA) sample obtained from the subject the presence of at least one genetic biomarker in one or more of the following genes: AKT1, APC, BRAF, CDKN2A, CTNNB1, EGFR, FBXW7, FGFR2, GNAS, HRAS, KRAS, NRAS, PIK3CA, PPP2R1A, PTEN, or TP53. In some embodiments, the cancer is a Stage I cancer. In some embodiments, the cancer is bladder cancer or an upper-tract urothelial cancer (UTUC). In some embodiments, the at least one mutation comprises an inactivating modification, and wherein the at least one mutation is in a tumor suppressor gene. In some embodiments, the modifications are independently selected from single base substitutions, insertions, deletions, translocations, fusions, breaks, duplications, or amplifications. In some embodiments, the methods further include administering to the subject one or more therapeutic interventions (e.g., one or more of: surgery, adjuvant chemotherapy, neoadjuvant chemotherapy, radiation therapy, immunotherapy, targeted therapy, immune checkpoint inhibitors, or combinations thereof).

In some embodiments, provided herein are systems for generating a report for a patient that include: at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL; b) at least one computer database including: i) a first reference distribution of mutation allele frequency in control samples for each mutation in the set of genes; and ii) a second reference distribution of mutation allele frequency in samples collected from patients having a cancer for each mutation in the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value. In some embodiments of systems for generating a report for a patient, the systems further include at least one device configured to detect the presence of at least one genetic biomarker (e.g., at least one mutation) in a TERT promoter.

In some embodiments, provided herein are systems for generating a report for a patient that include: at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A; b) at least one computer database including: i) a first reference distribution of mutation allele frequency in control samples for each mutation in the set of genes; and ii) a second reference distribution of mutation allele frequency in samples collected from patients having a cancer for each mutation in the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value. In some embodiments, provided herein are systems for generating a report for a patient that include: at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A; b) at least one computer database including: i) a first reference distribution of mutation allele frequency in control samples for each mutation in the set of genes; and ii) a second reference distribution of mutation allele frequency in samples collected from patients having a cancer for each mutation in the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value. In some embodiments, provided herein are systems for generating a report for a patient that include: at least one device configured to assay a TP53 gene in a biological sample collected from the patient to determine mutation allele frequency of TP53; b) at least one computer database including: i) a first reference distribution of mutation allele frequency in control samples for TP53; and ii) a second reference distribution of mutation allele frequency in samples collected from patients having a cancer for TP53; c) a computer-readable program code comprising instructions to execute the following: i) inputting the mutation allele frequency in the biological sample of TP53; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value.

In some embodiments, provided herein are systems for generating a report to identify a cancer treatment for a patient that include: a) at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments of systems for generating a report to identify a cancer treatment for a patient, the systems further include at least one device configured to detect the presence of at least one genetic biomarker (e.g., at least one mutation) in a TERT promoter.

In some embodiments, provided herein are systems for generating a report to identify a cancer treatment for a patient that include: a) at least one device configured to assay a set of genes in a biological sample to determine mutation allele frequency of each mutation in the set of genes in a sample collected from the patient, wherein the set of genes comprises one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments, provided herein are systems for generating a report to identify a cancer treatment for a patient that include: a) at least one device configured to assay a set of genes in a biological sample to determine mutation allele frequency of each mutation in the set of genes comprises one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments, provided herein are systems for generating a report to identify a cancer treatment for a patient that include: a) at least one device configured to assay a TP53 gene in a biological sample collected from the patient to determine mutation allele frequency of TP53; b) at least one computer database comprising: i) a first reference distribution of mutation allele frequency in control samples for TP53; ii) a second reference distribution of mutation allele frequency in samples collected from patients having a cancer for TP53; and iii) a listing of cancer treatment with efficacy linked to a biological state of TP53; c) a computer-readable program code comprising instructions to execute the following: i) inputting the mutation allele frequency in the biological sample of TP53; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments, provided herein are systems for generating a report for a patient to identify the patient as a candidate for increased monitoring, further diagnostic testing, or both that include: a) at least one device configured to assay a set of genes in a biological sample to determine mutation allele frequency of each mutation in the set of genes in a sample collected from the patient, wherein the set of genes in a sample collected from the patient, wherein the set of genes comprises one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments of systems for generating a report for a patient to identify the patient as a candidate for increased monitoring, further diagnostic testing, or both, the systems further include at least one device configured to detect the presence of at least one genetic biomarker (e.g., at least one mutation) in a TERT promoter.

In some embodiments, provided herein are systems for generating a report for a patient to identify the patient as a candidate for increased monitoring, further diagnostic testing, or both that include: a) at least one device configured to assay a set of genes in a biological sample to determine mutation allele frequency of each mutation in the set of genes in a sample collected from the patient, wherein the set of genes in a sample collected from the patient, wherein the set of genes comprises one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments, provided herein are systems for generating a report for a patient to identify the patient as a candidate for increased monitoring, further diagnostic testing, or both that include: a) at least one device configured to assay a set of genes in a biological sample to determine mutation allele frequency of each mutation in the set of genes comprises one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A; b) at least one computer database comprising: i) a first reference distribution of mutation allele frequency in control samples for each mutation in the set of genes; ii) a second reference distribution of mutation allele frequency in samples collected from patients having a cancer for each mutation in the set of genes; and iii) a listing of cancer treatment with efficacy linked to a biological state of at least one member of the set of genes; c) a computer-readable program code comprising instructions to execute the following: i) inputting the mutation allele frequency in the biological sample of each mutation in the set of genes; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient. In some embodiments, provided herein are systems for generating a report for a patient to identify the patient as a candidate for increased monitoring, further diagnostic testing, or both that include: a) at least one device configured to assay a TP53 gene in a biological sample collected from the patient to determine mutation allele frequency of TP53; b) at least one computer database comprising: i) a first reference distribution of mutation allele frequency in control samples for TP53; ii) a second reference distribution of mutation allele frequency in samples collected from patients having a cancer for TP53; and iii) a listing of cancer treatment with efficacy linked to a biological state of TP53; c) a computer-readable program code comprising instructions to execute the following: i) inputting the mutation allele frequency in the biological sample of TP53; ii) comparing the mutation allele frequency to the first reference distribution; iii) comparing the mutation allele frequency to the second reference distribution; and iv) calculating a score that indicates the likelihood that the patient has a cancer; d) a computer-readable program code comprising instructions to generate a report that indicates the patient as having a cancer if the score is higher than a reference value; or a report that indicates the patient as not having a cancer if the score is not higher than the reference value; and e) a computer-readable program code comprising instructions to identify for the patient at least one cancer treatment from the listing of cancer treatments in (b) (iii) when the patient is identified as having a cancer in step (d), wherein the calculated score provides an indication that the identified cancer treatment will be effective in the patient.

In some embodiments of systems for generating a report for a patient, systems for generating a report to identify a cancer treatment for a patient, or systems for generating a report for a patient to identify the patient as a candidate for increased monitoring, further diagnostic testing, or both, the systems further include a computer-readable program code comprising instructions to execute the following: i) determining a mutation allele frequency in the sample for two or more of the genetic biomarkers; ii) obtaining a score that indicates the likelihood that the subject has a cancer by comparing the mutation allele frequency of each mutation in the selected genetic biomarkers against a reference distribution of mutation allele frequency for each mutation in control samples; and ii) identifying the subject as having a cancer when the score is higher than a reference value for the score. In some embodiments of systems for generating a report for a patient, systems for generating a report to identify a cancer treatment for a patient, or systems for generating a report for a patient to identify the patient as a candidate for increased monitoring, further diagnostic testing, or both, the systems further include a computer-readable program code comprising instructions to execute the following instructions: i) selecting one genetic biomarker with the highest score that indicates the probability that the subject has a cancer from the two or more genetic biomarkers; and ii) comparing the score for the selected genetic biomarker to the reference value. In some embodiments of systems for generating a report for a patient, systems for generating a report to identify a cancer treatment for a patient, or systems for generating a report for a patient to identify the patient as a candidate for increased monitoring, further diagnostic testing, or both, the score is Stouffer's Z-score. In some embodiments of systems for generating a report for a patient, systems for generating a report to identify a cancer treatment for a patient, or systems for generating a report for a patient to identify the patient as a candidate for increased monitoring, further diagnostic testing, or both, the systems further include a computer-readable program code comprising instructions to execute the following instructions: i) determining a mutation allele frequency in the sample for two or more of the genetic biomarkers; and ii) comparing the mutation allele frequency of each mutation in the selected genetic biomarkers to the maximum mutation allele frequency of each mutation for each mutation in control samples.

In some embodiments of systems for generating a report for a patient, systems for generating a report to identify a cancer treatment for a patient, or systems for generating a report for a patient to identify the patient as a candidate for increased monitoring, further diagnostic testing, or both, the device configured to assay a set of genes comprises a device that employs a includes a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments of systems for generating a report for a patient, systems for generating a report to identify a cancer treatment for a patient, or systems for generating a report for a patient to identify the patient as a candidate for increased monitoring, further diagnostic testing, or both, the multiplex PCR-based sequencing assay comprises: a. assigning a unique identifier (UID) to each of a plurality of template molecules present in the sample; b. amplifying each uniquely tagged template molecule to create UID-families; and c. redundantly sequencing the amplification products. In some embodiments of systems for generating a report for a patient, systems for generating a report to identify a cancer treatment for a patient, or systems for generating a report for a patient to identify the patient as a candidate for increased monitoring, further diagnostic testing, or both, the system further includes a device configured to detect the presence of aneuploidy in a biological sample. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, the system further includes a device (e.g., a device that includes a multiplex immunoassay system) configured to detect the presence of aneuploidy in a biological sample. In some embodiments of systems for generating a report for a patient, systems for generating a report to identify a cancer treatment for a patient, or systems for generating a report for a patient to identify the patient as a candidate for increased monitoring, further diagnostic testing, or both that include: 1) at least one device configured to assay one or more (e.g., 1, 2, 3, 4, 5, 6, 7, 8, 9, 10, 11, 12, 13, 14, 16, or 16) of the following genes: NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS, and 2) at least one device configured to detect the presence of a genetic biomarker (e.g., at least one mutation) in a TERT promoter, the system further includes a device (e.g., a device that includes a multiplex immunoassay system) configured to detect the presence of aneuploidy in a biological sample. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A, the system further includes a device (e.g., a device that includes a multiplex immunoassay system) configured to detect the presence of aneuploidy in a biological sample. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A, the system further includes a device (e.g., a device that includes a multiplex immunoassay system) configured to detect the presence of aneuploidy in a biological sample. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay TP53, the system further includes a device (e.g., a device that includes a multiplex immunoassay system) configured to detect the presence of aneuploidy in a biological sample. The presence of aneuploidy can be detected on one or more chromosomes or chromosomal arms that are associated with cancer. In some embodiments, the presence of aneuploidy is detected on one or more of chromosomal arms 5q, 8q, and/or 9p. In some embodiments, the presence of aneuploidy is detected on one or more of chromosomal arms 4p, 7q, 8q, and/or 9q In some embodiments of systems for generating a report for a patient, systems for generating a report to identify a cancer treatment for a patient, or systems for generating a report for a patient to identify the patient as a candidate for increased monitoring, further diagnostic testing, or both, the sensitivity of the system in identifying a subject as having cancer is improved as compared to conventional systems for generating a report for a patient. In some embodiments of systems for generating a report for a patient, systems for generating a report to identify a cancer treatment for a patient, or systems for generating a report for a patient to identify the patient as a candidate for increased monitoring, further diagnostic testing, or both, the specificity of the system in identifying a subject as having cancer is improved as compared to conventional systems for generating a report for a patient. In some embodiments of systems for generating a report for a patient, systems for generating a report to identify a cancer treatment for a patient, or systems for generating a report for a patient to identify the patient as a candidate for increased monitoring, further diagnostic testing, or both, the first and second reference distribution of mutation allele frequency values are input into the system from a location that is remote from the at least one computer database. In some embodiments of systems for generating a report for a patient, systems for generating a report to identify a cancer treatment for a patient, or systems for generating a report for a patient to identify the patient as a candidate for increased monitoring, further diagnostic testing, or both, first and second reference distribution of mutation allele frequency values are input into the system over an internet connection. In some embodiments of systems for generating a report for a patient, systems for generating a report to identify a cancer treatment for a patient, or systems for generating a report for a patient to identify the patient as a candidate for increased monitoring, further diagnostic testing, or both, the report is in electronic or paper format.

In some embodiments of systems for generating a report for a patient, systems for generating a report to identify a cancer treatment for a patient, or systems for generating a report for a patient to identify the patient as a candidate for increased monitoring, further diagnostic testing, or both, the cancer is any of the variety of cancer types described herein (see, e.g., section entitled "Cancers"). In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay comprises one or more (e.g., 1, 2, 3, 4, 5, 6, 7, 8, 9, or 10) of the following genes: TP53, PIK3CA, FGFR3, KRAS, ERBB2, CDKN2A, MLL, HRAS, MET, and/or VHL and at least one a device configured to detect the presence of aneuploidy in a biological sample, the cancer is bladder cancer or an upper-tract urothelial carcinoma. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, 12, 13, 14, 15, 16, 17, or 18) of the following genes: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and/or CDKN2A and at least one a device configured to detect the presence of aneuploidy in a biological sample, the cancer is cervical cancer, endometrial cancer, ovarian cancer, or fallopian tubal cancer. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay one or more (e.g., 1, 2, 3, 4, 5, 6, 7, 8, 9, 10, 11, or 12) of the following genes: PTEN, TP53, PIK3CA, PIK3R1, CTNNB1, KRAS, FGFR2, POLE, APC, FBXW7, RNF43, and/or PPP2R1A and at least one a device configured to detect the presence of aneuploidy in a biological sample, the cancer is endometrial cancer. In some embodiments of systems for generating a report for a patient, systems for generating a report to identify a cancer treatment for a patient, or systems for generating a report for a patient to identify the patient as a candidate for increased monitoring, further diagnostic testing, or both that include at least one device configured to assay TP53 and at least one a device configured to detect the presence of aneuploidy in a biological sample, the cancer is a high-grade serous carcinoma. In some embodiments of systems for generating a report for a patient or systems for generating a report to identify a cancer treatment for a patient, the patient is identified as a candidate for increased monitoring, further diagnostic testing, or both (e.g. any of the variety of increased monitoring or further diagnostic methods described herein).

Many of the currently approved tests for earlier cancer detection are procedural in nature, and include colonoscopy, mammography, and cervical cytology analysis. To date, the vast majority of cancer patients evaluated with mutation-based liquid biopsies have advanced stage disease. Yet another issue with liquid biopsies is the identification of the underlying organ of origin. Because the same gene mutations drive multiple tumor types, liquid biopsies based on such alterations cannot generally identify the location of the primary tumor giving rise to a positive blood test. Described herein is a non-invasive combinatorial blood test (e.g., a test that combines DNA markers and protein markers) for the early detection and localization of many common cancers.

This document provides methods and materials for assessing and/or treating mammals (e.g., humans) having, or suspected of having, cancer. In some embodiments, this document provides methods and materials for identifying a mammal as having cancer. For example, a sample (e.g., a blood sample) obtained from a mammal can be assessed to determine if the mammal has cancer based, at least in part, on the presence or absence of one or more biomarkers (e.g., genetic biomarkers) and/or an elevated level of one or more biomarkers (e.g., peptide biomarkers). In some embodiments, this document provides methods and materials for identifying the location (e.g., the anatomic site) of a cancer in a mammal. For example, a sample (e.g., a blood sample) obtained from a mammal can be assessed to determine the location of the cancer in the mammal based, at least in part, on the presence or absence of one or more biomarkers (e.g., genetic biomarkers) and/or an elevated level of one or more biomarkers (e.g., peptide biomarkers). In some embodiments, this document provides methods and materials for identifying a mammal as having cancer, and administering one or more pharmacological interventions to treat the mammal. For example, a sample (e.g., a blood sample) obtained from a mammal can be assessed to determine if the mammal has cancer based, at least in part, on the presence or absence of one or more biomarkers (e.g., genetic biomarkers) and/or an elevated level of one or more biomarkers (e.g., peptide biomarkers), and administering one or more cancer treatments to the mammal.

As demonstrated herein, an analysis of only 2,001 bp of genomic DNA could detect at least one mutation in 82% of eight common cancer types. A test (CancerSEEK) was designed which assessed the levels of 10 circulating proteins as well as mutations of these 2,001 bp in circulating cell-free DNA. This test was applied to 1,005 patients with cancers of the liver, ovary, esophagus, stomach, pancreas, colorectum, lung, or breast. CancerSEEK tests were positive in a median of 70% of the eight cancer types, while fewer than 1% of 812 normal individuals scored positively. The sensitivities ranged from 69% to 98% for the detection of five cancer types (liver, ovary, esophagus, stomach, and pancreas) for which there are no screening tests available for average-risk individuals. Moreover, the source of the cancer could be localized to a small number of anatomic sites in a median of 84% of the patients scoring positive in the CancerSEEK assay.

Having the ability to use a blood test having very high specificity (e.g., by combining DNA markers and protein markers) can allow clinicians to detect cancers at earlier stages resulting in earlier treatment with fewer unnecessary follow-up procedures, less anxiety, and/or reduced cancer deaths.

In general, one aspect of this document features a method for identifying a mammal as having cancer. The method can include, or consist essentially of, detecting one or more genetic biomarkers in circulating DNA in a blood sample obtained from a mammal; detecting an elevated level of one or more peptide biomarkers in the blood sample obtained from a mammal; and identifying the mammal as having cancer when the presence of one or more genetic biomarkers is detected in circulating DNA in said blood sample, when an elevated level of one or more peptide biomarkers is detected in said blood sample, or both. The mammal can be a human. The blood sample can be a plasma sample. The cancer can be a Stage I cancer. The cancer can be a liver cancer, an ovary cancer, an esophageal cancer, a stomach cancer, a pancreatic cancer, a colorectal cancer, a lung cancer, a breast cancer, or a prostate cancer. The one or more genetic biomarkers can include one or more modifications in one or more genes. The one or more modifications can include inactivating modifications, and the one or more genes can include tumor suppressor genes. The one or more modifications can independently be selected from single base substitutions, insertions, and deletions. The one or more genes are can include NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. The one or more modifications can independently be selected from the modifications set forth in Table 5. The step of detecting the presence of one or more genetic biomarkers can be performed using a multiplex PCR-based sequencing assay. The multiplex PCR-based sequencing assay can include assigning a unique identifier (UID) to each template molecule; amplifying each uniquely tagged template molecule to create UID-families; and redundantly sequencing the amplification products. The one or more peptide biomarkers can include prolactin, OPN, IL-6, CEA, CA125, HGF, Myeloperoxidase, CA19-9, Midkine, and/or TIMP-1. The step of detecting the level of one or more peptide biomarkers can be performed using a multiplex immunoassay system. The method also can include identifying a location of said cancer. The method also can include administering to the mammal one or more cancer treatments. The one or more cancer treatments can include surgery, chemotherapy, hormone therapy, targeted therapy, radiation therapy, and combinations thereof.

In another aspect, this document features a method for treating a mammal having cancer. The method can include, or consist essentially of, detecting one or more genetic biomarkers in circulating DNA in a blood sample obtained from a mammal; detecting an elevated level of one or more peptide biomarkers in the blood sample obtained from a mammal; and administering one or more cancer treatments to said mammal when the presence of one or more genetic biomarkers is detected in circulating DNA in said blood sample, when an elevated level of one or more peptide biomarkers is detected in said blood sample, or both. The one or more cancer treatments can include surgery, chemotherapy, hormone therapy, targeted therapy, radiation therapy, and combinations thereof. The mammal can be a human. The blood sample can be a plasma sample. The cancer can be a Stage I cancer. The cancer can be a liver cancer, an ovary cancer, an esophageal cancer, a stomach cancer, a pancreatic cancer, a colorectal cancer, a lung cancer, a breast cancer, or a prostate cancer. The one or more genetic biomarkers can include one or more modifications in one or more genes. The one or more modifications can include inactivating modifications, and the one or more genes can include tumor suppressor genes. The one or more modifications can independently be selected from single base substitutions, insertions, and deletions. The one or more genes are can include NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. The one or more modifications can independently be selected from the modifications set forth in Table 5. The step of detecting the presence of one or more genetic biomarkers can be performed using a multiplex PCR-based sequencing assay. The multiplex PCR-based sequencing assay can include assigning a unique identifier (UID) to each template molecule; amplifying each uniquely tagged template molecule to create UID-families; and redundantly sequencing the amplification products. The one or more peptide biomarkers can include prolactin, OPN, IL-6, CEA, CA125, HGF, Myeloperoxidase, CA19-9, Midkine, and/or TIMP-1. The step of detecting the level of one or more peptide biomarkers can be performed using a multiplex immunoassay system.

In another aspect, this document features a method for identifying the location of a cancer in a mammal. The method can include, or consist essentially of, detecting one or more genetic biomarkers in circulating DNA in a blood sample obtained from a mammal; detecting an elevated level of one or more peptide biomarkers in the blood sample obtained from a mammal; and identifying the location of the cancer in the mammal when the presence of one or more genetic biomarkers is detected in circulating DNA in said blood sample, when an elevated level of one or more peptide biomarkers is detected in said blood sample, or both. The mammal can be a human. The blood sample can be a plasma sample. The cancer can be a Stage I cancer. The cancer can be a liver cancer, an ovary cancer, an esophageal cancer, a stomach cancer, a pancreatic cancer, a colorectal cancer, a lung cancer, a breast cancer, or a prostate cancer. The one or more genetic biomarkers can include one or more modifications in one or more genes. The one or more modifications can include inactivating modifications, and the one or more genes can include tumor suppressor genes. The one or more modifications can independently be selected from single base substitutions, insertions, and deletions. The one or more genes are can include NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS. The one or more modifications can independently be selected from the modifications set forth in Table 5. The step of detecting the presence of one or more genetic biomarkers can be performed using a multiplex PCR-based sequencing assay. The multiplex PCR-based sequencing assay can include assigning a unique identifier (UID) to each template molecule; amplifying each uniquely tagged template molecule to create UID-families; and redundantly sequencing the amplification products. The one or more peptide biomarkers can include prolactin, OPN, IL-6, CEA, CA125, HGF, Myeloperoxidase, CA19-9, Midkine, and/or TIMP-1. The step of detecting the level of one or more peptide biomarkers can be performed using a multiplex immunoassay system.

Provided herein are methods for identifying the presence of a cancer in a human subject comprising: detecting in a first biological sample isolated from the human subject the presence of one or more genetic alterations in cell-free DNA derived from a gene selected from the group consisting of: AKT1, APC, BRAF, CDKN2, CTNNB1, FBXW7, FGFR2, GNAS, HRAS, KRAS, PPP2R1A, TP53, PTEN, PIK3CA, EGFR and NRAS, and combinations thereof; detecting a level of one or more protein biomarkers in a second biological sample isolated from the human subject, wherein the protein biomarker is selected from the group consisting of: carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3, and combinations thereof; comparing the detected levels of the one or more protein biomarkers to one or more reference levels of the protein biomarkers; and identifying the presence of the cancer in the human subject when the presence of one or more genetic alterations in the cell-free DNA is detected, the detected levels of the one or more protein biomarkers are higher than the reference levels of the one or more protein biomarkers, or both. In some embodiments, the first biological sample comprises blood, plasma, urine, cerebrospinal fluid, saliva, sputum, bronchoalveolar lavage, bile, lymphatic fluid, cyst fluid, stool, ascites, and combinations thereof. In some embodiments, the first biological sample, the second biological sample, or both comprises plasma. In some embodiments, the first and second biological samples are the same.

In some embodiments of identifying the presence of a cancer in a human subject, the step of detecting the presence of one or more genetic alterations in cell-free DNA in the first biological sample comprises amplifying an amplicon comprising codons and their surrounding splice sites, wherein the codons are selected from the group consisting of: codons 16-18 of AKT1; codons 1304-1311 or 1450-1459 of APC; codons 591-602 of BRAF; codons 51-58 or 76-88 of CDKN2A; codons 31-39 or 38-47 of CTNNB1; codons 856-868 of EGFR; codons 361-371, 464-473, 473-483, or 498-507 of FBXW7; codons 250-256 of FGFR2; codons 199-208 of GNAS; codons 7-19 of HRAS; codons 7-14, 57-65, or 143-148 of KRAS; codons 3-15 or 54-63 of NRAS; codons 80-90, 343-348, 541-551, or 1038-1050 of PIK3CA; codons 175-187 of PPP2R1A; codons 90-98, 125-132, 133-146, 145-154 of PTEN; codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, or 374-386 of TP53, and combinations thereof. In some embodiments, the step of detecting the presence of one or more genetic alterations in cell-free DNA in the first biological sample comprises sequencing gene regions comprising codons and their surrounding splice sites, wherein the codons are selected from the group consisting of: codons 16-18 of AKT1; codons 1304-1311 or 1450-1459 of APC; codons 591-602 of BRAF; codons 51-58 or 76-88 of CDKN2A; codons 31-39 or 38-47 of CTNNB1; codons 856-868 of EGFR; codons 361-371, 464-473, 473-483, or 498-507 of FBXW7; codons 250-256 of FGFR2; codons 199-208 of GNAS; codons 7-19 of HRAS; codons 7-14, 57-65, or 143-148 of KRAS; codons 3-15 or 54-63 of NRAS; codons 80-90, 343-348, 541-551, or 1038-1050 of PIK3CA; codons 175-187 of PPP2R1A; codons 90-98, 125-132, 133-146, 145-154 of PTEN; codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, or 374-386 of TP53, and combinations thereof. In some embodiments, the step of detecting the presence of one or more genetic alterations in cell-free DNA in the first biological sample comprises sequencing gene regions comprising codons and their surrounding splice from each of: codons 16-18 of AKT1; codons 1304-1311 and 1450-1459 of APC; codons 591-602 of BRAF; codons 51-58 and 76-88 of CDKN2A; codons 31-39 and 38-47 of CTNNB1; codons 856-868 of EGFR; codons 361-371, 464-473, 473-483, and 498-507 of FBXW7; codons 250-256 of FGFR2; codons 199-208 of GNAS; codons 7-19 of HRAS; codons 7-14, 57-65, and 143-148 of KRAS; codons 3-15 and 54-63 of NRAS; codons 80-90, 343-348, 541-551, and 1038-1050 of PIK3CA; codons 175-187 of PPP2R1A; codons 90-98, 125-132, 133-146, 145-154 of PTEN; codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, and 374-386 of TP53, and combinations thereof.

In some embodiments of identifying the presence of a cancer in a human subject, the one or more protein biomarkers include CA19-9. In some embodiments, the reference level of the CA19-9 protein biomarker is 92 U/mL. In some embodiments, the one or more protein biomarkers include CEA. In some embodiments, the reference level of the CEA protein biomarker is 7.5 ng/mL. In some embodiments, the one or more protein biomarkers include HGF. In some embodiments, the reference level of the HGF protein biomarker is 0.89 ng/mL. In some embodiments, the one or more protein biomarkers include OPN. In some embodiments, the reference level of the OPN protein biomarker is 158 ng/mL. In some embodiments, the one or more protein biomarkers include CA125. In some embodiments, the reference level of the CA125 protein biomarker is 577 U/mL. In some embodiments, the one or more protein biomarkers include AFP. In some embodiments, the reference level of the AFP protein biomarker is 21 ng/mL. In some embodiments, the one or more protein biomarkers include prolactin. In some embodiments, the reference level of the prolactin protein biomarker is 145 ng/mL. In some embodiments, the one or more protein biomarkers include TIMP-1. In some embodiments, the reference level of the TIMP-1 protein biomarker is 177 ng/mL. In some embodiments, the one or more protein biomarkers include follistatin. In some embodiments, the reference level of the follistatin protein biomarker is 2 ng/ml In some embodiments, the one or more protein biomarkers include G-CSF. In some embodiments, the reference level of the G-CSF protein biomarker is 800 pg/mL. In some embodiments, the one or more protein biomarkers include CA15-3. In some embodiments, the reference level of the CA15-3 protein biomarker is 98 U/mL.

In some embodiments of identifying the presence of a cancer in a human subject, the presence of the cancer in the human subject is identified when: (i) the presence of one or more genetic alterations in cell-free DNA derived is detected, and (ii) the detected levels of the one or more protein biomarkers are higher than the reference levels of the one or more protein biomarkers.

In some embodiments of identifying the presence of a cancer in a human subject, the presence of one or more genetic alterations in cell-free DNA in the first biological sample is detected by amplifying the cell-free DNA to form families of amplicons in which each member of a family is derived from a single template molecule in the cell-free DNA, wherein each member of a family is marked by a common oligonucleotide barcode, and wherein each family is marked by a distinct oligonucleotide barcode. In some embodiments, the oligonucleotide barcode is introduced into the template molecule by a step of amplifying with a population of primers which collectively contain a plurality of oligonucleotide barcodes. In some embodiments, the oligonucleotide barcode is endogenous to the template molecule, and an adapter comprising a DNA synthesis priming site is ligated to an end of the template molecule adjacent to the oligonucleotide barcode.

In some embodiments of identifying the presence of a cancer in a human subject, a therapeutic intervention is administered to the subject when the presence of cancer is identified. In some embodiments, the therapeutic intervention is selected from the group consisting of: adoptive T cell therapy, radiation therapy, surgery, administration of a chemotherapeutic agent, administration of an immune checkpoint inhibitor, administration of a targeted therapy, administration of a kinase inhibitor, administration of a signal transduction inhibitor, administration of a bispecific antibody, administration of a monoclonal antibody, and combinations thereof. In some embodiments, cancer, and wherein the therapeutic intervention is more effective than if the therapeutic intervention were to be administered to a human subject at a later time.

In some embodiments of identifying the presence of a cancer in a human subject, the presence of cancer in the human subject is detected at a time prior to diagnosis of the human subject with cancer. In some embodiments, the presence of cancer in the human subject is detected at a time prior to the human subject exhibiting symptoms associated with cancer.

In some embodiments of identifying the presence of a cancer in a human subject, the human subject is human subjected to a radiologic scanning of an organ or body region to identify the location of the cancer. In some embodiments, the human subject is human subjected to whole body radiologic scanning to identify the location of the cancer. In some embodiments, the scanning is a Positron emission tomography-computed tomography (PET-CT) scan.

In some embodiments, the cancer is selected from the group consisting of: pancreatic cancer, colon cancer, esophageal cancer, stomach cancer, ovarian cancer, liver cancer, lung cancer, and breast cancer, and combinations thereof.

Also provided herein are methods for identifying the presence of cancer in a human subject comprising: detecting a level of one or more protein biomarkers in a first biological sample isolated from the human subject, wherein the one or more protein biomarkers are selected from the group consisting of: carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3, and combinations thereof; comparing the detected levels of the one or more protein biomarkers to one or more reference levels of the protein biomarkers; and identifying the presence of cancer in the human subject when the detected levels of the one or more protein biomarkers are higher than the reference levels of the one or more protein biomarkers.

Provided herein are methods for identifying the presence of pancreatic cancer in a human subject comprising: detecting in a first biological sample isolated from the human subject the presence of one or more genetic alterations in cell-free DNA derived from a gene selected from the group consisting of: KRAS, TP53, CDKN2A, SMAD4, and combinations thereof; detecting a level of one or more protein biomarkers in a second biological sample isolated from the human subject, wherein the one or more protein biomarkers are selected from the group consisting of: carbohydrate antigen 19-9 (CA19-9), carcinoembryonic antigen (CEA), hepatocyte growth factor (HGF), osteopontin (OPN), and combinations thereof; comparing the detected levels of the one or more protein biomarker to one or more reference levels of the protein biomarkers; and identifying the presence of pancreatic cancer in the human subject when the presence of one or more genetic alterations in the cell-free DNA is detected, the detected levels of the one or more protein biomarkers are higher than the reference levels of the one or more protein biomarkers, or both. In some embodiments, the first biological sample comprises blood, plasma, urine, cerebrospinal fluid, saliva, sputum, broncho-alveolar lavage, bile, lymphatic fluid, cyst fluid, stool, ascites, and combinations thereof. In some embodiments, the first biological sample, the second biological sample, or both comprises plasma. In some embodiments, the first and second biological samples are the same.

In some embodiments of methods for identifying the presence of pancreatic cancer in a human subject, the one or more genetic alterations occur in codons 12 or 61 of the KRAS gene. In some embodiments, the one or more protein biomarkers include CA19-9. In some embodiments, the reference level of the CA19-9 protein biomarker is 100 U/mL. In some embodiments, the one or more protein biomarkers include CEA. In some embodiments, the reference level of the CEA protein biomarker is 7.5 ng/mL. In some embodiments, the one or more protein biomarkers include HGF. In some embodiments, the reference level of the HGF protein biomarker is 0.92 ng/mL. In some embodiments, the one or more protein biomarkers include OPN. In some embodiments, the reference level of the OPN protein biomarker is 158 ng/mL. In some embodiments, detecting the level of the one or more protein biomarkers comprises detecting the levels of each of CA19-9, CEA, HGF, and OPN; and comparing the detected levels of the one or more protein biomarkers to one or more reference levels of the protein biomarker comprises comparing the detected levels of each of CA19-9, CEA, HGF, and OPN to a reference level of each of CA19-9, CEA, HGF, and OPN.

In some embodiments of methods for identifying the presence of pancreatic cancer in a human subject, the presence of pancreatic cancer in the human subject is identified when: (i) the presence of one or more genetic alterations in cell-free DNA derived from the KRAS gene are detected, and (ii) the detected levels of the one or more protein biomarkers are higher than the reference levels of the one or more protein biomarkers. In some embodiments of methods for identifying the presence of pancreatic cancer in a human subject, the one or more genetic alterations are detected by amplifying the cell-free DNA to form families of amplicons in which each member of a family is derived from a single template molecule in the cell-free DNA, wherein each member of a family is marked by a common oligonucleotide barcode, and wherein each family is marked by a distinct oligonucleotide barcode. In some embodiments, the oligonucleotide barcode is introduced into the template molecule by a step of amplifying with a population of primers which collectively contain a plurality of oligonucleotide barcodes. In some embodiments, the oligonucleotide barcode is endogenous to the template molecule, and an adapter comprising a DNA synthesis priming site is ligated to an end of the template molecule adjacent to the oligonucleotide barcode.

In some embodiments, a therapeutic intervention to the human subject when the presence of pancreatic cancer is identified. In some embodiments, the therapeutic intervention is selected from the group consisting of: adoptive T cell therapy, radiation therapy, surgery, administration of a chemotherapeutic agent, administration of an immune checkpoint inhibitor, administration of a targeted therapy, administration of a kinase inhibitor, administration of a signal transduction inhibitor, administration of a bispecific antibody, administration of a monoclonal antibody, and combinations thereof. In some embodiments, the therapeutic intervention is administered at a time when the human subject has an early-stage pancreatic cancer, and wherein the therapeutic intervention is more effective than if the therapeutic intervention were to be administered to a human subject at a later time.

In some embodiments, the presence of pancreatic cancer in the human subject is detected at a time prior to diagnosis of the human subject with pancreatic cancer. In some embodiments, the presence of pancreatic cancer in the human subject is detected at a time prior to the human subject exhibiting symptoms associated with pancreatic cancer.

Also provided herein are methods for identifying the presence of pancreatic cancer in a human subject comprising: detecting a level of one or more protein biomarkers in a first biological sample isolated from the human subject, wherein the one or more protein biomarkers are selected from the group consisting of: carbohydrate antigen 19-9 (CA19-9), carcinoembryonic antigen (CEA), hepatocyte growth factor (HGF), osteopontin (OPN), and combinations thereof; comparing the detected levels of the one or more protein biomarker to one or more reference levels of the protein biomarkers; and identifying the presence of pancreatic cancer in the human subject when the detected levels of the one or more protein biomarkers are higher than the reference levels of the one or more protein biomarkers.

Provided herein are methods for identifying the presence of a cancer in a human subject comprising: detecting in a first biological sample isolated from the subject the presence of one or more genetic alterations in cell-free DNA derived from a gene selected from the group consisting of: AKT1, APC, BRAF, CDKN2, CTNNB1, FBXW7, FGFR2, GNAS, HRAS, KRAS, PPP2R1A, TP53, PTEN, PIK3CA, EGFR and NRAS, and combinations thereof; detecting in a second biological sample isolated from the subject the absence of one or more genetic alterations in DNA derived from a gene selected from the group consisting of: AKT1, APC, BRAF, CDKN2, CTNNB1, FBXW7, FGFR2, GNAS, HRAS, KRAS, PPP2R1A, TP53, PTEN, PIK3CA, EGFR and NRAS, and combinations thereof, wherein the second biological sample is isolated from white blood cells of the subject; identifying the presence of the cancer in the subject when the one or more genetic alterations that are detected in the first sample are not detected in the second sample. In some embodiments, the first biological sample, the second biological sample, or both comprise blood, plasma, urine, cerebrospinal fluid, saliva, sputum, broncho-alveolar lavage, bile, lymphatic fluid, cyst fluid, stool, ascites, and combinations thereof. In some embodiments, the first biological sample, the second biological sample, or both comprises plasma. In some embodiments, the first and second biological samples are the same. In some embodiments of identifying the presence of a cancer in a human subject, the methods further comprise detecting a level of one or more protein biomarkers in a third biological sample isolated from the subject, wherein the protein biomarker is selected from the group consisting of: carbohydrate antigen 19-9 (CA19-9), carcinoembryonic antigen (CEA), hepatocyte growth factor (HGF), osteopontin (OPN), CA125, AFP, prolactin, TIMP-1, follistatin, G-CSF, and CA15-3 and combinations thereof; comparing the detected levels of the one or more protein biomarkers to one or more reference levels of the protein biomarkers; and identifying the presence of the cancer in the subject when the presence of one or more genetic alterations in the cell-free DNA is detected in the first sample, the absence of one or more genetic alterations is detected in DNA from the second sample, and the detected levels of the one or more protein biomarkers are higher than the reference levels of the one or more protein biomarkers. In some embodiments, the third biological sample is the same as the first biological sample.

In some embodiments of identifying the presence of a cancer in a human subject, the step of detecting the presence of one or more genetic alterations in cell-free DNA in the first biological sample, the step of detecting the absence of one or more genetic alterations in DNA in the second biological sample, or both comprises amplifying an amplicon comprising codons and their surrounding splice sites, wherein the codons are selected from the group consisting of: codons 16-18 of AKT1; codons 1304-1311 or 1450-1459 of APC; codons 591-602 of BRAF; codons 51-58 or 76-88 of CDKN2A; codons 31-39 or 38-47 of CTNNB1; codons 856-868 of EGFR; codons 361-371, 464-473, 473-483, or 498-507 of FBXW7; codons 250-256 of FGFR2; codons 199-208 of GNAS; codons 7-19 of HRAS; codons 7-14, 57-65, or 143-148 of KRAS; codons 3-15 or 54-63 of NRAS; codons 80-90, 343-348, 541-551, or 1038-1050 of PIK3CA; codons 175-187 of PPP2R1A; and codons 90-98, 125-132, 133-146, 145-154 of PTEN; and codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, or 374-386 of TP53. In some embodiments, the step of detecting the presence of one or more genetic alterations in cell-free DNA in the first biological sample, the step of detecting the absence of one or more genetic alterations in DNA in the second biological sample, or both comprises sequencing gene regions comprising codons and their surrounding splice sites, wherein the codons are selected from the group consisting of: codons 16-18 of AKT1; codons 1304-1311 or 1450-1459 of APC; codons 591-602 of BRAF; codons 51-58 or 76-88 of CDKN2A; codons 31-39 or 38-47 of CTNNB1; codons 856-868 of EGFR; codons 361-371, 464-473, 473-483, or 498-507 of FBXW7; codons 250-256 of FGFR2; codons 199-208 of GNAS; codons 7-19 of HRAS; codons 7-14, 57-65, or 143-148 of KRAS; codons 3-15 or 54-63 of NRAS; codons 80-90, 343-348, 541-551, or 1038-1050 of PIK3CA; codons 175-187 of PPP2R1A; and codons 90-98, 125-132, 133-146, 145-154 of PTEN; and codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, or 374-386 of TP53. In some embodiments, the step of detecting the presence of one or more genetic alterations in cell-free DNA in the first biological sample, the step of detecting the absence of one or more genetic alterations in DNA in the second biological sample, or both comprises sequencing gene regions comprising codons and their surrounding splice from each of: codons 16-18 of AKT1; codons 1304-1311 and 1450-1459 of APC; codons 591-602 of BRAF; codons 51-58 and 76-88 of CDKN2A; codons 31-39 and 38-47 of CTNNB1; codons 856-868 of EGFR; codons 361-371, 464-473, 473-483, and 498-507 of FBXW7; codons 250-256 of FGFR2; codons 199-208 of GNAS; codons 7-19 of HRAS; codons 7-14, 57-65, and 143-148 of KRAS; codons 3-15 and 54-63 of NRAS; codons 80-90, 343-348, 541-551, or 1038-1050 of PIK3CA; codons 175-187 of PPP2R1A; and codons 90-98, 125-132, 133-146, 145-154 of PTEN; and codons 10-22, 25-32, 33-40, 40-52, 52-64, 82-94, 97-110, 112-125, 123-125, 126-132, 132-142, 150-163, 167-177, 175-186, 187-195, 195-206, 207-219, 219-224, 226-237, 232-245, 248-261, 261-268, 272-283, 279-290, 298-307, 307-314, 323-331, 333-344, 344-355, 367-375, and 374-386 of TP53.

In some embodiments of identifying the presence of a cancer in a human subject, the one or more protein biomarkers include CA19-9. In some embodiments, the reference level of the CA19-9 protein biomarker is 92 U/mL. In some embodiments, the one or more protein biomarkers include CEA. In some embodiments, the reference level of the CEA protein biomarker is 7.5 ng/mL. In some embodiments, the one or more protein biomarkers include HGF. In some embodiments, the reference level of the HGF protein biomarker is 0.89 ng/mL. In some embodiments, the one or more protein biomarkers include OPN. In some embodiments, the reference level of the OPN protein biomarker is 158 ng/mL. In some embodiments, the one or more protein biomarkers include CA125. In some embodiments, the reference level of the CA125 protein biomarker is 577 U/mL. In some embodiments, the one or more protein biomarkers include AFP. In some embodiments, the reference level of the AFP protein biomarker is 21 ng/mL. In some embodiments, the one or more protein biomarkers include prolactin. In some embodiments, the reference level of the prolactin protein biomarker is 145 ng/mL. In some embodiments, the one or more protein biomarkers include TIMP-1. In some embodiments, the reference level of the TIMP-1 protein biomarker is 177 ng/mL. In some embodiments, the one or more protein biomarkers include follistatin. In some embodiments, the reference level of the follistatin protein biomarker is 2 ng/ml. In some embodiments, the one or more protein biomarkers include G-CSF. In some embodiments, the reference level of the G-CSF protein biomarker is 800 pg/mL. In some embodiments, the one or more protein biomarkers include CA15-3. In some embodiments, the reference level of the CA15-3 protein biomarker is 98 U/mL.

In some embodiments of identifying the presence of a cancer in a human subject, the presence of one or more genetic alterations in cell-free DNA in the first biological sample, the absence of one or more genetic alterations in DNA in the second biological sample, or both are detected by amplifying the cell-free DNA to form families of amplicons in which each member of a family is derived from a single template molecule in the cell-free DNA, wherein each member of a family is marked by a common oligonucleotide barcode, and wherein each family is marked by a distinct oligonucleotide barcode. In some embodiments, the oligonucleotide barcode is introduced into the template molecule by a step of amplifying with a population of primers which collectively contain a plurality of oligonucleotide barcodes. In some embodiments, the oligonucleotide barcode is endogenous to the template molecule, and an adapter comprising a DNA synthesis priming site is ligated to an end of the template molecule adjacent to the oligonucleotide barcode.

In some embodiments, a therapeutic intervention is administered to the subject when the presence of cancer is identified. In some embodiments, the therapeutic intervention is selected from the group consisting of: adoptive T cell therapy, radiation therapy, surgery, administration of a chemotherapeutic agent, administration of an immune checkpoint inhibitor, administration of a targeted therapy, administration of a kinase inhibitor, administration of a signal transduction inhibitor, administration of a bispecific antibody, administration of a monoclonal antibody, and combinations thereof. In some embodiments, the therapeutic intervention is administered at a time when the subject has an early-stage cancer, and wherein the therapeutic intervention is more effective than if the therapeutic intervention were to be administered to a subject at a later time.

In some embodiments of identifying the presence of a cancer in a human subject, the presence of cancer in the subject is detected at a time prior to diagnosis of the subject with cancer. In some embodiments, the presence of cancer in the subject is detected at a time prior to the subject exhibiting symptoms associated with cancer.

In some embodiments of identifying the presence of a cancer in a human subject, the human subject is human subjected to a radiologic scanning of an organ or body region to identify the location of the cancer. In some embodiments, the human subject is human subjected to whole body radiologic scanning to identify the location of the cancer. In some embodiments, the scanning is a Positron emission tomography-computed tomography (PET-CT) scan.

In some embodiments of identifying the presence of a cancer in a human subject, the cancer is selected from the group consisting of: pancreatic cancer, colon cancer, esophageal cancer, stomach cancer, ovarian cancer, liver cancer, lung cancer, and breast cancer, and combinations thereof.

Figure 19:
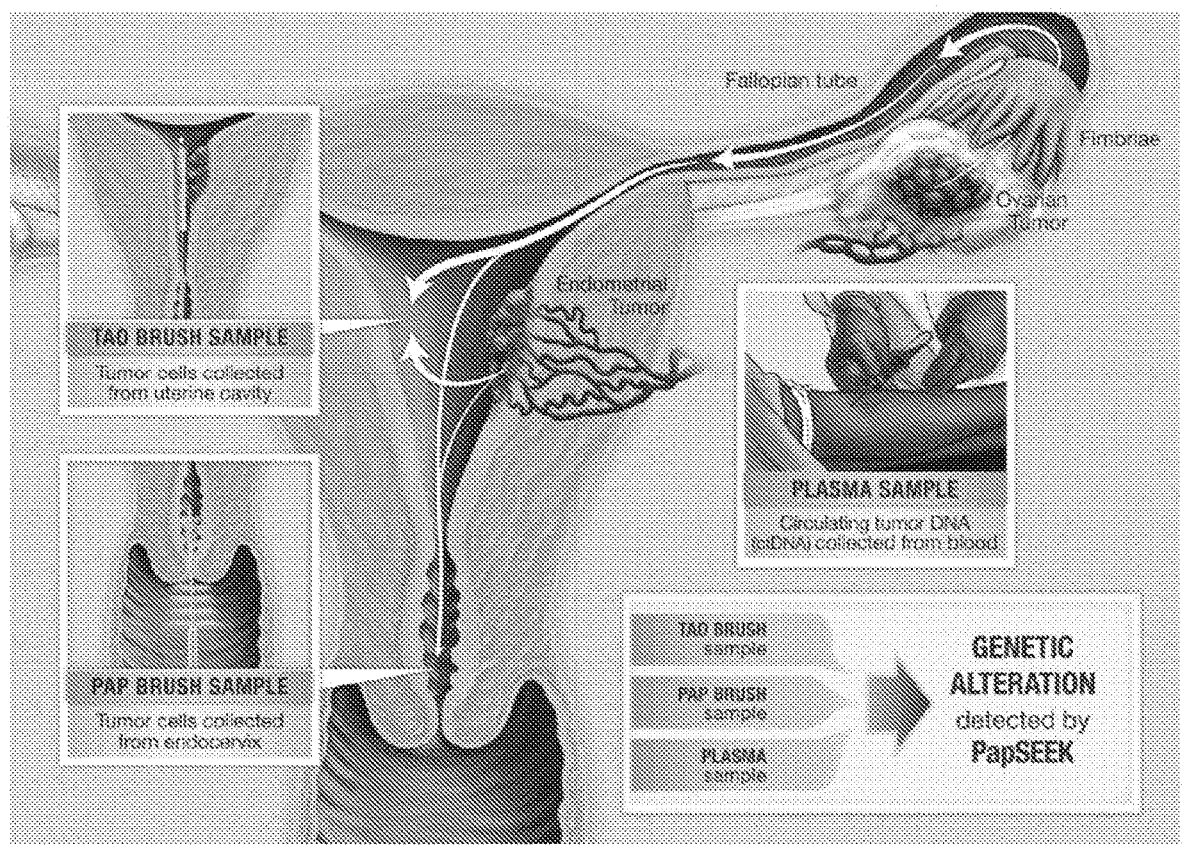
FIG. 19 contains a schematic of an exemplary PapSEEK test for the detection of tumor DNA in the Pap brush, Tao brush, and plasma samples of patients with endometrial or ovarian cancers. Tumor cells shed from ovarian or endometrial cancers are carried into the uterine cavity, where they can be collected by the Tao brush. The tumor cells that pass down into the endocervical canal can be captured by the Pap brush used in the routine Pap test. These brushes are dipped into a liquid fixative, from which DNA is isolated and sequenced. The sequences are analyzed for somatic mutations and aneuploidy. Additionally, tumor DNA shed into the bloodstream can be detected by ctDNA analysis.

As described in more detail herein, it has been shown that DNA from sampled fluid (e.g., fluid containing cells sampled from the endocervical canal) can be used in an assay (e.g., a PCR-based, multiplex test) to simultaneously assess genetic alterations that commonly occur in endometrial or ovarian cancers (FIG. 19). Additionally, as described in more detail herein and without limitation, two ways to increase sensitivity were identified. First, intrauterine sampling (with a "Tao brush") was tested, a method that allows sample collection closer to the anatomical site of the tumors. Second, in a recent study, it was shown that testing for mutations in both saliva and plasma from the same individual increased the sensitivity of detecting head and neck tumors (Wang et al., Detection of somatic mutations and HPV in the saliva and plasma of patients with head and neck squamous cell carcinomas. Sci Transl Med 7, 293ra104 (2015)). Based on this precedent, it was shown that testing for mutations in both the plasma and Pap test fluid can increase sensitivity for cancers (e.g., ovarian cancers).

In some aspects, provided herein are methods of detecting endometrial and ovarian cancers based on genetic analyses of DNA recovered from fluids (e.g., fluids obtained during a routine Papanicolaou (Pap) test). In some embodiments, this new test, called PapSEEK, incorporates assays for mutations in one or more of 18 genes and/or an assay for aneuploidy. In some embodiment, method provided herein to detect gynecologic cancers are used at a stage when the cancers are more likely to be curable. In some embodiments, PapSEEK can be combined with assays for mutations in one or more genes in nucleic acids present in a plasma sample.

In some embodiments, provided herein are methods of detecting ovarian or endometrial cancer in a subject that include detecting in a sample obtained from the subject the presence of one or more mutations in one or more genes selected from the group consisting of: NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, and CDKN2A, detecting in the sample the presence of aneuploidy, or both, wherein the presence of one or more mutations in NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A, the presence of aneuploidy, or both indicates that the subject has ovarian or endometrial cancer. In some embodiments, the step of detecting the presence of one or more mutations in NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, CDKN2A is performed using a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments, the step of detecting the presence of one or more mutations in NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, CDKN2A is performed by increasing the sensitivity of massively parallel sequencing instruments with an error reduction technique that allows for the detection of rare mutant alleles in a range of 1 mutant template among 100 to 1,000,000 wild-type templates. For example, the step of detecting one or more mutations can be performed by increasing the sensitivity of massively parallel sequencing instruments with an error reduction technique comprising: a) molecularly assigning a unique identifier (UID) to each template molecule, b) amplifying each uniquely tagged template molecule to create UID-families, and c) redundantly sequencing the amplification products. In some embodiments, methods provided herein further include conducting cytology on the sample, wherein presence of the one or more mutations in NRAS, PTEN, FGFR2, KRAS, POLE, AKT1, TP53, RNF43, PPP2R1A, MAPK1, CTNNB1, PIK3CA, FBXW7, PIK3R1, APC, EGFR, BRAF, or CDKN2A, the presence of aneuploidy, and/or a positive cytology indicates that the subject has ovarian or endometrial cancer. In some embodiments, the step of detecting in the sample the presence of aneuploidy comprises detecting the presence of one or more alterations on one or more of chromosome arms 4p, 7q, 8q, and 9q. In some embodiments, the step of detecting in the sample the presence of aneuploidy comprises amplifying interspersed nucleotide elements. In some embodiments, methods provided herein further include detecting in a second sample comprising circulating tumor DNA (ctDNA) the presence of at least one mutation in one or more genes selected from the group consisting of: AKT1, APC, BRAF, CDKN2A, CTNNB1, EGFR, FBXW7, FGFR2, GNAS, HRAS, KRAS, NRAS, PIK3CA, PPP2R1A, PTEN, and TP53. In some embodiments, the second sample includes plasma. In some embodiments, the sample is collected via intrauterine sampling. In some embodiments, the sample is collected with a Tao brush. In some embodiments, methods further include administering to the subject a therapy (e.g., adjuvant chemotherapy, neoadjuvant chemotherapy, radiation therapy, immunotherapy, targeted therapy, immune checkpoint inhibitors, and combinations thereof).

In some embodiments, provided herein are methods of detecting endometrial cancer in a subject that include detecting in a sample obtained from the subject the presence of one or more mutations in one or more genes selected from the group consisting of: PTEN, TP53, PIK3CA, PIK3R1, CTNNB1, KRAS, FGFR2, POLE, APC, FBXW7, RNF43, and PPP2R1A, detecting in the sample the presence of aneuploidy, or both, wherein the presence of one or more mutations in PTEN, TP53, PIK3CA, PIK3R1, CTNNB1, KRAS, FGFR2, POLE, APC, FBXW7, RNF43, and PPP2R1A, the presence of aneuploidy, or both indicates that the subject has endometrial cancer. In some embodiments, the step of detecting the presence of one or more mutations in PTEN, TP53, PIK3CA, PIK3R1, CTNNB1, KRAS, FGFR2, POLE, APC, FBXW7, RNF43, and PPP2R1A is performed using a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments, the step of detecting the presence of one or more mutations in PTEN, TP53, PIK3CA, PIK3R1, CTNNB1, KRAS, FGFR2, POLE, APC, FBXW7, RNF43, and PPP2R1A is performed by increasing the sensitivity of massively parallel sequencing instruments with an error reduction technique that allows for the detection of rare mutant alleles in a range of 1 mutant template among 100 to 1,000,000 wild-type templates. For example, the step of detecting one or more mutations can be performed by increasing the sensitivity of massively parallel sequencing instruments with an error reduction technique comprising: a) molecularly assigning a unique identifier (UID) to each template molecule, b) amplifying each uniquely tagged template molecule to create UID-families, and c) redundantly sequencing the amplification products. In some embodiments, methods provided herein further include conducting cytology on the sample, wherein presence of the one or more mutations in PTEN, TP53, PIK3CA, PIK3R1, CTNNB1, KRAS, FGFR2, POLE, APC, FBXW7, RNF43, and PPP2R1A, the presence of aneuploidy, and/or a positive cytology indicates that the subject has endometrial cancer. In some embodiments, the step of detecting in the sample the presence of aneuploidy comprises detecting the presence of one or more alterations on one or more of chromosome arms 4p, 7q, 8q, and 9q. In some embodiments, the step of detecting in the sample the presence of aneuploidy comprises amplifying interspersed nucleotide elements. In some embodiments, methods provided herein further include detecting in a second sample comprising circulating tumor DNA (ctDNA) the presence of at least one mutation in one or more genes selected from the group consisting of: AKT1, APC, BRAF, CDKN2A, CTNNB1, EGFR, FBXW7, FGFR2, GNAS, HRAS, KRAS, NRAS, PIK3CA, PPP2R1A, PTEN, and TP53. In some embodiments, the second sample includes plasma. In some embodiments, the sample is collected via intrauterine sampling. In some embodiments, the sample is collected with a Tao brush. In some embodiments, methods further include administering to the subject a therapy (e.g., adjuvant chemotherapy, neoadjuvant chemotherapy, radiation therapy, immunotherapy, targeted therapy, immune checkpoint inhibitors, and combinations thereof).

In some embodiments, provided herein are methods of detecting ovarian cancer in a subject that include detecting in a sample obtained from the subject the presence of one or more mutations in TP53, detecting in the sample the presence of aneuploidy, or both, wherein the presence of one or more mutations in TP53, the presence of aneuploidy, or both indicates that the subject has ovarian cancer. In some embodiments, the step of detecting the presence of one or more mutations in TP53 is performed using a PCR-based multiplex assay, using a PCR-based singleplex assay, a digital PCR assay, a droplet digital PCR (ddPCR) assay, a microarray assay, a next-generation sequencing assay, a Sanger sequencing assay, a quantitative PCR assay, or a ligation assay. In some embodiments, the step of detecting the presence of one or more mutations in TP53 is performed by increasing the sensitivity of massively parallel sequencing instruments with an error reduction technique that allows for the detection of rare mutant alleles in a range of 1 mutant template among 100 to 1,000,000 wild-type templates. For example, the step of detecting one or mutations can be performed by increasing the sensitivity of massively parallel sequencing instruments with an error reduction technique comprising: a) molecularly assigning a unique identifier (UID) to each template molecule, b) amplifying each uniquely tagged template molecule to create UID-families, and c) redundantly sequencing the amplification products. In some embodiments, methods provided herein further include conducting cytology on the sample, wherein presence of the one or more mutations in TP53, the presence of aneuploidy, and/or a positive cytology indicates that the subject has ovarian cancer. In some embodiments, the step of detecting in the sample the presence of aneuploidy comprises detecting the presence of one or more alterations on one or more of chromosome arms 4p, 7q, 8q, and 9q. In some embodiments, the step of detecting in the sample the presence of aneuploidy comprises amplifying interspersed nucleotide elements. In some embodiments, methods provided herein further include detecting in a second sample comprising circulating tumor DNA (ctDNA) the presence of at least one mutation in one or more genes selected from the group consisting of: AKT1, APC, BRAF, CDKN2A, CTNNB1, EGFR, FBXW7, FGFR2, GNAS, HRAS, KRAS, NRAS, PIK3CA, PPP2R1A, PTEN, and TP53. In some embodiments, the second sample includes plasma. In some embodiments, the sample is collected via intrauterine sampling. In some embodiments, the sample is collected with a Tao brush. In some embodiments, methods further include administering to the subject a therapy (e.g., adjuvant chemotherapy, neoadjuvant chemotherapy, radiation therapy, immunotherapy, targeted therapy, immune checkpoint inhibitors, and combinations thereof).

Provided herein are methods of detecting bladder cancer or an upper tract urothelial carcinoma in a subject that include: detecting in a urinary sample obtained from the subject the presence of one or more mutations in one or more genes selected from the group consisting of: TP53, PIK3CA, FGFR3, KRAS, ERBB2, CDKN2A, MLL, HRAS, MET, and VHL, detecting in the sample the presence of at least one mutation in a TERT promoter, and detecting in the sample the presence of aneuploidy, wherein presence of one or more mutations in the group consisting of: TP53, PIK3CA, FGFR3, KRAS, ERBB2, CDKN2A, MLL, HRAS, MET, and VHL, the presence of the at least one mutation in the TERT promoter, or the presence of aneuploidy indicates that the subject has bladder cancer. In some embodiments of methods of detecting bladder cancer or an upper tract urothelial carcinoma in a subject, the one or more genes are TP53, FGFR3, or both. In some embodiments of methods of detecting bladder cancer or an upper tract urothelial carcinoma in a subject, the one or more mutations in TP53, PIK3CA, FGFR3, KRAS, ERBB2, CDKN2A, MLL, HRAS, MET, or VHL, the one or more mutations in the TERT promoter, or both, are present in 0.03% or fewer of the urinary cells in the sample.

In some embodiments of methods of detecting bladder cancer or an upper tract urothelial carcinoma in a subject, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a PCR based multiplex assay, a Sanger sequencing assay, a next-generation sequencing assay, a quantitative PCR assay, a droplet digital PCR (ddPCR) assay, or a microarray technique. In some embodiments of methods of detecting bladder cancer or an upper tract urothelial carcinoma in a subject, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a Sanger Sequencing assay. In some embodiments of methods of detecting bladder cancer or an upper tract urothelial carcinoma in a subject, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a next generation sequencing assay.

In some embodiments of methods of detecting bladder cancer or an upper tract urothelial carcinoma in a subject, the step of detecting in the sample the presence of aneuploidy comprises detecting the presence of one or more alterations on one or more of chromosome arms 5q, 8q, and 9p. In some embodiments of methods of detecting bladder cancer or an upper tract urothelial carcinoma in a subject, the step of detecting the presence of aneuploidy comprises amplifying long interspersed nucleotide elements (LINEs).

In some embodiments of methods of detecting bladder cancer or an upper tract urothelial carcinoma in a subject, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed by increasing the sensitivity of massively parallel sequencing instruments with an error reduction technique that allows for the detection of rare mutant alleles in a range of 1 mutant template among 5,000 to 1,000,000 wild-type templates. In some embodiments of methods of detecting bladder cancer or an upper tract urothelial carcinoma in a subject, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed by increasing the sensitivity of massively parallel sequencing instruments with an error reduction technique that includes: a) assigning a unique identifier (UID) to each template molecule, b) amplifying each uniquely tagged template molecule to create UID-families, and c) redundantly sequencing the amplification products.

In some embodiments of methods of detecting bladder cancer or an upper tract urothelial carcinoma in a subject, the method further includes performing cytology on the sample, wherein presence of the one or more mutations in TP53, PIK3CA, FGFR3, KRAS, ERBB2, CDKN2A, MLL, HRAS, MET, VHL, the presence of the at least one mutation in the TERT promoter, the presence of aneuploidy, or a positive cytology indicates that the subject has bladder cancer.

In some embodiments of methods of detecting bladder cancer in a subject, the method further includes administering transuretral resection of the bladder (TURB), intravesical BCG (Bacillus Calmette-Guerin), intravesical chemotherapy, adjuvant chemotherapy, neoadjuvant chemotherapy, cystectomy or cystoprostatectomy, radiation therapy, immunotherapy, immune checkpoint inhibitors, or any combination thereof.

In some embodiments of methods of detecting an upper tract urothelial carcinoma in a subject, the method further includes administering transurethral resection, intravesical BCG (Bacillus Calmette-Guerin), intravesical chemotherapy, adjuvant chemotherapy, neoadjuvant chemotherapy, ureterectomy or nephroureterectomy, radiation therapy, immunotherapy, immune checkpoint inhibitors, or any combination thereof.

In some embodiments of methods of detecting bladder cancer or an upper tract urothelial carcinoma in a subject, the cancer is a low-grade tumor. In some embodiments of methods of detecting bladder cancer or an upper tract urothelial carcinoma in a subject in which the cancer is a low-grade tumor, the low-grade tumor is a papillary urothelial neoplasms of low malignant potential (PUNLMP) or a non-invasive low grade papillary urothelial carcinoma. In some embodiments of methods of detecting bladder cancer or an upper tract urothelial carcinoma in a subject in which the cancer is a low-grade tumor, the method further includes administering transuretral resection of the bladder (TURB).

In some embodiments of methods of detecting bladder cancer or an upper tract urothelial carcinoma in a subject, the subject has previously undergone treatment for bladder cancer or an upper tract urothelial carcinoma. In some embodiments of methods of detecting bladder cancer or an upper tract urothelial carcinoma in a subject in which the subject has previously undergone treatment for bladder cancer or an upper tract urothelial carcinoma, the method includes detecting in a urinary sample obtained from the subject the presence of one or more mutations in TP53, FGFR3, or both. In some embodiments of methods of detecting bladder cancer or an upper tract urothelial carcinoma in a subject in which the subject has previously undergone treatment for bladder cancer or an upper tract urothelial carcinoma, one or more mutations in TP53, PIK3CA, FGFR3, KRAS, ERBB2, CDKN2A, MLL, HRAS, MET, or VHL, one or more mutations in the TERT promoter, or both, are present in 0.03% or fewer of the urinary cells in the sample. In some embodiments of methods of detecting bladder cancer or an upper tract urothelial carcinoma in a subject in which the subject has previously undergone treatment for bladder cancer or an upper tract urothelial carcinoma, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a PCR based multiplex assay. In some embodiments of methods of detecting bladder cancer or an upper tract urothelial carcinoma in a subject in which the subject has previously undergone treatment for bladder cancer or an upper tract urothelial carcinoma, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a Sanger Sequencing assay. In some embodiments of methods of detecting bladder cancer or an upper tract urothelial carcinoma in a subject in which the subject has previously undergone treatment for bladder cancer or an upper tract urothelial carcinoma, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed using a next generation sequencing assay.

In some embodiments of methods of detecting bladder cancer or an upper tract urothelial carcinoma in a subject in which the subject has previously undergone treatment for bladder cancer or an upper tract urothelial carcinoma, the step of detecting in the sample the presence of aneuploidy comprises detecting the presence of one or more alterations on one or more of chromosome arms 5q, 8q, and 9p. In some embodiments of methods of detecting bladder cancer or an upper tract urothelial carcinoma in a subject in which the subject has previously undergone treatment for bladder cancer or an upper tract urothelial carcinoma, the step of detecting the presence of aneuploidy comprises amplifying long interspersed nucleotide elements (LINESs).

In some embodiments of methods of detecting bladder cancer or an upper tract urothelial carcinoma in a subject in which the subject has previously undergone treatment for bladder cancer or an upper tract urothelial carcinoma, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed by increasing the sensitivity of massively parallel sequencing instruments with an error reduction technique that allows for the detection of rare mutant alleles in a range of 1 mutant template among 5,000 to 1,000,000 wild-type templates. In some embodiments of methods of detecting bladder cancer or an upper tract urothelial carcinoma in a subject in which the subject has previously undergone treatment for bladder cancer or an upper tract urothelial carcinoma, the step of detecting the presence of one or more mutations in TP53, PIK3CA, FGFR3, KRAS, ERBB2, CDKN2A, MLL, HRAS, MET, VHL, the step of detecting the presence of at least one mutation in the TERT promoter, or both is performed by increasing the sensitivity of massively parallel sequencing instruments with an error reduction technique that includes: a) assigning a unique identifier (UID) to each template molecule, b) amplifying each uniquely tagged template molecule to create UID-families, and c) redundantly sequencing the amplification products.

In some embodiments of methods of detecting bladder cancer or an upper tract urothelial carcinoma in a subject in which the subject has previously undergone treatment for bladder cancer or an upper tract urothelial carcinoma, the method further includes conducting cytology on the sample, wherein presence of the one or more mutations in TP53, PIK3CA, FGFR3, KRAS, ERBB2, CDKN2A, MLL, HRAS, MET, VHL, the presence of the at least one mutation in the TERT promoter, the presence of aneuploidy, or a positive cytology indicates that the subject has bladder cancer.

In some embodiments of methods of detecting bladder cancer in a subject in which the subject has previously undergone treatment for bladder cancer or an upper tract urothelial carcinoma, the method further includes administering transuretral resection of the bladder (TURB), intravesical BCG (Bacillus Calmette-Guerin), intravesical chemotherapy, adjuvant chemotherapy, neoadjuvant chemotherapy, cystectomy or cystoprostatectomy, radiation therapy, immunotherapy, immune checkpoint inhibitors, or any combinations of the above.

In some embodiments of methods of detecting an upper tract urothelial carcinoma in a subject in which the subject has previously undergone treatment for bladder cancer or an upper tract urothelial carcinoma, the method further includes administering transurethral resection, intravesical BCG (Bacillus Calmette-Guerin), intravesical chemotherapy, adjuvant chemotherapy, neoadjuvant chemotherapy, ureterectomy or nephroureterectomy, radiation therapy, immunotherapy, immune checkpoint inhibitors, or any combination thereof.

This document provides methods and materials for identifying one or more chromosomal anomalies (e.g., aneuploidy). In some cases, this document provides methods and materials for using amplicon-based sequencing data to identify a mammal as having a disease or disorder associated with one or more chromosomal anomalies. For example, methods and materials described herein can be applied to a sample obtained from a mammal to identify the mammal as having one or more chromosomal anomalies. For example, methods and materials described herein can be applied to a sample obtained from a mammal to identify the mammal as having a disease or disorder associated with one or more chromosomal anomalies. For example, a prenatal mammal can be identified as having a disease or disorder based, at least in part, on the presence of one or more aneuploidies. This document also provides methods and materials for identifying and/or treating a disease associated with one or more chromosomal anomalies. In some cases, one or more chromosomal anomalies can be identified in DNA obtained from a sample obtained from a mammal. For example, a mammal identified as having cancer based, at least in part, on the presence of one or more chromosomal anomalies can be treated with one or more cancer treatments.

As demonstrated herein, a new approach (called WALDO for Within-Sample-AneupLoidy-DetectiOn, can be used to evaluate the sequencing data obtained from amplicons to identify the presence of one or more chromosomal anomalies (e.g., aneuploidy). For example, WALDO can employ supervised machine learning to detect the small changes in multiple chromosome arms that are often present in cancers. As described herein, WALDO was used to search for chromosome arm gains and losses in 1,677 tumors as well as in 1,522 liquid biopsies of blood from cancer patients or normal individuals. Aneuploidy was detected in 95% of cancer biopsies and in 22% of liquid biopsies. Using single nucleotide polymorphisms (SNPs) within the amplified interspersed nucleotide elements (LINEs), WALDO concomitantly assessed allelic imbalances, microsatellite instability, and sample identification. WALDO can be used on samples containing only a few nanograms (ng) of DNA and having as little as 1% neoplastic content.

Having the ability to use amplicon-based sequencing reads to detect one or more chromosomal anomalies provides a unique and unrealized opportunity to achieve high coverage depth with improved sensitivity at relatively low cost. Moreover, the ability to use amplicon-based sequencing reads allows the detection of one or more chromosomal anomalies (e.g., aneuploidies) from samples containing limited amounts of DNA. This approach can be used in a variety of applications including, but not limited to, diagnostics (e.g., prenatal diagnostics and/or cancer diagnostics) and forensic science.

In general, one aspect of this document features a method for detecting aneuploidy in a genome of a mammal. The method includes, or consists essentially of, sequencing a plurality of amplicons obtained from a sample obtained from the mammal to obtain sequencing reads; grouping the sequencing reads into clusters of genomic intervals; calculating sums of distributions of the sequencing reads in each genomic interval using the equation $\Sigma_1^I R_i \sim N(\Sigma_1^I \mu_i, \Sigma_1^I \sigma_i^2)$, where $R_i$ is the number of sequencing reads, I is the number of clusters on a chromosome arm, N is a Gaussian distribution with parameters $\mu_i$ and $\sigma_i^2$, where $\mu_i$ is the mean number of sequencing reads in each genomic interval, and where $\sigma_i^2$ is the variance of sequencing reads in each genomic interval; calculating a Z-score of a chromosome arm using the quantile function $1-CDF(\Sigma_1^I \mu_i, \Sigma_1^I \sigma_i^2)$; and identifying the presence of an aneuploidy in the genome of the mammal when the Z-score is outside a significance threshold. The plurality of amplicons can include from about 10,000 amplicons to about 1,000,000 amplicons (e.g., the plurality of amplicons can include about 38,000 amplicons). The genomic intervals can include from about 100 nucleotides to about 125,000,000 nucleotides (e.g., the genomic intervals can include about 500,000 nucleotides). The mammal can be a human. The sample can be a liquid biopsy. The liquid biopsy can be blood, urine, saliva, cyst fluid, sputum, tissue, stool, pap smears, or cerebral spinal fluid. The liquid biopsy can be a blood sample (e.g., a plasma sample). The blood sample can include cell free fetal DNA. The sample can include a neoplastic cell fraction. The neoplastic cell fraction in the sample can include less than about 1% (e.g., less than about 0.5%) of the entire sample. The amplicons can include unique long interspersed nucleotide elements (LINEs). The sequencing step also can include amplifying DNA from the sample obtained from the mammal to obtain the amplicons. The amplifying can be performed using a single primer pair. The amplicons can include about 100 to about 140 base pairs. Each amplicon can be sequenced between 1 and 20 times. The method can include about 100,000 to about 25 million sequencing reads. Each cluster can include about two hundred genomic intervals. The method also can include supervised machine learning. The supervised machine learning can employ a support vector machine model.

In another aspect, this document features a method for detecting one or more polymorphisms in a genome of a mammal. The method includes, or consists essentially of, sequencing a plurality of amplicons obtained from a sample from the mammal to obtain variant sequencing reads; sequencing a plurality of amplicons obtained from a reference sample from the mammal to obtain reference sequencing reads; grouping the variant sequencing reads and the reference sequencing reads into clusters of genomic intervals; selecting a chromosome arm having a sum of the variant sequencing reads and the reference sequencing reads on both alleles that is greater than about 3; determining a variant-allele frequency (VAF) of the selected chromosome arm, wherein said VAF is the number of variant sequencing reads/total number of sequencing reads; and identifying the presence of one or more polymorphisms on said selected chromosome arm of the mammal if the VAF is between about 0.2 and about 0.8. The sequencing step can include assigning a unique identifier (UID) to each amplicon, amplifying each uniquely tagged amplicon to create UID-families, and redundantly sequencing the amplification products. The sequencing step can further include calculating a Z-score of a variant on said selected chromosome arm using the equation $$Z \sim \frac{\sum_{i=1}^{k} w_i Z_i}{\sqrt{\sum_{i=1}^{k} w_i^2}},$$

where $w_i$ is UID depth at a variant i, $Z_i$ is the Z-score of variant i, and k is the number of variants observed on the chromosome arm. The one or more polymorphisms can include single base substitutions, insertions, deletions, indels, and/or combinations thereof. The pluralities of amplicons can include from about 10,000 amplicons to about 1,000,000 amplicons (e.g., the pluralities of amplicons can include about 38,000 amplicons). The genomic intervals can include from about 100 nucleotides to about 125,000,000 nucleotides (e.g., the genomic intervals can include about 500,000 nucleotides). The mammal can be a human. The sample can be a liquid biopsy. The liquid biopsy can be blood, urine, saliva, cyst fluid, sputum, tissue, stool, pap smears, or cerebral spinal fluid. The liquid biopsy can be a blood sample (e.g., a plasma sample). The blood sample can include cell free fetal DNA. The sample can include a neoplastic cell fraction. The neoplastic cell fraction in the sample can include less than about 1% (e.g., less than about 0.5%) of the entire sample. The amplicons can include unique long interspersed nucleotide elements (LINEs). The sequencing step also can include amplifying DNA from the sample obtained from the mammal to obtain the amplicons. The amplifying can be performed using a single primer pair. The amplicons can include about 100 to about 140 base pairs. Each amplicon can be sequenced between 1 and 20 times. The method can include about 100,000 to about 25 million sequencing reads. Each cluster can include about two hundred genomic intervals. The method also can include supervised machine learning. The supervised machine learning can employ a support vector machine model.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXAMPLES

Example 1: Detection and Localization of Surgically Resectable Cancers with a Multi-Analyte Liquid Biopsy Many of the currently approved tests for earlier cancer detection are procedural in nature, and include colonoscopy, mammography, and cervical cytology analysis. To date, the vast majority of cancer patients evaluated with mutation-based liquid biopsies have advanced stage disease. Yet another issue with liquid biopsies is the identification of the underlying organ of origin. Because the same gene mutations drive multiple tumor types, liquid biopsies based on such alterations cannot generally identify the location of the primary tumor giving rise to a positive blood test.

This Example describes a new blood test, called CancerSEEK, which addresses the problematic issues described above. The test utilizes combined assays for genetic alterations and protein biomarkers and has the capacity not only to identify the presence of relatively early cancers but also to pinpoint the organ of origin of these cancers (FIG. 1).

CancerSEEK is a widely applicable, non-invasive test for most cancers. The eight cancer types studied here account for 360,000 (60%) of the estimated cancer deaths in the U.S. in 2017 and their earlier detection could conceivably reduce deaths from these diseases. At the time of this disclosure, the cost of CancerSEEK is less than $500, which is comparable or lower than other screening tests for single cancers, such as colonoscopy, while this test can detect at least eight different cancer types.

Materials and Methods

Plasma, White Blood Cell and Tumor DNA Samples

The study was approved by the Institutional Review Boards for Human Research at each institution, and samples were obtained after informed consent was obtained. Patients with stage I to III cancer, who had undergone surgical resection at the participating institutions were included in the study. Blood was collected from patients before any therapy was undertaken (i.e., before neoadjuvant therapy in those patients receiving neoadjuvant therapy) and before surgery in all patients. If sample was drawn on the day of surgery, then care was taken to ensure that the blood was collected prior to the administration of anesthesia, as anesthesia can increase the levels of circulating biomarkers (Cohen et al., 2017 *Proc Natl Acad Sci USA* 114:10202-10207). General demographics, surgical pathology, and AJCC stage (7$^{th}$ edition) were documented. The 'healthy' cohort consisted of peripheral blood samples obtained from 812 individuals of median age 55 (IQR interquartile range 28 to 65) with no history of cancer. The cancer and healthy control samples were processed in an identical manner. Plasma samples from 46 of the 1,005 cancer patients and 181 of the 812 normal samples had been previously evaluated with a different approach (Cohen et al., 2017 *Proc Natl Acad Sci USA* 114: 10202-10207) (Table 2).

DNA was purified from an average of 7.5 mL plasma using a QIASymphony circulating DNA kit (cat #1091063), as specified by the manufacturer. DNA from peripheral WBCs was also purified with the QIAsymphony DP DNA Midi Kit (Cat #937255) as specified by the manufacturer. Tumor tissues were formalin-fixed and paraffin-embedded (FFPE) according to standard histopathologic procedures and also purified with a QIAsymphony DP DNA Midi Kit (Cat #937255).

Mutation Detection and Analysis

For amplification of DNA from plasma, 61 primer pairs were designed (see below) to amplify 66 to 80 bp segments containing regions of interest from 16 genes.

The 61 primer pairs were divided into two non-overlapping sets each containing either 28 or 33 primer pairs. Each of these two primer sets were used to amplify DNA in six independent 25 µl reactions as described elsewhere (see, e.g., Wang et al., 2016 *Elife* 5) except that 15 cycles were used for the initial amplification. The PCR products were purified with AMPure XP beads (Beckman Coulter, PA, USA) and 1% of the purified PCR products were then amplified in a second round of PCR as described elsewhere (see, e.g., Wang et al., 2016 *Elife* 5), but using 21 cycles. PCR products from the second round of amplification were then purified with AMPure and sequenced on an Illumina MiSeq or HiSeq 4000 instrument.

The template-specific portion of the reads was matched to reference sequences using custom scripts written in SQL and C#. Reads from a common template molecule were then grouped based on the unique identifier sequences (UIDs) that were incorporated as molecular barcodes as described elsewhere (see, e.g., Kinde et al., 2011 *Proc Natl Acad Sci USA* 108:9530-9535). Artefactual mutations introduced during the sample preparation or sequencing steps were reduced by requiring a mutation to be present in >90% of reads in each UID family. Redundant reads arising from optical duplication were eliminated by requiring reads with the same UID and sample index to be at least 5,000 pixels apart when located on the same tile. Mutations that met one of the two following criteria were considered (i) present in the COSMIC database (Forbes et al., 2017 *Nucleic Acids Res* 45:D777-D783), or (ii) predicted to be inactivating in tumor suppressor genes (nonsense mutations, out-of-frame insertions or deletions, canonical splice site mutations). Synonymous mutations, except those at exon ends, and intronic mutations, except for those at splice sites, were excluded.

Evaluation of Plasma Proteins

The Bioplex 200 platform (Biorad, Hercules CA) was used to determine the concentration of multiple target proteins in the plasma samples. Luminex bead based immunoassays (Millipore, Bilerica NY) were performed following the manufacturers protocols and concentrations were determined using 5 parameter log curve fits (using Bioplex Manager 6.0) with vendor provided standards and quality controls. The HCCBP1MAG-58K panel was used to detect FGF2, Osteopontin, sFas, IL-8/CXCL8, Prolactin, HE4, HGF, AFP, CA125, IL6, CA15-3, TGFa, CYFRA21-1, CEA, CA19-9 and Leptin. The HANG2MAG-12K panel was used to detect PAR, sPECAM-1, TSP-2, sEGFR, AXL and sHER2/sEGFR2/sErbB2. The HCMBMAG-22K panel was used to detect DKK1, GDF15, Osteoprotegerin (OPG) and Neuron-specific enolase (NSE). The HCCBP4MAG-58K panels was used to detect Kallikrein-6, CD44, Midkine and Mesothelin. The HAGP1MAG-12K panel was used to detect Follistatin, G-CSF, Angiopoietin-2 and Endoglin. The HCCBP3MAG-58K panel was used to detect SHBG, Galectin and Myeloperoxidase. The HTMP1MAG-54K panel was used to detect TIMP-1 and TIMP-2. LRG-1 and Vitronectin were not included in this study since they could not be reproducibly evaluated with a single immunoassay platform.

Algorithm for Classifying ctDNA Status

The classification of a sample's ctDNA status was obtained from a statistical test comparing the normalized mutation frequencies of the sample of interest to the distributions of the normalized mutation frequencies of, respectively, normal and cancer samples in the training set. Specifically, the mutant allele frequency (MAF), defined as the ratio between the number of supermutants and the number of UIDs, was first normalized based on the observed MAFs for each mutation in a set of normal controls. Following this mutation-specific normalization, the MAF of each mutation in each well was compared to two reference distributions of MAFs: 1) a distribution built from the normal control plasmas in the training set plus a set of 188 WBCs from unrelated, healthy individuals 2) a distribution built from the cancers' samples in a training set that included only mutations found in plasma that were also present with MAF >5% in the corresponding primary tumors. Corresponding p-values, $p^N$ and $p^C$, were thus obtained. For each mutation, the log ratio of these two p-values was calculated, and the minimum and maximum of these log ratios across the six wells were eliminated so that the results would be less sensitive to outliers. An "omega" score was then determined according to the following formula:

$$\Omega = \sum_{i=1}^{4} w_i * \log \frac{p_i^C}{p_i^N},$$

where $w_i$ is the proportion of UIDs in well i out of the total number of UIDs for that mutation present across the four wells. When a mutation identified in a plasma sample had $\Omega>1$, and was not identified in the primary tumor of the patient, DNA from white blood cells (WBCs) of the same patient whenever WBCs were available (23% of the cancer patients was evaluated. WBC DNA was tested with the same 61-amplicon panel to ensure that the plasma mutation was not a result of Clonal Hematopoiesis of Indeterminate Potential (Jaiswal et al., 2014 *N Engl J Med* 371:2488-2498). WBCs from the normal individuals were evaluated identically whenever a mutation with $\Omega>1$ was found in the plasma. Any mutation that was identified in the WBCs as well as in the plasma was excluded from the analysis. The requirement for exclusion was that the ratio between the max MAF in the plasma and the max MAF in the WBC was less than 100.

The mutation with the greatest $\Omega$ score in each patient or normal control was then deemed the "top mutation" and is listed in Table 3. This score was used in the logistic regression as well as the concentrations of the following 10 proteins, selected via an optimization step, Prolactin, OPN, IL6, CEA, CA125, HGF, Myeloperoxidase, CA19-9, Midkine, and TIMP-1. To be conservative, a non-linear transformation was applied to the features used by Logistic Regression. Specifically, if a protein's concentration in the sample of interest was lower than the 95th percentile of the concentration found for that same protein among the normal samples in the training set, then the protein's concentration was set equal to zero; otherwise the log of that concentration was used. For the Ω score, the same log-threshold transformation was used but with a constant threshold equal to 1. The R glmnet package (version 2.10-13) was then used to perform the Logistic Regression, with the lambda parameter set to zero as described elsewhere (see, e.g., Friedman et al., 2010 Journal of Statistical Software 33:74862). The importance of each feature was evaluated by multiplying its coefficient (see below) times the difference of the feature's mean between normal and cancer samples. Ten rounds of 10-fold cross-validations were performed. The classification calls obtained in an average round of 10-fold cross-validation (CV) are listed for each of the 812 normal individuals and 1,005 cancer patients in Table 2.

Logistic Regression Model Coefficients and Importance Scores.

| Feature | Logistic Regression Coefficient | Importance Score |
|---|---|---|
| Ω score | 1.77E+00 | 7.55E+00 |
| CA-125 | 4.15E-02 | 1.37E+00 |
| CEA | 2.33E-04 | 1.17E+00 |
| CA19-9 | 1.20E-02 | 5.18E-01 |
| Prolactin | 3.51E-05 | 4.76E-01 |
| HGF | 2.45E-03 | 3.03E-01 |
| OPN | 1.45E-05 | 1.72E-01 |
| Myeloperoxidase | 5.40E-03 | 9.31E-02 |
| TIMP-1 | 7.34E-06 | 7.05E-02 |

For prediction of cancer type, the same 11 features (mutation score and levels of ten proteins) were used plus patient gender and the other 29 proteins evaluated in this study. Cancer type prediction was performed only on the cancer samples that were correctly classified as cancer by Logistic Regression. Random Forest, as implemented in the randomForest package (version 4.6-12) (see, e.g., Liaw et al., 2001 R news 2:18-22) was used for this prediction. Ten rounds of 10-fold CV were performed and, for consistency, in each round and in each fold the same partition used by Logistic Regression was used by Random Forest. The classification calls obtained in an average round of 10-fold CV (the same round for which cancer status is reported in Table 3), are listed in Table 6.

For determining the concordance between mutations identified in the plasma with those identified in primary tumors (Table 5), only the 155 cases in which a mutation could be identified with high confidence in the plasma were considered (Ω score >3, Table 3) and in which the primary tumor contained any mutation that was present at a mutant allele fraction of >5% (Table 1). This approach allowed us to avoid scoring tumors that had low neoplastic contents.

Sample Identification

To confirm that plasma, WBC, and primary tumor DNA samples originated from the same patient primers were utilized that could be used to amplify ~38,000 unique long interspersed nucleotide elements (LINEs) from throughout the genome as described elsewhere (see, e.g., Kinde et al., 2012 PloS one 7:e41162). These ~38,000 LINEs contain 26,220 common polymorphisms which can establish or refute sample identity among plasma, white blood cell and tumor samples. The genotype at each polymorphic location was identified, and the percent concordance between the samples of interest was calculated. Concordance was defined as the number of matched polymorphic sites that were identical in both samples divided by the total number of genotypes that had adequate coverage in both samples. Two samples were considered a match if concordance was >0.99 and at least 5,000 amplicons had adequate coverage.

Statistical Analysis

Continuous variables were reported as means and standard deviations or medians and range as deemed necessary while categorical variables were reported as whole numbers and percentages. Confidence intervals (CI) for sensitivities were calculated using a binomial distribution. P-values were calculated with a one sided binomial test using the R stats package (version 3.3.1).

Results

Figure 2:
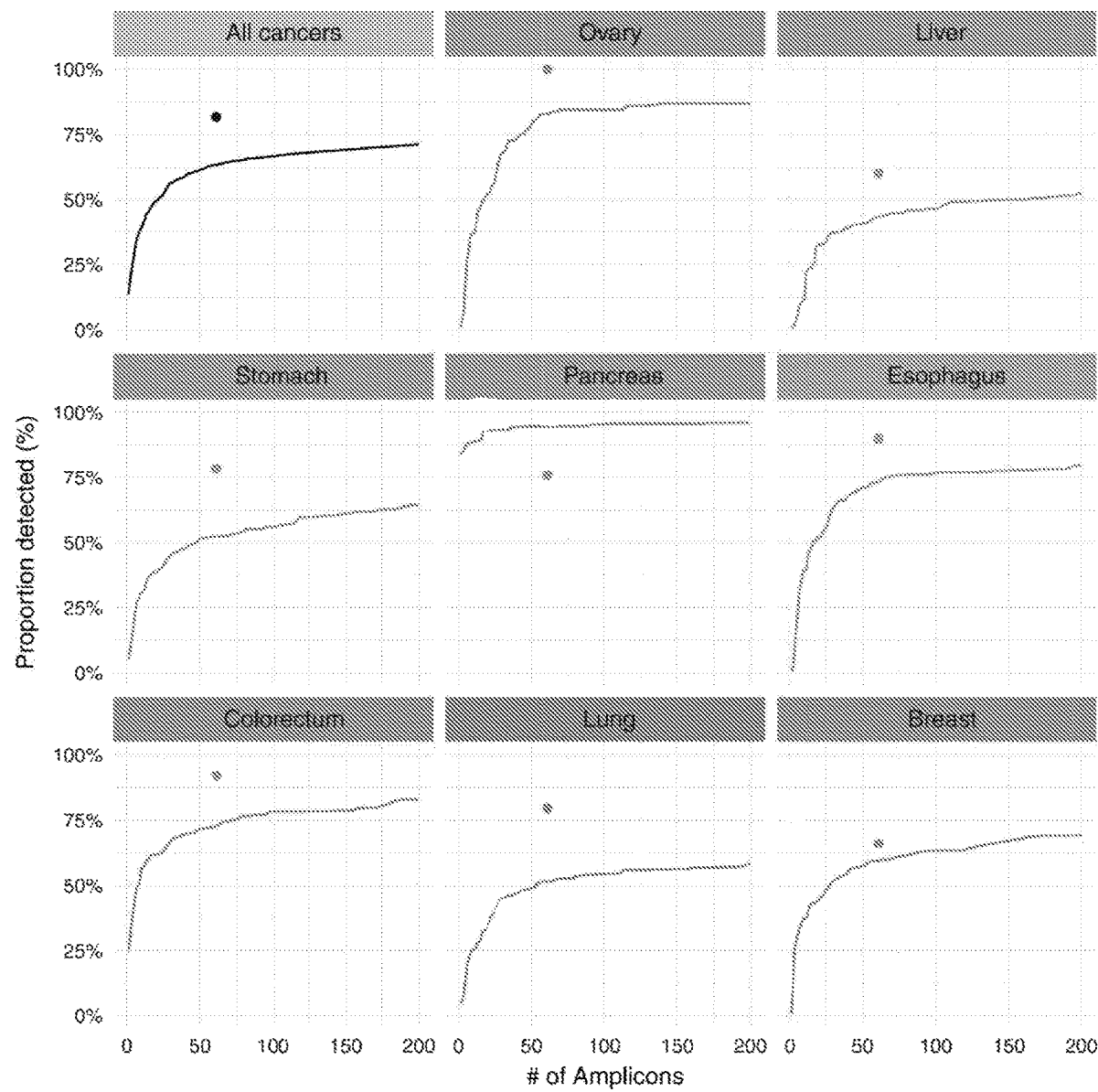
FIG. 2 contains graphs showing the development of a PCR-based assay to identify tumor-specific mutations in plasma samples. Colored curves indicate the proportion of cancers of the eight types evaluated in this study that can be detected with an increasing number of short (<40 bp) amplicons. The sensitivity of detection increases with the number of amplicons but plateaus at ~60 amplicons. Colored dots indicate the fraction of cancers detected using the 61-amplicon panel used in 805 cancers evaluated in our study, which averaged 82% (see main text). Publicly available sequencing data was obtained from the Catalog of Somatic Mutations in Cancer (COSMIC) repository.

To identify a panel of protein and gene markers that might be used to detect many solid tumors at a stage prior to the emergence of distant metastases, a PCR-based assay was designing that could simultaneously assess multiple regions of driver genes that are commonly mutated in a variety of cancer types. Four challenges confronted this design. First, the test must query a sufficient number of bases to allow a large number of cancers to be detected. Second, each queried base must be sequenced thousands of times to detect mutations present at low prevalence. Third, the more bases that are queried the more likely that artifactual mutations will be identified, reducing the signal-to-noise ratio. And fourth, a test that can be implemented in a screening setting must be cost effective and high throughput, limiting the amount of sequencing that must be performed. To meet these contrasting challenges, a minimum number of short amplicons was identified that would allow detection of at least one driver gene in each of the eight tumor types evaluated. Using Publicly available sequencing data was used to determine that there was a fractional power law relationship between the number of amplicons required and the sensitivity of detection, with a plateau at ~60 amplicons (FIG. 2). Raising the number of amplicons above a threshold level would not detect substantially more cancers but would increase the probability of false positive results. This decreasing marginal utility defined the optimal number of amplicons.

Based on these data, a 61-amplicon panel was designed with each amplicon querying an average of 33 bp within one of 16 genes (see Materials and Methods). As shown in FIG. 2, this panel would theoretically detect 41% (liver) to 95% (pancreas) of the cancers in the Catalog of Somatic Mutations in Cancer (COSMIC) dataset (Forbes et al., 2017 Nucleic Acids Res 45:D777-D783). In practice, the panel performed considerably better, detecting at least one mutation in 82%, two mutations in 47%, and more than two mutations in 8% of the 805 cancers evaluated in our study (dots in FIG. 2, FIG. 3, and Table 1). A larger fraction of tumors was detected than predicted by the COSMIC dataset because the PCR-based sequencing assay was more sensitive for detecting mutations than conventional genome-wide sequencing. Based on this analysis of the DNA from primary tumor tissues, the predicted maximum detection capability of circulating tumor DNA (ctDNA) varied by tumor type, ranging from 60% for liver cancers to 100% for ovarian cancers (FIG. 2).

Armed with this small but robust panel of amplicons, two approaches were developed that enabled the detection of the rare mutations expected to be present in plasma. First, a multiplex-PCR was used to directly and uniquely label each original template molecule with a DNA barcode. This design minimized the errors inherent to massively parallel sequencing and made efficient use of the small amount of cell-free DNA present in plasma. Additionally, the total amount of DNA recovered from plasma was divided into multiple aliquots and independent assays were performed on each replicate. This decreased the number of DNA molecules per well; however, it increased the fraction of each mutant molecule per well making it easier to assay. Because the sensitivity of detection is often limited by the fraction of mutant alleles in each replicate, this partitioning strategy allowed an increase in the signal-to-noise ratio and identification of mutations present at lower prevalence than possible if all of the plasma DNA was evaluated at once.

The second component of CancerSEEK is based on protein biomarkers. The literature was searched to find proteins potentially useful for early detection and cancer diagnosis in at least one of the eight cancer types described above with sensitivities >10% and specificities >99%. 41 potential protein biomarkers were identified and evaluated in preliminary studies on plasma samples from individuals without cancer and from cancer patients. 39 of these proteins could be reproducibly evaluated through a single immunoassay platform and these were then used to assay all plasma samples. Ten of these 39 proteins proved to be useful for discriminating cancer patients from healthy controls, and are set forth below.

Protein biomarkers analyzed and included in exemplary CancerSEEK test.

| Protein | Evaluated in this study | Included in exemplary CancerSEEK test | Used for cancer type identification |
|---|---|---|---|
| AFP | Yes | No | Yes |
| Angiopoietin-2 | Yes | No | Yes |
| AXL | Yes | No | Yes |
| CA125 | Yes | Yes | Yes |
| CA15-3 | Yes | No | Yes |
| CA19-9 | Yes | Yes | Yes |
| CD44 | Yes | No | Yes |
| CEA | Yes | Yes | Yes |
| CYFRA 21-1 | Yes | No | Yes |
| DKK1 | Yes | No | Yes |
| Endoglin | Yes | No | Yes |
| FGF2 | Yes | No | Yes |
| Follistatin | Yes | No | Yes |
| Galectin-3 | Yes | No | Yes |
| G-CSF | Yes | No | Yes |
| GDF15 | Yes | No | Yes |
| HE4 | Yes | No | Yes |
| HGF | Yes | Yes | Yes |
| IL-6 | Yes | Yes | Yes |
| IL-8 | Yes | No | Yes |
| Kallikrein-6 | Yes | No | Yes |
| Leptin | Yes | No | Yes |
| LRG-1 | No | No | No |
| Mesothelin | Yes | No | Yes |
| Midkine | Yes | Yes | Yes |
| Myeloperoxidase | Yes | Yes | Yes |
| NSE | Yes | No | Yes |
| OPG | Yes | No | Yes |
| OPN | Yes | Yes | Yes |
| PAR | Yes | No | Yes |
| Prolactin | Yes | Yes | Yes |
| sEGFR | Yes | No | Yes |
| sFas | Yes | No | Yes |
| SHBG | Yes | No | Yes |
| sHER2/sEGFR2/sErbB2 | Yes | No | Yes |
| sPECAM-1 | Yes | No | Yes |
| TGFa | Yes | No | Yes |
| Thrombospondin-2 | Yes | No | Yes |
| TIMP-1 | Yes | Yes | Yes |
| TIMP-2 | Yes | No | Yes |
| Vitronectin | No | No | No |

This study included 1,005 patients with Stage I to III cancers of the ovary, liver, esophagus, pancreas, stomach, colorectum, lung, or breast. No patient received neo-adjuvant chemotherapy prior to blood sample collection. None had evident distant metastasis at the time of study entry and all underwent surgical resection with the intent to cure. The median age at diagnosis was 64 (range 22 to 93). The eight cancer types were chosen because they are common and because no blood-based tests for earlier detection of them are in common clinical use. The histopathological and clinical characteristics of the patients are summarized in Table 2.

The most common stage at presentation was American Joint Commission on Cancer (AJCC) stage II, accounting for 49% of patients, with the remaining patients harboring stage I (20%), or stage III (31%) disease. The number of samples per stage for each of the eight tumor types is summarized below. A total of 812 individuals of median age 55 (range 17 to 88) with no known history of cancer, high-grade dysplasia, autoimmune disease, or chronic kidney disease acted as the healthy control cohort.

Cancer patients evaluated in this study by tumor type and stage.

| Tumor Type | AJCC Stage | Patients (n) | Proportion of cases (%) |
|---|---|---|---|
| Breast | I | 32 | 15 |
| | II | 114 | 55 |
| | III | 63 | 30 |
| | I-III | 209 | — |
| Colorectum | I | 77 | 20 |
| | II | 191 | 49 |
| | III | 120 | 31 |
| | I-III | 388 | — |
| Esophagus | I | 5 | 11 |
| | II | 29 | 64 |
| | III | 11 | 24 |
| | I-III | 45 | — |
| Liver | I | 5 | 11 |
| | II | 19 | 43 |
| | III | 20 | 45 |
| | I-III | 44 | — |
| Lung | I | 46 | 44 |
| | II | 27 | 26 |
| | III | 31 | 30 |
| | I-III | 104 | — |
| Ovary | I | 9 | 17 |
| | II | 4 | 7 |
| | III | 41 | 76 |
| | I-III | 54 | — |
| Pancreas | I | 4 | 4 |
| | II | 83 | 89 |
| | III | 6 | 6 |
| | I-III | 93 | — |
| Stomach | I | 21 | 31 |
| | II | 30 | 44 |
| | III | 17 | 25 |
| | I-III | 68 | — |

CancerSEEK evaluates levels of 10 proteins and mutations in 2,001 genomic positions; each genomic position could be mutated in several ways (single base substitutions, insertions, or deletions). The presence of a mutation in an assayed gene or an elevation in the level of any of these proteins would classify a patient as positive. Rigorous statistical methods were employed to ensure the accuracy of the test. Log ratios were used to evaluate mutations and incorporated them into a logistic regression algorithm that took into account both mutation data and protein biomarker levels to score CancerSEEK test results. The mean sensitivities and specificities were determined by ten iterations of 10-fold cross-validations. The receiver operating characteristic (ROC) curves for the entire cohort of cancer patients and controls in one representative iteration is shown in FIG. 4A.

The median sensitivity of CancerSEEK among the eight cancer types evaluated was 70% ($p<10^{-96}$ one-sided binomial test) and ranged from 98% in liver cancers to 33% in breast cancers (FIG. 4C). At this sensitivity, the specificity was >99%, i.e., only 6 of the individuals without known cancers scored positive.

Figure 4:
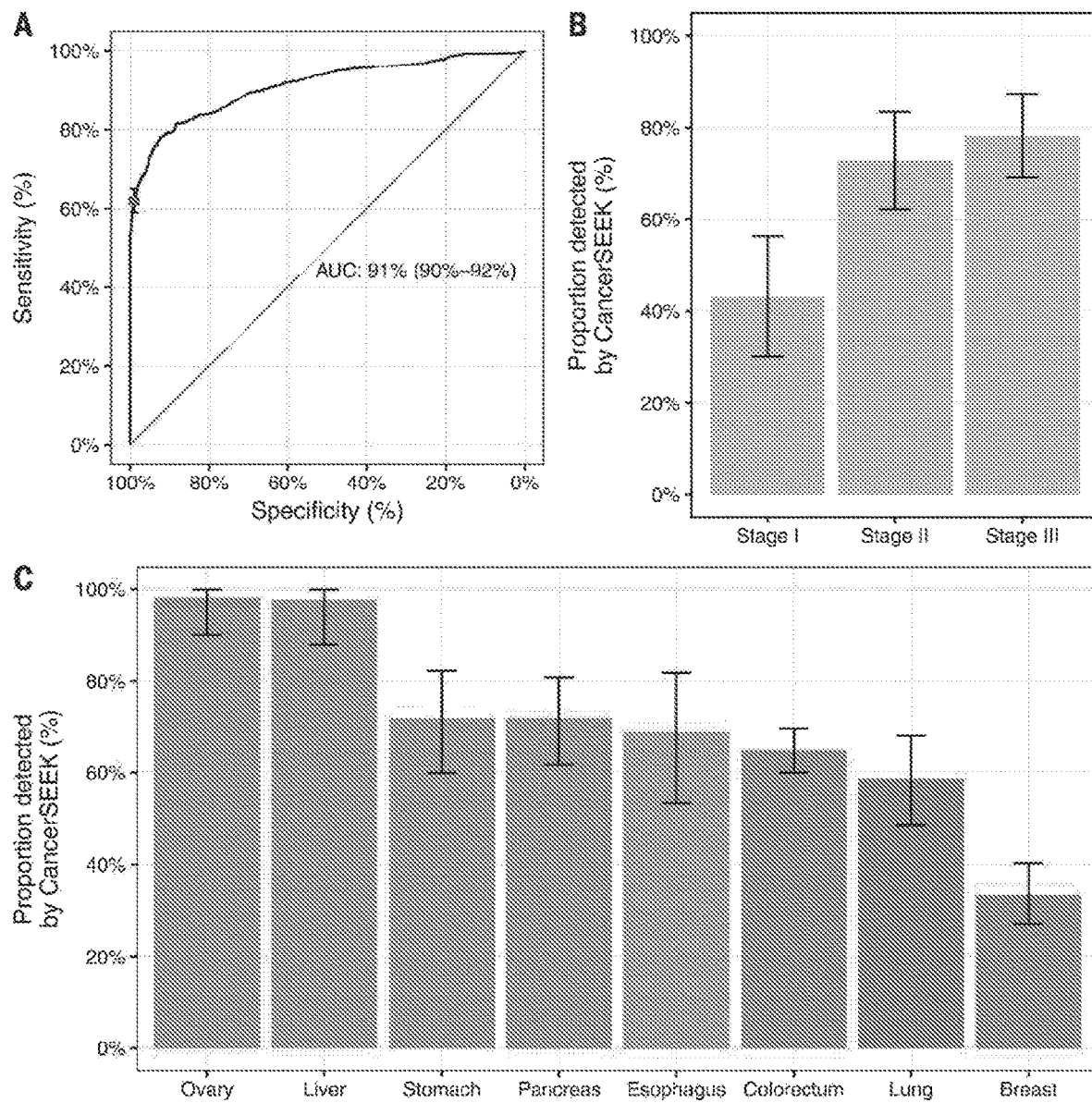
FIG. 4 contains graphs showing the performance of CancerSEEK. (A) A receiver operator characteristic (ROC) curve for CancerSEEK. The red point on the curve indicate the test's average performance (61%) at >99% specificity. Error bars represent 95% confidence intervals for sensitivity and specificity at this particular point. The median performance among the 8 cancer types assessed was 70%, as noted in the main text. (B) Sensitivity of CancerSEEK by stage. Error bars represent standard errors of the median. (C) Sensitivity of CancerSEEK by tumor type. Error bars represent 95% confidence intervals.
Figure 5:
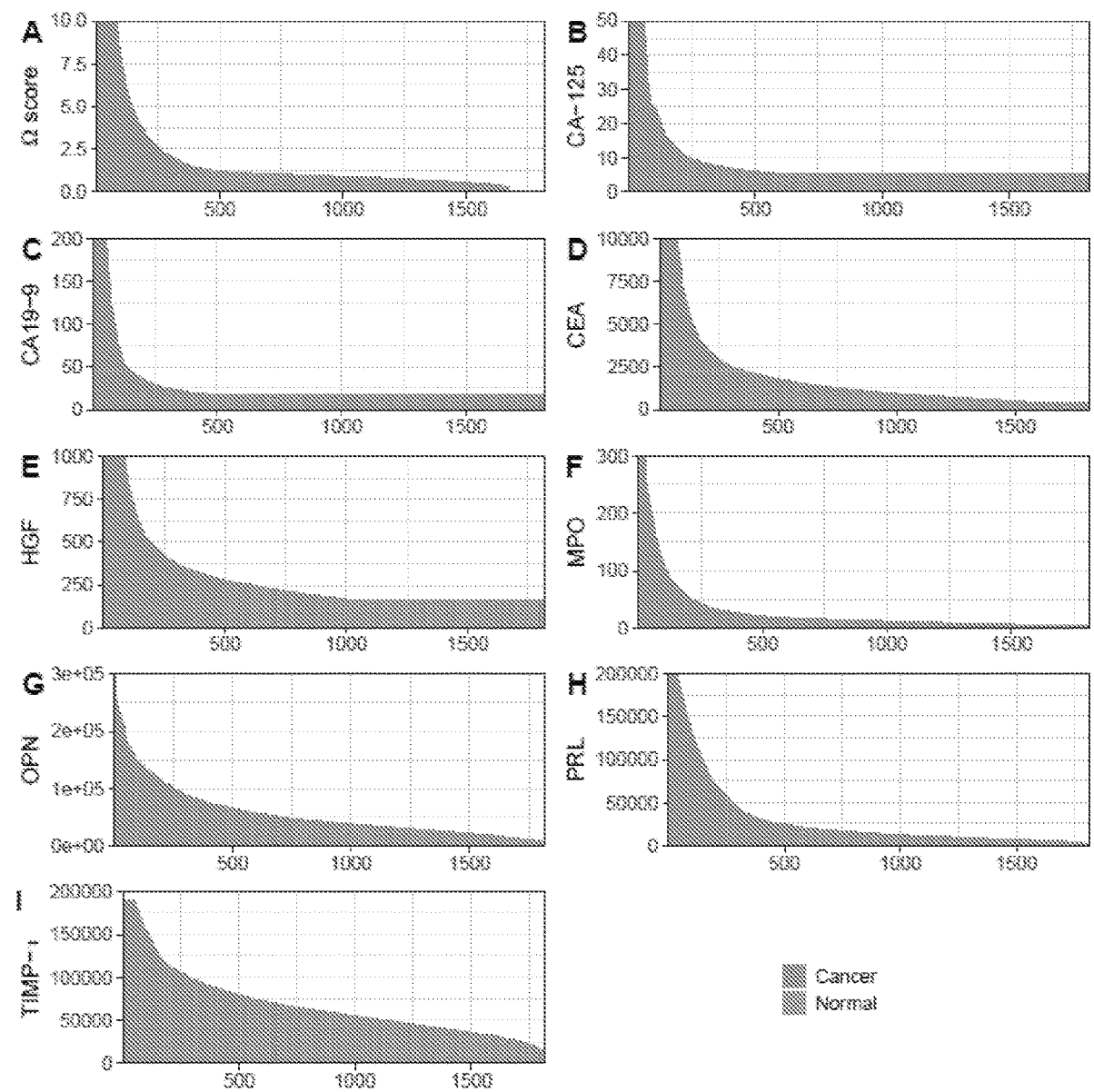
FIG. 5 contains waterfall plots of the ctDNA and eight protein features used in CancerSEEK illustrate the separation between healthy donors and healthy patients. Values are sorted from high (left) to low (right). Each column represents an individual patient sample (red, cancer patient; blue, healthy control).
Figure 6:
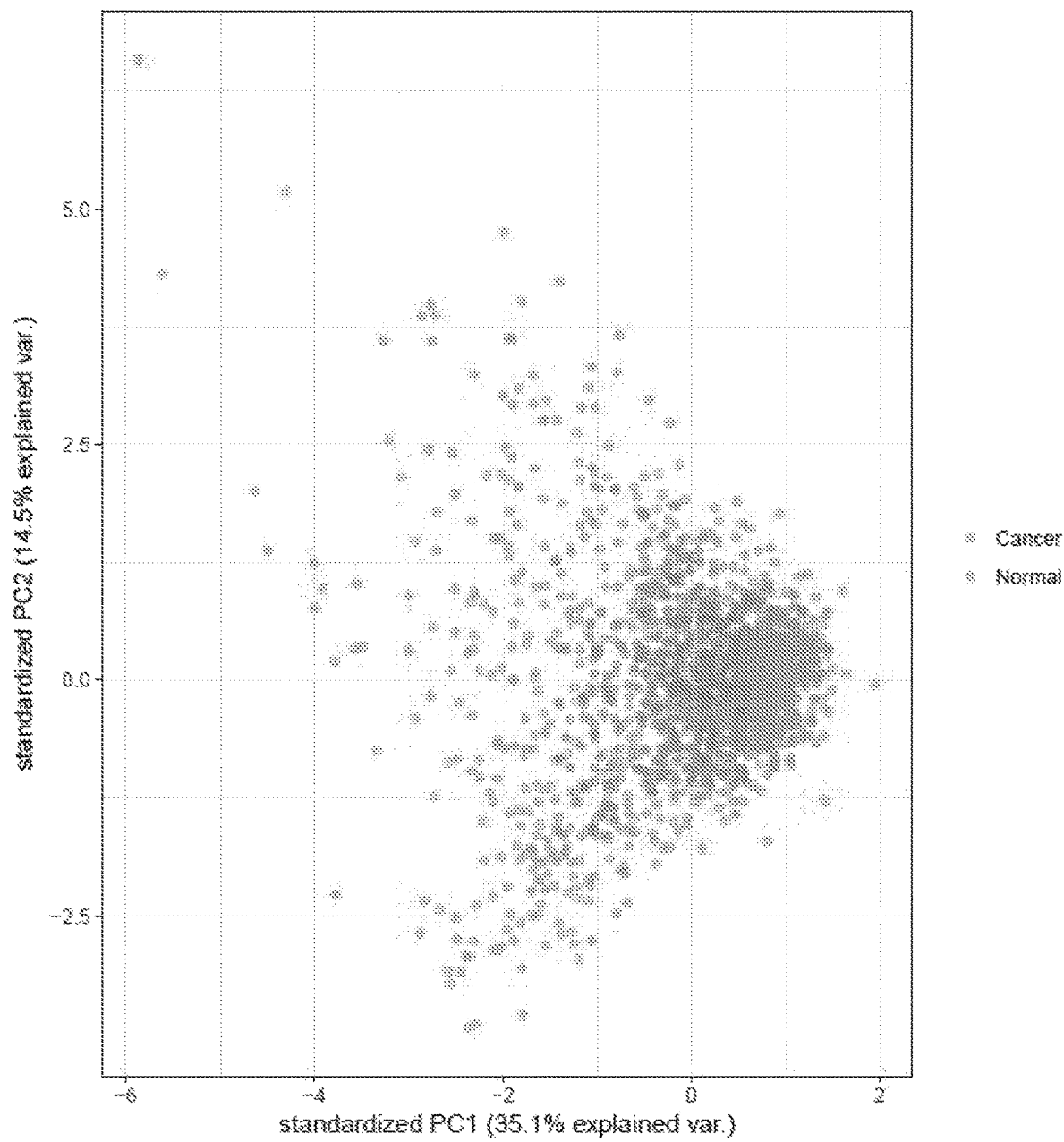
FIG. 6 contains a graph showing the principle component analysis of the ctDNA and eight protein features used in CancerSEEK. Each dot represents an individual patient sample (red, cancer patient; blue, healthy control).
Figure 7:
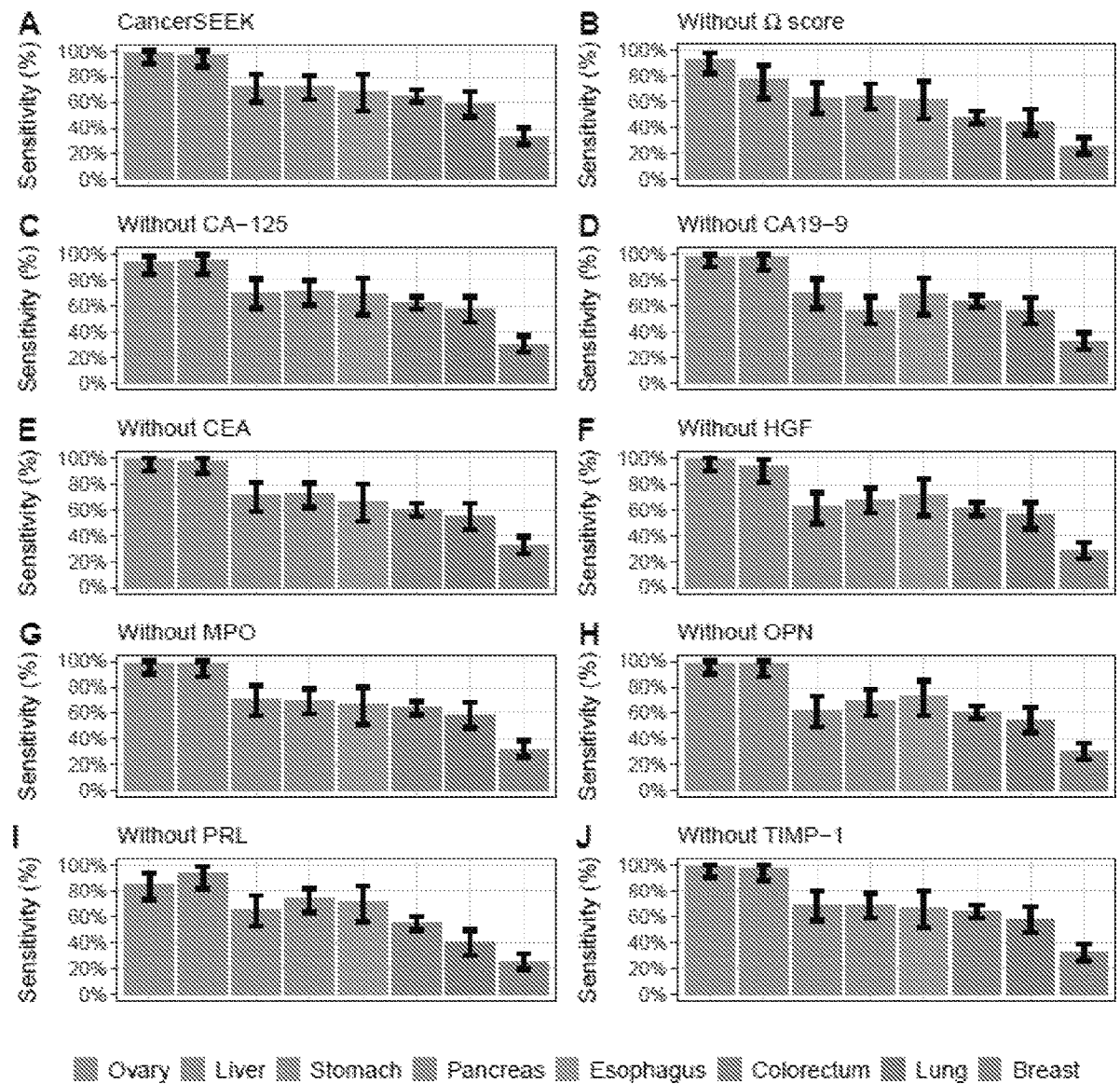
FIG. 7 contains graphs showing the effect of individual CancerSEEK features on sensitivity. (A) Sensitivity of CancerSEEK by tumor type as in FIG. 4C. (B-J) Each panel displays the sensitivity achieved when a particular CancerSEEK feature is excluded from the logistic regression. The difference in sensitivity relative to that achieved by CancerSEEK reflects the relative contribution of each biomarker to the performance of the CancerSEEK test.

The features of the test that were most important to the algorithm were the presence of a ctDNA mutation followed by elevations of Prolactin, OPN, IL-6, CEA, CA125, HGF, Myeloperoxidase, CA19-9, Midkine, and TIMP-1 protein levels. Waterfall plots for each of the ctDNA and protein features used in CancerSEEK illustrate their distribution among individuals with and without cancer (FIG. 4). The importance ranking of the ctDNA and protein features used in CancerSEEK are provided below and a principal component analysis displaying the clustering of individuals with and without cancer is shown in FIG. 5. The complete dataset, including the levels of all proteins studied and the mutations identified in the plasma samples, are provided in Table 3 and Table 4. The probabilistic rather than deterministic nature of the approach used here to call a sample positive is evident from FIG. 6; each panel represents the sensitivity of CancerSEEK when one specific feature was excluded from the analysis.

A screening test is advantageously able to detect cancers at early stages. The median sensitivity of CancerSEEK was 73% for the most common stage evaluated (Stage II), similar (78%) for Stage III cancers, and lower (43%) for Stage I cancers (FIG. 4B). The sensitivities for the earliest stage cancers (Stage I) were highest for liver (100%) and lowest for esophageal cancer (20%).

The basis of liquid biopsy is that mutant DNA templates in plasma are derived from dying cancer cells and thus serve as exquisitely specific markers for neoplasia. To test this expectation, tumor tissue from 155 patients in whom ctDNA could be detected at statistically significant levels and in whom primary tumors were available were evaluated. The mutation in the plasma was identical to a mutation found in the primary tumor of the same individual in 138 (90%) of these 155 cases (Table 5). This concordance between plasma and primary tumor was evident in all 8 cancer types, and ranged from 100% in ovarian and pancreatic cancers to 82% in stomach cancers.

A major limitation of conventional liquid biopsies is their inability to determine the cancer type in patients who test positive, thereby posing challenges for clinical follow-up. In addition to increasing the sensitivity of detection, the combination of protein biomarkers and ctDNA helped identify the type of cancer that might exist with a positive CancerSEEK test. Supervised machine learning was used to predict the underlying cancer type in patients with positive CancerSEEK tests. The input algorithm took into account the gender of the patient and the protein and ctDNA biomarker data. One of the main purposes of such predictions is to determine the most appropriate follow up test for cancer diagnosis or monitoring after a positive CancerSEEK test. Patients with esophageal and gastric cancers were grouped together, as the optimal follow-up for individuals potentially affected with these two cancers would be endoscopy.

Figure 8:
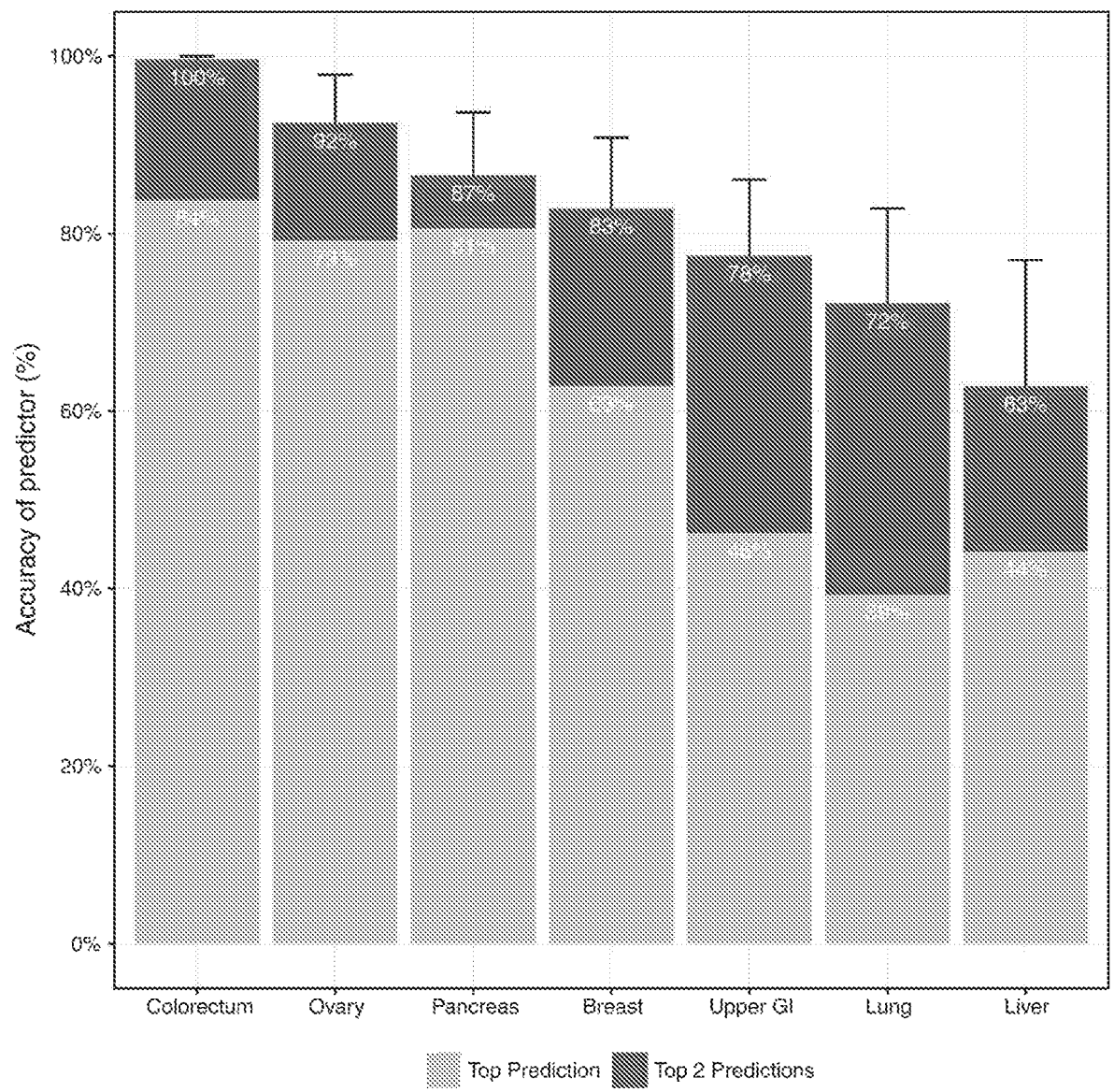
FIG. 8 contains a graph showing identification of cancer type by supervised machine learning for patients classified by CancerSEEK as positive. Percentages correspond to the proportion of patients correctly classified by one of the two most likely types (sum of light and dark blue bars) or the most likely type (light blue bar). Predictions for all patients for all cancer types are provided in Table 6. Error bars represent 95% confidence intervals.

An algorithm was used to study the 617 patients scoring positive in the CancerSEEK Test. Without any clinical information about the patients, the source of the cancer was localized to two anatomic sites in a median of 83% of these patients (FIG. 8, Table 6; $p<10^{-77}$ one-sided binomial test). Furthermore, the source of the positive test was localized to a single organ in a median of 63% these patients (FIG. 8, Table 6; $p<10^{-47}$ one-sided binomial test). The accuracy of prediction varied with tumor type and was best for colorectal cancers and lowest for lung cancers as shown below (see, also, FIG. 8).

Confusion matrix of top predictions from cancer type localization results.

| | | Breast | Colo-rectum | Liver | Lung | Ovary | Pancreas | Upper GI |
|---|---|---|---|---|---|---|---|---|
| Predicted cancer type | Breast | 63% | 3% | 2% | 8% | 4% | 3% | 3% |
| | Colo-rectum | 26% | 84% | 30% | 48% | 15% | 15% | 44% |
| | Liver | 0% | 1% | 44% | 2% | 0% | 0% | 4% |
| | Lung | 4% | 2% | 0% | 39% | 2% | 1% | 4% |
| | Ovary | 3% | 0% | 0% | 2% | 79% | 0% | 0% |
| | Pancreas | 4% | 2% | 9% | 2% | 0% | 81% | 0% |
| | Upper GI | 0% | 9% | 14% | 0% | 0% | 0% | 46% |

The results described herein demonstrate that a blood test based on genes and proteins can be used to detect a major fraction (median of 70%) of eight major cancer types. In the majority of the samples that scored positive, the underlying cancer type could be predicted simply from the test results without any prior knowledge of the patient's medical history or disease status. The specificity of CancerSEEK was high, with less than 1% of 812 individuals without known cancers scoring positive.

Example 2: Combination Approach to Liquid Biopsy Cancer Screening Tests with Increased Sensitivity and High Specificity There is a strong correlation between tumor stage and prognosis in many cancers (see, e.g., Ansari et al., 2017 *Br J Surg* 104(5):600-607). Very few patients with cancers of the lung, colon, esophagus, or stomach who have distant metastasis at the time of diagnosis survive for more than five years (see, e.g., Howlader et al., 2016 SEER Cancer Statistics Review, 1975-2013, National Cancer Institute. Bethesda, MD). It is therefore evident that earlier detection of cancers is one key to reducing deaths from these diseases.

Biomarkers in the circulation provide one of the best ways, in principle, to detect cancers at an earlier stage. Historically, the type of biomarkers used to monitor cancers were proteins (see, e.g., Liotta et al., 2003 *Clin Adv Hematol Oncol* 1(8):460-462). More recently, mutant DNA has been explored as a biomarker as DNA released from the dying cells can escape into bodily fluids such as urine, stool, and plasma (see, e.g., Haber et al., 2014 Cancer Discov 4(6): 650-661; Dawson et al., 2013 *N Engl J Med* 368(13):1199-1209; Bettegowda et al., 2014 Science translational medicine 6(224):224ra224; Kinde et al., 2013 *Science translational medicine* 5(167):167ra164; Wang et al., 2015 *Science translational medicine* 7(293):293ra104; Wang et al., 2015 *Proc Natl Acad Sci USA* 112(31): 9704-9709; Wang et al., 2016 *Elife* 5; Springer et al., 2015 *Gastroenterology* 149(6):1501-1510; Forshew et al., 2012 *Science translational medicine* 4(136):136ra168; Vogelstein et al., 1999 *Proc Natl Acad Sci USA* 96(16):9236-9241; and Dressman et al., 2003 *Proc Natl Acad Sci USA* 100(15):8817-8822). The concept underlying this approach, often called "liquid biopsies" is that cancer cells, like normal self-renewing cells, turn over frequently. However, studies of circulating tumor DNA (ctDNA) indicate that while ctDNA is elevated in >85% of patients with advanced forms of many cancer types, a considerably smaller fraction of patients with earlier stages of cancer have detectable levels of ctDNA in their plasma (see, e.g., Bettegowda et al., 2014 *Science translational medicine* 6(224):224ra224; and Wang et al., 2015 *Science translational medicine* 7(293): 293ra104).

This Example describes using a combination approach to cancer screening tests which increases the sensitivity of detection of resectable or otherwise treatable cancers under conditions that preserve high specificity. For example, the assays described in this Example combine detection of mutations in ctDNA with detection of threshold protein markers in plasma.

Materials and Methods

Plasma, White Blood Cell and Tumor DNA Samples

DNA was purified from plasma using a QIASymphony circulating DNA kit (Qiagen, cat #1091063). Custom primers containing a unique identifier (UID) and amplicon specific sequences (Table 38) were used to amplify plasma DNA, and the resulting products were sequenced on an Illumina MiSeq or HiSeq instrument. Protein biomarker plasma concentrations were determined using Luminex bead based immunoassays on the Bioplex 200 platform (Biorad, Hercules CA). Plasma samples were scored as positive if the sample contained a KRAS mutation or if the concentration of CA19-9, CEA, HGF, or OPN was greater than 100 U/mL, 7.5 ng/mL, 0.92 ng/mL, or 158 ng/mL, respectively. All samples were obtained following approval by the Institutional Review Boards for Human Research at each institution and informed consent.

Samples were obtained following approval by the Institutional Review Boards for Human Research at each institution and informed consent. Patients with Stage IA, IB, IIA or IIB (considered resectable) who had had peripheral blood collected prior to surgery, had not received neoadjuvant therapy, and had undergone surgical resection at the participating institutions between April 2011 and May 2016 were included in the study. General demographics, surgical pathology, and AJCC stage (7th edition) were documented. The 'healthy' cohort consisted of peripheral blood samples obtained from 185 individuals of average age 64 with no history of cancer. The pancreatic cancer and healthy control samples were collected and processed in an identical manner.

DNA was purified from 3.75 mL plasma using a QIASymphony circulating DNA kit (cat #1091063), as specified by the manufacturer. Tumor tissues were formalin-fixed and paraffin embedded (FFPE) according to standard histopathologic procedures and macro-dissected under a microscope to ensure a neoplastic cellularity of >30%. DNA was purified with a QIAsymphony DP DNA Midi Kit (Cat #937255) as specified by the manufacturer. DNA concentrations were assessed by fluorescence using SYBR Green I (Thermo Cat #S7585).

Mutation Detection and Analysis

For amplification of DNA from plasma, primer pairs were designed to amplify 66 to 80 bp segments containing regions of interest from the KRAS and TP53 genes (Table 11 and Table 12). These primers were used to amplify DNA in six independent 25 µl reactions as described elsewhere (see, e.g., Wang et al., 2015 Proc Natl Acad Sci USA 112(31): 9704-9709). Reactions were purified with AMPure XP beds (Beckman Coulter, PA, USA) and eluted in 50 µl of Buffer EB (Qiagen). A fraction (5 µl) of purified PCR products were then amplified in a second round of PCR, as described elsewhere (see, e.g., Wang et al., 2015 Proc Natl Acad Sci USA 112(31): 9704-9709). The PCR products were purified with AMPure and sequenced on an Illumina MiSeq or HiSeq 4000 instrument.

The template-specific portion of the reads was matched to reference sequences using custom scripts written in SQL and C#. Reads from a common template molecule were then grouped based on the unique identifier sequences (UIDs) that were incorporated as molecular barcodes (see, e.g., Allen et al., 2017 Ann Surg 265(1):185-191). Artefactual mutations introduced during the sample preparation or sequencing steps were reduced by requiring a mutation to be present in >90% of reads in each UID family.

Evaluation of Plasma Proteins

The Bioplex 200 platform (Biorad, Hercules CA) was used to determine the concentration of multiple target proteins in the plasma samples. Luminex bead based immunoassays were performed following the manufacturers protocols and concentrations were determined using 5 parameter log curve fits (using Bioplex Manager 6.0) with vendor provided standards and quality controls. Plasma samples were diluted 6-fold for assay of CA19-9, CEA, HGF, OPN and prolactin and 5-fold for assay of midkine. Plasma samples were scored as positive if the concentration of CA19-9, CEA, HGF, or OPN was greater than 100 U/mL, 7.5 ng/mL, 0.92 ng/mL, or 158 ng/mL, respectively. The dynamic ranges of these immunoassays for CA19-9, CEA, HGF, OPN, prolactin, and midkine were 2.74-2,000 U/mL, 78.19-57,000 pg/mL, 27.43-20,000 pg/mL, 548.7-400,000 pg/mL, 137.17-100,000 pg/mL, and 13.72-10,000 pg/mL, respectively.

Algorithm for Classifying ctDNA Status

The classification of a sample's ctDNA status was obtained from a statistical test comparing the normalized mutation frequencies of the sample of interest to a distribution of normal controls. Specifically, the MAF, defined as the ratio between the number of supermutants and the number of UIDs, was first normalized based on the observed MAFs in a set of normal controls for each mutation. Following this mutation-specific normalization, the MAF of each mutation in each well was compared to a reference distribution of MAFs built from normal controls with all mutations included, and a p-value was calculated from this distribution. The lowest p-value among all mutations detected in a given sample was deemed the "top mutation". The classification of a sample's ctDNA status was based on whether the p-value of this top mutation was below or above a given threshold. The threshold was selected based on a desired specificity observed among an independent set of normal controls. Thus, no training was performed on any other sample except these controls; in particular, neither the 182 healthy controls nor the 221 pancreatic cancer patients described in the main text were included in the controls used for training the algorithm.

Statistical Analysis

Continuous variables were reported as means and standard deviations or medians and range as deemed necessary while categorical variables were reported as whole numbers and percentages. Confidence intervals (CI) for sensitivities were calculated using a binomial distribution. Survival curves were estimated using Kaplan-Meier method and differences between curves were investigated with the log-rank test. Statistically significant variables in the univariate analyses were subjected to multivariable Cox proportional hazard regression model.

Hazard ratio (HR) and 95% confidence interval (CI) for variables included in the multivariable model were reported. A p-value <0.05 was considered to be statistically significant.

Results
Characteristics of Patients with PDAC and Presumed Healthy Controls

Two hundred and twenty-one patients with surgically resectable pancreatic cancer were evaluated in this study. The histopathological and clinical characteristics of these patients are summarized in Table 7. A total of 182 individuals of similar age with no known history of cancer, autoimmune disease, or chronic kidney disease acted as the healthy control cohort.

Figure 12:
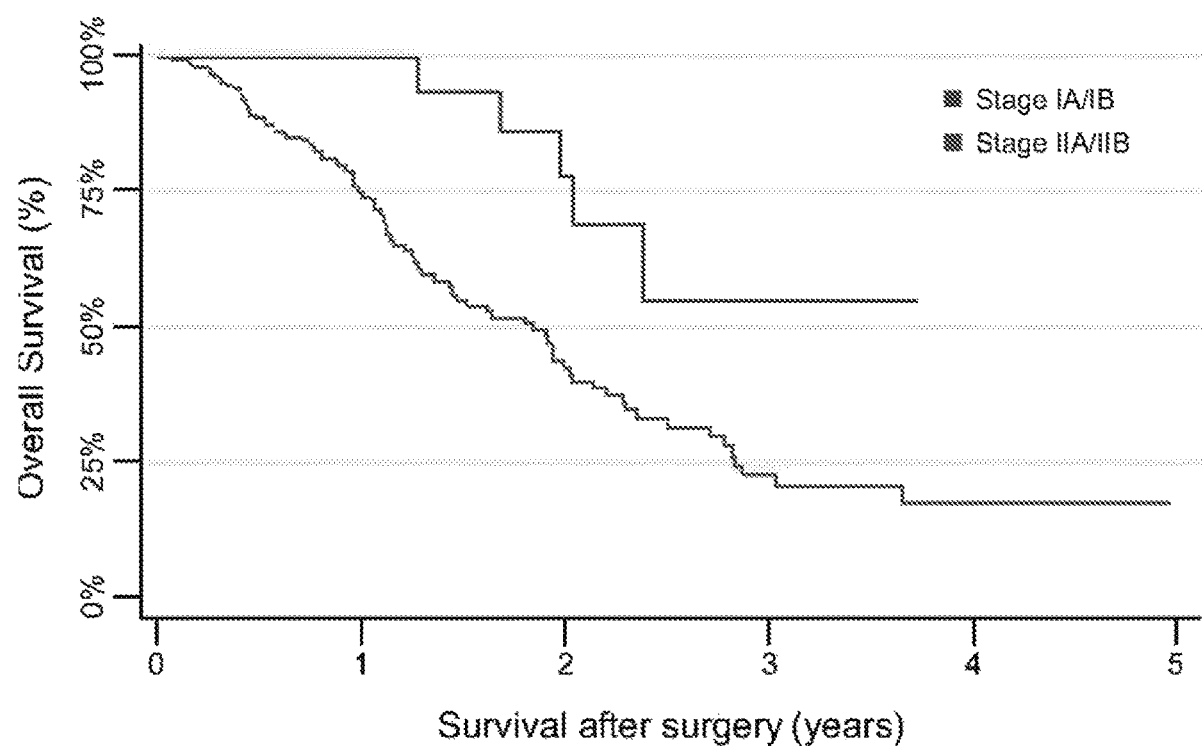
FIG. 12 contains a Kaplan-Meier survival plot of the 221 PDAC patients included in this study stratified by AJCC stage (stage IA or IB: blue curve, stage IIA or IIB: red curve).

Twenty percent of the patients had no symptoms typically associated with pancreatic cancer. The size of the primary tumors at presentation ranged from 0.6 cm to 13 cm, with a median size of 3.0 cm. The most common stage at presentation was American Joint Commission on cancer stage (AJCC) Stage IIB, accounting for 77% of patients, with the remaining patients harboring Stage IA (5%), Stage IB (8%) or Stage IIA (10%) (Table 7). Patient survival correlated with stage, as graphically depicted in FIG. 12 and as expected from prior clinical studies (see, e.g., Allen et al., 2017 *Ann Surg* 265(1):185-191).

PCR-Based Assay to Identify Tumor-Specific KRAS Mutations in Plasma Samples

Figure 11:
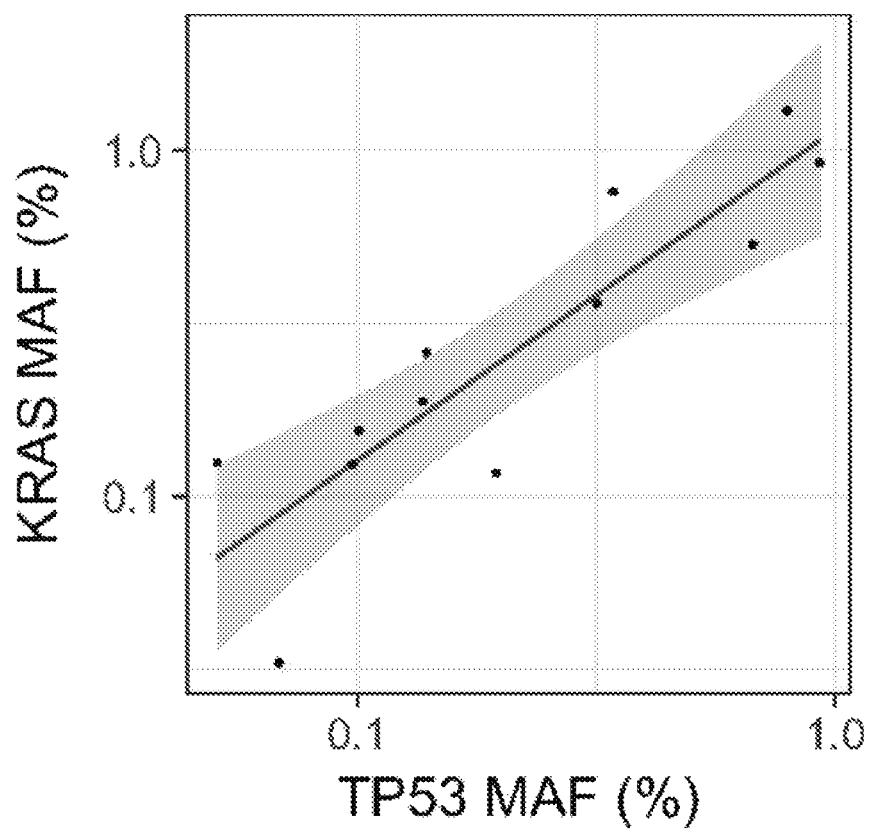
FIG. 11 contains a graph showing that mutant allele frequencies (MAFs) of KRAS and TP53 mutations are strongly correlated (Pearson's r=0.885) in the plasma of the 12 patients whose plasma contained detectable amounts of both mutations, providing validation of the reliability of the ctDNA assay and its quantitative nature. Shaded region represents the 95% confidence interval.

A PCR-based assay was designed that could simultaneously assess the two codons (codons 12 and 61) of the KRAS gene that are most frequently mutated in PDAC as well as surrounding codons. The assay employed a sensitive technology called the Safe-Sequencing System (Safe-SeqS) (see, e.g., Kinde et al., 2011 *Proc Natl Acad Sci USA* 108(23):9530-9535). Safe-SeqS incorporates molecular barcodes that uniquely label each template molecule, thereby drastically minimizing the errors that routinely occur in massively parallel sequencing. This approach can identify one mutant template among as many as 10,000 normal templates. Using this technology, KRAS mutations in the plasma of 66 of the 221 (30%: 95% CI 24-36%) pancreatic cancer cases (see below, and Table 8) were identified. Sixty-two (94%) and four (6%) of the mutations were at codons 12, and 61, respectively, with G>T transversions most commonly observed (Table 8). Mutations were found more frequently in Stage II patients than in Stage I patients (see below, Table 8, and FIG. 9A). Additionally, while the mutant allele frequency did not correlate with tumor size (Table 8, and FIG. 11A), mutations were found more frequently in larger tumors than in smaller tumors (see below, Table 8, and FIG. 9B).

Proportion of samples stratified by AJCC stage detected with each individual assay and all combinations thereof.

| Assay Type | Proportion of samples detected (95% confidence interval) | | | | |
|---|---|---|---|---|---|
| | Stage IA (12 cases) | Stage IB (17 cases) | Stage IIA (22 cases) | Stage IIB (170 cases) | Stage I & II (221 cases) |
| KRAS ctDNA | 25% (5-57%) | 0% (0-20%) | 18% (5-40%) | 35% (28-42%) | 30% (24-36%) |
| CA19-9 | 17% (2-48%) | 41% (18-67%) | 36% (17-59%) | 54% (46-62%) | 49% (43-56%) |
| CEA + HGF + OPN | 25% (5-57%) | 6% (0-29%) | 14% (3-35%) | 19% (14-26%) | 18% (13-24%) |
| KRAS ctDNA + CA19-9 | 33% (10-65%) | 41% (18-67%) | 50% (28-72%) | 65% (58-72%) | 60% (53-67%) |
| KRAS ctDNA Mutations + CEA + HGF + OPN | 33% (10-65%) | 6% (0-29%) | 32% (14-55%) | 47% (39-55%) | 42% (35-48%) |
| CA19-9 + CEA + HGF + OPN | 25% (5-57%) | 47% (23-72%) | 36% (17-59%) | 59% (52-67%) | 54% (47-61%) |
| Combination Assay | 33% (10-65%) | 47% (23-72%) | 50% (28-72%) | 69% (62-76%) | 64% (57-70%) |

Proportion of samples stratified by tumor size detected with each individual assay and all combinations thereof.

| Assay Type | Proportion of samples detected (95% confidence interval) | | | | | | |
|---|---|---|---|---|---|---|---|
| | ≤1.5 cm (24 cases) | 1.5-2.0 cm (12 cases) | 2.0-2.5 cm (47 cases) | 2.5-3.0 cm (38 cases) | 3.0-3.5 cm (36 cases) | 3.5-4.0 cm (22 cases) | >4.0 cm (42 cases) |
| KRAS ctDNA | 21% (7-42%) | 17% (2-48%) | 9% (2-20%) | 32% (18-49%) | 42% (26-59%) | 45% (24-68%) | 43% (28-59%) |
| CA19-9 | 25% (10-47%) | 33% (10-65%) | 43% (28-58%) | 45% (29-62%) | 58% (41-74%) | 59% (36-79%) | 67% (50-80%) |
| CEA + HGF + OPN | 25% (10-47%) | 8% (0-38%) | 17% (8-31%) | 21% (10-37%) | 8% (2-22%) | 18% (5-40%) | 24% (12-39%) |
| KRAS ctDNA + CA19-9 | 38% (19-59%) | 50% (21-79%) | 47% (32-62%) | 55% (38-71%) | 78% (61-90%) | 73% (50-89%) | 74% (58-86%) |
| KRAS ctDNA Mutations + CEA + HGF + OPN | 38% (19-59%) | 25% (5-57%) | 26% (14-40%) | 47% (31-64%) | 47% (30-65%) | 55% (32-76%) | 50% (34-66%) |
| CA19-9 + CEA + HGF + OPN | 38% (19-59%) | 33% (10-65%) | 47% (32-62%) | 53% (36-69%) | 64% (46-79%) | 64% (41-83%) | 67% (50-80%) |
| Combination Assay | 46% (26-67%) | 50% (21-79%) | 51% (36-66%) | 61% (43-76%) | 81% (64-92%) | 77% (55-92%) | 74% (58-86%) |

Protein biomarkers in various cancer types.

| Cancer Type | # Cases | % CA19-9 | % CEA | % CA125 | % AFP | % Prolactin | % HGF | % OPN | % TIMP-1 | % Follistatin | % G-CSF | % CA15-3 |
|---|---|---|---|---|---|---|---|---|---|---|---|---|
| Breast | 150 | 3% | 4% | 1% | 1% | 8% | 3% | 3% | 0% | 1% | 3% | 1% |
| CRC | 322 | 5% | 17% | 0% | 1% | 10% | 11% | 8% | 8% | 10% | 9% | 0% |
| Esophagus | 43 | 7% | 5% | 0% | 0% | 2% | 33% | 19% | 26% | 2% | 14% | 5% |
| Gastric | 65 | 11% | 15% | 0% | 5% | 3% | 34% | 20% | 11% | 8% | 8% | 3% |

| Cancer Type | # Cases | % CA19-9 | % CEA | % CA125 | % AFP | % Prolactin | % HGF | % OPN | % TIMP-1 | % Follistatin | % G-CSF | % CA15-3 |
|---|---|---|---|---|---|---|---|---|---|---|---|---|
| Liver | 53 | 21% | 9% | 6% | 40% | 11% | 25% | 28% | 17% | 8% | 6% | 6% |
| Lung | 109 | 4% | 13% | 0% | 1% | 11% | 1% | 2% | 0% | 0% | 0% | 3% |
| Ovarian | 86 | 13% | 1% | 12% | 3% | 20% | 3% | 3% | 10% | 1% | 0% | 19% |
| Pancreas | 412 | 52% | 8% | 0% | 0% | 0% | 7% | 6% | 7% | 8% | 1% | 0% |

The number of mutant templates in the plasma could be calculated from the mutant allele fraction and the concentration of DNA in each plasma sample (Table 8). This number was often very low, with 15 (23%) of the patients with detectable KRAS mutations having <2 mutant templates per ml of plasma. The average number of mutant templates per mL of plasma was 9.4 (Table 8). These results emphasize that extremely sensitive techniques can be used to detect the mutations in early stage pancreatic cancer patients. KRAS mutations were only observed in one of the 221 individuals in the presumed healthy cohort, a 69-year-old male with no known cancer.

The basis for the liquid biopsy concept is that the mutant DNA templates identified in the circulation are derived from cancers. It was therefore important to determine whether the KRAS mutations identified in these patients' plasma samples were also present in their primary carcinomas. Primary carcinomas from 50 of the 66 patients with detectable KRAS mutations in their plasma were obtained. In all 50 cases, the mutation found in the plasma was identical to that found in the primary carcinoma, providing another, orthogonal measure of specificity.

Simultaneous Assessment of CA19-9 and KRAS Mutations in Plasma

It was sought to determine whether a combination of the KRAS ctDNA test with CA19-9, the PDAC biomarker, would result in improved sensitivity compared with the KRAS ctDNA test alone. Recent studies have shown that CA19-9 can be elevated in patients with pancreatic cancer two years prior to diagnosis (see, e.g., O'Brien et al., 2015 *Clin Cancer Res* 21(3):622-631). However, CA19-9 elevations have also been observed in non-malignant conditions, and 5% of the population cannot produce the CA19-9 antigen due to germline genetic variation, limiting its use for screening purposes (see, e.g., Lennon et al., 2010 Diagnostic and Therapeutic Response Markers. *Pancreatic Cancer*, (Springer New York, New York, NY), pp 675-701). However, it was reasoned that CA19-9 might prove useful as a screening biomarker if the threshold for scoring a result as positive was sufficiently high. A threshold of 100 U/mL was chosen based on prior data that this level is not found among healthy individuals who do not have a clinical history of pancreaticobiliary disease (see, Kim et al., 2004 *J Gastroenterol Hepatol* 19(2):182-186).

Figure 9:
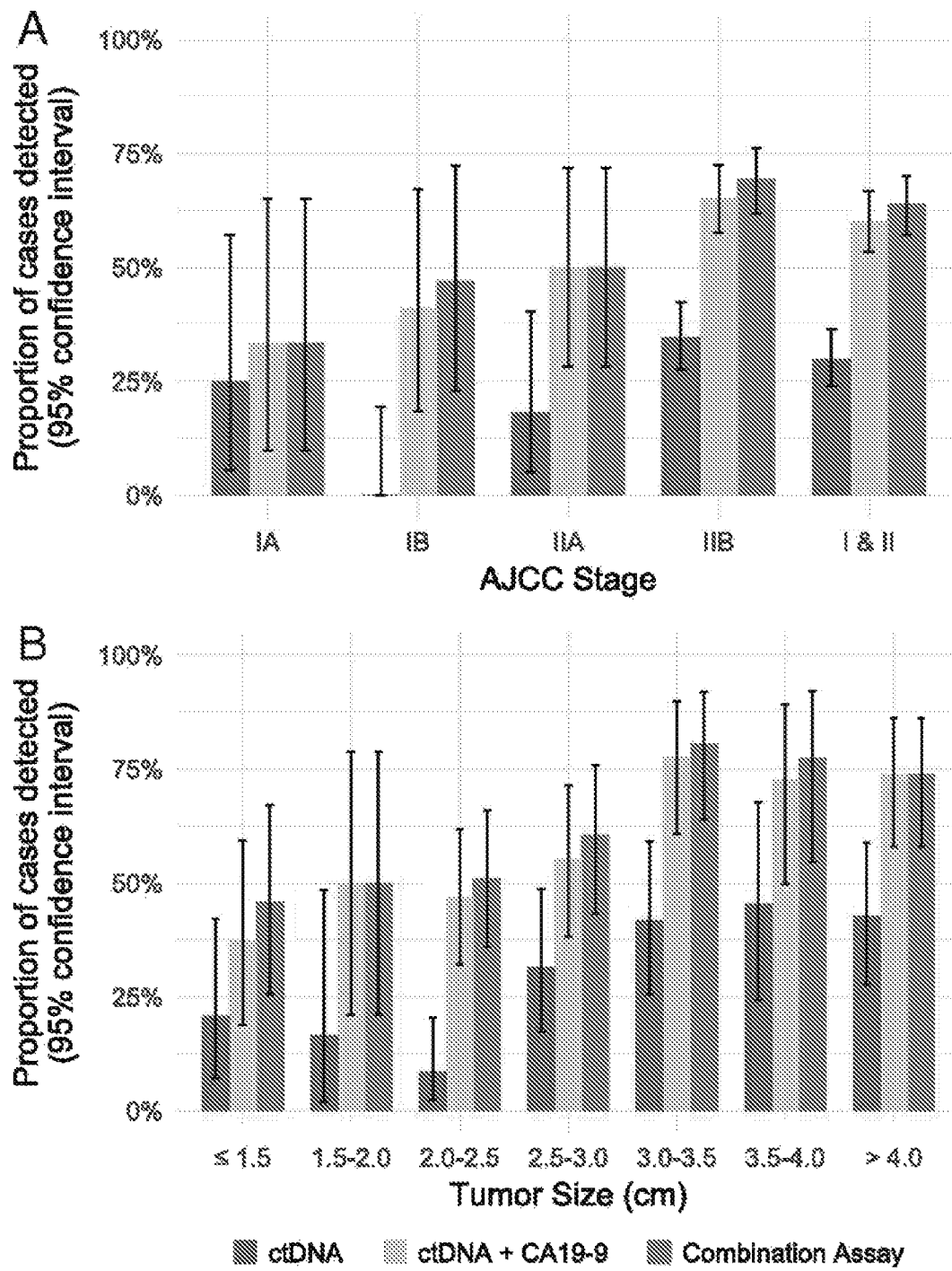
FIG. 9 contains graphs combining ctDNA KRAS mutations with protein biomarkers increases sensitivity for early detection of PDAC. (A) Sensitivities of ctDNA KRAS mutations alone, ctDNA KRAS mutations plus CA19-9, and ctDNA KRAS mutations with CA19-9 and other proteins (combination assay) with respect to AJCC stage. (B) Sensitivities of ctDNA KRAS mutations alone, ctDNA KRAS mutations plus CA19-9, and ctDNA KRAS mutations with CA19-9 and other proteins (combination assay) with respect to tumor size. Error bars represent 95% confidence intervals.
Figure 10:
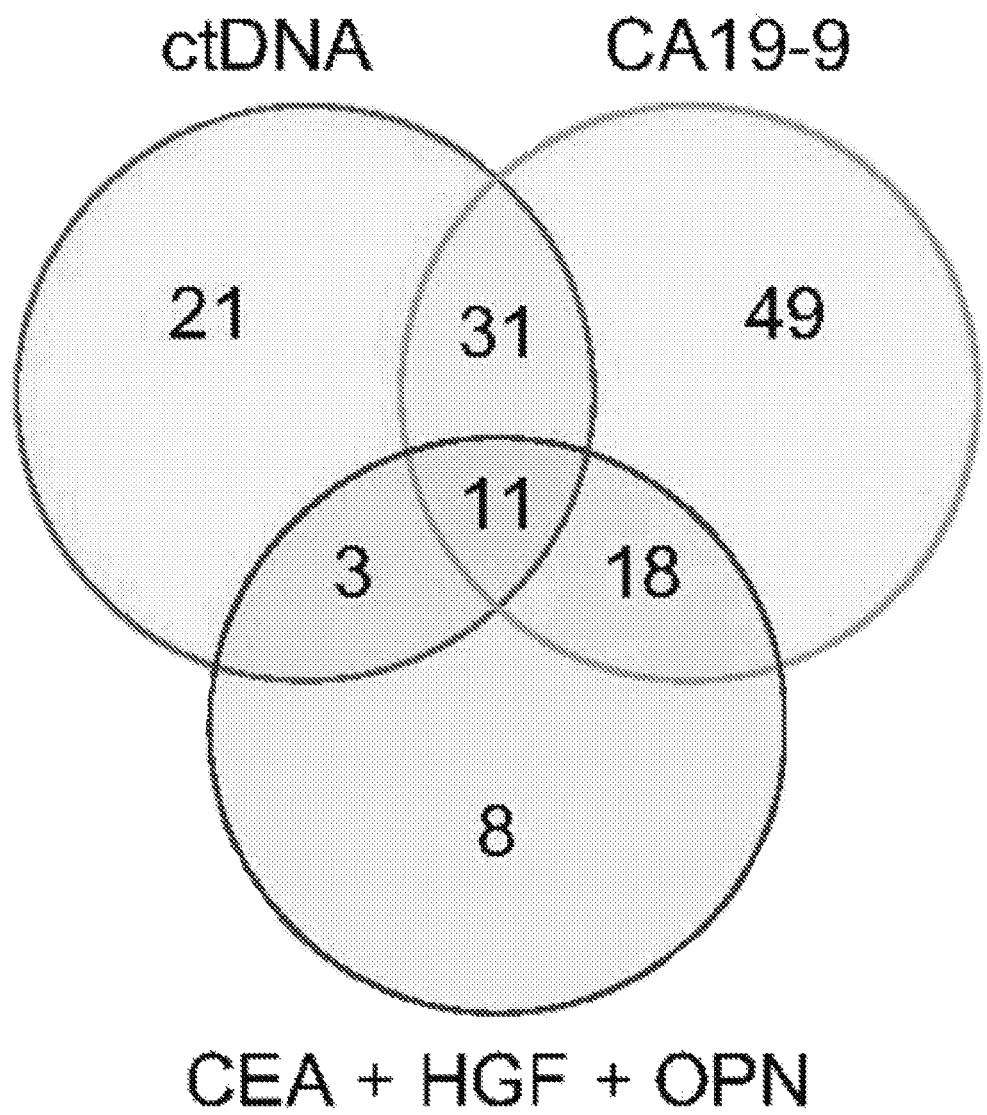
FIG. 10 contains a diagram showing that combining ctDNA and protein markers increases sensitivity because a large proportion of patients are detected by only one marker. Number of patients detected by ctDNA KRAS mutations (red circle), CA19-9 (green circle), and the three other protein biomarkers (blue circle), and combinations thereof (overlapping regions). Eighty patients (36% of the total) were not detectable by any of the three makers.

Using this predefined high threshold, CA19-9 was detected in 109 of the 221 (49%: 95% CI 43-56%) patients with pancreatic cancer, and in none of the 182 healthy controls, confirming its specificity when used in this way (Table 8, and Table 9). As expected, the number of patients with detectable CA19-9 levels increased with stage and tumor size (FIG. 9, and Table 8). A question addressed in the current study was whether these two biomarkers—KRAS mutations and a positive CA19-9 score—were independent indicators of the presence of disease. It was found that the overlap was only partial, as indicated in the Venn diagram in FIG. 10. Though 42 patients (19%) had elevated CA19-9 levels as well as detectable KRAS mutations in their plasma, 91 additional patients had either mutations in KRAS or elevated CA19-9, but not both (FIG. 10). Thus, the combined sensitivity of these analyses was 60% (95% CI 53-67%), higher than the sensitivity of either alone (FIG. 9). As such, this Example demonstrates that the two assays could be combined without substantially increasing the false positive rate because each was extremely specific at the thresholds used.

Increasing Sensitivity by Inclusion of Other Protein Biomarkers

Encouraged by the results described above, it was sought to further increase sensitivity by combining ctDNA KRAS mutations and CA19-9 with other protein biomarkers (Table 10). In a pilot study on a small number of pancreatic cancer samples independent from those studied here, the potential utility of other proteins that had been found to be elevated in cancer, including alpha-fetoprotein (AFP), CA15-3, leptin, IL-6, carcinoembryonic antigen (CEA), CA-125, interleukin 8 (IL-8), sFas, prolactin, osteopontin (OPN), basic fibroblast growth factor (FGF2), hepatocyte growth factor (HGF), cytokeratin-19 fragment (CYFRA 21-1), human epididymis protein 4 (HE4), transforming growth factor alpha (TGF-α), growth/differentiation factor 15 (GDF15), dickkopf-related protein 1 (DKK1), neuron specific enolase (NSE), osteoprotegerin (OPG), TIMP metallopeptidase inhibitor 1 (TIMP-1), TIMP metallopeptidase inhibitor 2 (TIMP-2), mesothelin, midkine, kallikrein-6, CD44, AXL receptor tyrosine kinase, soluble human epidermal growth factor receptor 2 (sHER2), soluble epidermal growth factor receptor (sEGFR), soluble urokinase-type plasminogen activator receptor (suPAR), and soluble platelet endothelial cell adhesion molecule (sPECAM-1) was evaluated. Of these 29 protein biomarkers, five—CEA (see, e.g., Nazli et al., 2000 *Hepatogastroenterology* 47(36):1750-1752), HGF (see, e.g., Di Renzo et al., 1995 *Cancer Res* 55(5):1129-1138), midkine (see, e.g., Ikematsu et al., 2000 *Br J Cancer* 83(6):701-706), OPN (see, e.g., Koopmann et al., 2004 *Cancer Epidemiol Biomarkers Prev* 13(3):487-491), and prolactin (see, e.g., Levina et al., 2009 *Cancer Res* 69(12):5226-5233)—were chosen for further analysis.

Figure 14:
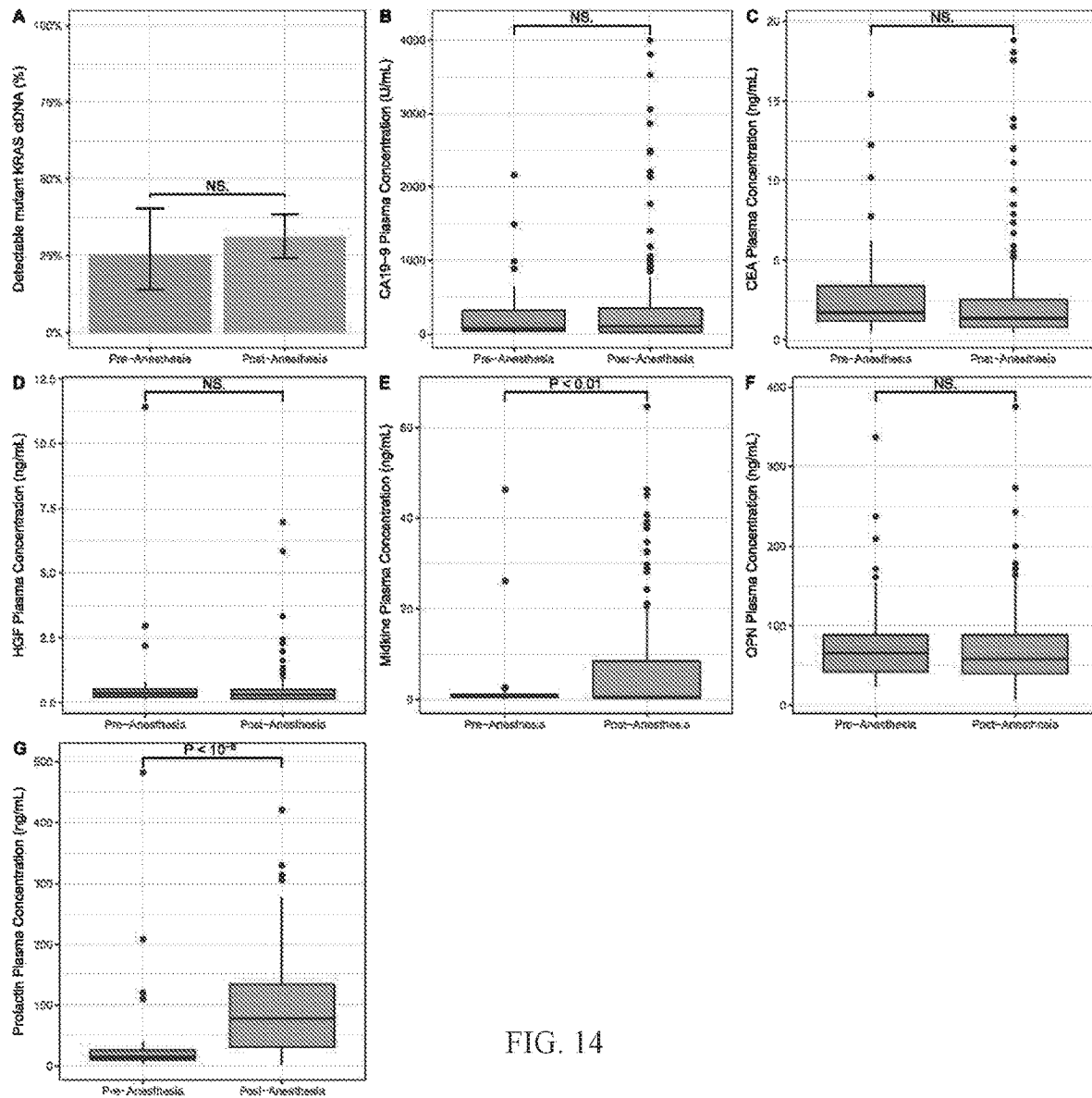
FIG. 14 contains graphs showing that levels of prolactin (G) and midkine (E) were significantly elevated in samples that were collected after the administration of anesthesia but before surgical excision. In contrast, no difference was observed in the proportion of samples with mutant KRAS ctDNA (A), CA19-9 plasma concentration (B), CEA plasma concentration (C), HGF plasma concentration (D), and OPN plasma concentration (F) between samples that were collected before or after the administration of anesthesia. N.S. not significant, P>0.05 (Exact permutation t-test).

When the levels of these five markers were evaluated in plasmas from the 221 patient pancreatic cancer cohort, an association between the plasma concentrations of prolactin and midkine and surgical site (P<0.01, $\chi^2$ test, degrees of freedom=5) was observed, suggesting that blood collection conditions might have elevated the levels of these two markers. There was no significant correlation between CA19-9, CEA, HGF, or OPN levels and collection sites, nor was there any correlation between the presence of KRAS ctDNA mutations and collection site (P>0.01, $\chi^2$ test, degrees of freedom=5). Upon further investigation, it was noted that the levels of prolactin and midkine were significantly elevated in samples that were collected after the administration of anesthesia but before surgical excision (FIG. 14). The results on prolactin were consistent with previous studies showing that anesthetics elevate the levels of this protein (see, e.g., Thorpe et al., 2007 *PLoS One*

Figure 15:
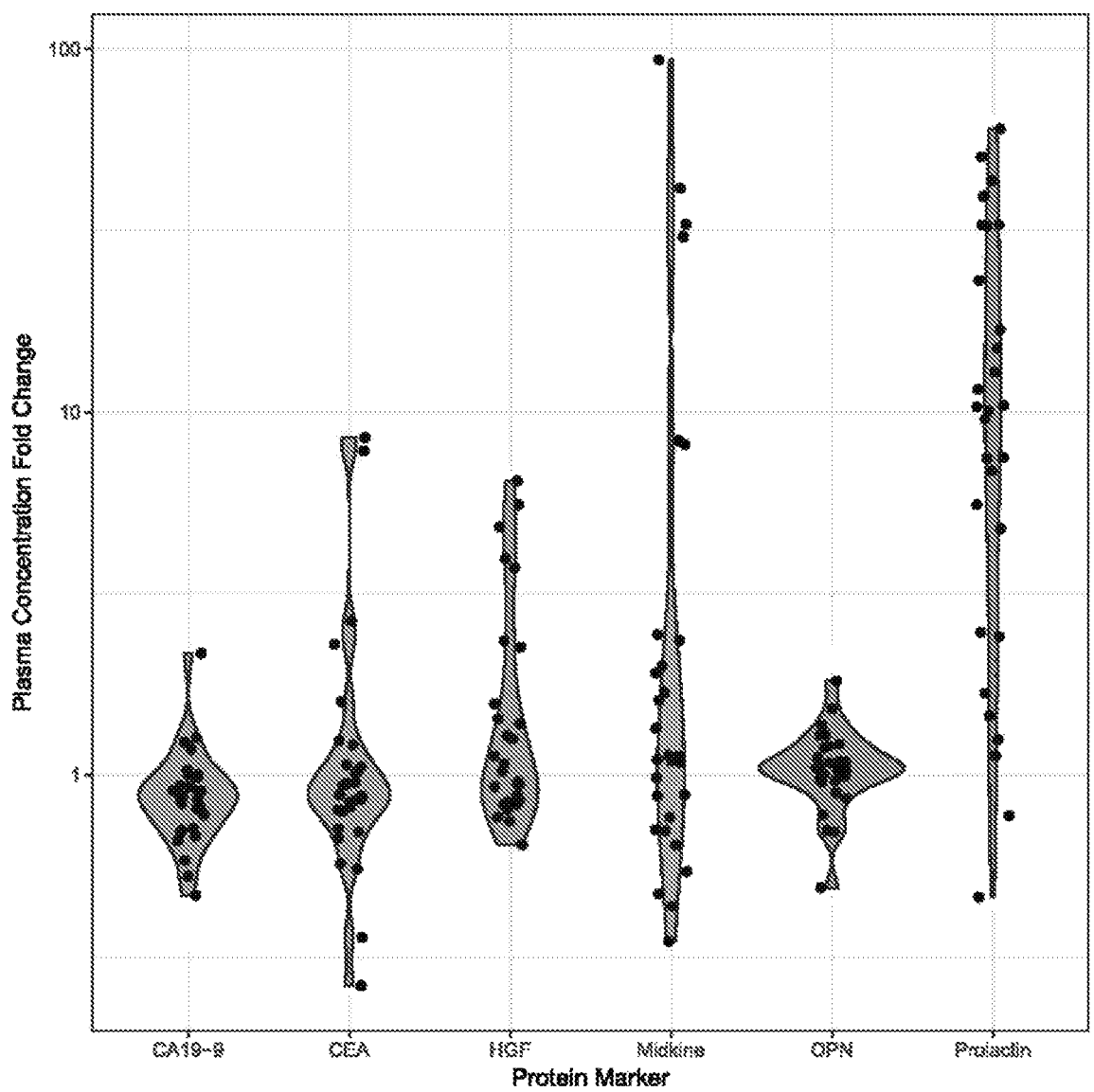
FIG. 15 contains a graph showing fold change in protein biomarker levels from 29 pairs plasma samples collected before and immediately after the administration of anesthesia. Of the six markers evaluated, only prolactin and midkine were found to be elevated by anesthesia, in perfect according with the correlation between collection site and protein levels.

2(12):e1281). To ensure that anesthesia did not affect the levels of the other protein biomarkers described above, paired plasma samples were collected before and immediately after the administration of anesthesia in 29 new patients. The only proteins found to be elevated by anesthesia were prolactin and midkine (FIG. 15), in perfect accordance with the correlation between collection site and protein levels noted above. Prolactin and midkine were therefore excluded from further analysis.

Figure 13:
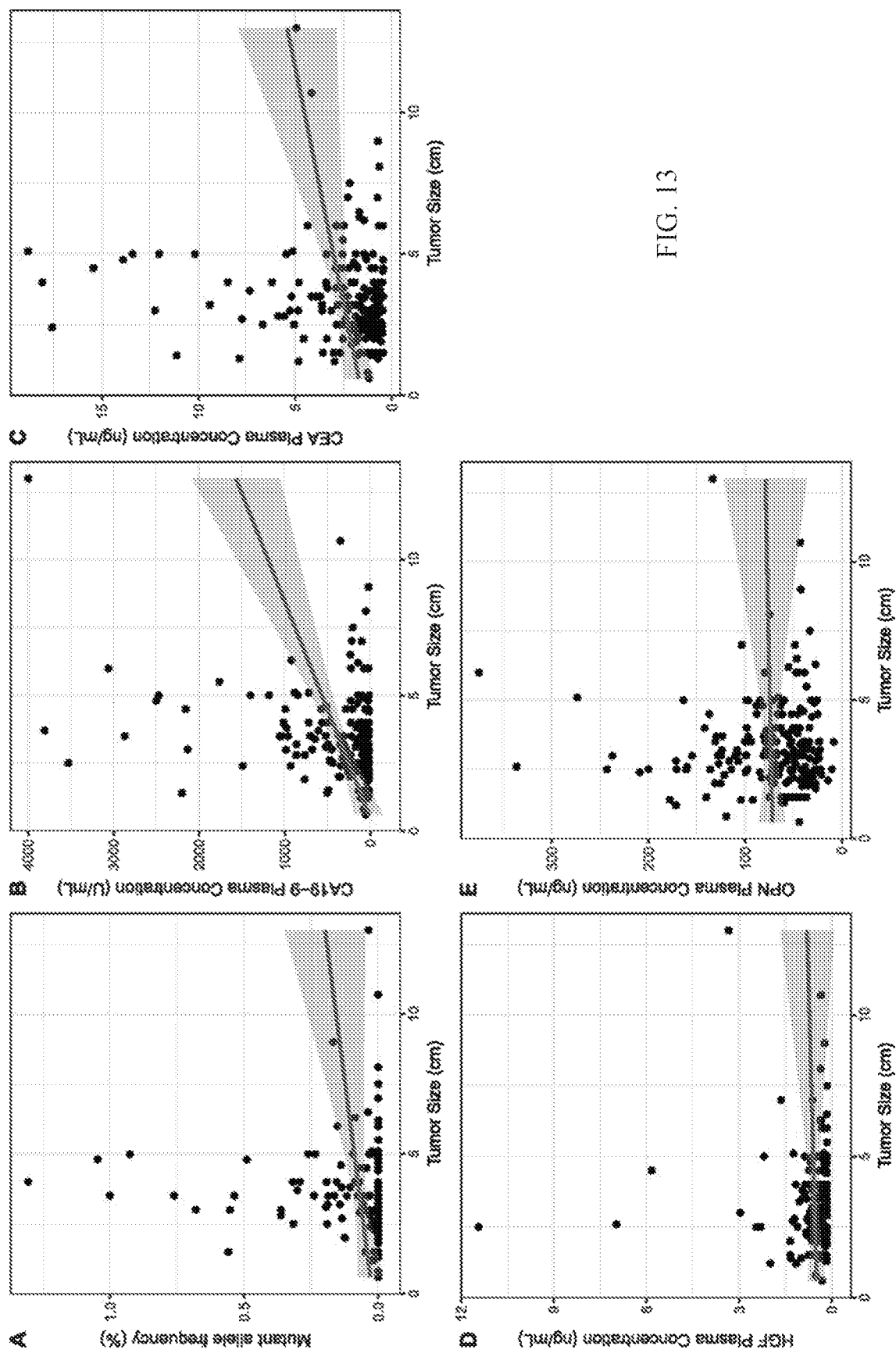
FIG. 13 contains graphs showing correlations between triplex assay markers and tumor size. (A) KRAS mutations were found more frequently in larger tumors than smaller tumors, but the mutant allele frequency did not correlate with tumor size (Pearson's r=0.039). (B) In patients with elevated CA19-9, CA19-9 plasma concentration weakly correlates with tumor size (Pearson's r=0.287). (C-E) Plasma levels of CEA, HGF, and OPN were less dependent on tumor size than KRAS mutations or CA19-9 (CEA Pearson's r=0.153; HGF Pearson's r=0.037; OPN Pearson's r=0.018). Shaded regions represent 95% confidence intervals.

Unlike CA19-9, no predefined threshold exists for the use of CEA, HGF, or OPN as markers for pancreatic cancer. As a result, appropriate thresholds were determined in an independent set of 273 plasma samples from healthy controls. To be conservative, thresholds for each protein that were 10% higher than the maximum values observed in any of the 273 normal plasma samples were chosen. Notably, when these thresholds were applied to the independent test set of 182 plasma samples, all three protein markers maintained 100% specificity (Table 9). The sensitivity of each of these three markers was less than that obtained with KRAS mutations or CA19-9 when each marker was used alone, but their levels were less dependent on stage and size than KRAS mutations or CA19-9 (FIG. 13, and Table 8). In combination with KRAS mutations and CA19-9 assays, this five-member biomarker panel ("combination assay") detected 141 (64%: 95% CI 57-70%) of the 221 resectable cancers (Table 7, FIG. 9A, FIG. 10, and Table 8).

Some of the patients detectable by the combination assay were of particular note. Forty-five (20%) patients had no symptoms classically associated with pancreatic cancer (Table 8). The combination assay identified 27 (60%) of these individuals, of whom 19 (70%) had no evidence of recurrence with a median follow up of 12 (range 3-16) months (Table 8). Of the 29 patients with the earliest stages of disease (Stages IA and IB) recognized by the AJCC, 12 (41%) were detectable using the combination assay (FIG. 9A), of whom 7 (58%) had no evidence of recurrence at the study termination with a median follow up of 19 (range 2-25) months.

Figure 16:
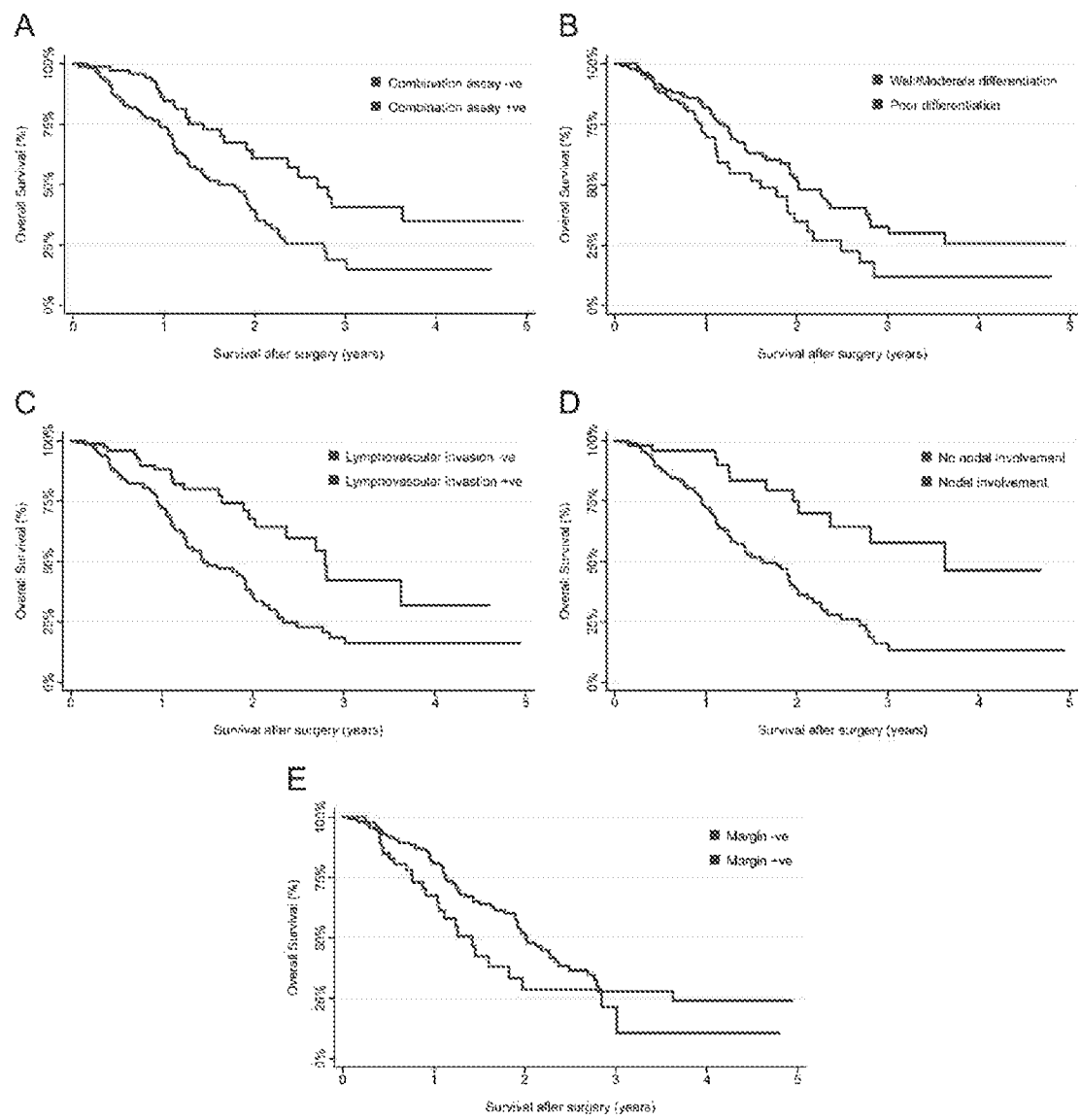
FIG. 16 contains Kaplan-Meier survival plots stratified by independent predictors of overall survival identified by multivariate analysis: (A) combination assay status (HR=1.76, 95% CI, 1.10-2.84, p=0.018); (B) grade of differentiation (poorly differentiated, HR=1.72, 95% CI 1.11-2.66, p=0.015); (C) lymphovascular invasion (present, HR=1.81, 95% CI 1.06-3.09, p=0.028); (D) nodal disease (present, HR=2.35, 95% CI 1.20-4.61, p=0.013); (E) margin status (HR=1.59, 95% CI 1.01-2.55, p=0.050)
Figure 17:
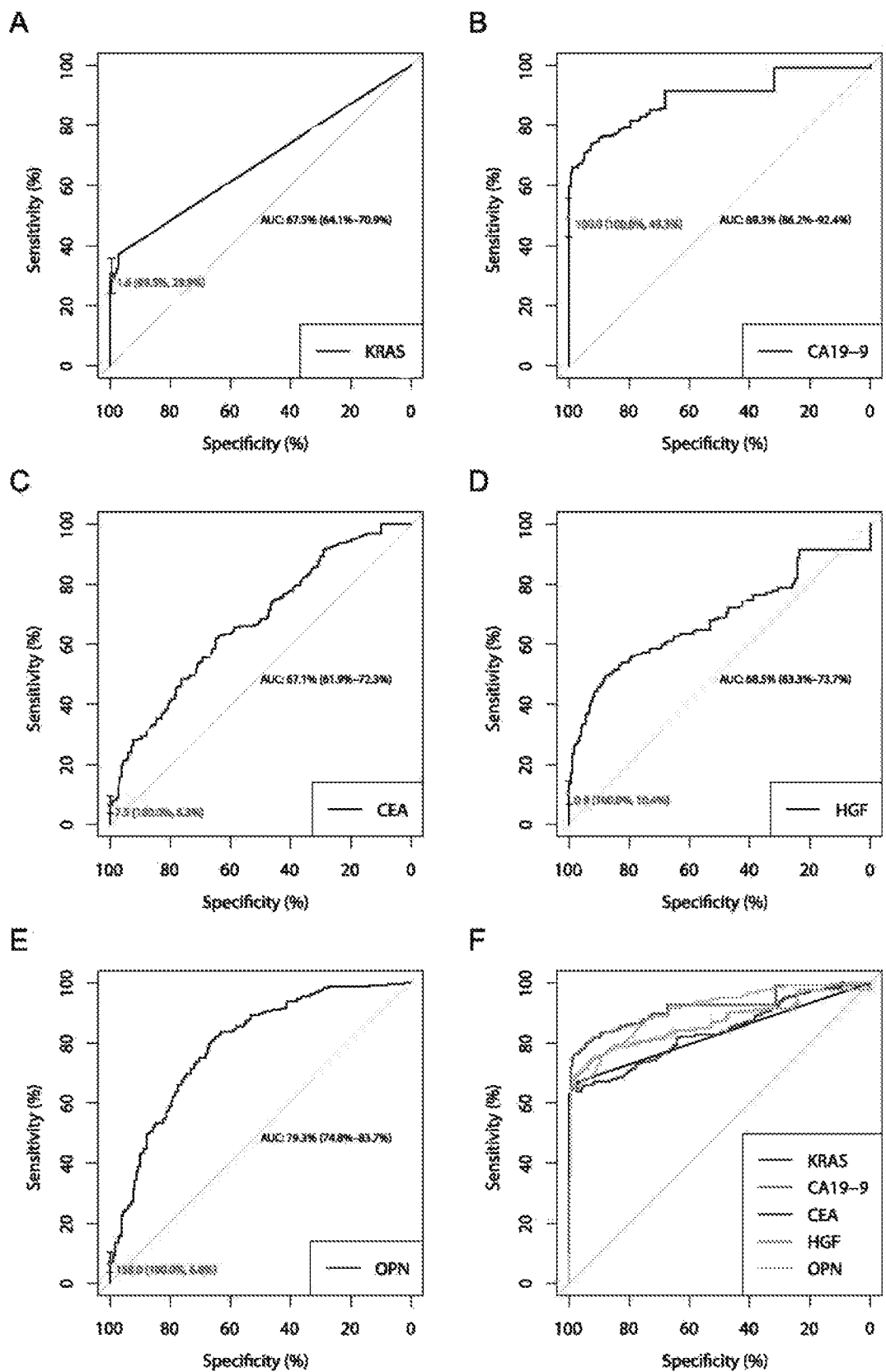
FIG. 17 contains receiver operator characteristic (ROC) curves for (A) KRAS mutations, (B) CA19-9, (C) CEA, (D) HGF, (E) OPN, and (F) Combination assay. (A-E) ROC curves demonstrate the performance of each combination assay biomarker individually. The red points on the curves indicate the marker performance at the thresholds used in the combination assay. Error bars represent 95% confidence intervals for sensitivity and specificity at the particular threshold (red font). (D) ROC curves demonstrating the performance of the combination assay when the KRAS threshold was varied and CA19-9, CEA, HGF, and OPN thresholds were fixed at the levels used in the combination assay (black curve), the CA19-9 threshold was varied and KRAS, CEA, HGF, and OPN thresholds were fixed at the levels used in the combination assay (red curve), the CEA threshold was varied and KRAS, CA19-9, HGF, and OPN thresholds were fixed at the levels used in the combination assay (blue curve), the HGF threshold was varied and KRAS, CA19-9, CEA, and OPN thresholds were fixed at the levels used in the combination assay (green curve), and the OPN threshold was varied and KRAS, CA19-9, CEA, and HGF thresholds were fixed at the levels used in the combination assay (orange curve). The intersection of these three curves designates the overall performance of the triplex assay (64% sensitivity, 99.5% sensitivity).
Figure 18:
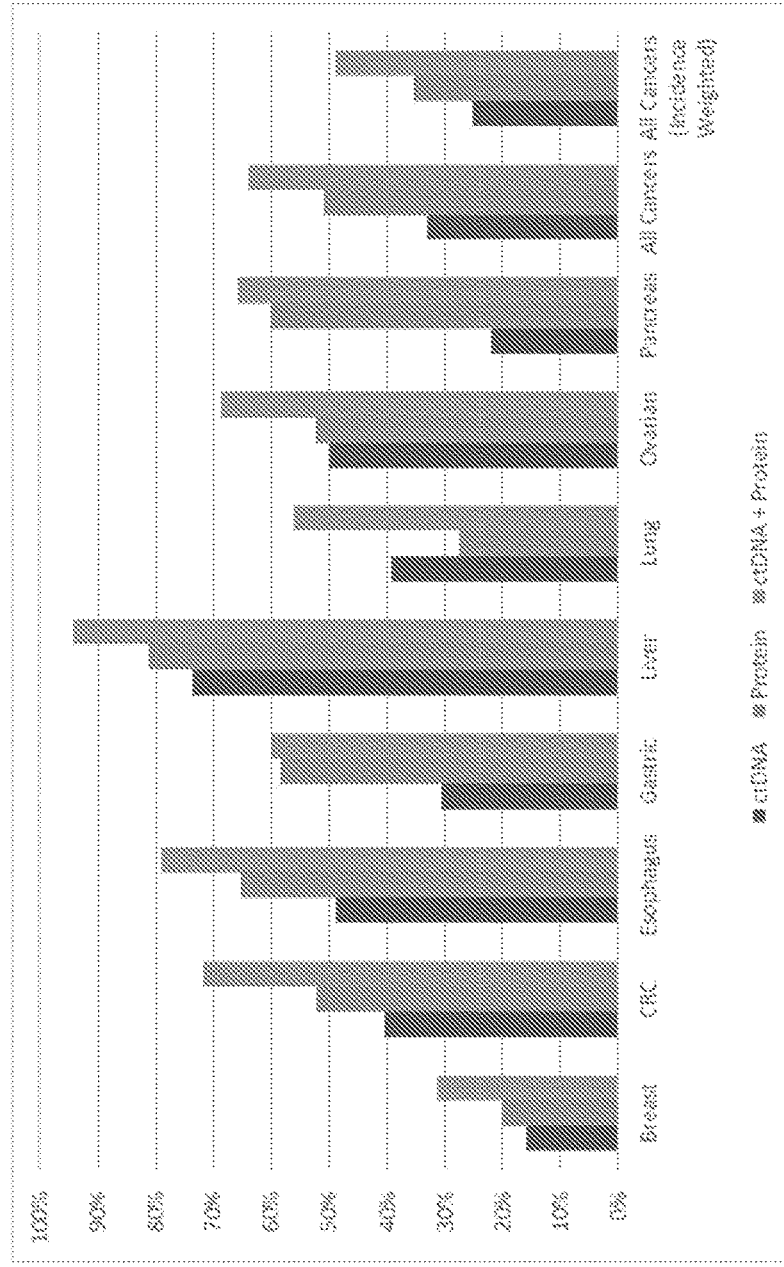
FIG. 18 shows performance of marker panel for identifying cancer in 8 cancer types. (A) Numerical data. (B) Graphical data.

Another notable but sobering result from this study was that patients with poorer survival were more likely to have a positive test. Of the entire 221 pancreatic cancer patients studied, 122 (56%) patients were alive at the termination of the study, with a median follow-up of 13 (7-21) months. It was found that the combination assay provided prognostic value that was independent of conventional clinical and histopathologic features. In particular, multivariate analyses showed that the independent predictors of overall survival were combination assay status (HR=1.76, 95% CI, 1.10-2.84, p=0.018), increasing age (HR=1.04, 95% CI 1.02-1.06, p=0.001), grade of differentiation (poorly differentiated, HR=1.72, 95% CI 1.11-2.66, p=0.015), lymphovascular invasion (present, HR=1.81, 95% CI 1.06-3.09, p=0.028), nodal disease (present, HR=2.35, 95% CI 1.20-4.61, p=0.013), and margin status (HR=1.59, 95% CI 1.01-2.55, p=0.050) (Table 7, FIG. 16).

TP53 in a Multiplex Assay

While nearly all pancreatic cancers harbor mutations within KRAS, a large fraction (~75%) also contains mutations in TP53 (see, e.g., Jones et al., 2008 Science 321 (5897):1801-1806; Biankin et al., 2012 Nature 491(7424): 399-405; and Waddell et al., 2015 Nature 518(7540):495-501). Furthermore, TP53 is the mostly commonly mutated gene in cancer (see, e.g., Vogelstein et al., 2013 Science 339(6127):1546-1558), making it an attractive target for ctDNA detection in future studies involving other tumor types. To determine whether the mutant allele frequencies of TP53 in the plasma correlated with those of KRAS, and also to determine whether a mutant TP53 assay in plasma might add to the sensitivity of the mutant KRAS assay, the 152 carcinomas for which matched tumor and plasma samples were available were evaluated. Mutations at one of the "hotspots" identified in genome-wide studies of PDAC (see, e.g., Jones et al., 2008 Science 321(5897):1801-1806) were first searched for. A total of 64 (42%) carcinomas contained a TP53 mutation at one of these positions. It was then determined whether these same mutations could be identified in the plasma of these 64 patients, using Safe-SeqS-based assays similar to that described above for KRAS but using primers specific for particular TP53 mutations.

Figure 3:
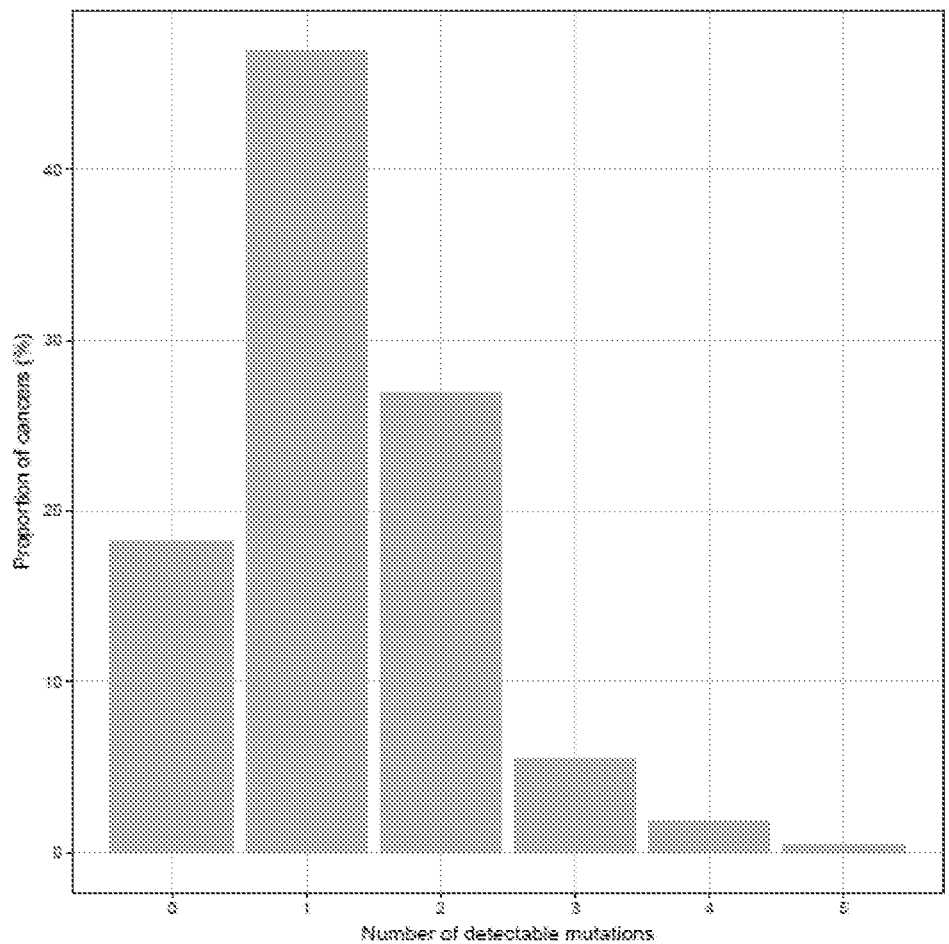
FIG. 3 contains a graph showing the distribution of the number of detectable mutations within the 805 primary tumors evaluated.

TP53 mutations in 13 (20%) of the 64 plasma samples (see below) were identified. Two observations were of interest. First, 12 of the 13 plasma samples containing a detectable TP53 mutation also contained a detectable KRAS mutation. Thus, TP53 mutation assays did not substantially increase sensitivity for pancreatic cancer detection, as expected from the high prevalence of KRAS mutations noted above. Second, there was a strong correlation between the mutant allele frequencies of TP53 and KRAS mutations in the plasma of the 12 patients whose plasma contained detectable amounts of both mutations (FIG. 3, Pearson's r=0.885). This provides yet another validation of the reliability of the ctDNA assay and its quantitative nature.

List of Exemplary TP53 Mutations Detected in PDAC Patients

| Sample ID # | Plasma DNA concentration (ng/mL) | Mutation identified in plasma | Mutant mean allele frequency (%) | Mutant fragments/ mL plasma |
| --- | --- | --- | --- | --- |
| PANC 335 | 13.28 | TP53 p.R196*, c.586C > T | 0.795 | 32.5 |
| PANC 336 | 13.67 | TP53 p.G266E, c.797G > A | 0.929 | 39.1 |
| PANC 552 | 19.44 | TP53 p.R175H, c.524G > A | 0.673 | 40.3 |
| PANC 387 | 11.11 | TP53 p.R175H, c.524G > A | 0.195 | 6.7 |
| PANC 467 | 6.76 | TP53 p.R248Q, c.743G > A | 0.344 | 7.2 |
| PANC 468 | 10.28 | TP53 p.S241F, c.722C > T | 0.139 | 4.4 |
| PANC 469 | 5.98 | TP53 p.C238F, c.713G > T | 0.051 | 0.9 |
| PANC 545 | 12.23 | TP53 p.Y236C, c.707A > G | 0.137 | 5.2 |
| PANC 547 | 10.73 | TP53 p.Y234C, c.701A > G | 0.069 | 2.3 |
| PANC 552 | 10.00 | TP53 p.C238Y, c.713G > A | 0.317 | 9.8 |
| PANC 692 | 9.83 | TP53 p.V272M, c.814G > A | 0.101 | 3.1 |
| PANCA 1105 | 11.49 | TP53 p.H193Y, c.577C > T | 0.098 | 3.5 |
| PANCA 1109 | 27.57 | TP53 p.Y234C, c.701A > G | 0.351 | 29.8 |

List of Exemplary CDKN2A Mutations Detected in PDAC Patients

| Sample ID # | Mutation identified in plasma | Mutation identified in tumor tissue | Mutant mean allele frequency % |
|---|---|---|---|
| PANC 335 PLS1 | CDKN2A p.R58*, c.172C > T | CDKN2A p.R58*, c.172C > T | 0.432 |
| PANC 552 PLS 1 | CDKN2A p.D84G, c.251A > G | CDKN2A p.D84G, c.251A > G | 0.166 |
| PANC 641 PLS 1 | CDKN2A g.21971208G > T (splice site) | CDKN2A g.21971208G > T (splice site) | 0.143 |
| PANC 447 PLS | CDKN2A p.R80*, c.238C > T | CDKN2A p.R80*, c.238C > T | 0.102 |
| PANC 398 PLS 1 | CDKN2A p.V51D, c.152T > A | CDKN2A p.V51D, c.152T > A | 0.091 |
| PANC 609 PLS 1 | CDKN2A p.R80*, c.238C > T | CDKN2A p.R80*, c.238C > T | 0.071 |
| PANC 455 PLS | CDKN2A p.H83Y, c.247C > T | CDKN2A p.H83Y, c.247C > T | 0.061 |
| PANC 517 PLS 1A | CDKN2A p.R58*, c.172C > T | CDKN2A p.R58*, c.172C > T | 0.026 |
| PANC 547 PLS 1 | CDKN2A p.R58*, c.172C > T | CDKN2A p.R58*, c.172C > T | 0.026 |
| PANC 648 PLS 1 | CDKN2A p.A76T, c.226G > A | CDKN2A p.A76T, c.226G > A | 0.016 |
| PANC 715 PLS 1 | CDKN2A p.M54fs, c.162 > G | CDKN2A p.M54fs, c.162 > G | 0.014 |
| PANC 763 PLS 1 | CDKN2A p.H83Y, c.247C > T | CDKN2A p.H83Y, c.247C > T | 0.013 |
| PANC 509 PLS 1 | CDKN2A p.H83Y, c.247C > T | CDKN2A p.H83Y, c.247C > T | 0.012 |
| PANC 545 PLS 1 | CDKN2A p.R80fs, c.239ACCCG> | CDKN2A p.R80fs, c.239ACCCG> | 0.011 |
| PANC 634 PLS 1 | CDKN2A p.A76T, c.226G > A | CDKN2A p.A76T, c.226G > A | 0.006 |

Example 3: Sensitivity and Specificity of ctDNA and Protein Biomarkers

Materials and Methods

Phase A

Healthy Cohort: Ten thousand non-symptomatic women are recruited. The age range of participants is 65 to 75 years, as this range captures patients at maximum risk for cancers of the eight types that are the target of detection. Women with oophorectomies, known cancer of any type other than non-melanoma skin cancer, are excluded from the study. Plasma from each participant is obtained at study entry. In participants who test positive, as well as in a random sample of participants with negative tests, one additional sample of plasma is drawn at 3 months following the first test. When both tests are positive for the same mutation, a whole body PET/CT scan is performed. If the PET/CT exam is positive, patients are managed as deemed appropriate by their physicians. This management includes yearly follow-up ctDNA tests. Yearly follow-up of patients via electronic questionnaires, combined with phone interviews when necessary, are obtained on all individuals, whether their tests are positive or negative.

Management Cohorts: Two hundred patients with Stage III colon cancers and 50 patients with resectable pancreatic cancers are recruited from at least 10 sites across Australia, New Zealand and Singapore. Tumor samples are tested to identify mutations that can be used for subsequent ctDNA tests. Plasma samples are collected on all patients prior to surgery (including those randomized to receive routine care). Additional plasma samples are collected at 3, 6, and 12 months in patients whose ctDNA tests are positive prior to surgery. No further ctDNA analyses are performed in ctDNA-negative patients or those randomized to receive routine care. Patients are randomized 1:1 to ctDNA-informed management (with treatment escalation or de-escalation compared to standard of care, or to routine care [blinded to ctDNA test results]).

Phase B

Healthy Cohort: Forty thousand more non-symptomatic women are recruited. The inclusion and exclusion criteria are the same as in Phase A. Other than the longer follow-up and larger number of patients, there are at least two other differences between Phase A and Phase B. First, protein biomarkers that passed the specificity threshold (>99.5%) in Phase A samples are included. Patients who test positive for one or more of these protein biomarkers are managed identically to those with positive ctDNA results. Second, a "control" Healthy Cohort is added. These represents individuals recruited from the same population but in whom no blood samples are taken to assess disease or guide management. These controls are used to assess the ability of the screening tests to detect disease before they would ordinarily be detected on the basis of symptoms or standard medical care of healthy individuals. Comparisons between stage and survival in the screened and control cohorts are also made.

Management Cohorts: One thousand more patients with Stage III colon cancers (a total of 1200 patients) and 210 more patients with resectable pancreatic cancers (for a total of 250 patients) are recruited, but now at 30 sites rather than 10 sites. Similarly, to Phase A, tumor samples are collected at surgery in all new patients and mutations identified so that they can be used in subsequent ctDNA tests. Additionally, protein biomarkers for colorectal or pancreatic cancers that passed the specificity threshold (>99.5%) in Phase A are included. Patients who test positive for these protein biomarkers are managed identically to those with positive ctDNA results. Plasma samples are collected on all patients prior to surgery and at 3, 6, and 12 months in patients whose ctDNA tests are positive prior to surgery. Patients are randomized 1:1 to ctDNA-informed management (with treatment escalation or de-escalation compared to standard of care, or to routine care [blinded to ctDNA result]).

Evaluations

The Safe-SeqS-based ctDNA test that is used in the Healthy Cohort incorporates 61 amplicons representing the most commonly mutated regions of cancer driver genes. It is estimated that ~70% of the eight cancer types to be targeted have mutations in at least one of the regions covered by these amplicons. The fraction of plasmas that have mutations in at least one of these amplicons is less than 70% because not all cancers give rise to ctDNA (see Bettegowda et al., Sci Transl Med. 2014 Feb. 19; 6(224):224ra24. doi: 10.1126/scitranslmed.3007094.).

For the Management Cohort, a targeted sequencing assay is first used to identify at least one mutation in the FFPE-cancer obtained from surgery or biopsy. This Safe-SeqS-based test employs 128 amplicons and we have used it to detect at least one pathogenic driver gene mutation in 395 of 401 colorectal cancers and in 200 of 200 pancreatic cancers tested. One specific amplicon that detects a mutation in each individual patient's tumor is then used to evaluate the plasma from that patient at the specified time points—in other words, a fully personalized assay.

In addition to the tests on circulating tumor DNA (ctDNA), a panel of ~25 protein biomarkers is assessed using a Luminex platform on a subset of plasma samples from the Healthy Cohort. The assays for these proteins have been well-established. If the thresholds for positivity are set to a high level, they provide additional information that can be combined with the ctDNA test results to improve sensitivity without compromising specificity. Markers that exhibit >99.5% specificity in Phase A are incorporated into Phase B of the study.

Example 4: Detecting Gynecologic Malignancies Using a Combination Approach Cancer Screening Tests Diagnosis of gynecologic malignancy (e.g., cervical cancers, ovarian cancers, and endometrial cancers) often includes the Papanicolaou (Pap) test, transvaginal ultrasound (TVUS), and/or detection of the CA-25 biomarker. However, screening with current diagnostic approaches is not recommended for the general population, as it leads to "important harms, including major surgical interventions in women who do not have cancer" (see, e.g., Moyer, 2012 *Annals of internal medicine* 157:900-904). Thus, new diagnostic approaches are urgently needed.

This Example describes a new blood test, called Pap-SEEK, which addresses the problematic issues described above. In this test, DNA from sampled fluid (e.g., fluid containing cells sampled from the endocervical canal) can be used in an assay (e.g., a PCR-based, multiplex test) to simultaneously assess genetic alterations that commonly occur in endometrial or ovarian cancers (FIG. 19). Overall, 1915 samples from 1658 individuals were included in the studies described herein, including 656 patients with endometrial or ovarian cancers and 1002 healthy controls. The age, race, histopathologic diagnosis, stage and other clinical information for the cancer patients are provided in Table 13. The samples tested from these patients are listed in Table 14.

Materials and Methods

Patient Samples

All samples for this study were obtained according to protocols approved by the Institutional Review Boards of the Johns Hopkins Medical Institutions (Baltimore, MD), McGill University (Montreal, QC, Canada), Gothenburg University (Gothenburg, Sweden), BioreclamationIVT (Chestertown, MD), Memorial Sloan Kettering Cancer Center (New York City, NY), and the Danish Scientific Ethical Committee (Copenhagen, Denmark). Demographic, clinical, and pathologic staging data were collected for each patient with cancer are listed in Table 13. The average age of 714 women without cancer used for Pap brush analysis was 34 (range: 17 to 67 years). The average age of 125 women without cancer used for Tao brush analysis was 29 (range: 18 to 74 years). All histopathology was re-reviewed by board-certified pathologists. DNA was extracted from tumors, Pap smear fluid, and plasma as described elsewhere (see, e.g., Kinde et al., 2011 *Proc Natl Acad Sci USA* 108:9530-9535; and Bettegowda et al., 2014 *Sci Transl Med* 6:224ra224). For intrauterine sampling, Tao Brush IUMC Endometrial Sampler (Cook Medical Inc., Bloomington, IN) was gently inserted to the level of the uterine fundus. The outer sheath was then pulled back and the brush was rotated 360 degrees clockwise and then counterclockwise. Then the outer sheath was pushed again and the device was removed. The sample was placed into Thin-Prep buffer, from which DNA was purified using an AllPrep DNA kit (Qiagen, Germany) according to the manufacturer's instructions. Purified DNA from all samples was quantified as described elsewhere (see, e.g., Rago et al., 2007 *Cancer research* 67:9364-9370).

Healthy controls included patients with normal cytology findings on Pap smears and no history of gynecologic tumors. Ovarian cancer patients with history of tubal ligation were excluded from the study.

Somatic Mutation Detection and Analysis

DNA from Pap smear fluid, Tao brush samples, or primary tumors was amplified in three multiplex PCR reactions consisting of 139 primer pairs that were designed to amplify 110 to 142 bp segments, as described elsewhere (see, e.g., Wang et al., 2016 *Elife* 5). These segments contain regions of interest from the following 18 genes: AKT1, APC, BRAF, CDKN2A, CTNNB1, EGFR, FBXW7, FGFR2, KRAS, MAPK1, NRAS, PIK3CA, PIK3R1, POLE, PPP2R1A, PTEN, RNF43, and TP53. For each sample, three multiplex reactions, each containing non-overlapping amplicons, were performed, as described elsewhere (see, e.g., Wang et al., 2016 *Elife* 5). Each sample was assessed in two duplicate wells. DNA from plasma was amplified in two multiplex PCR reactions consisting of 61 primer pairs that were designed to amplify 67 to 81 bp segments. Each sample was assessed in six duplicate wells. These segments contained regions of interest from the following genes: AKT1, APC, BRAF, CDKN2A, CTNNB1, EGFR, FBXW7, FGFR2, GNAS, HRAS, KRAS, NRAS, PIK3CA, PPP2R1A, PTEN, and TP53.

Safe-SeqS, an error-reduction technology for detection of low frequency mutations (see, e.g., Kinde et al., 2011 *Proc Natl Acad Sci USA* 108:9530-9535), was used for all sequencing analyses. One primer in each pair included a unique identifier sequence (UIDs), consisting of 14 degenerate bases with an equal chance of being an A, C, T, or G. High quality sequence reads were selected based on quality scores, which were generated by the sequencing instrument to indicate the probability a base was called in error. Reads from a common template molecule were then grouped based on the UIDs that were incorporated as molecular barcodes. Artifactual mutations introduced during the sample preparation or sequencing steps were reduced by requiring a mutation to be present in >90% of reads in each UID family (i.e., to be scored as a "supermutant") (see, e.g., Kinde et al., 2011 *Proc Natl Acad Sci USA* 108:9530-9535).

Statistical Analysis of Sequencing Data

All Pap brush and Tao brush samples were analyzed using a mutant allele fraction (MAF)-based approach. Mutations that met one of the two following criteria were considered (i) present in the COSMIC database (see, e.g., Forbes et al., 2017 *Nucleic Acids Res* 45:D777-D783), or (ii) predicted to be inactivating in tumor suppressor genes (nonsense mutations, out-of-frame insertions or deletions, canonical splice site mutations). Synonymous mutations, except those at exon ends (see, e.g., Jung et al., 2015 *Nat Genet* 47:1242-1248), and intronic mutations, except for those at splice sites, were excluded. The MAF in the sample of interest was first normalized based on the distribution of MAFs for the same mutation in the control group. Following this mutation-specific normalization, a p-value was obtained by comparing the MAF of each mutation in each well with a reference distribution of MAFs built from normal controls where all mutations were included. The Stouffer's Z-score was then calculated from the p-values of two wells, weighted by their number of UIDs.

A sample was scored as positive when any of its mutations had a value above the corresponding thresholds for any of the following three criteria: 1) the difference between its MAF and the corresponding maximum MAF observed for that mutation in the controls, 2) the ratio of its Stouffer's Z-score to the average of the highest six non-zero Stouffer's Z-scores for the same mutation in the controls, or 3) its Stouffer's Z-score alone when the mutation was not seen in the controls.

Sensitivity and specificity were obtained from a 10-fold cross validation. In each round, Pap brush samples from 90% of the 714 women without cancer served as controls. In each of the ten rounds, the remaining 10% of the Pap brush samples from women without cancer were scored to obtain specificity. All other samples were scored once in each of the 10 rounds for a total of ten times, and were considered to be positive overall if they scored positive more than half of the time (i.e. 5 or more rounds). The mutations in the samples that scored positive are listed in Table 15.

The analysis of the plasma samples was done using an empirical Bayes approach. A Beta distribution was first fitted based on the MAFs in a set of controls using maximum likelihood estimation. The MAFs of all mutations were then adjusted accordingly. A p-value was calculated for each mutation in each well by comparison to the distribution of adjusted MAFs among the controls. An overall p-value for every mutation was obtained as the product of the p-values from all 6 wells. Sensitivity and specificity were obtained from a 10-fold cross validation. In each round, normal plasma samples from 192 healthy individuals served as controls, as for the Pap brush samples described above. A sample was considered to be positive if it was positive in 5 or more rounds. The mutations in the samples that scored positive are listed in Table 17.

Confidence intervals for sensitivities and specificities were calculated assuming binomial distributions with the actual sensitivities and specificities set as the corresponding success probabilities.

Aneuploidy Detection and Analysis

For each sample, a single primer pair was used to amplify ~38,000 loci of long interspersed nucleotide elements (LINEs) throughout the genome (see, e.g., Kinde et al., 2012 PLoS One 7:e41162). Massively parallel sequencing was performed on Illumina instruments. One of the primers include an UID to as a molecular barcode as described above to reduce error rates associated with PCR and sequencing. The sequencing data were then processed to identify significant single chromosomal arm gains or losses, as well as allelic imbalance on 39 chromosome arms, using Within-Sample AneupLoidy DetectiOn (WALDO) software (see, e.g., Example 6). WALDO incorporates a support vector machine (SVM) to discriminate between aneuploid and euploid samples. The SVM was trained using 3150 synthetic aneuploid samples with low neoplastic content and 677 euploid peripheral white blood cell (WBC) samples. A sample was scored as positive (aneuploid), if the SVM discriminant score exceeded a given threshold, or if significant gains of chromosome arms 7q and 8q were observed.

These chromosome arms are frequently gained in both endometrial and ovarian cancers (see, e.g., Cancer Genome Atlas Research, 2013 Nature 497:67-73; and Cancer Genome Atlas Research, 2011 Nature 474:609-615).

Results

Evaluation of Somatic Mutations in Pap Brush Samples from Patients with Endometrial or Ovarian Cancer The amount of DNA shed from neoplastic cells was expected to be a minor fraction of the total DNA in the Pap brush samples, with most DNA emanating from normal cells. Therefore, a sensitive, PCR-based error-reduction technology, called Safe-Sequencing System (Safe-SeqS), was used to identify mutations in these samples (see Methods and Materials). In brief, primers were designed to amplify 139 regions, covering 9,392 distinct nucleotide positions within the 18 genes of interest (Table 39). Three multiplex PCR reactions, each containing non-overlapping amplicons, were then performed on each sample.

This assay was applied to Pap brush samples of 382 women with endometrial cancer, 245 women with ovarian cancer, and 714 women without cancer. It was found that 81% of the patients with endometrial cancers had detectable mutations, including 78% of patients with early-stage (stages I and II) disease and 89% of the patients with late-stage disease (stages III and IV; Table S2). The most commonly mutated genes were PTEN (64%), TP53 (41%), PIK3CA (31%), PIK3R1 (29%), CTNNB1 (21%), KRAS (18%), FGFR2 (11%), POLE (9%), APC (9%), FBXW7 (8%), RNF43 (7%), and PPP2R1A (5%). The median mutant allele fraction (MAF) was 4.0% (95% confidence interval (CI): 3.5% to 4.5%) (Table 15).

Figure 20:
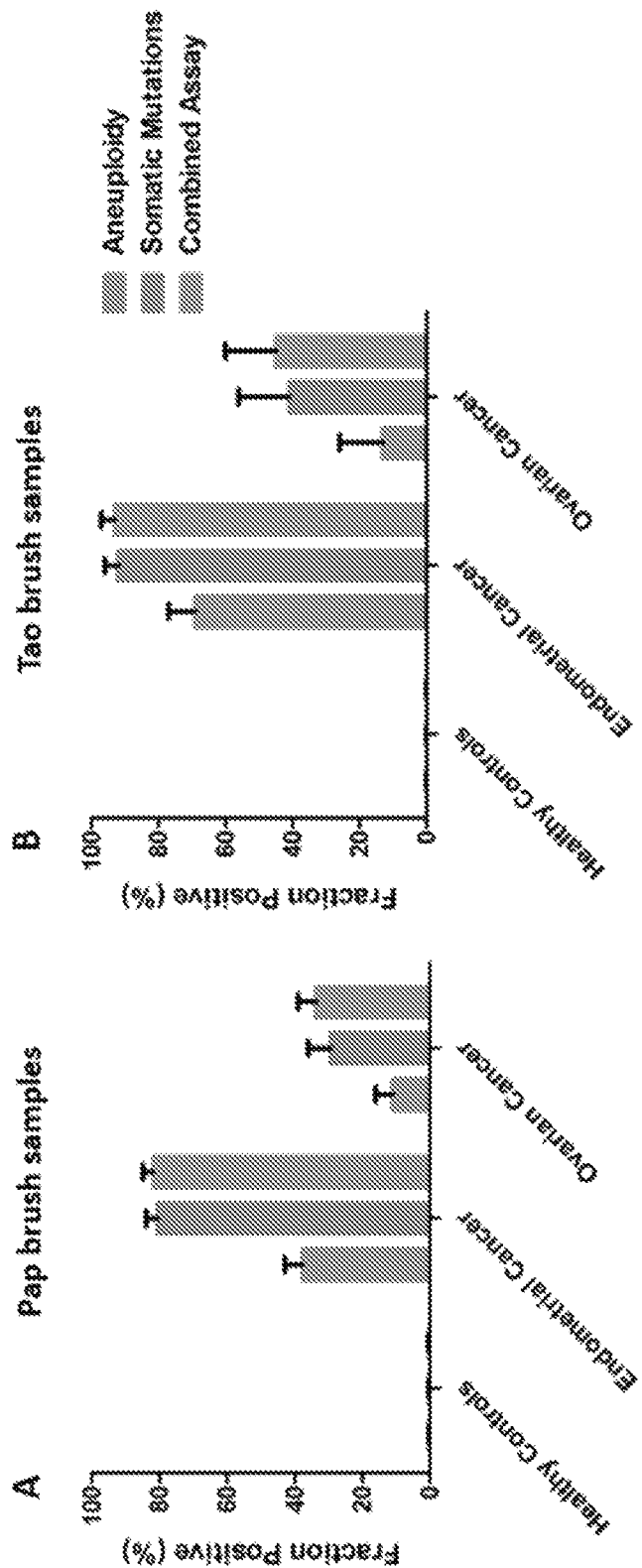
FIG. 20 contains graphs showing detection of aneuploidy and somatic mutations (PapSEEK) in Pap brush (A) and Tao brush samples (B) from healthy controls and patients with endometrial and ovarian cancers. Error bars represent 95% confidence intervals.

Twenty-nine percent of 245 ovarian cancer patients harbored detectable mutations in their Pap brush samples. These included 28% of patients with early-stage disease and 30% of patients with late-stage disease (Table 14). The most commonly mutated genes were TP53 (74%). The median MAF was 0.54% (95% CI: 0.4% % to 0.87%) (Table 15). This assay was also applied to 714 women without cancer and found that 1.3% had a detectable mutation, yielding a specificity of 98.7% (95% CI: 97.6% to 99.4%) (FIG. 20).

Tumor tissue was available from 83% and 84% of endometrial and ovarian cancer patients who donated Pap brush samples, respectively. Using the same multiplex assay applied to the Pap brush samples, a driver gene mutation was identified in 98% and 82% of the endometrial and ovarian cancer tissues, respectively (Table 16). Of the endometrial and ovarian cancer patients with a driver mutation identified in their primary tumor, 85% and 29%, respectively, had mutations in their Pap brush samples. Conversely, of the positive Pap brush samples from patients with endometrial or ovarian cancers, 93% contained at least one driver gene mutation that was identical to that observed in their primary tumor. The fraction of Pap brush samples with mutations that were also found in the primary tumors was higher in endometrial cancer patients (97%) than in ovarian cancer patients (73%).

Evaluation of Aneuploidy in Pap Brush Samples

In addition to somatic mutations, aneuploidy is found in the great majority of endometrial and ovarian cancers (see, e.g., Cancer Genome Atlas Research, 2013 Nature 497:67-73; Cancer Genome Atlas Research, 2011 Nature 474:609-615; and Vogelstein et al., 2013 Science 339:1546-1558). To assess aneuploidy, a PCR-based was used method to amplify ~38,000 loci of long interspersed nucleotide elements (LINEs) with a single primer pair. LINEs have spread throughout the genome via retrotransposition and are found on all 39 non-acrocentric autosomal arms. After sequencing, the data was processed to identify gains or losses on single chromosome arms.

Aneuploidy was detected in the Pap brush samples of 38% (n=382) of patients with endometrial cancer, including 34% and 51% of those with early- and late-stage disease, respectively (Table 14). Aneuploidy was also detected in the Pap brush samples of 11% (n=245) of ovarian cancer patients, including 15% and 9.3% of those with early- and late-stage disease, respectively (Table 14). In endometrial and ovarian cancers, the most commonly altered arms were 4p, 7q, 8q, and 9q. In contrast, when the aneuploidy assay was applied to the Pap brush samples of 714 women without cancer, only one woman was positive (FIG. 20).

Figure 21:
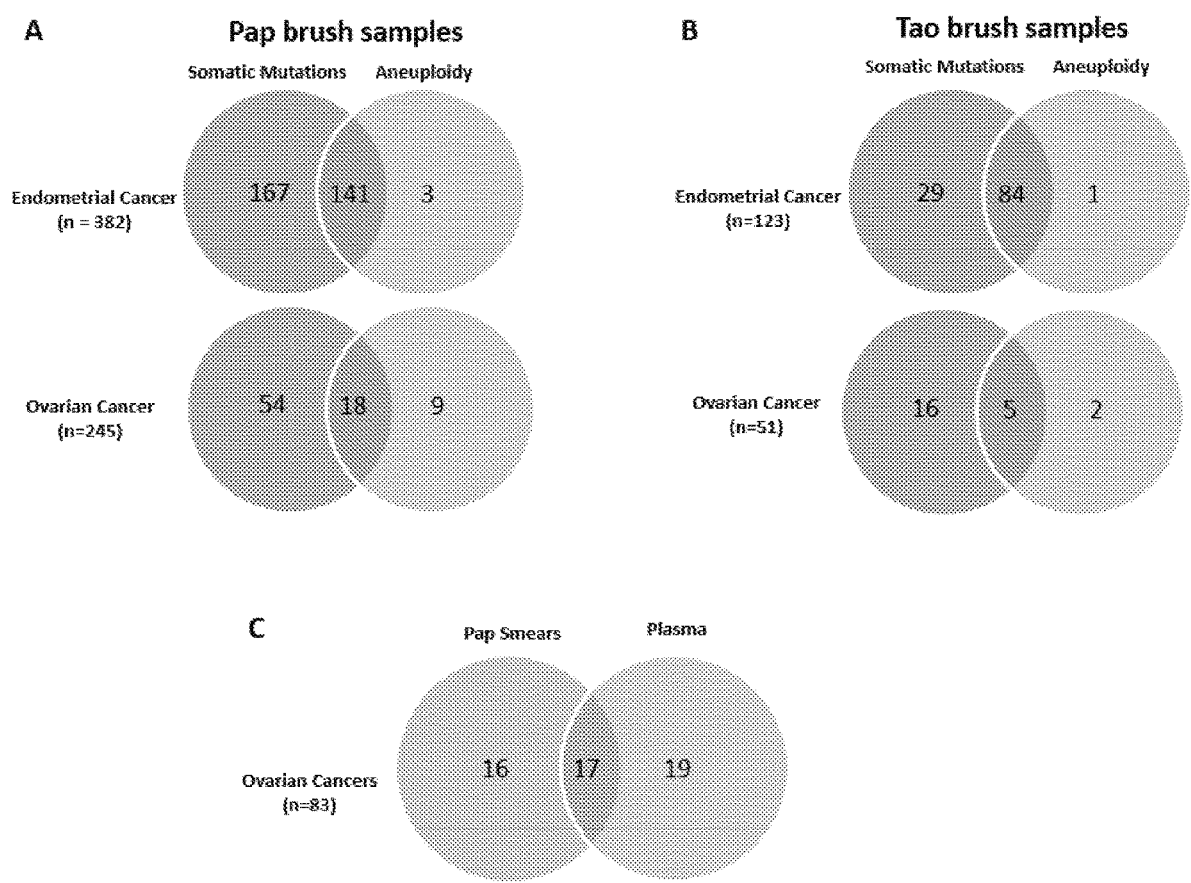
FIG. 21 contains Venn diagrams showing that combined testing for somatic mutations and aneuploidy increased sensitivity for both ovarian and endometrial cancers, in the Pap (A) as well as the Tao brush (B) samples. For ovarian cancer, combined testing of Pap brush and plasma samples also increased sensitivity compared to testing either sample type alone (C).
Figure 22:
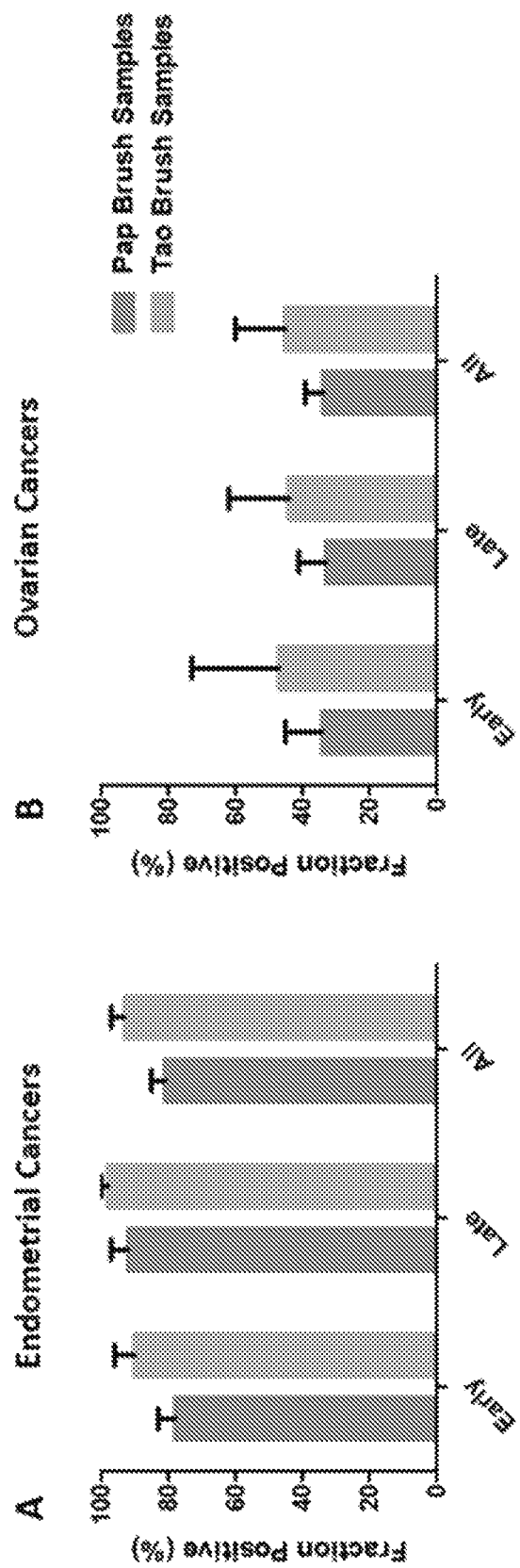
FIG. 22 contains graphs showing detection of endometrial (A) or ovarian cancers (B) in Pap or Tao brush samples with PapSEEK, by stage. Error bars represent 95% confidence intervals.

Even if a sample does not contain a genetic alteration in one of the 18 genes assessed, it might still be aneuploid and detectable by methods provided herein. This conjecture was supported by identification of six patients (three with endometrial and three with ovarian cancers) who had no mutations in their Pap brush samples or primary tumors (when available), but whose Pap brush samples displayed aneuploidy. The combined test incorporating the above-described assays for mutations plus aneuploidy, was dubbed "PapSEEK." PapSEEK scores a sample as positive if it either harbors a mutation or an abnormal chromosome arm number. Eighty-one percent of the Pap brush samples from women with endometrial cancers were PapSEEK-positive, including 78% of patients with early-stage disease and 92% of patients with late-stage disease (FIG. 21 and FIG. 22). Thirty-three percent of the Pap brush samples from women with ovarian cancers were PapSEEK-positive, including 34% of patients with early-stage disease and 33% of patients with late-stage disease (FIG. 21 and FIG. 22). Only 1.4% of the Pap brush samples from 714 women without cancer were PapSEEK-positive, yielding a specificity of 98.6% (95% CI: 97.4% to 99.3%) (FIG. 20).

Evaluation of Tao Brush Samples from Patients with Ovarian or Endometrial Cancers A more direct, minimally invasive sampling of the intrauterine cavity (rather than the endocervical canal) might increase the sensitivity of this approach for detecting gynecologic cancers. To explore this possibility, intrauterine samples were collected using a Tao brush, which is a flexible, narrow brush covered by a retractable outer sheath that allows direct sampling of the entire endometrial cavity without injury to the myometrium or contamination from the cervical canal. It has been approved by the Food and Drug Administration for endometrial sampling and can be used in an outpatient setting without the need for anesthesia. Advantageous to a potential screening test, it is well-tolerated by patients.

PapSEEK was applied to Tao brush samples collected from 123 patients with endometrial cancers, 51 patients with ovarian cancers, and 125 women without cancer. Ninety-three percent of the Tao brush samples from endometrial cancer patients contained genetic alterations detected by PapSEEK, including 90% and 98% of patients with early-, and late-stage disease, respectively (FIG. 22). The most commonly mutated genes in the Tao brush samples were PTEN (63%), TP53 (42%), PIK3CA (36%), PIK3R1 (20%), KRAS (17%), CTNNB1 (15%), FGFR2 (15%), RNF43 (11%), PPP2R1A (7%), POLE (7%), and FBXW7 (6%), similar to that observed in the Pap brush samples. The median MAF was 24.7% (95% CI: 21.3% to 26.9%), considerably higher than observed in the Pap brush samples, in which the median MAF was 4.0% (95% CI: 3.5% to 4.5%; Table S4).

Genetic alterations detectable by PapSEEK were found in 45% (95% CI: 31% to 60%) of the Tao brush samples from 51 women with ovarian cancers, including 47% and 44% of patients with early-, and late-stage, respectively (FIG. 22). The most commonly mutated genes were TP53 (86%), consistent with the data on Pap brush samples. The median MAF was 0.88% (95% CI: 0.61% to 2.8%), which was higher than in the Pap brush samples (median 0.54%; 95% CI: 0.4% to 0.87%; Table 15).

PapSEEK was applied to the Tao brush samples from 125 women without cancer. None (0%) of these women tested positive for mutations, yielding a specificity of 100% (95% CI: 97% to 100%; FIG. 20).

Tao brush and Pap brush samples were available from the same women in 145 patients (103 with endometrial and 42 with ovarian cancers). In endometrial cancers, PapSEEK was positive in 91% of the Tao brush samples and in 81% of the Pap brush samples (p=0.02, mid-P McNemar test). Similarly, the fraction of ovarian cancer patients with a positive PapSEEK test was higher for Tao brush (45%) than for Pap brush (17%; p=0.002, mid-P McNemar test; Table 13).

Tumor tissue was available from 90% and 88% of patients with endometrial and ovarian cancers who donated Tao brush samples, respectively. PapSEEK identified driver gene mutations in 97% and 80% of the endometrial and ovarian cancer tissues, respectively (Table 16). Of the endometrial and ovarian cancer patients with a driver mutation identified in their primary tumor, 93% and 42%, respectively, had mutations detectable in their Tao brush samples. Conversely, of the positive Tao brush samples from patients with endometrial or ovarian cancers, 91% contained at least one driver gene mutation that was identical to that observed in their primary tumor. The fraction of Tao brush samples with mutations that were also found in the primary tumors was higher in endometrial cancer patients (97%) than in ovarian cancer patients (53%).

Evaluation of ctDNA in Patients with Ovarian Cancers

Ovarian cancers that were inaccessible by Pap or Tao brush sampling due to anatomical or other factors might be detectable by circulating tumor DNA (ctDNA) in plasma. This was tested in 83 ovarian cancer patients who had donated both Pap brush and plasma samples. Due to the smaller size of degraded ctDNA, primers were designed to amplify short 67 to 81 bp DNA fragments, covering 1,931 distinct nucleotide positions within 16 genes of interest. To demonstrate the specificity of this assay, it was applied it to plasma samples from 192 healthy individuals; none (0%) tested positive, yielding a specificity of 100% (95% CI: 98% to 100%).

Figure 23:
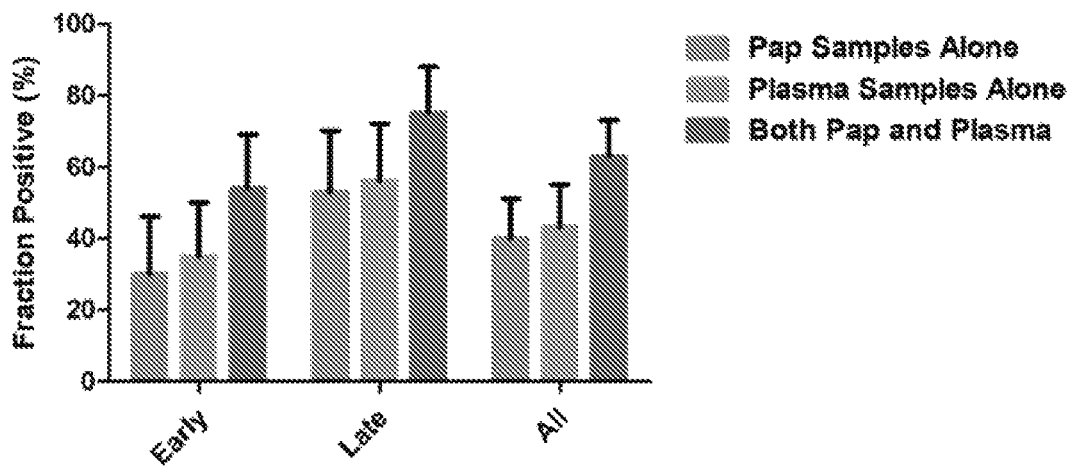
FIG. 23 contains a graph showing detection of ovarian cancer in Pap and plasma samples. Error bars represent 95% confidence intervals.

It was found that 43% (95% CI: 33% to 55%) of the plasma from the 83 patients with ovarian cancers had detectable ctDNA. The mutations detected are listed in Table 17. As expected, the sensitivity for ctDNA in plasma was higher in patients with late-stage tumors than early-stage tumors (56% vs. 35%; FIG. 23). For early-stage disease, the median MAF in the plasma was 0.85%, which was less than the median MAF (5.7%) in the Pap smears. At least one of the mutations identified in the plasma could be identified in 88% of the corresponding primary tumor.

In the Pap brush samples from this same cohort of 83 patients, 40% were positive by the PapSEEK test. The individuals scoring positive in their Pap brush and plasma samples only partially overlapped (FIG. 21). As a result, 63% (95% CI: 51% to 73%) of patients were positive with at least one of the two tests. Those who tested positive included 54% of patients with early-stage disease and 75% with late-stage disease, respectively (Table 13, FIG. 23).

DISCUSSION

Figure 24:
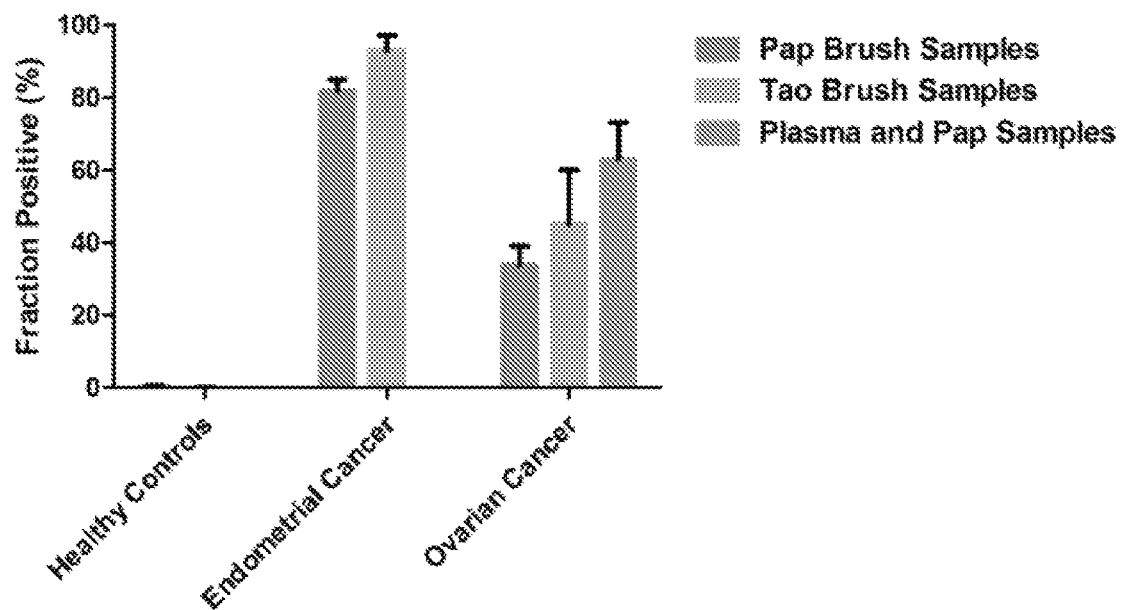
FIG. 24 contains a graph showing detection of endometrial and ovarian cancers with PapSEEK in the Pap brush, Tao brush, and plasma samples. Error bars represent 95% confidence intervals.

As described herein, a multiplex PCR-based test (PapSEEK) was designed and applied to detect genetic alterations in Pap brush or Tao brush samples. These samples are minimally invasively and conveniently obtained during routine office visits. The majority of endometrial cancers could be detected with PapSEEK: 93% with Tao Brush and 81% with Pap brush. A substantial fraction of ovarian cancers could also be detected with PapSEEK: 45% with Tao Brush and 33% with Pap brush. The specificity of PapSEEK was high, with only 0% and 1.4% of women without cancer testing positive with Tao and Pap brush samples, respectively (FIG. 24). It was also demonstrated that assays for ctDNA in plasma could be used in conjunction with PapSEEK on Pap brush samples, increasing the sensitivity of detecting ovarian cancer to 63%.

It was notable that the sensitivity for detecting early-stage ovarian cancers was as high as that for late-stage disease (47% vs. 44% for Tao; 34% vs. 33% for Pap). Without wishing to be bound by theory, there are at least two possible explanations for this unexpected but enticing finding. First, it has been shown that some ovarian cancers originate in the fallopian tubes, which could facilitate their early detection with PapSEEK when tumor cells are shed into the uterine cavity. Second, in late-stage tumors, the fallopian tubes are often matted and obliterated by the disease and thus less likely to serve as a conduit for tumor cells to pass into the uterus or endocervical canal. In this setting, the addition of ctDNA analysis in plasma to Pap or Tao brush sampling may be particularly beneficial.

A subset of samples tested herein was composed of high-grade, early-stage cancers. Currently available diagnostic modalities have low sensitivities for these lesions (see, e.g., Fishman et al., 2005 *Am J Obstet Gynecol* 192:1214-1221; Sharma et al., 2012 *Ultrasound Obstet Gynecol* 40:338-344; and Hamilton et al., 2006 *British journal of cancer* 94:642-646). Though the high-grade subtypes comprise only about 10% of incident endometrial cancers, they account for more than 40% of deaths from the disease (see, e.g., Moore et al., 2011 *Clin Obstet Gynecol* 54:278-291). As these high-grade cancers often arise from a background of atrophic endometrium and can metastasize prior to visible abnormalities on imaging, transvaginal ultrasound has a limited role in screening and early diagnosis. Thus it was encouraging that PapSEEK detected 85% (n=34) and 89% (n=9) of high-grade endometrial cancers confined to the endometrium in the Pap and Tao brush samples, respectively. In the case of ovarian cancers, the tested cohort included only a small number of early-stage, high-grade cases, consistent with the unfortunate fact that these cancers are often diagnosed only at advanced stages. Nevertheless, the finding that 36% (n=11) were positive with combined Pap and plasma sample testing, and that 80% (n=5) were positive in Tao brush samples, is notable.

The study described herein was retrospective. The samples that were examined were derived from patients with known cancers, even though a substantial fraction was from patients with early-stage lesions. In a screening setting, the cancers would advantageously be at an earlier stage, and the sensitivities for detection would be expected to be closer to the sensitivity for early-stage cancers observed in the present study. Moreover, the age ranges of the controls and cases are typically better matched in a prospective study than in the present retrospective study. Some of the ovarian cancer patients who had mutations detectable in their Pap brush or Tao brush samples did not have the identical mutations in their primary tumors. This was not an issue with endometrial cancers, wherein at least one mutation in the brush samples was nearly always (97%) found in the corresponding primary tumors. But this phenomenon was observed in ovarian cancer patients, particularly with the Tao brush. At least one mutation identifiable in the Pap brush could be identified in 73% of the corresponding primary ovarian tumors, while the same was true for only 53% of the Tao brush samples.

Without wishing to be bound by theory, one possible explanation for the discordance between the mutations in brush samples and ovarian cancers from the same patients is that the assay detects mutations that do not exist in vivo, representing technical artifacts. It is not believed that this is likely, however, given that the specificity of the assays was 100% and 99% in Tao brush and Pap brush samples, respectively, from women without cancer. Another possible explanation is tumor heterogeneity. Only a small part of the tumors that were analyzed was sampled and sequenced, and the additional mutations found in the Pap smear or intrauterine samples could represent mutations from other parts of the tumor. It is also possible that some mutations were from small synchronous endometrial cancers or early, premalignant endometrial lesions that were unnoted by the pathologist. A significant proportion of women with ovarian cancer have synchronous endometrial cancer, with risk factors including Lynch syndrome, polycystic ovarian syndrome, perimenopause, obesity, nulliparity, and unopposed estrogen replacement therapy (see, e.g., Al Hilli et al., 2012 *Gynecologic oncology* 125:109-113; Walsh et al., 2005 *Obstetrics and gynecology* 106:693-699; Zaino et al., 2001 *Gynecologic oncology* 83:355-362; and Song et al., 2014 *Int J Gynecol Cancer* 24:520-527).

Though tumor heterogeneity, or multiple synchronous tumors are feasible explanations that are often used to explain discordances in liquid biopsy studies, without wishing to be bound by theory, it is possible that clonal expansions of non-malignant cells may play a role in the present observations. Clonal proliferations that are not considered neoplastic have been described in the uterine lavage, bone marrow, skin, and other tissues (see, e.g., Steensma et al., 2015 *Blood* 126:9-16; Coombs et al., 2017 *Cell Stem Cell* 21(3):374-382; Young et al., 2016 *Nat Commun* 7:12484; Krimmel et al., 2016 *Proc Natl Acad Sci USA* 113:6005-6010; and Nair et al., 2016 *PLoS Med* 13:e1002206). Of particular interest are the clonal proliferations of endometrial cells that cause endometriosis, a sometimes debilitating condition that affects millions of women. It has recently been shown that these lesions, which can occur throughout the abdomen and are derived from endometrium, are clonal proliferations that can be driven by the same mutations detected in endometrial cancers (see, e.g., Anglesio et al., 2017 *N Engl J Med* 376:1835-1848). Without wishing to be bound by theory, it is possible that the hormonal and physiologic changes contributing to or resulting from ovarian cancers stimulate or select for such clonal proliferations in the endometrial lining. On one hand, this possibility argues against the exquisite specificity that is the conceptual basis for all liquid biopsies. On the other hand, it could actually enhance the sensitivity of detection of ovarian cancers, without diminishing specificity, if large clonal proliferations are almost exclusively found in women with gynecologic malignancies. Clonal proliferations that account for >0.03% of the total cells in the endometrial lining are detectable by methods provided herein.

Example 5: Detecting Urologic Malignancies Using a Combination Approach Cancer Screening Tests According to the American Cancer Society, 79,030 new cases of bladder cancer (BC) and 18,540 deaths are estimated to occur in the United States alone in 2017 (see, e.g., Siegel et al., 2017 *CA Cancer J Clin* 67:7-30), with many BC patients suffer with multiple relapses prior to progression, providing ample lead-time for early detection and treatment prior to metastasis (see, e.g., Netto, 2013 *Adv Anat Pathol* 20:175-203). Urine cytology and cystoscopy with transurethral biopsy (TURB) are currently the gold standard for diagnosis and follow-up in bladder cancer. While urine cytology has value for the detection of high-grade neoplasms, it is unable to detect the vast majority of low-grade tumors (see, e.g., Netto et al., 2016 *Urol Clin North Am* 43:63-76; Lotan et al., 2003 *Urology* 61:109-18; and Zhang et al., 2016 *Cancer Cytopathol* 124:552-564). This fact, together with the high cost and invasive nature of repeated cystoscopy and TURB procedures, have led to many attempts to develop novel noninvasive strategies including urine or serum based genetic and protein assays for screening and surveillance (see, e.g., Kawauchi et al., 2009 *Hum Pathol* 40:1783-1789; Kruger et al., 2003 *Int J Oncol* 23:41-48; Skacel et al., 2003 *J Urol* 169:2101-2105; Sarosdy et al., 2006 *J Urol* 176:44-47; Moonen et al., 2007 *Eur Urol* 51:1275-80; Fradet et al., 1997 *Can J Urol* 4:400-405; Yafi et al., 2015 *Urol Oncol* 33:66.e25-66.e31; Serizawa et al., 2010 *Int J Cancer* 129(1):78-87; Kinde et al., 2013 *Cancer Res* 73:7162-7167; Hurst et al., 2014 *Eur Urol* 65:367-369; Wang et al., 2014 *Oncotarget* 5:12428-12439; Ralla et al., 2014 *Crit Rev Clin Lab Sci* 51:200-231; Ellinger et al., 2015 *Expert Rev Mol Diagn* 15:505-516; Bansal et al., 2014 *Clin Chim Acta* 436:97-103; Goodison et al., 2012 *PLoS One* 7:e47469; and Allory et al., 2014 *Eur Urol* 65:360-366). Currently available U.S. Food and Drug Administration (FDA) approved assays include ImmunoCyt test (Scimedx Corp), nuclear matrix protein 22 (NMP22) immunoassay test (Matritech), and multitarget FISH (UroVysion) (see, e.g., Kawauchi et al., 2009 *Hum Pathol* 40:1783-1789; Kruger et al., 2003 *Int J Oncol* 23:41-48; Skacel et al., 2003 *J Urol* 169:2101-2105; Sarosdy et al., 2006 *J Urol* 176:44-47; Moonen et al., 2007 *Eur Urol* 51:1275-80; Fradet et al., 1997 *Can J Urol* 4:400-405; and Yafi et al., 2015 *Urol Oncol* 33:66.e25-66.e31). Sensitivities between 62% and 69% and specificities between 79% and 89% have been reported for some of these tests; however, due to assay performance inconsistencies, cost or required technical expertise, integration of such assays into routine clinical practice has not yet occurred. Further, because urine cytology is relatively insensitive for the detection of recurrence, cystoscopies are performed as often as every three months in such patients in the U.S., and the cost of managing these patients is in aggregate higher than the cost of managing any other type of cancer, and amounts to 3 billion dollars annually (see, e.g., Netto et al., 2010 *Pathology* 42:384-394).

Further, the annual incidence of these upper tract urothelial carcinomas (UTUCs) in Western countries is 1-2 cases per 100,000, but occurs at a much higher rate in populations exposed to aristolochic acid (AA) (Chen et al., 2012 *Proc Natl Acad Sci USA*, 109(21): 8241-8246; and Grollman et al., 2013 *Environ Mol Mutagen*, 54(1): 1-7; and Lai et al., 2010 *J Natl Cancer Inst*, 102(3):179-186). Nephroureterectomy can be curative for patients with UTUC when it is detected at an early stage (Li et al., 2008 *Eur Urol.* 54(5): 1127-34). However, these cancers are largely silent until the onset of overt clinical symptoms, typically hematuria, and as a result, most patients are diagnosed only at an advanced stage (Roupret et al., 2015 *Eur Urol.* 68(5):868-79). Diagnostic tests for the detection of early-stage UTUC are not currently available.

A broadly applicable approach for non-invasive detection of cancer (e.g., an early-stage cancer such as BCs or UTUCs) could be both medically and economically important.

Figure 25:
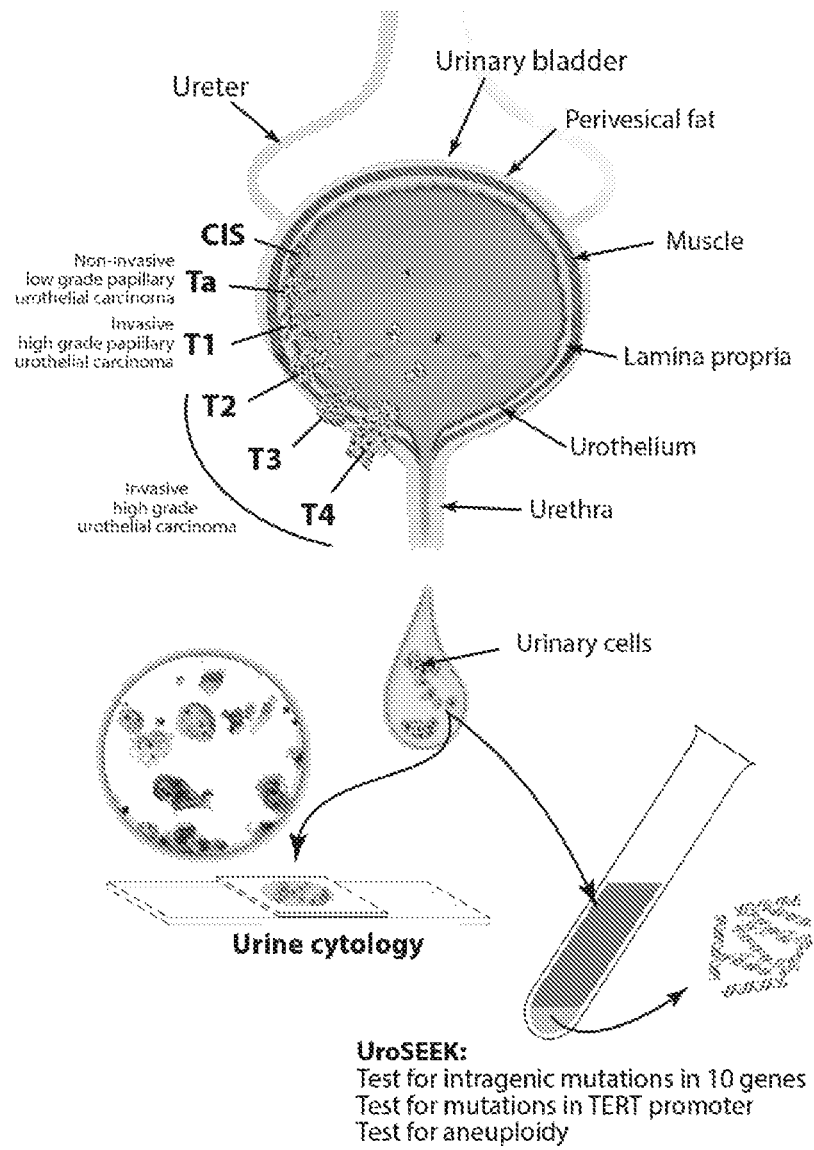
FIG. 25 contains a schematic drawing of an exemplary approach used to evaluate urinary cells in this study.
Figure 31:
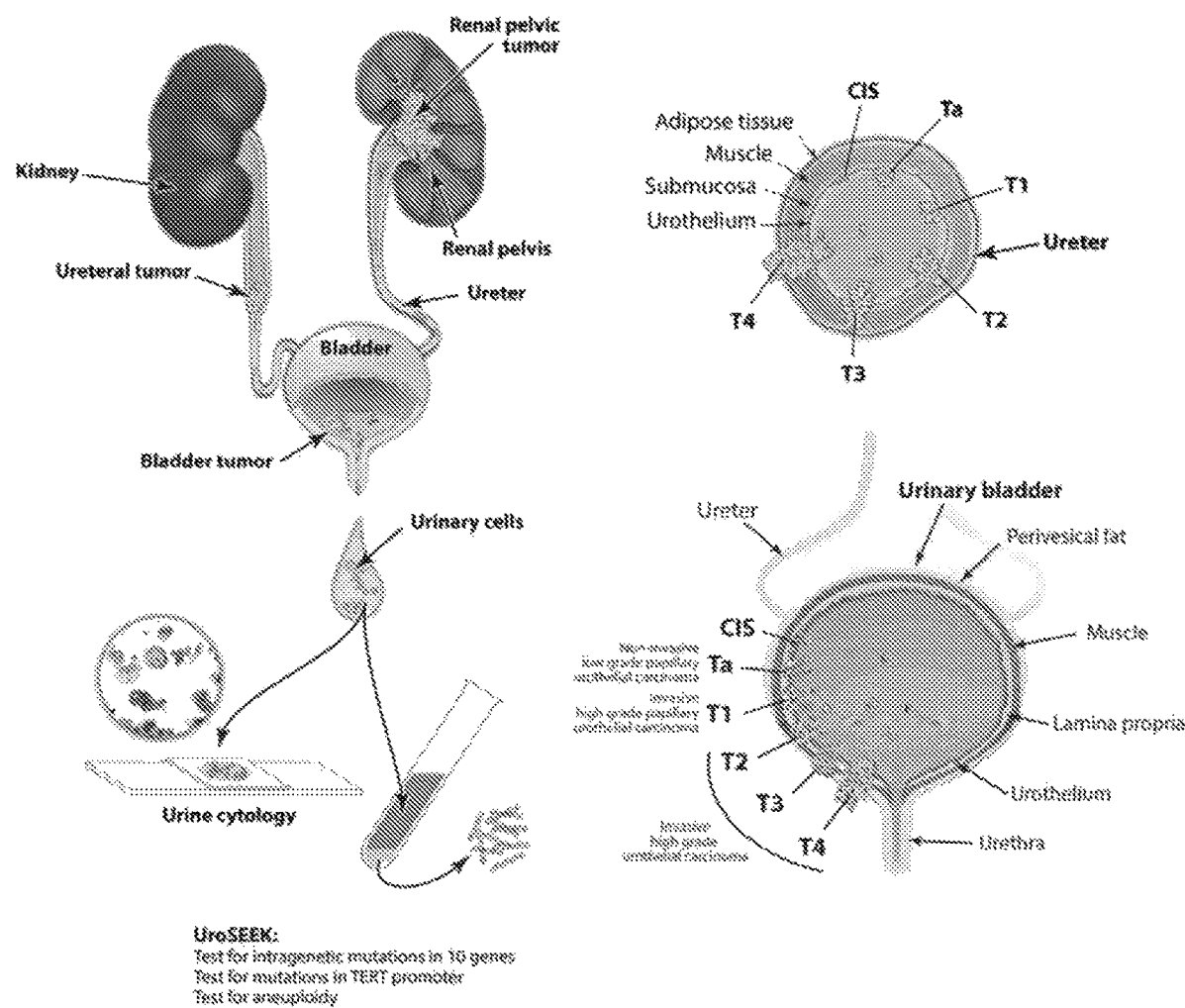
FIG. 31 contains a schematic diagram of an exemplary non-invasive detection of upper tract urothelial cancer (UTUC) through genetic analysis of urinary cell DNA. Upper urinary tract tumors arise in the renal pelvis and/or ureter and are in direct contact with urine. Urine contains a mixture of normal cells that are constitutively shed from various sites along the urinary system, along with malignant cells when present (blue). The UroSEEK assay relies on mutational analyses of genes frequently mutated in urinary cancers along with a determination of chromosome losses and gains.

This Example describes a new blood test, called UroSEEK, which addresses the problematic issues described above. In this test, DNA from urine samples can be used in an assay (e.g., a PCR-based, multiplex test) to simultaneously assess genetic alterations that commonly occur in BCs or UTUCs. A schematic of the approach used in the bladder cancer study is provided in FIG. 25, and a schematic of the approach used in the UTUC study is provided in FIG. 31.

Materials and Methods

Patients and Samples

Urine samples were collected prospectively from patients in four participating institutions including Johns Hopkins Hospital, Baltimore, MD, USA; A.C. Camargo Cancer Center, Sao Paulo, Brazil; Osaka University Hospital, Osaka, Japan; and Hacettepe University Hospital, Ankara, Turkey. The study was approved by the institutional Review Boards of Johns Hopkins Hospital and all other participating institutions. Proper material transfer agreements were obtained. Patients with a known history of malignancy other than bladder cancer were excluded from the study. The study included two cohorts of patients.

The Early Detection cohort comprised 570 patients who were referred to a urology clinic in one of the above hospitals because of hematuria or lower urinary tract symptoms (Table 18). The second cohort (322 patients) represented patients with prior established diagnosis of Bladder Cancer (BC) who are on surveillance for disease recurrence (Surveillance Cohort). These patients' primary tumors harbored mutations in at least one of the 11 genes assessed through the multiplex or singleplex assays. A minimum follow-up of 12 months was from date of urine collection was required for cases with no evidence of incident or recurrent tumors in the Early Detection or Surveillance cohorts, respectively. Urine samples were collected prior to any procedures, such as cystoscopy, performed during the patients' visits. A total of 892 urine samples were analyzed in the study, composed of two type of samples. The first was residual urinary cells after processing with standard BD SurePath™ liquid-based cytology protocols (Becton Dickinson and Company; Franklin Lakes, NJ, USA). To allow for standard-of-care, residual SurePath® fluids were kept refrigerated for 6-8 weeks prior to submission for DNA purification to allow for any potential need for repeat cytology processing of the same sample. The second sample type was composed of bio-banked fresh urine samples in which 15-25 mL of voided urine samples were stored at 4° C. for up to 60 min prior to centrifugation (10 min at 500 g) and the pellets stored at minus 80° C. prior to DNA purification. Urines from 188 healthy individuals of average age 26 were also obtained and processed identically to the bio-banked fresh urine samples.

Formalin-fixed paraffin-embedded (FFPE) tumor tissue samples from trans-urethral resections (TURB) or cystectomies were collected in 413 of the 892 cases. When several different tumors from the same patient were available (because of recurrences), the earliest tumor tissue obtained following the donation of the urine sample was used in the Early Detection Cohort. In the surveillance cohort, the tumors preceding the donation of the urine sample was used in 146 of the 322 patients. In the other 176 Surveillance cases, the earliest tissue obtained following the donation of the urine sample was used. A genitourinary pathologist reviewed all histologic slides to confirm the diagnosis and select a representative tumor area with as high tumor cellularity as possible for that case. Corresponding FFPE blocks were cored with a sterile 16-gauge needle. One to three cores were obtained per tumor and placed in 1.5 mL sterile tubes for DNA purification, as described elsewhere (see, e.g., Kinde et al., 2013 Cancer Res 73:7162-7167). Electronic medical records were reviewed to obtain medical history and follow up data in all patients.

UTUC Cohort Studied

Sequential patients with UTUC scheduled to undergo a radical unilateral nephroureterectomy at National Taiwan University Hospital in 2012-2016 were asked to participate in the study. All patients provided informed consent using the consent form and study design reviewed and approved by the Institutional Review Boards at National Taiwan University and Stony Brook University. A total of 56 UTUC patients were enrolled in the study after excluding four patients with gross hematuria and one patient with a tumor-urine DNA mismatch by identity testing. Urinary cell DNA from 188 urine samples donated by healthy individuals in the U.S. of average age 40, range 19 to 60 years old, was used to assess the specificity of the UroSEEK test. White blood cell (WBC) DNA from 94 normal individuals from the U.S. was used to evaluate the technical specificity of the PCR analysis.

Biological Samples—UTUC Cohort

Urine samples were obtained from patients one day prior to surgery. Urinary cells were isolated by centrifugation at 581 g for 10 minutes at room temperature, washed thrice in saline using the same centrifugation conditions, and stored frozen until DNA was isolated using a Qiagen kit #937255 (Germantown, MD). DNA was purified from fresh-frozen resected samples of upper tract tumors and renal cortex by standard phenol-chloroform extraction procedures as described elsewhere (see, e.g., Chen et al., 2012 Proc Natl Acad Sci USA, 109(21): 8241-8246; and Jelakovic et al., 2012 Kidney Int. 81(6):559-67). One upper urinary tract tumor per patient was analyzed; for cases with tumors at multiple sites, renal pelvic tumors were preferentially selected whenever available. Formalin-fixed, paraffin-embedded tumor samples were staged and graded by a urologic pathologist, and the presence of one or more upper tract urothelial carcinomas was confirmed by histopathology for each enrolled subject. Pertinent clinical and demographic data were obtained by a chart review of each subject. eGFR was calculated by the MDRD equation (see, e.g., Levey et al., 2006 Ann Intern Med. 145(4):247-54) and used to determine CKD stage (see, e.g., Levey et al., 2005 Kidney Int. 67(6):2089-100).

DNA Adduct Analysis

AL-DNA adduct (7-(deoxyadenosin-N6-yl) aristolactam I; dA-AL-I) levels in 2 μg of DNA from the normal renal cortex of UTUC patients were quantified by ultra-performance liquid chromatography-electrospray ionization/multistage mass spectrometry (UPLC-ESI/MSn) with a linear quadrupole ion trap mass spectrometer (LTQ Velos Pro, Thermo Fisher Scientific, San Jose, CA) as described elsewhere (see, e.g., Yun et al., 2012 Chem Res Toxicol. 2012 25 (5): 1119-31).

Mutation Analysis

Three separate assays were used to search for abnormalities in urinary cell DNA. First, a multiplex PCR was used to detect mutations in regions of ten genes commonly mutated in urologic malignancies CDKN2A, ERBB2, FGFR3, HRAS, KRAS, MET, MLL, PIK3CA, TP53, and VHL (see, e.g., Netto, 2011 Nat Rev Urol 9:41-51; Mo et al., 2007 J Clin Invest 117:314-325; Sarkis et al., 1993 J Natl Cancer Inst 85:53-59; Lin et al., 2010 Urol Oncol 28:597-602; Sarkis et al., 1994 J Urol 152:388-392; Sarkis et al., 1995 J Clin Oncol 13:1384-1390; Wu, 2005 Nat Rev Cancer 5:713-725; and Cancer Genome Atlas Research Network, 2014 Nature 507:315-322). The primer pairs used for this multiplex PCR were divided in a total of three multiplex reactions, each containing non-overlapping amplicons (see below). These primers were used to amplify DNA in 25 μL reactions as described elsewhere (see, e.g., Kinde et al., 2011 Proc Natl Acad Sci USA 108:9530-9535) except that 15 cycles were used for the initial amplification. Second, the TERT promoter region was evaluated. A single amplification primer was used to amplify a 73-bp segment containing the region of the TERT promoter known to harbor mutations in BC (see, e.g., Kinde et al., 2013 Cancer Res 73:7162-7167). The conditions used to amplify it were the same as used in the multiplex reactions described above except that Phusion GC Buffer (Thermo-Fisher) instead of HF buffer was used and 20 cycles were used for the initial amplification. The TERT promoter region could not be included in the multiplex PCR because of the high GC content of the former. PCR products were purified with AMPure XP beads (Beckman Coulter, PA, USA) and 0.25% of the purified PCR products (multiplex) or 0.0125% of the PCR products (TERT singleplex) were then amplified in a second round of PCR, as described elsewhere (see, e.g., Wang et al., 2016 Elife 5:10.7554/eLife.15175). The PCR products from the second round of amplification were then purified with AMPure and sequenced on an Illumina instrument. For each mutation identified, the mutant allele frequency (MAF) was determined by dividing the number of uniquely identified reads with mutations (see, e.g., Kinde et al., 2011 Proc Natl Acad Sci USA 108:9530-9535) by the number of total uniquely identified reads. Each DNA sample was assessed in two independent PCRs, for both the TERT promoter and multiplex assays, and samples were scored as positive only if both PCRs showed the same mutation. The mutant allele frequencies and number of UIDs listed in Table 19, Table 20, Table 22, and Table 23 refer to the average of the two independent assays.

To evaluate the statistical significance of putative mutations, DNA from white blood cells of 188 unrelated normal individuals were assessed. A variant observed in the samples from cancer patient was only scored as a mutation if it was observed at a much higher MAF than observed in normal WBCs. Specifically, the classification of a sample's ctDNA status was based on two complementary criteria applied to each mutation: 1) the difference between the average MAF in the sample of interest and the corresponding maximum MAF observed for that same mutation in a set of controls, and 2) the Stouffer's Z-score obtained by comparing the MAF in the sample of interest to a distribution of normal controls. To calculate the Z-score, the MAF in the sample of interest was first normalized based on the mutation-specific distributions of MAFs observed among all controls. Following this mutation-specific normalization, a P-value was obtained by comparing the MAF of each mutation in each well with a reference distribution of MAFs built from normal controls where all mutations were included. The Stouffer's Z-score was then calculated from the p-values of two wells, weighted by their number of UIDs. The sample was classified as positive if either the difference or the Stouffer's Z-score of its mutations was above the thresholds determined from the normal WBCs. The threshold for the difference parameter was defined by the highest MAF observed in any normal WBCs. The threshold for the Stouffer's Z-score was chosen to allow one false positive among the 188 normal urine samples studied.

Analysis of Aneuploidy.

Aneuploidy was assessed with Fast-SeqS, which uses a single primer pair to amplify ~38,000 loci scattered throughout the genome (see, e.g., Kinde et al., 2012 PLoS One 7:e41162). After massively parallel sequencing, gains or losses of each of the 39 chromosome arms covered by the assay were determined using a bespoke statistical learning method. A Support vector machine (SVM) was used to discriminate between aneuploid and euploid samples. The SVM was trained using 3150 low neoplastic cell fraction synthetic aneuploid samples and 677 euploid peripheral white blood cell (WBC) samples. Samples were scored as positive when the genome-wide aneuploidy score was >0.7 and there was at least one gain or loss of a chromosome arm.

Identity Checks.

A multiplex reaction containing 26 primers detecting 31 common SNPs on chromosomes 10 and 20 was performed using the amplification conditions described above for the multiplex PCR. The primers used for this identity evaluation are listed in FIG. 34 (Table 42) for bladder cancer cohorts and FIG. 33 (Table 41) for UTUC cohorts.

Statistical Analysis

Performance characteristics of urine cytology, UroSEEK and its three components was calculated using MedCalc statistical software (medcalc.org/calc/diagnostic_test.php).

Results

Early Detection Cohort Characteristics.

A flow diagram indicating the number of patients evaluated in this study and the major results is provided in FIG. 26.

A total 570 patients were included in the Early Detection cohort, each with one urine sample analyzed. 90% of the patients had hematuria, 3% had lower urinary tract symptoms (LUTS), and 9% had other indications suggesting they were at risk for BC. The median age of the participants was 58 years (range 5 to 89) (Table 18). 70% of the patients were male. 175 (31%) of patients developed BC after a median follow-up period of 18 months (range 0 to 40 months). For each patient who developed BC, two other patients were selected who presented with similar symptoms but did not develop BC during the follow-up period. By design, then, the fraction of cases in this cohort developing BC was higher than the fraction (5%) of patients with similar presentations that would have developed BC in standard clinical practice. The characteristics of the tumors developing in the 570 patients are summarized below.

Demographic, Clinical and Genetic Features of the Early Detection Cohort.

| Gender | n | % | Ten-gene multiplex positive | TERT positive | Aneuploidy positive | UroSEEK positive | Cytology Positive* | UroSEEK or Cytology positive* |
|---|---|---|---|---|---|---|---|---|
| Males without recurrence | 172 | 59% | 3 (2%) | 10 (6%) | 2 (1%) | 13 (8%) | 0 (0%) | 13 (8%) |
| Males with recurrence | 32 | 11% | 26 (81%) | 21 (66%) | 19 (59%) | 29 (91%) | 16 (50%) | 30 (94%) |
| Females without recurrence | 81 | 28% | 2 (2%) | 2 (2%) | 1 (1%) | 5 (6%) | 0 (0%) | 5 (6%) |
| Females with recurrence | 9 | 3% | 4 (44%) | 4 (44%) | 3 (33%) | 6 (67%) | 1 (11%) | 6 (67%) |
| Indication | | | | | | | | |
| Hematuria without recurrence | 346 | 61% | 6 (2%) | 15 (4%) | 5 (1%) | 22 (6%) | 0 (0%) | 17 (5%) |
| Hematuria with recurrence | 163 | 29% | 108 (66%) | 90 (55%) | 76 (47%) | 134 (82%) | 18 (11%) | 32 (2%) |
| LUTS without recurrence | 11 | 2% | 0 (0%) | 2 (18%) | 0 (0%) | 2 (18%) | 0 (0%) | 2 (18%) |
| LUTS with recurrence | 3 | 1% | 2 (67%) | 1 (33%) | 0 (0%) | 2 (67%) | 1 (33%) | 2 (67%) |
| Other without recurrence | 38 | 7% | 1 (3%) | 0 (0%) | 1 (3%) | 2 (5%) | 0 (0%) | 2 (5%) |
| Other with recurrence | 9 | 2% | 9 (100%) | 8 (89%) | 5 (56%) | 9 (100%) | 2 (22%) | 9 (100%) |
| Detected Tumor Diagnosis | | | | | | | | |
| PUNLMP | 2 | 1% | 0 (0%) | 1 (50%) | 0 (0%) | 1 (50%) | 0 (0%) | 0 (0%) |
| CIS | 7 | 5% | 4 (57%) | 4 (57%) | 1 (14%) | 6 (86%) | 3 (43%) | 6 (86%) |
| LGTCC | 31 | 21% | 15 (48%) | 18 (58%) | 9 (29%) | 22 (71%) | 0 (0%) | 4 (13%) |
| HGTCC | 49 | 33% | 34 (69%) | 28 (57%) | 26 (53%) | 40 (82%) | 4 (8%) | 11 (22%) |
| INTCC | 61 | 41% | 48 (79%) | 36 (59%) | 35 (57%) | 57 (93%) | 9 (15%) | 16 (26%) |
| Cytology diagnosis* | | | | | | | | |
| Positive | 21 | 6% | 16 (76%) | 12 (57%) | 16 (76%) | 20 (95%) | N/A | N/A |
| Atypical | 105 | 30% | 21 (20%) | 21 (30%) | 12 (11%) | 30 (29%) | N/A | N/A |
| Negative | 221 | 64% | 4 (2%) | 9 (4%) | 1 (0.4%) | 12 (5%) | N/A | N/A |

*Cytology was available on only a subset of cases.
N/A Not Available.

Genetic Analysis in Bladder Cancer Cohorts.

Three separate tests were performed for genetic abnormalities that might be found in urinary cells derived from BC (FIG. 26). First, mutations were evaluated in selected regions of ten genes that have been shown to be frequently altered in urothelial tumors (Table 19). For this purpose, a specific set of primers were designed that allowed detection of mutations in as few as 0.03% of urinary cells. The capacity to detect such low mutant fractions was a result of the incorporation of molecular barcodes in each of the primers, thereby substantially reducing the artifacts associated with massively parallel sequencing. Second, TERT promoter mutations were evaluated. A singleplex PCR was used for this analysis because the unusually high GC-content of the TERT promoter precluded its inclusion in the multiplex PCR design. Third, the extent of aneuploidy was evaluated using a technique in which a single PCR is used to co-amplify ~38,000 members of a subfamily of long interspersed nucleotide element-1 (L1 retrotransposons, also called LINEs). L1 retrotransposons, like other human repeats, have spread throughout the genome via retrotransposition and are found on all 39 non-acrocentric autosomal arms.

Figure 27:
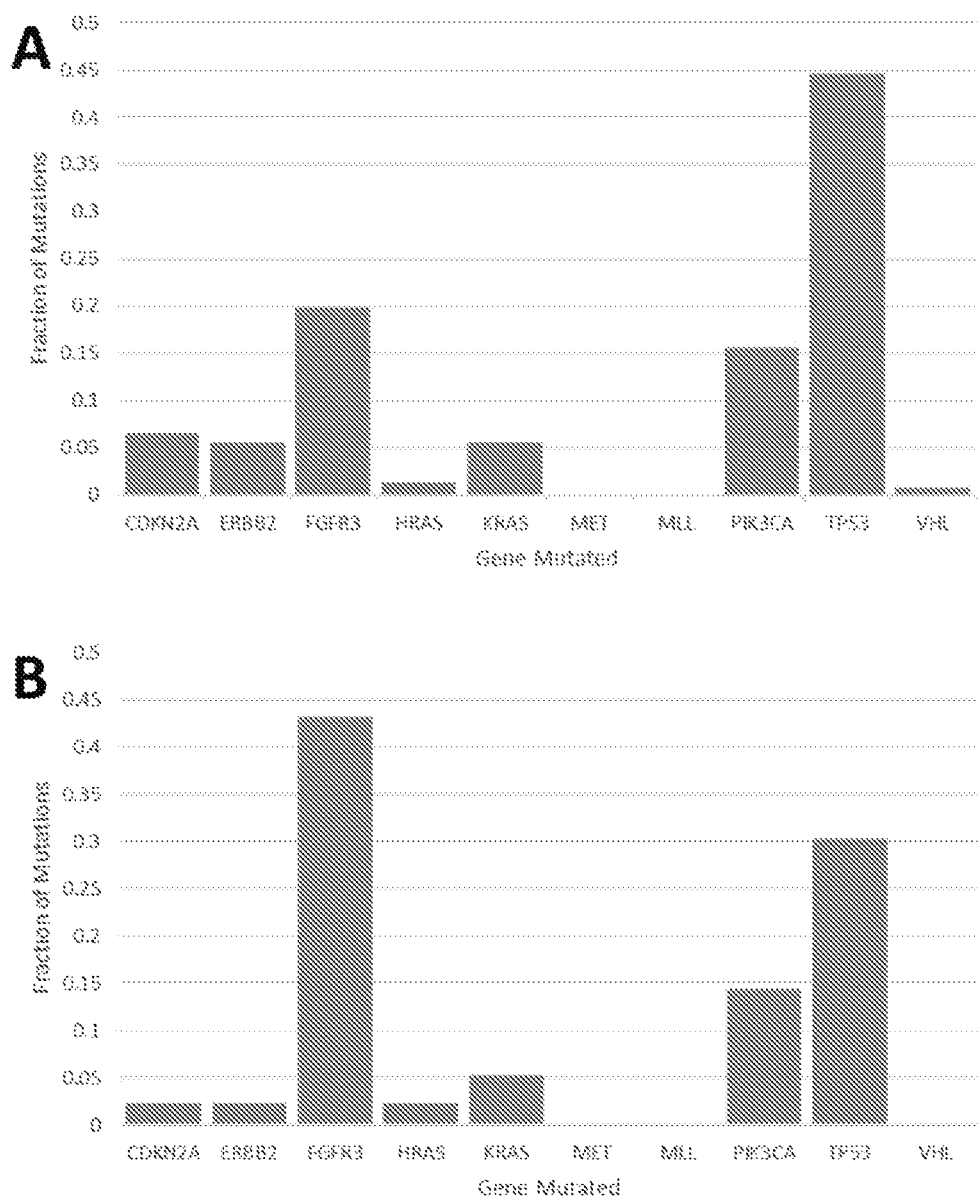
FIG. 27 contains graphs showing the fraction of mutations found in the ten-gene panel in 231 urinary cell samples assessed in the Early Detection Cohort (A) and 132 urinary cell samples assessed in the Surveillance Cohort (B).

The multiplex assay detected mutations in 68% of the 175 urinary cell samples from the individuals that developed BC during the course of this study (95% CI 61% to 75%) (Table 19). A total of 246 mutations were detected in 8 of the ten target genes (FIG. 27A and Table 19). The mean mutant allele frequency in the urinary cells with detectable mutations was 18% and ranged from 0.17% to 99%. The most commonly altered genes were TP53 (45% of the total mutations) and FGFR3 (20% of the total mutations; FIG. 27A). At the thresholds used, 1.7% of the 395 patients in the Early Detection Cohort who did not develop BC during the course of the study had a detectable mutation in any of the ten genes. At the same thresholds, none of the 188 urinary cell samples from healthy individuals had any mutation in any of the ten genes assayed (100% specificity, 95% CI 98% to 100%).

Mutations in the TERT promoter were detected in 57% of the 175 urinary cell samples from the patients that developed cancer during the study interval (95% CI 49% to 64%; Table 20). The mean TERT mutant allele frequency in the urinary cells was 14% and ranged from 0.18% to 78%. Mutations were detected in 3 positions: 98% of the mutations were at hg1295228 (79%) and hg 1295250 (19%), which are 66 and 88 bp upstream of the transcription start site, respectively. These positions have been previously shown to be involved in the appropriate transcriptional regulation of TERT. In particular, the mutant alleles recruit the GABPA/B1 transcription factor, resulting in the H3K4me2/3 mark of active chromatin and reversing the epigenetic silencing present in normal cells. 4% of the 395 patients in this cohort who did not develop BC during the course of the study had a detectable mutation in the TERT promoter. Only one of the 188 urinary samples from healthy individuals harbored a TERT promoter mutation.

Aneuploidy was detected in 46% (95% CI 39% to 54%) of the 175 urinary cell samples from the patients that developed BC during the course of the study (Table 20 and Table 21). The most commonly altered arms were 5q, 8q, and 9p. All three of these arms harbor well-known oncogenes and tumor suppressor genes which have been shown to undergo copy number alterations in many cancers, including BC. 1.5% of the urinary cell samples from the 395 patients who did not develop BC during the course of the study exhibited aneuploidy. None of the 188 urinary samples from healthy individuals exhibited aneuploidy when assessed with the same technology.

Comparison with Primary Tumors

Tumor samples from 102 of the patients enrolled in this cohort were available for comparison and were studied with the same three assays used to study the urinary cell samples (Table 20). In 91 (89%) of these 102 cancers, at least one mutation in the eleven genes studied were mutated (in the 10-gene panel or in the TERT promoter). Moreover, at least one of the mutations identified in the urine samples from these 102 patients was also identified in 83% of the corresponding BC (Table 19, and Table 20). Analysis of the BCs also shed light on the basis for "false negatives", i.e., the reason that 21% of urine samples from patients who developed BC had no detectable mutations in the 11 genes tested. The reason could either have been that the corresponding BC did not harbor a mutation in these 11 genes or that it did, but the fraction of neoplastic cells in the urine sample was not high enough to allow its detection with the assays used. At least one mutation in at least one of the 11 genes in 62% of the primary tumors was identified from patients with false negative urine tests for mutations (Table 22, and Table 23). The results indicate that 38% of the 29 false negative tests for mutations were due to the fact that none of the queried mutations were present in the tumor and that the other 62% of the false negatives were due to insufficient amounts of cancer cells in the urine.

UroSEEK: Biomarkers in Combination.

Figure 28:
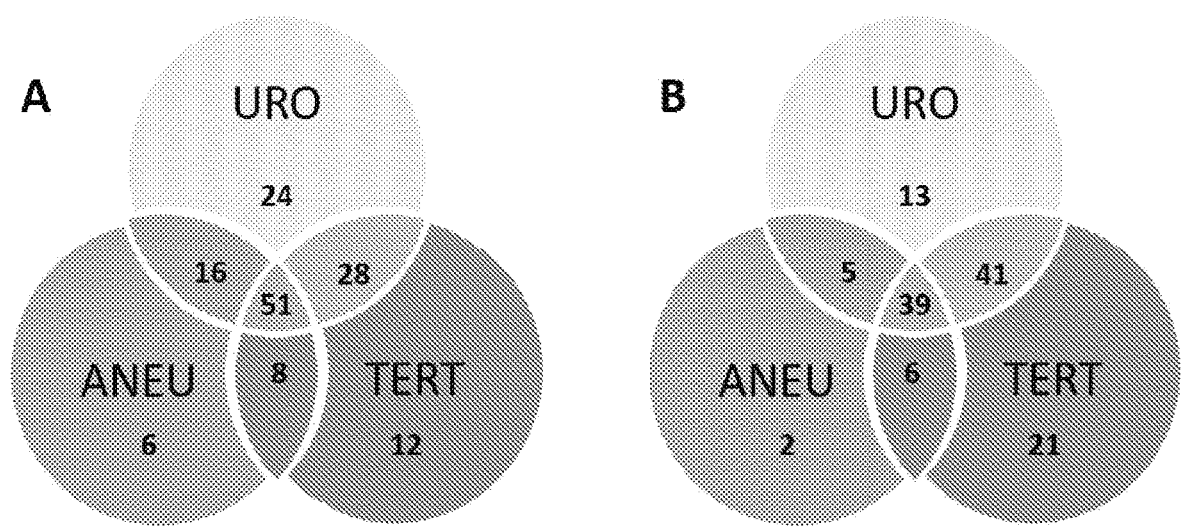
FIG. 28 contains Venn Diagrams of the distribution of samples that were positive by each of the three assays for the Early Detection Cohort (A) and the Surveillance Cohort (B). URO=Ten gene panel, TERT=TERT promoter region, ANEU=Aneuploidy test.

As noted above, the ten-gene multiplex assay, the TERT singleplex assay, and the aneuploidy assays yielded 68%, 57%, and 46% sensitivities, respectively, when used separately (Table 19, Table 20, and Table 21). 45 samples without TERT promoter mutations could be detected by mutations in one of the other ten genes (FIG. 28A and Table 19). Conversely, 35 samples without detectable mutations in the multiplex assay could be detected by virtue of TERT promoter mutations (FIG. 28A and Table 20). Ten of the urinary cell samples without any detectable mutations in the 11 genes could be detected by the assay for aneuploidy (FIG. 28A and Table 21). Thus, when the three assays were used together (test termed "UroSEEK"), and a positive result in either assay was sufficient to score a sample as positive, the sensitivity rose to 83% (95% CI 76% to 88%). Only one of the 188 samples from healthy individuals was scored positive by UroSEEK (specificity 99.5%, CI 97% to 100%). Twenty-six (6.5%) of the 395 patients in this cohort who did not develop BC during the course of the study scored positive by the UroSEEK test (specificity 93%, CI 91% to 96%). On average, UroSEEK positivity preceded the diagnosis of BC by 2.3 months, and in eight cases by more than a year (FIG. 29A and Table 18).

UroSEEK Plus Cytology

As both cytology and UroSEEK tests are non-invasive and can be performed on the same urine sample, their performance in combination was assessed. There were 347 patients in the Early Detection cohort in whom cytology was available (Table 18). Among the 40 patients who developed biopsy-proven cancer in this cohort, 17 were positive by cytology (43% sensitivity). None of the 299 patients that did not develop cancer were positive by cytology (100% specificity). UroSEEK was positive in 100% of the 17 cancer patients whose urines were positive by cytology and in 95% of the 23 cancer patients whose urines were negative by cytology. Thus, in combination, UroSEEK plus cytology afforded 95% (95% CI 83% to 99%) sensitivity, a 12% increase over UroSEEK and a 52% increase over cytology. Among the 299 patients in the early detection cohort who did not develop BC during the course of the study, 20 (6.6%) were positive by UroSEEK or cytology, giving the combination of UroSEEK and cytology a specificity of 93% (95% CI 90% to 96%).

Surveillance Cohort Characteristics

The strategy for surveillance was different than the one used for early detection. Patients in whom a BC was surgically excised for treatment and diagnosis generally have tumor tissue available, and in most such tumors, a mutation can be identified. For example, it was found during the course of this study that a mutation in at least one of the 11 queried genes was present in 95.2% of BCs evaluated. All patients selected for the surveillance study had biopsy confirmed BC and had a urine sample collected 0-5 years after surgery. A total of 322 patients that donated urines and whose BC contained a mutation in at least one of the 11 genes analyzed were evaluated. It was determined whether a single urine sample taken a relatively short time following surgical excision of the BC could reveal residual disease in these 322 patients, as evidenced by later recurrence. 187 (58%) of the 322 patients developed clinically evident BC after a median follow-up period of 10.7 months (range 0 to 51 months). The histopathologic types and tumor stages of these patients are summarized below and detailed Table 24. The median age of the participants was 62 (range 20 to 93). As expected from the demographics of BC, 75% of the patients were male.

their urine sample (false positives). The mean interval between a positive TERT test and the diagnosis of recurrent BC was 7 months (range 0 to 40 months).

Aneuploidy was detected in 30% (95% CI 24% to 37%) of the urinary cell samples from the patients that developed recurrent BC during the course of the study (Table 27). The most commonly altered arms were 8p, 8q, and 9p, as in the Early Detection cohort. Two percent of the 135 patients who Demographic, clinical and genetic features of the Surveillance cohort.

| Gender | n | % | Ten-gene multiplex positive | TERT positive | Aneuploidy positive | UroSEEK positive | Cytology Positive* | UroSEEK or Cytology positive* |
|---|---|---|---|---|---|---|---|---|
| Males without recurrence | 59 | 30% | 3 (5%) | 8 (14%) | 3 (5%) | 10 (17%) | 0 (0%) | 8 (14%) |
| Males with recurrence | 90 | 45% | 45 (50%) | 53 (59%) | 20 (22%) | 59 (66%) | 20 (22%) | 53 (59%) |
| Females without recurrence | 17 | 9% | 5 (29%) | 3 (18%) | 0 (0%) | 6 (35%) | 0 (0%) | 6 (35%) |
| Females with recurrence | 33 | 17% | 15 (45%) | 19 (58%) | 11 (33%) | 33 (100%) | 6 (18%) | 19 (58%) |
| Original Tumor Diagnosis | | | | | | | | |
| PUNLMP | 12 | 4% | 5 (42%) | 2 (17%) | 1 (8%) | 6 (50%) | 0 (0%) | 2 (17%) |
| CIS | 25 | 8% | 11 (44%) | 13 (52%) | 6 (24%) | 14 (56%) | 5 (20%) | 10 (40%) |
| LGTCC | 107 | 35% | 27 (25%) | 34 (32%) | 8 (7%) | 41 (38%) | 0 (0%) | 59 (55%) |
| HGTCC | 62 | 20% | 22 (36%) | 24 (39%) | 10 (16%) | 30 (49%) | 4 (7%) | 16 (26%) |
| INTCC | 104 | 34% | 39 (38%) | 47 (45%) | 29 (28%) | 54 (52%) | 20 (19%) | 34 (33%) |
| Original Tumor Stage | | | | | | | | |
| pTis | 25 | 8% | 11 (44%) | 13 (52%) | 6 (24%) | 14 (56%) | 5 (20%) | 10 (40%) |
| pTa | 181 | 58% | 54 (30%) | 60 (33%) | 19 (19%) | 77 (43%) | 4 (2%) | 77 (43%) |
| pT1 | 71 | 23% | 28 (39%) | 35 (49%) | 22 (31%) | 39 (55%) | 14 (20%) | 23 (32%) |
| pT2 | 23 | 7% | 9 (9%) | 9 (39%) | 7 (30%) | 12 (52%) | 5 (22%) | 10 (43%) |
| pT3 | 9 | 3% | 1 (11%) | 2 (22%) | 0 | 2 (22%) | 1 (11%) | 1 (11%) |
| pT4 | 1 | 0.3% | 1 (100%) | 1 (100%) | 0 | 1 (100%) | N/A | N/A |
| Routine cytology diagnosis* | | | | | | | | |
| Positive | 30 | 15% | 21 (21%) | 25 (83%) | 20 (67%) | 27 (90%) | N/A | N/A |
| Atypical | 95 | 48% | 38 (40%) | 43 (45%) | 18 (19%) | 50 (53%) | N/A | N/A |
| Negative | 71 | 36% | 12 (17%) | 13 (18%) | 3 (4%) | 19 (27%) | N/A | N/A |

*Cytology was available on only a subset of cases.
N/A Not Available.

Genetic Analysis of Surveillance Cohort

The multiplex assay in urinary cells detected mutations in 49% of the urinary cell samples from patients that developed recurrent BC during the study interval (95% CI 45% to 60%; Table 24 and Table 25). The mean mutant allele frequency in the urinary cells with detectable mutations was 16% and ranged from 0.08% to 93%. The most commonly altered genes were FGFR3 (43% of the 134 mutations) and TP53 (30% of the 134 mutations; FIG. 27B). Seven percent of the 135 patients who did not develop recurrent BC during the course of the study had a detectable mutation in their urinary cell sample (these are considered to be false positives; see Discussion). The mean interval between a positive multiplex assay test and the diagnosis of recurrent BC was 7 months (range 0 to 51 months).

Mutations in the TERT promoter were detected in 51% of the urinary cell samples from patients that developed recurrent BC during the study interval (95% CI 44% to 58%; Table 26). The mean TERT mutant allele frequency in the urinary cells with detectable mutations was 6% and ranged from 0.23% to 43%. Mutations were detected in the same three positions observed in the urinary cells of the Early Detection cohort. 10% (95% CI 83% to 94%) of the 135 patients who did not develop recurrent BC during the course of the study had a detectable TERT promoter mutation in did not develop recurrent BC during the course of the study exhibited aneuploidy in at least one of their urinary cell samples.

Markers in Combination—Surveillance Cohort

As noted above, the ten-gene multiplex assay, the TERT singleplex assay, and the aneuploidy assays yielded 49%, 51%, and 30% sensitivities, respectively, when used separately (Table 25, Table 26, and Table 27). Thirty-two samples without TERT promoter mutations could be detected by mutations in one of the other ten genes (FIG. 28B and Table 25). Conversely, 41 samples without detectable mutations in the multiplex assay could be detected by virtue of TERT promoter mutations. Three of the urinary cell samples without any detectable mutations could be detected by the assay for aneuploidy. Thus, the sensitivity of Uro-SEEK was 66% (95% CI 59% to 73%). Fourteen percent of the 135 patients in this cohort who did not develop BC during the course of the study scored positive by the UroSEEK test, yielding a specificity of 86% (95% CI 77% to 91%). On average, UroSEEK positivity preceded the diagnosis of BC by 7 months, and in 47 cases by more than one year (FIG. 29B and Table 24).

There were 196 patients in the Surveillance cohort for whom cytology was available (Table 24). Among the 120 patients who developed recurrent BC in this cohort, 30

(25%) were positive by cytology. Conversely, no positive cytology results were observed in patients whose tumors did not recur. UroSEEK was positive in 90% of the recurrent BC patients whose urines were positive by cytology and in 61% of the 90 recurrent BC patients whose urines were negative by cytology. Thus in combination, UroSEEK plus cytology afforded 71% sensitivity (95% CI 61.84% to 78.77) (FIG. 28D and Table 22). Among the 76 patients who did not develop recurrent BC during the course of the study and in whom cytology was available, 18% scored as positive by either cytology or UroSEEK, affording a specificity of 82% (95% CI 71% to 90%;).

Figure 30:
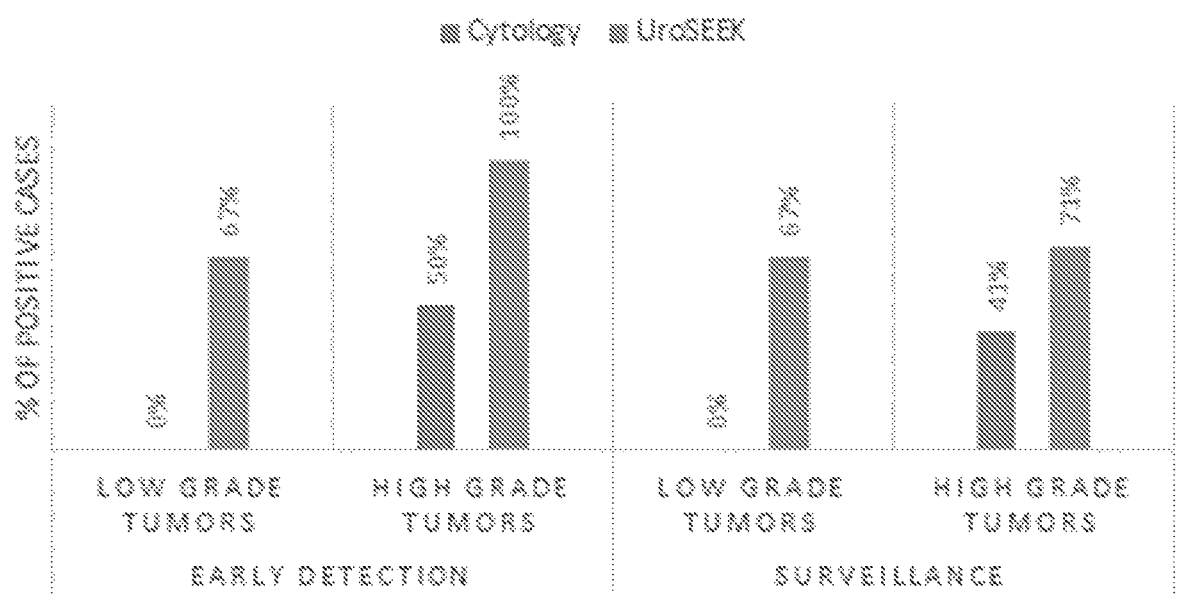
FIG. 30 contains bar graphs showing the performance of cytology compared to UroSEEK in diagnosis of low and high grade urothelial neoplasms in the Early Detection Cohort and the Surveillance Cohort.

Low Vs. High Grade Urothelial Neoplasms in Both Early Detection and Surveillance Cohorts The advantage of UroSEEK over cytology was particularly evident in low-grade tumors (Papillary urothelial neoplasms of low malignant potential and non-invasive low grade papillary urothelial carcinomas). There were a total of 49 low-grade tumors evaluated in this study in whom cytology was available (six from the Early Detection cohort and 43 from the Surveillance cohort). None of these low-grade tumors were detected by cytology (0% sensitivity; 95% CI 0.0% to 6.7%). In contrast, UroSEEK detected 67% (95% CI 51% to 81%) of the low-grade tumors (identical rate of 67% in both cohorts; FIG. 30). Analogously, there were a total of 102 high-grade tumors (in-situ urothelial carcinoma, non-invasive high grade papillary urothelial carcinoma or infiltrating high grade urothelial carcinoma) evaluated in this study in whom cytology was available (34 from the Early Detection cohort and 68 in the Surveillance cohort). Cytology was positive in 45% of these patients (50% and 41% in the Early Detection and Surveillance cohorts, respectively) while UroSEEK was positive in 80% of them (100% and 71% in the Early Detection and Surveillance cohorts, respectively; see below.

Summary of the Performance of Cytology Vs. UroSEEK.

| Biopsy Outcome Diagnosis | n | Cytology | | | | UroSEEK | | | |
|---|---|---|---|---|---|---|---|---|---|
| | | Positive test | Negative test | Sensitivity | 95% CI | Positive test | Negative test | Sensitivity | 95% CI |
| PUNLMP/LGTCC | 49 | 0 | 49 | 0% | 0.00% to 6.06% | 33 | 16 | 67% | 54.36% to 79.38% |
| CIS/HGTCC/INTCC | 102 | 46 | 56 | 45% | 33.63% to 52.21% | 82 | 20 | 80% | 71.03% to 86.39% |
| Total | 151 | | | | | | | | |

UTUC Cohort Characteristics

Thirty-two females and twenty-four males ranging in age from 39-85 years participated in the study (see below; individual data are in Table 28). This gender distribution, atypical of UTUC patients in Western countries where males predominate (Shariat et al., 2011 *World J Urol.* 29(4):481-6), is consistent with previous epidemiologic studies of Taiwanese individuals with known exposures to AA (see, e.g., Chen et al., 2012 *Proc Natl Acad Sci USA,* 109(21): 8241-8246). Tobacco use was reported by 18% of this cohort, all males. Based on estimated glomerular filtration rate (eGFR) values, renal function was unimpaired (chronic kidney disease (CKD) stage 0-2) in 45% of the subjects, while mild-to-moderate renal disease (CKD stage 3) or severe disease (CKD stages 4-5) was noted for 43% and 12% of the cohort, respectively.

Demographic, Clinical and Genetic Features of the UTUC Cohort Stratified by UroSEEK Results.

| | n | % | Ten-gene multiplex positive | TERT positive | Aneuploidy positive | UroSEEK positive |
|---|---|---|---|---|---|---|
| All subjects | 56 | 100% | 64% | 29% | 39% | 75% |
| Gender | | | | | | |
| Males | 24 | 43% | 71% | 33% | 54% | 83% |
| Females | 32 | 57% | 59% | 25% | 28% | 69% |
| CKD stage | | | | | | |
| 0-2 | 25 | 45% | 68% | 36% | 44% | 76% |
| 3A | 14 | 25% | 50% | 21% | 43% | 71% |
| 3B | 10 | 18% | 80% | 20% | 40% | 80% |
| 4 | 4 | 7% | 25% | 50% | 0% | 50% |
| 5 | 3 | 5% | 100% | 0% | 33% | 100% |
| Tumor grade | | | | | | |
| Low | 6 | 11% | 67% | 50% | 17% | 67% |
| High | 50 | 89% | 64% | 26% | 42% | 76% |

|  | n | % | Ten-gene multiplex positive | TERT positive | Aneuploidy positive | UroSEEK positive |
|---|---|---|---|---|---|---|
| Tumor stage |  |  |  |  |  |  |
| Ta | 11 | 20% | 73% | 55% | 45% | 82% |
| T1 | 8 | 14% | 50% | 0% | 38% | 75% |
| T2 | 10 | 18% | 80% | 20% | 10% | 80% |
| T3 | 24 | 43% | 67% | 33% | 54% | 79% |
| T4 | 3 | 5% | 0% | 0% | 0% | 0% |
| Upper urinary tract tumor site |  |  |  |  |  |  |
| Lower ureter | 17 | 30% | 76% | 18% | 35% | 76% |
| Upper ureter | 1 | 2% | 100% | 0% | 0% | 100% |
| Ureterovesical junction | 2 | 4% | 0% | 0% | 0% | 0% |
| Lower ureter and upper ureter | 2 | 4% | 100% | 50% | 50% | 100% |
| Renal pelvis | 21 | 38% | 57% | 38% | 38% | 76% |
| Renal pelvis and lower ureter | 4 | 7% | 75% | 25% | 50% | 100% |
| Renal pelvis and upper ureter | 5 | 9% | 40% | 40% | 60% | 60% |
| Renal pelvis, lower ureter, upper ureter | 4 | 7% | 75% | 25% | 50% | 75% |
| Synchronous bladder cancer |  |  |  |  |  |  |
| Present | 21 | 38% | 52% | 29% | 33% | 62% |
| Absent | 35 | 63% | 71% | 29% | 43% | 83% |
| UTUC risk factors |  |  |  |  |  |  |
| Aristolactam-DNA adducts present | 54 | 96% | 65% | 30% | 39% | 74% |
| Smoking history | 10 | 18% | 70% | 30% | 60% | 70% |

CKD, chronic kidney disease.

Tumors were confined to a single site along the upper urinary tract in the majority of cases (38% renal pelvis; 39% ureter), while multifocal tumors affecting both renal pelvis and ureter occurred in 23% of the patients. Synchronous bladder cancer (diagnosed within 3 months prior to nephroureterectomy) was present in 38%. Histologically, 89% of the tumors were classified as high grade, with the majority categorized as muscle-invasive (T2-T4, 66%).

Mutational Analysis—UTUC Cohort

Figure 32:
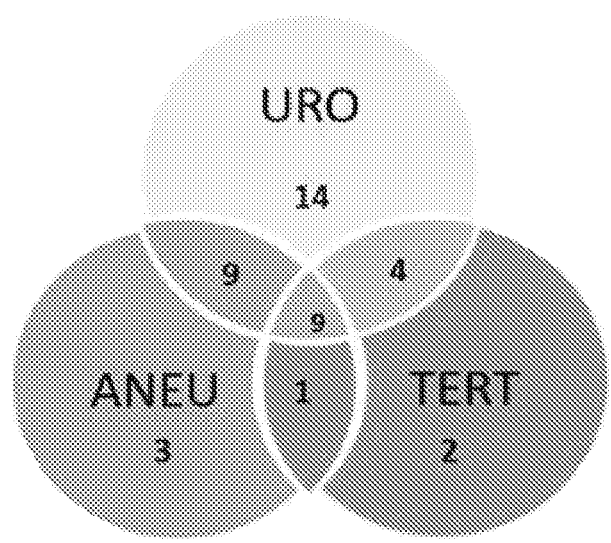
FIG. 32 contains a Venn diagram showing the distribution of positive results for each of the three UroSEEK assays.
Figure 33:
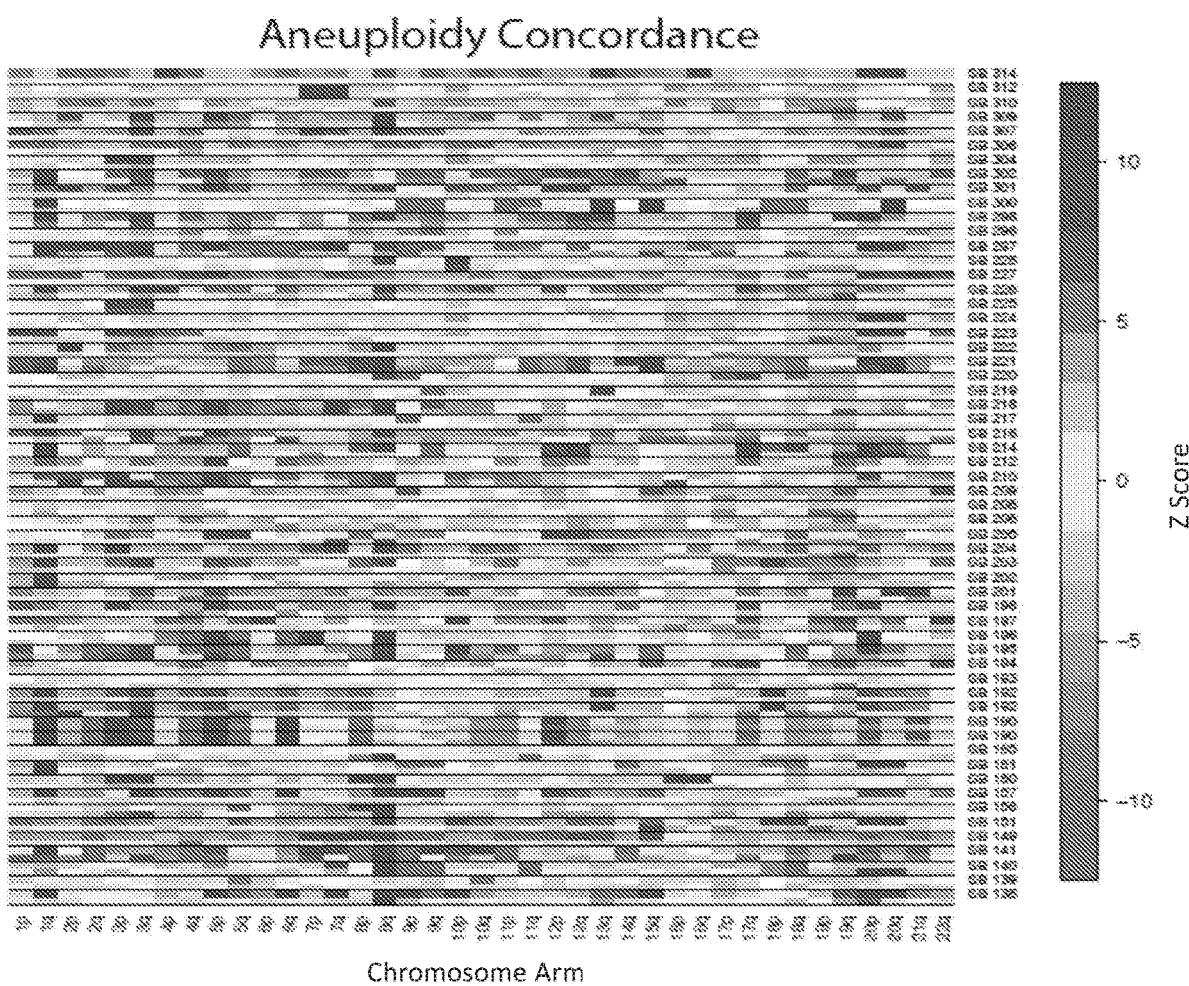
FIG. 33 contains a graph showing a comparison of copy number variations in matched tumor and urinary cell DNA samples from the UTUC cohort. Primary tumor is shown in the top of each section and urinary cell DNA on the bottom. Chromosome gains are in blue while losses are in red. Significance levels for gains and losses were set at Z scores >3 and <−3, respectively. X axis is Chromosome Arm. Y axis is Z score.

Three separate tests were performed for genetic abnormalities that might be found in urinary cells derived from UTUCs (FIG. 32, Table 29, Table 30, Table 31, and FIG. 33). First, mutations were evaluated in selected exomic regions of ten genes (CDKN2A, ERBB2, FGFR3, HRAS, KRAS, MET, MLL, PIK3CA, TP53, and VHL) that are frequently altered in urologic tumors (Sfakianos et al., 2015). For this purpose, a specific set of multiplex primers were designed that allowed detection of mutations in as few as 0.03% of urinary cells (Table 40). The capacity to detect such low mutant fractions was a result of the incorporation of molecular barcodes in each of the primers, thereby substantially reducing the artifacts associated with massively parallel sequencing. Second, TERT promoter mutations were evaluated, based on prior evidence that TERT promoter mutations are often found in UTUCs. A singleplex PCR was used for this analysis because the unusually high GC-content of the TERT promoter precluded its inclusion in the multiplex PCR design. Third, the extent of aneuploidy was evaluated using a technique in which a single PCR is used to co-amplify ~38,000 members of a subfamily of long interspersed nucleotide element-1 (L1 retrotransposons). L1 retrotransposons, like other human repeats, have spread throughout the genome via retrotransposition and are found on all 39 non-acrocentric autosomal arms.

Figure 34:
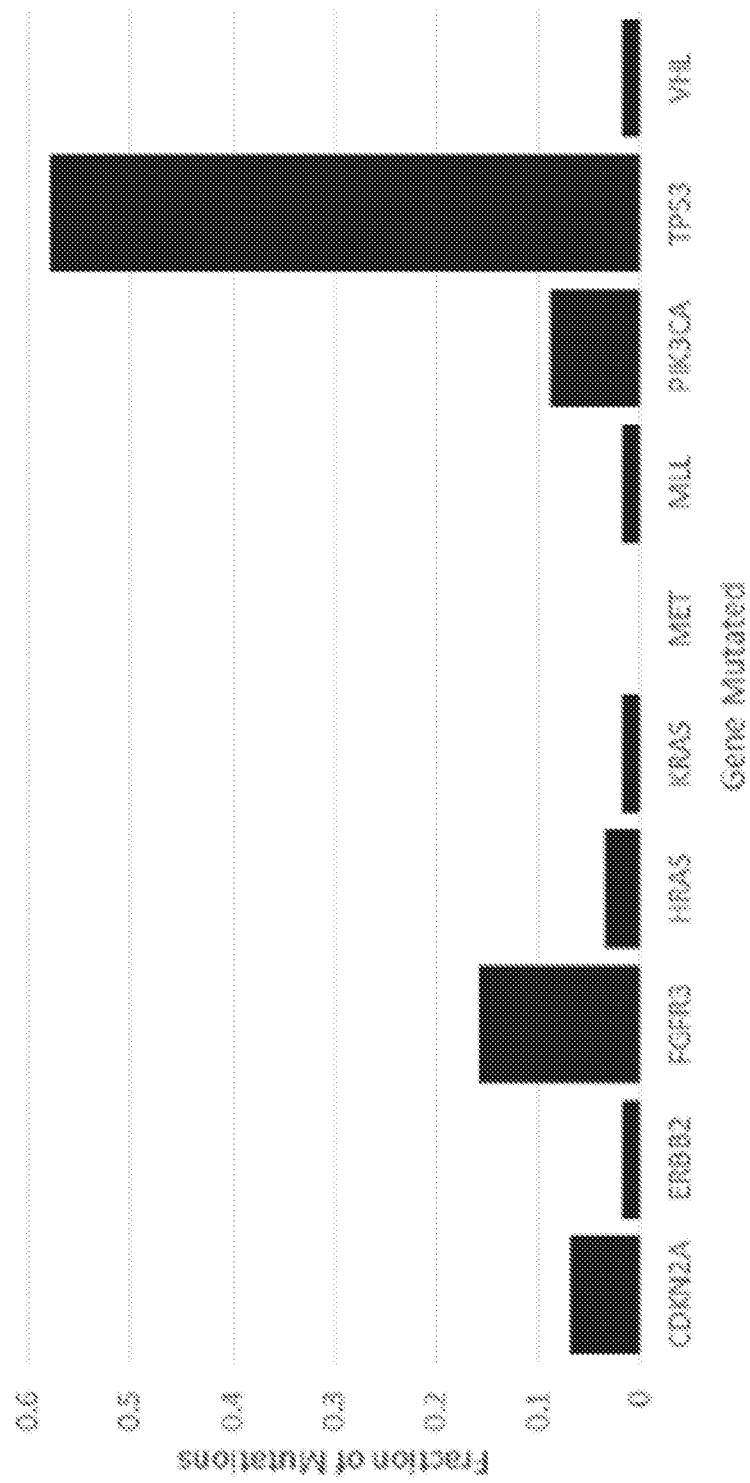
FIG. 34 contains a graph showing the fraction of total mutations for each gene in the 10-gene panel used to analyze urinary cell DNA from UTUC patients.

The multiplex assay detected mutations in 36 of the 56 urinary cell samples from UTUC patients (64%, 95% CI 51% to 76% (Table 29). A total of 57 mutations were detected in nine of the ten target genes (FIG. 34). The median mutant allele frequency (MAF) in the urinary cells was 5.6% and ranged from 0.3% to 80%. The most commonly altered genes were TP53 (58% of the 57 mutations) and FGFR3 (16% of the 57 mutations) (Table 18). None of the 188 urinary cell samples from healthy individuals had a detectable mutation in any of the ten genes assayed (100% specificity, CI 97.5% to 100%).

Mutations in the TERT promoter were detected in 16 of the 56 urinary cell samples from UTUC patients (29%, 95% CI 18% to 42%) (Table 30). The median TERT MAF in the urinary cells was 2.22% and ranged from 0.59% to 46.3%. One of the 188 urinary samples from healthy individuals harbored a mutation (TERT g.1295250C>T with a MAF of 0.39%). In the UTUC urinary cell samples, mutations were detected in three positions: 94% of the mutations were at hg1295228 (67%) and hg1295250 (28%), which are 69 and 91 bp upstream of the transcription start site, respectively. These positions have been previously shown to be involved in the appropriate transcriptional regulation of TERT. In particular, the mutant alleles recruit the GABPA/B1 transcription factor, resulting in the H3K4me2/3 mark of active chromatin and reversing the epigenetic silencing present in normal cells.

Aristolochic Acid Exposure in the UTUC Cohort

The activated metabolites of aristolochic acid bind covalently to the exocyclic amino groups in purine bases, with a preference for dA, leading to characteristic A>T transversions. To determine whether the individuals in the cohort had been exposed to AA, renal cortical DNA adducts were qualified using mass spectrometry. All but two of the 56 patients had detectable aristolactam (AL)-DNA adducts with levels ranging from 0.4 to 68 dA-AL adducts per $10^8$ nucleotides. Moreover, the A>T signature mutation associated with AA was highly represented in the mutational spectra of TP53 (18/32 A>T) and HRAS (2/2 A>T) found in urinary cells (Table 30).

Aneuploidy Analysis in the UTUC Cohort

Aneuploidy was detected in 22 of the 56 urinary cell samples from UTUC patients (39%, 95% CI 28% to 52%, Table 31, and FIG. 33) but in none of the 188 urinary cell samples from healthy individuals. The most commonly altered arms were 1q, 7q, 8q, 17p, and 18q. Some of these arms harbor well-known tumor oncogenes or suppressor genes that have been shown to undergo changes in copy numbers in many cancers (Vogelstein et al., 2013).

Comparison with Primary Tumors—the UTUC Cohort

Tumor samples from all 56 patients enrolled in this study were available for comparison and were studied with the same three assays used to analyze the urinary cell samples. This comparison served two purposes. First, it allowed determining if the mutations identified in the urinary cells were derived from the available tumor specimen from the same patient. There were a total of 39 UTUC cases in which a mutation could be identified in the urinary cells. In 35 (90%) of these 39 cases, at least one of the mutations identified in the urine sample (Table 29 and Table 30) was also identified in the corresponding tumor DNA sample (Table 32 and Table 33). When all 80 mutations identified in the urinary cells were considered, 63 (79%) were identified in the corresponding tumor sample (Table 32 and Table 33). In any of the three assays, the discrepancies between urine and tumor samples might be explained by the fact that only one tumor per patient was accessible, even though more than one anatomically distinct tumor was often evident clinically. Additionally, DNA was extracted from only one piece of tissue from each tumor, and intratumoral heterogeneity could have been responsible for some of the discrepancies.

The tumor data helped determine why 17 of the 56 urinary cell samples from UTUC patients did not contain detectable mutations. The reason could either have been that the primary tumors did not harbor a mutation present in the gene panel or that the primary tumor did contain such a mutation but the fraction of neoplastic cells in the urine sample was not high enough to allow its detection. From the evaluation of the primary tumor samples, it was found that four (24%) of the 17 urine samples without detectable mutations were from patients whose tumors did not contain any of the queried mutations (Table 32). The conclusion was that the main reason for failure of the mutation test was an insufficient number of cancer cells in the urine, and this accounted for 13 (76%) of the 17 failures.

Figure 35:
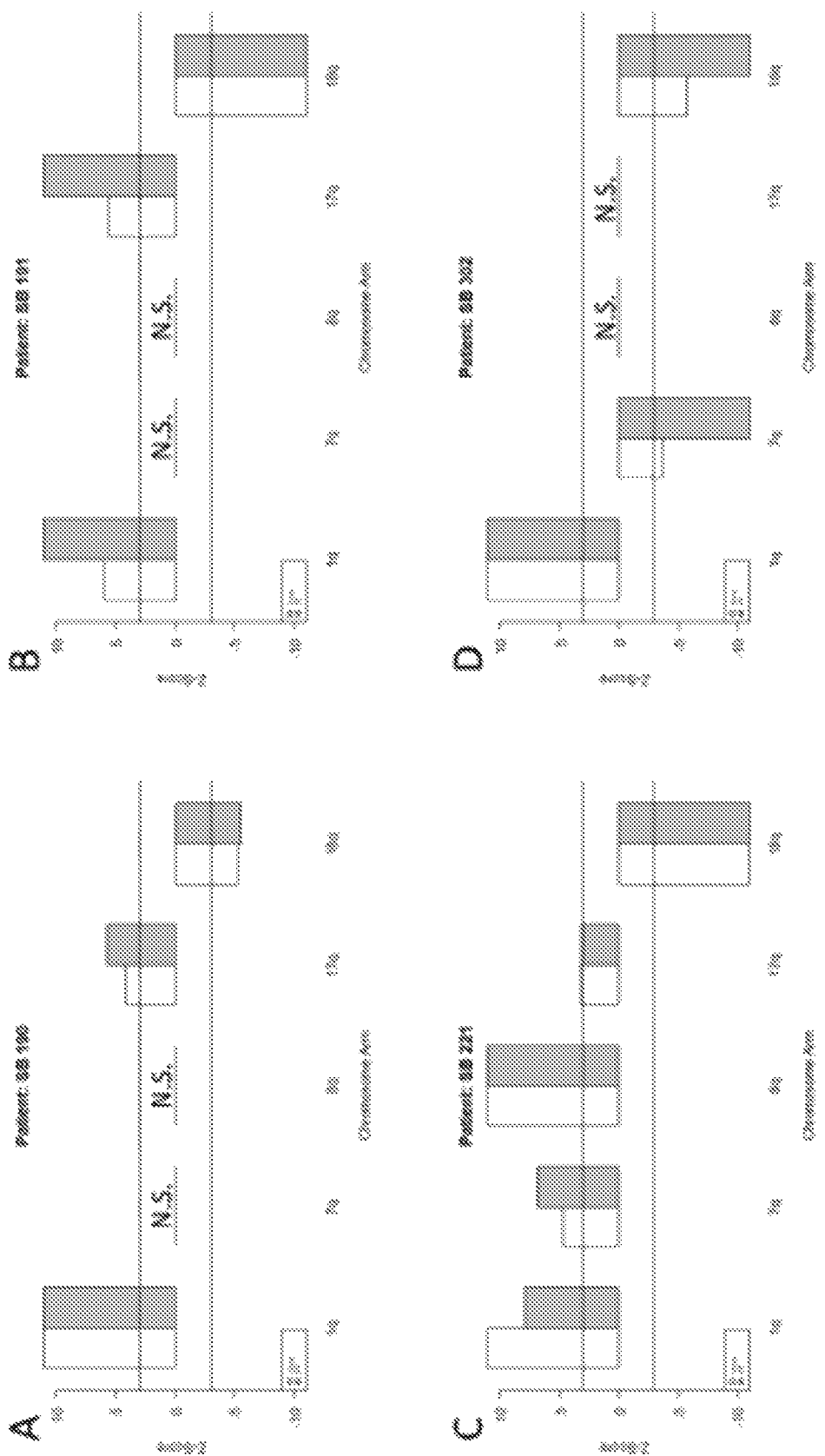
FIG. 35 contains graphs showing comparisons of copy number variations in matched tumor and urinary cell DNA samples from four individual UTUC patients (FIGS. 35A-D). Z-scores >3 or <−3 were considered as significant for chromosome gains or losses, respectively. N.S. indicates not significant. Data for all 56 patients are provided in Table 28.

There were 22 cases in which aneuploidy was observed in the urinary cell samples. Overall, 96% of the chromosome gains or losses observed in the urinary cells were also observed in the primary tumors (examples in FIG. 35). Conversely, there were 34 cases in which aneuploidy was not observed in the urinary cell samples. Evaluation of the 56 tumors with the same assay showed that all but three were aneuploid, so as with mutations, the main reason for failure of the aneuploidy assay was insufficient amounts of neoplastic DNA in the urinary cells.

Biomarkers in Combination—the UTUC Cohort

There are two factors that can limit sensitivity for genetically-based biomarkers. First, a sample can only be scored as positive for the biomarker if it contains DNA from a sufficient number of neoplastic cells to be detected by the assay. Second, the tumor from which the neoplastic cells were derived must harbor the genetic alteration that is queried. Combination assays can increase sensitivity by assessing more genetic alterations, and are thereby more likely to detect at least one genetic alteration present in the tumor. However, mutations in clinical samples often are present at low allele frequencies (Table 29 and Table 30), requiring high coverage of every base queried. It would be prohibitively expensive to perform whole exome sequencing at 10,000× coverage. In this study, the selected regions of 11 genes (including TERT) were carefully evaluated together with copy number analysis of 39 chromosome arms. Even if a tumor does not contain a genetic alteration in one of the 11 genes assessed, it might still be aneuploid and detectable by the urinary cell assay for aneuploidy. The sensitivity of aneuploidy detection is less than that of the mutation assays. Simulations showed that DNA containing a minimum of 1% neoplastic cells is required for reliable aneuploidy detection, while mutations present in as few as 0.03% of the DNA templates can be detected by the mutation assays used in this study. Nevertheless, urinary cell samples that had relatively high fractions of neoplastic cells but did not contain a detectable mutation in the 11 queried genes should still be detectable by virtue of their aneuploidy because, as noted above, 53/56 UTUCs studied here were aneuploid. Additionally, some of the mutations in the 11 genes queried, such as large insertions or deletions or complex changes, might be undetectable by mutation-based assays but a sample with such an undetectable mutation could still score positive in a test for aneuploidy.

To determine whether these theoretical arguments made a difference in practice, biomarker performance was evaluated with the combined approaches, collectively called UroSEEK. As noted above, the ten-gene multiplex assay, the TERT singleplex assay, and the aneuploidy assays yielded 64, 29%, and 39% sensitivities, respectively, when used separately. Twenty-three samples without TERT promoter mutations tested positive for mutations in one of the other ten genes (Venn diagram in FIG. 32). Conversely, three samples without detectable mutations with the multiplex assay scored positive for TERT promoter mutations (FIG. 32). And, three of the urinary cell samples without any detectable mutations were positive for aneuploidy (FIG. 32). Thus, when the three assays were used together, and a positive result in any one assay was sufficient to score a sample as positive, the sensitivity rose to 75% (95% CI 62.2% to 84.6%). Only one of the 188 samples from healthy individuals scored positive in the UroSEEK test (specificity 99.5%, CI 97.5 to 100%).

To determine the basis for the increased sensitivity afforded by the combination assays, data from the primary tumors of the three patients whose urinary cell samples exhibited aneuploidy but did not harbor detectable mutations were evaluated. It was found that these three tumors did not contain any mutations in the 11 queried genes, explaining why these same assays were negative when applied to urinary cell DNA. As noted above, these three tumors were aneuploid, thus affording the opportunity to detect these copy number variations in the urinary cell samples.

Correlation with Clinical Features

A cancer biomarker should advantageously be able to detect tumors at an early stage, enabling surgical removal of the lesions prior to widespread metastasis. UroSEEK was sensitive in detecting both early and late tumors. It scored positive in 15 (79%) of 19 patients with stage Ta or T1 tumors and in 27 (73%) of 37 patients with stage T2-T4 tumors. Ten-year cancer specific survival rates show that 91% of UTUC patients with stage T1 malignancies are expected to be cured by surgery, compared to only 78%, 34% and 0% of patients with stage 2, 3, or 4 tumors, respectively.

UroSEEK sensitivity was independent of a variety of clinical parameters other than tumor stage, including gender, CKD stage, tumor grade, tumor location and risk factors for developing UTUC, indicating that the assay is suitable for evaluation of diverse patient populations. Furthermore, UroSEEK was considerably more sensitive than urine cytology in this cohort. Cytology was available in 42 cases, and of these only four (9.5%) were diagnosed as carcinoma cytologically. Even if samples scored as "suspicious for malignancy" by cytology were considered as positive, the sensitivity was only 26% (including the four scored as positive and seven scored as suspicious). UroSEEK detected all four cases scored as positive by cytology, five of the seven cases scored as suspicious for malignancy, and 22 of the 31 samples scored by cytology as inconclusive or negative.

Example 6: Detection of Aneuploidy in Patients with Cancer Through Amplification of Long Interspersed Nucleotide Elements (LINEs)

This Example describes a new approach for amplicon-based aneuploidy detection. This approach, called WALDO for Within-Sample-AneupLoidy-DetectiOn (WALDO), employs supervised machine learning to detect the small changes in multiple chromosome arms that are often present in cancers. It is shown herein that WALDO can be applied to identify chromosome arm gains or losses with improved sensitivity and equivalent specificity compared to previous approaches. Furthermore, machine learning can be incorporated to make genome-wide aneuploidy calls, in which samples are classified according to their aneuploidy status. This Example reports WALDO results on thousands of samples, including tissues of ten different tumor types as well as liquid biopsies of plasma from cancer patients. When two samples are available for comparison, WALDO can be used to assess genetic relatedness or to find somatic mutations within the LINEs. Thus, this approach can be used to provide an estimate of somatic mutation load, evaluate carcinogen signatures, and detect microsatellite instability (FIG. 1).

Materials and Methods

Samples

A total of 1,678 tumors were evaluated in this study (see below).

| Sample Source | Sample Type | Number of Samples | Number of Samples Including Replicates | Matched Normal | Mutation Data |
|---|---|---|---|---|---|
| Peripheral white-blood-cell (WBC) | Normal | 176 | 677 | N/A | No |
| Tumor | Breast Invasive Carcinoma (BRCA) | 45 | 45 | No | No |
| Tumor | Colon Adenocarcinoma and Rectum Adenocarcinoma (COAD; COADREAD) | 536 | 536 | No | No |
| Tumor | Colorectal Adenoma | 32 | 32 | N/A | No |
| Tumor | Esophageal Carcinoma (ESCA) | 42 | 42 | No | No |
| Tumor | Head and Neck Squamous Cell Carcinoma (HNSC) | 96 | 96 | No | No |
| Tumor | Liver Heptaocellular Carcinoma (LIHC) | 56 | 56 | No | No |
| Tumor | Ovarian Serous Cystadenocarcinoma (OV) | 157 | 157 | No | No |
| Tumor | Pancreatic Adenocarcinoma (PAAD) | 345 | 345 | No | No |
| Tumor | Stomatic Adenocarcinoma (STAD) | 28 | 28 | No | No |
| Tumor | Uterine Corpus Endometrial Carcinoma (UCEC) | 296 | 296 | No | No |
| Tumor (Cell Line) | Mismatch Repair Deficient Colorectal Carcinoma | 6 | 6 | Yes | No |
| Plasma | Normal | 402 | 566 | N/A | No |
| Plasma | Pancreatic Adenocarcinoma (PAAD) | 547 | 547 | No | Yes |
| Plasma | Breast Invasive Carcinoma (BRCA) | 28 | 28 | No | Yes |
| Plasma | Colon Adenocarcinoma and Rectum Adenocarcinoma (COAD; COADREAD) | 167 | 167 | No | Yes |
| Plasma | Esophageal Carcinoma (ESCA) | 17 | 17 | No | Yes |
| Plasma | Liver Heptaocellular Carcinoma (LIHC) | 54 | 54 | No | Yes |
| Plasma | Stomatic Adenocarcinoma (STAD) | 16 | 16 | No | Yes |
| Plasma | Ovarian Serous Cystadenocarcinoma (OV) | 14 | 14 | No | Yes |
| Plasma | Lung | 113 | 113 | No | Yes |

The number of cancers of each histopathologic subtype are listed in the Appendices. The tumors were formalized fixed and paraffin-embedded (FFPE). In all cases, DNA was purified using QIAsymphony (cat #937255). Peripheral white blood cells (WBCs) were purified from the blood of 176 healthy individuals. Plasma was purified from 566 healthy individuals and 982 patients with cancer. DNA was purified from WBCs and plasma using Qiagen kit numbers (cat #1091063) and (cat #937255) respectively. The majority of the plasma samples used in this study has been independently evaluated for mutations in one of twelve commonly mutated genes. The fraction of mutant alleles in these plasma samples was used as an estimate of their neoplastic cell content. All individuals participating in the study provided written informed consent after approval by the institutional review boards of the hospitals at which they were collected.

Fast-SeqS

For each DNA sample evaluated, FAST-SeqS was used to amplify approximately 38,000 amplicons with a single primer pair (Kinde et al., 2012 *PloS ONE* 7:e41162). Massively parallel sequencing was performed on Illumina instruments (HiSeq 2500, HiSeq 4000, or MiSeq). During amplification, degenerate bases at the 5' end of the primer were used as molecular barcodes to uniquely label each DNA template molecule as described elsewhere (see, e.g., Kinde et al., 2011 *Proceedings of the National Academy of Sciences* 108:9530-9535). This ensured that each DNA template molecule was counted only once. In all instances in this paper, the term "reads" refers to uniquely identified reads. Depending on the experiment, each read was sequenced between 1 and 20 times. For each WBC and tumor DNA sample, 100,000 to 25 million reads were used for analysis. For each plasma DNA sample, 100,000 to 15 million reads were used. Replicates of normal DNA were included in every sequencing experiment and used to evaluate stochastic and experimental variability.

Sample Alignment and Genomic Interval Grouping

Bowtie2 was used to align reads to human reference genome assembly GRC37. 37,669 exact matches (33,844 excluding the sex chromosomes) to the reference genome were identified. These exact matches allowed inclusion of common polymorphisms. The polymorphisms included 24,720 single nucleotide polymorphisms (SNPs) and 1,500 insertion and deletion (indel) polymorphisms, with minor allele frequencies were >1% in the 1000 Genomes database (Consortium 2012 *Nature* 491:56-65).

In light of experimental and stochastic variation, the number of reads that mapped to each genomic region of any euploid sample was expected to be variable. To minimize this variability, clusters of 500-kb genomic intervals with similar read depth across all chromosomes in multiple euploid samples were identified. This step permitted estimation of the expected variability in read depth in a sample when no aneuploidy was present. Genomic intervals smaller and larger than 500 kb were tested, and it was found that 500 kb yielded reasonable performance in the assays described below at reasonable computational expense.

Clustering of the 500-kb genomic intervals was performed as follows. Each test sample was matched to euploid samples that had similar amplicon sizes. This was done because smaller amplicons will be over-represented in the amplicons generated from DNA that is of small size prior to amplification. The size of the amplicons generated by Fast-SeqS range from 100 to 140 bp (Kinde et al., 2012 *PloS ONE* 7: c41162). The size of plasma DNA is 140 to 180 bp (Diehl et al., 2005) *Proceedings of the National Academy of Sciences of the United States of America* 102:16368-16373; Chan et al., 2004 *Clinical chemistry* 50:88-92; Jahr et al., 2001 *Cancer research* 61:1659-1665; and Giacona et al., 1998 *Pancreas* 17:89-97), so the largest LINE amplicons will be substantially underrepresented in plasma DNA compared to WBC DNA, for example. It was found that seven euploid samples was sufficient for comparison to any test sample; using more than seven euploid samples did not substantially increase performance. The seven euploid samples were derived from a collection of 677 WBC or 566 plasma DNA from normal individuals, collectively termed the "euploid reference set". For each test sample p, the seven normal samples with the smallest Euclidean distance to p were selected, defined as $D(p,q)=\sqrt{\Sigma_n(q_n-p_n)^2}$ where, $p_n$ and $q_n$ are the fraction of amplicons of size n in samples p and q, and the sum is over all amplicon sizes in the two samples. Before calculating the Euclidian distances between the test samples from the samples in the euploid reference set, the following amplicons were excluded: (i) Using maximum likelihood estimates, the amplicons were ranked by variance among the seven euploid samples and the top 1% excluded. (ii), any amplicons with <10 reads in one sample but >50 reads in any of the other six samples were removed. In each sample, the 500-kb genomic intervals were scaled by subtracting the mean and dividing by the standard deviation of reads in each sample.

Figure 45:
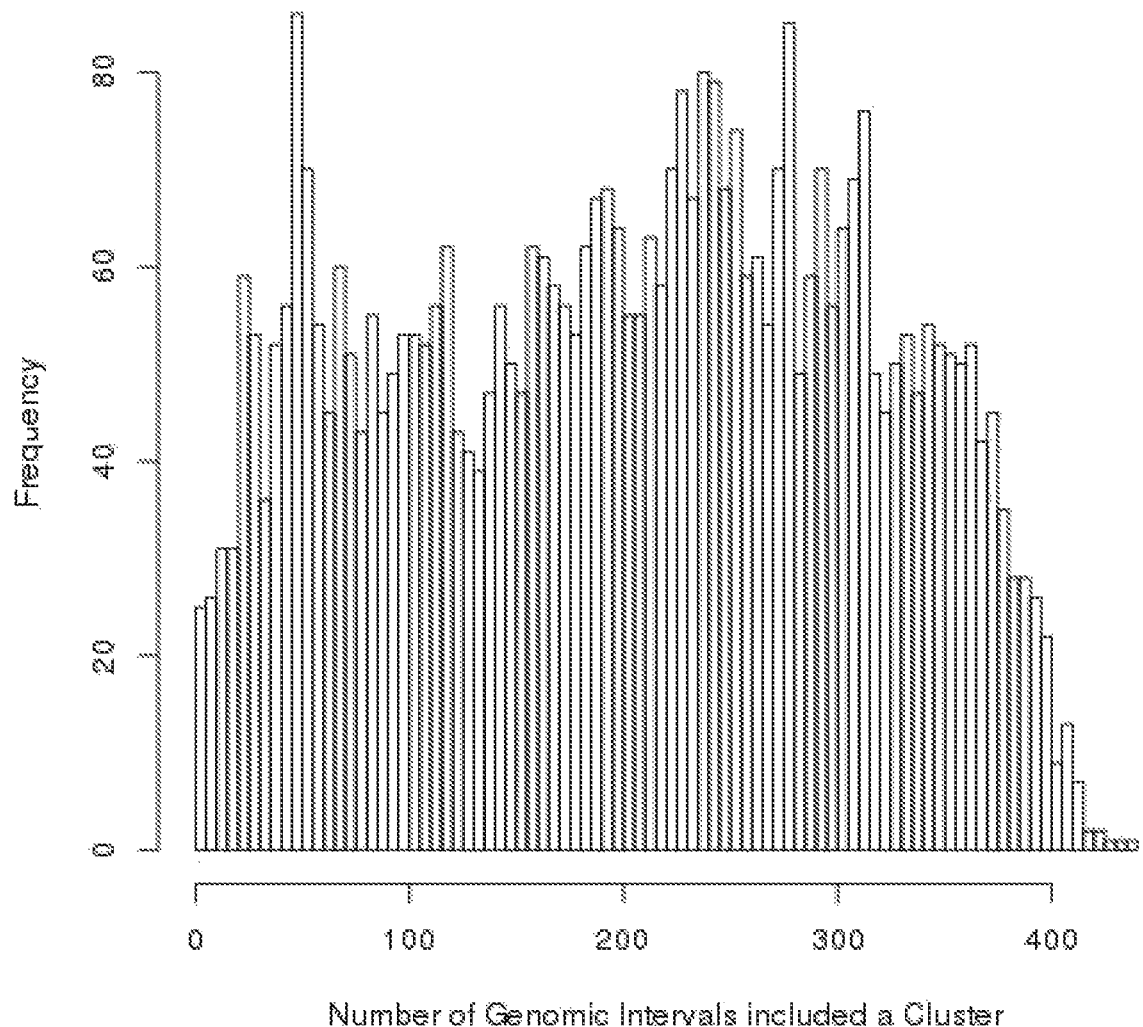
FIG. 45 contains a graph showing a distribution of the number of genomic intervals included in a cluster for a representative normal WBC sample.
Figure 46:
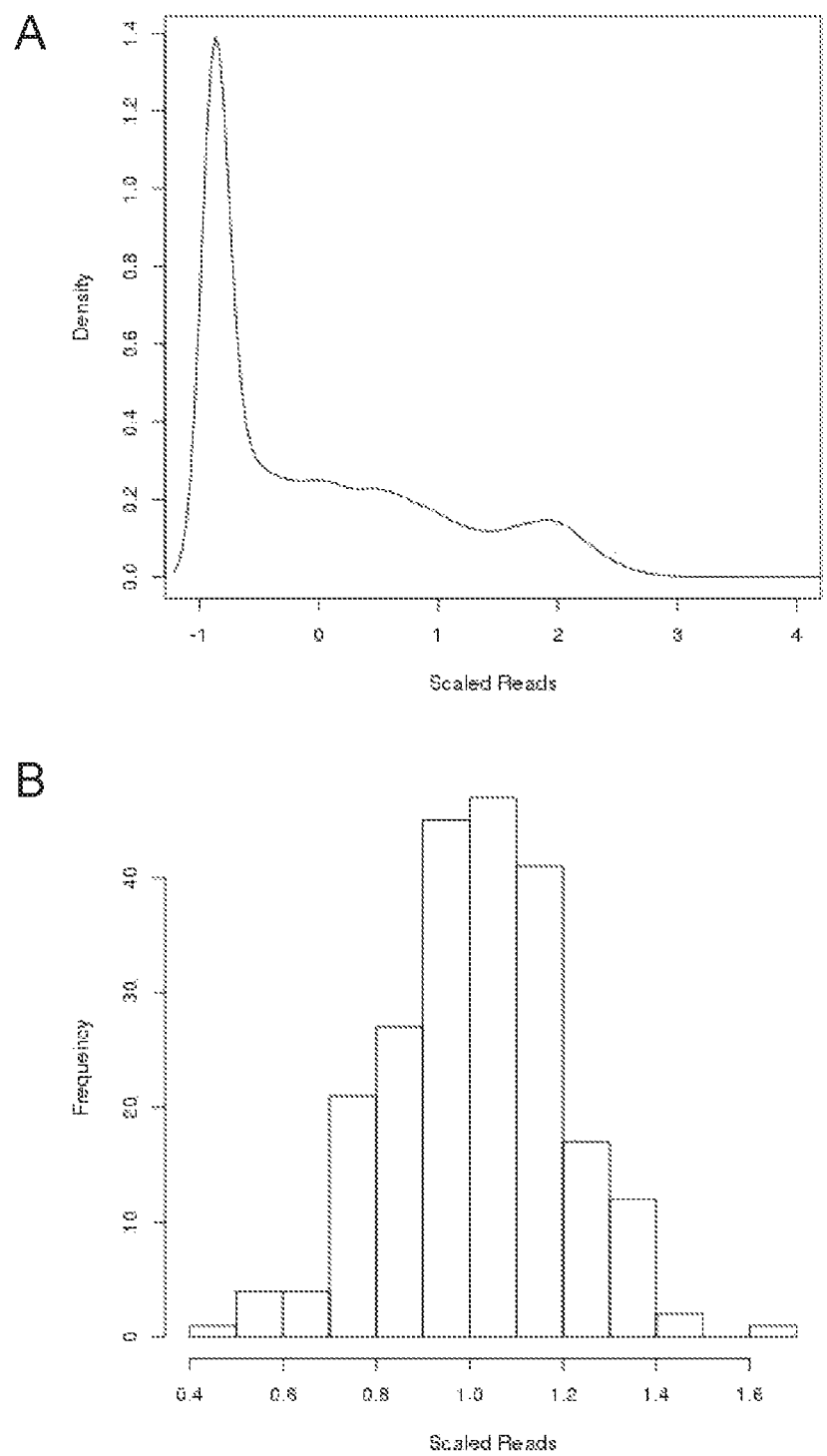
FIG. 46 contains graphs showing distributions of scaled reads. (A) Distribution of scaled reads illustrating that reads in FAST-SeqS amplicon sequencing were not randomly distributed. (B) Representative cluster for a normal WBC sample illustrating the normality of the scaled reads in a cluster. (C) Representative cluster for an aneuploid primary tumor sample illustrating the normality of the scaled reads in a cluster.
Figure 46:
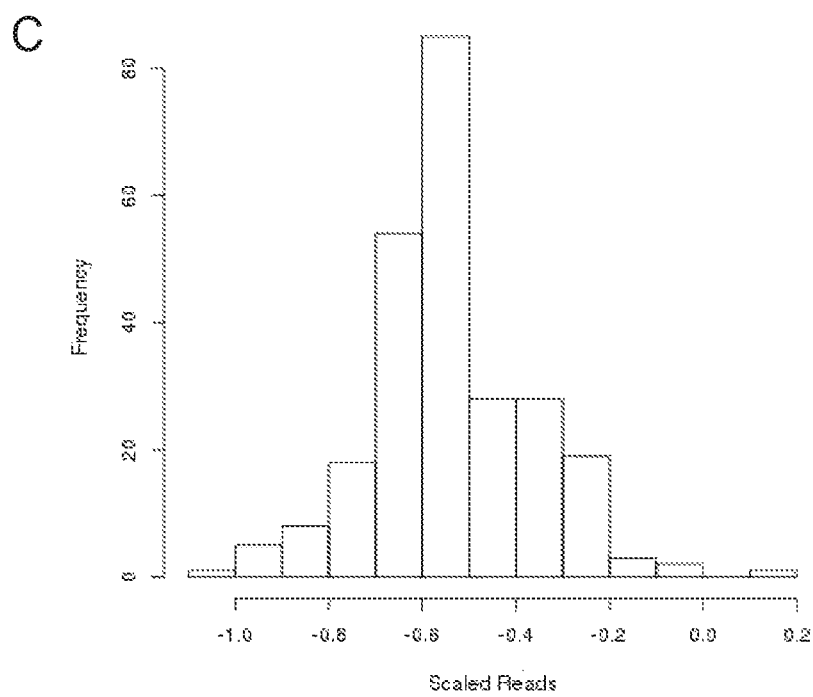

The scaled 500-kb genomic intervals were then clustered across the seven selected normal samples in the following way. First, each 500-kb genomic interval i was assigned to a primary cluster $C_i$. Next, the reads in genomic interval i across all samples was compared to the average number of read in the seven samples in all other genomic intervals i' that occurred on the remaining 21 autosomal chromosomes. Insignificant results (paired t-test p>0.05, f-test p>0.05) were tested fro during the search for similarity. If the average number of reads in genomic interval i' was not significantly different from the number of reads in genomic interval i, it was added to cluster $C_i$. This process was repeated for each of the 4361 genomic intervals, yielding 4361 clusters. Every interval i belonged to its primary cluster but the same interval also belonged to an average of 176 other clusters (range of 100 to 252 clusters among 190 representative samples). The number of unique clusters was less than the 4361 because some clusters were composed of the same 500-kb genomic intervals. The number of unique clusters was typically 4310 to 4330 among 190 representative samples. Clusters contained an average of approximately two hundred 500-kb genomic intervals (see FIG. 45). Scaled reads were not randomly distributed (see FIG. 46A). However, the distribution of scaled reads within the ~200 genomic intervals in each cluster followed an approximately normal distribution (example in FIG. 46B-C).

Identifying Chromosome Arm Gains or Losses in a Test Sample

WALDO used the seven euploid samples described above only to define clusters of genomic intervals with similar amplification properties. The statistical tests for aneuploidy in WALDO were based on the read distributions within the test sample and independently of the read distributions in any euploid sample. For a test sample, maximum likelihood was used to estimate the means μ and variances $\sigma^2$ of the genomic intervals in each of the 4,361 clusters defined by the seven euploid samples that were chosen to match it on the basis of amplicon length. The robustness of these estimates was improved by iteratively removing outlying genomic intervals within the test sample from the clusters.

Figure 47:
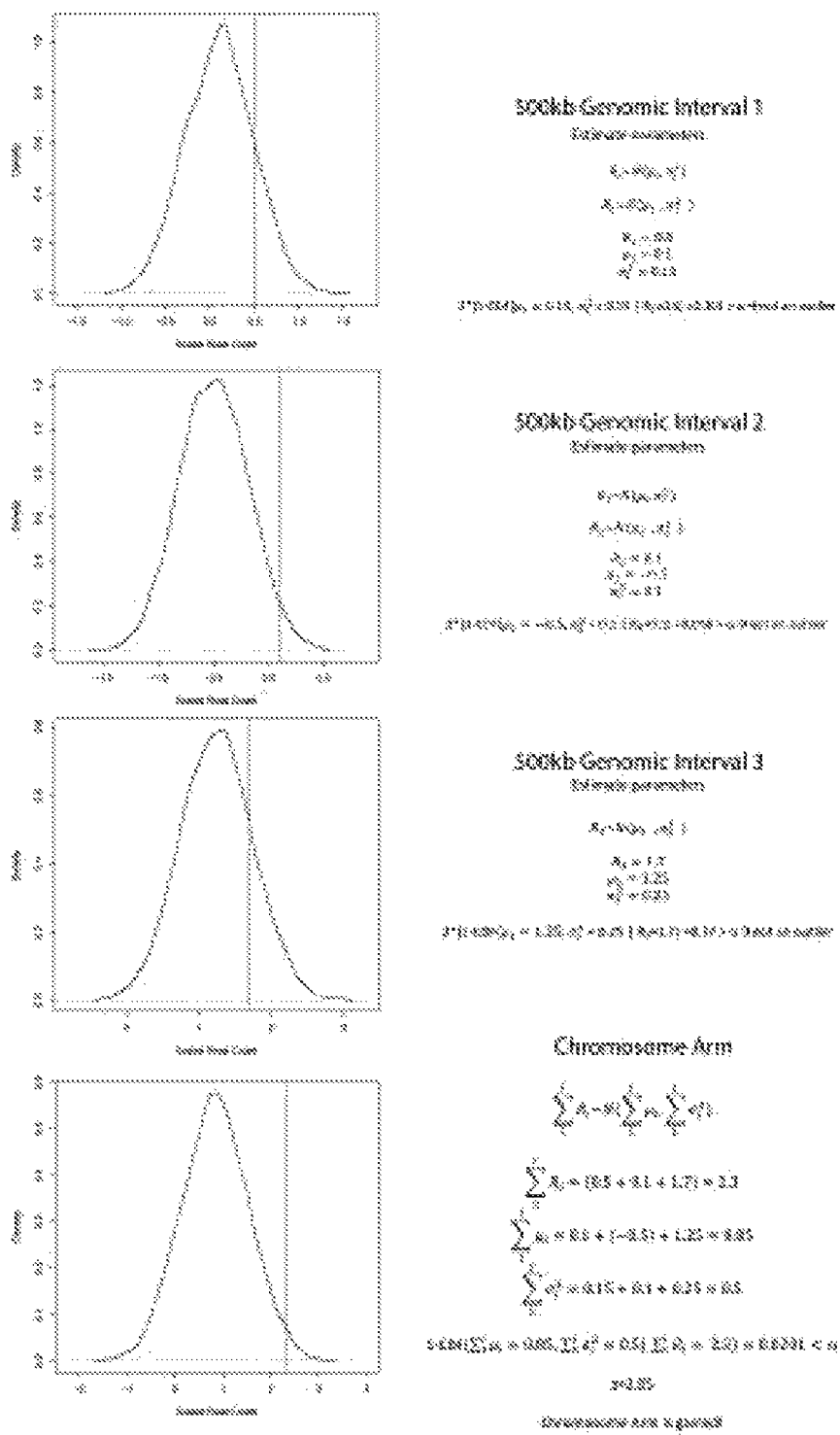
FIG. 47 contains graphs showing an example of the statistical procedure to identify a chromosome arm gain or loss.

Clusters containing fewer than 10 genomic intervals were not included in the analysis. For each cluster, any 500-kb genomic interval meeting the criteria min (2*CDF($\mu$, $\sigma_i^2$), 2*(1−CDF($\mu$, $\sigma_i^2$))<0.01 was removed from all clusters. Next, the $\mu$ and $\sigma^2$ parameters of each cluster were re-estimated by maximum likelihood. The two steps were repeated until no outlying genomic intervals remained. The statistical significance of the total reads was then estimated from all 500-kb genomic intervals on the arm. Because sums of normally distributed random variables are also normally distributed random variables, the calculation was straight-forward (see FIG. 47). For each chromosome arm, $\Sigma_1^I R_i \sim N(\Sigma_1^I \mu_i, \Sigma_1^I \sigma_i^2)$ was calculated, where $R_i$ is the scaled reads and I is the number of clusters on the arm. Z-scores were produced using the quantile function $1-CDF(\Sigma_1^I \mu_i, \Sigma_1^I \sigma_i^2)$. Positive Z-scores>$\alpha$ represented gains and negative Z-scores<−$\alpha$ represented losses, where $\alpha$ was the selected significance threshold.

Arm Level Allelic Imbalance

Figure 48:
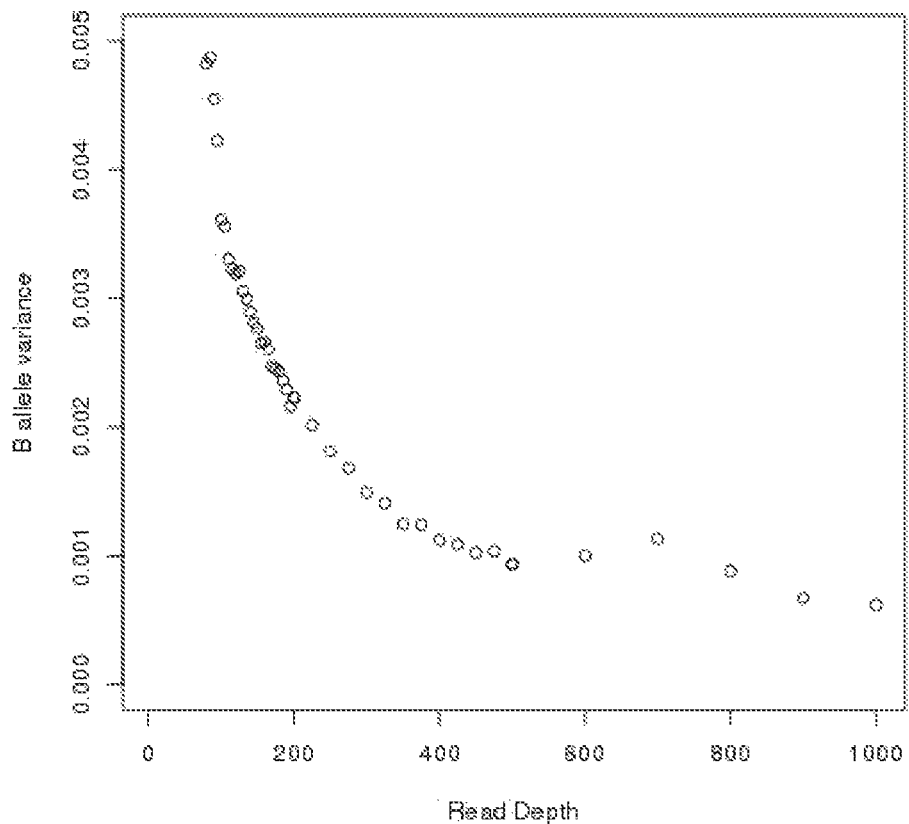
FIG. 48 contains a graph showing an empirical estimation of the variance of the B-allele frequency for heterozygous SNPs as a function of read depth. Increasing UID depth improved the estimation of the B-allele frequency for heterozygous SNPs.

Common polymorphisms from 1000 Genomes (24,720 single nucleotide and 1,500 indels, MAF>1%) were used as candidate heterozygous sites. For each of the 677 normal samples, polymorphic sites were identified that could be confidently called as heterozygous and diploid. Polymorphisms were defined as those with variant-allele frequencies (VAF) (0.4<VAF<0.6), where VAF=#non-reference reads/total reads. VAFs were modeled at these sites as random variables taken from a normal distribution with $\mu=0.5$; the variance $\sigma^2$ was estimated by maximum likelihood as a function of read depth (FIG. 48). To determine whether the alleles on a chromosome arm in a test sample were unbalanced, the subset of polymorphic sites was identified at which both alleles were present and in which the sum of the reads on both alleles was >25. The observed VAF was then compared with the normal distribution, using the expected variance for the observed read depth, yielding a two-sided P-value. All p-values on a chromosome arm were Z-transformed and combined with a weighted Stouffer's method, with the observed read depth at each site used as its weight. The formula used for this calculation was $$Z \sim \frac{\sum_{i=1}^{k} w_i Z_i}{\sqrt{\sum_{i=1}^{k} w_i^2}},$$

where $w_i$ is UID depth at variant i, $Z_i$ is the Z-score of variant i, and k is the number of variants observed on the chromosome arm. A chromosome arm was scored as having an allelic imbalance if the resulting Z score was greater than the selected statistical significance threshold $\alpha$ (one-sided test).

Generation of Synthetic Aneuploid Samples

Data from 63 presumably euploid samples was selected, each containing at least 9 million reads, and each derived from the DNA of normal WBCs. Synthetic aneuploid samples were created by adding (or subtracting) reads from several chromosome arms to the reads from these normal DNA samples. Reads from 1, 5, 10, 15, 20, or 25 randomly selected chromosome arms were added to or subtracted from each sample. The additions and subtractions were designed to represent neoplastic cell fractions ranging from 0.5% to 10% and resulted in synthetic samples containing exactly nine million reads. The reads from each chromosome arm was added or subtracted uniformly. For example, when five chromosome arms that were lost were modeled, each was lost to the identical degree and we did not incorporate tumor heterogeneity into the model. Furthermore, synthetic samples containing two or more of the same extra chromosome arms were not created, such as synthetic cells containing 4 copies of chromosome 3p. This simplified approach did not comprehensively cover all biologically plausible aneuploidy events. However, limiting the possible combinations of altered arms made sample generation computationally tractable, and the resulting support vector machine worked well in practice.

Figure 37:
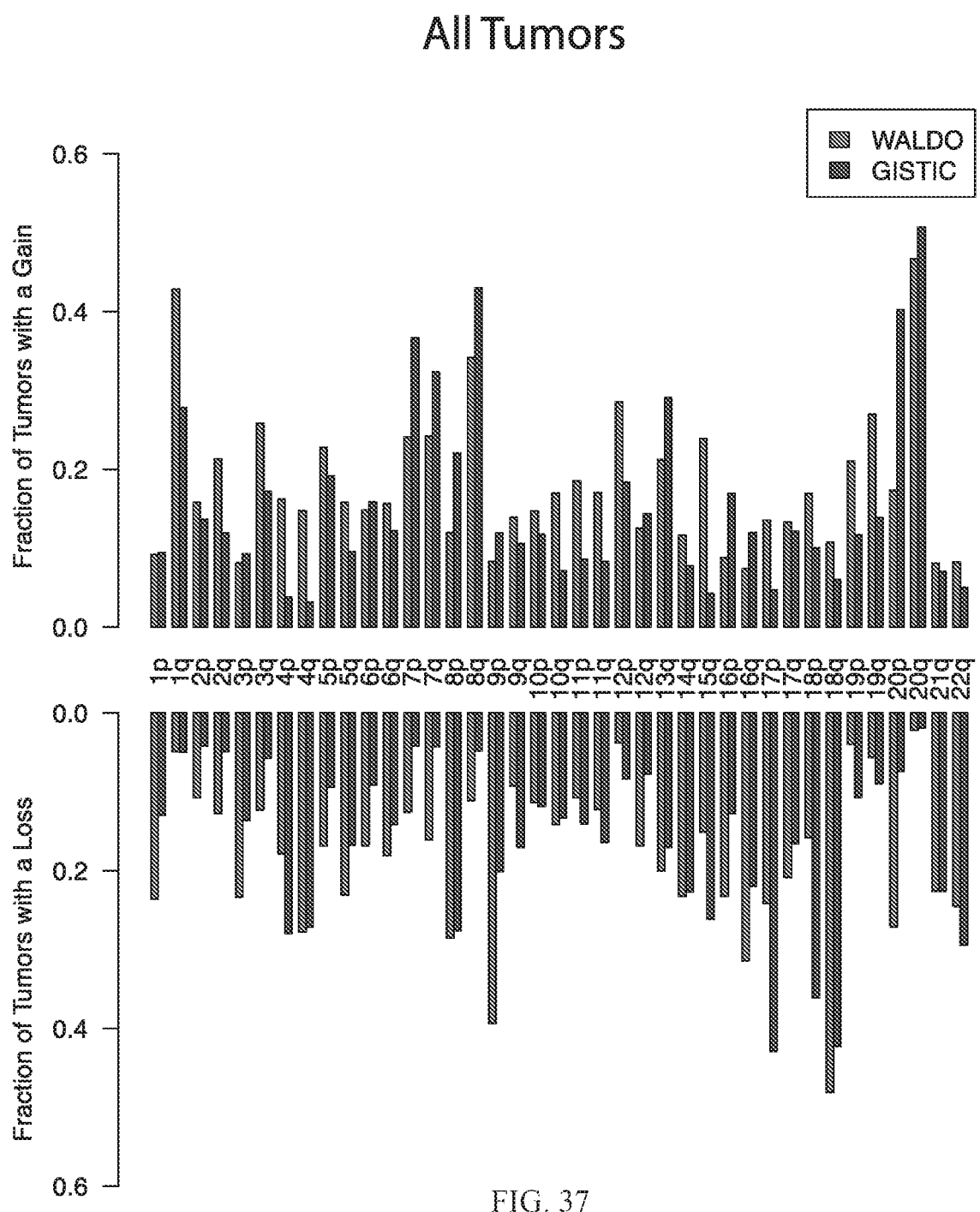
FIG. 37 contains a graph showing individual chromosome arm gains and losses that were identified in nine cancer types. The average fraction of tumors with a gain or loss in each chromosome arm are depicted in the figure. The same nine tumor types were analyzed in both cohorts, but there was no overlap between the samples assessed by WALDO (red) or GISTIC (blue). WALDO employed the data from LINE sequencing of tumors reported here while GISTIC employed the data from Affymetrix SNP6.0 arrays provided by the TCGA.

The synthetically generated samples in which reads from only a single chromosome arm were added or subtracted enabled us to estimate the performance of WALDO when only a single chromosome arm of interest was gained or lost. The synthetic set in which 5-25 chromosome arms were altered permitted assessment of the performance of WALDO in typical samples derived from cancers. As shown in FIG. 37, most cancers have gains or losses of multiple chromosomes. The algorithms used to generate the synthetic samples are shown as pseudocode in FIG. 49 and FIG. 50.

Genome-Wide Aneuploidy Detection

A two-class support vector machine (SVM; Cortes 1995 *Machine learning* 20:273-297) was trained to discriminate between euploid samples and the synthetic samples in which the reads from 5 to 25 chromosome arms were added or subtracted. The training set contained 677 WBC negative samples (presumably euploid WBCs containing 3 million-15 million reads) and 3150 positive samples, all synthetic as described above. SVM training was done with the e1071 package in R, using radial basis kernel and default parameters (Meyer et al., 2015 *R package version*:1.6-3). Each sample had 39 Z-score features, representing chromosome arm gains and losses. 677 synthetic samples were randomly sampled so that the sizes of the negative and positive classes were equivalent, and this was repeated ten times. Each sample to be classified was scored by all ten SVMs, and the ten scores were averaged to yield a final score.

Figure 51:
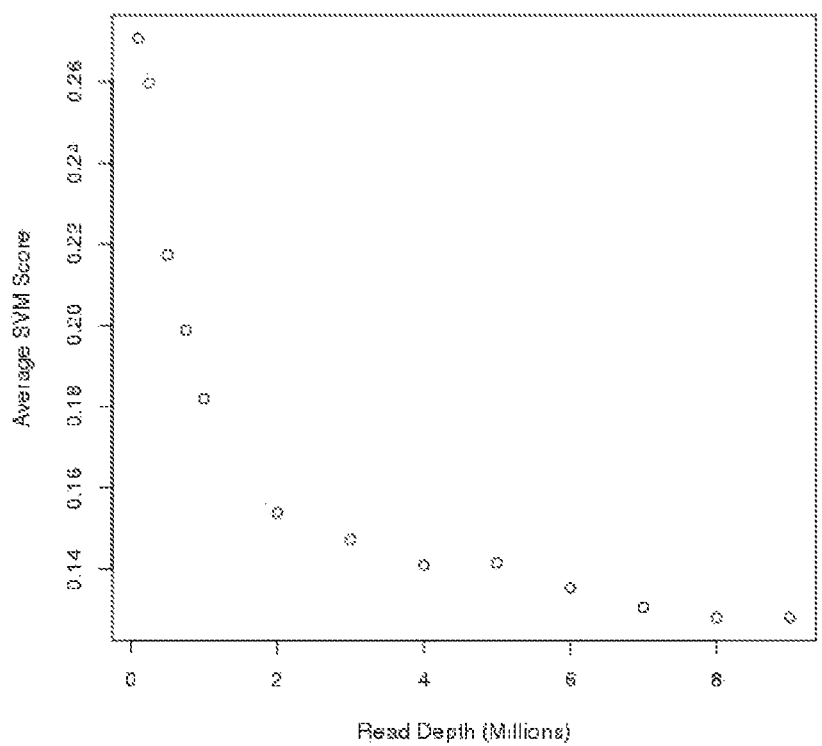
FIG. 51 contains a graph showing a distribution of genome wide aneuploidy scores (SVM Scores) as a function of read depth. Lower read depth was more likely to produce higher scores, and failing to correct for UID depth, can produce false positives.

The number of reads from the data on experimental samples can vary widely, particularly when the samples are derived from sources with limited amounts of DNA such as plasma. Samples with low reads can generate artificially high SVM scores if read depth is not taken into account. Read depth was therefore controlled for by modeling the change in SVM scores as a function of read depth in the normal samples. In particular, each of the 63 WBC euploid samples was randomly down-sampled to yield ten replicates of lower read euploid samples of read depth ranging from 100,000 to 9 million. All down-sampled euploid samples were scored using the 10 SVMs were and the scores were averaged. This procedure yielded 630 SVM scores for the down-sampled euploid samples at each read depth. All scores were converted to ratios by finding the sample at each read depth with the minimum SVM score and dividing all scores at the same depth by that value. The average ratio r at each depth decreased monotonically as a function of increasing read depth (FIG. 51). The relation between read depth and SVM score was modeled using the following equation (A=−7.076*10^−7 and B=−1.946*10^−1). Raw SVM scores were corrected by dividing by the ratio r, using the formula log (1−1/r)=Ax+B.

To score a sample as aneuploid, it was first determined whether any single chromosome arm in it was lost or gained in a statistically significant manner. A statistically significant gain of a single chromosome arm was defined as one whose Z-score was >4$\sigma$ above the maximum Z-score observed in the 677 normal WBC samples. Similarly, a statistically significant loss of a single chromosome arm was defined as one whose Z-score was <−4° below the minimum Z-score observed in the 677 normal WBC samples. Allelic imbalance based on SNPs was defined for a chromosome arm whose Z-score was Z-score was >4° above the maximum Z-score observed in the 677 normal WBC samples. Only samples in which no single chromosome arm was gained or lost when defined in this way were subjected to SVM analysis. The rationale for this process was that the SVM was designed to identify samples with large numbers of chromosome arm gains or losses but relatively low neoplastic cell fractions. The SVM was not designed to detect aneuploidy in samples with neoplastic cell fractions >10%, which were easily identified through evaluation of their Z-scores and comparison to the 677 normal samples as described in the first part of this paragraph.

Somatic Sequence Mutations and Microsatellite Instability (MSI)

When matched normal samples were available, it was attempted to detect somatic single base substitution (SBS), insertion and deletion (indel) mutations based on LINE amplicon sequences and alignments. In such cases, the molecular barcoding approach for error reduction was used. For SBS, only amplicons that have at least 200 reads and 50 unique molecular barcodes were considered. For indels, reads that were observed in at least two clusters on the sequencing instrument were considered. The SBS mutations were identified by directly comparing amplicons from the test sample with amplicons from the matched normal, and did not require any alignment to the reference genome. Amplicons with fewer than 50 reads in the matched normal sample were excluded. A somatic SBS was defined as one in which at least five reads from the test sample differed from any normal read by exactly one nucleotide substitution.

Indels were called in a similar way. Amplicons from the test sample and matched normal sample to were first aligned the reference genome (GRc37) with Bowtie2 (Langmead 2012 *Nature Methods* 9:357-359). A somatic indel was defined as one in which at least ten reads from the test sample differed from any normal read by virtue of the same insertion or deletion.

Microsatellite instability in a test sample was determined by counting the number of somatic indels in mononucleotide tracts of >3 nucleotides. There were 17,488 of these mononucleotide tracts in the LINE amplicons that were studied. It was expected that somatic indels in monotracts would be rare in a normal sample. Therefore, the null distribution of counts could be modeled as Poisson ($\lambda=1$), where $\lambda$ is the mean number of somatic indels in a monotract in a normal sample. A sample was called as harboring MSI if the number of somatic indels was statistically significant. To evaluate how often normal samples would be scored as MSI using this process, the total reads in normal samples was randomly split into two equal partitions. The first partition was used as the reference sample and the second partition was used as a test sample.

Sample Matching

To compare one sample to another, amplicons were first aligned to the reference genome GRC37 with Bowtie2. The 1000 Genomes common polymorphisms were used to identify the genotypes at 26,220 sites in each sample. Each polymorphic site was called as "0" (homozygous reference, >0.95 reads matching reference allele, minimum of ten reads), "1" (heterozygous, 0.05-0.95 UIDS matching either reference or alternate allele, minimum of ten reads of each allele), or "2" (homozygous alternate, >0.95 UIDs matching alternate allele, minimum of ten reads). Concordance was defined as the number of matched polymorphic sites that were identical in both samples (i.e., were both "0", both "1", or both "2") divided by the total number of genotypes that had adequate coverage in both samples. Two samples were considered a match if concordance was >0.98 and at least 15,000 amplicons had adequate coverage.

TCGA Somatic Copy Number Alterations

The most recent Cancer Genome Atlas Level 4 somatic copy number alteration files from Firehose were downloaded (Aggregate_AnalysisFeatures.Level_4.2016 012800.0.0), from GISTIC analysis (Beroukhim et al., 2007 *Proceedings of the National Academy of Sciences* 104: 20007-20012) of Affymetrix SNP6 arrays. 9 TCGA tumor types were selected that matched our cohorts of primary tumor samples (Breast invasive carcinoma (BRCA), colon adenocarcinoma (COAD), colon or rectal adenocarcinoma (COADREAD), esophageal carcinoma (ESCA), head and neck squamous cell carcinoma (HNSC), liver hepatocellular carcinoma (LIHC), ovarian serous cystadenocarcinoma (OV), pancreatic adenocarcinoma (PAAD), stomach adenocarcinoma (STAD), and uterine corpus endometrial carcinoma (UCEC)). A total of 6276 samples were available (Breast invasive carcinoma (BRCA): 1081, colon adenocarcinoma, colon or rectal adenocarcinoma (COAD;COADREAD): 2755, esophageal carcinoma (ESCA): 185, head and neck squamous cell carcinoma (HNSC): 523, liver hepatocellular carcinoma (LIHC): 371, ovarian serous cystadenocarcinoma (OV): 580, pancreatic adenocarcinoma (PAAD): 185, stomach adenocarcinoma (STAD): 442, uterine corpus endometrial carcinoma (UCEC): 540). The data consisted of GISTIC $\log_2$ ratios representing gains or losses of each chromosome arm (Mermel et al., 2011 *Genome biology* 12:R41). Ratios >0.2 or <0.2 were considered gains or losses (Laddha et al., 2014 *Molecular cancer research* 12:485-490).

Comparison with a Prior Technique for Detecting Single Chromosome Arm Alterations The fraction of reads that mapped to each chromosome arm in each of the 677 WBC samples, and their averages and standard deviations, were calculated (Kinde et al., 2011 *Proceedings of the National Academy of Sciences* 108:9530-9535). The score for each arm was computed as: $z_{i,chrN} = (chrN_i - \mu_{chrN})/\sigma_{chrN}$, where $chrN_i$ represents the normalized read counts for that chromosome arm and $\mu_{chrN}$ and $\sigma_{chrN}$ represent the mean and standard deviation of the normalized reads counts.

Results

Statistical Principles Underlying WALDO

Unlike most conventional approaches for assessing copy number changes, WALDO does not compare normalized read counts from each chromosome arm in a test sample to the fraction of reads in each chromosome arm in other samples. Such conventional comparisons are subject to batch effects and other artifacts associated with variables that are difficult to control. To evaluate whole genome sequencing data, aneuploidy was detected by comparing the read counts of LINEs within 4361 genomic intervals each containing 500-kb of sequence. The read counts within the 500-kb genomic intervals within a sample were only compared to the read counts of other genomic intervals within the same sample-hence the "Within-Sample" designation in WALDO.

In euploid samples, the number of LINE reads within each 500-kb genomic interval should track with the number of reads in certain other genomic regions. Genomic intervals that track together do so because the amplicons within them amplify to similar extents. Here, such genomic regions that track together are called "clusters". It is possible identify clusters from sequencing data on euploid samples. In a test sample, it is determined whether the number of reads in each genomic interval in each pre-defined cluster is within the expected bound of the other clusters from that same sample. If the reads within a genomic interval are outside the statistically expected bound, and there are many such outsiders on the same chromosome arm, then that chromosome arm is classified as aneuploid. The statistical basis of this test is described in the Materials and Methods. In brief, while the number of reads at each LINE is not randomly distributed across the genome, the distribution of scaled reads within each cluster is approximately Normal. A convenient property of Normal distributions is that the sum of multiple Normal distributions is also a Normal distribution. It is thus possible to compute the theoretical mean and variance of the summed reads on each chromosome arm simply by summing the means and variances of all the clusters represented on that chromosome arm.

WALDO also employs several other innovations that make it applicable to the analysis of PCR-generated amplicons from clinical samples. One of these innovations is controlling amplification bias stemming from the strong dependence of the data on the size of the initial template. Another is the use of a Support Vector Machine (SVM) to enable the detection of aneuploidy in samples containing low neoplastic fractions. The conceptual and statistical bases for WALDO are detailed in the Materials and Methods section herein.

Evaluation of Chromosome Arm Gains and Losses in Primary Tumor Samples

Figure 39:
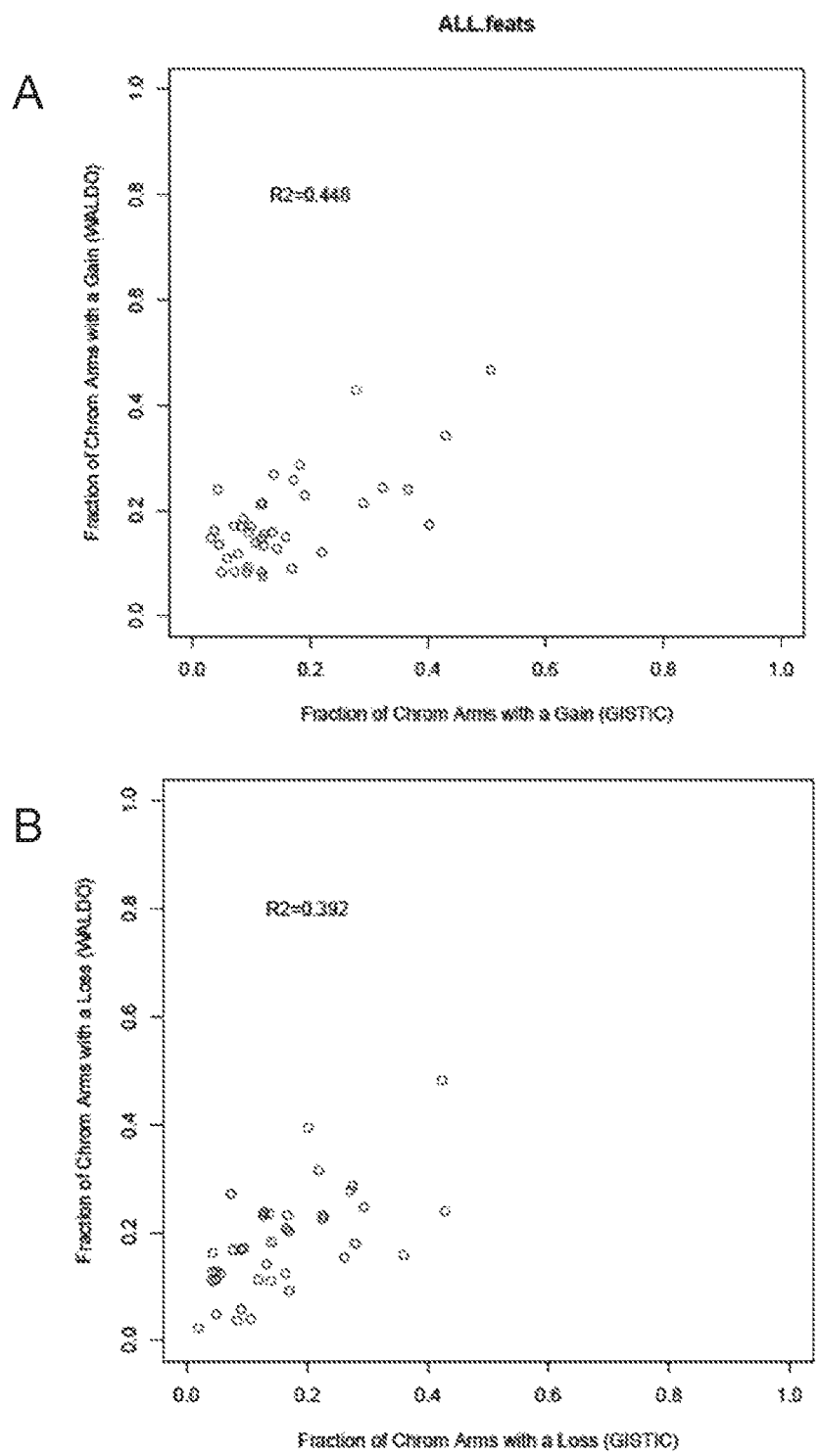
FIG. 39 contains graphs showing aneuploidy correlation comparisons of cancers detected using FAST-SeqS and WALDO compared to The Cancer Genome Atlas (TCGA) using Affymetrix SNP6.0 and GISTIC across 9 different cancer types. (A) Correlation of the fraction of chromosome arm gains. (B) Correlation of the fraction of chromosome arm losses.

WALDO was first used to study chromosome arm gains and losses in 1,677 primary tumor samples from ten cancer types. One of the outputs of WALDO is a z-score for each of the 39 non-acrocentric arms on the autosomal chromosomes. The z-scores for each of these chromosome arms in each of the primary tumor samples evaluated in this study are provided in Table 35. These results were compared with those obtained by The Cancer Genome Atlas (TCGA) on independent samples of the same tumor types (Zack et al., 2013 *Nature genetics* 45:1134-1140; and Beroukhim et al., 2007 *Proceedings of the National Academy of Sciences* 104:20007-20012). The fraction of tumor samples having a gain or a loss in each chromosome arm was identified in our data and in TCGA, considering all tumor types together and each tumor type individually. As shown in the top half of FIG. 37, the fraction of samples in all cancer types scored as a gain by WALDO or as a gain by TCGA's algorithm (GISTIC) is shown for each chromosome arm, and the fraction of samples with a loss is shown in the bottom half. The correlations between arm-level gains scored in this study and those in TCGA are shown in FIG. 39A ($R^2=0=45$) and arm-level losses are shown in FIG. 39B ($R^2=0.39$). Considering that the samples were from completely different patients, the specific chromosome arms gained and lost in both datasets were remarkably similar. The chromosome arms with the most gains were 1q, 3q, 7p, 7q, 8q, and 20q and relatively few losses were observed on these arms. Those with the most losses were 4p, 4q, 8p, and 18q and relatively few gains were observed on these arms. The arms with fewest gains or losses were 10p, 16p, 19p, and 19q.

Figure 40:
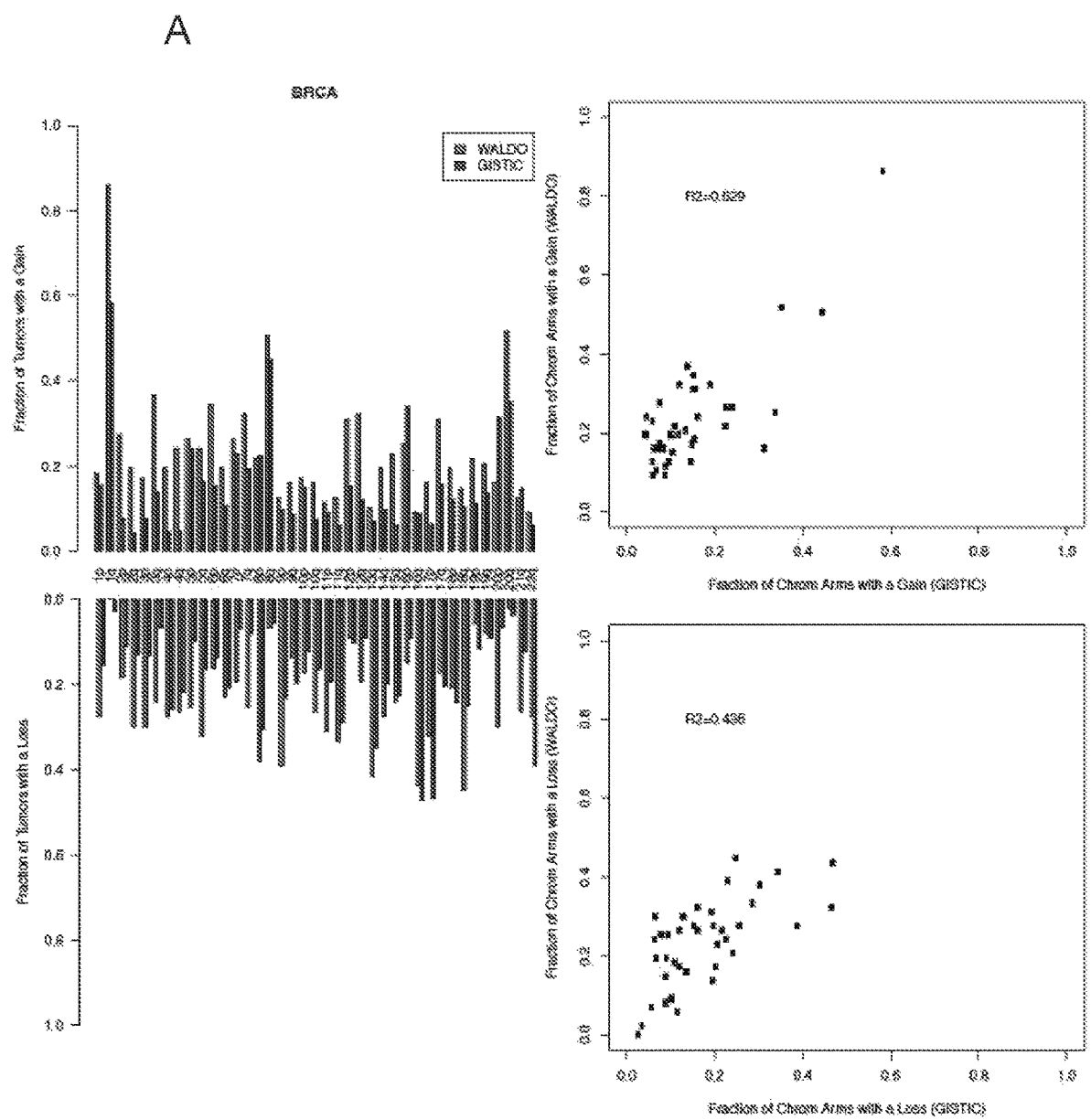
FIG. 40 contains graphs showing aneuploidy comparisons of individual cancer types that were detected using the WALDO framework compared to The Cancer Genome Atlas (TCGA). For each cancer type, the fraction of each chromosome arms gained and lost were compared. The correlation of these gains and losses in WALDO to TCGA was compared. Each sub-figure represents a different cancer type. (A) Breast invasive carcinoma (BRCA). (B) Colon adenocarcinoma and rectum adenocarcinoma (COAD; COADREAD). (C) Esophageal carcinoma (ESCA). (D) Head and neck squamous cell carcinoma (HNSC). (E) Liver hepatocellular carcinoma (LIHC). (F) Pancreatic adenocarcinoma (PAAD). (G) Ovarian serous cystadenocarcinoma (OV). (H) stomach adenocarcinoma (STAD). (I) Uterine corpus endometrial carcinoma (UCEC).
Figure 40:
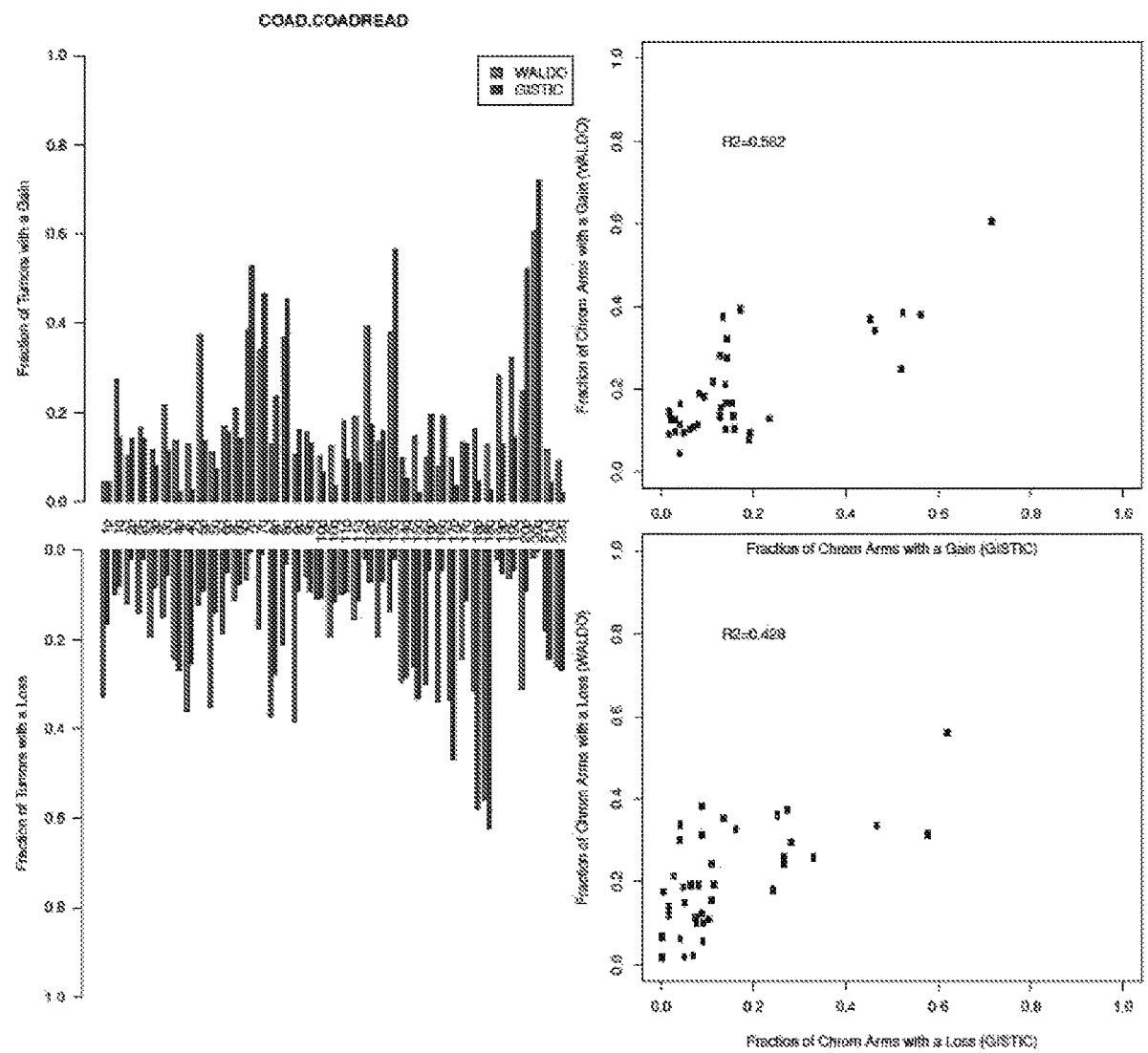
Figure 40:
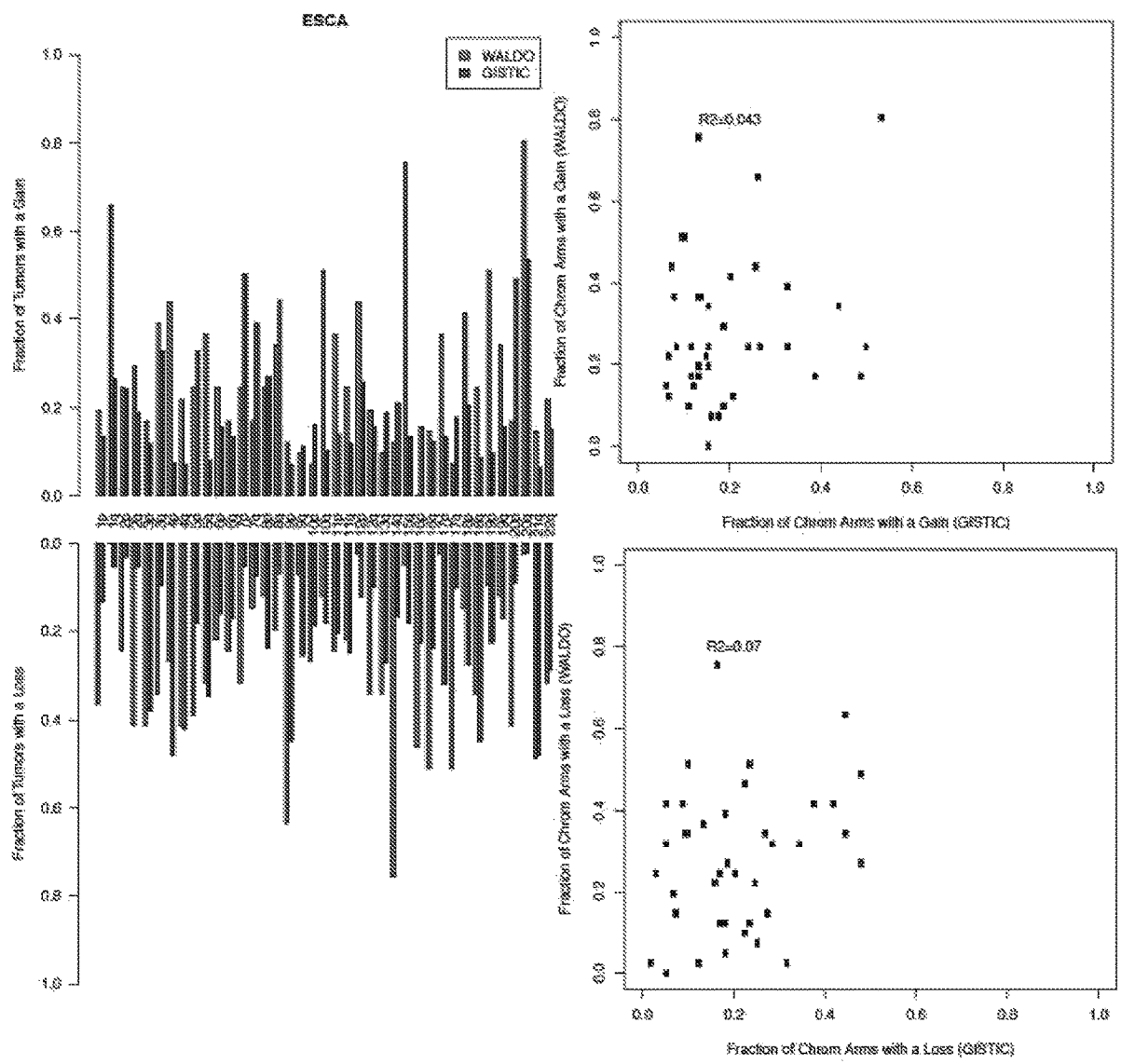
Figure 40:
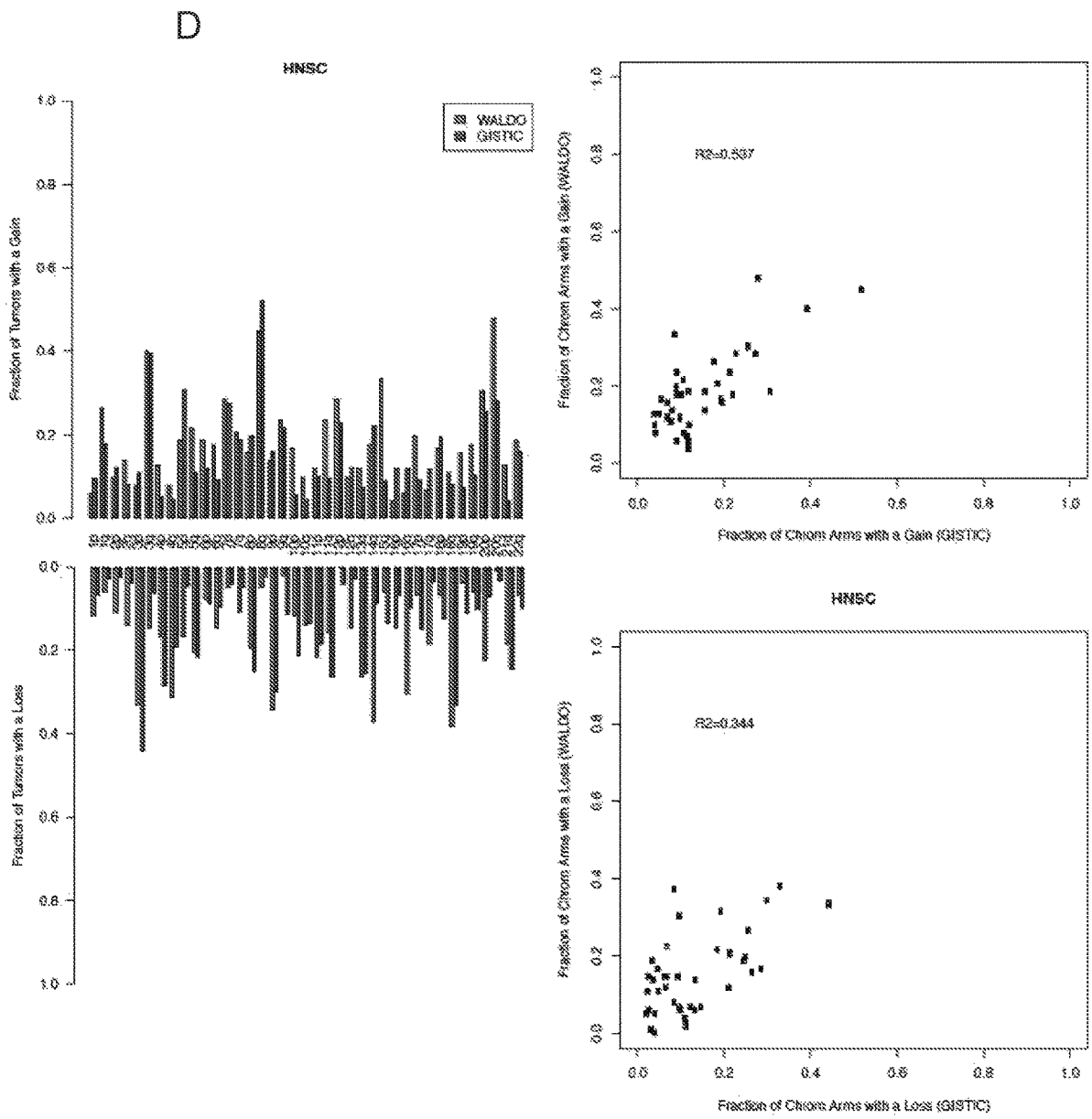
Figure 40:
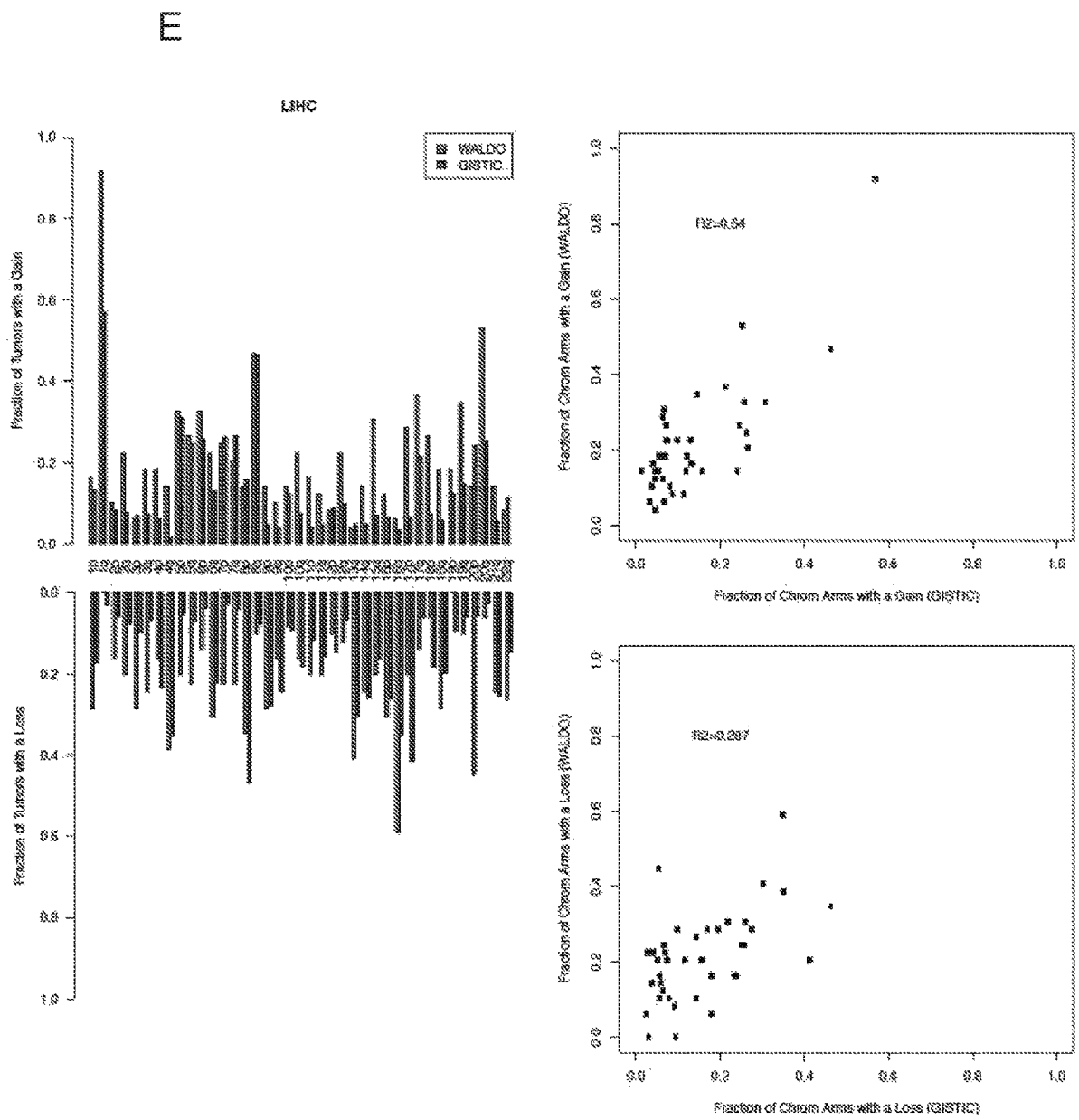
Figure 40:
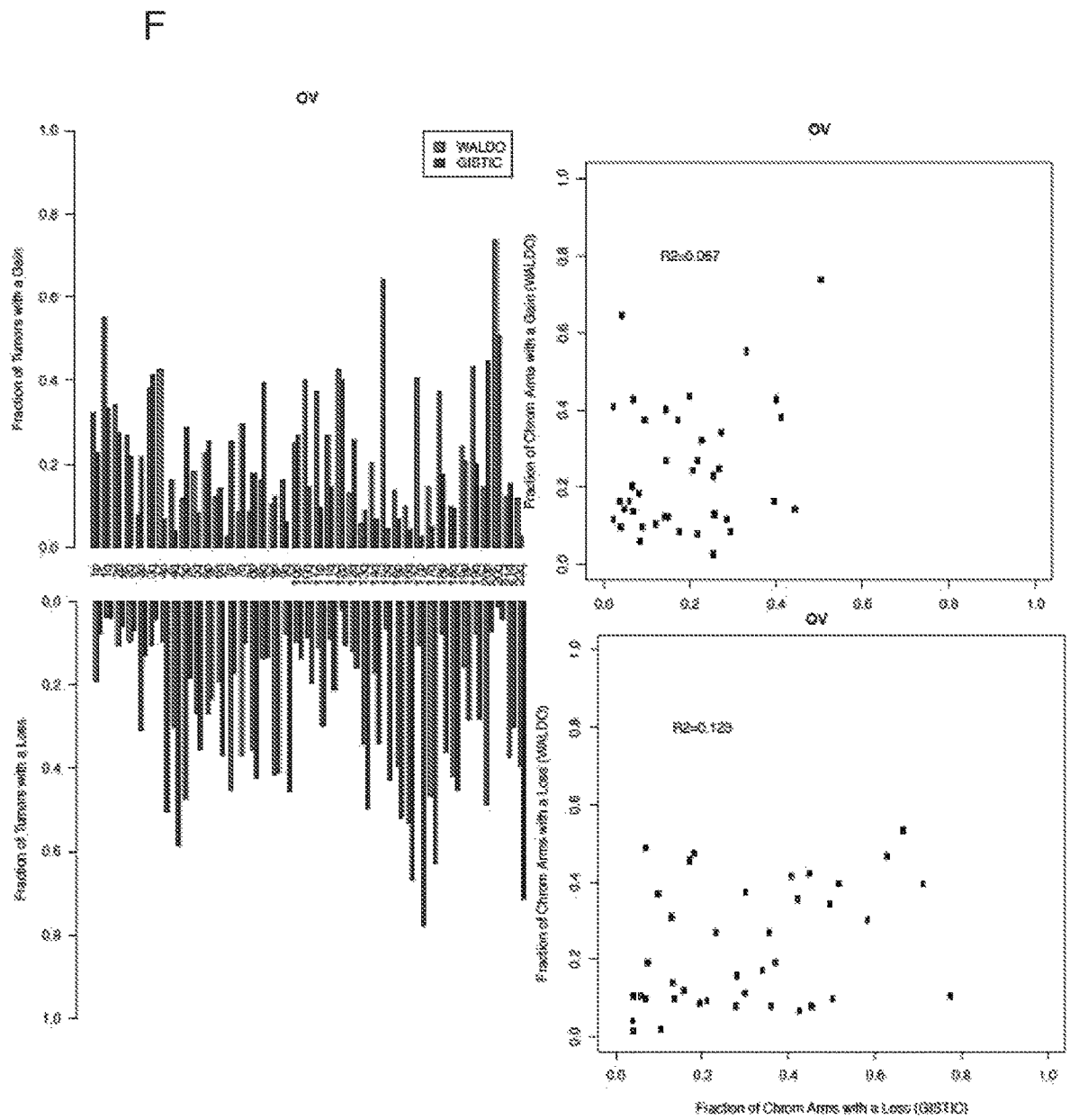
Figure 40:
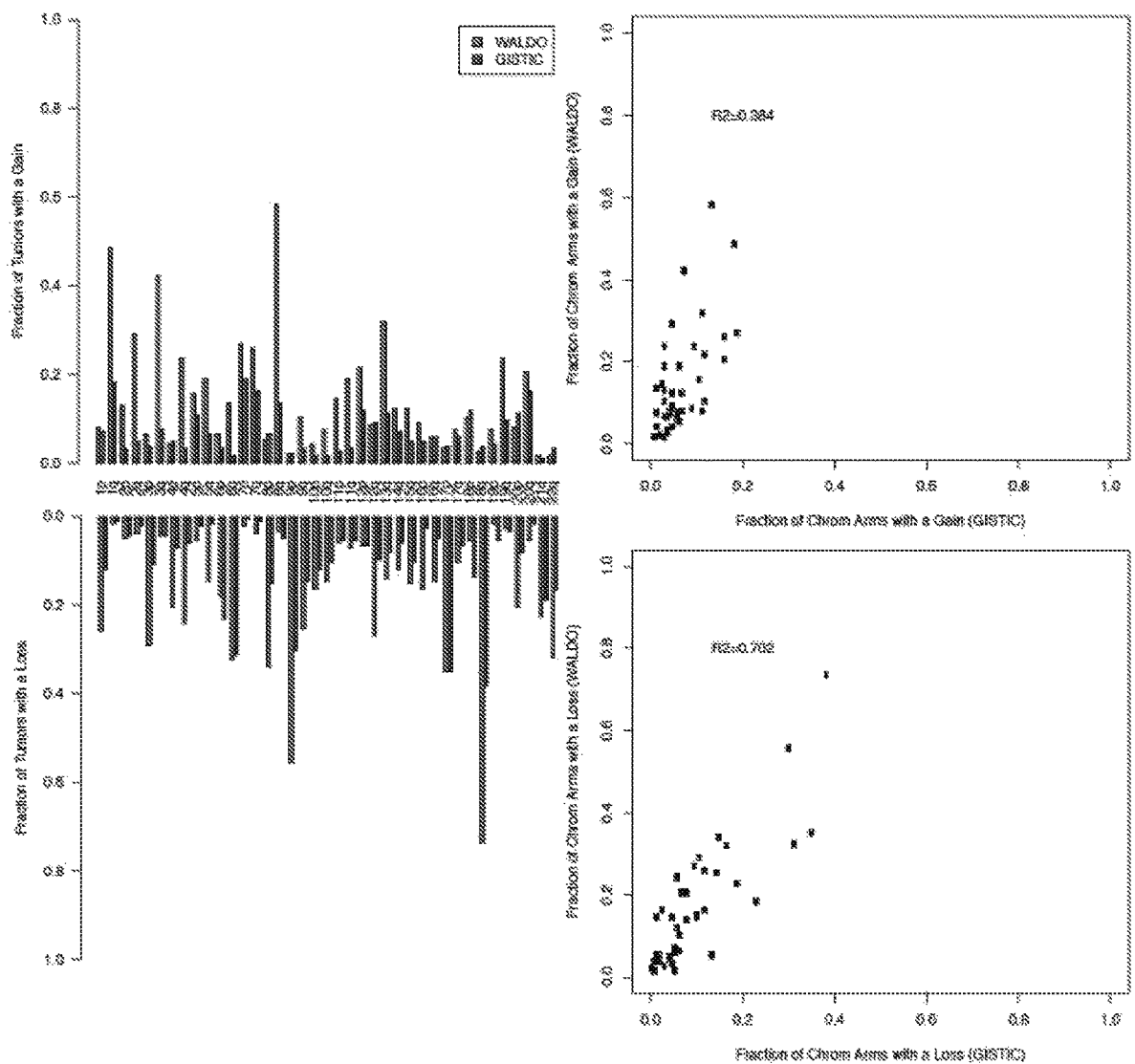
Figure 40:
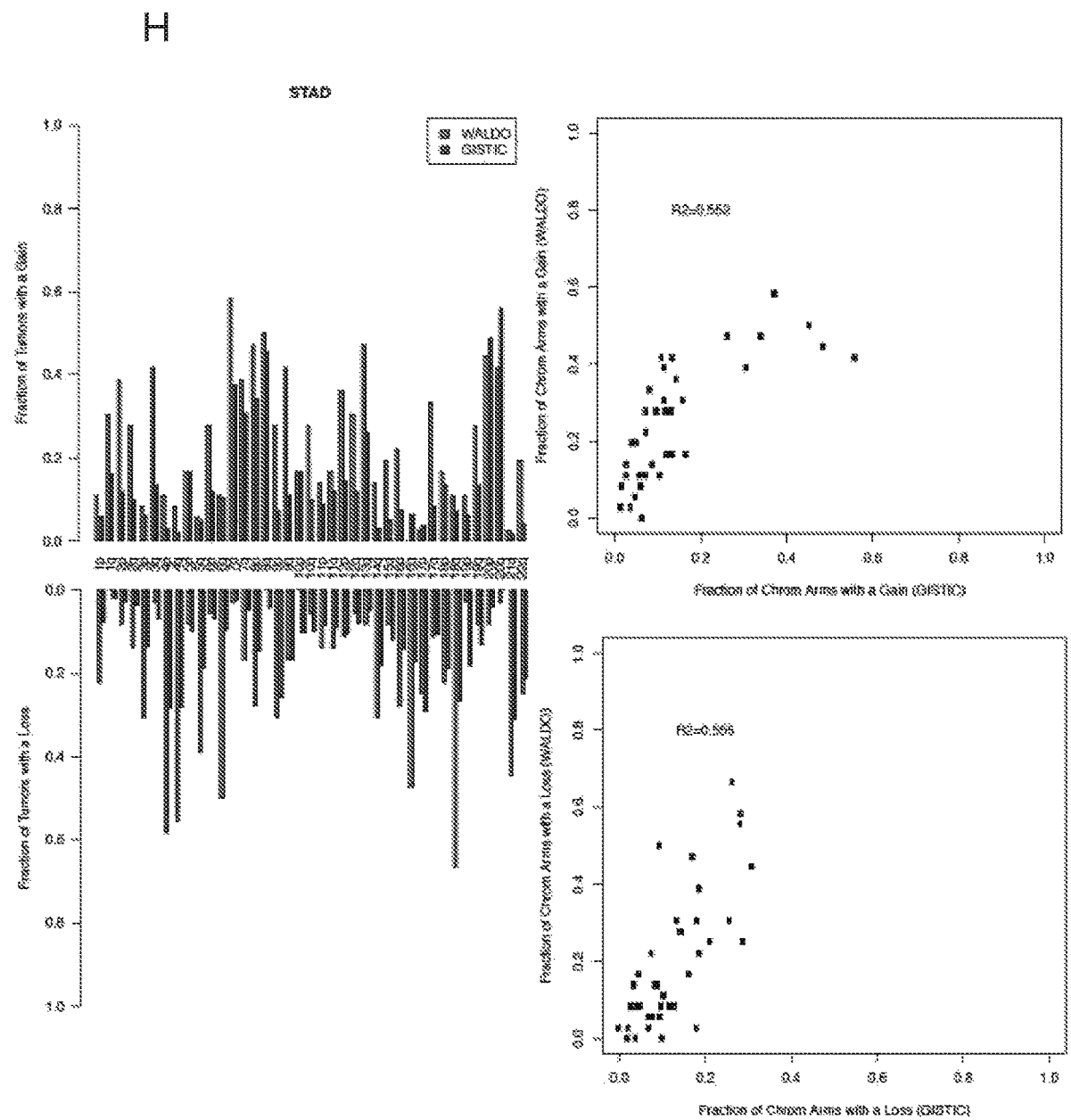
Figure 40:
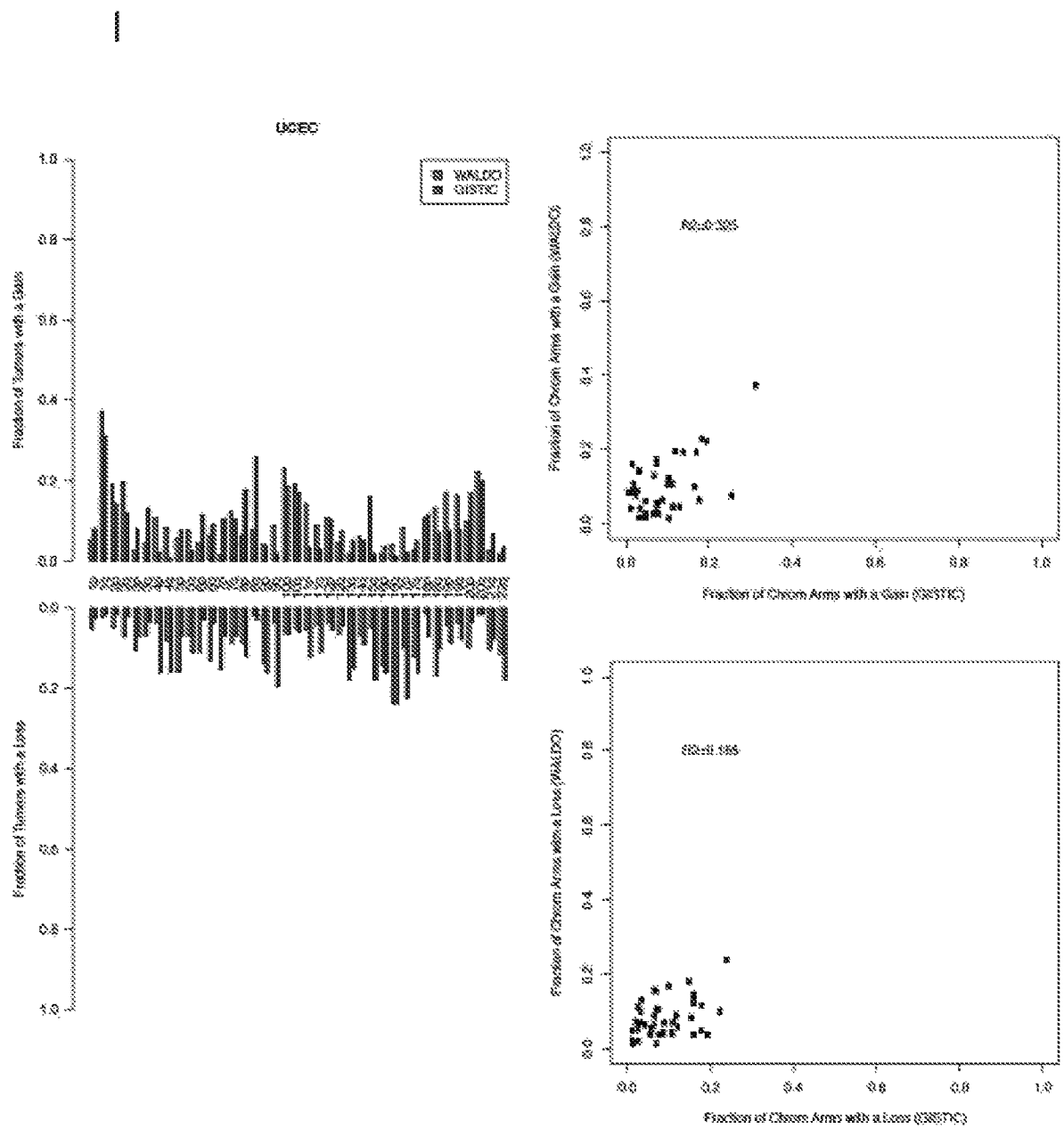

Similarly high correlations were observed for many of the specific tumor types in those cases in which a sufficient number of cancers were available for comparison (see below, and FIG. 40).

| | Gain Correlation | Loss Correlation | WALDO Samples | GISTIC Samples |
|---|---|---|---|---|
| BRCA | 0.629 | 0.436 | 89 | 181 |
| COAD; COADREAD | 0.582 | 0.428 | 536 | 2755 |
| ESCA | 0.043 | 0.07 | 42 | 185 |
| HNSC | 0.537 | 0.344 | 96 | 523 |
| LIHC | 0.64 | 0.287 | 56 | 371 |
| OV | 0.067 | 0.123 | 157 | 580 |
| PAAD | 0.384 | 0.702 | 345 | 185 |
| STAD | 0.552 | 0.555 | 28 | 442 |
| UCEC | 0.325 | 0.165 | 296 | 540 |

The highest correlations were for pancreatic adenocarcinomas and liver cancers ($R^2=0.70$ and $R^2=0.64$, respectively). An interesting outcome of this analysis was the large number of chromosome arms that were aneuploid in the great majority of cancer cases. The median number of chromosome arms that were lost or gained per cancer was 14, with interquartile range of 5 to 22. This large number was used for the development of the Support Vector Machine described below.

32 benign tumors of the colon (colorectal adenomas) were also evaluated. It was found that 25 of them displayed gains or losses of chromosomes. The median number of chromosome arms that were lost or gained per benign tumor was 4, with interquartile range of 1 to 9.75. No benign tumors have yet been studied by TCGA, so comparison was not possible. However, comparison to colorectal cancers showed that the benign tumors had many fewer chromosome arm changes than observed in cancers. Additionally, the chromosome arms altered in the adenomas overlapped with those in the cancers, and the directionality of the changes (gains vs. losses) was preserved.

WALDO also allows determination of allelic imbalances based on the SNPs with the LINEs that are concomitantly sequenced. This provides a totally independent measure of chromosome arm changes than provided by the number of reads across the 500-kb genomic intervals. Note that measurements of allelic imbalance represent the ratios between the number of reads of the reference allele vs. those of the variant allele. This ratio will be the same whether the chromosome arm containing the reference allele is gained or the arm containing the variant allele is lost. Nevertheless, without wishing to be bound by theory, one would expect that there would be a strong relationship between the chromosomes exhibiting allelic imbalances and those exhibiting either gains or losses in the same tumor. It was found that 63% of chromosome arms with allelic imbalance also had a significant gain or loss at the same chromosome arm. Other uses of the SNPs within the LINEs are described herein.

Next, the sensitivity and specificity of WALDO to call single chromosome arm gains or losses was compared (see Materials and Methods). Both methods were applied to LINE amplicon sequencing data from 677 normal peripheral white blood cell (WBC) samples, with each WBC sample independently amplified and sequenced to an average depth of 9.5M reads. This experimental data was augmented by 24,570 synthetic samples with single chromosome alterations (see Materials and Methods). Sensitivity was computed as the total number of correctly identified altered arms divided by the total number of altered arms in the synthetic samples. Specificity was computed as 1 minus the total number of incorrectly called altered arms divided by the total number of normal arms in the experimental data from the normal WBC samples. For both WALDO and the previous method, three significance thresholds (±1.96, ±3.0, ±5.0) and three neoplastic cell fractions (1%, 5%, 10%) were considered. For all thresholds and neoplastic cell fractions, WALDO had higher specificity and sensitivity (see below, and Table 34).

| Dilution | Threshold | WALDO Sensitivity | WALDO Specificity | Z Score Sensitivity | Z Score Specificity |
|---|---|---|---|---|---|
| 0.010 | 1.96> or <− 1.96 | 0.221 | 0.969 | 0.144 | 0.952 |
| 0.010 | 3> or <− 3 | 0.031 | 0.999 | 0.020 | 0.995 |
| 0.010 | 5> or <− 5 | 0.000 | 1.000 | 0.000 | 1.000 |
| 0.050 | 1.96> or <− 1.96 | 0.969 | 0.969 | 0.899 | 0.952 |
| 0.050 | 3> or <− 3 | 0.917 | 0.999 | 0.748 | 0.995 |
| 0.050 | 5> or <− 5 | 0.671 | 1.000 | 0.443 | 1.000 |
| 0.100 | 1.96> or <− 1.96 | 0.999 | 0.969 | 0.988 | 0.952 |
| 0.100 | 3> or <− 3 | 0.995 | 0.999 | 0.957 | 0.995 |
| 0.100 | 5> or >− 5 | 0.957 | 1.000 | 0.839 | 1.000 |

To further evaluate the ability of WALDO to detect single chromosome abnormalities, DNA from patients with trisomy 21 was also evaluated. The DNA from individuals with trisomies were physically mixed at a ratio of 2 ng of normal DNA and 0.2 ng of Trisomy 21 DNA. The mixtures were created to replicate typical fetal fractions in noninvasive prenatal testing (approximately 10%). Using polymorphisms in the LINE amplicons, the trisomy admixture rate of the samples (range 7.7%-10.4%) was estimated. Using a z threshold of 2.5, it was found that as few as 2M reads could detect trisomy 21 at fetal fractions typically observed (Sensitivity 95%). 16 normal WBC were then sampled at various read depths. At 2M reads using the same threshold, the specificity was 100%. Sensitivities and specificities at other read depths and other admixtures of trisomy 21 samples are summarized in FIG. 41.

Aneuploidy Detection in Samples with Low Fractions of Neoplastic Cell DNA

Many potential applications of aneuploidy detection in cancer involve identifying a relatively small fraction of DNA from neoplastic cells within a large pool of DNA derived from normal cells. One notable application is liquid biopsy, i.e., the evaluation of bodily fluids such as urine, saliva, cyst fluid, or sputum for evidence of cancer. Given that aneuploidy is a general feature of cancers of virtually all types (see FIG. 37), detecting aneuploidy could be used for this purpose.

To employ WALDO for liquid biopsies, a 2-stage approach was used. The first employed a search for individual chromosome arm gains or losses or allelic imbalance, as described above. Simulations with synthetic DNA showed that this approach could detect an individual chromosome arm gain or loss with sensitivities >90% at specificities >99% when the fraction of DNA contributed by the neoplastic cells was >5% of the total DNA. To detect aneuploidy in samples with lower fractions of neoplastic cell DNA, that fact that the median number of chromosome arm gains or losses per tumor was high (Kinde et al., 2012 PloS ONE 7:e41162) was exploited. A variety of approaches to distinguish samples containing low fractions of neoplastic DNA with multiple chromosome abnormalities from euploid samples was therefore considered. These approaches included counting the number of significant arms, combining scores of the most significant arms, and summing squared window-based Z-scores. Based on synthetic samples, it was found that the optimum approach was obtained with a Support Vector Machine (among many machine learning algorithms tested). The Support Vector Machine training was designed to be generally applicable to any cancer type rather than based on patterns of gains and losses typical of specific cancer types. With synthetic samples, the Support Vector Machine could detect aneuploidy in 78% of samples with a neoplastic cell fraction of 1% at a specificity of 99% as determined by cross validation. This Support Vector Machine-based algorithm was therefore incorporated into WALDO for the evaluation of clinical samples with low neoplastic composition (see FIG. 38).

Figure 38:
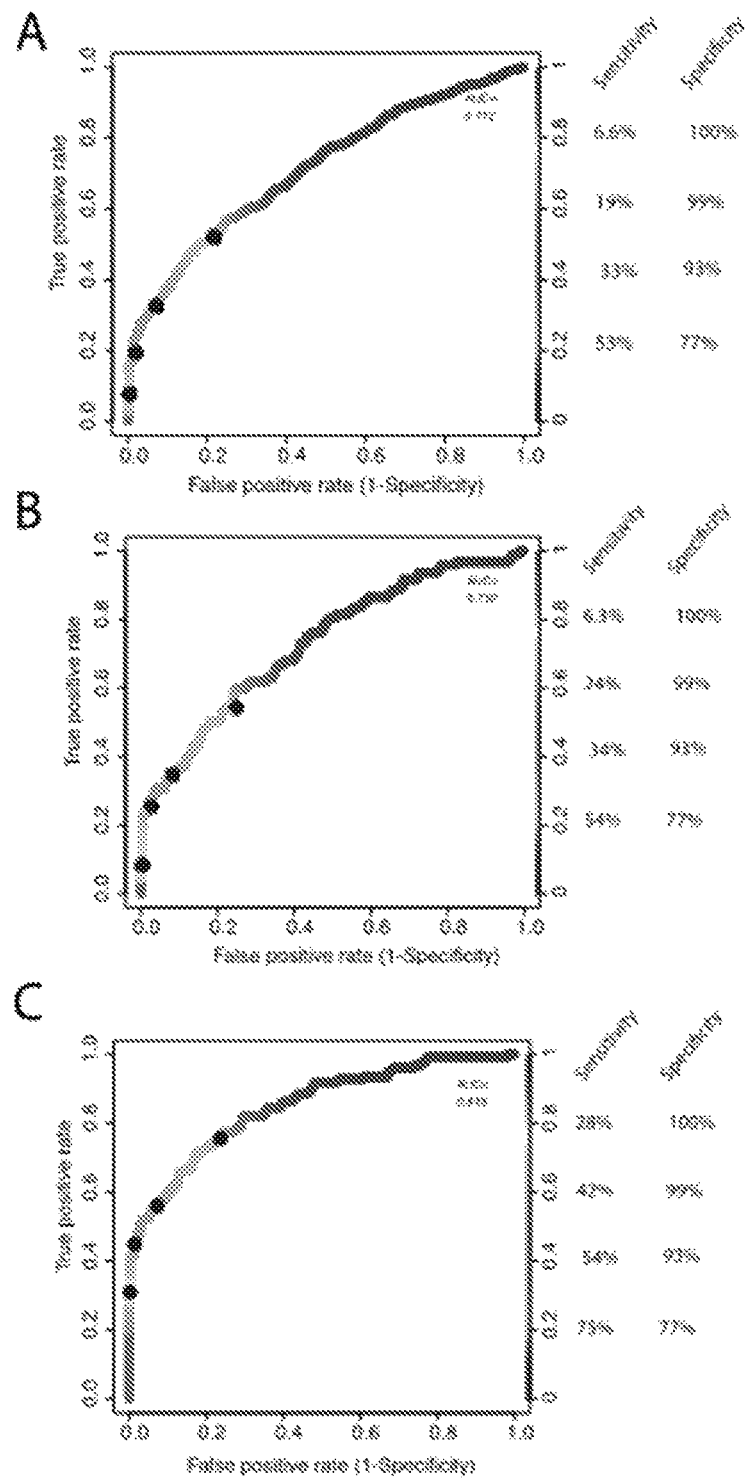
FIG. 38 shows aneuploidy detected in plasma samples from cancer patients. Receiver operating characteristics (ROC) and area under the curve (AUC) are shown for three ranges of neoplastic cell fractions. True positives were defined as those samples from cancer patients scoring positive while false positives were defined as those from normal individuals scoring positive. The neoplastic cell fraction of each plasma samples was estimated from driver gene sequencing data as described in the text. (A) Samples with neoplastic cell fractions <0.5%. (B) Samples with neoplastic cell fractions ranging from 0.5-1%. (C) Samples with neoplastic cell fractions >1%.

WALDO was then used to attempt to evaluate aneuploidy in plasma samples from 961 cancer patients and 566 healthy individuals (see Materials and Methods). Cancers of 8 different types were evaluated (see Table 36). The neoplastic cell fraction of each cancer sample was considered to be the mutant allele fractions determined from deep sequencing data. Samples were divided into those with neoplastic cell fractions >1% (122 samples), between 0.5% and 1% (96 samples) and <0.5% (738 samples). Sensitivity was defined as the proportion of cancer patient samples scored as aneuploid, while specificity was defined as 1 minus the fraction of healthy patient samples scored as aneuploid. Receiver operating curves (ROC) are shown in FIG. 38 for these three ranges of neoplastic fractions. At stringent specificity (99%), aneuploidy was identified in 42% of samples with neoplastic cell fractions >1% (see FIG. 38A). As expected, sensitivity decreased with decreasing neoplastic cell fractions (see FIG. 38B, 38C). At 99% specificity, WALDO detected aneuploidy in 24% of samples with neoplastic cell fractions of 0.5 to 1% and in 19% of samples with neoplastic cell fractions of 0 to 0.5%. The specific cancer type of the patient was not highly correlated with positive aneuploidy calls. However, the number of template molecules that were assessed did correlate with sensitivity.

In plasma samples with higher neoplastic cell content, it was possible to determine which chromosome arms were gained or lost. Among 558 of the plasma samples that had a paired primary tumor, 188 samples had a significant chromosome arm gain or loss and 54% had a concordant gain or loss in the primary tumor. In samples with low neoplastic content, none of the individual arms were gained or lost at statistically significant levels but the Support Vector Machine component of WALDO was presumably able to pick out small deviations in multiple chromosome arms that distinguished them from euploid samples.

Sample Matching

DNA profiling with short tandem repeats is a well-established forensic technique that is now routinely used. Carefully curated SNP panels have also been developed to ensure sample identity, such as between tumor and normal specimens from the same patients (Kidd et al., 2006 *Forensic science international* 164:20-32; and Pengelly et al., 2013 *Genome medicine* 5:89). The LINEs amplified in FAST-SeqS contain 26,220 common polymorphisms, including variants detected in >1% in 1000 Genomes (Consortium 2012 *Nature* 491:56-65). These polymorphisms theoretically provide a powerful way to profile DNA samples evaluated for aneuploidy without any additional work or cost. To determine whether such identification was possible in practice, a measure of concordance between any two samples was designed (see Materials and Methods). This to measure concordance was then used in replicates of 176 normal WBC samples to one another, using ~5 replicates per sample, for a total of 676 WBC samples. The input to WALDO was 676 samples, without specifying the sample name, so there were a total of 456,976 (676×676) possible matches. WALDO correctly matched all replicate samples with high concordance (>99.9%), without any false matching. Next, this protocol was performed on 970 plasma samples and 1,684 tumor samples. The 558 plasma samples should match the corresponding primary tumor samples and no other matches should be observed. This produced 7,038,409 ((970+1,683)×(970+1,683)) possible matches. Nearly all the 2653 samples matched as expected, i.e., only to themselves or to the corresponding primary tumors, with concordance >99.8%. However, two plasma samples were found that did not match to the expected primary tumors and 12 plasma samples that matched to other plasma samples that were purportedly derived from different donors. In all these "mismatched cases", the FastSeqS data indicated high concordances (>99.8%). The mismatches were therefore most likely a result of mislabeling of the samples and illustrated the utility of sample identity check with WALDO.
Mutation Load, Carcinogenic Signatures, Microsatellite Instability When two samples, a normal and a cancer, are available from the same patient, LINE mutations that are in one sample but not the other can conceivably be discerned. For this application, molecular barcoding to reduce sequencing errors (see, e.g., Kinde et al., 2011 *Proceedings of the National Academy of Sciences* 108:9530-9535) can be used, as is achieved through the experimental and bioinformatics components of WALDO (see Materials and Methods).

Figure 42:
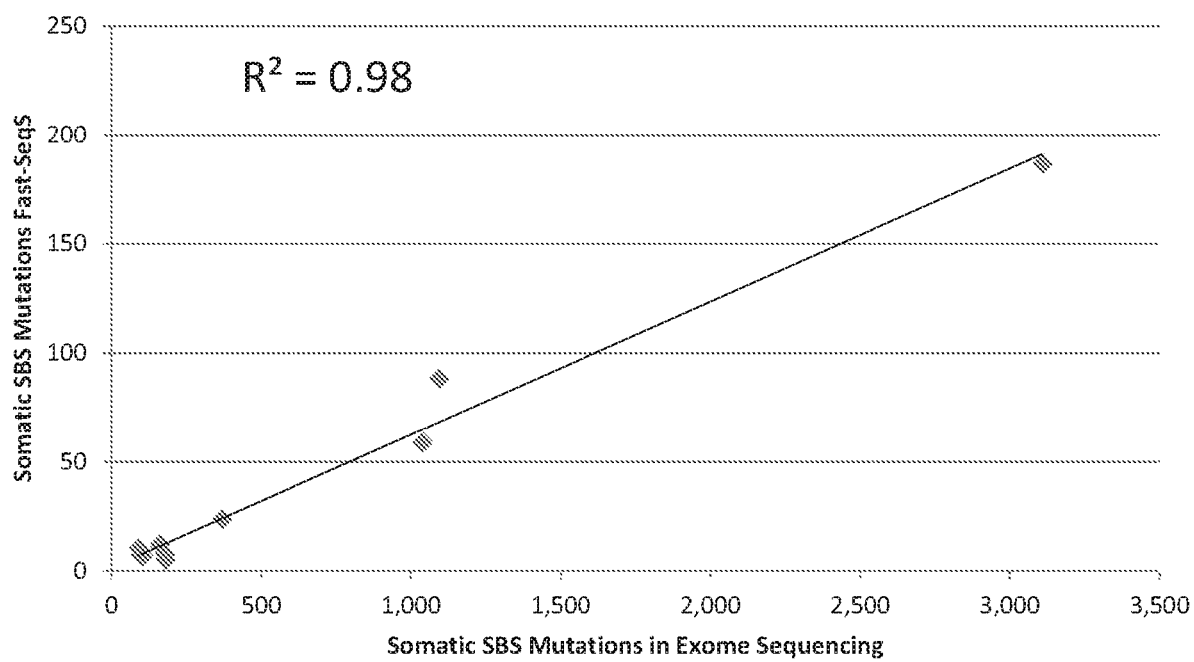
FIG. 42 contains a graph showing a comparison of the total number of somatic single base substitutions (SBS) that were detected in Exome Sequence vs WALDO.
Figure 43:
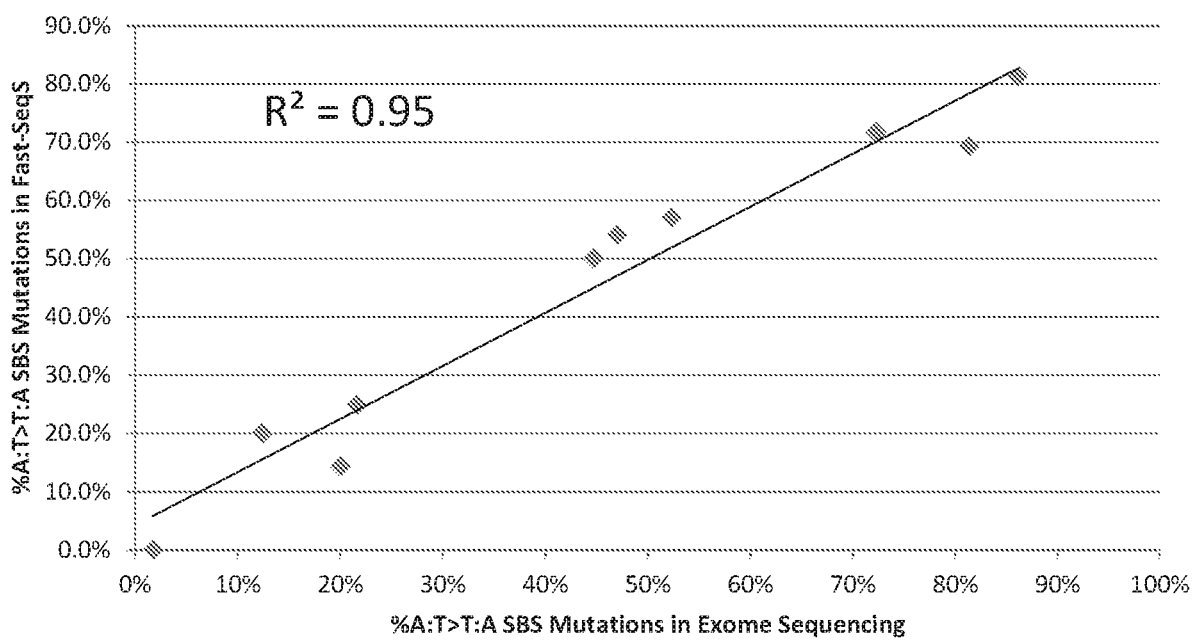
FIG. 43 contains a graph showing a comparison of the percentages of single base substitution mutations that are A:T>T:A Mutations that were detected via Exome sequencing vs WALDO.
Figure 44:
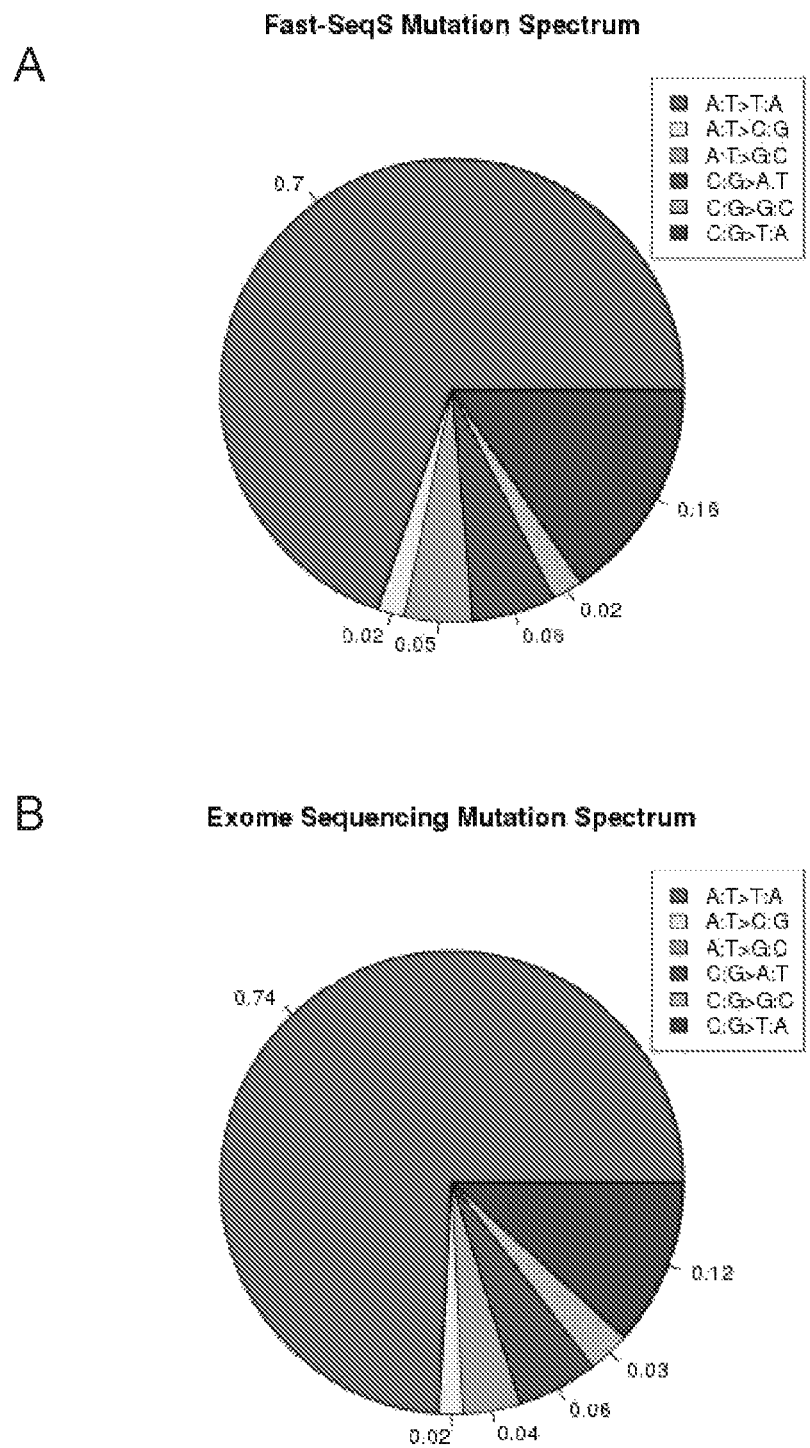
FIG. 44 contains graphs showing the spectrums of single base substitution (SBS) mutations. (A) SBS identified by WALDO. (B) SBS identified by exome sequencing.

To determine whether somatic mutation detection was feasible, ten urothelial carcinomas of the upper urinary tract (UTUCs) and normal tissues from the same patients were evaluated. These samples had previously been analyzed by exomic sequencing (Hoang et al., 2013 *Science translational medicine* 5:197ra102-197ra102). For each tumor sample, the number of somatic mutations were counted and the spectrum of single base substitutions (SBS) (A→T, A→C, etc.). It was found that the number of SBS in LINEs was highly correlated with the number of SBS in the exomes of these tumors ($R^2$=0.98, p<2.6*$10^{-8}$). The spectrum of mutations in the LINEs was similarly correlated with the spectrum of mutations in exonic sequences ($R^2$=0.95, p<1.8*$10^{-6}$). Noticeably, six of these tumors were from patients exposed to aristolochic acid and the pathognomonic signature (A→T, T→A) of this mutagen was prominent in these six tumors (see FIG. 42, FIG. 43, and FIG. 44).

The LINEs assessed by WALDO harbor 17,488 mononucleotide tracts of >3 nucleotides. Because mononucleotide tracts are particularly sensitive to defects in mismatch repair, it was determined whether WALDO could be used to assess mismatch repair deficiency. For this purpose, the number of indels in the 17,488 LINE mononucleotide tracts were assessed. It was found the number of indels in six mismatch repair-deficient colorectal cancers averaged 35 and ranged from 10 to 67. Normal tissues from these patients harbored only zero or one indel, and the difference between the cancers and normal tissues was highly significant (p<7.2*104).

Example 7: Genome-Wide Quantification of Rare Mutations by Bottleneck Sequencing The accumulation of random somatic mutations in the nuclear and mitochondrial genome over time underlies fundamental theories of carcinogenesis, neurodegeneration, and aging (see, e.g., Stratton et al., 2009 *Nature* 458:719-724; Kennedy et al., 2012 *Mech Ageing Dev* 133:118-126; and Vijg et al., 2014 *Current opinion in genetics & development* 26:141-149). Direct observation of these rare mutations in the human body with age therefore has the potential to enhance our understanding of human disease. Currently, no simple high-throughput method exists to directly and systematically quantify somatic mutational load in normal, non-diseased human tissues at a genome-wide level. Next-generation DNA sequencing (NGS) technologies address this issue, but their sequencing error rate limits the detection of rare mutations (see, e.g., Albertini et al., 1990 *Annu Rev Genet* 24:305-326; and Cole et al., 1994 *Mutat Res* 304:33-105).

This Example describes a Bottleneck Sequencing System (BotSeqS) technology designed to accurately detect rare point mutations in any molecularly-barcoded library in a completely unbiased fashion. BotSeqS, a next-generation sequencing method that simultaneously quantifies rare somatic point mutations across the mitochondrial and nuclear genomes. BotSeqS combines molecular barcoding with a simple dilution step immediately prior to library amplification. In this Example, BotSeqS is used to show age and tissue-dependent accumulations of rare mutations and demonstrate that somatic mutational burden in normal tissues can vary by several orders of magnitude, depending on biologic and environmental factors. This Example also shows major differences between the mutational patterns of the mitochondrial and nuclear genomes in normal tissues. Lastly, the mutation spectra of normal tissues were different from each other, but similar to those of the cancers that arose in them. This technology can provide insights into the number and nature of genetic alterations in normal tissues and can be used to address a variety of fundamental questions about the genomes of diseased tissues.

Materials and Methods

Human Tissue Samples

Normal, non-diseased tissues for this study were acquired from five different sources (Table 43). For COL229 to COL237 and SIN230, colon or duodenum was obtained from consented patients at the Johns Hopkins Hospital with the approval of its Institutional Review Board. For COL373 to COL375 and BRA01 to BRA09, flash frozen, post-mortem colon and brain was requested from the NIH NeuroBioBank (neurobiobank.nih.gov), with the request being approved and fulfilled by University of Maryland Brain and Tissue Bank (Baltimore, Maryland) and University of Miami Brain Endowment Bank (Miami, Florida). For KID034 to KID038, flash frozen, post-mortem kidney cortex blocks (200 mg) were purchased from Windber Research Institute (Windber, Pennsylvania). COL238 and COL239 were as reported elsewhere (see, e.g., Parsons et al., 1995 *Science* 268:738-740; Hamilton et al., 1995 *The New England journal of medicine* 332:839-847; and De Vos et al., 2004 *American journal of human genetics* 74:954-964). SA_117, SA_118, SA_119, AA_105, AA_124, and AA_126 were as reported elsewhere (see, e.g., Hoang et al., 2013 *Science translational medicine* 5:197ra102). The initial rationale for the sample size for colon and brain was to acquire at least three individuals in each age group in order to understand the average trend of somatic mutational patterns for each age group. Age groups for colon and brain were selected based on human body growth and maintenance: early body development at <10 years, fully grown young adult body at ~20-40 years, and old, maintained adult body at >90 years. For colon, one tissue from the young child age group (SIN230) was later determined to be duodenum, leaving only two individuals representing the young child age group for colon epithelium. For normal kidney, criteria for kidney acquisition were an age-matched and non-smoking control group for the kidneys of smokers and aristolochic acid-exposed samples. All normal kidney controls were Caucasian and therefore less likely to originate from a high risk AA-exposed population (e.g. Asia). From the same kidney tissue source, three aliquots of flash frozen, post-mortem normal kidney from a five month old individual were available as technical replicates and to further test an age-trend for non-carcinogen exposed normal kidneys.

Preparation of Illumina Y-Adapter-Ligated Molecules

Genomic DNA (34 ng to 1 µg) in 55 µL TE buffer was fragmented using BioRuptor (Diagenode) at high intensity for 15 s on and 90 s off, using 7 cycles at 3° C. After random fragmentation, Illumina Y-adapters were ligated to the DNA fragments using TruSeq DNA PCR-Free kit (Illumina) according to a standard low DNA input Illumina protocol with selection for 350 bp insert sizes. This resulted in adapter-ligated molecules in a total volume of 20 µL.

Dilution of Y-Adapter-Ligated Molecules

Five ten-fold serial dilutions were performed in 96-well PCR plates starting with 2 µL of adapter-ligated molecules (prior to PCR) in 18 µL of dilution buffer (TE containing 1 ng/µL pBlueScript). Samples were mixed by gently pipetting with a multichannel pipette. Two µL of each sample was then transferred into 18 µL of fresh dilution buffer using a multichannel pipette. The mixing and transferring was repeated for a total of five serial dilutions. Only 2 µL of each dilution (1/10 total volume) was used as template for each PCR. A $10^3$-fold dilution was accomplished as follows: (i) use of 2 µL of the total 20 µL of adapter-ligated molecules (10-fold dilution); (ii) mixing 2 µL of adapter-ligated molecules with dilution buffer in a total volume of 20 µL (10-fold dilution); and (iii) use of 2 µL of diluted adapter-ligated molecules from the total 20 µL volume in the PCR reaction (10-fold dilution, see below). The five serial dilutions resulted in final dilution factors of $10^3$, $10^4$, $10^5$, $10^6$, and $10^7$.

PCR Amplification of Diluted Y-Adapter-Ligated Molecules

Custom HPLC-purified PCR primers (IDT), TS-PCR Oligo1 (5'-AATGATACGGCGACCACCGAG*A; SEQ ID NO:808) and TS-PCR Oligo2 (5'-CAAGCAGAAGACGGCATACGA*G; SEQ ID NO:809), were designed with one phosphorothioated bond (*) at the 3' end. PCR was performed in 50 µL total volume with 0.5 µM TS-PCR Oligo1, 0.5 µM TS-PCR Oligo2, Q5 2× HotStart High-Fidelity Master Mix (NEB) at 1× final concentration, and 2 µL of diluted adapter-ligated molecules as template. PCR was performed in Thermo HyBaid PCR Express HBPX Thermal Cycler. The following PCR program was used: 1) 98° C. for 30 s 2) 98° C. for 10 s, 69° C. for 30 s, 72° C. for 30 s for 18 cycles, and 3) 72° for 2 min. PCR reactions were purified with AMPure XP (Agilent) at 1.0× bead-to-sample ratio according to the manufacturer's protocol.

MiSeq Run and Analysis

A subset of amplified BotSeqS sequencing libraries was evaluated on an Illumina MiSeq instrument (~5 M clusters passed filter per library) to empirically deduce the optimal dilution. The "optimal dilution" was determined to result in 5 to 10 PCR duplicates per molecule when scaled to ½ lane of a HiSeq instrument (~70 M clusters passed filter per library in Rapid Run mode). For example, for an input of 500 ng gDNA into the TruSeq PCR-free library prep (selecting for 350 bp insert size), amplified libraries from the 104-, 105-, 106-fold dilutions were sequenced at 2×50 bp depth on MiSeq. Three different well-barcoded samples (which were also molecularly barcoded) were multiplexed in one MiSeq lane to test three dilutions of each sample. The .bam output files were uploaded into Galaxy, and Picard's Estimate Library Complexity Tool (Galaxy Tool Version 1.56.0) was executed using the default parameters. Optimal dilutions showed distributions ranging from one to four members per family with singletons comprising ~60-80% of total counts. In general, with an input of 500 ng of gDNA into the TruSeq PCR-free library prep, the 105-fold dilution yielded ~10 members per family on a subsequent HiSeq run used for BotSeqS. From our sequencing data, we estimate the average number of high quality clusters required to identify one rare mutation in colonic tissues was (1) 30 M in a normal child, (2) 12 M in a normal young adult, and (3) 5.8 M in a normal old adult.

Whole-Genome Sequencing

Thirty-two whole-genome sequencing (WGS) libraries were generated from the 34 individuals in this study. In the remaining two individuals without WGS, COL238 and COL239, Sanger sequence was performed to exclude clonal variants in the BotSeqS data. Of the final 20 µL of adapter-ligated molecules used to prepare BotSeqS libraries (prior to dilution), 10 µL was used to amplify a library for whole-genome sequencing using TruSeq PCR Primer Cocktail (Illumina) and TruSeq PCR Master Mix (Illumina) according to TruSeq PCR protocol. PCR reactions were purified with AMPure XP (Agilent) at 1.0× bead-to-sample ratio according to the manufacturer's instructions. The libraries were PE sequenced 2×100 bp on Illumina HiSeq at >30× coverage.

Spike-In Sensitivity Experiment

Two DNA mixtures were prepared from the DNA of normal spleen samples PEN93 and PEN95. Whole genome sequence data was available from these two samples (see, e.g., Jiao et al., 2011 *Science* 331:1199-1203) and SNPs in PEN93 that were not present in PEN95 could be identified. Both mixtures contained the same amount of PEN95 DNA, but the low spike-in mix contained only 10% of the PEN93 DNA contained in the high spike-in mix. BotSeqS libraries from these samples were first analyzed using the normal BotSeqS pipeline to minimize clonal and germline mutations. Indeed only a total of two mutations were detected among the two libraries; these two mutations likely represented rare mutations in the PEN95 sample, and suggest a mutation frequency of $\sim 8 \times 10^{-7}$ mutation/bp. Next, the data were processed through the BotSeqS pipeline without filtering out mutations that were present in dbSNP (build 130 and 142). Seven PEN93-specific SNPs in the low spike-in and 89 PEN93-specific SNPs in the high spike-in mixtures were identified. After normalizing for the number of sequenced bases, the "mutation frequency" (number of PEN93-specific SNPs/bp) was $2.71 \times 10^{-6}$ for the low spike-in and $2.01 \times 10^{-5}$ for the high spike-in samples. The difference between the low spike-in and the high spike-in was 7.4-fold, within the range expected from the 10-fold dilution given the relatively low number of mutations identified in the low spike-in sample.

Characterization of BotSeqS Specificity

As one measure of specificity, we identified rare mutations as usual except that we used mutations that were present in only one strand rather than in both. Specifically, mutations were present in ≥90% of the Watson family members and the reference sequence was present in ≥90% of the Crick family members, or vice versa, but satisfied our other criteria for being "rare". False Watson and Crick pairings were then created, where the Watson strand had overlapping but different coordinates than the Crick strand, and vice versa, to determine if they contained the same mutation by chance. BotSeqS works by having low coverage throughout the genome, generated through the bottleneck dilution step, and precluded this analysis in the nuclear DNA. Instead, mtDNA were used because of the multiple copies of mtDNA per cell. The coverage of mtDNA with BotSeqS is much higher than that of nuclear DNA and facilitated the identification of overlapping molecules. 30 BotSeqS control libraries were processed this way and a total of 146 mtDNA mutations were identified present in one strand only. Using this dataset, each sample was then searched for overlapping molecules and identified 27 examples. None of the 27 false Watson and Crick pairs shared the same artifactual mutation.

Non-random shearing could produce another type of artifact, falsely suggesting that the Watson and Crick strands of a family were actually derived from two different molecules that coincidentally had the same genomic coordinate. To test for such artifacts, Watson and Crick family pairs were identified that contained the variant in the Watson strand and the reference sequence in the Crick strand, or vice versa, but this time included heterozygous germline variants rather than just the rare variants, and in nuclear DNA rather than in mtDNA. There are many more heterozygous variants in nuclear DNA than in mtDNA because the mtDNA is derived only from the oocyte. The discordances of interest could arise as a result of mispairing of a Watson strand with a Crick strand derived from a different template molecule—i.e., non-random shearing. Alternatively, discordances could result from an amplification error in one of the two strands during an early PCR cycle. Using our WGS data, we first identified 8,535,891 nuclear heterozygous variants observed among the 30 DNA samples used for the control BotSeqS libraries (median of 268,180 variants per library with range 121,851 to 529,922, with the same common variants present in many libraries). From the 8,535,891 nuclear heterozygous variants, we identified a total of 3,960,818 families (median of 123,134 families per library with range 65,832 to 222, 135) for which both strands could be evaluated. Of these, 3,960,807 families had the concordant sequence at the variant position in both strands; only 11 heterozygous variants were discordant (i.e., the variant was present in ≥90% of the Watson family members and the reference sequence was present in ≥90% of the Crick family members, or vice versa). The rate of discordant germline heterozygous variants was thus $2.78 \times 10^{-6}$ (11 out of 3,960,818) per bp. This rate is compatible with the known error rate of high fidelity DNA polymerases and could easily represent an amplification error that occurred in one of the two strands during the first PCR cycle, so represents an overestimate of shearing artifacts. Furthermore, it is important to note that BotSeqS eliminates such amplification errors by requiring mutations to be observed on both strands. Because BotSeqS requires mutations to be observed on both strands, the actual false positive rate can be estimated to be $\sim(\frac{1}{3})(2.78 \times 10^{-6})(2.78 \times 10^{-6}) = 2.58 \times 10^{-12}$.

Generation of BotSeqS Change and Molecule Tables

Sequence alignments and variant calling were performed with the Illumina secondary analysis package (CASAVA 1.8) using ELANDv2 matching to the GRCh37/hg19 human reference genome. High-quality reads were selected for further analysis only if they satisfied all of the following criteria: (i) passed chastity filter, (ii) read mapped in a proper pair, (iii) ≤5 mismatches to reference sequence, and (iv) perfect identity to reference sequence within the first and last five bases of each read. Sequencing reads were grouped into families based on identical paired-end endogenous barcodes. The members of a family were further subdivided into the two possible sequencing orientations to determine the number of Watson and Crick-derived family members. Watson and Crick families had identical genomic coordinates with each end sequenced in opposite reads. Quality scores of identical changes within a family were calculated as the average among the family members. The output for each BotSeqS library was two annotated tables of changes and template molecules (i.e., families).

Selection of High Quality Changes and Molecules

Custom algorithms were written in Microsoft SQL Server Management Studio to query the changes and molecules tables for each BotSeqS library. Selection criteria are detailed in Table 44-Table 48. In general, selection was based on quality, clonality, and mappability of single base pair substitutions. For example, it is known that one of the major sources of errors facing all short read alignment and variant callers are artifacts that arise when variants map to repetitive regions in the genome, including low complexity regions and copy number variants (see, e.g., Li et al., 2014 *Bioinformatics* 30:2843-2851). The BotSeqS pipeline eliminates this universal error in a downstream step by filtering out the genomic noise from repetitive DNA and structural variants (detailed in Table 48). Indels were excluded because they are prone to alignment artifacts and are ~10 times less frequent than spontaneous point mutations. High quality single-base substitutions were defined as those with average quality scores (within the family) of ≥Q30 and with ≥2 reads and ≥90% mutation fraction in both the Watson and Crick strands. Variants were considered to be clonal if the variant position was present in the WGS data from that sample or observed in >1 template molecules (i.e., both strands of more than one UID). Any positions present in dbSNP130 or dbSNP142 were also excluded. It was noticed that the dbSNP filtering drastically minimized recurrent sequencing or mapping artifacts and highly mutable regions. For example, homopolymer tracts (≥8 bp) are mutation hotspots that flood the mutation list. It was observed that nearly all were filtered out with dbSNP142. Finally, families that harbored >1 mutation were excluded as possible mapping artifacts.

Calculation of Mutation Frequency

Mutation frequencies were determined for each BotSeqS library (see Table 51) by dividing the total number of rare mutations by the total bp sequenced. The total bp sequenced was defined by number of families×2× read length of each family. The average length of the libraries was ~500 bp such that the 100 bp paired-end reads were unlikely to overlap. Only templates with perfect identity to the reference sequence in the first and last 5 bp of every read were considered. The reads were further trimmed by excluding cycle 6 and 7 to ensure quality. Therefore, the actual read length was 88 bases (100−7−5=88). For the samples from which technical replicate BotSeqS libraries were generated, the average mutation frequency of the technical replicates was considered the mutation frequency for the sample.

Validation of Somatic Mutations

All rare mutations from the nuclear and mtDNA genome passed visual inspection of the sequencing reads. For rare nuclear mutations, Sanger sequencing was performed on a representative set (514 out of 876 mutations). Of these, 514 of 514(100%) were confirmed to be invisible by Sanger sequencing (excluding the COL238 and COL239 samples that did not have a matched WGS). This demonstrated that these mutations were neither present in the germline nor present in a highly clonal fashion. Mutations confirmed to be absent upon Sanger sequencing are indicated in Table 50.

Comparison to Cancer Genomes

Nineteen MAF files representing nuclear somatic mutations from 19 TCGA tumor types were downloaded at synapse.org/#!Synapse: syn1729383 (see, e.g., Kandoth et al., 2013 Nature 502:333-339). From the TCGA data, only single-base substitutions were considered and somatic mutations from ultra-mutated tumors were excluded. Mitochondrial DNA somatic mutations from colorectal and renal tumors were derived from supplementary file 2 of Ju et al. (2014 *eLife* 3).

Statistics

For study design, no prior power analysis or randomization was performed because the variance was initially unknown. The goal of the study was to find major, biologically meaningful differences between the cohorts. To find major differences, sample sizes can be small. Even with the small sample size, however, no violations of the assumptions of the tests were detected, including violations about the homogeneity of variances. T-test and ANOVA analyses were performed using GraphPad Prism 5.0f. Fisher's exact test was performed using R version 3.2.2. Principal component analysis was performed in R. All analyzed samples were reported in the manuscript.

Results

Principles Underlying BotSeqS

The principal feature of BotSeqS is the dilution of any type of a sequencing library prior to PCR amplification. This dilution creates a bottleneck and permits an efficient, random sampling of double-stranded template molecules with a minimal amount of sequencing. Rare mutations, which would normally be masked by an abundance of wild-type sequences in conventional libraries, account for much more of the signal at the corresponding genomic position in a bottlenecked library. Dilution also increases the likelihood that both the "Watson" and "Crick" strands of a DNA molecule will be sequenced redundantly, a feature critical for the high accuracy of BotSeqS and the relatively small amount of sequencing required to implement it. The presence of the same rare mutation on both strands can substantially decrease artifacts and increase specificity (see, e.g., Schmitt et al., 2012 *PNAS USA* 109:14508-14513). Finally, the random nature of dilution allows DNA molecules from both nuclear and mitochondrial genomes to be assessed from one library.

Generation of BotSeqS Libraries

A standard Illumina TruSeq PCR-Free kit was used to generate 44 BotSeqS libraries from the normal tissues of 34 individuals (Table 43). This included nine individuals with one or two technical replicates. In addition, 10 of our 12 cohorts had more than one biological replicate, each containing two to six individuals.

Figure 52:
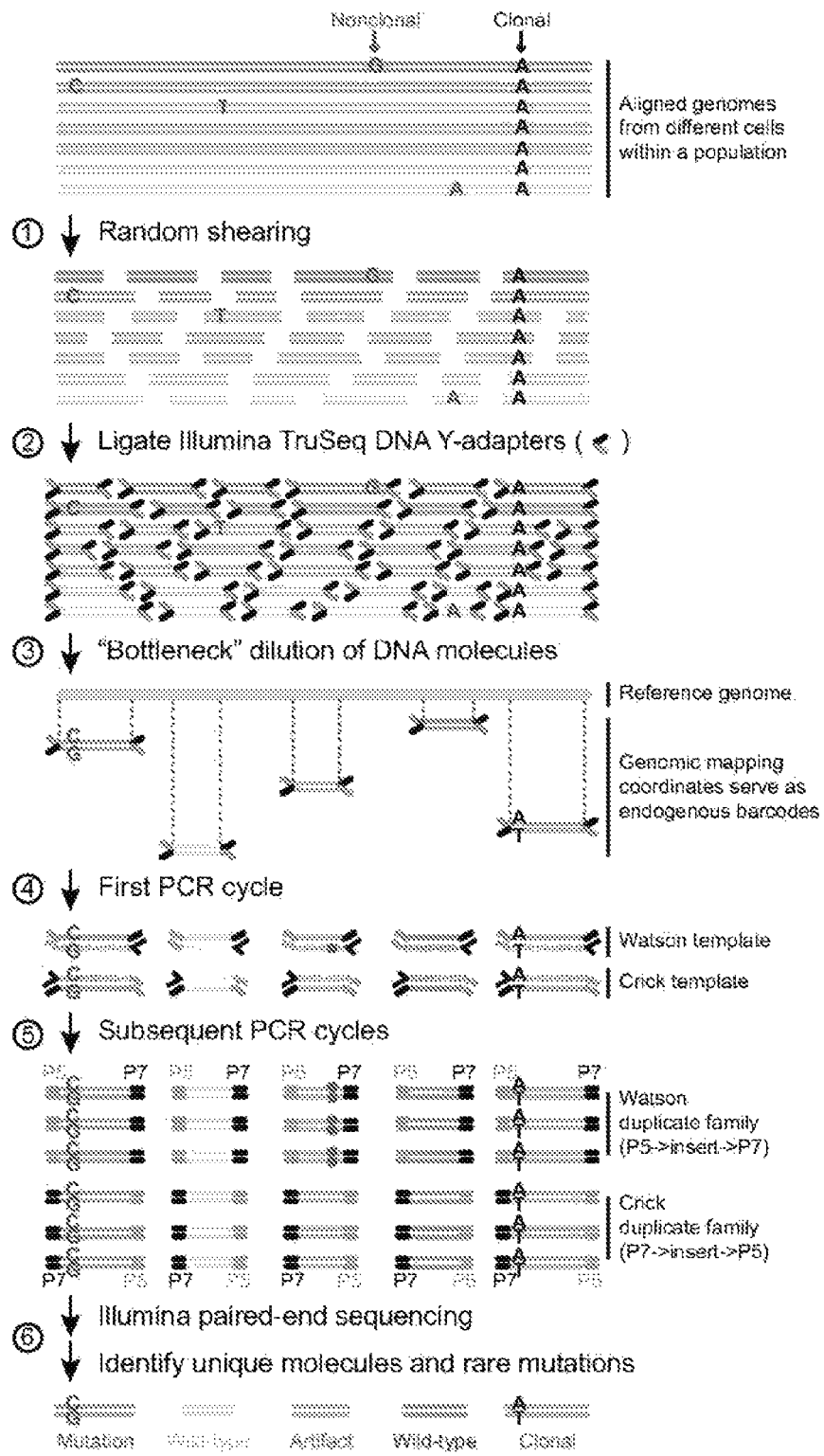
FIG. 52 contains a schematic showing an exemplary overview of a bottleneck sequencing methodology. Each color at the top of the figure represents double-stranded DNA from a genome of one cell within a population. Random, nonclonal point mutations (red) are private to individual cells. In contrast, clonal reference changes (A in black) are present in all genomes within the cell population. (step 1) Random shearing generates variably sized DNA molecules. (step 2) Noncomplementary single-stranded regions of the Illumina Y-adapters (P5 in gray and P7 in black) are represented as forked structures ligated to both ends of each DNA molecule. (step 3) Dilution decreases the number of DNA molecules (five are shown) from the original population in a random manner. Ends of the DNA molecules align uniquely to the reference genome. Mapping coordinates are used as unique molecule "barcodes" during data processing. (step 4) PCR primer (black arrowhead) anneals and primer extends (hashed lines) the Watson and Crick template of the original DNA molecule independently. The red asterisk represents an error generated during PCR of the library. (step 5) Watson and Crick templates generate two families of PCR duplicates. Orientation of P5 (gray) and P7 (black) containing adapters to the DNA molecule (insert) distinguishes the two families. P5 and P7 sequences dictate which end will be sequenced in read 1 vs. read 2, respectively, on the Illumina flow cell. Red asterisks represent the PCR error propagated in the Watson but not the Crick family members. In contrast to artifacts, real mutations (C:G mutation in red) will be present in both the Watson and Crick family members. (step 6) The BotSeqS pipeline identifies and quantifies the number of unique DNA molecules and point mutations (C:G in red) in the sequencing data by eliminating artifacts and clonal changes (A:T in black).
Figure 53:
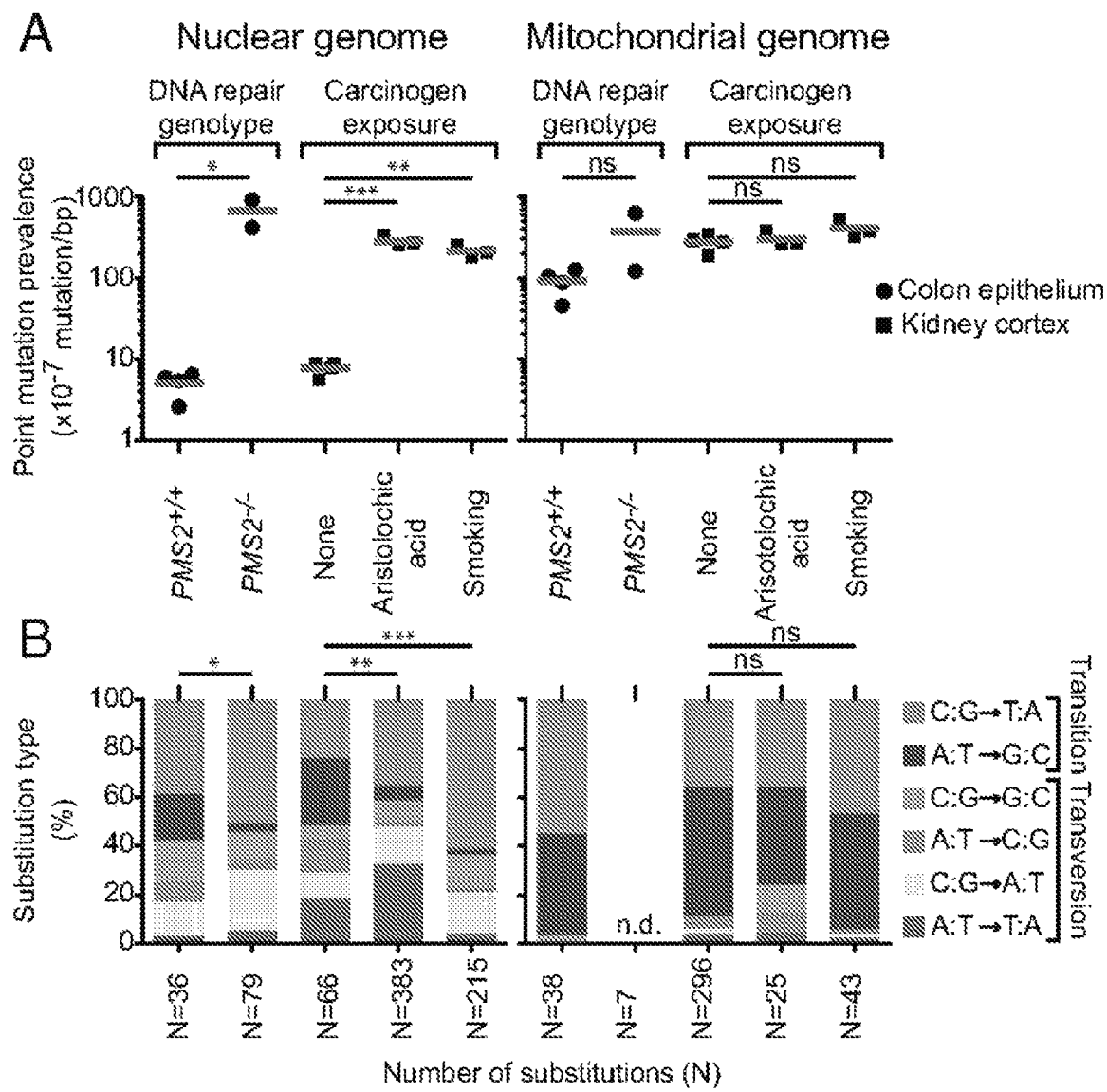
FIG. 53 contains graphs showing nuclear point mutations increase in normal tissues from individuals with defects in DNA repair or with exposure to environmental carcinogens compared with controls. (A) Comparison of point mutation prevalences in nuclear (Left) and mitochondrial (Right) genome in age-matched normal colon epithelium (filled circle) with different DNA mismatch repair genotypes ($PMS2^{++}$ or $PMS2^{-/-}$) or in age-matched normal kidney cortex (filled square) without (none) or with (aristolochic acid or smoking) carcinogen exposure. Red lines represent average. *$P<0.05$, t test; $P<0.001$ and *$P<0.0001$, one-way ANOVA with Bonferroni multiple comparison posttest; ns, not significant, indicates $P>0.05$. (B) Stacked columns representing the substitution frequencies (y axis) of each substitution out of the six possible types (see legend). Cohort labels are indicated in A directly above each column. Number of substitutions (N) generating each mutational spectrum is indicated on the x axis. n.d., not determined due to an insufficient number of mutations (N=7) for mutational spectrum analysis. *$P=0.04$, Fisher's exact test; $P=2.6\times10^{-8}$ and *$P=1.5\times10^{-16}$, Fisher's exact test with Bonferroni multiple comparison correction; ns, not significant, indicates $P>0.05$. All statistical tests in this figure were two-tailed.

The preparation of BotSeqS libraries starts with the random shearing of genomic DNA (FIG. 52). This fragments the genomes into variably-sized DNA molecules, each possessing unique end coordinates called endogenous barcodes (see, e.g., Kinde et al., 2011 *PNAS USA* 108:9530-9535). Following ligation of standard sequencing adapters to the DNA molecules, the library is diluted to reduce the number of molecules in the population. To identify the correct dilution factor, a ten-fold dilution series was assessed on a MiSeq instrument (FIG. 53). After dilution, PCR amplification of the library generates multiple copies (duplicates) of each DNA molecule. The endogenous barcodes enables the grouping of sequencing reads into families, also known as UIDs, for unique identifiers (see, e.g., Kinde et al., 2011 *PNAS USA* 108:9530-9535); each family represents the PCR-derived progeny of a single-stranded template and each member of a family represents the sequence from a single cluster on the Illumina instrument. In the following, we consider the Watson strand to be the sequence derived from the first read of the sequencing instrument (Illumina adapter P5) and the Crick strand to be the sequence derived from the second read (Illumina adapter P7) of each member of the family (FIG. 52). To be considered a potential mutation, BotSeqS required that the identical sequence change be observed in ≥90% of the Watson and in ≥90% of the Crick family members and that each family be composed of at least two members. BotSeqS libraries were analyzed using an Illumina HiSeq 2500 instrument on rapid run mode with paired-end reads of 100 bases each. A median of 70 million (M) clusters per library passed the standard Illumina quality filters (range 37 to 188 M clusters per library; Table 43).

BotSeqS Data Processing Pipeline

Figure 56:
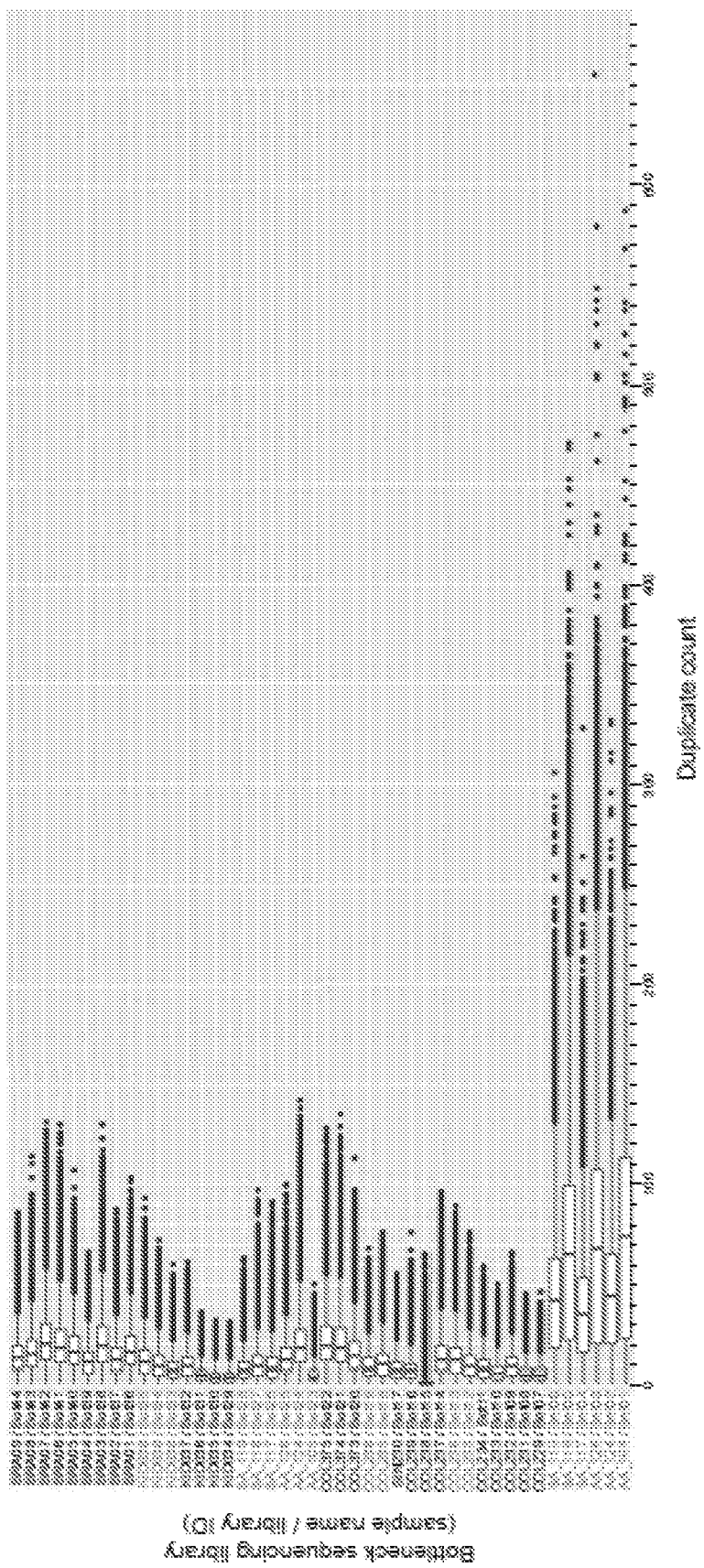
FIG. 56 contains a graph showing family member counts of 44 BotSeqS libraries reported in this study. Horizontal box and whisker plots for 44 BotSeqS libraries (y-axis) and number of members per family (duplicate count, x-axis). White boxes represent the first to third quartile range with the hash mark indicating the median. Whiskers represent 1.5*IQR (interquartile range) and data points outside the whiskers are shown as outliers. An average of 3.97 M (range 0.38 to 10.91 M) unfiltered families per library were assessed. Families were identified through the BotSeqS pipeline using the genomic mapping coordinates as unique molecule identifiers. Names in blue indicate technical replicate samples. Note that Bot01-Bot06 and Bot23-28 were performed on the same samples with a 100-fold difference in dilution (see Table 43).

The goal of the BotSeqS pipeline was to accurately identify rare, somatic point mutations and to calculate the frequency of these mutations in the sample. To process the data for this purpose, raw sequencing data were input into Illumina's secondary analysis package (CASAVA 1.8) with ELANDv2 mapping to GRCh37/hg19 human reference genome. The BotSeqS pipeline begins by selecting high quality reads for analysis (see Materials and Methods). The data are then organized into two tables for each BotSeqS library: (i) a "change" table listing all differences from the reference sequence and (ii) a unique molecule table listing all families. Importantly, each table contains strand information; almost half (median 45%, range 8% to 62%) of the unique molecules from each BotSeqS library had both the Watson and Crick strands represented in the dataset, ensuring specificity in the subsequent mutation analysis. Moreover, most BotSeqS libraries (37 of 44) had a median number of family members between 5 and 20 (FIG. 56), further demonstrating that the libraries underwent successful bottlenecking.

Figure 57:
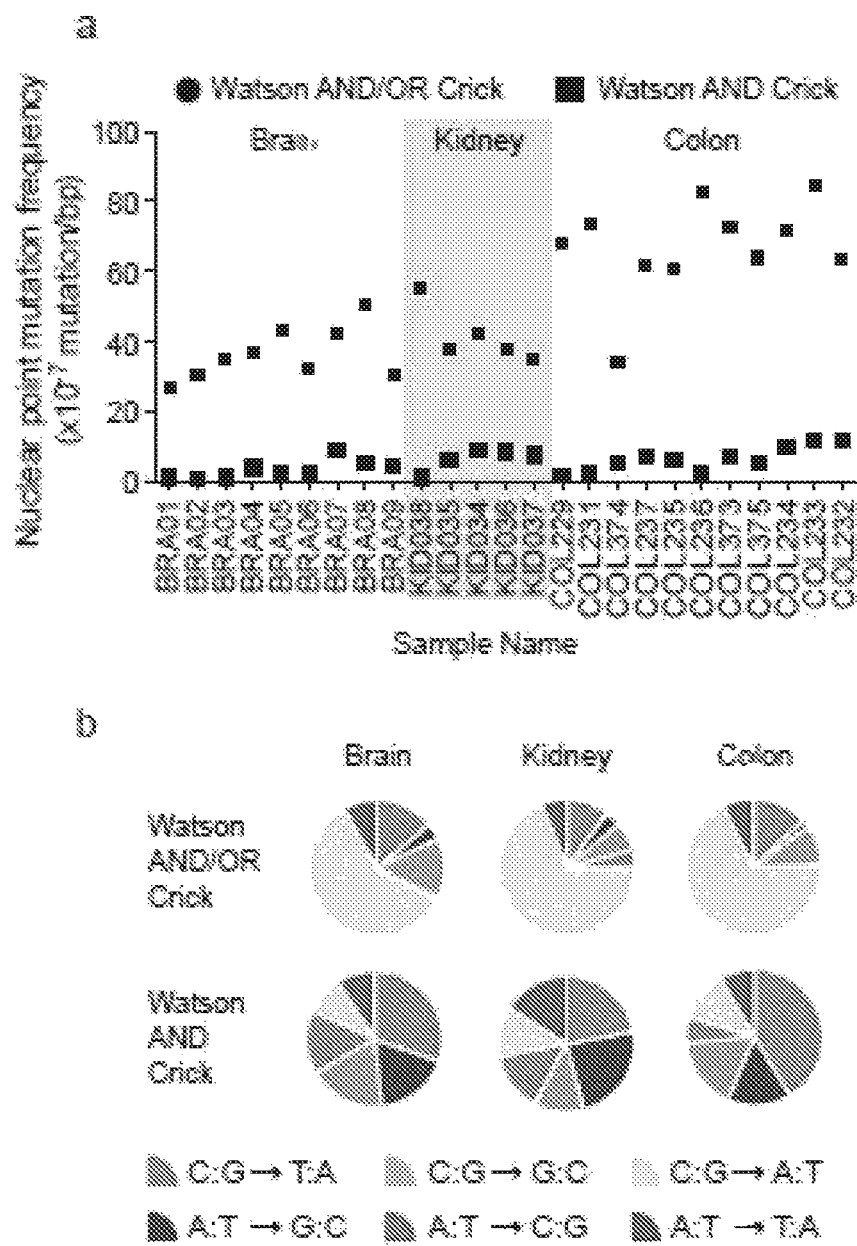
FIG. 57 contains graphs showing Consideration of both Watson and Crick family members decreases artifacts, specifically G>T transversions. (A) Nuclear point mutation frequencies (y-axis) considering mutations observed in "Watson AND/OR Crick" (black circle) or "Watson AND Crick" families (black square) in normal tissues derived from brain frontal cortex (left side), kidney cortex (middle, shaded), or colon epithelium (right side). Specifically, "OR" mutations represent ≥90% mutation fraction in Watson family with a minimum of two Watson reads or ≥90% mutation fraction Crick family with a minimum of two Crick reads. Note that the "OR" mutations have only the Watson or Crick families represented in the data but not both. "AND" mutations represent ≥90% mutation fraction in Watson family with a minimum of two Watson reads and ≥90% mutation fraction Crick family with a minimum of two Crick reads. "AND" mutations are an internal subset of the "AND/OR" dataset, which is a modified version of the BotSeqS pipeline. Twenty-five individuals are organized by increasing age within each tissue. (B) Pie charts of the frequencies of each nuclear substitution out of the six possible substitution types (see legend) from a considering Watson AND/OR Crick (top pies) or Watson AND Crick (bottom pies) in each normal tissue type. The number of nuclear mutations generating mutational spectra for Watson AND/OR Crick was n=616 for brain, n=1,257 for kidney, n=2,542 for colon and for Watson AND Crick was n=33 for brain, n=74 for kidney, n=99 for colon.

To identify rare, somatic mutations, it was necessary to eliminate germline and clonal variants from the BotSeqS data (we defined clonal as those present in both strands of more than one template molecule). We performed whole genome sequencing (WGS) of the same DNA sample or the same libraries that had been diluted for BotSeqS for 32 of the 34 individuals in this study (Table 43). For the remaining two individuals (COL238 and COL239), Sanger sequencing was performed to eliminate clonal variants, demonstrating that WGS was not necessary for BotSeqS. The vast majority (median 92%, range 88-94%) of variants were found to be germline, easily identifiable from the matched WGS dataset. In addition to clonality, we eliminated potential artifacts by considering only well-mapped positions and by using other filters (Table 44-Table 48 and Materials and Methods). The requirement for mutations to be present on both strands was indeed necessary because, in the absence of this filter, there was a large number of G>T transversions (FIG. 57), known to represent artifacts in NGS library preparations (see, e.g., Costello et al., 2013 *Nucleic acids research* 41:e67). A "spike-in" validation experiment was further performed by mixing one individual's normal DNA (PEN93) into another individual's normal DNA (PEN95) at two different ratios. Using BotSeqS, it was possible to detect PEN93-specific SNPs in both samples with a 7.4-fold difference in frequency between the low and high spike-ins, within the expected error of the intended 10-fold difference (see Materials and Methods).

From the 44 BotSeqS libraries, a total of 666 and 876 rare somatic point mutations were identified in mtDNA and nuclear DNA, respectively (Table 49 and Table 50). All rare mutations passed visual inspection and a subset was Sanger-sequenced to confirm that the mutations were not germline or highly prevalent in the samples evaluated (see Materials and Methods). As expected from previous studies, point mutation frequencies of mtDNA ($1.40 \pm 1.29 \times 10^{-5}$ mutation/ bp, mean±s.d.) were significantly higher than those of nuclear DNA ($5.23 \pm 3.47 \times 10^{-7}$) in 25 control individuals (two-tailed t-test, P<0.0001; Table 51). The specificity of BotSeqS was further determined using discordant germline heterozygous calls to estimate a false positive rate of $2.58 \times 10^{-12}$ (see Materials and Methods).

Mutation Frequencies Vary with DNA Repair Capacity and Carcinogen Exposure

It was first asked if BotSeqS can detect the elevated levels of mutations in the normal tissues of mismatch repair deficient individuals. Individuals with biallelic inactivating germline mutations in mismatch repair machinery show higher levels of mutation in both normal and tumor tissues (see, e.g., Parsons et al., 1995 *Science* 268:738-740; and Shlien et al., 2015 *Nature genetics* 47:257-262). Therefore, DNA was tested from normal colon epithelium of individuals (COL238 and COL239) with biallelic germline inactivating mutations in the Post-Meiotic Segregation 2 (PMS2) gene. Using BotSeqS, it was found that the average mutation frequency of nuclear DNA in these two siblings ($6.63 \pm 3.47 \times 10^{-5}$ mutations/bp; ages 16 and 18) was significantly higher than that in similarly aged individuals ($5.13 \pm 1.73 \times 10^{-7}$ for COL235, COL236, COL237, COL374; average age 24) with proficient mismatch repair (two-tailed t-test, P<0.05, FIG. 53a). This 129-fold increase in nuclear mutation frequency was associated with a significant difference in the nuclear mutational spectrum between PMS2$^{+/+}$ and PMS2$^{-/-}$ cohorts (Fisher's exact test, P=0.04, FIG. 53b).

It was also tested if BotSeqS could identify a high number of mutations in the normal tissues of individuals exposed to environmental carcinogens. Genome-wide sequencing of upper tract urothelial carcinomas was previously performed, representing a cancer type associated with exposure to aristolochic acid (AA) or smoking (see, e.g., Hoang et al., 2013 *Science translational medicine* 5:197ra102). Mutagens in tobacco smoke as well as AA are metabolized to form DNA-adducts in the normal kidney cortex (see, e.g., Hoang et al., 2013 *Science translational medicine* 5:197ra102; and Randerath et al., 1989 *Journal of the National Cancer Institute* 81:341-347). Four age-matched normal kidney cortices from individuals (KID034, KID035, KID036, KID037; average age 64 years) without known exposure to tobacco smoke or to AA were compared with the normal kidney cortex of three heavy smokers (SA_117, SA_118, SA_119; average age 65 years) as well as with three individuals who had been exposed to AA (AA_105, AA_124, AA_126; average age 79 years). The nuclear point mutation frequencies in smokers and AA-exposed kidneys were significantly higher, by 27- and 36-fold, respectively, than in the non-exposed controls (one-way ANOVA with Bonferroni multiple comparison post-test, P<0.0001 for AA and P<0.001 for smoking) (FIG. 53a). This increased number of mutations in the nuclear genome was associated with a significantly altered nuclear mutational spectrum (Fisher's exact test with Bonferroni multiple comparison correction, $P = 2.58 \times 10^{-8}$ for AA and $P = 1.51 \times 10^{-15}$ for smoking) (FIG. 53b). Interestingly, the mtDNA point mutation frequencies and spectra between the non-exposed and exposed groups were not significantly different, despite the dramatic difference in their nuclear genomes (FIG. 53a, b).

Rare Mutations Accumulate with Age

Many lines of evidence indicate that the human body accumulates random mutations with age. BotSeqS was designed to directly measure differences such as these and we tested whether rare point mutation frequencies in the DNA of three normal human tissues were dependent upon age. Normal colonic epithelium from 11 individuals showed mutation frequencies that significantly increased with age, by an average of 30-fold in mtDNA and 6.1-fold in nuclear DNA, over 91 years (see below and FIG. 54; one-way ANOVA with Bonferroni multiple comparison post-test, P<0.001 for both). Similarly, mutation frequencies increased by an average of 19-fold in mtDNA and 6.5-fold in nuclear DNA over 64 years in normal kidney cortices. The mutation frequencies in brain frontal cortex also significantly increased with age, albeit more slowly, by 7.3-fold in mtDNA and 5.7-fold in nuclear DNA over 90 years (one-way ANOVA with Bonferroni multiple comparison post-test, P<0.001 for mtDNA and P<0.05 for nuclear).

| Normal Genome | Tissue | Number of Individuals | Mutation Frequency ($\times 10^{-7}$ mutations/bp) Young Child | Young Adult | Old Adult | Average Lifespan (years) | Lifespan Fold-Difference |
|---|---|---|---|---|---|---|---|
| mtDNA | Brain | 9 | 18 ± 7 | 43 ± 6 | 131 ± 18 | 89.5 | 7.3 |
|  | Kidney | 5 | 15 | nd | 277 ± 64 | 63.8 | 18.5 |
|  | Colon | 11 | 12 ± 17 | 112 ± 43 | 365 ± 103 | 90.8 | 30.4 |
| Nuclear | Brain | 9 | 1.1 ± 0.3 | 2.2 ± 1.1 | 6.3 ± 2.3 | 89.5 | 5.7 |
|  | Kidney | 5 | 1.2 | nd | 7.8 ± 1.5 | 63.8 | 6.5 |
|  | Colon | 11 | 1.8 ± 0.5 | 5.5 ± 1.6 | 11 ± 1.5 | 90.8 | 6.1 | nd, not determined

Figure 58:
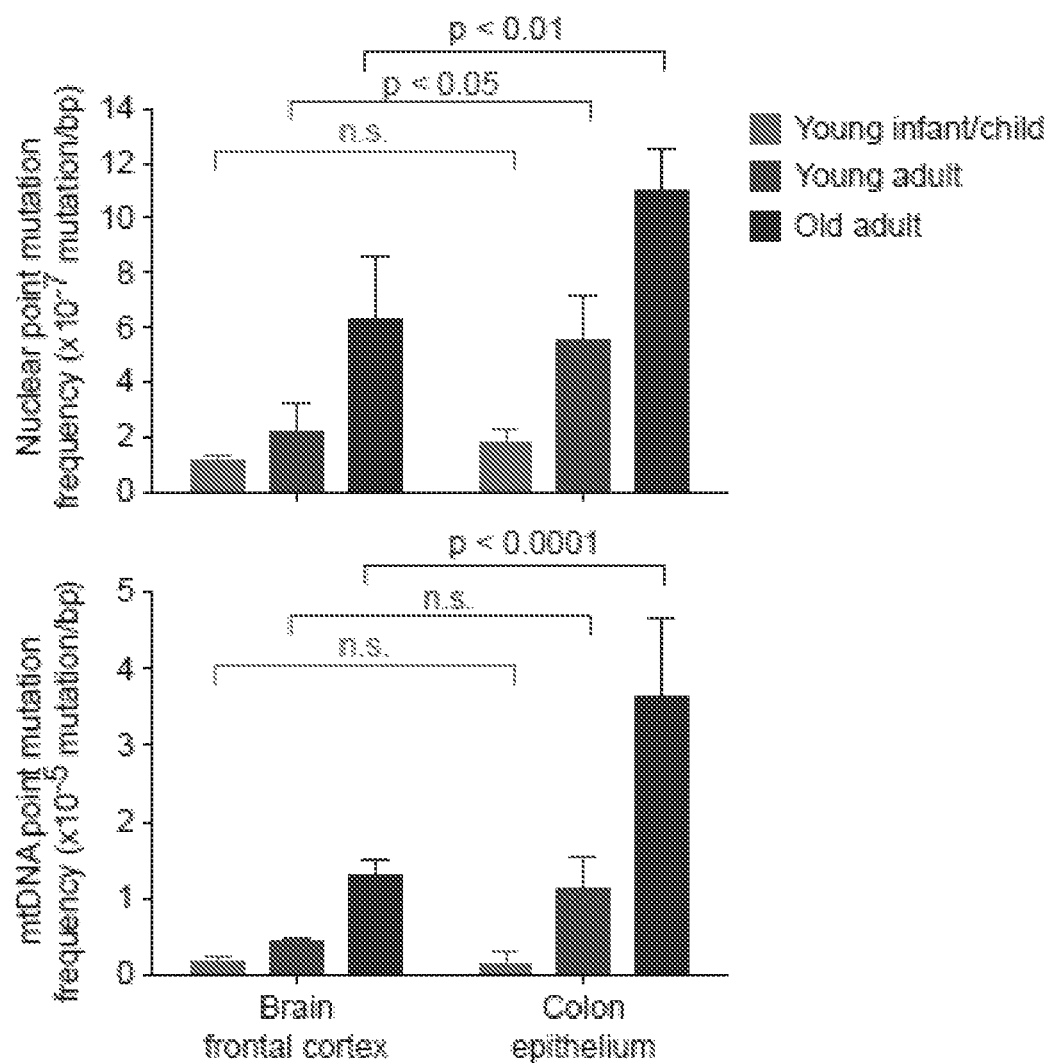
FIG. 58 contains graphs showing rare point mutations accumulate in normal tissues of the colon more than in brain. Point mutation frequency (y-axis) in nuclear (top graph) and mitochondrial (bottom graph) genome in normal brain frontal cortex (left side) and normal colon epithelium (right side) grouped by age (young infant/child in green, young adult in purple, old adult in blue). Averages of each age cohort are shown with error bars representing the standard deviations. Two-way ANOVA with Bonferroni multiple comparison post-test was performed using GraphPad Prism™ 5.0f software with P values reported above bars. n.s. (not significant) indicates P>0.05. For brain, the number of individuals and average age of group are as follows-infant/child: n=3, 3.5 years old (y/o) (BRA01, BRA02, BRA03); young adult: n=3 individuals, 22 y/o (BRA04, BRA05, BRA06); and old adult: n=3, 93 y/o (BRA07, BRA08, BRA09). For colon, infant/child: n=2, 5.5 y/o (COL229, COL231); young adult: n=6, 28 (COL235, COL236, COL237, COL373, COL374, COL375); old adult: n=3, 96 y/o (COL232, COL233, COL234).

Within the dataset, point mutation frequencies in brain versus colonic tissues in three different age groups (children <10 years; adults between 20 and 40 years; and old adults ≥90 years) could be directly compared. Interestingly, the nuclear mutation frequency in colon was not significantly different from that of the brain in children ($1.81 \pm 0.45 \times 10^{-7}$ in colon vs. $1.06 \pm 0.27 \times 10^{-7}$ in brain, two-way ANOVA with Bonferroni multiple comparison post-test, P>0.05). However, the mutation frequency in the colon was significantly higher than that of the brain in young adults ($5.51 \pm 1.62 \times 10^{-7}$ in colon vs. $2.16 \pm 1.11 \times 10^{-7}$ in brain, two-way ANOVA with Bonferroni multiple comparison post-test, P<0.05) as well as in old adults ($1.10 \pm 0.15 \times 10^{-6}$ in colon vs. $6.29 \pm 2.31 \times 10^{-7}$ in brain, two-way ANOVA with Bonferroni multiple comparison post-test, P<0.01) (FIG. 58). No significant differences were found between the mtDNA mutation frequency of the colon versus that of brain in relatively young individuals (children or young adults). However, the mtDNA mutation frequency in the colon was significantly higher than that of the brain in old individuals ($3.65 \pm 1.03 \times 10^{-5}$ in colon vs. $1.31 \pm 0.18 \times 10^{-5}$ in brain, two-way ANOVA with Bonferroni multiple comparison post-test, P<0.0001) (FIG. 58).

The Mutational Patterns in mtDNA are Very Different from Those of Nuclear DNA

Figure 54:
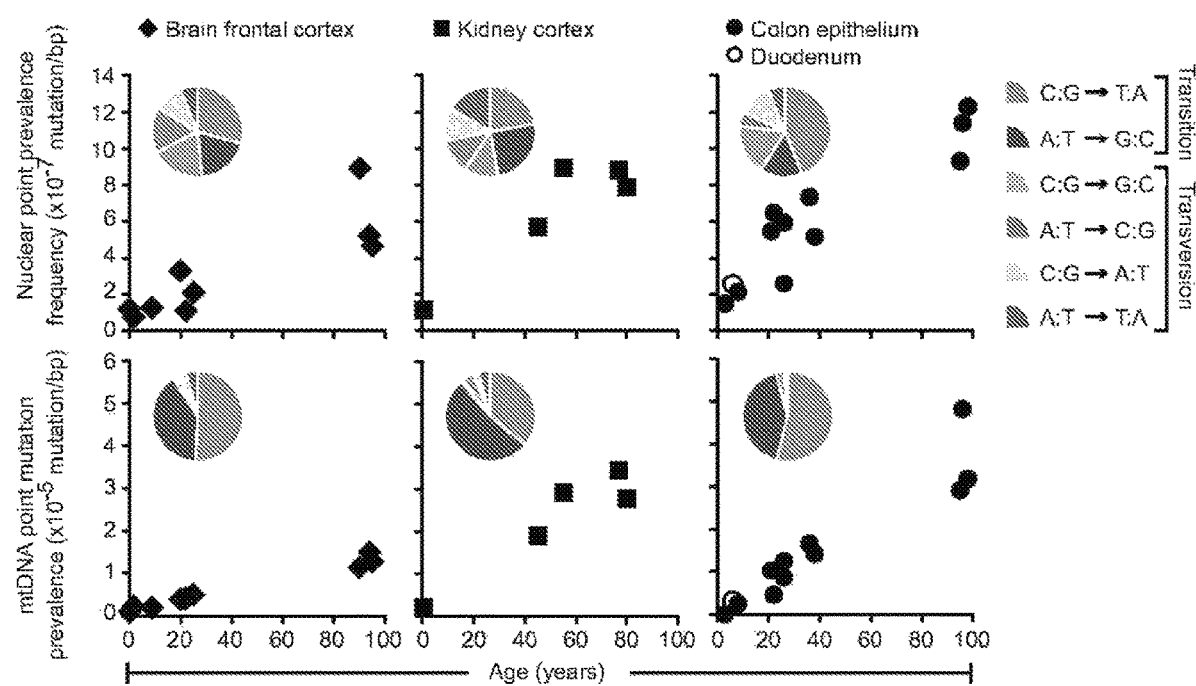
FIG. 54 contains graphs showing normal human tissues accumulate point mutations over a lifetime with genome-specific and tissue-specific mutational patterns. Point mutation prevalences in nuclear (Top) and mitochondrial (Bottom) genome measured in four normal tissue types (brain frontal cortex of 9 individuals, kidney cortex of 5 individuals, colon epithelium of 11 individuals, and duodenum of 1 individual). Twenty-six total individuals were assessed, with each individual contributing to one normal tissue type. Pie chart Insets show the prevalences of each substitution out of the six possible substitution types (see pie chart legend, right side). Each pie chart was compiled from the individuals represented in their respective scatter plots, with the exception that duodenum was omitted. The number of substitutions generating the pie charts for the nuclear genome was n=31 for brain, n=73 for kidney, and n=94 for colon, and for the mitochondrial genome was n=181 for brain, n=299 for kidney, and n=116 for colon.

The spectra of the rare point mutations in each normal tissue studied were examined. Mutations in mtDNA were dominated by transitions (97% in colon, 89% in kidney, and 91% in brain) with a heavy strand bias, as expected from previous studies[12] (FIG. 54 and Table 49). The ratio of transitions to transversions was strikingly different in mtDNA (average of 15.3) compared to nuclear DNA (average of 1.1) in all three tissues.

Figure 59:
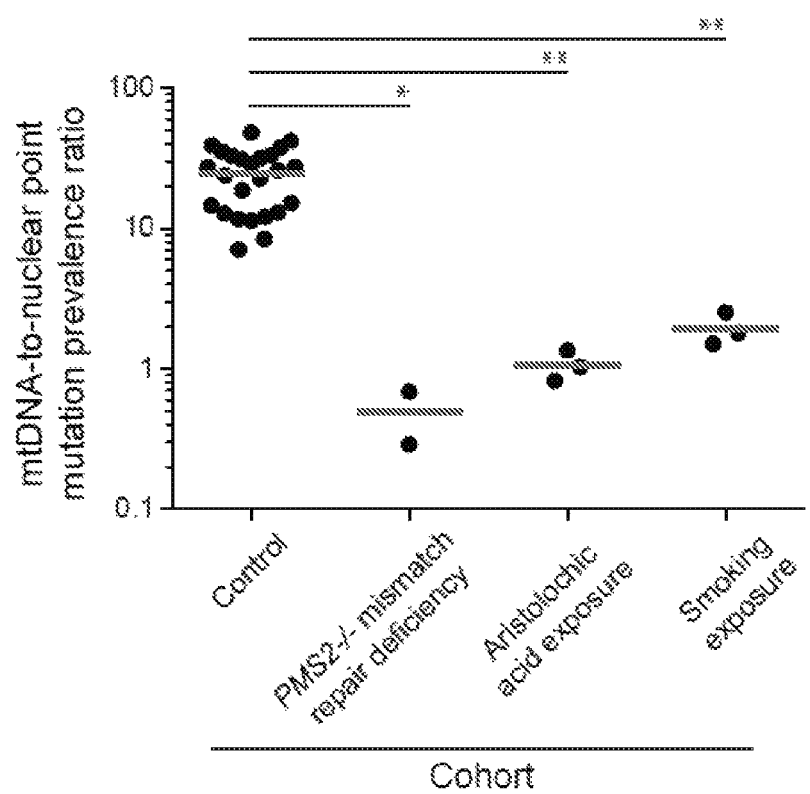
FIG. 59 contains a graph showing Mitochondrial and nuclear point mutation frequencies in normal tissues from the same individual. Data points represent the ratio between mitochondrial to nuclear point mutation frequencies (y-axis) within the normal tissue of the same individual. Individuals were grouped into four cohorts (x-axis) with n=24 individuals for Control (see Table 51), n=2 individuals (COL238, COL239) for DNA repair defect PMS2−/−, n=3 individuals (AA_105, AA_124, AA_126) for aristolochic acid exposure, and n=3 individuals (SA_117, SA_118, SA_119) for smoking exposure. One ratio from the control cohort (COL229) was zero and omitted from this analysis. Average (red line) ratio for each cohort is 24.5 for Control, 0.5 for DNA repair defect PMS2−/−, 1.1 for aristolochic acid exposure, and 2.0 for smoking exposure. *P<0.05, **P<0.01, one-way ANOVA with Bonferroni multiple comparison post-test.

To further assess the differences in mutation frequencies between the two genomes, we calculated the ratio between mtDNA-to-nuclear mutation frequencies for each individual (Table 51). Point mutation frequencies in the mtDNA were on average 24.5-fold higher than the nuclear genome in normal tissues (control cohort, FIG. 59). In patients with exposure histories or DNA repair defects, the ratios were significantly smaller due to the concomitantly greater number of nuclear (but not mitochondrial) DNA mutations in such individuals compared to those from the control cohort (one-way ANOVA with Bonferroni multiple comparison post-test, P<0.05) (FIG. 59).

Mutational Spectra are Tissue-Specific

Though rare mutations in mtDNA are dominated by transitions, there are still tissue-specific mtDNA differences that can be appreciated from the pie charts in FIG. 3. For example, mitochondrial C:G to T:A transitions were more prominent, and A:T to G:C transitions less prominent, in normal colon (54% and 42%, respectively) and brain (51% and 40%) compared to normal kidney tissues (36% and 53%, respectively). The mutation spectra in the nuclear DNA of all three tissues were much more diverse. For example, C:G to T:A transitions predominated in normal colon (44% in colon compared to 22% in kidney and 29% in brain), while normal kidney and brain harbored a proportionately greater fraction of A:T to G:C transitions (25% in kidney and 19% in brain compared to 15% in colon) as well as A:T to C:G transversions (12% in kidney and 16% in brain compared to 5% in colon). Moreover, A:T to T:A transversions were more frequent in kidney (16%) compared to colon (6%) and brain (6%). Pairwise comparisons of the mutational spectra within each genome revealed significant differences between the substitution pattern of kidney and colon (Fisher's exact test with Bonferroni multiple comparison correction, P=0.0029 in mtDNA and P=0.0312 in nuclear DNA).

Figure 60:
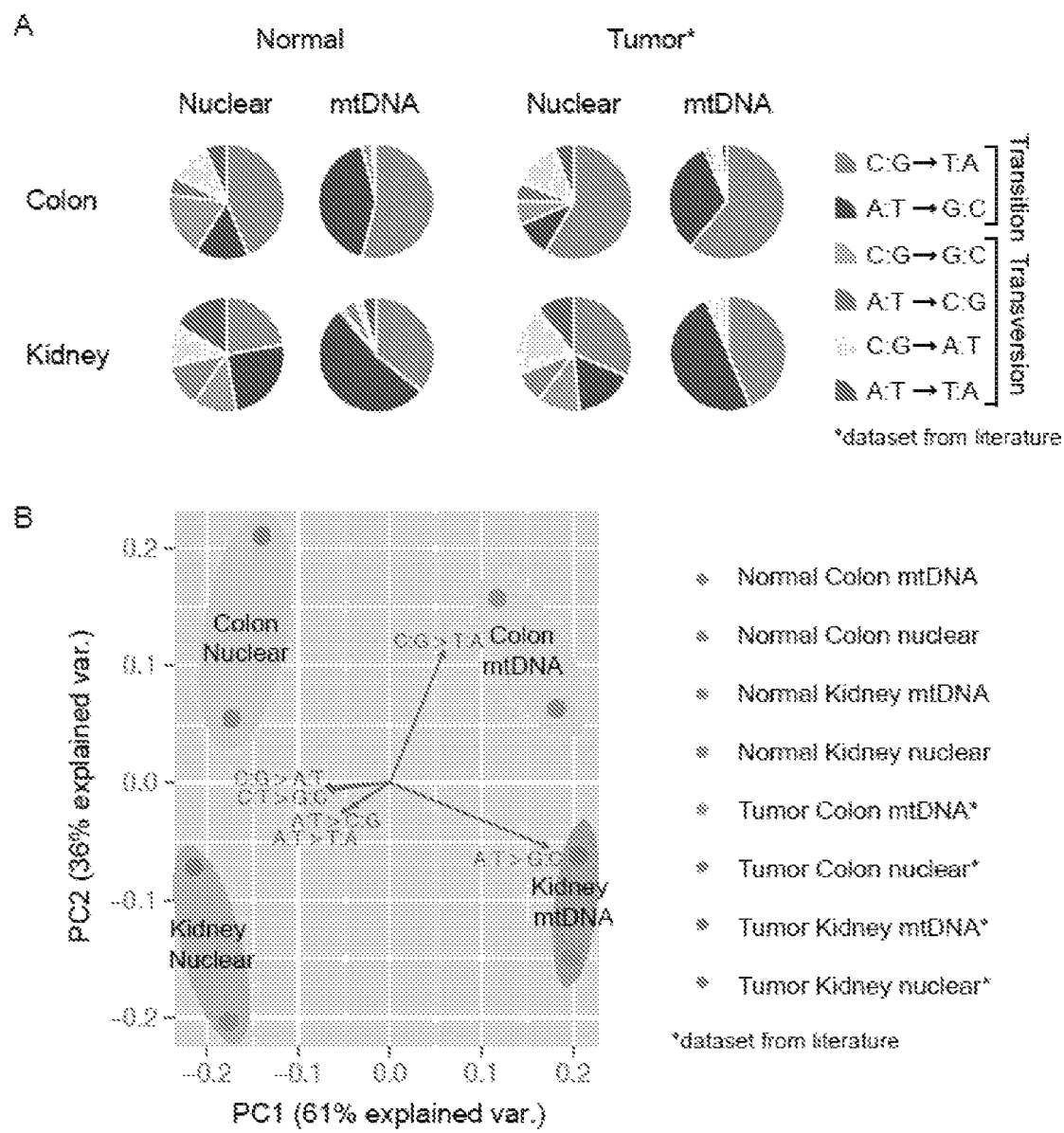
FIG. 60 contains graphs showing Normal tissues and tumors derived from the same tissue type have similar mutation spectra. (A) Pie charts of nuclear and mitochondrial frequencies of each substitution out of the six possible substitution types (see legend) comparing normal (left side) and tumors (right side) derived from colon (top) and kidney (bottom). "Normal" represents the rare mutational spectra data derived from normal tissues shown in FIG. 54. "Nuclear tumor mutations" represent clonal mutation data from colorectal carcinomas (COAD/READ) or clear cell renal carcinoma (KIRC) from the TCGA dataset #!Synapse:syn1729383 found at the website of synapse.org. "mtDNA tumor mutations" from colon and kidney were acquired from "colorectal" and "renal" tumor types in supplementary file 2 of Ju et al. (2014 cLife 3). For normal tissues, the number of substitutions assessed was as follows: colon nuclear n=94 from 13 individuals, colon mtDNA n=116 from 12 individuals, kidney nuclear n=73 from 7 individuals, and kidney mtDNA n=299 from five individuals. For tumor tissue, the number of substitutions assessed was as follows: colorectal carcinoma nuclear n=18,538 from 193 individuals, colorectal carcinoma mtDNA n=64 from 76 individuals, clear cell renal cell carcinoma nuclear n=24,559 from 417 individuals, and renal carcinoma mtDNA n=16 from 23 individuals. (B) Principal component analysis (PCA) of mutational spectra from the cohorts indicated in (A). PCA performed and graphed using R software.

The spectra of the rare mutations found in normal kidney and colon tissues were compared to the clonal DNA mutations in cancers derived from the cells of these organs, using publically available data for the latter (see, e.g., Ju et al., 2014 *eLife* 3; and Kandoth et al., 2013 *Nature* 502:333-339). Brain frontal cortex was excluded in this analysis because it was not clear what tumor type should be used for comparison. To search for similarities and differences among normal and tumor mutational spectra, principal component analysis was performed on the nuclear and mtDNA spectra derived from the data on normal kidney cortex, normal colon epithelium, clear cell renal carcinoma, and colorectal carcinoma. It was found that the spectra of the rare mutations in normal colon and kidney tissues were very similar to those of the corresponding cancer type (FIG. 60).

Example 8: Safe Sequencing System

Genetic mutations underlie many aspects of life and death including, for example, evolution and disease, respectively (see, e.g., Luria et al., 1943 *Genetics* 28:491-511; Roach et al., 2010 *Science* 328:636-639; Durbin et al., 2010 *Nature* 467:1061-1073; Shibata, 2011 *Carcinogenesis* 32:123-128; McMahon et al., 2007 *N Engl J Med* 356:2614-2621; Eastman et al., 1998 *J Infect Dis* 177:557-564; Chiu et al., 2008 *Proc Natl Acad Sci USA* 105:20458-20463; and Fan et al., 2008 *Proc Natl Acad Sci USA* 105:16266-16271). Detection of such mutations, particularly at a stage prior to their becoming dominant in the population, will likely be essential to optimize diagnoses and/or therapy. For example, in neoplastic diseases, which are all driven by somatic mutations, the applications of rare mutant detection are manifold; they can be used to help identify residual disease at surgical margins or in lymph nodes, to follow the course of therapy when assessed in plasma, and perhaps to identify patients with early, surgically curable disease when evaluated in stool, sputum, plasma, and other bodily fluids (see, e.g., Hoque et al., 2003 *Cancer Res* 63:5723-5726; Thunnissen et al., 2003 *J Clin Pathol* 56:805-810; and Diehl et al., 2008 *Gastroenterology* 135:489-498).

This Example describes a "Safe-SeqS" (Safe-Sequencing System) to achieve a very high level of accuracy and sensitivity from sequence data. Safe-SeqS can be used to assess the fidelity of a polymerase, the accuracy of in vitro synthesized nucleic acid synthesis, and the prevalence of mutations in nuclear or mitochondrial nucleic acids of normal cells. Safe-SeqS can also be used to detect and/or quantify mosaicsm and somatic mutations. See, also, WO 2012/142213, incorporated herein by reference in its entirety.

Materials and Methods

Endogenous UIDs

Genomic DNA from human pancreas or cultured lymphoblastoid cells was prepared using Qiagen kits. The pancreas DNA was used for the capture experiment and the lymphoblastoid cells were used for the inverse PCR experiment. DNA was quantified by optical absorbance and with qPCR. DNA was fragmented to an average size of ~200 bp by acoustic shearing (Covaris), then end-repaired, A-tailed, and ligated to Y-shaped adapters according to standard Illumina protocols. The ends of each template molecule provide endogenous UIDs corresponding to their chromosomal positions. After PCR-mediated amplification of the libraries with primer sequences within the adapters, DNA was captured with a filter containing 2,594 nt corresponding to six cancer genes. After capture, 18 cycles of PCR were performed to ensure sufficient amounts of template for sequencing on an Illumina GA IIx instrument.

For the inverse PCR experiments (FIG. 65), we ligated custom adapters (IDT, Table 57) instead of standard Y-shaped Illumina adapters to sheared cellular DNA. These adapters retained the region complementary to the universal sequencing primer but lacked the grafting sequences required for hybridization to the Illumina GA IIx flow cell. The ligated DNA was diluted into 96 wells and the DNA in each column of 8 wells was amplified with a unique forward primer containing one of 12 index sequences at its 5' end plus a standard reverse primer (Table 57). Amplifications were performed using Phusion HotStart I (NEB) in 50 uL reactions containing 1× Phusion HF buffer, 0.5 mM dNTPs, 0.5 uM each forward and reverse primer (both 5'-phosphorylated), and 1 U of Phusion polymerase. The following cycling conditions were used: one cycle of 98° C. for 30 s; and 16 cycles of 98° C. for 10 s, 65° C. for 30 s, and 72° C. for 30 s. All 96 reactions were pooled and then purified using a Qiagen MinElute PCR Purification Kit (cat. no. 28004) and a QIAquick Gel Extraction kit (cat. no. 28704). To prepare the circular templates necessary for inverse PCR, DNA was diluted to ~1 ng/uL and ligated with T4 DNA Ligase (Enzymatics) for 30 minutes at room temperature in a 600 uL reaction containing 1× T4 DNA Ligation Buffer and 18,000 U of T4 DNA Ligase. The ligation reaction was purified using a Qiagen MinElute kit. Inverse PCR was performed using Phusion Hot Start I on 90 ng of circular template distributed in twelve 50 uL reactions, each containing 1× Phusion HF Buffer, 0.25 mM dNTPs, 0.5 uM each of KRAS forward and reverse primers (Table 57) and 1 U of Phusion polymerase. The KRAS-specific primers both contained grafting sequences for hybridization to the Illumina GA IIx flow cell (Table 57). The following cycling conditions were used: one cycle of 98° C. for 2 minutes; and 37 cycles of 98° C. for 10 seconds, 61° C. for 15 seconds, and 72° C. for 10 seconds. The final purification was performed with a NucleoSpin Extract II kit (Macherey-Nagel) and eluted in 20 uL NE Buffer. The resulting DNA fragments contained UIDs composed of three sequences: two endogenous ones, represented by the two ends of the original sheared fragments plus the exogenous sequence introduced during the indexing amplification. As 12 exogenous sequences were used, this increased the number of distinct UIDs by 12-fold over that obtained without exogenous UIDs. This number could easily be increased by using a greater number of distinct primers.

Exogenous UIDs

Genomic DNA from normal human colonic mucosae or blood lymphocytes was prepared using Qiagen kits. The DNA from colonic mucosae was used for the experiments on CTNNB1 and mitochondrial DNA, while the lymphocyte DNA was used for the experiments on CTNNB1 and on polymerase fidelity. DNA was quantified with Digital PCR using primers that amplified single-copy genes from human cells (Analysis of Polymerase Fidelity and CTNNB1), qPCR (mitochondrial DNA), or by optical absorbance (oligonucleotides). Each strand of each template molecule was encoded with a 12 or 14 base UID using two cycles of amplicon-specific PCR, as described in the text and FIG. 63. The amplicon-specific primers both contained universal tag sequences at their 5' ends for a later amplification step. The UIDs constituted 12 or 14 random nucleotide sequences appended to the 5' end of the forward amplicon-specific primers (Table 57). These primers can generate 16.8 and 268 million distinct UIDs, respectively. It is important that the number of distinct UIDs greatly exceed the number of original template molecules to minimize the probability that two different original templates acquired the same UID. The UID assignment PCR cycles included Phusion Hot Start II (NEB) in a 45 uL reaction containing 1× Phusion HF buffer, 0.25 mM dNTPs, 0.5 uM each forward (containing 12-14 Ns) and reverse primers, and 2 U of Phusion polymerase. To keep the final template concentrations <1.5 ng/uL, multiple wells were used to create some libraries. The following cycling conditions were employed: one incubation of 98° C. for 30 seconds (to activate the Phusion Hot Start II); and two cycles of 98° C. for 10 seconds, 61° C. for 120 seconds, and 72° C. for 10 seconds. To ensure complete removal of the first round primers, each well was digested with 60 U of a single strand DNA specific nuclease (Exonuclease-I; Enzymatics) at 37° C. for 1 hour. After a 5 minute heat-inactivation at 98° C., primers complementary to the introduced universal tags (Table 57) were added to a final concentration of 0.5 uM each. These primers contained two terminal phosphorothioates to make them resistant to any residual Exonuclease-I activity. They also contained 5' grafting sequences necessary for hybridization to the Illumina GA IIx flow cell. Finally, they contained an index sequence between the grafting sequence and the universal tag sequence. This index sequence enables the PCR products from multiple different individuals to be simultaneously analyzed in the same flow cell compartment of the sequencer. The following cycling conditions were used for the subsequent 25 cycles of PCR: 98° C. for 10 seconds and 72° C. for 15 seconds. No intermediate purification steps were performed in an effort to reduce the losses of template molecules.

After the second round of amplification, wells were consolidated and purified using a Qiagen QIAquick PCR Purification Kit (cat. no. 28104) and eluted in 50 uL EB Buffer (Qiagen). Fragments of the expected size were purified after agarose (mtDNA libraries) or polyacrylamide (all other libraries) gel electrophoresis. For agarose gel purification, the eight 6-uL aliquots were loaded into wells of a 2% Size Select Gel (Invitrogen) and bands of the expected size were collected in EB Buffer as specified by the manufacturer. For polyacrylamide gel purification, ten 5-uL aliquots were loaded into wells of a 10% TBE Polyacrylamide Gel (Invitrogen). Gel slices containing the fragments of interest were excised, crushed, and eluted as described elsewhere (see, e.g., Durbin et al., 2010 Nature 467:1061-1073).

Analysis of Phusion Polymerase Fidelity

Amplification of a fragment of human genomic DNA within the BMX (RefSeq Accession NM_203281.2) gene was first performed using the PCR conditions described above. The template was diluted so that an average of one template molecule was present in every 10 wells of a 96-well PCR plate. Fifty uL PCR reactions were then performed in 1× Phusion HF buffer, 0.25 mM dNTPs, 0.5 uM each forward and reverse primers (Table 57), and 2 U of Phusion polymerase. The cycling conditions were one cycle of 98° C. for 30 seconds; and 19 cycles of 98° C. for 10 seconds, 61° C. for 120 seconds, and 72° C. for 10 seconds. The primers were removed by digestion with 60 U of Exonuclease-I at 37° C. for 1 hour followed by a 5 minute heat-inactivation at 98° C. No purification of the PCR product was performed, either before or after Exonuclease-I digestion. The entire contents of each well were then used as templates for the exogenous UIDs strategy described above.

Sequencing

Sequencing of all the libraries described above was performed using an Illumina GA IIx instrument as specified by the manufacturer. The total length of the reads used for each experiment varied from 36 to 73 bases. Base-calling and sequence alignment was performed with the Eland pipeline (Illumina). Only high quality reads meeting the following criteria were used for subsequent analysis: (i) the first 25 bases passed the standard Illumina chastity filter; (ii) every base in the read had a quality score ≥20; and (iii)≤3 mismatches to expected sequences. For the exogenous UID libraries, we additionally required the UIDs to have a quality score ≥30. A relatively high frequency of errors was noticed at the ends of the reads in the endogenous UID libraries prepared with the standard Illumina protocol, presumably introduced during shearing or end-repair, so the first and last three bases of these tags were excluded from analysis.

Safe-SeqS Analysis

High quality reads were grouped into UID-families based on their endogenous or exogenous UIDs. Only UID-families with two or more members were considered. Such UID-families included the vast majority (≥99%) of the sequencing reads. To ensure that the same data was used for both conventional and Safe-SeqS analysis, UID-families containing only one member were also excluded from conventional analysis. Furthermore, a base was only identified as "mutant" in conventional sequencing analysis if the same variant was identified in at least two members of at least one UID-family (i.e., two mutations) when comparing conventional analysis to that of Safe-SeqS with exogenous UIDs. For comparison with Safe-SeqS with endogenous UIDs, we required at least two members of each of two UID-families (i.e., four mutations) to identify a position as "mutant" in conventional analysis. With either endogenous or exogenous UIDs, a super-mutant was defined as a UID-family in which ≥95% of members shared the identical mutation. Thus, UID-families with <20 members had to be 100% identical at the mutant position, while a 5% combined replication and sequencing error rate was permitted in UID-families with more members. To determine polymerase fidelity using Safe-SeqS, and to compare the results with previous analyses of Phusion polymerase fidelity, it was necessary to realize that the previous analyses would only detect mutations present in both strands of the PCR products (see, e.g., Shibata, 2011 *Carcinogenesis* 32:123-128). This would be equivalent to analyzing PCR products generated with one less cycle with Safe-SeqS, and the appropriate correction was made in Table 53A. Unless otherwise specified, all values listed in the text and Tables represent means and standard deviations.

Results

Endogenous UIDs

Figure 62:
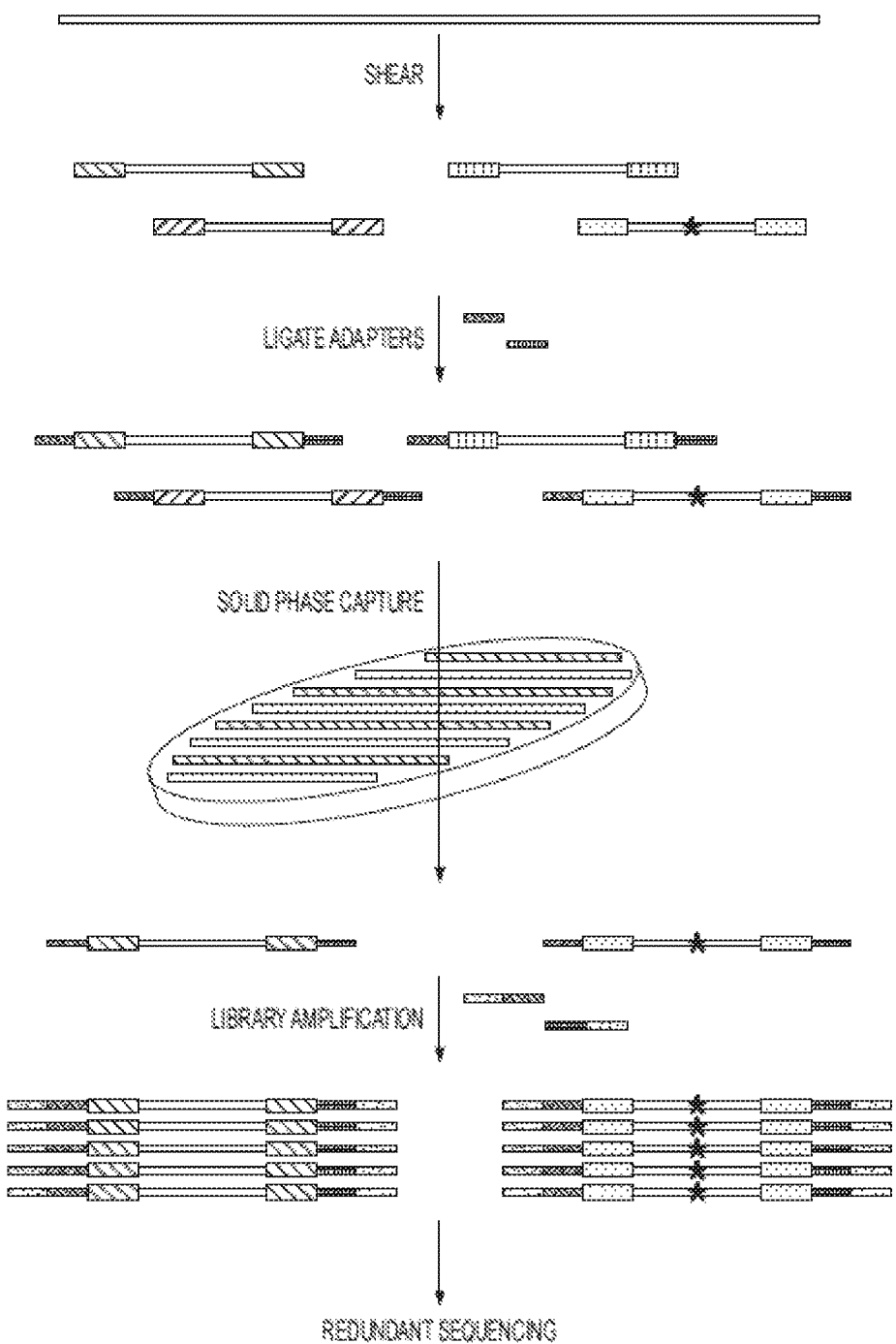
FIG. 62 contains a schematic showing an exemplary Safe-SeqS with endogenous UIDs plus capture. The sequences of the ends of each fragment produced by random shearing (variously shaded bars) serve as the unique identifiers (UIDs). These fragments are ligated to adapters (earth hatched and cross hatched bars) so they can subsequently be amplified by PCR. One uniquely identifiable fragment is produced from each strand of the double-stranded template; only one strand is shown. Fragments of interest are captured on a solid phase containing oligonucleotides complementary to the sequences of interest. Following PCR amplification to produce UID-families with primers containing 5' "grafting"

UIDs, sometimes called barcodes or indexes, can be assigned to nucleic acid fragments in many ways. These include the introduction of exogenous sequences through PCR or ligation. Even more simply, randomly sheared genomic DNA inherently contains UIDs consisting of the sequences of the two ends of each sheared fragment (FIG. 62 and FIG. 65). Paired-end sequencing of these fragments yields UID-families that can be analyzed as described above. To employ such endogenous UIDs in Safe-SeqS, two separate approaches were used: one designed to evaluate many genes simultaneously and the other designed to evaluate a single gene fragment in depth (FIG. 62 and FIG. 65, respectively).

For the evaluation of multiple genes, standard Illumina sequencing adapters were ligated to the ends of sheared DNA fragments to produce a standard sequencing library, then captured genes of interest on a solid phase. In this experiment, a library made from the DNA of ~15,000 normal cells was used, and 2,594 bp from six genes were targeted for capture. After excluding known single nucleotide polymorphisms, 25,563 apparent mutations, corresponding to $2.4\times10^{-4}$±mutations/bp, were also identified (Table 52). Based on previous analyses of mutation rates in human cells, at least 90% of these apparent mutations were likely to represent mutations introduced during template and library preparation or base-calling errors. Note that the error rate determined here ($2.4\times10^{-4}$ mutations/bp) is considerably lower than usually reported in experiments using the Illumina instrument because we used very stringent criteria for base calling.

With Safe-SeqS analysis of the same data, it was determined that 69,505 original template molecules were assessed in this experiment (i.e., 69,505 UID-families, with an average of 40 members per family, were identified, Table 52). All of the polymorphic variants identified by conventional analysis were also identified by Safe-SeqS. However, only 8 super-mutants were observed among these families, corresponding to $3.5\times10^{-6}$ mutations/bp. Thus Safe-SeqS decreased the presumptive sequencing errors by at least 70-fold.

Safe-SeqS analysis can also determine which strand of a template is mutated, thus an additional criteria for calling mutations could require that the mutation appears in only one or in both strands of the originally double stranded template. Massively parallel sequencers are able to obtain sequence information from both ends of a template in two sequential reads. (This type of sequencing experiment is called a "paired end" run on the Illumina platform, but similar experiments can be done on other sequencing platforms where they may be called by another name.) The two strands of a double stranded template can be differentiated by the observed orientation of the sequences and the order in which they appear when sequence information is obtained from both ends. For example, a UID strand pair could consist of the following two groups of sequences when each end of a template is sequenced in sequential reads: 1) A sequence in the sense orientation that begins at position 100 of chromosome 2 in the first read followed by a sequence in the antisense orientation that begins at position 400 of chromosome 2 in the second read; and 2) A sequence in the antisense orientation that begins at position 400 of chromosome 2 in the first read followed by a sequence in the sense orientation that begins at position 100 of chromosome 2 in the second read. In the capture experiment described above, 42,222 of 69,505 UIDs (representing 21,111 original double stranded molecules) in the region of interest represented UID strand pairs. These 42,222 UIDs encompassed 1,417, 838 bases in the region of interest. When allowing a mutation to only occur within UID strand pairs (whether in one or both strands), two super-mutants were observed, yielding a mutation rate of $1.4\times10^{-6}$ super-mutants/bp. When requiring that a mutation occur in only one strand of a UID strand pair, only one super-mutant was observed, yielding a mutation rate of $7.1\times10^{-7}$ super-mutants/bp. When requiring that a mutation occur in both strands of a UID strand pair, only one super-mutant was observed, yielding a mutation rate of $7.1\times10^{-7}$ super-mutants/bp. Thus, requiring that mutations occur in only one or in both strands of templates can further increase the specificity of Safe-SeqS.

A strategy employing endogenous UIDs was also used to reduce false positive mutations upon deep sequencing of a single region of interest. In this case, a library prepared as described above from ~1,750 normal cells was used as template for inverse PCR employing primers complementary to a gene of interest, so the PCR products could be directly used for sequencing (FIG. 65). With conventional analysis, an average of $2.3\times10^{-4}$ mutations/bp were observed, similar to that observed in the capture experiment (Table 52). Given that only 1,057 independent molecules from normal cells were assessed in this experiment, as determined through Safe-SeqS analysis, all mutations observed with conventional analysis likely represented false positives (Table 52). With Safe-SeqS analysis of the same data, no super-mutants were identified at any position.

Exogenous UIDs

Though the results described above show that Safe-SeqS can increase the reliability of massively parallel sequencing, the number of different molecules that can be examined using endogenous UIDs is limited. For fragments sheared to an average size of 150 bp (range 125-175), 36 base paired-end sequencing can evaluate a maximum of ~7,200 different molecules containing a specific mutation (2 reads×2 orientations×36 bases/read×50 base variation on either end of the fragment). In practice, the actual number of UIDs is smaller because the shearing process is not entirely random.

To make more efficient use of the original templates, a Safe-SeqS strategy was developed that employed a minimum number of enzymatic steps. This strategy also permitted the use of degraded or damaged DNA, such as found in clinical specimens or after bisulfite-treatment for the examination of cytosine methylation. As depicted in FIG. 63, this strategy employs two sets of PCR primers. The first set is synthesized with standard phosphoramidite precursors and contained sequences complementary to the gene of interest on the 3' end and different tails at the 5' ends of both the forward and reverse primers. The different tails allowed universal amplification in the next step. Finally, there was a stretch of 12 to 14 random nucleotides between the tail and the sequence-specific nucleotides in the forward primer. The random nucleotides form the UIDs. An equivalent way to assign UIDs to fragments, not used in this study, would employ 10,000 forward primers and 10,000 reverse primers synthesized on a microarray. Each of these 20,000 primers would have gene-specific primers at their 3'-ends and one of 10,000 specific, predetermined, non-overlapping UID sequences at their 5'-ends, allowing for $10^8$ (i.e., $[10^4]^2$) possible UID combinations. In either case, two cycles of PCR are performed with the primers and a high-fidelity polymerase, producing a uniquely tagged, double-stranded DNA fragment from each of the two strands of each original template molecule (FIG. 63). The residual, unused UID assignment primers are removed by digestion with a single-strand specific exonuclease, without further purification, and two new primers are added. Alternatively or in addition to such digestion, one can use a silica column that selectively retains larger-sized fragments or one can use solid phase reversible immobilization (SPRI) beads under conditions that selectively retain larger fragments to eliminate smaller, non-specific, amplification artifacts. This purification may potentially help in reducing primer-dimer accumulation in later steps. The new primers, complementary to the tails introduced in the UID assignment cycles, contain grafting sequences at their 5' ends, permitting solid-phase amplification on the Illumina instrument, and phosphorothioate residues at their 3' ends to make them resistant to any remaining exonuclease. Following 25 additional cycles of PCR, the products are loaded on the Illumina instrument. As shown below, this strategy allowed us to evaluate the majority of input fragments and was used for several illustrative experiments.

Analysis of DNA Polymerase Fidelity

Measurement of the error rates of DNA polymerases is essential for their characterization and dictates the situations in which these enzymes can be used. The error rate of Phusion polymerase was measured, as this polymerase has one of the lowest reported error frequencies of any commercially available enzyme and therefore poses a particular challenge for an in vitro-based approach. A single human DNA template molecule, comprising a segment of an arbitrarily chosen human gene, was first amplified through 19 rounds of PCR. The PCR products from these amplifications, in their entirety, were used as templates for Safe-SeqS as described in FIG. 63. In seven independent experiments of this type, the number of UID-families identified by sequencing was 624,678±421,274, which is consistent with an amplification efficiency of 92±9.6% per round of PCR.

The error rate of Phusion polymerase, estimated through cloning of PCR products encoding β-galactosidase in plasmid vectors and transformation into bacteria, is reported by the manufacturer to be $4.4 \times 10^{-7}$ errors/bp/PCR cycle. Even with very high stringency base-calling, conventional analysis of the Illumina sequencing data revealed an apparent error rate of $9.1 \times 10^{-6}$ errors/bp/PCR cycle, more than an order of magnitude higher than the reported Phusion polymerase error rate (Table 53A). In contrast, Safe-SeqS of the same data revealed an error rate of $4.5 \times 10^{-7}$ errors/bp/PCR cycle, nearly identical to that measured for Phusion polymerase in biological assays (Table 53A). The vast majority (>99%) of these errors were single base substitutions (Table 54A), consistent with previous data on the mutation spectra created by other prokaryotic DNA polymerases (Tindall et al. 1988 *Biochemistry* 27:6008-6013; de Boer et al., 1988 *Genetics* 118:181-191; Eckert et al., 1990 *Nucleic Acids Res* 18:3739-3744).

Safe-SeqS also allowed a determination of the total number of distinct mutational events and an estimation of PCR cycle in which the mutation occurred. There were 19 cycles of PCR performed in wells containing a single template molecule in these experiments. If a polymerase error occurred in cycle 19, there would be only one super-mutant produced (from the strand containing the mutation). If the error occurred in cycle 18 there should be two super-mutants (derived from the mutant strands produced in cycle 19), etc. Accordingly, the cycle in which the error occurred is related to the number of super-mutants containing that error. The data from seven independent experiments demonstrate a relatively consistent number of observed total polymerase errors ($2.2 \pm 1.1 \times 10^{-6}$ distinct mutations/bp), in good agreement with the expected number of observations from simulations ($1.5 \pm 0.21 \times 10^{-6}$ distinct mutations/bp). The data also show a highly variable timing of occurrence of polymerase errors among experiments (Table 55). This kind of information is difficult to derive using conventional analysis of the same next-generation sequencing data, in part because of the prohibitively high apparent mutation rate noted above.

Analysis of Oligonucleotide Composition

A small number of mistakes during the synthesis of oligonucleotides from phoshoramidite precursors are tolerable for most applications, such as routine PCR or cloning. However, for synthetic biology, wherein many oligonucleotides must be joined together, such mistakes present a major obstacle to success. Clever strategies for making the gene construction process more efficient have been devised (see, e.g., Kosuri et al., 2010 *Nat Biotechnol* 28:1295-129; and Matzas et al., 2010 *Nat Biotechnol* 28:1291-1294), but all such strategies would benefit from more accurate synthesis of the oligonucleotides themselves. Determining the number of errors in synthesized oligonucleotides is difficult because the fraction of oligonucleotides containing errors can be lower than the sensitivity of conventional next-generation sequencing analyses.

To determine whether Safe-SeqS could be used for this determination, standard phosphoramidite chemistry was used to synthesize an oligonucleotide containing 31 bases that were designed to be identical to that analyzed in the polymerase fidelity experiment described above. In the synthetic oligonucleotide, the 31 bases were surrounded by sequences complementary to primers that could be used for the UID assignment steps of Safe-SeqS (FIG. 63). By performing Safe-SeqS on ~300,000 oligonucleotides, it was found that there were $8.9 \pm 0.28 \times 10^{-4}$ super-mutants/bp and that these errors occurred throughout the oligonucleotides (FIG. 66A). The oligonucleotides contained a large number of insertion and deletion errors, representing 8.2±0.63% and 25±1.5% of the total super-mutants, respectively. Importantly, both the position and nature of the errors were highly reproducible among seven independent replicates of this experiment performed on the same batch of oligonucleotides (FIG. 66A). This nature and distribution of errors had little in common with that of the errors produced by Phusion polymerase (FIG. 66B and Table 56), which were distributed in the expected stochastic pattern among replicate experiments. The number of errors in the oligonucleotides synthesized with phosphoramidites was ~60 times higher than in the equivalent products synthesized by Phusion polymerase. These data, in toto, indicate that the vast majority of errors in the former were generated during their synthesis rather than during the Safe-SeqS procedure.

Does Safe-SeqS preserve the ratio of mutant:normal sequences in the original templates? To address this question, two 31-base oligonucleotides of identical sequence with the exception of nt 15 (50:50 C/G instead of T) were synthesized and mixed them at nominal mutant/normal fractions of 3.3% and 0.33%. Through Safe-SeqS analysis of the oligonucleotide mixtures, it was found that the ratios were 2.8% and 0.27%, respectively. Thus, the UID assignment and amplification procedures used in Safe-SeqS do not greatly alter the proportion of variant sequences and thereby provide a reliable estimate of that proportion when unknown. This is also supported by the reproducibility of variant fractions when analyzed in independent Safe-SeqS experiments (FIG. 66A).

Analysis of DNA Sequences from Normal Human Cells

The exogenous UID strategy (FIG. 63) was then used to determine the prevalence of rare mutations in a small region of the CTNNB1 gene from ~100,000 normal human cells from three unrelated individuals. Through comparison with the number of UID-families obtained in the Safe-SeqS experiments (Table 53B), it was calculated that the majority (78±9.8%) of the input fragments were converted into UID-families. There was an average of 68 members/UID-family, easily fulfilling the required redundancy for Safe-SeqS (FIG. 67). Conventional analysis of the Illumina sequencing data revealed an average of 118,488±11,357 mutations among the ~560 Mb of sequence analyzed per sample, corresponding to an apparent mutation prevalence of $2.1\pm0.16\times10^{-4}$ mutations/bp (Table 53B). Only an average of 99±78 super-mutants were observed in the Safe-SeqS analysis. The vast majority (>99%) of super-mutants were single base substitutions and the calculated mutation rate was $9.0\pm3.1\times10^{-6}$ mutations/bp (Table 54B). Safe-SeqS thereby reduced the apparent frequency of mutations in genomic DNA by at least 24-fold (FIG. 64).

One possible strategy to increase the specificity of Safe-SeqS is to perform the library amplification (and possibly the UID assignment cycles) in multiple wells. This can be accomplished in as few as 2 or as many as 384 wells using standard PCR plates, or scaled up to many more wells when using a microfluidic device (thousands to millions). When performed this way, indexing sequences can be introduced into the templates that are unique to the wells in which the template is amplified. Rare mutations, thus, should give rise to two super-mutants (i.e., one from each strand), both with the same well index sequence. When performing Safe-SeqS with exogenous UIDs on the CTNNB1 templates described above and diluted into 10 wells (each well yielding templates amplified with a different index sequence), the mutation rate was further reduced from $9.0\pm3.1\times10^{-6}$ to $3.7\pm1.2\times10^{-6}$ super-mutants/bp. Thus, analyzing templates in multiple compartments—in a manner that yields differentially encoded templates based on the compartment in which templates were amplified—may be an additional strategy to increase the specificity of Safe-SeqS.

Analysis of DNA Sequences from Mitochondrial DNA

The identical strategy was applied to a short segment of mitochondrial DNA in ~1,000 cells from each of seven unrelated individuals. Conventional analysis of the Illumina sequencing libraries produced with the Safe-SeqS procedure (FIG. 63) revealed an average of 30,599±12,970 mutations among the ~150 Mb of sequence analyzed per sample, corresponding to an apparent mutation prevalence of $2.1\pm0.94\times10^{-4}$ mutations/bp (Table 53C). Only 135±61 super-mutants were observed in the Safe-SeqS analysis. As with the CTNNB1 gene, the vast majority of mutations were single base substitutions, though occasional single base deletions were also observed (Table 54C). The calculated mutation rate in the analyzed segment of mtDNA was $1.4\pm0.68\times10^{-5}$ mutations/bp (Table 53C). Thus, Safe-SeqS thereby reduced the apparent frequency of mutations in genomic DNA by at least 15-fold.

Example 9: Detection of Genetic and Protein Biomarkers in Combination with Detection of Aneuploidy Samples from a number of patients were tested for the presence of genetic biomarkers (NRAS, CTNNB1, PIK3CA, FBXW7, APC, EGFR, BRAF, CDKN2A, PTEN, FGFR2, HRAS, KRAS, AKT1, TP53, PPP2R1A, and/or GNAS) and protein biomarkers (CA19-9, CEA, HGF, OPN, CA125, prolactin, TIMP-1, and/or MPO). The same samples were also tested for the presence of aneuploidy using WALDO methods described herein. The results are shown in Table 59. As can be seen, the genetic and protein biomarker test can complement the aneuploidy test (e.g., some patients are negative for the genetic and protein biomarker test while being positive for aneuploidy, and vice versa), such that the presence of cancer can be more accurately and completely detected using both tests.

Once a subject, is identified as having cancer by the genetic and protein biomarker test, the aneuploidy test, or both, the subject can undergo further diagnostic testing and/or increased monitoring (e.g., any of the variety of further diagnostic testing and/or increased monitoring methods described herein) and/or be administered a therapeutic intervention (e.g., any of the variety of therapeutic interventions described herein).

REFERENCES

Certain of the following references are referred to herein. The contents of each of the following references is incorporated herein by reference in its entirety.

AlHilli et al., Incidence and factors associated with synchronous ovarian and endometrial cancer: a population-based case-control study. Gynecologic oncology 125, 109-113 (2012).

Allen P J, et al. (2017) Multi-institutional Validation Study of the American Joint Commission on Cancer (8th Edition) Changes for T and N Staging in Patients With Pancreatic Adenocarcinoma. Ann Surg 265(1):185-191.

Allory Y, Beukers W, Sagrera A, Flandez M, Marques M, Marquez M, van der Keur K A, Dyrskjot L, Lurkin I, Vermeij M, Carrato A, Lloreta J, Lorente J A, Carrillo-de Santa Pau E, Masius R G, Kogevinas M, Steyerberg E W, van Tilborg A A, Abas C, Orntoft T F, Zuiverloon T C, Malats N, Zwarthoff E C, Real F X (2014) Telomerase reverse transcriptase promoter mutations in bladder cancer: high frequency across stages, detection in urine, and lack of association with outcome. Eur Urol 65:360-366.

Andre T, et al. (2009) Improved overall survival with oxaliplatin, fluorouracil, and leucovorin as adjuvant treatment in stage II or III colon cancer in the MOSAIC trial. J Clin Oncol 27(19):3109-3116.

Anglesio et al., Cancer-Associated Mutations in Endometriosis without Cancer. N Engl J Med 376, 1835-1848 (2017).

Ansari D, et al. (2017) Relationship between tumour size and outcome in pancreatic ductal adenocarcinoma. Br J Surg 104(5):600-607.

Arnold et al., G. A. Stevens, M. Ezzati, J. Ferlay, J. J. Miranda, I. Romieu, R. Dikshit, D. Forman, I. Soerjomataram, Global burden of cancer attributable to high body-mass index in 2012: a population-based study. The Lancet. Oncology 16, 36-46 (2015).

Bahuva R, Walsh R M, Kapural L, & Stevens T (2013) Morphologic abnormalities are poorly predictive of visceral pain in chronic pancreatitis. Pancreas 42(1):6-10.

Bansal N, Gupta A, Sankhwar S N, Mahdi A A (2014) Low- and high-grade bladder cancer appraisal via serum-based proteomics approach. Clin Chim Acta 436:97-103.

Barkan G A, Wojcik E M, Nayar R, Savic-Prince S, Quek M L, Kurtycz D F, Rosenthal D L (2016) The Paris System for Reporting Urinary Cytology: The Quest to Develop a Standardized Terminology. Adv Anat Pathol 23:193-201.

Bettegowda C, et al. (2014) Detection of circulating tumor DNA in early- and late-stage human malignancies. Science translational medicine 6(224):224ra224.

Biankin A V, et al. (2012) Pancreatic cancer genomes reveal aberrations in axon guidance pathway genes. Nature 491 (7424):399-405.

Bozic I, et al. (2013) Evolutionary dynamics of cancer in response to targeted combination therapy. Elife 2:e00747.

Buys et al., Effect of screening on ovarian cancer mortality: the Prostate, Lung, Colorectal and Ovarian (PLCO) Cancer Screening Randomized Controlled Trial. JAMA 305, 2295-2303 (2011).

Cancer Genome Atlas Research Network (2014) Comprehensive molecular characterization of urothelial bladder carcinoma. Nature 507:315-322.

Capello M, et al. (2017) Sequential Validation of Blood-Based Protein Biomarker Candidates for Early-Stage Pancreatic Cancer. J Natl Cancer Inst 109(4).

Chai H, Brown R E (2009) Field effect in cancer—an update. Ann Clin Lab Sci 39:331-337

Chari S T, et al. (2005) Probability of pancreatic cancer following diabetes: a population-based study. Gastroenterology 129(2):504-511.

Cheng L, Montironi R, Lopez-Beltran A (2017) TERT Promoter Mutations Occur Frequently in Urothelial Papilloma and Papillary Urothelial Neoplasm of Low Malignant Potential. Eur Urol 71:497-498.

Cheung et al., High frequency of PIK3R1 and PIK3R2 mutations in endometrial cancer elucidates a novel mechanism for regulation of PTEN protein stability. Cancer Discov 1, 170-185 (2011).

Clarke-Pearson D L (2009) Clinical practice. Screening for ovarian cancer. N Engl J Med 361(2):170-177.

Coombs et al., Therapy-Related Clonal Hematopoiesis in Patients with Non-hematologic Cancers Is Common and Associated with Adverse Clinical Outcomes. Cell Stem Cell, (2017).

Cowan M L, Springer S, Nguyen D, Taheri D, Guner G, Mendoza Rodriguez M A, Wang Y, Kinde I, Del Carmen Rodriguez Pena M, VandenBussche C J, Olson M T, Cunha I, Fujita K, Ertoy D, Kinzler K, Bivalacqua T, Papadopoulos N, Vogelstein B, Netto G J (2016) Detection of TERT promoter mutations in primary adenocarcinoma of the urinary bladder. Hum Pathol 53:8-13.

Davis R, Jones J S, Barocas D A, Castle E P, Lang E K, Leveillee R J, Messing E M, Miller S D, Peterson A C, Turk™, Weitzel W, American Urological Association (2012) Diagnosis, evaluation and follow-up of asymptomatic microhematuria (AMH) in adults: AUA guideline. J Urol 188:2473-2481.

Dawson S J, et al. (2013) Analysis of circulating tumor DNA to monitor metastatic breast cancer. N Engl J Med 368 (13):1199-1209.

Di Renzo M F, et al. (1995) Overexpression and amplification of the met/HGF receptor gene during the progression of colorectal cancer. Clin Cancer Res 1(2):147-154.

Di Renzo M F, Poulsom R, Olivero M, Comoglio P M, & Lemoine N R (1995) Expression of the Met/hepatocyte growth factor receptor in human pancreatic cancer. Cancer Res 55(5):1129-1138.

Dimashkieh H, Wolff D J, Smith T M, Houser P M, Nietert P J, Yang J (2013) Evaluation of urovysion and cytology for bladder cancer detection: a study of 1835 paired urine samples with clinical and histologic correlation. Cancer Cytopathol 121:591-597.

Dong T, Liu C C, Petricoin E F, & Tang L L (2014) Combining markers with and without the limit of detection. Stat Med 33(8):1307-1320.

Dressman D, Yan H, Traverso G, Kinzler K W, & Vogelstein B (2003) Transforming single DNA molecules into fluorescent magnetic particles for detection and enumeration of genetic variations. Proc Natl Acad Sci USA 100(15): 8817-8822.

Dy G K, et al. (2009) Long-term survivors of metastatic colorectal cancer treated with systemic chemotherapy alone: a North Central Cancer Treatment Group review of 3811 patients, N0144. Clin Colorectal Cancer 8(2):88-93.

Eckert et al., Genomics of Ovarian Cancer Progression Reveals Diverse Metastatic Trajectories Including Intraepithelial Metastasis to the Fallopian Tube. Cancer Discov 6, 1342-1351 (2016).

Egawa S, et al. (2004) Clinicopathological aspects of small pancreatic cancer. Pancreas 28(3):235-240.

Ellinger J, Muller S C, Dietrich D (2015) Epigenetic biomarkers in the blood of patients with urological malignancies. Expert Rev Mol Diagn 15:505-516.

El-Tanani M K, et al. (2006) The regulation and role of osteopontin in malignant transformation and cancer. Cytokine Growth Factor Rev 17(6):463-474.

Erickson et al., Detection of somatic TP53 mutations in tampons of patients with high-grade serous ovarian cancer. Obstetrics and gynecology 124, 881-885 (2014).

Fishman et al., The role of ultrasound evaluation in the detection of early-stage epithelial ovarian cancer. Am J Obstet Gynecol 192, 1214-1221; discussion 1221-1212 (2005).

Forbes et al., COSMIC: somatic cancer genetics at high-resolution. Nucleic Acids Res 45, D777-D783 (2017).

Forshew T, et al. (2012) Noninvasive identification and monitoring of cancer mutations by targeted deep sequencing of plasma DNA. Science translational medicine 4(136):136ra168.

Fradet Y, Lockhard C (1997) Performance characteristics of a new monoclonal antibody test for bladder cancer: ImmunoCyt trade mark. Can J Urol 4:400-405.

Frokjaer J B, Olesen S S, & Drewes A M (2013) Fibrosis, atrophy, and ductal pathology in chronic pancreatitis are associated with pancreatic function but independent of symptoms. Pancreas 42(7):1182-1187.

Geldenhuys, Murray, Sensitivity and specificity of the Pap smear for glandular lesions of the cervix and endometrium. Acta cytologica 51, 47-50 (2007).

Genovese G, et al. (2014) Clonal hematopoiesis and blood-cancer risk inferred from blood DNA sequence. N Engl J Med 371 (26): 2477-2487.

Gerlinger et al., Intratumor heterogeneity and branched evolution revealed by multiregion sequencing. N Engl J Med 366, 883-892 (2012).

Gilbert et al., Assessment of symptomatic women for early diagnosis of ovarian cancer: results from the prospective DOVE pilot project. The Lancet. Oncology 13, 285-291 (2012).

Goodison S, Chang M, Dai Y, Urquidi V, Rosser C J (2012) A multi-analyte assay for the non-invasive detection of bladder cancer. PLoS One 7:e47469.

Gopalakrishna A, Fantony J J, Longo T A, Owusu R, Foo W C, Dash R, Denton B T, Inman B A (2017) Anticipatory Positive Urine Tests for Bladder Cancer. Ann Surg Oncol 24:1747-1753.

Haber D A & Velculescu V E (2014) Blood-based analyses of cancer: circulating tumor cells and circulating tumor DNA. Cancer Discov 4(6):650-661.

Hajdinjak T (2008) UroVysion FISH test for detecting urothelial cancers: meta-analysis of diagnostic accuracy and comparison with urinary cytology testing. Urol Oncol 26:646-651.

Hamilton et al., Uterine papillary serous and clear cell carcinomas predict for poorer survival compared to grade 3 endometrioid corpus cancers. British journal of cancer 94, 642-646 (2006).

Herbst R S, Heymach J V, & Lippman S M (2008) Lung cancer. N Engl J Med 359(13):1367-1380.

Horn S, Figl A, Rachakonda P S, Fischer C, Sucker A, Gast A, Kadel S, Moll I, Nagore E, Hemminki K, Schadendorf D, Kumar R (2013) TERT promoter mutations in familial and sporadic melanoma. Science 339:959-961.

Howlader et al., SEER Cancer Statistics Review, 1975-2014, National Cancer Institute. (2017).

Howlader N, et al. (2016) SEER Cancer Statistics Review, 1975-2013, National Cancer Institute. Bethesda, MD, http://seer.cancer.gov/csr/1975_2013/, based on November 2015 SEER data submission, posted to the SEER web site, April 2016.

Huang A C, et al. (2017) T-cell invigoration to tumour burden ratio associated with anti-PD-1 response. Nature 545(7652):60-65.

Huang F W, Hodis E, Xu M J, Kryukov G V, Chin L, Garraway L A (2013) Highly recurrent TERT promoter mutations in human melanoma. Science 339:957-959.

Hurst C D, Platt F M, Knowles M A (2014) Comprehensive mutation analysis of the TERT promoter in bladder cancer and detection of mutations in voided urine. Eur Urol 65:367-369.

Ikematsu S, et al. (2000) Serum midkine levels are increased in patients with various types of carcinomas. Br J Cancer 83(6):701-706.

International Agency for Research on Cancer. (2016) WHO Classification of Tumours of the Urinary System and Male Genital Organs. World Health Organization; 4 edition Ishikawa O, et al. (1999) Minute carcinoma of the pancreas measuring 1 cm or less in diameter—collective review of Japanese case reports. Hepatogastroenterology 46(25):8-15.

Jacobs et al., Ovarian cancer screening and mortality in the UK Collaborative Trial of Ovarian Cancer Screening (UKCTOCS): a randomised controlled trial. Lancet 387, 945-956 (2016).

Jacobs et al., Sensitivity of transvaginal ultrasound screening for endometrial cancer in postmenopausal women: a case-control study within the UKCTOCS cohort. The Lancet. Oncology 12, 38-48 (2011).

Jaiswal S, et al. (2014) Age-related clonal hematopoiesis associated with adverse outcomes. N Engl J Med 371 (26): 2488-2498.

Jones S, et al. (2008) Core signaling pathways in human pancreatic cancers revealed by global genomic analyses. Science 321(5897):1801-1806.

Jung et al., Intron retention is a widespread mechanism of tumor-suppressor inactivation. Nat Genet 47, 1242-1248 (2015).

Jung K W, et al. (2007) Clinicopathological aspects of 542 cases of pancreatic cancer: a special emphasis on small pancreatic cancer. J Korean Med Sci 22 Suppl: S79-85.

K. N. Moore, A. N. Fader, Uterine papillary serous carcinoma. Clin Obstet Gynecol 54, 278-291 (2011).

Kalinich M, et al. (2017) An RNA-based signature enables high specificity detection of circulating tumor cells in hepatocellular carcinoma. Proc Natl Acad Sci USA 114 (5):1123-1128.

Kandoth et al., Integrated genomic characterization of endometrial carcinoma. Nature 497, 67-73 (2013).

Karst et al., Modeling high-grade serous ovarian carcinogenesis from the fallopian tube. Proc Natl Acad Sci USA 108, 7547-7552 (2011).

Kawauchi S, Sakai H, Ikemoto K, Eguchi S, Nakao M, Takihara H, Shimabukuro T, Furuya T, Oga A, Matsuyama H, Takahashi M, Sasaki K (2009) 9p21 Index as Estimated by Dual-Color Fluorescence in Situ Hybridization is Useful to Predict Urothelial Carcinoma Recurrence in Bladder Washing Cytology. Hum Pathol 40:1783-1789.

Khadra M H, Pickard R S, Charlton M, Powell P H, Neal D E (2000) A prospective analysis of 1,930 patients with hematuria to evaluate current diagnostic practice. J Urol 163:524-527.

Killela P J, Reitman Z J, Jiao Y, Bettegowda C, Agrawal N, Diaz L A, Jr, Friedman A H, Friedman H, Gallia G L, Giovanella B C, Grollman A P, He T C, He Y, Hruban R H, Jallo G I, Mandahl N, Mecker A K, Mertens F, Netto G J, Rasheed B A, Riggins G J, Rosenquist T A, Schiffman M, Shih I, Theodorescu D, Torbenson M S, Velculescu V E, Wang T L, Wentzensen N, Wood L D, Zhang M, Mclendon R E, Bigner D D, Kinzler K W, Vogelstein B, Papadopoulos N, Yan H (2013) TERT promoter mutations occur frequently in gliomas and a subset of tumors derived from cells with low rates of self-renewal. Proc Natl Acad Sci USA 110:6021-6026.

Kim J E, et al. (2004) Clinical usefulness of carbohydrate antigen 19-9 as a screening test for pancreatic cancer in an asymptomatic population. J Gastroenterol Hepatol 19(2): 182-186.

Kinde et al., FAST-SeqS: a simple and efficient method for the detection of aneuploidy by massively parallel sequencing. PLoS One 7, e41162 (2012).

Kinde I, et al. (2013) Evaluation of DNA from the Papanicolaou test to detect ovarian and endometrial cancers. Science translational medicine 5(167):167ra164.

Kinde I, Munari E, Faraj S F, Hruban R H, Schoenberg M, Bivalacqua T, Allaf M, Springer S, Wang Y, Diaz L A, Jr, Kinzler K W, Vogelstein B, Papadopoulos N, Netto G J (2013) TERT promoter mutations occur early in urothelial neoplasia and are biomarkers of early disease and disease recurrence in urine. Cancer Res 73:7162-7167.

Kinde I, Wu J, Papadopoulos N, Kinzler K W, & Vogelstein B (2011) Detection and quantification of rare mutations with massively parallel sequencing. Proc Natl Acad Sci USA 108(23):9530-9535.

Kobayashi et al., A randomized study of screening for ovarian cancer: a multicenter study in Japan. Int J Gynecol Cancer 18, 414-420 (2008).

Koopmann J, et al. (2004) Evaluation of osteopontin as biomarker for pancreatic adenocarcinoma. Cancer Epidemiol Biomarkers Prev 13(3):487-491.

Krimmel et al., Ultra-deep sequencing detects ovarian cancer cells in peritoneal fluid and reveals somatic TP53 mutations in noncancerous tissues. Proc Natl Acad Sci USA 113, 6005-6010 (2016).

Kruger S, Mess F, Bohle A, Feller A C (2003) Numerical aberrations of chromosome 17 and the 9p21 locus are independent predictors of tumor recurrence in non-invasive transitional cell carcinoma of the urinary bladder. Int J Oncol 23:41-48.

Kurman, Shih Ie, Molecular pathogenesis and extraovarian origin of epithelial ovarian cancer—shifting the paradigm. Human pathology 42, 918-931 (2011).

Kurman, Shih Ie, The Dualistic Model of Ovarian Carcinogenesis: Revisited, Revised, and Expanded. Am J Pathol 186, 733-747(2016).

Kurman, Shih Ie, The origin and pathogenesis of epithelial ovarian cancer: a proposed unifying theory. The American journal of surgical pathology 34, 433-443 (2010).

Le Calvez-Kelm F, et al. (2016) KRAS mutations in blood circulating cell-free DNA: a pancreatic cancer case-control. Oncotarget 7(48):78827-78840.

Lee et al., A candidate precursor to serous carcinoma that originates in the distal fallopian tube. The Journal of pathology 211, 26-35 (2007).

Lennon A M & Goggins M (2010) Diagnostic and Therapeutic Response Markers. Pancreatic Cancer, (Springer New York, New York, N Y), pp 675-701.

Lennon A M, et al. (2014) The Early Detection of Pancreatic Cancer: What Will It Take to Diagnose and Treat Curable Pancreatic Neoplasia? Cancer Res 74(13):3381-3389.

Levina V V, et al. (2009) Biological significance of prolactin in gynecologic cancers. Cancer Res 69(12):5226-5233.

Lin H H, Ke H L, Huang S P, Wu W J, Chen Y K, Chang L L (2010) Increase sensitivity in detecting superficial, low grade bladder cancer by combination analysis of hypermethylation of E-cadherin, p16, p14, RASSF1A genes in urine. Urol Oncol 28:597-602.

Liotta L A & Petricoin E F, 3rd (2003) The promise of proteomics. Clin Adv Hematol Oncol 1(8):460-462.

Locker G Y, et al. (2006) ASCO 2006 update of recommendations for the use of tumor markers in gastrointestinal cancer. J Clin Oncol 24(33):5313-5327.

Lotan Y, Roehrborn C G (2003) Sensitivity and specificity of commonly available bladder tumor markers versus cytology: results of a comprehensive literature review and meta-analyses. Urology 61:109-18; discussion 118.

Meden, Fattahi-Meibodi, C A 125 in benign gynecological conditions. Int J Biol Markers 13, 231-237 (1998).

Menon et al., Risk Algorithm Using Serial Biomarker Measurements Doubles the Number of Screen-Detected Cancers Compared With a Single-Threshold Rule in the United Kingdom Collaborative Trial of Ovarian Cancer Screening. J Clin Oncol 33, 2062-2071 (2015).

Mishriki S F, Nabi G, Cohen N P (2008) Diagnosis of urologic malignancies in patients with asymptomatic dipstick hematuria: prospective study with 13 years' follow-up. Urology 71:13-16.

Mo L, Zheng X, Huang H Y, Shapiro E, Lepor H, Cordon-Cardo C, Sun T T, Wu X R (2007) Hyperactivation of Ha-ras oncogene, but not Ink4a/Arf deficiency, triggers bladder tumorigenesis. J Clin Invest 117:314-325.

Moertel C G, et al. (1995) Fluorouracil plus levamisole as effective adjuvant therapy after resection of stage III colon carcinoma: a final report. Ann Intern Med 122(5): 321-326.

Moonen P M, Merkx G F, Peelen P, Karthaus H F, Smeets D F, Witjes J A (2007). UroVysion compared with cytology and quantitative cytology in the surveillance of non-muscle-invasive bladder cancer. Eur Urol 51:1275-80; discussion 1280.

Moore et al., The use of multiple novel tumor biomarkers for the detection of ovarian carcinoma in patients with a pelvic mass. Gynecologic oncology 108, 402-408 (2008).

Moyer, Screening for ovarian cancer: U.S. Preventive Services Task Force reaffirmation recommendation statement. Annals of internal medicine 157, 900-904 (2012).

N. Cancer Genome Atlas Research, Integrated genomic analyses of ovarian carcinoma. Nature 474, 609-615 (2011).

Nair et al., Genomic Analysis of Uterine Lavage Fluid Detects Early Endometrial Cancers and Reveals a Prevalent Landscape of Driver Mutations in Women without Histopathologic Evidence of Cancer: A Prospective Cross-Sectional Study. PLoS Med 13, e1002206 (2016).

Nazli O, Bozdag A D, Tansug T, Kir R, & Kaymak E (2000) The diagnostic importance of CEA and C A 19-9 for the early diagnosis of pancreatic carcinoma. Hepatogastroenterology 47(36):1750-1752.

Netto G J (2011) Molecular biomarkers in urothelial carcinoma of the bladder: are we there yet?. Nat Rev Urol 9:41-51.

Netto G J (2013) Clinical applications of recent molecular advances in urologic malignancies: no longer chasing a "mirage"?. Adv Anat Pathol 20:175-203.

Netto G J, Epstein J I (2010) Theranostic and prognostic biomarkers: genomic applications in urological malignancies. Pathology 42:384-394.

Netto G J, Tafe L J (2016) Emerging Bladder Cancer Biomarkers and Targets of Therapy. Urol Clin North Am 43:63-76.

Ng et al., Significance of endometrial cells in the detection of endometrial carcinoma and its precursors. Acta cytologica 18, 356-361 (1974).

Nguyen D, Taheri D, Springer S, Cowan M, Guner G, Mendoza Rodriguez M A, Wang Y, Kinde I, Vanden-Bussche C J, Olson M T, Ricardo B F, Cunha I, Fujita K, Ertoy D, Kinzler K W, Bivalacqua T J, Papadopoulos N, Vogelstein B, Netto G J (2016) High prevalence of TERT promoter mutations in micropapillary urothelial carcinoma. Virchows Arch 469:427-434.

O'Brien D P, et al. (2015) Serum CA19-9 is significantly upregulated up to 2 years before diagnosis with pancreatic cancer: implications for early disease detection. Clin Cancer Res 21(3):622-631.

Rago et al., Serial assessment of human tumor burdens in mice by the analysis of circulating DNA. Cancer research 67, 9364-9370 (2007).

Rahib L, et al. (2014) Projecting cancer incidence and deaths to 2030: the unexpected burden of thyroid, liver, and pancreas cancers in the United States. Cancer Res 74(11): 2913-2921.

Ralla B, Stephan C, Meller S, Dietrich D, Kristiansen G, Jung K (2014) Nucleic acid-based biomarkers in body fluids of patients with urologic malignancies. Crit Rev Clin Lab Sci 51:200-231.

Rodriguez Pena M D C, Tregnago A C, Eich M L, Springer S, Wang Y, Taheri D, Ertoy D, Fujita K, Bezerra S M, Cunha I W, Raspollini M R, Yu L, Bivalacqua T J, Papadopoulos N, Kinzler K W, Vogelstein B, Netto G J (2017) Spectrum of genetic mutations in de novo PUNLMP of the urinary bladder. Virchows Arch.

Ryan D P, Hong T S, & Bardeesy N (2014) Pancreatic adenocarcinoma. N Engl J Med 371(22):2140-2141.

Sarkis A S, Bajorin D F, Reuter V E, Herr H W, Netto G, Zhang Z F, Schultz P K, Cordon-Cardo C, Scher H I (1995) Prognostic value of p53 nuclear overexpression in patients with invasive bladder cancer treated with neoadjuvant MVAC. J Clin Oncol 13:1384-1390.

Sarkis A S, Dalbagni G, Cordon-Cardo C, Melamed J, Zhang Z F, Sheinfeld J, Fair W R, Herr H W, Reuter V E (1994) Association of P53 nuclear overexpression and tumor progression in carcinoma in situ of the bladder. J Urol 152:388-392.

Sarkis A S, Dalbagni G, Cordon-Cardo C, Zhang Z F, Sheinfeld J, Fair W R, Herr H W, Reuter V E (1993) Nuclear overexpression of p53 protein in transitional cell bladder carcinoma: a marker for disease progression. J Natl Cancer Inst 85:53-59.

Sarosdy M F, Kahn P R, Ziffer M D, Love W R, Barkin J, Abara E O, Jansz K, Bridge J A, Johansson S L, Persons D L, Gibson J S (2006) Use of a multitarget fluorescence in situ hybridization assay to diagnose bladder cancer in patients with hematuria. J Urol 176:44-47.

Schnatz et al., Clinical significance of atypical glandular cells on cervical cytology. Obstetrics and gynecology 107, 701-708 (2006).

Scott G A, Laughlin T S, Rothberg P G (2014) Mutations of the TERT promoter are common in basal cell carcinoma and squamous cell carcinoma. Mod Pathol 27:516-523.

Semrad T J, Fahrni A R, Gong I Y, & Khatri V P (2015) Integrating Chemotherapy into the Management of Oligometastatic Colorectal Cancer: Evidence-Based Approach Using Clinical Trial Findings. Ann Surg Oncol 22 Suppl 3:S855-862.

Serizawa R R, Ralfkiaer U, Steven K, Lam G W, Schmiedel S, Schuz J, Hansen A B, Horn T, Guldberg P (2010) Integrated genetic and epigenetic analysis of bladder cancer reveals an additive diagnostic value of FGFR3 mutations and hypermethylation events. Int J Cancer.

Sharma et al., Risk of epithelial ovarian cancer in asymptomatic women with ultrasound-detected ovarian masses: a prospective cohort study within the UK collaborative trial of ovarian cancer screening (UKCTOCS). Ultrasound Obstet Gynecol 40, 338-344 (2012).

Siegel R L, Miller K D, Jemal A (2017) Cancer Statistics, 2017. CA Cancer J Clin 67:7-30.

Siravegna et al., Integrating liquid biopsies into the management of cancer. Nat Rev Clin Oncol 14, 531-548 (2017).

Skacel M, Fahmy M, Brainard J A, Pettay J D, Biscotti C V, Liou L S, Procop G W, Jones J S, Ulchaker J, Zippe C D, Tubbs R R (2003) Multitarget fluorescence in situ hybridization assay detects transitional cell carcinoma in the majority of patients with bladder cancer and atypical or negative urine cytology. J Urol 169:2101-2105.

Song et al., Prognostic factors in women with synchronous endometrial and ovarian cancers. Int J Gynecol Cancer 24, 520-527 (2014).

Springer S, et al. (2015) A Combination of Molecular Markers and Clinical Features Improve the Classification of Pancreatic Cysts. Gastroenterology 149(6):1501-1510.

Steensma et al., Clonal hematopoiesis of indeterminate potential and its distinction from myelodysplastic syndromes. Blood 126, 9-16(2015).

Stern J L, Theodorescu D, Vogelstein B, Papadopoulos N, Cech T R (2015) Mutation of the TERT promoter, switch to active chromatin, and monoallelic TERT expression in multiple cancers. Genes Dev 29:2219-2224.

Takahashi T, Habuchi T, Kakehi Y, Mitsumori K, Akao T, Terachi T, Yoshida O (1998) Clonal and chronological genetic analysis of multifocal cancers of the bladder and upper urinary tract. Cancer Res 58:5835-5841.

Tao, Direct intrauterine sampling: the IUMC Endometrial Sampler. Diagnostic cytopathology 17, 153-159 (1997).

Thomas D S, et al. (2015) Evaluation of serum CEA, CYFRA21-1 and CA125 for the early detection of colorectal cancer using longitudinal preclinical samples. Br J Cancer 113(2):268-274.

Thorpe J D, et al. (2007) Effects of blood collection conditions on ovarian cancer serum markers. PLoS One 2(12): e1281.

Tsuchiya R, et al. (1986) Collective review of small carcinomas of the pancreas. Ann Surg 203(1):77-81.

Uhlen M, et al. (2015) Proteomics. Tissue-based map of the human proteome. Science 347 (6220): 1260419.

Vogelstein B & Kinzler K W (1999) Digital PCR. Proc Natl Acad Sci USA 96(16):9236-9241.

Vogelstein B, Papadopoulos N, Velculescu V E, Zhou S, Diaz L A, Jr, Kinzler K W (2013) Cancer genome landscapes. Science 339:1546-1558.

Waddell N, et al. (2015) Whole genomes redefine the mutational landscape of pancreatic cancer. Nature 518 (7540):495-501.

Walsh et al., Coexisting ovarian malignancy in young women with endometrial cancer. Obstetrics and gynecology 106, 693-699 (2005).

Wang K, Liu T, Ge N, Liu L, Yuan X, Liu J, Kong F, Wang C, Ren H, Yan K, Hu S, Xu Z, Bjorkholm M, Fan Y, Zhao S, Liu C, Xu D (2014) TERT promoter mutations are associated with distant metastases in upper tract urothelial carcinomas and serve as urinary biomarkers detected by a sensitive castPCR. Oncotarget 5:12428-12439.

Wang Y, et al. (2015) Detection of somatic mutations and HPV in the saliva and plasma of patients with head and neck squamous cell carcinomas. Science translational medicine 7(293):293ra104.

Wang Y, et al. (2015) Detection of tumor-derived DNA in cerebrospinal fluid of patients with primary tumors of the brain and spinal cord. Proc Natl Acad Sci USA 112(31): 9704-9709.

Wang Y, et al. (2016) Diagnostic potential of tumor DNA from ovarian cyst fluid. Elife 5.

Wein A J, Kavoussi L R, Novick A C, Partin A W, Peters C A (2012) Campbell-Walsh Urology. Saunders, Philadelphia.

Wilcox C M, et al. (2015) Chronic pancreatitis pain pattern and severity are independent of abdominal imaging findings. Clin Gastroenterol Hepatol 13(3):552-560; quiz e528-559.

Wu et al., Endometrial brush biopsy (Tao brush). Histologic diagnosis of 200 cases with complementary cytology: an accurate sampling technique for the detection of endometrial abnormalities. American journal of clinical pathology 114, 412-418 (2000).

Wu X R (2005) Urothelial tumorigenesis: a tale of divergent pathways. Nat Rev Cancer 5:713-725.

Xie M, et al. (2014) Age-related mutations associated with clonal hematopoietic expansion and malignancies. Nat Med 20 (12): 1472-1478.

Yafi F A, Brimo F, Steinberg J, Aprikian A G, Tanguay S, Kassouf W (2015) Prospective analysis of sensitivity and specificity of urinary cytology and other urinary biomarkers for bladder cancer. Urol Oncol 33:66.e25-66.e31.

Young et al., Clonal hematopoiesis harbouring AML-associated mutations is ubiquitous in healthy adults. Nat Commun 7, 12484 (2016).

Zaino et al., Simultaneously detected endometrial and ovarian carcinomas—a prospective clinicopathologic study of 74 cases: a gynecologic oncology group study. Gynecologic oncology 83, 355-362 (2001).

Zhai et al., High-grade serous carcinomas arise in the mouse oviduct via defects linked to the human disease. The Journal of pathology 243, 16-25 (2017).

Zhang M L, Rosenthal D L, VandenBussche C J (2016) The cytomorphological features of low-grade urothelial neoplasms vary by specimen type. Cancer Cytopathol 124: 552-564

Zhao et al., Histologic follow-up results in 662 patients with Pap test findings of atypical glandular cells: results from a large academic womens hospital laboratory employing sensitive screening methods. Gynecologic oncology 114, 383-389 (2009).

Zhou W, et al. (1998) Identifying markers for pancreatic cancer by gene expression analysis. Cancer Epidemiol Biomarkers Prev 7(2):109-112.

What is claimed is:

1. A method for identifying the presence of cancer in a human comprising:

a) sequencing at least a portion of each of at least 12 genes from cell-free DNA derived from a plasma sample from said human, wherein said at least 12 genes are selected from NRAS, CTNNB1, PIK3CA, FBXW7, APC, EGFR, BRAF, CDKN2A, PTEN, FGFR2, HRAS, KRAS, AKT1, TP53, PPP2R1A, and GNAS, wherein said human has not been determined to have cancer, and wherein the sequencing of at least a portion of each of the at least 12 genes detects the presence or absence of at least the following mutations:

when the at least 12 genes comprise NRAS, a 175G>A, 35G>A, and 182A>G mutation in NRAS, when the at least 12 genes comprise CTNNB1, a 134C>T, 121A>G, 127G>A, 133T>G, 113G>A, 110C>T, 104T>G, 98C>A, 101G>T, and 100G>A mutation in CTNNB1, when the at least 12 genes comprise PIK3CA, a 3140A>G, 3137C>T, 1635G>T, 1624G>A, 1634A>C, 1633G>A, 3141T>G, 3132T>A, 3145G>C, 241G>A, 1637A>G, 1030G>A, 3140A>T, 1035T>A, 3131A>G, 263G>A, 1638G>T, and 1633G>C mutation in PIK3CA, when the at least 12 genes comprise FBXW7, a 1393C>T, 1514G>A, 1394G>A, 1436G>A, 1435C>T, 1412insA, 1105G>T, and 1099C>T mutation in FBXW7, when the at least 12 genes comprise APC, a 3916G>T, 4348C>T, 3927delAAAGA, and 393 1insA mutation in APC, when the at least 12 genes comprise EGFR, a 2570G>A, 2590G>A, 2588G>A, 2603A>G, and 2573T>G mutation in EGFR, when the at least 12 genes comprise BRAF, a 1798G>A, 1781A>G, 1801A>G, 1799T>A, 1796C>T, 1785T>G, 1790T>G, 1792G>A, and 1786G>C mutation in BRAF, when the at least 12 genes comprise CDKN2A, a 226G>A, 251A>T, 172C>T, 236C>T, 250G>T, 227C>T, 151G>C, 247C>T, 260G>A, and 262G>T mutation in CDKN2A, when the at least 12 genes comprise PTEN, a 388C>G, 406T>C, 377C>T, 376G>T, 275A>C, 389G>A, 451G>A, and 388C>T in PTEN, when the at least 12 genes comprise FGFR2, a 758C>G mutation in FGFR2, when the at least 12 genes comprise HRAS, a 35G>A, 38G>T, and 34G>A mutation in HRAS, when the at least 12 genes comprise KRAS, a 38G>A, 34G>T, 35G>A, 181C>A, 35G>T, 437C>T, 436G>A, 40G>A, 32C>T, 35G>C, 34G>A, 169G>A, 38G>T, 34G>C, 31G>A, 176C>A, 35G>T, 183A>C, 175G>A, and 183A>T mutation in KRAS,
when the at least 12 genes comprise AKT1, a 49G>A mutation in AKT1,
when the at least 12 genes comprise TP53, a 747G>T, 742C>T, 818G>T, 473G>A, 743G>A, 818G>A, 844C>T, 455C>T, 817C>T, 527G>T, 524G>A, 733G>A, and 659A>G mutation in TP53,
when the at least 12 genes comprise PPP2R1A, a 547C>T, 544C>T, and 551C>T mutation in PPP2R1A, and
when the at least 12 genes comprise GNAS, a 602G>A, 601C>T, 608T>C, and 601C>A mutation in GNAS;
b) sequencing at least a portion of each of said at least 12 genes from genomic DNA derived from a white blood cell sample from the human to detect in the genomic DNA the presence or absence of each of the mutations detected as present or absent in said cell-free DNA;
c) detecting a level of each of at least four of the following protein biomarkers derived from a plasma sample obtained from the human: CA19-9, CEA, HGF, OPN, CA125, AFP, prolactin, TIMP-1, follistatin, G-CSF, and CA15-3;
d) comparing the detected levels of each of the at least four protein biomarkers to reference levels of each of the protein biomarkers; and
e) identifying the presence of cancer in the human when:
i) at least one of the mutations is detected as present in said cell-free DNA and is detected as absent in said genomic DNA; or
ii) the detected level of at least one of said at least four protein biomarkers is higher than its reference level.

2. The method of claim 1, wherein the at least four protein biomarkers include CA19-9.

3. The method of claim 2, wherein the reference level of the CA19-9 protein biomarker is 92 U/mL.

4. The method of claim 1, wherein the at least four protein biomarkers include CEA.

5. The method of claim 4, wherein the reference level of the CEA protein biomarker is 7.5 ng/mL.

6. The method of claim 1, wherein the at least four protein biomarkers include CA125.

7. The method of claim 6, wherein the reference level of the CA125 protein biomarker is 577 U/mL.

8. The method of claim 1, wherein the at least four protein biomarkers include CA15-3.

9. The method of claim 8, wherein the reference level of the CA15-3 protein biomarker is 98 U/mL.

10. The method of claim 1, wherein the presence or absence of said at least one mutation in said at least 12 genes in said cell-free DNA from the plasma sample, or the presence or absence of said at least one mutation in said at least 12 genes in the genomic DNA from the white blood cell sample, or both are detected by amplifying the cell-free DNA, the genomic DNA, or both to form families of amplicons in which each member of a family is derived from a single template molecule in the cell-free DNA or genomic DNA, wherein each member of a family comprises a common oligonucleotide barcode, and wherein each family comprises a distinct oligonucleotide barcode.

11. The method of claim 10, wherein the oligonucleotide barcode is introduced into the template molecule by a step of amplifying with a population of primers which collectively contain a plurality of oligonucleotide barcodes.

12. The method of claim 10, wherein the oligonucleotide barcode is endogenous to the template molecule, and an adapter comprising a DNA synthesis priming site is ligated to an end of the template molecule adjacent to the oligonucleotide barcode.

13. The method of claim 1, further comprising administering a therapeutic intervention to the subject.

14. The method of claim 1, wherein the cancer is selected from the group consisting of: pancreatic cancer, colon cancer, ovarian cancer, liver cancer, lung cancer, breast cancer, and upper GI cancer.

15. A method for identifying the presence of cancer in a human comprising:
a) sequencing at least a portion of each of at least 12 genes from cell-free DNA derived from a plasma sample from said human, wherein said at least 12 genes are selected from NRAS, CTNNB1, PIK3CA, FBXW7, APC, EGFR, BRAF, CDKN2A, PTEN, FGFR2, HRAS, KRAS, AKT1, TP53, PPP2R1A, and GNAS,
wherein said human has not been determined to have cancer, and
wherein the sequencing of at least a portion of each of the at least 12 genes detects the presence or absence of at least the following mutations:
when the at least 12 genes comprise NRAS, a 175G>A, 35G>A, and 182A>G mutation in NRAS,
when the at least 12 genes comprise CTNNB1, a 134C>T, 121A>G, 127G>A, 133T>G, 113G>A, 110C>T, 104T>G, 98C>A, 101G>T, and 100G>A mutation in CTNNB1,
when the at least 12 genes comprise PIK3CA, a 3140A>G, 3137C>T, 1635G>T, 1624G>A, 1634A>C, 1633G>A, 3141T>G, 3132T>A, 3145G>C, 241G>A, 1637A>G, 1030G>A, 3140A>T, 1035T>A, 3131A>G, 263G>A, 1638G>T, and 1633G>C mutation in PIK3CA,
when the at least 12 genes comprise FBXW7, a 1393C>T, 1514G>A, 1394G>A, 1436G>A, 1435C>T, 1412insA, 1105G>T, and 1099C>T mutation in FBXW7,
when the at least 12 genes comprise APC, a 3916G>T, 4348C>T, 3927delAAAGA, and 393 1insA mutation in APC,
when the at least 12 genes comprise EGFR, a 2570G>A, 2590G>A, 2588G>A, 2603A>G, and 2573T>G mutation in EGFR,
when the at least 12 genes comprise BRAF, a 1798G>A, 1781A>G, 1801A>G, 1799T>A, 1796C>T, 1785T>G, 1790T>G, 1792G>A, and 1786G>C mutation in BRAF,
when the at least 12 genes comprise CDKN2A, a 226G>A, 251A>T, 172C>T, 236C>T, 250G>T, 227C>T, 151G>C, 247C>T, 260G>A, and 262G>T mutation in CDKN2A,
when the at least 12 genes comprise PTEN, a 388C>G, 406T>C, 377C>T, 376G>T, 275A>C, 389G>A, 451G>A, and 388C>T in PTEN,
when the at least 12 genes comprise FGFR2, a 758C>G mutation in FGFR2,
when the at least 12 genes comprise HRAS, a 35G>A, 38G>T, and 34G>A mutation in HRAS,
when the at least 12 genes comprise KRAS, a 38G>A, 34G>T, 35G>A, 181C>A, 35G>T, 437C>T, 436G>A, 40G>A, 32C>T, 35G>C, 34G>A, 169G>A, 38G>T, 34G>C, 31G>A, 176C>A, 35G>T, 183A>C, 175G>A, and 183A>T mutation in KRAS,
when the at least 12 genes comprise AKT1, a 49G>A mutation in AKT1,
when the at least 12 genes comprise TP53, a 747G>T, 742C>T, 818G>T, 473G>A, 743G>A, 818G>A, 844C>T, 455C>T, 817C>T, 527G>T, 524G>A, 733G>A, and 659A>G mutation in TP53,
when the at least 12 genes comprise PPP2R1A, a 547C>T, 544C>T, and 551C>T mutation in PPP2R1A, and
when the at least 12 genes comprise GNAS, a 602G>A, 601C>T, 608T>C, and 601C>A mutation in GNAS;
b) sequencing at least a portion of each of said at least 12 genes from genomic DNA derived from a white blood cell sample from the human to detect in the genomic DNA the presence or absence of each of said mutations detected as present or absent in said cell-free DNA;
c) detecting a level of each of at least four of the following protein biomarkers derived from a plasma sample obtained from the human: CA19-9, CEA, HGF, OPN, CA125, AFP, prolactin, TIMP-1, follistatin, G-CSF, and CA15-3;
d) comparing the detected levels of each of the at least four protein biomarkers to reference levels of each of the protein biomarkers; and
e) identifying the presence of cancer in the human by:
  i) detecting at least one of the mutations as present in said cell-free DNA and as absent in said genomic DNA; and
  ii) detecting the level of at least one of said at least four protein biomarkers as higher than its reference level.

\* \* \* \* \*